US012697398B2

(12) United States Patent
Chen et al.

(10) Patent No.: US 12,697,398 B2
(45) Date of Patent: Aug. 4, 2026

(54) COMPOSITIONS AND METHODS COMPRISING VIRAL VECTOR SYSTEMS FOR MULTIPLEXED ACTIVATION OF ENDOGENOUS GENES AS IMMUNOTHERAPY AND VIRAL-BASED IMMUNE-GENE THERAPY

(71) Applicant: YALE UNIVERSITY, New Haven, CT (US)

(72) Inventors: Sidi Chen, Milford, CT (US); Guangchuan Wang, West Haven, CT (US); Ryan D. Chow, San Jose, CA (US); Feifei Zhang, New Haven, CT (US)

(73) Assignee: Yale University, New Haven, CT (US)

( * ) Notice: Subject to any disclaimer, the term of this patent is extended or adjusted under 35 U.S.C. 154(b) by 1073 days.

(21) Appl. No.: 17/771,202

(22) PCT Filed: Oct. 23, 2020

(86) PCT No.: PCT/US2020/057113
§ 371 (c)(1),
(2) Date: Apr. 22, 2022

(87) PCT Pub. No.: WO2021/108050
PCT Pub. Date: Jun. 3, 2021

(65) Prior Publication Data
US 2022/0387626 A1     Dec. 8, 2022

Related U.S. Application Data

(60) Provisional application No. 62/924,973, filed on Oct. 23, 2019.

(51) Int. Cl.
| | |
|---|---|
| *A61K 48/00* | (2006.01) |
| *A61K 38/17* | (2006.01) |
| *A61K 38/19* | (2006.01) |
| *A61K 39/00* | (2006.01) |
| *A61P 35/00* | (2006.01) |
| *C12N 9/22* | (2006.01) |
| *C12N 15/10* | (2006.01) |
| *C12N 15/11* | (2006.01) |
| *C12N 15/86* | (2006.01) |

(52) U.S. Cl.
CPC ........ *A61K 48/0058* (2013.01); *A61K 38/177* (2013.01); *A61K 38/1774* (2013.01); *A61K 38/195* (2013.01); *A61K 39/0011* (2013.01); *A61K 48/0083* (2013.01); *A61P 35/00* (2018.01); *C12N 9/22* (2013.01); *C12N 15/1082* (2013.01); *C12N 15/11* (2013.01); *C12N 15/86* (2013.01); *C12N 2310/20* (2017.05); *C12N 2710/10343* (2013.01)

(58) Field of Classification Search
None
See application file for complete search history.

(56) References Cited

U.S. PATENT DOCUMENTS

| | | | | |
|---|---|---|---|---|
| 10,968,426 B2 * | 4/2021 | Meissner | ............. | C12N 5/0696 |
| 2002/0098542 A1 | 7/2002 | Sharpe et al. | | |
| 2003/0223971 A1 * | 12/2003 | Kurtzman | ............ | C07K 14/565 |
| | | | | 435/235.1 |
| 2019/0194653 A1 | 6/2019 | Amit et al. | | |

FOREIGN PATENT DOCUMENTS

WO     WO-2018053542 A1 *     3/2018     .........     G01N 33/5014

OTHER PUBLICATIONS

Narimatsu et al. (Glycobiology 28.5 (2018): 295-305.) (Year: 2018).*
Yoo et al., Scientific Reports 9.1 (2019): 4712. (Year: 2019).*
Lane-Reticker et al., Immunotherapy 10.3 (2018): 167-170. (Year: 2018).*
Gilbert et al., Cell 159.3 (2014): 647-661. (Year: 2014).*
Manguso et al., Nature 547.7664 (2017): 413-418. (Year: 2017).*
Steel et al., Molecular Therapy 21.3 (2013): 680-687. (Year: 2013).*
Codina, et al. "Convergent identification and interrogation of tumor-intrinsic factors that modulate cancer immunity in vivo." Cell systems 8.2 (2019): 136-151.
Qi, et al. "Repurposing CRISPR as an RNA-guided platform for sequence-specific control of gene expression." Cell 152.5 (2013): 1173-1183.
Gilbert, et al. "CRISPR-mediated modular RNA-guided regulation of transcription in eukaryotes." Cell 154.2 (2013): 442-451.
Konermann, et al. "Genome-scale transcriptional activation by an engineered CRISPR-Cas9 complex." Nature 517.7536 (2015): 583-588.
Chavez, et al. "Highly efficient Cas9-mediated transcriptional programming." Nature methods 12.4 (2015): 326-328.
Tanenbaum, et al. "A protein-tagging system for signal amplification in gene expression and fluorescence imaging." Cell 159.3 (2014): 635-646.
International Search Report and Written Opinion, Dated Jul. 23, 2021, for International Application No. PCT/US2020/057113.
Partial Supplementary European Search Report issued in App. No. EP20891848, dated Sep. 21, 2023, 13 pages.
Wang Guangchuan et al: "Multiplexed activation of endogenous genes by CRISPRa elicits potent antitumor immunity", Nature Immulogy, Nature Publishing Group US, New York, vol. 20, No. 11, Oct. 14, 2019 (Oct. 14, 2019), pp. 1494-1505, XP036912475, ISSN: 1529-2908, DOI: 10.1038/S41590-019-0500-4 [retrieved on Oct. 14, 2019].
Wangensteen Kirk J. et al: "Combinatorial genetics in liver repopulation and carcinogenesis with a in vivo CRISPR activation platform", Hepatology, vol. 68, No. 2, Aug. 1, 2018 (Aug. 1, 2018), pp. 663-676, XP055876179, US ISSN: 0270-9139, DOI: 10.1002/hep. 29626.

* cited by examiner

*Primary Examiner* — Maria G Leavitt
*Assistant Examiner* — Brendan Thomas Tinsley
(74) *Attorney, Agent, or Firm* — Saul Ewing, LLP; Kathryn Doyle; Lukas Pfannenstiel

(57)     ABSTRACT

The present invention includes compositions and methods comprising viral vector systems for multiplexed activation of endogenous genes as immunotherapy and viral-based immune-gene therapy.

4 Claims, 37 Drawing Sheets

Specification includes a Sequence Listing.

Fig. 4A pGW011b: AAV-EFS-dSpCas9-sPA

| TR | EFS | NLS | dSpCas9 | NLS | sPA | ITR |

+ pGW045: AAV-U6-sg(ms2)-EF1a-MCP-p65-HSF1-WPRE

| ITR | U6 | sg(ms2) | EF1a | MCP | NLS | p65 | HSF1 | WPRE | ITR |

| Gene | gRNA target sequence | SEQ ID NO: | Gene | gRNA target sequence | SEQ ID NO: |
|---|---|---|---|---|---|
| CD70 | GCTTCAGTTTGTCTGTGGGA | 86 | TNFSF9 (4-1BBL) | CCCTCCCTCCCTTCCCTCCC | 139 |
| | ATTCACTGAGCATCTATTAG | 87 | | ACAGGGCCTGGACAGGGAAG | 140 |
| | ATCAGGAAGCATCCGCATCC | 88 | | AGAAAGTTCCGGGAGTCGAG | 141 |
| CD80 | GAGAGTTCTGAATCAGGGTG | 89 | TL1A (TNFSF15) | CAGAGGGCTGTCAGAGGGAG | 142 |
| | TCCAGGCCTGTTCTGAGCAC | 90 | | AACTTGGTTTCTGTTGTAGG | 143 |
| | GGACCTTTGAGTTGCCCTCA | 91 | | ATTCCCTAGCCGGGCAGGGC | 144 |
| CD83 | CCAAGTCCGCGTTGCTGCTG | 92 | CD30L(TNFSF8) | AATTGTAGCGAGATAGACGA | 145 |
| | ATCTGCATGACCCACTCGAT | 93 | | GTGGTTGGTGTACACTCACG | 146 |
| | GTTTGAGGGTCATCTAGCTG | 94 | | CGTTCTGTGGCTGAGCCTAA | 147 |
| CD86 | GCAGGCAGGAGTGGGTGGGT | 95 | TAP1 | TGCAGGCAACTTGCAGACTG | 148 |
| | CTTTGTAGATTATTCGAGTT | 96 | | TTCACGCAAGCAAGTTAAGG | 149 |
| | GAGTTCGGTTTCAGTCTTGA | 97 | | CGTGCCGTTCTACCAGCATT | 150 |
| IFNa4 | AAAGAGAATTGGAAAGCAAG | 98 | B2M | ACGACCTCCGGATCTGAGTC | 151 |
| | TGTGTACATCTCTCTTAAAT | 99 | | CCGTGATATTTCAAACAGCC | 152 |
| | CAGGCTCTCAGAGAACCTGT | 100 | | AGCATCAACAGCTAGGAGAC | 153 |
| IFNb1 | GAAATTCCTCTGAGGCAGAA | 101 | Tapasin | GCGGAGTCTAGGCTGATAAA | 154 |
| | CCTGTGCTATTTATAAGGGA | 102 | | GGTCTGGGAACGCGGGAGTG | 155 |
| | GTGAGAATGATCTTCCTTCA | 103 | | TATTTATTGGTCACTTCACT | 156 |
| IFNg | AGAGTTTCCTTTCGACTCCT | 104 | TAPBPR | CTCCAGCCCTCTCATAGTTG | 157 |
| | TTAAGATGGTGACAGATAGG | 105 | | AGGATTTAACATGGACTGAA | 158 |
| | ATACCTGATCGAAGGCTCCT | 106 | | CTGTGATCGAACAGACGAGA | 159 |
| CXCL9 | AAACCCTACTCTCAGATCCC | 107 | ERp57(PDIA3) | GCAGTGTGGCAGCCGCCGAT | 160 |
| | TAGTTCTTCTAGGTCAGCTG | 108 | | AACAGCTGGTAACTGCCGAT | 161 |
| | TAACCACAAATTGATCGTCC | 109 | | CTGCCGTCACGCAGCGTCGGG | 162 |
| CXCL10 | ACTTTGGAGATGACTCAGCA | 110 | Calreticulin | GGTCGCACTATGGGCCAATG | 163 |
| | TTTATTGTGACCCATGAACT | 111 | | GTAGGTCTAAACCAGTCAAA | 164 |
| | GCAATGCCCTCGGTTTACAG | 112 | | GGGTCGACCACGCGTTGTGG | 165 |
| IL-2 | TTTCAAAGAGTCTACCTGTG | 113 | ERAP1 | TGATAGGGAATGCATTCTCC | 166 |
| | GCAATTTATACTGTTAATGC | 114 | | ACTTTGAGTTCCCGAAGCCC | 167 |
| | TCCATTCAGTCAGTGTATGG | 115 | | CAAGCCTAAGGGATCTAGCC | 168 |
| CXCL3 | CACACTCATCAAGAGCCCGG | 116 | NLRC5/CITA | AGCTGGCCGTGCAGAGAGGA | 169 |
| | GTGGGCAAGAAGCGAAGGAA | 117 | | TCATCTGGGAGATGAGCCTC | 170 |
| | AGAGGACACACGTGTGCTAC | 118 | | TTCGGTTGGCATTCGGCTAA | 171 |
| CCL5 | AGGCAGAGTCATACTTCCAA | 119 | TAP2 | GGGTCTGAGATGCTTTGAAA | 172 |
| | CTACCCTGGCTCCCTATAAA | 120 | | GGCGCCTGTCAATTTGCGGG | 173 |
| | TTATGACAGCAACAAGTGTT | 121 | | TTGCTAGTAGCGGCCTTGGA | 174 |
| CD40L | TGGTGTCTTCTGACCAAGAA | 122 | Cystatin C (x) | CTAGTCTGTTCTTGCCTTGT | 175 |
| | TCGTCGCAACCCACACTTCC | 123 | | GGGAGGGTGGCCGCCGGAAA | 176 |
| | TTAACTAATCCTGAGTAAGG | 124 | | GAATCTGGCAGCTCTTTAAG | 177 |
| OX40L/TNFSF4 | AAGTCACTCAATTCATAACT | 125 | Cystatin B | GGACGCTAAGAAGGGGTTTGG | 178 |
| | CAACTCCCTGTTAGCCCGGA | 126 | | CTGTCACCACCCTCCGTTCC | 179 |
| GITRL(TNFSF18) | AGTGCTTAGCAGTGTTCCAA | 127 | | CTTCACGTCCTTTCCCTGAA | 180 |
| | GCACCAGGCCAAACATACAA | 128 | Calnexin | TGGGAAGGCGCTTCGAGCGA | 181 |
| | CACTACAAGGGAAGTTCAGA | 129 | | TTCTTAGATCTTGCGCAAAG | 182 |
| Flt3L | CGCCACCTAGTGGTAACAAG | 130 | | CCACGAAGAATAGCCCTAGG | 183 |
| | GGGCCCTGAAAAGGATAGCGA | 131 | Sec61a1 | AGCGGCCGGTGGCCCATCCC | 184 |
| | TTCTACATACACTTCGAAGC | 132 | | GCTGTCGGGAAGACGACTGT | 185 |
| LIGHT (TNFRSF14) | TGTGACTCAGGTGGGATGGA | 133 | | GCACACGCCCAGTTCCGGTG | 186 |
| | GAGGAGGTACGTGAGGAAAG | 134 | Sec61b | TCGCAGACTCTTGGATGACT | 187 |
| | CAGTGAGAGTGATCGACCGG | 135 | | AATCTTTACAGGCATATCTC | 188 |
| B7-H2 (ICOSL) | GAGACTTGGGCATGAGTTAC | 136 | | TCACACGGCCCAGTTGTTGT | 189 |
| | AACCCAATCGGCTGCTGAGC | 137 | Sec61g | GTACATCTAATTCCTCATTG | 190 |
| | CCGCCTGTGCCCAATTAGCC | 138 | | TTCAAACTATTCTCCATTCC | 191 |
| | | | | GACTTTCTGCTTATTATTCA | 192 |

Fig. 7

| Gene Name | Guide Sequence | SEQ ID NO: | Gene Name | Guide Sequence | SEQ ID NO: |
|---|---|---|---|---|---|
| TNFRSF14 | CCCACCTCACTCACACACTC | 193 | CD86 | AGAGAAACAACACCACAGCC | 247 |
| TNFRSF14 | GGGACCCTCGGCTGCTCCCC | 194 | CD86 | CTTTGTCATGTTTGTGGATG | 248 |
| TNFRSF14 | GAGAACTCGCCCCTCCCATC | 195 | CD86 | CCAAGCAAGAGCACTGTCCC | 249 |
| TNFRSF14 | TCCCCCTTCTACAGGAAACC | 196 | CD86 | TCCAAATAACTTCTGCCGGC | 250 |
| TNFRSF14 | GTGGACTGGAATGGTGCAGG | 197 | CD86 | TTTGTAGTCATTCTCATCAG | 251 |
| TNFRSF14 | ACCCACAGGGCCCCTTTATT | 198 | CD86 | GCTTTACACTCATGCTCCGA | 252 |
| TNFRSF14 | AAACACAGATGGACTTTGGG | 199 | SEC61A1 | CCCGGCGGGGCCCCGCGCGCC | 253 |
| TNFRSF14 | AAAAATGTCAGTCAGCGCCC | 200 | SEC61A1 | GCGCGGCGAAGCGCGGCGGC | 254 |
| TNFSF18 | TTTATGTTCTGAGTTTGTGT | 201 | SEC61A1 | GCCCCTTCCCGACAGGCCCC | 255 |
| TNFSF18 | AAAGCACAAGGGAAGTTCAG | 202 | SEC61A1 | CCGGCATGCAGCGGGGCTCC | 256 |
| TNFSF18 | TTTTCTAACACAGTGACAGA | 203 | SEC61A1 | GAGGTCTCGGCGAAGCGGCG | 257 |
| TNFSF18 | CTTAAGTGCTGACTCTCATT | 204 | SEC61A1 | GGTGTGCGGCTGCGCAGACT | 258 |
| TNFSF18 | ACCAGATCAAATACAACAAA | 205 | SEC61A1 | TAACGCGAGAGCGCGCGGGG | 259 |
| TNFSF18 | AGCAATATGGTAATTAGTAG | 206 | CXCL3 | GAAGGCGACGGCCCCGCCCC | 260 |
| TNFSF4 | TTTTTTTCCTCTGGGCTAAC | 207 | CXCL3 | CCCGTATCCGACTCCACCCC | 261 |
| TNFSF4 | ACAGTCACTCAAATCAGAAC | 208 | CXCL3 | GGTGGACTCACTGCCTCTCC | 262 |
| TNFSF4 | TTTAACGCTGCAACTTTTGC | 209 | CXCL3 | CATTTTCTGCCCCAAATTCC | 263 |
| IFNG | AGAGTTTCCTTTAGACTCCT | 210 | CXCL3 | TGCACGGGGGTTACTCTGGA | 264 |
| IFNG | TAAATACCAGCAGCCAGAGG | 211 | CXCL3 | GAGGCGTAGGCGTCACCAGT | 265 |
| IFNG | ATCCTCAGGAGACTTCAATT | 212 | CXCL3 | AGATCGATCCGGAGTCCCGA | 266 |
| IFNG | AACTAAGGTTTTGTGGCATT | 213 | CXCL9 | TGTTCTCTAAAGAATTTCTC | 267 |
| IFNG | AAGATGAGATGGTGACAGAT | 214 | CXCL9 | GACCACAAACTTGATTGTGC | 268 |
| PDIA3 | CGGAGCGCGGGGCGGGGCCG | 215 | CXCL9 | AAACCCTAGTCTCAGATCCA | 269 |
| PDIA3 | GCTGTGTGGCAGCCGCTGAT | 216 | CXCL9 | TTTCTCTCCTAAACTCTGAT | 270 |
| PDIA3 | CAGGGGCTAGGGCCGGGTCC | 217 | CXCL10 | TCCCTCTGCTCCTCTTTTTT | 271 |
| PDIA3 | CCCAGGTTTCGGCTCACCCC | 218 | CXCL10 | CTGCAACATGGGACTTCCCC | 272 |
| PDIA3 | GGCTGCGCGTCGCCTTCGTC | 219 | CXCL10 | TTATTGTAGCCTCCAAGTTA | 273 |
| PDIA3 | GGCGAGTGTCTGGGCGAGCG | 220 | CXCL10 | GTTGACTTAGCAAAACCTGC | 274 |
| PDIA3 | GGCTGGGCCCGGTCCTGGGC | 221 | ERAP1 | TCGGTCCCCAACTTGAGCAC | 275 |
| PDIA3 | ACCAACTCGTTACCGCCGAG | 222 | ERAP1 | GGGTTAGGGGCATGCAGGAA | 276 |
| B2M | AAGAAAAGGAAACTGAAAAC | 223 | ERAP1 | TGGACTTGTCAGCGCCTGCC | 277 |
| B2M | AGACAGGTGACGGTCCCTGC | 224 | ERAP1 | TTTCACTGTTTAGCGTTGCG | 278 |
| B2M | GTGCCCAGCCAATCAGGACA | 225 | ERAP1 | TTTCTCTCACACTAAAAGAA | 279 |
| B2M | GAAAGTCCCTCTCTCTAACC | 226 | ERAP1 | CTGAACAATGATGTGAGCT | 280 |
| B2M | CAAGCCAGCGACGCAGTGCC | 227 | ERAP1 | TTCCGTTCCTCATTGACTAT | 281 |
| B2M | GAGTCTCGTGATGTTTAAGA | 228 | ERAP1 | TAGTTCCTTGCCATATCCTA | 282 |
| B2M | TGAGTTTGCTGTCTGTACAT | 229 | ERAP1 | AAACAGTCAGCAAAACACTG | 283 |
| NLRC5 | CAGGGGCAAGGGCTGGTGCC | 230 | ERAP1 | TCGGTCCCCAACTTGAGCAC | 284 |
| NLRC5 | CCACTATTCCAGACTCCAAA | 231 | ERAP1 | GGGTTAGGGGCATGCAGGAA | 285 |
| NLRC5 | GGAGTTGGGGGGACTGTGTC | 232 | ERAP1 | TGGACTTGTCAGCGCCTGCC | 286 |
| NLRC5 | TTCTCAGATGTGTCTCCGGC | 233 | ERAP1 | TTTCACTGTTTAGCGTTGCG | 287 |
| NLRC5 | GAAGAACAAGGTCTAGCGGA | 234 | CANX | GCCGGGAGTGAGGCAGGAAG | 288 |
| NLRC5 | GACACAAGGAGCTGCAGTCG | 235 | CANX | GCTACTCAGGGGCCAGGGGC | 289 |
| CCL5 | TCTAGATGAGAGAGCAGTGA | 236 | CANX | GCGGGACTTGGCGCCGGCTG | 290 |
| CCL5 | GAGACAGAGACTCGAATTTC | 237 | CANX | TGTTGGTTGGGCGGGAGGTG | 291 |
| CCL5 | AAGAAAACTGAAATAGCCTC | 238 | CANX | CGATGCCCACGCCGGCCAAC | 292 |
| CCL5 | ATTTTGGAAACTCCCCTTAG | 239 | CANX | TCTTCGTGGAGTGTGAAGAT | 293 |
| CCL5 | GCCCTTTATAGGGCCAGTTG | 240 | CANX | ACCGTCCCATACGCCCCTA | 294 |
| CCL5 | TTATGATACCGGCCAATGCT | 241 | CANX | ATGTCGGGGCTTGCGCGGGA | 295 |
| TNFSF9 | TGGCCGCGGGCGGAGGGGCG | 242 | CD83 | ACTTGGCTCCCTGCCTTCCC | 296 |
| TNFSF9 | GGGCGTGGCCGCGGGCGGAG | 243 | CD83 | GTACTGACTGATAACCTCCC | 297 |
| TNFSF9 | GAAAGGCTCTGGGCTGGGAA | 244 | CD83 | ACACGCATACACAACATTTT | 298 |
| TNFSF9 | CGCAGAGTCACGGGGACGAG | 245 | CD83 | TACAGACTTGTATGTTTCCA | 299 |
| TNFSF9 | AAAGCGGAGAGAGATCCGAG | 246 | CD83 | TAATAGGAGACACTCTCCTT | 300 |

Fig. 8A

| Gene Name | Guide Sequence | SEQ ID NO: | Gene Name | Guide Sequence | SEQ ID NO: |
|---|---|---|---|---|---|
| TNFSF9 | AGCTGCTTGGCTACAAAAGG | 301 | CD83 | GACGGGGGCGGGGACGGGGG | 356 |
| TNFSF9 | TTGGAAGGCCGGAAACGGAA | 302 | CD83 | CCGCCCCCGCGCGCCCGGGC | 357 |
| CD70 | GGCGGGGAGGGGTTGGGGGC | 303 | CD83 | GCGCACGCGGCGAGGGCGGC | 358 |
| CD70 | ATGTCTCCTGCCTGAAGGTC | 304 | CD83 | CCCCGCGTGACGCCCAGCGC | 359 |
| CD70 | CAGGATGCAGGCAGTGGCCC | 305 | CD83 | CGACGCGAACTCGGGGCGCC | 360 |
| CD70 | CAACTGCCTCCACCCACTTT | 306 | TAP2 | GGGTCTCGCGCGCCCCCTCC | 361 |
| CD70 | ATGTCCGGCCGGTCGAGGGG | 307 | TAP2 | CGCTTTCGCTTCCCCAGCCA | 362 |
| CD70 | TCAGACTGGCAGCGGTTGGA | 308 | TAP2 | AGGCGAGTGAGACTCATTGC | 363 |
| CD70 | GGCAACTCTGAGGCTCACCC | 309 | TAP2 | GGCTCCAGTTCCGCTGTCTG | 364 |
| CD70 | GGGACTTGAGCAATTGGCGA | 310 | TAP2 | TTCATTCTGGGCTGGGCCGC | 365 |
| CALR | CAGGGGCGGGCCCAAGGGCT | 311 | TAP2 | TACAGTGCGAACCAGAGTTC | 366 |
| CALR | GTCAGGTTGGTTTGAGAGGC | 312 | TAP2 | TCTCGCGCGCCCCCTCCCGG | 367 |
| CALR | CCGAACGCTGGGTTCCCAGA | 313 | TAP2 | AGTAAAATACAGTTGTCTCA | 368 |
| CALR | GTGGTGAGGCCAATAGAAAT | 314 | TAP2 | AGGCGAGTGAGACTCATTGC | 369 |
| CALR | GGCATAGACCAATGACAAAG | 315 | TAP2 | GCTCCAGTTCCGCTGTCTGC | 370 |
| CALR | CAATGGAAAAAGACGGCCAT | 316 | TAP2 | TACAGTGCGAACCAGAGTTC | 371 |
| CALR | TGGGTATAAAAGTGCAAGGC | 317 | TAP1 | CGGCGCCGCCAGGAGGCGCC | 372 |
| CALR | CTTCGTCGGTTCACTATGTT | 318 | TAP1 | GGAGGCAGGGAGAGGCGAGA | 373 |
| CST3 | GCGGGGAGAGGCAGGGGAGG | 319 | TAP1 | TTCCCACCCCAGCCTCAGGG | 374 |
| CST3 | GGGGAGAGGCAGGGGAGGCG | 320 | TAP1 | AAAGCAGCCCCGCAGCACCC | 375 |
| CST3 | GAGGGAGAAGGGAGGTGGGA | 321 | TAP1 | GGCTGCCTCGTCACTTGTCT | 376 |
| CST3 | GGGAGGGAAGGGGATGGATG | 322 | TAP1 | ACTGGTGCAAGTGGAAAGGC | 377 |
| CST3 | GCAGGGGAGGCTGGGATGGG | 323 | TAP1 | GCGCGGCGCTAACGTGTGTA | 378 |
| CST3 | GAGGCCGGGAGGGGCTGGGA | 324 | SEC61G | AGCGCAGCGCGACGTGCGCC | 379 |
| CST3 | AAGGACAGGGAAGCCTGGAG | 325 | SEC61G | CTCTTCCAGGAAGCGTGGCC | 380 |
| CST3 | ACTGATAGGGAGGGACCTGG | 326 | SEC61G | CGCCCACTCCTCCGTCCTAT | 381 |
| CSTB | GCGGGGCGCGGGGCGGGGCG | 327 | SEC61G | TAGACTCACACTCCTAAGGA | 382 |
| CSTB | GGGAGGAGGCACTTTGGCTT | 328 | SEC61G | GCGCACTGAGGTTTCGCGTA | 383 |
| CSTB | GGGAGGGAGCGCCCCCCTCC | 329 | SEC61G | GCATTGCGGAGCTCGCTAGT | 384 |
| CSTB | TGGGTCTCCGCGCCCAGCGC | 330 | SEC61G | CGTTATCCCTTTTTTCCGGC | 385 |
| CSTB | AGTCCCCTGCGGGGTCGCGG | 331 | IFNB1 | TGAAAGGGAGAAGTGAAAGT | 386 |
| CSTB | GCCCCGCAAGAAGGGACGCG | 332 | IFNB1 | ATGGTCCTCTCTCTATTCAG | 387 |
| CSTB | GGAAAGACGATACCAGCCCC | 333 | IFNA4 | GAAGACTTTGCTCTGTGCAT | 388 |
| CSTB | ACCTGGCCACCACTCGCCGC | 334 | IFNA4 | TATTTTTCACCTGCACTCAA | 389 |
| ICOSLG | GGGCGGGGCGGGGACGGGGC | 335 | IFNA4 | CAACTAGGGAATTTAGAAAA | 390 |
| ICOSLG | GGGGCGCTGCGCGGCGGCTC | 336 | SEC61B | ACTGACTCAGGCCCCGCCCC | 391 |
| ICOSLG | CGGCGCCCAGGTCCGCGTCC | 337 | SEC61B | ATCCAAAGGAAGGAGGCCGG | 392 |
| ICOSLG | CGAGACCGCCCCGGGACAGG | 338 | SEC61B | AGACGACCCAGGCGTCCCTG | 393 |
| ICOSLG | TCGCCAGAGGAGCCAGGCCG | 339 | SEC61B | AGGACCTTGCCTGCAAGTCC | 394 |
| ICOSLG | GTGTGCCCGTCGGCCGGAGG | 340 | SEC61B | GTCTCTACTTCCCATACAGC | 395 |
| ICOSLG | GGCAGGTCGGCCTGTCCGCC | 341 | SEC61B | GTAGGGATTGGACTTTCTGA | 396 |
| ICOSLG | CTGGGCAGAGCCGAACTTTC | 342 | SEC61B | GTCTGTAGCAGACTGTCTAC | 397 |
| CD80 | TTCTCCTCCCCTAGGCCGCC | 343 | TNFSF15 | TTCCAATCCAAAATCCTGCA | 398 |
| CD80 | GCCTCCCTCACCACCGTGCA | 344 | TNFSF15 | ACCCGCAGCAAGCACCACCA | 399 |
| CD80 | GCTTTTGTAGAGGCTGTGGC | 345 | TNFSF15 | TAAACTTGCCCAAAGCCATG | 400 |
| CD80 | CAAACACCCTGTCCAACTCC | 346 | TNFSF15 | GTGGCACTGGACCAAGCTGG | 401 |
| CD80 | TAGAAGAAGACGGCAGCAGA | 347 | TNFSF15 | TCTTGAACACAAATGAATCT | 402 |
| CD80 | AATGGTGCCCGAGAAGAGTG | 348 | TNFSF15 | CAAGGTTTCTCTCCTATCAT | 403 |
| CD80 | CATGAAACACCACGAGCACC | 349 | TNFSF15 | TGTGCTCTTGAAGAGGGGAG | 404 |
| CD86 | TTAAAGAAAGTTAGCTGGGT | 350 | TNFSF15 | CTCCTTCCTTCGTTTACAGA | 405 |
| CD86 | GAGTTTAAACTGCAAGGAAA | 351 | TNFSF15 | GTGCATTCTCTAGCAGGGTA | 406 |
| CD86 | TCAAAATCTGTAGAGAAAAG | 352 | TNFSF15 | AACTTGGTTTCTGTTGTAGG | 407 |
| CD86 | TTAAATTTCTTCCTCAAGTG | 353 | TNFSF8 | GGGGAGGTCTTCTGAGCCAC | 408 |
| CD86 | GCTCATCTTAACGTCATGTC | 354 | TNFSF8 | AGCTGCACCTTCTTTCAGCG | 409 |
| CD86 | CTCCCTTTGGGGGTTTCCCA | 355 | TNFSF8 | CCCAGCAAGGACTCATTATC | 410 |
|  |  |  | TNFSF8 | TTGAACAGGAAGGCGTTTTG | 411 |

Fig. 8B

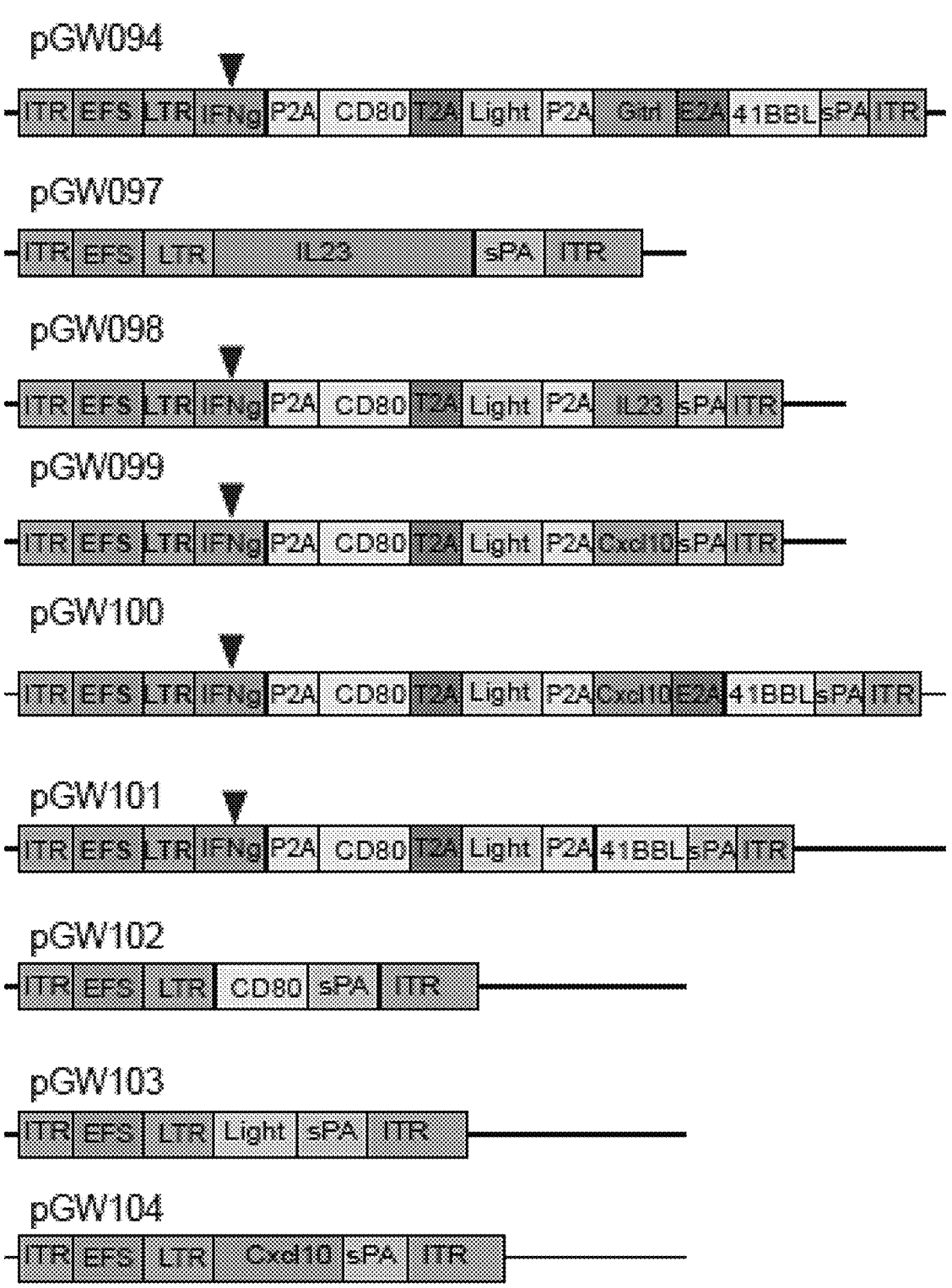
Fig. 15, continued

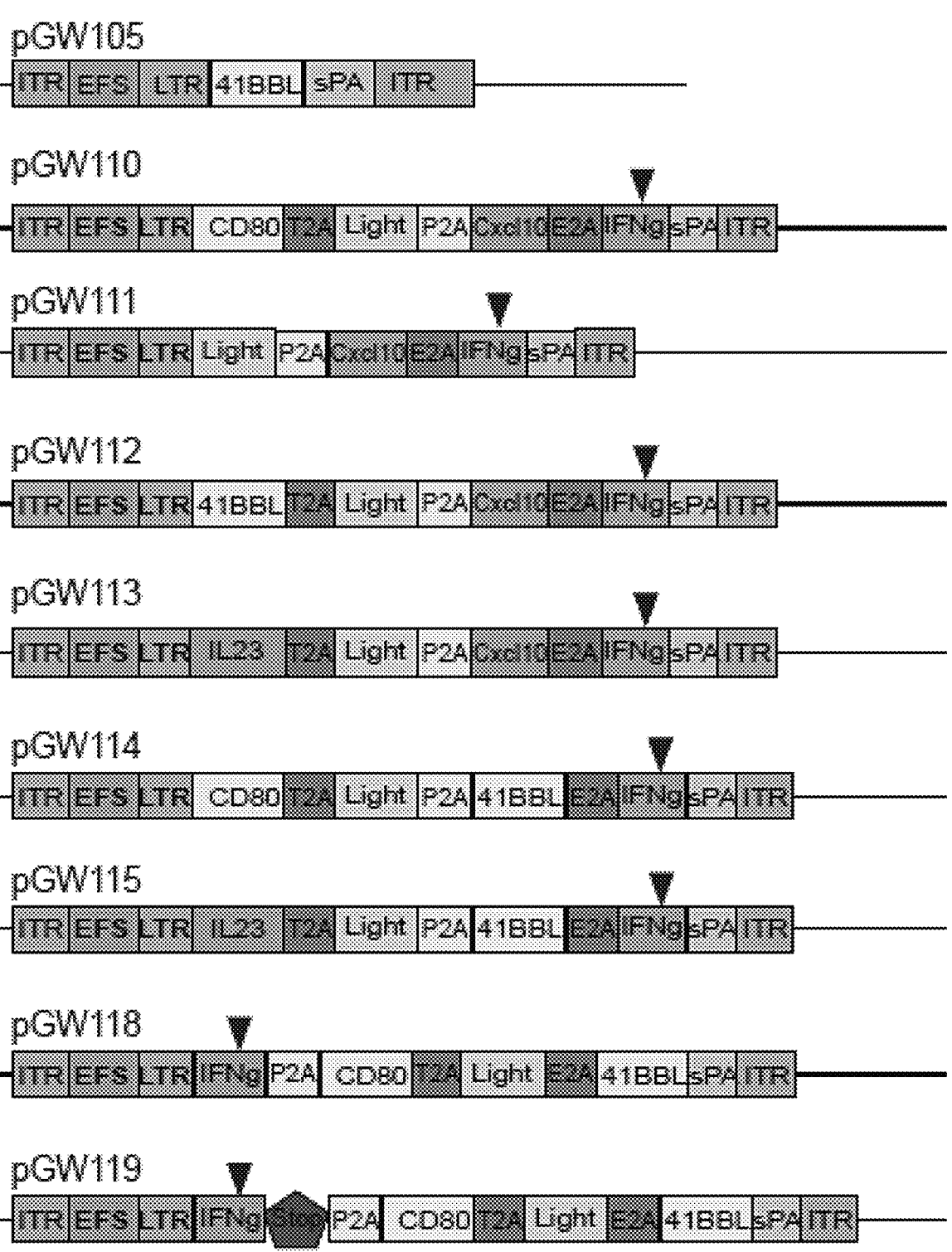
Fig. 15, continued

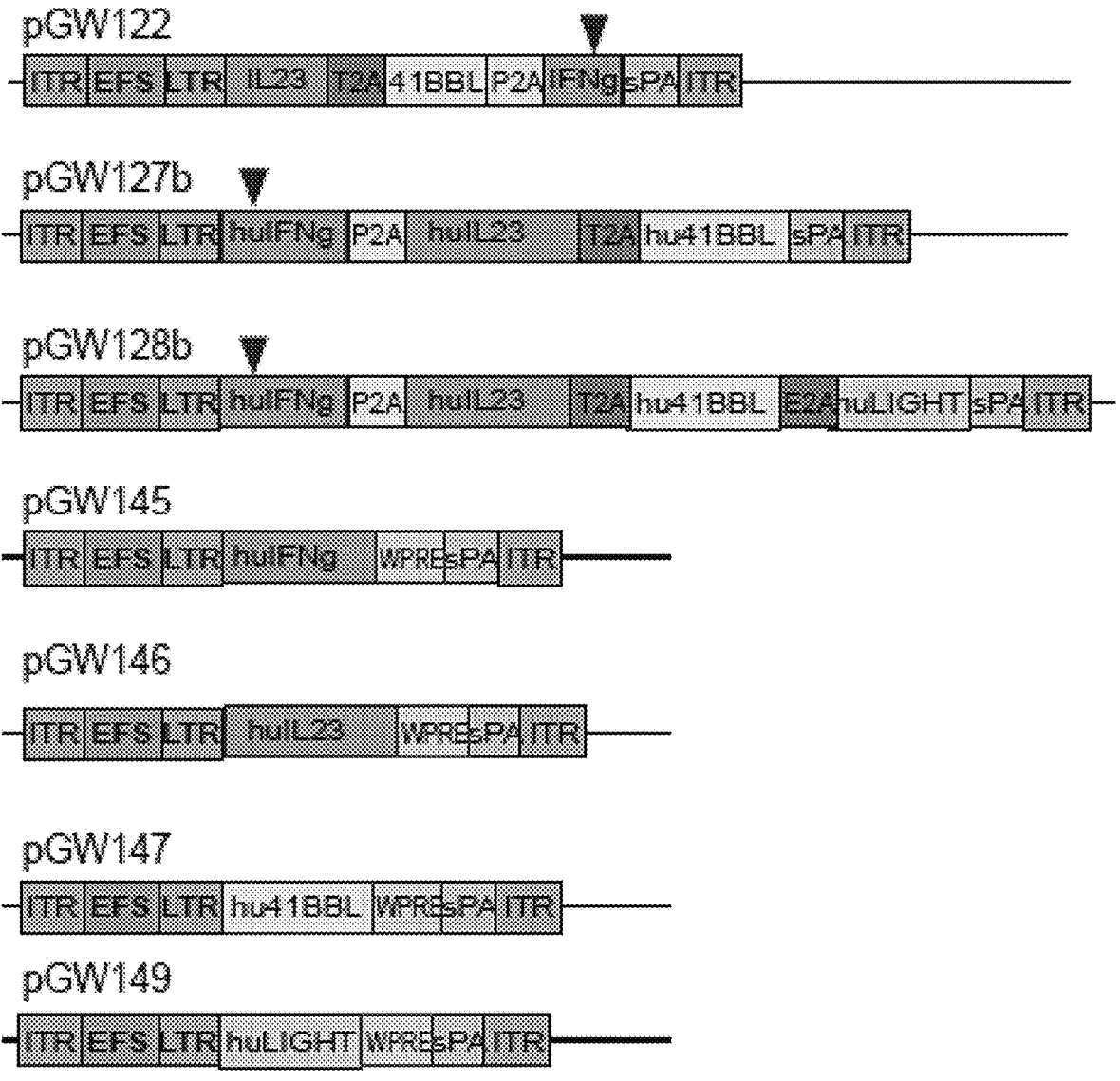
Fig. 15, continued

COMPOSITIONS AND METHODS COMPRISING VIRAL VECTOR SYSTEMS FOR MULTIPLEXED ACTIVATION OF ENDOGENOUS GENES AS IMMUNOTHERAPY AND VIRAL-BASED IMMUNE-GENE THERAPY

CROSS-REFERENCE TO RELATED APPLICATIONS

The present application is a 35 U.S.C. § 371 national phase application of, and claims priority to, International Application No. PCT/US2020/057113 filed Oct. 23, 2020, which is entitled to priority under 35 U.S.C. § 119 (e) to U.S. Provisional Patent Application No. 62/924,973, filed Oct. 23, 2019, all of which applications are hereby incorporated by reference in their entireties herein.

STATEMENT REGARDING FEDERALLY SPONSORED RESEARCH OR DEVELOPMENT

This invention was made with government support under CA238295, CA231112, CA209992 and CA225498 awarded by the National Institutes of Health; and under W81XWH-17-1-0235 and W81XWH-20-1-0072 awarded by the United States Army Medical Research and Material Command. The government has certain rights in the invention.

SEQUENCE LISTING

The instant application contains a Sequence Listing which has been submitted in ASCII format via EFS-Web and is hereby incorporated by reference in its entirety. Said ASCII copy, created on Apr. 21, 2022, is named "047162-7254US1_SequenceListing_ST25.txt" and is 579 kilobytes in size.

BACKGROUND OF THE INVENTION

Immunotherapy has transformed cancer treatment by leveraging the patient's own immune system against the tumor, thereby turning several previously lethal cancers into manageable diseases for a subset of patients. Major types of immunotherapy include checkpoint blockade, adoptive cell transfer, human recombinant cytokines, and cancer vaccines. Although antigen recognition is a key process in the anti-tumor immune response, there has been limited success using cancer vaccines in the clinic over the past several decades. Traditional cancer vaccines are often dendritic cell-based vaccines such as sipuleucel-T. Recent advances of peptide- and RNA-based vaccines showed that targeted delivery of multiple mutated neoantigens can generate a strong anti-tumor effect, providing direct clinical evidence of effective cancer vaccines against late-stage melanoma. Tumor cells harbor a multitude of mutations that frequently encode mutated, partially truncated, or amplified genes that are immunogenic. However, many of these mutations might not be expressed at levels sufficient to elicit an effective T-cell-mediated response. Synthesis of these peptides or transcripts is possible with parallel protein- or RNA-synthesis, but the cost of this approach is proportional to the number of mutations identified.

A need exists for new types of cancer vaccines that can elicit strong, durable, and specific immune responses against cancer antigens, while maintaining efficacy, versatility, and cost-effectiveness. The present invention addresses this need.

SUMMARY OF THE INVENTION

As described herein, the present invention relates to compositions and methods comprising viral vector systems for multiplexed activation of endogenous genes as immunotherapy and viral-based immune-gene therapy.

In one aspect, the invention comprises a method of developing a cancer immunotherapy. The method comprises a) administering a CRISPR activation (CRISPRa) system comprising an sgRNA library to a cancer cell, thereby generating a modified cell, b) administering the modified cell to an immunocompetent mammal whereby the mammal develops cancer, c) determining the sgRNAs and thereby the targeted genes that are depleted in the cancer, and d) designing a cancer immunotherapy that targets the depleted genes.

In certain embodiments, the sgRNA library comprises the nucleotide sequences set forth in SEQ ID NOs. 86-192 or SEQ ID NOs. 193-411.

In certain embodiments, the mammal is a mouse.

In certain embodiments, the CRISPRa system comprises a vector comprising the nucleotide sequence set forth in SEQ ID NO: 1.

In certain embodiments, determining the genes that are depleted in the cancer comprises nucleotide sequencing and analysis.

In certain embodiments, designing a cancer therapy that targets the depleted genes comprises packaging the open reading frames (ORFs) of the depleted genes in a vector.

In certain embodiments, the vector is an adeno-associated viral (AAV) vector or an adenoviral vector.

In another aspect, the invention includes a method of treating cancer in a subject in need thereof. The method comprises administering a therapeutically effective amount of the cancer immunotherapy generated by any of the methods contemplated herein.

In another aspect, the invention includes a composition comprising a vector comprising an open reading frame (ORF) of at least one gene selected from the group consisting of CD80, Light, CXCL10, 4-1BBL, GITRL, IL2, IL-23, and IFNg.

In certain embodiments, the vector comprises the nucleotide sequence set forth in any one of SEQ ID NOs: 2, 3, and 24-58.

In certain embodiments, the vector is an AAV vector or an adenoviral vector.

In another aspect, the invention includes a vector comprising a nucleic acid sequence that is 85%, 90%, 95%, 96%, 97%, 98%, 99%, or 100% identical to any one of SEQ ID NOs: 1-18 or 24-58.

In another aspect, the invention includes a vector comprising at least one nucleic acid sequence that is 85%, 90%, 95%, 96%, 97%, 98%, 99%, or 100% identical to any one of SEQ ID NOs: 73-84.

In certain embodiments, the vector is an AAV vector or an adenoviral vector.

In another aspect, the invention includes a composition comprising any of the vectors contemplated herein.

In another aspect, the invention includes a method of treating cancer in a subject in need thereof. The method comprises administering to the subject a therapeutically effective amount of any of the compositions contemplated herein.

In certain embodiments, the cancer is selected from the group consisting of triple-negative breast cancer, melanoma, pancreatic cancer, or a solid tumor.

In certain embodiments, the method further comprises administering an additional treatment to the subject.

BRIEF DESCRIPTION OF THE DRAWINGS

The following detailed description of specific embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

FIG. 1A is a schematic of the experiment design. The APCM sgRNA library was introduced into E0771, a triple-negative breast cancer cell line, by infection with lentiviruses at M.O.I=0.2-0.3. After 7 days of in vitro culture under puromycin selection, $2*10^6$ of APCM library-transduced cells were intravenously injected into immunocompetent C57BL/6J mice. The resulting metastatic tumors in the lungs were collected, and the immune-mediated sgRNA depletion and enrichment was readout by illumina sequencing. FIG. 1B shows Kaplan-Meier survival curves of mice transplanted with E0771-Vector (n=10) or E0771-APCM library (n=15) formed metastatic tumors. Log-rank test, E0771-APCM vs. E0771-Vector, p=0.2000. FIG. 1C depicts the correlations within tumor samples and cell samples. FIG. 1D is a scatter plot of genes whose activation may lead to elevated immune destruction. Average sgRNA representation across metastatic tumors in C57BL/6J mice (n=14) was plotted against average sgRNA library representation in cultured cell pool (n=2). Screen was performed in immunocompetent C57BL/6J mice by intravenously injecting library-transduced E0771 to form metastatic tumors. The linearized sgRNA population regression was used to call depletion under immune pressure. Error bars: Data points in this figure are presented as mean±s.e.m. Asterisks: *p<0.05, p<0.01, *p<0.001.

FIGS. 3A-3C illustrate the design and characterization of an adenoviral CRISPRa system. FIG. 3A is a schematic of the designs of adenoviral dSpCas9-based CRISPRa systems, that use a single construct to deliver all CRISPRa components. Depicted are pGW029 (SEQ ID NO: 4), pGW035 (SEQ ID NO: 5), and pGW063 (SEQ ID NO: 6). FIG. 3B shows results from an experiment wherein Ox40l-targeted sgRNA was cloned into a construct from FIG. 3A and the activation efficiency tested in vitro. 4 days post-transfection, expression levels of Ox40l were determined by quantitative RT-PCR. FIG. 3C shows the cytopathic effects in HEK293FT cells caused by the adenoviral CRISPRa system. Upper panel: AdTrack (adenoviral CMV-EGFP) were rescued, and the expression of GFP and cytopathic effects were observed, demonstrating the robustness of the adenoviral engineering and rescue system. Lower panel: the CRISPRa system was cloned into adenoviral constructs (U6-sgRNA-EFS-LTR-dSpCas9-p65-HSF1-sPA) and the adenoviruses were rescued. 4-6 days post-infection of the adenovirus, cytopathic effects on HEK293FT were observed.

FIGS. 4A-4B illustrate an AAV based one-vector system with dSaCas9. FIG. 4A is a diagram illustrating a dSaCas9-based AIO (all-in-one) CRISPRa system, using a single AAV vector to deliver all CRISPRa components. FIG. 4B shows in vitro activation of the Pmel gene with the AIO CRISPRa system. Pmel was targeted with the MO CRISPRa system and 4 days post-infection expression levels of Pmel were determined by quantitative RT-PCR.

FIG. 5A is a schematic of the design of a dSaCas9-based dual-AAV delivery CRISPRa system. FIG. 5B shows results from in vitro testing of the dSaCas9-based dual-AAV CRISPRa system. Pmel targeted sgRNA was cloned into with the dual AAV-CRISPRa system. Four days post-infection, expression levels of Pmel were determined by quantitative RT-PCR.

FIG. 6A is a schematic of the design of a dSpCas9-based dual-AAV delivery of CRISPRa system. FIG. 6B shows results of in vitro testing. Pmel targeted sgRNA was cloned into with the dual AAV-CRISPRa system. 6 days post-infection, expression levels of Pmel were determined by quantitative RT-PCR.

FIG. 7 is a table illustrating sgRNA sequences for an AAV-APCM library (SEQ ID NOs: 86-192).

FIGS. 8A-8B illustrate sgRNA sequences for an AAV-APCM library designed/optimized specifically for human genes (SEQ ID NOs: 193-411).

FIG. 9A shows tumor growth curves of orthotopic breast tumor formed by E0771-dCas9-VP64 in mice treated with PBS (n=10 mice), AAV-Vector (n=10), or AAV-APCM (n=8) by intratumoral administration at indicated times (arrows). Two-way ANOVA: AAV-Vector vs. PBS, p=0.0054; AAV-APCM vs. PBS, p<0.0001; AAV-APCM vs. AAV-Vector, p=0.0139. FIG. 9B illustrates the therapeutic effects of dual-AAV delivered APCM CRISPRa into tumor-bearing mice. The growth curves of E0771 syngeneic tumors in mice treated by intratumoral injection of PBS (n=5 mice), AAV-dCas9+Vector (n=5), or AAV-dCas9+APCM (n=5) at the indicated time points (arrows). Two-way ANOVA: AAV-dCas9+Vector vs. PBS, p=0.1586; AAV-dCas9+APCM vs. PBS, p<0.0001; AAV-dCas9+APCM vs. AAV-dCas9+Vector, p<0.0001. FIG. 9C shows an experimental design for evaluating the systemic anti-tumor effects of AAV-APCM. $2*10^6$ or $0.2*10^6$E0771-dCas9-VP64 tumor cells were transplanted into the left or right flank of C57BL/6J mice respectively to model local and distant tumors. AAV-p-MAEGI was administered only into the local tumors at the indicated times (arrows). FIGS. 9D-9E are growth curves of E0771-dCas9-VP64 local (FIG. 9D) and distant (FIG. 9E) tumors in mice treated with PBS (n=11), AAV-Vector (n=11), or AAV-APCM (n=17). FIG. 9D: Local tumors, two-way ANOVA: AAV-Vector vs. PBS, p=0.0001; AAV-APCM vs. PBS, p<0.0001; AAV-APCM vs. AAV-Vector, p=0.0130. FIG. 9E: Distant tumor: two-way ANOVA: AAV-Vector vs. PBS, p=0.2308; AAV-APCM vs. PBS, p=0.011; AAV-APCM vs. AAV-Vector, p=0.1407. FIG. 9F shows survival curves of the E0771 breast tumor bearing mice treated with PBS (n=6), AAV-Vector (n=13), or AAV-APCM (n=12). Log-rank test, AAV-Vector vs. PBS, p=0.1115; AAV-APCM vs. PBS, p=0.0022; AAV-APCM vs. AAV-Vector, p=0.1178. FIG. 9G show growth curves of Pan02-dCas9-VP64 tumors in C57BL/6J mice treated with PBS (n=6 mice), AAV-Vector (n=6), AAV-APCM (n=7), or AAV-p-MAEGI (n=8) at indicated times (blue arrows). Two-way ANOVA: AAV-Vector vs. PBS, p<0.0001; AAV-APCM vs. PBS, p<0.0001; AAV-p-MAEGI vs. PBS, p<0.0001; AAV-APCM vs. AAV-Vector, p=0.4432; AAV-p-MAEGI vs. AAV-Vector, p<0.0001. Error bars: Data points in this figure are presented as mean±s.e.m. Asterisks: *p<0.05, p<0.01, *p<0.001.

FIG. 10A left: AAV-CRISPRa-mediated transcriptional activation of Cd80, Light, Cxcl10, Gitrl, 41bbl, and IFNg, normalized to vector-transduced controls (n=8, multiple t-test, AAV-sgRNAs versus vector Cd80, P=0.01; Light, P=0.00001; Cxcl10, P=0.0003; Gitrl, P=0.0004; 41bbl, P=0.00002; Ifnγ, P<0.0001); FIG. 10A right: Co-transfection of Dual AAV-CRISPRa-mediated transcriptional activation of Cd80, Light, Cxcl10, Gitrl, 41bbl, and IFNg, normalized to control (n=4). FIG. 10B shows the expression of CD80, 41BBL, and Gitrl in dual-AAV-CRISPRa infected cells as assessed by flow cytometry. FIG. 10C shows the therapeutic effects of intratumoral injected AAV-CRISPRa. Dual-AAV mediated activation of Cd80, light/Tnfsf14, Cxcl10, 4-1BBL/Tnfsf9, and Ifng (CLC4I). Growth curves of E0771 tumors treated with PBS (n=6), AAV-dCas9+Vector (n=6), AAV-dCas9+CLCG4 (dual AAV delivered CRISRPa of Clcg (n=6). Two-way ANOVA: AAV-dCas9+Vector vs. PBS, p=0.9675; AAV-dCas9+Clcg4 vs. PBS, p<0.0001; AAV-dCas9+Clcg4 vs. AAV-dCas9+Vector, p=0.0028. FIG. 10D illustrates express Cd80, Light, Cxcl10, 41bbl, or/and IFNg using AAV polycistronic ORFs. Both transfection and AAV infection lead to high levels' expression of these molecules. FIG. 10E illustrates the therapeutic effects of intratumoral injected AAV-ORFs expressing Cd80, Light, Cxcl10, 41bbl (orfClc4, n=6), or AAV expressing Cd80, Light, Cxcl10, 41bbl, Ifng (orfClc4I, n=6). FIG. 10F illustrates the therapeutic effects of intratumoral injected AAV-ORFs expressing Cd80, Light, Cxcl10, 41bbl, Ifng (orfClc4I, n=5). Two-way ANOVA: AAV-orfCLC4 vs. PBS, p<0.0001; AAV-Vector vs. PBS, p=0.0041; AAV-orfCLC4 vs. AAV-Vector, p=0.0038. Two-way ANOVA: AAV-orfCLC4I vs. PBS, p=0.6182; AAV-orfCLC4I vs. PBS, p<0.0001. Error bars: Data points in this figure are presented as mean±s.e.m. Asterisks: *p<0.05, p<0.01, *p<0.001.

FIG. 11A shows flow cytometry quantification of CD45+ immune cells in tumor microenvironment at DPI=30. Percentage of CD45+ immune cells out of total cells in tumors treated with PBS, dual-AAV-vector, dual-AAV-Clcg4, AAV-orfClc4, AAV-orfClc4I (n=5 mice per group; two-tailed Mann-Whitney test: AAV-dCas9+Clcg4 vs. PBS, P=0.0931; AAV-orfClc4I vs. PBS, P=0.0411). FIG. 11B shows percentage of CD8+ T cells out of total cells in tumors treated with PBS, dual-AAV-vector, dual-AAV-Clcg4, AAV-orfClc4, AAV-orfClc4I (n=5 mice per group; two-tailed Mann-Whitney test: AAV-dCas9+Clcg4 vs. PBS, P=0.0411; AAV-orfClc4I vs. PBS, P=0.0411). FIG. 11C shows percentage of CD4+ T cells out of total cells in tumors treated with PBS, dual-AAV-vector, dual-AAV-Clcg4, AAV-orfClc4, AAV-orfClc4I (n=5 mice per group; two-tailed Mann-Whitney test: AAV-dCas9+Clcg4 vs. PBS, P=0.1320; AAV-orfClc4I vs. PBS, P=0.0152). FIG. 11D shows flow cytometry quantification of PD1+CD8+ T cells out of total CD8+ T cells in tumors treated with PBS, dual-AAV-vector, dual-AAV-Clcg4, AAV-orfClc4, AAV-orfClc4I (n=5 mice per group; two-tailed Mann-Whitney test: AAV-dCas9+Clcg4 vs. PBS, P=0.1797; AAV-orfClc4I vs. PBS, P=0.026). FIG. 11E shows flow cytometry quantification of monocytes out of total cells in tumors treated with PBS, dual-AAV-vector, dual-AAV-Clcg4, AAV-orfClc4, AAV-orfClc4l (n=5 mice per group; two-tailed Mann-Whitney test: AAV-dCas9+Clcg4 vs. PBS, P=0.0411; AAV-orfClc4l vs. PBS, P=0.6991). FIG. 11F shows flow cytometry quantification of dendritic cells out of total cells in tumors treated with PBS, dual-AAV-vector, dual-AAV-Clcg4, AAV-orfClc4, AAV-orfClc4l (n=5 mice per group; two-tailed Mann-Whitney test: AAV-dCas9+Clcg4 vs. PBS, P=0.0411; AAV-orfClc4I vs. PBS, P=0.5887). Error bars: Data points in this figure are presented as mean±s.e.m. Asterisks: *p<0.05, p<0.01, *p<0.001.

FIG. 12A illustrates the therapeutic effects of intra-tumoral injected AAV-CRISPR activating Cd80, light, Cxcl10, 4-1BBL, Gitrl and Ifng (Clcg4I). Growth curves of E0771 tumors treated with PBS (n=5), AAV-Vector (pGW045; n=5), or AAV-Clcg4I (pGW045-Clcg4I). Two-way ANOVA: AAV-Vector vs. PBS, p=0.0871; AAV-Clcg4 vs. PBS, p<0.0001; AAV-Clcg4 vs. AAV-Vector, p=0.0009.

FIGS. 12B-12C illustrate further optimization of the combinatorial genes pool by removing one gene in each pool. FIG. 12B shows growth curves of E0771 tumors treated with PBS (n=4), AAV-Vector (n=4), AAV-Clcg4I (n=4), or AAV-Clcg4Iminus1 (n=4). Two-way ANOVA: AAV-Vector vs. PBS, p=0.0002; AAV-Clcg4I vs. AAV-Vector, p=0.0002. FIG. 12C shows growth curves of E0771 tumors treated with AAV-Clcg4I (n=4), or AAV-Clcg4I minus1 (n=4). Two-way ANOVA: AAV-Clcg4I vs. 41BBL, p<0.0001; AAV-Clcg4I vs. -IFNg, p=0.05; AAV-Clcg4I vs. -CD80, p=0.095; AAV-Clcg4I vs. -Light, p=0.05; AAV-Clcg4I vs. -Gitrl, p=0.0116. FIG. 12D shows growth curves of B16F10 melanoma treated with PBS (n=4), AAV-Vector (n=5), AAV-p67:Clc4I (Cd80, Light, Cxcl10, 41bbl, Ifng; n=5), AAV-P72:IFNg (n=4). Two-way ANOVA: AAV-Vector vs. PBS, p=0.3495; AAV-p67:Clc4I vs. Vector, p=0.0012; AAV-p72:IFNg vs. PBS, p<0.0001. FIG. 12E shows growth curves of E0771 tumors treated with PBS (n=6), AAV-Vector (n=6), AAV-P72:IFNg (n=6), AAV-p94:IClG4 (Ifng, Cd80, Light, Gitrl, 41bbl; n=6). FIG. 12F shows growth curves of E0771 tumors treated with AAV-Vector (n=5), AAV-polycistronic P119:IFNg-STOP-CD80-Light-Cxcl10-41BBL (n=5), AAV-polycistronic P118:IFNg-CD80-Light-Cxcl10-41BBL (n=5), AAV-polycistronic P100:IFNg-CD80-Light-Cxcl10 (n=5), AAV-P67: CD80-Light-Cxcl10-41BBL-IFNg (n=5). Two-way ANOVA: AAV-Vector vs. PBS, p=0.0455; AAV-p94:ICLG4 vs. Vector, p=0.0111; AAV-p72:IFNg vs. PBS, p<0.0001. Error bars: Data points in this figure are presented as mean±s.e.m. Asterisks: *p<0.05, p<0.01, *p<0.001.

FIG. 13A Upper panel: Representative flow cytometry plots demonstrating AAV-ORFs-mediated expression of IFNg in different AAV constructs transfected E0771 cells; low panel (left): the percentage of IFNg expressing cells in different constructs-transfected E0771 cells; low panel (right): the median fluorescent intensity (MFI) of IFNg-APC in different constructs-transfected E0771 cells. FIG. 13B Upper panel: Representative flow cytometry plots demonstrating AAV-ORFs-mediated expression of CD80 in different AAV constructs transfected E0771 cells; low panel (left): the percentage of CD80+ cells in different constructs-transfected E0771 cells; low panel (right): the median fluorescent intensity (MFI) of CD80-PE in different constructs-transfected E0771 cells.

FIG. 14A Upper panel: Representative flow cytometry plots demonstrating AAV-ORFs-mediated expression of CD80 and 41BBL in AAV-infected E0771 or MA1NC cells; lower panel: the percentage of CD80 and 41BBL positive cells in different AAV-infected E0771 and MA1NC cells. FIG. 14B Upper panel: Representative flow cytometry plots demonstrating AAV-ORFs-mediated expression of IL23 and IFNg in AAV-infected E0771 or MA1NC cells; lower panel: the percentage of IL23 and IFNg positive cells in different AAV-infected E0771 and MA1NC cells. FIG. 14C shows tumor growth curves of E0771 tumors treated with PBS (n=5), AAV-Vector (n=10), AAV-IL23 (n=5), AAV-IFNg (n=6), Pooled AAVs (IFNg+CD80+LIGHT+CXCL10+41BBL; n=5). FIG. 14D shows tumor growth curves of E0771 tumors treated AAV-Vector (n=5), AAV-IFNg (n=4), AAV-IFNg+AAV-IL23 (n=5), pooled AAVs (IFNg+CXCL10+41BBL; n=5), pooled AAVs (IFNg+LIGHT+41BBL; n=5), pooled AAV (IFNg+LIGHT+CXCL10+41BBL; n=5). FIG. 14E shows tumor growth curves of E0771 tumors treated AAV-Vector (n=11), AAV-IFNg (n=10), AAV-IL23 (n=10), AAV-IFNg+AAV-IL23 (n=4). FIG. 14F shows tumor growth curves of E0771 tumors treated AAV-Vector (n=5), AAV-IFNg (n=5), AAV-IL23 (n=5), AAV-IFNg+AAV-IL23+AAV-41BBL (n=5). Error bars: Data points in this figure are presented as mean±s.e.m. Asterisks: *p<0.05, p<0.01, *p<0.001.

DETAILED DESCRIPTION

Definitions

Figures 1A, 1B:
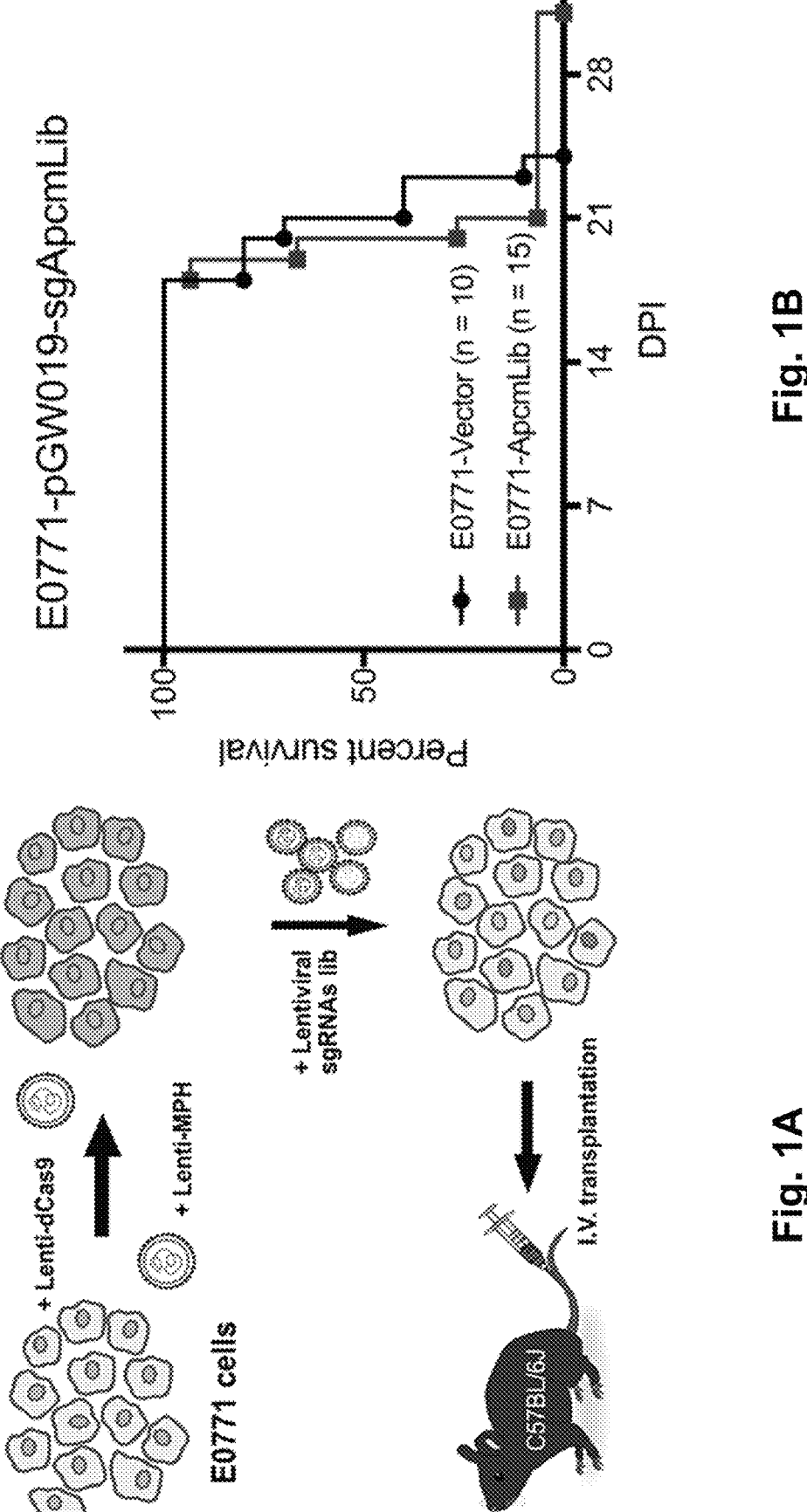
FIGS. 1A-1D illustrate an in vivo CRISPRa screen to pinpoint the genetic factors that can enhance host immune surveillance and tumor destruction.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the As used herein, the term "autologous" is meant to refer to any material derived from the same individual to which it is later to be re-introduced into the individual.

"Allogeneic" refers to any material derived from a different animal of the same species.

As used herein, the term "bp" refers to base pair.

The term "complementary" refers to the degree of anti-parallel alignment between two nucleic acid strands. Complete complementarity requires that each nucleotide be across from its opposite. No complementarity requires that each nucleotide is not across from its opposite. The degree of complementarity determines the stability of the sequences to be together or anneal/hybridize. Furthermore, various DNA repair functions as well as regulatory functions are based on base pair complementarity.

The term "CRISPR/Cas" or "clustered regularly inter-spaced short palindromic repeats" or "CRISPR" refers to DNA loci containing short repetitions of base sequences followed by short segments of spacer DNA from previous exposures to a virus or plasmid. Bacteria and archaea have evolved adaptive immune defenses termed CRISPR/CRISPR-associated (Cas) systems that use short RNA to direct degradation of foreign nucleic acids. In bacteria, the CRISPR system provides acquired immunity against invading foreign DNA via RNA-guided DNA cleavage.

The "CRISPR/Cas9" system or "CRISPR/Cas9-mediated gene editing" refers to a type II CRISPR/Cas system that has been modified for genome editing/engineering. It is typically comprised of a "guide" RNA (gRNA) and a non-specific CRISPR-associated endonuclease (Cas9). "Guide RNA (gRNA)" is used interchangeably herein with "short guide RNA (sgRNA)" or "single guide RNA (sgRNA). The sgRNA is a short synthetic RNA composed of a "scaffold" sequence necessary for Cas9-binding and a user-defined ~20 nucleotide "spacer" or "targeting" sequence which defines the genomic target to be modified. The genomic target of Cas9 can be changed by changing the targeting sequence present in the sgRNA.

"CRISPRa" system refers to a modification of the CRISPR-Cas9 system that functions to activate or increase gene expression. In certain embodiments, the CRISPRa system is comprised of a catalytically dead RNA/DNA guided endonuclease, such as dCas9, dCas12a/dCpf1, dCas12b/dC2c1, dCas12c/dC2c3, dCas12d/dCasY, dCas12e/dCasX, dCas13a/dC2c2, dCas13b, dCas13c, dCas14, dead Cascade complex, or others; at least one transcriptional activator; and at least one sgRNA that functions to increase expression of at least one gene of interest. The term "activation" as used herein refers to an increase in gene expression of one or more genes.

"dCas9" as used herein refers to a catalytically dead Cas9 protein that lacks endonuclease activity. "dSaCas9" refers to dCas9 derived from *Staphylococcus aureus*. dSpCas9" refers to dCas9 derived from *Streptococcus pyogenes.*

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the noncoding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "knockdown" as used herein refers to a decrease in gene expression of one or more genes.

The term "knockout" as used herein refers to the ablation of gene expression of one or more genes.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient vectors for gene delivery. HIV, SIV, and FIV are all examples of lentiviruses. Vectors derived from lentiviruses offer the means to achieve significant levels of gene transfer in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

A "mutation" as used herein is a change in a DNA sequence resulting in an alteration from a given reference sequence (which may be, for example, an earlier collected DNA sample from the same subject). The mutation can comprise deletion and/or insertion and/or duplication and/or substitution of at least one deoxyribonucleic acid base such as a purine (adenine and/or thymine) and/or a pyrimidine (guanine and/or cytosine). Mutations may or may not produce discernible changes in the observable characteristics (phenotype) of an organism (subject).

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron (s).

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T".

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Parenteral" administration of an immunogenic composition includes, e.g., subcutaneous (s.c.), intravenous (i.v.), intramuscular (i.m.), or intrasternal injection, or infusion techniques.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means. Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

A "sample" or "biological sample" as used herein means a biological material from a subject, including but is not limited to organ, tissue, exosome, blood, plasma, saliva, urine and other body fluid. A sample can be any source of material obtained from a subject.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

A "target site" or "target sequence" refers to a genomic nucleic acid sequence that defines a portion of a nucleic acid to which a binding molecule may specifically bind under conditions sufficient for binding to occur.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject. As used herein, "vaccinating" means administering a substance to a subject that induces an immune response against a disease.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention includes compositions and methods for treating cancer. In certain embodiments, the invention includes methods for treating cancer using a viral vector based (such as Adenovirus or AAV-based) composition that utilizes the CRISPR activation (CRISPRa) system to activate endogenous genes. In certain embodiments, the invention includes use of the CRISPRa system to identify key factors for generating direct ORF-based immune-gene therapies.

It was discovered herein that direct activation of endogenous genes using a single vector system is an effective means to amplify tumor-associated antigens to enhance anti-tumor immune responses. Highly multiplexed and customizable endogenous neoantigen activation using a single vector system has not yet been demonstrated prior to this disclosure. The present invention demonstrates the feasibility of using CRISPR technologies with RNA-guided precise genetic manipulations. The CRISPR activation (CRISPRa) system, based on dead Cas9 without nuclease activity (dCas9) (Qi et al. (20131) Cell 152, 1173-1183), enables simple and flexible regulation of gene expression with dCas9—transcriptional activation domain fusion (Gilbert et al. (2013) Cell 154, 442-451), which is further augmented by the recruitment of synergistic activation mediators (SAM) (Konermann, et al. (2015) Nature 517, 583-588; Chavez, et al. (2015) Nat Methods 12, 326-328; Tanenbaum, et al. (2014) Cell 159, 635-646). Herein, the CRISPRa system was harnessed to manipulate endogenous gene expression to magnify anti-tumor immune responses. The approach was developed into multiplexed tumor vaccination strategies.

Another aspect of the invention includes compositions and methods comprising off-the-shelf endogenous gene vaccination cancer vaccines. The off-the-shelf versions have fixed components, which can have multiple forms, including single component or multi-component vaccines. The compositions of these forms of cancer vaccines and their preclinical efficacy showed that they can be an effective means of prophylactic and therapeutic agents.

CRISPR Activation (CRISPRa) System

The CRISPR activation (CRISPRa) system is comprised of a catalytically inactive RNA-guided endonuclease or other endonucleases, such as but not limited to dCas9, dCas12a/dCpf1, dCas12b/dC2c1, dCas12c/dC2c3, dCas12d/dCasY, dCas12e/dCasX, dCas13a/dC2c2, dCas13b, dCas13c, dCas14, dead Cascade complex, or others. The CRISPRa system also comprises at least one transcriptional activator, and at least one sgRNA that functions to increase expression of at least one gene of interest. Like a standard CRISPR-Cas9 system, CRISPRa systems rely on sgRNAs to guide Cas9 to intended targets. However, while a standard CRISPR-Cas9 system creates breaks in DNA through the endonuclease activity of Cas9 and then manipulates DNA repair mechanisms for gene editing, CRISPRa systems are modified and employ transcriptional activators to increase expression of genes of interest.

"dCas9" refers to a catalytically dead Cas9 protein that lacks endonuclease activity. This can be accomplished by introducing point mutations in the two catalytic residues (D10A and H840A) of the gene encoding Cas9. In doing so, dCas9 is unable to cleave dsDNA but retains the ability to target and bind DNA. This alone is often enough to attenuate if not outright block transcription of the targeted gene if the gRNA positions dCas9 in a way that prevents transcriptional factors and RNA polymerase from accessing the DNA. However, this ability to bind DNA can also be exploited for activation since dCas9 has modifiable regions, typically the N and C terminus of the protein, that can be used to attach transcriptional activators. dCas9 can be derived, for example, from *S. pyogenes* (dSpCas9), *S. aureus* (dSaCas9) *N. meningiditis, S. thermopilus, F. novicida, C. jejuni, B. laterosporus*, or from other species.

Targeting specificity of the CRISPRa system is determined by complementary base-pairing of a small guide RNA (sgRNA) to the genomic loci. sgRNA is a chimeric noncoding RNA that can be subdivided into three regions: a base-pairing sequence, a dCas9-binding hairpin and a terminator. When designing a synthetic sgRNA, only the base-pairing sequence is modified. Secondary variables must also be considered: off-target effects (for which a simple BLAST run of the base-pairing sequence is required), maintenance of the dCas9-binding hairpin structure, and ensuring that no restriction sites are present in the modified sgRNA, as this may pose a problem in downstream cloning steps. Due to the simplicity of sgRNA design, this technology is amenable to genome-wide scaling.

Transcriptional activators are protein domains or whole proteins that can be linked to dCas9 or sgRNAs and assist in the recruitment of important co-factors as well as RNA Polymerase for transcription of the gene(s) targeted by the system. Transcriptional activators have a DNA binding domain and a domain for activation of transcription. The activation domain can recruit general transcription factors or RNA polymerase to the gene sequence. Activation domains can also function by facilitating transcription by stalled RNA polymerases, and in eukaryotes can act to move nucleosomes on the DNA or modify histones to increase gene expression. These activators can be introduced into the system through attachment to dCas9 or to the sgRNA. Transcriptional activators can be either mammalian cellular endogenous proteins that have activator function, activators from other species such as viruses, microbials or plants, their partial or mutant variants, engineered activators, or other forms of activators that can increase gene expression. A list of applicable viral activators include but are not limited to: VP16, VP32, VP64, VP160, HBx, NS proteins, and VMW65. A list of applicable microbial activators include but are not limited to: Lac operons and GAL4. A list of applicable mammalian cellular transcriptional activators include but are not limited to: CAP, ACTN1, ACTN2, ACTN2, ACTN4, ACTN4, ANKRD1, APEX1, ARID5B, ARL2BP, ASCC1, ASXL1, ATN1, ATXN7L3, ATXN7L3, ATXN7L3, BCL9, BCL9L, BCL10, BCL10, BICRA, BIRC2, BRCA1, BRD7, CALCOCO1, CALCOCO1, CAL-COCO1, CALCOCO1, CARM1, CARM1, CARM1, CBFB, CCAR1, CCAR1, CCAR1, CCAR1, CCAR2, CCDC62, CEBPA, CENPJ, CITED1, CITED1, CITED2, CITED2, CITED2, CITED2, CITED2, CITED4, CITED4, CITED4, COPSS, CREBBP, CREBBP, CREBBP, CTBP2, CTNNB1, CTNNB1, CTNNB1, CTNNB1, CTNNB1, DAXX, DAXX, DCAF6, DCC, DDX17, DHX9, DR1, DYRK1B, EDF1, ELF3, ELOB, ENY2, ENY2, ENY2, EP300, EP300, EP300, FAM129B, FGF2, FHLS, FOXC1, GATA3, GATA3, GATA3, GATA4, GM20517, GMEB1, GMEB2, GPS2, GPS2, GTF2A2, GTF2A2, HAND1, HCFC1, HCFC1, HELZ2, HIF3A, HINFP, HIPK2, HMGA1, HMGA1, HMGA1B, HMGB2, HYAL2, ING4, ISL1, JADEL JMJD6, JMY, JMY, JUN, JUN, JUNB, JUND, JUP, JUP, KAT2A, KAT2B, KAT2B, KATS, KATS, KAT6A, KDM1A, KDMSA, KMT2C, KMT2D, LPIN1, LPIN1, LPIN2, LPIN2, LPIN3, MAGED1, MAK, MAML1, MAML1, MAML1, MAML1, MAML2, MAML2, MAML3, MAML3, MAML3, MCIDAS, MED1, MED1, MED1, MED1, MED1, MED1, MED6, MED12, MED12, MED12, MED12L, MED13, MED14, MED16, MED17, MED17, MED20, MED21, MED24, MED27, MED31, MEF2A, MMS19, MRTFA, MRTFB, MRTFB, MTA1, MTA1, MTA1, MTA1, MTA2, MTA3, MTDH, MYCBP, MYOCD, MYOD1, MYSM1, MYT1L, NACA, NCOA1, NCOA1, NCOA1, NCOA1, NCOA1, NCOA2, NCOA2, NCOA2, NCOA2, NCOA2, NCOA2, NCOA3, NCOA3, NCOA3, NCOA3, NCOA3, NCOA6, NCOA6, NCOA7, NEUROD1, NEUROG3, NFE2L1, NKX2-2, NME2, NPAT, NPM1, NR1D1, NR1D2, NR1H2, NR1H3, NR1H3, NR1H4, NR1H5, NR1I2, NR1I3, NR3C1, NRBF2, NRIP1, NRIP1, NRIP1, NRL, NSD3, NUP98, NUPR1, PARK7, PCBD1, PDLIM1, PER2, PHF2, PKN1, PMF1, PMF1, PML, PML, PML, POU2AF1, POU3F1, POU3F2, POU3F2, POU4F1, POU4F2, POU5F1, PPARA, PPARD, PPARD, PPARG, PPARG, PPARG, PPARGC1A, PPARGC1A, PPARGC1A, PPARGC1A, PPARGC1A, PPARGC1A, PPARGC1B, PPARGC1B, PPRC1, PRDM16, PRKCB, PRMT2, PRPF6, PRRX1, PSIP1, PSMC3IP, PSMC3IP, PSMD9, PSMD9, PUS1, RAP2C, RARA, RARA, RARB, RARG, RBM14, RBM14, RBM39, RBPMS, RERE, REXO4, RNF20, RRP1B, RUVBL1, RXRB, SCAND1, SERTAD2, SETD3, SFR1, SFR1, SIX3, SLC30A9, SLC30A9, SMARCA2, SMARCA4, SMARCB1, SMARCB1, SMARCD3, SNW1, SNW1, SOX4, SOX11, SOX11, SOX12, SOX17, SP4, SRA1, SRA1, SRA1, SRA1, SRA1, SRA1, SS18, SS18, SS18L1, SS18L2, SUB1, SUB1, SUPT3, SUPT7L, TADA1, TADA1, TADA2A, TADA2B, TADA3, TADA3, TADA3, TAF1, TAF5L, TAF6L, TAF6L, TAF7, TAF7, TAF7L, TAF9, TAF11, TAF11, TAF12, TCF3, TDRD3, TFAP2A, TFAP2A, TFAP2A, TFAP2B, TFAP2B, TFAP2B, TGFB1I1, THRA, THRAP3, THRAP3, THRAP3, THRB, TRIM24, TRIM24, TRIM28, TRIP4, TRIP4, TRRAP, TSG101, UBE2L3, UBE3A, USP16, USP21, USP22, USP22, UTF1, UTF1, VDR, VGLL2, WBP2, WBP2, WBP2NL, WDR77, WNT3A, WWC1, WWOX, WWTR1, WWTR1, YAF2, YAP1, YAP1, ZBTB18, ZCCHC12, ZCCHC12, ZCCHC18, ZMIZ2.

Applicable CRISPRa systems demonstrated to be capable of activating transcription in mammalian species include but are not limited to: VP64-p65-Rta (VPR), Synergistic Activation Mediator (SAM), Suntag, p300, and VP160.

One example of a transcriptional activator (or transactivator domain) is VP64. VP64 is made up of four copies of VP16, a viral protein sequence of 16 amino acids that is used for transcriptional activation. Embodiments of the invention include various forms of VP64, for example a nucleic acid comprising dCas9 and/or VP64, or plasmids or vectors that encode the dCas9 and/or VP64 genes. One non-limiting example includes pcDNA-dCas9-VP64 (Plasmid #47107, from Addgene). Additional elements can be present in the nucleic acid encoding dCas9 and/or VP64, as in for example lenti vector EF1a-NLS-dCas9(N863)-VP64-2A-Blast-WPRE (Plasmid #61425 from Addgene), which additionally encodes a 2A Blast resistance marker. Another non-limiting example includes plasmid pLV hUbC-VP64 dCas9 VP64-

T2A-GFP (Plasmid #59791 from Addgene) that co-expresses human optimized *S. pyogenes* dCas9 fused to two copies of VP64 and GFP.

Certain embodiments of the invention utilize the VP64-p65-Rta, or VPR, in which a VP64 transcriptional activator is joined to the C terminus of dCas9. In the dCas9-VPR protein, the transcription factors p65 and Rta are added to the C terminus of dCas9-VP64. Therefore, all three transcription factors are targeted to the same gene. The use of three transcription factors, as opposed to solely VP64, results in increased expression of targeted genes. dCas9-VPR can be used to increase expression of multiple genes within the same cell by putting multiple sgRNAs into the same cell.

In certain embodiments, the invention utilizes the Synergistic Activation Mediator (SAM) system. SAM makes use of not only VP64 but also sgRNA 2.0, which contains a sequence to recruit a viral protein fused to even more effectors (p65-hsf1). In one embodiment the SAM complex comprises dCas9-VP64, sgRNA, MS2-p65HSF-1. In one embodiment, the CRISPRa system comprises a nucleic acid encoding dCas9-VP64, a nucleic acid encoding MS2-p65-HSF1, and a genome-scale lentiviral SAM CRISPRa sgRNA library. Administering this type of CRISPRa system to a plurality of cells results in a highly diverse population of cells encompassing the entire sgRNA library.

The invention should be construed to work with any alternative activator, such as VP16, VP160, p65AD, p300 or any other transcriptional activator.

The invention should also be construed to work with any dCas9/CRISPRa system or any other adaptor system known in the art, including but not limited to: 1) RNA Scaffolds, which also utilizes sgRNA 2.0 and recruits 3 viral proteins fused to VP64, 2) Suntag, which sports a protruding chain of 10 peptide epitopes that are recognized by an entourage of antibodies fused to VP64, 3) The epigenetic editor p300, which deposits activating H3K27ac. 4) VP160, which is also known as CRISPR-on and has ten times the VPs of VP16, and 5) VP64-dCas9-BFP-VP64, which makes use of that much neglected N-terminus.

The CRISPRa systems disclosed herein can be used with an sgRNA library. With regard to any and all sgRNA libraries disclosed herein, it should be understood by one of ordinary skill in the art that when it is stated that the library comprises at least one sgRNA, it should be construed that the library can comprise one or more sgRNAs, all sgRNAs in the library, and all integer values and numerical ranges of sgRNAs there between. For example, an sgRNA library comprising a total of 219 sgRNAs (e.g. SEQ ID NOs. 193-411) can comprise one sgRNA, all 219 sgRNAs, or and any and all integer values between 1 and 219. In other words, the library could include 1, 10, 20, 50, 100, 150, 200, or 219 sgRNAs and any and all values in between.

CRISPRa Screen Assisted Rational Design of Off-the-Shelf Viral Immune Gene Therapies Provided herein is a method of developing an off-the-shelf viral immune gene therapy. The method utilizes an in vivo CRISPRa screen to unbiasedly pinpoint the genetic factors that enhance host immune surveillance and tumor destruction ("rational design", or "immune gene therapy rationalization"). In one embodiment, the method comprises administering an APCM sgRNA library (e.g. SEQ ID NOs: 86-192) to a cell (e.g. a cancer cell) or population of cells. "APCM" refers to an approach of multiplexed immune gene therapy (abbreviated for <u>A</u>ntigen <u>P</u>resentation <u>C</u>RISPR <u>M</u>anipulation; <u>A</u>ntigen <u>P</u>resentation and <u>C</u>o-stimulation <u>M</u>anipulation; and/or <u>A</u>ntigen <u>P</u>resentation, <u>C</u>o-stimulation and <u>M</u>igration) wherein a plurality of APCM genes are activated by the CRISPRa system using sgRNAs specific for these antigen presentation genes, or by overexpression with cDNA expressing ORFs, or by other gene activation/expression/delivery approaches, or by the combination(s) of above. The cell(s) are cultured in vitro, thereby generating a modified cell or population of cells, then injected into a mammal (e.g. a mouse). Tumor cells are collected from the mammal and analyzed to determine which genes are depleted (e.g. sgRNA depletion and enrichment readout by Illumina sequencing). Specifically, sgRNAs that that are depleted by the mammal's immune system in the resulting tumors, identifying the genes that confer immune recognition of tumor cells. This novel screening approach is based on immune rejection, e.g. identifies the strongest immune factors. By using this method, one can identify which combination of genes should be targeted, e.g. those that are rejected by the immune system, rather than guessing. Genes that are depleted by the method are highly immunogenic and work the best. This method can be used for different tumor/cancer types, as each tumor/cancer type may involve a different set of genes that are immunogenic. Thus, different therapies can be designed to target different combinations of genes from different types of cancers.

In one aspect, the invention provides a method of developing a cancer therapy (e.g. a rationalized immune gene therapy). The method comprises administering a CRISPR activation (CRISPRa) system comprising a sgRNA library to a cancer cell, thereby generating a modified cell, administering the modified cell to a mammal whereby the mammal develops cancer, determining the genes that are depleted in the cancer cell from the mammal, and designing a cancer therapy that targets the depleted genes (e.g immune promoting genes).

In certain embodiments, the sgRNA library comprises the nucleotide sequences set forth in SEQ ID NOs. 86-192 (FIG. 7). In certain embodiments, the sgRNA library comprises an AAV-APCM library (AAV-Apcm) designed/optimized specifically for human genes. Such gRNAs were designed to target the same set of immune genes as above, yielding a library of 219 sgRNAs (SEQ ID NOs: 193-411) (FIGS. 8A-8B).

In certain embodiments, the mammal is a mouse. Other mammals can be used include but are not limited to dogs, cats, pigs, and humans.

In certain embodiments, the CRISPRa system comprises a vector comprising the nucleotide sequence set forth in SEQ ID NO: 1.

Determining the genes that are depleted in the cancer cell can be achieved by any means known to one of ordinary skill in the art, for example, nucleotide sequencing and analysis.

In certain embodiments, designing a cancer therapy that targets the depleted genes comprises packaging the open reading frames (ORFs) of the depleted genes in a vector. In certain embodiments, the vector is an adeno-associated viral (AAV) vector.

Compositions

Certain aspects of the invention comprise vectors and compositions comprising vectors. In certain embodiments, the vectors and compostions are useful for treating cancer.

In one aspect, the invention provides an off-the-shelf therapy useful for treating cancer (e.g. triple negative breast cancer). In one embodiment, the therapy comprises CLC4, which targets CD80, Light, CXCL10, and 4-1BBL genes. In one embodiment, the therapy comprises CLC4I, which targets CD80, Light, CXCL10, 4-1BBL, and IFNG. In one embodiment, the therapy comprises CLC4G, which targets CD80, Light, CXCL10, 4-1BBL, and GITRL. These therapies can be in the form of MAEGI (CRISPRa-based pooled activation), direct ORF-based viral immune gene therapy (AAV expressing concatenated ORFs), or other forms.

In one aspect, the invention provides a composition comprising a vector comprising an open reading frame (ORF) of at least one gene selected from the group consisting of CD80, Light, CXCL10, 4-1BBL, GITRL, IL2, IL-23, and IFNg. The invention should be construed to include ORFs from any number or any combination of the genes selected from the group consisting of CD80, Light, CXCL10, 4-1BBL, GITRL, IL2, IL-23, and IFNg. For example, the vector can comprise one or more ORFs from one or more of the aforementioned genes. The vector can comprise one or more ORFs from any combination of the gene selected from the group consisting of CD80, Light, CXCL10, 4-1BBL, GITRL, IL2, IL-23, and IFNg. For example, the vector can comprise ORFs from one, two, three, four, five, six, seven, or eight genes selected from the group consisting of CD80, Light, CXCL10, 4-1BBL, GITRL, IL2, IL-23, and IFNg.

In one aspect, the invention provides a composition comprising a vector comprising the open reading frames (ORFs) of CD80, Light, CXCL10, 4-1BBL and IFNG genes. In another aspect, the invention provides a vector comprising the open reading frames (ORFs) of CD80, Light, CXCL10, and 4-1BBL. In certain embodiments, vector is an AAV vector. In certain embodiments, the vector comprises the nucleotide sequence set forth in SEQ ID NO: 2 or SEQ ID NO: 3.

In one aspect, the invention provides a composition comprising a vector comprising the open reading frames (ORFs) of IL-23, 4-1BBL, and IFNg genes. In one aspect, the invention provides a composition comprising a vector comprising the open reading frames (ORFs) of IL-23, Light, CXCL10, 4-1BBL and IFNg genes. In one aspect, the invention provides a composition comprising a vector comprising the open reading frames (ORFs) of IFNg, CD80, Light, and 4-1BBL and genes. In one aspect, the invention provides a composition comprising a vector comprising the open reading frames (ORFs) of IL-23, 4-1BBL, and IFNg genes. In one aspect, the invention provides a composition comprising a vector comprising the open reading frames (ORFs) of CD80, 41BBL, IL23 and IFNg genes.

In one aspect, the invention provides a composition comprising an adenoviral-based dSpCas9 CRISPRa system that utilizes a single vector to deliver all CRISPRa components. In one embodiment, the vector comprises pGW029 (SEQ ID NO: 4). In one embodiment, the vector comprises pGW035 (SEQ ID NO: 5), In one embodiment, the vector comprises pGW063 (SEQ ID NO: 6), In another aspect, the invention provides a composition comprising a dSaCas9-based AIO (all-in-one) CRISPRa system, which uses a single AAV vector to deliver all CRISPRa components. In one embodiment, the vector comprises pZB3 (SEQ ID NO: 10).

In another aspect, the invention provides a composition comprising an AAV based two-vector system with dSaCas9. In this system, the dSaCas9 enzyme is on a separate vector from the other CRISPRa components. In one embodiment, the vector which contains the dSaCas9 is pGW060 (SEQ ID NO: 12) and the vector that contains the other CRISPRa components is pGW047 (SEQ ID NO:11).

In another aspect, the invention provides a composition comprising an AAV based two-vector system with dSpCas9. In this system, the dSpCas9 enzyme is on a separate vector from the other CRISPRa components. In one embodiment, the vector which contains the dSpCas9 is pGW011b (SEQ ID NO: 56) and the vector that contains the other CRISPRa components is pGW045 (SEQ ID NO: 13).

In another aspect, the invention provides a composition comprising an AAV based two-vector system with dCas12/dCpf1. In certain embodiments, the composition comprises one or more vectors selected from the group consisting of pRC119 (SEQ ID NO: 14), pRC120 (SEQ ID NO: 15), pRC121b (SEQ ID NO: 16), pRC124 (SEQ ID NO: 17), and pRC126 (SEQ ID NO: 18).

In one aspect, the invention includes a vector comprising SEQ ID NO: 1. In another aspect, the invention includes a vector comprising SEQ ID NO: 2. In another aspect, the invention includes a vector comprising SEQ ID NO: 3. In another aspect, the invention includes a vector comprising SEQ ID NO: 4. In another aspect, the invention includes a vector comprising SEQ ID NO: 5. In another aspect, the invention includes a vector comprising SEQ ID NO: 6. In another aspect, the invention includes a vector comprising SEQ ID NO: 7. In another aspect, the invention includes a vector comprising SEQ ID NO: 8. In another aspect, the invention includes a vector comprising SEQ ID NO: 9. In another aspect, the invention includes a vector comprising SEQ ID NO: 10. In another aspect, the invention includes a vector comprising SEQ ID NO: 11. In another aspect, the invention includes a vector comprising SEQ ID NO: 12. In another aspect, the invention includes a vector comprising SEQ ID NO: 13. In another aspect, the invention includes a vector comprising SEQ ID NO: 14. In another aspect, the invention includes a vector comprising SEQ ID NO: 15. In another aspect, the invention includes a vector comprising SEQ ID NO: 16. In another aspect, the invention includes a vector comprising SEQ ID NO: 17. In another aspect, the invention includes a vector comprising SEQ ID NO: 18. In another aspect, the invention includes a vector comprising SEQ ID NO: 24. In another aspect, the invention includes a vector comprising SEQ ID NO: 25. In another aspect, the invention includes a vector comprising SEQ ID NO: 26. In another aspect, the invention includes a vector comprising SEQ ID NO: 27. In another aspect, the invention includes a vector comprising SEQ ID NO: 28. In another aspect, the invention includes a vector comprising SEQ ID NO: 29. In another aspect, the invention includes a vector comprising SEQ ID NO: 30. In another aspect, the invention includes a vector comprising SEQ ID NO: 31. In another aspect, the invention includes a vector comprising SEQ ID NO: 32. In another aspect, the invention includes a vector comprising SEQ ID NO: 33. In another aspect, the invention includes a vector comprising SEQ ID NO: 34. In another aspect, the invention includes a vector comprising SEQ ID NO: 35. In another aspect, the invention includes a vector comprising SEQ ID NO: 36. In another aspect, the invention includes a vector comprising SEQ ID NO: 37. In another aspect, the invention includes a vector comprising SEQ ID NO: 38. In another aspect, the invention includes a vector comprising SEQ ID NO: 39. In another aspect, the invention includes a vector comprising SEQ ID NO: 40. In another aspect, the invention includes a vector comprising SEQ ID NO: 41. In another aspect, the invention includes a vector comprising SEQ ID NO: 42. In another aspect, the invention includes a vector comprising SEQ ID NO: 43. In another aspect, the invention includes a vector comprising SEQ ID NO: 44. In another aspect, the invention includes a vector comprising SEQ ID NO: 45. In another aspect, the invention includes a vector comprising SEQ ID NO: 46. In another aspect, the invention includes a vector comprising SEQ ID NO: 47. In another aspect, the invention includes a vector comprising SEQ ID NO: 48. In another aspect, the invention includes a vector comprising SEQ ID NO: 49. In another aspect, the invention includes a vector comprising SEQ ID NO: 50. In another aspect, the invention includes a vector comprising SEQ ID NO: 51. In another aspect, the invention includes a vector comprising SEQ ID NO: 52. In another aspect, the invention includes a vector comprising SEQ ID NO: 53. In another aspect, the invention includes a vector comprising SEQ ID NO: 54. In another aspect, the invention includes a vector comprising SEQ ID NO: 55. In another aspect, the invention includes a vector comprising SEQ ID NO: 56.

Figure 15:
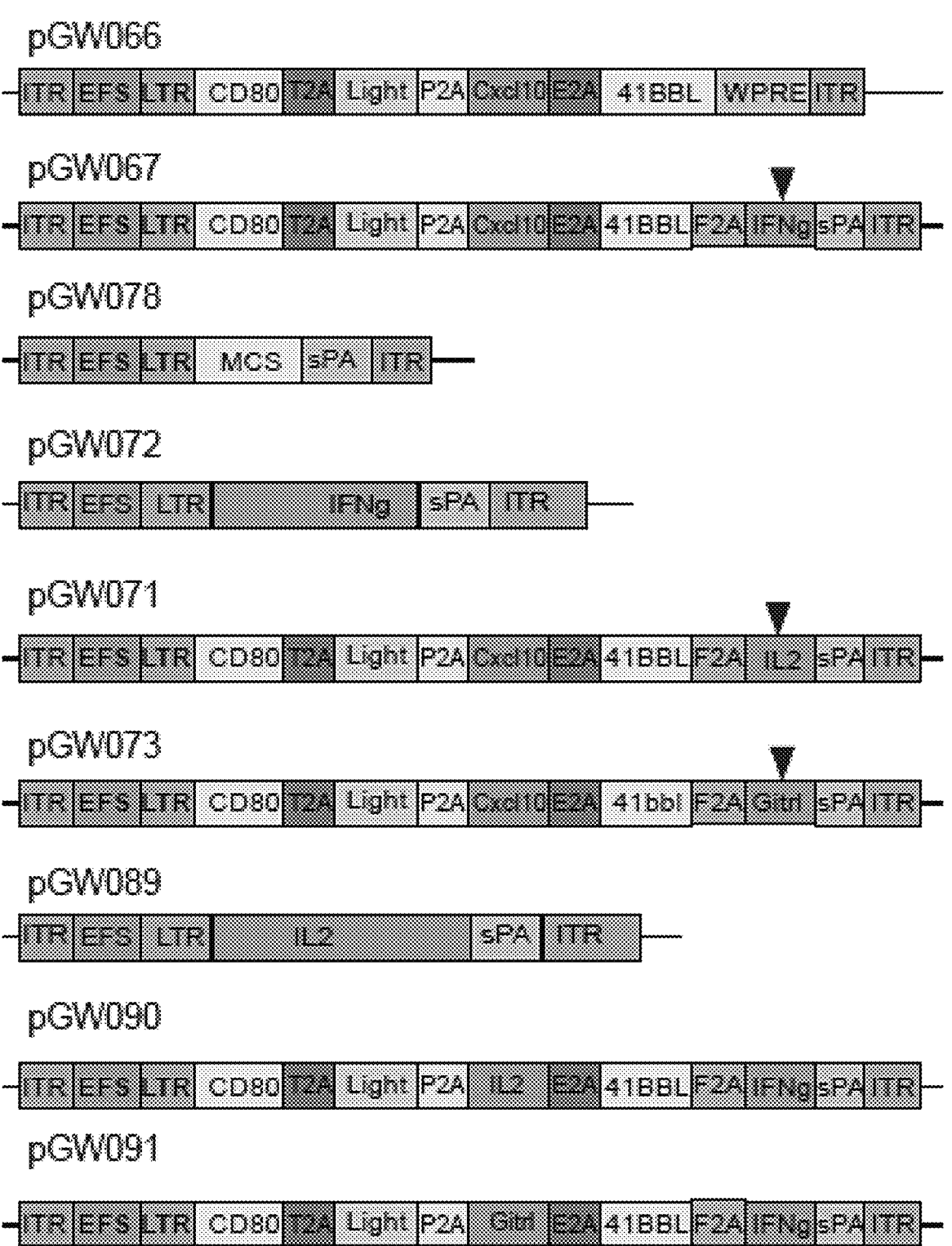
FIG. 15 depicts schematics of the construct designs for AAV-ORFs. Constructs include: pGW066 inserts (including ITR): 4542 bp (SEQ ID NO: 2); pGW067 inserts (including ITR): 4513 bp (SEQ ID NO: 3); pGW071 inserts (including ITR): 4556 bp (SEQ ID NO: 24); pGW072 inserts (including ITR): 1360 bp (SEQ ID NO: 25); pGW073 inserts (including ITR): 4567 bp (SEQ ID NO: 26); pGW078 inserts (including ITR): 895 bp (SEQ ID NO: 27); pGW071 inserts (including ITR): 4556 bp (SEQ ID NO: 24); pGW089 inserts (including ITR): 1401 bp (SEQ ID NO: 57); pGW090 inserts (including ITR): 4726 bp (SEQ ID NO: 28); pGW091 inserts (including ITR): 4738 bp (SEQ ID NO: 29); pGW094 inserts (including ITR): 4723 bp (SEQ ID NO:58); pGW096 inserts (including ITR): 5209 bp (SEQ ID NO: 30); pGW097 inserts (including ITR): 1899 bp (SEQ ID NO: 31); pGW098 inserts (including ITR): 4207 bp (SEQ ID NO: 32); pGW099 inserts (including ITR): 3496 bp (SEQ ID NO: 33); pGW100 inserts (including ITR): 4498 bp (SEQ ID NO: 34); pGW101 inserts (including ITR): 4132 bp (SEQ ID NO: 35); pGW102 inserts (including ITR): 1816 bp (SEQ ID NO: 36); pGW103 inserts (including ITR): 1612 bp (SEQ ID NO: 37); pGW104 inserts (including ITR): 1189 bp (SEQ ID NO: 38); pGW105 inserts (including ITR): 1822 bp (SEQ ID NO: 39); pGW110 inserts (including ITR): 4080 bp (SEQ ID NO: 40); pGW111 inserts (including ITR): 3093 bp (SEQ ID NO: 41); pGW112 inserts (including ITR): 4083 bp (SEQ ID NO: 42); pGW113 inserts (including ITR): 4161 bp (SEQ ID NO: 43); pGW114 inserts (including ITR): 4713 bp (SEQ ID NO: 44); pGW115 inserts (including ITR): 4794 bp (SEQ ID NO: 45); pGW118 inserts (including ITR): 4133 bp (SEQ ID NO: 46); pGW119 inserts (including ITR): 4133 bp (SEQ ID NO: 47); pGW122 inserts (including ITR): 4002 bp (SEQ ID NO: 48); pGW127b inserts (including ITR): 3852 bp (SEQ ID NO: 49); pGW128b inserts (including ITR): 4671 bp (SEQ ID NO: 50); pGW145 inserts (including ITR): 2023 bp (SEQ ID NO: 51); pGW146 inserts (including ITR): 2509 bp (SEQ ID NO: 52); pGW147 inserts (including ITR): 2287 bp (SEQ ID NO: 53); pGW149 inserts (including ITR): 2260 bp (SEQ ID NO: 54)

In certain aspects, the invention includes an AAV-ORF immune gene therapy construct. In certain aspects, the invention includes any of the constructs/vectors depicted in FIG. 15. In certain aspects, the invention includes a vector comprising a nucleotide sequence encoding at least one of the following components: Ori, flOri, AmpR promoter, AmpR, AAV-ITR, EFS core promoter, LTR promoter, EFS-LTR promoter, T2A, P2A, E2A, WPRE, short-PolyA, ORF-Cd80, ORF-Light, ORF-Cxcl10, ORF-41BBL, ORF-IFNg, ORF-Il2, ORF-Gitrl, ORF-Il23, ORF-hIFNg, ORF-hIL23, ORF-h41BBL, ORF-hLIGHT(remove-EQLI), CGKRK. In certain aspects, the invention includes a vector comprising the nucleotide sequence set forth in any one of SEQ ID NOs: 59-85.

In certain aspects, the invention includes a vector comprising a nucleotide sequence encoding at least one ORF selected from the group consisting of ORF-Light, ORF-Cxcl10, ORF-41BBL, ORF-IFNg, ORF-Il2, ORF-Gitrl, ORF-Il23, ORF-hIFNg, ORF-hIL23, ORF-h41BBL, ORF-hLIGHT, or any combination thereof. In certain embodiments, the vector comprises one, two, three, four, five, six, seven, eight, nine, ten, or eleven ORF sequences selected from the group consisting of ORF-Light, ORF-Cxcl10, ORF-41BBL, ORF-IFNg, ORF-Il2, ORF-Gitrl, ORF-Il23, ORF-hIFNg, ORF-hIL23, ORF-h41BBL, and ORF-hLIGHT. In certain embodiments, the vector comprises at least one nucleotide sequence selected from the group consisting of SEQ ID NOs: 73-84. In certain embodiments, the vector comprises one, two, three, four, five, six, seven, eight, nine, ten, or eleven nucleotide sequences selected from the group consisting of SEQ ID NOs: 73-84.

Tolerable variations of any one of the vectors or component parts will be known to those of skill in the art. For example, in some embodiments the vector or component part comprises a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of the nucleic acid sequence set forth in SEQ ID NO: 1-18 or 24-85.

Methods of Treatment

The present invention includes methods for treating or preventing cancer in a subject comprising administering to the subject a therapeutically effective amount of any of the compositions disclosed herein. This composition can be utilized as a prophylactic treatment, a therapeutic treatment, a personalized, subject-specific treatment, and/or a method of turning a 'cold' tumor into a 'hot' tumor, thus making it more susceptible to immunotherapy.

One aspect of the invention includes a method of treating cancer in a subject in need thereof comprising administering to the subject a therapeutically effective amount of a composition comprising a vector comprising a CRISPRa system, wherein the CRISPRa system increases expression of at least one endogenous gene, thus treating the cancer in the subject.

The vector can be any vector that can carry the gene, including but not limited to, standard viral vectors, chimeric viral vectors, other viral vectors, bacterial vectors, yeast vectors, DNA vectors, mRNA, protein carriers, nanomaterials, or other delivery vehicles. Applicable standard viral vectors for delivery include the vectors from the following types of viruses: dsDNA viruses (e.g. Adenoviruses, Herpesviruses, Poxviruses), ssDNA viruses (+ strand or "sense") DNA (e.g. Parvoviruses), dsRNA viruses (e.g. Reoviruses), (+)ssRNA viruses (+ strand or sense) RNA (e.g. Picornaviruses, Togaviruses), (−)ssRNA viruses (− strand or antisense) RNA (e.g. Orthomyxoviruses, Rhabdoviruses), ssRNA-RT viruses (+ strand or sense) RNA with DNA intermediate in life-cycle (e.g. Retroviruses), and dsDNA-RT viruses DNA with RNA intermediate in life-cycle (e.g. Hepadnaviruses).

In certain embodiments of the invention, the cells are packaged into an AAV vector. Applicable AAV serotypes include, but are not limited to, AAV1, AAV2, AAV3, AAV4, AAV5, AAV6, AAV7, AAV8, AAV9, AAV10, AAV11, AAV12, artificial variants such as AAV.rh10, AAV.rh32/33, AAV.rh43, AAV.rh64R1, rAAV2-retro, AAV-DJ, AAV-PHP.B, AAV-PHP.S, AAV-PHP.eB, or other engineered versions of AAV. In one embodiment, the AAV vector is AAV9. In one embodiment, the CRISPRa system is cloned into an AAV vector.

The cell or cells utilized in the invention can be from any source known to one of ordinary skill in the art. The cells of the invention may be autologous, allogeneic or xenogeneic with respect to the subject undergoing treatment. In some embodiments, the cell is from a cancer cell line. In some embodiments, the cell is from the subject. In some embodiments, the cell from the subject is a cancer cell. In further embodiments, the cancer cell is from a tumor. In some embodiments, the subject is a mammal. In further embodiments, the subject is a human.

The cells or vectors of the present invention may be administered in a manner appropriate to the disease to be treated or prevented. The quantity and frequency of administration will be determined by such factors as the condition of the patient, and the type and severity of the patient's disease, although appropriate dosages may be determined by clinical trials. Cells or vectors of the invention can be administered in dosages and routes and at times to be determined in appropriate pre-clinical and clinical experimentation and trials. Cell and vector compositions may be administered multiple times at various dosages. Administration of the cells or vectors of the invention may be combined with other methods useful to treat the desired disease or condition as determined by those of skill in the art. In one embodiment, administering the therapeutically effective amount of the composition comprises a one dose, a two dose, a three dose, a four dose, or a multi-dose treatment. The administration of the modified cells or vectors of the invention may be carried out in any convenient manner known to those of skill in the art. In one embodiment, the cells are administered intratumorally.

The invention includes compositions and methods for treating cancer. Types of cancer that can be treated include, but are not limited to, Acute Lymphoblastic Leukemia (ALL), Acute Myeloid Leukemia (AML), Adrenocortical Carcinoma, AIDS-Related Cancers, Kaposi Sarcoma, AIDS-Related Lymphoma, Primary CNS Lymphoma, Anal Cancer, Appendix Cancer (Gastrointestinal Carcinoid Tumors), Astrocytomas, Atypical Teratoid/Rhabdoid Tumor, Brain Cancer, Basal Cell Carcinoma of the Skin, Bile Duct Cancer, Bladder Cancer, Bone Cancer (includes Ewing Sarcoma and Osteosarcoma and Malignant Fibrous Histiocytoma), Brain Tumors, Breast Cancer, Bronchial Tumors, Burkitt Lymphoma, Non-Hodgkin Lymphoma, Carcinoid Tumors, Carcinoma of Unknown Primary, Cardiac (Heart) Tumors, Embryonal Tumors, Germ Cell Tumor, Primary CNS Lymphoma, Cervical Cancer, Cholangiocarcinoma, Chordoma, Chronic Lymphocytic Leukemia (CLL), Chronic Myelogenous Leukemia (CML), Chronic Myeloproliferative Neoplasms, Colorectal Cancer, Craniopharyngioma, Cutaneous T-Cell Lymphoma (Mycosis Fungoides and Sézary Syndrome), Ductal Carcinoma In Situ (DCIS), Endometrial Cancer, Ependymoma, Esophageal Cancer, Esthesioneuroblastoma, Ewing Sarcoma, Extracranial Germ Cell Tumor, Eye Cancer, Intraocular Melanoma, Fallopian Tube Cancer, Fibrous Histiocytoma of Bone, Osteosarcoma, Gallbladder Cancer, Gastric Cancer, Stomach Cancer, Gastrointestinal Carcinoid Tumor, Gastrointestinal Stromal Tumors (GIST), Central Nervous System Germ Cell Tumors, Extracranial Germ Cell Tumors, Extragonadal Germ Cell Tumors, Ovarian Germ Cell Tumors, Testicular Cancer, Gestational Trophoblastic Disease, Hairy Cell Leukemia, Head and Neck Cancer, Heart Tumors, Hepatocellular (Liver) Cancer, Histiocytosis (Langerhans Cell), Hodgkin Lymphoma, Hypopharyngeal Cancer, Intraocular Melanoma, Islet Cell Tumors, Pancreatic Neuroendocrine Tumors, Kidney Cancer, Renal Cell Cancer, Langerhans Cell Histiocytosis, Laryngeal Cancer, Leukemia, Lip and Oral Cavity Cancer, Liver Cancer, Lung Cancer (Non-Small Cell and Small Cell), Lymphoma, Male Breast Cancer, Malignant Fibrous Histiocytoma of Bone and Osteosarcoma, Melanoma, Intraocular (Eye) Melanoma, Merkel Cell Carcinoma (Skin Cancer), Malignant Mesothelioma, Metastatic Cancer, Metastatic Squamous Neck Cancer with Occult Primary, Midline Tract Carcinoma With NUT Gene Changes, Mouth Cancer, Multiple Endocrine Neoplasia Syndromes, Multiple Myeloma/Plasma Cell Neoplasms, Mycosis Fungoides (Lymphoma), Myelodysplastic Syndromes, Myelodysplastic/Myeloproliferative Neoplasms, Nasal Cavity and Paranasal Sinus Cancer, Nasopharyngeal Cancer, Neuroblastoma, Non-Small Cell Lung Cancer, Oral Cancer, and Oropharyngeal Cancer, Ovarian Cancer, Pancreatic Cancer, Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Primary Central Nervous System (CNS) Lymphoma, Primary Peritoneal Cancer, Prostate Cancer, Rectal Cancer, Recurrent Cancer, Retinoblastoma, Rhabdomyosarcoma, Salivary Gland Cancer, Sarcoma, Vascular Tumors, Uterine Sarcoma, Sézary Syndrome (Lymphoma), Small Cell Lung Cancer, Small Intestine Cancer, Soft Tissue Sarcoma, Squamous Cell Carcinoma, Stomach (Gastric) Cancer, Throat Cancer, Thymoma, Thymic Carcinoma, Thyroid Cancer, Transitional Cell Cancer of the Renal Pelvis and Ureter, Carcinoma of Unknown Primary, Ureter and Renal Pelvis, Transitional Cell Cancer, Urethral Cancer, Uterine Cancer, Vaginal Cancer, Vulvar Cancer, Wilms Tumor, and combinations thereof.

Certain embodiments of the invention further comprise administering an additional treatment to the subject. Certain embodiments of the invention include treating the subject with a combination of a composition of the present invention and an additional treatment. Examples of additional treatments include but are not limited to, chemotherapy, radiation, surgery, medication, immune checkpoint inhibitors, immune checkpoint blockade (ICB) antibodies, immune checkpoint inhibitors that block CTLA-4 or PD1, anti-CTLA4 monoclonal antibody, anti-PD1 monoclonal antibody, and -PD-L monoclonal antibody, adoptive cell transfer, human recombinant cytokines, cancer vaccines, immunotherapy, targeted therapy, hormone therapy, stem cell transplant, precision medicine, non-specific immunotherapy (e.g. cytokines and chemokines, such as IL-2, IL-7, IL-12, IL-15, IL-18, IL-23, IFNa, IFNb, IFNg, TNFa), oncolytic virus therapy, cell therapy (e.g. adoptive transfer of TILs, TCR-T, CAR-T, CAR-NK, CAR-macrophage, or other forms of naïve, patient-isolated or engineered primary cells), cancer vaccines (e.g. conventional DC vaccine), Ipilimumab (Yervoy), Nivolumab (Opdivo), Pembrolizumab (Keytruda), Atezolizumab (Tecentriq), Avelumab (Bavencio), Durvalumab (Imfinzi), Anti-LAG-3, anti-TIM1, Anti-TIM3, Anti-CSF-R, IDO inhibitor, OX-40 agonist, GITR agonist, CD80 agonist, CD86 agonist, ICOS agonist, ICOSLG agonist, CD276 agonist, VTCN1 agonist, TNFSF14 agonist, TNFSF9 agonist, TNFSF4 agonist, CD70 agonist, CD40 agonist, LGALS9 agonist, CD80 inhibitor, CD86 inhibitor, ICOS inhibitor, ICOSLG inhibitor, CD276 inhibitor, VTCN1 inhibitor, TNFSF14 inhibitor, TNFSF9 inhibitor, TNFSF4 inhibitor, CD70 inhibitor, CD40 inhibitor, LGALS9 inhibitor, TLR9 agonist, CD20 antibody, CD80 antibody, TIGIT antibody, B7-H1 antibody, B7-H2 antibody, B7-H3 antibody, B7-H4 antibody, CD28 antibody, CD47 antibody, anti-BTLA, anti-Galetin9, anti-IL15R, anti-GD2. In some embodiments the monoclonal antibody is fully human, humanized or chimeric.

In certain embodiments, administering a composition of the present invention alters the tumor microenvironment. In certain embodiments, administering the composition augments host immune responses against established tumors.

Introduction of Nucleic Acids

In certain embodiments an expression system is used for the introduction of gRNAs and (d)Cas9 proteins into the cells of interest. Typically employed options include but are not limited to plasmids and viral vectors such as adeno-associated virus (AAV) vector, adenoviral vector or lentivirus vector.

Methods of introducing nucleic acids into a cell include physical, biological and chemical methods. Physical methods for introducing a polynucleotide, such as RNA, into a host cell include calcium phosphate precipitation, lipofection, particle bombardment, microinjection, electroporation, and the like. RNA can be introduced into target cells using commercially available methods which include electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany). RNA can also be introduced into cells using cationic liposome mediated transfection using lipofection, using polymer encapsulation, using peptide mediated transfection, or using biolistic particle delivery systems such as "gene guns" (see, for example, Nishikawa, et al. Hum Gene Ther., 12(8):861-70 (2001).

Biological methods for introducing a polynucleotide of interest into a host cell include the use of DNA and RNA vectors. Viral vectors have become the most widely used method for introducing genes into mammalian, e.g., human cells. Other viral vectors can include as listed above. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the nucleic acids in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Moreover, the nucleic acids may be introduced by any means, such as transducing the cells, transfecting the cells, and electroporating the cells. One nucleic acid may be introduced by one method and another nucleic acid may be introduced into the cell by a different method.

RNA

In one embodiment, the nucleic acids introduced into cell are RNA. In another embodiment, the RNA is mRNA that comprises in vitro transcribed RNA or synthetic RNA. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA.

PCR can be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has a cap on the 5' end and a 3' poly(A) tail which determine ribosome binding, initiation of translation and stability mRNA in the cell. On a circular DNA template, for instance, plasmid DNA, RNA polymerase produces a long concatameric product which may not be suitable for expression in eukaryotic cells. The transcription of plasmid DNA linearized at the end of the 3' UTR results in normal sized mRNA which may not be effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is by molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001);

Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

In some embodiments, the RNA is electroporated into the cells, such as in vitro transcribed RNA.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the mRNAs with different structures and combination of their domains.

One advantage of RNA transfection methods of the invention is that RNA transfection is essentially transient and vector-free. A RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of cells with in vitro-transcribed RNA (IVT-RNA) makes use of two different strategies both of which have been successively tested in various animal models. Cells are transfected with in vitro-transcribed RNA by means of lipofection or electroporation. It is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct is delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Sources of Cells

In one embodiment, cells are obtained from a subject. Non-limiting examples of subjects include humans, dogs, cats, mice, rats, pigs and transgenic species thereof. Preferably, the subject is a human. Cells can be obtained from a number of sources, including peripheral blood mononuclear cells, bone marrow, lymph node tissue, spleen tissue, umbilical cord, cancer cells and tumors. In certain embodiments, any number of cell lines available in the art, may be used. In certain embodiments, cells can be obtained from a unit of blood collected from a subject using any number of techniques known to the skilled artisan, such as Ficoll separation. In one embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, cells are isolated from peripheral blood. Alternatively, cells can be isolated from umbilical cord. In any event, a specific subpopulation of cells can be further isolated by positive or negative selection techniques.

Cells can also be frozen. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

Pharmaceutical Compositions

Pharmaceutical compositions of the present invention may comprise the vector or modified cell as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

It can generally be stated that a pharmaceutical composition comprising the modified cells described herein may be administered at a dosage of $10^4$ to $10^9$ cells/kg body weight, in some instances $10^5$ to $10^6$ cells/kg body weight, including all integer values within those ranges. Compositions of the invention may also be administered multiple times at these dosages. The cells or vectors can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

The administration of the modified cells or vectors of the invention may be carried out in any convenient manner known to those of skill in the art. The cells or vectors of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullarly, intracystically intramuscularly, by intravenous (i.v.) injection, parenterally or intraperitoneally. In other instances, the cells of the invention are injected directly into a site of inflammation in the subject, a local disease site in the subject, a lymph node, an organ, a tumor, and the like.

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, Sambrook et al. (2012) *Molecular Cloning: A Laboratory Manual, fourth edition*. Cold Spring Harbor NY, Cold Spring Harbor Lab Press; Freshney, R.I. (2010) *Culture of Animal Cells: A Manual of Basic Technique and Specialized Applications, sixth edition*. John Wiley & Sons; Ausubel et al. (2002) *Short Protocols in Molecular Biology*. John Wiley & Sons; Coligan et al. (2002) *Current Protocols in Immunology*. John Wiley & Sons. These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

The materials and methods employed in these experiments are now described.

APCM sgRNA library: The APCM library was designed by first selecting a small set of genes that elicit immune responses: B2M, B7-H2 (ICOSL), Calnexin, Calreticulin, CCL5, CD30L(TNFSF8), CD40L, CD70, CD80, CD83, CD86, CXCL10, CXCL3, CXCL9, Cystatin B, Cystatin C (x), ERAP1, ERp57(PDIA3), Flt3L, GITRL(TNFSF18), IFNa4, IFNb1, IFNg, IL-2, LIGHT (TNFRSF14), NLRC5/CITA, OX40L/TNFSF4, Sec61a1, Sec61b, Sec61g, TAP1, TAP2, Tapasin, TAPBPR, TL1A (TNFSF15), and TNFSF9

(4-1BBL). SgRNA sequences were designed to target these genes in mice, yielding a library of 107 sgRNAs (SEQ ID NOs. 86-192) (FIG. 7). The sgRNAs were cloned into a viral vector and packaged.

CLC4 (CD80-Light-CXCL10-4-1BBL), CLC4G (CD80-Light-CXCL10-4-1BBL-GITRL) and CLC4I (CD80-Light-CXCL10-4-1BBL-IFNG): AAV-ORF-CLC4 was generated by concatenating ORFs of the CD80, Light, CXCL10, and 4-1BBL genes and expressing in an AAV vector (SEQ ID NO: 2). AAV-ORF-CLC4I was generated by concatenating ORFs of the CD80, Light, CXCL10, 4-1BBL, and IFNG genes expressing in an AAV vector (SEQ ID NO: 3). AAV-o-MAEGI-CLC4G was generated by cloning sgRNAs targeting the 5 genes into the AAV-CRISPRa vector (pGW059), and packaging into an AAV virus as a small pool: CD80-sg2 (NM_009855): TCCAGGCCTGTTCTGAGCAC (SEQ ID NO: 19), LIGHT (TNFRSF14)-sg2 (NM_019418): GAGGAGGTACGT GAGGAAAG (SEQ ID NO: 20), CXCL10-sg3 (NM_021274): GCAATGCCCTCGGTT TACAG (SEQ ID NO: 21), TNFSF9 (4-1BBL)-sg2 (NM_009404): ACAGGGCCTGG ACAGGGAAG (SEQ ID NO: 22), GITRL(TNFSF18)-sg1 (NM_183391): AGTGCTTAGCAGTGTTCCAA (SEQ ID NO: 23).

TABLE 1

Vectors used in the invention

| Vector name | Function | SEQ ID NO: |
|---|---|---|
| pGW059 | Lenti CRISPRa screen vector | 1 |
| pGW066 | AAV-ORF-CLC4 | 2 |
| pGW067 | AAV-ORF-CLC4I | 3 |
| pGW029 | Adenovirus one vector dSpCas9 | 4 |
| pGW035 | Adenovirus one vector dSpCas9 | 5 |
| pGW063 | Adenovirus one vector dSpCas9 | 6 |
| pAdEasy-1 | Adenovirus packaging or helper | 7 |
| pAD_Track8509 | Adenovirus packaging or helper | 8 |
| pAdTrack-CMV Sequences_190476 | Adenovirus packaging or helper | 9 |
| pZB3 | AAV dSaCas9 one vector | 10 |
| pGW047 | AAV dSaCas9 two vector | 11 |
| pGW060 | AAV dSaCas9 two vector | 12 |
| pGW045 | AAV dSpCas9 two vector | 13 |
| pRC119 | AAV two vector dCas12a/dCpf1 | 14 |
| pRC120 | AAV two vector dCas12a/dCpf1 | 15 |
| pRC121b | AAV two vector dCas12a/dCpf1 | 16 |
| pRC124 | AAV two vector dCas12a/dCpf1 | 17 |
| pRC126 | AAV two vector dCas12a/dCpf1 | 18 |
| pGW071 | AAV vector expressing Cd80-T2A-light-P2A-cxcl10-E2A-41bb-F2A-Il2 | 24 |
| pGW072 | AAV vector expressing IFNg | 25 |
| pGW073 | AAV vector expressing Cd80-T2A-light-P2A-cxcl10-E2A-41bb-F2A-Gitrl | 26 |
| pGW078 | AAV vector (base) | 27 |
| pGW089 | AAV vector expressing Il2 | 57 |
| pGW090 | AAV vector expressing Cd80-T2A-light-P2A-IL2-E2A-41bb-F2A-Ifng | 28 |
| pGW091 | AAV vector expressing Cd80-T2A-light-P2A-GITRL-E2A-41bb-F2A-Ifng | 29 |
| pGW094 | AAV vector expressing Ifng-P2A-Cd80-T2A-light-P2A-Gitrl-E2A-41BBL | 58 |
| pGW096 | AAV vector expressing Ifng-P2A-Cd80-T2A-light-P2A-IL23-E2A-41BBL-sPA | 30 |
| pGW097 | AAV vector expressing IL23 | 31 |
| pGW098 | AAV vector expressing Ifng-P2A-Cd80-T2A-light-P2A-IL23 | 32 |
| pGW099 | AAV vector expressing IFNg-P2A-Cd80-T2A-light-P2A-cxcl10 | 33 |
| pGW100 | AAV vector expressing Ifng-P2A-Cd80-T2A-light-P2A-Cxcl10-E2A-41BBL | 34 |
| pGW101 | AAV vector expressing Ifng-P2A-Cd80-T2A-light-E2A-41BBL | 35 |

TABLE 1-continued

| | Vectors used in the invention | |
|---|---|---|
| Vector name | Function | SEQ ID NO: |
| pGW102 | AAV vector expressing Cd80 | 36 |
| pGW103 | AAV vector expressing Light | 37 |
| pGW104 | AAV vector expressing Cxcl10 | 38 |
| pGW105 | AAV vector expressing 41bbL | 39 |
| pGW110 | AAV vector expressing Cd80-T2A-Light-P2A-Cxcl10-E2A-IFNg | 40 |
| pGW111 | AAV vector expressing Light-P2A-Cxcl10-E2A-IFNg | 41 |
| pGW112 | AAV vector expressing 41BBL-T2A-Light-P2A-Cxcl10-E2A-IFNg | 42 |
| pGW113 | AAV vector expressing IL23-T2A-Light-P2A-Cxcl10-E2A-IFNg | 43 |
| pGW114 | AAV vector expressing Cd80-T2A-Light-P2A-41BBL-E2A-IFNg | 44 |
| pGW115 | AAV vector expressing IL23-T2A-Light-P2A-41BBL-E2A-IFNg | 45 |
| pGW118 | AAV vector expressing Ifng-P2A-Cd80-T2A-light-E2A-41BBL | 46 |
| pGW119 | AAV vector expressing Ifng-STOP-P2A-Cd80-T2A-light-E2A-41BBL | 47 |
| pGW122 | AAV vector expressing IL23-T2A-41BBL-P2A-IFNg | 48 |
| pGW127b | AAV vector expressing hIFNg-P2A-hIL23-T2A-h41BBL | 49 |
| pGW128b | AAV vector expressing hIFNg-P2A-hIL23-T2A-h41BBL-E2A-hLight | 50 |
| pGW145 | AAV vector expressing hIFNg | 51 |
| pGW146 | AAV vector expressing hIL23 | 52 |
| pGW147 | AAV vector expressing h41BBL | 53 |
| pGW149 | AAV vector expressing hLIGHT(Remove-EQLI)-RSR | 54 |
| pGW036 | AAV vector expressing dSaCas9-VP64 | 55 |
| pGW011b | AAV vector expressing EFS-dCAS9-spA | 56 | pGW059 Lenti CRISPRa Screen Vector
(SEQ ID NO: 1)
ttaatgtagtcttatgcaatactcttgtagtcttgcaacatggta acgatgagttagcaacatgccttacaaggagagaaaaagcaccgt gcatgccgattggtggaagtaaggtggtacgatcgtgccttatta ggaaggcaacagacgggtctgacatggattggacgaaccactgaa ttgccgcattgcagagatattgtatttaagtgcctagctcgatac ataaacgggtctctctggttagaccagatctgagcctgggagctc tctggctaactagggaacccactgcttaagcctcaataaagcttg ccttgagtgcttcaagtagtgtgtgcccgtctgttgtgtgactct ggtaactagagatccctcagacccttttagtcagtgtggaaaatc tctagcagtggcgcccgaacagggacttgaaagcgaaagggaaac cagaggagctctctcgacgcaggactcggcttgctgaagcgcgca cggcaagaggcgaggggcggcgactggtgagtacgccaaaaattt tgactagcggaggctagaaggagagagatgggtgcgagagcgtca gtattaagcggggggagaattagatcgcgatgggaaaaaattcggt taaggccaggggggaaagaaaaaatataaattaaaacatatagtat gggcaagcagggagctagaacgattcgcagttaatcctggcctgt tagaaacatcagaaggctgtagacaaatactgggacagctacaac catcccttcagacaggatcagaagaacttagatcattatataata cagtagcaacccctctattgtgtgcatcaaaggatagagataaaag -continued acaccaaggaagctttagacaagatagaggaagagcaaaacaaaa gtaagaccaccgcacagcaagcggccgctgatcttcagacctgga ggaggagatatgagggacaattggagaagtgaattatataaatat aaagtagtaaaaattgaaccattaggagtagcacccaccaaggca aagagaagagtggtgcagagagaaaaaagagcagtgggaatagga gctttgttccttgggttcttgggagcagcaggaagcactatgggc gcagcgtcaatgacgctgacggtacaggccagacaattattgtct ggtatagtgcagcagcagaacaatttgctgagggctattgaggcg caacagcatctgttgcaactcacagtctggggcatcaagcagctc caggcaagaatcctggctgtggaaagatacctaaaggatcaacag ctcctggggatttggggttgctctggaaaactcatttgcaccact gctgtgccttggaatgctagttggagtaataaatctctggaacag atttggaatcacacgacctggatggagtgggacagagaaattaac aattacacaagcttaatacactccttaattgaagaatcgcaaaac cagcaagaaaagaatgaacaagaattattggaattagataaatgg gcaagtttgtggaattggtttaacataacaaattggctgtggtat ataaaattattcataatgatagtaggaggcttggtaggtttaaga atagtttttgctgtactttctatagtgaatagagttaggcaggga tattcaccattatcgtttcagacccacctcccaaccccgaggggga ccctctagagatccgacgcgccatctctaggcccgcgccggcccc

```
ctcgcacggacttgtgggagaagctcggctactccctgccccgg ttaatttgcatataatatttcctagtaactatagagagcttaatgt gcgataaaagacagataatctgttcttttttaatactagctacatt ttacatgataggcttggatttctataacttcgtatagcatacatt atacgaagttataaacagcacaaaaggaaactcaccctaactgta aagtaattgtgtgttttgagactataaGtatcccttggagaaCCA cctTGTTGgGAGACGggatacCGTCTCtgtttAagagctaAGCTG gccAACATGAGGATCACCCATGTCTGCAGggcCAGCTtagcaagt taaaataaggctagtccgttatcaacttggccAACATGAGGATCA CCCATGTCTGCAGggccaagtggcaccgagtcggtgcTTTTTTGG ATCCaagcttggcgtaactagatcttgagacaaatggcagtattc atccacaattttaaaagaaaagggggggattgggggggtacagtgca ggggaaagaatagtagacataatagcaacagacatacaaactaaa gaattacaaaaacaaattacaaaaattcaaaattttcgggtttat tacagggacagcagagatccactttggcgccggctcgaggggggcc cgggtgcaaagatggataaagtttttaaacagagaggaatctttgc agctaatggaccttctaggtcttgaaaggagtgggaattggctcc ggtgcccgtcagtgggcagagcgcacatcgcccacagtccccgag aagttggggggagggtcggcaattgatccggtgcctagagaagg tggcgcggggtaaactgggaaagtgatgtcgtgtactggctccgc cttttttcccgagggtgggggagaaccgtatataagtgcagtagtc gccgtgaacgttcttttttcgcaacgggtttgccgccagaacacag gtaagtgccgtgtgtggttcccgcgggcctggcctctttacgggt tatggcccttgcgtgccttgaattacttccactggctgcagtacg tgattcttgatcccgagcttcgggttggaagtgggtgggagagtt cgaggccttgcgcttaaggagcccttcgcctcgtgcttgagttg aggcctggcctgggcgctggggccgccgcgtgcgaatctggtggc accttcgcgcctgtctcgctgctttcgataagtctctagccattt aaaattttttgatgacctgctgcgacgctttttttctggcaagata gtcttgtaaatgcgggccaagatctgcacactggtatttcggttt ttggggccgcgggcggcgacgggccgtgcgtcccagcgcacat gttcggcgaggcggggcctgcgagcgcggccaccgagaatcggac gggggtagtctcaagctggccggcctgctctggtgcctggcctcg cgccgccgtgtatcgccccgccctgggcggcaaggctggcccggt cggcaccagttgcgtgagcggaaagatggccgcttcccggccctg ctgcagggagctcaaaatggaggacgcggcgctcgggagagcggg cgggtgagtcacccacacaaaggaaaagggcctttccgtcctcag ccgtcgcttcatgtgactccacggagtaccgggcgccgtccaggc acctcgattagttctcgagctttttggagtacgtcgtctttaggtt gggggggagggggtttttatgcgatggagtttccccacactgagtggg tggagactgaagttaggccagcttggcacttgatgtaattctcct
```

```
tggaatttgccctttttgagtttggatcttggttcattctcaagc ctcagacagtggttcaaagtttttttcttccatttcaggtgtcgt gacgtacggccaccatgaccgagtacaagcccacggtgcgcctcg ccacccgcgacgacgtgccccaggggccgtacgcaccctcgccgccg cgttcgccgactaccccgccacgcgccacaccgtcgatccggacc gccacatcgagcgggtcaccgagctgcaagaactcttcctcacgc gcgtcgggctcgacatcggcaaggtgtgggtcgcggacgacggcg ccgccgtggcggtctggaccacgccggagagcgtcgaagcggggg cggtgttcgccgagatcggcccgcgcatggccgagttgagcggtt cccggctggccgcgcagcaacagatggaaggcctcctggcgccgc accggcccaaggagcccgcgtggttcctggccaccgtcggagtct cgcccgaccaccagggcaagggtctgggcagcgccgtcgtgctcc ccggagtggaggcggccgagcgcgccggggtgcccgccttcctgg agacctccgcgcccgcaacctccccttctacgagcggctcggct tcaccgtcaccgccgacgtcgaggtgcccgaaggaccgcgcacct ggtgcatgacccgcaagcccggtgccGGATCCGGCGCAACAAACT

TCTCTCTGCTGAAACAAGCCGGAGATGTCGAAGAGAATCCTGGAC

CGatggaagacgccaaaaacataaagaaaggcccggcgccattct atccgctggaagatggaaccgctggagagcaactgcataaggcta tgaagagatacgccctggttcctggaacaattgcttttacagatg cacatatcgaggtggacatcacttacgctgagtacttcgaaatgt ccgttcggttggcagaagctatgaaacgatatgggctgaatacaa atcacagaatcgtcgtatgcagtgaaaactctcttcaattctta tgccggtgttgggcgcgttatttatcggagttgcagttgcgcccg cgaacgacatttataatgaacgtgaattgctcaacagtatgggca tttcgcagcctaccgtggtgttcgtttccaaaaaggggttgcaaa aaattttgaacgtgcaaaaaaagctcccaatcatccaaaaaatta ttatcatggattctaaaacggattaccagggatttcagtcgatgt acacgttcgtcacatctcatctacctcccggttttaatgaatacg attttgtgccagagtccttcgatagggacaagacaattgcactga tcatgaactcctctggatctactggtctgcctaaaggtgtcgctc tgcctcatagaactgcctgcgtgagattctcgcatgccagagatc ctatttttggcaatcaaatcattccggatactgcgattttaagtg ttgttccattccatcacggttttggaatgtttactacactcggat atttgatatgtggatttcgagtcgtcttaatgtatagatttgaag aGgagctgtttctgaggagccttcaggattacaagattcaaagtg cgctgctggtgccaacccttattctccttcttcgccaaaagcactc tgattgacaaatacgatttatctaatttacacgaaattgcttctg gtggcgctcccctctctaaggaagtcggggaagcggttgccaaga ggttccatctgccaggtatcaggcaaggatatgggctcactgaga
```

-continued

```
ctacatcagctattctgattacacccgaggggatgatgatgaaaccgg gcgcggtcggtaaagttgttccattttttgaagcgaaggttgtgg atctggataccgggaaaacgctgggcgttaatcaaagaggcgaac tgtgtgtgagaggtcctatgattatgtccggttatgtaaacaatc cggaagcgaccaacgccttgattgacaaggatggatggctacatt ctggagacatagcttactgggacgaagacgaacacttcttcatcg ttgaccgcctgaagtctctgattaagtacaaaggctatcaggtgg ctcccgctgaattggaatccatcttgctccaacaccccaacatct tcgacgcaggtgtcgcaggtcttcccgacgatgacgccggtgaac ttcccgccgccgttgttgtttggagcacggaaagacgatgacgg aaaaagagatcgtggattacgtcgccagtcaagtaacaaccgcga aaaagttgcgcggaggagttgtgtttgtggacgaagtaccgaaag gtcttaccggaaaactcgacgcaagaaaaatcagagagatcctca taaaggccaagaagggcggaaagatcgccgtgTAAgaattcacgc gttaagtcgacaatcaacctctggattacaaaatttgtgaaagat tgactggtattcttaactatgttgctccttttacgctatgtggat acgctgctttaatgcctttgtatcatgctattgcttcccgtatgg ctttcattttctcctccttgtataaatcctggttgctgtctcttt atgaggagttgtggcccgttgtcaggcaacggcgtggtgtgca ctgtgtttgctgacgcaacccccactggttggggcattgccacca cctgtcagctcctttccgggacttttcgctttcccctccctattg ccacggcggaactcatcgccgcctgccttgcccgctgctggacag gggctcggctgttgggcactgacaattccgtggtgttgtcgggga aatcatcgtcctttccttggctgctcgcctgtgttgccacctgga ttctgcgcgggacgtccttctgctacgtccctcggccctcaatc cagcggaccttccttcccgcggcctgctgccggctctgcggcctc ttccgcgtcttcgccttcgccctcagacgagtcggatctcccttt gggccgcctccccgcgtcgactttaagaccaatgacttacaaggc agctgtagatcttagccactttttaaaagaaaagggggactgga agggctaattcactcccaacgaagacaagatctgctttttgcttg tactgggtctctctggttagaccagatctgagcctgggagctctc tggctaactagggaacccactgcttaagcctcaataaagcttgcc ttgagtgcttcaagtagtgtgtgcccgtctgttgtgtgactctgg taactagagatccctcagacccttttagtcagtgtggaaaatctc tagcagtacgtatagtagttcatgtcatcttattattcagtattt ataacttgcaaagaaatgaatatcagagagtgagaggaacttgtt tattgcagcttataatggttacaaataaagcaatagcatcacaaa tttcacaaataaagcatttttttcactgcattctagttgtggttt gtccaaactcatcaatgtatcttatcatgtctggctctagctatc ccgcccctaactccgcccatccgcccctaactccgcccagttcc gcccattctccgccccatggctgactaattttttttatttatgca
```

-continued

```
gaggccgaggccgcctcggcctctgagctattccagaagtagtga ggaggcttttttggaggcctagggacgtacccaattcgccctata gtgagtcgtattacgcgcgctcactggccgtcgttttacaacgtc gtgactgggaaaaccctggcgttacccaacttaatcgccttgcag cacatcccccttttcgccagctggcgtaatagcgaagaggcccgca ccgatcgcccttcccaacagttgcgcagcctgaatggcgaatggg acgcgccctgtagcggcgcattaagcgcggcgggtgtggtggtta cgcgcagcgtgaccgctacacttgccagcgccctagcgcccgctc ctttcgctttcttcccttcctttctcgccacgttcgccggctttc cccgtcaagctctaaatcgggggctcccttaggggttccgatttta gtgctttacggcacctcgaccccaaaaaacttgattagggtgatg gttcacgtagtgggccatcgccctgatagacggtttttcgccctt tgacgttggagtccacgttctttaatagtggactcttgttccaaa ctggaacaacactcaaccctatctcggtctattcttttgatttat aagggattttgccgatttcggcctattggttaaaaaatgagctga tttaacaaaaatttaacgcgaattttaacaaaatattaacgctta caatttaggtggcacttttcggggaaatgtgcgcggaacccctat ttgtttatttttctaaatacattcaaatatgtatccgctcatgag acaataaccctgataaatgcttcaataatattgaaaaaggaagag tatgagtattcaacatttccgtgtcgcccttattcccttttttgc ggcattttgccttcctgtttttgctcacccagaaacgctggtgaa agtaaaagatgctgaagatcagttgggtgcacgagtgggttacat cgaactggatctcaacagcggtaagatccttgagagttttcgccc cgaagaacgttttccaatgatgagcacttttaaagttctgctatg tggcgcggtattatcccgtattgacgccgggcaagagcaactcgg tcgccgcatacactattctcagaatgacttggttgagtactcacc agtcacagaaaagcatcttacggatggcatgacagtaagagaatt atgcagtgctgccataaccatgagtgataacactgcggccaactt acttctgacaacgatcggaggaccgaaggagctaaccgcttttttt gcacaacatgggggatcatgtaactcgccttgatcgttgggaacc ggagctgaatgaagccataccaaacgacgagcgtgacaccacgat gcctgtagcaatggcaacaacgttgcgcaaactattaactggcga actacttactctagcttcccggcaacaattaatagactggatgga ggcggataaagttgcaggaccacttctgcgctcggcccttccggc tggctggtttattgctgataaatctggagccggtgagcgtgggtc tcgcggtatcattgcagcactggggccagatggtaagccctcccg tatcgtagttatctacacgacggggagtcaggcaactatggatga acgaaatagacagatcgctgagataggtgcctcactgattaagca ttggtaactgtcagaccaagtttactcatatatactttagattga tttaaaacttcattttttaatttaaaaggatctaggtgaagatcct
```

-continued ttttgataatctcatgaccaaaatcccttaacgtgagttttcgtt ccactgagcgtcagaccccgtagaaaagatcaaaggatcttcttg agatcctttttttctgcgcgtaatctgctgcttgcaaacaaaaaa accaccgctaccagcggtggtttgtttgccggatcaagagctacc aactctttttccgaaggtaactggcttcagcagagcgcagatacc aaatactgttcttctagtgtagccgtagttaggccaccacttcaa gaactctgtagcaccgcctacatacctcgctctgctaatcctgtt accagtggctgctgccagtggcgataagtcgtgtcttaccgggtt ggactcaagacgatagttaccggataaggcgcagcggtcgggctg aacggggggttcgtgcacacagcccagcttggagcgaacgaccta caccgaactgagatacctacagcgtgagctatgagaaagcgccac gcttcccgaagggagaaaggcggacaggtatccggtaagcggcag ggtcggaacaggagagcgcacgagggagcttccaggggggaaacgc ctggtatctttatagtcctgtcgggtttcgccacctctgacttga gcgtcgatttttgtgatgctcgtcaggggggcggagcctatggaa aaacgccagcaacgcggcctttttacggttcctggccttttgctg gccttttgctcacatgttctttcctgcgttatcccctgattctgt ggataaccgtattaccgcctttgagtgagctgataccgctcgccg cagccgaacgaccgagcgcagcgagtcagtgagcgaggaagcgga agagcgcccaatacgcaaaccgcctctccccgcgcgttggccgat tcattaatgcagctggcacgacaggtttcccgactggaaagcggg cagtgagcgcaacgcaattaatgtgagttagctcactcattaggc accccaggctttacactttatgcttccggctcgtatgttgtgtgg aattgtgagcggataacaatttcacacaggaaacagctatgacca tgattacgccaagcgcgcaattaaccctcactaaagggaacaaaa gctggagctgcaagc pGW066 AAV-ORF-CLC4

(SEQ ID NO: 2)

CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

-continued

TCTTTGTTTCGTTTTCTGTTCTGCGCCGTTACAGATCTGGCTAAC

TAccggtgccaccatggccttgcaattgtcagttgatgcaggatac accactcctcaagtttccatgtccaaggctcattcttctctttgt gctgctgattcgtctttcacaagtgtcttcagatgttgatgaaca actgtccaagtcagtgaaagataaggtattgctgccttgccgtta caactctcctcatgaagatgagtctgaagaccgaatctactggca aaaacatgacaaagtggtgctgtctgtcattgctgggaaactaaa agtgtggcccgagtataagaaccggactttatatgacaacactac ctactctcttatcatcctgggcctggtcctttcagaccggggcac atacagctgtgtcgttcaaaagaaggaaagaggaacgtatgaagt taaacacttggctttagtaaagttgtccatcaaagctgacttctc tacccccaacataactgagtctggaaacccatctgcagacactaa aaggattacctgctttgcttccgggggtttcccaaagcctcgctt ctcttggttggaaaatggaagagaattacctggcatcaatacgac aatttcccaggatcctgaatctgaattgtacaccattagtagcca actagatttcaatacgactcgcaaccacaccattaagtgtctcat taaatatggagatgctcacgtgtcagaggacttcacctgggaaaa acccccagaagaccctcctgatagcaagaacacacttgtgctctt tggggcaggattcggcgcagtaataacagtcgtcgtcatcgttgt catcatcaaatgcttctgtaagcacagaagctgtttcagaagaaa tgaggcaagcagagaaacaaacaacagccttaccttcgggcctga agaagcattagctgaacagaccgtcttccttcgtacgGGCAGTGG

AGAGGGCAGAGGAAGTCTGCTAACATGCGGTGACGTCGAGGAGAA

TCCTGGCCCAatggagagtgtggtacagccttcagtgtttgtggt ggatggacagacggacatcccattcaggcggctggaacagaacca ccggagacggcgctgtggcactgtccaggtcagcctggccctggt gctgctgctaAgtgctgggctggccactcagggctggtttctcct gagactgcatcaacgtcttggagacatagtagctcatctgccaga tggaggcaaaggctcctgggagaagctgatacaagatcaacgatc tcaccaggccaacccagcagcacatcttacaggagccaacgccag cttgataggtattggtggacctctgttatggggagacacgacttgg cctggccttcttgaggggcttgacgtatcatgatggggccctggt gaccatggagcccggttactactatgtgtactccaaagtgcagct gagcggcgtgggctgcccccaggggctggccaatggcctccccat cacccatggactatacaagcgcacatcccgctacccgaaggagtt agaactgctggtcagtcggcggtcaccctgtggccgggccaacag ctcccgagtctggtgggacagcagcttcctgggcggcgtggtaca tctggaggctggggaagaggtggtggtccgcgtgcctggaaaccg cctggtcagaccacgtgacggcaccaggtcctatttcggagcttt catggtcactagtGGATCCGGCGCAACAAACTTCTCTCTGCTGAA -continued ACAAGCCGGAGATGTCGAAGAGAATCCTGGACCGatgaacccaag tgctgccgtcattttctgcctcatcctgctgggtctgagtgggac tcaagggatccctctcgcaaggacggtccgctgcaactgcatcca tatcgatgacgggccagtgagaatgagggccatagggaagcttga aatcatccctgcgagcctatcctgcccacgtgttgagatcattgc cacgatgaaaaagaatgatgagcagagatgtctgaatccggaatc taagaccatcaagaatttaatgaaagcgtttagccaaaaaaggtc taaaagggctcctgctagcagcggtacccagtgcaccaactacgc cctgctgaagctggccggcgatgtggagagcaaccccgggcccat ggaccagcacacacttgatgtggaggataccgcggatgccagaca tccagcaggtacttcgtgcccctcggatgcggcgctcctcagaga taccgggctcctcgcggacgctgcgctcctctcagatactgtgcg ccccacaaatgccgcgctccccacggatgctgcctaccctgcggt taatgttcgggatcgcgaggccgcgtggccgcctgcactgaactt ctgttcccgccacccaaagctctatggcctagtcgctctttggtttt gctgcttctgatcgccgcctgtgttcctatcttcacccgcaccga gcctcggccagcgctcacaatcaccacctcgcccaacctgggtac ccgagagaataatgcagaccaggtcacccctgtttcccacattgg ctgccccaacactacacaacagggctctcctgtgttcgccaagct actggctaaaaaccaagcatcgttgtgcaatacaactctgaactg gcacagccaagatggagctgggagctcataccctatctcaaggtct gaggtacgaagaagacaaaaaggagttggtggtagacagtcccgg gctctactacgtattttttggaactgaagctcagtccaacattcac aaacacaggccacaaggtgcagggctgggtctctcttgttttgca agcaaagcctcaggtagatgactttgacaacttggccctgacagt ggaactgttcccttgctccatggagaacaagttagtggaccgttc ctggagtcaactgttgctcctgaaggctggccaccgcctcagtgt gggtctgagggcttatctgcatggagcccaggatgcatacagaga ctgggagctgtcttatcccaacaccaccagctttggactctttct tAtgaaacccgacaacccatgggaatgaGaattcacgcgttaagt cgacaatcaacctctggattacaaaatttgtgaaagattgactgg tattcttaactatgttgctccttttacgctatgtggatacgctgc tttaatgcctttgtatcatgctattgcttcccgtatggctttcat tttctcctccttgtataaatcctggttgctgtctctttatgagga gttgtggcccgttgtcaggcaacgtggcgtggtgtgcactgtgtt tgctgacgcaacccccactggttggggcattgccaccacctgtca gctcctttccgggactttcgctttccccctccctattgccacggc ggaactcatcgccgcctgccttgcccgctgctggacaggggctcg gctgttgggcactgacaattccgtggtgttgtcggggaaatcatc gtcctttccttggctgctcgcctgtgttgccacctggattctgcg cgggacgtccttctgctacgtcccttcggccctcaatccagcgga -continued ccttccttcccgcggcctgctgccggctctgcggcctcttccgcg tcttcgccttcgccctcagacgagtcggatctcccctttgggccgc ctccccgcgtcgactttaagaccaatgacGGCCGCAGGAACCCCT

AGTGATGGAGTTGGCCACTCCCTCTCTGCGCGCTCGCTCGCTCAC

TGAGGCCGGGCGACCAAAGGTCGCCCGACGCCCGGGCTTTGCCCG

GGCGGCCTCAGTGAGCGAGCGAGCGCGCAGCTGCCTGCAGGGGCG

CCTGATGCGGTATTTTCTCCTTACGCATCTGTGCGGTATTTCACA

CCGCATACGTCAAAGCAACCATAGTACGCGCCCTGTAGCGGCGCA

TTAAGCGCGGCGGGTGTGGTGGTTACGCGCAGCGTGACCGCTACA

CTTGCCAGCGCCTTAGCGCCCGCTCCTTTCGCTTTCTTCCCTTCC

TTTCTCGCCACGTTCGCCGGCTTTCCCCGTCAAGCTCTAAATCGG

GGGCTCCCTTTAGGGTTCCGATTTAGTGCTTTACGGCACCTCGAC

CCCAAAAAACTTGATTTGGGTGATGGTTCACGTAGTGGGCCATCG

CCCTGATAGACGGTTTTTCGCCCTTTGACGTTGGAGTCCACGTTC

TTTAATAGTGGACTCTTGTTCCAAACTGGAACAACACTCAACTCT

ATCTCGGGCTATTCTTTTGATTTATAAGGGATTTTGCCGATTTCG

GTCTATTGGTTAAAAAATGAGCTGATTTAACAAAAATTTAACGCG

AATTTTAACAAAATATTAACGTTTACAATTTTATGGTGCACTCTC

AGTACAATCTGCTCTGATGCCGCATAGTTAAGCCAGCCCCGACAC

CCGCCAACACCCGCTGACGCGCCCTGACGGGCTTGTCTGCTCCCG

GCATCCGCTTACAGACAAGCTGTGACCGTCTCCGGGAGCTGCATG

TGTCAGAGGTTTTCACCGTCATCACCGAAACGCGCGAGACGAAAG

GGCCTCGTGATACGCCTATTTTTATAGGTTAATGTCATGATAATA

ATGGTTTCTTAGACGTCAGGTGGCACTTTTCGGGGAAATGTGCGC

GGAACCCCTATTTGTTTATTTTTCTAAATACATTCAAATATGTAT

CCGCTCATGAGACAATAACCCTGATAAATGCTTCAATAATATTGA

AAAAGGAAGAGTATGAGTATTCAACATTTCCGTGTCGCCCTTATT

CCCTTTTTTGCGGCATTTTGCCTTCCTGTTTTTGCTCACCCAGAA

ACGCTGGTGAAAGTAAAAGATGCTGAAGATCAGTTGGGTGCACGA

GTGGGTTACATCGAACTGGATCTCAACAGCGGTAAGATCCTTGAG

AGTTTTCGCCCCGAAGAACGTTTTCCAATGATGAGCACTTTTAAA

GTTCTGCTATGTGGCGCGGTATTATCCCGTATTGACGCCGGGCAA

GAGCAACTCGGTCGCCGCATACACTATTCTCAGAATGACTTGGTT

GAGTACTCACCAGTCACAGAAAAGCATCTTACGGATGGCATGACA

GTAAGAGAATTATGCAGTGCTGCCATAACCATGAGTGATAACACT

GCGGCCAACTTACTTCTGACAACGATCGGAGGACCGAAGGAGCTA

ACCGCTTTTTTGCACAACATGGGGGATCATGTAACTCGCCTTGAT

CGTTGGGAACCGGAGCTGAATGAAGCCATACCAAACGACGAGCGT

GACACCACGATGCCTGTAGCAATGGCAACAACGTTGCGCAAACTA

TTAACTGGCGAACTACTTACTCTAGCTTCCCGGCAACAATTAATA

-continued

GACTGGATGGAGGCGGATAAAGTTGCAGGACCACTTCTGCGCTCG

GCCCTTCCGGCTGGCTGGTTTATTGCTGATAAATCTGGAGCCGGT

GAGCGTGGAAGCCGCGGTATCATTGCAGCACTGGGGCCAGATGGT

AAGCCCTCCCGTATCGTAGTTATCTACACGACGGGGAGTCAGGCA

ACTATGGATGAACGAAATAGACAGATCGCTGAGATAGGTGCCTCA

CTGATTAAGCATTGGTAACTGTCAGACCAAGTTTACTCATATATA

CTTTAGATTGATTTAAAACTTCATTTTTAATTTAAAAGGATCTAG

GTGAAGATCCTTTTTGATAATCTCATGACCAAAATCCCTTAACGT

GAGTTTTCGTTCCACTGAGCGTCAGACCCCGTAGAAAAGATCAAA

GGATCTTCTTGAGATCCTTTTTTTCTGCGCGTAATCTGCTGCTTG

CAAACAAAAAACCACCGCTACCAGCGGTGGTTTGTTTGCCGGAT

CAAGAGCTACCAACTCTTTTTCCGAAGGTAACTGGCTTCAGCAGA

GCGCAGATACCAAATACTGTTCTTCTAGTGTAGCCGTAGTTAGGC

CACCACTTCAAGAACTCTGTAGCACCGCCTACATACCTCGCTCTG

CTAATCCTGTTACCAGTGGCTGCTGCCAGTGGCGATAAGTCGTGT

CTTACCGGGTTGGACTCAAGACGATAGTTACCGGATAAGGCGCAG

CGGTCGGGCTGAACGGGGGGTTCGTGCACACAGCCCAGCTTGGAG

CGAACGACCTACACCGAACTGAGATACCTACAGCGTGAGCTATGA

GAAAGCGCCACGCTTCCCGAAGGGAGAAAGGCGGACAGGTATCCG

GTAAGCGGCAGGGTCGGAACAGGAGAGCGCACGAGGGAGCTTCCA

GGGGGAAACGCCTGGTATCTTTATAGTCCTGTCGGGTTTCGCCAC

CTCTGACTTGAGCGTCGATTTTTGTGATGCTCGTCAGGGGGGCGG

AGCCTATGGAAAAACGCCAGCAACGCGGCCTTTTTACGGTTCCTG

GCCTTTTGCTGGCCTTTTGCTCACATGT pGW067 AAV-ORF-CLC41

(SEQ ID NO: 3)

CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccatggcttgcaattgtcagttgatgcaggatac

-continued accactcctcaagtttccatgtccaaggctcattcttctctttgt gctgctgattcgtcttttcacaagtgtgtcttcagatgttgatgaaca actgtccaagtcagtgaaagataaggtattgctgccttgccgtta caactctcctcatgaagatgagtctgaagaccgaatctactggca aaaacatgacaaagtggtgctgtctgtcattgTtgggaaactaaa agtgtggcccgagtataagaaccggactttatatgacaacactac ctactctcttatcatcctgggcctggtcctttcagaccggggcac atacagctgtgtcgttcaaaagaaggaaagaggaacgtatgaagt taaacacttggctttagtaaagttgtccatcaaagctgacttctc tacccccaacataactgagtctggaaacccatctgcagacactaa aaggattacctgctttgcttccggggggtttcccaaagcctcgctt ctcttggttggaaaatggaagagaattacctggcatcaatacgac aatttcccaggatcctgaatctgaattgtacaccattagtagcca actagatttcaatacgactcgcaaccacaccattaagtgtctcat taaatatggagatgctcacgtgtcagaggacttcacctgggaaaa accccccagaagaccctcctgatagcaagaacacacttgtgctctt tggggcaggattcggcgcagtaataacagtcgtcgtcatcgttgt catcatcaaatgcttctgtaagcacagaagctgtttcagaagaaa tgaggcaagcagagaaacaaacaacagccttaccttcgggcctga agaagcattagctgaacagaccgtcttccttcgtacgGGCAGTGG

AGAGGGCAGAGGAAGTCTGCTAACATGCGGTGACGTCGAGGAGAA

TCCTGGCCCAatggagagtgtggtacagccttcagtgtttgtggt ggatggacagacggacatcccattcaggcggctggaacagaacca ccggagacggcgctgtggcactgtccaggtcagcctggccctggt gctgctgctaggtgctgggctggccactcagggctggtttctcct gagactgcatcaacgtcttggagacatagtagctcatctgccaga tggaggcaaaggctcctgggagaagctgatacaagatcaacgatc tcaccaggccaacccagcagcacatcttacaggagccaacgccag cttgataggtattggtggacctctgttatgggagacacgacttgg cctggccttcttgaggggcttgacgtatcatgatggggccctggt gaccatggagcccggttactactatgtgtactccaaagtgcagct gagcggcgtgggctgcccccagggggctggccaatggcctccccat cacccatggactatacaagcgcacatcccgctacccgaaggagtt agaactgctggtcagtcggcggtcaccctgtggccgggccaacag ctcccgagtctggtgggacagcagcttcctgggcggcgtggtaca tctggaggctggggaagaggtggtggtccgcgtgcctggaaaccg cctggtcagaccacgtgacggcaccaggtcctatttcggagcttt catggtcactagtGGATCCGGCGCAACAAACTTCTCTCTGCTGAA ACAAGCCGGAGATGTCGAAGAGAATCCTGGACCGatgaacccaag tgctgccgtcattttctgcctcatcctgctgggtctgagtgggac -continued

```
tcaagggatccctctcgcaaggacggtccgctgcaactgcatcca tatcgatgacgggccagtgagaatgagggccatagggaagcttga aatcatccctgcgagcctatcctgcccacgtgttgagatcattgc cacgatgaaaaagaatgatgagcagagatgtctgaatccggaatc taagaccatcaagaatttaatgaaagcgtttagccaaaaaaggtc taaaagggctcctgctagcagcggtacccagtgcaccaactacgc cctgctgaagctggccggcgatgtggagagcaaccccgggcccat ggaccagcacacacttgatgtggaggataccgcggatgccagaca tccagcaggtacttcgtgcccctcggatgcggcgctcctcagaga taccgggctcctcgcggacgctgcgctcctctcagatactgtgcg ccccacaaatgccgcgctccccacggatgctgcctaccctgcggt taatgttcgggatcgcgaggccgcgtggccgcctgcactgaactt ctgttcccgccacccaaagctctatggcctagtcgctttggtttt gctgcttctgatcgccgcctgtgttcctatcttcacccgcaccga gcctcggccagcgctcacaatcaccacctcgcccaacctgggtac ccgagagaataatgcagaccaggtcacccctgtttcccacattgg ctgccccaacactacacaacagggctctcctgtgttcgccaagct actggctaaaaaccaagcatcgttgtgcaatacaactctgaactg gcacagccaagatggagctgggagctcatacctatctcaaggtct gaggtacgaagaagacaaaaaggagttggtggtagacagtcccgg gctctactacgtattttttggaactgaagctcagtccaacattcac aaacacaggccacaaggtgcagggctgggtctctcttgttttgca agcaaagcctcaggtagatgactttgacaacttggccctgacagt ggaactgttcccttgctccatggagaacaagttagtggaccgttc ctggagtcaactgttgctcctgaaggctggccaccgcctcagtgt gggtctgagggcttatctgcatggagcccaggatgcatacagaga ctgggagctgtcttatcccaacaccaccagctttggactctttct tgtgaaacccgacaacccatgggaaggcatatgcggtaccgtgaa gcagaccctgaacttcgatctgctgaagctggccggcgatgtgga gagcaaccccgggcccatgaacgctacacactgcatcttggcttt gcagctcttcctcatggctgtttctggctgttactgccacggcac agtcattgaaagcctagaaagtctgaataactattttaactcaag tggcatagatgtggaagaaaagagtctcttcttggatatctggag gaactggcaaaaggatggtgacatgaaaatcctgcagagccagat tatctctttctacctcagactctttgaagtcttgaaagacaatca ggccatcagcaacaacataagcgtcattgaatcacacctgattac taccttcttcagcaacagcaaggcgaaaaaggatgcattcatgag tattgccaagtttgaggtcaacaacccacaggtccagcgccaagc attcaatgagctcatccgagtggtccaccagctgttgccggaatc cagcctcaggaagcggaaaaggagtcgctgctgaGAATTCAATAA

AAGATCTTTATTTTCATTAGATCTGTGTGTTGGTTTTTTGTGTGC
```

-continued

```
GGCCGCAGGAACCCCTAGTGATGGAGTTGGCCACTCCCTCTCTGC

GCGCTCGCTCGCTCACTGAGGCCGGGCGACCAAAGGTCGCCCGAC

GCCCGGGCTTTGCCCGGGCGGCCTCAGTGAGCGAGCGAGCGCGCA

GCTGCCTGCAGGGGCGCCTGATGCGGTATTTTCTCCTTACGCATC

TGTGCGGTATTTCACACCGCATACGTCAAAGCAACCATAGTACGC

GCCCTGTAGCGGCGCATTAAGCGCGGCGGGTGTGGTGGTTACGCG

CAGCGTGACCGCTACACTTGCCAGCGCCTTAGCGCCCGCTCCTTT

CGCTTTCTTCCCTTCCTTTCTCGCCACGTTCGCCGGCTTTCCCCG

TCAAGCTCTAAATCGGGGGCTCCCTTTAGGGTTCCGATTTAGTGC

TTTACGGCACCTCGACCCCAAAAAACTTGATTTGGGTGATGGTTC

ACGTAGTGGGCCATCGCCCTGATAGACGGTTTTTCGCCCTTTGAC

GTTGGAGTCCACGTTCTTTAATAGTGGACTCTTGTTCCAAACTGG

AACAACACTCAACTCTATCTCGGGCTATTCTTTTGATTTATAAGG

GATTTTGCCGATTTCGGTCTATTGGTTAAAAAATGAGCTGATTTA

ACAAAAATTTAACGCGAATTTTAACAAAATATTAACGTTTACAAT

TTTATGGTGCACTCTCAGTACAATCTGCTCTGATGCCGCATAGTT

AAGCCAGCCCCGACACCCGCCAACACCCGCTGACGCGCCCTGACG

GGCTTGTCTGCTCCCGGCATCCGCTTACAGACAAGCTGTGACCGT

CTCCGGGAGCTGCATGTGTCAGAGGTTTTCACCGTCATCACCGAA

ACGCGCGAGACGAAAGGGCCTCGTGATACGCCTATTTTTATAGGT

TAATGTCATGATAATAATGGTTTCTTAGACGTCAGGTGGCACTTT

TCGGGGAAATGTGCGCGGAACCCCTATTTGTTTATTTTTCTAAAT

ACATTCAAATATGTATCCGCTCATGAGACAATAACCCTGATAAAT

GCTTCAATAATATTGAAAAAGGAAGAGTATGAGTATTCAACATTT

CCGTGTCGCCCTTATTCCCTTTTTTGCGGCATTTTGCCTTCCTGT

TTTTGCTCACCCAGAAACGCTGGTGAAAGTAAAAGATGCTGAAGA

TCAGTTGGGTGCACGAGTGGGTTACATCGAACTGGATCTCAACAG

CGGTAAGATCCTTGAGAGTTTTCGCCCCGAAGAACGTTTTCCAAT

GATGAGCACTTTTAAAGTTCTGCTATGTGGCGCGGTATTATCCCG

TATTGACGCCGGGCAAGAGCAACTCGGTCGCCGCATACACTATTC

TCAGAATGACTTGGTTGAGTACTCACCAGTCACAGAAAAGCATCT

TACGGATGGCATGACAGTAAGAGAATTATGCAGTGCTGCCATAAC

CATGAGTGATAACACTGCGGCCAACTTACTTCTGACAACGATCGG

AGGACCGAAGGAGCTAACCGCTTTTTTGCACAACATGGGGGATCA

TGTAACTCGCCTTGATCGTTGGGAACCGGAGCTGAATGAAGCCAT

ACCAAACGACGAGCGTGACACCACGATGCCTGTAGCAATGGCAAC

AACGTTGCGCAAACTATTAACTGGCGAACTACTTACTCTAGCTTC

CCGGCAACAATTAATAGACTGGATGGAGGCGGATAAAGTTGCAGG

ACCACTTCTGCGCTCGGCCCTTCCGGCTGGCTGGTTTATTGCTGA

TAAATCTGGAGCCGGTGAGCGTGGAAGCCGCGGTATCATTGCAGC
```

-continued

ACTGGGGCCAGATGGTAAGCCCTCCCGTATCGTAGTTATCTACAC

GACGGGGAGTCAGGCAACTATGGATGAACGAAATAGACAGATCGC

TGAGATAGGTGCCTCACTGATTAAGCATTGGTAACTGTCAGACCA

AGTTTACTCATATATACTTTAGATTGATTTAAAACTTCATTTTTA

ATTTAAAAGGATCTAGGTGAAGATCCTTTTTGATAATCTCATGAC

CAAAATCCCTTAACGTGAGTTTTCGTTCCACTGAGCGTCAGACCC

CGTAGAAAAGATCAAAGGATCTTCTTGAGATCCTTTTTTTCTGCG

CGTAATCTGCTGCTTGCAAACAAAAAAACCACCGCTACCAGCGGT

GGTTTGTTTGCCGGATCAAGAGCTACCAACtcttttttccgAAggt

AActggcttcAgcAgAgcgcAgAtAccAAAtActgttcTTCTAGT

GTAGCCGTAGTTAGGCCACCACTTCAAGAACTCTGTAGCACCGCC

TACATACCTCGCTCTGCTAATCCTGTTACCAGTGGCTGCTGCCAG

TGGCGATAAGTCGTGTCTTACCGGGTTGGACTCAAGACGATAGTT

ACCGGATAAGGCGCAGCGGTCGGGCTGAACGGGGGGTTCGTGCAC

ACAGCCCAGCTTGGAGCGAACGACCTACACCGAACTGAGATACCT

ACAGCGTGAGCTATGAGAAAGCGCCACGCTTCCCGAAGGGAGAAA

GGCGGACAGGTATCCGGTAAGCGGCAGGGTCGGAACAGGAGAGCG

CACGAGGGAGCTTCCAGGGGGAAACGCCTGGTATCTTTATAGTCC

TGTCGGGTTTCGCCACCTCTGACTTGAGCGTCGATTTTTGTGATG

CTCGTCAGGGGGCGGAGCCTATGGAAAAACGCCAGCAACGCGGC

CTTTTTACGGTTCCTGGCCTTTTGCTGGCCTTTTGCTCACATGT pGW029 Adenovirus One Vector dSpCas9

(SEQ ID NO: 4)

CTACAGGGCGCGTCCATTCGCCATTCAGGATCGAATTAATTCTTA

ATTAACATCATCAATAATATACCTTAttttggattgaagccaata tgataatgagggggtggagtttgtgacgtggcgcggggcgtggga acggggcgggtgacgtagtagtgtggcggaagtgtgatgttgcaa gtgtggcggaacacatgtaagcgacggatgtggcaaaagtgacgt ttttggtgtgcgccggtgtacacaggaagtgacaattttcgcgcg gttttaggcggatgttgtagtaaatttgggcgtaaccgagtaaga tttggccattttcgcgggaaaactgaataagaggaagtgaaatct gaataatttgtgttactcatagcgcgtaaTACTggtaccgcggc cgcctcgagtCTAGAAAGAgggcctatttcccatgattccttcat atttgcatatacgatacaaggctgttagagagataattagaatta atttgactgtaaacacaaagatattagtacaaaatacgtgacgta gaaagtaataatttcttgggtagtttgcagttttaaaattatgtt ttaaaatggactatcatatgcttaccgtaacttgaaagtatttcg atttcttggctttatatatcttGTGGAAAGGACGAAACACCggaa gagcgagctcttctgtttttagagctaggccAACATGAGGATCACC CATGTCTGCAGggcctagcaagttaaaataaggctagtccgttat caacttggccAACATGAGGATCACCCATGTCTGCAGggccaagtg gcaccgagtcggtgcTTTTTTGctagcGTCAGTGGGCAGAGCGCA -continued

CATCGCCCACAGTCCCCGAGAAGTTGGGGGGAGGGGTCGGCAATT

GAACGGGTGCCTAGAGAAGGTGGCGCGGGGTAAACTGGGAAAGTG

ATGTCGTGTACTGGCTCCGCCTTTTTCCCGAGGGTGGGGGAGAAC

CGTATATAAGTGCAGTAGTCGCCGTGAACGTTCTTTTTCGCAACG

GGTTTGCCGCCAGAACACAGCTGAAGCTTCGAGGGGCTCGCATCT

CTCCTTCACGCGCCCGCCGCCCTACCTGAGGCCGCCATCCACGCC

GGTTGAGTCGCGTTCTGCCGCCTCCCGCCTGTGGTGCCTCCTGAA

CTGCGTCCGCCGTCTAGGTAAGTTTAAAGCTCAGGTCGAGACCGG

GCCTTTGTCCGGCGCTCCCTTGGAGCCTACCTAGACTCAGCCGGC

TCTCCACGCTTTGCCTGACCCTGCTTGCTCAACTCTACGTCTTTG

TTTCGTTTTCTGTTCTGCGCCGTTACAGATCCAAGctcGTACGgc caccATGAAAAGGCCGGCGGCCACGAAAAAGGCCGGCCAGGCAAA

AAAGAAAAAGGACAAGAAGTACAGCATCGGCCTGGCCATCGGCAC

CAACTCTGTGGGCTGGGCCGTGATCACCGACGAGTACAAGGTGCC

CAGCAAGAAATTCAAGGTGCTGGGCAACACCGACCGGCACAGCAT

CAAGAAGAACCTGATCGGAGCCCTGCTGTTCGACAGCGGCGAAAC

AGCCGAGGCCACCCGGCTGAAGAGAACCGCCAGAAGAAGATACAC

CAGACGGAAGAACCGGATCTGCTATCTGCAAGAGATCTTCAGCAA

CGAGATGGCCAAGGTGGACGACAGCTTCTTCCACAGACTGGAAGA

GTCCTTCCTGGTGGAAGAGGATAAGAAGCACGAGCGGCACCCCAT

CTTCGGCAACATCGTGGACGAGGTGGCCTACCACGAGAAGTACCC

CACCATCTACCACCTGAGAAAGAAACTGGTGGACAGCACCGACAA

GGCCGACCTGCGGCTGATCTATCTGGCCCTGGCCCACATGATCAA

GTTCCGGGGCCACTTCCTGATCGAGGGCGACCTGAACCCCGACAA

CAGCGACGTGGACAAGCTGTTCATCCAGCTGGTGCAGACCTACAA

CCAGCTGTTCGAGGAAAACCCCATCAACGCCAGCGGCGTGGACGC

CAAGGCCATCCTGTCTGCCAGACTGAGCAAGAGCAGACGGCTGGA

AAATCTGATCGCCCAGCTGCCCGGCGAGAAGAAGAATGGCCTGTT

CGGCAACCTGATTGCCCTGAGCCTGGGCCTGACCCCCAACTTCAA

GAGCAACTTCGACCTGGCCGAGGATGCCAAACTGCAGCTGAGCAA

GGACACCTACGACGACGACCTGGACAACCTGCTGGCCCAGATCGG

CGACCAGTACGCCGACCTGTTTCTGGCCGCCAAGAACCTGTCCGA

CGCCATCCTGCTGAGCGACATCCTGAGAGTGAACACCGAGATCAC

CAAGGCCCCCCTGAGCGCCTCTATGATCAAGAGATACGACGAGCA

CCACCAGGACCTGACCCTGCTGAAAGCTCTCGTGCGGCAGCAGCT

GCCTGAGAAGTACAAAGAGATTTTCTTCGACCAGAGCAAGAACGG

CTACGCCGGCTACATTGACGGCGGAGCCAGCCAGGAAGAGTTCTA

CAAGTTCATCAAGCCCATCCTGGAAAAGATGGACGGCACCGAGGA

ACTGCTCGTGAAGCTGAACAGAGAGGACCTGCTGCGGAAGCAGCG

GACCTTCGACAACGGCAGCATCCCCCACCAGATCCACCTGGGAGA

GCTGCACGCCATTCTGCGGCGGCAGGAAGATTTTTACCCATTCCT

GAAGGACAACCGGGAAAAGATCGAGAAGATCCTGACCTTCCGCAT

CCCCTACTACGTGGGCCCTCTGGCCAGGGGAAACAGCAGATTCGC

CTGGATGACCAGAAAGAGCGAGGAAACCATCACCCCCTGGAACTT

CGAGGAAGTGGTGGACAAGGGCGCTTCCGCCCAGAGCTTCATCGA

GCGGATGACCAACTTCGATAAGAACCTGCCCAACGAGAAGGTGCT

GCCCAAGCACAGCCTGCTGTACGAGTACTTCACCGTGTATAACGA

GCTGACCAAAGTGAAATACGTGACCGAGGGAATGAGAAAGCCCGC

CTTCCTGAGCGGCGAGCAGAAAAAGGCCATCGTGGACCTGCTGTT

CAAGACCAACCGGAAAGTGACCGTGAAGCAGCTGAAAGAGGACTA

CTTCAAGAAAATCGAGTGCTTCGACTCCGTGGAAATCTCCGGCGT

GGAAGATCGGTTCAACGCCTCCCTGGGCACATACCACGATCTGCT

GAAAATTATCAAGGACAAGGACTTCCTGGACAATGAGGAAAACGA

GGACATTCTGGAAGATATCGTGCTGACCCTGACACTGTTTGAGGA

CAGAGAGATGATCGAGGAACGGCTGAAAACCTATGCCCACCTGTT

CGACGACAAAGTGATGAAGCAGCTGAAGCGGCGGAGATACACCGG

CTGGGGCAGGCTGAGCCGGAAGCTGATCAACGGCATCCGGGACAA

GCAGTCCGGCAAGACAATCCTGGATTTCCTGAAGTCCGACGGCTT

CGCCAACAGAAACTTCATGCAGCTGATCCACGACGACAGCCTGAC

CTTTAAAGAGGACATCCAGAAAGCCCAGGTGTCCGGCCAGGGCGA

TAGCCTGCACGAGCACATTGCCAATCTGGCCGGCAGCCCCGCCAT

TAAGAAGGGCATCCTGCAGACAGTGAAGGTGGTGGACGAGCTCGT

GAAAGTGATGGGCCGGCACAAGCCCGAGAACATCGTGATCGAAAT

GGCCAGAGAGAACCAGACCACCCAGAAGGGACAGAAGAACAGCCG

CGAGAGAATGAAGCGGATCGAAGAGGGCATCAAAGAGCTGGGCAG

CCAGATCCTGAAAGAACACCCCGTGGAAAACACCCAGCTGCAGAA

CGAGAAGCTGTACCTGTACTACCTGCAGAATGGGCGGGATATGTA

CGTGGACCAGGAACTGGACATCAACCGGCTGTCCGACTACGATGT

GGACCACATCGTGCCTCAGAGCTTTCTGAAGGACGACTCCATCGA

CAACAAGGTGCTGACCAGAAGCGACAAGGCCCGGGGCAAGAGCGA

CAACGTGCCCTCCGAAGAGGTCGTGAAGAAGATGAAGAACTACTG

GCGGCAGCTGCTGAACGCCAAGCTGATTACCCAGAGAAAGTTCGA

CAATCTGACCAAGGCCGAGAGAGGCGGCCTGAGCGAACTGGATAA

GGCCGGCTTCATCAAGAGACAGCTGGTGGAAACCCGGCAGATCAC

AAAGCACGTGGCACAGATCCTGGACTCCCGGATGAACACTAAGTA

CGACGAGAATGACAAGCTGATCCGGGAAGTGAAAGTGATCACCCT

GAAGTCCAAGCTGGTGTCCGATTTCCGGAAGGATTTCCAGTTTTA

CAAAGTGCGCGAGATCAACAACTACCACCACGCCCACGACGCCTA

CCTGAACGCCGTCGTGGGAACCGCCCTGATCAAAAAGTACCCTAA

GCTGGAAAGCGAGTTCGTGTACGGCGACTACAAGGTGTACGACGT

GCGGAAGATGATCGCCAAGAGCGAGCAGGAAATCGGCAAGGCTAC

CGCCAAGTACTTCTTCTACAGCAACATCATGAACTTTTTCAAGAC

CGAGATTACCCTGGCCAACGGCGAGATCCGGAAGCGGCCTCTGAT

CGAGACAAACGGCGAAACCGGGGAGATCGTGTGGGATAAGGGCCG

GGATTTTGCCACCGTGCGGAAAGTGCTGAGCATGCCCCAAGTGAA

TATCGTGAAAAAGACCGAGGTGCAGACAGGCGGCTTCAGCAAAGA

GTCTATCCTGCCCAAGAGGAACAGCGATAAGCTGATCGCCAGAAA

GAAGGACTGGGACCCTAAGAAGTACGGCGGCTTCGACAGCCCCAC

CGTGGCCTATTCTGTGCTGGTGGTGGCCAAAGTGGAAAAGGGCAA

GTCCAAGAAACTGAAGAGTGTGAAAGAGCTGCTGGGGATCACCAT

CATGGAAAGAAGCAGCTTCGAGAAGAATCCCATCGACTTTCTGGA

AGCCAAGGGCTACAAAGAAGTGAAAAAGGACCTGATCATCAAGCT

GCCTAAGTACTCCCTGTTCGAGCTGGAAAACGGCCGGAAGAGAAT

GCTGGCCTCTGCCGGCGAACTGCAGAAGGGAAACGAACTGGCCCT

GCCCTCCAAATATGTGAACTTCCTGTACCTGGCCAGCCACTATGA

GAAGCTGAAGGGCTCCCCCGAGGATAATGAGCAGAAACAGCTGTT

TGTGGAACAGCACAAGCACTACCTGGACGAGATCATCGAGCAGAT

CAGCGAGTTCTCCAAGAGAGTGATCCTGGCCGACGCTAATCTGGA

CAAAGTGCTGTCCGCCTACAACAAGCACCGGGATAAGCCCATCAG

AGAGCAGGCCGAGAATATCATCCACCTGTTTACCCTGACCAATCT

GGGAGCCCCTGCCGCCTTCAAGTACTTTGACACCACCATCGACCG

GAAGAGGTACACCAGCACCAAAGAGGTGCTGGACGCCACCCTGAT

CCACCAGAGCATCACCGGCCTGTACGAGACACGGATCGACCTGTC

TCAGCTGGGAGGCGACagcgctGGAggacctaagaaaaagaggaa ggtgggatccGGACGGGCTGACGCATTGGACGATTTTGATCTGGA

TATGCTGGGAAGTGACGCCCTCGATGATTTTGACCTTGACATGCT

TGGTTCGGATGCCCTTGATGACTTTGACCTCGACATGCTCGGCAG

TGACGCCCTTGATGATTTCGACCTGGACATGCTGATTAACtgtac aggaagcggagccactaacttctccctgttgaaacaagcagggga tgtcgaagagaatcccgggccaGCCACCATGGCTTCAAACTTTAC

TCAGTTCGTGCTCGTGGACAATGGTGGGACAGGGGATGTGACAGT

GGCTCCTTCTAATTTCGCTAATGGGGTGGCAGAGTGGATCAGCTC

CAACTCACGGAGCCAGGCCTACAAGGTGACATGCAGCGTCAGGCA

GTCTAGTGCCCAGAAGAGAAAGTATACCATCAAGGTGGAGGTCCC

CAAAGTGGCTACCCAGACAGTGGGCGGAGTCGAACTGCCTGTCGC

CGCTTGGAGGTCCTACCTGAACATGGAGCTCACTATCCCAATTTT

CGCTACCAATTCTGACTGTGAACTCATCGTGAAGGCAATGCAGGG

GCTCCTCAAAGACGGTAATCCTATCCCTTCCGCCATCGCCGCTAA

CTCAGGTATCTACAGCGCTGGAGGAGGTGGAAGCGGAGGAGGAGG

AAGCGGAGGAGGAGGTAGCGGACCTAAGAAAAAGAGGAAGGTGGC

GGCCGCTGGATCCCCTTCAGGGCAGATCAGCAACCAGGCCCTGGC 51
52

TCTGGCCCCTAGCTCCGCTCCAGTGCTGGCCCAGACTATGGTGCC

CTCTAGTGCTATGGTGCCTCTGGCCCAGCCACCTGCTCCAGCCCC

TGTGCTGACCCCAGGACCACCCCAGTCACTGAGCGCTCCAGTGCC

CAAGTCTACACAGGCCGGCGAGGGGACTCTGAGTGAAGCTCTGCT

GCACCTGCAGTTCGACGCTGATGAGGACCTGGGAGCTCTGCTGGG

GAACAGCACCGATCCCGGAGTGTTCACAGATCTGGCCTCCGTGGA

CAACTCTGAGTTTCAGCAGCTGCTGAATCAGGGCGTGTCCATGTC

TCATAGTACAGCCGAACCAATGCTGATGGAGTACCCCGAAGCCAT

TACCCGGCTGGTGACCGGCAGCCAGCGGCCCCCCGACCCCGCTCC

AACTCCCCTGGGAACCAGCGGCCTGCCTAATGGGCTGTCCGGAGA

TGAAGACTTCTCAAGCATCGCTGATATGGACTTTAGTGCCCTGCT

GTCACAGATTTCCTCTAGTGGGCAGGGAGGAGGTGGAAGCGGCTT

CAGCGTGGACACCAGTGCCCTGCTGGACCTGTTCAGCCCCTCGGT

GACCGTGCCCGACATGAGCCTGCCTGACCTTGACAGCAGCCTGGC

CAGTATCCAAGAGCTCCTGTCTCCCCAGGAGCCCCCCAGGCCTCC

CGAGGCAGAGAACAGCAGCCCGGATTCAGGGAAGCAGCTGGTGCA

CTACACAGCGCAGCCGCTGTTCCTGCTGGACCCCGGCTCCGTGGA

CACCGGGAGCAACGACCTGCCGGTGCTGTTTGAGCTGGGAGAGGG

CTCCTACTTCTCCGAAGGGGACGGCTTCGCCGAGGACCCCACCAT

CTCCCTGCTGACAGGCTCGGAGCCTCCCAAAGCCAAGGACCCCAC

TGTCTCCTAAGAATTCgatatcaagcttAATAAAAGATCTTTATT

TTCATTAGATCTGTGTGTTGGTTTTTTGTGTagatctGGGCGTGG

Ttaagggtgggaaagaatatataaggtgggggtcttatgtagttt tgtatctgttttgcagcagccgccgccgccatgagcaccaactcg tttgatggaagcattgtgagctcatatttgacaacgcgcatgccc ccatgggccggggtgcgtcagaatgtgatgggctccagcattgat ggtcgccccgtcctgcccgcaaactctactaccttgacctacgag accgtgtctggaacgccgttggagactgcagcctccgccgccgct tcagccgctgcagccaccgcccgcgggattgtgactgactttgct ttcctgagcccgcttgcaagcagtgcagcttcccgttcatccgcc cgcgatgacaagttgacggctcttttggcacaattggattctttg acccgggaacttaatgtcgtttctcagcagctgttggatctgcgc cagcaggtttctgccctgaaggcttcctcccctcccaatgcggtt taaaacataaataaaaaaccagactctgtttggatttggatcaag caagtgtcttgctgtctttatttaggggttttgcgcgcgcggtag gcccgggaccagcggtctcggtcgttgagggtcctgtgtattttt tccaggacgtggtaaaggtgactctggatgttcagatacatgggc ataagcccgtctctggggtggaggtagcaccactgcagagcttca tgctgcggggtggtgttgtagatgatccagtcgtagcaggagcgc tgggcgtggtgcctaaaaatgtctttcagtagcaagctgattgcc aggggcaggcccttggtgtaagtgtttacaaagcggttaagctgg gatgggtgcatacgtgggggatatgagatgcatcttggactgtatt

5 tttaggttggctatgttcccagccatatccctccggggggattcatg ttgtgcagaaccaccagcacagtgtatccggtgcacttgggaaat ttgtcatgtagcttagaaggaaatgcgtggaagaacttggagacg

10 cccttgtgacctccaagattttccatgcattcgtccataatgatg gcaatgggcccacgggcggcggcctgggcgaagatatttctggga tcactaacgtcatagttgtgttccaggatgagatcgtcataggcc attttttacaaagcgcgggcggagggtgccagactgcggtataatg

15 gttccatccggcccaggggcgtagttaccctcacagatttgcatt tcccacgctttgagttcagatgggggggatcatgtctacctgcggg gcgatgaagaaacggtttccgggggtaggggagatcagctgggaa

20 gaaagcaggttcctgagcagctgcgacttaccgcagccggtgggc ccgtaaatcacacctattaccgggtgcaactggtagttaagagag ctgcagctgccgtcatccctgagcaggggggccacttcgttaagc

25 atgtccctgactcgcatgttttccctgaccaaatccgccagaagg cgctcgccgcccagcgatagcagttcttgcaaggaagcaaagttt ttcaacggtttgagaccgtccgccgtaggcatgctttttgagcgtt

30 tgaccaagcagttccaggcggtcccacagctcggtcacctgctct acggcatctcgatccagcatatctcctcgtttcgcggggttggggc ggctttcgctacggcagtagtcggtgctcgtccagacgggcca

35 gggtcatgtctttccacgggcgcagggtcctcgtcagcgtagtct gggtcacggtgaaggggtgcgctccgggctgcgcgctggccaggg tgcgcttgaggctggtcctgctggtgctgaagcgctgccggtctt

40 cgccctgcgcgtcggccaggtagcatttgaccatggtgtcatagt ccagcccctccgcggcgtggcccttggcgcgcagcttgcccttgg aggaggcgccgcacgaggggcagtgcagacttttgagggcgtaga

45 gcttgggcgcgagaaataccgattccggggagtaggcatccgcgc cgcaggccccgcagacggtctcgcattccacgagccaggtgagct ctggccgttcggggtcaaaaaccaggtttcccccatgctttttga

50 tgcgtttcttacctctggtttccatgagccggtgtccacgctcgg tgacgaaaaggctgtccgtgtcccgtatacagactnnngtttaa acgaattcnnntataaaatgcaaggtgctgctcaaaaaatcaggc aaagcctcgcgcaaaaaagaaagcacatcgtagtcatgctcatgc

55 agataaaggcaggtaagctccggaaccaccacagaaaaagacacc attttttctctcaaacatgtctgcgggtttctgcataaacacaaaa taaaataacaaaaaaacatttaaacattagaagcctgtcttacaa

60 caggaaaaacaaccctttataagcataagacggactacggccatgc cggcgtgaccgtaaaaaaaactggtcaccgtgattaaaaagcacca ccgacagctcctcggtcatgtccggagtcataatgtaagactcgg

taaacacatcaggttgattcatcggtcagtgctaaaaagcgaccg

-continued aaatagcccggggggaatacataccccgcaggcgtagagacaacatt acagcccccataggaggtataacaaaattaataggagagaaaaac acataaacacctgaaaaaccctcctgcctaggcaaaatagcaccc tcccgctccagaacaacatacagcgcttcacagcggcagcctaac agtcagccttaccagtaaaaaagaaaacctattaaaaaaacacca ctcgacacggcaccagctcaatcagtcacagtgtaaaaaagggcc aagtgcagagcgagtatatataggactaaaaaatgacgtaacggt taaagtccacaaaaaacaccccagaaaaccgcacgcgaacctacgc ccagaaacgaaagccaaaaaacccacaacttcctcaaatcgtcac ttccgttttcccacgttacgtaacttcccattttaagaaaactac aattcccaacacatacaagttactccgccctaaaacctacgtcac ccgcccgttcccacgcccgcgccacgtcacaaactccacccccc tcattatcatattggcttcaatccaaaataaggtatattattgat gattaattaattaaggatcccggtgtgaaataccgcacagatgcg taaggagaaaataccgcatcaggcgctcttacgcttcctcgctca ctgactcgctgcgctcggtcgttcggctgcggcgagcggtatcag ctcactcaaaggcggtaatacggttatccacagaatcaggggata acgcaggaaagaacatgtgagcaaaaggccagcaaaaggccagga accgtaaaaaggccgcgttgctggcgtttttccataggctccgcc cccctgacgagcatcacaaaaatcgacgctcaagtcagaggtggc gaaacccgacaggactataaagataccaggcgtttccccctggaa gctccctcgtgcgctctcctgttccgaccctgccgcttaccggat acctgtccgcctttctcccttcgggaagcgtggcgctttctcata gctcacgctgtaggtatctcagttcggtgtaggtcgttcgctcca agctgggctgtgtgcacgaaccccccgttcagcccgaccgctgcg ccttatccggtaactatcgtcttgagtccaacccggtaagacacg acttatcgccactggcagcagccactggtaacaggattagcagag cgaggtatgtaggcggtgctacagagttcttgaagtggtggccta actacggctacactagaaggacagtatttggtatctgcgctctgc tgaagccagttaccttcggaaaaagagttggtagctcttgatccg gcaaacaaaccaccgctggtagcggtggtttttttgtttgcaagc agcagattacgcgcagaaaaaaaggatctcaagaagatcctttga tcttttctacggggtctgacgctcagtggaacgaaaactcacgtt aagggattttggtcatgagattatcaaaaaggatcttcacctaga tccttttaaattaaaaatgaagttttaaatcaatctaaagtatat atgagtaaacttggtctgacagttaccaatgcttaatcagtgagg cacctatctcagcgatctgtctatttcgttcatccatagttgcct gactccccgtcgtgtagataactacgatacgggagggcttaccat ctggccccagtgctgcaatgataccgcgagacccacgctcaccgg ctccagatttatcagcaataaaccagccagccggaagggccgagc gcagaagtggtcctgcaactttatccgcctccatccagtctatta -continued attgttgccgggaagctagagtaagtagttcgccagttaatagtt tgcgcaacgttgttgnnnnnnaaaaaggatcttcacctagatcct tttcacgtagaaagccagtccgcagaaacggtgctgacccggat gaatgtcagctactgggctatctggacaagggaaaacgcaagcgc aaagagaaagcaggtagcttgcagtgggcttacatggcgatagct agactgggcggttttatggacagcaagcgaaccggaattgccagc tggggcgccctctggtaaggttgggaagccctgcaaagtaaactg gatggctttctcgccgccaaggatctgatggcgcaggggatcaag ctctgatcaagagacaggatgaggatcgtttcgcatgattgaaca agatggattgcacgcaggttctccggccgcttgggtggagaggct attcggctatgactgggcacaacagacaatcggctgctctgatgc cgccgtgttccggctgtcagcgcaggggcgcccggttcttttttgt caagaccgacctgtccggtgccctgaatgaactgcaagacgaggc agcgcggctatcgtggctggccacgacgggcgttccttgcgcagc tgtgctcgacgttgtcactgaagcgggaagggactggctgctatt gggcgaagtgccggggcaggatctcctgtcatctcaccttgctcc tgccgagaaagtatccatcatggctgatgcaatgcggcggctgca tacgcttgatccggctacctgcccattcgaccaccaagcgaaaca tcgcatcgagcgagcacgtactcggatggaagccggtcttgtcga tcaggatgatctgacgaggagcatcaggggctcgcgccagccga actgttcgccaggctcaaggcgagcatgcccgacggcgaggatct cgtcgtgacccatggcgatgcctgcttgccgaatatcatggtgga aaatggccgcttttctggattcatcgactgtggccggctgggtgt ggcggaccgctatcaggacatagcgttggctacccgtgatattgc tgaggagcttggcggcgaatgggctgaccgcttcctcgtgcttta cggtatcgccgctcccgattcgcagcgcatcgccttctatcgcct tcttgacgagttcttctgaattttgttaaaattttttgttaaatca gctcattttttaaccaataggccgaaatcggcaacatcccttata aatcaaaagaatagaccgcgatagggttgagtgttgttccagttt ggaacaagagtccactattaaagaacgtggactccaacgtcaaag ggcgaaaaaccgtctatcagggcgatggcccactacgtgaaccat cacccaaatcaagtttttgcggtcgaggtgccgtaaagctctaa atcggaaccctaaagggagcccccgatttagagcttgacggggaa agccggcgaacgtggcgagaaaggaagggaagaaagcgaaaggag cgggcgctaggcgctggcaagtgtagcggtcacgctgcgcgtaa ccaccacacccgcgcgcttaatgcgccg pGW035 Adenovirus One Vector dSpCas9

(SEQ ID NO: 5)

CTACAGGGCGCGTCCATTCGCCATTCAGGATCGAATTAATTCTTA

ATTAACATCATCAATAATATACCTTAttttggattgaagccaata tgataatgaggggggtggagtttgtgacgtggcgcggggcgtggga -continued

```
acggggcgggtgacgtagtagtgtggcggaagtgtgatgttgcaa gtgtggcggaacacatgtaagcgacggatgtggcaaaagtgacgt ttttggtgtgcgccggtgtacacaggaagtgacaattttcgcgcg gttttaggcggatgttgtagtaaatttgggcgtaaccgagtaaga tttggccattttcgcgggaaaactgaataagaggaagtgaaatct gaataattttgtgttactcatagcgcgtaaTACTggtaccgcggc cgcctcgagtCTAGAAAGAgggcctatttcccatgattccttcat atttgcatatacgatacaaggctgttagagagataattagaatta atttgactgtaaacacaaagatattagtacaaaatacgtgacgta gaaagtaataatttcttgggtagtttgcagttttaaaattatgtt ttaaaatggactatcatatgcttaccgtaacttgaaagtatttcg atttcttggctttatatatcttGTGGAAAGGACGAAACACCggaa gagcgagctcttctgttttagagctaggccAACATGAGGATCACC CATGTCTGCAGggcctagcaagttaaaataaggctagtccgttat caacttggccAACATGAGGATCACCCATGTCTGCAGggccaagtg gcaccgagtcggtgcTTTTTTGctagcGTCAGTGGGCAGAGCGCA

CATCGCCCACAGTCCCCGAGAAGTTGGGGGGGAGGGGTCGGCAATT

GAACGGGTGCCTAGAGAAGGTGGCGCGGGGTAAACTGGGAAAGTG

ATGTCGTGTACTGGCTCCGCCTTTTTCCCGAGGGTGGGGGAGAAC

CGTATATAAGTGCAGTAGTCGCCGTGAACGTTCTTTTTCGCAACG

GGTTTGCCGCCAGAACACAGCTGAAGCTTCGAGGGGCTCGCATCT

CTCCTTCACGCGCCCGCCGCCCTACCTGAGGCCGCCATCCACGCC

GGTTGAGTCGCGTTCTGCCGCCTCCCGCCTGTGGTGCCTCCTGAA

CTGCGTCCGCCGTCTAGGTAAGTTTAAAGCTCAGGTCGAGACCGG

GCCTTTGTCCGGCGCTCCCTTGGAGCCTACCTAGACTCAGCCGGC

TCTCCACGCTTTGCCTGACCCTGCTTGCTCAACTCTACGTCTTTG

TTTCGTTTTCTGTTCTGCGCCGTTACAGATCCAAGctcGTACGgc caccATGAAAAGGCCGGCGGCCACGAAAAAGGCCGGCCAGGCAAA

AAAGAAAAAGGACAAGAAGTACAGCATCGGCCTGGCCATCGGCAC

CAACTCTGTGGGCTGGGCCGTGATCACCGACGAGTACAAGGTGCC

CAGCAAGAAATTCAAGGTGCTGGGCAACACCGACCGGCACAGCAT

CAAGAAGAACCTGATCGGAGCCCTGCTGTTCGACAGCGGCGAAAC

AGCCGAGGCCACCCGGCTGAAGAGAACCGCCAGAAGAAGATACAC

CAGACGGAAGAACCGGATCTGCTATCTGCAAGAGATCTTCAGCAA

CGAGATGGCCAAGGTGGACGACAGCTTCTTCCACAGACTGGAAGA

GTCCTTCCTGGTGGAAGAGGATAAGAAGCACGAGCGGCACCCCAT

CTTCGGCAACATCGTGGACGAGGTGGCCTACCACGAGAAGTACCC

CACCATCTACCACCTGAGAAAGAAACTGGTGGACAGCACCGACAA

GGCCGACCTGCGGCTGATCTATCTGGCCCTGGCCCACATGATCAA

GTTCCGGGGCCACTTCCTGATCGAGGGCGACCTGAACCCCGACAA

CAGCGACGTGGACAAGCTGTTCATCCAGCTGGTGCAGACCTACAA
```

-continued

```
CCAGCTGTTCGAGGAAAACCCCATCAACGCCAGCGGCGTGGACGC

CAAGGCCATCCTGTCTGCCAGACTGAGCAAGAGCAGACGGCTGGA

AAATCTGATCGCCCAGCTGCCCGGCGAGAAGAAGAATGGCCTGTT

CGGCAACCTGATTGCCCTGAGCCTGGGCCTGACCCCCAACTTCAA

GAGCAACTTCGACCTGGCCGAGGATGCCAAACTGCAGCTGAGCAA

GGACACCTACGACGACGACCTGGACAACCTGCTGGCCCAGATCGG

CGACCAGTACGCCGACCTGTTTCTGGCCGCCAAGAACCTGTCCGA

CGCCATCCTGCTGAGCGACATCCTGAGAGTGAACACCGAGATCAC

CAAGGCCCCCCTGAGCGCCTCTATGATCAAGAGATACGACGAGCA

CCACCAGGACCTGACCCTGCTGAAAGCTCTCGTGCGGCAGCAGCT

GCCTGAGAAGTACAAAGAGATTTTCTTCGACCAGAGCAAGAACGG

CTACGCCGGCTACATTGACGGCGGAGCCAGCCAGGAAGAGTTCTA

CAAGTTCATCAAGCCCATCCTGGAAAAGATGGACGGCACCGAGGA

ACTGCTCGTGAAGCTGAACAGAGAGGACCTGCTGCGGAAGCAGCG

GACCTTCGACAACGGCAGCATCCCCCACCAGATCCACCTGGGAGA

GCTGCACGCCATTCTGCGGCGGCAGGAAGATTTTTACCCATTCCT

GAAGGACAACCGGGAAAAGATCGAGAAGATCCTGACCTTCCGCAT

CCCCTACTACGTGGGCCCTCTGGCCAGGGGAAACAGCAGATTCGC

CTGGATGACCAGAAAGAGCGAGGAAACCATCACCCCCTGGAACTT

CGAGGAAGTGGTGGACAAGGGCGCTTCCGCCCAGAGCTTCATCGA

GCGGATGACCAACTTCGATAAGAACCTGCCCAACGAGAAGGTGCT

GCCCAAGCACAGCCTGCTGTACGAGTACTTCACCGTGTATAACGA

GCTGACCAAAGTGAAATACGTGACCGAGGGAATGAGAAAGCCCGC

CTTCCTGAGCGGCGAGCAGAAAAAGGCCATCGTGGACCTGCTGTT

CAAGACCAACCGGAAAGTGACCGTGAAGCAGCTGAAAGAGGACTA

CTTCAAGAAAATCGAGTGCTTCGACTCCGTGGAAATCTCCGGCGT

GGAAGATCGGTTCAACGCCTCCCTGGGCACATACCACGATCTGCT

GAAAATTATCAAGGACAAGGACTTCCTGGACAATGAGGAAAACGA

GGACATTCTGGAAGATATCGTGCTGACCCTGACACTGTTTGAGGA

CAGAGAGATGATCGAGGAACGGCTGAAAACCTATGCCCACCTGTT

CGACGACAAAGTGATGAAGCAGCTGAAGCGGCGGAGATACACCGG

CTGGGGCAGGCTGAGCCGGAAGCTGATCAACGGCATCCGGGACAA

GCAGTCCGGCAAGACAATCCTGGATTTCCTGAAGTCCGACGGCTT

CGCCAACAGAAACTTCATGCAGCTGATCCACGACGACAGCCTGAC

CTTTAAAGAGGACATCCAGAAAGCCCAGGTGTCCGGCCAGGGCGA

TAGCCTGCACGAGCACATTGCCAATCTGGCCGGCAGCCCCGCCAT

TAAGAAGGGCATCCTGCAGACAGTGAAGGTGGTGGACGAGCTCGT

GAAAGTGATGGGCCGGCACAAGCCCGAGAACATCGTGATCGAAAT

GGCCAGAGAGAACCAGACCACCCAGAAGGGACAGAAGAACAGCCG

CGAGAGAATGAAGCGGATCGAAGAGGGCATCAAAGAGCTGGGCAG
```

-continued

```
CCAGATCCTGAAAGAACACCCCGTGGAAAACACCCAGCTGCAGAA

CGAGAAGCTGTACCTGTACTACCTGCAGAATGGGCGGGATATGTA

CGTGGACCAGGAACTGGACATCAACCGGCTGTCCGACTACGATGT

GGACCACATCGTGCCTCAGAGCTTTCTGAAGGACGACTCCATCGA

CAACAAGGTGCTGACCAGAAGCGACAAGGCCCGGGGCAAGAGCGA

CAACGTGCCCTCCGAAGAGGTCGTGAAGAAGATGAAGAACTACTG

GCGGCAGCTGCTGAACGCCAAGCTGATTACCCAGAGAAAGTTCGA

CAATCTGACCAAGGCCGAGAGAGGCGGCCTGAGCGAACTGGATAA

GGCCGGCTTCATCAAGAGACAGCTGGTGGAAACCCGGCAGATCAC

AAAGCACGTGGCACAGATCCTGGACTCCCGGATGAACACTAAGTA

CGACGAGAATGACAAGCTGATCCGGGAAGTGAAAGTGATCACCCT

GAAGTCCAAGCTGGTGTCCGATTTCCGGAAGGATTTCCAGTTTTA

CAAAGTGCGCGAGATCAACAACTACCACCACGCCCACGACGCCTA

CCTGAACGCCGTCGTGGGAACCGCCCTGATCAAAAAGTACCCTAA

GCTGGAAAGCGAGTTCGTGTACGGCGACTACAAGGTGTACGACGT

GCGGAAGATGATCGCCAAGAGCGAGCAGGAAATCGGCAAGGCTAC

CGCCAAGTACTTCTTCTACAGCAACATCATGAACTTTTTCAAGAC

CGAGATTACCCTGGCCAACGGCGAGATCCGGAAGCGGCCTCTGAT

CGAGACAAACGGCGAAACCGGGGAGATCGTGTGGGATAAGGGCCG

GGATTTTGCCACCGTGCGGAAAGTGCTGAGCATGCCCCAAGTGAA

TATCGTGAAAAAGACCGAGGTGCAGACAGGCGGCTTCAGCAAAGA

GTCTATCCTGCCCAAGAGGAACAGCGATAAGCTGATCGCCAGAAA

GAAGGACTGGGACCCTAAGAAGTACGGCGGCTTCGACAGCCCCAC

CGTGGCCTATTCTGTGCTGGTGGTGGCCAAAGTGGAAAAGGGCAA

GTCCAAGAAACTGAAGAGTGTGAAAGAGCTGCTGGGGATCACCAT

CATGGAAAGAAGCAGCTTCGAGAAGAATCCCATCGACTTTCTGGA

AGCCAAGGGCTACAAAGAAGTGAAAAAGGACCTGATCATCAAGCT

GCCTAAGTACTCCCTGTTCGAGCTGGAAAACGGCCGGAAGAGAAT

GCTGGCCTCTGCCGGCGAACTGCAGAAGGGAAACGAACTGGCCCT

GCCCTCCAAATATGTGAACTTCCTGTACCTGGCCAGCCACTATGA

GAAGCTGAAGGGCTCCCCCGAGGATAATGAGCAGAAACAGCTGTT

TGTGGAACAGCACAAGCACTACCTGGACGAGATCATCGAGCAGAT

CAGCGAGTTCTCCAAGAGAGTGATCCTGGCCGACGCTAATCTGGA

CAAAGTGCTGTCCGCCTACAACAAGCACCGGGATAAGCCCATCAG

AGAGCAGGCCGAGAATATCATCCACCTGTTTACCCTGACCAATCT

GGGAGCCCCTGCCGCCTTCAAGTACTTTGACACCACCATCGACCG

GAAGAGGTACACCAGCACCAAAGAGGTGCTGGACGCCACCCTGAT

CCACCAGAGCATCACCGGCCTGTACGAGACACGGATCGACCTGTC

TCAGCTGGGAGGCGACAgcgctGGAGGAGGTGGAAGCGGAGGAGG

AGGAAGCGGAGGAGGAGGTAGCggacctaagaaaaagaggaaggt ggcggccgctggatccGGACGGGCTGACGCATTGGACGATTTTGA
```

-continued

```
TCTGGATATGCTGGGAAGTGACGCCCTCGATGATTTTGACCTTGA

CATGCTTGGTTCGGATGCCCTTGATGACTTTGACCTCGACATGCT

CGGCAGTGACGCCCTTGATGATTTCGACCTGGACATGCTGATTAA

Ctgtacaggaagcggagccactaacttctccctgttgaaacaagc aggggatgtcgaagagaatcccgggccaGCCACCATGGCTTCAAA

CTTTACTCAGTTCGTGCTCGTGGACAATGGTGGGACAGGGGATGT

GACAGTGGCTCCTTCTAATTTCGCTAATGGGGTGGCAGAGTGGAT

CAGCTCCAACTCACGGAGCCAGGCCTACAAGGTGACATGCAGCGT

CAGGCAGTCTAGTGCCCAGAAGAGAAAGTATACCATCAAGGTGGA

GGTCCCCAAAGTGGCTACCCAGACAGTGGGCGGAGTCGAACTGCC

TGTCGCCGCTTGGAGGTCCTACCTGAACATGGAGCTCACTATCCC

AATTTTCGCTACCAATTCTGACTGTGAACTCATCGTGAAGGCAAT

GCAGGGGCTCCTCAAAGACGGTAATCCTATCCCTTCCGCCATCGC

CGCTAACTCAGGTATCTACAGCGCTGGAGGAGGTGGAAGCGGAGG

AGGAGGAAGCGGAGGAGGAGGAGGTAGCGGACCTAAGAAAAAGAGGAA

GGTGGCGGCCGCTGGATCCCCTTCAGGGCAGATCAGCAACCAGGC

CCTGGCTCTGGCCCCTAGCTCCGCTCCAGTGCTGGCCCAGACTAT

GGTGCCCTCTAGTGCTATGGTGCCTCTGGCCCAGCCACCTGCTCC

AGCCCCTGTGCTGACCCCAGGACCACCCCAGTCACTGAGCGCTCC

AGTGCCCAAGTCTACACAGGCCGGCGAGGGGACTCTGAGTGAAGC

TCTGCTGCACCTGCAGTTCGACGCTGATGAGGACCTGGGAGCTCT

GCTGGGGAACAGCACCGATCCCGGAGTGTTCACAGATCTGGCCTC

CGTGGACAACTCTGAGTTTCAGCAGCTGCTGAATCAGGGCGTGTC

CATGTCTCATAGTACAGCCGAACCAATGCTGATGGAGTACCCCGA

AGCCATTACCCGGCTGGTGACCGGCAGCCAGCGGCCCCCCGACCC

CGCTCCAACTCCCCTGGGAACCAGCGGCCTGCCTAATGGGCTGTC

CGGAGATGAAGACTTCTCAAGCATCGCTGATATGGACTTTAGTGC

CCTGCTGTCACAGATTTCCTCTAGTGGGCAGGGAGGAGGTGGAAG

CGGCTTCAGCGTGGACACCAGTGCCCTGCTGGACCTGTTCAGCCC

CTCGGTGACCGTGCCCGACATGAGCCTGCCTGACCTTGACAGCAG

CCTGGCCAGTATCCAAGAGCTCCTGTCTCCCCAGGAGCCCCCCAG

GCCTCCCGAGGCAGAGAACAGCAGCCCGGATTCAGGGAAGCAGCT

GGTGCACTACACAGCGCAGCCGCTGTTCCTGCTGGACCCCGGCTC

CGTGGACACCGGGAGCAACGACCTGCCGGTGCTGTTTGAGCTGGG

AGAGGGCTCCTACTTCTCCGAAGGGGACGGCTTCGCCGAGGACCC

CACCATCTCCCTGCTGACAGGCTCGGAGCCTCCCAAAGCCAAGGA

CCCCACTGTCTCCTAAGAATTCgatatcaagcttAATAAAAGATC

TTTATTTTCATTAGATCTGTGTGTTGGTTTTTTGTGTagatctGG

GCGTGGTtaagggtgggaaagaatatataaggtgggggtcttatg tagttttgtatctgttttgcagcagccgccgccgccatgagcacc
```

-continued

```
aactcgtttgatggaagcattgtgagctcatatttgacaacgcgc atgcccccatgggccggggtgcgtcagaatgtgatgggctccagc attgatggtcgccccgtcctgcccgcaaactctactaccttgacc tacgagaccgtgtctggaacgccgttggagactgcagcctccgcc gccgcttcagccgctgcagccaccgcccgcgggattgtgactgac tttgcttttcctgagcccgcttgcaagcagtgcagcttccgttca tccgcccgcgatgacaagttgacggctcttttggcacaattggat tctttgacccgggaacttaatgtcgtttctcagcagctgttggat ctgcgccagcaggtttctgccctgaaggcttcctcccctcccaat gcggtttaaaacataaataaaaaaccagactctgtttggatttgg atcaagcaagtgtcttgctgtctttatttaggggttttgcgcgcg cggtaggcccgggaccagcggtctcggtcgttgagggtcctgtgt attttttccaggacgtggtaaaggtgactctggatgttcagatac atgggcataagcccgtctctggggtggaggtagcaccactgcaga gcttcatgctgcggggtggtgttgtagatgatccagtcgtagcag gagcgctgggcgtggtgcctaaaaatgtctttcagtagcaagctg attgccaggggcaggcccttggtgtaagtgtttacaaagcggtta agctgggatgggtgcatacgtggggatatgagatgcatcttggac tgtattttaggttggctatgttcccagccatatccctccgggga ttcatgttgtgcagaaccaccagcacagtgtatccggtgcacttg ggaaatttgtcatgtagcttagaaggaaatgcgtggaagaacttg gagacgcccttgtgacctccaagattttccatgcattcgtccata atgatggcaatgggcccacgggcggcggcctgggcgaagatattt ctgggatcactaacgtcatagttgtgttccaggatgagatcgtca taggccattttttacaaagcgcgggcggagggtgccagactgcggt ataatggttccatccggcccaggggcgtagttaccctcacagatt tgcatttcccacgctttgagttcagatggggggatcatgtctacc tgcggggcgatgaagaaaacggtttccggggtaggggagatcagc tgggaagaaagcaggttcctgagcagctgcgacttaccgcagccg gtgggcccgtaaatcacacctattaccgggtgcaactggtagtta agagagctgcagctgccgtcatccctgagcagggggggccacttcg ttaagcatgtccctgactcgcatgttttccctgaccaaatccgcc agaaggcgctcgccgcccagcgatagcagttcttgcaaggaagca aagttttcaacggtttgagaccgtccgccgtaggcatgctttg agcgtttgaccaagcagttccaggcggtcccacagctcggtcacc tgctctacggcatctcgatccagcatatctcctcgtttcgcgggt tggggcggctttcgctgtacggcagtagtcggtgctcgtccagac gggccagggtcatgtctttccacgggcgcagggtcctcgtcagcg tagtctgggtcacggtgaaggggtgcgctccgggctgcgcgctgg ccaggggtgcgcttgaggctggtcctgctggtgctgaagcgctgcc ggtcttcgccctgcgcgtcggccaggtagcatttgaccatggtgt
```

-continued

```
catagtccagcccctccgcgcggcgtggcccttggcgcgcagcttgc 5    ccttggaggaggcgccgcacgaggggcagtgcagactttgaggg cgtagagcttgggcgcgagaaataccgattccggggagtaggcat ccgcgccgcaggccccgcagacggtctcgcattccacgagccagg tgagctctggccgttcggggtcaaaaaccaggtttcccccatgct 10   ttttgatgcgtttcttacctctggtttccatgagccggtgtccac gctcggtgacgaaaaggctgtccgtgtccccgtatacagactnnn gtttaaacgaattcnnntataaaatgcaaggtgctgctcaaaaaa 15   tcaggcaaagcctcgcgcaaaaaagaaagcacatcgtagtcatgc tcatgcagataaaggcaggtaagctccggaaccaccacagaaaaa gacaccattttttctctcaaacatgtctgcgggtttctgcataaac 20   acaaaataaaataacaaaaaaacatttaaacattagaagcctgtc ttacaacaggaaaaacaacccttataagcataagacggactacgg ccatgccggcgtgaccgtaaaaaaactggtcaccgtgattaaaaa 25   gcaccaccgacagctcctcggtcatgtccggagtcataatgtaag actcggtaaacacatcaggttgattcatcggtcagtgctaaaaag cgaccgaaatagcccggggggaatacatacccgcaggcgtagagac 30   aacattacagcccccataggaggtataacaaaattaataggagag aaaaacacatataaacacctgaaaaaccctcctgcctaggcaaaata gcaccctcccgctccagaacaacatacagcgcttcacagcggcag 35   cctaacagtcagccttaccagtaaaaaagaaaacctattaaaaaa acaccactcgacacggcaccagctcaatcagtcacagtgtaaaaa agggccaagtgcagagcgagtatatataggactaaaaaatgacgt 40   aacggttaaagtccacaaaaaacacccagaaaaccgcacgcgaac ctacgcccagaaacgaaagccaaaaaacccacaacttcctcaaat cgtcacttccgttttcccacgttacgtaacttcccattttaagaa 45   aactacaattcccaacacatacaagttactccgccctaaaaccta cgtcacccgccccgttcccacgccccgcgccacgtcacaaactcc acccccctcattatcatattggcttcaatccaaaataaggtatatt 50   attgatgattaattaattaaggatcccggtgtgaaataccgcaca gatgcgtaaggagaaaataccgcatcaggcgctcttacgcttcct cgctcactgactcgctgcgctcggtcgttcggctgcggcgagcgg tatcagctcactcaaaggcggtaatacggttatccacagaatcag 55   gggataacgcaggaaagaacatgtgagcaaaaggccagcaaaagg ccaggaaccgtaaaaaggccgcgttgctggcgtttttccataggc tccgcccccctgacgagcatcacaaaaatcgacgctcaagtcaga 60   ggtggcgaaacccgacaggactataaagataccaggcgtttcccc ctggaagctccctcgtgcgctctcctgttccgaccctgccgctta ccggatacctgtccgcctttctccccttcgggaagcgtggcgcttt
     ctcatagctcacgctgtaggtatctcagttcggtgtaggtcgttc
```

-continued

```
gctccaagctgggctgtgtgcacgaacccccgttcagcccgacc gctgcgccttatccggtaactatcgtcttgagtccaaccggtaa gacacgacttatcgccactggcagcagccactggtaacaggatta gcagagcgaggtatgtaggcggtgctacagagttcttgaagtggt ggcctaactacggctacactagaaggacagtatttggtatctgcg ctctgctgaagccagttaccttcggaaaaagagttggtagctctt gatccggcaaacaaaccaccgctggtagcggtggtttttttgttt gcaagcagcagattacgcgcagaaaaaaaggatctcaagaagatc ctttgatcttttctacggggtctgacgctcagtggaacgaaaact cacgttaagggattttggtcatgagattatcaaaaaggatcttca cctagatccttttaaattaaaaatgaagttttaaatcaatctaaa gtatatatgagtaaacttggtctgacagttaccaatgcttaatca gtgaggcacctatctcagcgatctgtctatttcgttcatccatag ttgcctgactccccgtcgtgtagataactacgatacgggagggct taccatctggccccagtgctgcaatgataccgcgagacccacgct caccggctccagatttatcagcaataaaccagccagccggaaggg ccgagcgcagaagtggtcctgcaactttatccgcctccatccagt ctattaattgttgccgggaagctagagtaagtagttcgccagtta atagtttgcgcaacgttgttgnnnnnnaaaaaggatcttcaccta gatccttttcacgtagaaagccagtccgcagaaacggtgctgacc ccggatgaatgtcagctactgggctatctggacaaggaaaacgc aagcgcaaagagaaagcaggtagcttgcagtgggcttacatggcg atagctagactgggcggttttatggacagcaagcgaaccggaatt gccagctggggcgccctctggtaaggttgggaagccctgcaaagt aaactggatggctttctcgccgccaaggatctgatggcgcagggg atcaagctctgatcaagagacaggatgaggatcgtttcgcatgat tgaacaagatggattgcacgcaggttctccggccgcttgggtgga gaggctattcggctatgactgggcacaacagacaatcggctgctc tgatgccgccgtgttccggctgtcagcgcaggggcgcccggttct ttttgtcaagaccgacctgtccggtgccctgaatgaactgcaaga cgaggcagcgcggctatcgtggctggccacgacgggcgttccttg cgcagctgtgctcgacgttgtcactgaagcgggaagggactggct gctattgggcgaagtgccggggcaggatcctctgtcatctcacct tgctcctgccgagaaagtatccatcatggctgatgcaatgcggcg gctgcatacgcttgatccggctacctgcccattcgaccaccaagc gaaacatcgcatcgagcgagcacgtactcggatggaagccggtct tgtcgatcaggatgatctggacgaggagcatcaggggctcgcgcc agccgaactgttcgccaggctcaaggcgagcatgcccgacgcga ggatctcgtcgtgacccatggcgatgcctgcttgccgaatatcat ggtggaaaatggccgcttttctggattcatcgactgtggccggct gggtgtggcggaccgctatcaggacatagcgttggctaccgtga
```

-continued

```
tattgctgaggagcttggcggcgaatgggctgaccgcttcctcgt gctttacggtatcgccgctcccgattcgcagcgcatcgccttcta tcgccttcttgacgagttcttctgaattttttgttaaaattttttgtt aaatcagctcattttttaaccaataggccgaaatcggcaacatcc cttataaatcaaaagaatagaccgcgatagggttgagtgttgttc cagtttggaacaagagtccactattaaagaacgtggactccaacg tcaaagggcgaaaaaccgtctatcagggcgatggcccactacgtg aaccatcacccaaatcaagttttttgcggtcgaggtgccgtaaag ctctaaatcggaaccctaaagggagcccccgatttagagcttgac ggggaaagccggcgaacgtggcgagaaaggaagggaagaaagcga aaggagcgggcgctagggcgctggcaagtgtagcggtcacgctgc gcgtaaccaccacacccgcgcgcttaatgcgccg pGW063 Adenovirus One Vector dSpCas9
                                      (SEQ ID NO: 6)
AATTAATTAAGCTAGCATCATCAATAATATACCTTATTTTGGATT

GAAGCCAATATGATAATGAGGGGGTGGAGTTTGTGACGTGGCGCG

GGGCGTGGGAACGGGGCGGGTGACGTAGTAGTGTGGCGGAAGTGT

GATGTTGCAAGTGTGGCGGAACACATGTAAGCGACGGATGTGGCA

AAAGTGACGTTTTTGGTGTGCGCCGGTGTACACAGGAAGTGACAA

TTTTCGCGCGGTTTTAGGCGGATGTTGTAGTAAATTTGGGCGTAA

CCGAGTAAGATTTGGCCATTTTCGCGGGAAAACTGAATAAGAGGA

AGTGAAATCTGAATAATTTTGTGTTACTCATAGCGCGTAATATTT

GTCTAGGGAGATCCGGTACcgcggccgcctcgagtCTAGAAAGAg ggcctatttcccatgattccttcatatttgcatatacgatacaag gctgttagagagataattagaattaatttgactgtaaacacaaag atattagtacaaaatacgtgacgtagaaagtaataatttcttggg tagtttgcagttttaaaattatgtttttaaaatggactatcatatg cttaccgtaacttgaaagtatttcgatttcttggctttatatatc ttGTGGAAAGGACGAAACACCggaagagcgagctcttctgttttta gagctaggccAACATGAGGATCACCCATGTCTGCAGggcctagca agttaaaataaggctagtccgttatcaacttggccAACATGAGGA TCACCCATGTCTGCAGggccaagtggcaccgagtcggtgcTTTTT TGctagcGTCAGTGGGCAGAGCGCACATCGCCCACAGTCCCCGAG

AAGTTGGGGGGAGGGGTCGGCAATTGAACGGGTGCCTAGAGAAGG

TGGCGCGGGGTAAACTGGGAAAGTGATGTCGTGTACTGGCTCCGC

CTTTTTCCCGAGGGTGGGGGAGAACCGTATATAAGTGCAGTAGTC

GCCGTGAACGTTCTTTTTCGCAACGGGTTTGCCGCCAGAACACAG

CTGAAGCTTCGAGGGGCTCGCATCTCTCCTTCACGCGCCCGCCGC

CCTACCTGAGGCCGCCATCCACGCCGGTTGAGTCGCGTTCTGCCG

CCTCCCGCCTGTGGTGCCTCCTGAACTGCGTCCGCCGTCTAGGTA

AGTTTAAAGCTCAGGTCGAGACCGGGCCTTTGTCCGGCGCTCCCT
```

-continued

```
TGGAGCCTACCTAGACTCAGCCGGCTCTCCACGCTTTGCCTGACC

CTGCTTGCTCAACTCTACGTCTTTGTTTCGTTTTCTGTTCTGCGC

CGTTACAGATCCAAGctcGTACGgccaccATGAAAAGGCCGGCGG

CCACGAAAAAGGCCGGCCAGGCAAAAAAGAAAAAGGACAAGAAGT

ACAGCATCGGCCTGGCCATCGGCACCAACTCTGTGGGCTGGGCCG

TGATCACCGACGAGTACAAGGTGCCCAGCAAGAAATTCAAGGTGC

TGGGCAACACCGACCGGCACAGCATCAAGAAGAACCTGATCGGAG

CCCTGCTGTTCGACAGCGGCGAAACAGCCGAGGCCACCCGGCTGA

AGAGAACCGCCAGAAGAAGATACACCAGACGGAAGAACCGGATCT

GCTATCTGCAAGAGATCTTCAGCAACGAGATGGCCAAGGTGGACG

ACAGCTTCTTCCACAGACTGGAAGAGTCCTTCCTGGTGGAAGAGG

ATAAGAAGCACGAGCGGCACCCCATCTTCGGCAACATCGTGGACG

AGGTGGCCTACCACGAGAAGTACCCCACCATCTACCACCTGAGAA

AGAAACTGGTGGACAGCACCGACAAGGCCGACCTGCGGCTGATCT

ATCTGGCCCTGGCCCACATGATCAAGTTCCGGGGCCACTTCCTGA

TCGAGGGCGACCTGAACCCCGACAACAGCGACGTGGACAAGCTGT

TCATCCAGCTGGTGCAGACCTACAACCAGCTGTTCGAGGAAAACC

CCATCAACGCCAGCGGCGTGGACGCCAAGGCCATCCTGTCTGCCA

GACTGAGCAAGAGCAGACGGCTGGAAAATCTGATCGCCCAGCTGC

CCGGCGAGAAGAAGAATGGCCTGTTCGGCAACCTGATTGCCCTGA

GCCTGGGCCTGACCCCCAACTTCAAGAGCAACTTCGACCTGGCCG

AGGATGCCAAACTGCAGCTGAGCAAGGACACCTACGACGACGACC

TGGACAACCTGCTGGCCCAGATCGGCGACCAGTACGCCGACCTGT

TTCTGGCCGCCAAGAACCTGTCCGACGCCATCCTGCTGAGCGACA

TCCTGAGAGTGAACACCGAGATCACCAAGGCCCCCCTGAGCGCCT

CTATGATCAAGAGATACGACGAGCACCACCAGGACCTGACCCTGC

TGAAAGCTCTCGTGCGGCAGCAGCTGCCTGAGAAGTACAAAGAGA

TTTTCTTCGACCAGAGCAAGAACGGCTACGCCGGCTACATTGACG

GCGGAGCCAGCCAGGAAGAGTTCTACAAGTTCATCAAGCCCATCC

TGGAAAAGATGGACGGCACCGAGGAACTGCTCGTGAAGCTGAACA

GAGAGGACCTGCTGCGGAAGCAGCGGACCTTCGACAACGGCAGCA

TCCCCCACCAGATCCACCTGGGAGAGCTGCACGCCATTCTGCGGC

GGCAGGAAGATTTTTACCCATTCCTGAAGGACAACCGGGAAAAGA

TCGAGAAGATCCTGACCTTCCGCATCCCCTACTACGTGGGCCCTC

TGGCCAGGGGAAACAGCAGATTCGCCTGGATGACCAGAAAGAGCG

AGGAAACCATCACCCCCTGGAACTTCGAGGAAGTGGTGGACAAGG

GCGCTTCCGCCCAGAGCTTCATCGAGCGGATGACCAACTTCGATA

AGAACCTGCCCAACGAGAAGGTGCTGCCCAAGCACAGCCTGCTGT

ACGAGTACTTCACCGTGTATAACGAGCTGACCAAAGTGAAATACG

TGACCGAGGGAATGAGAAAGCCCGCCTTCCTGAGCGGCGAGCAGA

AAAAGGCCATCGTGGACCTGCTGTTCAAGACCAACCGGAAAGTGA
```

-continued

```
CCGTGAAGCAGCTGAAAGAGGACTACTTCAAGAAAATCGAGTGCT

TCGACTCCGTGGAAATCTCCGGCGTGGAAGATCGGTTCAACGCCT

CCCTGGGCACATACCACGATCTGCTGAAAATTATCAAGGACAAGG

ACTTCCTGGACAATGAGGAAAACGAGGACATTCTGGAAGATATCG

TGCTGACCCTGACACTGTTTGAGGACAGAGAGATGATCGAGGAAC

GGCTGAAAACCTATGCCCACCTGTTCGACGACAAAGTGATGAAGC

AGCTGAAGCGGCGGAGATACACCGGCTGGGGCAGGCTGAGCCGGA

AGCTGATCAACGGCATCCGGGACAAGCAGTCCGGCAAGACAATCC

TGGATTTCCTGAAGTCCGACGGCTTCGCCAACAGAAACTTCATGC

AGCTGATCCACGACGACGCCTGACCTTTAAAGAGGACATCCAGA

AAGCCCAGGTGTCCGGCCAGGGCGATAGCCTGCACGAGCACATTG

CCAATCTGGCCGGCAGCCCCGCCATTAAGAAGGGCATCCTGCAGA

CAGTGAAGGTGGTGGACGAGCTCGTGAAAGTGATGGGCCGGCACA

AGCCCGAGAACATCGTGATCGAAATGGCCAGAGAGAACCAGACCA

CCCAGAAGGGACAGAAGAACAGCCGCGAGAGAATGAAGCGGATCG

AAGAGGGCATCAAAGAGCTGGGCAGCCAGATCCTGAAAGAACACC

CCGTGGAAAACACCCAGCTGCAGAACGAGAAGCTGTACCTGTACT

ACCTGCAGAATGGGCGGGATATGTACGTGGACCAGGAACTGGACA

TCAACCGGCTGTCCGACTACGATGTGGACCACATCGTGCCTCAGA

GCTTTCTGAAGGACGACTCCATCGACAACAAGGTGCTGACCAGAA

GCGACAAGGCCCGGGGCAAGAGCGACAACGTGCCCTCCGAAGAGG

TCGTGAAGAAGATGAAGAACTACTGGCGGCAGCTGCTGAACGCCA

AGCTGATTACCCAGAGAAAGTTCGACAATCTGACCAAGGCCGAGA

GAGGCGGCCTGAGCGAACTGGATAAGGCCGGCTTCATCAAGAGAC

AGCTGGTGGAAACCCGGCAGATCACAAAGCACGTGGCACAGATCC

TGGACTCCCGGATGAACACTAAGTACGACGAGAATGACAAGCTGA

TCCGGGAAGTGAAAGTGATCACCCTGAAGTCCAAGCTGGTGTCCG

ATTTCCGGAAGGATTTCCAGTTTTACAAAGTGCGCGAGATCAACA

ACTACCACCACGCCCACGACGCCTACCTGAACGCCGTCGTGGGAA

CCGCCCTGATCAAAAAGTACCCTAAGCTGGAAAGCGAGTTCGTGT

ACGGCGACTACAAGGTGTACGACGTGCGGAAGATGATCGCCAAGA

GCGAGCAGGAAATCGGCAAGGCTACCGCCAAGTACTTCTTCTACA

GCAACATCATGAACTTTTTCAAGACCGAGATTACCCTGGCCAACG

GCGAGATCCGGAAGCGGCCTCTGATCGAGACAAACGGCGAAACCG

GGGAGATCGTGTGGGATAAGGGCCGGGATTTTGCCACCGTGCGGA

AAGTGCTGAGCATGCCCCAAGTGAATATCGTGAAAAAGACCGAGG

TGCAGACAGGCGGCTTCAGCAAAGAGTCTATCCTGCCCAAGAGGA

ACAGCGATAAGCTGATCGCCAGAAAGAAGGACTGGGACCCTAAGA

AGTACGGCGGCTTCGACAGCCCCACCGTGGCCTATTCTGTGCTGG

TGGTGGCCAAAGTGGAAAAGGGCAAGTCCAAGAAACTGAAGAGTG
```

-continued

```
TGAAAGAGCTGCTGGGGATCACCATCATGGAAAGAAGCAGCTTCG

AGAAGAATCCCATCGACTTTCTGGAAGCCAAGGGCTACAAAGAAG

TGAAAAAGGACCTGATCATCAAGCTGCCTAAGTACTCCCTGTTCG

AGCTGGAAAACGGCCGGAAGAGAATGCTGGCCTCTGCCGGCGAAC

TGCAGAAGGGAAACGAACTGGCCCTGCCCTCCAAATATGTGAACT

TCCTGTACCTGGCCAGCCACTATGAGAAGCTGAAGGGCTCCCCCG

AGGATAATGAGCAGAAACAGCTGTTTGTGGAACAGCACAAGCACT

ACCTGGACGAGATCATCGAGCAGATCAGCGAGTTCTCCAAGAGAG

TGATCCTGGCCGACGCTAATCTGGACAAAGTGCTGTCCGCCTACA

ACAAGCACCGGGATAAGCCCATCGAGAGCAGGCCGAGAATATCA

TCCACCTGTTTACCCTGACCAATCTGGGAGCCCCTGCCGCCTTCA

AGTACTTTGACACCACCATCGACCGGAAGAGGTACACCAGCACCA

AAGAGGTGCTGGACGCCACCCTGATCCACCAGAGCATCACCGGCC

TGTACGAGACACGGATCGACCTGTCTCAGCTGGGAGGCGACagcg ctGGAGGAGGTGGAAGCGGAGGAGGAGGAAGCGGAGGAGGAGGTA GCggacctaagaaaaagaggaaggtggcggccgctgGATCCCCTT

CAGGGCAGATCAGCAACCAGGCCCTGGCTCTGGCCCCTAGCTCCG

CTCCAGTGCTGGCCCAGACTATGGTGCCCTCTAGTGCTATGGTGC

CTCTGGCCCAGCCACCTGCTCCAGCCCCTGTGCTGACCCCAGGAC

CACCCCAGTCACTGAGCGCTCCAGTGCCCAAGTCTACACAGGCCG

GCGAGGGGACTCTGAGTGAAGCTCTGCTGCACCTGCAGTTCGACG

CTGATGAGGACCTGGGAGCTCTGCTGGGGAACAGCACCGATCCCG

GAGTGTTCACAGATCTGGCCTCCGTGGACAACTCTGAGTTTCAGC

AGCTGCTGAATCAGGGCGTGTCCATGTCTCATAGTACAGCCGAAC

CAATGCTGATGGAGTACCCCGAAGCCATTACCCGGCTGGTGACCG

GCAGCCAGCGGCCCCCCGACCCCGCTCCAACTCCCCTGGGAACCA

GCGGCCTGCCTAATGGGCTGTCCGGAGATGAAGACTTCTCAAGCA

TCGCTGATATGGACTTTAGTGCCCTGCTGTCACAGATTTCCTCTA

GTGGGCAGGGAGGAGGTGGAAGCGGCTTCAGCGTGGACACCAGTG

CCCTGCTGGACCTGTTCAGCCCCTCGGTGACCGTGCCCGACATGA

GCCTGCCTGACCTTGACAGCAGCCTGGCCAGTATCCAAGAGCTCC

TGTCTCCCCAGGAGCCCCCCAGGCCTCCCGAGGCAGAGAACAGCA

GCCCGGATTCAGGGAAGCAGCTGGTGCACTACACAGCGCAGCCGC

TGTTCCTGCTGGACCCCGGCTCCGTGGACACCGGGAGCAACGACC

TGCCGGTGCTGTGTTTGAGCTGGGAGAGGGCTCCTACTTCTCCGAAG

GGGACGGCTTCGCCGAGGACCCCACCATCTCCCTGCTGACAGGCT

CGGAGCCTCCCAAAGCCAAGGACCCCACTGTCTCCTAAGAATTCC

TGCAGCCCGGGGGATCCACTAGTTCTAGAGCGGCCGCCACCGCGG

GGAGATCCAGACATGATAAGATACATTGATGAGTTTGGACAAACC

ACAACTAGAATGCAGTGAAAAAAATGCTTTATTTGTGAAATTTGT

GATGCTATTGCTTTATTTGTAACCATTATAAGCTGCAATAAACAA
```

-continued

```
GTTAACAACAACAATTGCATTCATTTTATGTTTCAGGTTCAGGGG

GAGGTGTGGGAGGTTTTTTAAAGCAAGTAAAACCTCTACAAATGT

GGTATGGCTGATTATGATCCCGGCTGCCTCGCGCGTTTCGGTGAT

GACGGTGAAAACCTCTTGACACATGCAGCTCCCGGAGACGGTCAC

AGCTTGTCTGTAAGCGGATGCCGGGAGCAGACAAGCCCGTCAGGG

CGCGTCAGCGGGTGTTGGCGGGTGTCGGGGCGCAGCCATGAGGTC

GACTCTAGTCCCCGCGGTGGCAGATCTGGAAGGTGCTGAGGTACG

ATGAGACCCGCACCAGGTGCAGACCCTGCGAGTGTGGCGGTAAAC

ATATTAGGAACCAGCCTGTGATGCTGGATGTGACCGAGGAGCTGA

GGCCCGATCACTTGGTGCTGGCCTGCACCCGCGCTGAGTTTGGCT

CTAGCGATGAAGATACAGATTGAGGTACTGAAATGTGTGGGCGTG

GCTTAAGGGTGGGAAAGAATATATAAGGTGGGGGTCTTATGTAGT

TTTGTATCTGTTTTGCAGCAGCCGCCGCCGCCATGAGCACCAACT

CGTTTGATGGAAGCATTGTGAGCTCATATTTGACAACGCGCATGC

CCCCATGGGCCGGGGTGCGTCAGAATGTGATGGGCTCCAGCATTG

ATGGTCGCCCCGTCCTGCCCGCAAACTCTACTACCTTGACCTACG

AGACCGTGTCTGGAACGCCGTTGGAGACTGCAGCCTCCGCCGCCG

CTTCAGCCGCTGCAGCCACCGCCCGCGGGATTGTGACTGACTTTG

CTTTCCTGAGCCCGCTTGCAAGCAGTGCAGCTTCCCGTTCATCCG

CCCGCGATGACAAGTTGACGGCTCTTTTGGCACAATTGGATTCTT

TGACCCGGGAACTTAATGTCGTTTCTCAGCAGCTGTTGGATCTGC

GCCAGCAGGTTTCTGCCCTGAAGGCTTCCTCCCCTCCCAATGCGG

TTTAAAACATAAATAAAAAACCAGACTCTGTTTGGATTTGGATCA

AGCAAGTGTCTTGCTGTCTTTATTTAGGGGTTTTGCGCGCGCGGT

AGGCCCGGGACCAGCGGTCTCGGTCGTTGAGGGTCCTGTGTATTT

TTTCCAGGACGTGGTAAAGGTGACTCTGGATGTTCAGATACATGG

GCATAAGCCCGTCTCTGGGGTGGAGGTAGCACCACTGCAGAGCTT

CATGCTGCGGGGTGGTGTTGTAGATGATCCAGTCGTAGCAGGAGC

GCTGGGCGTGGTGCCTAAAAATGTCTTTCAGTAGCAAGCTGATTG

CCAGGGGCAGGCCCTTGGTGTAAGTGTTTACAAAGCGGTTAAGCT

GGGATGGGTGCATACGTGGGGATATGAGATGCATCTTGGACTGTA

TTTTTAGGTTGGCTATGTTCCCAGCCATATCCCTCCGGGGATTCA

TGTTGTGCAGAACCACCAGCACAGTGTATCCGGTGCACTTGGGAA

ATTTGTCATGTAGCTTAGAAGGAAATGCGTGGAAGAACTTGGAGA

CGCCCTTGTGACCTCCAAGATTTTCCATGCATTCGTCCATAATGA

TGGCAATGGGCCCACGGGCGGCGGCCTGGGCGAAGATATTTCTGG

GATCACTAACGTCATAGTTGTGTTCCAGGATGAGATCGTCATAGG

CCATTTTTACAAAGCGCGGGCGGAGGGTGCCAGACTGCGGTATAA

TGGTTCCATCCGGCCCAGGGGCGTAGTTACCCTCACAGATTTGCA

TTTCCCACGCTTTGAGTTCAGATGGGGGGGATCATGTCTACCTGCG
```

-continued

```
GGGCGATGAAGAAAACGGTTTCCGGGGTAGGGGAGATCAGCTGGG

AAGAAAGCAGGTTCCTGAGCAGCTGCGACTTACCGCAGCCGGTGG

GCCCGTAAATCACACCTATTACCGGGTGCAACTGGTAGTTAAGAG

AGCTGCAGCTGCCGTCATCCCTGAGCAGGGGGGCCACTTCGTTAA

GCATGTCCCTGACTCGCATGTTTTCCCTGACCAAATCCGCCAGAA

GGCGCTCGCCGCCCAGCGATAGCAGTTCTTGCAAGGAAGCAAAGT

TTTTCAACGGTTTGAGACCGTCCGCCGTAGGCATGCTTTTGAGCG

TTTGACCAAGCAGTTCCAGGCGGTCCCACAGCTCGGTCACCTGCT

CTACGGCATCTCGATCCAGCATATCTCCTCGTTTCGCGGGTTGGG

GCGGCTTTCGCTGTACGGCAGTAGTCGGTGCTCGTCCAGACGGGC

CAGGGTCATGTCTTTCCACGGGCGCAGGGTCCTCGTCAGCGTAGT

CTGGGTCACGGTGAAGGGGTGCGCTCCGGGCTGCGCGCTGGCCAG

GGTGCGCTTGAGGCTGGTCCTGCTGGTGCTGAAGCGCTGCCGGTC

TTCGCCCTGCGCGTCGGCCAGGTAGCATTTGACCATGGTGTCATA

GTCCAGCCCCTCCGCGCGTGGCCCTTGGCGCGCAGCTTGCCCTT

GGAGGAGGCGCCGCACGAGGGGCAGTGCAGACTTTTGAGGGCGTA

GAGCTTGGGCGCGAGAAATACCGATTCCGGGGAGTAGGCATCCGC

GCCGCAGGCCCCGCAGACGGTCTCGCATTCCACGAGCCAGGTGAG

CTCTGGCCGTTCGGGGTCAAAAACCAGGTTTCCCCCATGCTTTTT

GATGCGTTTCTTACCTCTGGTTTCCATGAGCCGGTGTCCACGCTC

GGTGACGAAAAGGCTGTCCGTGTCCCCGTATACAGACTTGAGAGG

CCTGTCCTCGACCGATGCCCTTGAGAGCCTTCAACCCAGTCAGCT

CCTTCCGGTGGGCGCGGGGCATGACTATCGTCGCCGCACTTATGA

CTGTCTTCTTTATCATGCAACTCGTAGGACAGGTGCCGGCAGCGC

TCTGGGTCATTTTCGGCGAGGACCGCTTTCGCTGGAGCGCGACGA

TGATCGGCCTGTCGCTTGCGGTATTCGGAATCTTGCACGCCCTCG

CTCAAGCCTTCGTCACTGGTCCCGCCACCAAACGTTTCGGCGAGA

AGCAGGCCATTATCGCCGGCATGGCGGCCGACGCGCTGGGCTACG

TCTTGCTGGCGTTCGCGACGCGAGGCTGGATGGCCTTCCCCATTA

TGATTCTTCTCGCTTCCGGCGGCATCGGGATGCCCGCGTTGCAGG

CCATGCTGTCCAGGCAGGTAGATGACGACCATCAGGGACAGCTTC

AAGGCCAGCAAAAGGCCAGGAACCGTAAAAAGGCCGCGTTGCTGG

CGTTTTTCCATAGGCTCCGCCCCCCTGACGAGCATCACAAAAATC

GACGCTCAAGTCAGAGGTGGCGAAACCCGACAGGACTATAAAGAT

ACCAGGCGTTTCCCCCTGGAAGCTCCCTCGTGCGCTCTCCTGTTC

CGACCCTGCCGCTTACCGGATACCTGTCCGCCTTTCTCCCTTCGG

GAAGCGTGGCGCTTTCTCATAGCTCACGCTGTAGGTATCTCAGTT

CGGTGTAGGTCGTTCGCTCCAAGCTGGGCTGTGTGCACGAACCCC

CCGTTCAGCCCGACCGCTGCGCCTTATCCGGTAACTATCGTCTTG

AGTCCAACCCGGTAAGACACGACTTATCGCCACTGGCAGCAGCCA

CTGGTAACAGGATTAGCAGAGCGAGGTATGTAGGCGGTGCTACAG
```

-continued

```
AGTTCTTGAAGTGGTGGCCTAACTACGGCTACACTAGAAGGACAG

TATTTGGTATCTGCGCTCTGCTGAAGCCAGTTACCTTCGGAAAAA

GAGTTGGTAGCTCTTGATCCGGCAAACAAACCACCGCTGGTAGCG

GTGGTTTTTTTGTTTGCAAGCAGCAGATTACGCGCAGAAAAAAAG

GATCTCAAGAAGATCCTTTGATCTTTTCTACGGGGTCTGACGCTC

AGTGGAACGAAAACTCACGTTAAGGGATTTTGGTCATGAGATTAT

CAAAAAGGATCTTCACCTAGATCCTTTTAAATTAAAAATGAAGTT

TTAAATCAATCTAAAGTATATATGAGTAAACTTGGTCTGACAGTT

ACCAATGCTTAATCAGTGAGGCACCTATCTCAGCGATCTGTCTAT

TTCGTTCATCCATAGTTGCCTGACTCCCCGTCGTGTAGATAACTA

CGATACGGGAGGGCTTACCATCTGGCCCCAGTGCTGCAATGATAC

CGCGAGACCCACGCTCACCGGCTCCAGATTTATCAGCAATAAACC

AGCCAGCCGGAAGGGCCGAGCGCAGAAGTGGTCCTGCAACTTTAT

CCGCCTCCATCCAGTCTATTAATTGTTGCCGGGAAGCTAGAGTAA

GTAGTTCGCCAGTTAATAGTTTGCGCAACGTTGTTGCCATTGCTG

CAGGCATCGTGGTGTCACGCTCGTCGTTTGGTATGGCTTCATTCA

GCTCCGGTTCCCAACGATCAAGGCGAGTTACATGATCCCCCATGT

TGTGCAAAAAAGCGGTTAGCTCCTTCGGTCCTCCGATCGTTGTCA

GAAGTAAGTTGGCCGCAGTGTTATCACTCATGGTTATGGCAGCAC

TGCATAATTCTCTTACTGTCATGCCATCCGTAAGATGCTTTTCTG

TGACTGGTGAGTACTCAACCAAGTCATTCTGAGAATAGTGTATGC

GGCGACCGAGTTGCTCTTGCCCGGCGTCAACACGGGATAATACCG

CGCCACATAGCAGAACTTTAAAAGTGCTCATCATTGGAAAACGTT

CTTCGGGGCGAAAACTCTCAAGGATCTTACCGCTGTTGAGATCCA

GTTCGATGTAACCCACTCGTGCACCCAACTGATCTTCAGCATCTT

TTACTTTCACCAGCGTTTCTGGGTGAGCAAAAACAGGAAGGCAAA

ATGCCGCAAAAAAGGGAATAAGGGCGACACGGAAATGTTGAATAC

TCATACTCTTCCTTTTTCAATATTATTGAAGCATTTATCAGGGTT

ATTGTCTCATGAGCGGATACATATTTGAATGTATTTAGAAAAATA

AACAAATAGGGGTTCCGCGCACATTTCCCCGAAAAGTGCCACCTG

ACGTCTAAGAAACCATTATTATCATGACATTAACCTATAAAAATA

GGCGTATCACGAGGCCCTTTCGTCTTCAAGAA
``` pAdEasy-1 Adenovirus Packaging or Helper (SEQ ID NO: 7)

```
attgtgagctcatatttgacaacgcgcatgcccccatgggccggg gtgcgtcagaatgtgatgggctccagcattgatggtcgccccgtc ctgcccgcaaactctactaccttgacctacgagaccgtgtctgga acgccgttggagactgcagcctccgccgccgcttcagccgctgca gccaccgcccgcgggattgtgactgactttgctttcctgagcccg cttgcaagcagtgcagcttccgttcatccgcccgcgatgacaag ttgacggctcttttggcacaattggattctttgacccgggaactt
```

-continued

```
aatgtcgtttctcagcagctgttggatctgcgccagcaggtttct gccctgaaggcttcctcccctcccaatgcggtttaaaacataaat aaaaaaccagactctgtttggatttggatcaagcaagtgtcttgc tgtctttatttaggggtttttgcgcgcgcggtaggcccgggaccag cggtctcggtcgttgagggtcctgtgtatttttttccaggacgtgg taaaggtgactctggatgttcagatacatgggcataagcccgtct ctggggtggaggtagcaccactgcagagcttcatgctgcggggtg gtgttgtagatgatccagtcgtagcaggagcgctgggcgtggtgc ctaaaaatgtctttcagtagcaagctgattgccaggggcaggccc ttggtgtaagtgtttacaaagcggttaagctgggatgggtgcata cgtggggatatgagatgcatcttggactgtattttttaggttggct atgttcccagccatatccctccggggattcatgttgtgcagaacc accagcacagtgtatccggtgcacttgggaaatttgtcatgtagc ttagaaggaaatgcgtggaagaacttggagacgcccttgtgacct ccaagattttccatgcattcgtccataatgatggcaatgggccca cgggcggcggcctgggcgaagatatttctgggatcactaacgtca tagttgtgttccaggatgagatcgtcataggccatttttacaaag cgcgggcggagggtgccagactgcggtataatggttccatccggc ccaggggcgtagttaccctcacagatttgcatttcccacgctttg agttcagatggggggatcatgtctacctgcggggcgatgaagaaa acggtttccggggtaggggagatcagctgggaagaaagcaggttc ctgagcagctgcgacttaccgcagccggtgggcccgtaaatcaca cctattaccggctgcaactggtagttaagagagctgcagctgccg tcatccctgagcaggggggccacttcgttaagcatgtccctgact cgcatgtttccctgaccaaatccgccagaaggcgctcgccgccc agcgatagcagttcttgcaaggaagcaaagtttttcaacggtttg agaccgtccgccgtaggcatgcttttgagcgtttgaccaagcagt tccaggcggtcccacagctcggtcacctgctctacggcatctcga tccagcatatctcctcgtttcgcgggttggggcggctttcgctgt acggcagtagtcggtgctcgtccagacgggccagggtcatgtctt tccacgggcgcagggtcctcgtcagcgtagtctgggtcacggtga aggggtgcgctccgggctgcgcgctggccagggtgcgcttgaggc tggtcctgctggtgctgaagcgctgccggtcttcgccctgcgcgt cggccaggtagcatttgaccatggtgtcatagtccagcccctccg cggcgtggcccttggcgcgcagcttgcccttggaggaggcgccgc acgagggcagtgcagacttttgagggcgtagagcttgggcgcga gaaataccgattccggggagtaggcatccgcgccgcaggccccgc agacggtctcgcattccacgagccaggtgagctctggccgttcgg ggtcaaaaaccaggtttcccccatgcttttttgatgcgtttcttac ctctggtttccatgagccggtgtccacgctcggtgacgaaaggc tgtccgtgtccccgtatacagacttgagaggcctgtcctcgagcg
```

-continued

```
gtgttccgcggtcctcctcgtatagaaactcggaccactctgaga caaaggctcgcgtccaggccagcacgaaggaggctaagtgggagg ggtagcggtcgttgtccactaggggggtccactcgctccagggtgt gaagacacatgtcgccctcttcggcatcaaggaaggtgattggtt tgtaggtgtaggccacgtgaccgggtgttcctgaaggggggctat aaaaggggggtggggcgcgttcgtcctcactctcttccgcatcgc tgtctgcgagggccagctgttggggtgagtactccctctgaaaag cgggcatgacttctgcgctaagattgtcagtttccaaaaacgagg aggatttgatattcacctggcccgcggtgatgcctttgagggtgg ccgcatccatctggtcagaaaagacaatcttttttgttgtcaagct tggtggcaaacgacccgtagagggcgttggacagcaacttggcga tggagcgcagggtttggtttttgtcgcgatcggcgcgctccttgg ccgcgatgtttagctgcacgtattcgcgcgcaacgcaccgccatt cgggaaagacggtggtgcgctcgtcgggcaccaggtgcacgcgcc aaccgcggttgtgcagggtgacaaggtcaacgctggtggctacct ctccgcgtaggcgctcgttggtccagcagaggcggccgcccttgc gcgagcagaatggcggtaggggggtctagctgcgtctcgtccgggg ggtctgcgtccacggtaaagacccgggcagcaggcgcgcgtcga agtagtctatcttgcatccttgcaagtctagcgcctgctgccatg cgcgggcggcaagcgcgcgctcgtatgggttgagtgggggacccc atggcatggggtgggtgagcgcggaggcgtacatgccgcaaatgt cgtaaacgtagaggggctctctgagtattccaagatatgtagggt agcatcttccaccgcggatgctggcgcgcacgtaatcgtatagtt cgtgcgagggagcgaggaggtcgggaccgaggttgctacgggcgg gctgctctgctcggaagactatctgcctgaagatggcatgtgagt tggatgatatggttggacgctggaagacgttgaagctggcgtctg tgagacctaccgcgtcacgcacgaaggaggcgtaggagtcgcgca gcttgttgaccagctcggcggtgacctgcacgtctagggcgcagt agtccagggtttccttgatgatgtcatacttatcctgtccctttt ttttccacagctcgcggttgaggacaaactcttcgcggtctttcc agtactcttggatcggaaacccgtcggcctccgaacggtaagagc ctagcatgtagaactggttgacggcctggtaggcgcagcatccct tttctacgggtagcgcgtatgcctgcgcggccttccggagcgagg tgtgggtgagcgcaaaggtgtccctgaccatgactttgaggtact ggtatttgaagtcagtgtcgtcgcatccgccctgctcccagagca aaaagtccgtgcgcttttttggaacgcggatttggcagggcgaagg tgacatcgttgaagagtatctttcccgcgcgaggcataaagttgc gtgtgatgcggaagggtcccggcacctcggaacggttgttaatta cctgggcggcgagcacgatctcgtcaaagccgttgatgttgtggc ccacaatgtaaagttccaagaagcgcgggatgcccttgatggaag
```

-continued

```
gcaattttttaagttcctcgtaggtgagctcttcaggggagctga gcccgtgctctgaaagggcccagtctgcaagatgagggttggaag cgacgaatgagctccacaggtcacgggccattagcatttgcaggt ggtcgcgaaaggtcctaaactggcgacctatggccattttttctg gggtgatgcagtagaaggtaagcgggtcttgttcccagcggtccc atccaaggttcgcggctaggtctcgcgcggcagtcactagaggct catctccgccgaacttcatgaccagcatgaagggcacgagctgct tcccaaaggcccccatccaagtataggtctctacatcgtaggtga caaagagacgctcggtgcgaggatgcgagccgatcgggaagaact ggatctcccgccaccaattggaggagtggctattgatgtggtgaa agtagaagtccctgcgacgggccgaacactcgtgctggcttttgt aaaaacgtgcgcagtactggcagcggtgcacgggctgtacatcct gcacgaggttgacctgacgaccgcgcacaaggaagcagagtggga atttgagcccctcgcctggcgggtttggctggtggtcttctactt cggctgcttgtccttgaccgtctggctgctcgaggggagttacgg tggatcggaccaccacgccgcgcgagcccaaagtccagatgtccg cgcgcggcggtcggagcttgatgacaacatcgcgcagatgggagc tgtccatggtctggagctcccgcggcgtcaggtcaggcgggagct cctgcaggtttacctcgcatagacgggtcaggcgcgcgggctagat ccaggtgatacctaatttccaggggctggttggtggcggcgtcga tggcttgcaagaggccgcatccccgcggcgcgactacggtaccgc gcggcgggcggtgggccgcgggggtgtccttggatgatgcatcta aaagcggtgacgcgggcgagccccgaggtaggggggggctccgg acccgccgggagaggggggcaggggcacgtcggcgccgcgcgggg caggagctggtgctgcgcgcgtaggttgctggcgaacgcgacgac gcggcggttgatctcctgaatctggcgcctctgcgtgaagacgac gggcccggtgagcttgaacctgaaagagagttcgacagaatcaat ttcggtgtcgttgacggcggcctggcgcaaaatctcctgcacgtc tcctgagttgtcttgataggcgatctcggccatgaactgctcgat ctcttcctcctggagatctccgcgtccggctcgctccacggtggc ggcgaggtcgttggaaatgcgggccatgagctgcgagaaggcgtt gaggcctccctcgttccagacgcggctgtagaccacgcccccttc ggcatcgcgggcgcgcatgaccacctgcgcgagattgagctccac gtgccgggcgaagacggcgtagtttcgcaggcgctgaaagaggta gttgagggtggtggcggtgtgttctgccacgaagaagtacataac ccagcgtcgcaacgtggattcgttgatatcccccaaggcctcaag gcgctccatggcctcgtagaagtccacggcgaagttgaaaaactg ggagttgcgcgccgacacggttaactcctcctccagaagacggat gagctcggcgacagtgtcgcgcacctcgcgctcaaaggctacagg ggcctcttcttcttcttcaatctcctcttccataagggcctcccc ttcttcttcttctggcggcggtgggggagggggggacacggcggcg
```

-continued

```
acgacggcgcaccgggaggcggtcgacaaagcgctcgatcatctc cccgcggcgacggcgcatggtctcggtgacggcgcggccgttctc gcgggggcgcagttggaagacgccgcccgtcatgtcccggttatg ggttggcggggggctgccatgcggcagggatacggcgctaacgat gcatctcaacaattgttgtgtaggtactccgccgccgagggacct gagcgagtccgcatcgaccggatcggaaaacctctcgagaaaggc gtctaaccagtcacagtcgcaaggtaggctgagcaccgtggcggg cggcagcgggcggcggtcggggttgtttctggcggaggtgctgct gatgatgtaattaaagtaggcggtcttgagacggcggatggtcga cagaagcaccatgtccttgggtccggcctgctgaatgcgcaggcg gtcggccatgccccaggcttcgttttgacatcggcgcaggtcttt gtagtagtcttgcatgagcctttctaccggcacttcttcttctcc ttcctcttgtcctgcatctcttgcatctatcgctgcggcggcggc ggagtttggccgtaggtggcgccctcttcctcccatgcgtgtgac cccgaagcccctcatcggctgaagcagggctaggtcggcgacaac gcgctcggctaatatggcctgctgcacctgcgtgagggtagactg gaagtcatccatgtccacaaagcggtggtatgcgcccgtgttgat ggtgtaagtgcagttggccataacggaccagttaacggtctggtg acccggctgcgagagctcggtgtacctgagacgcgagtaagccct cgagtcaaatacgtagtcgttgcaagtccgcaccaggtactggta tcccaccaaaaagtgcggcggcggctggcggtagaggggccagcg tagggtggccggggctccgggggcgagatcttccaacataaggcg atgatatccgtagatgtacctggacatccaggtgatgccggcggc ggtggtggaggcgcgcggaaagtcgcggacgcggttccagatgtt gcgcagcggcaaaaagtgctccatggtcgggacgctctggccggt caggcgcgcgcaatcgttgacgctctagcgtgcaaaaggagagcc tgtaagcgggcactcttccgtggtctggtggataaattcgcaagg gtatcatggcggacgaccggggttcgagccccgtatccggccgtc cgccgtgatccatgcggttaccgcccgcgtgtcgaacccaggtgt gcgacgtcagacaacggggagtgctcctttttggcttccttccag gcgcggcggctgctgcgctagcttttttggccactggccgcgcgc agcgtaagcggttaggctggaaagcgaaagcattaagtggctcgc tccctgtagccggagggttattttccaagggttgagtcgcgggac ccccggttcgagtctcggaccggccggactgcggcgaacgggggt ttgcctccccgtcatgcaagaccccgcttgcaaattcctccggaa acagggacgagcccctttttttgcttttcccagatgcatccggtgc tgcggcagatgcgccccctcctcagcagcggcaagagcaagagc agcggcagacatgcagggcaccctcccctcctcctaccgcgtcag gaggggcgacatccgcggttgacgcggcagcagatggtgattacg aaccccgcgggcgccgggcccggcactacctggacttggaggagg
```

-continued

```
gcgagggcctggcgcggctaggagcgccctctcctgagcggcacc caagggtgcagctgaagcgtgatacgcgtgaggcgtacgtgccgc ggcagaacctgtttcgcgaccgcgagggagaggagcccgaggaga tgcgggatcgaaagttccacgcagggcgcgagctgcggcatggcc tgaatcgcgagcggttgctgcgcgaggaggactttgagcccgacg cgcgaaccgggattagtcccgcgcgcgcacacgtggcggccgccg acctggtaaccgcatacgagcagacggtgaaccaggagattaact ttcaaaaaagctttaacaaccacgtgcgtacgcttgtggcgcgcg aggaggtggctataggactgatgcatctgtgggactttgtaagcg cgctggagcaaaacccaaatagcaagccgctcatggcgcagctgt tccttatagtgcagcacagcagggacaacgaggcattcagggatg cgctgctaaacatagtagagcccgagggccgctggctgctcgatt tgataaacatcctgcagagcatagtggtgcaggagcgcagcttga gcctggctgacaaggtggccgccatcaactattccatgcttagcc tgggcaagtttttacgcccgcaagatataccatacccccttacgttc ccatagacaaggaggtaaagatcgaggggttctacatgcgcatgg cgctgaaggtgcttaccttgagcgacgacctgggcgtttatcgca acgagcgcatccacaaggccgtgagcgtgagccggcggcgcgagc tcagcgaccgcgagctgatgcacagcctgcaaagggccctggctg gcacgggcagcggcgatagagaggccgagtcctactttgacgcgg gcgctgacctgcgctgggccccaagccgacgcgccctggaggcag ctggggccggacctgggctggcggtggcacccgcgcgcgctggca acgtcggcggcgtggaggaatatgacgaggacgatgagtacgagc cagaggacggcgagtactaagcggtgatgtttctgatcagatgat gcaagacgcaacggacccggcggtgcgggcggcgctgcagagcca gccgtccggccttaactccacggacgactggcgccaggtcatgga ccgcatcatgtcgctgactgcgcgcaatcctgacgcgttccggca gcagccgcaggccaaccggctctccgcaattctggaagcggtggt cccggcgcgcgcaaaccccacgcacgagaaggtgctggcgatcgt aaacgcgctggccgaaaacagggccatccggcccgacgaggccgg cctggtctacgacgcgctgcttcagcgcgtggctcgttacaacag cggcaacgtgcagaccaacctggaccggctggtggggggatgtgcg cgaggccgtggcgcagcgtgagcgcgcgcagcagcagggcaacct gggctccatggttgcactaaacgccttcctgagtacacagcccgc caacgtgccgcggggacaggaggactacaccaactttgtgagcgc actgcggctaatggtgactgagacaccgcaaagtgaggtgtacca gtctgggccagactattttttccagaccagtagacaaggcctgca gaccgtaaacctgagccaggctttcaaaaacttgcaggggctgtg ggggggtgcgggctcccacaggcgaccgcgcgaccgtgtctagctt gctgacgcccaactcgcgcctgttgctgctgctaatagcgccctt cacggacagtggcagcgtgtcccgggacacataccttaggtcactt
```

-continued

```
gctgacactgtaccgcgaggccataggtcaggcgcatgtggacga gcatactttccaggagattacaagtgtcagccgcgcgctggggca ggaggacacgggcagcctggaggcaaccctaaactacctgctgac caaccggcggcagaagatcccctcgttgcacagtttaaacagcga ggaggagcgcattttgcgctacgtgcagcagagcgtgagccttaa cctgatgcgcgacggggtaacgcccagcgtggcgctggacatgac cgcgcgcaacatggaaccgggcatgtatgcctcaaaccggccgtt tatcaaccgcctaatggactacttgcatcgcgcggccgccgtgaa ccccgagtatttcaccaatgccatcttgaacccgcactggctacc gcccctggtttctacaccggggggattcgaggtgcccgagggtaa cgatggattcctctgggacgacatagacgacagcgtgttttcccc gcaaccgcagaccctgctagagttgcaacagcgcgagcaggcaga ggcggcgctgcgaaaggaaagcttccgcaggccaagcagcttgtc cgatctaggcgctgcggccccgcggtcagatgctagtagcccatt tccaagcttgatagggtctcttaccagcactcgcaccacccgccc gcgcctgctgggcgaggaggagtacctaaacaactcgctgctgca gccgcagcgcgaaaaaaacctgcctccggcatttcccaacaacgg gatagagagcctagtggacaagatgagtagatgggaagacgtacgc gcaggagcacagggacgtgccaggcccgcgcccgcccacccgtcg tcaaaggcacgaccgtcagcggggtctggtgtgggaggacgatga ctcggcagacgacagcagcgtcctggatttgggagggagtggcaa cccgtttgcgcaccttcgccccaggctggggagaatgttttaaaa aaaaaaagcatgatgcaaaataaaaaactcaccaaggccatggc accgagcgttggttttcttgtattcccccttagtatgcggcgcgcg gcgatgtatgaggaaggtcctcctccctcctacgagagtgtggtg agcgcggcgccagtggcggcggcgctgggttctcccttcgatgct cccctggacccgccgtttgtgcctccgcggtacctgcggcctacc gggggggagaaacagcatccgttactctgagttggcacccctattc gacaccacccgtgtgtacctggtggacaacaagtcaacggatgtg gcatccctgaactaccagaacgaccacagcaactttctgaccacg gtcattcaaaacaatgactacagcccgggggggaggcaagcacacag accatcaatcttgacgaccggtcgcactggggcggcgacctgaaa accatcctgcataccaacatgccaaatgtgaacgagttcatgttt accaataagtttaaggcgcgggtgatggtgtcgcgcttgcctact aaggacaatcaggtggagctgaaatacgagtgggtggagttcacg ctgcccgagggcaactactccgagaccatgaccatagaccttatg aacaacgcgatcgtggagcactacttgaaagtgggcagacagaac ggggttctggaaagcgacatcggggtaaagtttgacacccgcaac ttcagactggggtttgaccccgtcactggtcttgtcatgcctggg gtatatacaaacgaagccttccatccagacatcattttgctgcca
```

-continued ggatgcggggtggacttcacccacagccgcctgagcaacttgttg ggcatccgcaagcggcaacccttccaggagggctttaggatcacc tacgatgatctggagggtggtaacattcccgcactgttggatgtg gacgcctaccaggcgagcttgaaagatgacaccgaacagggcggg ggtggcgcaggcggcagcaacagcagtggcagcggcgcggaagag aactccaacgcggcagccgcggcaatgcagccggtggaggacatg aacgatcatgccattcgcggcgacacctttgccacacgggctgag gagaagcgcgctgaggccgaagcagcggccgaagctgccgcccc gctgcgcaacccgaggtcgagaagcctcagaagaaaccggtgatc aaaccccctgacagaggacagcaagaaacgcagttacaacctaata agcaatgacagcaccttcacccagtaccgcagctggtaccttgca tacaactacggcgaccctcagaccggaatccgctcatggaccctg ctttgcactcctgacgtaacctgcggctcggagcaggtctactgg tcgttgccagacatgatgcaagaccccgtgaccttccgctccacg cgccagatcagcaactttccggtggtgggcgccgagctgttgccc gtgcactccaagagcttctacaacgaccaggccgtctactcccaa ctcatccgccagtttacctctctgacccacgtgttcaatcgcttt cccgagaaccagattttggcgcgccccgccagcccccaccatcacc accgtcagtgaaaacgttcctgctctcacagatcacgggacgcta ccgctgcgcaacagcatcggaggagtccagcgagtgaccattact gacgccagacgccgcacctgcccctacgtttacaaggccctgggc atagtctcgccgcgcgtcctatcgagccgcacttttttgagcaagc atgtccatccttatatcgcccagcaataacacaggctggggcctg cgcttcccaagcaagatgtttggcggggccaagaagcgctccgac caacacccagtgcgcgtgcgcgggcactaccgcgcgcccctgggcc gcgcacaaacgcggccgcactgggcgcaccaccgtcgatgacgcc atcgacgcggtggtggaggaggcgcgcaactacacgcccacgccg ccaccagtgtccacagtggacgcggccattcagaccgtggtgcgc ggagcccggcgctatgctaaaatgaagagacggcggaggcgcgta gcacgtcgccaccgccgccgacccggcactgccgcccaacgcgcg gcggcggccctgcttaaccgcgcacgtcgcaccggccgacgggcg gccatgcgggccgctcgaaggctggccgcgggtattgtcactgtg cccccaggtccaggcgacgagcggccgccgcagcagccgcggcc attagtgctatgactcagggtcgcaggggcaacgtgtattgggtg cgcgactcggttagcggcctgcgcgtgcccgtgcgcacccgcccc ccgcgcaactagattgcaagaaaaaactacttagactcgtactgt tgtatgtatccagcggcggcggcgcgcaacgaagctatgtccaag cgcaaaatcaaagaagagatgctccaggtcatcgcgccggagatc tatggccccccgaagaaggaagagcaggattacaagccccgaaag ctaaagcgggtcaaaaagaaaaagaaagatgatgatgatgaactt gacgacgaggtggaactgctgcacgctaccgcgcccaggcgacgg gtacagtggaaaggtcgacgcgtaaaacgtgttttgcgacccggc accaccgtagtctttacgcccggtgagcgctccacccgcacctac aagcgcgtgtatgatgaggtgtacggcgacgaggacctgcttgag caggccaacgagcgcctcgggggagtttgcctacggaaagcggcat aaggacatgctggcgttgccgctggacgagggcaacccaacacct agcctaaagcccgtaacactgcagcaggtgctgcccgcgcttgca ccgtccgaagaaaagcgcggcctaaagcgcgagtctggtgacttg gcacccaccgtgcagctgatggtacccaagcgccagcgactggaa gatgtcttggaaaaaatgaccgtggaacctgggctggagcccgag gtccgcgtgcggccaatcaagcaggtggcgccgggactgggcgtg cagaccgtggacgttcagatacccactaccagtagcaccagtatt gccaccgccacagagggcatggagacacaaacgtccccggttgcc tcagcggtggcggatgccgcggtgcaggcggtcgctgcggccgcg tccaagacctctacggaggtgcaaacggaccgtggatgtttcgc gtttcagcccccggcgcccgcgccgttcgaggaagtacggcgcc gccagcgcgctactgcccgaatatgccctacatccttccattgcg cctacccccggctatcgtggctacacctaccgccccagaagacga gcaactacccgacgccgaaccaccactggaacccgccgccgccgt cgccgtcgccagccgtgctggccccgatttccgtgcgcagggtg gctcgcgaaggaggcaggaccctggtgctgccaacagcgcgctac cacccagcatcgtttaaaagccggtctttgtggttcttgcagat atgcccctcacctgccgcctccgtttcccggtgccgggattccga ggaagaatgcaccgtaggaggggcatggccgccacggcctgacg ggcggcatgcgtcgtgcgcaccaccggcggcggcgcgcgtcgcac cgtcgcatgcgcggcggtatcctgcccctccttattccactgatc gccgcggcgattggcgccgtgcccggaattgcatccgtggccttg caggcgcagagacactgattaaaaacaagttgcatgtggaaaaat caaaataaaaagtctggactctcacgctcgcttggtcctgtaact atttttgtagaatggaagacatcaactttgcgtctctggccccgcg acacggctcgcgcccgttcatgggaaactggcaagatatcggcac cagcaatatgagcggtggcgccttcagctggggctcgctgtggag cggcattaaaaatttcggttccaccgttaagaactatggcagcaa ggcctggaacagcagcacaggccagatgctgagggataagttgaa agagcaaaatttccaacaaaaggtggtagatggcctggcctctgg cattagcggggtggtggacctggccaaccaggcagtgcaaaataa gattaacagtaagcttgatccccgccctcccgtagaggagcctcc accggccgtggagacagtgtctccagaggggcgtggcgaaaagcg tccgcgccccgacagggaagaaactctggtgacgcaaatagacga gcctccctcgtacgaggaggcactaaagcaaggcctgcccaccac ccgtcccatcgcgcccatggctaccggagtgctgggccagcacac -continued

```
acccgtaacgctggacctgcctcccccgccgacacccagcagaa acctgtgctgccaggcccgaccgccgttgttgtaaccgtcctag ccgcgcgtccctgcgccgcgccgccagcggtccgcgatcgttgcg gcccgtagccagtggcaactggcaaagcacactgaacagcatcgt gggtctgggggtgcaatccctgaagcgccgacgatgcttctgata gctaacgtgtcgtatgtgtgtcatgtatgcgtccatgtcgccgcc agaggagctgctgagccgccgcgcgcccgctttccaagatggcta cccccttcgatgatgccgcagtggtcttacatgcacatctcgggcc aggacgcctcggagtacctgagccccgggctggtgcagtttgccc gcgccaccgagacgtacttcagcctgaataacaagtttagaaacc ccacggtggcgcctacgcacgacgtgaccacagaccggtcccagc gtttgacgctgcggttcatccctgtggaccgtgaggatactgcgt actcgtacaaggcgcggttcaccctagctgtgggtgataaccgtg tgctggacatggcttccacgtactttgacatccgcggcgtgctgg acaggggccctactttaagccctactctggcactgcctacaacg ccctggctcccaagggtgccccaaatccttgcgaatgggatgaag ctgctactgctcttgaaataaaacctagaagaagaggacgatgaca acgaagacgaagtagacgagcaagctgagcagcaaaaaactcacg tatttgggcaggcgccttattctggtataaatattacaaaggagg gtattcaaataggtgtcgaaggtcaaacacctaaatatgccgata aaacatttcaacctgaacctcaaataggagaatctcagtggtacg aaacagaaattaatcatgcagctgggagagtcctaaaaaagacta ccccaatgaaaccatgttacggttcatatgcaaaacccacaaatg aaaatggagggcaaggcattcttgtaaagcaacaaaatggaaagc tagaaagtcaagtggaaatgcaattttttctcaactactgaggcag ccgcaggcaatggtgataacttgactcctaaagtggtattgtaca gtgaagatgtagatatagaaaccccagacactcatatttcttaca tgcccactattaaggaaggtaactcacgagaactaatgggccaac aatctatgcccaacaggcctaattacattgcttttagggacaatt ttattggtctaatgtattacaacagcacgggtaatatgggtgttc tggcgggccaagcatcgcagttgaatgctgttgtagatttgcaag acagaaacacagagctttcataccagctttttgcttgattccattg gtgatagaaccaggtacttttctatgtggaatcaggctgttgaca gctatgatccagatgttagaattattgaaaatcatggaactgaag atgaacttccaaattactgctttccactgggaggtgtgattaata cagagactcttaccaaggtaaaaacctaaaacaggtcaggaaaatg gatgggaaaaagatgctacagaattttcagataaaaatgaaataa gagttggaaataattttgccatggaaatcaatctaaatgccaacc tgtggagaaatttcctgtactccaacatagcgctgtatttgcccg acaagctaaagtacagtccttccaacgtaaaaatttctgataacc caaacacctacgactacatgaacaagcgagtggtggctcccgggc
```

-continued

```
tagtggactgctacattaaccttggagcacgctggtcccttgact atatggacaacgtcaacccatttaaccaccaccgcaatgctggcc tgcgctaccgctcaatgttgctgggcaatggtcgctatgtgccct tccacatccaggtgcctcagaagttctttgccattaaaaaacctcc ttctcctgccgggctcatacacctacgagtggaacttcaggaagg atgttaacatggttctgcagagctccctaggaaatgacctaaggg ttgacggagccagcattaagtttgatagcatttgcctttacgcca ccttcttccccatggcccacaacaccgcctccacgcttgaggcca tgcttagaaacgacaccaacgaccagtcctttaacgactatctct ccgccgccaacatgctctaccctatacccgccaacgctaccaacg tgcccatatccatcccctcccgcaactgggcggctttccgcggct gggccttcacgcgcgccttaagactaaggaaaccccatcactgggct cgggctacgacccttattacacctactctggctctatacctacc tagatggaaccttttacctcaaccacacctttaagaaggtggcca ttacctttgactcttctgtcagctggcctggcaatgaccgcctgc ttaccccaacgagtttgaaattaagcgctcagttgacggggagg gttacaacgttgcccagtgtaacatgaccaaagactggttcctgg tacaaatgctagctaactataacattggctaccagggcttctata tcccagagagctacaaggaccgcatgtactccttctttagaaact tccagcccatgagccgtcaggtggtggatgatactaaatacaagg actaccaacaggtgggcatcctacaccaacacaacaactctggat ttgttggctaccttgcccccaccatgcgcgaaggacaggcctacc ctgctaacttcccctatccgcttataggcaagaccgcagttgaca gcattacccagaaaaagtttcttgcgatcgcacccttggcgca tcccattctccagtaacttatgtccatgggcgcactcacagacc tgggccaaaaccttctctacgccaactccgcccacgcgctagaca tgacttttgaggtggatcccatggacgagcccacccttctttatg ttttgtttgaagtctttgacgtggtccgtgtgcaccagccgcacc gcggcgtcatcgaaaccgtgtacctgcgcacgcccttctcggccg gcaacgccacaacataaagaagcaagcaacatcaacaacagctgc cgccatgggctccagtgagcaggaactgaaagccattgtcaaaga tcttggttgtgggccatattttttgggcacctatgacaagcgctt tccaggctttgtttctccacacaagctcgcctgcgcgccatagtcaa tacggccggtcgcgagactgggggcgtacactggatggcctttgc ctggaacccgcactcaaaaacatgctacctctttgagccctttgg cttttctgaccagcgactcaagcaggtttaccagtttgagtacga gtcactcctgcgccgtagcgccattgcttcttcccccgaccgctg tataacgctggaaaagtccacccaaagcgtacaggggcccaactc ggccgcctgtggactattctgctgcatgtttctccacgcctttgc caactggccccaaactcccatggatcacaaccccaccatgaacct
```

-continued tattaccggggtacccaactccatgctcaacagtccccaggtaca gcccaccctgcgtcgcaaccaggaacagctctacagcttcctgga gcgccactcgccctacttccgcagccacagtgcgcagattaggag cgccacttcttttttgtcacttgaaaaacatgtaaaaataatgtac tagagacactttcaataaaggcaaatgcttttatttgtacactct cgggtgattatttacccccaccccttgccgtctgcgccgtttaaaa atcaaaggggttctgccgcgcatcgctatgcgccactggcaggga cacgttgcgatactggtgtttagtgctccacttaaactcaggcac aaccatccgcggcagctcggtgaagttttcactccacaggctgcg caccatcaccaacgcgtttagcaggtcgggcgccgatatcttgaa gtcgcagttggggcctccgccctgcgcgcgcgagttgcgatacac agggttgcagcactggaacactatcagcgccgggtggtgcacgct ggccagcacgctcttgtcggagatcagatccgcgtccaggtcctc cgcgttgctcagggcgaacggagtcaactttggtagctgccttcc caaaaagggcgcgtgcccaggctttgagttgcactcgcaccgtag tggcatcaaaaggtgaccgtgcccggtctgggcgttaggatacag cgcctgcataaaagccttgatctgcttaaaagccacctgagcctt tgcgccttcagagaagaacatgccgcaagacttgccggaaaactg attggccggacaggccgcgtcgtgcacgcagcaccttgcgtcggt gttggagatctgcaccacatttcggccccaccggttcttcacgat cttggccttgctagactgctccttcagcgcgcgctgcccgttttc gctcgtcacatccatttcaatcacgtgctccttatttatcataat gcttccgtgtagacacttaagctcgccttcgatctcagcgcagcg gtgcagccacaacgcgcagcccgtgggctcgtgatgcttgtaggt cacctctgcaaacgactgcaggtacgcctgcaggaatcgccccat catcgtcacaaaggtcttgttgctggtgaaggtcagctgcaaccc gcggtgctcctcgttcagccaggtcttgcatacggccgccagagc ttccacttggtcaggcagtagtttgaagttcgcctttagatcgtt atccacgtggtacttgtccatcagcgcgcgcgcagcctccatgcc cttctcccacgcagacacgatcggcacactcagcgggttcatcac cgtaatttcactttccgcttcgctgggctcttcctcttcctcttg cgtccgcataccacgcgccactgggtcgtcttcattcagccgccg cactgtgcgcttacctcctttgccatgcttgattagcaccggtgg gttgctgaaacccaccatttgtagcgccacatcttctctttcttc ctcgctgtccacgattacctctggtgatggcgggcgctcgggctt gggagaagggcgcttctttttcttcttgggcgcaatggccaaatc cgccgccgaggtcgatggccgcgggctgggtgtgcgcggcaccag cgcgtcttgtgatgagtcttcctcgtcctcggactcgatacgccg cctcatccgcttttttgggggcgcccggggaggcggcggcgacgg ggacggggacgacacgtcctccatggttggggggacgtcgcgccgc accgcgtccgcgctcgggggtggtttcgcgctgctcctcttcccg -continued actggccatttccttctcctataggcagaaaaagatcatggagtc agtcgagaagaaggacagcctaaccgcccccctctgagttcgccac caccgcctccaccgatgccgccaacgcgcctaccaccttccccgt cgaggcaccccgcttgaggaggaggaagtgattatcgagcagga cccaggttttgtaagcgaagacgacgaggaccgctcagtaccaac agaggataaaaagcaagaccaggacaacgcagaggcaaacgagga acaagtcgggcgggggacgaaaggcatggcgactacctagatgt gggagacgacgtgctgttgaagcatctgcagcgccagtgcgccat tatctgcgacgcgttgcaagagcgcagcgatgtgcccctcgccat agcggatgtcagccttgcctacgaacgccacctattctcaccgcg cgtaccccccaaacgccaagaaaacggcacatgcgagcccaaccc gcgcctcaacttctacccccgtatttgccgtgccagaggtgcttgc cacctatcacatcttttttccaaaactgcaagataccccctatcctg ccgtgccaaccgcagccgagcggacaagcagctggccttgcggca gggcgctgtcataacctgatatcgcctcgctcaacgaagtgccaaa aatctttgagggtcttggacgcgacgagaagcgcgcggcaaacgc tctgcaacaggaaaacagcgaaaatgaaagtcactctggagtgtt ggtggaactcgagggtgacaacgcgcgcctagccgtactaaaacg cagcatcgaggtcacccactttgcctacccggcacttaacctacc ccccaaggtcatgagcacagtcatgagtgagctgatcgtgcgccg tgcgcagcccctggagagggatgcaaatttgcaagaacaaacaga ggagggcctacccgcagttggcgacgagcagctagcgcgctggct tcaaacgcgcgagcctgccgacttggaggagcgacgcaaactaat gatggccgcagtgctcgttaccgtgggagcttgagtgcatgcagcg gttctttgctgacccggagatgcagcgcaagctagaggaaacatt gcactacacctttcgacagggctacgtacgccaggcctgcaagat ctccaacgtggagctctgcaacctggtctcctaccttggaatttt gcacgaaaaccgccttgggcaaaacgtgcttcattccacgctcaa gggcgaggcgcgccgcgactacgtccgcgactgcgtttacttatt tctatgctacacctggcagacggccatgggcgtttggcagcagtg cttggaggagtgcaacctcaaggagctgcagaaactgctaaagca aaacttgaaggacctatggacggccttcaacgagcgctccgtggc cgcgcacctggcggacatcattttccccgaacgcctgcttaaaac cctgcaacagggtctgccagacttcaccagtcaaagcatgttgca gaacttaggaactttatcctagagcgctcaggaatcttgcccgc cacctgctgtgcacttcctagcgactttgtgcccattaagtaccg cgaatgccctccgccgcctttggggccactgctaccttctgcagct agccaactaccttgcctaccactctgacataatggaagacgtgag cggtgacggtctactggagtgtcactgtcgctgcaacctatgcac cccgcaccgctccctggtttgcaattcgcagctgcttaacgaaag -continued tcaaattatcggtacctttgagctgcagggtccctcgcctgacga aaagtccgcggctccggggttgaaactcactccggggctgtggac gtcggcttaccttcgcaaatttgtacctgaggactaccacgccca cgagattaggttctacgaagaccaatcccgcccgcctaatgcgga gcttaccgcctgcgtcattacccagggccacattcttggccaatt gcaagccatcaacaaagcccgccaagagtttctgctacgaaaggg acggggggtttacttggacccccagtccggcgaggagctcaaccc aatcccccgccgcgcagccctatcagcagcagccgcgggccct tgcttcccaggatggcacccaaaaagaagctgcagctgccgccgc cacccacgacgaggaggaatactgggacagtcaggcagaggagg ttttggacgaggaggaggaggacatgatggaagactgggagagcc tagacgaggaagcttccgaggtcgaagaggtgtcagacgaaacac cgtcaccctcggtcgcattcccctcgccggcgccccagaaatcgg caaccggttccagcatggctacaacctccgctcctcaggcgccgc cggcactgcccgttcgccgacccaaccgtagatgggacaccactg gaaccagggccggtaagtccaagcagccgccgccgttagcccaag agcaacaacagcgccaaggctaccgctcatggcgcgggcacaaga acgccatagttgcttgcttgcaagactgtgggggcaacatctcct tcgcccgccgctttcttctctaccatcacggcgtggccttcccc gtaacatcctgcattactaccgtcatctctacagcccatactgca ccggcggcagcggcagcaacagcagcggccacacagaagcaaagg cgaccggatagcaagactctgacaaagcccaagaaatccacagcg gcggcagcagcaggaggaggagcgctgcgtctggcgcccaacgaa cccgtatcgacccgcgagcttagaaacaggattttttcccactctg tatgctatatttcaacagagcaggggccaagaacaagagctgaaa ataaaaaacaggtctctgcgatccctcacccgcagctgcctgtat cacaaaagcgaagatcagcttcggcgcacgctggaagacgcggag gctctcttcagtaaatactgcgcgctgactcttaaggactagttt cgcgccctttctcaaatttaagcgcgaaaactacgtcatctccag cggccacacccggcgccagcacctgttgtcagcgccattatgagc aaggaaattcccacgccctacatgtggagttaccagccacaaatg ggacttgcggctggagctgcccaagactactcaacccgaataaac tacatgagcgcgggaccccacatgatatcccgggtcaacggaata cgcgcccaccgaaaccgaattctcctggaacaggcggctattacc accacacctcgtaataaccttaatcccgtagttggcccgctgcc ctggtgtaccaggaaagtcccgctcccaccactgtggtacttccc agagacgcccaggccgaagttcagatgactaactcaggggcgcag cttgcgggcggctttcgtcacagggtgcggtcgcccgggcaggg ataactcacctgacaatcagagggcgaggtattcagctcaacgac gagtcggtgagctcctcgcttggtctccgtccggacgggacatt cagatcggcggcgccggccgctcttcattcacgcctcgtcaggca -continued atcctaactctgcagacctcgtcctctgagccgcgctctggaggc attggaactctgcaatttattgaggagtttgtgccatcggtctac tttaaccccttctcgggacctcccggccactatccggatcaattt attcctaactttgacgcggtaaaggactcggcggacggctacgac tgaatgttaagtggagaggcagagcaactgcgcctgaaacacctg gtccactgtcgccgccacaagtgctttgcccgcgactccggtgag ttttgctactttgaattgcccgaggatcatatcgagggcccggcg cacggcgtccggcttaccgcccagggagagcttgcccgtagcctg attcgggagtttacccagcgccccctgctagttgagcgggacagg ggacccgtgttctcactgtgatttgcaactgtcctaaccctgga ttacatcaagatcctctagttaatgtcaggtcgcctaagtcgatt aactagagtacccggggatcttattccctttaactaataaaaaaa aataataaagcatcacttacttaaaatcagttagcaaatttctgt ccagtttattcagcagcacctccttgccctcctcccagctctggt attgcagcttcctcctggctgcaaactttctccacaatctaaatg gaatgtcagttcctcctgttcctgtccatccgcacccactatct tcatgttgttgcagatgaagcgcgcaagaccgtctgaagatacct tcaaccccgtgtatccatatgacacggaaaccggtcctccaactg tgccttttcttactcctcccttgtatccccaatgggtttcaag agagtcccctggggtactctctttgcgcctatccgaacctctag ttacctccaatggcatgcttgcgctcaaaatgggcaacggcctct ctctggacgaggccggcaaccttacctcccaaaatgtaaccactg tgagcccacctctcaaaaaaaccaagtcaaacataaacctggaaa tatctgcacccctcacagttacctcagaagccctaactgtggctg ccgccgcacctctaatggtcgcgggcaacacactcaccatgcaat cacaggccccgctaaccgtgcacgactccaaacttagcattgcca cccaaggaccccctcacagtgtcagaaggaaagctagccctgcaaa catcaggcccctcaccaccaccgatagcagtacccttactatca ctgcctcacccccctctaactactgccactggtagcttgggcattg acttgaaagagcccatttatacacaaaatggaaaactaggactaa agtacggggctcctttgcatgtaacagacgacctaaacactttga ccgtagcaactggtccaggtgtgactattaataatacttccttgc aaactaaagttactggagccttgggtttttgattcacaaggcaata tgcaacttaatgtagcaggaggactaaggattgattctcaaaaca gacgccttatacttgatgttagttatccgtttgatgctcaaaacc aactaaatctaagactaggacagggccctcttttttataaaactcag cccacaacttggatattaactacaacaaaggcctttacttgtttta cagcttcaaacaattccaaaaagcttgaggttaacctaagcactg ccaaggggttgatgtttgacgctacagccatagccattaatgcag gagatgggcttgaatttggttcacctaatgcaccaaacacaaatc -continued

```
ccctcaaaacaaaaattggccatggcctagaatttgattcaaaca aggctatggttcctaaactaggaactggccttagttttgacagca caggtgccattacagtaggaaacaaaaataatgataagctaactt tgtggaccacaccagctccatctcctaactgtagactaaatgcag agaaagatgctaaactcactttggtcttaacaaaatgtggcagtc aaatacttgctacagtttcagttttggctgttaaaggcagtttgg ctccaatatctggaacagttcaaagtgctcatcttattataagat ttgacgaaaatggagtgctactaaacaattccttcctggacccag aatattggaactttagaaatggagatcttactgaaggcacagcct atacaaacgctgttggatttatgcctaacctatcagcttatccaa aatctcacggtaaaactgccaaaagtaacattgtcagtcaagttt acttaaacggagacaaaactaaacctgtaacactaaccattacac taaacggtacacaggaaacaggagacacaactccaagtgcatact ctatgtcattttcatgggactggtctggccacaactacattaatg aaatatttgccacatcctcttacactttttcatacattgcccaag aataaagaatcgtttgtgttatgtttcaacgtgtttattttttcaa ttgcagaaaatttcaagtcattttttcattcagtagtatagcccca ccaccacatagcttatacagatcaccgtaccttaatcaaactcac agaaccctagtattcaacctgccacctccctcccaacacacagag tacacagtcctttctccccggctggccttaaaaagcatcatatca tgggtaacagacatattcttaggtgttatattccacacggtttcc tgtcgagccaaacgctcatcagtgatattaataaactccccgggc agctcacttaagttcatgtcgctgtccagctgctgagccacaggc tgctgtccaacttgcggttgcttaacgggcggcgaaggagaagtc cacgcctacatgggggtagagtcataatcgtgcatcaggataggg cggtggtgctgcagcagcgcgcgaataaaactgctgccgccgccgc tccgtcctgcaggaatacaacatggcagtggtctcctcagcgatg attcgcaccgcccgcagcataaggcgccttgtcctccgggcacag cagcgcaccctgatctcacttaaatcagcacagtaactgcagcac agcaccacaatattgttcaaaatcccacagtgcaaggcgctgtat ccaaagctcatggcgggggaccacagaacccacgtggccatcatac cacaagcgcaggtagattaagtggcgacccctcataaacacgctg gacataaacattacctcttttggcatgttgtaattcaccacctcc cggtaccatataaacctctgattaaacatggcgccatccaccacc atcctaaaccagctggccaaaacctgcccgccggctatacactgc agggaaccgggactggaacaatgacagtggagagcccaggactcg taaccatggatcatcatgctcgtcatgatatcaatgttggcacaa cacaggcacacgtgcatacacttcctcaggattacaagctcctcc cgcgttagaaccatatcccagggaacaacccattcctgaatcagc gtaaatccacactgcaggaagacctcgcacgtaactcacgttg tgcattgtcaaagtgttacattcgggcagcagcggatgatcctcc
```

-continued

```
agtatggtagcgcgggtttctgtctcaaaaggaggtagacgatcc ctactgtacggagtgcgccgagacaaccgagatcgtgttggtcgt agtgtcatgccaaatggaacgccggacgtagtcatatttcctgaa gcaaaaccaggtgcgggcgtgacaaacagatctgcgtctccggtc tcgccgcttagatcgctctgtgtagtagttgtagtatatccactc tctcaaagcatccaggcgcccctggcttcgggttctatgtaaac tccttcatgcgccgctgccctgataacatccaccaccgcagaata agccacacccagccaacctacacattcgttctgcgagtcacacac gggaggagcgggaagagctggaagaaccatgttttttttttttatt ccaaaagattatccaaaacctcaaaatgaagatctattaagtgaa cgcgctcccctccggtggcgtggtcaaactctacagccaaagaac agataatggcatttgtaagatgttgcacaatggcttccaaaaggc aaacggccctcacgtccaagtggacgtaaaggctaaacccttcag ggtgaatctcctctataaacattccagcaccttcaaccatgccca aataattctcatctcgccaccttctcaatatatctctaagcaaat cccgaatattaagtccggccattgtaaaaatctgctccagagcgc cctccaccttcagcctcaagcagcgaatcatgattgcaaaaattc aggttcctcacagacctgtataagattcaaaagcggaacattaac aaaaataccgcgatcccgtaggtcccttcgcagggccagctgaac ataatcgtgcaggtctgcacggaccagcgcggccacttccccgcc aggaaccatgacaaaagaacccacactgattatgacacgcatact cggagctatgctaaccagcgtagccccgatgtaagcttgttgcat gggcggcgatataaaatgcaaggtgctgctcaaaaaatcaggcaa agcctcgcgcaaaaaagaaagcacatcgtagtcatgctcatgcag ataaaggcaggtaagctccggaaccaccacagaaaaagacaccat ttttctctcaaacatgtctgcgggtttctgcataaacacaaaata aaataacaaaaaaacatttaaacattagaagcctgtcttacaaca ggaaaaacaacccttataagcataagacggactacggccatgccg gcgtgaccgtaaaaaaactggtcaccgtgattaaaaagcaccacc gacagctcctcggtcatgtccggagtcataatgtaagactcggta aacacatcaggttgattcacatcggtcagtgctaaaaagcgaccg aaatagcccgggggaatacatacccgcaggcgtagagacaacatt acagcccccataggaggtataacaaaattaataggagagaaaaac acataaacacctgaaaaaccctcctgcctaggcaaaatagcaccc tcccgctccagaacaacatacagcgcttccacagcggcagccata acagtcagccttaccagtaaaaaagaaaacctattaaaaaaacac cactcgacacggcaccagctcaatcagtcacagtgtaaaaaaggg ccaagtgcagagcgagtatatataggactaaaaaatgacgtaacg gttaaagtccacaaaaaacacccagaaaccgcacgcgaacctac gcccagaaacgaaagccaaaaaacccacaacttcctcaaatcgtc
```

-continued

```
acttccgttttcccacgttacgtcacttcccatttttaagaaaact acaattcccaacacatacaagttactccgccctaaaacctacgtc acccgccccgttcccacgccccgcgccacgtcacaaactccaccc cctcattatcatattggcttcaatccaaaataaggtatattattg atgatgttaattaacatgcatggatcctacgtctcgaccgatgcc cttgagagccttcaacccagtcagctccttccggtgggcgcgggg catgactatcgtcgccgcacttatgactgtcttctttatcatgca actcgtaggacaggtgccggcagcgctctgggtcattttcggcga ggaccgctttcgctggagcgcgacgatgatcggcctgtcgcttgc ggtattcggaatcttgcacgccctcgctcaagccttcgtcactgg tcccgccaccaaacgtttcggcgagaagcaggccattatcgccgg catggcggccgacgcgctgggctacgtcttgctggcgttcgcgac gcgaggctggatggccttccccattatgattcttctcgcttccgg cggcatcgggatgcccgcgttgcaggccatgctgtccaggcaggt agatgacgaccatcagggacagcttcaaggatcgctcgcggctct taccagcctaacttcgatcattggaccgctgatcgtcacggcgat ttatgccgcctcggcgagcacatggaacgggtggcatggattgt aggcgccgccctataccttgtctgcctccccgcgttgcgtcgcgg tgcatggagccgggccacctcgacctgaatggaagccggcggcac ctcgctaacggattcaccactccaagaattggagccaatcaattc ttgcggagaactgtgaatgcgcaaaccaacccttggcagaacata tccatcgcgtccgccatctccagcagccgcacgcggcgcatctcg ggcagcgttgggtcctggccacgggtgcgcatgatcgtgctcctg tcgttgaggacccggctaggctggcgggggttgccttactggttag cagaatgaatcaccgatacgcgagcgaacgtgaagcgactgctgc tgcaaaacgtctgcgacctgagcaacaacatgaatggtcttcggt ttccgtgtttcgtaaagtctggaaacgcggaagtcagcgccctgc accattatgttccggatctgcatcgcaggatgctgctggctaccc tgtggaacacctacatctgtattaacgaagcgctggcattgaccc tgagtgattttttctctggtcccgccgcatccataccgccagttgt ttaccctcacaacgttccagtaaccgggcatgttcatcatcagta acccgtatcgtgagcatcctctctcgtttcatcggtatcattacc cccatgaacagaaatcccccttacacggaggcatcagtgaccaaa caggaaaaaaccgcccttaacatggcccgctttatcagaagccag acattaacgcttctggagaaactcaacgagctggacgcggatgaa caggcagacatctgtgaatcgcttcacgaccacgctgatgagctt taccgcagctgcctcgcgcgtttcggtgatgacggtgaaaacctc tgacacatgcagctcccggagacggtcacagcttgtctgtaagcg gatgccgggagcagacaagcccgtcagggcgcgtcagcgggtgtt ggcgggtgtcggggcgcagccatgacccagtcacgtagcgatagc ggagtgtatactggcttaactatgcggcatcagagcagattgtac
```

-continued

```
tgagagtgcaccatatgcggtgtgaaataccgcacagatgcgtaa ggagaaaataccgcatcaggcgctcttccgcttcctcgctcactg actcgctgcgctcggtcgttcggctgcggcgagcggtatcagctc actcaaaggcggtaatacggttatccacagaatcaggggataacg caggaaagaacatgtgagcaaaaggccagcaaaaggccaggaacc gtaaaaaggccgcgttgctggcgtttttccataggctccgcccccc ctgacgagcatcacaaaaatcgacgctcaagtcagaggtggcgaa acccgacaggactataaagataccaggcgtttccccctggaagct ccctcgtgcgctctcctgttccgaccctgccgcttaccggatacc tgtccgcctttctcccttcgggaagcgtggcgctttctcatagct cacgctgtaggtatctcagttcggtgtaggtcgttcgctccaagc tgggctgtgtgcacgaaccccccgttcagcccgaccgctgcgcct tatccggtaactatcgtcttgagtccaacccggtaagacacgact tatcgccactggcagcagccactggtaacaggattagcagagcga ggtatgtaggcggtgctacagagttcttgaagtggtggcctaact acggctacactagaaggacagtatttggtatctgcgctctgctga agccagttaccttcggaaaaagagttggtagctcttgatccggca aacaaaccaccgctggtagcggtggtttttttgtttgcaagcagc agattacgcgcagaaaaaaaggatctcaagaagatcctttgatct tttctacggggtctgacgctcagtggaacgaaaactcacgttaag ggattttggtcatgagattatcaaaaaggatcttcacctagatcc ttttaaattaaaaatgaagtttttaaatcaatctaaagtatatatg agtaaacttggtctgacagttaccaatgcttaatcagtgaggcac ctatctcagcgatctgtctatttcgttcatccatagttgcctgac tccccgtcgtgtagataactacgatacgggagggcttaccatctg gccccagtgctgcaatgataccgcgagacccacgctcaccggctc cagatttatcagcaataaaccagccagccggaagggccgagcgca gaagtggtcctgcaactttatccgcctccatccagtctattaatt gttgccgggaagctagagtaagtagttcgccagttaatagtttgc gcaacgttgttgccattgctgcaggcatcgtggtgtcacgctcgt cgtttggtatggcttcattcagctccggttcccaacgatcaaggc gagttacatgatcccccatgttgtgcaaaaaagcggttagctcct tcggtcctccgatcgttgtcagaagtaagttggccgcagtgttat cactcatggttatggcagcactgcataattctcttactgtcatgc catccgtaagatgcttttctgtgactggtgagtactcaaccaagt cattctgagaatagtgtatgcggcgaccgagttgctcttgcccgg cgtcaacacgggataataccgcgccacatagcagaactttaaaag tgctcatcattggaaaacgttcttcggggcgaaaactctcaagga tcttaccgctgttgagatccagttcgatgtaacccactcgtgcac ccaactgatcttcagcatcttttactttcaccagcgtttctgggt
```

-continued

```
gagcaaaaacaggaaggcaaaatgccgcaaaaaagggaataagggg cgacacggaaatgttgaatactcatactcttccttttttcaatatt attgaagcatttatcagggttattgtctcatgagcggatacatat ttgaatgtatttagaaaaataaacaaatagggggttccgcgcacat ttccccgaaaagtgccacctgtctagctacgaattcttcgacagc ttcgaaactagaatcgatttcgaaactagcttaagggtgggaaag aatatataaggtgggggtcttatgtagttttgtatctgtttttgca gcagccgccgccgccatgagcaccaactcgtttgatggaagc
``` pAD_Track8509 Adenovirus Packaging or Helper
(SEQ ID NO: 8)

```
ttaattaannntcccttccagctctctgccccttttggattgaag ccaatatgataatgaggggggtggagtttgtgacgtggcgcggggc gtgggaacggggcgggtgacgtagtagtgtggcggaagtgtgatg ttgcaagtgtggcggaacacatgtaagcgacggatgtggcaaaag tgacgtttttggtgtgcgccggtgtacacaggaagtgacaatttt cgcgcggtttaggcggatgttgtagtaaatttgggcgtaaccga gtaagatttggccattttcgcgggaaaactgaataagaggaagtg aaatctgaataattttgtgttactcatagcgcgtaannncgcgtt aagatacattgatgagtttggacaaaccacaactagaatgcagtg aaaaaaatgctttatttgtgaaatttgtgatgctattgctttatt tgtaaccattataagctgcaataaacaagttaacaacaacaattg cattcattttatgtttcaggttcaggggggaggtgtgggaggtttt ttaaagcaagtaaaacctctacaaatgtggtatggctgattatga tcagttatctagatccggtggatctgagtccggacttgtacagct cgtccatgccgagagtgatcccggcggcggtcacgaactccagca ggaccatgtgatcgcgcttctcgttgggctctttgctcagggcgg actgggtgctcaggtagtggttgtcgggcagcagcacgggggccgt cgccgatggggggtgttctgctggtagtggtcggcgagctgcacgc tgccgtcctcgatgttgtggcggatcttgaagttcaccttgatgc cgttcttctgcttgtcggccatgatatagacgttgtggctgttgt agttgtactccagcttgtgccccaggatgttgccgtcctccttga agtcgatgcccttcagctcgatgcggttcaccagggtgtcgccct cgaacttcacctcggcgcgggtcttgtagttgccgtcgtccttga agaagatggtgcgctcctggacgtagccttcgggcatggcggact tgaagaagtcgtgctgcttcatgtggtcggggtagcggctgaagc actgcacgccgtaggtcagggtggtcacgagggtgggccagggca cgggcagcttgccggtggtgcagatgaacttcagggtcagcttgc cgtaggtggcatcgccctcgccctcgccggacacgctgaacttgt ggccgtttacgtcgccgtccagctcgaccaggatgggcaccaccc cggtgaacagctcctcgcccttgctcaccatggtggcgaccggta gcgctagcggatctgacggttcactaaaccagctctgcttatata gacctcccaccgtacacgcctaccgcccatttgcgtcaatggggc
```

-continued

```
ggagttgttacgacattttggaaagtcccgttgattttggtgcca aaacaaactcccattgacgtcaatggggtggagacttggaaatcc ccgtgagtcaaaccgctatccacgcccattgatgtactgccaaaa ccgcatcaccatggtaatagcgatgactaatacgtagatgtactg ccaagtaggaaagtcccataaggtcatgtactgggcataatgcca ggcgggccatttaccgtcattgacgtcaatagggggcgtacttgg catatgatacacttgatgtactgccaagtgggcagtttaccgtaa atactccacccattgacgtcaatggaaagtccctattggcgttac tatgggaacatacgtcattattgacgtcaatgggcgggggtcgtt gggcggtcagccaggcgggccatttaccgtaagttatgtaacgcg gaactccatatatgggctatgaactaatgaccccgtaattgatta ctattannnctagcagatctggtaccgtcgacgcggccgcgatat cctcgagaagctttctagagnnntaagggtgggaaagaatatata aggtgggggtcttatgtagttttgtatctgtttttgcagcagccgc cgccgccatgagcaccaactcgtttgatggaagcattgtgagctc atatttgacaacgcgcatgcccccatgggccggggtgcgtcagaa tgtgatgggctccagcattgatggtcgccccgtcctgcccgcaaa ctctactaccttgacctacgagaccgtgtctggaacgccgttgga gactgcagcctccgccgccgcttcagccgctgcagccaccgcccg cgggattgtgactgactttgctttcctgagcccgcttgcaagcag tgcagcttcccgttcatccgcccgcgatgacaagttgacggctct tttggcacaattggattctttgaccccgggaacttaatgtcgtttc tcagcagctgttggatctgcgccagcaggtttctgccctgaaggc ttcctcccctcccaatgcggtttaaaacataaataaaaaaccaga ctctgtttggatttggatcaagcaagtgtcttgctgtctttattt aggggtttttgcgcgcgcggtaggcccgggaccagcggtctcggtc gttgagggtcctgtgtattttttccaggacgtggtaaaggtgact ctggatgttcagatacatgggcataagcccgtctctggggtggag gtagcaccactgcagagcttcatgctgcggggtggtgttgtagat gatccagtcgtagcaggagcgctgggcgtggtgcctaaaaatgtc tttcagtagcaagctgattgccaggggcaggcccttggtgtaagt gtttacaaagcggttaagctgggatgggtgcatacgtggggatat gagatgcatcttgactgtattttttaggttggctatgttcccagc catatccctccggggattcatgttgtgcagaaccaccagcacagt gtatccggtgcacttgggaaatttgtcatgtagcttagaaggaaa tgcgtggaagaacttggagacgcccttgtgacctccaagattttc catgcattcgtccataatgatggcaatgggcccacgggcggcggc ctgggcgaagatatttctgggatcactaacgtcatagttgtgttc caggatgagatcgtcataggccatttttacaaagcgcgggcggag ggtgccagactgcggtataatggttccatccggcccaggggcgta
```

-continued

```
gttaccctcacagatttgcatttcccacgctttgagttcagatgg ggggatcatgtctacctgcggggcgatgaagaaaacggtttccgg ggtaggggagatcagctgggaagaaagcaggttcctgagcagctg cgacttaccgcagccggtgggccgtaaatcacacctattaccgg gtgcaactggtagttaagagagctgcagctgccgtcatccctgag caggggggccacttcgttaagcatgtccctgactcgcatgttttc cctgaccaaatccgccagaaggcgctcgccgcccagcgatagcag ttcttgcaaggaagcaaagttttttcaacggtttgagaccgtccgc cgtaggcatgcttttgagcgtttgaccaagcagttccaggcggtc ccacagctcggtcacctgctctacggcatctcgatccagcatatc tcctcgtttcgcgggttggggcggctttcgctgtacggcagtagt cggtgctcgtccagacgggccagggtcatgtctttccacgggcgc agggtcctcgtcagcgtagtctgggtcacggtgaaggggtgcgct ccgggctgcgcgctggccagggtgcgcttgaggctggtcctgctg gtgctgaagcgctgccggtcttcgccctgcgcgtcggccaggtag catttgaccatggtgtcatagtccagcccctccgcggcgtggccc ttggcgcgcagcttgcccttggaggaggcgccgcacgaggggcag tgcagactttgagggcgtagagcttgggcgcgagaaataccgat tccgggagtaggcatccgcgccgcaggccccgcagacggtctcg cattccacgagccaggtgagctctggccgttcggggtcaaaaacc aggtttcccccatgcttttgatgcgtttcttacctctggtttcc atgagccggtgtccacgctcggtgacgaaaaggctgtccgtgtcc ccgtatacagactnnngtttaaacgaattcnnntatataaaatgcaa ggtgctgctcaaaaaatcaggcaaagcctcgcgcaaaaaagaaag cacatcgtagtcatgctcatgcagataaaggcaggtaagctccgg aaccaccacagaaaaagacaccattttttctctcaaacatgtctgc gggtttctgcataaacacaaataaaataacaaaaaaacatttaa acattagaagcctgtcttacaacaggaaaaacaacccttataagc ataagacggactacggccatgccggcgtgaccgtaaaaaaactgg tcaccgtgattaaaaagcaccaccgacagctcctcggtcatgtcc ggagtcataatgtaagactcggtaaacacatcaggttgattcatc ggtcagtgctaaaaagcgaccgaaatagcccgggggaatacatac ccgcaggcgtagagacaacattacagcccccataggaggtataac aaaattaataggagagaaaaacacataaacacctgaaaaaccctc ctgcctaggcaaaatagcaccctcccgctccagaacaacatacag cgcttcacagcggcagcctaacagtcagccttaccagtaaaaaag aaaacctattaaaaaaacaccactcgacacggcaccagctcaatc agtcacagtgtaaaaaagggcaagtgcagagcgagtatatatag gactaaaaaatgacgtaacggttaaagtccacaaaaaacacccag aaaaccgcacgcgaacctacgcccagaaacgaaagccaaaaaacc cacaacttcctcaaatcgtcacttccgttttcccacgttacgtaa
```

-continued

```
cttcccattttaagaaaactacaattcccaacacatacaagttac tccgccctaaaacctacgtcacccgcccgttcccacgccccgcg ccacgtcacaaactccacccctcattatcatattggcttcaatc caaaataaggtatattattgatgatnnnttaattaaggatccnnn cggtgtgaaataccgcacagatgcgtaaggagaaaataccgcatc aggcgctcttccgcttcctcgctcactgactcgctgcgctcggtc gttcggctgcggcgagcggtatcagctcactcaaaggcggtaata cggttatccacagaatcaggggataacgcaggaaagaacatgtga gcaaaaggccagcaaaaggccaggaaccgtaaaaaggccgcgttg ctggcgtttttccataggctccgcccccctgacgagcatcacaaa aatcgacgctcaagtcagaggtggcgaaacccgacaggactataa agataccaggcgtttccccctggaagctccctcgtgcgctctcct gttccgaccctgccgcttaccggatacctgtccgcctttctccct tcgggaagcgtggcgctttctcatagctcacgctgtaggtatctc agttcggtgtaggtcgttcgctccaagctgggctgtgtgcacgaa ccccccgttcagcccgaccgctgcgccttatccggtaactatcgt cttgagtccaacccggtaagacacgacttatcgccactggcagca gccactggtaacaggattagcagagcgaggtatgtaggcggtgct acagagttcttgaagtggtggcctaactacggctacactagaagg acagtatttggtatctgcgctctgctgaagccagttaccttcgga aaaagagttggtagctcttgatccggcaaacaaaccaccgctggt agcggtggtttttttgtttgcaagcagcagattacgcgcagaaaa aaaggatctcaagaagatcctttgatcttttctacggggtctgac gctcagtggaacgaaaactcacgttaagggattttggtcatgaga ttatcaaaaaggatcttcacctagatcctttttaaattaaaaatga agttttaaatcaatctaaagtatatatgagtaaacttggtctgac agttaccaatgcttaatcagtgaggcacctatctcagcgatctgt ctatttcgttcatccatagttgcctgactccccgtcgtgtagata actacgatacgggagggcttaccatctggccccagtgctgcaatg ataccgcgagacccacgctcaccggctccagatttatcagcaata aaccagccagccggaagggccgagcgcagaagtggtcctgcaact ttatccgcctccatccagtctattaattgttgccgggaagctaga gtaagtagttcgccagttaatagtttgcgcaacgttgttgnnnnn naaaaaggatcttcacctagatcctttttcacgtagaaagccagtc cgcagaaacggtgctgaccccggatgaatgtcagctactgggcta tctggacaagggaaaacgcaagcgcaaagagaaagcaggtagctt gcagtgggcttacatggcgatagctagactgggcggttttatgga cagcaagcgaaccggaattgccagctggggcgccctctggtaagg ttgggaagccctgcaaagtaaactggatggctttctcgccgccaa ggatctgatggcgcaggggatcaagctctgatcaagagacaggat
```

-continued

```
gaggatcgtttcgcatgattgaacaagatggattgcacgcaggtt ctccggccgcttgggtggagaggctattcggctatgactgggcac aacagacaatcggctgctctgatgccgccgtgttccggctgtcag cgcaggggcgcccggttcttttttgtcaagaccgacctgtccggtg ccctgaatgaactgcaagacgaggcagcgcggctatcgtggctgg ccacgacgggcgttccttgcgcagctgtgctcgacgttgtcactg aagcgggaagggactggctgctattgggcgaagtgccggggcagg atctcctgtcatctcaccttgctcctgccgagaaagtatccatca tggctgatgcaatgcggcggctgcatacgcttgatccggctacct gcccattcgaccaccaagcgaaacatcgcatcgagcgagcacgta ctcggatggaagccggtcttgtcgatcaggatgatctggacgaag agcatcaggggctcgcgccagccgaactgttcgccaggctcaagg cgagcatgcccgacggcgaggatctcgtcgtgacccatggcgatg cctgcttgccgaatatcatggtggaaaatggccgcttttctggat tcatcgactgtggccggctgggtgtggcggaccgctatcaggaca tagcgttggctacccgtgatattgctgaagagcttggcggcgaat gggctgaccgcttcctcgtgctttacggtatcgccgctcccgatt cgcagcgcatcgccttctatcgccttcttgacgagttcttctgaa ttttgttaaaattttttgttaaatcagctcatttttttaaccaatag gccgaaatcggcaacatcccttataaatcaaaagaatagaccgcg ataggggttgagtgttgttccagtttggaacaagagtccactatta aagaacgtggactccaacgtcaaagggcgaaaaaccgtctatcag ggcgatggcccactacgtgaaccatcacccaaatcaagttttttg cggtcgaggtgccgtaaagctctaaatcggaaccctaaagggagc ccccgatttagagcttgacggggaaagccggcgaacgtggcgaga aaggaagggaagaaagcgaaaggagcgggcgctagggcgctggca agtgtagcggtcacgctgcgcgtaaccaccacacccgcgcgctta atgcgccg
``` pAdTrack-CMV Sequence190476 Adenovirus
Packaging or Helper (SEQ ID NO: 9)
```
tgttaacttgtttattgcagcttataatggttacaaataaagcaa tagcatcacaaatttcacaaataaagcattttttttcactgcattc tagttgtggtttgtccaaactcatcaatgtatcttaacgcggagg tttatcgacgatctgctagtgattaatagtaatcaattacgggt cattagttcatagcccatatatggagttccgcgttacataactta cggtaaatggcccgcctggctgaccgcccaacgaccccgcccat tgacgtcaataatgacgtatgttcccatagtaacgccaataggga ctttccattgacgtcaatgggtggagtatttacggtaaactgccc acttggcagtacatcaagtgtatcatatgccaagtacgcccccta ttgacgtcaatgacggtaaatggcccgcctggcattatgcccagt acatgaccttatgggactttcctacttggcagtacatctacgtat
```

-continued

```
tagtcatcgctattaccatggtgatgcggttttggcagtacatca atgggcgtggatagcggtttgactcacggggatttccaagtctcc accccattgacgtcaatgggagtttgttttggcaccaaaatcaac gggactttccaaaatgtcgtaacaactccgccccattgacgcaaa tgggcggtaggcgtgtacggtgggaggtctatataagcagagctg gtttagtgaaccgtcagatccgctagcgctaccggtcgccaccat ggtgagcaagggcgaggagctgttcaccggggtggtgcccatcct ggtcgagctggacggcgacgtaaacggccacaagttcagcgtgtc cggcgagggcgagggcgatgccacctacggcaagctgaccctgaa gttcatctgcaccaccggcaagctgcccgtgccctggcccaccct cgtgaccaccctgacctacggcgtgcagtgcttcagccgctaccc cgaccacatgaagcagcacgacttcttcaagtccgccatgcccga aggctacgtccaggagcgcaccatcttcttcaaggacgacggcaa ctacaagacccgcgccgaggtgaagttcgagggcgacaccctggt gaaccgcatcgagctgaagggcatcgacttcaaggaggacggcaa catcctggggcacaagctggagtacaactacaacagccacaacgt ctatatcatggccgacaagcagaagaacggcatcaaggtgaactt caagatccgccacaacatcgaggacggcagcgtgcagctcgccga ccactaccagcagaacacccccatcggcgacggccccgtgctgct gcccgacaaccactacctgagcacccagtccgccctgagcaaaga ccccaacgagaagcgcgatcacatggtcctgctggagttcgtgac cgccgccgggatcactctcggcatggacgagctgtacaagtccgg actcagatccaccggatctagataactgatcataatcagccatac cacatttgtagaggttttacttgctttaaaaaacctcccacacct ccccctgaacctgaaacataaaatgaatgcaattgttgttgttaa cttgtttattgcagcttataatggttacaaataaagcaatagcat cacaaatttcacaaataaagcattttttttcactgcattctagttg tggtttgtccaaactcatcaatgtatcttaacgcgatcaagctag cttgctagactcgactgactataataataaaacgccaactttgac ccggaacgcggaaaacacctgagaaaaacacctgggcgagtctcc acgtaaacggtcaaagtccccgcggccctagacaaatattacgcg ctatgagtaacacaaaattattcagatttcacttcctcttattca gttttcccgcgaaaatggccaaatcttactcggttacgcccaaat ttactacaacatccgcctaaaaccgcgcgaaaattgtcacttcct gtgtacaccggcgcacaccaaaaacgtcacttttgccacatccgt cgcttacatgtgttccgccacacttgcaacatcacacttccgcca cactactacgtcacccgccccgttcccacgccccgcgccacgtca caaactccacccctcattatcatattggcttcaatccaaaataa ggtatattattgatgatgttaattaagaattaattcgatcctgaa tggcgaatggacgcgccctgtagcggcgcattaagcgcggcgggt gtggtggttacgcgcagcgtgaccgctacacttgccagcgccta
```

-continued gcgcccgctcctttcgctttcttcccttcctttctcgccacgttc gccggctttccccgtcaagctctaaatcggggggctcccctttaggg ttccgatttagtgctttacggcacctcgaccccaaaaaacttgat tagggtgatggttcacgtagtgggccatcgccctgatagacggtt tttcgccctttgacgttggagtccacgttctttaatagtggactc ttgttccaaactggaacaacactcaaccctatctcggtctattct tttgatttataagggattttgccgatttcggcctattggttaaaa aatgagctgatttaacaaaaattttaacaaaattcagaagaactc gtcaagaaggcgatagaaggcgatgcgctgcgaatcgggagcggc gataccgtaaagcacgaggaagcggtcagcccattcgccgccaag ctcttcagcaatatcacgggtagccaacgctatgtcctgatagcg gtccgccacacccagccggccacagtcgatgaatccagaaaagcg gccattttccaccatgatattcggcaagcaggcatcgccatgggt cacgacgagatcctcgccgtcgggcatgctcgccttgagcctggc gaacagttcggctggcgcgagcccctgatgctcttcgtccagatc atcctgatcgacaagaccggcttccatccgagtacgtgctcgctc gatgcgatgtttcgcttggtggtcgaatgggcaggtagccggatc aagcgtatgcagccgccgcattgcatcagccatgatggatacttt ctcggcaggagcaaggtgagatgacaggagatcctgccccggcac ttcgcccaatagcagccagtcccttcccgcttcagtgacaacgtc gagcacagctgcgcaaggaacgcccgtcgtggccagccacgatag ccgcgctgcctcgtcttgcagttcattcagggcaccggacaggtc ggtcttgacaaaaagaaccgggcgcccctgcgctgacagccggaa cacggcggcatcagagcagccgattgtctgttgtgcccagtcata gccgaatagcctctccacccaagcggccggagaacctgcgtgcaa tccatcttgttcaatcatgcgaaacgatcctcatcctgtctcttg atcagagcttgatcccctgcgccatcagatccttggcggcaagaa agccatccagtttactttgcagggcttcccaaccttaccagaggg cgccccagctggcaattccggttcgcttgctgtccataaaaccgc ccagtctagctatcgccatgtaagcccactgcaagctacctgctt tctctttgcgcttgcgttttccttgtccagatagcccagtagct gacattcatccggggtcagcaccgtttctgcggactggctttcta cgtgaaaaggatctaggtgaagatcctttttgataatctcatggc tgcagcaatggcaacaacgttgcgcaaactattaactggcgaact acttactctagcttcccggcaacaattaatagactggatggaggc ggataaagttgcaggaccacttctgcgctcggcccttccggctgg ctggtttattgctgataaatctggagccggtgagcgtgggtctcg cggtatcattgcagcactggggccagatggtaagccctcccgtat cgtagttatctacacgacggggagtcaggcaactatggatgaacg aaatagacagatcgctgagataggtgcctcactgattaagcattg -continued gtaactgtcagaccaagtttactcatatatactttagattgattt aaaacttcattttttaatttaaaaggatctaggtgaagatcctttt tgataatctcatgaccaaaatcccttaacgtgagttttcgttcca ctgagcgtcagaccccgtagaaaagatcaaaggatcttcttgaga tccttttttttctgcgcgtaatctgctgcttgcaaacaaaaaaacc accgctaccagcggtggtttgtttgccggatcaagagctaccaac tcttttccgaaggtaactggcttcagcagagcgcagataccaaa tactgtccttctagtgtagccgtagttaggccaccacttcaagaa ctctgtagcaccgcctacatacctcgctctgctaatcctgttacc agtggctgctgccagtggcgataagtcgtgtcttaccgggttgga ctcaagacgatagttaccggataaaggcgcagcggtcgggctgaac ggggggttcgtgcacacagcccagcttggagcgaacgacctacac cgaactgagatacctacagcgtgagctatgagaaagcgccacgct tcccgaagggagaaaggcggacaggtatccggtaagcggcagggt cggaacaggagagcgcacgagggagcttccaggggggaaacgcctg gtatctttatagtcctgtcgggtttcgccacctctgacttgagcg tcgatttttgtgatgctcgtcaggggggcggagcctatggaaaaa cgccagcaacgcggcctttttacggttcctggccttttgctggcc ttttgctcacatgttctttcctgcgttatcccctgattctgtgga taaccgtattaccgcctttgagtgagctgataccgctcgccgcag ccgaacgaccgagcgcagcgagtcagtgagcgaggaagcggaaga gcgcctgatgcggtattttctccttacgcatctgtgcggtatttc acaccgcatatggatccatgcatgttaattaacatcatcaataat ataccttattttggattgaagccaatatgataatgagggggtgga gtttgtgacgtggcgcggggcgtgggaacggggcgggtgacgtag gttttagggcggagtaacttgtatgtgttgggaattgtagttttc ttaaaatgggaagtgacgtaacgtgggaaaacggaagtgacgatt tgaggaagttgtgggtttttggctttcgtttctgggcgtaggtt cgcgtgcggttttctgggtgtttttttgtggacttaaccgttacg tcattttttagtcctatatatactcgctctgcacttggcccttttt ttacctgtgactgattgagctggtgccgtgtcgagtggtgttttt tttaataggttttcttttttactggtaaggctgactgttatggct gccgctgtggaagcgctgtatgttgttctggagcgggagggtgct attttgcctaggcaggagggttttcaggtgtttatgtgtttttttc tctcctattaattttgttatacctcctatgggggcgtgtaatgttg tctctacgcctgcgggtatgtattcccccgggctatttcggtcgc tttttagcactgaccgatgtgaatcaacctgatgtgtttaccgag tcttacattatgactccggacatgaccgaggagctgtcggtggtg cttttttaatcacggtgaccagttttttttacggtcacgccggcatg gccgtagtccgtcttatgcttataagggttgttttttcctgttgta agacaggcttctaatgtttaaatgtttttttttgttattttatttttg -continued

```
tgtttatgcagaaacccgcagacatgtttgagagaaaaatggtgt ctttttctgtggtggttccggagcttacctgcctttatctgcatg agcatgactacgatgtgctttcttttttgcgcgaggctttgcctg attttttgagcagcaccttgcattttatatcgccgcccatgcaac aagctattgaattcgtttaaactccctctcaagtctgtatacggg gacacggacagcctttcgtcaccgagcgtggacaccggctcatg gaaaccagaggtaagaaacgcatcaaaaagcatgggggaaacctg gttttttgaccccgaacggccagagctcacctggctcgtggaatgc gagaccgtctgcgggggcctgcggcgcggatgcctactccccggaa tcggtatttctcgcgcccaagctctacgccctcaaaagtctgcac tgcccctcgtgcggcgcctcctccaagggcaagctgcgcgccaag ggccacgccgcggagggctggactatgacaccatggtcaaatgc tacctggccgacgcgcagggcgaagaccggcagcgcttcagcacc agcaggaccagcctcaagcgcaccctggccagcgcgcagcccgga gcgcacccttcaccgtgacccagactacgctgacgaggaccctg cgcccgtggaaagacatgaccctggcccgtctggacgagcaccga ctactgccgtacagcgaaagccgccccaacccgcgaaacgaggag atatgctggatcgagatgccgtagagcaggtgaccgagctgtggg accgcctggaactgcttggtcaaacgctcaaaagcatgcctacgg cggacggtctcaaaccgttgaaaaactttgcttccttgcaagaac tgctatcgctgggcggcgagcgccttctggcggatttggtcaggg aaaacatgcgagtcagggacatgcttaacgaagtggccccccctgc tcagggatgacggcagctgcagctctcttaactaccagttgcagc cggtaataggtgtgatttacgggcccaccggctgcggtaagtcgc agctgctcaggaacctgctttcttcccagctgatctcccctaccc cggaaaccgttttcttcatcgccccgcaggtagacatgatccccc catctgaactcaaagcgtgggaaatgcaaatctgtgagggtaact acgcccctgggccggatggaaccattataccgcagtctggcaccc tccgcccgcgctttgtaaaaatggcctatgacgatctcatcctgg aacacaactatgacgttagtgatcccagaaatatcttcgcccagg ccgccgcccgtgggcccattgccatcattatggacgaatgcatgg aaaatcttggaggtcacaagggcgtctccaagttcttccacgcat ttccttctaagctacatgacaaatttcccaagtgcaccggataca ctgtgctggtggttctgcacaacatgaatccccggagggatatgg ctgggaacatagccaacctaaaaatacagtccaagatgcatctca tatccccacgtatgcacccatcccagcttaaccgctttgtaaaca cttacaccaagggcctgcccctggcaatcagcttgctactgaaag acatttttaggcaccacgcccagcgctcctgctacgactggatca tctacaacaccacccgcagcatgaagctctgcagtggtgctacc tccaccccagagacgggcttatgcccatgtatctgaacatccaga
```

-continued

```
gtcacctttaccacgtcctggaaaaaatacacacaggaccctcaacg accgagaccgctggtcccgggcctaccgcgcgcgcaaaacccta aataaagacagcaagacacttgcttgatccaaatccaaacagagt ctggttttttatttatgttttaaaccgcattgggaggggaggaag ccttcagggcagaaacctgctggcgcagatccaacagctgctgag aaacgacattaagttcccgggtcaaagaatccaattgtgccaaaa gagccgtcaacttgtcatcgcgggcggatgaacgggaagctgcac tgcttgcaagcgggctcaggaaagcaaagtcagtcacaatcccgc gggcggtggctgcagcggctgaagcggcggcggaggctgcagtct ccaacggcgttccagacacggtctcgtaggtcaaggtagtagagt ttgcgggcaggacggggcgaccatcaatgctggagcccatcacat tctgacgcacccggcccatgggggcatgcgcgttgtcaaatatg agctcacaatgcttccatcaaacgagttggtgctcatggcggcgg cggctgctgcaaaacagatacaaaactacataagacccccacctt atatattctttcccacccttaaccacgcccagatcctctagcagt gataaacgtctaatagtaatcaattacggggtcattagttcatag cccatatatggagttccgcgttacataacttacggtaaatggccc gcctggctgaccgcccaacgacccccgcccattgacgtcaataat gacgtatgttcccatagtaacgccaatagggactttccattgacg tcaatgggtggagtatttacggtaaactgcccacttggcagtaca tcaagtgtatcatatgccaagtacgcccctattgacgtcaatga cggtaaatggcccgcctggcattatgcccagtacatgaccttatg ggactttcctacttggcagtacatctacgtattagtcatcgctat taccatggtgatgcggttttggcagtacatcaatgggcgtggata gcggtttgactcacggggatttccaagtctccacccattgacgt caatgggagtttgttttggcaccaaaatcaacgggactttccaaa atgtcgtaacaactccgccccattgacgcaaatgggcggtaggcg tgtacggtgggaggtctatataagcagagctggtttagtgaaccg tcagatccgctagagatctggtaccgtcgacgcggccgctcgagc ctaagcttctagataagatatccgatccaccggatctagataact gatcataatcagccataccacatttgtagaggttttacttgcttt aaaaaacctcccacacctcccctgaacctgaaacataaaatgaa tgcaattgttgt
``` pZB3 AAV dSaCas9 One Vector (SEQ ID NO: 10)

```
aaaacctctgacacatgcagctcccggagacggtcacagcttgtc tgtaagcggatgccggggagcagacaagcccgtcagggcgcgtcag cgggtgttggcgggtgtcggggctggcttaactatgcggcatcag agcagattgtactgagagtgcaccataaaaattgtaaacgttaata ttttgttaaaattcgcgttaaattttttgttaaatcagctcatttt ttaaccaatagaccgaaatcggcaaaatcccttataaatcaaaag aatagcccgagatagagttgagtgttgttccagtttggaacaaga
```

-continued gtccactattaaagaacgtggactccaacgtcaaagggcgaaaaa ccgtctatcagggcgatggcccactacgtgaaccatcacccaaat caagttttttggggtcgaggtgccgtaaagcactaaatcggaacc ctaaagggagccccgatttagagcttgacggggaaagccggcga acgtggcgagaaaggaagggaagaaagcgaaaggagcgggcgcta aggcgctggcaagtgtagcggtcacgctgcgcgtaaccaccacac ccgccgcgcttaatgcgccgctacagggcgcgtactatggttgct ttgacgtatgcggtgtgaaataccgcacagatgcgtaaggagaaa ataccgcatcaggcgccctgcaggcagctgcgcgctcgctcgct cactgaggccgcccgggcaaagcccgggcgtcgggcgacctttgg tcgcccggcctcagtgagcgagcgagcgcgcagagagggagtggc caactccatcactagggggttcctgcggccgcgagggcctatttcc catgattccttcatatttgcatatcgatacaaggctgttagaga gataattggaattaatttgactgtaaacacaaagatattagtaca aaatacgtgacgtagaaagtaataatttcttgggtagtttgcagt tttaaaattatgtttaaaatggactatcatatgcttaccgtaac ttgaaagtatttcgatttcttggctttatatatcttgtggaaagg acgaaacaccgggagaccacggcaggtctcagttttagtactctg gaggccAACATGAGGATCACCCATGTCTGCAGggccaacagaatc tactaaaacaaggcaaaatgccgtgtttatctcgtcaacttgttg gcgagatttttttggccgcctcgaggtacttatataaggggggtgg gggcgcgttcgtcctcagtcgcgatcgaacactcgagccgagcag acgtgcctacgaccgaccggtgccaccatggccccaaagaagaa gcggaaggtcggtatccacggagtcccagcagccaagcggaacta catcctgggcctggccatcggcatcaccagcgtgggctacggcat catcgactacgagacacgggacgtgatcgatgccggcgtgcggct gttcaaagaggccaacgtggaaaacaacgagggcaggcggagcaa gagaggcgccagaaggctgaagcggcggaggcggcatagaatcca gagagtgaagaagctgctgttcgactacaacctgctgaccgacca cagcgagctgagcggcatcaacccctacgaggccagagtgaaggg cctgagccagaagctgagcgaggaagagttctctgccgccctgct gcacctggccaagagaagaggcgtgcacaacgtgaacgaggtgga agaggacaccggcaacgagctgtccaccaaagagcagatcagccg gaacagcaaggccctggaagagaaatacgtggccgaactgcagct ggaacggctgaagaaagacggcgaagtgcggggcagcatcaacag attcaagaccagcgactacgtgaaagaagccaaacagctgctgaa ggtgcagaaggcctaccaccagctggaccagagcttcatcgacac ctacatcgacctgctggaaacccggcggacctactatgagggacc tggcgagggcagcccccttcggctggaaggacatcaaagaatggta cgagatgctgatgggccactgcacctacttccccgaggaactgcg -continued gagcgtgaagtacgcctacaacgccgacctgtacaacgccctgaa cgacctgaacaatctcgtgatcaccagggacgagaacgagaagct ggaatattacgagaagttccagatcatcgagaacgtgttcaagca gaagaagaagcccaccctgaagcagatcgccaaagaaatcctcgt gaacgaagaggatattaagggctacagagtgaccagcaccggcaa gcccgagttcaccaacctgaaggtgtaccacgacatcaaggacat taccgcccggaaagagattattgagaacgccgagctgctggatca gattgccaagatcctgaccatctaccagagcagcgaggacatcca ggaagaactgaccaatctgaactccgagctgacccaggaagagat cgagcagatctctaatctgaagggctataccggcacccacaacct gagcctgaaggccatcaacctgatcctggacgagctgtggcacac caacgacaaccagatcgctatcttcaaccggctgaagctggtgcc caagaaggtggacctgtcccagcagaaagagatccccaccacct ggtggacgacttcatcctgagccccgtcgtgaagagaagcttcat ccagagcatcaaagtgatcaacgccatcatcaagaagtacggcct gcccaacgacatcattatcgagctggcccgcgagaagaactccaa ggacgcccagaaaatgatcaacgagatgcagaagcggaaccggca gaccaacgagcggatcgaggaaatcatccggaccaccggcaaaga gaacgccaagtacctgatcgagaagatcaagctgcacgacatgca ggaaggcaagtgcctgtacagcctggaagccatccctctggaaga tctgctgaacaacccccttcaactatgaggtggaccacatcatccc cagaagcgtgtccttcgacaacagcttcaacaacaaggtgctcgt gaagcaggaagaagccagcaagaagggcaaccggaccccattcca gtacctgagcagcagcgacagcaagatcagctacgaaaaccttcaa gaagcacatcctgaatctggccaagggcaagggcagaatcagcaa gaccaagaaagagtatctgctggaagaacgggacatcaacaggtt ctccgtgcagaaagacttcatcaaccggaacctggtggataccag atacgccaccagaggcctgatgaacctgctgcgggagctacttcag agtgaacaacctggacgtgaaagtgaagtccatcaatggcggctt caccagctttctgcggcggaagtggaagtttaagaaagagcggaa caagggtacaagcaccacgccgaggacgccctgatcattgccaa cgccgatttcatcttcaaagagtggaagaaactggacaaggccaa aaaagtgatggaaaaccagatgttcgaggaaaagcaggccgagag catgcccgagatcgaaaccgagcaggagtacaaagagatcttcat cacccccaccagatcaagcacattaaggacttcaaggactacaa gtacagccaccgggtggacaagaagcctaatagagagctgattaa cgacaccctgtactccacccggaaggacgacaagggcaacaccct gatcgtgaacaatctgaacggcctgtacgacaaggacaatgacaa gctgaaaaagctgatcaacaagagccccgaaaagctgctgatgta ccaccacgaccccagacctaccagaaactgaagctgattatgga acagtacggcgacgagaagaatcccctgtacaagtactacgagga -continued

```
aaccgggaactacctgaccaagtactccaaaaaggacaacggccc cgtgatcaagaagattaagtattacggcaacaaactgaacgccca tctggacatcaccgacgactaccccaacagcagaaacaaggtcgt gaagctgtccctgaagccctacagattcgacgtgtacctggacaa tggcgtgtacaagttcgtgaccgtgaagaatctggatgtgatcaa aaaagaaaactactacgaagtgaatagcaagtgctatgaggaagc taagaagctgaagaagatcagcaaccaggccgagtttatcgcctc cttctacaacaacgatctgatcaagatcaacggcgagctgtatag agtgatcggcgtgaacaacgacctgctgaaccggatcgaagtgaa catgatcgacatcacctaccgcgagtacctggaaaacatgaacga caagaggccccccaggatcattaagacaatcgcctccaagaccca gagcattaagaagtacagcacagacattctgggcaacctgtatga agtgaaatctaagaagcaccctcagatcatcaaaaagggcaaaag gccggcggccacgaaaaaggccggccaggcaaaaaagaaaaaggg atccgaggccagcggttccggacgggctgacgcattggacgattt tgatctggatatgctgggaagtgacgccctcgatgattttgacct tgacatgcttggttcggatgcccttgatgactttgacctcgacat gctcggcagtgacgcccttgatgattcgacctggacatgctgat taactctagaagttccggatctccgaaaaagaaacgcaaagttgg ttcgggaggtggttcgggtggctctggatcagtgctgcctcaggc tcctgctcctgcaccagctccagccatggtgtctgcactggctca ggcaccagcacccgtgcctgtgctggctcctggacctccacaggc tgtggctccaccagcccctaaacctacacaggccggcgagggcac actgtctgaagctctgctgcagctgcagttcgacgacgaggatct gggagccctgctgggaaacagcaccgatcctgccgtgttcaccga cctggccagcgtggacaacagcgagttccagcagctgctgaacca gggcatccctgtggcccctcacaccaccgagcccatgctgatgga ataccccgaggccatcacccggctcgtgacaggcgctcagaggcc tcctgatccagctcctgcccctctgggagcaccaggcctgcctaa tggactgctgtctggcgacgaggacttcagctctatcgccgatat ggatttctcagccttgctgtcaggcggtggtagtggtgggagcgg tagtgacctttcccatccgcccccaaggggccatctggatgagct gacaaccacacttgagtccatgaccgaggatctgaacctggactc accccctgaccccggaattgaacgagattctggataccttcctgaa cgacgagtgcctcttgcatgccatgcatatcagcacaggactgtc catcttcgacacatctctgttttaggaattcaaataaaatacgaa atgaaataaaatacgaaatgcaattgggccgcaggaaccccctagt gatggagttggccactccctctctgcgcgctcgctcgctcactga ggccgggcgaccaaaggtcgcccgacgcccgggctttgcccgagc ggcctcagtgagcgagcgagcgcgcagctgcctgcaggacatgtg
```

-continued

```
agcaaaaggccagcaaaaggccaggaaccgtaaaaaggccgcgtt gctggcgtttttccataggctccgcccccctgacgagcatcacaa aaatcgacgctcaagtcagaggtggcgaaacccgacaggactata aagataccaggcgtttccccctggaagctccctcgtgcgctctcc tgttccgaccctgccgcttaccggatacctgtccgcctttctccc ttcgggaagcgtggcgctttctcatagctcacgctgtaggtatct cagttcggtgtaggtcgttcgctccaagctgggctgtgtgcacga accccccgttcagcccgaccgctgcgccttatccggtaactatcg tcttgagtccaacccggtaagacacgacttatcgccactggcagc agccactggtaacaggattagcagagcgaggtatgtaggcggtgc tacagagttcttgaagtggtggcctaactacggctacactagaag aacagtatttggtatctgcgctctgctgaagccagttaccttcgg aaaaagagttggtagctcttgatccggcaaacaaaccaccgctgg tagcggtggtttttttgtttgcaagcagcagattacgcgcagaaa aaaaggatctcaagaagatcctttgatcttttctacggggtctga cgctcagtggaacgaaaactcacgttaagggattttggtcatgag attatcaaaaaggatcttcacctagatccttttaaattaaaaatg aagttttaaatcaatctaaagtatatatgagtaaacttggtctga cagttaccaatgcttaatcagtgaggcacctatctcagcgatctg tctatttcgttcatccatagttgcctgactccccgtcgtgtagat aactacgatacgggagggcttaccatctggccccagtgctgcaat gataccgcggcttccacgctcaccggctccagatttatcagcaat aaaccagccagccggaagggccgagcgcagaagtggtcctgcaac tttatccgcctccatccagtctattaattgttgccgggaagctag agtaagtagttcgccagttaatagtttgcgcaacgttgttgccat tgctacaggcatcgtggtgtcacgctcgtcgtttggtatggcttc attcagctccggttcccaacgatcaaggcgagttacatgatcccc catgttgtgcaaaaaagcggttagctccttcggtcctccgatcgt tgtcagaagtaagttggccgcagtgttatcactcatggttatggc agcactgcataattctcttactgtcatgccatccgtaagatgctt ttctgtgactggtgagtactcaaccaagtcattctgagaatagtg tatgcggcgaccgagttgctcttgcccggcgtcaatacgggataa taccgcgccacatagcagaactttaaaagtgctcatcattggaaa acgttcttcggggcgaaaactctcaaggatcttaccgctgttgag atccagttcgatgtaacccactcgtgcacccaactgatcttcagc atcttttactttcaccagcgtttctgggtgagcaaaaacaggaag gcaaaatgccgcaaaaaagggaataagggcgacacggaaatgttg aatactcatactcttcctttttcaatattattgaagcatttatca gggttattgtctcatgagcggatacatatttgaatgtatttagaa aaataaacaaatagggggttccgcgcacatttccccgaaaagtgcc acctgacgtctaagaaaccattattatcatgacattaacctataa
```

-continued aaataggcgtatcacgaggccctttcgtctcgcgcgtttcggtga tgacggtg pGW047 AAV dSaCas9 Two Vector (SEQ ID NO: 11)

cctgcaggcagctgcgcgctcgctcgctcactgaggccgcccggg caaagcccgggcgtcgggcgacctttggtcgcccggcctcagtga gcgagcgagcgcgcagagagggagtggccaactccatcactaggg gttcctgcggccgcacgcgttctagaaagagggcctatttcccat gattccttcatatttgcatatacgatacaaggctgttagagagat aattggaattaatttgactgtaaacacaaagatattagtacaaaa tacgtgacgtagaaagtaataatttcttgggtagtttgcagtttt aaaattatgttttaaaatggactatcatatgcttaccgtaacttg aaagtatttcgatttcttggctttatatatcttgtggaaaggacg aaacaccggaagagcgagctcttctgttttagtactctggaggcc aacatgaggatcacccatgtctgcagggccaacagaatctactaa aacaaggcaaaatgccgtgtttatctcgtcaactggccaacatga ggatcacccatgtctgcagggcctgttggcgagattttttttgcta gctgcaaagatggataaagttttaaacagagaggaatctttgcag ctaatggaccttctaggtcttgaaaggagtgggaattggctccgg tgcccgtcagtgggcagagcgcacatcgcccacagtccccgagaa gttggggggaggggtcggcaattgaaccggtgcctagagaaggtg gcgcggggtaaactgggaaagtgatgtcgtgtactggctccgcct tttttcccgagggtgggggagaaccgtatataagtgcagtagtcgc cgtgaacgttctttttcgcaacgggtttgccgccagaacacaggt aagtgccgtgtgtggttcccgcgggcctggcctctttacgggtta tggcccttgcgtgccttgaattacttccacctggctgcagtacgt gattcttgatcccgagcttcgggttggaagtgggtgggagagttc gaggccttgcgcttaaggagcccccttcgcctcgtgcttgagttga ggcctggcctgggcgctggggccgccgcgtgcgaatctggtggca ccttcgcgcctgtctcgctgctttcgataagtctctagccattta aaattttttgatgacctgctgcgacgctttttttctggcaagatag tcttgtaaatgcgggccaagatctgcacactggtatttcggtttt tggggccgcgggcggcgacggggcccgtgcgtcccagcgcacatg ttcggcgaggcggggcctgcgagcgcggccaccgagaatcggacg ggggtagtctcaagctggccggcctgctctggtgcctggcctcgc gccgccgtgtatcgccccgccctgggcggcaaggctggcccggtc ggcaccagttgcgtgagcggaaagatggccgcttccggccctgc tgcagggagctcaaaatgaaggacgcggcgctcgggagagcgggc gggtgagtcacccacacaaaggaaaagggcctttccgtcctcagc cgtcgcttcatgtgactccacggagtaccgggcgccgtccaggca cctcgattagttctcgagcttttggagtacgtcgtctttaggttg -continued ggggggagggtttttatgcgatggagtttccccacactgagtgggt ggagactgaagttaggccagcttggcacttgatgtaattctcctt ggaatttgcccttttttgagtttggatcttggttcattctcaagcc tcagacagtggttcaaagttttttttcttccatttcaggtgtcgtg acgtacggccaccatggcttcaaactttactcagttcgtgctcgt ggacaatggtgggacaggggatgtgacagtggctccttctaattt cgctaatggggtggcagagtggatcagctccaactcacggagcca ggcctacaaggtgacatgcagcgtcaggcagtctagtgcccagaa gagaaagtataccatcaaggtggaggtccccaaagtggctaccca gacagtgggcggagtcgaactgcctgtcgccgcttggaggtcctta cctgaacatggagctcactatcccaattttcgctaccaattctga ctgtgaactcatcgtgaaggcaatgcagggggctcctcaaagacgg taatcctatcccttccgccatcgcgctaactcaggtatctacag cgctggaggaggtggaagcggaggaggaggaagcggaggaggagg tagcggacctaagaaaaagaggaaggtggcggccgctggatcccc ttcagggcagatcagcaaccaggccctggctctggcccctagctc cgctccagtgctggcccagactatggtgccctctagtgctatggt gcctctggcccagccacctgctccagcccctgtgctgaccccagg accaccccagtcactgagcgctccagtgcccaagtctacacaggc cggcgaggggactctgagtgaagctctgctgcacctgcagttcga cgctgatgaggacctgggagctctgctggggaacagcaccgatcc cggagtgttcacagatctggcctccgtggacaactctgagtttca gcagctgctgaatcagggcgtgtccatgtctcatagtacagccga accaatgctgatggagtaccccgaagccattacccggctggtgac cggcagccagcggcccccgaccccgctccaactcccctgggaac cagcggcctgcctaatgggctgtccggagatgaagacttctcaag catcgctgatatggactttagtgccctgctgtcacagatttcctc tagtgggcagggaggaggtggaagcggcttcagcgtggacaccag tgccctgctggacctgttcagccccctcggtgaccgtgcccgacat gagcctgcctgaccttgacagcagcctggccagtatccaagagct cctgtctccccaggagcccccaggcctcccgaggcagagaacag cagcccggattcagggaagcagctggtgcactacacagcgcagcc gctgttcctgctggaccccggctccgtggacaccgggagcaacga cctgccggtgctgtttgagctgggagagggctcctacttctccga aggggacggcttcgccgaggaccccaccatctccctgctgacagg ctcggagcctcccaaagccaaggaccccactgtctcctaagaatt cacgcgttaagtcgacaatcaacctctggattacaaaatttgtga aagattgactggtattcttaactatgttgctcctttttacgctatg tggatacgctgctttaatgcctttgtatcatgctattgcttcccg tatggctttcattttctcctccttgtataaatcctggttgctgtc tctttatgaggagttgtggcccgttgtcaggcaacgtggcgtggt -continued

```
gtgcactgtgtttgctgacgcaacccccactggttggggcattgc caccacctgtcagctcctttccgggactttcgcttcccctccc tattgccacggcggaactcatcgccgcctgccttgcccgctgctg gacaggggctcggctgttgggcactgacaattccgtggtgttgtc ggggaaatcatcgtcctttccttggctgctcgcctgtgttgccac ctggattctgcgcgggacgtccttctgctacgtcccttcggccct caatccagcggaccttccttcccgcggcctgctgccggctctgcg gcctcttccgcgtcttcgccttcgccctcagacgagtcggatctc cctttgggccgcctccccgcgtcgactttaagaccaatgacgtgc ggaccgagcggccgcaggaacccctagtgatggagttggccactc cctctctgcgcgctcgctcgctcactgaggccgggcgaccaaagg tcgcccgacgcccgggctttgcccgggcggcctcagtgagcgagc gagcgcgcagctgcctgcaggggcgcctgatgcggtattttctcc ttacgcatctgtgcggtatttcacaccgcatacgtcaaagcaacc atagtacgcgccctgtagcggcgcattaagcgcggcgggtgtggt ggttacgcgcagcgtgaccgctacacttgccagcgccctagcgcc cgctcctttcgctttcttcccttcctttctcgccacgttcgccgg ctttccccgtcaagctctaaatcgggggctccctttagggttccg atttagtgctttacggcacctcgaccccaaaaaacttgatttggg tgatggttcacgtagtgggccatcgccctgatagacggttttttcg ccctttgacgttggagtccacgttctttaatagtggactcttgtt ccaaactggaacaacactcaaccctatctcgggctattcttttga tttataagggattttgccgatttcggcctattggttaaaaaatga gctgatttaacaaaaatttaacgcgaattttaacaaaatattaac gtttacaattttatggtgcactctcagtacaatctgctctgatgc cgcatagttaagccagccccgacacccgccaacacccgctgacgc gccctgacgggcttgtctgctcccggcatccgcttacagacaagc tgtgaccgtctccgggagctgcatgtgtcagaggttttcaccgtc atcaccgaaacgcgcgagacgaaagggcctcgtgatacgcctatt tttataggttaatgtcatgataataatggtttcttagacgtcagg tggcacttttcggggaaatgtgcgcggaacccctatttgtttatt tttctaaatacattcaaatatgtatccgctcatgagacaataacc ctgataaatgcttcaataatattgaaaaaggaagagtatgagtat tcaacatttccgtgtcgcccttattcccttttttgcggcattttg ccttcctgtttttgctcacccagaaacgctggtgaaagtaaaaga tgctgaagatcagttgggtgcacgagtgggttacatcgaactgga tctcaacagcggtaagatccttgagagttttcgccccgaagaacg ttttccaatgatgagcacttttaaagttctgctatgtggcgcggt attatcccgtattgacgccgggcaagagcaactcggtcgccgcat acactattctcagaatgacttggttgagtactcaccagtcacaga
```

-continued

```
aaagcatcttacggatggcatgacagtaagagaattatgcagtgc tgccataaccatgagtgataaacactgcggccaacttacttctgac aacgatcggaggaccgaaggagctaaccgcttttttgcacaacat gggggatcatgtaactcgccttgatcgttgggaaccggagctgaa tgaagccataccaaacgacgagcgtgacaccacgatgcctgtagc aatggcaacaacgttgcgcaaactattaactggcgaactacttac tctagcttcccggcaacaattaatagactggatggaggcggataa agttgcaggaccacttctgcgctcggcccttccggctggctggtt tattgctgataaatctggagccggtgagcgtgggtctcgcggtat cattgcagcactggggccagatggtaagccctcccgtatcgtagt tatctacacgacggggagtcaggcaactatggatgaacgaaatag acagatcgctgagataggtgcctcactgattaagcattggtaact gtcagaccaagtttactcatatatactttagattgatttaaaact tcattttaatttaaaaggatctaggtgaagatcctttttgataa tctcatgaccaaaatcccttaacgtgagttttcgttccactgagc gtcagaccccgtagaaaagatcaaaggatcttcttgagatccttt ttttctgcgcgtaatctgctgcttgcaaacaaaaaaaccaccgct accagcggtggtttgtttgccggatcaagagctaccaactctttt tccgaaggtaactggcttcagcagagcgcagataccaaatactgt ccttctagtgtagccgtagttaggccaccacttcaagaactctgt agcaccgcctacatacctcgctctgctaatcctgttaccagtggc tgctgccagtggcgataagtcgtgtcttaccgggttggactcaag acgatagttaccggataaggcgcagcggtcgggctgaacggggggg ttcgtgcacacagcccagcttggagcgaacgacctacaccgaact gagatacctacagcgtgagctatgagaaagcgccacgcttcccga agggagaaaggcggacaggtatccggtaagcggcagggtcggaac aggagagcgcacgagggagcttccaggggaaacgcctggtatct ttatagtcctgtcgggtttcgccacctctgacttgagcgtcgatt tttgtgatgctcgtcaggggggcggagcctatggaaaaacgccag caacgcggcctttttacggttcctggccttttgctggccttttgc tcacatgt
``` pGW060 AAV dSaCas9 Two Vector (SEQ ID NO: 12)

```
cctgcaggcagctgcgcgctcgctcgctcactgaggccgcccggg cgtcgggcgacctttggtcgcccggcctcagtgagcgagcgagcg cgcagagagggagtggccaactccatcactaggggttcctgcggc ctctagaaaggatctgcgatcgctccggtgcccgtcagtgggcag agcgcacatcgcccacagtccccgagaagttggggggaggggtcg gcaattgaacgggtgcctagagaaggtggcgcggggtaaactggg aaagtgatgtcgtgtactggctccgcctttttcccgagggtgggg gagaaccgtatataagtgcagtagtcgccgtgaacgttctttttc gcaacgggtttgccgccagaacacagctgaagcttcgaggggctc
```

-continued gcatctctccttcacgcgcccgccgccctacctgaggccgccatc cacgccggttgagtcgcgttctgccgcctcccgcctgtggtgcct cctgaactgcgtccgccgtctaggtaagtttaaagctcaggtcga gaccgggcctttgtccggcgctcccttggagcctacctagactca gccggctctccacgctttgcctgaccctgcttgctcaactctacg tctttgtttcgttttctgttctgcgccgttacagatctggctaac taccggtgccaccatggccccaaagaagaagcggaaggtcggtat ccacggagtcccagcagccaagcggaactacatcctgggcctggc catcggcatcaccagcgtgggctacggcatcatcgactacgagac acgggacgtgatcgatgccggcgtgcggctgttcaaagaggccaa cgtggaaaacaacgagggcaggcggagcaagagaggcgccagaag gctgaagcggcggaggcggcatagaatccagagagtgaagaagct gctgttcgactacaacctgctgaccgaccacagcgagctgagcgg catcaacccctacgaggccagagtgaagggcctgagccagaagct gagcgaggaagagttctctgccgccctgctgcacctggccaagag aagaggcgtgcacaacgtgaacgaggtggaagaggacaccggcaa cgagctgtccaccaaagagcagatcagccggaacagcaaggccct ggaagagaaatacgtggccgaactgcagctggaacggctgaagaa agacggcgaagtgcggggcagcatcaacagattcaagaccagcga ctacgtgaaagaagccaaacagctgctgaaggtgcagaaggccta ccaccagctggaccagagcttcatcgacacctacatcgacctgct ggaaacccggcggacctactatgagggacctggcgagggcagccc cttcggctggaaggacatcaaagaatggtacgagatgctgatggg ccactgcacctacttccccgaggaactgcggagcgtgaagtacgc ctacaacgccgacctgtacaacgccctgaacgacctgaacaatct cgtgatcaccagggacgagaacgagaagctggaatattacgagaa gttccagatcatcgagaacgtgttcaagcagaagaagaagcccac cctgaagcagatcgccaaagaaatcctcgtgaacgaagaggatat taagggctacaagagtgaccagcaccggcaagcccgagttcacca cctgaaggtgtaccacgacatcaaggacattaccgcccggaaaga gattattgagaacgccgagctgctggatcagattgccaagatcct gaccatctaccagagcagcgaggacatccaggaagaactgaccaa tctgaactccgagctgacccaggaagagatcgagcagatctctaa tctgaagggctataccggcacccacaacctgagcctgaaggccat caacctgatcctggacgagctgtggcacaccaacgacaaccagat cgctatcttcaaccggctgaagctggtgcccaagaaggtggacct gtcccagcagaaagagatccccaccacccctggtgacgacttcat cctgagccccgtcgtgaagaagaagcttcatccagagcatcaaagt gatcaacgccatcatcaagaagtacggcctgcccaacgacatcat tatcgagctggcccgcgagaagaactccaaggacgcccagaaaat -continued gatcaacgagatgcagaagcggaaccggcagaccaacgagcggat cgaggaaatcatccggaccaccggcaaagagaacgccaagtacct gatcgagaagatcaagctgcacgacatgcaggaaggcaagtgcct gtacagcctggaagccatccctctggaagatctgctgaacaaccc cttcaactatgaggtggaccacatcatccccagaagcgtgtccctt cgacaacagcttcaacaacaaggtgctcgtgaagcaggaagaagc cagcaagaagggcaaccggacccccattccagtacctgagcagcag cgacagcaagatcagctacgaaaccttcaagaagcacatcctgaa tctggccaagggcaagggcagaatcagcaagaccaagaaagagta tctgctggaagaacgggacatcaacaggttctccgtgcagaaaga cttcatcaaccggaacctggtggataccagatacgccaccagagg cctgatgaacctgctgcgcgagctacttcagagtgaacaacctgga cgtgaaagtgaagtccatcaatggcggcttcaccagctttctgcg gcggaagtggaagtttaagaaagagcggaacaagggggtacaagca ccacgccgaggacgccctgatcattgccaacgccgatttcatctt caaagagtggaagaaactggacaaggccaaaaaagtgatggaaaa ccagatgttcgaggaaaagcaggccgagagcatgcccgagatcga aaccgagcaggagtacaaagagatcttcatcaccccccaccagat caagcacattaaggacttcaaggactacaagtacagccaccgggt ggacaagaagcctaatagagagctgattaacgacaccctgtactc caccccggaaggacgacaagggcaacaccctgatcgtgaacaatct gaacggcctgtacgacaaggacaatgacaagctgaaaaagctgat caacaagagccccgaaaagctgctgatgtaccaccacgacccccca gacctaccagaaactgaagctgattatggaacagtacggcgacga gaagaatcccctgtacaagtactacgaggaaaccgggaactacct gaccaagtactccaaaaaggacaacggcccccgtgatcaagaagat taagtattacggcaacaaactgaacgcccatctggacatcaccga cgactaccccaacagcagaaacaaggtcgtgaagctgtccctgaa gccctacagattcgacgtgtacctggacaatggcgtgtacaagtt cgtgaccgtgaagaatctggatgtgatcaaaaaagaaaactacta cgaagtgaatagcaagtgctatgaggaagctaagaagctgaagaa gatcagcaaccaggccgagtttatcgcctccttctacaacaacga tctgatcaagatcaacggcgagctgtatagagtgatcggcgtgaa caacgacctgctgaaccggatcgaagtgaacatgatcgacatcac ctaccgcgagtacctggaaaacatgaacgacaagaggcccccccag gatcattaagacaatcgcctccaagacccagagcattaagaagta cagcacagacattctgggcaacctgtatgaagtgaaatctaagaa gcaccctcagatcatcaaaaagggcaaaaggccggcggccacgaa aaaggccggccaggcaaaaaagaaaaagggatccggacgggctga cgcattggacgattttgatctggatatgctgggaagtgacgccct cgatgattttgaccttgacatgcttggttcggatgcccttgatga -continued ctttgacctcgacatgctcggcagtgacgcccttgatgatttcga cctggacatgctgatttaagaattcacgcgttaagtcgacaatca acctctggattacaaaatttgtgaaagattgactggtattcttaa ctatgttgctccttttacgctatgtggatacgctgctttaatgcc tttgtatcatgctattgcttcccgtatggctttcattttctcctc cttgtataaatcctggttgctgtctctttatgaggagttgtggcc cgttgtcaggcaacgtggcgtggtgtgcactgtgtttgctgacgc aaccccactggttggggcattgccaccacctgtcagctcctttc cgggactttcgctttcccctccctattgccacggcggaactcat cgccgcctgccttgcccgctgctggacaggggctcggctgttggg cactgacaattccgtggtgttgtcggggaaatcatcgtcctttcc ttggctgctcgcctgtgttgccacctggattctgcgcgggacgtc cttctgctacgtcccttcggccctcaatccagcggaccttccttc ccgcggcctgctgccggctctgcggcctcttccgcgtcttcgcct tcgccctcagacgagtcggatctcccttgggccgcctccccgcg tcgactttaagaccaatgacggccgcaggaaccctagtgatgga gttggccactccctctctgcgcgctcgctcgctcactgaggccgg gcgaccaaaggtcgcccgacgcccgggctttgcccgggcggcctc agtgagcgagcgagcgcgcagctgcctgcaggggcgcctgatgcg gtattttctccttacgcatctgtgcggtatttcacaccgcatacg tcaaagcaaccatagtacgcgccctgtagcggcgcattaagcgcg gcgggtgtggtggttacgcgcagcgtgaccgctacacttgccagc gccttagcgcccgctcctttcgctttcttcccttcctttctcgcc acgttcgccggctttccccgtcaagctctaaatcggggctccct ttagggttccgatttagtgctttacggcacctcgaccccaaaaaa cttgatttgggtgatggttcacgtagtgggccatcgccctgatag acggtttttcgcccttgacgttggagtccacgttctttaatagt ggactcttgttccaaactggaacaacactcaactctatctcgggc tattcttttgatttataagggattttgccgatttcggtctattgg ttaaaaaatgagctgatttaacaaaaatttaacgcgaattttaac aaaatattaacgtttacaatttttatggtgcactctcagtacaatc tgctctgatgccgcatagttaagccagccccgacacccgccaaca cccgctgacgcgccctgacgggcttgtctgctcccggcatccgct tacagacaagctgtgaccgtctccgggagctgcatgtgtcagagg ttttcaccgtcatcaccgaaacgcgcgagacgaaagggcctcgtg atacgcctatttttataggttaatgtcatgataataatggtttct tagacgtcaggtggcacttttcggggaaatgtgcgcggaacccct atttgtttattttctaaatacattcaaatatgtatccgctcatg agacaataaccctgataaatgcttcaataatattgaaaaaggaag agtatgagtattcaacatttccgtgtcgcccttattccctttttt -continued gcggcattttgccttcctgtttttgctcacccagaaacgctggtg aaagtaaaagatgctgaagatcagttgggtgcacgagtgggttac atcgaactggatctcaacagcggtaagatccttgagagttttcgc cccgaagaacgttttccaatgatgagcacttttaaagttctgcta tgtggcgcggtattatcccgtattgacgccgggcaagagcaactc ggtcgccgcatacactattctcagaatgacttggttgagtactca ccagtcacagaaaagcatcttacggatggcatgacagtaagagaa ttatgcagtgctgccataaccatgagtgataacactgcggccaac ttacttctgacaacgatcggaggaccgaaggagctaaccgctttt ttgcacaacatgggggatcatgtaactcgccttgatcgttgggaa ccggagctgaatgaagccataccaaacgacgagcgtgacaccacg atgcctgtagcaatggcaacaacgttgcgcaaactattaactggc gaactacttactctagcttcccggcaacaattaatagactggatg gaggcggataaagttgcaggaccacttctgcgctcggcccttccg gctggctggtttattgctgataaatctggagccggtgagcgtgga agccgcggtatcattgcagcactggggccagatggtaagccctcc cgtatcgtagttatctacacgacggggagtcaggcaactatggat gaacgaaatagacagatcgctgagataggtgcctcactgattaag cattggtaactgtcagaccaagtttactcatatatactttagatt gatttaaaacttcatttttaatttaaaaggatctaggtgaagatc cttttttgataatctcatgaccaaaatcccttaacgtgagttttcg ttccactgagcgtcagaccccgtagaaaagatcaaaggatcttct tgagatcctttttttctgcgcgtaatctgctgcttgcaaacaaaa aaaccaccgctaccagcggtggtttgtttgccggatcaagagcta ccaactctttttccgaaggtaactggcttcagcagagcgcagata ccaaatactgttcttctagtgtagccgtagttaggccaccacttc aagaactctgtagcaccgcctacatacctcgctctgctaatcctg ttaccagtggctgctgccagtggcgataagtcgtgtcttaccggg ttggactcaagacgatagttaccggataaggcgcagcggtcgggc tgaacggggggttcgtgcacacagcccagcttggagcgaacgacc tacaccgaactgagatacctacagcgtgagctatgagaaagcgcc acgcttcccgaagggagaaaggcggacaggtatccggtaagcggc agggtcggaacaggagagcgcacgagggagcttccagggggaaac gcctggtatctttatagtcctgtcgggtttcgccacctctgactt gagcgtcgatttttgtgatgctcgtcaggggggcggagcctatgg aaaaacgccagcaacgcggcctttttacggttcctggccttttgc tggcctttttgctcacatgt pGW045 AAV dSpCas9 Two Vector
(SEQ ID NO: 13)
cctgcaggcagctgcgcgctcgctcgctcactgaggccgcccggg caaagcccgggcgtcgggcgacctttggtcgcccggcctcagtga gcgagcgagcgcgcagagagggagtggccaactccatcactaggg -continued gttcctgcggccgcaCGCGTTCTAGAAAGAgggcctatttcccat gattccttcatatttgcatatacgatacaaggctgttagagagat aattggaattaatttgactgtaaacacaaagatattagtacaaaa tacgtgacgtagaaagtaataaatttcttgggtagtttgcagtttt aaaattatgtttttaaaatggactatcatatgcttaccgtaacttg aaagtatttcgatttcttggctttatatatcttGTGGAAAGGACG AAACACCggaagagcgagctcttctgtttttagagctaggccAACA TGAGGATCACCCATGTCTGCAGggcctagcaagttaaaataaggc tagtccgttatcaacttggccAACATGAGGATCACCCATGTCTGC AGggccaagtggcaccgagtcggtgcTTTTTTGGATCCaagcttg gcgtaactagatcttgagacaaatggGACAGCAGAGATCCAGTTT

GGTTAATTAGCTAGCTGCAAAGATGGATAAAGTTTTAAACAGAGA

GGAATCTTTGCAGCTAATGGACCTTCTAGGTCTTGAAAGGAGTGG

GAATTGGCTCCGGTGCCCGTCAGTGGGCAGAGCGCACATCGCCCA

CAGTCCCCGAGAAGTTGGGGGGAGGGGTCGGCAATTGAACCGGTG

CCTAGAGAAGGTGGCGCGGGGTAAACTGGGAAAGTGATGTCGTGT

ACTGGCTCCGCCTTTTTCCCGAGGGTGGGGGAGAACCGTATATAA

GTGCAGTAGTCGCCGTGAACGTTCTTTTTCGCAACGGGTTTGCCG

CCAGAACACAGGTAAGTGCCGTGTGTGGTTCCCGCGGGCCTGGCC

TCTTTACGGGTTATGGCCCTTGCGTGCCTTGAATTACTTCCACCT

GGCTGCAGTACGTGATTCTTGATCCCGAGCTTCGGGTTGGAAGTG

GGTGGGAGAGTTCGAGGCCTTGCGCTTAAGGAGCCCCTTCGCCTC

GTGCTTGAGTTGAGGCCTGGCCTGGGCGCTGGGGCCGCCGCGTGC

GAATCTGGTGGCACCTTCGCGCCTGTCTCGCTGCTTTCGATAAGT

CTCTAGCCATTTAAAATTTTTGATGACCTGCTGCGACGCTTTTTT

TCTGGCAAGATAGTCTTGTAAATGCGGGCCAAGATCTGCACACTG

GTATTTCGGTTTTTGGGGCCGCGGGCGGCGACGGGGCCCGTGCGT

CCCAGCGCACATGTTCGGCGAGGCGGGGCCTGCGAGCGCGGCCAC

CGAGAATCGGACGGGGGTAGTCTCAAGCTGGCCGGCCTGCTCTGG

TGCCTGGCCTCGCGCCGCCGTGTATCGCCCCGCCCTGGGCGGCAA

GGCTGGCCCGGTCGGCACCAGTTGCGTGAGCGGAAAGATGGCCGC

TTCCCGGCCCTGCTGCAGGGAGCTCAAAATGAAGGACGCGGCGCT

CGGGAGAGCGGGCGGGTGAGTCACCCACACAAAGGAAAAGGGCCT

TTCCGTCCTCAGCCGTCGCTTCATGTGACTCCACGGAGTACCGGG

CGCCGTCCAGGCACCTCGATTAGTTCTCGAGCTTTTGGAGTACGT

CGTCTTTAGGTTGGGGGGAGGGGTTTTATGCGATGGAGTTTCCCC

ACACTGAGTGGGTGGAGACTGAAGTTAGGCCAGCTTGGCACTTGA

TGTAATTCTCCTTGGAATTTGCCCTTTTTGAGTTTGGATCTTGGT

TCATTCTCAAGCCTCAGACAGTGGTTCAAAGTTTttttcttccat ttcaggtgtcgtgacgtacggccaccatggcttcaaactttacTC

AGTTCGTGCTCGTGGACAATGGTGGGACAGGGGATGTGACAGTGG

CTCCTTCTAATTTCGCTAATGGGGTGGCAGAGTGGATCAGCTCCA

ACTCACGGAGCCAGGCCTACAAGGTGACATGCAGCGTCAGGCAGT

CTAGTGCCCAGAAGAGAAAGTATACCATCAAGGTGGAGGTCCCCA

AAGTGGCTACCCAGACAGTGGGCGGAGTCGAACTGCCTGTCGCCG

CTTGGAGGTCCTACCTGAACATGGAGCTCACTATCCCAATTTTCG

CTACCAATTCTGACTGTGAACTCATCGTGAAGGCAATGCAGGGGC

TCCTCAAAGACGGTAATCCTATCCCTTCCGCCATCGCCGCTAACT

CAGGTATCTACAGCGCTGGAGGAGGTGGAAGCGGAGGAGGAGGAA

GCGGAGGAGGAGGTAGCGGACCTAAGAAAAAGAGGAAGGTGGCGG

CCGCTGGATCCCCTTCAGGGCAGATCAGCAACCAGGCCCTGGCTC

TGGCCCCTAGCTCCGCTCCAGTGCTGGCCCAGACTATGGTGCCCT

CTAGTGCTATGGTGCCTCTGGCCCAGCCACCTGCTCCAGCCCCTG

TGCTGACCCCAGGACCACCCCAGTCACTGAGCGCTCCAGTGCCCA

AGTCTACACAGGCCGGCGAGGGGACTCTGAGTGAAGCTCTGCTGC

ACCTGCAGTTCGACGCTGATGAGGACCTGGGAGCTCTGCTGGGGA

ACAGCACCGATCCCGGAGTGTTCACAGATCTGGCCTCCGTGGACA

ACTCTGAGTTTCAGCAGCTGCTGAATCAGGGCGTGTCCATGTCTC

ATAGTACAGCCGAACCAATGCTGATGGAGTACCCCGAAGCCATTA

CCCGGCTGGTGACCGGCAGCCAGCGGCCCCCCGACCCCGCTCCAA

CTCCCCTGGGAACCAGCGGCCTGCCTAATGGGCTGTCCGGAGATG

AAGACTTCTCAAGCATCGCTGATATGGACTTTAGTGCCCTGCTGT

CACAGATTTCCTCTAGTGGGCAGGGAGGAGGTGGAAGCGGCTTCA

GCGTGGACACCAGTGCCCTGCTGGACCTGTTCAGCCCCTCGGTGA

CCGTGCCCGACATGAGCCTGCCTGACCTTGACAGCAGCCTGGCCA

GTATCCAAGAGCTCCTGTCTCCCCAGGAGCCCCCCAGGCCTCCCG

AGGCAGAGAACAGCAGCCCGGATTCAGGGAAGCAGCTGGTGCACT

ACACAGCGCAGCCGCTGTTCCTGCTGGACCCCGGCTCCGTGGACA

CCGGGAGCAACGACCTGCCGGTGCTGTTTGAGCTGGGAGAGGGCT

CCTACTTCTCCGAAGGGGACGGCTTCGCCGAGGACCCCACCATCT

CCCTGCTGACAGGCTCGGAGCCTCCCAAAGCCAAGGACCCCACTG

TCTCCTAAGaattcacgcgttaagtcgacaatcaacctctggatt acaaaatttgtgaaagattgactggtattcttaactatgttgctc cttttacgctatgtggatacgctgctttaatgcctttgtatcatg ctattgcttcccgtatggctttcattttctcctccttgtataaat cctggttgctgtctctttatgaggagttgtggcccgttgtcaggc aacgtggcgtggtgtgcactgtgtttgctgacgcaacccccactg gttggggcattgccaccacctgtcagctcctttccgggactttcg ctttccccctccctattgccacggcggaactcatcgccgcctgcc ttgcccgctgctggacagggctcggctgttgggcactgacaatt ccgtggtgttgtcggggaaatcatcgtcctttccttggctgctcg -continued

```
cctgtgttgccacctggattctgcgcgggacgtccttctgctacg tcccttcggccctcaatccagcggaccttccttcccgcggcctgc tgccggctctgcggcctcttccgcgtcttcgccttcgccctcaga cgagtcggatctcccctttgggccgcctccccgcgtcgactttaag accaatgacgtgcggaccgagcggccgcaggaacccctagtgatg gagttggccactccctctctgcgcgctcgctcgctcactgaggcc gggcgaccaaaggtcgcccgacgcccgggctttgcccgggcggcc tcagtgagcgagcgagcgcgcagctgcctgcaggggcgcctgatg cggtattttctccttacgcatctgtgcggtatttcacaccgcata cgtcaaagcaaccatagtacgcgccctgtagcggcgcattaagcg cggcgggtgtggtggttacgcgcagcgtgaccgctacacttgcca gcgccctagcgcccgctcctttcgctttcttcccttcctttctcg ccacgttcgccggctttccccgtcaagctctaaatcggggggctcc ctttagggttccgatttagtgctttacggcacctcgaccccaaaa aacttgatttgggtgatggttcacgtagtgggccatcgccctgat agacggtttttcgccctttgacgttggagtccacgttctttaata gtggactcttgttccaaactggaacaacactcaaccctatctcgg gctattcttttgatttataagggattttgccgatttcggcctatt ggttaaaaaatgagctgatttaacaaaaatttaacgcgaatttta acaaaatattaacgtttacaatttttatggtgcactctcagtacaa tctgctctgatgccgcatagttaagccagccccgacacccgccaa caccgctgacgcgccctgacgggcttgtctgctcccggcatccg cttacagacaagctgtgaccgtctccgggagctgcatgtgtcaga ggttttcaccgtcatcaccgaaacgcgcgagacgaaagggcctcg tgatacgcctatttttataggttaatgtcatgataataatggttt cttagacgtcaggtggcacttttcggggaaatgtgcgcggaaccc ctatttgtttatttttctaaatacattcaaatatgtatccgctca tgagacaataaccctgataaatgcttcaataatattgaaaaagga agagtatgagtattcaacatttccgtgtcgcccttattccctttt ttgcggcattttgccttcctgtttttgctcacccagaaacgctgg tgaaagtaaaagatgctgaagatcagttgggtgcacgagtgggtt acatcgaactggatctcaacagcggtaagatccttgagagttttc gccccgaagaacgttttccaatgatgagcacttttaaagttctgc tatgtggcgcggtattatcccgtattgacgccgggcaagagcaac tcggtcgccgcatacactattctcagaatgacttggttgagtact caccagtcacagaaaagcatcttacggatggcatgacagtaagag aattatgcagtgctgccataaccatgagtgataacactgcggcca acttacttctgacaacgatcggaggaccgaaggagctaaccgctt ttttgcacaacatgggggatcatgtaactcgccttgatcgttggg aaccggagctgaatgaagccataccaaacgacgagcgtgacacca
```

-continued

```
cgatgcctgtagcaatggcaacaacgttgcgcaaactattaactg gcgaactacttactctagcttcccggcaacaattaatagactgga tggaggcggataaagttgcaggaccacttctgcgctcggcccttc cggctggctggtttattgctgataaatctggagccggtgagcgtg ggtctcgcggtatcattgcagcactggggccagatggtaagccct cccgtatcgtagttatctacacgacggggagtcaggcaactatgg atgaacgaaatagacagatcgctgagataggtgcctcactgatta agcattggtaactgtcagaccaagtttactcatatatactttaga ttgatttaaaacttcattttttaatttaaaaggatctaggtgaaga tcctttttgataatctcatgaccaaaatcccttaacgtgagtttt cgttccactgagcgtcagaccccgtagaaaagatcaaaggatctt cttgagatcctttttttctgcgcgtaatctgctgcttgcaaacaa aaaaaccaccgctaccagcggtggtttgtttgccggatcaagagc taccaactctttttccgaaggtaactggcttcagcagagcgcaga taccaaatactgtccttctagtgtagccgtagttaggccaccact tcaagaactctgtagcaccgcctacatacctcgctctgctaatcc tgttaccagtggctgctgccagtggcgataagtcgtgtcttaccg ggttggactcaagacgatagttaccggataaggcgcagcggtcgg gctgaacggggggttcgtgcacacagcccagcttggagcgaacga cctacaccgaactgagatacctacagcgtgagctatgagaaagcg ccacgcttcccgaagggagaaaggcggacaggtatccggtaagcg gcagggtcggaacaggagagcgcacgagggagcttccaggggggaa acgcctggtatctttatagtcctgtcgggtttcgccacctctgac ttgagcgtcgatttttgtgatgctcgtcaggggggcggagcctat ggaaaaacgccagcaacgcggcctttttacggttcctggccttttt gctggccttttgctcacatgt
``` pRC119AAV Two Vector dCas11a/dCpf1

(SEQ ID NO: 14)
```
cctgcaggcagctgcgcgctcgctcgctcactgaggccgcccggg caaagcccgggcgtcgggcgacctttggtcgcccggcctcagtga gcgagcgagcgcgcagagagggagtggccaactccatcactaggg gttcctgcggccgcacgcgttctaggtcttgaaaggagtgggaat tggctccggtgcccgtcagtgggcagagcgcacatcgcccacagt ccccgagaagttggggggaggggtcggcaattgatccggtgccta gagaaggtggcgcggggtaaactgggaaagtgatgtcgtgtactg gctccgcctttttcccgagggtgggggagaaccgtatataagtgc agtagtcgccgtgaacgttctttttcgcaacgggtttgccgccag aacacaggTGTCGTGACGCGcGTACGgccaccatgacacagttcg agggctttaccaacctgtatcaggtgagcaagacactgcggtttg agctgatcccacagggcaagaccctgaagcacatccaggagcagg gcttcatcgaggaggacaaggcccgcaatgatcactacaaggagc tgaagcccatcatcgatcggatctacaagaccctatgccgaccagt
```

-continued gcctgcagctggtgcagctggattgggagaacctgagcgccgcca tcgactcctatagaaaggagaaaaccgaggagacaaggaacgccc tgatcgaggagcaggccacatatcgcaatgccatccacgactact tcatcggccggacagacaacctgaccgatgccatcaataagagac acgccgagatctacaagggcctgttcaaggccgagctgtttaatg gcaaggtgctgaagcagctgggcaccgtgaccacaaccgagcacg agaacgccctgctgcggagcttcgacaagtttacaacctacttct ccggctttttatagaaacaggaagaacgtgttcagcgccgaggata tcagcacagccatcccacaccgcatcgtgcaggacaacttcccca agtttaaggagaattgtcacatcttcacacgcctgatcaccgccg tgcccagcctgcgggagcactttgagaacgtgaagaaggccatcg gcatcttcgtgagcacctccatcgaggaggtgtttttccttcccttt tttataaccagctgctgacacagacccagatcgacctgtataacc agctgctgggaggaatctctcgggaggcaggcaccgagaagatca agggcctgaacgaggtgctgaatctggccatccagaagaatgatg agacagcccacatcatcgcctccctgccacacagattcatcccc tgtttaagcagatcctgtccgataggaacaccctgtctttcatcc tggaggagtttaagagcgacgaggaagtgatccagtccttctgca agtacaagacactgctgagaaacgagaacgtgctggagacagccg aggccctgtttaacgagctgaacagcatcgacctgacacacatct tcatcagccacaagaagctggagacaatcagcagcgccctgtgcg accactgggatacactgaggaatgccctgtatgagcggagaatct ccgagctgacaggcaagatcaccaagtctgccaaggagaaggtgc agcgcagcctgaagcacgaggatatcaacctgcaggagatcatct ctgccgcaggcaaggagctgagcgaggccttcaagcagaaaacca gcgagatcctgtcccacgcacacgccgccctggatcagccactgc ctacaaccctgaagaagcaggaggagaaggagatcctgaagtctc agctggacagcctgctgggcctgtaccacctgctggactggtttg ccgtggatgagtccaacgaggtggaccccgagttctctgcccggc tgaccggcatcaagctggagatggagccttctctgagcttctaca acaaggccagaaattatgccaccaagaagccctactccgtggaga agttcaagctgaacttttcagatgcctacactggccagaggctggg acgtgaatagagagaagaacaatggcgccatcctgtttgtgaaga acggcctgtactatctgggcatcatgccaaagcagaagggcaggt ataaggccctgagcttcgagcccacagagaaaaccagcgagggct ttgataagatgtactatgactacttccctgatgccgccaagatga tcccaaagtgcagcacccagctgaaggccgtgacagcccactttc agacccacacaacccccatcctgctgtccaacaatttcatcgagc ctctggagatcacaaaggagatctacgacctgaacaatcctgaga aggagccaaagaagtttcagacagcctacgccaagaaaaccggcg -continued accagaagggctacagagagggccctgtgcaagtggatcgacttca caagggattttctgtccaagtataccaagacaacctctatcgatc tgtctagcctgcggccatcctctcagtataaggacctgggcgagt actatgccgagctgaatccctgctgtaccacatcagcttccaga gaatcgccgagaaggagatcatggatgccgtggagacaggcaagc tgtacctgttccagatctataacaaggactttgccaagggccacc acggcaagcctaatctgcacacactgtattggaccggcctgtttt ctccagagaacctggccaagacaagcatcaagctgaatggccagg ccgagctgttctaccgccctaagtccaggatgaagaggatggcac accggctgggagagaagatgctgaacaagaagctgaaggatcaga aaaccccaatccccgacaccctgtaccaggagctgtacgactatg tgaatcacagactgtcccacgacctgtctgatgaggccagggccc tgctgcccaacgtgatcaccaaggaggtgtctcacgagatcatca aggataggcgctttaccagcgacaagttcttttttccacgtgccta tcacactgaactatcaggccgccaattcccccatctaagttcaacc agagggtgaatgcctacctgaaggagcacccccgagacacctatca tcggcatcgcccgggggcgagagaaacctgatctatatcacagtga tcgactccaccggcaagatcctggagcagcggagcctgaacacca tccagcagtttgattaccagaagaagctggacaacagggagaagg agagggtggcagcaaggcaggcctggtctgtggtgggcacaatca aggatctgaagcagggctatctgagccaggtcatccacgagatcg tggacctgatgatccactaccaggccgtggtggtgctggagaacc tgaatttcggctttaagagcaagaggaccggcatcgccgagaagg ccgtgtaccagcagttcgagaagatgctgatcgataagctgaatt gcctggtgctgaaggactatccagcagagaaagtgggaggcgtgc tgaacccataccagctgacagaccagttcacctcctttgccaaga tgggcacccagtctggcttcctgttttacgtgcctgccccatata catctaagatcgatcccctgaccggcttcgtggacccccttcgtgt ggaaaaccatcaagaatcacgagagccgcaagcacttcctggagg gcttcgactttctgcactacgacgtgaaaaccggcgacttcatcc tgcactttaagatgaacagaaatctgtccttccagaggggcctgc ccggctttatgcctgcatgggatatcgtgttcgagaagaacgaga cacagtttgacgccaagggcacccctttcatcgccggcaagagaa tcgtgccagtgatcgagaatcacagattcaccggcagataccggg acctgtatcctgccaacgagctgatcgccctgctggaggagaagg gcatcgtgttcagggatggctccaacatcctgccaaagctgctgg agaatgacgattctcacgccatcgacacgatggtggccctgatcc gcagcgtgctgcagatgcggaactccaatgccgccacaggcgagg actatatcaacagccccgtgcgcgatctgaatggcgtgtgcttcg actcccggtttcagaacccagagtggccaatggacgccgatgcca atggcgcctaccacatcgccctgaagggccagctgctgctgaatc -continued acctgaaggagagcaaggatctgaagctgcagaacggcatctcca atcaggactggctggcctacatccaggagctgcgcaacaaaaggc cggcggccacgaaaaaggccggccaggcaaaaaagaaaaagGGCA

GTGGTAGTGGAGAAGAGCTGTTGTCAAAAAATTATCACTTGGAGA

ATGAGGTAGCCCGCCTTAAGAAAGGCAGCGGATCAGGCGAGGAAC

TTCTGAGCAAGAATTACCATCTCGAAAACGAAGTGGCACGCTTGA

AGAAGGGTTCAGGTTCCGGGGAGGAGCTCCTCTCCAAGAACTACC

ACCTGGAGAACGAAGTCGCTCGCCTGAAGAAAtgaAATAAAAGAT

CTTTATTTTCATTAGATCTGTGTGTTGGTTTTTTTGTGTGcggacc gagcggccgcaggaacccctagtgatggagttggccactccctct ctgcgcgctcgctcgctcactgaggccgggcgaccaaaggtcgcc cgacgcccgggctttgcccgggcggcctcagtgagcgagcgagcg cgcagctgcctgcaggggcgcctgatgcggtattttctccttacg catctgtgcggtatttcacaccgcatacgtcaaagcaaccatagt acgcgccctgtagcggcgcattaagcgcggcgggtgtggtggtta cgcgcagcgtgaccgctacacttgccagcgccctagcgcccgctc ctttcgctttcttcccttcctttctcgccacgttcgccggctttc cccgtcaagctctaaatcggggggctccctttagggttccgatttta gtgctttacggcacctcgaccccaaaaaacttgatttgggtgatg gttcacgtagtgggccatcgccctgatagacggtttttcgcccctt tgacgttggagtccacgttctttaatagtggactcttgttccaaa ctggaacaacactcaacccctatctcgggctattcttttgatttat aagggattttgccgatttcggcctattggttaaaaaaatgagctga tttaacaaaaatttaacgcgaatttttaacaaaatattaacgtttta caattttatggtgcactctcagtacaatctgctctgatgccgcat agttaagccagccccgacacccgccaacacccgctgacgcgccct gacgggcttgtctgctcccggcatccgcttacagacaagctgtga ccgtctccgggagctgcatgtgtcagaggttttcaccgtcatcac cgaaacgcgcgagacgaaagggcctcgtgatacgcctattttttat aggttaatgtcatgataataatggtttcttagacgtcaggtggca cttttcggggaaatgtgcgcggaacccctatttgtttattttttct aaatacattcaaatatgtatccgctcatgagacaataaccctgat aaatgcttcaataatattgaaaaaggaagagtatgagtattcaac atttccgtgtcgcccttattcccttttttgcggcattttgccttc ctgttttttgctcacccagaaacgctggtgaaagtaaaagatgctg aagatcagttgggtgcacgagtgggttacatcgaactggatctca acagcggtaagatccttgagagttttcgccccgaagaacgttttc caatgatgagcacttttaaagttctgctatgtggcgcggtattat cccgtattgacgccgggcaagagcaactcggtcgccgcatacact attctcagaatgacttggttgagtactcaccagtcacagaaaagc atcttacggatggcatgacagtaagagaattatgcagtgctgcca taaccatgagtgataacactgcggccaacttacttctgacaacga tcggaggaccgaaggagctaaccgcttttttgcacaacatggggg atcatgtaactcgccttgatcgttgggaaccggagctgaatgaag ccataccaaacgacgagcgtgacaccacgatgcctgtagcaatgg caacaacgttgcgcaaactattaactggcgaactacttactctag cttcccggcaacaattaatagactggatggaggcggataaagttg caggaccacttctgcgctcggcccttccggctggctggttttattg ctgataaatctggagccggtgagcgtgggtctcgcggtatcattg cagcactggggccagatggtaagccctcccgtatcgtagttatct acacgacggggagtcaggcaactatggatgaacgaaatagacaga tcgctgagataggtgcctcactgattaagcattggtaactgtcag accaagtttactcatatatactttagattgatttaaaacttcatt tttaatttaaaaggatctaggtgaagatcctttttgataatctca tgaccaaaatcccttaacgtgagttttcgttccactgagcgtcag accccgtagaaaagatcaaaggatcttcttgagatcctttttttc tgcgcgtaatctgctgcttgcaaacaaaaaaaccaccgctaccag cggtggtttgtttgccggatcaagagctaccaactctttttccga aggtaactggcttcagcagagcgcagataccaaatactgtccttc tagtgtagccgtagttaggccaccacttcaagaactctgtagcac cgcctacatacctcgctctgctaatcctgttaccagtggctgctg ccagtggcgataagtcgtgtcttaccgggttggactcaagacgat agttaccggataaggcgcagcggtcgggctgaacggggggttcgt gcacacagcccagcttggagcgaacgacctacaccgaactgagat acctacagcgtgagctatgagaaagcgccacgcttcccgaaggga gaaaggcggacaggtatccggtaagcggcagggtcggaacaggag agcgcacgagggagcttccaggggggaaacgcctggtatctttata gtcctgtcgggtttcgccacctctgacttgagcgtcgatttttgt gatgctcgtcaggggggcggagcctatggaaaaacgccagcaacg cggcctttttacggttcctggccttttgctggccttttgctcaca tgt pRC120AAV Two Vector dCas12a/dCpf1
(SEQ ID NO: 15)
cctgcaggcagctgcgcgctcgctcgctcactgaggccgcccggg caaagcccgggcgtcgggcgacctttggtcgcccggcctcagtga gcgagcgagcgcgcagagagggagtggccaactccatcactaggg gttcctgcggccgcacgcgttctaggtcttgaaaggagtgggaat tggctccggtgcccgtcagtgggcagagcgcacatcgcccacagt ccccgagaagttgggggggagggagtcggcaattgatccggtgccta gagaaggtggcgcggggtaaactgggaaagtgatgtcgtgtactg gctccgcctttttcccgagggtggggggagaaccgtatataagtgc agtagtcgccgtgaacgttcttttttcgcaacgggtttgccgccag -continued

```
aacacaggTGTCGTGACGCGcGTACGgccaccatgtcaaagctgg agaaattcaccaactgttatagcctgtctaagaccctgcgcttca aggcaatcccagtgggcaagacacaagagaacattgacaacaaac ggctcctggtggaggatgagaagagggctgaagattacaagggcg ttaagaagctgctggataggtactatctgtcattcatcaacgatg tcctccacagtatcaagctgaagaatctgaacaattacatttctc tgttccggaagaagacacggaccgagaaggagaacaaagagctgg agaatctggagatcaacctgaggaaagaaatagctaaggctttca aagggaacgagggttacaagtccctgttcaagaaagacattatcg agactattctgcctgagttcctggacgataaagatgagatcgccc tcgtcaattccttcaatgggtttaccacagcctttaccggcttct tcgacaatagagagaatatgttctctgaagaggccaaatccacta gcatcgcctttcgctgcataaacgagaacctgactaggtacatca gcaatatggacatctttgagaaagtcgatgccatattcgacaaac atgaggtgcaggagattaaggagaagatcctgaactcagattacg atgtcgaagatttcttcgagggagagttcttcaacttcgtgctca cacaagagggcattgatgtgtacaatgcaatcattggagggttcg tgacagagagtggcgagaagataaagggcctgaacgagtatatca acctctacaaccagaaaaccaagcagaaactgcctaagttcaagc cactgtacaaacaagtgctctcagatagggaaagcctgagcttct acggtgaagggtatacatcagatgaagaagtgctcgaagtgttcc gcaacaccctcaataagaacagtgaaatcttctcttcaatcaaga agctggagaaactgttcaagaatttcgatgagtactcctctgccg gaatctttgtgaagaatggccctgcaatatccactattagcaaag acatctttggcgagtggaacgttatcagggataagtggaatgccg agtacgatgatattcatctcaagaagaaagccgtggttacagaga aatacgaggatgatagacgcaagagctttaagaagattggtagct tctctctcgaacagctgcaggagtacgccgacgctgacctgtcag tcgtggagaaactcaaggagatcataatccagaaggtggatgaaa tctacaaagtgtatggaagctctgagaaactcttcgatgcagact ttgttctggagaagagtctgaagaagaacgacgcagtggttgcta tcatgaaggacctgctggattctgttaagtctttcgagaattaca ttaaggcattctttggtgaagggaaggagacaaatagggacgaga gcttctatggcgactttgttctggcctacgacatcctcctcaagg ttgaccacatctatgacgctatacggaattacgttacccagaagc cctatagcaaagacaagttcaagctgtatttccagaatccacagt ttatgggtgggtgggataaagacaaagaaacagattacagggcca ctatcctgcggtacggcagcaaatactatctggctatcatggata agaagtacgccaaatgcctccagaagatcgacaaggacgacgtga acggtaactacgagaagatcaattacaagctcctgccaggaccta
```

-continued

```
acaagatgctgcccaaggtgttcttctccaagaaatggatggcct actataacccaagcgaggacattcagaagatatacaagaatgggga cattcaagaagggcgatatgttcaacctcaacgactgccacaagc tgattgatttcttcaaggatagcatttctcgctatcccaagtggt ctaatgcatacgatttcaacttcagcgagactgagaagtacaaag acatcgctggcttctaccgggaggtggaagagcaaggctataagg tgtcattcgaatccgcttctaagaaggaagtggataagctcgtgg aagagggtaagctgtacatgttccagatatacaacaaagacttca gcgataagagccacggcactccaaacctccatactatgtatttca agctgctgtttgacgagaacaaccacggacagattaggctgtcag gaggcgcagaactcttcatgcgcagagcttcactgaagaaggagg aactcgttgtccacccagccaatagccctatagccaataagaatc cagacaatcctaagaaaaccactactctgtcttacgatgtgtata aggataagagattctctgaagatcagtacgaactgcacatacccca ttgccattaacaagtgccctaagaacatcttcaagattaacacag aggttagagtgctcctgaaacacgacgataaccccttatgttatag gcattgctcgcggagagagaaacctgctgtacatcgtcgtggtgg acggcaaaggcaacatcgtggaacagtacagtctcaatgaaatca ttaacaatttcaacggaatccgcattaagaccgactaccattctc tcctcgacaagaaggagaaagaaaggttcgaagcaagacagaatt ggacaagtatagagaatatcaaagaactgaaggctgggtacatct ctcaggttgtgcacaagatatgtgagctggtggagaagtacgacg ctgttatcgccctcgcggacctgaatagcggcttcaagaactcca gggtgaaggtggagaagcaggtgtatcagaagttcgagaagatgc tgatcgacaagctcaactatatggtggacaagaaatccaatcctt gcgctactggtggagccctgaagggctatcaaatcaccaataagt tcgaatctttcaagtctatgagcacccagaatggcttcatcttct acatacccgcatggctgacatccaagattgatccctctaccggat ttgttaatctgctcaagactaagtacacctctattgctgactcaa agaagttcatatcatcatttgaccgcatcatgtacgtgccagaag aggacctgttcgagtttgccctggattacaagaatttctctctcgga ctgacgccgactacatcaagaagtggaagctctactcttatggta atcggattcgcatattccgcaatcccaagaagaataacgtgttcg attgggaggaagtttgcctcaccagcgcttacaaggagctgttca ataagtatgggattaactaccagcagggcgacataagagccctgc tgtgcgaacaatctgataaggcattctattcctctttcatggcac tgatgtcactgatgctgcaaatgcgcaattccatcaccggaagaa cagacgtggcctttctgatctctcctgtcaagaactcagatggca tcttctacgattcccgcaactatgaagcacaggagaatgctatcc tgcctaagaatgccgatgcaaatggagccctataacatcgccagaa aggtcctctgggccataggacaattcaagaaagctgaagatgaga
```

-continued

```
agctggacaaggtgaagatcgccatttcaaacaaagagtggctcg aatatgctcagacctcagtgaagcataaaaggccggcggccacga aaaaggccggccaggcaaaaaagaaaaagGGCAGCGGTAGTGGGG

AGGAGCTTCTTTCTAAAAATTATCATCTTGAAAATGAAGTGGCAC

GACTCAAGAAAGGCTCTGGGTCCGGTGAGGAACTCCTGTCCAAGA

ACTATCATCTTGAAAACGAAGTCGCCCGCCTTAAAAAAGGCTCAG

GCTCAGGTGAAGAATTGTTGAGCAAAAACTATCACCTTGAGAATG

AGGTTGCCCGGCTCAAAAAGGGTCTGGCAGCGGCGAGGAACTCC

TTTCAAAGAACTACCATCTCGAAAATGAAGTTGCTCGGTTGAAGA

AGGGTTCAGGATCTGGCGAGGAGCTTCTGTCCAAGAACTACCATT

TGGAGAACGAGGTCGCAAGACTTAAAAAAtgaAATAAAAGATCTT

TATTTTCATTAGATCTGTGTGTTGGTTTTTTGTGTGCggaccgag cggccgcaggaacccctagtgatggagttggccactccctctctg cgcgctcgctcgctcactgaggccgggcgaccaaaggtcgcccga cgcccgggctttgcccgggcggcctcagtgagcgagcgagcgcgc agctgcctgcaggggcgcctgatgcggtattttctcttacgcat ctgtgcggtatttcacaccgcatacgtcaaagcaaccatagtacg cgccctgtagcggcgcattaagcgcggcgggtgtggtggttacgc gcagcgtgaccgctacacttgccagcgccctagcgcccgctcctt tcgctttcttcccttccttctcgccacgttcgccggctttcccc gtcaagctctaaatcggggctcccttagggttccgatttagtg ctttacggcacctcgaccccaaaaaacttgatttgggtgatggtt cacgtagtgggccatcgccctgatagacggtttttcgccctttga cgttggagtccacgttctttaatagtggactcttgttccaaactg gaacaacactcaaccctatctcgggctattcttttgatttataag ggattttgccgatttcggcctattggttaaaaaatgagctgattt aacaaaaatttaacgcgaatttttaacaaaatattaacgtttacaa ttttatggtgcactctcagtacaatctgctctgatgccgcatagt taagccagccccgacacccgccaacacccgctgacgcgccctgac gggcttgtctgctcccggcatccgcttacagacaagctgtgaccg tctccgggagctgcatgtgtcagaggttttcaccgtcatcaccga aacgcgcgagacgaaagggcctcgtgatacgcctatttttatagg ttaatgtcatgataataatggtttcttagacgtcaggtggcactt ttcggggaaatgtgcgcggaacccctatttgtttatttttctaaa tacattcaaatatgtatccgctcatgagacaataaccctgataaa tgcttcaataatattgaaaaaggaagagtatgagtattcaacatt tccgtgtcgcccttattccctttttttgcggcattttgccttcctg ttttgctcacccagaaacgctggtgaaagtaaaagatgctgaag atcagttgggtgcacgagtgggttacatcgaactggatctcaaca gcggtaagatccttgagagttttcgccccgaagaacgttttccaa
```

-continued

```
tgatgagcacttttaaagttctgctatgtggcgcggtattatccc gtattgacgccgggcaagagcaactcggtcgccgcatacactatt ctcagaatgacttggttgagtactcaccagtcacagaaaagcatc ttacggatggcatgacagtaagagaattatgcagtgctgccataa ccatgagtgataacactgcggccaacttacttctgacaacgatcg gaggaccgaaggagctaaccgcttttttgcacaacatgggggatc atgtaactcgccttgatcgttgggaaccggagctgaatgaagcca taccaaacgacgagcgtgacaccacgatgcctgtagcaatggcaa caacgttgcgcaaactattaactggcgaactacttactctagctt cccggcaacaattaatagactggatggaggcggataaagttgcag gaccacttctgcgctcggcccttccggctggctggtttattgctg ataaatctggagccggtgagcgtgggtctcgcggtatcattgcag cactggggccagatggtaagccctcccgtatcgtagttatctaca cgacggggagtcaggcaactatggatgaacgaaatagacagatcg ctgagataggtgcctcactgattaagcattggtaactgtcagacc aagtttactcatatatactttagattgatttaaaacttcattttt aatttaaaaggatctaggtgaagatcctttttgataatctcatga ccaaaatcccttaacgtgagttttcgttccactgagcgtcagacc ccgtagaaaagatcaaaggatcttcttgagatcctttttttctgc gcgtaatctgctgcttgcaaacaaaaaaaccaccgctaccagcgg tggtttgtttgccggatcaagagctaccaactctttttttccgaagg taactggcttcagcagagcgcagataccaaatactgtccttctag tgtagccgtagttaggccaccacttcaagaactctgtagcaccgc ctacatacctcgctctgctaatcctgttaccagtggctgctgcca gtggcgataagtcgtgtcttaccgggttggactcaagacgatagt taccggataaggcgcagcggtcgggctgaacggggggttcgtgca cacagcccagcttggagcgaacgacctacaccgaactgagatacc tacagcgtgagctatgagaaagcgccacgcttcccgaagggagaa aggcggacaggtatccggtaagcggcagggtcggaacaggagagc gcacgagggagcttccaggggaaacgcctggtatctttatagtc ctgtcgggtttcgccacctctgacttgagcgtcgatttttgtgat gctcgtcagggggggggagcctatggaaaaacgccagcaacgcgg cctttttacggttcctggccttttgctggccttttgctcacatgt
``` pRC121b AAV Two Vector dCas11a/dCpf1

(SEQ ID NO: 16)

```
CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG
```

-continued

```
AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccatgGGCCCAGCCGCCAAACGAGTCAAGCTGGA

TGGCCCCGATATCGTCATGACTCAATCACCCTCATCACTGTCAGC

CAGCGTCGGTGACCGGGTAACAATTACTTGTAGATCATCAACTGG

GGCCGTCACTACCTCCAACTATGCCAGTTGGGTTCAAGAGAAACC

CGGCAAGCTCTTTAAGGGACTGATCGGTGGGACCAATAATCGGGC

CCCCGGTGTGCCTTCTCGCTTTAGCGGGAGTTTGATAGGCGATAA

AGCCACATTGACAATATCATCTCTTCAACCCGAGGACTTCGCTAC

CTATTTTTGTGCTTTGTGGTATAGTAACCATTGGGTATTTGGCCA

AGGAACTAAGGTAGAGTTGAAGCGGGGGGGCGGCGGCTCTGGTGG

AGGAGGTAGTGGGGGCGGTGGCTCTTCCGAGGGGGGTTCCGAAGT

AAAGCTTTTGGAGAGCGGCGGCGGCCTGGTCCAGCCTGGAGGATC

TCTCAAGCTTAGCTGCGCCGTCAGCGGCTTTTCCCTCACTGATTA

TGGTGTAAATTGGGTGAGGCAGGCTCCAGGCAGGGGGTTGGAGTG

GATAGGGGTGATATGGGGGGATGGCATCACAGATTATAATTCTGC

ACTTAAGGATAGGTTTATTATCAGTAAGGACAACGGTAAGAACAC

CGTTTATCTTCAGATGTCTAAGGTGCGGTCCGATGATACTGCCCT

CTATTATTGTGTAACCGGCCTTTTCGATTACTGGGGCCAAGGGAC

TTTGGTAACCGTGTCATCATATCCCTATGACGTCCCTGACTACGC

AGGGGGAGGAGGGGGATCCGGTGGCGGTGGTAGTGGAGGAGGTGG

ATCTGGAGGAGGGGGAAGCggtaccCCAGCTGCGAAACGAGTTAA

ATTGGATGGTGGTGGCGGGTCCTCAGGTTTGCCCAATGGATTGGA

TGGTGATGAAGACTTCTCAGACATCGCAGATATGGACTTTAGTGC

CTTGCTGAGCCAAATCTCATCTGGCTCATCAGGTCTTCCCAACGG

ATTGGATGGCGATGAGGACTTTTCCGACATCGCAGACATGGACTT

TTCCGCTCTGTTGAGCCAGATAAGTTCTGGCTCCTCCGGACTCCC

TAATGGCTTGGATGGAGATGAGGATTTTAGCGATATAGCAGACAT

GGATTTTAGCGCATTGCTCTCACAAATCTCCAGTGGCGGGGGTGG

TAGTGGATTTTCAGTGGATACTTCCGCACTTCTCGATTTGTTTTC

TCCCAGTGTCACCGTCCCAGACATGAGTCTTCCTGACCTCGACTC

TTCTCTCGCCAGTATTCAGGAACTGCTCAGTCCACAGGAGCCTCC

TCGCCCTCCTGAAGCAGAGAATAGTTCCCCAGATTCAGGAAAGCA

GCTGGTGCACTACACAGCACAGCCACTGTTCCTCTTGGACCCTGG
```

-continued

```
GAGTGTAGACACAGGCTCAAACGATCTCCCCGTTCTTTTTGAACT

TGGCGAAGGTTCCTATTTTAGCGAGGGGGACGGATTCGCCGAGGA

CCCTACTATCAGTCTCCTTACAGGTAGCGAGCCACCCAAAGCTAA

AGACCCCACCGTGAGCTAGTGActcgagGATTCGTCAGTAGGGTT

GTAAAGGTTTTTCTTTTCCTGAGAAAACAACCTTTTGTTTTCTCA

GGTTTTGCTTTTTGGCCTTTCCCTAGCTTTAAAAAAAAAAAAGCA

AAACTCACCGAGGCAGTTCCATAGGATGGCtagcAAGATCCTGGT

ATTGGTCTGCGAgaagagcgagctcttcaatcaacctctggatta caaaatttgtgaaagattgactggtattcttaactatgttgctcc ttttacgctatgtggatacgctgctttaatgcctttgtatcatgc tattgcttcccgtatggctttcattttctcctccttgtataaatc ctggttgctgtctctttatgaggagttgtggcccgttgtcaggca acgtggcgtggtgtgcactgtgtttgctgacgcaacccccactgg ttggggcattgccaccacctgtcagctccttttccgggacttttcgc tttcccctccctattgccacggcggaactcatcgccgcctgcct tgcccgctgctggacaggggctcggctgttgggcactgacaattc cgtggtgttgtcggggaaatcatcgtcctttccttggctgctcgc ctgtgttgccacctggattctgcgcgggacgtccttctgctacgt cccttcggccctcaatccagcggaccttccttcccgcggcctgct gccggctctgcgggcctcttccgcgtcttcgccttcgccctcagac gagtcggatctccctttgggccgcctccccgcgtcgactttaaga ccaatCGGCCGCAGGAACCCCTAGTGATGGAGTTGGCCACTCCCT

CTCTGCGCGCTCGCTCGCTCACTGAGGCCGGGCGACCAAAGGTCG

CCCGACGCCCGGGCTTTGCCCGGGCGGCCTCAGTGAGCGAGCGAG

CGCGCAGCTGCCTGCAGGGGCGCCTGATGCGGTATTTTCTCCTTA

CGCATCTGTGCGGTATTTCACACCGCATACGTCAAAGCAACCATA

GTACGCGCCCTGTAGCGGCGCATTAAGCGCGGCGGGTGTGGTGGT

TACGCGCAGCGTGACCGCTACACTTGCCAGCGCCTTAGCGCCCGC

TCCTTTCGCTTTCTTCCCTTCCTTTCTCGCCACGTTCGCCGGCTT

TCCCCGTCAAGCTCTAAATCGGGGGCTCCCTTTAGGGTTCCGATT

TAGTGCTTTACGGCACCTCGACCCCAAAAAACTTGATTTGGGTGA

TGGTTCACGTAGTGGGCCATCGCCCTGATAGACGGTTTTTCGCCC

TTTGACGTTGGAGTCCACGTTCTTTAATAGTGGACTCTTGTTCCA

AACTGGAACAACACTCAACTCTATCTCGGGCTATTCTTTTGATTT

ATAAGGGATTTTGCCGATTTCGGTCTATTGGTTAAAAAATGAGCT

GATTTAACAAAAATTTAACGCGAATTTTAACAAAATATTAACGTT

TACAATTTTATGGTGCACTCTCAGTACAATCTGCTCTGATGCCGC

ATAGTTAAGCCAGCCCCGACACCCGCCAACACCCGCTGACGCGCC

CTGACGGGCTTGTCTGCTCCCGGCATCCGCTTACAGACAAGCTGT

GACCGTCTCCGGGAGCTGCATGTGTCAGAGGTTTTCACCGTCATC
```

-continued

ACCGAAACGCGCGAGACGAAAGGGCCTCGTGATACGCCTATTTTT

ATAGGTTAATGTCATGATAATAATGGTTTCTTAGACGTCAGGTGG

CACTTTTCGGGGAAATGTGCGCGGAACCCCTATTTGTTTATTTTT

CTAAATACATTCAAATATGTATCCGCTCATGAGACAATAACCCTG

ATAAATGCTTCAATAATATTGAAAAAGGAAGAGTATGAGTATTCA

ACATTTCCGTGTCGCCCTTATTCCCTTTTTTGCGGCATTTTGCCT

TCCTGTTTTTGCTCACCCAGAAACGCTGGTGAAAGTAAAAGATGC

TGAAGATCAGTTGGGTGCACGAGTGGGTTACATCGAACTGGATCT

CAACAGCGGTAAGATCCTTGAGAGTTTTCGCCCCGAAGAACGTTT

TCCAATGATGAGCACTTTTAAAGTTCTGCTATGTGGCGCGGTATT

ATCCCGTATTGACGCCGGGCAAGAGCAACTCGGTCGCCGCATACA

CTATTCTCAGAATGACTTGGTTGAGTACTCACCAGTCACAGAAAA

GCATCTTACGGATGGCATGACAGTAAGAGAATTATGCAGTGCTGC

CATAACCATGAGTGATAACACTGCGGCCAACTTACTTCTGACAAC

GATCGGAGGACCGAAGGAGCTAACCGCTTTTTTGCACAACATGGG

GGATCATGTAACTCGCCTTGATCGTTGGGAACCGGAGCTGAATGA

AGCCATACCAAACGACGAGCGTGACACCACGATGCCTGTAGCAAT

GGCAACAACGTTGCGCAAACTATTAACTGGCGAACTACTTACTCT

AGCTTCCCGGCAACAATTAATAGACTGGATGGAGGCGGATAAAGT

TGCAGGACCACTTCTGCGCTCGGCCCTTCCGGCTGGCTGGTTTAT

TGCTGATAAATCTGGAGCCGGTGAGCGTGGAAGCCGCGGTATCAT

TGCAGCACTGGGGCCAGATGGTAAGCCCTCCCGTATCGTAGTTAT

CTACACGACGGGGAGTCAGGCAACTATGGATGAACGAAATAGACA

GATCGCTGAGATAGGTGCCTCACTGATTAAGCATTGGTAACTGTC

AGACCAAGTTTACTCATATATACTTTAGATTGATTTAAAACTTCA

TTTTTAATTTAAAAGGATCTAGGTGAAGATCCTTTTTGATAATCT

CATGACCAAAATCCCTTAACGTGAGTTTTCGTTCCACTGAGCGTC

AGACCCCGTAGAAAAGATCAAAGGATCTTCTTGAGATCCTTTTTT

TCTGCGCGTAATCTGCTGCTTGCAAACAAAAAAACCACCGCTACC

AGCGGTGGTTTGTTTGCCGGATCAAGAGCTACCAACTCTTTTTCC

GAAGGTAACTGGCTTCAGCAGAGCGCAGATACCAAATACTGTTCT

TCTAGTGTAGCCGTAGTTAGGCCACCACTTCAAGAACTCTGTAGC

ACCGCCTACATACCTCGCTCTGCTAATCCTGTTACCAGTGGCTGC

TGCCAGTGGCGATAAGTCGTGTCTTACCGGGTTGGACTCAAGACG

ATAGTTACCGGATAAGGCGCAGCGGTCGGGCTGAACGGGGGGTTC

GTGCACACAGCCCAGCTTGGAGCGAACGACCTACACCGAACTGAG

ATACCTACAGCGTGAGCTATGAGAAAGCGCCACGCTTCCCGAAGG

GAGAAAGGCGGACAGGTATCCGGTAAGCGGCAGGGTCGGAACAGG

AGAGCGCACGAGGGAGCTTCCAGGGGGAAACGCCTGGTATCTTTA

TAGTCCTGTCGGGTTTCGCCACCTCTGACTTGAGCGTCGATTTTT

-continued

GTGATGCTCGTCAGGGGGGCGGAGCCTATGGAAAAACGCCAGCAA

CGCGGCCTTTTTACGGTTCCTGGCCTTTTGCTGGCCTTTTGCTCA

CATGT pRC124AAV Two Vector dCas12a/dCpf1

(SEQ ID NO: 17)

CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccatgCCCGCTGCGAAACGAGTTAAATTGGATgg atcctcaaagctggagaaattcaccaactgttatagcctgtctaa gaccctgcgcttcaaggcaatcccagtgggcaagacacaagagaa cattgacaacaaacggctcctggtggaggatgagaagagggctga agattacaagggcgttaagaagctgctggataggtactatctgtc attcatcaacgatgtcctccacagtatcaagctgaagaatctgaa caattacatttctctgttccggaagaagacacggaccgagaagga gaacaaagagctggagaatctggagatcaacctgaggaaagaaat agctaaggctttcaaagggaacgagggttacaagtccctgttcaa gaaagacattatcgagactattctgcctgagttcctggacgataa agatgagatcgccctcgtcaattccttcaatgggtttaccacagc ctttaccggcttcttcgacaatagagagaatatgttctctgaaga ggccaaatccactagcatcgcctttcgctgcataaacgagaacct gactaggtacatcagcaatatggacatctttgagaaagtcgatgc catattcgacaaacatgaggtgcaggagattaaggagaagatcct gaactcagattacgatgtcgaagatttcttcgagggagagttctt caacttcgtgctcacacaagagggcattgatgtgtacaatgcaat cattggagggttcgtgacagagagtggcgagaagataaagggcct gaacgagtatatcaacctctacaaccagaaaaccaagcagaaact gcctaagttcaagccactgtacaaacaagtgctctcagataggga aagcctgagcttctacggtgaagggtatacatcagatgaagaagt gctcgaagtgttccgcaacaccctcaataagaacagtgaaatctt -continued ctcttcaatcaagaagctggagaaactgttcaagaatttcgatga gtactcctctgccggaatctttgtgaagaatggccctgcaatatc cactattagcaaagacatctttggcgagtggaacgttatcaggga taagtggaatgccgagtacgatgatattcatctcaagaagaaagc cgtggttacagagaaatacgaggatgatagacgcaagagctttaa gaagattggtagcttctctctcgaacagctgcaggagtacgccga cgctgacctgtcagtcgtggagaaactcaaggagatcataatcca gaaggtggatgaaatctacaaagtgtatggaagctctgagaaact cttcgatgcagactttgttctggagaagagtctgaagaagaacga cgcagtggttgctatcatgaaggacctgctggattctgttaagtc tttcgagaattacattaaggcattctttggtgaagggaaggagac aaatagggacgagagcttctatggcgactttgttctggcctacga catcctcctcaaggttgaccacatctatgacgctatacggaatta cgttacccagaagccctatagcaaagacaagttcaagctgtattt ccagaatccacagtttatgggtgggtgggataaagacaaagaaac agattacagggccactatcctgcggtacggcagcaaatactatct ggctatcatggataagaagtacgccaaatgcctccagaagatcga caaggacgacgtgggtaccagtCCAGCTGCGAAACGAGTTAAATT

GGATGGTGGTGGCGGGTCCTCAGGTTTGCCCAATGGATTGGATGG

TGATGAAGACTTCTCAGACATCGCAGATATGGACTTTAGTGCCTT

GCTGAGCCAAATCTCATCTGGCTCATCAGGTCTTCCCAACGGATT

GGATGGCGATGAGGACTTTTCCGACATCGCAGACATGGACTTTTC

CGCTCTGTTGAGCCAGATAAGTTCTGGCTCCTCCGGACTCCCTAA

TGGCTTGGATGGAGATGAGGATTTTAGCGATATAGCAGACATGGA

TTTTAGCGCATTGCTCTCACAAATCTCCAGTGGCGGGGGTGGTAG

TGGATTTTCAGTGGATACTTCCGCACTTCTCGATTTGTTTTCTCC

CAGTGTCACCGTCCCAGACATGAGTCTTCCTGACCTCGACTCTTC

TCTCGCCAGTATTCAGGAACTGCTCAGTCCACAGGAGCCTCCTCG

CCCTCCTGAAGCAGAGAATAGTTCCCCAGATTCAGGAAAGCAGCT

GGTGCACTACACAGCACAGCCACTGTTCCTCTTGGACCCTGGGAG

TGTAGACACAGGCTCAAACGATCTCCCCGTTCTTTTTGAACTTGG

CGAAGGTTCCTATTTTAGCGAGGGGGACGGATTCGCCGAGGACCC

TACTATCAGTCTCCTTACAGGTAGCGAGCCACCCAAAGCTAAAGA

CCCCACCGTGAGCTAGTGActcgagGATTCGTCAGTAGGGTTGTA

AAGGTttttcttttcctgagaaaacaaccttttgttttctcaggt tttgcttttggcctTTCCCTAGCTTTAAAAAAAAAAAAGCAAAA CTCACCGAGGCAGTTCCATAGGATGGCtagcAAGATCCTGGTATT GGTCTGCGAgaagagcgagctcttcaatcaacctctggattacaa aatttgtgaaagattgactggtattcttaactatgttgctccttt tacgctatgtggatacgctgctttaatgcctttgtatcatgctat -continued tgcttcccgtatggctttcattttctcctccttgtataaatcctg gttgctgtctctttatgaggagttgtggcccgttgtcaggcaacg tggcgtggtgtgcactgtgtttgctgacgcaaccccactggttg gggcattgccaccacctgtcagctcctttccgggactttcgctttt ccccctccctattgccacggcggaactcatcgccgcctgccttgc ccgctgctggacaggggctcggctgttgggcactgacaattccgt ggtgttgtcggggaaatcatcgtcctttccttggctgctcgcctg tgttgccacctggattctgcgcgggacgtccttctgctacgtccc ttcggccctcaatccagcggaccttccttcccgcggcctgctgcc ggctctgcggcctcttccgcgtcttcgccttcgccctcagacgag tcggatctcccctttgggccgcctccccgcCGGCCGCAGGAACCCC

TAGTGATGGAGTTGGCCACTCCCTCTCTGCGCGCTCGCTCGCTCA

CTGAGGCCGGGCGACCAAAGGTCGCCCGACGCCCGGGCTTTGCCC

GGGCGGCCTCAGTGAGCGAGCGAGCGCGCAGCTGCCTGCAGGGGC

GCCTGATGCGGTATTTTCTCCTTACGCATCTGTGCGGTATTTCAC

ACCGCATACGTCAAAGCAACCATAGTACGCGCCCTGTAGCGGCGC

ATTAAGCGCGGCGGGTGTGGTGGTTACGCGCAGCGTGACCGCTAC

ACTTGCCAGCGCCTTAGCGCCCGCTCCTTTCGCTTTCTTCCCTTC

CTTTCTCGCCACGTTCGCCGGCTTTCCCCGTCAAGCTCTAAATCG

GGGGCTCCCTTTAGGGTTCCGATTTAGTGCTTTACGGCACCTCGA

CCCCAAAAAACTTGATTTGGGTGATGGTTCACGTAGTGGGCCATC

GCCCTGATAGACGGTTTTTCGCCCTTTGACGTTGGAGTCCACGTT

CTTTAATAGTGGACTCTTGTTCCAAACTGGAACAACACTCAACTC

TATCTCGGGCTATTCTTTTGATTTATAAGGGATTTTGCCGATTTC

GGTCTATTGGTTAAAAAATGAGCTGATTTAACAAAAATTTAACGC

GAATTTTAACAAAATATTAACGTTTACAATTTTATGGTGCACTCT

CAGTACAATCTGCTCTGATGCCGCATAGTTAAGCCAGCCCCGACA

CCCGCCAACACCCGCTGACGCGCCCTGACGGGCTTGTCTGCTCCC

GGCATCCGCTTACAGACAAGCTGTGACCGTCTCCGGGAGCTGCAT

GTGTCAGAGGTTTTCACCGTCATCACCGAAACGCGCGAGACGAAA

GGGCCTCGTGATACGCCTATTTTTATAGGTTAATGTCATGATAAT

AATGGTTTCTTAGACGTCAGGTGGCACTTTTCGGGGAAATGTGCG

CGGAACCCCTATTTGTTTATTTTTCTAAATACATTCAAATATGTA

TCCGCTCATGAGACAATAACCCTGATAAATGCTTCAATAATATTG

AAAAAGGAAGAGTATGAGTATTCAACATTTCCGTGTCGCCCTTAT

TCCCTTTTTTGCGGCATTTTGCCTTCCTGTTTTTGCTCACCCAGA

AACGCTGGTGAAAGTAAAAGATGCTGAAGATCAGTTGGGTGCACG

AGTGGGTTACATCGAACTGGATCTCAACAGCGGTAAGATCCTTGA

GAGTTTTCGCCCCGAAGAACGTTTTCCAATGATGAGCACTTTTAA

AGTTCTGCTATGTGGCGCGGTATTATCCCGTATTGACGCCGGGCA

AGAGCAACTCGGTCGCCGCATACACTATTCTCAGAATGACTTGGT

-continued

TGAGTACTCACCAGTCACAGAAAAGCATCTTACGGATGGCATGAC

AGTAAGAGAATTATGCAGTGCTGCCATAACCATGAGTGATAACAC

TGCGGCCAACTTACTTCTGACAACGATCGGAGGACCGAAGGAGCT

AACCGCTTTTTTGCACAACATGGGGGATCATGTAACTCGCCTTGA

TCGTTGGGAACCGGAGCTGAATGAAGCCATACCAAACGACGAGCG

TGACACCACGATGCCTGTAGCAATGGCAACAACGTTGCGCAAACT

ATTAACTGGCGAACTACTTACTCTAGCTTCCCGGCAACAATTAAT

AGACTGGATGGAGGCGGATAAAGTTGCAGGACCACTTCTGCGCTC

GGCCCTTCCGGCTGGCTGGTTTATTGCTGATAAATCTGGAGCCGG

TGAGCGTGGAAGCCGCGGTATCATTGCAGCACTGGGGCCAGATGG

TAAGCCCTCCCGTATCGTAGTTATCTACACGACGGGGAGTCAGGC

AACTATGGATGAACGAAATAGACAGATCGCTGAGATAGGTGCCTC

ACTGATTAAGCATTGGTAACTGTCAGACCAAGTTTACTCATATAT

ACTTTAGATTGATTTAAAACTTCATTTTTAATTTAAAAGGATCTA

GGTGAAGATCCTTTTTGATAATCTCATGACCAAAATCCCTTAACG

TGAGTTTTCGTTCCACTGAGCGTCAGACCCCGTAGAAAAGATCAA

AGGATCTTCTTGAGATCCTTTTTTTCTGCGCGTAATCTGCTGCTT

GCAAACAAAAAAACCACCGCTACCAGCGGTGGTTTGTTTGCCGGA

TCAAGAGCTACCAACTCTTTTTCCGAAGGTAACTGGCTTCAGCAG

AGCGCAGATACCAAATACTGTTCTTCTAGTGTAGCCGTAGTTAGG

CCACCACTTCAAGAACTCTGTAGCACCGCCTACATACCTCGCTCT

GCTAATCCTGTTACCAGTGGCTGCTGCCAGTGGCGATAAGTCGTG

TCTTACCGGGTTGGACTCAAGACGATAGTTACCGGATAAGGCGCA

GCGGTCGGGCTGAACGGGGGGTTCGTGCACACAGCCCAGCTTGGA

GCGAACGACCTACACCGAACTGAGATACCTACAGCGTGAGCTATG

AGAAAGCGCCACGCTTCCCGAAGGGAGAAAGGCGGACAGGTATCC

GGTAAGCGGCAGGGTCGGAACAGGAGAGCGCACGAGGGAGCTTCC

AGGGGGAAACGCCTGGTATCTTTATAGTCCTGTCGGGTTTCGCCA

CCTCTGACTTGAGCGTCGATTTTTGTGATGCTCGTCAGGGGGGCG

GAGCCTATGGAAAAACGCCAGCAACGCGGCCTTTTTACGGTTCCT

GGCCTTTTGCTGGCCTTTTGCTCACATGT pRC126AAV Two Vector dCas12a/dCpf1
(SEQ ID NO: 18)
CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

-continued
GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccATGCCCGCTGCGAAACGAGTTAAATTGGATGG

TGGTGGCGGGTCCTCAGGTTTGCCCAATGGATTGGATGGTGATGA

AGACTTCTCAGACATCGCAGATATGGACTTTAGTGCCTTGCTGAG

CCAAATCTCATCTGGCTCATCAGGTCTTCCCAACGGATTGGATGG

CGATGAGGACTTTTCCGACATCGCAGACATGGACTTTTCCGCTCT

GTTGAGCCAGATAAGTTCTGGCTCCTCCGGACTCCCTAATGGCTT

GGATGGAGATGAGGATTTTAGCGATATAGCAGACATGGATTTTAG

CGCATTGCTCTCACAAATCTCCAGTGGCGGGGGTGGTAGTGGATT

TTCAGTGGATACTTCCGCACTTCTCGATTTGTTTTCTCCCAGTGT

CACCGTCCCAGACATGAGTCTTCCTGACCTCGACTCTTCTCTCGC

CAGTATTCAGGAACTGCTCAGTCCACAGGAGCCTCCTCGCCCTCC

TGAAGCAGAGAATAGTTCCCCAGATTCAGGAAAGCAGCTGGTGCA

CTACACAGCACAGCCACTGTTCCTCTTGGACCCTGGGAGTGTAGA

CACAGGCTCAAACGATCTCCCCGTTCTTTTTGAACTTGGCGAAGG

TTCCTATTTTAGCGAGGGGGACGGATTCGCCGAGGACCCTACTAT

CAGTCTCCTTACAGGTAGCGAGCCACCCAAAGCTAAAGACCCCAC

CGTGAGCGGTGGTGGCGGGTCCGGTaacggtaactacgagaagat caattacaagctcctgccaggacctaacaagatgctgcccaaggt gttcttctccaagaaatggatggcctactataacccaagcgagga cattcagaagatatacaagaatgggacattcaagaagggcgatat gttcaacctcaacgactgccacaagctgattgatttcttcaagga tagcatttctcgctatcccaagtggtctaatgcatacgatttcaa cttcagcgagactgagaagtacaaagacatcgctggcttctaccg ggaggtggaagagcaaggctataaggtgtcattcgaatccgcttc taagaaggaagtggataagctcgtggaagagggtaagctgtacat gttccagatatacaacaaagacttcagcgataagagccacggcac tccaaacctccatactatgtatttcaagctgctgtttgacgagaa caaccacggacagattaggctgtcaggaggcgcagaactcttcat gcgcagagcttcactgaagaaggaggaactcgttgtccacccagc caatagccctatagccaataagaatccagacaatcctaagaaaac cactactctgtcttacgatgtgtataaggataagagattctctga agatcagtacgaactgcacatacccattgccattaacaagtgccc taagaacatcttcaagattaacacagaggttagagtgctcctgaa acacgacgataaccccttatgttataggcattgctcgcggagagag -continued

```
aaacctgctgtacatcgtcgtggtggacggcaaaggcaacatcgt ggaacagtacagtctcaatgaaatcattaacaatttcaacggaat ccgcattaagaccgactaccattctctcctcgacaagaaggagaa agaaaggttcgaagcaagacagaattggacaagtatagagaatat caaagaactgaaggctgggtacatctctcaggttgtgcacaagat atgtgagctggtggagaagtacgacgcgtgttatcgccctcgcgga cctgaatagcggcttcaagaactccagggtgaaggtggagaagca ggtgtatcagaagttcgagaagatgctgatcgacaagctcaacta tatggtggacaagaaatccaatccttgcgctactggtggagccct gaagggctatcaaatcaccaataagttcgaatctttcaagtctat gagcacccagaatggcttcatcttctacatacccgcatggctgac atccaagattgatccctctaccggattgttaatctgctcaagac taagtacacctctattgctgactcaaagaagttcatatcatcatt tgaccgcatcatgtacgtgccagaagaggacctgttcgagtttgc cctggattacaagaatttctctcggactgacgccgactacatcaa gaagtggaagctctactcttatggtaatcggattcgcatattccg caatcccaagaagaataacgtgttcgattgggaggaagtttgcct caccagcgcttacaaggagctgttcaataagtatgggattaacta ccagcagggcgacataagagccctgctgtgcgaacaatctgataa ggcattctattcctctttcatggcactgatgtcactgatgctgca aatgcgcaattccatcaccggaagaacagacgtggcctttctgat ctctcctgtcaagaactcagatggcatcttctacgattcccgcaa ctatgaagcacaggagaatgctatcctgcctaagaatgccgatgc aaatggagcctataacatcgccagaaaggtcctctgggccatagg acaattcaagaaagctgaagatgagaagctggacaaggtgaagat cgccatttcaaacaaagagtggctcgaatatgctcagacctcagt gaagcatggtaccCCCGCTGCGAAACGAGTTAAATTGGATGGTGG

TGGCGGGTCCTCAGGTTTGCCCAATGGATTGGATGGTGATGAAGA

CTTCTCAGACATCGCAGATATGGACTTTAGTGCCTTGCTGAGCCA

AATCTCATCTGGCTCATCAGGTCTTCCCAACGGATTGGATGGCGA

TGAGGACTTTTCCGACATCGCAGACATGGACTTTTCCGCTCTGTT

GAGCCAGATAAGTTCTGGCTCCTCCGGACTCCCTAATGGCTTGGA

TGGAGATGAGGATTTTAGCGATATAGCAGACATGGATTTTAGCGC

ATTGCTCTCACAAATCTCCAGTGGCGGGGGTGGTAGTGGATTTTC

AGTGGATACTTCCGCACTTCTCGATTTGTTTTCTCCCAGTGTCAC

CGTCCCAGACATGAGTCTTCCTGACCTCGACTCTTCTCTCGCCAG

TATTCAGGAACTGCTCAGTCCACAGGAGCCTCCTCGCCCTCCTGA

AGCAGAGAATAGTTCCCCAGATTCAGGAAAGCAGCTGGTGCACTA

CACAGCACAGCCACTGTTCCTCTTGGACCCTGGGAGTGTAGACAC

AGGCTCAAACGATCTCCCCGTTCTTTTTGAACTTGGCGAAGGTTC
```

-continued

```
CTATTTTAGCGAGGGGGACGGATTCGCCGAGGACCCTACTATCAG

TCTCCTTACAGGTAGCGAGCCACCCAAAGCTAAAGACCCCACCGT

GAGCTAGTGActcgagAATAAAAGATCTTTATTTTCATTAGATCT

GTGTGTTGGTTTTTTGTGTCGGCCGCAGGAACCCCTAGTGATGGA

GTTGGCCACTCCCTCTCTGCGCGCTCGCTCGCTCACTGAGGCCGG

GCGACCAAAGGTCGCCCGACGCCCGGGCTTTGCCCGGGCGGCCTC

AGTGAGCGAGCGAGCGCGCAGCTGCCTGCAGGGGCGCCTGATGCG

GTATTTTCTCCTTACGCATCTGTGCGGTATTTCACACCGCATACG

TCAAAGCAACCATAGTACGCGCCCTGTAGCGGCGCATTAAGCGCG

GCGGGTGTGGTGGTTACGCGCAGCGTGACCGCTACACTTGCCAGC

GCCTTAGCGCCCGCTCCTTTCGCTTTCTTCCCTTCCTTTCTCGCC

ACGTTCGCCGGCTTTCCCCGTCAAGCTCTAAATCGGGGGCTCCCT

TTAGGGTTCCGATTTAGTGCTTTACGGCACCTCGACCCCAAAAAA

CTTGATTTGGGTGATGGTTCACGTAGTGGGCCATCGCCCTGATAG

ACGGTTTTTCGCCCTTTGACGTTGGAGTCCACGTTCTTTAATAGT

GGACTCTTGTTCCAAACTGGAACAACACTCAACTCTATCTCGGGC

TATTCTTTTGATTTATAAGGGATTTTGCCGATTTCGGTCTATTGG

TTAAAAAATGAGCTGATTTAACAAAAATTTAACGCGAATTTTAAC

AAAATATTAACGTTTACAATTTTATGGTGCACTCTCAGTACAATC

TGCTCTGATGCCGCATAGTTAAGCCAGCCCCGACACCCGCCAACA

CCCGCTGACGCGCCCTGACGGGCTTGTCTGCTCCCGGCATCCGCT

TACAGACAAGCTGTGACCGTCTCCGGGAGCTGCATGTGTCAGAGG

TTTTCACCGTCATCACCGAAACGCGCGAGACGAAAGGGCCTCGTG

ATACGCCTATTTTTATAGGTTAATGTCATGATAATAATGGTTTCT

TAGACGTCAGGTGGCACTTTTCGGGGAAATGTGCGCGGAACCCCT

ATTTGTTTATTTTTCTAAATACATTCAAATATGTATCCGCTCATG

AGACAATAACCCTGATAAATGCTTCAATAATATTGAAAAAGGAAG

AGTATGAGTATTCAACATTTCCGTGTCGCCCTTATTCCCTTTTTT

GCGGCATTTTGCCTTCCTGTTTTTGCTCACCCAGAAACGCTGGTG

AAAGTAAAAGATGCTGAAGATCAGTTGGGTGCACGAGTGGGTTAC

ATCGAACTGGATCTCAACAGCGGTAAGATCCTTGAGAGTTTTCGC

CCCGAAGAACGTTTTCCAATGATGAGCACTTTTAAAGTTCTGCTA

TGTGGCGCGGTATTATCCCGTATTGACGCCGGGCAAGAGCAACTC

GGTCGCCGCATACACTATTCTCAGAATGACTTGGTTGAGTACTCA

CCAGTCACAGAAAAGCATCTTACGGATGGCATGACAGTAAGAGAA

TTATGCAGTGCTGCCATAACCATGAGTGATAACACTGCGGCCAAC

TTACTTCTGACAACGATCGGAGGACCGAAGGAGCTAACCGCTTTT

TTGCACAACATGGGGGATCATGTAACTCGCCTTGATCGTTGGGAA

CCGGAGCTGAATGAAGCCATACCAAACGACGAGCGTGACACCACG

ATGCCTGTAGCAATGGCAACAACGTTGCGCAAACTATTAACTGGC

GAACTACTTACTCTAGCTTCCCGGCAACAATTAATAGACTGGATG
```

GAGGCGGATAAAGTTGCAGGACCACTTCTGCGCTCGGCCCTTCCG

GCTGGCTGGTTTATTGCTGATAAATCTGGAGCCGGTGAGCGTGGA

AGCCGCGGTATCATTGCAGCACTGGGGCCAGATGGTAAGCCCTCC

CGTATCGTAGTTATCTACACGACGGGGAGTCAGGCAACTATGGAT

GAACGAAATAGACAGATCGCTGAGATAGGTGCCTCACTGATTAAG

CATTGGTAACTGTCAGACCAAGTTTACTCATATATACTTTAGATT

GATTTAAAACTTCATTTTTAATTTAAAAGGATCTAGGTGAAGATC

CTTTTTGATAATCTCATGACCAAAATCCCTTAACGTGAGTTTTCG

TTCCACTGAGCGTCAGACCCCGTAGAAAAGATCAAAGGATCTTCT

TGAGATCCTTTTTTTCTGCGCGTAATCTGCTGCTTGCAAACAAAA

AAACCACCGCTACCAGCGGTGGTTTGTTTGCCGGATCAAGAGCTA

CCAACTCTTTTTCCGAAGGTAACTGGCTTCAGCAGAGCGCAGATA

CCAAATACTGTTCTTCTAGTGTAGCCGTAGTTAGGCCACCACTTC

AAGAACTCTGTAGCACCGCCTACATACCTCGCTCTGCTAATCCTG

TTACCAGTGGCTGCTGCCAGTGGCGATAAGTCGTGTCTTACCGGG

TTGGACTCAAGACGATAGTTACCGGATAAGGCGCAGCGGTCGGGC

TGAACGGGGGGTTCGTGCACACAGCCCAGCTTGGAGCGAACGACC

TACACCGAACTGAGATACCTACAGCGTGAGCTATGAGAAAGCGCC

ACGCTTCCCGAAGGGAGAAAGGCGGACAGGTATCCGGTAAGCGGC

AGGGTCGGAACAGGAGAGCGCACGAGGGAGCTTCCAGGGGGAAAC

GCCTGGTATCTTTATAGTCCTGTCGGGTTTCGCCACCTCTGACTT

GAGCGTCGATTTTTGTGATGCTCGTCAGGGGGGCGGAGCCTATGG

AAAAACGCCAGCAACGCGGCCTTTTTACGGTTCCTGGCCTTTTGC

TGGCCTTTTGCTCACATGT pGW071-pAAV_EFSLTR-Cd80-T2A-light-
P2A-Cxcl10-E2A-41bb-F2A-I12-sPA
                    (SEQ ID NO: 24)
CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccatggccttgcaattgtcagttgatgcaggatac accactcctcaagtttccatgtccaaggctcattcttctctttgt gctgctgattcgtctttcacaagtgtcttcagatgttgatgaaca actgtccaagtcagtgaaagataaggtattgctgccttgccgtta caactctcctcatgaagatgagtctgaagaccgaatctactggca aaaacatgacaaagtggtgctgtctgtcattgTtgggaaactaaa agtgtggcccgagtataagaaccggactttatatgacaacactac ctactctcttatcatcctgggcctggtcctttcagaccggggcac atacagctgtgtcgttcaaaagaaggaaagaggaacgtatgaagt taaacacttggctttagtaaagttgtccatcaaagctgacttctc tacccccaacataactgagtctggaaacccatctgcagacactaa aaggattacctgctttgcttccggggggtttcccaaagcctcgctt ctcttggttggaaaatggaagagaattacctggcatcaatacgac aatttcccaggatcctgaatctgaattgtacaccattagtagcca actagatttcaatacgactcgcaaccacaccattaagtgtctcat taaatatggagatgctcacgtgtcagaggacttcacctgggaaaa accccccagaagaccctcctgatagcaagaacacacttgtgctctt tggggcaggattcggcgcagtaataacagtcgtcgtcatcgttgt catcatcaaatgcttctgtaagcacagaagctgtttcagaagaaa tgaggcaagcagagaaacaaacaacagccttaccttcgggcctga agaagcattagctgaacagaccgtcttccttcgtacgGGCAGTGG

AGAGGGCAGAGGAAGTCTGCTAACATGCGGTGACGTCGAGGAGAA

TCCTGGCCCAatggagagtgtggtacagccttcagtgtttgtggt ggatggacagacggacatcccattcaggcggctggaacagaacca ccggagacggcgctgtggcactgtccaggtcagcctggccctggt gctgctgctaggtgctgggctggccactcagggctggtttctcct gagactgcatcaacgtcttggagacatagtagctcatctgccaga tggaggcaaaggctcctgggagaagctgatacaagatcaacgatc tcaccaggccaacccagcagcacatcttacaggagccaacgccag cttgataggtattggtggacctctgttatgggagacacgacttgg cctggccttcttgagggggcttgacgtatcatgatggggccctggt gaccatggagcccggttactactatgtgtactccaaagtgcagct gagcggcgtgggctgcccccagggggctggccaatggcctccccat cacccatggactatacaagcgcacatcccgctacccgaaggagtt agaactgctggtcagtcggcggtcaccctgtggccgggccaacag ctcccgagtctggtgggacagcagcttcctgggcggcgtggtaca tctggaggctggggaagaggtggtggtccgcgtgcctggaaaccg cctggtcagaccacgtgacggcaccaggtcctatttcggagcttt catggtcactagtGGATCCGGCGCAACAAACTTCTCTCTGCTGAA ACAAGCCGGAGATGTCGAAGAGAATCCTGGACCGatgaacccaag -continued tgctgccgtcattttctgcctcatcctgctgggtctgagtgggac tcaagggatccctctcgcaaggacggtccgctgcaactgcatcca tatcgatgacgggccagtgagaatgagggccatagggaagcttga aatcatccctgcgagcctatcctgcccacgtgttgagatcattgc cacgatgaaaaagaatgatgagcagagatgtctgaatccggaatc taagaccatcaagaatttaatgaaagcgtttagccaaaaaaggtc taaaagggctcctgctagcagcggtacccagtgcaccaactacgc cctgctgaagctggccggcgatgtggagagcaaccccgggcccat ggaccagcacacacttgatgtggaggataccgcggatgccagaca tccagcaggtacttcgtgcccctcggatgcggcgctcctcagaga taccgggctcctcgcggacgctgcgctcctctcagatactgtgcg ccccacaaatgccgcgctccccacggatgctgcctaccctgcggt taatgttcgggatcgcgaggccgcgtggccgcctgcactgaactt ctgttcccgccacccaaagctctatggcctagtcgctttggtttt gctgcttctgatcgccgcctgtgttcctatcttcacccgcaccga gcctcggccagcgctcacaatcaccacctcgcccaacctgggtac ccgagagaataatgcagaccaggtcaccccctgtttcccacattgg ctgccccaacactacacaacagggctctcctgtgttcgccaagct actggctaaaaaccaagcatcgttgtgcaatacaactctgaactg gcacagccaagatggagctgggagctcatacctatctcaaggtct gaggtacgaagaagacaaaaaggagttggtggtagacagtcccgg gctctactacgtattttttggaactgaagctcagtccaacattcac aaacacaggccacaaggtgcagggctgggtctctcttgttttgca agcaaagcctcaggtagatgactttgacaacttggccctgacagt ggaactgttccccttgctccatggagaacaagttagtggaccgttc ctggagtcaactgttgctcctgaaggctggccaccgcctcagtgt gggtctgagggcttatctgcatggagcccaggatgcatacagaga ctgggagctgtcttatcccaacaccaccagctttggactctttct tgtgaaacccgacaacccatgggaaggcatatgcggtaccgtgaa gcagaccctgaacttcgatctgctgaagctggccggcgatgtgga gagcaacccgggcccatgtacagcatgcagctcgcatcctgtgt cacattgacacttgtgctccttgtcaacagcgcacccacttcaag ctccacttcaagctctacagcggaagcacagcagcagcagcagca gcagcagcagcagcagcagcacctggagcagctgttgatggacct acaggagctcctgagcaggatggagaattacaggaacctgaaact ccccaggatgctcaccttcaaattttacttgcccaagcaggccac agaattgaaagatcttcagtgcctagaagatgaacttggacctct gcggcatgttctggatttgactcaaagcaaaagctttcaattgga agatgctgagaatttcatcagcaatatcagagtaactgttgtaaa actaaagggctctgacaacacatttgagtgccaattcgatgatga gtcagcaactgtggtggactttctgaggagatggatagccttctg -continued tcaaagcatcatctcaacaagccctcaataaGAATTCAATAAAAG

ATCTTTATTTTCATTAGATCTGTGTGTTGGTTTTTTGTGTGCGGC

CGCAGGAACCCCTAGTGATGGAGTTGGCCACTCCCTCTCTGCGCG

CTCGCTCGCTCACTGAGGCCGGGCGACCAAAGGTCGCCCGACGCC

CGGGCTTTGCCCGGGCGGCCTCAGTGAGCGAGCGAGCGCGCAGCT

GCCTGCAGGGGCGCCTGATGCGGTATTTTCTCCTTACGCATCTGT

GCGGTATTTCACACCGCATACGTCAAAGCAACCATAGTACGCGCC

CTGTAGCGGCGCATTAAGCGCGGCGGGTGTGGTGGTTACGCGCAG

CGTGACCGCTACACTTGCCAGCGCCTTAGCGCCCGCTCCTTTCGC

TTTCTTCCCTTCCTTTCTCGCCACGTTCGCCGGCTTTCCCCGTCA

AGCTCTAAATCGGGGGCTCCCTTTAGGGTTCCGATTTAGTGCTTT

ACGGCACCTCGACCCCAAAAAACTTGATTTGGGTGATGGTTCACG

TAGTGGGCCATCGCCCTGATAGACGGTTTTTCGCCCTTTGACGTT

GGAGTCCACGTTCTTTAATAGTGGACTCTTGTTCCAAACTGGAAC

AACACTCAACTCTATCTCGGGCTATTCTTTTGATTTATAAGGGAT

TTTGCCGATTTCGGTCTATTGGTTAAAAAATGAGCTGATTTAACA

AAAATTTAACGCGAATTTTAACAAAATATTAACGTTTACAATTTT

ATGGTGCACTCTCAGTACAATCTGCTCTGATGCCGCATAGTTAAG

CCAGCCCCGACACCCGCCAACACCCGCTGACGCGCCCTGACGGGC

TTGTCTGCTCCCGGCATCCGCTTACAGACAAGCTGTGACCGTCTC

CGGGAGCTGCATGTGTCAGAGGTTTTCACCGTCATCACCGAAACG

CGCGAGACGAAAGGGCCTCGTGATACGCCTATTTTTATAGGTTAA

TGTCATGATAATAATGGTTTCTTAGACGTCAGGTGGCACTTTTCG

GGGAAATGTGCGCGGAACCCCTATTTGTTTATTTTTCTAAATACA

TTCAAATATGTATCCGCTCATGAGACAATAACCCTGATAAATGCT

TCAATAATATTGAAAAAGGAAGAGTATGAGTATTCAACATTTCCG

TGTCGCCCTTATTCCCTTTTTTGCGGCATTTTGCCTTCCTGTTTT

TGCTCACCCAGAAACGCTGGTGAAAGTAAAAGATGCTGAAGATCA

GTTGGGTGCACGAGTGGGTTACATCGAACTGGATCTCAACAGCGG

TAAGATCCTTGAGAGTTTTCGCCCCGAAGAACGTTTTCCAATGAT

GAGCACTTTTAAAGTTCTGCTATGTGGCGCGGTATTATCCCGTAT

TGACGCCGGGCAAGAGCAACTCGGTCGCCGCATACACTATTCTCA

GAATGACTTGGTTGAGTACTCACCAGTCACAGAAAAGCATCTTAC

GGATGGCATGACAGTAAGAGAATTATGCAGTGCTGCCATAACCAT

GAGTGATAACACTGCGGCCAACTTACTTCTGACAACGATCGGAGG

ACCGAAGGAGCTAACCGCTTTTTTGCACAACATGGGGGATCATGT

AACTCGCCTTGATCGTTGGGAACCGGAGCTGAATGAAGCCATACC

AAACGACGAGCGTGACACCACGATGCCTGTAGCAATGGCAACAAC

GTTGCGCAAACTATTAACTGGCGAACTACTTACTCTAGCTTCCCG

GCAACAATTAATAGACTGGATGGAGGCGGATAAAGTTGCAGGACC

-continued

ACTTCTGCGCTCGGCCCTTCCGGCTGGCTGGTTTATTGCTGATAA

ATCTGGAGCCGGTGAGCGTGGAAGCCGCGGTATCATTGCAGCACT

GGGGCCAGATGGTAAGCCCTCCCGTATCGTAGTTATCTACACGAC

GGGGAGTCAGGCAACTATGGATGAACGAAATAGACAGATCGCTGA

GATAGGTGCCTCACTGATTAAGCATTGGTAACTGTCAGACCAAGT

TTACTCATATATACTTTAGATTGATTTAAAACTTCATTTTTAATT

TAAAAGGATCTAGGTGAAGATCcttttttgataatctcatgaccaa aatcccttaacgtgagttttcgttccactgaGCGTCAGACCCCGT

AGAAAAGATCAAAGGATCTTCTTGAGATCCTTTTTTTCTGCGCGT

AATCTGCTGCTTGCAAACAAAAAAACCACCGCTACCAGCGGTGGT

TTGTTTGCCGGATCAAGAGCTACCAACTCTTTTTCCGAAGGTAAC

TGGCTTCAGCAGAGCGCAGATACCAAATACTGTTCTTCTAGTGTA

GCCGTAGTTAGGCCACCACTTCAAGAACTCTGTAGCACCGCCTAC

ATACCTCGCTCTGCTAATCCTGTTACCAGTGGCTGCTGCCAGTGG

CGATAAGTCGTGTCTTACCGGGTTGGACTCAAGACGATAGTTACC

GGATAAGGCGCAGCGGTCGGGCTGAACGGGGGGTTCGTGCACACA

GCCCAGCTTGGAGCGAACGACCTACACCGAACTGAGATACCTACA

GCGTGAGCTATGAGAAAGCGCCACGCTTCCCGAAGGGAGAAAGGC

GGACAGGTATCCGGTAAGCGGCAGGGTCGGAACAGGAGAGCGCAC

GAGGGAGCTTCCAGGGGGAAACGCCTGGTATCTTTATAGTCCTGT

CGGGTTTCGCCACCTCTGACTTGAGCGTCGATTTTTGTGATGCTC

GTCAGGGGGGCGGAGCCTATGGAAAAACGCCAGCAACGCGGCCTT

TTTACGGTTCCTGGCCTTTTGCTGGCCTTTTGCTCACATGT pGWO72-pAAV_EFSLTR-IFNg-sPA (SEQ ID NO: 25)

CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccatgaacgctacacactgcatcttggctttgca gctcttcctcatggctgtttctggctgttactgccacggcacagt -continued cattgaaagcctagaaagtctgaataactattttaactcaagtgg catagatgtggaagaaaagagtctcttcttggatatctggaggaa ctggcaaaaggatggtgacatgaaaatcctgcagagccagattat ctctttctacctcagactctttgaagtcttgaaagacaatcaggc catcagcaacaacataagcgtcattgaatcacacctgattactac cttcttcagcaacagcaaggcgaaaaaggatgcattcatgagtat tgccaagtttgaggtcaacaacccacaggtccagcgccaagcatt caatgagctcatccgagtggtccaccagctgttgccggaatccag cctcaggaagcggaaaaggagtcgctgctgaGAATTCAATAAAAG

ATCTTTATTTTCATTAGATCTGTGTGTTGGTTTTTTGTGTGCGGC

CGCAGGAACCCCTAGTGATGGAGTTGGCCACTCCCTCTCTGCGCG

CTCGCTCGCTCACTGAGGCCGGGCGACCAAAGGTCGCCCGACGCC

CGGGCTTTGCCCGGGCGGCCTCAGTGAGCGAGCGAGCGCGCAGCT

GCCTGCAGGGGCGCCTGATGCGGTATTTTCTCCTTACGCATCTGT

GCGGTATTTCACACCGCATACGTCAAAGCAACCATAGTACGCGCC

CTGTAGCGGCGCATTAAGCGCGGCGGGTGTGGTGGTTACGCGCAG

CGTGACCGCTACACTTGCCAGCGCCTTAGCGCCCGCTCCTTTCGC

TTTCTTCCCTTCCTTTCTCGCCACGTTCGCCGGCTTTCCCCGTCA

AGCTCTAAATCGGGGGCTCCCTTTAGGGTTCCGATTTAGTGCTTT

ACGGCACCTCGACCCCAAAAAACTTGATTTGGGTGATGGTTCACG

TAGTGGGCCATCGCCCTGATAGACGGTTTTTCGCCCTTTGACGTT

GGAGTCCACGTTCTTTAATAGTGGACTCTTGTTCCAAACTGGAAC

AACACTCAACTCTATCTCGGGCTATTCTTTTGATTTATAAGGGAT

TTTGCCGATTTCGGTCTATTGGTTAAAAAATGAGCTGATTTAACA

AAAATTTAACGCGAATTTTAACAAAATATTAACGTTTACAATTTT

ATGGTGCACTCTCAGTACAATCTGCTCTGATGCCGCATAGTTAAG

CCAGCCCCGACACCCGCCAACACCCGCTGACGCGCCCTGACGGGC

TTGTCTGCTCCCGGCATCCGCTTACAGACAAGCTGTGACCGTCTC

CGGGAGCTGCATGTGTCAGAGGTTTTCACCGTCATCACCGAAACG

CGCGAGACGAAAGGGCCTCGTGATACGCCTATTTTTATAGGTTAA

TGTCATGATAATAATGGTTTCTTAGACGTCAGGTGGCACTTTTCG

GGGAAATGTGCGCGGAACCCCTATTTGTTTATTTTTCTAAATACA

TTCAAATATGTATCCGCTCATGAGACAATAACCCTGATAAATGCT

TCAATAATATTGAAAAAGGAAGAGTATGAGTATTCAACATTTCCG

TGTCGCCCTTATTCCCTTTTTTGCGGCATTTTGCCTTCCTGTTTT

TGCTCACCCAGAAACGCTGGTGAAAGTAAAAGATGCTGAAGATCA

GTTGGGTGCACGAGTGGGTTACATCGAACTGGATCTCAACAGCGG

TAAGATCCTTGAGAGTTTTCGCCCCGAAGAACGTTTTCCAATGAT

GAGCACTTTTAAAGTTCTGCTATGTGGCGCGGTATTATCCCGTAT

TGACGCCGGGCAAGAGCAACTCGGTCGCCGCATACACTATTCTCA

-continued

```
GAATGACTTGGTTGAGTACTCACCAGTCACAGAAAAGCATCTTAC

GGATGGCATGACAGTAAGAGAATTATGCAGTGCTGCCATAACCAT

GAGTGATAACACTGCGGCCAACTTACTTCTGACAACGATCGGAGG

ACCGAAGGAGCTAACCGCTTTTTTGCACAACATGGGGGATCATGT

AACTCGCCTTGATCGTTGGGAACCGGAGCTGAATGAAGCCATACC

AAACGACGAGCGTGACACCACGATGCCTGTAGCAATGGCAACAAC

GTTGCGCAAACTATTAACTGGCGAACTACTTACTCTAGCTTCCCG

GCAACAATTAATAGACTGGATGGAGGCGGATAAAGTTGCAGGACC

ACTTCTGCGCTCGGCCCTTCCGGCTGGCTGGTTTATTGCTGATAA

ATCTGGAGCCGGTGAGCGTGGAAGCCGCGGTATCATTGCAGCACT

GGGGCCAGATGGTAAGCCCTCCCGTATCGTAGTTATCTACACGAC

GGGGAGTCAGGCAACTATGGATGAACGAAATAGACAGATCGCTGA

GATAGGTGCCTCACTGATTAAGCATTGGTAACTGTCAGACCAAGT

TTACTCATATATACTTTAGATTGATTTAAAACTTCATTTTTAATT

TAAAAGGATCTAGGTGAAGATCCTTTTTGATAATCTCATGACCAA

AATCCCTTAACGTGAGTTTTCGTTCCACTGAGCGTCAGACCCCGT

AGAAAAGATCAAAGGATCTTCTTGAGATCCTTTTTTTCTGCGCGT

AATCTGCTGCTTGCAAACAAAAAAACCACCGCTACCAGCGGTGGT

TTGTTTGCCGGATCAAGAGCTACCAACTctttttccgAAggtAAc tggcttcAgcAgAgcgcAgAtAccAAAtActgttcTTCTAGTGTA

GCCGTAGTTAGGCCACCACTTCAAGAACTCTGTAGCACCGCCTAC

ATACCTCGCTCTGCTAATCCTGTTACCAGTGGCTGCTGCCAGTGG

CGATAAGTCGTGTCTTACCGGGTTGGACTCAAGACGATAGTTACC

GGATAAGGCGCAGCGGTCGGGCTGAACGGGGGGTTCGTGCACACA

GCCCAGCTTGGAGCGAACGACCTACACCGAACTGAGATACCTACA

GCGTGAGCTATGAGAAAGCGCCACGCTTCCCGAAGGGAGAAAGGC

GGACAGGTATCCGGTAAGCGGCAGGGTCGGAACAGGAGAGCGCAC

GAGGGAGCTTCCAGGGGGAAACGCCTGGTATCTTTATAGTCCTGT

CGGGTTTCGCCACCTCTGACTTGAGCGTCGATTTTTGTGATGCTC

GTCAGGGGGGCGGAGCCTATGGAAAAACGCCAGCAACGCGGCCTT

TTTACGGTTCCTGGCCTTTTGCTGGCCTTTTGCTCACATGT
``` pGW073-pAAV_EFSLTR-Cd80-T2A-light-
P2A-Cxcl10-E2A-41bb-F2A-Gitrl (SEQ ID NO: 26)
```
CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC
```

-continued

```
GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccatggccttgcaattgtcagttgatgcaggatac accactcctcaagtttccatgtccaaggctcattcttctctttgt gctgctgattcgtcttcacaagtgtcttcagatgttgatgaaca actgtccaagtcagtgaaagataaggtattgctgccttgccgtta caactcctcatgaagatgagtctgaagaccgaatctactggca aaaacatgacaaagtggtgctgtctgtcattgTtgggaaactaaa agtgtggcccgagtataagaaccggactttatatgacaacactac ctactctcttatcatcctgggcctggtcctttcagaccggggcac atacagctgtgtcgttcaaaagaaggaaagaggaacgtatgaagt taaacacttggctttagtaaagttgtccatcaaagctgacttctc taccccaacataactgagtctggaaacccatctgcagacactaa aaggattacctgctttgcttccggggggtttcccaaagcctcgctt ctcttggttggaaaatggaagagaattacctggcatcaatacgac aatttcccaggatcctgaatctgaattgtacaccattagtagcca actagatttcaatacgactcgcaaccacaccattaagtgtctcat taaatatggagatgctcacgtgtcagaggacttcacctgggaaaa accccagaagaccctcctgatagcaagaacacacttgtgctctt tggggcaggattcggcgcagtaataacagtcgtcgtcatcgttgt catcatcaaatgcttctgtaagcacagaagctgtttcagaagaaa tgaggcaagcagagaaacaaacaacagccttaccttcgggcctga agaagcattagctgaacagaccgtcttccttcgtacgGGCAGTGG

AGAGGGCAGAGGAAGTCTGCTAACATGCGGTGACGTCGAGGAGAA

TCCTGGCCCAatggagagtgtggtacagccttcagtgtttgtggt ggatggacagacggacatcccattcaggcggctggaacagaacca ccggagacggcgctgtggcactgtccaggtcagcctggccctggt gctgctgctaggtgctgggctggccactcagggctggtttctcct gagactgcatcaacgtcttggagacatagtagctcatctgccaga tggaggcaaaggctcctgggagaagctgatacaagatcaacgatc tcaccaggccaacccagcagcacatcttacaggagccaacgccag cttgataggtattggtggacctctgttatgggagacacgacttgg cctggccttcttgaggggcttgacgtatcatgatggggccctggt gaccatggagcccggttactactatgtgtactccaaagtgcagct gagcggcgtgggctgcccccagggggctggccaatggcctccccat cacccatggactatacaagcgcacatcccgctacccgaaggagtt
```

-continued

```
agaactgctggtcagtcggcggtcaccctgtggccgggccaacag ctcccgagtctggtgggacagcagcttcctgggcggcgtggtaca tctggaggctggggaagaggtggtggtccgcgtgcctggaaaccg cctggtcagaccacgtgacggcaccaggtcctatttcggagcttt catggtcactagtGGATCCGGCGCAACAAACTTCTCTCTGCTGAA ACAAGCCGGAGATGTCGAAGAGAATCCTGGACCGatgaacccaag tgctgccgtcattttctgcctcatcctgctgggtctgagtgggac tcaagggatccctctcgcaaggacggtccgctgcaactgcatcca tatcgatgacgggccagtgagaatgagggccataggggaagcttga aatcatccctgcgagcctatcctgcccacgtgttgagatcattgc cacgatgaaaaagaatgatgagcagagatgtctgaatccggaatc taagaccatcaagaatttaatgaaagcgtttagccaaaaaaggtc taaaagggctcctgctagcagcggtacccagtgcaccaactacgc cctgctgaagctggccggcgatgtggagagcaacccgggcccat ggaccagcacacacttgatgtggaggataccgcggatgccagaca tccagcaggtacttcgtgccctcggatgcggcgctcctcagaga taccgggctcctcgcggacgctgcgctcctctcagatactgtgcg ccccacaaatgccgcgctccccacggatgctgcctaccctgcggt taatgttcgggatcgcgaggccgcgtggccgcctgcactgaactt ctgttcccgccacccaaagctctatggcctagtcgctttggtttt gctgcttctgatcgccgcctgtgttcctatcttcacccgcaccga gcctcggccagcgctcacaatcaccacctcgcccaacctgggtac ccgagagaataatgcagaccaggtcaccccctgtttcccacattgg ctgccccaacactacacaacagggctctcctgtgttcgccaagct actggctaaaaaccaagcatcgttgtgcaatacaactctgaactg gcacagccaagatggagctgggagctcatacctatctcaaggtct gaggtacgaagaagacaaaaaggagttggtggtagacagtcccgg gctctactacgtatttttggaactgaagctcagtccaacattcac aaacacaggccacaaggtgcagggctgggtctctcttgttttgca agcaaagcctcaggtagatgactttgacaacttggccctgacagt ggaactgttccttgctccatggagaacaagttagtggaccgttc ctggagtcaactgttgctcctgaaggctggccaccgcctcagtgt gggtctgagggcttatctgcatggagcccaggatgcatacagaga ctgggagctgtcttatcccaacaccaccagctttggactctttct tgtgaaacccgacaacccatgggaaggcatatgcggtaccgtgaa gcagaccctgaacttcgatctgctgaagctggccggcgatgtgga gagcaacccgggcccatggaggaaatgcctttgagagagtcaag tcctcaaagggcagagaggtgcaagaagtcatggctcttgtgcat agtggctctgttactgatgctgctctgttctttgggtacactgat ctatacttcactcaagccaactgccatcgagtcctgcatggttaa
```

-continued

```
   gtttgaactatcatcctcaaaatggcacatgacatctcccaaacc tcactgtgtgaatacgacatctgatgggaagctgaagatactgca 5 gagtggcacatatttaatctacggccaagtgattcctgtggataa gaaatacataaaagacaatgcccccttcgtagtacagatatataa aaagaatgatgtcctacaaactctaatgaatgattttcaaatctt 10 gcctataggagggggtttatgaactgcatgctggagataacatata tctgaagttcaactctaaagaccatattcagaaaaataacacata ctggggatcatcttaatgcctgatctaccattcatctcttagGA

15 ATTCAATAAAAGATCTTTATTTTCATTAGATCTGTGTGTTGGTTT

TTTGTGTGCGGCCGCAGGAACCCCTAGTGATGGAGTTGGCCACTC

CCTCTCTGCGCGCTCGCTCGCTCACTGAGGCCGGGCGACCAAAGG

20 TCGCCCGACGCCCGGGCTTTGCCCGGGCGGCCTCAGTGAGCGAGC

GAGCGCGCAGCTGCCTGCAGGGGCGCCTGATGCGGTATTTTCTCC

TTACGCATCTGTGCGGTATTTCACACCGCATACGTCAAAGCAACC

ATAGTACGCGCCCTGTAGCGGCGCATTAAGCGCGGCGGGTGTGGT

25 GGTTACGCGCAGCGTGACCGCTACACTTGCCAGCGCCTTAGCGCC

CGCTCCTTTCGCTTTCTTCCCTTCCTTTCTCGCCACGTTCGCCGG

CTTTCCCCGTCAAGCTCTAAATCGGGGGCTCCCTTTAGGGTTCCG

30 ATTTAGTGCTTTACGGCACCTCGACCCCAAAAAACTTGATTTGGG

TGATGGTTCACGTAGTGGGCCATCGCCCTGATAGACGGTTTTTCG

CCCTTTGACGTTGGAGTCCACGTTCTTTAATAGTGGACTCTTGTT

35 CCAAACTGGAACAACACTCAACTCTATCTCGGGCTATTCTTTTGA

TTTATAAGGGATTTTGCCGATTTCGGTCTATTGGTTAAAAAATGA

GCTGATTTAACAAAAATTTAACGCGAATTTTAACAAAATATTAAC

40 GTTTACAATTTTATGGTGCACTCTCAGTACAATCTGCTCTGATGC

CGCATAGTTAAGCCAGCCCCGACACCCGCCAACACCCGCTGACGC

GCCCTGACGGGCTTGTCTGCTCCCGGCATCCGCTTACAGACAAGC

45 TGTGACCGTCTCCGGGAGCTGCATGTGTCAGAGGTTTTCACCGTC

ATCACCGAAACGCGCGAGACGAAAGGGCCTCGTGATACGCCTATT

TTTATAGGTTAATGTCATGATAATAATGGTTTCTTAGACGTCAGG

50 TGGCACTTTTCGGGGAAATGTGCGCGGAACCCCTATTTGTTTATT

TTTCTAAATACATTCAAATATGTATCCGCTCATGAGACAATAACC

CTGATAAATGCTTCAATAATATTGAAAAAGGAAGAGTATGAGTAT

55 TCAACATTTCCGTGTCGCCCTTATTCCCTTTTTTGCGGCATTTTG

CCTTCCTGTTTTTGCTCACCCAGAAACGCTGGTGAAAGTAAAAGA

TGCTGAAGATCAGTTGGGTGCACGAGTGGGTTACATCGAACTGGA

60 TCTCAACAGCGGTAAGATCCTTGAGAGTTTTCGCCCCGAAGAACG

TTTTCCAATGATGAGCACTTTTAAAGTTCTGCTATGTGGCGCGGT

ATTATCCCGTATTGACGCCGGGCAAGAGCAACTCGGTCGCCGCAT

ACACTATTCTCAGAATGACTTGGTTGAGTACTCACCAGTCACAGA

65 AAAGCATCTTACGGATGGCATGACAGTAAGAGAATTATGCAGTGC
```

-continued

```
TGCCATAACCATGAGTGATAACACTGCGGCCAACTTACTTCTGAC

AACGATCGGAGGACCGAAGGAGCTAACCGCTTTTTTGCACAACAT

GGGGGATCATGTAACTCGCCTTGATCGTTGGGAACCGGAGCTGAA

TGAAGCCATACCAAACGACGAGCGTGACACCACGATGCCTGTAGC

AATGGCAACAACGTTGCGCAAACTATTAACTGGCGAACTACTTAC

TCTAGCTTCCCGGCAACAATTAATAGACTGGATGGAGGCGGATAA

AGTTGCAGGACCACTTCTGCGCTCGGCCCTTCCGGCTGGCTGGTT

TATTGCTGATAAATCTGGAGCCGGTGAGCGTGGAAGCCGCGGTAT

CATTGCAGCACTGGGGCCAGATGGTAAGCCCTCCCGTATCGTAGT

TATCTACACGACGGGGAGTCAGGCAACTATGGATGAACGAAATAG

ACAGATCGCTGAGATAGGTGCCTCACTGATTAAGCATTGGTAACT

GTCAGACCAAGTTTACTCATATATACTTTAGATTGATTTAAAACT

TCATTTTTAATTTAAAAGGATCTAGGTGAAGATcctttttgataa tctcatgaccaaaatcccttaacgtgagttttcgttccactgAGC

GTCAGACCCCGTAGAAAAGATCAAAGGATCTTCTTGAGATCCTTT

TTTTCTGCGCGTAATCTGCTGCTTGCAAACAAAAAAACCACCGCT

ACCAGCGGTGGTTTGTTTGCCGGATCAAGAGCTACCAACTCTTTT

TCCGAAGGTAACTGGCTTCAGCAGAGCGCAGATACCAAATACTGT

TCTTCTAGTGTAGCCGTAGTTAGGCCACCACTTCAAGAACTCTGT

AGCACCGCCTACATACCTCGCTCTGCTAATCCTGTTACCAGTGGC

TGCTGCCAGTGGCGATAAGTCGTGTCTTACCGGGTTGGACTCAAG

ACGATAGTTACCGGATAAGGCGCAGCGGTCGGGCTGAACGGGGGG

TTCGTGCACACAGCCCAGCTTGGAGCGAACGACCTACACCGAACT

GAGATACCTACAGCGTGAGCTATGAGAAAGCGCCACGCTTCCCGA

AGGGAGAAAGGCGGACAGGTATCCGGTAAGCGGCAGGGTCGGAAC

AGGAGAGCGCACGAGGGAGCTTCCAGGGGGAAACGCCTGGTATCT

TTATAGTCCTGTCGGGTTTCGCCACCTCTGACTTGAGCGTCGATT

TTTGTGATGCTCGTCAGGGGGGCGGAGCCTATGGAAAAACGCCAG

CAACGCGGCCTTTTTACGGTTCCTGGCCTTTTGCTGGCCTTTTGC

TCACATGT
``` pGW078-pAAV_EFSLTR-AgeI&EcoRI-sPA (SEQ ID NO: 27)

```
CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC
```

-continued

```
GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccacctgaGAATTCAATAAAAGATCTTTATTTTCATT

AGATCTGTGTGTTGGTTTTTTGTGTGCGGCCGCAGGAACCCCTAG

TGATGGAGTTGGCCACTCCCTCTCTGCGCGCTCGCTCGCTCACTG

AGGCCGGGCGACCAAAGGTCGCCCGACGCCCGGGCTTTGCCCGGG

CGGCCTCAGTGAGCGAGCGAGCGCGCAGCTGCCTGCAGGGGCGCC

TGATGCGGTATTTTCTCCTTACGCATCTGTGCGGTATTTCACACC

GCATACGTCAAAGCAACCATAGTACGCGCCCTGTAGCGGCGCATT

AAGCGCGGCGGGTGTGGTGGTTACGCGCAGCGTGACCGCTACACT

TGCCAGCGCCCTAGCGCCCGCTCCTTTCGCTTTCTTCCCTTCCTT

TCTCGCCACGTTCGCCGGCTTTCCCCGTCAAGCTCTAAATCGGGG

GCTCCCTTTAGGGTTCCGATTTAGTGCTTTACGGCACCTCGACCC

CAAAAAACTTGATTTGGGTGATGGTTCACGTAGTGGGCCATCGCC

CTGATAGACGGTTTTTCGCCCTTTGACGTTGGAGTCCACGTTCTT

TAATAGTGGACTCTTGTTCCAAACTGGAACAACACTCAACTCTAT

CTCGGGCTATTCTTTTGATTTATAAGGGATTTTGCCGATTTCGGT

CTATTGGTTAAAAAATGAGCTGATTTAACAAAAATTTAACGCGAA

TTTTAACAAAATATTAACGTTTACAATTTTATGGTGCACTCTCAG

TACAATCTGCTCTGATGCCGCATAGTTAAGCCAGCCCCGACACCC

GCCAACACCCGCTGACGCGCCCTGACGGGCTTGTCTGCTCCCGGC

ATCCGCTTACAGACAAGCTGTGACCGTCTCCGGGAGCTGCATGTG

TCAGAGGTTTTCACCGTCATCACCGAAACGCGCGAGACGAAAGGG

CCTCGTGATACGCCTATTTTTATAGGTTAATGTCATGATAATAAT

GGTTTCTTAGACGTCAGGTGGCACTTTTCGGGGAAATGTGCGCGG

AACCCCTATTTGTTTATTTTTCTAAATACATTCAAATATGTATCC

GCTCATGAGACAATAACCCTGATAAATGCTTCAATAATATTGAAA

AAGGAAGAGTATGAGTATTCAACATTTCCGTGTCGCCCTTATTCC

CTTTTTTGCGGCATTTTGCCTTCCTGTTTTTGCTCACCCAGAAAC

GCTGGTGAAAGTAAAAGATGCTGAAGATCAGTTGGGTGCACGAGT

GGGTTACATCGAACTGGATCTCAACAGCGGTAAGATCCTTGAGAG

TTTTCGCCCCGAAGAACGTTTTCCAATGATGAGCACTTTTAAAGT

TCTGCTATGTGGCGCGGTATTATCCCGTATTGACGCCGGGCAAGA

GCAACTCGGTCGCCGCATACACTATTCTCAGAATGACTTGGTTGA

GTACTCACCAGTCACAGAAAAGCATCTTACGGATGGCATGACAGT

AAGAGAATTATGCAGTGCTGCCATAACCATGAGTGATAACACTGC

GGCCAACTTACTTCTGACAACGATCGGAGGACCGAAGGAGCTAAC
```

-continued

CGCTTTTTTGCACAACATGGGGGATCATGTAACTCGCCTTGATCG

TTGGGAACCGGAGCTGAATGAAGCCATACCAAACGACGAGCGTGA

CACCACGATGCCTGTAGCAATGGCAACAACGTTGCGCAAACTATT

AACTGGCGAACTACTTACTCTAGCTTCCCGGCAACAATTAATAGA

CTGGATGGAGGCGGATAAAGTTGCAGGACCACTTCTGCGCTCGGC

CCTTCCGGCTGGCTGGTTTATTGCTGATAAATCTGGAGCCGGTGA

GCGTGGAAGCCGCGGTATCATTGCAGCACTGGGGCCAGATGGTAA

GCCCTCCCGTATCGTAGTTATCTACACGACGGGGAGTCAGGCAAC

TATGGATGAACGAAATAGACAGATCGCTGAGATAGGTGCCTCACT

GATTAAGCATTGGTAACTGTCAGACCAAGTTTACTCATATATACT

TTAGATTGATTTAAAACTTCATTTTTAATTTAAAAGGATCTAGGT

GAAGATCCTTTTTGATAATCTCATGACCAAAATCCCTTAACGTGA

GTTTTCGTTCCACTGAGCGTCAGACCCCGTAGAAAAGATCAAAGG

ATCTTCTTGAGATCCTTTTTTTCTGCGCGTAATCTGCTGCTTGCA

AACAAAAAAACCACCGCTACCAGCGGTGGTTTGTTTGCCGGATCA

AGAGCTACCAACTCTTTTTCCGAAGGTAACTGGCTTCAGCAGAGC

GCAGATACCAAATACTGTTCTTCTAGTGTAGCCGTAGTTAGGCCA

CCACTTCAAGAACTCTGTAGCACCGCCTACATACCTCGCTCTGCT

AATCCTGTTACCAGTGGCTGCTGCCAGTGGCGATAAGTCGTGTCT

TACCGGGTTGGACTCAAGACGATAGTTACCGGATAAGGCGCAGCG

GTCGGGCTGAACGGGGGGTTCGTGCACACAGCCCAGCTTGGAGCG

AACGACCTACACCGAACTGAGATACCTACAGCGTGAGCTATGAGA

AAGCGCCACGCTTCCCGAAGGGAGAAAGGCGGACAGGTATCCGGT

AAGCGGCAGGGTCGGAACAGGAGAGCGCACGAGGGAGCTTCCAGG

GGGAAACGCCTGGTATCTTTATAGTCCTGTCGGGTTTCGCCACCT

CTGACTTGAGCGTCGATTTTTGTGATGCTCGTCAGGGGGCGGAG

CCTATGGAAAAACGCCAGCAACGCGGCCTTTTTACGGTTCCTGGC

CTTTTGCTGGCCTTTTGCTCACATGT pGW090-pAAV_EFSLTR-Cd80-T2A-light-
P2A-IL2-E2A-41bb-F2A-Ifng (SEQ ID NO: 28)
CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

-continued

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccatggccttgcaattgtcagttgatgcaggatac accactcctcaagtttccatgtccaaggctcattcttctctttgt gctgctgattcgtctttcacaagtgtcttcagatgttgatgaaca actgtccaagtcagtgaaagataaggtattgctgccttgccgtta caactctcctcatgaagatgagtctgaagaccgaatctactggca aaaacatgacaaagtggtgctgtctgtcattgTtgggaaactaaa agtgtggcccgagtataagaaccggacttatatgacaacactac ctactctcttatcatcctgggcctggtccttcagaccggggcac atacagctgtgtcgttcaaaagaaggaaagaggaacgtatgaagt taaacacttggctttagtaaagttgtccatcaaagctgacttctc tacccccaacataactgagtctggaaacccatctgcagacactaa aaggattacctgctttgcttccgggggtttcccaaagcctcgctt ctcttggttggaaaatggaagagaattacctggcatcaatacgac aatttcccaggatcctgaatctgaattgtacaccattagtagcca actagatttcaatacgactcgcaaccacaccattaagtgtctcat taaatatggagatgctcacgtgtcagaggacttcacctgggaaaa accccagaagaccctcctgatagcaagaacacacttgtgctctt tggggcaggattcggcgcagtaataacagtcgtcgtcatcgttgt catcatcaaatgcttctgtaagcacagaagctgtttcagaagaaa tgaggcaagcagagaaacaaacaacagccttaccttcgggcctga agaagcattagctgaacagaccgtcttccttcgtacgGGCAGTGG

AGAGGGCAGAGGAAGTCTGCTAACATGCGGTGACGTCGAGGAGAA

TCCTGGCCCAatggagagtgtggtacagccttcagtgtttgtggt ggatggacagacggacatcccattcaggcggctggaacagaacca ccggagacggcgctgtggcactgtccaggtcagcctggccctggt gctgctgctaggtgctgggctggccactcagggctggtttctcct gagactgcatcaacgtcttggagacatagtagctcatctgccaga tggaggcaaaggctcctgggagaagctgatacaagatcaacgatc tcaccaggccaacccagcagcacatcttacaggagccaacgccag cttgataggtattggtggacctctgttatgggagacacgacttgg cctggccttcttgaggggcttgacgtatcatgatggggccctggt gaccatggagcccggttactactatgtgtactccaaagtgcagct gagcggcgtgggctgcccccagggggctggccaatggcctccccat cacccatggactatacaagcgcacatcccgctacccgaaggagtt agaactgctggtcagtcggcggtcaccctgtggccgggccaacag ctcccgagtctggtgggacagcagcttcctgggcggcgtggtaca -continued

```
tctggaggctggggaagaggtggtggtccgcgtgcctggaaaccg cctggtcagaccacgtgacggcaccaggtcctatttcggagcttt catggtcactagtGGATCCGGCGCAACAAACTTCTCTCTGCTGAA ACAAGCCGGAGATGTCGAAGAGAATCCTGGACCGatgtacagcat gcagctcgcatcctgtgtcacattgacacttgtgctccttgtcaa cagcgcacccacttcaagctccacttcaagctctacagcggaagc acagcagcagcagcagcagcagcagcagcagcagcagcacctgga gcagctgttgatggacctacaggagctcctgagcaggatggagaa ttacaggaacctgaaactccccaggatgctcaccttcaaattttta cttgcccaagcaggccacagaattgaaagatcttcagtgcctaga agatgaacttggacctctgcggcatgttctggatttgactcaaag caaaagctttcaattggaagatgctgagaatttcatcagcaatat cagagtaactgttgtaaaactaaagggctctgacaacacatttga gtgccaattcgatgatgagtcagcaactgtggtggactttctgag gagatggatagccttctgtcaaagcatcatctcaacaagccctca agctagcagcggtacccagtgcaccaactacgccctgctgaagct ggccggcgatgtggagagcaaccccgggcccatggaccagcacac acttgatgtggaggataccgcggatgccagacatccagcaggtac ttcgtgcccctcggatgcggcgctcctcagagataccgggctcct cgcggacgctgcgctcctctcagatactgtgcgccccacaaatgc cgcgctccccacggatgctgcctaccctgcggttaatgttcggga tcgcgaggccgcgtggccgcctgcactgaacttctgttcccgcca cccaaagctctatggcctagtcgctttggttttgctgcttctgat cgccgcctgtgttcctatcttcacccgcaccgagcctcggccagc gctcacaatcaccacctcgcccaacctgggtacccgagagaataa tgcagaccaggtcacccctgtttcccacattggctgccccaacac tacacaacagggctctcctgtgttcgccaagctactggctaaaaa ccaagcatcgttgtgcaatacaactctgaactggcacagccaaga tggagctgggagctcatacctatctcaaggtctgaggtacgaaga agacaaaaaggagttggtggtagacagtcccgggctctactacgt attttttggaactgaagctcagtccaacattcacaaacacaggcca caaggtgcagggctgggtctctcttgttttgcaagcaaagcctca ggtagatgactttgacaacttggccctgacagtggaactgttccc ttgctccatggagaacaagttagtggaccgttcctggagtcaact gttgctcctgaaggctggccaccgcctcagtgtgggtctgagggc ttatctgcatggagcccaggatgcatacagagactgggagctgtc ttatcccaacaccaccagctttggactctttcttgtgaaacccga caacccatgggaaggcatatgcggtaccgtgaagcagaccctgaa cttcgatctgctgaagctggccggcgatgtggagagcaaccccgg gcccatgaacgctacacactgcatcttggctttgtcagctcttcct catggctgtttctggctgttactgccacggcacagtcattgaaag
```

-continued

```
cctagaaagtctgaataactattttaactcaagtggcatagatgt ggaagaaaagagtctcttcttggatatctggaggaactggcaaaa ggatggtgacatgaaaatcctgcagagccagattatctctttcta cctcagactctttgaagtcttgaaagacaatcaggccatcagcaa caacataagcgtcattgaatcacacctgattactaccttcttcag caacagcaaggcgaaaaggatgcattcatgagtattgccaagtt tgaggtcaacaacccacaggtccagcgccaagcattcaatgagct catccgagtggtccaccagctgttgccggaatccagcctcaggaa gcggaaaaggagtcgctgctgaGAATTCAATAAAAGATCTTTATT

TTCATTAGATCTGTGTGTTGGTTTTTTGTGTGCGGCCGCAGGAAC

CCCTAGTGATGGAGTTGGCCACTCCCTCTCTGCGCGCTCGCTCGC

TCACTGAGGCCGGGCGACCAAAGGTCGCCCGACGCCCGGGCTTTG

CCCGGGCGGCCTCAGTGAGCGAGCGAGCGCGCAGCTGCCTGCAGG

GGCGCCTGATGCGGtattttctccttacgcatctgtgcggtattt cacaccgcatacgtcaaagcaaCCATAGTACGCGCCCTGTAGCGG

CGCATTAAGCGCGGCGGGTGTGGTGGTTACGCGCAGCGTGACCGC

TACACTTGCCAGCGCCTTAGCGCCCGCTCCTTTCGCTTTCTTCCC

TTCCTTTCTCGCCACGTTCGCCGGCTTTCCCCGTCAAGCTCTAAA

TCGGGGGCTCCCTTTAGGGTTCCGATTTAGTGCTTTACGGCACCT

CGACCCCAAAAAACTTGATTTGGGTGATGGTTCACGTAGTGGGCC

ATCGCCCTGATAGACGGTTTTTCGCCCTTTGACGTTGGAGTCCAC

GTTCTTTAATAGTGGACTCTTGTTCCAAACTGGAACAACACTCAA

CTCTATCTCGGGCTATTCTTTTGATTTATAAGGGATTTTGCCGAT

TTCGGTCTATTGGTTAAAAAATGAGCTGATTTAACAAAAATTTAA

CGCGAATTTTAACAAAATATTAACGTTTACAATTTTATGGTGCAC

TCTCAGTACAATCTGCTCTGATGCCGCATAGTTAAGCCAGCCCCG

ACACCCGCCAACACCCGCTGACGCGCCCTGACGGGCTTGTCTGCT

CCCGGCATCCGCTTACAGACAAGCTGTGACCGTCTCCGGGAGCTG

CATGTGTCAGAGGTTTTCACCGTCATCACCGAAACGCGCGAGACG

AAAGGGCCTCGTGATACGCCTATTTTTATAGGTTAATGTCATGAT

AATAATGGTTTCTTAGACGTCAGGTGGCACTTTTCGGGGAAATGT

GCGCGGAACCCCTATTTGTTTATTTTTCTAAATACATTCAAATAT

GTATCCGCTCATGAGACAATAACCCTGATAAATGCTTCAATAATA

TTGAAAAAGGAAGAGTATGAGTATTCAACATTTCCGTGTCGCCCT

TATTCCCTTTTTTGCGGCATTTTGCCTTCCTGTTTTTGCTCACCC

AGAAACGCTGGTGAAAGTAAAAGATGCTGAAGATCAGTTGGGTGC

ACGAGTGGGTTACATCGAACTGGATCTCAACAGCGGTAAGATCCT

TGAGAGTTTTCGCCCCGAAGAACGTTTTCCAATGATGAGCACTTT

TAAAGTTCTGCTATGTGGCGCGGTATTATCCCGTATTGACGCCGG

GCAAGAGCAACTCGGTCGCCGCATACACTATTCTCAGAATGACTT
```

-continued

```
GGTTGAGTACTCACCAGTCACAGAAAAGCATCTTACGGATGGCAT

GACAGTAAGAGAATTATGCAGTGCTGCCATAACCATGAGTGATAA

CACTGCGGCCAACTTACTTCTGACAACGATCGGAGGACCGAAGGA

GCTAACCGCTTTTTTGCACAACATGGGGGATCATGTAACTCGCCT

TGATCGTTGGGAACCGGAGCTGAATGAAGCCATACCAAACGACGA

GCGTGACACCACGATGCCTGTAGCAATGGCAACAACGTTGCGCAA

ACTATTAACTGGCGAACTACTTACTCTAGCTTCCCGGCAACAATT

AATAGACTGGATGGAGGCGGATAAAGTTGCAGGACCACTTCTGCG

CTCGGCCCTTCCGGCTGGCTGGTTTATTGCTGATAAATCTGGAGC

CGGTGAGCGTGGAAGCCGCGGTATCATTGCAGCACTGGGGCCAGA

TGGTAAGCCCTCCCGTATCGTAGTTATCTACACGACGGGGAGTCA

GGCAACTATGGATGAACGAAATAGACAGATCGCTGAGATAGGTGC

CTCACTGATTAAGCATTGGTAACTGTCAGACCAAGTTTACTCATA

TATACTTTAGATTGATTTAAAACTTCATTTTTAATTTAAAAGGAT

CTAGGTGAAGATCCTTTTTGATAATCTCATGACCAAAATCCCTTA

ACGTGAGTTTTCGTTCCACTGAGCGTCAGACCCCGTAGAAAAGAT

CAAAGGATCTTCTTGAGATCCTTTTTTTCTGCGCGTAATCTGCTG

CTTGCAAACAAAAAAACCACCGCTACCAGCGGTGGTTTGTTTGCC

GGATCAAGAGCTACCAACTCTTTTTCCGAAGGTAACTGGCTTCAG

CAGAGCGCAGATACCAAATACTGTTCTTCTAGTGTAGCCGTAGTT

AGGCCACCACTTCAAGAACTCTGTAGCACCGCCTACATACCTCGC

TCTGCTAATCCTGTTACCAGTGGCTGCTGCCAGTGGCGATAAGTC

GTGTCTTACCGGGTTGGACTCAAGACGATAGTTACCGGATAAGGC

GCAGCGGTCGGGCTGAACGGGGGGTTCGTGCACACAGCCCAGCTT

GGAGCGAACGACCTACACCGAACTGAGATACCTACAGCGTGAGCT

ATGAGAAAGCGCCACGCTTCCCGAAGGGAGAAAGGCGGACAGGTA

TCCGGTAAGCGGCAGGGTCGGAACAGGAGAGCGCACGAGGGAGCT

TCCAGGGGGAAACGCCTGGTATCTTTATAGTCCTGTCGGGTTTCG

CCACCTCTGACTTGAGCGTCGATTTTTGTGATGCTCGTCAGGGGG

GCGGAGCCTATGGAAAAACGCCAGCAACGCGGCCTTTTTACGGTT

CCTGGCCTTTTGCTGGCCTTTTGCTCACATGT
``` pGW091-pAAV_EFSLTR-Cd80-T2A-light-
P2A-GITRL-E2A-41bb-F2A-Ifng (SEQ ID NO: 29)

```
CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC
```

-continued

```
GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccatggccttgcaattgtcagttgatgcaggatac accactcctcaagtttccatgtccaaggctcattcttctctttgt gctgctgattcgtctttcacaagtgtcttcagatgttgatgaaca actgtccaagtcagtgaaagataaggtattgctgccttgccgtta caactctcctcatgaagatgagtctgaagaccgaatctactggca aaaacatgacaaagtggtgctgtctgtcattgTtgggaaactaaa agtgtggcccgagtataagaaccggactttatatgacaacactac ctactctcttatcatcctgggcctggtcctttcagaccggggcac atacagctgtgtcgttcaaaagaaggaaagaggaacgtatgaagt taaacacttggctttagtaaagttgtccatcaaagctgacttctc taccccaacataactgagtctggaaacccatctgcagacactaa aaggattacctgctttgcttccgggggtttcccaaagcctcgctt ctcttggttggaaaatggaagagaattacctggcatcaatacgac aatttcccaggatcctgaatctgaattgtacaccattagtagcca actagatttcaatacgactcgcaaccacaccattaagtgtctcat taaatatggagatgctcacgtgtcagaggacttcacctgggaaaa accccagaagaccctcctgatagcaagaacacacttgtgctctt tggggcaggattcggcgcagtaataacagtcgtcgtcatcgttgt catcatcaaatgcttctgtaagcacagaagctgtttcagaagaaa tgaggcaagcagagaaacaaacaacagccttaccttcgggcctga agaagcattagctgaacagaccgtcttccttcgtacgGGCAGTGG

AGAGGGCAGAGGAAGTCTGCTAACATGCGGTGACGTCGAGGAGAA

TCCTGGCCCAatggagagtgtggtacagccttcagtgtttgtggt ggatggacagacggacatcccattcaggcggctggaacagaacca ccggagacggcgctgtggcactgtccaggtcagcctggccctggt gctgctgctaggtgctgggctggccactcagggctggtttctcct gagactgcatcaacgtcttggagacatagtagctcatctgccaga tggaggcaaaggctcctgggagaagctgatacaagatcaacgatc tcaccaggccaacccagcagcacatcttacaggagccaacgccag cttgataggtattggtggacctctgttatgggagacacgacttgg cctggccttcttgaggggcttgacgtatcatgatggggccctggt gaccatggagcccggttactactatgtgtactccaaagtgcagct gagcggcgtgggctgcccccagggggctggccaatggcctccccat cacccatggactatacaagcgcacatcccgctacccgaaggagtt
```

-continued agaactgctggtcagtcggcggtcaccctgtggccgggccaacag ctcccgagtctggtgggacagcagcttcctgggcggcgtggtaca tctggaggctggggaagaggtggtggtccgcgtgcctggaaaccg cctggtcagaccacgtgacggcaccaggtcctatttcggagcttt catggtcactagtGGATCCGGCGCAACAAACTTCTCTCTGCTGAA ACAAGCCGGAGATGTCGAAGAGAATCCTGGACCGatggaggaaat gcctttgagagagtcaagtcctcaaagggcagagaggtgcaagaa gtcatggctcttgtgcatagtggctctgttactgatgctgctctg ttctttgggtacactgatctatacttcactcaagccaactgccat cgagtcctgcatggttaagtttgaactatcatcctcaaaatggca catgacatctcccaaacctcactgtgtgaatacgacatctgatgg gaagctgaagatactgcagagtggcacatatttaatctacggcca agtgattcctgtggataagaaatacataaaagacaatgccccctt cgtagtacagatatataaaaagaatgatgtcctacaaactctaat gaatgattttcaaatcttgcctataggaggggtttatgaactgca tgctggagataacatatatctgaagttcaactctaaagaccatat tcagaaaaataacacatactgggggatcatcttaatgcctgatct accattcatctctgctagcagcggtacccagtgcaccaactacgc cctgctgaagctggccggcgatgtggagagcaaccccgggcccat ggaccagcacacacttgatgtggaggataccgcggatgccagaca tccagcaggtacttcgtgcccctcggatgcggcgctcctcagaga taccgggctcctcgcggacgctgcgctcctctcagatactgtgcg ccccacaaatgccgcgctcccacggatgctgcctaccctgcggt taatgttcgggatcgcgaggccgcgtggccgcctgcactgaactt ctgttcccgccacccaaagctctatggcctagtcgctttggtttt gctgcttctgatcgccgcctgtgttcctatcttcacccgcaccga gcctcggccagcgctcacaatcaccacctcgcccaacctgggtac ccgagagaataatgcagaccaggtcacccctgtttcccacattgg ctgccccaacactacacaacagggctctcctgtgttcgccaagct actggctaaaaaccaagcatcgttgtgcaatacaactctgaactg gcacagccaagatgagctgggagctcatacctatctcaaggtct gaggtacgaagaagacaaaaaggagttggtggtagacagtcccgg gctctactacgtattttttggaactgaagctcagtccaacattcac aaacacaggccacaaggtgcagggctgggtctctcttgttttgca agcaaagcctcaggtagatgactttgacaacttggccctgacagt ggaactgttccccttgctccatggagaacaagttagtggaccgttc ctggagtcaactgttgctcctgaaggctggcaccgcctcagtgt gggtctgagggcttatctgcatggagcccaggatgcatacagaga ctgggagctgtcttatcccaacaccaccagctttggactctttct tgtgaaacccgacaacccatgggaaggcatatgcggtaccgtgaa gcagaccctgaacttcgatctgctgaagctggccggcgatgtgga gagcaaccccgggcccatgaacgctacacactgcatcttggcttt gcagctcttcctcatggctgtttctggctgttactgccacggcac agtcattgaaagcctagaaagtctgaataactattttaacctcaag tggcatagatgtggaagaaaagagtctcttcttggatatctggag gaactggcaaaaggatggtgacatgaaaatcctgcagagccagat tatctctttctacctcagactcttttgaagtcttgaaagacaatca ggccatcagcaacaacataagcgtcattgaatcacacctgattac taccttcttcagcaacagcaaggcgaaaaaggatgcattcatgag tattgccaagtttgaggtcaacaacccacaggtccagcgccaagc attcaatgagctcatccgagtggtccaccagctgttgccggaatc cagcctcaggaagcggaaaaggagtcgctgctgaGAATTCAATAA

AAGATCTTTATTTTCATTAGATCTGTGTGTTGGTTTTTTGTGTGC

GGCCGCAGGAACCCCTAGTGATGGAGTTGGCCACTCCCTCTCTGC

GCGCTCGCTCGCTCACTGAGGCCGGGCGACCAAAGGTCGCCCGAC

GCCCGGGCTTTGCCCGGGCGGCCTCAGTGAGCGAGCGAGCGCGCA

GCTGCCTGCAGGGGCGCCTGATGCGGtattttctccttacgcatc tgtgcggtatttcacaccgcatacgtcaaagcaaCCATAGTACGC

GCCCTGTAGCGGCGCATTAAGCGCGGCGGGTGTGGTGGTTACGCG

CAGCGTGACCGCTACACTTGCCAGCGCCTTAGCGCCCGCTCCTTT

CGCTTTCTTCCCTTCCTTTCTCGCCACGTTCGCCGGCTTTCCCCG

TCAAGCTCTAAATCGGGGGCTCCCTTTAGGGTTCCGATTTAGTGC

TTTACGGCACCTCGACCCCAAAAAACTTGATTTGGGTGATGGTTC

ACGTAGTGGGCCATCGCCCTGATAGACGGTTTTTCGCCCTTTGAC

GTTGGAGTCCACGTTCTTTAATAGTGGACTCTTGTTCCAAACTGG

AACAACACTCAACTCTATCTCGGGCTATTCTTTTGATTTATAAGG

GATTTTGCCGATTTCGGTCTATTGGTTAAAAAATGAGCTGATTTA

ACAAAAATTTAACGCGAATTTTAACAAAATATTAACGTTTACAAT

TTTATGGTGCACTCTCAGTACAATCTGCTCTGATGCCGCATAGTT

AAGCCAGCCCCGACACCCGCCAACACCCGCTGACGCGCCCTGACG

GGCTTGTCTGCTCCCGGCATCCGCTTACAGACAAGCTGTGACCGT

CTCCGGGAGCTGCATGTGTCAGAGGTTTTCACCGTCATCACCGAA

ACGCGCGAGACGAAAGGGCCTCGTGATACGCCTATTTTTATAGGT

TAATGTCATGATAATAATGGTTTCTTAGACGTCAGGTGGCACTTT

TCGGGGAAATGTGCGCGGAACCCCTATTTGTTTATTTTTCTAAAT

ACATTCAAATATGTATCCGCTCATGAGACAATAACCCTGATAAAT

GCTTCAATAATATTGAAAAAGGAAGAGTATGAGTATTCAACATTT

CCGTGTCGCCCTTATTCCCTTTTTTGCGGCATTTTGCCTTCCTGT

TTTTGCTCACCCAGAAACGCTGGTGAAAGTAAAAGATGCTGAAGA

TCAGTTGGGTGCACGAGTGGGTTACATCGAACTGGATCTCAACAG

CGGTAAGATCCTTGAGAGTTTTCGCCCCGAAGAACGTTTTCCAAT

-continued

GATGAGCACTTTTAAAGTTCTGCTATGTGGCGCGGTATTATCCCG

TATTGACGCCGGGCAAGAGCAACTCGGTCGCCGCATACACTATTC

TCAGAATGACTTGGTTGAGTACTCACCAGTCACAGAAAAGCATCT

TACGGATGGCATGACAGTAAGAGAATTATGCAGTGCTGCCATAAC

CATGAGTGATAACACTGCGGCCAACTTACTTCTGACAACGATCGG

AGGACCGAAGGAGCTAACCGCTTTTTTGCACAACATGGGGGATCA

TGTAACTCGCCTTGATCGTTGGGAACCGGAGCTGAATGAAGCCAT

ACCAAACGACGAGCGTGACACCACGATGCCTGTAGCAATGGCAAC

AACGTTGCGCAAACTATTAACTGGCGAACTACTTACTCTAGCTTC

CCGGCAACAATTAATAGACTGGATGGAGGCGGATAAAGTTGCAGG

ACCACTTCTGCGCTCGGCCCTTCCGGCTGGCTGGTTTATTGCTGA

TAAATCTGGAGCCGGTGAGCGTGGAAGCCGCGGTATCATTGCAGC

ACTGGGGCCAGATGGTAAGCCCTCCCGTATCGTAGTTATCTACAC

GACGGGGAGTCAGGCAACTATGGATGAACGAAATAGACAGATCGC

TGAGATAGGTGCCTCACTGATTAAGCATTGGTAACTGTCAGACCA

AGTTTACTCATATATACTTTAGATTGATTTAAAACTTCATTTTTA

ATTTAAAAGGATCTAGGTGAAGATCCTTTTTGATAATCTCATGAC

CAAAATCCCTTAACGTGAGTTTTCGTTCCACTGAGCGTCAGACCC

CGTAGAAAAGATCAAAGGATCTTCTTGAGATCCTTTTTTTCTGCG

CGTAATCTGCTGCTTGCAAACAAAAAAACCACCGCTACCAGCGGT

GGTTTGTTTGCCGGATCAAGAGCTACCAACTCTTTTTCCGAAGGT

AACTGGCTTCAGCAGAGCGCAGATACCAAATACTGTTCTTCTAGT

GTAGCCGTAGTTAGGCCACCACTTCAAGAACTCTGTAGCACCGCC

TACATACCTCGCTCTGCTAATCCTGTTACCAGTGGCTGCTGCCAG

TGGCGATAAGTCGTGTCTTACCGGGTTGGACTCAAGACGATAGTT

ACCGGATAAGGCGCAGCGGTCGGGCTGAACGGGGGGTTCGTGCAC

ACAGCCCAGCTTGGAGCGAACGACCTACACCGAACTGAGATACCT

ACAGCGTGAGCTATGAGAAAGCGCCACGCTTCCCGAAGGGAGAAA

GGCGGACAGGTATCCGGTAAGCGGCAGGGTCGGAACAGGAGAGCG

CACGAGGGAGCTTCCAGGGGGAAACGCCTGGTATCTTTATAGTCC

TGTCGGGTTTCGCCACCTCTGACTTGAGCGTCGATTTTTGTGATG

CTCGTCAGGGGGGCGGAGCCTATGGAAAAACGCCAGCAACGCGGC

CTTTTTACGGTTCCTGGCCTTTTGCTGGCCTTTTGCTCACATGT pGW096-pAAV_EFSLTR-Ifng-P2A-Cd80-T2A-light-
P2A-IL23-E2A-41BBL-sPA
(SEQ ID NO: 30)
CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccatgaacgctacacactgcatcttggctttgca gctcttcctcatggctgtttctggctgttactgccacggcacagt cattgaaagcctagaaagtctgaataactattttaactcaagtgg catagatgtggaagaaaagagtctcttcttggatatctggaggaa ctggcaaaaggatggtgacatgaaaatcctgcagagccagattat ctctttctacctcagactctttgaagtcttgaaagacaatcaggc catcagcaacaacataagcgtcattgaatcacacctgattactac cttcttcagcaacagcaaggcgaaaaaggatgcattcatgagtat tgccaagtttgaggtcaacaacccacaggtccagcgccaagcatt caatgagctcatccgagtggtccaccagctgtgttgccggaatccag cctcaggaagcggaaaaggagtcgctgcGGATCCGGCGCAACAAA

CTTCTCTCTGCTGAAACAAGCCGGAGATGTCGAAGAGAATCCTGG

ACCGatggcttgcaattgtcagttgatgcaggatacaccactcct caagtttccatgtccaaggctcattcttctctttgtgctgctgat tcgtctttcacaagtgtcttcagatgttgatgaacaactgtccaa gtcagtgaaagataaggtattgctgccttgccgttacaactctcc tcatgaagatgagtctgaagaccgaatctactggcaaaaacatga caaagtggtgctgtctgtcattgTtgggaaactaaaagtgtggcc cgagtataagaaccggactttatatgacaacactacctactctct tatcatcctgggcctggtcctttcagaccggggcacatacagctg tgtcgttcaaaagaaggaaagaggaacgtatgaagttaaacactt ggctttagtaaagttgtccatcaaagctgacttctctacccccaa cataactgagtctggaaacccatctgcagacactaaaaggattac ctgctttgcttccgggggtttcccaaagcctcgcttctcttggtt ggaaaatggaagagaattacctggcatcaatacgacaatttccca ggatcctgaatctgaattgtacaccattagtagccaactagattt caatacgactcgcaaccacaccattaagtgtctcattaaatatgg agatgctcacgtgtcagaggacttcacctgggaaaaaaccccaga agaccctcctgatagcaagaacacacttgtgctctttggggcagg attcggcgcagtaataacagtcgtcgtcatcgttgtcatcatcaa atgcttctgtaagcacagaagctgtttcagaagaaatgaggcaag -continued

```
cagagaaacaaacaacagccttaccttcgggcctgaagaagcatt agctgaacagaccgtcttccttcgtacgGGCAGTGGAGAGGGCAG

AGGAAGTCTGCTAACATGCGGTGACGTCGAGGAGAATCCTGGCCC

Aatggagagtgtggtacagccttcagtgtttgtggtggatggaca gacggacatcccattcaggcggctggaacagaaccaccggagacg gcgctgtggcactgtccaggtcagcctggccctggtgctgctgct aggtgctgggctggccactcagggctggtttctcctgagactgca tcaacgtcttggagacatagtagctcatctgccagatggaggcaa aggctcctgggagaagctgatacaagatcaacgatctcaccaggc caacccagcagcacatcttacaggagccaacgccagcttgatagg tattggtggacctctgttatgggagacacgacttggcctggcctt cttgaggggcttgacgtatcatgatggggccctggtgaccatgga gcccggttactactatgtgtactccaaagtgcagctgagcggcgt gggctgcccccaggggctggccaatggcctccccatcacccatgg actatacaagcgcacatcccgctacccgaaggagttagaactgct ggtcagtcggcggtcaccctgtggccgggccaacagctcccgagt ctggtgggacagcagcttcctgggcggcgtggtacatctggaggc tggggaagaggtggtggtccgcgtgcctggaaaccgcctggtcag accacgtgacggcaccaggtcctatttcggagctttcatggtcac tagtGGATCCGGCGCAACAAACTTCTCTCTGCTGAAACAAGCCGG

AGATGTCGAAGAGAATCCTGGACCGATGTGTCCTCAGAAGCTAAC

CATCTCCTGGTTTGCCATCGTTTTGCTGGTGTCTCCACTCATGGC

CATGTGGGAGCTGGAGAAAGACGTTTATGTTGTAGAGGTGGACTG

GACTCCCGATGCCCCTGGAGAAACAGTGAACCTCACCTGTGACAC

GCCTGAAGAAGATGACATCACCTGGACCTCAGACCAGAGACATGG

AGTCATAGGCTCTGGAAAGACCCTGACCATCACTGTCAAAGAGTT

TCTAGATGCTGGCCAGTACACCTGCCACAAAGGAGGCGAGACTCT

GAGCCACTCACATCTGCTGCTCCACAAGAAGGAAAATGGAATTTG

GTCCACTGAAATTTTAAAAAATTTCAAAAACAAGACTTTCCTGAA

GTGTGAAGCACCAAATTACTCCGGACGGTTCACGTGCTCATGGCT

GGTGCAAAGAAACATGGACTTGAAGTTCAACATCAAGAGCAGTAG

CAGTTCCCCTGACTCTCGGGCAGTGACATGTGGAATGGCGTCTCT

GTCTGCAGAGAAGGTCACACTGGACCAAAGGGACTATGAGAAGTA

TTCAGTGTCCTGCCAGGAGGATGTCACCTGCCCAACTGCCGAGGA

GACCCTGCCCATTGAACTGGCGTTGGAAGCACGGCAGCAGAATAA

ATATGAGAACTACAGCACCAGCTTCTTCATCAGGGACATCATCAA

ACCAGACCCGCCCAAGAACTTGCAGATGAAGCCTTTGAAGAACTC

ACAGGTGGAGGTCAGCTGGGAGTACCCTGACTCCTGGAGCACTCC

CCATTCCTACTTCTCCCTCAAGTTCTTTGTTCGAATCCAGCGCAA

GAAAGAAAAGATGAAGGAGACAGAGGAGGGGTGTAACCAGAAAGG

TGCGTTCCTCGTAGAGAAGACATCTACCGAAGTCCAATGCAAAGG
```

-continued

```
CGGGAATGTCTGCGTGCAAGCTCAGGATCGCTATTACAATTCCTC

ATGCAGCAAGTGGGCATGTGTTCCCTGCAGGGTCCGATCCgctag cagcggtacccagtgcaccaactacgccctgctgaagctggccgg cgatgtggagagcaacccgggcccatggaccagcacacacttga tgtggaggataccgcggatgccagacatccagcaggtacttcgtg cccctcggatgcggcgctcctcagagataccgggctcctcgcgga cgctgcgctcctctcagatactgtgcgccccacaaatgccgcgct ccccacggatgctgcctaccctgcggttaatgttcgggatcgcga ggccgcgtggccgcctgcactgaacttctgttcccgccacccaaa gctctatggcctagtcgctttggttttgctgcttctgatcgccgc ctgtgttcctatcttcacccgcaccgagcctcggccagcgctcac aatcaccacctcgcccaacctgggtacccgagagaataatgcaga ccaggtcacccctgtttcccacattggctgccccaacactacaca acagggctctcctgtgttcgccaagctactggctaaaaaccaagc atcgttgtgcaatacaactctgaactggcacagccaagatggagc tgggagctcatacctatctcaaggtctgaggtacgaagaagacaa aaaggagttggtggtagacagtcccgggctctactacgtattttt ggaactgaagctcagtccaacattcacaaacacaggccacaaggt gcagggctgggtctctcttgtttgcaagcaaagcctcaggtaga tgactttgacaacttggccctgacagtggaactgttcccttgctc catggagaacaagttagtggaccgttcctggagtcaactgttgct cctgaaggctggccaccgcctcagtgtgggtctgagggcttatct gcatggagcccaggatgcatacagagactgggagctgtcttatcc caacaccaccagctttggactctttcttgtgaaacccgacaaccc atgggaatgaGAATTCAATAAAAGATCTTTATTTTCATTAGATCT

GTGTGTTGGTTTTTTGTGTGCGGCCGCAGGAACCCCTAGTGATGG

AGTTGGCCACTCCCTCTCTGCGCGCTCGCTCGCTCACTGAGGCCG

GGCGACCAAAGGTCGCCCGACGCCCGGGCTTTGCCCGGGCGGCCT

CAGTGAGCGAGCGAGCGCGCAGCTGCCTGCAGGGGCGCCTGATGC

GGTATTTTCTCCTTACGCATCTGTGCGGTATTTCACACCGCATAC

GTCAAAGCAACCATAGTACGCGCCCTGTAGCGGCGCATTAAGCGC

GGCGGGTGTGGTGGTTACGCGCAGCGTGACCGCTACACTTGCCAG

CGCCTTAGCGCCCGCTCCTTTCGCTTTCTTCCCTTCCTTTCTCGC

CACGTTCGCCGGCTTTCCCCGTCAAGCTCTAAATCGGGGGCTCCC

TTTAGGGTTCCGATTTAGTGCTTTACGGCACCTCGACCCCAAAAA

ACTTGATTTGGGTGATGGTTCACGTAGTGGGCCATCGCCCTGATA

GACGGTTTTTCGCCCTTTGACGTTGGAGTCCACGTTCTTTAATAG

TGGACTCTTGTTCCAAACTGGAACAACACTCAACTCTATCTCGGG

CTATTCTTTTGATTTATAAGGGATTTTGCCGATTTCGGTCTATTG

GTTAAAAAATGAGCTGATTTAACAAAAATTTAACGCGAATTTTAA
```

-continued

CAAAATATTAACGTTTACAATTTTATGGTGCACTCTCAGTACAAT

CTGCTCTGATGCCGCATAGTTAAGCCAGCCCCGACACCCGCCAAC

ACCCGCTGACGCGCCCTGACGGGCTTGTCTGCTCCCGGCATCCGC

TTACAGACAAGCTGTGACCGTCTCCGGGAGCTGCATGTGTCAGAG

GTTTTCACCGTCATCACCGAAACGCGCGAGACGAAAGGGCCTCGT

GATACGCCTATTTTTATAGGTTAATGTCATGATAATAATGGTTTC

TTAGACGTCAGGTGGCACTTTTCGGGGAAATGTGCGCGGAACCCC

TATTTGTTTATTTTTCTAAATACATTCAAATATGTATCCGCTCAT

GAGACAATAACCCTGATAAATGCTTCAATAATATTGAAAAAGGAA

GAGTATGAGTATTCAACATTTCCGTGTCGCCCTTATTCCCTTTTT

TGCGGCATTTTGCCTTCCTGTTTTTGCTCACCCAGAAACGCTGGT

GAAAGTAAAAGATGCTGAAGATCAGTTGGGTGCACGAGTGGGTTA

CATCGAACTGGATCTCAACAGCGGTAAGATCCTTGAGAGTTTTCG

CCCCGAAGAACGTTTTCCAATGATGAGCACTTTTAAAGTTCTGCT

ATGTGGCGCGGTATTATCCCGTATTGACGCCGGGCAAGAGCAACT

CGGTCGCCGCATACACTATTCTCAGAATGACTTGGTTGAGTACTC

ACCAGTCACAGAAAAGCATCTTACGGATGGCATGACAGTAAGAGA

ATTATGCAGTGCTGCCATAACCATGAGTGATAACACTGCGGCCAA

CTTACTTCTGACAACGATCGGAGGACCGAAGGAGCTAACCGCTTT

TTTGCACAACATGGGGGATCATGTAACTCGCCTTGATCGTTGGGA

ACCGGAGCTGAATGAAGCCATACCAAACGACGAGCGTGACACCAC

GATGCCTGTAGCAATGGCAACAACGTTGCGCAAACTATTAACTGG

CGAACTACTTACTCTAGCTTCCCGGCAACAATTAATAGACTGGAT

GGAGGCGGATAAAGTTGCAGGACCACTTCTGCGCTCGGCCCTTCC

GGCTGGCTGGTTTATTGCTGATAAATCTGGAGCCGGTGAGCGTGG

AAGCCGCGGTATCATTGCAGCACTGGGGCCAGATGGTAAGCCCTC

CCGTATCGTAGTTATCTACACGACGGGGAGTCAGGCAACTATGGA

TGAACGAAATAGACAGATCGCTGAGATAGGTGCCTCACTGATTAA

GCATTGGTAACTGTCAGACCAAGTTTACTCATATATACTTTAGAT

TGATTTAAAACTTCATTTTTAATTTAAAAGGATCTAGGTGAAGAT

CCTTTTTGATAATCTCATGACCAAAATCCCTTAACGTGAGTTTTC

GTTCCACTGAGCGTCAGACCCCGTAGAAAAGATCAAAGGATCTTC

TTGAGATCCTTTTTTTCTGCGCGTAATCTGCTGCTTGCAAACAAA

AAAACCACCGCTACCAGCGGTGGTTTGTTTGCCGGATCAAGAGCT

ACCAACTCTTTTTCCGAAGGTAACTGGCTTCAGCAGAGCGCAGAT

ACCAAATACTGTTCTTCTAGTGTAGCCGTAGTTAGGCCACCACTT

CAAGAACTCTGTAGCACCGCCTACATACCTCGCTCTGCTAATCCT

GTTACCAGTGGCTGCTGCCAGTGGCGATAAGTCGTGTCTTACCGG

GTTGGACTCAAGACGATAGTTACCGGATAAGGCGCAGCGGTCGGG

CTGAACGGGGGGTTCGTGCACACAGCCCAGCTTGGAGCGAACGAC

CTACACCGAACTGAGATACCTACAGCGTGAGCTATGAGAAAGCGC

-continued

CACGCTTCCCGAAGGGAGAAAGGCGGACAGGTATCCGGTAAGCGG

CAGGGTCGGAACAGGAGAGCGCACGAGGGAGCTTCCAGGGGGAAA

CGCCTGGTATCTTTATAGTCCTGTCGGGTTTCGCCACCTCTGACT

TGAGCGTCGATTTTTGTGATGCTCGTCAGGGGGGCGGAGCCTATG

GAAAAACGCCAGCAACGCGGCCTTTTTACGGTTCCTGGCCTTTTG

CTGGCCTTTTGCTCACATGT pGW097-pAAV_EFSLTR-IL23-sPA (SEQ ID NO: 31)

CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccacATGTGTCCTCAGAAGCTAACCATCTCCTGGTTT

GCCATCGTTTTGCTGGTGTCTCCACTCATGGCCATGTGGGAGCTG

GAGAAAGACGTTTATGTTGTAGAGGTGGACTGGACTCCCGATGCC

CCTGGAGAAACAGTGAACCTCACCTGTGACACGCCTGAAGAAGAT

GACATCACCTGGACCTCAGACCAGAGACATGGAGTCATAGGCTCT

GGAAAGACCCTGACCATCACTGTCAAAGAGTTTCTAGATGCTGGC

CAGTACACCTGCCACAAAGGAGGCGAGACTCTGAGCCACTCACAT

CTGCTGCTCCACAAGAAGGAAAATGGAATTTGGTCCACTGAAATT

TTAAAAAATTTCAAAAACAAGACTTTCCTGAAGTGTGAAGCACCA

AATTACTCCGGACGGTTCACGTGCTCATGGCTGGTGCAAAGAAAC

ATGGACTTGAAGTTCAACATCAAGAGCAGTAGCAGTTCCCCTGAC

TCTCGGGCAGTGACATGTGGAATGGCGTCTCTGTCTGCAGAGAAG

GTCACACTGGACCAAAGGGACTATGAGAAGTATTCAGTGTCCTGC

CAGGAGGATGTCACCTGCCCAACTGCCGAGGAGACCCTGCCCATT

GAACTGGCGTTGGAAGCACGGCAGCAGAATAAATATGAGAACTAC

AGCACCAGCTTCTTCATCAGGGACATCATCAAACCAGACCCGCCC

AAGAACTTGCAGATGAAGCCTTTGAAGAACTCACAGGTGGAGGTC

AGCTGGGAGTACCCTGACTCCTGGAGCACTCCCCATTCCTACTTC

-continued

TCCCTCAAGTTCTTTGTTCGAATCCAGCGCAAGAAAGAAAAGATG

AAGGAGACAGAGGAGGGGTGTAACCAGAAAGGTGCGTTCCTCGTA

GAGAAGACATCTACCGAAGTCCAATGCAAAGGCGGGAATGTCTGC

GTGCAAGCTCAGGATCGCTATTACAATTCCTCATGCAGCAAGTGG

GCATGTGTTCCCTGCAGGGTCCGATCCTAGGAATTCAATAAAAGA

TCTTTATTTTCATTAGATCTGTGTGTTGGTTTTTTGTGTGCGGCC

GCAGGAACCCCTAGTGATGGAGTTGGCCACTCCCTCTCTGCGCGC

TCGCTCGCTCACTGAGGCCGGGCGACCAAAGGTCGCCCGACGCCC

GGGCTTTGCCCGGGCGGCCTCAGTGAGCGAGCGAGCGCGCAGCTG

CCTGCAGGGGCGCCTGATGCGGTATTTTCTCCTTACGCATCTGTG

CGGTATTTCACACCGCATACGTCAAAGCAACCATAGTACGCGCCC

TGTAGCGGCGCATTAAGCGCGGCGGGTGTGGTGGTTACGCGCAGC

GTGACCGCTACACTTGCCAGCGCCTTAGCGCCCGCTCCTTTCGCT

TTCTTCCCTTCCTTTCTCGCCACGTTCGCCGGCTTTCCCCGTCAA

GCTCTAAATCGGGGGCTCCCTTTAGGGTTCCGATTTAGTGCTTTA

CGGCACCTCGACCCCAAAAAACTTGATTTGGGTGATGGTTCACGT

AGTGGGCCATCGCCCTGATAGACGGTTTTTCGCCCTTTGACGTTG

GAGTCCACGTTCTTTAATAGTGGACTCTTGTTCCAAACTGGAACA

ACACTCAACTCTATCTCGGGCTATTCTTTTGATTTATAAGGGATT

TTGCCGATTTCGGTCTATTGGTTAAAAAATGAGCTGATTTAACAA

AAATTTAACGCGAATTTTAACAAAATATTAACGTTTACAATTTTA

TGGTGCACTCTCAGTACAATCTGCTCTGATGCCGCATAGTTAAGC

CAGCCCCGACACCCGCCAACACCCGCTGACGCGCCCTGACGGGCT

TGTCTGCTCCCGGCATCCGCTTACAGACAAGCTGTGACCGTCTCC

GGGAGCTGCATGTGTCAGAGGTTTTCACCGTCATCACCGAAACGC

GCGAGACGAAAGGGCCTCGTGATACGCCTATTTTTATAGGTTAAT

GTCATGATAATAATGGTTTCTTAGACGTCAGGTGGCACTTTTCGG

GGAAATGTGCGCGGAACCCCTATTTGTTTATTTTTCTAAATACAT

TCAAATATGTATCCGCTCATGAGACAATAACCCTGATAAATGCTT

CAATAATATTGAAAAAGGAAGAGTATGAGTATTCAACATTTCCGT

GTCGCCCTTATTCCCTTTTTTGCGGCATTTTGCCTTCCTGTTTTT

GCTCACCCAGAAACGCTGGTGAAAGTAAAAGATGCTGAAGATCAG

TTGGGTGCACGAGTGGGTTACATCGAACTGGATCTCAACAGCGGT

AAGATCCTTGAGAGTTTTCGCCCCGAAGAACGTTTTCCAATGATG

AGCACTTTTAAAGTTCTGCTATGTGGCGCGGTATTATCCCGTATT

GACGCCGGGCAAGAGCAACTCGGTCGCCGCATACACTATTCTCAG

AATGACTTGGTTGAGTACTCACCAGTCACAGAAAAGCATCTTACG

GATGGCATGACAGTAAGAGAATTATGCAGTGCTGCCATAACCATG

AGTGATAACACTGCGGCCAACTTACTTCTGACAACGATCGGAGGA

CCGAAGGAGCTAACCGCTTTTTTGCACAACATGGGGGATCATGTA

ACTCGCCTTGATCGTTGGGAACCGGAGCTGAATGAAGCCATACCA

-continued

AACGACGAGCGTGACACCACGATGCCTGTAGCAATGGCAACAACG

TTGCGCAAACTATTAACTGGCGAACTACTTACTCTAGCTTCCCGG

CAACAATTAATAGACTGGATGGAGGCGGATAAAGTTGCAGGACCA

CTTCTGCGCTCGGCCCTTCCGGCTGGCTGGTTTATTGCTGATAAA

TCTGGAGCCGGTGAGCGTGGAAGCCGCGGTATCATTGCAGCACTG

GGGCCAGATGGTAAGCCCTCCCGTATCGTAGTTATCTACACGACG

GGGAGTCAGGCAACTATGGATGAACGAAATAGACAGATCGCTGAG

ATAGGTGCCTCACTGATTAAGCATTGGTAACTGTCAGACCAAGTT

TACTCATATATACTTTAGATTGATTTAAAACTTCATTTTTAATTT

AAAAGGATCTAGGTGAAGATCCTTTTTGATAATCTCATGACCAAA

ATCCCTTAACGTGAGTTTTCGTTCCACTGAGCGTCAGACCCCGTA

GAAAAGATCAAAGGATCTTCTTGAGATCCTTTTTTTTCTGCGCGTA

ATCTGCTGCTTGCAAACAAAAAAACCACCGCTACCAGCGGTGGTT

TGTTTGCCGGATCAAGAGCTACCAACTCTTTTTCCGAAGGTAACT

GGCTTCAGCAGAGCGCAGATACCAAATACTGTTCTTCTAGTGTAG

CCGTAGTTAGGCCACCACTTCAAGAACTCTGTAGCACCGCCTACA

TACCTCGCTCTGCTAATCCTGTTACCAGTGGCTGCTGCCAGTGGC

GATAAGTCGTGTCTTACCGGGTTGGACTCAAGACGATAGTTACCG

GATAAGGCGCAGCGGTCGGGCTGAACGGGGGGTTCGTGCACACAG

CCCAGCTTGGAGCGAACGACCTACACCGAACTGAGATACCTACAG

CGTGAGCTATGAGAAAGCGCCACGCTTCCCGAAGGGAGAAAGGCG

GACAGGTATCCGGTAAGCGGCAGGGTCGGAACAGGAGAGCGCACG

AGGGAGCTTCCAGGGGGAAACGCCTGGTATCTTTATAGTCCTGTC

GGGTTTCGCCACCTCTGACTTGAGCGTCGATTTTTGTGATGCTCG

TCAGGGGGGCGGAGCCTATGGAAAAACGCCAGCAACGCGGCCTTT

TTACGGTTCCTGGCCTTTTGCTGGCCTTTTGCTCACATGT pGW098-pAAV_EFSLTR-Ifng-P2A-Cd80-T2A-light-
P2A-IL23-sPA (SEQ ID NO: 32)

CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

-continued

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccatgaacgctacacactgcatcttggctttgca gctcttcctcatggctgtttctggctgttactgccacggcacagt cattgaaagcctagaaagtctgaataactattttaactcaagtgg catagatgtggaagaaaagagtctcttcttggatatctggaggaa ctggcaaaaggatggtgacatgaaaatcctgcagagccagattat ctctttctacctcagactctttgaagtcttgaaagacaatcaggc catcagcaacaacataagcgtcattgaatcacacctgattactac cttcttcagcaacagcaaggcgaaaaaggatgcattcatgagtat tgccaagtttgaggtcaacaacccacaggtccagcgccaagcatt caatgagctcatccgagtggtccaccagctgttgccggaatccag cctcaggaagcggaaaaggagtcgctgcGGATCCGGCGCAACAAA

CTTCTCTCTGCTGAAACAAGCCGGAGATGTCGAAGAGAATCCTGG

ACCGatggcttgcaattgtcagttgatgcaggatacaccactcct caagtttccatgtccaaggctcattcttctctttgtgctgctgat tcgtctttcacaagtgtcttcagatgttgatgaacaactgtccaa gtcagtgaaagataaggtattgctgccttgccgttacaactctcc tcatgaagatgagtctgaagaccgaatctactggcaaaaacatga caaagtggtgctgtctgtcattgTtgggaaactaaaagtgtggcc cgagtataagaaccggactttatatgacaacactacctactctct tatcatcctgggcctggtcctttcagaccggggcacatacagctg tgtcgttcaaaagaaggaaagaggaacgtatgaagttaaacactt ggctttagtaaagttgtccatcaaagctgacttctctacccccaa cataactgagtctggaaacccatctgcagacactaaaaggattac ctgctttgcttccggggggtttcccaaagcctcgcttctcttggtt ggaaaatggaagagaattacctggcatcaatacgacaatttccca ggatcctgaatctgaattgtacaccattagtagccaactagattt caatacgactcgcaaccacaccattaagtgtctcattaaatatgg agatgctcacgtgtcagaggacttcacctgggaaaaaccccaga agaccctcctgatagcaagaacacacttgtgctctcttggggcagg attcggcgcagtaataacagtcgtcgtcatcgttgtcatcatcaa atgcttctgtaagcacagaagctgtttcagaagaaatgaggcaag cagagaaacaaacaacagccttaccttcgggcctgaagaagcatt agctgaacagaccgtcttccttcgtacgGGCAGTGGAGAGGGCAG

AGGAAGTCTGCTAACATGCGGTGACGTCGAGGAGAATCCTGGCCC

Aatggagagtgtggtacagccttcagtgtttgtggtggatggaca gacggacatcccattcaggcggctggaacagaaccaccggagacg gcgctgtggcactgtccaggtcagcctggccctggtgctgctgct aggtgctgggctggccactcagggctggtttctcctgagactgca -continued tcaacgtcttggagacatagtagctcatctgccagatggaggcaa aggctcctgggagaagctgatacaagatcaacgatctcaccaggc 5 caacccagcagcacatcttacaggagccaacgccagcttgatagg tattggtggacctctgttatgggagacacgacttggcctggcctt cttgaggggcttgacgtatcatgatggggccctggtgaccatgga 10 gcccggttactactatgtgtactccaaagtgcagctgagcggcgt gggctgcccccaggggctggccaatggcctccccatcacccatgg actatacaagcgcacatcccgctacccgaaggagttagaactgct 15 ggtcagtcggcggtcaccctgtggccgggccaacagctcccgagt ctggtgggacagcagcttcctgggcggcgtggtacatctggaggc tggggaagaggtggtggtccgcgtgcctggaaaccgcctggtcag 20 accacgtgacggcaccaggtcctatttcggagctttcatggtcac tagtGGATCCGGCGCAACAAACTTCTCTCTGCTGAAACAAGCCGG

AGATGTCGAAGAGAATCCTGGACCGATGTGTCCTCAGAAGCTAAC

CATCTCCTGGTTTGCCATCGTTTTGCTGGTGTCTCCACTCATGGC

25 CATGTGGGAGCTGGAGAAAGACGTTTATGTTGTAGAGGTGGACTG

GACTCCCGATGCCCCTGGAGAAACAGTGAACCTCACCTGTGACAC

GCCTGAAGAAGATGACATCACCTGGACCTCAGACCAGAGACATGG

30 AGTCATAGGCTCTGGAAAGACCCTGACCATCACTGTCAAAGAGTT

TCTAGATGCTGGCCAGTACACCTGCCACAAAGGAGGCGAGACTCT

GAGCCACTCACATCTGCTGCTCCACAAGAAGGAAAATGGAATTTG

35 GTCCACTGAAATTTTAAAAAATTTCAAAAACAAGACTTTCCTGAA

GTGTGAAGCACCAAATTACTCCGGACGGTTCACGTGCTCATGGCT

GGTGCAAAGAAACATGGACTTGAAGTTCAACATCAAGAGCAGTAG

40 CAGTTCCCCTGACTCTCGGGCAGTGACATGTGGAATGGCGTCTCT

GTCTGCAGAGAAGGTCACACTGGACCAAAGGGACTATGAGAAGTA

TTCAGTGTCCTGCCAGGAGGATGTCACCTGCCCAACTGCCGAGGA

45 GACCCTGCCCATTGAACTGGCGTTGGAAGCACGGCAGCAGAATAA

ATATGAGAACTACAGCACCAGCTTCTTCATCAGGGACATCATCAA

ACCAGACCCGCCCAAGAACTTGCAGATGAAGCCTTTGAAGAACTC

50 ACAGGTGGAGGTCAGCTGGGAGTACCCTGACTCCTGGAGCACTCC

CCATTCCTACTTCTCCCTCAAGTTCTTTGTTCGAATCCAGCGCAA

GAAAGAAAAGATGAAGGAGACAGAGGAGGGGGTGTAACCAGAAAGG

55 TGCGTTCCTCGTAGAGAAGACATCTACCGAAGTCCAATGCAAAGG

CGGGAATGTCTGCGTGCAAGCTCAGGATCGCTATTACAATTCCTC

ATGCAGCAAGTGGGCATGTGTTCCCTGCAGGGTCCGATCCtgaGA

ATTCAATAAAAGATCTTTATTTTCATTAGATCTGTGTGTTGGTTT

TTTGTGTGCGGCCGCAGGAACCCCTAGTGATGGAGTTGGCCACTC

CCTCTCTGCGCGCTCGCTCGCTCACTGAGGCCGGGCGACCAAAGG

TCGCCCGACGCCCGGGCTTTGCCCGGGCGGCCTCAGTGAGCGAGC

65 GAGCGCGCAGCTGCCTGCAGGGGCGCCTGATGCGGTATTTTCTCC

-continued

```
TTACGCATCTGTGCGGTATTTCACACCGCATACGTCAAAGCAACC

ATAGTACGCGCCCTGTAGCGGCGCATTAAGCGCGGCGGGTGTGGT

GGTTACGCGCAGCGTGACCGCTACACTTGCCAGCGCCTTAGCGCC

CGCTCCTTTCGCTTTCTTCCCTTCCTTTCTCGCCACGTTCGCCGG

CTTTCCCCGTCAAGCTCTAAATCGGGGGCTCCCTTTAGGGTTCCG

ATTTAGTGCTTTACGGCACCTCGACCCCAAAAAACTTGATTTGGG

TGATGGTTCACGTAGTGGGCCATCGCCCTGATAGACGGTTTTTCG

CCCTTTGACGTTGGAGTCCACGTTCTTTAATAGTGGACTCTTGTT

CCAAACTGGAACAACACTCAACTCTATCTCGGGCTATTCTTTTGA

TTTATAAGGGATTTTGCCGATTTCGGTCTATTGGTTAAAAAATGA

GCTGATTTAACAAAAATTTAACGCGAATTTTAACAAAATATTAAC

GTTTACAATTTTATGGTGCACTCTCAGTACAATCTGCTCTGATGC

CGCATAGTTAAGCCAGCCCCGACACCCGCCAACACCCGCTGACGC

GCCCTGACGGGCTTGTCTGCTCCCGGCATCCGCTTACAGACAAGC

TGTGACCGTCTCCGGGAGCTGCATGTGTCAGAGGTTTTCACCGTC

ATCACCGAAACGCGCGAGACGAAAGGGCCTCGTGATACGCCTATT

TTTATAGGTTAATGTCATGATAATAATGGTTTCTTAGACGTCAGG

TGGCACTTTTCGGGGAAATGTGCGCGGAACCCCTATTTGTTTATT

TTTCTAAATACATTCAAATATGTATCCGCTCATGAGACAATAACC

CTGATAAATGCTTCAATAATATTGAAAAAGGAAGAGTATGAGTAT

TCAACATTTCCGTGTCGCCCTTATTCCCTTTTTTGCGGCATTTTG

CCTTCCTGTTTTTGCTCACCCAGAAACGCTGGTGAAAGTAAAAGA

TGCTGAAGATCAGTTGGGTGCACGAGTGGGTTACATCGAACTGGA

TCTCAACAGCGGTAAGATCCTTGAGAGTTTTCGCCCCGAAGAACG

TTTTCCAATGATGAGCACTTTTAAAGTTCTGCTATGTGGCGCGGT

ATTATCCCGTATTGACGCCGGGCAAGAGCAACTCGGTCGCCGCAT

ACACTATTCTCAGAATGACTTGGTTGAGTACTCACCAGTCACAGA

AAAGCATCTTACGGATGGCATGACAGTAAGAGAATTATGCAGTGC

TGCCATAACCATGAGTGATAACACTGCGGCCAACTTACTTCTGAC

AACGATCGGAGGACCGAAGGAGCTAACCGCTTTTTTGCACAACAT

GGGGGATCATGTAACTCGCCTTGATCGTTGGGAACCGGAGCTGAA

TGAAGCCATACCAAACGACGAGCGTGACACCACGATGCCTGTAGC

AATGGCAACAACGTTGCGCAAACTATTAACTGGCGAACTACTTAC

TCTAGCTTCCCGGCAACAATTAATAGACTGGATGGAGGCGGATAA

AGTTGCAGGACCACTTCTGCGCTCGGCCCTTCCGGCTGGCTGGTT

TATTGCTGATAAATCTGGAGCCGGTGAGCGTGGAAGCCGCGGTAT

CATTGCAGCACTGGGGCCAGATGGTAAGCCCTCCCGTATCGTAGT

TATCTACACGACGGGGAGTCAGGCAACTATGGATGAACGAAATAG

ACAGATCGCTGAGATAGGTGCCTCACTGATTAAGCATTGGTAACT

GTCAGACCAAGTTTACTCATATATACTTTAGATTGATTTAAAACT
```

-continued

```
TCATTTTTAATTTAAAAGGATCTAGGTGAAGATCCTTTTTGATAA

TCTCATGACCAAAATCCCTTAACGTGAGTTTTCGTTCCACTGAGC

GTCAGACCCCGTAGAAAAGATCAAAGGATCTTCTTGAGATCCTTT

TTTTCTGCGCGTAATCTGCTGCTTGCAAACAAAAAAACCACCGCT

ACCAGCGGTGGTTTGTTTGCCGGATCAAGAGCTACCAACTCTTTT

TCCGAAGGTAACTGGCTTCAGCAGAGCGCAGATACCAAATACTGT

TCTTCTAGTGTAGCCGTAGTTAGGCCACCACTTCAAGAACTCTGT

AGCACCGCCTACATACCTCGCTCTGCTAATCCTGTTACCAGTGGC

TGCTGCCAGTGGCGATAAGTCGTGTCTTACCGGGTTGGACTCAAG

ACGATAGTTACCGGATAAGGCGCAGCGGTCGGGCTGAACGGGGGG

TTCGTGCACACAGCCCAGCTTGGAGCGAACGACCTACACCGAACT

GAGATACCTACAGCGTGAGCTATGAGAAAGCGCCACGCTTCCCGA

AGGGAGAAAGGCGGACAGGTATCCGGTAAGCGGCAGGGTCGGAAC

AGGAGAGCGCACGAGGGAGCTTCCAGGGGGAAACGCCTGGTATCT

TTATAGTCCTGTCGGGTTTCGCCACCTCTGACTTGAGCGTCGATT

TTTGTGATGCTCGTCAGGGGGGCGGAGCCTATGGAAAAACGCCAG

CAACGCGGCCTTTTTACGGTTCCTGGCCTTTTGCTGGCCTTTTGC

TCACATGT pGW099-pAAV_EFSLTR-IFNg-P2A-Cd80-T2A-light-
P2A-Cxcl10
                                    (SEQ ID NO: 33)
CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccatgaacgctacacactgcatcttggctttgca gctcttcctcatggctgtttctggctgttactgccacggcacagt cattgaaagcctagaaagtctgaataactattttaactcaagtgg catagatgtggaagaaaagagtctcttcttggatatctggaggaa ctggcaaaaggatggtgacatgaaaatcctgcagagccagattat ctctttctacctcagactctttgaagtcttgaaagacaatcaggc
```

-continued

```
catcagcaacaacataagcgtcattgaatcacacctgattactac cttcttcagcaacagcaaggcgaaaaaggatgcattcatgagtat tgccaagtttgaggtcaacaacccacaggtccagcgccaagcatt caatgagctcatccgagtggtccaccagctgttgccggaatccag cctcaggaagcggaaaaggagtcgctgcGGATCCGGCGCAACAAA

CTTCTCTCTGCTGAAACAAGCCGGAGATGTCGAAGAGAATCCTGG

ACCGatggcttgcaattgtcagttgatgcaggatacaccactcct caagtttccatgtccaaggctcattcttctctttgtgctgctgat tcgtctttcacaagtgtcttcagatgttgatgaacaactgtccaa gtcagtgaaagataaggtattgctgccttgccgttacaactctcc tcatgaagatgagtctgaagaccgaatctactggcaaaaacatga caaagtggtgctgtctgtcattgTtgggaaactaaaagtgtggcc cgagtataagaaccggactttatatgacaacactacctactctct tatcatcctgggcctggtcctttcagaccggggcacatacagctg tgtcgttcaaaagaaggaaagaggaacgtatgaagttaaacactt ggctttagtaaagttgtccatcaaagctgacttctctacccccaa cataactgagtctggaaacccatctgcagacactaaaaggattac ctgctttgcttccgggggtttcccaaagcctcgcttctcttggtt ggaaaatggaagagaattacctggcatcaatacgacaatttccca ggatcctgaatctgaattgtacaccattagtagccaactagattt caatacgactcgcaaccacaccattaagtgtctcattaaatatgg agatgctcacgtgtcagaggacttcacctgggaaaaaccccccaga agaccctcctgatagcaagaacacacttgtgctctcttggggcagg attcggcgcagtaataacagtcgtcgtcatcgttgtcatcatcaa atgcttctgtaagcacagaagctgtttcagaagaaatgaggcaag cagagaaacaaacaacagccttaccttcgggcctgaagaagcatt agctgaacagaccgtcttccttcgtacgGGCAGTGGAGAGGGCAG

AGGAAGTCTGCTAACATGCGGTGACGTCGAGGAGAATCCTGGCCC

Aatggagagtgtggtacagccttcagtgtttgtggtggatggaca gacggacatcccattcaggcggctggaacagaaccaccggagacg gcgctgtggcactgtccaggtcagcctggccctggtgctgctgct aggtgctgggctggccactcagggctggtttctcctgagactgca tcaacgtcttggagacatagtagctcatctgccagatggaggcaa aggctcctgggagaagctgatacaagatcaacgatctcaccaggc caacccagcagcacatcttacaggagccaacgccagcttgatagg tattggtggacctctgttatgggagacacgacttggcctggcctt cttgaggggcttgacgtatcatgatggggccctggtgaccatgga gcccggttactactatgtgtactccaaagtgcagctgagcggcgt gggctgcccccaggggctggccaatggcctccccatcacccatgg actatacaagcgcacatcccgctacccgaaggagttagaactgct ggtcagtcggcggtcaccctgtggccgggccaacagctcccgagt
```

-continued

```
     ctggtgggacagcagcttcctgggcggcgtggtacatctggaggc tggggaagaggtggtggtccgcgtgcctggaaaccgcctggtcag accacgtgacggcaccaggtcctatttcggagctttcatggtcac tagtGGATCCGGCGCAACAAACTTCTCTCTGCTGAAACAAGCCGG 10   AGATGTCGAAGAGAATCCTGGACCGatgaacccaagtgctgccgt cattttctgcctcatcctgctgggtctgagtgggactcaagggat ccctctcgcaaggacggtccgctgcaactgcatccatatcgatga cgggccagtgagaatgagggccatagggaagcttgaaatcatccc 15   tgcgagcctatcctgcccacgtgttgagatcattgccacgatgaa aaagaatgatgagcagagatgtctgaatccggaatctaagaccat caagaatttaatgaaagcgtttagccaaaaaaggtctaaaagggc 20   tccttgaGAATTCAATAAAAGATCTTTATTTTCATTAGATCTGTG

TGTTGGTTTTTTGTGTGCGGCCGCAGGAACCCCTAGTGATGGAGT

TGGCCACTCCCTCTCTGCGCGCTCGCTCGCTCACTGAGGCCGGGC

25   GACCAAAGGTCGCCCGACGCCCGGGCTTTGCCCGGGCGGCCTCAG

TGAGCGAGCGAGCGCGCAGCTGCCTGCAGGGGCGCCTGATGCGGT attttctccttacgcatctgtgcggtatttcacaccgcatacgtc 30   aaagcaacCATAGTACGCGCCCTGTAGCGGCGCATTAAGCGCGGC

GGGTGTGGTGGTTACGCGCAGCGTGACCGCTACACTTGCCAGCGC

CTTAGCGCCCGCTCCTTTCGCTTTCTTCCCTTCCTTTCTCGCCAC

35   GTTCGCCGGCTTTCCCCGTCAAGCTCTAAATCGGGGGCTCCCTTT

AGGGTTCCGATTTAGTGCTTTACGGCACCTCGACCCCAAAAAACT

TGATTTGGGTGATGGTTCACGTAGTGGGCCATCGCCCTGATAGAC

40   GGTTTTTCGCCCTTTGACGTTGGAGTCCACGTTCTTTAATAGTGG

ACTCTTGTTCCAAACTGGAACAACACTCAACTCTATCTCGGGCTA

TTCTTTTGATTTATAAGGGATTTTGCCGATTTCGGTCTATTGGTT

AAAAAATGAGCTGATTTAACAAAAATTTAACGCGAATTTTAACAA

45   AATATTAACGTTTACAATTTTATGGTGCACTCTCAGTACAATCTG

CTCTGATGCCGCATAGTTAAGCCAGCCCCGACACCCGCCAACACC

CGCTGACGCGCCCTGACGGGCTTGTCTGCTCCCGGCATCCGCTTA

50   CAGACAAGCTGTGACCGTCTCCGGGAGCTGCATGTGTCAGAGGTT

TTCACCGTCATCACCGAAACGCGCGAGACGAAAGGGCCTCGTGAT

ACGCCTATTTTTATAGGTTAATGTCATGATAATAATGGTTTCTTA

55   GACGTCAGGTGGCACTTTTCGGGGAAATGTGCGCGGAACCCCTAT

TTGTTTATTTTTCTAAATACATTCAAATATGTATCCGCTCATGAG

ACAATAACCCTGATAAATGCTTCAATAATATTGAAAAAGGAAGAG

60   TATGAGTATTCAACATTTCCGTGTCGCCCTTATTCCCTTTTTTGC

GGCATTTTGCCTTCCTGTTTTTGCTCACCCAGAAACGCTGGTGAA

AGTAAAAGATGCTGAAGATCAGTTGGGTGCACGAGTGGGTTACAT

65   CGAACTGGATCTCAACAGCGGTAAGATCCTTGAGAGTTTTCGCCC
```

-continued

CGAAGAACGTTTTCCAATGATGAGCACTTTTAAAGTTCTGCTATG

TGGCGCGGTATTATCCCGTATTGACGCCGGGCAAGAGCAACTCGG

TCGCCGCATACACTATTCTCAGAATGACTTGGTTGAGTACTCACC

AGTCACAGAAAAGCATCTTACGGATGGCATGACAGTAAGAGAATT

ATGCAGTGCTGCCATAACCATGAGTGATAACACTGCGGCCAACTT

ACTTCTGACAACGATCGGAGGACCGAAGGAGCTAACCGCTTTTTT

GCACAACATGGGGGATCATGTAACTCGCCTTGATCGTTGGGAACC

GGAGCTGAATGAAGCCATACCAAACGACGAGCGTGACACCACGAT

GCCTGTAGCAATGGCAACAACGTTGCGCAAACTATTAACTGGCGA

ACTACTTACTCTAGCTTCCCGGCAACAATTAATAGACTGGATGGA

GGCGGATAAAGTTGCAGGACCACTTCTGCGCTCGGCCCTTCCGGC

TGGCTGGTTTATTGCTGATAAATCTGGAGCCGGTGAGCGTGGAAG

CCGCGGTATCATTGCAGCACTGGGGCCAGATGGTAAGCCCTCCCG

TATCGTAGTTATCTACACGACGGGGAGTCAGGCAACTATGGATGA

ACGAAATAGACAGATCGCTGAGATAGGTGCCTCACTGATTAAGCA

TTGGTAACTGTCAGACCAAGTTTACTCATATATACTTTAGATTGA

TTTAAAACTTCATTTTTAATTTAAAAGGATCTAGGTGAAGATCCT

TTTTGATAATCTCATGACCAAAATCCCTTAACGTGAGTTTTCGTT

CCACTGAGCGTCAGACCCCGTAGAAAAGATCAAAGGATCTTCTTG

AGATCCTTTTTTTCTGCGCGTAATCTGCTGCTTGCAAACAAAAAA

ACCACCGCTACCAGCGGTGGTTTGTTTGCCGGATCAAGAGCTACC

AACTCTTTTTCCGAAGGTAACTGGCTTCAGCAGAGCGCAGATACC

AAATACTGTTCTTCTAGTGTAGCCGTAGTTAGGCCACCACTTCAA

GAACTCTGTAGCACCGCCTACATACCTCGCTCTGCTAATCCTGTT

ACCAGTGGCTGCTGCCAGTGGCGATAAGTCGTGTCTTACCGGGTT

GGACTCAAGACGATAGTTACCGGATAAGGCGCAGCGGTCGGGCTG

AACGGGGGGTTCGTGCACACAGCCCAGCTTGGAGCGAACGACCTA

CACCGAACTGAGATACCTACAGCGTGAGCTATGAGAAAGCGCCAC

GCTTCCCGAAGGGAGAAAGGCGGACAGGTATCCGGTAAGCGGCAG

GGTCGGAACAGGAGAGCGCACGAGGGAGCTTCCAGGGGGAAACGC

CTGGTATCTTTATAGTCCTGTCGGGTTTCGCCACCTCTGACTTGA

GCGTCGATTTTTGTGATGCTCGTCAGGGGGGCGGAGCCTATGGAA

AAACGCCAGCAACGCGGCCTTTTTACGGTTCCTGGCCTTTTGCTG

GCCTTTTGCTCACATGT pGW100-pAAV_EFSLTR-Ifng-P2A-Cd80-T2A-light-
P2A-Cxcl10-E2A-41BBL-sPA (SEQ ID NO: 34)

CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

-continued

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccatgaacgctacacactgcatcttggctttgca gctcttcctcatggctgtttctggctgttactgccacggcacagt cattgaaagcctagaaagtctgaataactattttaactcaagtgg catagatgtggaagaaaagagtctcttcttggatatctggaggaa ctggcaaaaggatggtgacatgaaaatcctgcagagccagattat ctctttctacctcagactctttgaagtcttgaaagacaatcaggc catcagcaacaacataagcgtcattgaatcacacctgattactac cttcttcagcaacagcaaggcgaaaaaggatgcattcatgagtat tgccaagtttgaggtcaacaacccacaggtccagcgccaagcatt caatgagctcatccgagtggtccaccagctgttgccggaatccag cctcaggaagcggaaaaggagtcgctgcGGATCCGGCGCAACAAA

CTTCTCTCTGCTGAAACAAGCCGGAGATGTCGAAGAGAATCCTGG

ACCGatggcttgcaattgtcagttgatgcaggatacaccactcct caagtttccatgtccaaggctcattcttctctttgtgctgctgat tcgtctttcacaagtgtcttcagatgttgatgaacaactgtccaa gtcagtgaaagataaggtattgctgccttgccgttacaactctcc tcatgaagatgagtctgaagaccgaatctactggcaaaaacatga caaagtggtgctgtctgtcattgTtgggaaactaaaagtgtggcc cgagtataagaaccggacttttatatgacaacactacctactctct tatcatcctgggcctggtcctttcagaccggggcacatacagctg tgtcgttcaaaagaaggaaagaggaacgtatgaagttaaacacatt ggctttagtaaagttgtccatcaaagctgacttctctaccccccaa cataactgagtctggaaacccatctgcagacactaaaaggattac ctgctttgcttccggggggtttcccaaagcctcgcttctcttggtt ggaaaatggaagagaattacctggcatcaatacgacaatttccca ggatcctgaatctgaattgtacaccattagtagccaactagattt caatacgactcgcaaccacaccattaagtgtctcattaaatatgg agatgctcacgtgtcagaggacttcacctgggaaaaaccccccaga agacctcctgatagcaagaacacacttgtgctctttggggcagg attcggcgcagtaataacagtcgtcgtcatcgttgtcatcatcaa atgcttctgtaagcacagaagctgtttcagaagaaatgaggcaag -continued

```
cagagaaacaaacaacagccttaccttcgggcctgaagaagcatt agctgaacagaccgtcttccttcgtacgGGCAGTGGAGAGGGCAG

AGGAAGTCTGCTAACATGCGGTGACGTCGAGGAGAATCCTGGCCC

Aatggagagtgtggtacagccttcagtgtttgtggtggatggaca gacggacatcccattcaggcggctggaacagaaccaccggagacg gcgctgtggcactgtccaggtcagcctggccctggtgctgctgct aAgtgctgggctggccactcagggctggtttctcctgagactgca tcaacgtcttggagacatagtagctcatctgccagatggaggcaa aggctcctgggagaagctgatacaagatcaacgatctcaccaggc caacccagcagcacatcttacaggagccaacgccagcttgatagg tattggtggacctctgttatgggagacacgacttggcctggcctt cttgaggggcttgacgtatcatgatggggccctggtgaccatgga gcccggttactactatgtgtactccaaagtgcagctgagcggcgt gggctgcccccaggggctggccaatggcctccccatcacccatgg actatacaagcgcacatcccgctacccgaaggagttagaactgct ggtcagtcggcggtcaccctgtggccgggccaacagctcccgagt ctggtgggacagcagcttcctgggcggcgtggtacatctggaggc tggggaagaggtggtggtccgcgtgcctggaaaccgcctggtcag accacgtgacggcaccaggtcctatttcggagctttcatggtcac tagtGGATCCGGCGCAACAAACTTCTCTCTGCTGAAACAAGCCGG AGATGTCGAAGAGAATCCTGGACCGatgaacccaagtgctgccgt cattttctgcctcatcctgctgggctctgagtgggactcaaggga ccctctcgcaaggacggtccgctgcaactgcatccatatcgatga cgggccagtgagaatgagggccataggggaagcttgaaatcatcc tgcgagcctatcctgcccacgtgttgagatcattgccacgatgaa aaagaatgatgagcagagatgtctgaatccggaatctaagaccat caagaatttaatgaaagcgtttagccaaaaaaggtctaaaagggc tcctgctagcagcggtacccagtgcaccaactacgccctgctgaa gctggccggcgatgtggagagcaaccccgggcccatggaccagca cacacttgatgtggaggataccgcggatgccagacatccagcagg tacttcgtgcccctcggatgcggcgctcctcagagataccgggct cctcgcggacgctgcgctcctctcagatactgtgcgccccacaaa tgccgcgctccccacggatgctgcctaccctgcggttaatgttcg ggatcgcgaggccgcgtggccgcctgcactgaacttctgttcccg ccacccaaagctctatggcctagtcgctttggttttgctgcttct gatcgccgcctgtgttcctatcttcacccgcaccgagcctcggcc agcgctcacaatcaccacctcgcccaacctgggtacccgagagaa taatgcagaccaggtcacccctgtttcccacattggctgcccaa cactacacaacagggctctcctgtgttcgccaagctactggctaa aaaccaagcatcgttgtgcaatacaactctgaactggcacagcca
```

-continued

```
agatggagctgggagctcataccttctcaaggtctgaggtacga agaagacaaaaaggagttggtggtagacagtcccgggctctacta cgtattttttggaactgaagctcagtccaacattcacaaacacagg ccacaaggtgcagggctgggtctctcttgttttgcaagcaaagcc tcaggtagatgactttgacaacttggccctgacagtggaactgtt ccccttgctccatggagaacaagttagtggaccgttcctggagtca actgttgctcctgaaggctggccaccgcctcagtgtgggtctgag ggcttatctgcatggagcccaggatgcatacagagactgggagct gtcttatcccaacaccaccagctttggactcttttcttgtgaaacc cgacaaacccatgggaatgaGAATTCAATAAAAGATCTTTATTTTC

ATTAGATCTGTGTGTTGGTTTTTTGTGTGCGGCCGCAGGAACCCC

TAGTGATGGAGTTGGCCACTCCCTCTCTGCGCGCTCGCTCGCTCA

CTGAGGCCGGGCGACCAAAGGTCGCCCGACGCCCGGGCTTTGCCC

GGGCGGCCTCAGTGAGCGAGCGAGCGCGCAGCTGCCTGCAGGGGC

GCCTGATGCGGTATTTTCTCCTTACGCATCTGTGCGGTATTTCAC

ACCGCATACGTCAAAGCAACCATAGTACGCGCCCTGTAGCGGCGC

ATTAAGCGCGGCGGGTGTGGTGGTTACGCGCAGCGTGACCGCTAC

ACTTGCCAGCGCCTTAGCGCCCGCTCCTTTCGCTTTCTTCCCTTC

CTTTCTCGCCACGTTCGCCGGCTTTCCCCGTCAAGCTCTAAATCG

GGGGCTCCCTTTAGGGTTCCGATTTAGTGCTTTACGGCACCTCGA

CCCCAAAAAACTTGATTTGGGTGATGGTTCACGTAGTGGGCCATC

GCCCTGATAGACGGTTTTTCGCCCTTTGACGTTGGAGTCCACGTT

CTTTAATAGTGGACTCTTGTTCCAAACTGGAACAACACTCAACTC

TATCTCGGGCTATTCTTTTGATTTATAAGGGATTTTGCCGATTTC

GGTCTATTGGTTAAAAAATGAGCTGATTTAACAAAAATTTAACGC

GAATTTTAACAAAATATTAACGTTTACAATTTTATGGTGCACTCT

CAGTACAATCTGCTCTGATGCCGCATAGTTAAGCCAGCCCCGACA

CCCGCCAACACCCGCTGACGCGCCCTGACGGGCTTGTCTGCTCCC

GGCATCCGCTTACAGACAAGCTGTGACCGTCTCCGGGAGCTGCAT

GTGTCAGAGGTTTTCACCGTCATCACCGAAACGCGCGAGACGAAA

GGGCCTCGTGATACGCCTATTTTTATAGGTTAATGTCATGATAAT

AATGGTTTCTTAGACGTCAGGTGGCACTTTTCGGGGAAATGTGCG

CGGAACCCCTATTTGTTTATTTTTCTAAATACATTCAAATATGTA

TCCGCTCATGAGACAATAACCCTGATAAATGCTTCAATAATATTG

AAAAAGGAAGAGTATGAGTATTCAACATTTCCGTGTCGCCCTTAT

TCCCTTTTTTGCGGCATTTTGCCTTCCTGTTTTTGCTCACCCAGA

AACGCTGGTGAAAGTAAAAGATGCTGAAGATCAGTTGGGTGCACG

AGTGGGTTACATCGAACTGGATCTCAACAGCGGTAAGATCCTTGA

GAGTTTTCGCCCCGAAGAACGTTTTCCAATGATGAGCACTTTTAA

AGTTCTGCTATGTGGCGCGGTATTATCCCGTATTGACGCCGGGCA

AGAGCAACTCGGTCGCCGCATACACTATTCTCAGAATGACTTGGT
```

-continued

-continued

TGAGTACTCACCAGTCACAGAAAAGCATCTTACGGATGGCATGAC

AGTAAGAGAATTATGCAGTGCTGCCATAACCATGAGTGATAACAC

TGCGGCCAACTTACTTCTGACAACGATCGGAGGACCGAAGGAGCT

AACCGCTTTTTTGCACAACATGGGGGATCATGTAACTCGCCTTGA

TCGTTGGGAACCGGAGCTGAATGAAGCCATACCAAACGACGAGCG

TGACACCACGATGCCTGTAGCAATGGCAACAACGTTGCGCAAACT

ATTAACTGGCGAACTACTTACTCTAGCTTCCCGGCAACAATTAAT

AGACTGGATGGAGGCGGATAAAGTTGCAGGACCACTTCTGCGCTC

GGCCCTTCCGGCTGGCTGGTTTATTGCTGATAAATCTGGAGCCGG

TGAGCGTGGAAGCCGCGGTATCATTGCAGCACTGGGGCCAGATGG

TAAGCCCTCCCGTATCGTAGTTATCTACACGACGGGGAGTCAGGC

AACTATGGATGAACGAAATAGACAGATCGCTGAGATAGGTGCCTC

ACTGATTAAGCATTGGTAACTGTCAGACCAAGTTTACTCATATAT

ACTTTAGATTGATTTAAAACTTCATTTTTAATTTAAAAGGATCTA

GGTGAAGATCCTTTTTGATAATCTCATGACCAAAATCCCTTAACG

TGAGTTTTCGTTCCACTGAGCGTCAGACCCCGTAGAAAAGATCAA

AGGATCTTCTTGAGATCCTTTTTTTCTGCGCGTAATCTGCTGCTT

GCAAACAAAAAAACCACCGCTACCAGCGGTGGTTTGTTTGCCGGA

TCAAGAGCTACCAACTCTTTTTCCGAAGGTAACTGGCTTCAGCAG

AGCGCAGATACCAAATACTGTTCTTCTAGTGTAGCCGTAGTTAGG

CCACCACTTCAAGAACTCTGTAGCACCGCCTACATACCTCGCTCT

GCTAATCCTGTTACCAGTGGCTGCTGCCAGTGGCGATAAGTCGTG

TCTTACCGGGTTGGACTCAAGACGATAGTTACCGGATAAGGCGCA

GCGGTCGGGCTGAACGGGGGGTTCGTGCACACAGCCCAGCTTGGA

GCGAACGACCTACACCGAACTGAGATACCTACAGCGTGAGCTATG

AGAAAGCGCCACGCTTCCCGAAGGGAGAAAGGCGGACAGGTATCC

GGTAAGCGGCAGGGTCGGAACAGGAGAGCGCACGAGGGAGCTTCC

AGGGGGAAACGCCTGGTATCTTTATAGTCCTGTCGGGTTTCGCCA

CCTCTGACTTGAGCGTCGATTTTTGTGATGCTCGTCAGGGGGGCG

GAGCCTATGGAAAAACGCCAGCAACGCGGCCTTTTTACGGTTCCT

GGCCTTTTGCTGGCCTTTTGCTCACATGT pGW101-pAAV_EFSLTR-Ifng-P2A-Cd80-T2A-light-
E2A-41BBL-sPA
(SEQ ID NO: 35)
CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccatgaacgctacacactgcatcttggctttgca gctcttcctcatggctgtttctggctgttactgccacggcacagt cattgaaagcctagaaagtctgaataactattttaactcaagtgg catagatgtggaagaaaagagtctcttcttggatatctggaggaa ctggcaaaaggatggtgacatgaaaatcctgcagagccagattat ctctttctacctcagactctttgaagtcttgaaagacaatcaggc catcagcaacaacataagcgtcattgaatcacacctgattactac cttcttcagcaacagcaaggcgaaaaaggatgcattcatgagtat tgccaagtttgaggtcaacaacccacaggtccagcgccaagcatt caatgagctcatccgagtggtccaccagctgttgccggaatccag cctcaggaagcggaaaaggagtcgctgcGGATCCGGCGCAACAAA

CTTCTCTCTGCTGAAACAAGCCGGAGATGTCGAAGAGAATCCTGG

ACCGAtggcttgcaattgtcagttgatgcaggatacaccactcct caagtttccatgtccaaggctcattcttctctttgtgctgctgat tcgtctttcacaagtgtcttcagatgttgatgaacaactgtccaa gtcagtgaaagataaggtattgctgccttgccgttacaactctcc tcatgaagatgagtctgaagaccgaatctactggcaaaaacatga caaagtggtgctgtctgtcattgTtgggaaactaaaagtgtggcc cgagtataagaaccggactttatatgacaacactacctactctct tatcatcctgggcctggtcctttcagaccgggggcacatacagctg tgtcgttcaaaagaaggaaagaggaacgtatgaagttaaacactt ggctttagtaaagttgtccatcaaagctgacttctctacccccaa cataactgagtctggaaacccatctgcagacactaaaaggattac ctgctttgcttccgggggtttcccaaagcctcgcttctcttggtt ggaaaatggaagagaattacctggcatcaatacgacaatttccca ggatcctgaatctgaattgtacaccattagtagccaactagattt caatacgactcgcaaccacaccattaagtgtctcattaaatatgg agatgctcacgtgtcagaggacttcacctgggaaaaaacccccaga agaccctcctgatagcaagaacacacttgtgctctttggggcagg attcggcgcagtaataacagtcgtcgtcatcgttgtcatcatcaa atgcttctgtaagcacagaagctgtttcagaagaaatgaggcaag cagagaaacaaacaacagccttaccttcgggcctgaagaagcatt agctgaacagaccgtcttccttcgtacgGGCAGTGGAGAGGGCAG -continued

```
AGGAAGTCTGCTAACATGCGGTGACGTCGAGGAGAATCCTGGCCC

Aatggagagtgtggtacagccttcagtgtttgtggtggatggaca gacggacatcccattcaggcggctggaacagaaccaccggagacg gcgctgtggcactgtccaggtcagcctggccctggtgctgctgct aggtgctgggctggccactcagggctggtttctcctgagactgca tcaacgtcttggagacatagtagctcatctgccagatggaggcaa aggctcctgggagaagctgatacaagatcaacgatctcaccaggc caacccagcagcacatcttacaggagccaacgccagcttgatagg tattggtggacctctgttatgggagacacgacttggcctggcctt cttgaggggcttgacgtatcatgatggggccctggtgaccatgga gcccggttactactatgtgtactccaaagtgcagctgagcggcgt gggctgcccccaggggctggccaatggcctccccatcacccatgg actatacaagcgcacatcccgctacccgaaggagttagaactgct ggtcagtcggcggtcaccctgtggccgggccaacagctcccgagt ctggtgggacagcagcttcctgggcggcgtggtacatctggaggc tggggaagaggtggtggtccgcgtgcctggaaaccgcctggtcag accacgtgacggcaccaggtcctatttcggagctttcatggtcac tagcagcggtacccagtgcaccaactacgccctgctgaagctggc cggcgatgtggagagcaaccccgggcccatggaccagcacacact tgatgtggaggataccgcggatgccagacatccagcaggtacttc gtgcccctcggatgcggcgctcctcagagataccgggctcctcgc ggacgctgcgctcctctcagatactgtgcgccccacaaatgccgc gctcccacggatgctgcctaccctgcggttaatgttcgggatcg cgaggccgcgtggccgcctgcactgaacttctgttcccgccaccc aaagctctatggcctagtcgctttggttttgctgcttctgatcgc cgcctgtgttcctatcttcacccgcaccgagcctcggccagcgct cacaatcaccacctcgcccaacctgggtacccgagagaataatgc agaccaggtcacccctgtttcccacattggctgccccaacactac acaacagggctctcctgtgttcgccaagctactggctaaaaacca agcatcgttgtgcaatacaactctgaactggcacagccaagatgg agctgggagctcatacctatctcaaggtctgaggtacgaagaaga caaaaaggagttggtggtagacagtcccgggctctactacgtatt tttggaactgaagctcagtccaacattcacaaacacaggccacaa ggtgcagggctgggtctctcttgttttgcaagcaaagcctcaggt agatgactttgacaacttggccctgacagtggaactgttcccttg ctccatggagaacaagttagtggaccgttcctggagtcaactgtt gctcctgaaggctggccaccgcctcagtgtgggtctgagggctta tctgcatggagcccaggatgcatacagagactgggagctgtctta tcccaacaccaccagctttggactctttcttgtgaaacccgacaa cccatgggaatgaGAATTCAATAAAAGATCTTTATTTTCATTAGA

TCTGTGTGTTGGTTTTTTGTGTGCGGCCGCAGGAACCCCTAGTGA
```

-continued

```
    TGGAGTTGGCCACTCCCTCTCTGCGCGCTCGCTCGCTCACTGAGG

CCGGGCGACCAAAGGTCGCCCGACGCCCGGGCTTTGCCCGGGCGG

CCTCAGTGAGCGAGCGAGCGCGCAGCTGCCTGCAGGGGCGCCTGA

TGCGgtattttctccttacgcatctgtgcggtatttcacaccgca tacgtcaaagcaACCATAGTACGCGCCCTGTAGCGGCGCATTAAG

10  CGCGGCGGGTGTGGTGGTTACGCGCAGCGTGACCGCTACACTTGC

CAGCGCCTTAGCGCCCGCTCCTTTCGCTTTCTTCCCTTCCTTTCT

CGCCACGTTCGCCGGCTTTCCCCGTCAAGCTCTAAATCGGGGGCT

15  CCCTTTAGGGTTCCGATTTAGTGCTTTACGGCACCTCGACCCCAA

AAAACTTGATTTGGGTGATGGTTCACGTAGTGGGCCATCGCCCTG

ATAGACGGTTTTTCGCCCTTTGACGTTGGAGTCCACGTTCTTTAA

20  TAGTGGACTCTTGTTCCAAACTGGAACAACACTCAACTCTATCTC

GGGCTATTCTTTTGATTTATAAGGGATTTTGCCGATTTCGGTCTA

TTGGTTAAAAAATGAGCTGATTTAACAAAAATTTAACGCGAATTT

25  TAACAAAATATTAACGTTTACAATTTTATGGTGCACTCTCAGTAC

AATCTGCTCTGATGCCGCATAGTTAAGCCAGCCCCGACACCCGCC

AACACCCGCTGACGCGCCCTGACGGGCTTGTCTGCTCCCGGCATC

30  CGCTTACAGACAAGCTGTGACCGTCTCCGGGAGCTGCATGTGTCA

GAGGTTTTCACCGTCATCACCGAAACGCGCGAGACGAAAGGGCCT

CGTGATACGCCTATTTTTATAGGTTAATGTCATGATAATAATGGT

35  TTCTTAGACGTCAGGTGGCACTTTTCGGGGAAATGTGCGCGGAAC

CCCTATTTGTTTATTTTTCTAAATACATTCAAATATGTATCCGCT

CATGAGACAATAACCCTGATAAATGCTTCAATAATATTGAAAAAG

40  GAAGAGTATGAGTATTCAACATTTCCGTGTCGCCCTTATTCCCTT

TTTTGCGGCATTTTGCCTTCCTGTTTTTGCTCACCCAGAAACGCT

GGTGAAAGTAAAAGATGCTGAAGATCAGTTGGGTGCACGAGTGGG

45  TTACATCGAACTGGATCTCAACAGCGGTAAGATCCTTGAGAGTTTT

TCGCCCCGAAGAACGTTTTCCAATGATGAGCACTTTTAAAGTTCT

GCTATGTGGCGCGGTATTATCCCGTATTGACGCCGGGCAAGAGCA

50  ACTCGGTCGCCGCATACACTATTCTCAGAATGACTTGGTTGAGTA

CTCACCAGTCACAGAAAAGCATCTTACGGATGGCATGACAGTAAG

AGAATTATGCAGTGCTGCCATAACCATGAGTGATAACACTGCGGC

55  CAACTTACTTCTGACAACGATCGGAGGACCGAAGGAGCTAACCGC

TTTTTTGCACAACATGGGGGATCATGTAACTCGCCTTGATCGTTG

GGAACCGGAGCTGAATGAAGCCATACCAAACGACGAGCGTGACAC

60  CACGATGCCTGTAGCAATGGCAACAACGTTGCGCAAACTATTAAC

TGGCGAACTACTTACTCTAGCTTCCCGGCAACAATTAATAGACTG

GATGGAGGCGGATAAAGTTGCAGGACCACTTCTGCGCTCGGCCCT

65  TCCGGCTGGCTGGTTTATTGCTGATAAATCTGGAGCCGGTGAGCG

TGGAAGCCGCGGTATCATTGCAGCACTGGGGCCAGATGGTAAGCC
```

-continued

```
CTCCCGTATCGTAGTTATCTACACGACGGGGAGTCAGGCAACTAT

GGATGAACGAAATAGACAGATCGCTGAGATAGGTGCCTCACTGAT

TAAGCATTGGTAACTGTCAGACCAAGTTTACTCATATATACTTTA

GATTGATTTAAAACTTCATTTTTAATTTAAAAGGATCTAGGTGAA

GATCcttttttgataatctcatgaccaaaatcccttaacgtgagtt ttcgttccactgaGCGTCAGACCCCGTAGAAAAGATCAAAGGATC

TTCTTGAGATCCTTTTTTTCTGCGCGTAATCTGCTGCTTGCAAAC

AAAAAAACCACCGCTACCAGCGGTGGTTTGTTTGCCGGATCAAGA

GCTACCAACTCTTTTTCCGAAGGTAACTGGCTTCAGCAGAGCGCA

GATACCAAATACTGTTCTTCTAGTGTAGCCGTAGTTAGGCCACCA

CTTCAAGAACTCTGTAGCACCGCCTACATACCTCGCTCTGCTAAT

CCTGTTACCAGTGGCTGCTGCCAGTGGCGATAAGTCGTGTCTTAC

CGGGTTGGACTCAAGACGATAGTTACCGGATAAGGCGCAGCGGTC

GGGCTGAACGGGGGGTTCGTGCACACAGCCCAGCTTGGAGCGAAC

GACCTACACCGAACTGAGATACCTACAGCGTGAGCTATGAGAAAG

CGCCACGCTTCCCGAAGGGAGAAAGGCGGACAGGTATCCGGTAAG

CGGCAGGGTCGGAACAGGAGAGCGCACGAGGGGAGCTTCCAGGGG

AAACGCCTGGTATCTTTATAGTCCTGTCGGGTTTCGCCACCTCTG

ACTTGAGCGTCGATTTTTGTGATGCTCGTCAGGGGGGCGGAGCCT

ATGGAAAAACGCCAGCAACGCGGCCTTTTTACGGTTCCTGGCCTT

TTGCTGGCCTTTTGCTCACATGT pGW102-pAAV_EFSLTR-Cd80-sPA (SEQ ID NO: 36)
CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccatggcttgcaattgtcagttgatgcaggatac accactcctcaagtttccatgtccaaggctcattcttctctttgt gctgctgattcgtctttcacaagtgtcttcagatgttgatgaaca actgtccaagtcagtgaaagataaggtattgctgccttgccgtta
```

-continued

```
caactctcctcatgaagatgagtctgaagaccgaatctactggca aaaacatgacaaagtggtgctgtctgtcattgTtgggaaactaaa agtgtggcccgagtataagaaccggacttttatatgacaacactac ctactctcttatcatcctgggcctggtccttcagaccggggcac atacagctgtgtcgttcaaaagaaggaaagaggaacgtatgaagt taaacacttggctttagtaaagttgtccatcaaagctgacttctc tacccccaacataactgagtctggaaacccatctgcagacactaa aaggattacctgctttgcttccgggggtttcccaaagcctcgctt ctcttggttggaaaatggaagagaattacctggcatcaatacgac aatttcccaggatcctgaatctgaattgtacaccattagtagcca actagatttcaatacgactcgcaaccacaccattaagtgtctcat taaatatggagatgctcacgtgtcagaggacttcacctgggaaaa acccccagaagaccctcctgatagcaagaacacacttgtgctctt tggggcaggattcggcgcagtaataacagtcgtcgtcatcgttgt catcatcaaatgcttctgtaagcacagaagctgtttcagaagaaa tgaggcaagcagagaaacaaacaacagccttaccttcgggcctga agaagcattagctgaacagaccgtcttccttcgttagGAATTCAA

TAAAAGATCTTTATTTTCATTAGATCTGTGTGTTGGTTTTTTGTGT

TGCGGCCGCAGGAACCCCTAGTGATGGAGTTGGCCACTCCCTCTC

TGCGCGCTCGCTCGCTCACTGAGGCCGGGCGACCAAAGGTCGCCC

GACGCCCGGGCTTTGCCCGGGCGGCCTCAGTGAGCGAGCGAGCGC

GCAGCTGCCTGCAGGGGCGCCTGATGCGGTATTTTCTCCTTACGC

ATCTGTGCGGTATTTCACACCGCATACGTCAAAGCAACCATAGTA

CGCGCCCTGTAGCGGCGCATTAAGCGCGGCGGGTGTGGTGGTTAC

GCGCAGCGTGACCGCTACACTTGCCAGCGCCTTAGCGCCCGCTCC

TTTCGCTTTCTTCCCTTCCTTTCTCGCCACGTTCGCCGGCTTTCC

CCGTCAAGCTCTAAATCGGGGGCTCCCTTTAGGGTTCCGATTTAG

TGCTTTACGGCACCTCGACCCCAAAAAACTTGATTTGGGTGATGG

TTCACGTAGTGGGCCATCGCCCTGATAGACGGTTTTTCGCCCTTT

GACGTTGGAGTCCACGTTCTTTAATAGTGGACTCTTGTTCCAAAC

TGGAACAACACTCAACTCTATCTCGGGCTATTCTTTTGATTTATA

AGGGATTTTGCCGATTTCGGTCTATTGGTTAAAAAATGAGCTGAT

TTAACAAAAATTTAACGCGAATTTTAACAAAATATTAACGTTTAC

AATTTTATGGTGCACTCTCAGTACAATCTGCTCTGATGCCGCATA

GTTAAGCCAGCCCCGACACCCGCCAACACCCGCTGACGCGCCCTG

ACGGGCTTGTCTGCTCCCGGCATCCGCTTACAGACAAGCTGTGAC

CGTCTCCGGGAGCTGCATGTGTCAGAGGTTTTCACCGTCATCACC

GAAACGCGCGAGACGAAAGGGCCTCGTGATACGCCTATTTTTATA

GGTTAATGTCATGATAATAATGGTTTCTTAGACGTCAGGTGGCAC

TTTTCGGGGAAATGTGCGCGGAACCCCTATTTGTTTATTTTTCTA
```

-continued

AATACATTCAAATATGTATCCGCTCATGAGACAATAACCCTGATA

AATGCTTCAATAATATTGAAAAAGGAAGAGTATGAGTATTCAACA

TTTCCGTGTCGCCCTTATTCCCTTTTTTGCGGCATTTTGCCTTCC

TGTTTTTGCTCACCCAGAAACGCTGGTGAAAGTAAAAGATGCTGA

AGATCAGTTGGGTGCACGAGTGGGTTACATCGAACTGGATCTCAA

CAGCGGTAAGATCCTTGAGAGTTTTCGCCCCGAAGAACGTTTTCC

AATGATGAGCACTTTTAAAGTTCTGCTATGTGGCGCGGTATTATC

CCGTATTGACGCCGGGCAAGAGCAACTCGGTCGCCGCATACACTA

TTCTCAGAATGACTTGGTTGAGTACTCACCAGTCACAGAAAAGCA

TCTTACGGATGGCATGACAGTAAGAGAATTATGCAGTGCTGCCAT

AACCATGAGTGATAACACTGCGGCCAACTTACTTCTGACAACGAT

CGGAGGACCGAAGGAGCTAACCGCTTTTTTTGCACAACATGGGGGA

TCATGTAACTCGCCTTGATCGTTGGGAACCGGAGCTGAATGAAGC

CATACCAAACGACGAGCGTGACACCACGATGCCTGTAGCAATGGC

AACAACGTTGCGCAAACTATTAACTGGCGAACTACTTACTCTAGC

TTCCCGGCAACAATTAATAGACTGGATGGAGGCGGATAAAGTTGC

AGGACCACTTCTGCGCTCGGCCCTTCCGGCTGGCTGGTTTATTGC

TGATAAATCTGGAGCCGGTGAGCGTGGAAGCCGCGGTATCATTGC

AGCACTGGGGCCAGATGGTAAGCCCTCCCGTATCGTAGTTATCTA

CACGACGGGGAGTCAGGCAACTATGGATGAACGAAATAGACAGAT

CGCTGAGATAGGTGCCTCACTGATTAAGCATTGGTAACTGTCAGA

CCAAGTTTACTCATATATACTTTAGATTGATTTAAAACTTCATTT

TTAATTTAAAAGGATCTAGGTGAAGATCCTTTTTTGATAATCTCAT

GACCAAAATCCCTTAACGTGAGTTTTCGTTCCACTGAGCGTCAGA

CCCCGTAGAAAAGATCAAAGGATCTTCTTGAGATCCTTTTTTTCT

GCGCGTAATCTGCTGCTTGCAAACAAAAAAACCACCGCTACCAGC

GGTGGTTTGTTTGCCGGATCAAGAGCTACCAACTCTTTTTCCGAA

GGTAACTGGCTTCAGCAGAGCGCAGATACCAAATACTGTTCTTCT

AGTGTAGCCGTAGTTAGGCCACCACTTCAAGAACTCTGTAGCACC

GCCTACATACCTCGCTCTGCTAATCCTGTTACCAGTGGCTGCTGC

CAGTGGCGATAAGTCGTGTCTTACCGGGTTGGACTCAAGACGATA

GTTACCGGATAAGGCGCAGCGGTCGGGCTGAACGGGGGGTTCGTG

CACACAGCCCAGCTTGGAGCGAACGACCTACACCGAACTGAGATA

CCTACAGCGTGAGCTATGAGAAAGCGCCACGCTTCCCGAAGGGAG

AAAGGCGGACAGGTATCCGGTAAGCGGCAGGGTCGGAACAGGAGA

GCGCACGAGGGAGCTTCCAGGGGGAAACGCCTGGTATCTTTATAG

TCCTGTCGGGTTTCGCCACCTCTGACTTGAGCGTCGATTTTTGTG

ATGCTCGTCAGGGGGGCGGAGCCTATGGAAAAACGCCAGCAACGC

GGCCTTTTTACGGTTCCTGGCCTTTTGCTGGCCTTTTGCTCACAT

GT

-continued pGW103-pAAV_EFSLTR-Light-sPA (SEQ ID NO: 37)

CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccatggagagtgtggtacagccttcagtgtttgt ggtggatggacagacggacatcccattcaggcggctggaacagaa ccaccggagacggcgctgtggcactgtccaggtcagcctggccct ggtgctgctgctaggtgctgggctggccactcagggctggtttct cctgagactgcatcaacgtcttggagacatagtagctcatctgcc agatggaggcaaaggctcctgggagaagctgatacaagatcaacg atctcaccaggccaacccagcagcacatcttacaggagccaacgc cagcttgataggtattggtggacctctgttatgggagacacgact tggcctggccttcttgaggggcttgacgtatcatgatggggccct ggtgaccatggagcccggttactactatgtgtactccaaagtgca gctgagcggcgtgggctgcccccaggggctggccaatggcctccc catcacccatggactatacaagcgcacatcccgctacccgaagga gttagaactgctggtcagtcggcggtcaccctgtggccgggccaa cagctcccgagtctggtgggacagcagcttcctgggcggcgtggt acatctggaggctggggaagaggtggtggtccgcgtgcctggaaa ccgcctggtcagaccacgtgacggcaccaggtcctatttcggagc tttcatggtctgaGAATTCAATAAAAGATCTTTATTTTCATTAGA

TCTGTGTGTTGGTTTTTTGTGTGCGGCCGCAGGAACCCCTAGTGA

TGGAGTTGGCCACTCCCTCTCTGCGCGCTCGCTCGCTCACTGAGG

CCGGGCGACCAAAGGTCGCCCGACGCCCGGGCTTTGCCCGGGCGG

CCTCAGTGAGCGAGCGAGCGCGCAGCTGCCTGCAGGGGCGCCTGA

TGCGGTATTTTCTCCTTACGCATCTGTGCGGTATTTCACACCGCA

TACGTCAAAGCAACCATAGTACGCGCCCTGTAGCGGCGCATTAAG

CGCGGCGGGTGTGGTGGTTACGCGCAGCGTGACCGCTACACTTGC

CAGCGCCTTAGCGCCCGCTCCTTTCGCTTTCTTCCCTTCCTTTCT

CGCCACGTTCGCCGGCTTTCCCCGTCAAGCTCTAAATCGGGGGCT

CCCTTTAGGGTTCCGATTTAGTGCTTTACGGCACCTCGACCCCAA

AAAACTTGATTTGGGTGATGGTTCACGTAGTGGGCCATCGCCCTG

ATAGACGGTTTTTCGCCCTTTGACGTTGGAGTCCACGTTCTTTAA

TAGTGGACTCTTGTTCCAAACTGGAACAACACTCAACTCTATCTC

GGGCTATTCTTTTGATTTATAAGGGATTTTGCCGATTTCGGTCTA

TTGGTTAAAAAATGAGCTGATTTAACAAAAATTTAACGCGAATTT

TAACAAAATATTAACGTTTACAATTTTATGGTGCACTCTCAGTAC

AATCTGCTCTGATGCCGCATAGTTAAGCCAGCCCCGACACCCGCC

AACACCCGCTGACGCGCCCTGACGGGCTTGTCTGCTCCCGGCATC

CGCTTACAGACAAGCTGTGACCGTCTCCGGGAGCTGCATGTGTCA

GAGGTTTTCACCGTCATCACCGAAACGCGCGAGACGAAAGGGCCT

CGTGATACGCCTATTTTTATAGGTTAATGTCATGATAATAATGGT

TTCTTAGACGTCAGGTGGCACTTTTCGGGGAAATGTGCGCGGAAC

CCCTATTTGTTTATTTTTCTAAATACATTCAAATATGTATCCGCT

CATGAGACAATAACCCTGATAAATGCTTCAATAATATTGAAAAAG

GAAGAGTATGAGTATTCAACATTTCCGTGTCGCCCTTATTCCCTT

TTTTGCGGCATTTTGCCTTCCTGTTTTTGCTCACCCAGAAACGCT

GGTGAAAGTAAAAGATGCTGAAGATCAGTTGGGTGCACGAGTGGG

TTACATCGAACTGGATCTCAACAGCGGTAAGATCCTTGAGAGTTT

TCGCCCCGAAGAACGTTTTCCAATGATGAGCACTTTTAAAGTTCT

GCTATGTGGCGCGGTATTATCCCGTATTGACGCCGGGCAAGAGCA

ACTCGGTCGCCGCATACACTATTCTCAGAATGACTTGGTTGAGTA

CTCACCAGTCACAGAAAAGCATCTTACGGATGGCATGACAGTAAG

AGAATTATGCAGTGCTGCCATAACCATGAGTGATAACACTGCGGC

CAACTTACTTCTGACAACGATCGGAGGACCGAAGGAGCTAACCGC

TTTTTTGCACAACATGGGGGATCATGTAACTCGCCTTGATCGTTG

GGAACCGGAGCTGAATGAAGCCATACCAAACGACGAGCGTGACAC

CACGATGCCTGTAGCAATGGCAACAACGTTGCGCAAACTATTAAC

TGGCGAACTACTTACTCTAGCTTCCCGGCAACAATTAATAGACTG

GATGGAGGCGGATAAAGTTGCAGGACCACTTCTGCGCTCGGCCCT

TCCGGCTGGCTGGTTTATTGCTGATAAATCTGGAGCCGGTGAGCG

TGGAAGCCGCGGTATCATTGCAGCACTGGGGCCAGATGGTAAGCC

CTCCCGTATCGTAGTTATCTACACGACGGGGAGTCAGGCAACTAT

GGATGAACGAAATAGACAGATCGCTGAGATAGGTGCCTCACTGAT

TAAGCATTGGTAACTGTCAGACCAAGTTTACTCATATATACTTTA

GATTGATTTAAAACTTCATTTTTAATTTAAAAGGATCTAGGTGAA

GATCCTTTTTGATAATCTCATGACCAAAATCCCTTAACGTGAGTT

TTCGTTCCACTGAGCGTCAGACCCCGTAGAAAAGATCAAAGGATC

TTCTTGAGATCCTTTTTTTCTGCGCGTAATCTGCTGCTTGCAAAC

AAAAAAACCACCGCTACCAGCGGTGGTTTGTTTGCCGGATCAAGA

GCTACCAACTCTTTTTCCGAAGGTAACTGGCTTCAGCAGAGCGCA

GATACCAAATACTGTTCTTCTAGTGTAGCCGTAGTTAGGCCACCA

CTTCAAGAACTCTGTAGCACCGCCTACATACCTCGCTCTGCTAAT

CCTGTTACCAGTGGCTGCTGCCAGTGGCGATAAGTCGTGTCTTAC

CGGGTTGGACTCAAGACGATAGTTACCGGATAAGGCGCAGCGGTC

GGGCTGAACGGGGGGTTCGTGCACACAGCCCAGCTTGGAGCGAAC

GACCTACACCGAACTGAGATACCTACAGCGTGAGCTATGAGAAAG

CGCCACGCTTCCCGAAGGGAGAAAGGCGGACAGGTATCCGGTAAG

CGGCAGGGTCGGAACAGGAGAGCGCACGAGGGAGCTTCCAGGGGG

AAACGCCTGGTATCTTTATAGTCCTGTCGGGTTTCGCCACCTCTG

ACTTGAGCGTCGATTTTTGTGATGCTCGTCAGGGGGGCGGAGCCT

ATGGAAAAACGCCAGCAACGCGGCCTTTTTACGGTTCCTGGCCTT

TTGCTGGCCTTTTGCTCACATGT pGW104-pAAV_EFSLTR-Cxcl10-sPA (SEQ ID NO: 38)

CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccatgaacccaagtgctgccgtcattttctgcct catcctgctgggtctgagtgggactcaagggatccctctcgcaag gacggtccgctgcaactgcatccatatcgatgacgggccagtgag aatgagggccatagggaagcttgaaatcatccctgcgagcctatc ctgcccacgtgttgagatcattgccacgatgaaaaagaatgatga gcagagatgtctgaatccggaatctaagaccatcaagaatttaat gaaagcgtttagccaaaaaaggtctaaaagggctccttgaGAATT

CAATAAAAGATCTTTATTTTCATTAGATCTGTGTGTTGGTTTTTT

GTGTGCGGCCGCAGGAACCCCTAGTGATGGAGTTGGCCACTCCCT

CTCTGCGCGCTCGCTCGCTCACTGAGGCCGGGCGACCAAAGGTCG

CCCGACGCCCGGGCTTTGCCCGGGCGGCCTCAGTGAGCGAGCGAG

-continued

CGCGCAGCTGCCTGCAGGGGCGCCTGATGCGGTATTTTCTCCTTA

CGCATCTGTGCGGTATTTCACACCGCATACGTCAAAGCAACCATA

GTACGCGCCCTGTAGCGGCGCATTAAGCGCGGCGGGTGTGGTGGT

TACGCGCAGCGTGACCGCTACACTTGCCAGCGCCTTAGCGCCCGC

TCCTTTCGCTTTCTTCCCTTCCTTTCTCGCCACGTTCGCCGGCTT

TCCCCGTCAAGCTCTAAATCGGGGGCTCCCTTTAGGGTTCCGATT

TAGTGCTTTACGGCACCTCGACCCCAAAAAACTTGATTTGGGTGA

TGGTTCACGTAGTGGGCCATCGCCCTGATAGACGGTTTTTCGCCC

TTTGACGTTGGAGTCCACGTTCTTTAATAGTGGACTCTTGTTCCA

AACTGGAACAACACTCAACTCTATCTCGGGCTATTCTTTTGATTT

ATAAGGGATTTTGCCGATTTCGGTCTATTGGTTAAAAAATGAGCT

GATTTAACAAAAATTTAACGCGAATTTTAACAAAATATTAACGTT

TACAATTTTATGGTGCACTCTCAGTACAATCTGCTCTGATGCCGC

ATAGTTAAGCCAGCCCCGACACCCGCCAACACCCGCTGACGCGCC

CTGACGGGCTTGTCTGCTCCCGGCATCCGCTTACAGACAAGCTGT

GACCGTCTCCGGGAGCTGCATGTGTCAGAGGTTTTCACCGTCATC

ACCGAAACGCGCGAGACGAAAGGGCCTCGTGATACGCCTATTTTT

ATAGGTTAATGTCATGATAATAATGGTTTCTTAGACGTCAGGTGG

CACTTTTCGGGGAAATGTGCGCGGAACCCCTATTTGTTTATTTTT

CTAAATACATTCAAATATGTATCCGCTCATGAGACAATAACCCTG

ATAAATGCTTCAATAATATTGAAAAAGGAAGAGTATGAGTATTCA

ACATTTCCGTGTCGCCCTTATTCCCTTTTTTGCGGCATTTTGCCT

TCCTGTTTTTGCTCACCCAGAAACGCTGGTGAAAGTAAAAGATGC

TGAAGATCAGTTGGGTGCACGAGTGGGTTACATCGAACTGGATCT

CAACAGCGGTAAGATCCTTGAGAGTTTTCGCCCCGAAGAACGTTT

TCCAATGATGAGCACTTTTAAAGTTCTGCTATGTGGCGCGGTATT

ATCCCGTATTGACGCCGGGCAAGAGCAACTCGGTCGCCGCATACA

CTATTCTCAGAATGACTTGGTTGAGTACTCACCAGTCACAGAAAA

GCATCTTACGGATGGCATGACAGTAAGAGAATTATGCAGTGCTGC

CATAACCATGAGTGATAACACTGCGGCCAACTTACTTCTGACAAC

GATCGGAGGACCGAAGGAGCTAACCGCTTTTTTGCACAACATGGG

GGATCATGTAACTCGCCTTGATCGTTGGGAACCGGAGCTGAATGA

AGCCATACCAAACGACGAGCGTGACACCACGATGCCTGTAGCAAT

GGCAACAACGTTGCGCAAACTATTAACTGGCGAACTACTTACTCT

AGCTTCCCGGCAACAATTAATAGACTGGATGGAGGCGGATAAAGT

TGCAGGACCACTTCTGCGCTCGGCCCTTCCGGCTGGCTGGTTTAT

TGCTGATAAATCTGGAGCCGGTGAGCGTGGAAGCCGCGGTATCAT

TGCAGCACTGGGGCCAGATGGTAAGCCCTCCCGTATCGTAGTTAT

CTACACGACGGGGAGTCAGGCAACTATGGATGAACGAAATAGACA

GATCGCTGAGATAGGTGCCTCACTGATTAAGCATTGGTAACTGTC

-continued

AGACCAAGTTTACTCATATATACTTTAGATTGATTTAAAACTTCA

TTTTTAATTTAAAAGGATCTAGGTGAAGATCCTTTTTGATAATCT

CATGACCAAAATCCCTTAACGTGAGTTTTCGTTCCACTGAGCGTC

AGACCCCGTAGAAAAGATCAAAGGATCTTCTTGAGATCCTTTTTT

TCTGCGCGTAATCTGCTGCTTGCAAACAAAAAAACCACCGCTACC

AGCCGGTGGTTTGTTTGCCGGATCAAGAGCTACCAACTCTTTTTCC

GAAGGTAACTGGCTTCAGCAGAGCGCAGATACCAAATACTGTTCT

TCTAGTGTAGCCGTAGTTAGGCCACCACTTCAAGAACTCTGTAGC

ACCGCCTACATACCTCGCTCTGCTAATCCTGTTACCAGTGGCTGC

TGCCAGTGGCGATAAGTCGTGTCTTACCGGGTTGGACTCAAGACG

ATAGTTACCGGATAAGGCGCAGCGGTCGGGCTGAACGGGGGGTTC

GTGCACACAGCCCAGCTTGGAGCGAACGACCTACACCGAACTGAG

ATACCTACAGCGTGAGCTATGAGAAAGCGCCACGCTTCCCGAAGG

GAGAAAGGCGGACAGGTATCCGGTAAGCGGCAGGGTCGGAACAGG

AGAGCGCACGAGGGAGCTTCCAGGGGGAAACGCCTGGTATCTTTA

TAGTCCTGTCGGGTTTCGCCACCTCTGACTTGAGCGTCGATTTTT

GTGATGCTCGTCAGGGGGGCGGAGCCTATGGAAAAACGCCAGCAA

CGCGGCCTTTTTACGGTTCCTGGCCTTTTGCTGGCCTTTTGCTCA

CATGT pGW105-pAAV_EFSLTR-41bbL-sPA (SEQ ID NO: 39)

CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccatggaccagcacacacttgatgtggaggatac cgcggatgccagacatccagcaggtacttcgtgcccctcggatgc ggcgctcctcagagataccgggctcctcgcggacgctgcgctcct ctcagatactgtgcgccccacaaatgccgcgctccccacggatgc tgcctaccctgcggttaatgttcgggatcgcgaggccgcgtggcc gcctgcactgaacttctgttcccgccacccaaagctctatggcct -continued

```
agtcgctttggttttgctgcttctgatcgccgcctgtgttcctat cttcacccgcaccgagcctcggccagcgctcacaatcaccacctc gcccaacctgggtacccgagagaataatgcagaccaggtcacccc tgtttcccacattggctgccccaacactacacaacagggctctcc tgtgttcgccaagctactggctaaaaaccaagcatcgttgtgcaa tacaactctgaactggcacagccaagatggagctgggagctcata cctatctcaaggtctgaggtacgaagaagacaaaaaggagttggt ggtagacagtcccgggctctactacgtattttttggaactgaagct cagtccaacattcacaaacacaggccacaaggtgcagggctgggt ctctcttgttttgcaagcaaagcctcaggtagatgactttgacaa cttggccctgacagtggaactgttcccttgctccatggagaacaa gttagtggaccgttcctggagtcaactgttgctcctgaaggctgg ccaccgcctcagtgtgggtctgagggcttatctgcatggagccca ggatgcatacagagactgggagctgtcttatcccaacaccaccag ctttggactctttcttgtgaaacccgacaacccatgggaatgaGA

ATTCAATAAAAGATCTTTATTTTCATTAGATCTGTGTGTTGGTTT

TTTGTGTGCGGCCGCAGGAACCCCTAGTGATGGAGTTGGCCACTC

CCTCTCTGCGCGCTCGCTCGCTCACTGAGGCCGGGCGACCAAAGG

TCGCCCGACGCCCGGGCTTTGCCCGGGCGGCCTCAGTGAGCGAGC

GAGCGCGCAGCTGCCTGCAGGGGCGCCTGATGCGGTATTTTCTCC

TTACGCATCTGTGCGGTATTTCACACCGCATACGTCAAAGCAACC

ATAGTACGCGCCCTGTAGCGGCGCATTAAGCGCGGCGGGTGTGGT

GGTTACGCGCAGCGTGACCGCTACACTTGCCAGCGCCTTAGCGCC

CGCTCCTTTCGCTTTCTTCCCTTCCTTTCTCGCCACGTTCGCCGG

CTTTCCCCGTCAAGCTCTAAATCGGGGGCTCCCTTTAGGGTTCCG

ATTTAGTGCTTTACGGCACCTCGACCCCAAAAAACTTGATTTGGG

TGATGGTTCACGTAGTGGGCCATCGCCCTGATAGACGGTTTTTCG

CCCTTTGACGTTGGAGTCCACGTTCTTTAATAGTGGACTCTTGTT

CCAAACTGGAACAACACTCAACTCTATCTCGGGCTATTCTTTTGA

TTTATAAGGGATTTTGCCGATTTCGGTCTATTGGTTAAAAAATGA

GCTGATTTAACAAAAATTTAACGCGAATTTTAACAAAATATTAAC

GTTTACAATTTTATGGTGCACTCTCAGTACAATCTGCTCTGATGC

CGCATAGTTAAGCCAGCCCCGACACCCGCCAACACCCGCTGACGC

GCCCTGACGGGCTTGTCTGCTCCCGGCATCCGCTTACAGACAAGC

TGTGACCGTCTCCGGGAGCTGCATGTGTCAGAGGTTTTCACCGTC

ATCACCGAAACGCGCGAGACGAAAGGGCCTCGTGATACGCCTATT

TTTATAGGTTAATGTCATGATAATAATGGTTTCTTAGACGTCAGG

TGGCACTTTTCGGGGAAATGTGCGCGGAACCCCTATTTGTTTATT

TTTCTAAATACATTCAAATATGTATCCGCTCATGAGACAATAACC

CTGATAAATGCTTCAATAATATTGAAAAAGGAAGAGTATGAGTAT
```

-continued

```
TCAACATTTCCGTGTCGCCCTTATTCCCTTTTTTGCGGCATTTTG

CCTTCCTGTTTTTGCTCACCCAGAAACGCTGGTGAAAGTAAAAGA

TGCTGAAGATCAGTTGGGTGCACGAGTGGGTTACATCGAACTGGA

TCTCAACAGCGGTAAGATCCTTGAGAGTTTTCGCCCCGAAGAACG

TTTTCCAATGATGAGCACTTTTAAAGTTCTGCTATGTGGCGCGGT

ATTATCCCGTATTGACGCCGGGCAAGAGCAACTCGGTCGCCGCAT

ACACTATTCTCAGAATGACTTGGTTGAGTACTCACCAGTCACAGA

AAAGCATCTTACGGATGGCATGACAGTAAGAGAATTATGCAGTGC

TGCCATAACCATGAGTGATAACACTGCGGCCAACTTACTTCTGAC

AACGATCGGAGGACCGAAGGAGCTAACCGCTTTTTTGCACAACAT

GGGGGATCATGTAACTCGCCTTGATCGTTGGGAACCGGAGCTGAA

TGAAGCCATACCAAACGACGAGCGTGACACCACGATGCCTGTAGC

AATGGCAACAACGTTGCGCAAACTATTAACTGGCGAACTACTTAC

TCTAGCTTCCCGGCAACAATTAATAGACTGGATGGAGGCGGATAA

AGTTGCAGGACCACTTCTGCGCTCGGCCCTTCCGGCTGGCTGGTT

TATTGCTGATAAATCTGGAGCCGGTGAGCGTGGAAGCCGCGGTAT

CATTGCAGCACTGGGGCCAGATGGTAAGCCCTCCCGTATCGTAGT

TATCTACACGACGGGGAGTCAGGCAACTATGGATGAACGAAATAG

ACAGATCGCTGAGATAGGTGCCTCACTGATTAAGCATTGGTAACT

GTCAGACCAAGTTTACTCATATATACTTTAGATTGATTTAAAACT

TCATTTTTAATTTAAAAGGATCTAGGTGAAGATCcttttgataa tctcatgaccaaaatcccttaacgtgagttttcgttccactgaGC

GTCAGACCCCGTAGAAAAGATCAAAGGATCTTCTTGAGATCCTTT

TTTTCTGCGCGTAATCTGCTGCTTGCAAACAAAAAAACCACCGCT

ACCAGCGGTGGTTTGTTTGCCGGATCAAGAGCTACCAACTCTTTT

TCCGAAGGTAACTGGCTTCAGCAGAGCGCAGATACCAAATACTGT

TCTTCTAGTGTAGCCGTAGTTAGGCCACCACTTCAAGAACTCTGT

AGCACCGCCTACATACCTCGCTCTGCTAATCCTGTTACCAGTGGC

TGCTGCCAGTGGCGATAAGTCGTGTCTTACCGGGTTGGACTCAAG

ACGATAGTTACCGGATAAGGCGCAGCGGTCGGGCTGAACGGGGGG

TTCGTGCACACAGCCCAGCTTGGAGCGAACGACCTACACCGAACT

GAGATACCTACAGCGTGAGCTATGAGAAAGCGCCACGCTTCCCGA

AGGGAGAAAGGCGGACAGGTATCCGGTAAGCGGCAGGGTCGGAAC

AGGAGAGCGCACGAGGGAGCTTCCAGGGGGAAACGCCTGGTATCT

TTATAGTCCTGTCGGGTTTCGCCACCTCTGACTTGAGCGTCGATT

TTTGTGATGCTCGTCAGGGGGCGGAGCCTATGGAAAAACGCCAG

CAACGCGGCCTTTTTACGGTTCCTGGCCTTTTGCTGGCCTTTTGC

TCACATGT
```

-continued pGW110-pAAV_EFS-LTR-Cd80-T2A-Light-
P2A-Cxcl10-E2A-IFNg-WPRE (SEQ ID NO: 40)

CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccatggcttgcaattgtcagttgatgcaggatac accactcctcaagtttccatgtccaaggctcattcttctctttgt gctgctgattcgtctttcacaagtgtcttcagatgttgatgaaca actgtccaagtcagtgaaagataaggtattgctgccttgccgtta caactctcctcatgaagatgagtctgaagaccgaatctactggca aaaacatgacaaagtggtgctgtctgtcattgctgggaaactaaa agtgtggcccgagtataagaaccggactttatatgacaacactac ctactctcttatcatcctgggcctggtcctttcagaccggggcac atacagctgtgtcgttcaaaagaaggaaagaggaacgtatgaagt taaacacttggctttagtaaagttgtccatcaaagctgacttctc taccccaacataactgagtctggaaacccatctgcagacactaa aaggattacctgctttgcttccggggggtttcccaaagcctcgctt ctcttggttggaaaatggaagagaattacctggcatcaatacgac aatttcccaggatcctgaatctgaattgtacaccattagtagcca actagatttcaatacgactcgcaaccacaccattaagtgtctcat taaatatggagatgctcacgtgtcagaggacttcacctgggaaaa acccccagaagaccctcctgatagcaagaacacacttgtgctctt tggggcaggattcggcgcagtaataacagtcgtcgtcatcgttgt catcatcaaatgcttctgtaagcacagaagctgtttcagaagaaa tgaggcaagcagagaaacaaacaacagccttaccttcgggcctga agaagcattagctgaacagaccgtcttccttcgtacgGGCAGTGG

AGAGGGCAGAGGAAGTCTGCTAACATGCGGTGACGTCGAGGAGAA

TCCTGGCCCAatggagagtgtggtacagccttcagtgtttgtggt ggatggacagacggacatcccattcaggcggctggaacagaacca -continued ccggagacggcgctgtggcactgtccaggtcagcctggccctggt gctgctgctaAgtgctgggctggccactcagggctggtttctcct gagactgcatcaacgtcttggagacatagtagctcatctgccaga tggaggcaaaggctcctgggagaagctgatacaagatcaacgatc tcaccaggccaacccagcagcacatcttacaggagccaacgccag cttgataggtattggtggacctctgttatgggagacacgacttgg cctggccttcttgaggggcttgacgtatcatgatggggccctggt gaccatggagcccggttactactatgtgtactccaaagtgcagct gagcggcgtgggctgcccccagggggctggccaatggcctcccat cacccatggactatacaagcgcacatcccgctacccgaaggagtt agaactgctggtcagtcggcggtcaccctgtggccgggccaacag ctcccgagtctggtgggacagcagcttcctgggcggcgtggtaca tctggaggctggggaagaggtggtggtccgcgtgcctggaaaccg cctggtcagaccacgtgacgggcaccaggtcctatttcggagcttt catggtcactagtGGATCCGGCGCAACAAACTTCTCTCTGCTGAA ACAAGCCGGAGATGTCGAAGAGAATCCTGGACCGatgaacccaag tgctgccgtcattttctgcctcatcctgctgggtctgagtgggac tcaagggatccctctcgcaaggacggtccgctgcaactgcatcca tatcgatgacgggccagtgagaatgagggccataggg gaagcttga aatcatccctgcgagcctatcctgcccacgtgttgagatcattgc cacgatgaaaaagaatgatgagcagagatgtctgaatccggaatc taagaccatcaagaattaatgaaagcgtttagccaaaaaggtc taaaagggctcctagcggtacccagtgcaccaactacgccctgct gaagctggccggcgatgtggagagcaaccccgggcccgctagcat gaacgctacacactgcatcttggctttgcagctcttcctcatggc tgtttctggctgttactgccacggcacagtcattgaaagcctaga aagtctgaataactattttaacctcaagtggcatagatgtggaaga aaagagtctcttcttggatatctggaggaactggcaaaaggatgg tgacatgaaaatcctgcagagccagattatctctttctacctcag actctttgaagtcttgaaagacaatcaggccatcagcaacaacat aagcgtcattgaatcacacctgattactaccttcttcagcaacag caaggcgaaaaaggatgcattcatgagtattgccaagtttgaggt caacaacccacaggtgcagcgccaagcattcaatgagctcatccg agtggtccaccagctgttgccggaatccagcctcaggaagcggaa aaggagtcgctgctgaGaattcacgcgttaagtcgacaatcaacc tctggattacaaaatttgtgaaagattgactggtattcttaacta tgttgctccttttacgctatgtggatacgctgctttaatgccttt gtatcatgctattgcttcccgtatggctttcattttctcctcctt gtataaatcctggttgctgtctctttatgaggagttgtggcccgt tgtcaggcaacgtggcgtggtgtgcactgtgtttgctgacgcaac ccccactggttggggcattgccaccacctgtcagctcctttccgg -continued

```
gactttcgctttccccctccctattgccacggcggaactcatcgc cgcctgccttgcccgctgctggacaggggctcggctgttgggcac tgacaattccgtggtgttgtcggggaaatcatcgtcctttccttg gctgctcgcctgtgttgccacctggattctgcgcgggacgtcctt ctgctacgtcccttcggccctcaatccagcggaccttccttcccg cggcctgctgccggctctgcgcggcctcttccgcgtcttcgccttcg ccctcagacgagtcggatctcccctttgggccgcctccccgcgtcg actttaagaccaatgacGGCCGCAGGAACCCCTAGTGATGGAGTT

GGCCACTCCCTCTCTGCGCGCTCGCTCGCTCACTGAGGCCGGGCG

ACCAAAGGTCGCCCGACGCCCGGGCTTTGCCCGGGCGGCCTCAGT

GAGCGAGCGAGCGCGCAGCTGCCTGCAGGGGCGCCTGATGCGGTA

TTTTCTCCTTACGCATCTGTGCGGTATTTCACACCGCATACGTCA

AAGCAACCATAGTACGCGCCCTGTAGCGGCGCATTAAGCGCGGCG

GGTGTGGTGGTTACGCGCAGCGTGACCGCTACACTTGCCAGCGCC

TTAGCGCCCGCTCCTTTCGCTTTCTTCCCTTCCTTTCTCGCCACG

TTCGCCGGCTTTCCCCGTCAAGCTCTAAATCGGGGGCTCCCTTTA

GGGTTCCGATTTAGTGCTTTACGGCACCTCGACCCCAAAAAACTT

GATTTGGGTGATGGTTCACGTAGTGGGCCATCGCCCTGATAGACG

GTTTTTCGCCCTTTGACGTTGGAGTCCACGTTCTTTAATAGTGGA

CTCTTGTTCCAAACTGGAACAACACTCAACTCTATCTCGGGCTAT

TCTTTTGATTTATAAGGGATTTTGCCGATTTCGGTCTATTGGTTA

AAAAATGAGCTGATTTAACAAAAATTTAACGCGAATTTTAACAAA

ATATTAACGTTTACAATTTTATGGTGCACTCTCAGTACAATCTGC

TCTGATGCCGCATAGTTAAGCCAGCCCCGACACCCGCCAACACCC

GCTGACGCGCCCTGACGGGCTTGTCTGCTCCCGGCATCCGCTTAC

AGACAAGCTGTGACCGTCTCCGGGAGCTGCATGTGTCAGAGGTTT

TCACCGTCATCACCGAAACGCGCGAGACGAAAGGGCCTCGTGATA

CGCCTATTTTTATAGGTTAATGTCATGATAATAATGGTTTCTTAG

ACGTCAGGTGGCACTTTTCGGGGAAATGTGCGCGGAACCCCTATT

TGTTTATTTTTCTAAATACATTCAAATATGTATCCGCTCATGAGA

CAATAACCCTGATAAATGCTTCAATAATATTGAAAAAGGAAGAGT

ATGAGTATTCAACATTTCCGTGTCGCCCTTATTCCCTTTTTTGCG

GCATTTTGCCTTCCTGTTTTTGCTCACCCAGAAACGCTGGTGAAA

GTAAAAGATGCTGAAGATCAGTTGGGTGCACGAGTGGGTTACATC

GAACTGGATCTCAACAGCGGTAAGATCCTTGAGAGTTTTCGCCCC

GAAGAACGTTTTCCAATGATGAGCACTTTTAAAGTTCTGCTATGT

GGCGCGGTATTATCCCGTATTGACGCCGGGCAAGAGCAACTCGGT

CGCCGCATACACTATTCTCAGAATGACTTGGTTGAGTACTCACCA

GTCACAGAAAAGCATCTTACGGATGGCATGACAGTAAGAGAATTA

TGCAGTGCTGCCATAACCATGAGTGATAACACTGCGGCCAACTTA
```

-continued

```
CTTCTGACAACGATCGGAGGACCGAAGGAGCTAACCGCTTTTTTG

CACAACATGGGGGATCATGTAACTCGCCTTGATCGTTGGGAACCG

GAGCTGAATGAAGCCATACCAAACGACGAGCGTGACACCACGATG

CCTGTAGCAATGGCAACAACGTTGCGCAAACTATTAACTGGCGAA

CTACTTACTCTAGCTTCCCGGCAACAATTAATAGACTGGATGGAG

GCGGATAAAGTTGCAGGACCACTTCTGCGCTCGGCCCTTCCGGCT

GGCTGGTTTATTGCTGATAAATCTGGAGCCGGTGAGCGTGGAAGC

CGCGGTATCATTGCAGCACTGGGGCCAGATGGTAAGCCCTCCCGT

ATCGTAGTTATCTACACGACGGGGAGTCAGGCAACTATGGATGAA

CGAAATAGACAGATCGCTGAGATAGGTGCCTCACTGATTAAGCAT

TGGTAACTGTCAGACCAAGTTTACTCATATATACTTTAGATTGAT

TTAAAACTTCATTTTTAATTTAAAAGGATCTAGGTGAAGATCCTT

TTTGATAATCTCATGACCAAAATCCCTTAACGTGAGTTTTCGTTC

CACTGAGCGTCAGACCCCGTAGAAAAGATCAAAGGATCTTCTTGA

GATCCTTTTTTTCTGCGCGTAATCTGCTGCTTGCAAACAAAAAAA

CCACCGCTACCAGCGGTGGTTTGTTTGCCGGATCAAGAGCTACCA

ACTCTTTTTCCGAAGGTAACTGGCTTCAGCAGAGCGCAGATACCA

AATACTGTTCTTCTAGTGTAGCCGTAGTTAGGCCACCACTTCAAG

AACTCTGTAGCACCGCCTACATACCTCGCTCTGCTAATCCTGTTA

CCAGTGGCTGCTGCCAGTGGCGATAAGTCGTGTCTTACCGGGTTG

GACTCAAGACGATAGTTACCGGATAAGGCGCAGCGGTCGGGCTGA

ACGGGGGGTTCGTGCACACAGCCCAGCTTGGAGCGAACGACCTAC

ACCGAACTGAGATACCTACAGCGTGAGCTATGAGAAAGCGCCACG

CTTCCCGAAGGGAGAAAGGCGGACAGGTATCCGGTAAGCGGCAGG

GTCGGAACAGGAGAGCGCACGAGGGAGCTTCCAGGGGGAAACGCC

TGGTATCTTTATAGTCCTGTCGGGTTTCGCCACCTCTGACTTGAG

CGTCGATTTTTGTGATGCTCGTCAGGGGGGCGGAGCCTATGGAAA

AACGCCAGCAACGCGGCCTTTTTACGGTTCCTGGCCTTTTGCTGG

CCTTTTGCTCACATGT pGW111-pAAV_EFS-LTR-Light-P2A-Cxc10-E2A-
IFNg-WPRE (SEQ ID NO: 41)
CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC
```

-continued

```
CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccatggagagtgtggtacagccttcagtgtttgt ggtggatggacagacggacatcccattcaggcggctggaacagaa ccaccggagacggcgctgtggcactgtccaggtcagcctggccct ggtgctgctgctaAgtgctgggctggccactcagggctggtttct cctgagactgcatcaacgtcttggagacatagtagctcatctgcc agatggaggcaaaggctcctgggagaagctgatacaagatcaacg atctcaccaggccaacccagcagcacatcttacaggagccaacgc cagcttgataggtattggtggacctctgttatgggagacacgact tggcctggccttcttgaggggcttgacgtatcatgatggggccct ggtgaccatggagcccggttactactatgtgtactccaaagtgca gctgagcggcgtgggctgcccccaggggctggccaatggcctccc catcacccatggactatacaagcgcacatcccgctacccgaagga gttagaactgctggtcagtcggcggtcaccctgtggccgggccaa cagctcccgagtctggtgggacagcagcttcctgggcggcgtggt acatctggaggctggggaagaggtggtggtccgcgtgcctggaaa ccgcctggtcagaccacgtgacggcaccaggtcctatttcggagc tttcatggtcactagtGGATCCGGCGCAACAAACTTCTCTCTGCT GAAACAAGCCGGAGATGTCGAAGAGAATCCTGGACCGatgaaccc aagtgctgccgtcattttctgcctcatcctgctgggtctgagtgg gactcaagggatccctctcgcaaggacggtccgctgcaactgcat ccatatcgatgacgggccagtgagaatgagggccatagggaagct tgaaatcatccctgcgagcctatcctgcccacgtgttgagatcat tgccacgatgaaaaagaatgatgagcagagatgtctgaatccgga atctaagaccatcaagaatttaatgaaagcgtttagccaaaaaag gtctaaaagggctcctagcggtacccagtgcaccaactacgccct gctgaagctggccggcgatgtggagagcaaccccgggccgctag catgaacgctacacactgcatcttggctttgcagctcttcctcat ggctgtttctggctgttactgccacggcacagtcattgaaagcct agaaagtctgaataactattttaactcaagtggcatagatgtgga agaaaagagtctcttcttggatatctggaggaactggcaaaagga tggtgacatgaaaatcctgcagagccagattatctctttctacct cagactctttgaagtcttgaaagacaatcaggccatcagcaacaa cataagcgtcattgaatcacacctgattactaccttcttcagcaa cagcaaggcgaaaaaggatgcattcatgagtattgccaagtttga ggtcaacaacccacaggtccagcgccaagcattcaatgagctcat ccgagtggtccaccagctgttgccggaatccagcctcaggaagcg
```

-continued

```
gaaaaggagtcgctgctgaGaattcacgcgttaagtcgacaatca acctctggattacaaaatttgtgaaagattgactggtattcttaa ctatgttgctccttttacgctatgtggatacgctgctttaatgcc tttgtatcatgctattgcttcccgtatggctttcattttctcctc cttgtataaatcctggttgctgtctctttatgaggagttgtggcc cgttgtcaggcaacgtggcgtggtgtgcactgtgtttgctgacgc aacccccactggttggggcattgccaccacctgtcagctcctttc cgggactttcgctttccccctccctattgccacggcggaactcat cgccgcctgccttgcccgctgctggacaggggctcggctgttggg cactgacaattccgtggtgttgtcggggaaatcatcgtcctttcc ttggctgctcgcctgtgttgccacctggattctgcgcgggacgtc cttctgctacgtcccttcggccctcaatccagcggaccttccttc ccgcggcctgctgccggctctgcggcctcttccgcgtcttcgcct tcgccctcagacgagtcggatctcccctttgggccgcctccccgcg tcgactttaagaccaatgacGGCCGCAGGAACCCCTAGTGATGGA

GTTGGCCACTCCCTCTCTGCGCGCTCGCTCGCTCACTGAGGCCGG

GCGACCAAAGGTCGCCCGACGCCCGGGCTTTGCCCGGGCGGCCTC

AGTGAGCGAGCGAGCGCGCAGCTGCCTGCAGGGGCGCCTGATGCG

GTATTTTCTCCTTACGCATCTGTGCGGTATTTCACACCGCATACG

TCAAAGCAACCATAGTACGCGCCCTGTAGCGGCGCATTAAGCGCG

GCGGGTGTGGTGGTTACGCGCAGCGTGACCGCTACACTTGCCAGC

GCCTTAGCGCCCGCTCCTTTCGCTTTCTTCCCTTCCTTTCTCGCC

ACGTTCGCCGGCTTTCCCCGTCAAGCTCTAAATCGGGGGCTCCCT

TTAGGGTTCCGATTTAGTGCTTTACGGCACCTCGACCCCAAAAAA

CTTGATTTGGGTGATGGTTCACGTAGTGGGCCATCGCCCTGATAG

ACGGTTTTTCGCCCTTTGACGTTGGAGTCCACGTTCTTTAATAGT

GGACTCTTGTTCCAAACTGGAACAACACTCAACTCTATCTCGGGC

TATTCTTTTGATTTATAAGGGATTTTGCCGATTTCGGTCTATTGG

TTAAAAAATGAGCTGATTTAACAAAAATTTAACGCGAATTTTAAC

AAAATATTAACGTTTACAATTTTATGGTGCACTCTCAGTACAATC

TGCTCTGATGCCGCATAGTTAAGCCAGCCCCGACACCCGCCAACA

CCCGCTGACGCGCCCTGACGGGCTTGTCTGCTCCCGGCATCCGCT

TACAGACAAGCTGTGACCGTCTCCGGGAGCTGCATGTGTCAGAGG

TTTTCACCGTCATCACCGAAACGCGCGAGACGAAAGGGCCTCGTG

ATACGCCTATTTTTATAGGTTAATGTCATGATAATAATGGTTTCT

TAGACGTCAGGTGGCACTTTTCGGGGAAATGTGCGCGGAACCCCT

ATTTGTTTATTTTTCTAAATACATTCAAATATGTATCCGCTCATG

AGACAATAACCCTGATAAATGCTTCAATAATATTGAAAAAGGAAG

AGTATGAGTATTCAACATTTCCGTGTCGCCCTTATTCCCTTTTTT

GCGGCATTTTGCCTTCCTGTTTTTGCTCACCCAGAAACGCTGGTG
```

-continued

AAAGTAAAAGATGCTGAAGATCAGTTGGGTGCACGAGTGGGTTAC

ATCGAACTGGATCTCAACAGCGGTAAGATCCTTGAGAGTTTTCGC

CCCGAAGAACGTTTTCCAATGATGAGCACTTTTAAAGTTCTGCTA

TGTGGCGCGGTATTATCCCGTATTGACGCCGGGCAAGAGCAACTC

GGTCGCCGCATACACTATTCTCAGAATGACTTGGTTGAGTACTCA

CCAGTCACAGAAAAGCATCTTACGGATGGCATGACAGTAAGAGAA

TTATGCAGTGCTGCCATAACCATGAGTGATAACACTGCGGCCAAC

TTACTTCTGACAACGATCGGAGGACCGAAGGAGCTAACCGCTTTT

TTGCACAACATGGGGGATCATGTAACTCGCCTTGATCGTTGGGAA

CCGGAGCTGAATGAAGCCATACCAAACGACGAGCGTGACACCACG

ATGCCTGTAGCAATGGCAACAACGTTGCGCAAACTATTAACTGGC

GAACTACTTACTCTAGCTTCCCGGCAACAATTAATAGACTGGATG

GAGGCGGATAAAGTTGCAGGACCACTTCTGCGCTCGGCCCTTCCG

GCTGGCTGGTTTATTGCTGATAAATCTGGAGCCGGTGAGCGTGGA

AGCCGCGGTATCATTGCAGCACTGGGGCCAGATGGTAAGCCCTCC

CGTATCGTAGTTATCTACACGACGGGGAGTCAGGCAACTATGGAT

GAACGAAATAGACAGATCGCTGAGATAGGTGCCTCACTGATTAAG

CATTGGTAACTGTCAGACCAAGTTTACTCATATATACTTTAGATT

GATTTAAAACTTCATTTTTAATTTAAAAGGATCTAGGTGAAGATC

CTTTTTGATAATCTCATGACCAAAATCCCTTAACGTGAGTTTTCG

TTCCACTGAGCGTCAGACCCCGTAGAAAAGATCAAAGGATCTTCT

TGAGATCCTTTTTTTCTGCGCGTAATCTGCTGCTTGCAAACAAAA

AAACCACCGCTACCAGCGGTGGTTTGTTTGCCGGATCAAGAGCTA

CCAACTCTTTTTCCGAAGGTAACTGGCTTCAGCAGAGCGCAGATA

CCAAATACTGTTCTTCTAGTGTAGCCGTAGTTAGGCCACCACTTC

AAGAACTCTGTAGCACCGCCTACATACCTCGCTCTGCTAATCCTG

TTACCAGTGGCTGCTGCCAGTGGCGATAAGTCGTGTCTTACCGGG

TTGGACTCAAGACGATAGTTACCGGATAAGGCGCAGCGGTCGGGC

TGAACGGGGGGTTCGTGCACACAGCCCAGCTTGGAGCGAACGACC

TACACCGAACTGAGATACCTACAGCGTGAGCTATGAGAAAGCGCC

ACGCTTCCCGAAGGGAGAAAGGCGGACAGGTATCCGGTAAGCGGC

AGGGTCGGAACAGGAGAGCGCACGAGGGAGCTTCCAGGGGGAAAC

GCCTGGTATCTTTATAGTCCTGTCGGGTTTCGCCACCTCTGACTT

GAGCGTCGATTTTTGTGATGCTCGTCAGGGGGGCGGAGCCTATGG

AAAAACGCCAGCAACGCGGCCTTTTTACGGTTCCTGGCCTTTTGC

TGGCCTTTTGCTCACATGT pGW112-pAAV_EFS-LTR-41BBL-T2A-Light-
P2A-Cxcl10-E2A-IFNg-WPRE
(SEQ ID NO: 42)

CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

-continued

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccatggaccagcacacacttgatgtggaggatac cgcggatgccagacatccagcaggtacttcgtgcccctcggatgc ggcgctcctcagagataccgggctcctcgcgggacgctgcgctcct ctcagatactgtgcgccccacaaatgccgcgctccccacggatgc tgcctaccctgcggttaatgttcgggatcgcgaggccgcgtggcc gcctgcactgaacttctgttcccgccacccaaagctctatggcct agtcgctttggttttgctgcttctgatcgccgcctgtgttcctat cttcacccgcaccgagcctcggccagcgctcacaatcaccacctc gcccaacctgggtacccgagagaataatgcagaccaggtcacccc tgtttcccacattggctgccccaacactacacaacagggctctcc tgtgttcgccaagctactggctaaaaaccaagcatcgttgtgcaa tacaactctgaactggcacagccaagatggagctgggagctcata cctatctcaaggtctgaggtacgaagaagacaaaaaggagttggt ggtagacagtcccgggctctactacgtattttttggaactgaagct cagtccaacattcacaaacacaggccacaaggtgcagggctgggt ctctcttgttttgcaagcaaagcctcaggtagatgactttgacaa cttggccctgacagtggaactgttcccttgctccatggagaacaa gttagtggaccgttcctggagtcaactgttgctcctgaaggctgg ccaccgcctcagtgtgggtctgagggcttatctgcatggagccca ggatgcatacagagactgggagctgtcttatcccaacaccaccag ctttggactctttcttgtgaaacccgacaacccatgggaaGGCAG

TGGAGAGGGCAGAGGAAGTCTGCTAACATGCGGTGACGTCGAGGA

GAATCCTGGCCCAatggagagtgtggtacagccttcagtgtttgt ggtggatggacagacggacatcccattcaggcggctggaacagaa ccaccggagacggcgctgtggcactgtccaggtcagcctggccct ggtgctgctgctaAgtgctgggctggccactcagggctggtttct cctgagactgcatcaacgtcttggagacatagtagctcatctgcc agatggaggcaaaggtcctgggagaagctgatacaagatcaacg atctcaccaggccaacccagcagcacatcttacaggagccaacgc -continued cagcttgataggtattggtggacctctgttatgggagacacgact tggcctggccttcttgaggggcttgacgtatcatgatggggccct ggtgaccatggagcccggttactactatgtgtactccaaagtgca gctgagcggcgtgggctgcccccaggggctggccaatggcctccc catcacccatggactatacaagcgcacatcccgctacccgaagga gttagaactgctggtcagtcggcggtcaccctgtggccgggccaa cagctcccgagtctggtgggacagcagcttcctgggcggcgtggt acatctggaggctggggaagaggtggtggtccgcgtgcctggaaa ccgcctggtcagaccacgtgacggcaccaggtcctatttcggagc tttcatggtcactagtGGATCCGGCGCAACAAACTTCTCTCTGCT GAAACAAGCCGGAGATGTCGAAGAGAATCCTGGACCGatgaaccc aagtgctgccgtcattttctgcctcatcctgctgggtctgagtgg gactcaagggatccctctcgcaaggacggtccgctgcaactgcat ccatatcgatgacgggccagtgagaatgagggccataggggaagct tgaaatcatccctgcgagcctatcctgcccacgtgttgagatcat tgccacgatgaaaaagaatgatgagcagagatgtctgaatccgga atctaagaccatcaagaatttaatgaaagcgtttagccaaaaaag gtctaaaagggctcctagcggtacccagtgcaccaactacgccct gctgaagctggccggcgatgtggagagcaaccccgggcccgctag catgaacgctacacactgcatcttggctttgcagctcttcctcat ggctgtttctggctgttactgccacggcacagtcattgaaagcct agaaagtctgaataactattttaactcaagtggcatagatgtgga agaaaagagtctcttcttggatatctggaggaactggcaaaagga tggtgacatgaaaatcctgcagagccagattatctctttctacct cagactctttgaagtcttgaaagacaatcaggccatcagcaacaa cataagcgtcattgaatcacacctgattactaccttcttcagcaa cagcaaggcgaaaaaggatgcattcatgagtattgccaagtttga ggtcaacaacccacaggtccagcgccaagcattcaatgagctcat ccgagtggtccaccagctgttgccggaatccagcctcaggaagcg gaaaaggagtcgctgctgaGaattcacgcgttaagtcgacaatca acctctggattacaaaatttgtgaaagattgactggtattcttaa ctatgttgctccttttacgctatgtggatacgctgctttaatgcc tttgtatcatgctattgcttcccgtatggctttcattttctcctc cttgtataaatcctggttgctgtctctttatgaggagttgtggcc cgttgtcaggcaacgtggcgtggtgtgcactgtgtttgctgacgc aaccccactggttggggcattgccaccacctgtcagctcctttc cgggactttcgctttccccctccctattgccacggcggaactcat cgccgcctgccttgcccgctgctggacaggggctcggctgttggg cactgacaattccgtggtgttgtcggggaaatcatcgtcctttcc ttggctgctcgcctgtgttgccacctggattctgcgcgggacgtc -continued cttctgctacgtcccttcggccctcaatccagcggaccttccttc ccgcggcctgctgccggctctgcggcctcttccgcgtcttcgcct tcgccctcagacgagtcggatctccctttgggccgcctccccgcg tcgactttaagaccaatgacGGCCGCAGGAACCCCTAGTGATGGA

GTTGGCCACTCCCTCTCTGCGCGCTCGCTCGCTCACTGAGGCCGG

GCGACCAAAGGTCGCCCGACGCCCGGGCTTTGCCCGGGCGGCCTC

AGTGAGCGAGCGAGCGCGCAGCTGCCTGCAGGGGCGCCTGATGCG

GTATTTTCTCCTTACGCATCTGTGCGGTATTTCACACCGCATACG

TCAAAGCAACCATAGTACGCGCCCTGTAGCGGCGCATTAAGCGCG

GCGGGTGTGGTGGTTACGCGCAGCGTGACCGCTACACTTGCCAGC

GCCTTAGCGCCCGCTCCTTTCGCTTTCTTCCCTTCCTTTCTCGCC

ACGTTCGCCGGCTTTCCCCGTCAAGCTCTAAATCGGGGGCTCCCT

TTAGGGTTCCGATTTAGTGCTTTACGGCACCTCGACCCCAAAAAA

CTTGATTTGGGTGATGGTTCACGTAGTGGGCCATCGCCCTGATAG

ACGGTTTTTCGCCCTTTGACGTTGGAGTCCACGTTCTTTAATAGT

GGACTCTTGTTCCAAACTGGAACAACACTCAACTCTATCTCGGGC

TATTCTTTTGATTTATAAGGGATTTTGCCGATTTCGGTCTATTGG

TTAAAAAATGAGCTGATTTAACAAAAATTTAACGCGAATTTTAAC

AAAATATTAACGTTTACAATTTTATGGTGCACTCTCAGTACAATC

TGCTCTGATGCCGCATAGTTAAGCCAGCCCCGACACCCGCCAACA

CCCGCTGACGCGCCCTGACGGGCTTGTCTGCTCCCGGCATCCGCT

TACAGACAAGCTGTGACCGTCTCCGGGAGCTGCATGTGTCAGAGG

TTTTCACCGTCATCACCGAAACGCGCGAGACGAAAGGGCCTCGTG

ATACGCCTATTTTTATAGGTTAATGTCATGATAATAATGGTTTCT

TAGACGTCAGGTGGCACTTTTCGGGGAAATGTGCGCGGAACCCCT

ATTTGTTTATTTTTCTAAATACATTCAAATATGTATCCGCTCATG

AGACAATAACCCTGATAAATGCTTCAATAATATTGAAAAAGGAAG

AGTATGAGTATTCAACATTTCCGTGTCGCCCTTATTCCCTTTTTT

GCGGCATTTTGCCTTCCTGTTTTTGCTCACCCAGAAACGCTGGTG

AAAGTAAAAGATGCTGAAGATCAGTTGGGTGCACGAGTGGGTTAC

ATCGAACTGGATCTCAACAGCGGTAAGATCCTTGAGAGTTTTCGC

CCCGAAGAACGTTTTCCAATGATGAGCACTTTTAAAGTTCTGCTA

TGTGGCGCGGTATTATCCCGTATTGACGCCGGGCAAGAGCAACTC

GGTCGCCGCATACACTATTCTCAGAATGACTTGGTTGAGTACTCA

CCAGTCACAGAAAAGCATCTTACGGATGGCATGACAGTAAGAGAA

TTATGCAGTGCTGCCATAACCATGAGTGATAACACTGCGGCCAAC

TTACTTCTGACAACGATCGGAGGACCGAAGGAGCTAACCGCTTTT

TTGCACAACATGGGGGATCATGTAACTCGCCTTGATCGTTGGGAA

CCGGAGCTGAATGAAGCCATACCAAACGACGAGCGTGACACCACG

ATGCCTGTAGCAATGGCAACAACGTTGCGCAAACTATTAACTGGC

GAACTACTTACTCTAGCTTCCCGGCAACAATTAATAGACTGGATG

-continued

```
GAGGCGGATAAAGTTGCAGGACCACTTCTGCGCTCGGCCCTTCCG

GCTGGCTGGTTTATTGCTGATAAATCTGGAGCCGGTGAGCGTGGA

AGCCGCGGTATCATTGCAGCACTGGGGCCAGATGGTAAGCCCTCC

CGTATCGTAGTTATCTACACGACGGGGAGTCAGGCAACTATGGAT

GAACGAAATAGACAGATCGCTGAGATAGGTGCCTCACTGATTAAG

CATTGGTAACTGTCAGACCAAGTTTACTCATATATACTTTAGATT

GATTTAAAACTTCATTTTTAATTTAAAAGGATCTAGGTGAAGATC

CTTTTTGATAATCTCATGACCAAAATCCCTTAACGTGAGTTTTCG

TTCCACTGAGCGTCAGACCCCGTAGAAAAGATCAAAGGATCTTCT

TGAGATCCTTTTTTTCTGCGCGTAATCTGCTGCTTGCAAACAAAA

AAACCACCGCTACCAGCGGTGGTTTGTTTGCCGGATCAAGAGCTA

CCAACTCTTTTTCCGAAGGTAACTGGCTTCAGCAGAGCGCAGATA

CCAAATACTGTTCTTCTAGTGTAGCCGTAGTTAGGCCACCACTTC

AAGAACTCTGTAGCACCGCCTACATACCTCGCTCTGCTAATCCTG

TTACCAGTGGCTGCTGCCAGTGGCGATAAGTCGTGTCTTACCGGG

TTGGACTCAAGACGATAGTTACCGGATAAGGCGCAGCGGTCGGGC

TGAACGGGGGGTTCGTGCACACAGCCCAGCTTGGAGCGAACGACC

TACACCGAACTGAGATACCTACAGCGTGAGCTATGAGAAAGCGCC

ACGCTTCCCGAAGGGAGAAAGGCGGACAGGTATCCGGTAAGCGGC

AGGGTCGGAACAGGAGAGCGCACGAGGGAGCTTCCAGGGGGAAAC

GCCTGGTATCTTTATAGTCCTGTCGGGTTTCGCCACCTCTGACTT

GAGCGTCGATTTTTGTGATGCTCGTCAGGGGGCGGAGCCTATGG

AAAAACGCCAGCAACGCGGCCTTTTTACGGTTCCTGGCCTTTTGC

TGGCCTTTTGCTCACATGT
``` pGW113-pAAV_EFS-LTR-IL23-T2A-Light-P2A-
Cxc10-E2A-IFNg-WPRE (SEQ ID NO: 43)
```
CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC
```

-continued

```
TAccggtgccaccATGTGTCCTCAGAAGCTAACCATCTCCTGGTT

TGCCATCGTTTTGCTGGTGTGTCTCCACTCATGGCCATGTGGGAGCT

GGAGAAAGACGTTTATGTTGTAGAGGTGGACTGGACTCCCGATGC

CCCTGGAGAAACAGTGAACCTCACCTGTGACACGCCTGAAGAAGA

TGACATCACCTGGACCTCAGACCAGAGACATGGAGTCATAGGCTC

TGGAAAGACCCTGACCATCACTGTCAAAGAGTTTCTAGATGCTGG

CCAGTACACCTGCCACAAAGGAGGCGAGACTCTGAGCCACTCACA

TCTGCTGCTCCACAAGAAGGAAAATGGAATTTGGTCCACTGAAAT

TTTAAAAAATTTCAAAAACAAGACTTTCCTGAAGTGTGAAGCACC

AAATTACTCCGGACGGTTCACGTGCTCATGGCTGGTGCAAAGAAA

CATGGACTTGAAGTTCAACATCAAGAGCAGTAGCAGTTCCCCTGA

CTCTCGGGCAGTGACATGTGGAATGGCGTCTCTGTCTGCAGAGAA

GGTCACACTGGACCAAAGGGACTATGAGAAGTATTCAGTGTCCTG

CCAGGAGGATGTCACCTGCCCAACTGCCGAGGAGACCCTGCCCAT

TGAACTGGCGTTGGAAGCACGGCAGCAGAATAAATATGAGAACTA

CAGCACCAGCTTCTTCATCAGGGACATCATCAAACCAGACCCGCC

CAAGAACTTGCAGATGAAGCCTTTGAAGAACTCACAGGTGGAGGT

CAGCTGGGAGTACCCTGACTCCTGGAGCACTCCCCATTCCTACTT

CTCCCTCAAGTTCTTTGTTCGAATCCAGCGCAAGAAAGAAAAGAT

GAAGGAGACAGAGGAGGGGTGTAACCAGAAAGGTGCGTTCCTCGT

AGAGAAGACATCTACCGAAGTCCAATGCAAAGGCGGGAATGTCTG

CGTGCAAGCTCAGGATCGCTATTACAATTCCTCATGCAGCAAGTG

GGCATGTGTTCCCTGCAGGGTCCGATCCGGCAGTGGAGAGGGCAG

AGGAAGTCTGCTAACATGCGGTGACGTCGAGGAGAATCCTGGCCC

Aatggagagtgtggtacagccttcagtgtttgtggtggatggaca gacggacatcccattcaggcggctggaacagaaccaccggagacg gcgctgtggcactgtccaggtcagcctggccctggtgctgctgct aAgtgctgggctggccactcagggctggtttctcctgagactgca tcaacgtcttggagacatagtagctcatctgccagatggaggcaa aggctcctgggagaagctgatacaagatcaacgatctcaccaggc caacccagcagcacatcttacaggagccaacgccagcttgatagg tattggtggacctctgttatgggagacacgacttggcctggcctt cttgaggggcttgacgtatcatgatggggccctggtgaccatgga gcccggttactactatgtgtactccaaagtgcagctgagcggcgt gggctgccccagggctggccaatggcctccccatcacccatgg actatacaagcgcacatcccgctacccgaaggagttagaactgct ggtcagtcggcggtcaccctgtggccgggccaacagctcccgagt ctggtgggacagcagcttcctgggcggcgtggtacatctggaggc tggggaagaggtggtggtccgcgtgcctggaaaccgcctggtcag accacgtgacggcaccaggtcctatttcggagctttcatggtcac
```

-continued

```
tagtGGATCCGGCGCAACAAACTTCTCTCTGCTGAAACAAGCCGG

AGATGTCGAAGAGAATCCTGGACCGatgaacccaagtgctgccgt cattttctgcctcatcctgctgggtctgagtgggactcaagggat ccctctcgcaaggacggtccgctgcaactgcatccatatcgatga cgggccagtgagaatgagggccatagggaagcttgaaatcatccc tgcgagcctatcctgcccacgtgttgagatcattgccacgatgaa aaagaatgatgagcagagatgtctgaatccggaatctaagaccat caagaatttaatgaaagcgtttagccaaaaaggtctaaaagggc tcctagcggtacccagtgcaccaactacgccctgctgaagctggc cggcgatgtggagagcaaccccgggcccgctagcatgaacgctac acactgcatcttggctttgcagctcttcctcatggctgtttctgg ctgttactgccacggcacagtcattgaaagcctagaaagtctgaa taactattttaactcaagtggcatagatgtggaagaaaagagtct cttcttggatatctggaggaactggcaaaaggatggtgacatgaa aatcctgcagagccagattatctctttctacctcagactctttga agtcttgaaagacaatcaggccatcagcaacaacataagcgtcat tgaatcacacctgattactaccttcttcagcaacagcaaggcgaa aaaggatgcattcatgagtattgccaagtttgaggtcaacaaccc acaggtccagcgccaagcattcaatgagctcatccgagtggtcca ccagctgttgccggaatccagcctcaggaagcggaaaaggagtcg ctgctgaGaattcacgcgttaagtcgacaatcaacctctggatta caaaatttgtgaaagattgactggtattcttaactatgttgctcc ttttacgctatgtggatacgctgctttaatgcctttgtatcatgc tattgcttcccgtatggctttcattttctcctccttgtataaatc ctggttgctgtctctttatgaggagttgtggcccgttgtcaggca acgtggcgtggtgtgcactgtgtttgctgacgcaaccccactgg ttggggcattgccaccacctgtcagctcctttccgggactttcgc tttccccctccctattgccacggcggaactcatcgccgcctgcct tgcccgctgctggacaggggctcggctgttgggcactgacaattc cgtggtgttgtcggggaaatcatcgtcctttccttggctgctcgc ctgtgttgccacctggattctgcgcgggacgtccttctgctacgt cccttcggccctcaatccagcggaccttccttcccgcggcctgct gccggctctgcggcctcttccgcgtcttcgccttcgccctcagac gagtcggatctccctttgggccgcctccccgcgtcgactttaaga ccaatgacGGCCGCAGGAACCCCTAGTGATGGAGTTGGCCACTCC

CTCTCTGCGCGCTCGCTCGCTCACTGAGGCCGGGCGACCAAAGGT

CGCCCGACGCCCGGGCTTTGCCCGGGCGGCCTCAGTGAGCGAGCG

AGCGCGCAGCTGCCTGCAGGGGCGCCTGATGCGGTATTTTCTCCT

TACGCATCTGTGCGGTATTTCACACCGCATACGTCAAAGCAACCA

TAGTACGCGCCCTGTAGCGGCGCATTAAGCGCGGCGGGTGTGGTG

GTTACGCGCAGCGTGACCGCTACACTTGCCAGCGCCTTAGCGCCC
```

-continued

```
GCTCCTTTCGCTTTCTTCCCTTCCTTTCTCGCCACGTTCGCCGGC

TTTCCCCGTCAAGCTCTAAATCGGGGGCTCCCTTTAGGGTTCCGA

TTTAGTGCTTTACGGCACCTCGACCCCAAAAAACTTGATTTGGGT

GATGGTTCACGTAGTGGGCCATCGCCCTGATAGACGGTTTTTCGC

CCTTTGACGTTGGAGTCCACGTTCTTTAATAGTGGACTCTTGTTC

CAAACTGGAACAACACTCAACTCTATCTCGGGCTATTCTTTTGAT

TTATAAGGGATTTTGCCGATTTCGGTCTATTGGTTAAAAAATGAG

CTGATTTAACAAAAATTTAACGCGAATTTTAACAAAATATTAACG

TTTACAATTTTATGGTGCACTCTCAGTACAATCTGCTCTGATGCC

GCATAGTTAAGCCAGCCCCGACACCCGCCAACACCCGCTGACGCG

CCCTGACGGGCTTGTCTGCTCCCGGCATCCGCTTACAGACAAGCT

GTGACCGTCTCCGGGAGCTGCATGTGTCAGAGGTTTTCACCGTCA

TCACCGAAACGCGCGAGACGAAAGGGCCTCGTGATACGCCTATTT

TTATAGGTTAATGTCATGATAATAATGGTTTCTTAGACGTCAGGT

GGCACTTTTCGGGGAAATGTGCGCGGAACCCCTATTTGTTTATTT

TTCTAAATACATTCAAATATGTATCCGCTCATGAGACAATAACCC

TGATAAATGCTTCAATAATATTGAAAAAGGAAGAGTATGAGTATT

CAACATTTCCGTGTCGCCCTTATTCCCTTTTTTGCGGCATTTTGC

CTTCCTGTTTTTGCTCACCCAGAAACGCTGGTGAAAGTAAAAGAT

GCTGAAGATCAGTTGGGTGCACGAGTGGGTTACATCGAACTGGAT

CTCAACAGCGGTAAGATCCTTGAGAGTTTTCGCCCCGAAGAACGT

TTTCCAATGATGAGCACTTTTAAAGTTCTGCTATGTGGCGCGGTA

TTATCCCGTATTGACGCCGGGCAAGAGCAACTCGGTCGCCGCATA

CACTATTCTCAGAATGACTTGGTTGAGTACTCACCAGTCACAGAA

AAGCATCTTACGGATGGCATGACAGTAAGAGAATTATGCAGTGCT

GCCATAACCATGAGTGATAACACTGCGGCCAACTTACTTCTGACA

ACGATCGGAGGACCGAAGGAGCTAACCGCTTTTTTGCACAACATG

GGGGATCATGTAACTCGCCTTGATCGTTGGGAACCGGAGCTGAAT

GAAGCCATACCAAACGACGAGCGTGACACCACGATGCCTGTAGCA

ATGGCAACAACGTTGCGCAAACTATTAACTGGCGAACTACTTACT

CTAGCTTCCCGGCAACAATTAATAGACTGGATGGAGGCGGATAAA

GTTGCAGGACCACTTCTGCGCTCGGCCCTTCCGGCTGGCTGGTTT

ATTGCTGATAAATCTGGAGCCGGTGAGCGTGGAAGCCGCGGTATC

ATTGCAGCACTGGGGCCAGATGGTAAGCCCTCCCGTATCGTAGTT

ATCTACACGACGGGGAGTCAGGCAACTATGGATGAACGAAATAGA

CAGATCGCTGAGATAGGTGCCTCACTGATTAAGCATTGGTAACTG

TCAGACCAAGTTTACTCATATATACTTTAGATTGATTTAAAACTT

CATTTTTAATTTAAAAGGATCTAGGTGAAGATCCTTTTTGATAAT

CTCATGACCAAAATCCCTTAACGTGAGTTTTCGTTCCACTGAGCG

TCAGACCCCGTAGAAAAGATCAAAGGATCTTCTTGAGATCCTTTT
```

-continued

TTTCTGCGCGTAATCTGCTGCTTGCAAACAAAAAAACCACCGCTA

CCAGCGGTGGTTTGTTTGCCGGATCAAGAGCTACCAACTCTTTTT

CCGAAGGTAACTGGCTTCAGCAGAGCGCAGATACCAAATACTGTT

CTTCTAGTGTAGCCGTAGTTAGGCCACCACTTCAAGAACTCTGTA

GCACCGCCTACATACCTCGCTCTGCTAATCCTGTTACCAGTGGCT

GCTGCCAGTGGCGATAAGTCGTGTCTTACCGGGTTGGACTCAAGA

CGATAGTTACCGGATAAGGCGCAGCGGTCGGGCTGAACGGGGGGT

TCGTGCACACAGCCCAGCTTGGAGCGAACGACCTACACCGAACTG

AGATACCTACAGCGTGAGCTATGAGAAAGCGCCACGCTTCCCGAA

GGGAGAAAGGCGGACAGGTATCCGGTAAGCGGCAGGGTCGGAACA

GGAGAGCGCACGAGGGAGCTTCCAGGGGGAAACGCCTGGTATCTT

TATAGTCCTGTCGGGTTTCGCCACCTCTGACTTGAGCGTCGATTT

TTGTGATGCTCGTCAGGGGGCGGAGCCTATGGAAAAACGCCAGC

AACGCGGCCTTTTTACGGTTCCTGGCCTTTTGCTGGCCTTTTGCT

CACATGT pGW114-pAAV_EFS-LTR-Cd80-T2A-Light-
P2A-41BBL-E2A-IFNg-WPRE (SEQ ID NO: 44)
CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccatggcttgcaattgtcagttgatgcaggatac accactcctcaagtttccatgtccaaggctcattcttctctttgt gctgctgattcgtctttcacaagtgtcttcagatgttgatgaaca actgtccaagtcagtgaaagataaggtattgctgccttgccgtta caactctcctcatgaagatgagtctgaagaccgaatctactggca aaaacatgacaaagtggtgctgtctgtcattgctgggaaactaaa agtgtggcccgagtataagaaccggactttatatgacaacactac ctactctcttatcatcctgggcctggtcctttcagaccggggcac atacagctgtgtcgttcaaaagaaggaaagaggaacgtatgaagt -continued taaacacttggctttagtaaagttgtccatcaaagctgacttctc tacccccaacataactgagtctggaaacccatctgcagacactaa aaggattacctgctttgcttccgggggtttcccaaagcctcgctt ctcttggttggaaaatggaagagaattacctggcatcaatacgac aatttcccaggatcctgaatctgaattgtacaccattagtagcca actagatttcaatacgactcgcaaccacaccattaagtgtctcat taaatatggagatgctcacgtgtcagaggacttcacctgggaaaa accccccagaagaccctcctgatagcaagaacacacttgtgctctt tggggcaggattcggcgcagtaataacagtcgtcgtcatcgttgt catcatcaaatgcttctgtaagcacagaagctgtttcagaagaaa tgaggcaagcagagaaacaaacaacagccttaccttcgggcctga agaagcattagctgaacagaccgtcttccttcgtacgGGCAGTGG

AGAGGGCAGAGGAAGTCTGCTAACATGCGGTGACGTCGAGGAGAA

TCCTGGCCCAatggagagtgtggtacagccttcagtgtttgtggt ggatggacagacggacatcccattcaggcggctggaacagaacca ccggagacggcgctgtggcactgtccaggtcagcctggccctggt gctgctgctaAgtgctgggctggccactcagggctggtttctcct gagactgcatcaacgtcttggagacatagtagctcatctgccaga tggaggcaaaggctcctgggagaagctgatacaagatcaacgatc tcaccaggccaacccagcagcacatcttacaggagccaacgccag cttgataggtattggtggacctctgttatggggagacacgacttgg cctggccttcttgaggggcttgacgtatcatgatggggccctggt gaccatggagcccggttactactatgtgtactccaaagtgcagct gagcggcgtgggctgcccccaggggctggccaatggcctccccat cacccatggactatacaagcgcacatcccgctacccgaaggagtt agaactgctggtcagtcggcggtcaccctgtggccgggccaacag ctcccgagtctggtgggacagcagcttcctgggcggcgtggtaca tctggaggctggggaagaggtggtggtccgcgtgcctggaaaccg cctggtcagaccacgtgacggcaccaggtcctatttcggagctttt catggtcactagtGGATCCGGCGCAACAAACTTCTCTCTGCTGAA ACAAGCCGGAGATGTCGAAGAGAATCCTGGACCGatggaccagca cacacttgatgtggaggataccgcggatgccagacatccagcagg tacttcgtgcccctcggatgcggcgctcctcagagataccgggct cctcgcggacgctgcgctcctctcagatactgtgcgccccacaaa tgccgcgctccccacggatgctgcctaccctgcggttaatgttcg ggatcgcgaggccgcgtggccgcctgcactgaacttctgttcccg ccacccaaagctctatggcctagtcgctttggttttgctgcttct gatcgccgcctgtgttcctatcttcaccgcaccgagcctcggcc agcgctcacaatcaccacctcgcccaacctgggtacccgagagaa taatgcagaccaggtcaccctgtttcccacattggctgccccaa cactacacaacagggctctcctgtgttcgccaagctactggctaa

```
aaaccaagcatcgttgtgcaatacaactctgaactggcacagcca agatggagctgggagctcatacctatctcaaggtctgaggtacga agaagacaaaaaggagttggtggtagacagtcccgggctctacta cgtattttggaactgaagctcagtccaacattcacaaacacagg ccacaaggtgcagggctgggtctctcttgttttgcaagcaaagcc tcaggtagatgactttgacaacttggccctgacagtggaactgtt cccttgctccatggagaacaagttagtggaccgttcctggagtca actgttgctcctgaaggctggccaccgcctcagtgtgggtctgag ggcttatctgcatggagcccaggatgcatacagagactgggagct gtcttatcccaacaccaccagctttggactctttcttgtgaaacc cgacaacccatgggaaagcggtacccagtgcaccaactacgccct gctgaagctggccggcgatgtggagagcaaccccgggccgctag catgaacgctacacactgcatcttggctttgcagctcttcctcat ggctgtttctggctgttactgccacggcacagtcattgaaagcct agaaagtctgaataactattttaactcaagtggcatagatgtgga agaaaagagtctcttcttggatatctggaggaactggcaaaagga tggtgacatgaaaatcctgcagagccagattatctctttctacct cagactctttgaagtcttgaaagacaatcaggccatcagcaacaa cataagcgtcattgaatcacacctgattactaccttcttcagcaa cagcaaggcgaaaaaggatgcattcatgagtattgccaagtttga ggtcaacaacccacaggtgcagcgccaagcattcaatgagctcat ccgagtggtccaccagctgttgccggaatccagcctcaggaagcg gaaaaggagtcgctgctgaGaattcacgcgttaagtcgacaatca acctctggattacaaaatttgtgaaagattgactggtattcttaa ctatgttgctcctttttacgctatgtggatacgctgctttaatgcc tttgtatcatgctattgcttcccgtatggctttcattttctcctc cttgtataaatcctggttgctgtctctttatgaggagttgtggcc cgttgtcaggcaacgtggcgtggtgtgcactgtgtttgctgacgc aacccccactggttggggcattgccaccacctgtcagctcctttc cgggactttcgctttccccctccctattgccacggcggaactcat cgccgcctgccttgcccgctgctggacaggggctcggctgttggg cactgacaattccgtggtgttgtcggggaaatcatcgtcctttcc ttggctgctcgcctgtgttgccacctggattctgcgcgggacgtc cttctgctacgtcccttcggccctcaatccagcggaccttccttc ccgcggcctgctgccggctctgcgggcctcttccgcgtcttcgcct tcgccctcagacgagtcggatctccctttgggccgcctccccgcg tcgactttaagaccaatgacGGCCGCAGGAACCCCTAGTGATGGA

GTTGGCCACTCCCTCTCTGCGCGCTCGCTCGCTCACTGAGGCCGG

GCGACCAAAGGTCGCCCGACGCCCGGGCTTTGCCCGGGCGGCCTC

AGTGAGCGAGCGAGCGCGCAGCTGCCTGCAGGGGCGCCTGATGCG
```

```
GTATTTTCTCCTTACGCATCTGTGCGGTATTTCACACCGCATACG

TCAAAGCAACCATAGTACGCGCCCTGTAGCGGCGCATTAAGCGCG

GCGGGTGTGGTGGTTACGCGCAGCGTGACCGCTACACTTGCCAGC

GCCTTAGCGCCCGCTCCTTTCGCTTTCTTCCCTTCCTTTCTCGCC

ACGTTCGCCGGCTTTCCCCGTCAAGCTCTAAATCGGGGGCTCCCT

TTAGGGTTCCGATTTAGTGCTTTACGGCACCTCGACCCCAAAAAA

CTTGATTTGGGTGATGGTTCACGTAGTGGGCCATCGCCCTGATAG

ACGGTTTTTCGCCCTTTGACGTTGGAGTCCACGTTCTTTAATAGT

GGACTCTTGTTCCAAACTGGAACAACACTCAACTCTATCTCGGGC

TATTCTTTTGATTTATAAGGGATTTTGCCGATTTCGGTCTATTGG

TTAAAAAATGAGCTGATTTAACAAAAATTTAACGCGAATTTTAAC

AAAATATTAACGTTTACAATTTTATGGTGCACTCTCAGTACAATC

TGCTCTGATGCCGCATAGTTAAGCCAGCCCCGACACCCGCCAACA

CCCGCTGACGCGCCCTGACGGGCTTGTCTGCTCCCGGCATCCGCT

TACAGACAAGCTGTGACCGTCTCCGGGAGCTGCATGTGTCAGAGG

TTTTCACCGTCATCACCGAAACGCGCGAGACGAAAGGGCCTCGTG

ATACGCCTATTTTTATAGGTTAATGTCATGATAATAATGGTTTCT

TAGACGTCAGGTGGCACTTTTCGGGGAAATGTGCGCGGAACCCCT

ATTTGTTTATTTTTCTAAATACATTCAAATATGTATCCGCTCATG

AGACAATAACCCTGATAAATGCTTCAATAATATTGAAAAAGGAAG

AGTATGAGTATTCAACATTTCCGTGTCGCCCTTATTCCCTTTTTT

GCGGCATTTTGCCTTCCTGTTTTTGCTCACCCAGAAACGCTGGTG

AAAGTAAAAGATGCTGAAGATCAGTTGGGTGCACGAGTGGGTTAC

ATCGAACTGGATCTCAACAGCGGTAAGATCCTTGAGAGTTTTCGC

CCCGAAGAACGTTTTCCAATGATGAGCACTTTTAAAGTTCTGCTA

TGTGGCGCGGTATTATCCCGTATTGACGCCGGGCAAGAGCAACTC

GGTCGCCGCATACACTATTCTCAGAATGACTTGGTTGAGTACTCA

CCAGTCACAGAAAAGCATCTTACGGATGGCATGACAGTAAGAGAA

TTATGCAGTGCTGCCATAACCATGAGTGATAACACTGCGGCCAAC

TTACTTCTGACAACGATCGGAGGACCGAAGGAGCTAACCGCTTTT

TTGCACAACATGGGGGATCATGTAACTCGCCTTGATCGTTGGGAA

CCGGAGCTGAATGAAGCCATACCAAACGACGAGCGTGACACCACG

ATGCCTGTAGCAATGGCAACAACGTTGCGCAAACTATTAACTGGC

GAACTACTTACTCTAGCTTCCCGGCAACAATTAATAGACTGGATG

GAGGCGGATAAAGTTGCAGGACCACTTCTGCGCTCGGCCCTTCCG

GCTGGCTGGTTTATTGCTGATAAATCTGGAGCCGGTGAGCGTGGA

AGCCGCGGTATCATTGCAGCACTGGGGCCAGATGGTAAGCCCTCC

CGTATCGTAGTTATCTACACGACGGGGAGTCAGGCAACTATGGAT

GAACGAAATAGACAGATCGCTGAGATAGGTGCCTCACTGATTAAG

CATTGGTAACTGTCAGACCAAGTTTACTCATATATACTTTAGATT

GATTTAAAACTTCATTTTTAATTTAAAAGGATCTAGGTGAAGATC
```

-continued

CTTTTTGATAATCTCATGACCAAAATCCCTTAACGTGAGTTTTCG

TTCCACTGAGCGTCAGACCCCGTAGAAAAGATCAAAGGATCTTCT

TGAGATCCTTTTTTTCTGCGCGTAATCTGCTGCTTGCAAACAAAA

AAACCACCGCTACCAGCGGTGGTTTGTTTGCCGGATCAAGAGCTA

CCAACTCTTTTTCCGAAGGTAACTGGCTTCAGCAGAGCGCAGATA

CCAAATACTGTTCTTCTAGTGTAGCCGTAGTTAGGCCACCACTTC

AAGAACTCTGTAGCACCGCCTACATACCTCGCTCTGCTAATCCTG

TTACCAGTGGCTGCTGCCAGTGGCGATAAGTCGTGTCTTACCGGG

TTGGACTCAAGACGATAGTTACCGGATAAGGCGCAGCGGTCGGGC

TGAACGGGGGGTTCGTGCACACAGCCCAGCTTGGAGCGAACGACC

TACACCGAACTGAGATACCTACAGCGTGAGCTATGAGAAAGCGCC

ACGCTTCCCGAAGGGAGAAAGGCGGACAGGTATCCGGTAAGCGGC

AGGGTCGGAACAGGAGAGCGCACGAGGGAGCTTCCAGGGGGAAAC

GCCTGGTATCTTTATAGTCCTGTCGGGTTTCGCCACCTCTGACTT

GAGCGTCGATTTTTGTGATGCTCGTCAGGGGGCGGAGCCTATGG

AAAAACGCCAGCAACGCGGCCTTTTTACGGTTCCTGGCCTTTTGC

TGGCCTTTTGCTCACATGT pGW115-pAAV_EFS-LTR-IL23-T2A-Light-P2A-
41BBL-E2A-IFNg-WPRE (SEQ ID NO: 45)
CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccATGTGTCCTCAGAAGCTAACCATCTCCTGGTT

TGCCATCGTTTTGCTGGTGTCTCCACTCATGGCCATGTGGGAGCT

GGAGAAAGACGTTTATGTTGTAGAGGTGGACTGGACTCCCGATGC

CCCTGGAGAAACAGTGAACCTCACCTGTGACACGCCTGAAGAAGA

TGACATCACCTGGACCTCAGACCAGAGACATGGAGTCATAGGCTC

TGGAAAGACCCTGACCATCACTGTCAAAGAGTTTCTAGATGCTGG

CCAGTACACCTGCCACAAAGGAGGCGAGACTCTGAGCCACTCACA

-continued

TCTGCTGCTCCACAAGAAGGAAAATGGAATTTGGTCCACTGAAAT

TTTAAAAAATTTCAAAAACAAGACTTTCCTGAAGTGTGAAGCACC

AAATTACTCCGGACGGTTCACGTGCTCATGGCTGGTGCAAAGAAA

CATGGACTTGAAGTTCAACATCAAGAGCAGTAGCAGTTCCCCTGA

CTCTCGGGCAGTGACATGTGGAATGGCGTCTCTGTCTGCAGAGAA

GGTCACACTGGACCAAAGGGACTATGAGAAGTATTCAGTGTCCTG

CCAGGAGGATGTCACCTGCCCAACTGCCGAGGAGACCCTGCCCAT

TGAACTGGCGTTGGAAGCACGGCAGCAGAATAAATATGAGAACTA

CAGCACCAGCTTCTTCATCAGGGACATCATCAAACCAGACCCGCC

CAAGAACTTGCAGATGAAGCCTTTGAAGAACTCACAGGTGGAGGT

CAGCTGGGAGTACCCTGACTCCTGGAGCACTCCCCATTCCTACTT

CTCCCTCAAGTTCTTTGTTCGAATCCAGCGCAAGAAAGAAAAGAT

GAAGGAGACAGAGGAGGGGTGTAACCAGAAAGGTGCGTTCCTCGT

AGAGAAGACATCTACCGAAGTCCAATGCAAAGGCGGGAATGTCTG

CGTGCAAGCTCAGGATCGCTATTACAATTCCTCATGCAGCAAGTG

GGCATGTGTTCCCTGCAGGGTCCGATCCGGCAGTGGAGAGGGCAG

AGGAAGTCTGCTAACATGCGGTGACGTCGAGGAGAATCCTGGCCC

Aatggagagtgtggtacagccttcagtgtttgtggtggatggaca gacggacatcccattcaggcggctggaacagaaccaccggagacg gcgctgtggcactgtccaggtcagcctggccctggtgctgctgct aAgtgctgggctggccactcagggctggtttctcctgagactgca tcaacgtcttggagacatagtagctcatctgccagatggaggcaa aggctcctgggagaagctgatacaagatcaacgatctcaccaggc caacccagcagcacatcttacaggagccaacgccagcttgatagg tattggtggacctctgttatgggagacacgacttggcctggcctt cttgaggggcttgacgtatcatgatggggccctggtgaccatgga gcccggttactactatgtgtactccaaagtgcagctgagcggcgt gggctgccccagggggctggccaatggcctccccatcacccatgg actatacaagcgcacatcccgctacccgaaggagttagaactgct ggtcagtcggcggtcaccctgtggccgggccaacagctcccgagt ctggtgggacagcagcttcctgggcggcgtggtacatctggaggc tggggaagaggtggtggtccgcgtgcctggaaaccgcctggtcag accacgtgacggcaccaggtcctatttcggagctttcatggtcac tagtGGATCCGGCGCAACAAACTTCTCTCTGCTGAAACAAGCCGG AGATGTCGAAGAGAATCCTGGACCGatggaccagcacacacttga tgtggaggataccgcggatgccagacatccagcaggtacttcgtg cccctcggatgcgcgctcctcagagataccgggctcctcgcgga cgctgcgctcctctcagatactgtgcgccccacaaatgccgcgct ccccacggatgctgcctaccctgcggttaatgttcgggatcgcga ggccgcgtggccgcctgcactgaacttctgttcccgccacccaaa

203

```
gctctatggcctagtcgctttggttttgctgcttctgatcgccgc ctgtgttcctatcttcacccgcaccgagcctcggccagcgctcac aatcaccacctcgcccaacctgggtacccgagagaataatgcaga ccaggtcacccctgtttcccacattggctgccccaacactacaca acagggctctcctgtgttcgccaagctactggctaaaaaccaagc atcgttgtgcaatacaactctgaactggcacagccaagatggagc tgggagctcatacctatctcaaggtctgaggtacgaagaagacaa aaaggagttggtggtagacagtcccgggctctactacgtattttt ggaactgaagctcagtccaacattcacaaacacaggccacaaggt gcagggctgggtctctcttgttttgcaagcaaagcctcaggtaga tgactttgacaacttggccctgacagtggaactgttccttgctc catggagaacaagttagtggaccgttcctggagtcaactgttgct cctgaaggctggccaccgcctcagtgtgggtctgagggcttatct gcatggagcccaggatgcatacagagactgggagctgtcttatcc caacaccaccagctttggactctttcttgtgaaacccgacaaccc atgggaaagcggtacccagtgcaccaactacgccctgctgaagct ggccggcgatgtggagagcaaccccgggcccgctagcatgaacgc tacacactgcatcttggctttgcagctcttcctcatggctgtttc tggctgttactgccacggcacagtcattgaaagcctagaaagtct gaataactattttaactcaagtggcatagatgtggaagaaaagag tctcttcttggatatctggaggaactggcaaaaggatggtgacat gaaaatcctgcagagccagattatctctttctacctcagactctt tgaagtcttgaaagacaatcaggccatcagcaacaacataagcgt cattgaatcacacctgattactaccttcttcagcaacagcaaggc gaaaaaggatgcattcatgagtattgccaagtttgaggtcaacaa cccacaggtccagcgccaagcattcaatgagctcatccgagtggt ccaccagctgttgccggaatccagcctcaggaagcggaaaaggag tcgctgctgaGaattcacgcgttaagtcgacaatcaacctctgga ttacaaaatttgtgaaagattgactggtattcttaactatgttgc tccttttacgctatgtggatacgctgctttaatgcctttgtatca tgctattgcttcccgtatggctttcattttctcctccttgtataa atcctggttgctgtctctttatgaggagttgtggcccgttgtcag gcaacgtggcgtggtgtgcactgtgtttgctgacgcaaccccac tggttggggcattgccaccacctgtcagctcctttccgggacttt cgctttcccctccctattgccacggcggaactcatcgccgcctg ccttgcccgctgctggacaggggctcggctgttgggcactgacaa ttccgtggtgttgtcggggaaatcatcgtcctttccttggctgct cgcctgtgttgccacctggattctgcgcgggacgtccttctgcta cgtcccttcggccctcaatccagcggaccttccttcccgcggcct gctgccggctctgcggcctcttccgcgtcttcgccttcgccctca gacgagtcggatctccctttgggccgcctccccgcgtcgactttta
```

204

```
      agaccaatgacGGCCGCAGGAACCCCTAGTGATGGAGTTGGCCAC

TCCCTCTCTGCGCGCTCGCTCGCTCACTGAGGCCGGGCGACCAAA

5    GGTCGCCCGACGCCCGGGCTTTGCCCGGGCGGCCTCAGTGAGCGA

GCGAGCGCGCAGCTGCCTGCAGGGGCGCCTGATGCGGTATTTTCT

CCTTACGCATCTGTGCGGTATTTCACACCGCATACGTCAAAGCAA

10    CCATAGTACGCGCCCTGTAGCGGCGCATTAAGCGCGGCGGGTGTG

GTGGTTACGCGCAGCGTGACCGCTACACTTGCCAGCGCCTTAGCG

CCCGCTCCTTTCGCTTTCTTCCCTTCCTTTCTCGCCACGTTCGCC

15    GGCTTTCCCCGTCAAGCTCTAAATCGGGGGCTCCCTTTAGGGTTC

CGATTTAGTGCTTTACGGCACCTCGACCCCAAAAAACTTGATTTG

GGTGATGGTTCACGTAGTGGGCCATCGCCCTGATAGACGGTTTTT

20    CGCCCTTTGACGTTGGAGTCCACGTTCTTTAATAGTGGACTCTTG

TTCCAAACTGGAACAACACTCAACTCTATCTCGGGCTATTCTTTT

GATTTATAAGGGATTTTGCCGATTTCGGTCTATTGGTTAAAAAAT

25    GAGCTGATTTAACAAAAATTTAACGCGAATTTTAACAAAATATTA

ACGTTTACAATTTTATGGTGCACTCTCAGTACAATCTGCTCTGAT

GCCGCATAGTTAAGCCAGCCCCGACACCCGCCAACACCCGCTGAC

30    GCGCCCTGACGGGCTTGTCTGCTCCCGGCATCCGCTTACAGACAA

GCTGTGACCGTCTCCGGGAGCTGCATGTGTCAGAGGTTTTCACCG

TCATCACCGAAACGCGCGAGACGAAAGGGCCTCGTGATACGCCTA

35    TTTTTATAGGTTAATGTCATGATAATAATGGTTTCTTAGACGTCA

GGTGGCACTTTTCGGGGAAATGTGCGCGGAACCCCTATTTGTTTA

TTTTTCTAAATACATTCAAATATGTATCCGCTCATGAGACAATAA

40    CCCTGATAAATGCTTCAATAATATTGAAAAAGGAAGAGTATGAGT

ATTCAACATTTCCGTGTCGCCCTTATTCCCTTTTTTGCGGCATTT

TGCCTTCCTGTTTTTGCTCACCCAGAAACGCTGGTGAAAGTAAAA

GATGCTGAAGATCAGTTGGGTGCACGAGTGGGTTACATCGAACTG

45    GATCTCAACAGCGGTAAGATCCTTGAGAGTTTTCGCCCCGAAGAA

CGTTTTCCAATGATGAGCACTTTTAAAGTTCTGCTATGTGGCGCG

GTATTATCCCGTATTGACGCCGGGCAAGAGCAACTCGGTCGCCGC

50    ATACACTATTCTCAGAATGACTTGGTTGAGTACTCACCAGTCACA

GAAAAGCATCTTACGGATGGCATGACAGTAAGAGAATTATGCAGT

GCTGCCATAACCATGAGTGATAACACTGCGGCCAACTTACTTCTG

55    ACAACGATCGGAGGACCGAAGGAGCTAACCGCTTTTTTGCACAAC

ATGGGGGATCATGTAACTCGCCTTGATCGTTGGGAACCGGAGCTG

AATGAAGCCATACCAAACGACGAGCGTGACACCACGATGCCTGTA

60    GCAATGGCAACAACGTTGCGCAAACTATTAACTGGCGAACTACTT

ACTCTAGCTTCCCGGCAACAATTAATAGACTGGATGGAGGCGGAT

AAAGTTGCAGGACCACTTCTGCGCTCGGCCCTTCCGGCTGGCTGG

65    TTTATTGCTGATAAATCTGGAGCCGGTGAGCGTGGAAGCCGCGGT
```

```
ATCATTGCAGCACTGGGGCCAGATGGTAAGCCCTCCCGTATCGTA

GTTATCTACACGACGGGGAGTCAGGCAACTATGGATGAACGAAAT

AGACAGATCGCTGAGATAGGTGCCTCACTGATTAAGCATTGGTAA

CTGTCAGACCAAGTTTACTCATATATACTTTAGATTGATTTAAAA

CTTCATTTTTAATTTAAAAGGATCTAGGTGAAGATCCTTTTTGAT

AATCTCATGACCAAAATCCCTTAACGTGAGTTTTCGTTCCACTGA

GCGTCAGACCCCGTAGAAAAGATCAAAGGATCTTCTTGAGATCCT

TTTTTTCTGCGCGTAATCTGCTGCTTGCAAACAAAAAAACCACCG

CTACCAGCGGTGGTTTGTTTGCCGGATCAAGAGCTACCAACTCTT

TTTCCGAAGGTAACTGGCTTCAGCAGAGCGCAGATACCAAATACT

GTTCTTCTAGTGTAGCCGTAGTTAGGCCACCACTTCAAGAACTCT

GTAGCACCGCCTACATACCTCGCTCTGCTAATCCTGTTACCAGTG

GCTGCTGCCAGTGGCGATAAGTCGTGTCTTACCGGGTTGGACTCA

AGACGATAGTTACCGGATAAGGCGCAGCGGTCGGGCTGAACGGGG

GGTTCGTGCACACAGCCCAGCTTGGAGCGAACGACCTACACCGAA

CTGAGATACCTACAGCGTGAGCTATGAGAAAGCGCCACGCTTCCC

GAAGGGAGAAAGGCGGACAGGTATCCGGTAAGCGGCAGGGTCGGA

ACAGGAGAGCGCACGAGGGAGCTTCCAGGGGGAAACGCCTGGTAT

CTTTATAGTCCTGTCGGGTTTCGCCACCTCTGACTTGAGCGTCGA

TTTTTGTGATGCTCGTCAGGGGGGCGGAGCCTATGGAAAAACGCC

AGCAACGCGGCCTTTTTACGGTTCCTGGCCTTTTGCTGGCCTTTT

GCTCACATGT
``` pGW118-pAAV_EFSLTR-Ifng-P2A-Cd80-T2A-light-
E2A-41BBL-sPA
(SEQ ID NO: 46)
```
CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccatgaacgctacacactgcatcttggctttgca gctcttcctcatggctgtttctggctgttactgccacggcacagt
```

```
cattgaaagcctagaaagtctgaataactattttaactcaagtgg catagatgtggaagaaaagagtctcttcttggatatctggaggaa ctggcaaaaggatggtgacatgaaaatcctgcagagccagattat ctctttctacctcagactctttgaagtcttgaaagacaatcaggc catcagcaacaacataagcgtcattgaatcacacctgattactac cttcttcagcaacagcaaggcgaaaaaggatgcattcatgagtat tgccaagtttgaggtcaacaacccacaggtccagcgccaagcatt caatgagctcatccgagtggtccaccagctgttgccggaatccag cctcaggaagcggaaaaggagtcgctgcGGATCCGGCGCAACAAA

CTTCTCTCTGCTGAAACAAGCCGGAGATGTCGAAGAGAATCCTGG

ACCGatggcttgcaattgtcagttgatgcaggatacaccactcct caagtttccatgtccaaggctcattcttctctttgtgctgctgat tcgtctttcacaagtgtcttcagatgttgatgaacaactgtccaa gtcagtgaaagataaggtattgctgccttgccgttacaactctcc tcatgaagatgagtctgaagaccgaatctactggcaaaaacatga caaagtggtgctgtctgtcattgTtgggaaactaaaagtgtggcc cgagtataagaaccggactttatatgacaacactacctactctct tatcatcctgggcctggtcctttcagaccggggcacatacagctg tgtcgttcaaaagaaggaaagaggaacgtatgaagttaaacactt ggctttagtaaagttgtccatcaaagctgacttctctacccccaa cataactgagtctggaaacccatctgcagacactaaaaggattac ctgctttgcttccggggggtttcccaaagcctcgcttctcttggtt ggaaaatggaagagaattacctggcatcaatacgacaatttccca ggatcctgaatctgaattgtacaccattagtagccaactagattt caatacgactcgcaaccacaccattaagtgtctcattaaatatgg agatgctcacgtgtcagaggacttcacctgggaaaaaccccccaga agacctcctgatagcaagaacacacttgtgctctttggggcagg attcggcgcagtaataacagtcgtcgtcatcgttgtcatcatcaa atgcttctgtaagcacagaagctgtttcagaagaaatgaggcaag cagagaaacaaacaacagccttaccttcgggcctgaagaagcatt agctgaacagaccgtcttccttcgtacgGGCAGTGGAGAGGGCAG

AGGAAGTCTGCTAACATGCGGTGACGTCGAGGAGAATCCTGGCCC

Aatggagagtgtggtacagccttcagtgtttgtggtggatggaca gacggacatcccattcaggcggctggaacagaaccaccggagacg gcgctgtggcactgtccaggtcagcctggccctggtgctgctgct aggtgctgggctggccactcagggctggtttctcctgagactgca tcaacgtcttggagacatagtagctcatctgccagatggaggcaa aggctcctgggagaagctgatacaagatcaacgatctcaccaggc caacccagcagcacatcttacaggagccaacgccagcttgatagg tattggtggacctctgttatgggagacacgacttggcctggcctt cttgagggggcttgacgtatcatgatggggccctggtgaccatgga
```

-continued

```
gcccggttactactatgtgtactccaaagtgcagctgagcggcgt gggctgcccccaggggctggccaatggcctccccatcacccatgg actatacaagcgcacatcccgctacccgaaggagttagaactgct ggtcagtcggcggtcaccctgtggccgggccaacagctcccgagt ctggtgggacagcagcttcctgggcggcgtggtacatctggaggc tggggaagaggtggtggtccgcgtgcctggaaaccgcctggtcag accacgtgacggcaccaggtcctatttcggagctttcatggtcac tagcagcggtacccagtgcaccaactacgccctgctgaagctggc cggcgatgtggagagcaaccccgggcccatggaccagcacacact tgatgtggaggataccgcggatgccagacatccagcaggtacttc gtgcccctcggatgcggcgctcctcagagataccgggctcctcgc ggacgctgcgctcctctcagatactgtgcgccccacaaatgccgc gctccccacggatgctgcctaccctgcggttaatgttcgggatcg cgaggccgcgtggccgcctgcactgaacttctgttcccgccaccc aaagctctatggcctagtcgctttggttttgctgcttctgatcgc cgcctgtgttcctatcttcacccgcaccgagcctcggccagcgct cacaatcaccacctcgcccaacctgggtacccgagagaataatgc agaccaggtcacccctgtttcccacattggctgccccaacactac acaacagggctctcctgtgttcgccaagctactggctaaaaacca agcatcgttgtgcaatacaactctgaactggcacagccaagatgg agctgggagctcatacctatctcaaggtctgaggtacgaagaaga caaaaaggagttggtggtagacagtcccgggctctactacgtatt tttggaactgaagctcagtccaacattcacaaacacaggccacaa ggtgcagggctgggtctctcttgttttgcaagcaaagcctcaggt agatgactttgacaacttggccctgacagtggaactgttcccttg ctccatggagaacaagttagtggaccgttcctggagtcaactgtt gctcctgaaggctggccaccgcctcagtgtgggtctgagggctta tctgcatggagcccaggatgcatacagagactgggagctgtctta tcccaacaccaccagctttggactctttcttgtgaaacccgacaa cccatgggaatgaGAATTCAATAAAAGATCTTTATTTTCATTAGA

TCTGTGTGTTGGTTTTTTGTGTGCGGCCGCAGGAACCCCTAGTGA

TGGAGTTGGCCACTCCCTCTCTGCGCGCTCGCTCGCTCACTGAGG

CCGGGCGACCAAAGGTCGCCCGACGCCCGGGCTTTGCCCGGGCGG

CCTCAGTGAGCGAGCGAGCGCGCAGCTGCCTGCAGGGGCGCCTGA

TGCGgtattttctccttacgcatctgtgcggtatttcacaccgca tacgtcaaagcaACCATAGTACGCGCCCTGTAGCGGCGCATTAAG

CGCGGCGGGTGTGGTGGTTACGCGCAGCGTGACCGCTACACTTGC

CAGCGCCTTAGCGCCCGCTCCTTTCGCTTTCTTCCCTTCCTTTCT

CGCCACGTTCGCCGGCTTTCCCCGTCAAGCTCTAAATCGGGGGCT

CCCTTTAGGGTTCCGATTTAGTGCTTTACGGCACCTCGACCCCAA
```

-continued

```
AAAACTTGATTTGGGTGATGGTTCACGTAGTGGGCCATCGCCCTG

ATAGACGGTTTTTCGCCCTTTGACGTTGGAGTCCACGTTCTTTAA

TAGTGGACTCTTGTTCCAAACTGGAACAACACTCAACTCTATCTC

GGGCTATTCTTTTGATTTATAAGGGATTTTGCCGATTTCGGTCTA

TTGGTTAAAAAATGAGCTGATTTAACAAAAATTTAACGCGAATTT

TAACAAAATATTAACGTTTACAATTTTATGGTGCACTCTCAGTAC

AATCTGCTCTGATGCCGCATAGTTAAGCCAGCCCCGACACCCGCC

AACACCCGCTGACGCGCCCTGACGGGCTTGTCTGCTCCCGGCATC

CGCTTACAGACAAGCTGTGACCGTCTCCGGGAGCTGCATGTGTCA

GAGGTTTTCACCGTCATCACCGAAACGCGCGAGACGAAAGGGCCT

CGTGATACGCCTATTTTTATAGGTTAATGTCATGATAATAATGGT

TTCTTAGACGTCAGGTGGCACTTTTCGGGGAAATGTGCGCGGAAC

CCCTATTTGTTTATTTTTCTAAATACATTCAAATATGTATCCGCT

CATGAGACAATAACCCTGATAAATGCTTCAATAATATTGAAAAAG

GAAGAGTATGAGTATTCAACATTTCCGTGTCGCCCTTATTCCCTT

TTTTGCGGCATTTTGCCTTCCTGTTTTTGCTCACCCAGAAACGCT

GGTGAAAGTAAAAGATGCTGAAGATCAGTTGGGTGCACGAGTGGG

TTACATCGAACTGGATCTCAACAGCGGTAAGATCCTTGAGAGTTTT

TCGCCCCGAAGAACGTTTTCCAATGATGAGCACTTTTAAAGTTCT

GCTATGTGGCGCGGTATTATCCCGTATTGACGCCGGGCAAGAGCA

ACTCGGTCGCCGCATACACTATTCTCAGAATGACTTGGTTGAGTA

CTCACCAGTCACAGAAAAGCATCTTACGGATGGCATGACAGTAAG

AGAATTATGCAGTGCTGCCATAACCATGAGTGATAACACTGCGGC

CAACTTACTTCTGACAACGATCGGAGGACCGAAGGAGCTAACCGC

TTTTTTGCACAACATGGGGGATCATGTAACTCGCCTTGATCGTTG

GGAACCGGAGCTGAATGAAGCCATACCAAACGACGAGCGTGACAC

CACGATGCCTGTAGCAATGGCAACAACGTTGCGCAAACTATTAAC

TGGCGAACTACTTACTCTAGCTTCCCGGCAACAATTAATAGACTG

GATGGAGGCGGATAAAGTTGCAGGACCACTTCTGCGCTCGGCCCT

TCCGGCTGGCTGGTTTATTGCTGATAAATCTGGAGCCGGTGAGCG

TGGAAGCCGCGGTATCATTGCAGCACTGGGGCCAGATGGTAAGCC

CTCCCGTATCGTAGTTATCTACACGACGGGGAGTCAGGCAACTAT

GGATGAACGAAATAGACAGATCGCTGAGATAGGTGCCTCACTGAT

TAAGCATTGGTAACTGTCAGACCAAGTTTACTCATATATACTTTA

GATTGATTTAAAACTTCATTTTTAATTTAAAAGGATCTAGGTGAA

GATCcttttttgataatctcatgaccaaaatcccttaacgtgagtt ttcgttccactgaGCGTCAGACCCCGTAGAAAAGATCAAAGGATC

TTCTTGAGATCCTTTTTTTCTGCGCGTAATCTGCTGCTTGCAAAC

AAAAAAACCACCGCTACCAGCGGTGGTTTGTTTGCCGGATCAAGA

GCTACCAACTCTTTTTCCGAAGGTAACTGGCTTCAGCAGAGCGCA

GATACCAAATACTGTTCTTCTAGTGTAGCCGTAGTTAGGCCACCA
```

CTTCAAGAACTCTGTAGCACCGCCTACATACCTCGCTCTGCTAAT

CCTGTTACCAGTGGCTGCTGCCAGTGGCGATAAGTCGTGTCTTAC

CGGGTTGGACTCAAGACGATAGTTACCGGATAAGGCGCAGCGGTC

GGGCTGAACGGGGGGTTCGTGCACACAGCCCAGCTTGGAGCGAAC

GACCTACACCGAACTGAGATACCTACAGCGTGAGCTATGAGAAAG

CGCCACGCTTCCCGAAGGGAGAAAGGCGGACAGGTATCCGGTAAG

CGGCAGGGTCGGAACAGGAGAGCGCACGAGGGAGCTTCCAGGGGG

AAACGCCTGGTATCTTTATAGTCCTGTCGGGTTTCGCCACCTCTG

ACTTGAGCGTCGATTTTTGTGATGCTCGTCAGGGGGGCGGAGCCT

ATGGAAAAACGCCAGCAACGCGGCCTTTTTACGGTTCCTGGCCTT

TTGCTGGCCTTTTGCTCACATGT pGW119-pAAV_EFSLTR-Ifng-STOP-P2A-Cd80-T2A-light-
P2A-E2A-41BBL-sPA (SEQ ID NO: 47)
CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccatgaacgctacacactgcatcttggctttgca gctcttcctcatggctgtttctggctgttactgccacggcacagt cattgaaagcctagaaagtctgaataactattttaactcaagtgg catagatgtggaagaaaagagtctcttcttggatatctggaggaa ctggcaaaaggatggtgacatgaaaatcctgcagagccagattat ctctttctacctcagactctttgaagtcttgaaagacaatcaggc catcagcaacaacataagcgtcattgaatcacacctgattactac cttcttcagcaacagcaaggcgaaaaaggatgcattcatgagtat tgccaagtttgaggtcaacaacccacaggtccagcgccaagcatt caatgagctcatccgagtggtccaccagctgttgccggaatccag cctcaggaagcggaaaaggagtcgctgcTGAATCCGGCGCAACAA

ACTTCTCTCTGCTGAAACAAGCCGGAGATGTCGAAGAGAATCCTG

GACCGatggcttgcaattgtcagttgatgcaggatacaccactcc tcaagtttccatgtccaaggctcattcttctctttgtgctgctga ttcgtctttcacaagtgtcttcagatgttgatgaacaactgtcca agtcagtgaaagataaggtattgctgccttgccgttacaactctc ctcatgaagatgagtctgaagaccgaatctactggcaaaaacatg acaaagtggtgctgtctgtcattgTtgggaaactaaaagtgtggc ccgagtataagaaccggactttatatgacaacactacctactctc ttatcatcctgggcctggtcctttcagaccggggcacatacagct gtgtcgttcaaaagaaggaaagaggaacgtatgaagttaaacact tggctttagtaaagttgtccatcaaagctgacttctctacccca acataactgagtctggaaacccatctgcagacactaaaaggatta cctgctttgcttccggggggtttcccaaagcctcgcttctcttggt tggaaaatggaagagaattacctggcatcaatacgacaatttccc aggatcctgaatctgaattgtacaccattagtagccaactagatt tcaatacgactcgcaaccacaccattaagtgtctcattaaatatg gagatgctcacgtgtcagaggacttcacctgggaaaaaaccccag aagaccctcctgatagcaagaacacacttgtgctctctttggggcag gattcggcgcagtaataacagtcgtcgtcatcgttgtcatcatca aatgcttctgtaagcacagaagctgtttcagaagaaatgaggcaa gcagagaaacaaacaacagcctaccttcgggcctgaagaagcat tagctgaacagaccgtcttccttcgtacgGGCAGTGGAGAGGGCA

GAGGAAGTCTGCTAACATGCGGTGACGTCGAGGAGAATCCTGGCC

CAatggagagtgtggtacagccttcagtgtttgtggtggatggac agacggacatcccattcaggcggctggaacagaaccaccggagac ggcgctgtggcactgtccaggtcagcctggccctggtgctgctgc taggtgctgggctggccactcagggctggtttctcctgagactgc atcaacgtcttggagacatagtagctcatctgccagatggaggca aaggctcctgggagaagctgatacaagatcaacgatctcaccagg ccaacccagcagcacatcttacaggagccaacgccagcttgatag gtattggtggacctctgttatgggagacacgacttggcctggcct tcttgaggggcttgacgtatcatgatggggccctggtgaccatgg agcccggttactactatgtgtactccaaagtgcagctgagcggcg tgggctgccccagggggctggccaatggcctccccatcacccatg gactatacaagcgcacatcccgctacccgaaggagttagaactgc tggtcagtcggcggtcaccctgtggccgggccaacagctcccgag tctggtgggacagcagcttcctgggcggcgtggtacatctggagg ctggggaagaggtggtggtccgcgtgcctggaaaccgcctggtca gaccacgtgacggcaccaggtcctatttcggagctttcatggtca ctagcagcggtacccagtgcaccaactacgccctgctgaagctgg ccggcgatgtggagagcaaccccgggcccatggaccagcacacac ttgatgtggaggataccgcggatgccagacatccagcaggtactt -continued

```
cgtgcccctcggatgcggcgctcctcagagataccgggctcctcg cggacgctgcgctcctctcagatactgtgcgccccacaaatgccg cgctccccacggatgctgcctaccctgcggttaatgttcgggatc gcgaggccgcgtggccgcctgcactgaacttctgttcccgccacc caaagctctatggcctagtcgctttggttttgctgcttctgatcg ccgcctgtgttcctatcttcacccgcaccgagcctcggccagcgc tcacaatcaccacctcgcccaacctgggtacccgagagaataatg cagaccaggtcacccctgtttcccacattggctgccccaacacta cacaacagggctctcctgtgttcgccaagctactggctaaaaacc aagcatcgttgtgcaatacaactctgaactggcacagccaagatg gagctgggagctcatacctatctcaaggtctgaggtacgaagaag acaaaaaggagttggtggtagacagtcccgggctctactacgtat ttttggaactgaagctcagtccaacattcacaaacacaggccaca aggtgcagggctgggtctctcttgttttgcaagcaaagcctcagg tagatgactttgacaacttggccctgacagtggaactgttccctt gctccatggagaacaagttagtggaccgttcctggagtcaactgt tgctcctgaaggctggccaccgcctcagtgtgggtctgagggctt atctgcatggagcccaggatgcatacagagactgggagctgtctt atcccaacaccaccagctttggactctttcttgtgaaacccgaca acccatgggaatgaGAATTCAATAAAAGATCTTTATTTTCATTAG

ATCTGTGTGTTGGTTTTTTGTGTGCGGCCGCAGGAACCCCTAGTG

ATGGAGTTGGCCACTCCCTCTCTGCGCGCTCGCTCGCTCACTGAG

GCCGGGCGACCAAAGGTCGCCCGACGCCCGGGCTTTGCCCGGGCG

GCCTCAGTGAGCGAGCGAGCGCGCAGCTGCCTGCAGGGGCGCCTG

ATGCGGTATTTTCTCCTTACGCATCTGTGCGGTATTTCACACCGC

ATACGTCAAAGCAACCATAGTACGCGCCCTGTAGCGGCGCATTAA

GCGCGGCGGGTGTGGTGGTTACGCGCAGCGTGACCGCTACACTTG

CCAGCGCCTTAGCGCCCGCTCCTTTCGCTTTCTTCCCTTCCTTTC

TCGCCACGTTCGCCGGCTTTCCCCGTCAAGCTCTAAATCGGGGGC

TCCCTTTAGGGTTCCGATTTAGTGCTTTACGGCACCTCGACCCCA

AAAAACTTGATTTGGGTGATGGTTCACGTAGTGGGCCATCGCCCT

GATAGACGGTTTTTCGCCCTTTGACGTTGGAGTCCACGTTCTTTA

ATAGTGGACTCTTGTTCCAAACTGGAACAACACTCAACTCTATCT

CGGGCTATTCTTTTGATTTATAAGGGATTTTGCCGATTTCGGTCT

ATTGGTTAAAAAATGAGCTGATTTAACAAAAATTTAACGCGAATT

TTAACAAAATATTAACGTTTACAATTTTATGGTGCACTCTCAGTA

CAATCTGCTCTGATGCCGCATAGTTAAGCCAGCCCCGACACCCGC

CAACACCCGCTGACGCGCCCTGACGGGCTTGTCTGCTCCCGGCAT

CCGCTTACAGACAAGCTGTGACCGTCTCCGGGAGCTGCATGTGTC

AGAGGTTTTCACCGTCATCACCGAAACGCGCGAGACGAAAGGGCC

TCGTGATACGCCTATTTTTATAGGTTAATGTCATGATAATAATGG
```

-continued

```
    TTTCTTAGACGTCAGGTGGCACTTTTCGGGGAAATGTGCGCGGAA

CCCCTATTTGTTTATTTTTCTAAATACATTCAAATATGTATCCGC

TCATGAGACAATAACCCTGATAAATGCTTCAATAATATTGAAAAA

GGAAGAGTATGAGTATTCAACATTTCCGTGTCGCCCTTATTCCCT

10  TTTTTGCGGCATTTTGCCTTCCTGTTTTTGCTCACCCAGAAACGC

TGGTGAAAGTAAAAGATGCTGAAGATCAGTTGGGTGCACGAGTGG

GTTACATCGAACTGGATCTCAACAGCGGTAAGATCCTTGAGAGTT

TTCGCCCCGAAGAACGTTTTCCAATGATGAGCACTTTTAAAGTTC

15  TGCTATGTGGCGCGGTATTATCCCGTATTGACGCCGGGCAAGAGC

AACTCGGTCGCCGCATACACTATTCTCAGAATGACTTGGTTGAGT

ACTCACCAGTCACAGAAAAGCATCTTACGGATGGCATGACAGTAA

20  GAGAATTATGCAGTGCTGCCATAACCATGAGTGATAACACTGCGG

CCAACTTACTTCTGACAACGATCGGAGGACCGAAGGAGCTAACCG

CTTTTTTGCACAACATGGGGGATCATGTAACTCGCCTTGATCGTT

25  GGGAACCGGAGCTGAATGAAGCCATACCAAACGACGAGCGTGACA

CCACGATGCCTGTAGCAATGGCAACAACGTTGCGCAAACTATTAA

CTGGCGAACTACTTACTCTAGCTTCCCGGCAACAATTAATAGACT

30  GGATGGAGGCGGATAAAGTTGCAGGACCACTTCTGCGCTCGGCCC

TTCCGGCTGGCTGGTTTATTGCTGATAAATCGGAGCCGGTGAGC

35  GTGGAAGCCGCGGTATCATTGCAGCACTGGGGCCAGATGGTAAGC

CCTCCCGTATCGTAGTTATCTACACGACGGGGAGTCAGGCAACTA

TGGATGAACGAAATAGACAGATCGCTGAGATAGGTGCCTCACTGA

40  TTAAGCATTGGTAACTGTCAGACCAAGTTTACTCATATATACTTT

AGATTGATTTAAAACTTCATTTTTAATTTAAAAGGATCTAGGTGA

AGATCcttttgataatctcatgaccaaaatcccttaacgtgagt 45  tttcgttccactgaGCGTCAGACCCCGTAGAAAAGATCAAAGGAT

CTTCTTGAGATCCTTTTTTTCTGCGCGTAATCTGCTGCTTGCAAA

CAAAAAAACCACCGCTACCAGCGGTGGTTTGTTTGCCGGATCAAG

50  AGCTACCAACTCTTTTTCCGAAGGTAACTGGCTTCAGCAGAGCGC

AGATACCAAATACTGTTCTTCTAGTGTAGCCGTAGTTAGGCCACC

ACTTCAAGAACTCTGTAGCACCGCCTACATACCTCGCTCTGCTAA

55  TCCTGTTACCAGTGGCTGCTGCCAGTGGCGATAAGTCGTGTCTTA

CCGGGTTGGACTCAAGACGATAGTTACCGGATAAGGCGCAGCGGT

CGGGCTGAACGGGGGGTTCGTGCACACAGCCCAGCTTGGAGCGAA

60  CGACCTACACCGAACTGAGATACCTACAGCGTGAGCTATGAGAAA

GCGCCACGCTTCCCGAAGGGAGAAAGGCGGACAGGTATCCGGTAA

GCGGCAGGGTCGGAACAGGAGAGCGCACGAGGGAGCTTCCAGGGG

65  GAAACGCCTGGTATCTTTATAGTCCTGTCGGGTTTCGCCACCTCT
```

-continued

GACTTGAGCGTCGATTTTTGTGATGCTCGTCAGGGGGCGGAGCC

TATGGAAAAACGCCAGCAACGCGGCCTTTTTACGGTTCCTGGCCT

TTTGCTGGCCTTTTGCTCACATGT pGW122-pAAV_EFS-LTR-IL23-T2A-41BBL-P2A-
IFNg-WPRE (SEQ ID NO: 48)
CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccATGTGTCCTCAGAAGCTAACCATCTCCTGGTT

TGCCATCGTTTTGCTGGTGTCTCCACTCATGGCCATGTGGGAGCT

GGAGAAAGACGTTTATGTTGTAGAGGTGGACTGGACTCCCGATGC

CCCTGGAGAAACAGTGAACCTCACCTGTGACACGCCTGAAGAAGA

TGACATCACCTGGACCTCAGACCAGAGACATGGAGTCATAGGCTC

TGGAAAGACCCTGACCATCACTGTCAAAGAGTTTCTAGATGCTGG

CCAGTACACCTGCCACAAAGGAGGCGAGACTCTGAGCCACTCACA

TCTGCTGCTCCACAAGAAGGAAAATGGAATTTGGTCCACTGAAAT

TTTAAAAAATTTCAAAAACAAGACTTTCCTGAAGTGTGAAGCACC

AAATTACTCCGGACGGTTCACGTGCTCATGGCTGGTGCAAAGAAA

CATGGACTTGAAGTTCAACATCAAGAGCAGTAGCAGTTCCCCTGA

CTCTCGGGCAGTGACATGTGGAATGGCGTCTCTGTCTGCAGAGAA

GGTCACACTGGACCAAAGGGACTATGAGAAGTATTCAGTGTCCTG

CCAGGAGGATGTCACCTGCCCAACTGCCGAGGAGACCCTGCCCAT

TGAACTGGCGTTGGAAGCACGGCAGCAGAATAAATATGAGAACTA

CAGCACCAGCTTCTTCATCAGGGACATCATCAAACCAGACCCGCC

CAAGAACTTGCAGATGAAGCCTTTGAAGAACTCACAGGTGGAGGT

CAGCTGGGAGTACCCTGACTCCTGGAGCACTCCCCATTCCTACTT

CTCCCTCAAGTTCTTTGTTCGAATCCAGCGCAAGAAAGAAAGAT

GAAGGAGACAGAGGAGGGGTGTAACCAGAAAGGTGCGTTCCTCGT

AGAGAAGACATCTACCGAAGTCCAATGCAAAGGCGGGAATGTCTG

-continued

CGTGCAAGCTCAGGATCGCTATTACAATTCCTCATGCAGCAAGTG

GGCATGTGTTCCCTGCAGGGTCCGATCCGGCAGTGGAGAGGGCAG

AGGAAGTCTGCTAACATGCGGTGACGTCGAGGAGAATCCTGGCCC

Aatggaccagcacacacttgatgtggaggataccgcggatgccag acatccagcaggtacttcgtgcccctcggatgcggcgctcctcag agataccgggctcctcgcggacgctgcgctcctctcagatactgt gcgccccacaaatgccgcgctccccacggatgctgcctaccctgc ggttaatgttcgggatcgcgaggccgcgtggccgcctgcactgaa cttctgttcccgccacccaaagctctatggcctagtcgctttggt tttgctgcttctgatcgccgcctgtgttcctatcttcacccgcac cgagcctcggccagcgctcacaatcaccacctcgcccaacctggg tacccgagagaataatgcagaccaggtcacccctgtttcccacat tggctgccccaacactacacaacagggctctcctgtgttcgccaa gctactggctaaaaaccaagcatcgttgtgcaatacaactctgaa ctggcacagccaagatggagctgggagctcatacctatctcaagg tctgaggtacgaagaagacaaaaaggagttggtggtagacagtcc cgggctctactacgtattttttggaactgaagctcagtccaacatt cacaaacacaggccacaaggtgcagggctgggtctctcttgtttt gcaagcaaagcctcaggtagatgactttgacaacttggccctgac agtggaactgttccccttgctccatggagaacaagttagtggaccg ttcctggagtcaactgttgctcctgaaggctggccaccgcctcag tgtgggtctgagggcttatctgcatggagcccaggatgcatacag agactgggagctgtcttatcccaacaccaccagctttggactctt tcttgtgaaacccgacaacccatgggaaGGATCCGGCGCAACAAA

CTTCTCTCTGCTGAAACAAGCCGGAGATGTCGAAGAGAATCCTGG

ACCGgctagcatgaacgctacacactgcatcttggctttgcagct cttcctcatggctgtttctggctgttactgccacggcacagtcat tgaaagcctagaaagtctgaataactattttaactcaagtggcat agatgtggaagaaaagagtctcttcttggatatctggaggaactg gcaaaaggatggtgacatgaaaatcctgcagagccagattatctc tttctacctcagactctttgaagtcttgaaagacaatcaggccat cagcaacaacataagcgtcattgaatcacacctgattactacctt cttcagcaacagcaaggcgaaaaaggatgcattcatgagtattgc caagtttgaggtcaacaacccacaggtccagcgccaagcattcaa tgagctcatccgagtggtccaccagctgttgccggaatccagcct caggaagcggaaaaggagtcgctgctgaGaattcacgcgttaagt cgacaatcaacctctggattacaaaatttgtgaaagattgactgg tattcttaactatgttgctccttttacgctatgtggatacgctgc tttaatgcctttgtatcatgctattgcttcccgtatggctttcat tttctcctccttgtataaatcctggttgctgtctctttatgagga gttgtggcccgttgtcaggcaacgtggcgtggtgtgcactgtgtt -continued

```
tgctgacgcaacccccactggttggggcattgccaccacctgtca gctcctttccgggactttcgctttcccctccctattgccacggc ggaactcatcgccgcctgccttgcccgctgctggacaggggctcg gctgttgggcactgacaattccgtggtgttgtcggggaaatcatc gtcctttccttggctgctcgcctgtgttgccacctggattctgcg cgggacgtccttctgctacgtcccttcggccctcaatccagcgga ccttccttcccgcggcctgctgccggctctgcggcctcttccgcg tcttcgccttcgccctcagacgagtcggatctcccttgggccgc ctccccgcgtcgactttaagaccaatgacGGCCGCAGGAACCCCT

AGTGATGGAGTTGGCCACTCCCTCTCTGCGCGCTCGCTCGCTCAC

TGAGGCCGGGCGACCAAAGGTCGCCCGACGCCCGGGCTTTGCCCG

GGCGGCCTCAGTGAGCGAGCGAGCGCGCAGCTGCCTGCAGGGGCG

CCTGATGCGGTATTTTCTCCTTACGCATCTGTGCGGTATTTCACA

CCGCATACGTCAAAGCAACCATAGTACGCGCCCTGTAGCGGCGCA

TTAAGCGCGGCGGGTGTGGTGGTTACGCGCAGCGTGACCGCTACA

CTTGCCAGCGCCTTAGCGCCCGCTCCTTTCGCTTTCTTCCCTTCC

TTTCTCGCCACGTTCGCCGGCTTTCCCCGTCAAGCTCTAAATCGG

GGGCTCCCTTTAGGGTTCCGATTTAGTGCTTTACGGCACCTCGAC

CCCAAAAAACTTGATTTGGGTGATGGTTCACGTAGTGGGCCATCG

CCCTGATAGACGGTTTTTCGCCCTTTGACGTTGGAGTCCACGTTC

TTTAATAGTGGACTCTTGTTCCAAACTGGAACAACACTCAACTCT

ATCTCGGGCTATTCTTTTGATTATAAGGGATTTTGCCGATTTCG

GTCTATTGGTTAAAAAATGAGCTGATTTAACAAAAATTTAACGCG

AATTTTAACAAAATATTAACGTTTACAATTTTATGGTGCACTCTC

AGTACAATCTGCTCTGATGCCGCATAGTTAAGCCAGCCCCGACAC

CCGCCAACACCCGCTGACGCGCCCTGACGGGCTTGTCTGCTCCCG

GCATCCGCTTACAGACAAGCTGTGACCGTCTCCGGGAGCTGCATG

TGTCAGAGGTTTTCACCGTCATCACCGAAACGCGCGAGACGAAAG

GGCCTCGTGATACGCCTATTTTTATAGGTTAATGTCATGATAATA

ATGGTTTCTTAGACGTCAGGTGGCACTTTTCGGGGAAATGTGCGC

GGAACCCCTATTTGTTTATTTTTCTAAATACATTCAAATATGTAT

CCGCTCATGAGACAATAACCCTGATAAATGCTTCAATAATATTGA

AAAAGGAAGAGTATGAGTATTCAACATTTCCGTGTCGCCCTTATT

CCCTTTTTTGCGGCATTTTGCCTTCCTGTTTTTGCTCACCCAGAA

ACGCTGGTGAAAGTAAAAGATGCTGAAGATCAGTTGGGTGCACGA

GTGGGTTACATCGAACTGGATCTCAACAGCGGTAAGATCCTTGAG

AGTTTTCGCCCCGAAGAACGTTTTCCAATGATGAGCACTTTTAAA

GTTCTGCTATGTGGCGCGGTATTATCCCGTATTGACGCCGGGCAA

GAGCAACTCGGTCGCCGCATACACTATTCTCAGAATGACTTGGTT

GAGTACTCACCAGTCACAGAAAAGCATCTTACGGATGGCATGACA
```

-continued

```
GTAAGAGAATTATGCAGTGCTGCCATAACCATGAGTGATAACACT

GCGGCCAACTTACTTCTGACAACGATCGGAGGACCGAAGGAGCTA

ACCGCTTTTTTGCACAACATGGGGGATCATGTAACTCGCCTTGAT

CGTTGGGAACCGGAGCTGAATGAAGCCATACCAAACGACGAGCGT

GACACCACGATGCCTGTAGCAATGGCAACAACGTTGCGCAAACTA

TTAACTGGCGAACTACTTACTCTAGCTTCCCGGCAACAATTAATA

GACTGGATGGAGGCGGATAAAGTTGCAGGACCACTTCTGCGCTCG

GCCCTTCCGGCTGGCTGGTTTATTGCTGATAAATCTGGAGCCGGT

GAGCGTGGAAGCCGCGGTATCATTGCAGCACTGGGGCCAGATGGT

AAGCCCTCCCGTATCGTAGTTATCTACACGACGGGGAGTCAGGCA

ACTATGGATGAACGAAATAGACAGATCGCTGAGATAGGTGCCTCA

CTGATTAAGCATTGGTAACTGTCAGACCAAGTTTACTCATATATA

CTTTAGATTGATTTAAAACTTCATTTTTAATTTAAAAGGATCTAG

GTGAAGATCCTTTTTGATAATCTCATGACCAAAATCCCTTAACGT

GAGTTTTCGTTCCACTGAGCGTCAGACCCCGTAGAAAAGATCAAA

GGATCTTCTTGAGATCCTTTTTTTCTGCGCGTAATCTGCTGCTTG

CAAACAAAAAAACCACCGCTACCAGCGGTGGTTTGTTTGCCGGAT

CAAGAGCTACCAACTCTTTTTCCGAAGGTAACTGGCTTCAGCAGA

GCGCAGATACCAAATACTGTTCTTCTAGTGTAGCCGTAGTTAGGC

CACCACTTCAAGAACTCTGTAGCACCGCCTACATACCTCGCTCTG

CTAATCCTGTTACCAGTGGCTGCTGCCAGTGGCGATAAGTCGTGT

CTTACCGGGTTGGACTCAAGACGATAGTTACCGGATAAGGCGCAG

CGGTCGGGCTGAACGGGGGGTTCGTGCACACAGCCCAGCTTGGAG

CGAACGACCTACACCGAACTGAGATACCTACAGCGTGAGCTATGA

GAAAGCGCCACGCTTCCCGAAGGGAGAAAGGCGGACAGGTATCCG

GTAAGCGGCAGGGTCGGAACAGGAGAGCGCACGAGGGAGCTTCCA

GGGGGAAACGCCTGGTATCTTTATAGTCCTGTCGGGTTTCGCCAC

CTCTGACTTGAGCGTCGATTTTTGTGATGCTCGTCAGGGGGGCGG

AGCCTATGGAAAAACGCCAGCAACGCGGCCTTTTTACGGTTCCTG

GCCTTTTGCTGGCCTTTTGCTCACATGT
``` pGW127b-pAAV_EFS-LTR-hIFNg-P2A-hIL23-
T2A-h41BBL-WPRE (SEQ ID NO: 49)

```
CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC
```

-continued

```
GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccATGAAATATACAAGTTATATCTTGGCTTTTCA

GCTCTGCATCGTTTTGGGTTCTCTTGGCTGTTACTGCCAGGACCC

ATATGTAAAGAAGCAGAAAACCTTAAGAAATATTTTAATGCAGG

TCATTCAGATGTAGCGGATAATGGAACTCTTTTCTTAGGCATTTT

GAAGAATTGGAAAGAGGAGAGTGACAGAAAAATAATGCAGAGCCA

AATTGTCTCCTTTTACTTCAAACTTTTTAAAAACTTTAAAGATGA

CCAGAGCATCCAAAAGAGTGTGGAGACCATCAAGGAAGACATGAA

TGTCAAGTTTTTCAATAGCAACAAAAAGAAACGAGATGACTTCGA

AAAGCTGACTAATTATTCGGTAACTGACTTGAATGTCCAACGCAA

AGCAATACATGAACTCATCCAAGTGATGGCTGAACTGTCGCCAGC

AGCTAAAACAGGGAAGCGAAAAAGGAGTCAGATGCTGTTTCGAGG

TCGAAGAGCATCCCAGGgcggaGGATCCGGCGCAACAAACTTCTC

TCTGCTGAAACAAGCCGGAGATGTCGAAGAGAATCCTGGACCGAT

GTGTCACCAGCAGTTGGTCATCTCTTGGTTTTCCCTGGTTTTTCT

GGCATCTCCCCTCGTGGCCATATGGGAACTGAAGAAAGATGTTTA

TGTCGTAGAATTGGATTGGTATCCGGATGCCCCTGGAGAAATGGT

GGTCCTCACCTGTGACACCCCTGAAGAAGATGGTATCACCTGGAC

CTTGGACCAGAGCAGTGAGGTCTTAGGCTCTGGCAAAACCCTGAC

CATCCAAGTCAAAGAGTTTGGAGATGCTGGCCAGTACACCTGTCA

CAAAGGAGGCGAGGTTCTAAGCCATTCGCTCCTGCTGCTTCACAA

AAAGGAAGATGGAATTTGGTCCACTGATATTTTAAAGGACCAGAA

AGAACCCAAAAATAAGACCTTTCTAAGATGCGAGGCCAAGAATTA

TTCTGGACGTTTCACCTGCTGGTGGCTGACGACAATCAGTACTGA

TTTGACATTCAGTGTCAAAAGCAGCAGAGGCTCTTCTGACCCCCA

AGGGGTGACGTGCGGAGCTGCTACACTCTCTGCAGAGAGAGTCAG

AGGGGACAACAAGGAGTATGAGTACTCAGTGGAGTGCCAGGAGGA

CAGTGCCTGCCCAGCTGCTGAGGAGAGTCTGCCCATTGAGGTCAT

GGTGGATGCCGTTCACAAGCTCAAGTATGAAAACTACACCAGCAG

CTTCTTCATCAGGGACATCATCAAACCTGACCCACCCAAGAACTT

GCAGCTGAAGCCATTAAAGAATTCTCGGCAGGTGGAGGTCAGCTG

GGAGTACCCTGACACCTGGAGTACTCCACATTCCTACTTCTCCCT

GACATTCTGCGTTCAGGTCCAGGGCAAGAGCAAGAGAGAAAAGAA

AGATAGAGTCTTCACGGACAAGACCTCAGCCACGGTCATCTGCCG

CAAAAATGCCAGCATTAGCGTGCGGGCCCAGGACCGCTACTATAG

CTCATCTTGGAGCGAATGGGCATCTGTGCCCTGCAGTGGCactAG
```

-continued

```
TGGAGAGGGCAGAGGAAGTCTGCTAACATGCGGTGACGTCGAGGA

GAATCCTGGCCCAATGGAATACGCCTCTGACGCTTCACTGGACCC

CGAAGCCCCGTGGCCTCCCGCGCCCCGCGCTCGCGCCTGCCGCGT

ACTGCCTTGGGCCCTGGTCGCGGGGCTGCTGCTGCTGCTGCTGCT

CGCTGCCGCCTGCGCCGTCTTCCTCGCCTGCCCCTGGGCCGTGTC

CGGGGCTCGCGCCTCGCCCGGCTCCGCGGCCAGCCCGAGACTCCG

CGAGGGTCCCGAGCTTTCGCCCGACGATCCCGCCGGCCTCTTGGA

CCTGCGGCAGGGCATGTTTGCGCAGCTGGTGGCCCAAAATGTTCT

GCTGATCGATGGGCCCCTGAGCTGGTACAGTGACCCAGGCCTGGC

AGGCGTGTCCCTGACGGGGGGCCTGAGCTACAAAGAGGACACGAA

GGAGCTGGTGGTGGCCAAGGCTGGAGTCTACTATGTCTTCTTTCA

ACTAGAGCTGCGGCGCGTGGTGGCCGGCGAGGGCTCAGGCTCCGT

TTCACTTGCGCTGCACCTGCAGCCACTGCGCTCTGCTGCTGGGGC

CGCCGCCCTGGCTTTGACCGTGGACCTGCCACCCGCCTCCTCCGA

GGCTCGGAACTCGGCCTTCGGTTTCCAGGGCCGCTTGCTGCACCT

GAGTGCCGGCCAGCGCCTGGGCGTCCATCTTCACACTGAGGCCAG

GGCACGCCATGCCTGGCAGCTTACCCAGGGCGCCACAGTCTTGGG

ACTCTTCCGGGTGACCCCCGAAATCCCAGCCGGACTCCCTTCACC

GAGGTCGGAATAAGaattcacgcgttaagtcgacaatcaacctct ggattacaaaatttgtgaaagattgactggtattcttaactatgt tgctccttttacgctatgtggatacgctgctttaatgcctttgta tcatgctattgcttcccgtatggctttcattttctcctccttgta taaatcctggttgctgtctctttatgaggagttgtggcccgttgt caggcaacgtggcgtggtgtgcactgtgtttgctgacgcaacccc cactggttggggcattgccaccacctgtcagctcctttccgggac tttcgctttccccctccctattgccacggcggaactcatcgccgc ctgccttgcccgctgctggacaggggctcggctgttgggcactga caattccgtggtgttgtcggggaaatcatcgtcctttccttggct gctcgcctgtgttgccacctggattctgcgcgggacgtccttctg ctacgtcccttcggccctcaatccagcggaccttccttcccgcgg cctgctgccggctctgcgggcctcttccgcgtcttcgccttcgcc tcagacgagtcggatctcccctttgggccgcctccccgcgtcgact ttaagaccaatgacGGCCGCAGGAACCCCTAGTGATGGAGTTGGC

CACTCCCTCTCTGCGCGCTCGCTCGCTCACTGAGGCCGGGCGACC

AAAGGTCGCCCGACGCCCGGGCTTTGCCCGGGCGGCCTCAGTGAG

CGAGCGAGCGCGCAGCTGCCTGCAGGGGCGCCTGATGCGGTATTT

TCTCCTTACGCATCTGTGCGGTATTTCACACCGCATACGTCAAAG

CAACCATAGTACGCGCCCTGTAGCGGCGCATTAAGCGCGGCGGGT

GTGGTGGTTACGCGCAGCGTGACCGCTACACTTGCCAGCGCCTTA

GCGCCCGCTCCTTTCGCTTTCTTCCCTTCCTTTCTCGCCACGTTC
```

-continued

GCCGGCTTTCCCCGTCAAGCTCTAAATCGGGGGCTCCCTTTAGGG

TTCCGATTTAGTGCTTTACGGCACCTCGACCCCAAAAAACTTGAT

TTGGGTGATGGTTCACGTAGTGGGCCATCGCCCTGATAGACGGTT

TTTCGCCCTTTGACGTTGGAGTCCACGTTCTTTAATAGTGGACTC

TTGTTCCAAACTGGAACAACACTCAACTCTATCTCGGGCTATTCT

TTTGATTTATAAGGGATTTTGCCGATTTCGGTCTATTGGTTAAAA

AATGAGCTGATTTAACAAAAATTTAACGCGAATTTTAACAAAATA

TTAACGTTTACAATTTTATGGTGCACTCTCAGTACAATCTGCTCT

GATGCCGCATAGTTAAGCCAGCCCCGACACCCGCCAACACCCGCT

GACGCGCCCTGACGGGCTTGTCTGCTCCCGGCATCCGCTTACAGA

CAAGCTGTGACCGTCTCCGGGAGCTGCATGTGTCAGAGGTTTTCA

CCGTCATCACCGAAACGCGCGAGACGAAAGGGCCTCGTGATACGC

CTATTTTTATAGGTTAATGTCATGATAATAATGGTTTCTTAGACG

TCAGGTGGCACTTTTCGGGGAAATGTGCGCGGAACCCCTATTTGT

TTATTTTTCTAAATACATTCAAATATGTATCCGCTCATGAGACAA

TAACCCTGATAAATGCTTCAATAATATTGAAAAAGGAAGAGTATG

AGTATTCAACATTTCCGTGTCGCCCTTATTCCCTTTTTTGCGGCA

TTTTGCCTTCCTGTTTTTGCTCACCCAGAAACGCTGGTGAAAGTA

AAAGATGCTGAAGATCAGTTGGGTGCACGAGTGGGTTACATCGAA

CTGGATCTCAACAGCGGTAAGATCCTTGAGAGTTTTCGCCCCGAA

GAACGTTTTCCAATGATGAGCACTTTTAAAGTTCTGCTATGTGGC

GCGGTATTATCCCGTATTGACGCCGGGCAAGAGCAACTCGGTCGC

CGCATACACTATTCTCAGAATGACTTGGTTGAGTACTCACCAGTC

ACAGAAAAGCATCTTACGGATGGCATGACAGTAAGAGAATTATGC

AGTGCTGCCATAACCATGAGTGATAACACTGCGGCCAACTTACTT

CTGACAACGATCGGAGGACCGAAGGAGCTAACCGCTTTTTTGCAC

AACATGGGGGATCATGTAACTCGCCTTGATCGTTGGGAACCGGAG

CTGAATGAAGCCATACCAAACGACGAGCGTGACACCACGATGCCT

GTAGCAATGGCAACAACGTTGCGCAAACTATTAACTGGCGAACTA

CTTACTCTAGCTTCCCGGCAACAATTAATAGACTGGATGGAGGCG

GATAAAGTTGCAGGACCACTTCTGCGCTCGGCCCTTCCGGCTGGC

TGGTTTATTGCTGATAAATCTGGAGCCGGTGAGCGTGGAAGCCGC

GGTATCATTGCAGCACTGGGGCCAGATGGTAAGCCCTCCCGTATC

GTAGTTATCTACACGACGGGGAGTCAGGCAACTATGGATGAACGA

AATAGACAGATCGCTGAGATAGGTGCCTCACTGATTAAGCATTGG

TAACTGTCAGACCAAGTTTACTCATATATACTTTAGATTGATTTA

AAACTTCATTTTTAATTTAAAAGGATCTAGGTGAAGATCCTTTTT

GATAATCTCATGACCAAAATCCCTTAACGTGAGTTTTCGTTCCAC

TGAGCGTCAGACCCCGTAGAAAAGATCAAAGGATCTTCTTGAGAT

CCTTTTTTTCTGCGCGTAATCTGCTGCTTGCAAACAAAAAAACCA

CCGCTACCAGCGGTGGTTTGTTTGCCGGATCAAGAGCTACCAACT

-continued

CTTTTTCCGAAGGTAACTGGCTTCAGCAGAGCGCAGATACCAAAT

ACTGTTCTTCTAGTGTAGCCGTAGTTAGGCCACCACTTCAAGAAC

TCTGTAGCACCGCCTACATACCTCGCTCTGCTAATCCTGTTACCA

GTGGCTGCTGCCAGTGGCGATAAGTCGTGTCTTACCGGGTTGGAC

TCAAGACGATAGTTACCGGATAAGGCGCAGCGGTCGGGCTGAACG

GGGGGTTCGTGCACACAGCCCAGCTTGGAGCGAACGACCTACACC

GAACTGAGATACCTACAGCGTGAGCTATGAGAAAGCGCCACGCTT

CCCGAAGGGAGAAAGGCGGACAGGTATCCGGTAAGCGGCAGGGTC

GGAACAGGAGAGCGCACGAGGGAGCTTCCAGGGGGAAACGCCTGG

TATCTTTATAGTCCTGTCGGGTTTCGCCACCTCTGACTTGAGCGT

CGATTTTTGTGATGCTCGTCAGGGGGGCGGAGCCTATGGAAAAAC

GCCAGCAACGCGGCCTTTTTACGGTTCCTGGCCTTTTGCTGGCCT

TTTGCTCACATGT pGW128b-pAAV_EFS-LTR-hIFNg-P2A-hIL23-
T2A-h41BBL-E2A-hLight-WPRE
                                    (SEQ ID NO: 50)
CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccATGAAATATACAAGTTATATCTTGGCTTTTCA

GCTCTGCATCGTTTTGGGTTCTCTTGGCTGTTACTGCCAGGACCC

ATATGTAAAAGAAGCAGAAAACCTTAAGAAATATTTAATGCAGG

TCATTCAGATGTAGCGGATAATGGAACTCTTTTCTTAGGCATTTT

GAAGAATTGGAAAGAGGAGAGTGACAGAAAAATAATGCAGAGCCA

AATTGTCTCCTTTTACTTCAAACTTTTTAAAAACTTTAAAGATGA

CCAGAGCATCCAAAAGAGTGTGGAGACCATCAAGGAAGACATGAA

TGTCAAGTTTTTCAATAGCAACAAAAAGAAACGAGATGACTTCGA

AAAGCTGACTAATTATTCGGTAACTGACTTGAATGTCCAACGCAA

AGCAATACATGAACTCATCCAAGTGATGGCTGAACTGTCGCCAGC

AGCTAAAACAGGGAAGCGAAAAAGGAGTCAGATGCTGTTTCGAGG

-continued

TCGAAGAGCATCCCAGggcggaGGATCCGGCGCAACAAACTTCTC

TCTGCTGAAACAAGCCGGAGATGTCGAAGAGAATCCTGGACCGAT

GTGTCACCAGCAGTTGGTCATCTCTTGGTTTTCCCTGGTTTTTCT

GGCATCTCCCCTCGTGGCCATATGGGAACTGAAGAAAGATGTTTA

TGTCGTAGAATTGGATTGGTATCCGGATGCCCCTGGAGAAATGGT

GGTCCTCACCTGTGACACCCCTGAAGAAGATGGTATCACCTGGAC

CTTGGACCAGAGCAGTGAGGTCTTAGGCTCTGGCAAAACCCTGAC

CATCCAAGTCAAAGAGTTTGGAGATGCTGGCCAGTACACCTGTCA

CAAAGGAGGCGAGGTTCTAAGCCATTCGCTCCTGCTGCTTCACAA

AAAGGAAGATGGAATTTGGTCCACTGATATTTTAAAGGACCAGAA

AGAACCCAAAAATAAGACCTTTCTAAGATGCGAGGCCAAGAATTA

TTCTGGACGTTTCACCTGCTGGTGGCTGACGACAATCAGTACTGA

TTTGACATTCAGTGTCAAAAGCAGCAGAGGCTCTTCTGACCCCCA

AGGGGTGACGTGCGGAGCTGCTACACTCTCTGCAGAGAGAGTCAG

AGGGGACAACAAGGAGTATGAGTACTCAGTGGAGTGCCAGGAGGA

CAGTGCCTGCCCAGCTGCTGAGGAGAGTCTGCCCATTGAGGTCAT

GGTGGATGCCGTTCACAAGCTCAAGTATGAAAACTACACCAGCAG

CTTCTTCATCAGGGACATCATCAAACCTGACCCACCCAAGAACTT

GCAGCTGAAGCCATTAAAGAATTCTCGGCAGGTGGAGGTCAGCTG

GGAGTACCCTGACACCTGGAGTACTCCACATTCCTACTTCTCCCT

GACATTCTGCGTTCAGGTCCAGGGCAAGAGCAAGAGAGAAAAGAA

AGATAGAGTCTTCACGGACAAGACCTCAGCCACGGTCATCTGCCG

CAAAAATGCCAGCATTAGCGTGCGGGCCCAGGACCGCTACTATAG

CTCATCTTGGAGCGAATGGGCATCTGTGCCCTGCAGTGGCAGTGG

AGAGGGCAGAGGAAGTCTGCTAACATGCGGTGACGTCGAGGAGAA

TCCTGGCCCAATGGAATACGCCTCTGACGCTTCACTGGACCCCGA

AGCCCCGTGGCCTCCCGCGCCCCGCGCTCGCGCCTGCCGCGTACT

GCCTTGGGCCCTGGTCGCGGGGCTGCTGCTGCTGCTGCTGCTCGC

TGCCGCCTGCGCCGTCTTCCTCGCCTGCCCCTGGGCCGTGTCCGG

GGCTCGCGCCTCGCCCGGCTCCGCGGCCAGCCCGAGACTCCGCGA

GGGTCCCGAGCTTTCGCCCGACGATCCCGCCGGCCTCTTGGACCT

GCGGCAGGGCATGTTTGCGCAGCTGGTGGCCCAAAATGTTCTGCT

GATCGATGGGCCCCTGAGCTGGTACAGTGACCCAGGCCTGGCAGG

CGTGTCCCTGACGGGGGGCCTGAGCTACAAAGAGGACACGAAGGA

GCTGGTGGTGGCCAAGGCTGGAGTCTACTATGTCTTCTTTCAACT

AGAGCTGCGGCGCGTGGTGGCCGGCGAGGGCTCAGGCTCCGTTTC

ACTTGCGCTGCACCTGCAGCCACTGCGCTCTGCTGCTGGGGCCGC

CGCCCTGGCTTTGACCGTGGACCTGCCACCCGCCTCCTCCGAGGC

TCGGAACTCGGCCTTCGGTTTCCAGGGCCGCTTGCTGCACCTGAG

TGCCGGCCAGCGCCTGGGCGTCCATCTTCACACTGAGGCCAGGGC

-continued

ACGCCATGCCTGGCAGCTTACCCAGGGCGCCACAGTCTTGGGACT

CTTCCGGGTGACCCCCGAAATCCCAGCCGGACTCCCTTCACCGAG

GTCGGAAGGTgctagcggtacccagtgcaccaactacgccctgct gaagctggccggcgatgtggagagcaaccccgggcccATGGAGGA

GAGTGTCGTACGGCCCTCAGTGTTTGTGGTGGATGGACAGACCGA

CATCCCATTCACGAGGCTGGGACGAAGCCACCGGAGACAGTCGTG

CAGTGTGGCCCGGGTGGGTCTGGGTCTCTTGCTGTTGCTGATGGG

GGCCGGGCTGGCCGTCCAAGGCTGGTTCCTCCTGCAGCTGCACTG

GCGTCTAGGAGAGATGGTCACCCGCCTGCCTGACGGACCTGCAGG

CTCCTGGGAGCAGCTGATACAAGAGCGAAGGTCTCACGAGGTCAA

CCCAGCAGCGCATCTCACAGGGGCCAACTCCAGCTTGACCGGCAG

CGGGGGGCCGCTGTTATGGGAGACTCAGCTGGGCCTGGCCTTCCT

GAGGGGCCTCAGCTACCACGATGGGGCCCTTGTGGTCACCAAAGC

TGGCTACTACTACATCTACTCCAAGGTGCAGCTGGGCGGTGTGGG

CTGCCCGCTGGGGCCTGGCCAGCACCATCACCCACGGCCTCTACAA

GCGCACACCCCGCTACCCCGAGGAGCTGGAGCTGTTGGTCAGCCA

GCAGTCACCCTGCGGACGGGCCACCAGCAGCTCCCGGGTCTGGTG

GGACAGCAGCTTCCTGGGTGGTGTGGTACACCTGGAGGCTGGGGA

GAAGGTGGTCGTCCGTGTGCTGGATGAACGCCTGGTTCGACTGCG

TGATGGTACCCGGTCTTACTTCGGGGCTTTCATGGTGGGTGGAGG

CGGTTGCGGAAAGCGTAAGTGAGaattcacgcgttaagtcgacaa tcaacctctggattacaaaatttgtgaaagattgactggtattct taactatgttgctccttttacgctatgtggatacgctgctttaat gcctttgtatcatgctattgcttcccgtatggctttcattttctc ctccttgtataaatcctggttgctgtctctttatgaggagttgtg gcccgttgtcaggcaacgtggcgtggtgtgcactgtgtttgctga cgcaacccccactggttggggcattgccaccacctgtcagctcct ttccgggactttcgctttccccctccctattgccacggcggaact catcgccgcctgccttgcccgctgctggacaggggctcggctgtt gggcactgacaattccgtggtgttgtcggggaaatcatcgtcctt tccttggctgctcgcctgtgttgccacctggattctgcgcgggac gtccttctgctacgtcccttcggccctcaatccagcggaccttcc ttcccgcggcctgctgccggctctgcgggcctcttccgcgtcttcg ccttcgccctcagacgagtcggatctccctttgggccgcctcccc gcgtcgactttaagaccaatgacGGCCGCAGGAACCCCTAGTGAT

GGAGTTGGCCACTCCCTCTCTGCGCGCTCGCTCGCTCACTGAGGC

CGGGCGACCAAAGGTCGCCCGACGCCCGGGCTTTGCCCGGGCGGC

CTCAGTGAGCGAGCGAGCGCGCAGCTGCCTGCAGGGGCGCCTGAT

GCGGTATTTTCTCCTTACGCATCTGTGCGGTATTTCACACCGCAT

ACGTCAAAGCAACCATAGTACGCGCCCTGTAGCGGCGCATTAAGC

GCGGCGGGTGTGGTGGTTACGCGCAGCGTGACCGCTACACTTGCC

-continued

AGCGCCTTAGCGCCCGCTCCTTTCGCTTTCTTCCCTTCCTTTCTC

GCCACGTTCGCCGGCTTTCCCCGTCAAGCTCTAAATCGGGGGCTC

CCTTTAGGGTTCCGATTTAGTGCTTTACGGCACCTCGACCCCAAA

AAACTTGATTTGGGTGATGGTTCACGTAGTGGGCCATCGCCCTGA

TAGACGGTTTTTCGCCCTTTGACGTTGGAGTCCACGTTCTTTAAT

AGTGGACTCTTGTTCCAAACTGGAACAACACTCAACTCTATCTCG

GGCTATTCTTTTGATTTATAAGGGATTTTGCCGATTTCGGTCTAT

TGGTTAAAAAATGAGCTGATTTAACAAAAATTTAACGCGAATTTT

AACAAAATATTAACGTTTACAATTTTATGGTGCACTCTCAGTACA

ATCTGCTCTGATGCCGCATAGTTAAGCCAGCCCCGACACCCGCCA

ACACCCGCTGACGCGCCCTGACGGGCTTGTCTGCTCCCGGCATCC

GCTTACAGACAAGCTGTGACCGTCTCCGGGAGCTGCATGTGTCAG

AGGTTTTCACCGTCATCACCGAAACGCGCGAGACGAAAGGGCCTC

GTGATACGCCTATTTTTATAGGTTAATGTCATGATAATAATGGTT

TCTTAGACGTCAGGTGGCACTTTTCGGGGAAATGTGCGCGGAACC

CCTATTTGTTTATTTTTCTAAATACATTCAAATATGTATCCGCTC

ATGAGACAATAACCCTGATAAATGCTTCAATAATATTGAAAAAGG

AAGAGTATGAGTATTCAACATTTCCGTGTCGCCCTTATTCCCTTT

TTTGCGGCATTTTGCCTTCCTGTTTTTGCTCACCCAGAAACGCTG

GTGAAAGTAAAAGATGCTGAAGATCAGTTGGGTGCACGAGTGGGT

TACATCGAACTGGATCTCAACAGCGGTAAGATCCTTGAGAGTTTT

CGCCCCGAAGAACGTTTTCCAATGATGAGCACTTTTAAAGTTCTG

CTATGTGGCGCGGTATTATCCCGTATTGACGCCGGGCAAGAGCAA

CTCGGTCGCCGCATACACTATTCTCAGAATGACTTGGTTGAGTAC

TCACCAGTCACAGAAAAGCATCTTACGGATGGCATGACAGTAAGA

GAATTATGCAGTGCTGCCATAACCATGAGTGATAACACTGCGGCC

AACTTACTTCTGACAACGATCGGAGGACCGAAGGAGCTAACCGCT

TTTTTGCACAACATGGGGGATCATGTAACTCGCCTTGATCGTTGG

GAACCGGAGCTGAATGAAGCCATACCAAACGACGAGCGTGACACC

ACGATGCCTGTAGCAATGGCAACAACGTTGCGCAAACTATTAACT

GGCGAACTACTTACTCTAGCTTCCCGGCAACAATTAATAGACTGG

ATGGAGGCGGATAAAGTTGCAGGACCACTTCTGCGCTCGGCCCTT

CCGGCTGGCTGGTTTATTGCTGATAAATCTGGAGCCGGTGAGCGT

GGAAGCCGCGGTATCATTGCAGCACTGGGGCCAGATGGTAAGCCC

TCCCGTATCGTAGTTATCTACACGACGGGGAGTCAGGCAACTATG

GATGAACGAAATAGACAGATCGCTGAGATAGGTGCCTCACTGATT

AAGCATTGGTAACTGTCAGACCAAGTTTACTCATATATACTTTAG

ATTGATTTAAAACTTCATTTTTAATTTAAAAGGATCTAGGTGAAG

ATCcttttgataatctcatgaccaaaatcccttaacgtgagttt tcgttccactgaGCGTCAGACCCCGTAGAAAAGATCAAAGGATCT -continued

TCTTGAGATCCTTTTTTTCTGCGCGTAATCTGCTGCTTGCAAACA

AAAAAACCACCGCTACCAGCGGTGGTTTGTTTGCCGGATCAAGAG

CTACCAACTCTTTTTCCGAAGGTAACTGGCTTCAGCAGAGCGCAG

ATACCAAATACTGTTCTTCTAGTGTAGCCGTAGTTAGGCCACCAC

TTCAAGAACTCTGTAGCACCGCCTACATACCTCGCTCTGCTAATC

CTGTTACCAGTGGCTGCTGCCAGTGGCGATAAGTCGTGTCTTACC

GGGTTGGACTCAAGACGATAGTTACCGGATAAGGCGCAGCGGTCG

GGCTGAACGGGGGGTTCGTGCACACAGCCCAGCTTGGAGCGAACG

ACCTACACCGAACTGAGATACCTACAGCGTGAGCTATGAGAAAGC

GCCACGCTTCCCGAAGGGAGAAAGGCGGACAGGTATCCGGTAAGC

GGCAGGGTCGGAACAGGAGAGCGCACGAGGGAGCTTCCAGGGGGA

AACGCCTGGTATCTTTATAGTCCTGTCGGGTTTCGCCACCTCTGA

CTTGAGCGTCGATTTTTGTGATGCTCGTCAGGGGGGCGGAGCCTA

TGGAAAAACGCCAGCAACGCGGCCTTTTTACGGTTCCTGGCCTTT

TGCTGGCCTTTTGCTCACATGT pGW145-pAAV_EFS-LTR-hIFNg-WPRE-sPA (SEQ ID NO: 51)

CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccATGAAATATACAAGTTATATCTTGGCTTTTCA

GCTCTGCATCGTTTTGGGTTCTCTTGGCTGTTACTGCCAGGACCC

ATATGTAAAAGAAGCAGAAAACCTTAAGAAATATTTTAATGCAGG

TCATTCAGATGTAGCGGATAATGGAACTCTTTTCTTAGGCATTTT

GAAGAATTGGAAAGAGGAGAGTGACAGAAAAATAATGCAGAGCCA

AATTGTCTCCTTTTACTTCAAACTTTTTAAAAACTTTAAAGATGA

CCAGAGCATCCAAAAGAGTGTGGAGACCATCAAGGAAGACATGAA

TGTCAAGTTTTTCAATAGCAACAAAAAGAAACGAGATGACTTCGA

AAAGCTGACTAATTATTCGGTAACTGACTTGAATGTCCAACGCAA

AGCAATACATGAACTCATCCAAGTGATGGCTGAACTGTCGCCAGC

-continued

```
AGCTAAAACAGGGAAGCGAAAAAGGAGTCAGATGCTGTTTCGAGG

TCGAAGAGCATCCCAGTGAGaattcacgcgttaagtcgacaatca acctctggattacaaaatttgtgaaagattgactggtattcttaa ctatgttgctccttttacgctatgtggatacgctgctttaatgcc tttgtatcatgctattgcttcccgtatggctttcattttctcctc cttgtataaatcctggttgctgtctctttatgaggagttgtggcc cgttgtcaggcaacgtggcgtggtgtgcactgtgtttgctgacgc aaccccactggttggggcattgccaccacctgtcagctcctttc cgggactttcgctttcccctcctattgccacggcggaactcat cgccgcctgccttgcccgctgctggacaggggctcggctgttggg cactgacaattccgtggtgttgtcggggaaatcatcgtcctttcc ttggctgctcgcctgtgttgccacctggattctgcgcgggacgtc cttctgctacgtcccttcggccctcaatccagcggaccttccttc ccgcggcctgctgccggctctgcggcctcttccgcgtcttcgcct tcgccctcagacgagtcggatctcccttgggccgcctccccgcg tcgactttaagaccaatgacGGCCGaataaaagatctttattttc attagatctgtgtgttggttttttgtgtgcggccgCAGGAACCCC

TAGTGATGGAGTTGGCCACTCCCTCTCTGCGCGCTCGCTCGCTCA

CTGAGGCCGGGCGACCAAAGGTCGCCCGACGCCCGGGCTTTGCCC

GGGCGGCCTCAGTGAGCGAGCGAGCGCGCAGCTGCCTGCAGGGGC

GCCTGATGCGGTATTTTCTCCTTACGCATCTGTGCGGTATTTCAC

ACCGCATACGTCAAAGCAACCATAGTACGCGCCCTGTAGCGGCGC

ATTAAGCGCGGCGGGTGTGGTGGTTACGCGCAGCGTGACCGCTAC

ACTTGCCAGCGCCTTAGCGCCCGCTCCTTTCGCTTTCTTCCCTTC

CTTTCTCGCCACGTTCGCCGGCTTTCCCCGTCAAGCTCTAAATCG

GGGGCTCCCTTTAGGGTTCCGATTTAGTGCTTTACGGCACCTCGA

CCCCAAAAAACTTGATTTGGGTGATGGTTCACGTAGTGGGCCATC

GCCCTGATAGACGGTTTTTCGCCCTTTGACGTTGGAGTCCACGTT

CTTTAATAGTGGACTCTTGTTCCAAACTGGAACAACACTCAACTC

TATCTCGGGCTATTCTTTTGATTTATAAGGGATTTTGCCGATTTC

GGTCTATTGGTTAAAAAATGAGCTGATTTAACAAAAATTTAACGC

GAATTTTAACAAAATATTAACGTTTACAATTTTATGGTGCACTCT

CAGTACAATCTGCTCTGATGCCGCATAGTTAAGCCAGCCCCGACA

CCCGCCAACACCCGCTGACGCGCCCTGACGGGCTTGTCTGCTCCC

GGCATCCGCTTACAGACAAGCTGTGACCGTCTCCGGGAGCTGCAT

GTGTCAGAGGTTTTCACCGTCATCACCGAAACGCGCGAGACGAAA

GGGCCTCGTGATACGCCTATTTTTATAGGTTAATGTCATGATAAT

AATGGTTTCTTAGACGTCAGGTGGCACTTTTCGGGGAAATGTGCG

CGGAACCCCTATTTGTTTATTTTTCTAAATACATTCAAATATGTA

TCCGCTCATGAGACAATAACCCTGATAAATGCTTCAATAATATTG
```

-continued

```
AAAAAGGAAGAGTATGAGTATTCAACATTTCCGTGTCGCCCTTAT

TCCCTTTTTTGCGGCATTTTGCCTTCCTGTTTTTGCTCACCCAGA

AACGCTGGTGAAAGTAAAAGATGCTGAAGATCAGTTGGGTGCACG

AGTGGGTTACATCGAACTGGATCTCAACAGCGGTAAGATCCTTGA

GAGTTTTCGCCCCGAAGAACGTTTTCCAATGATGAGCACTTTTAA

AGTTCTGCTATGTGGCGCGGTATTATCCCGTATTGACGCCGGGCA

AGAGCAACTCGGTCGCCGCATACACTATTCTCAGAATGACTTGGT

TGAGTACTCACCAGTCACAGAAAAGCATCTTACGGATGGCATGAC

AGTAAGAGAATTATGCAGTGCTGCCATAACCATGAGTGATAACAC

TGCGGCCAACTTACTTCTGACAACGATCGGAGGACCGAAGGAGCT

AACCGCTTTTTTGCACAACATGGGGGATCATGTAACTCGCCTTGA

TCGTTGGGAACCGGAGCTGAATGAAGCCATACCAAACGACGAGCG

TGACACCACGATGCCTGTAGCAATGGCAACAACGTTGCGCAAACT

ATTAACTGGCGAACTACTTACTCTAGCTTCCCGGCAACAATTAAT

AGACTGGATGGAGGCGGATAAAGTTGCAGGACCACTTCTGCGCTC

GGCCCTTCCGGCTGGCTGGTTTATTGCTGATAAATCTGGAGCCGG

TGAGCGTGGAAGCCGCGGTATCATTGCAGCACTGGGGCCAGATGG

TAAGCCCTCCCGTATCGTAGTTATCTACACGACGGGGAGTCAGGC

AACTATGGATGAACGAAATAGACAGATCGCTGAGATAGGTGCCTC

ACTGATTAAGCATTGGTAACTGTCAGACCAAGTTTACTCATATAT

ACTTTAGATTGATTTAAAACTTCATTTTTAATTTAAAAGGATCTA

GGTGAAGATCCTTTTTGATAATCTCATGACCAAAATCCCTTAACG

TGAGTTTTCGTTCCACTGAGCGTCAGACCCCGTAGAAAAGATCAA

AGGATCTTCTTGAGATCCTTTTTTTCTGCGCGTAATCTGCTGCTT

GCAAACAAAAAAACCACCGCTACCAGCGGTGGTTTGTTTGCCGGA

TCAAGAGCTACCAACTCTTTTTCCGAAGGTAACTGGCTTCAGCAG

AGCGCAGATACCAAATACTGTTCTTCTAGTGTAGCCGTAGTTAGG

CCACCACTTCAAGAACTCTGTAGCACCGCCTACATACCTCGCTCT

GCTAATCCTGTTACCAGTGGCTGCTGCCAGTGGCGATAAGTCGTG

TCTTACCGGGTTGGACTCAAGACGATAGTTACCGGATAAGGCGCA

GCGGTCGGGCTGAACGGGGGGTTCGTGCACACAGCCCAGCTTGGA

GCGAACGACCTACACCGAACTGAGATACCTACAGCGTGAGCTATG

AGAAAGCGCCACGCTTCCCGAAGGGAGAAAGGCGGACAGGTATCC

GGTAAGCGGCAGGGTCGGAACAGGAGAGCGCACGAGGGAGCTTCC

AGGGGGAAACGCCTGGTATCTTTATAGTCCTGTCGGGTTTCGCCA

CCTCTGACTTGAGCGTCGATTTTTGTGATGCTCGTCAGGGGGGCG

GAGCCTATGGAAAAACGCCAGCAACGCGGCCTTTTTACGGTTCCT

GGCCTTTTGCTGGCCTTTTGCTCACATGT
``` pGW146-pAAV_EFS-LTR-hIL23-WPRE-sPA
                                    (SEQ ID NO: 52)
```
CCTGCAGGCAGCTGCGCGCTCGCTCGCTCACTGAGGCCGCCCGGG

CGTCGGGCGACCTTTGGTCGCCCGGCCTCAGTGAGCGAGCGAGCG
```

-continued

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccATGTGTCACCAGCAGTTGGTCATCTCTTGGTT

TTCCCTGGTTTTTCTGGCATCTCCCCTCGTGGCCATATGGGAACT

GAAGAAAGATGTTTATGTCGTAGAATTGGATTGGTATCCGGATGC

CCCTGGAGAAATGGTGGTCCTCACCTGTGACACCCCTGAAGAAGA

TGGTATCACCTGGACCTTGGACCAGAGCAGTGAGGTCTTAGGCTC

TGGCAAAACCCTGACCATCCAAGTCAAAGAGTTTGGAGATGCTGG

CCAGTACACCTGTCACAAAGGAGGCGAGGTTCTAAGCCATTCGCT

CCTGCTGCTTCACAAAAAGGAAGATGGAATTTGGTCCACTGATAT

TTTAAAGGACCAGAAAGAACCCAAAAATAAGACCTTTCTAAGATG

CGAGGCCAAGAATTATTCTGGACGTTTCACCTGCTGGTGGCTGAC

GACAATCAGTACTGATTTGACATTCAGTGTCAAAAGCAGCAGAGG

CTCTTCTGACCCCCAAGGGGTGACGTGCGGAGCTGCTACACTCTC

TGCAGAGAGAGTCAGAGGGGACAACAAGGAGTATGAGTACTCAGT

GGAGTGCCAGGAGGACAGTGCCTGCCCAGCTGCTGAGGAGAGTCT

GCCCATTGAGGTCATGGTGGATGCCGTTCACAAGCTCAAGTATGA

AAACTACACCAGCAGCTTCTTCATCAGGGACATCATCAAACCTGA

CCCACCCAAGAACTTGCAGCTGAAGCCATTAAAGAATTCTCGGCA

GGTGGAGGTCAGCTGGGAGTACCCTGACACCTGGAGTACTCCACA

TTCCTACTTCTCCCTGACATTCTGCGTTCAGGTCCAGGGCAAGAG

CAAGAGAGAAAAGAAAGATAGAGTCTTCACGGACAAGACCTCAGC

CACGGTCATCTGCCGCAAAAATGCCAGCATTAGCGTGCGGGCCCA

GGACCGCTACTATAGCTCATCTTGGAGCGAATGGGCATCTGTGCC

CTGCAGTTGAGaattcacgcgttaagtcgacaatcaacctctgga ttacaaaatttgtgaaagattgactggtattcttaactatgttgc tcctttacgctatgtggatacgctgctttaatgcctttgtatca tgctattgcttcccgtatggctttcatttttctcctccttgtataa atcctggttgctgtctctttatgaggagttgtggcccgttgtcag -continued gcaacgtggcgtggtgtgcactgtgtttgctgacgcaacccccac tggttggggcattgccaccacctgtcagctcctttccgggacttt cgctttcccctccctattgccacggcggaactcatcgccgcctg ccttgcccgctgctggacaggggctcggctgttgggcactgacaa ttccgtggtgttgtcggggaaatcatcgtcctttccttggctgct cgcctgtgttgccacctggattctgcgcgggacgtccttctgcta cgtcccttcggccctcaatccagcggaccttccttcccgcggcct gctgccggctctgcgcgcctcttccgcgtcttcgccttcgccctca gacgagtcggatctccctttgggccgcctccccgcgtcgacttta agaccaatgacGGCCGaataaaaagatctttattttcattagatct gtgtgttggttttttgtgtgcggccgcCAGGAACCCCTAGTGATGG

AGTTGGCCACTCCCTCTCTGCGCGCTCGCTCGCTCACTGAGGCCG

GGCGACCAAAGGTCGCCCGACGCCCGGGCTTTGCCCGGGCGGCCT

CAGTGAGCGAGCGAGCGCGCAGCTGCCTGCAGGGGCGCCTGATGC

GGTATTTTCTCCTTACGCATCTGTGCGGTATTTCACACCGCATAC

GTCAAAGCAACCATAGTACGCGCCCTGTAGCGGCGCATTAAGCGC

GGCGGGTGTGGTGGTTACGCGCAGCGTGACCGCTACACTTGCCAG

CGCCTTAGCGCCCGCTCCTTTCGCTTTCTTCCCTTCCTTTCTCGC

CACGTTCGCCGGCTTTCCCCGTCAAGCTCTAAATCGGGGGCTCCC

TTTAGGGTTCCGATTTAGTGCTTTACGGCACCTCGACCCCAAAAA

ACTTGATTTGGGTGATGGTTCACGTAGTGGGCCATCGCCCTGATA

GACGGTTTTTCGCCCTTTGACGTTGGAGTCCACGTTCTTTAATAG

TGGACTCTTGTTCCAAACTGGAACAACACTCAACTCTATCTCGGG

CTATTCTTTTGATTTATAAGGGATTTTGCCGATTTCGGTCTATTG

GTTAAAAAATGAGCTGATTTAACAAAAATTTAACGCGAATTTTAA

CAAAATATTAACGTTTACAATTTTATGGTGCACTCTCAGTACAAT

CTGCTCTGATGCCGCATAGTTAAGCCAGCCCCGACACCCGCCAAC

ACCCGCTGACGCGCCCTGACGGGCTTGTCTGCTCCCGGCATCCGC

TTACAGACAAGCTGTGACCGTCTCCGGGAGCTGCATGTGTCAGAG

GTTTTCACCGTCATCACCGAAACGCGCGAGACGAAAGGGCCTCGT

GATACGCCTATTTTTATAGGTTAATGTCATGATAATAATGGTTTC

TTAGACGTCAGGTGGCACTTTTCGGGGAAATGTGCGCGGAACCCC

TATTTGTTTATTTTTCTAAATACATTCAAATATGTATCCGCTCAT

GAGACAATAACCCTGATAAATGCTTCAATAATATTGAAAAAGGAA

GAGTATGAGTATTCAACATTTCCGTGTCGCCCTTATTCCCTTTTT

TGCGGCATTTTGCCTTCCTGTTTTTGCTCACCCAGAAACGCTGGT

GAAAGTAAAAGATGCTGAAGATCAGTTGGGTGCACGAGTGGGTTA

CATCGAACTGGATCTCAACAGCGGTAAGATCCTTGAGAGTTTTCG

CCCCGAAGAACGTTTTCCAATGATGAGCACTTTTAAAGTTCTGCT

ATGTGGCGCGGTATTATCCCGTATTGACGCCGGGCAAGAGCAACT

CGGTCGCCGCATACACTATTCTCAGAATGACTTGGTTGAGTACTC

-continued

ACCAGTCACAGAAAAGCATCTTACGGATGGCATGACAGTAAGAGA

ATTATGCAGTGCTGCCATAACCATGAGTGATAACACTGCGGCCAA

CTTACTTCTGACAACGATCGGAGGACCGAAGGAGCTAACCGCTTT

TTTGCACAACATGGGGGATCATGTAACTCGCCTTGATCGTTGGGA

ACCGGAGCTGAATGAAGCCATACCAAACGACGAGCGTGACACCAC

GATGCCTGTAGCAATGGCAACAACGTTGCGCAAACTATTAACTGG

CGAACTACTTACTCTAGCTTCCCGGCAACAATTAATAGACTGGAT

GGAGGCGGATAAAGTTGCAGGACCACTTCTGCGCTCGGCCCTTCC

GGCTGGCTGGTTTATTGCTGATAAATCTGGAGCCGGTGAGCGTGG

AAGCCGCGGTATCATTGCAGCACTGGGGCCAGATGGTAAGCCCTC

CCGTATCGTAGTTATCTACACGACGGGGAGTCAGGCAACTATGGA

TGAACGAAATAGACAGATCGCTGAGATAGGTGCCTCACTGATTAA

GCATTGGTAACTGTCAGACCAAGTTTACTCATATATACTTTAGAT

TGATTTAAAACTTCATTTTTAATTTAAAAGGATCTAGGTGAAGAT

CCTTTTTGATAATCTCATGACCAAAATCCCTTAACGTGAGTTTTC

GTTCCACTGAGCGTCAGACCCCGTAGAAAAGATCAAAGGATCTTC

TTGAGATCCTTTTTTTCTGCGCGTAATCTGCTGCTTGCAAACAAA

AAAACCACCGCTACCAGCGGTGGTTTGTTTGCCGGATCAAGAGCT

ACCAACTCTTTTTCCGAAGGTAACTGGCTTCAGCAGAGCGCAGAT

ACCAAATACTGTTCTTCTAGTGTAGCCGTAGTTAGGCCACCACTT

CAAGAACTCTGTAGCACCGCCTACATACCTCGCTCTGCTAATCCT

GTTACCAGTGGCTGCTGCCAGTGGCGATAAGTCGTGTCTTACCGG

GTTGGACTCAAGACGATAGTTACCGGATAAGGCGCAGCGGTCGGG

CTGAACGGGGGGTTCGTGCACACAGCCCAGCTTGGAGCGAACGAC

CTACACCGAACTGAGATACCTACAGCGTGAGCTATGAGAAAGCGC

CACGCTTCCCGAAGGGAGAAAGGCGGACAGGTATCCGGTAAGCGG

CAGGGTCGGAACAGGAGAGCGCACGAGGGAGCTTCCAGGGGGAAA

CGCCTGGTATCTTTATAGTCCTGTCGGGTTTCGCCACCTCTGACT

TGAGCGTCGATTTTTGTGATGCTCGTCAGGGGGGCGGAGCCTATG

GAAAAACGCCAGCAACGCGGCCTTTTTACGGTTCCTGGCCTTTTG

CTGGCCTTTTGCTCACATGT pGW147-pAAV_EFS-LTR-h41BBL-WPRE-sPA (SEQ ID NO: 53)

CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

-continued

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TACcggtgccaccATGGAATACGCCTCTGACGCTTCACTGGACCC

CGAAGCCCCGTGGCCTCCCGCGCCCCGCGCTCGCGCCTGCCGCGT

ACTGCCTTGGGCCCTGGTCGCGGGGCTGCTGCTGCTGCTGCTGCT

CGCTGCCGCCTGCGCCGTCTTCCTCGCCTGCCCCTGGGCCGTGTC

CGGGGCTCGCGCCTCGCCCGGCTCCGCGGCCAGCCCGAGACTCCG

CGAGGGTCCCGAGCTTTCGCCCGACGATCCCGCCGGCCTCTTGGA

CCTGCGGCAGGGCATGTTTGCGCAGCTGGTGGCCCAAAATGTTCT

GCTGATCGATGGGCCCCTGAGCTGGTACAGTGACCCAGGCCTGGC

AGGCGTGTCCCTGACGGGGGGCCTGAGCTACAAAGAGGACACGAA

GGAGCTGGTGGTGGCCAAGGCTGGAGTCTACTATGTCTTCTTTCA

ACTAGAGCTGCGGCGCGTGGTGGCCGGCGAGGGCTCAGGCTCCGT

TTCACTTGCGCTGCACCTGCAGCCACTGCGCTCTGCTGCTGGGGC

CGCCGCCCTGGCTTTGACCGTGGACCTGCCACCCGCCTCCTCCGA

GGCTCGGAACTCGGCCTTCGGTTTCCAGGGCCGCTTGCTGCACCT

GAGTGCCGGCCAGCGCCTGGGCGTCCATCTTCACACTGAGGCCAG

GGCACGCCATGCCTGGCAGCTTACCCAGGGCGCCACAGTCTTGGG

ACTCTTCCGGGTGACCCCCGAAATCCCAGCCGGACTCCCTTCACC

GAGGTCGGAATGAGaattcacgcgttaagtcgacaatcaacctct ggattacaaaatttgtgaaagattgactggtattcttaactatgt tgctccttttacgctatgtggatacgctgctttaatgcctttgta tcatgctattgcttcccgtatggctttcattttctcctccttgta taaatcctggttgctgtctctttatgaggagttgtggcccgttgt caggcaacgtggcgtggtgtgcactgtgtttgctgacgcaaccccc actggttggggcattgccaccacctgtcagctcctttccgggggac tttcgctttccccctccctattgccacggcggaactcatcgccgc ctgccttgcccgctgctggacaggggctcggctgttgggcactga caattccgtggtgttgtcggggaaatcatcgtcctttccttggct gctcgcctgtgttgccacctggattctgcgcgggacgtccttctg ctacgtcccttcggccctcaatccagcggaccttccttcccgcgg cctgctgccggctctgcggcctcttccgcgtcttcgccttcgccc tcagacgagtcggatctccctttgggccgcctccccgcgtcgact ttaagaccaatgacGGCCgaataaaagatctttattttcattaga tctgtgtgttggttttttgtgtgcggccgcCAGGAACCCCTAGTGA

TGGAGTTGGCCACTCCCTCTCTGCGCGCTCGCTCGCTCACTGAGG

-continued

CCGGGCGACCAAAGGTCGCCCGACGCCCGGGCTTTGCCCGGGCGG

CCTCAGTGAGCGAGCGAGCGCGCAGCTGCCTGCAGGGGCGCCTGA

TGCGGTATTTTCTCCTTACGCATCTGTGCGGTATTTCACACCGCA

TACGTCAAAGCAACCATAGTACGCGCCCTGTAGCGGCGCATTAAG

CGCGGCGGGTGTGGTGGTTACGCGCAGCGTGACCGCTACACTTGC

CAGCGCCTTAGCGCCCGCTCCTTTCGCTTTCTTCCCTTCCTTTCT

CGCCACGTTCGCCGGCTTTCCCCGTCAAGCTCTAAATCGGGGGCT

CCCTTTAGGGTTCCGATTTAGTGCTTTACGGCACCTCGACCCCAA

AAAACTTGATTTGGGTGATGGTTCACGTAGTGGGCCATCGCCCTG

ATAGACGGTTTTTCGCCCTTTGACGTTGGAGTCCACGTTCTTTAA

TAGTGGACTCTTGTTCCAAACTGGAACAACACTCAACTCTATCTC

GGGCTATTCTTTTGATTTATAAGGGATTTTGCCGATTTCGGTCTA

TTGGTTAAAAAATGAGCTGATTTAACAAAAATTTAACGCGAATTT

TAACAAAATATTAACGTTTACAATTTTATGGTGCACTCTCAGTAC

AATCTGCTCTGATGCCGCATAGTTAAGCCAGCCCCGACACCCGCC

AACACCCGCTGACGCGCCCTGACGGGCTTGTCTGCTCCCGGCATC

CGCTTACAGACAAGCTGTGACCGTCTCCGGGAGCTGCATGTGTCA

GAGGTTTTCACCGTCATCACCGAAACGCGCGAGACGAAAGGGCCT

CGTGATACGCCTATTTTTATAGGTTAATGTCATGATAATAATGGT

TTCTTAGACGTCAGGTGGCACTTTTCGGGGAAATGTGCGCGGAAC

CCCTATTTGTTTATTTTTCTAAATACATTCAAATATGTATCCGCT

CATGAGACAATAACCCTGATAAATGCTTCAATAATATTGAAAAAG

GAAGAGTATGAGTATTCAACATTTCCGTGTCGCCCTTATTCCCTT

TTTTGCGGCATTTTGCCTTCCTGTTTTTGCTCACCCAGAAACGCT

GGTGAAAGTAAAAGATGCTGAAGATCAGTTGGGTGCACGAGTGGG

TTACATCGAACTGGATCTCAACAGCGGTAAGATCCTTGAGAGTTT

TCGCCCCGAAGAACGTTTTCCAATGATGAGCACTTTTAAAGTTCT

GCTATGTGGCGCGGTATTATCCCGTATTGACGCCGGGCAAGAGCA

ACTCGGTCGCCGCATACACTATTCTCAGAATGACTTGGTTGAGTA

CTCACCAGTCACAGAAAAGCATCTTACGGATGGCATGACAGTAAG

AGAATTATGCAGTGCTGCCATAACCATGAGTGATAACACTGCGGC

CAACTTACTTCTGACAACGATCGGAGGACCGAAGGAGCTAACCGC

TTTTTTGCACAACATGGGGGATCATGTAACTCGCCTTGATCGTTG

GGAACCGGAGCTGAATGAAGCCATACCAAACGACGAGCGTGACAC

CACGATGCCTGTAGCAATGGCAACAACGTTGCGCAAACTATTAAC

TGGCGAACTACTTACTCTAGCTTCCCGGCAACAATTAATAGACTG

GATGGAGGCGGATAAAGTTGCAGGACCACTTCTGCGCTCGGCCCT

TCCGGCTGGCTGGTTTATTGCTGATAAATCTGGAGCCGGTGAGCG

TGGAAGCCGCGGTATCATTGCAGCACTGGGGCCAGATGGTAAGCC

CTCCCGTATCGTAGTTATCTACACGACGGGGAGTCAGGCAACTAT

-continued

GGATGAACGAAATAGACAGATCGCTGAGATAGGTGCCTCACTGAT

TAAGCATTGGTAACTGTCAGACCAAGTTTACTCATATATACTTTA

GATTGATTTAAAACTTCATTTTTAATTTAAAAGGATCTAGGTGAA

GATCCTTTTTGATAATCTCATGACCAAAATCCCTTAACGTGAGTT

TTCGTTCCACTGAGCGTCAGACCCCGTAGAAAAGATCAAAGGATC

TTCTTGAGATCCTTTTTTTCTGCGCGTAATCTGCTGCTTGCAAAC

AAAAAAACCACCGCTACCAGCGGTGGTTTGTTTGCCGGATCAAGA

GCTACCAACTCTTTTTCCGAAGGTAACTGGCTTCAGCAGAGCGCA

GATACCAAATACTGTTCTTCTAGTGTAGCCGTAGTTAGGCCACCA

CTTCAAGAACTCTGTAGCACCGCCTACATACCTCGCTCTGCTAAT

CCTGTTACCAGTGGCTGCTGCCAGTGGCGATAAGTCGTGTCTTAC

CGGGTTGGACTCAAGACGATAGTTACCGGATAAGGCGCAGCGGTC

GGGCTGAACGGGGGGTTCGTGCACACAGCCCAGCTTGGAGCGAAC

GACCTACACCGAACTGAGATACCTACAGCGTGAGCTATGAGAAAG

CGCCACGCTTCCCGAAGGGAGAAAGGCGGACAGGTATCCGGTAAG

CGGCAGGGTCGGAACAGGAGAGCGCACGAGGGAGCTTCCAGGGGG

AAACGCCTGGTATCTTTATAGTCCTGTCGGGTTTCGCCACCTCTG

ACTTGAGCGTCGATTTTTGTGATGCTCGTCAGGGGGGCGGAGCCT

ATGGAAAAACGCCAGCAACGCGGCCTTTTTACGGTTCCTGGCCTT

TTGCTGGCCTTTTGCTCACATGT pGW149-pAAV_EFS-LTR-hLIGHT(Remove-EQLI)-
RSR-WPRE-sPA (SEQ ID NO: 54)

CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccATGGAGGAGAGTGTCGTACGGCCCTCAGTGTT

TGTGGTGGATGGACAGACCGACATCCCATTCACGAGGCTGGGACG

AAGCCACCGGAGACAGTCGTCAGTGTGGCCCGGGTGGGTCTGGG

TCTCTTGCTGTTGCTGATGGGGGCCGGGCTGGCCGTCCAAGGCTG

```
GTTCCTCCTGCAGCTGCACTGGCGTCTAGGAGAGATGGTCACCCG

CCTGCCTGACGGACCTGCAGGCTCCTGGCAAGAGCGAAGGTCTCA

CGAGGTCAACCCAGCAGCGCATCTCACAGGGGCCAACTCCAGCTT

GACCGGCAGCGGGGGCCGCTGTTATGGGAGACTCAGCTGGGCCT

GGCCTTCCTGAGGGGCCTCAGCTACCACGATGGGGCCCTTGTGGT

CACCAAAGCTGGCTACTACTACATCTACTCCAAGGTGCAGCTGGG

CGGTGTGGGCTGCCCGCTGGGCCTGGCCAGCACCATCACCCACGG

CCTCTACAAGCGCACACCCCGCTACCCCGAGGAGCTGGAGCTGTT

GGTCAGCCAGCAGTCACCCTGCGGACGGGCCACCAGCAGCTCCCG

GGTCTGGTGGGACAGCAGCTTCCTGGGTGGTGTGGTACACCTGGA

GGCTGGGGAGAAGGTGGTCGTCCGTGTGCTGGATGAACGCCTGGT

TCGACTGCGTGATGGTACCCGGTCTTACTTCGGGGCTTTCATGGT

GggtggaggcggttgcggaaagcgtaagTGAGaattcacgcgtta agtcgacaatcaacctctggattacaaaatttgtgaaagattgac tggtattcttaactatgttgctccttttacgctatgtggatacgc tgctttaatgcctttgtatcatgctattgcttcccgtatggcttt cattttctcctccttgtataaatcctggttgctgtctctttatga ggagttgtggcccgttgtcaggcaacgtggcgtggtgtgcactgt gtttgctgacgcaacccccactggttggggcattgccaccacctg tcagctcctttccgggactttcgctttcccctccctattgccac ggcggaactcatcgccgctgccttgcccgctgctggacaggggc tcggctgttgggcactgacaattccgtggtgttgtcggggaaatc atcgtcctttccttggctgctcgcctgtgttgccacctggattct gcgcgggacgtccttctgctacgtccttcggccctcaatccagc ggaccttccttcccgcggcctgctgccggctctgcggcctcttcc gcgtcttcgccttcgccctcagacgagtcggatctccctttgggc cgcctccccgcgtcgactttaagaccaatgacGGCCGaataaaag atctttattttcattagatctgtgtgttggttttttgtgtgcggc cgCAGGAACCCCTAGTGATGGAGTTGGCCACTCCCTCTCTGCGCG

CTCGCTCGCTCACTGAGGCCGGGCGACCAAAGGTCGCCCGACGCC

CGGGCTTTGCCCGGCGGCCTCAGTGAGCGAGCGAGCGCGCAGCT

GCCTGCAGGGGCGCCTGATGCGGTATTTTCTCCTTACGCATCTGT

GCGGTATTTCACACCGCATACGTCAAAGCAACCATAGTACGCGCC

CTGTAGCGGCGCATTAAGCGCGGCGGGTGTGGTGGTTACGCGCAG

CGTGACCGCTACACTTGCCAGCGCCTTAGCGCCCGCTCCTTTCGC

TTTCTTCCCTTCCTTTCTCGCCACGTTCGCCGGCTTTCCCCGTCA

AGCTCTAAATCGGGGGCTCCCTTTAGGGTTCCGATTTAGTGCTTT

ACGGCACCTCGACCCCAAAAAACTTGATTTGGGTGATGGTTCACG

TAGTGGGCCATCGCCCTGATAGACGGTTTTTCGCCCTTTGACGTT

GGAGTCCACGTTCTTTAATAGTGGACTCTTGTTCCAAACTGGAAC

AACACTCAACTCTATCTCGGGCTATTCTTTTGATTTATAAGGGAT
```

```
TTTGCCGATTTCGGTCTATTGGTTAAAAAATGAGCTGATTTAACA

AAAATTTAACGCGAATTTTAACAAAATATTAACGTTTACAATTTT

ATGGTGCACTCTCAGTACAATCTGCTCTGATGCCGCATAGTTAAG

CCAGCCCCGACACCCGCCAACACCCGCTGACGCGCCCTGACGGGC

TTGTCTGCTCCCGGCATCCGCTTACAGACAAGCTGTGACCGTCTC

CGGGAGCTGCATGTGTCAGAGGTTTTCACCGTCATCACCGAAACG

CGCGAGACGAAAGGGCCTCGTGATACGCCTATTTTTATAGGTTAA

TGTCATGATAATAATGGTTTCTTAGACGTCAGGTGGCACTTTTCG

GGGAAATGTGCGCGGAACCCCTATTTGTTTATTTTTCTAAATACA

TTCAAATATGTATCCGCTCATGAGACAATAACCCTGATAAATGCT

TCAATAATATTGAAAAAGGAAGAGTATGAGTATTCAACATTTCCG

TGTCGCCCTTATTCCCTTTTTTGCGGCATTTTGCCTTCCTGTTTT

TGCTCACCCAGAAACGCTGGTGAAAGTAAAAGATGCTGAAGATCA

GTTGGGTGCACGAGTGGGTTACATCGAACTGGATCTCAACAGCGG

TAAGATCCTTGAGAGTTTTCGCCCCGAAGAACGTTTTCCAATGAT

GAGCACTTTTAAAGTTCTGCTATGTGGCGCGGTATTATCCCGTAT

TGACGCCGGGCAAGAGCAACTCGGTCGCCGCATACACTATTCTCA

GAATGACTTGGTTGAGTACTCACCAGTCACAGAAAAGCATCTTAC

GGATGGCATGACAGTAAGAGAATTATGCAGTGCTGCCATAACCAT

GAGTGATAACACTGCGGCCAACTTACTTCTGACAACGATCGGAGG

ACCGAAGGAGCTAACCGCTTTTTTGCACAACATGGGGGATCATGT

AACTCGCCTTGATCGTTGGGAACCGGAGCTGAATGAAGCCATACC

AAACGACGAGCGTGACACCACGATGCCTGTAGCAATGGCAACAAC

GTTGCGCAAACTATTAACTGGCGAACTACTTACTCTAGCTTCCCG

GCAACAATTAATAGACTGGATGGAGGCGGATAAAGTTGCAGGACC

ACTTCTGCGCTCGGCCCTTCCGGCTGGCTGGTTTATTGCTGATAA

ATCTGGAGCCGGTGAGCGTGGAAGCCGCGGTATCATTGCAGCACT

GGGGCCAGATGGTAAGCCCTCCCGTATCGTAGTTATCTACACGAC

GGGGAGTCAGGCAACTATGGATGAACGAAATAGACAGATCGCTGA

GATAGGTGCCTCACTGATTAAGCATTGGTAACTGTCAGACCAAGT

TTACTCATATATACTTTAGATTGATTTAAAACTTCATTTTTAATT

TAAAAGGATCTAGGTGAAGATCCTTTTTGATAATCTCATGACCAA

AATCCCTTAACGTGAGTTTTCGTTCCACTGAGCGTCAGACCCCGT

AGAAAAGATCAAAGGATCTTCTTGAGATCCTTTTTTTCTGCGCGT

AATCTGCTGCTTGCAAACAAAAAAACCACCGCTACCAGCGGTGGT

TTGTTTGCCGGATCAAGAGCTACCAACTCTTTTTCCGAAGGTAAC

TGGCTTCAGCAGAGCGCAGATACCAAATACTGTTCTTCTAGTGTA

GCCGTAGTTAGGCCACCACTTCAAGAACTCTGTAGCACCGCCTAC

ATACCTCGCTCTGCTAATCCTGTTACCAGTGGCTGCTGCCAGTGG

CGATAAGTCGTGTCTTACCGGGTTGGACTCAAGACGATAGTTACC
```

-continued

```
GGATAAGGCGCAGCGGTCGGGCTGAACGGGGGGTTCGTGCACACA

GCCCAGCTTGGAGCGAACGACCTACACCGAACTGAGATACCTACA

GCGTGAGCTATGAGAAAGCGCCACGCTTCCCGAAGGGAGAAAGGC

GGACAGGTATCCGGTAAGCGGCAGGGTCGGAACAGGAGAGCGCAC

GAGGGAGCTTCCAGGGGGAAACGCCTGGTATCTTTATAGTCCTGT

CGGGTTTCGCCACCTCTGACTTGAGCGTCGATTTTTGTGATGCTC

GTCAGGGGGGCGGAGCCTATGGAAAAACGCCAGCAACGCGGCCTT

TTTTACGGTTCCTGGCCTTTTGCTGGCCTTTTGCTCACATGT
``` pGW036-EFS-dSaCas9-VP64

(SEQ ID NO: 55)

```
CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccatggcccaaagaagaagcggaaggtcggtat ccacggagtcccagcagccaagcggaactacatcctgggcctggc catcggcatcaccagcgtgggctacggcatcatcgactacgagac acgggacgtgatcgatgccggcgtgcggctgttcaaagaggccaa cgtggaaaacaacgagggcaggcggagcaagagaggcgccagaag gctgaagcggcggaggcggcatagaatccagagagtgaagaagct gctgttcgactacaacctgctgaccgaccacagcgagctgagcgg catcaacccctacgaggccagagtgaagggcctgagccagaagct gagcgaggaagagttctctgccgccctgctgcacctggccaagag aagaggcgtgcacaacgtgaacgaggtggaagaggacaccggcaa cgagctgtccaccaaagagcagatcagccggaacagcaaggccct ggaagagaaatacgtggccgaactgcagctggaacggctgaagaa agacggcgaagtgcggggcagcatcaacagattcaagaccagcga ctacgtgaaagaagccaaacagctgctgaaggtgcagaaggccta ccaccagctggaccagagcttcatcgacacctacatcgacctgct ggaaacccggcggacctactatgagggacctggcgagggcagccc cttcggctggaaggacatcaaagaatggtacgagatgctgatggg
```

-continued

```
ccactgcacctacttccccgaggaactgcggagcgtgaagtacgc ctacaacgccgacctgtacaacgccctgaacgacctgaacaatct cgtgatcaccagggacgagaacgagaagctggaatattacgagaa gttccagatcatcgagaacgtgttcaagcagaagaagaagcccac cctgaagcagatcgccaaagaaatcctcgtgaacgaagaggatat taagggctacagagtgaccagcaccggcaagcccgagttcaccaa cctgaaggtgtaccacgacatcaaggacattaccgcccggaaaga gattattgagaacgccgagctgctggatcagattgccaagatcct gaccatctaccagagcagcgaggacatccaggaagaactgaccaa tctgaactccgagctgacccaggaagagatcgagcagatctctaa tctgaagggctataccggcacccacaacctgagcctgaaggccat caacctgatcctggacgagctgtggcacaccaacgacaaccagat cgctatcttcaaccggctgaagctggtgcccaagaaggtggacct gtcccagcagaaagagatccccaccaccctggtggacgacttcat cctgagccccgtcgtgaagagaagcttcatccagagcatcaaagt gatcaacgccatcatcaagaagtacggcctgcccaacgacatcat tatcgagctggcccgcgagaagaactccaaggacgcccagaaaat gatcaacgagatgcagaagcggaaccggcagaccaacgagcggat cgaggaaatcatccggaccaccggcaaagagaacgccaagtacct gatcgagaagatcaagctgcacgacatgcaggaaggcaagtgcct gtacagcctggaagccatccctctggaagatctgctgaacaaccc cttcaactatgaggtggaccacatcatcccccagaagcgtgtcctt cgacaacagcttcaacaacaaggtgctcgtgaagcaggaagaagc cagcaagaagggcaaccggacccccattccagtacctgagcagcag cgacagcaagatcagctacgaaaccttcaagaagcacatcctgaa tctggccaagggcaagggcagaatcagcaagaccaagaaagagta tctgctggaagaacgggacatcaacaggttctccgtgcagaaaga cttcatcaaccggaacctggtggataccagatacgccaccagagg cctgatgaacctgctgcgcgagctacttcagagtgaacaacctgga cgtgaaagtgaagtccatcaatggcggcttcaccagctttctgcg gcggaagtggaagtttaagaaagagcggaacaagggtacaagca ccacgccgaggacgccctgatcattgccaacgccgatttcatctt caaagagtggaagaaactggacaaggccaaaaaagtgatggaaaa ccagatgttcgaggaaaagcaggccgagagcatgcccgagatcga aaccgagcaggagtacaaagagatcttcatcacccccaccagat caagcacattaaggacttcaaggactacaagtacagccaccgggt ggacaagagcctaatagagagctgattaacgacaccctgtactc cacccggaaggacgacaagggcaacaccctgatcgtgaacaatct gaacggcctgtacgacaaggacaatgacaagctgaaaaagctgat caacaagagccccgaaaagctgctgatgtaccaccacgacccccca
```

-continued gacctaccagaaactgaagctgattatggaacagtacggcgacga gaagaatcccctgtacaagtactacgaggaaaccgggaactacct gaccaagtactccaaaaaggacaacggccccgtgatcaagaagat taagtattacggcaacaaactgaacgcccatctggacatcaccga cgactaccccaacagcagaaacaaggtcgtgaagctgtccctgaa gccctacagattcgacgtgtacctggacaatggcgtgtacaagtt cgtgaccgtgaagaatctggatgtgatcaaaaaagaaaactacta cgaagtgaatagcaagtgctatgaggaagctaagaagctgaagaa gatcagcaaccaggccgagtttatcgcctccttctacaacaacga tctgatcaagatcaacggcgagctgtatagagtgatcggcgtgaa caacgacctgctgaaccggatcgaagtgaacatgatcgacatcac ctaccgcgagtacctggaaaacatgaacgacaagaggccccccag gatcattaagacaatcgcctccaagacccagagcattaagaagta cagcacagacattctgggcaacctgtatgaagtgaaatctaagaa gcaccctcagatcatcaaaaagggcaaaaggccggcggccacgaa aaaggccggccaggcaaaaaagaaaaagggatccGGACGGGCTGA

CGCATTGGACGATTTTGATCTGGATATGCTGGGAAGTGACGCCCT

CGATGATTTTGACCTTGACATGCTTGGTTCGGATGCCCTTGATGA

CTTTGACCTCGACATGCTCGGCAGTGACGCCCTTGATGATTTCGA

CCTGGACATGCTGATTTAAGAATTCAATAAAAGATCTTTATTTTC

ATTAGATCTGTGTGTTGGTTTTTTGTGTGCGGCCGCAGGAACCCC

TAGTGATGGAGTTGGCCACTCCCTCTCTGCGCGCTCGCTCGCTCA

CTGAGGCCGGGCGACCAAAGGTCGCCCGACGCCCGGGCTTTGCCC

GGGCGGCCTCAGTGAGCGAGCGAGCGCGCAGCTGCCTGCAGGGGC

GCCTGATGCGGTATTTTCTCCTTACGCATCTGTGCGGTATTTCAC

ACCGCATACGTCAAAGCAACCATAGTACGCGCCCTGTAGCGGCGC

ATTAAGCGCGGCGGGTGTGGTGGTTACGCGCAGCGTGACCGCTAC

ACTTGCCAGCGCCTTAGCGCCCGCTCCTTTCGCTTTCTTCCCTTC

CTTTCTCGCCACGTTCGCCGGCTTTCCCCGTCAAGCTCTAAATCG

GGGGCTCCCTTTAGGGTTCCGATTTAGTGCTTTACGGCACCTCGA

CCCCAAAAAACTTGATTTGGGTGATGGTTCACGTAGTGGGCCATC

GCCCTGATAGACGGTTTTTCGCCCTTTGACGTTGGAGTCCACGTT

CTTTAATAGTGGACTCTTGTTCCAAACTGGAACAACACTCAACTC

TATCTCGGGCTATTCTTTTGATTTATAAGGGATTTTGCCGATTTC

GGTCTATTGGTTAAAAAATGAGCTGATTTAACAAAAATTTAACGC

GAATTTTAACAAAATATTAACGTTTACAATTTTATGGTGCACTCT

CAGTACAATCTGCTCTGATGCCGCATAGTTAAGCCAGCCCCGACA

CCCGCCAACACCCGCTGACGCGCCCTGACGGGCTTGTCTGCTCCC

GGCATCCGCTTACAGACAAGCTGTGACCGTCTCCGGGAGCTGCAT

GTGTCAGAGGTTTTCACCGTCATCACCGAAACGCGCGAGACGAAA

GGGCCTCGTGATACGCCTATTTTTATAGGTTAATGTCATGATAAT

-continued

AATGGTTTCTTAGACGTCAGGTGGCACTTTTCGGGGAAATGTGCG

CGGAACCCCTATTTGTTTATTTTTCTAAATACATTCAAATATGTA

TCCGCTCATGAGACAATAACCCTGATAAATGCTTCAATAATATTG

AAAAAGGAAGAGTATGAGTATTCAACATTTCCGTGTCGCCCTTAT

TCCCTTTTTTGCGGCATTTTGCCTTCCTGTTTTTGCTCACCCAGA

AACGCTGGTGAAAGTAAAAGATGCTGAAGATCAGTTGGGTGCACG

AGTGGGTTACATCGAACTGGATCTCAACAGCGGTAAGATCCTTGA

GAGTTTTCGCCCCGAAGAACGTTTTCCAATGATGAGCACTTTTAA

AGTTCTGCTATGTGGCGCGGTATTATCCCGTATTGACGCCGGGCA

AGAGCAACTCGGTCGCCGCATACACTATTCTCAGAATGACTTGGT

TGAGTACTCACCAGTCACAGAAAAGCATCTTACGGATGGCATGAC

AGTAAGAGAATTATGCAGTGCTGCCATAACCATGAGTGATAACAC

TGCGGCCAACTTACTTCTGACAACGATCGGAGGACCGAAGGAGCT

AACCGCTTTTTTGCACAACATGGGGGATCATGTAACTCGCCTTGA

TCGTTGGGAACCGGAGCTGAATGAAGCCATACCAAACGACGAGCG

TGACACCACGATGCCTGTAGCAATGGCAACAACGTTGCGCAAACT

ATTAACTGGCGAACTACTTACTCTAGCTTCCCGGCAACAATTAAT

AGACTGGATGGAGGCGGATAAAGTTGCAGGACCACTTCTGCGCTC

GGCCCTTCCGGCTGGCTGGTTTATTGCTGATAAATCTGGAGCCGG

TGAGCGTGGAAGCCGCGGTATCATTGCAGCACTGGGGCCAGATGG

TAAGCCCTCCCGTATCGTAGTTATCTACACGACGGGGAGTCAGGC

AACTATGGATGAACGAAATAGACAGATCGCTGAGATAGGTGCCTC

ACTGATTAAGCATTGGTAACTGTCAGACCAAGTTTACTCATATAT

ACTTTAGATTGATTTAAAACTTCATTTTTAATTTAAAAGGATCTA

GGTGAAGATCCTTTTTGATAATCTCATGACCAAAATCCCTTAACG

TGAGTTTTCGTTCCACTGAGCGTCAGACCCCGTAGAAAAGATCAA

AGGATCTTCTTGAGATCCTTTTTTTCTGCGCGTAATCTGCTGCTT

GCAAACAAAAAAACCACCGCTACCAGCGGTGGTTTGTTTGCCGGA

TCAAGAGCTACCAACTCTTTTTCCGAAGGTAACTGGCTTCAGCAG

AGCGCAGATACCAAATACTGTTCTTCTAGTGTAGCCGTAGTTAGG

CCACCACTTCAAGAACTCTGTAGCACCGCCTACATACCTCGCTCT

GCTAATCCTGTTACCAGTGGCTGCTGCCAGTGGCGATAAGTCGTG

TCTTACCGGGTTGGACTCAAGACGATAGTTACCGGATAAGGCGCA

GCGGTCGGGCTGAACGGGGGGTTCGTGCACACAGCCCAGCTTGGA

GCGAACGACCTACACCGAACTGAGATACCTACAGCGTGAGCTATG

AGAAAGCGCCACGCTTCCCGAAGGGAGAAAGGCGGACAGGTATCC

GGTAAGCGGCAGGGTCGGAACAGGAGAGCGCACGAGGGAGCTTCC

AGGGGGAAACGCCTGGTATCTTTATAGTCCTGTCGGGTTTCGCCA

-continued

```
CCTCTGACTTGAGCGTCGATTTTTGTGATGCTCGTCAGGGGGGCG

GAGCCTATGGAAAAACGCCAGCAACGCGGCCTTTTTACGGTTCCT

GGCCTTTTGCTGGCCTTTTGCTCACATGT
``` pGW011b_pAAV-EFS-dCAS9-spA (SEQ ID NO: 56)
```
cctgcaggcagctgcgcgctcgctcgctcactgaggccgcccggg caaagcccgggcgtcgggcgacctttggtcgcccggcctcagtga gcgagcgagcgcgcagagagggagtggccaactccatcactaggg gttcctgcggccgcacgcgttctaggtcttgaaaggagtgggaat tggctccggtgcccgtcagtgggcagagcgcacatcgcccacagt ccccgagaagttggggggagggggtcggcaattgatccggtgccta gagaaggtggcgcggggtaaactgggaaagtgatgtcgtgtactg gctccgcctttttcccgagggtggggagaaccgtatataagtgc agtagtcgccgtgaacgttcttttcgcaacgggtttgccgccag aacacaggTGTCGTGACGCGcGTACGtaatacgactcactatagg gccgccaccATGAAAAGGCCGGCGGCCACGAAAAAGGCCGGCCAG

GCAAAAAAGAAAAAGGACAAGAAGTACAGCATCGGCCTGGCCATC

GGCACCAACTCTGTGGGCTGGGCCGTGATCACCGACGAGTACAAG

GTGCCCAGCAAGAAATTCAAGGTGCTGGGCAACACCGACCGGCAC

AGCATCAAGAAGAACCTGATCGGAGCCCTGCTGTTCGACAGCGGC

GAAACAGCCGAGGCCACCCGGCTGAAGAGAACCGCCAGAAGAAGA

TACACCAGACGGAAGAACCGGATCTGCTATCTGCAAGAGATCTTC

AGCAACGAGATGGCCAAGGTGGACGACAGCTTCTTCCACAGACTG

GAAGAGTCCTTCCTGGTGGAAGAGGATAAGAAGCACGAGCGGCAC

CCCATCTTCGGCAACATCGTGGACGAGGTGGCCTACCACGAGAAG

TACCCCACCATCTACCACCTGAGAAAGAAACTGGTGGACAGCACC

GACAAGGCCGACCTGCGGCTGATCTATCTGGCCCTGGCCCACATG

ATCAAGTTCCGGGGCCACTTCCTGATCGAGGGCGACCTGAACCCC

GACAACAGCGACGTGGACAAGCTGTTCATCCAGCTGGTGCAGACC

TACAACCAGCTGTTCGAGGAAAACCCCATCAACGCCAGCGGCGTG

GACGCCAAGGCCATCCTGTCTGCCAGACTGAGCAAGAGCAGACGG

CTGGAAAATCTGATCGCCCAGCTGCCCGGCGAGAAGAAGAATGGC

CTGTTCGGCAACCTGATTGCCCTGAGCCTGGGCCTGACCCCCAAC

TTCAAGAGCAACTTCGACCTGGCCGAGGATGCCAAACTGCAGCTG

AGCAAGGACACCTACGACGACGACCTGGACAACCTGCTGGCCCAG

ATCGGCGACCAGTACGCCGACCTGTTTCTGGCCGCCAAGAACCTG

TCCGACGCCATCCTGCTGAGCGACATCCTGAGAGTGAACACCGAG

ATCACCAAGGCCCCCCTGAGCGCCTCTATGATCAAGAGATACGAC

GAGCACCACCAGGACCTGACCCTGCTGAAAGCTCTCGTGCGGCAG

CAGCTGCCTGAAGTACAAAGAGATTTTCTTCGACCAGAGCAAG

AACGGCTACGCCGGCTACATTGACGGCGGAGCCAGCCAGGAAGAG

TTCTACAAGTTCATCAAGCCCATCCTGGAAAAGATGGACGGCACC
```

-continued

```
GAGGAACTGCTCGTGAAGCTGAACAGAGAGGACCTGCTGCGGAAG

CAGCGGACCTTCGACAACGGCAGCATCCCCCACCAGATCCACCTG

GGAGAGCTGCACGCCATTCTGCGGCGGCAGGAAGATTTTTACCCA

TTCCTGAAGGACAACCGGGAAAAGATCGAGAAGATCCTGACCTTC

CGCATCCCCTACTACGTGGGCCCTCTGGCCAGGGGAAACAGCAGA

TTCGCCTGGATGACCAGAAAGAGCGAGGAAACCATCACCCCCTGG

AACTTCGAGGAAGTGGTGGACAAGGGCGCTTCCGCCCAGAGCTTC

ATCGAGCGGATGACCAACTTCGATAAGAACCTGCCCAACGAGAAG

GTGCTGCCCAAGCACAGCCTGCTGTACGAGTACTTCACCGTGTAT

AACGAGCTGACCAAAGTGAAATACGTGACCGAGGGAATGAGAAAG

CCCGCCTTCCTGAGCGGCGAGCAGAAAAAGGCCATCGTGGACCTG

CTGTTCAAGACCAACCGGAAAGTGACCGTGAAGCAGCTGAAAGAG

GACTACTTCAAGAAAATCGAGTGCTTCGACTCCGTGGAAATCTCC

GGCGTGGAAGATCGGTTCAACGCCTCCCTGGGCACATACCACGAT

CTGCTGAAAATTATCAAGGACAAGGACTTCCTGGACAATGAGGAA

AACGAGGACATTCTGGAAGATATCGTGCTGACCCTGACACTGTTT

GAGGACAGAGAGATGATCGAGGAACGGCTGAAAACCTATGCCCAC

CTGTTCGACGACAAAGTGATGAAGCAGCTGAAGCGGCGGAGATAC

ACCGGCTGGGGCAGGCTGAGCCGGAAGCTGATCAACGGCATCCGG

GACAAGCAGTCCGGCAAGACAATCCTGGATTTCCTGAAGTCCGAC

GGCTTCGCCAACAGAAACTTCATGCAGCTGATCCACGACGACAGC

CTGACCTTTAAAGAGGACATCCAGAAAGCCCAGGTGTCCGGCCAG

GGCGATAGCCTGCACGAGCACATTGCCAATCTGGCCGGCAGCCCC

GCCATTAAGAAGGGCATCCTGCAGACAGTGAAGGTGGTGGACGAG

CTCGTGAAAGTGATGGGCCGGCACAAGCCCGAGAACATCGTGATC

GAAATGGCCAGAGAGAACCAGACCACCCAGAAGGGACAGAAGAAC

AGCCGCGAGAGAATGAAGCGGATCGAAGAGGGCATCAAAGAGCTG

GGCAGCCAGATCCTGAAAGAACACCCCGTGGAAAACACCCAGCTG

CAGAACGAGAAGCTGTACCTGTACTACCTGCAGAATGGGCGGGAT

ATGTACGTGGACCAGGAACTGGACATCAACCGGCTGTCCGACTAC

GATGTGGACCACATCGTGCCTCAGAGCTTTCTGAAGGACGACTCC

ATCGACAACAAGGTGCTGACCAGAAGCGACAAGGCCCGGGGCAAG

AGCGACAACGTGCCCTCCGAAGAGGTCGTGAAGAAGATGAAGAAC

TACTGGCGGCAGCTGCTGAACGCCAAGCTGATTACCCAGAGAAAG

TTCGACAATCTGACCAAGGCCGAGAGAGGCGGCCTGAGCGAACTG

GATAAGGCCGGCTTCATCAAGAGACAGCTGGTGGAAACCCGGCAG

ATCACAAAGCACGTGGCACAGATCCTGGACTCCCGGATGAACACT

AAGTACGACGAGAATGACAAGCTGATCCGGGAAGTGAAAGTGATC

ACCCTGAAGTCCAAGCTGGTGTCCGATTTCCGGAAGGATTTCCAG

TTTTACAAAGTGCGCGAGATCAACAACTACCACCACGCCCACGAC
```

GCCTACCTGAACGCCGTCGTGGGAACCGCCCTGATCAAAAAGTAC

CCTAAGCTGGAAAGCGAGTTCGTGTACGGCGACTACAAGGTGTAC

GACGTGCGGAAGATGATCGCCAAGAGCGAGCAGGAAATCGGCAAG

GCTACCGCCAAGTACTTCTTCTACAGCAACATCATGAACTTTTTC

AAGACCGAGATTACCCTGGCCAACGGCGAGATCCGGAAGCGGCCT

CTGATCGAGACAAACGGCGAAACCGGGGAGATCGTGTGGGATAAG

GGCCGGGATTTTGCCACCGTGCGGAAAGTGCTGAGCATGCCCCAA

GTGAATATCGTGAAAAAGACCGAGGTGCAGACAGGCGGCTTCAGC

AAAGAGTCTATCCTGCCCAAGAGGAACAGCGATAAGCTGATCGCC

AGAAAGAAGGACTGGGACCCTAAGAAGTACGGCGGCTTCGACAGC

CCCACCGTGGCCTATTCTGTGCTGGTGGTGGCCAAAGTGGAAAAG

GGCAAGTCCAAGAAACTGAAGAGTGTGAAAGAGCTGCTGGGGATC

ACCATCATGGAAAGAAGCAGCTTCGAGAAGAATCCCATCGACTTT

CTGGAAGCCAAGGGCTACAAAGAAGTGAAAAAGGACCTGATCATC

AAGCTGCCTAAGTACTCCCTGTTCGAGCTGGAAAACGGCCGGAAG

AGAATGCTGGCCTCTGCCGGCGAACTGCAGAAGGGAAACGAACTG

GCCCTGCCCTCCAAATATGTGAACTTCCTGTACCTGGCCAGCCAC

TATGAGAAGCTGAAGGGCTCCCCCGAGGATAATGAGCAGAAACAG

CTGTTTGTGGAACAGCACAAGCACTACCTGGACGAGATCATCGAG

CAGATCAGCGAGTTCTCCAAGAGAGTGATCCTGGCCGACGCTAAT

CTGGACAAAGTGCTGTCCGCCTACAACAAGCACCGGGATAAGCCC

ATCAGAGAGCAGGCCGAGAATATCATCCACCTGTTTACCCTGACC

AATCTGGGAGCCCCTGCCGCCTTCAAGTACTTTGACACCACCATC

GACCGGAAGAGGTACACCAGCACCAAAGAGGTGCTGGACGCCACC

CTGATCCACCAGAGCATCACCGGCCTGTACGAGACACGGATCGAC

CTGTCTCAGCTGGGAGGCGACagccctaagaaaaagaggaaggtg

AGCtgagaattcAATAAATAAAAGATCTTTATTTTCATTAGATCT

GTGTGTTGGTTTTTTGTGTGcggaccgagcggccgcaggaacccc tagtgatggagttggccactccctctctgcgcgctcgctcgctca ctgaggccgggcgaccaaaggtcgcccgacgcccgggctttgccc gggcggcctcagtgagcgagcgagcgcgcagctgcctgcaggggc gcctgatgcggtattttctccttacgcatctgtgcggtatttcac accgcatacgtcaaagcaaccatagtacgcgccctgtagcggcgc attaagcgcggcgggtgtggtggttacgcgcagcgtgaccgctac acttgccagcgccctagcgcccgctcctttcgctttcttcccttc ctttctcgccacgttcgccggctttccccgtcaagctctaaatcg ggggctccctttagggttccgatttagtgctttacggcacctcga ccccaaaaaacttgattgggtgatggttcacgtagtgggccatc gccctgatagacggtttttcgccctttgacgttggagtccacgtt ctttaatagtggactcttgttccaaactggaacaacactcaaccc tatctcgggctattcttttgatttataagggattttgccgatttc ggcctattggttaaaaaatgagctgatttaacaaaaatttaacgc gaattttaacaaaatattaacgtttacaattttatggtgcactct cagtacaatctgctctgatgccgcatagttaagccagccccgaca cccgccaacacccgctgacgcgccctgacgggcttgtctgctccc ggcatccgcttacagacaagctgtgaccgtctccgggagctgcat gtgtcagaggttttcaccgtcatcaccgaaacgcgcgagacgaaa gggcctcgtgatacgcctatttttataggttaatgtcatgataat aatggtttcttagacgtcaggtggcacttttcggggaaatgtgcg cggaacccctatttgtttattttttctaaatacattcaaatatgta tccgctcatgagacaataaccctgataaatgcttcaataatattg aaaaaggaagagtatgagtattcaacatttccgtgtcgcccttat tcccttttttgcggcattttgccttcctgttttttgctcacccaga aacgctggtgaaagtaaaagatgctgaagatcagttgggtgcacg agtgggttacatcgaactggatctcaacagcggtaagatccttga gagtttttcgccccgaagaacgttttccaatgatgagcacttttaa agttctgctatgtggcgcggtattatcccgtattgacgccgggca agagcaactcggtcgccgcatacactattctcagaatgacttggt tgagtactcaccagtcacagaaaagcatcttacggatggcatgac agtaagagaattatgcagtgctgccataaccatgagtgataacac tgcggccaacttacttctgacaacgatcggaggaccgaaggagct aaccgctttttttgcacaacatgggggatcatgtaactcgccttga tcgttgggaaccggagctgaatgaagccataccaaacgacgagcg tgacaccacgatgcctgtagcaatggcaacaacgttgcgcaaact attaactggcgaactacttactctagcttcccggcaacaattaat agactggatggaggcggataaagttgcaggaccacttctgcgctc ggcccttccggctggctggtttattgctgataaatctggagccgg tgagcgtgggtctcgcggtatcattgcagcactggggccagatgg taagccctcccgtatcgtagttatctacacgacggggagtcaggc aactatggatgaacgaaatagacagatcgctgagataggtgcctc actgattaagcattggtaactgtcagaccaagtttactcatatat actttagattgatttaaaacttcattttttaattttaaaaggatcta ggtgaagatcctttttgataatctcatgaccaaaatcccttaacg tgagttttcgttccactgagcgtcagaccccgtagaaaagatcaa aggatcttcttgagatcctttttttctgcgcgtaatctgctgctt gcaaacaaaaaaaccaccgctaccagcggtggtttgtttgccgga tcaagagctaccaactctttttccgaaggtaactggcttcagcag agcgcagataccaaatactgtccttctagtgtagccgtagttagg ccaccacttcaagaactctgtagcaccgcctacatacctcgctct gctaatcctgttaccagtggctgctgccagtggcgataagtcgtg tcttaccgggttggactcaagacgatagttaccggataaggcgca -continued gcggtcgggctgaacggggggttcgtgcacacagcccagcttgga gcgaacgacctacaccgaactgagatacctacagcgtgagctatg agaaagcgccacgcttcccgaagggagaaaggcggacaggtatcc ggtaagcggcagggtcggaacaggagagcgcacgagggagcttcc aggggggaaacgcctggtatctttatagtcctgtcgggtttcgcca cctctgacttgagcgtcgattttttgtgatgctcgtcaggggggcg gagcctatggaaaaacgccagcaacgcggccttttttacggttcct ggccttttgctggccttttgctcacatgt pGW089-pAAV-EFSLTR-IL2-sPA (SEQ ID NO: 57)

CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccacatgtacagcatgcagctcgcatcctgtgtcaca ttgacacttgtgctccttgtcaacagcgcacccacttcaagctcc acttcaagctctacagcggaagcacagcagcagcagcagcagcag cagcagcagcagcagcacctggagcagctgttgatggacctacag gagctcctgagcaggatggagaattacaggaacctgaaactcccc aggatgctcaccttcaaattttacttgcccaagcaggccacagaa ttgaaagatcttcagtgcctagaagatgaacttggacctctgcgg catgttctggatttgactcaaagcaaaagctttcaattggaagat gctgagaatttcatcagcaatatcagagtaactgttgtaaaacta aagggctctgacaacacatttgagtgccaattcgatgatgagtca gcaactgtggtggactttctgaggagatggatagccttctgtcaa agcatcatctcaacaagccctcaataaGAATTCAATAAAAGATCT

TTATTTTCATTAGATCTGTGTGTTGGTTTTTTGTGTGCGGCCGCA

GGAACCCCTAGTGATGGAGTTGGCCACTCCCTCTCTGCGCGCTCG

CTCGCTCACTGAGGCCGGGCGACCAAAGGTCGCCCGACGCCCGGG

CTTTGCCCGGGCGGCCTCAGTGAGCGAGCGAGCGCGCAGCTGCCT

GCAGGGGCGCCTGATGCGGTATTTTCTCCTTACGCATCTGTGCGG

-continued

TATTTCACACCGCATACGTCAAAGCAACCATAGTACGCGCCCTGT

AGCGGCGCATTAAGCGCGGCGGGTGTGGTGGTTACGCGCAGCGTG

ACCGCTACACTTGCCAGCGCCTTAGCGCCCGCTCCTTTCGCTTTC

TTCCCTTCCTTTCTCGCCACGTTCGCCGGCTTTCCCCGTCAAGCT

CTAAATCGGGGGCTCCCTTTAGGGTTCCGATTTAGTGCTTTACGG

CACCTCGACCCCAAAAAACTTGATTTGGGTGATGGTTCACGTAGT

GGGCCATCGCCCTGATAGACGGTTTTTCGCCCTTTGACGTTGGAG

TCCACGTTCTTTAATAGTGGACTCTTGTTCCAAACTGGAACAACA

CTCAACTCTATCTCGGGCTATTCTTTTGATTTATAAGGGATTTTG

CCGATTTCGGTCTATTGGTTAAAAAATGAGCTGATTTAACAAAAA

TTTAACGCGAATTTTAACAAAATATTAACGTTTACAATTTTATGG

TGCACTCTCAGTACAATCTGCTCTGATGCCGCATAGTTAAGCCAG

CCCCGACACCCGCCAACACCCGCTGACGCGCCCTGACGGGCTTGT

CTGCTCCCGGCATCCGCTTACAGACAAGCTGTGACCGTCTCCGGG

AGCTGCATGTGTCAGAGGTTTTCACCGTCATCACCGAAACGCGCG

AGACGAAAGGGCCTCGTGATACGCCTATTTTTATAGGTTAATGTC

ATGATAATAATGGTTTCTTAGACGTCAGGTGGCACTTTTCGGGGA

AATGTGCGCGGAACCCCTATTTGTTTATTTTTCTAAATACATTCA

AATATGTATCCGCTCATGAGACAATAACCCTGATAAATGCTTCAA

TAATATTGAAAAAGGAAGAGTATGAGTATTCAACATTTCCGTGTC

GCCCTTATTCCCTTTTTTGCGGCATTTTGCCTTCCTGTTTTTGCT

CACCCAGAAACGCTGGTGAAAGTAAAAGATGCTGAAGATCAGTTG

GGTGCACGAGTGGGTTACATCGAACTGGATCTCAACAGCGGTAAG

ATCCTTGAGAGTTTTCGCCCCGAAGAACGTTTTCCAATGATGAGC

ACTTTTAAAGTTCTGCTATGTGGCGCGGTATTATCCCGTATTGAC

GCCGGGCAAGAGCAACTCGGTCGCCGCATACACTATTCTCAGAAT

GACTTGGTTGAGTACTCACCAGTCACAGAAAAGCATCTTACGGAT

GGCATGACAGTAAGAGAATTATGCAGTGCTGCCATAACCATGAGT

GATAACACTGCGGCCAACTTACTTCTGACAACGATCGGAGGACCG

AAGGAGCTAACCGCTTTTTTGCACAACATGGGGGATCATGTAACT

CGCCTTGATCGTTGGGAACCGGAGCTGAATGAAGCCATACCAAAC

GACGAGCGTGACACCACGATGCCTGTAGCAATGGCAACAACGTTG

CGCAAACTATTAACTGGCGAACTACTTACTCTAGCTTCCCGGCAA

CAATTAATAGACTGGATGGAGGCGGATAAAGTTGCAGGACCACTT

CTGCGCTCGGCCCTTCCGGCTGGCTGGTTTATTGCTGATAAATCT

GGAGCCGGTGAGCGTGGAAGCCGCGGTATCATTGCAGCACTGGGG

CCAGATGGTAAGCCCTCCCGTATCGTAGTTATCTACACGACGGGG

AGTCAGGCAACTATGGATGAACGAAATAGACAGATCGCTGAGATA

GGTGCCTCACTGATTAAGCATTGGTAACTGTCAGACCAAGTTTAC

TCATATATACTTTAGATTGATTTAAAACTTCATTTTTAATTTAAA

-continued

AGGATCTAGGTGAAGATccttttttgataatctcatgaccaaaatc ccttaacgtgagttttcgttccactgAGCGTCAGACCCCGTAGAA

AAGATCAAAGGATCTTCTTGAGATCCTTTTTTTTCTGCGCGTAATC

TGCTGCTTGCAAACAAAAAAACCACCGCTACCAGCGGTGGTTTGT

TTGCCGGATCAAGAGCTACCAACTCTTTTTTCCGAAGGTAACTGGC

TTCAGCAGAGCGCAGATACCAAATACTGTTCTTCTAGTGTAGCCG

TAGTTAGGCCACCACTTCAAGAACTCTGTAGCACCGCCTACATAC

CTCGCTCTGCTAATCCTGTTACCAGTGGCTGCTGCCAGTGGCGAT

AAGTCGTGTCTTACCGGGTTGGACTCAAGACGATAGTTACCGGAT

AAGGCGCAGCGGTCGGGCTGAACGGGGGGTTCGTGCACACAGCCC

AGCTTGGAGCGAACGACCTACACCGAACTGAGATACCTACAGCGT

GAGCTATGAGAAAGCGCCACGCTTCCCGAAGGGAGAAAGGCGGAC

AGGTATCCGGTAAGCGGCAGGGTCGGAACAGGAGAGCGCACGAGG

GAGCTTCCAGGGGGAAACGCCTGGTATCTTTATAGTCCTGTCGGG

TTTCGCCACCTCTGACTTGAGCGTCGATTTTTGTGATGCTCGTCA

GGGGGGCGGAGCCTATGGAAAAACGCCAGCAACGCGGCCTTTTTA

CGGTTCCTGGCCTTTTGCTGGCCTTTTGCTCACATGT pGW094-pAAV_EFSLTR-Ifng-P2A-Cd80-T2A-
light-P2A-Gitrl-E2A-41BBL-sPA (SEQ ID NO: 58)

CCTGCAGGCAGCTGCGCGCTCGCTCGCTCACTGAGGCCGCCCGGG

CGTCGGGCGACCTTTGGTCGCCCGGCCTCAGTGAGCGAGCGAGCG

CGCAGAGAGGGAGTGGCCAACTCCATCACTAGGGGTTCCTGCGGC

CTCTAGAAAGGATCTGCGATCGCTCCGGTGCCCGTCAGTGGGCAG

AGCGCACATCGCCCACAGTCCCCGAGAAGTTGGGGGGAGGGGTCG

GCAATTGAACGGGTGCCTAGAGAAGGTGGCGCGGGGTAAACTGGG

AAAGTGATGTCGTGTACTGGCTCCGCCTTTTTCCCGAGGGTGGGG

GAGAACCGTATATAAGTGCAGTAGTCGCCGTGAACGTTCTTTTTC

GCAACGGGTTTGCCGCCAGAACACAGCTGAAGCTTCGAGGGGCTC

GCATCTCTCCTTCACGCGCCCGCCGCCCTACCTGAGGCCGCCATC

CACGCCGGTTGAGTCGCGTTCTGCCGCCTCCCGCCTGTGGTGCCT

CCTGAACTGCGTCCGCCGTCTAGGTAAGTTTAAAGCTCAGGTCGA

GACCGGGCCTTTGTCCGGCGCTCCCTTGGAGCCTACCTAGACTCA

GCCGGCTCTCCACGCTTTGCCTGACCCTGCTTGCTCAACTCTACG

TCTTTGTTTCGTTTTCTGTTCTGCGCCGTTACAGATCTGGCTAAC

TAccggtgccaccatgaacgctacacactgcatcttggctttgca gctcttcctcatggctgtttctggctgttactgccacggcacagt cattgaaagcctagaaagtctgaataactattttaactcaagtgg catagatgtggaagaaaagagtctcttcttggatatctggaggaa ctggcaaaaggatggtgacatgaaaatcctgcagagccagattat ctctttctacctcagactctttgaagtcttgaaagacaatcaggc catcagcaacaacataagcgtcattgaatcacacctgattactac -continued cttcttcagcaacagcaaggcgaaaaaggatgcattcatgagtat tgccaagtttgaggtcaacaacccacaggtccagcgccaagcatt caatgagctcatccgagtggtccaccagctgttgccggaatccag cctcaggaagcggaaaaggagtcgctgcGGATCCGGCGCAACAAA

CTTCTCTCTGCTGAAACAAGCCGGAGATGTCGAAGAGAATCCTGG

ACCGatggcttgcaattgtcagttgatgcaggatacaccactcct caagtttccatgtccaaggctcattcttctctttgtgctgctgat tcgtctttcacaagtgtcttcagatgttgatgaacaactgtccaa gtcagtgaaagataaggtattgctgccttgccgttacaactctcc tcatgaagatgagtctgaagaccgaatctactggcaaaaacatga caaagtggtgctgtctgtcattgTtgggaaactaaaagtgtggcc cgagtataagaaccggactttatatgacaacactacctactctct tatcatcctgggcctggtcctttcagaccggggcacatacagctg tgtcgttcaaaagaaggaaagaggaacgtatgaagttaaacactt ggctttagtaaagttgtccatcaaagctgacttctctacccccaa cataactgagtctggaaacccatctgcagacactaaaaggattac ctgctttgcttccggggggtttcccaaagcctcgcttctcttggtt ggaaaatggaagagaattacctggcatcaatacgacaatttccca ggatcctgaatctgaattgtacaccattagtagccaactagattt caatacgactcgcaaccacaccattaagtgtctcattaaatatgg agatgctcacgtgtcagaggacttcacctgggaaaaaaccccaga agaccctcctgatagcaagaacacacttgtgctctttggggcagg attcggcgcagtaataacagtcgtcgtcatcgttgtcatcatcaa atgcttctgtaagcacagaagctgtttcagaagaaatgaggcaag cagagaaacaaacaacagccttacccttcgggcctgaagaagcatt agctgaacagaccgtcttccttcgtacgGGCAGTGGAGAGGGCAG

AGGAAGTCTGCTAACATGCGGTGACGTCGAGGAGAATCCTGGCCC

Aatggagagtgtggtacagccttcagtgtttgtggtggatggaca gacggacatcccattcaggcggctggaacagaaccaccggagacg gcgctgtggcactgtccaggtcagcctggccctggtgctgctgct aggtgctgggctggccactcagggctggtttctcctgagactgca tcaacgtcttggagacatagtagctcatctgccagatggaggcaa aggctcctgggagaagctgatacaagatcaacgatctcaccaggc caacccagcagcacatcttacaggagccaacgccagcttgatagg tattggtggacctctgttatgggagacacgacttggcctggcctt cttgaggggcttgacgtatcatgatggggccctggtgaccatgga gcccggttactactatgtgtactccaaagtgcagctgagcggcgt gggctgcccccaggggctggccaatgcctccccatcacccatgg actatacaagcgcacatcccgctacccgaaggagttagaactgct ggtcagtcggcggtcaccctgtggccgggccaacagctcccgagt ctggtgggacagcagcttcctgggcggcgtggtacatctggaggc -continued tggggaagaggtggtggtccgcgtgcctggaaaccgcctggtcag accacgtgacggcaccaggtcctatttcggagctttcatggtcac tagtGGATCCGGCGCAACAAACTTCTCTCTGCTGAAACAAGCCGG AGATGTCGAAGAGAATCCTGGACCGatggaggaaatgcctttgag agagtcaagtcctcaaagggcagagaggtgcaagaagtcatggct cttgtgcatagtggctctgttactgatgctgctctgttctttggg tacactgatctatacttcactcaagccaactgccatcgagtcctg catggttaagtttgaactatcatcctcaaaatggcacatgacatc tcccaaacctcactgtgtgaatacgacatctgatgggaagctgaa gatactgcagagtggcacatatttaatctacggccaagtgattcc tgtggataagaaatacataaaagacaatgccccttcgtagtaca gatatataaaaagaatgatgtcctacaaactctaatgaatgattt tcaaatcttgcctataggaggggtttatgaactgcatgctggaga taacatatatctgaagttcaactctaaagaccatattcagaaaaa taacacatactgggggatcatcttaatgcctgatctaccattcat ctctgctagcagcggtacccagtgcaccaactacgccctgctgaa gctggccggcgatgtggagagcaaccccgggcccatggaccagca cacacttgatgtggaggataccgcggatgccagacatccagcagg tacttcgtgcccctcggatgcggcgctcctcagagataccgggct cctcgcggacgctgcgctcctctcagatactgtgcgccccacaaa tgccgcgctccccacggatgctgcctaccctgcggttaatgttcg ggatcgcgaggccgcgtggccgcctgcactgaacttctgttcccg ccacccaaagctctatggcctagtcgctttggttttgctgcttct gatcgccgcctgtgttcctatcttcacccgcaccgagcctcggcc agcgctcacaatcaccacctcgcccaacctgggtacccgagagaa taatgcagaccaggtcacccctgtttcccacattggctgccccaa cactacacaacagggctctcctgtgttcgccaagctactggctaa aaaccaagcatcgttgtgcaatacaactctgaactggcacagcca agatggagctgggagctcatacctatctcaaggtctgaggtacga agaagacaaaaaggagttggtggtagacagtcccgggctctacta cgtattttggaactgaagctcagtccaacattcacaaacacagg ccacaaggtgcagggctgggtctctcttgttttgcaagcaaagcc tcaggtagatgactttgacaacttggccctgacagtggaactgtt cccttgctccatggagaacaagttagtggaccgttcctggagtca actgttgctcctgaaggctggccaccgcctcagtgtgggtctgag ggcttatctgcatggagcccaggatgcatacagagactgggagct gtcttatcccaacaccaccagctttggactctttcttgtgaaacc cgacaacccatgggaatgaGAATTCAATAAAAGATCTTTATTTTC

ATTAGATCTGTGTGTTGGTTTTTTGTGTGCGGCCGCAGGAACCCC

TAGTGATGGAGTTGGCCACTCCCTCTCTGCGCGCTCGCTCGCTCA

-continued

CTGAGGCCGGGCGACCAAAGGTCGCCCGACGCCCGGGCTTTGCCC

GGGCGGCCTCAGTGAGCGAGCGAGCGCGCAGCTGCCTGCAGGGGC

GCCTGATGCGGTATTTTCTCCTTACGCATCTGTGCGGTATTTCAC

ACCGCATACGTCAAAGCAACCATAGTACGCGCCCTGTAGCGGCGC

ATTAAGCGCGGCGGGTGTGGTGGTTACGCGCAGCGTGACCGCTAC

ACTTGCCAGCGCCTTAGCGCCCGCTCCTTTCGCTTTCTTCCCTTC

CTTTCTCGCCACGTTCGCCGGCTTTCCCCGTCAAGCTCTAAATCG

GGGGCTCCCTTTAGGGTTCCGATTTAGTGCTTTACGGCACCTCGA

CCCCAAAAAACTTGATTTGGGTGATGGTTCACGTAGTGGGCCATC

GCCCTGATAGACGGTTTTTCGCCCTTTGACGTTGGAGTCCACGTT

CTTTAATAGTGGACTCTTGTTCCAAACTGGAACAACACTCAACTC

TATCTCGGGCTATTCTTTTGATTTATAAGGGATTTTGCCGATTTC

GGTCTATTGGTTAAAAAATGAGCTGATTTAACAAAAATTTAACGC

GAATTTTAACAAAATATTAACGTTTACAATTTTATGGTGCACTCT

CAGTACAATCTGCTCTGATGCCGCATAGTTAAGCCAGCCCCGACA

CCCGCCAACACCCGCTGACGCGCCCTGACGGGCTTGTCTGCTCCC

GGCATCCGCTTACAGACAAGCTGTGACCGTCTCCGGGAGCTGCAT

GTGTCAGAGGTTTTCACCGTCATCACCGAAACGCGCGAGACGAAA

GGGCCTCGTGATACGCCTATTTTTATAGGTTAATGTCATGATAAT

AATGGTTTCTTAGACGTCAGGTGGCACTTTTCGGGGAAATGTGCG

CGGAACCCCTATTTGTTTATTTTTCTAAATACATTCAAATATGTA

TCCGCTCATGAGACAATAACCCTGATAAATGCTTCAATAATATTG

AAAAAGGAAGAGTATGAGTATTCAACATTTCCGTGTCGCCCTTAT

TCCCTTTTTTGCGGCATTTTGCCTTCCTGTTTTTGCTCACCCAGA

AACGCTGGTGAAAGTAAAAGATGCTGAAGATCAGTTGGGTGCACG

AGTGGGTTACATCGAACTGGATCTCAACAGCGGTAAGATCCTTGA

GAGTTTTCGCCCCGAAGAACGTTTTCCAATGATGAGCACTTTTAA

AGTTCTGCTATGTGGCGCGGTATTATCCCGTATTGACGCCGGGCA

AGAGCAACTCGGTCGCCGCATACACTATTCTCAGAATGACTTGGT

TGAGTACTCACCAGTCACAGAAAAGCATCTTACGGATGGCATGAC

AGTAAGAGAATTATGCAGTGCTGCCATAACCATGAGTGATAACAC

TGCGGCCAACTTACTTCTGACAACGATCGGAGGACCGAAGGAGCT

AACCGCTTTTTTGCACAACATGGGGGATCATGTAACTCGCCTTGA

TCGTTGGGAACCGGAGCTGAATGAAGCCATACCAAACGACGAGCG

TGACACCACGATGCCTGTAGCAATGGCAACAACGTTGCGCAAACT

ATTAACTGGCGAACTACTTACTCTAGCTTCCCGGCAACAATTAAT

AGACTGGATGGAGGCGGATAAAGTTGCAGGACCACTTCTGCGCTC

GGCCCTTCCGGCTGGCTGGTTTATTGCTGATAAATCTGGAGCCGG

TGAGCGTGGAAGCCGCGGTATCATTGCAGCACTGGGGCCAGATGG

TAAGCCCTCCCGTATCGTAGTTATCTACACGACGGGGAGTCAGGC

AACTATGGATGAACGAAATAGACAGATCGCTGAGATAGGTGCCTC

-continued

ACTGATTAAGCATTGGTAACTGTCAGACCAAGTTTACTCATATAT

ACTTTAGATTGATTTAAAACTTCATTTTTAATTTAAAAGGATCTA

GGTGAAGATCCTTTTTGATAATCTCATGACCAAAATCCCTTAACG

TGAGTTTTCGTTCCACTGAGCGTCAGACCCCGTAGAAAAGATCAA

AGGATCTTCTTGAGATccttttttttctgcgcgtaatctgctgctt gcaaacaaaaaaaccaccgctaccAGCGGTGGTTTGTTTGCCGGA

TCAAGAGCTACCAACTCTTTTTCCGAAGGTAACTGGCTTCAGCAG

AGCGCAGATACCAAATACTGTTCTTCTAGTGTAGCCGTAGTTAGG

CCACCACTTCAAGAACTCTGTAGCACCGCCTACATACCTCGCTCT

GCTAATCCTGTTACCAGTGGCTGCTGCCAGTGGCGATAAGTCGTG

TCTTACCGGGTTGGACTCAAGACGATAGTTACCGGATAAGGCGCA

GCGGTCGGGCTGAACGGGGGGTTCGTGCACACAGCCCAGCTTGGA

GCGAACGACCTACACCGAACTGAGATACCTACAGCGTGAGCTATG

AGAAAGCGCCACGCTTCCCGAAGGGAGAAAGGCGGACAGGTATCC

GGTAAGCGGCAGGGTCGGAACAGGAGAGCGCACGAGGGAGCTTCC

AGGGGGAAACGCCTGGTATCTTTATAGTCCTGTCGGGTTTCGCCA

CCTCTGACTTGAGCGTCGATTTTTGTGATGCTCGTCAGGGGGGCG

GAGCCTATGGAAAAACGCCAGCAACGCGGCCTTTTTACGGTTCCT

GGCCTTTTGCTGGCCTTTTGCTCACATGT

Ori
                                        (SEQ ID NO: 59)
TTGAGATCCTTTTTTTCTGCGCGTAATCTGCTGCTTGCAAACAAA

AAAACCACCGCTACCAGCGGTGGTTTGTTTGCCGGATCAAGAGCT

ACCAACTCTTTTTCCGAAGGTAACTGGCTTCAGCAGAGCGCAGAT

ACCAAATACTGTTCTTCTAGTGTAGCCGTAGTTAGGCCACCACTT

CAAGAACTCTGTAGCACCGCCTACATACCTCGCTCTGCTAATCCT

GTTACCAGTGGCTGCTGCCAGTGGCGATAAGTCGTGTCTTACCGG

GTTGGACTCAAGACGATAGTTACCGGATAAGGCGCAGCGGTCGGG

CTGAACGGGGGGTTCGTGCACACAGCCCAGCTTGGAGCGAACGAC

CTACACCGAACTGAGATACCTACAGCGTGAGCTATGAGAAAGCGC

CACGCTTCCCGAAGGGAGAAAGGCGGACAGGTATCCGGTAAGCGG

CAGGGTCGGAACAGGAGAGCGCACGAGGGAGCTTCCAGGGGGAAA

CGCCTGGTATCTTTATAGTCCTGTCGGGTTTCGCCACCTCTGACT

TGAGCGTCGATTTTTGTGATGCTCGTCAGGGGGGCGGAGCCTATG

GAAA fl0ri
                                        (SEQ ID NO: 60)
ACGCGCCCTGTAGCGGCGCATTAAGCGCGGCGGGTGTGGTGGTTA

CGCGCAGCGTGACCGCTACACTTGCCAGCGCCTTAGCGCCCGCTC

CTTTCGCTTTCTTCCCTTCCTTTCTCGCCACGTTCGCCGGCTTTC

CCCGTCAAGCTCTAAATCGGGGGCTCCCTTTAGGGTTCCGATTTA

GTGCTTTACGGCACCTCGACCCCAAAAAACTTGATTTGGGTGATG

-continued
GTTCACGTAGTGGGCCATCGCCCTGATAGACGGTTTTTCGCCCTT

TGACGTTGGAGTCCACGTTCTTTAATAGTGGACTCTTGTTCCAAA

CTGGAACAACACTCAACTCTATCTCGGGCTATTCTTTTGATTTAT

AAGGGATTTTGCCGATTTCGGTCTATTGGTTAAAAAATGAGCTGA

TTTAACAAAAATTTAACGCGAATTTTAACAAAATATTAACGTTTA

CAATTT

AmpR Promoter
                                        (SEQ ID NO: 61)
CGCGGAACCCCTATTTGTTTATTTTTCTAAATACATTCAAATATG

TATCCGCTCATGAGACAATAACCCTGATAAATGCTTCAATAATAT

TGAAAAAGGAAGAGT

AmpR
                                        (SEQ ID NO: 62)
ATGAGTATTCAACATTTCCGTGTCGCCCTTATTCCCTTTTTTGCG

GCATTTTGCCTTCCTGTTTTTGCTCACCCAGAAACGCTGGTGAAA

GTAAAAGATGCTGAAGATCAGTTGGGTGCACGAGTGGGTTACATC

GAACTGGATCTCAACAGCGGTAAGATCCTTGAGAGTTTTCGCCCC

GAAGAACGTTTTCCAATGATGAGCACTTTTAAAGTTCTGCTATGT

GGCGCGGTATTATCCCGTATTGACGCCGGGCAAGAGCAACTCGGT

CGCCGCATACACTATTCTCAGAATGACTTGGTTGAGTACTCACCA

GTCACAGAAAAGCATCTTACGGATGGCATGACAGTAAGAGAATTA

TGCAGTGCTGCCATAACCATGAGTGATAACACTGCGGCCAACTTA

CTTCTGACAACGATCGGAGGACCGAAGGAGCTAACCGCTTTTTTG

CACAACATGGGGGATCATGTAACTCGCCTTGATCGTTGGGAACCG

GAGCTGAATGAAGCCATACCAAACGACGAGCGTGACACCACGATG

CCTGTAGCAATGGCAACAACGTTGCGCAAACTATTAACTGGCGAA

CTACTTACTCTAGCTTCCCGGCAACAATTAATAGACTGGATGGAG

GCGGATAAAGTTGCAGGACCACTTCTGCGCTCGGCCCTTCCGGCT

GGCTGGTTTATTGCTGATAAATCTGGAGCCGGTGAGCGTGGAAGC

CGCGGTATCATTGCAGCACTGGGGCCAGATGGTAAGCCCTCCCGT

ATCGTAGTTATCTACACGACGGGGAGTCAGGCAACTATGGATGAA

CGAAATAGACAGATCGCTGAGATAGGTGCCTCACTGATTAAGCAT

TGGTAA

AAV-ITR
                                        (SEQ ID NO: 63)
AGGAACCCCTAGTGATGGAGTTGGCCACTCCCTCTCTGCGCGCTC

GCTCGCTCACTGAGGCCGGGCGACCAAAGGTCGCCCGACGCCCGG

GCTTTGCCCGGGCGGCCTCAGTGAGCGAGCGAGCGCGCAGCTGCC

TGCAGG

EES core promoter
                                        (SEQ ID NO: 64)
GGGCAGAGCGCACATCGCCCACAGTCCCCGAGAAGTTGGGGGGAG

GGGTCGGCAATTGAACGGGTGCCTAGAGAAGGTGGCGCGGGGTAA

-continued

ACTGGGAAAGTGATGTCGTGTACTGGCTCCGCCTTTTTCCCGAGG

GTGGGGGAGAACCGTATATAAGTGCAGTAGTCGCCGTGAACGTTC

TTTTTCGCAACGGGTTTGCCGCCAGAACACAG

LTR promoter (SEQ ID NO: 65)
GGGGCTCGCATCTCTCCTTCACGCGCCCGCCGCCCTACCTGAGGC

CGCCATCCACGCCGGTTGAGTCGCGTTCTGCCGCCTCCCGCCTGT

GGTGCCTCCTGAACTGCGTCCGCCGTCTAGGTAAGTTTAAAGCTC

AGGTCGAGACCGGGCCTTTGTCCGGCGCTCCCTTGGAGCCTACCT

AGACTCAGCCGGCTCTCCACGCTTTGCCTGACCCTGCTTGCTCAA

CTCTACGTCTTTGTTTCGTTTTCTGTTCTGCGCCGTTACAGATC

EFS-LTR promoter (SEQ ID NO: 66)
GGGCAGAGCGCACATCGCCCACAGTCCCCGAGAAGTTGGGGGGAG

GGGTCGGCAATTGAACGGGTGCCTAGAGAAGGTGGCGCGGGGTAA

ACTGGGAAAGTGATGTCGTGTACTGGCTCCGCCTTTTTCCCGAGG

GTGGGGGAGAACCGTATATAAGTGCAGTAGTCGCCGTGAACGTTC

TTTTTCGCAACGGGTTTGCCGCCAGAACACAGCTGAAGCTTCGAG

GGGCTCGCATCTCTCCTTCACGCGCCCGCCGCCCTACCTGAGGCC

GCCATCCACGCCGGTTGAGTCGCGTTCTGCCGCCTCCCGCCTGTG

GTGCCTCCTGAACTGCGTCCGCCGTCTAGGTAAGTTTAAAGCTCA

GGTCGAGACCGGGCCTTTGTCCGGCGCTCCCTTGGAGCCTACCTA

GACTCAGCCGGCTCTCCACGCTTTGCCTGACCCTGCTTGCTCAAC

TCTACGTCTTTGTTTCGTTTTCTGTTCTGCGCCGTTACAGATC

T2A (SEQ ID NO: 67)
GAGGAAGTCTGCTAACATGCGGTGACGTCGAGGAGAATCCTGGCC

CAatggagagtgtggtacagcct

P2A (SEQ ID NO: 68)
actagtGGATCCGGCGCAACAAACTTCTCTCTGCTGAAACAAGCC

GGAGATGTCGAAGAGAATCCTGGACCG

E2A (SEQ ID NO: 69)
gctagcagcggtacccagtgcaccaactacgccctgctgaagctg gccggcgatgtggagagcaaccccgggccc

F2A (SEQ ID NO: 70)
ggcatatgcggtaccgtgaagcagaccctgaacttcgatctgctg aagctggccggcgatgtggagagcaaccccgggccc

WPRE (SEQ ID NO: 71)
aatcaacctctggattacaaaatttgtgaaagattgactggtatt cttaactatgttgctcctttttacgctatgtggatacgctgcttta atgcctttgtatcatgctattgcttcccgtatggctttcattttc tcctccttgtataaatcctggttgctgtctctttatgaggagttg tggcccgttgtcaggcaacgtggcgtggtgtgcactgtgtttgct gacgcaacccccactggttggggcattgccaccacctgtcagctc -continued ctttccgggactttcgctttccccctccctattgccacggcggaa ctcatcgccgcctgccttgcccgctgctggacaggggctcggctg ttgggcactgacaattccgtggtgttgtcggggaaatcatcgtcc tttccttggctgctcgcctgtgttgccacctggattctgcgcggg acgtccttctgctacgtcccttcggccctcaatccagcggacctt ccttcccgcggcctgctgccggctctgcggcctcttccgcgtctt cgccttcgccctcagacgagtcggatctcccttttgggccgcctcc ccgc short-PolyA (SEQ ID NO: 72)
AATAAAAGATCTTTATTTTCATTAGATCTGTGTGTTGGTTTTTTG

TGTG

ORF-Cd80

(SEQ ID NO: 73)
atggcttgcaattgtcagttgatgcaggatacaccactcctcaag tttccatgtccaaggctcattcttctctttgtgctgctgattcgt ctttcacaagtgtcttcagatgttgatgaacaactgtccaagtca gtgaaagataaggtattgctgccttgccgttacaactctcctcat gaagatgagtctgaagaccgaatctactggcaaaaacatgacaaa gtggtgctgtctgtcattgctgggaaactaaaagtgtggcccgag tataagaaccggactttatatgacaacactacctactctcttatc atcctgggcctggtcctttcagaccggggcacatacagctgtgtc gttcaaaagaaggaaagaggaacgtatgaagttaaacacttggct ttagtaaagttgtccatcaaagctgacttctctaccccccaacata actgagtctggaaacccatctgcagacactaaaaggattacctgc tttgcttccggggggtttcccaaagcctcgcttctcttggttggaa aatggaagagaattacctggcatcaatacgacaatttcccaggat cctgaatctgaattgtacaccattagtagccaactagatttcaat acgactcgcaaccacaccattaagtgtctcattaaatatggagat gctcacgtgtcagaggacttcacctgggaaaaaccccccagaagac cctcctgatagcaagaacacacttgtgctctttggggcaggattc ggcgcagtaataacagtcgtcgtcatcgttgtcatcatcaaatgc ttctgtaagcacagaagctgtttcagaagaaatgaggcaagcaga gaaacaaacaacagccttaccttcgggcctgaagaagcattagct gaacagaccgtcttcctt ORF-Light (SEQ ID NO: 74)
atggagagtgtggtacagccttcagtgtttgtggtggatggacag acggacatcccattcaggcggctggaacagaaccaccggagacgg cgctgtggcactgtccaggtcagcctggccctggtgctgctgcta ggtgctgggctggccactcagggctggtttctcctgagactgcat caacgtcttggagacatagtagctcatctgccagatggaggcaaa ggctcctgggagaagctgatacaagatcaacgatctcaccaggcc -continued aacccagcagcacatcttacaggagccaacgccagcttgataggt attggtggacctctgttatgggagacacgacttggcctggccttc ttgaggggcttgacgtatcatgatggggccctggtgaccatggag cccggttactactatgtgtactccaaagtgcagctgagcggcgtg ggctgcccccaggggctggccaatggcctccccatcacccatgga ctatacaagcgcacatcccgctacccgaaggagttagaactgctg gtcagtcggcggtcaccctgtggccgggccaacagctcccgagtc tggtgggacagcagcttcctgggcggcgtggtacatctggaggct ggggaagaggtggtggtccgcgtgcctggaaaccgcctggtcaga ccacgtgacggcaccaggtcctatttcggagctttcatggtc ORF-Cxc10

(SEQ ID NO: 75)

atgaacccaagtgctgccgtcattttctgcctcatcctgctgggt ctgagtgggactcaagggatccctctcgcaaggacggtccgctgc aactgcatccatatcgatgacgggccagtgagaatgagggccata gggaagcttgaaatcatccctgcgagcctatcctgcccacgtgtt gagatcattgccacgatgaaaaagaatgatgagcagagatgtctg aatccggaatctaagaccatcaagaatttaatgaaagcgtttagc caaaaaaggtctaaaagggctcct

ORF-41BBL (SEQ ID NO: 76)

atggaccagcacacacttgatgtggaggataccgcggatgccaga catccagcaggtacttcgtgcccctcggatgcggcgctcctcaga gataccgggctcctcgcggacgctgcgctcctctcagatactgtg cgccccacaaatgccgcgctcccacggatgctgcctaccctgcg gttaatgttcgggatcgcgaggccgcgtggccgcctgcactgaac ttctgttcccgccacccaaagctctatggcctagtcgctttggtt ttgctgcttctgatcgccgcctgtgttcctatcttcacccgcacc gagcctcggccagcgctcacaatcaccacctcgcccaacctgggt acccgagagaataatgcagaccaggtcacccctgtttcccacatt ggctgccccaacactacacaacagggctctcctgtgttcgccaag ctactggctaaaaaccaagcatcgttgtgcaatacaactctgaac tggcacagccaagatggagctgggagctcatacctatctcaaggt ctgaggtacgaagaagacaaaaaggagttggtggtagacagtccc gggctctactacgtattttttggaactgaagctcagtccaacattc acaaacacaggccacaaggtgcagggctgggtctctcttgttttg caagcaaagcctcaggtagatgactttgacaacttggccctgaca gtggaactgttcccttgctccatggagaacaagttagtggaccgt tcctggagtcaactgttgctcctgaaggctggccaccgcctcagt gtgggtctgagggcttatctgcatggagcccaggatgcatacaga gactgggagctgtcttatcccaacaccaccagctttggactcttt cttAtgaaacccgacaacccatgggaa -continued ORF-IFNg (SEQ ID NO: 77)

atgaacgctacacactgcatcttggctttgcagctcttcctcatg gctgtttctggctgttactgccacggcacagtcattgaaagccta gaaagtctgaataactattttaactcaagtggcatagatgtggaa gaaaagagtctcttcttggatatctggaggaactggcaaaaggat ggtgacatgaaaatcctgcagagccagattatctctttctacctc agactctttgaagtcttgaaagacaatcaggccatcagcaacaac ataagcgtcattgaatcacacctgattactaccttcttcagcaac agcaaggcgaaaaaggatgcattcatgagtattgccaagtttgag gtcaacaacccacaggtccagcgccaagcattcaatgagctcatc cgagtggtccaccagctgttgccggaatccagcctcaggaagcgg aaaaggagtcgctgctga

ORF-I12

(SEQ ID NO: 78)

atgtacagcatgcagctcgcatcctgtgtcacattgacacttgtg ctccttgtcaacagcgcacccacttcaagctccacttcaagctct acagcggaagcacagcagcagcagcagcagcagcagcagcagcag cagcacctggagcagctgttgatggacctacaggagctcctgagc aggatggagaattacaggaacctgaaactccccaggatgctcacc ttcaaattttacttgcccaagcaggccacagaattgaaagatctt cagtgcctagaagatgaacttggacctctgcggcatgttctggat ttgactcaaagcaaaagctttcaattggaagatgctgagaatttc atcagcaatatcagagtaactgttgtaaaactaaagggctctgac aacacatttgagtgccaattcgatgatgagtcagcaactgtggtg gactttctgaggagatggatagccttctgtcaaagcatcatctca acaagccctcaataaGAATTC ORF-Gitr (SEQ ID NO: 79)

atggaggaaatgcctttgagagagtcaagtcctcaaagggcagag aggtgcaagaagtcatggctcttgtgcatagtggctctgttactg atgctgctctgttctttgggtacactgatctatacttcactcaag ccaactgccatcgagtcctgcatggttaagtttgaactatcatcc tcaaaatggcacatgacatctcccaaacctcactgtgtgaatacg acatctgatgggaagctgaagatactgcagagtggcacatattta atctacggccaagtgattcctgtggataagaaatacataaaaagac aatgcccccttcgtagtacagatatataaaaagaatgatgtccta caaactctaatgaatgattttcaaatcttgcctataggaggggtt tatgaactgcatgctggagataacatatatctgaagttcaactct aaagaccatattcagaaaaataacacatactgggggatcatctta atgcctgatctaccattcatctct

ORF-I123

(SEQ ID NO: 80)

ATGTGTCCTCAGAAGCTAACCATCTCCTGGTTTGCCATCGTTTTG

CTGGTGTCTCCACTCATGGCCATGTGGGAGCTGGAGAAAGACGTT

-continued

TATGTTGTAGAGGTGGACTGGACTCCCGATGCCCCTGGAGAAACA

GTGAACCTCACCTGTGACACGCCTGAAGAAGATGACATCACCTGG

ACCTCAGACCAGAGACATGGAGTCATAGGCTCTGGAAAGACCCTG

ACCATCACTGTCAAAGAGTTTCTAGATGCTGGCCAGTACACCTGC

CACAAAGGAGGCGAGACTCTGAGCCACTCACATCTGCTGCTCCAC

AAGAAGGAAAATGGAATTTGGTCCACTGAAATTTTAAAAAATTTC

AAAAACAAGACTTTCCTGAAGTGTGAAGCACCAAATTACTCCGGA

CGGTTCACGTGCTCATGGCTGGTGCAAAGAAACATGGACTTGAAG

TTCAACATCAAGAGCAGTAGCAGTTCCCCTGACTCTCGGGCAGTG

ACATGTGGAATGGCGTCTCTGTCTGCAGAGAAGGTCACACTGGAC

CAAAGGGACTATGAGAAGTATTCAGTGTCCTGCCAGGAGGATGTC

ACCTGCCCAACTGCCGAGGAGACCCTGCCCATTGAACTGGCGTTG

GAAGCACGGCAGCAGAATAAATATGAGAACTACAGCACCAGCTTC

TTCATCAGGGACATCATCAAACCAGACCCGCCCAAGAACTTGCAG

ATGAAGCCTTTGAAGAACTCACAGGTGGAGGTCAGCTGGGAGTAC

CCTGACTCCTGGAGCACTCCCCATTCCTACTTCTCCCTCAAGTTC

TTTGTTCGAATCCAGCGCAAGAAAGAAAGATGAAGGAGACAGAG

GAGGGGTGTAACCAGAAAGGTGCGTTCCTCGTAGAGAAGACATCT

ACCGAAGTCCAATGCAAAGGCGGGAATGTCTGCGTGCAAGCTCAG

GATCGCTATTACAATTCCTCATGCAGCAAGTGGGCATGTGTTCCC

TGCAGGGTCCGATCCTAG

ORF-hIFNg (SEQ ID NO: 81)
ATGAAATATACAAGTTATATCTTGGCTTTTCAGCTCTGCATCGTT

TTGGGTTCTCTTGGCTGTTACTGCCAGGACCCATATGTAAAAGAA

GCAGAAAACCTTAAGAAATATTTTAATGCAGGTCATTCAGATGTA

GCGGATAATGGAACTCTTTTCTTAGGCATTTTGAAGAATTGGAAA

GAGGAGAGTGACAGAAAATAATGCAGAGCCAAATTGTCTCCTTT

TACTTCAAACTTTTTAAAAACTTTAAAGATGACCAGAGCATCCAA

AAGAGTGTGGAGACCATCAAGGAAGACATGAATGTCAAGTTTTTC

AATAGCAACAAAAAGAAACGAGATGACTTCGAAAAGCTGACTAAT

TATTCGGTAACTGACTTGAATGTCCAACGCAAAGCAATACATGAA

CTCATCCAAGTGATGGCTGAACTGTCGCCAGCAGCTAAAACAGGG

AAGCGAAAAAGGAGTCAGATGCTGTTTCGAGGTCGAAGAGCATCC

CAG

ORF-hIL23

(SEQ ID NO: 82)
TGTGTCACCAGCAGTTGGTCATCTCTTGGTTTTCCCTGGTTTTTC

TGGCATCTCCCCTCGTGGCCATATGGGAACTGAAGAAAGATGTTT

ATGTCGTAGAATTGGATTGGTATCCGGATGCCCCTGGAGAAATGG

TGGTCCTCACCTGTGACACCCCTGAAGAAGATGGTATCACCTGGA

CCTTGGACCAGAGCAGTGAGGTCTTAGGCTCTGGCAAACCCTGA

CCATCCAAGTCAAAGAGTTTGGAGATGCTGGCCAGTACACCTGTC

ACAAAGGAGGCGAGGTTCTAAGCCATTCGCTCCTGCTGCTTCACA

AAAAGGAAGATGGAATTTGGTCCACTGATATTTTAAAGGACCAGA

AAGAACCCAAAAATAAGACCTTTCTAAGATGCGAGGCCAAGAATT

ATTCTGGACGTTTCACCTGCTGGTGGCTGACGACAATCAGTACTG

ATTTGACATTCAGTGTCAAAAGCAGCAGAGGCTCTTCTGACCCCC

AAGGGGTGACGTGCGGAGCTGCTACACTCTCTGCAGAGAGAGTCA

GAGGGGACAACAAGGAGTATGAGTACTCAGTGGAGTGCCAGGAGG

ACAGTGCCTGCCCAGCTGCTGAGGAGAGTCTGCCCATTGAGGTCA

TGGTGGATGCCGTTCACAAGCTCAAGTATGAAAACTACACCAGCA

GCTTCTTCATCAGGGACATCATCAAACCTGACCCACCCAAGAACT

TGCAGCTGAAGCCATTAAAGAATTCTCGGCAGGTGGAGGTCAGCT

GGGAGTACCCTGACACCTGGAGTACTCCACATTCCTACTTCTCCC

TGACATTCTGCGTTCAGGTCCAGGGCAAGAGCAAGAGAGAAAAGA

AAGATAGAGTCTTCACGGACAAGACCTCAGCCACGGTCATCTGCC

GCAAAAATGCCAGCATTAGCGTGCGGGCCCAGGACCGCTACTATA

GCTCATCTTGGAGCGAATGGGCATCTGTGCCCTGCAGT

ORF-h41BBL (SEQ ID NO: 83)
ATGGAATACGCCTCTGACGCTTCACTGGACCCCGAAGCCCCGTGG

CCTCCCGCGCCCCGCGCTCGCGCCTGCCGCGTACTGCCTTGGGCC

CTGGTCGCGGGGCTGCTGCTGCTGCTGCTGCTCGCTGCCGCCTGC

GCCGTCTTCCTCGCCTGCCCCTGGGCCGTGTCCGGGGCTCGCGCC

TCGCCCGGCTCCGCGCCAGCCCGAGACTCCGCGAGGGTCCCGAG

CTTTCGCCCGACGATCCCGCCGGCCTCTTGGACCTGCGGCAGGGC

ATGTTTGCGCAGCTGGTGGCCCAAAATGTTCTGCTGATCGATGGG

CCCCTGAGCTGGTACAGTGACCCAGGCCTGGCAGGCGTGTCCCTG

ACGGGGGGCCTGAGCTACAAAGAGGACACGAAGGAGCTGGTGGTG

GCCAAGGCTGGAGTCTACTATGTCTTCTTTCAACTAGAGCTGCGG

CGCGTGGTGGCCGGCGAGGGCTCAGGCTCCGTTTCACTTGCGCTG

CACCTGCAGCCACTGCGCTCTGCTGCTGGGGCCGCCGCCCTGGCT

TTGACCGTGGACCTGCCACCCGCCTCCTCCGAGGCTCGGAACTCG

GCCTTCGGTTTCCAGGGCCGCTTGCTGCACCTGAGTGCCGGCCAG

CGCCTGGGCGTCCATCTTCACACTGAGGCCAGGGCACGCCATGCC

TGGCAGCTTACCCAGGGCGCCACAGTCTTGGGACTCTTCCGGGTG

ACCCCCGAAATCCCAGCCGGACTCCCTTCACCGAGGTCGGAA

ORF-hLIGHT(remove-EQLI)

(SEQ ID NO: 84)
ATGGAGGAGAGTGTCGTACGGCCCTCAGTGTTTGTGGTGGATGGA

CAGACCGACATCCCATTCACGAGGCTGGGACGAAGCCACCGGAGA

CAGTCGTGCAGTGTGGCCCGGGTGGGTCTGGGTCTCTTGCTGTTG

CTGATGGGGGCCGGGCTGGCCGTCCAAGGCTGGTTCCTCCTGCAG

CTGCACTGGCGTCTAGGAGAGATGGTCACCCGCCTGCCTGACGGA 257
258

-continued

```
CCTGCAGGCTCCTGGCAAGAGCGAAGGTCTCACGAGGTCAACCCA

GCAGCGCATCTCACAGGGGCCAACTCCAGCTTGACCGGCAGCGGG

GGGCCGCTGTTATGGGAGACTCAGCTGGGCCTGGCCTTCCTGAGG

GGCCTCAGCTACCACGATGGGGCCCTTGTGGTCACCAAAGCTGGC

TACTACTACATCTACTCCAAGGTGCAGCTGGGCGGTGTGGGCTGC

CCGCTGGGCCTGGCCAGCACCATCACCCACGGCCTCTACAAGCGC

ACACCCCGCTACCCCGAGGAGCTGGAGCTGTTGGTCAGCCAGCAG

TCACCCTGCGGACGGGCCACCAGCAGCTCCCGGGTCTGGTGGGAC

AGCAGCTTCCTGGGTGGTGTGGTACACCTGGAGGCTGGGGAGAAG

GTGGTCGTCCGTGTGCTGGATGAACGCCTGGTTCGACTGCGTGAT

GGTACCCGGTCTTACTTCGGGGCTTTCATGGTGCGKRK
```
                                        (SEQ ID NO: 85)
`tgcggaaagcgtaag`

The results of the experiments are now described.

Example 1: CRISPRa Screen Assisted Rational Design of an Off the Shelf Viral Immune Gene Therapy In order to develop an improved off-the-shelf viral immune gene therapy that is both simpler and more potent, an in vivo CRISPRa-based screen was devised using a sgRNA library to identify the key genes that are effective in Multiplexed Activation of Endogenous Genes as an Immunotherapy (MAEGI) or direct ORF-based viral immune gene therapy settings (FIG. 1A). By performing a CRISPRa in vivo depletion screen in the syngeneic systemic cancer model, a small number of genes that are depleted in the metastatic tumors in the lung were identified.

Figure 1C:
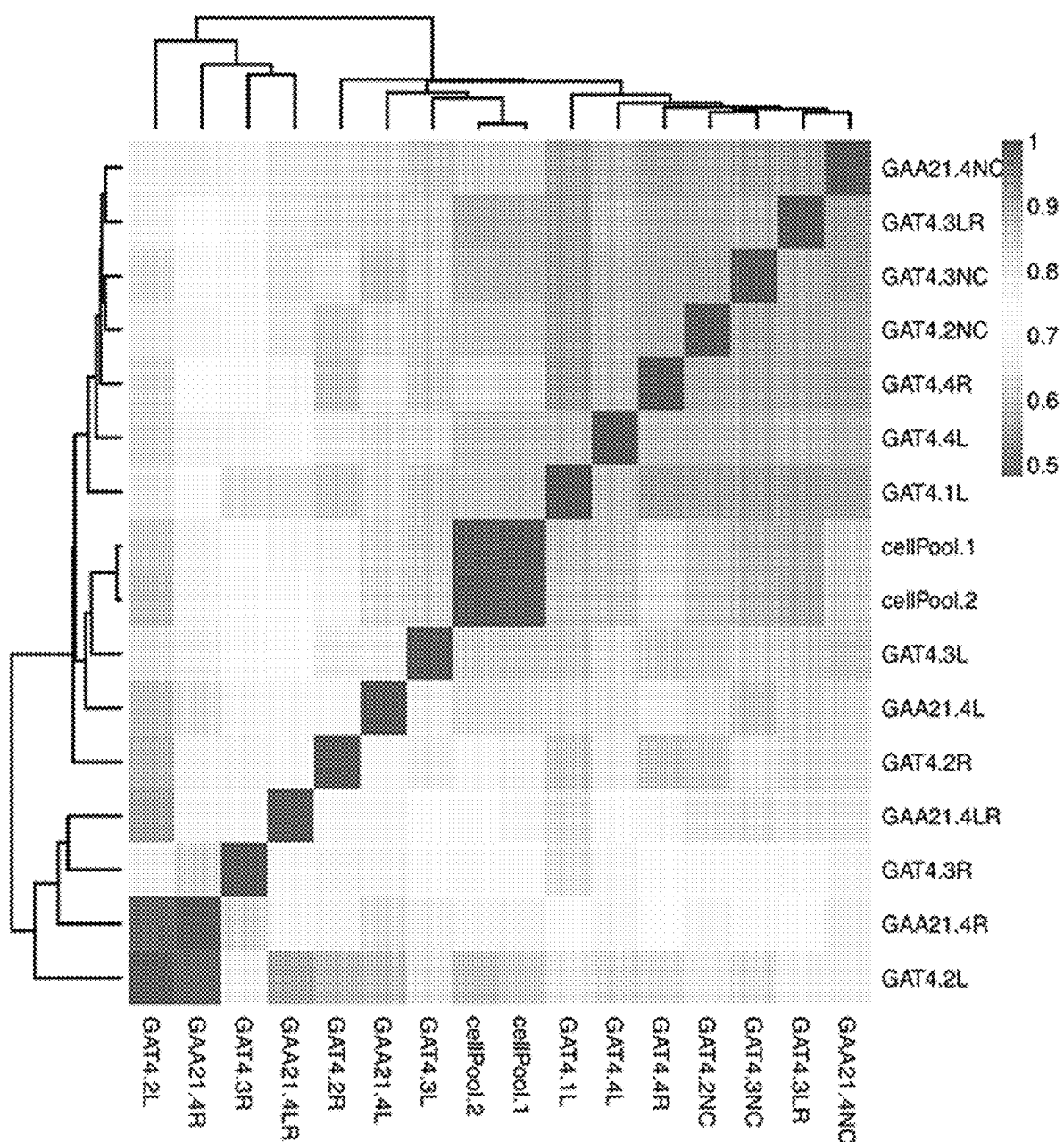
Figure 1D:
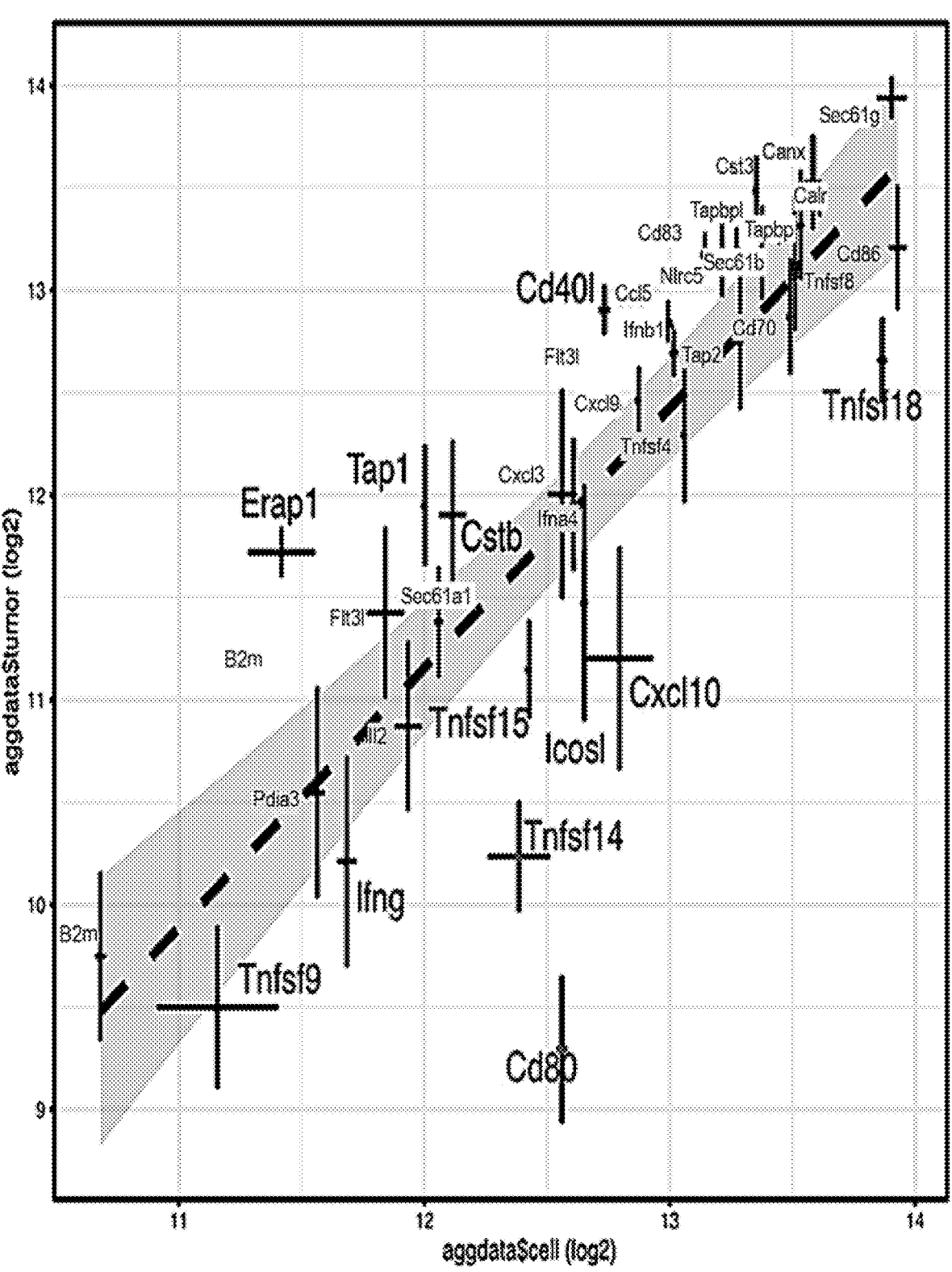
Figure 1E:
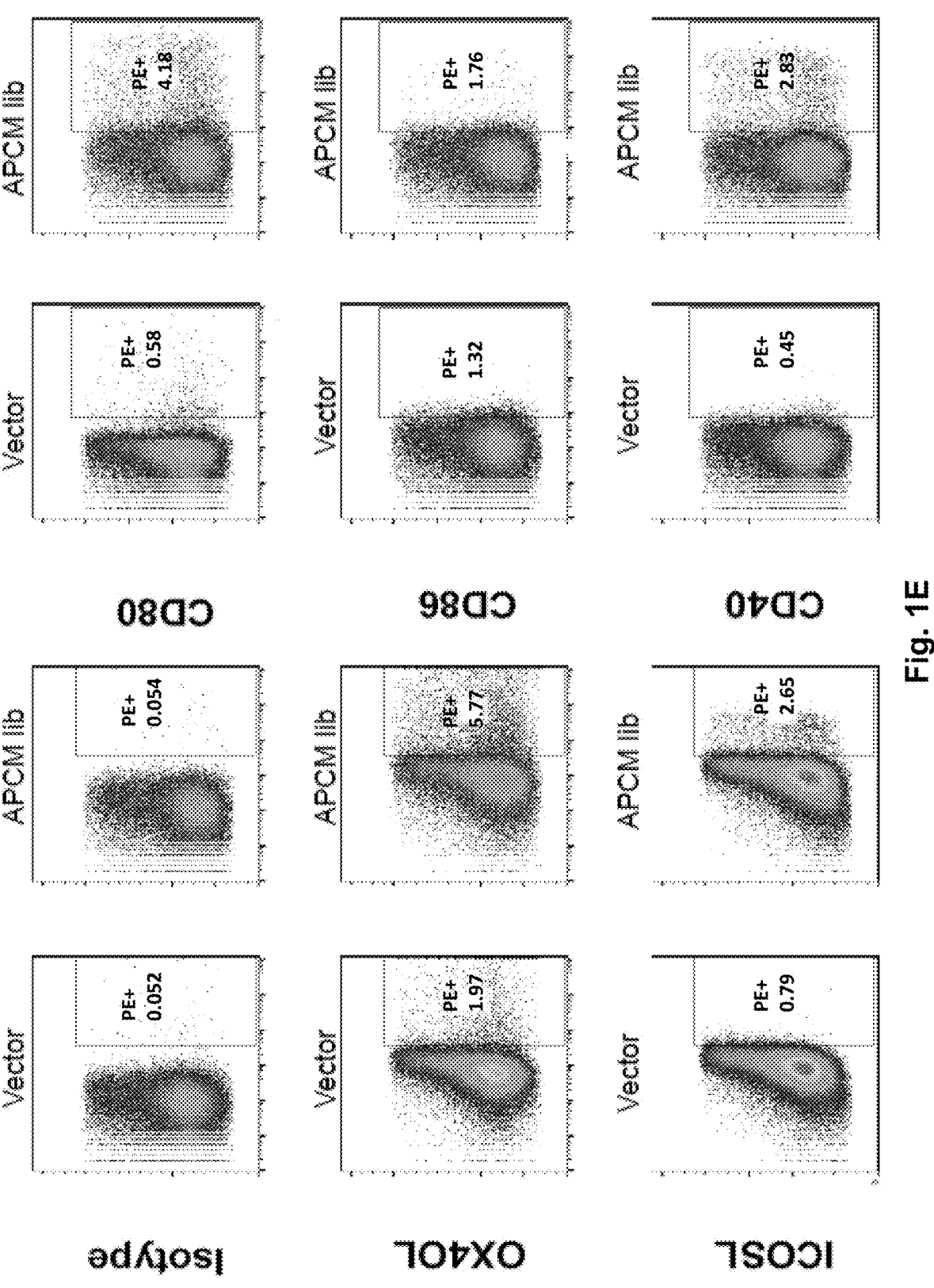
FIG. 1E depicts representative flow cytometry plots demonstrating CRISPRa-mediated expression of several representative costimulatory molecules, such as OX40L, ICOSL, CD80, CD86, and CD40 s in APCM sgRNA library transduced E0771 cells.
Figure 1F:
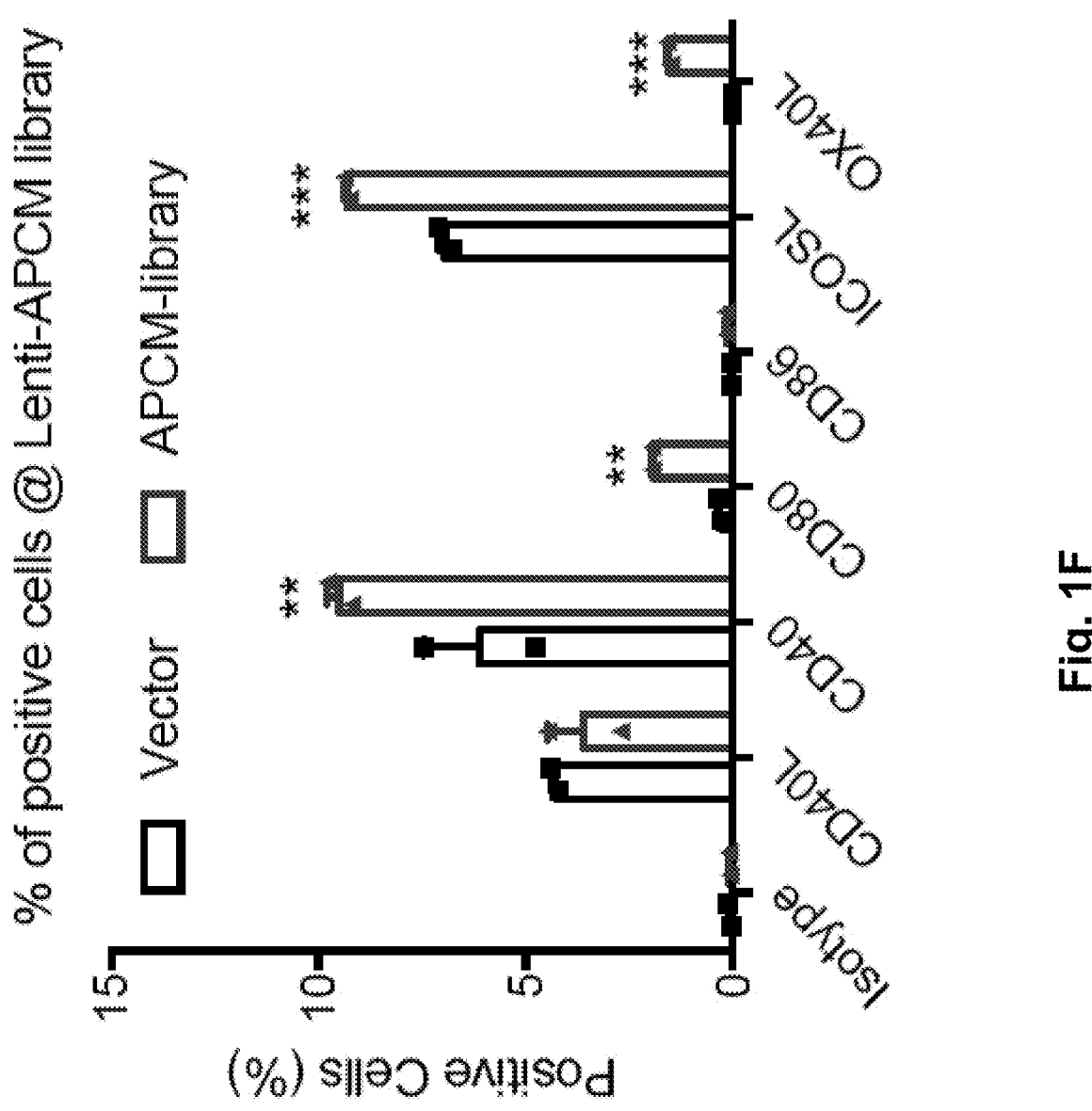
FIG. 1F shows the percentage of CD40, CD40L, CD80, CD86, OX40L, and ICOSL expressing cells in APCM sgRNA library transduced E0771 cells.

An APCM sgRNA library (SEQ ID NOs. 86-192) (FIG. 7) was introduced into E0771, a triple-negative breast cancer cell line, by infection with a lentiviral CRISPRa vector at M.O.I=0.2-0.3. After 7 days of in vitro culture under puromycin, 2*10⁶ of APCM library transduced cells were intravenously injected into immune-competent C57BL/6J mice (FIG. 1A). Mouse survival was then followed for 30 days (FIG. 1B). The metastatic tumors formed in the lungs of each animal were collected, and the immune-mediated sgRNA depletion and enrichment was readout by illumina sequencing (FIG. 1C). The abundance of sgRNAs within tumor samples and cell samples was then determined by mapping the sequenced reads to the library. The depleted genes were chosen in combinations (e.g. CLC4, CLC4G, CLC4I) as screen-rationalized, off-the-shelf viral immune gene therapy, either in the form of o-MAEGI or concatenated ORF (FIG. 1D).

Example 2: In Vivo Anti-Tumor Efficacy of AAV-o-MAEGI-CLC4, AAV-ORF-CLC4 and AAV-ORF-CLC4I in a Syngeneic Triple-Negative Breast Cancer Model Taking the top hits from the analysis of depleted gene expression in APCM-transduced tumors from Example 1, three off-the-shelf therapies were developed: CLC4 (CD80-Light-CXCL10-4-1BBL), CLC4G (CD80-Light-CXCL10-4-1BBL-Gitrl) and CLC4I (CD80-Light-CXCL10-4-1BBL-IFNG). These therapies were developed in the form of MAEGI (CRISPRa-based pooled activation) and direct ORF-based viral immune gene therapy (AAV expressing concatenated ORFs).

Figure 2:
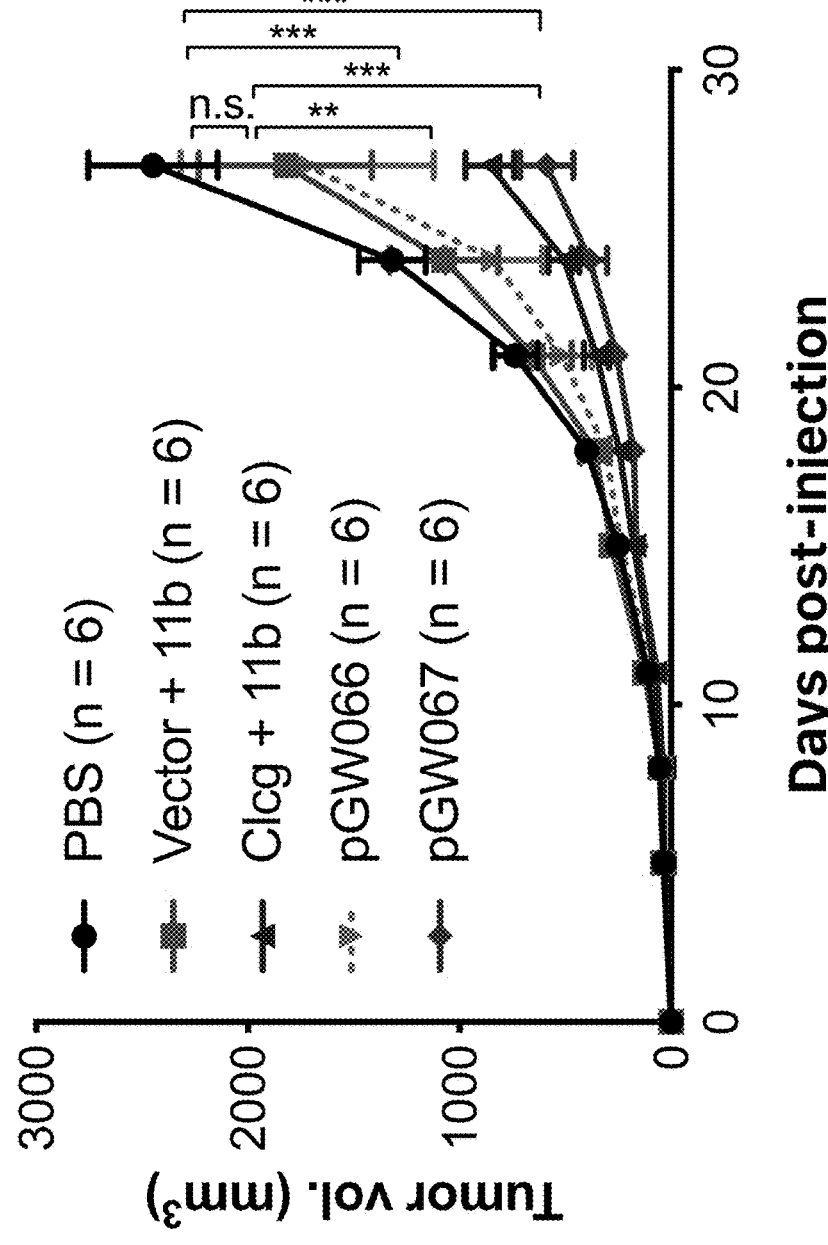
FIG. 2 illustrates in vivo efficacy of AAV-o-MAEGI-CLC4G, AAV-ORF-CLC4 and AAV-ORF-CLC4I in a syngeneic triple-negative breast cancer model. Therapeutic effects of intratumoral activation of CLC4I (Cd80, light/Tnfsf14, Cxcl10, 4-1BBL/Tnfsf9, Ifng or Gitrl) are shown. Tumor growth curves of E0771 tumors treated with PBS (n=6), AAV-dCas9+Vector (n=6), AAV-dCas9+CLC4G (dual AAV delivered CRISPRa of sgRNA library targeting CLC4G, i.e. o-MAEGI-CLC4G, n=6), AAV-orf-CLC4 (pGW066: AAV delivered open reading frame expression of CLC4, n=6), or AAV-orf-CLC4I (pGW067: AAV delivered open reading frame expression of Clcg and Ifng, n=6). Two-way ANOVA: AAV-dCas9+Vector vs. PBS, p=0.9675; AAV-dCas9+CLC4 vs. PBS, p<0.0001; AAV-orf-CLC4 vs. PBS, p=0.04; AAV-orf-CLC4I vs. PBS, p<0.0001; AAV-dCas9+CLC4G vs. AAV-dCas9+Vector, p<0.0001. Error bars: Data points in this figure are presented as mean±s.e.m. Asterisks: *p<0.05, p<0.01, *p<0.001.

The therapeutic effects of intratumoral activation of CLC4, CLC4G and CLC4I were assessed by injecting the AAV constructs into established E077 tumors. Mice were treated with PBS, AAV-dCas9+Vector, AAV-dCas9+CLC4 (dual AAV delivered CRISPRa of sgRNA library targeting CLC4G, i.e. o-MAEGI-CLC4G), AAV-orf-CLC4 (AAV delivered open reading frame expression of CD80-Light-CXCL10-4-1BBL), or AAV-orf-CLC4I (AAV delivered open reading frame expression of CD80-Light-CXCL10-4-1BBL-IFNG). Tumor growth was then followed over the next 27 days (FIG. 2). Tumors treated with empty vector plus the dCas9 AAV (Vector+11b) had slightly reduced but not significant growth compared to PBS-alone controls. Treatment with CLC4 (pGW066) resulted in a significant reduction in tumor volume. Treatment with CLC4G+11b (o-MAEGI) or CLC4I (pGW067) resulted in a highly significant reduction in tumor volume. The data demonstrated the in vivo therapeutic efficacy of these treatments.

Figure 3A:
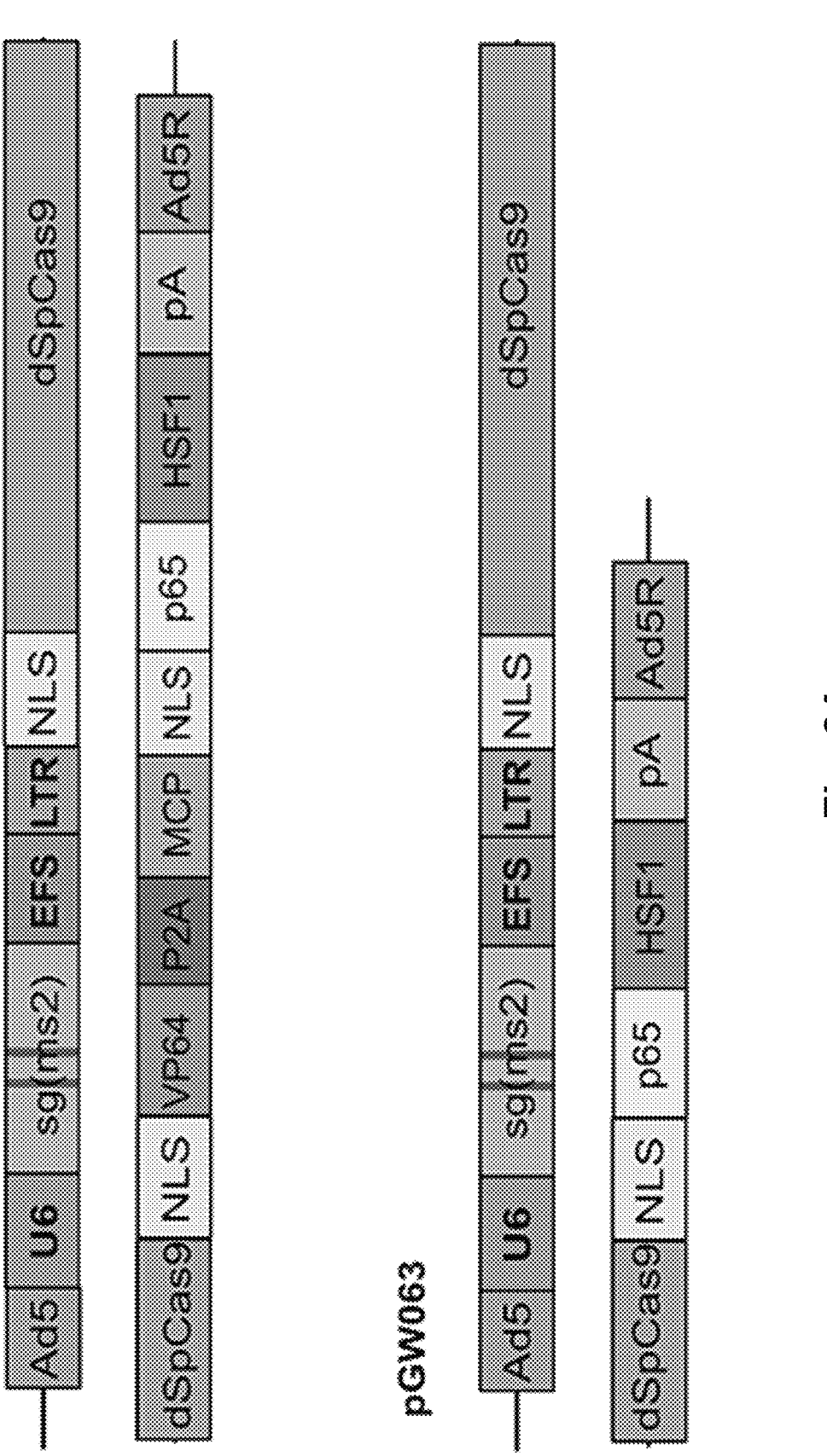
Figure 3B:
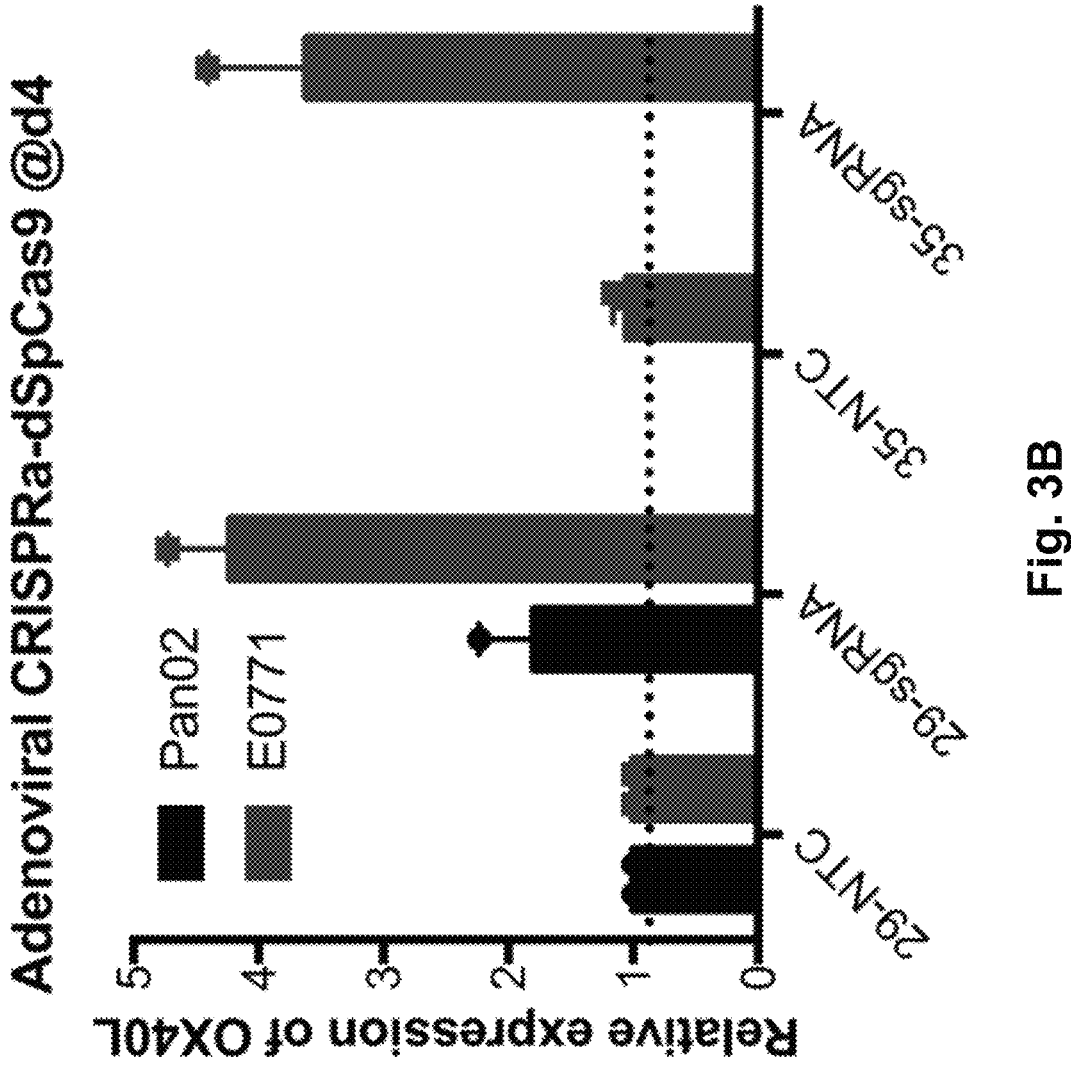
Figure 3C:
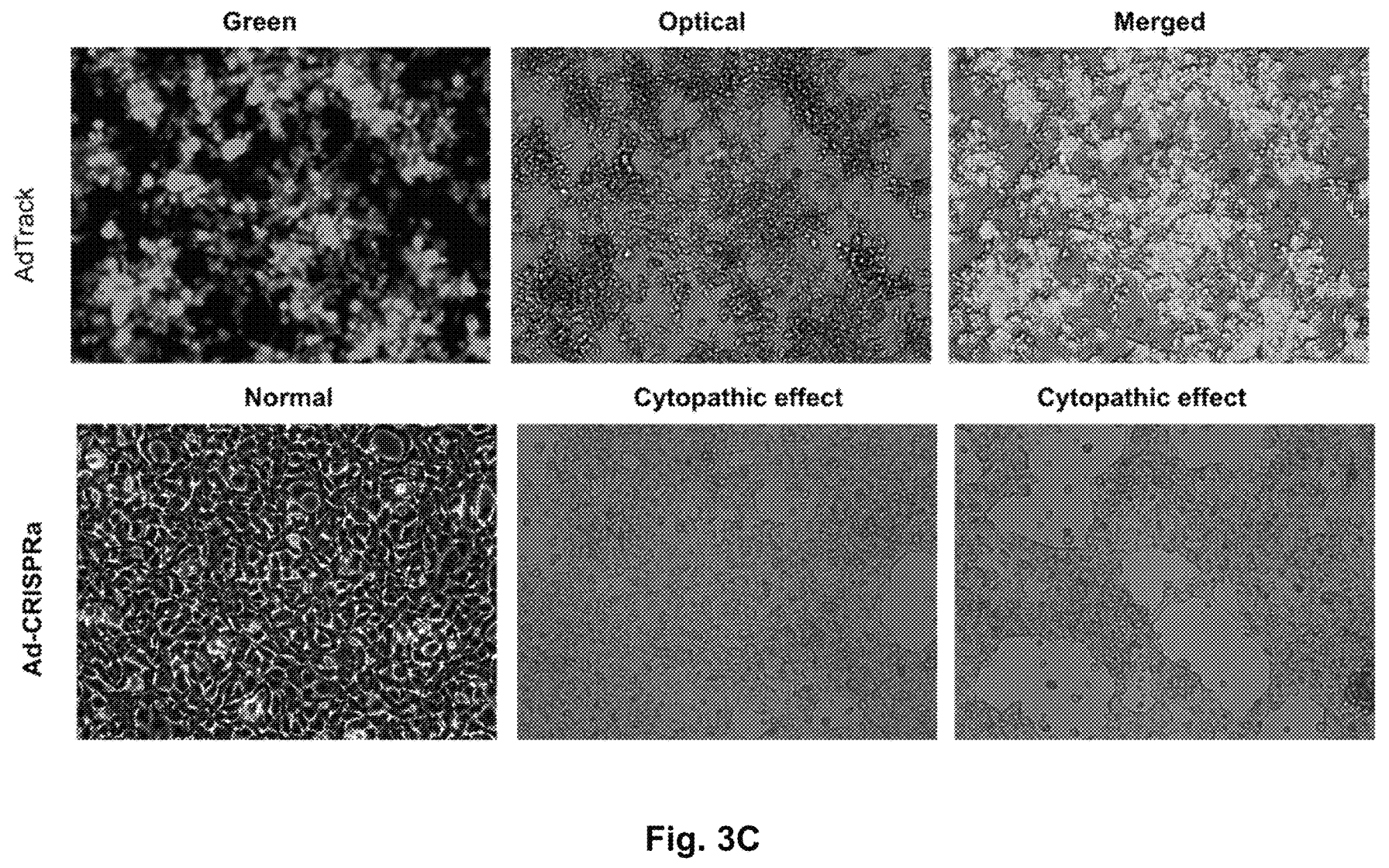

Example 3: Design and Characterization of Adenovirus-Based One-Vector CRISPRa Systems Adenoviral-based dSpCas9 CRISPRa systems were designed herein that utilize a single construct to deliver all CRISPRa components. The constructs, pGW029 (SEQ ID NO: 4), pGW035 (SEQ ID NO: 5), and pGW063 (SEQ ID NO: 6), are illustrated in FIG. 3A. In order to test this system in vitro, an sgRNA that targeted Ox40L was cloned into these constructs, and their activation efficacies were tested. Four days post-transfection, expression levels of Ox40L were determined by quantitative RT-PCR (FIG. 3B). The cytotoxic effects in HEK293FT cells caused by adenovirus production were then observed (FIG. 3C). Cells were transfected with AdTrack (adenoviral CMV-EGFP) constructs, and the expression of GFP and cytopathic effects were observed (FIG. 3C top row). In a similar study, the CRISPRa system was cloned into adenoviral constructs (U6-sgRNA-EFS-LTR-dSpCas9-p65-HSF1-sPA) and the adenoviruses were rescued. 4-6 days post-infection of the adenovirus, cytopathic effects on HEK293FT were observed (FIG. 3C, bottom row). These results demonstrated the robustness of the dSpCas9 CRISPRa adenoviral system.

Example 4: Design and Testing of CRISPRa AAV-Based Vector Systems

Figures 4A, 4B:
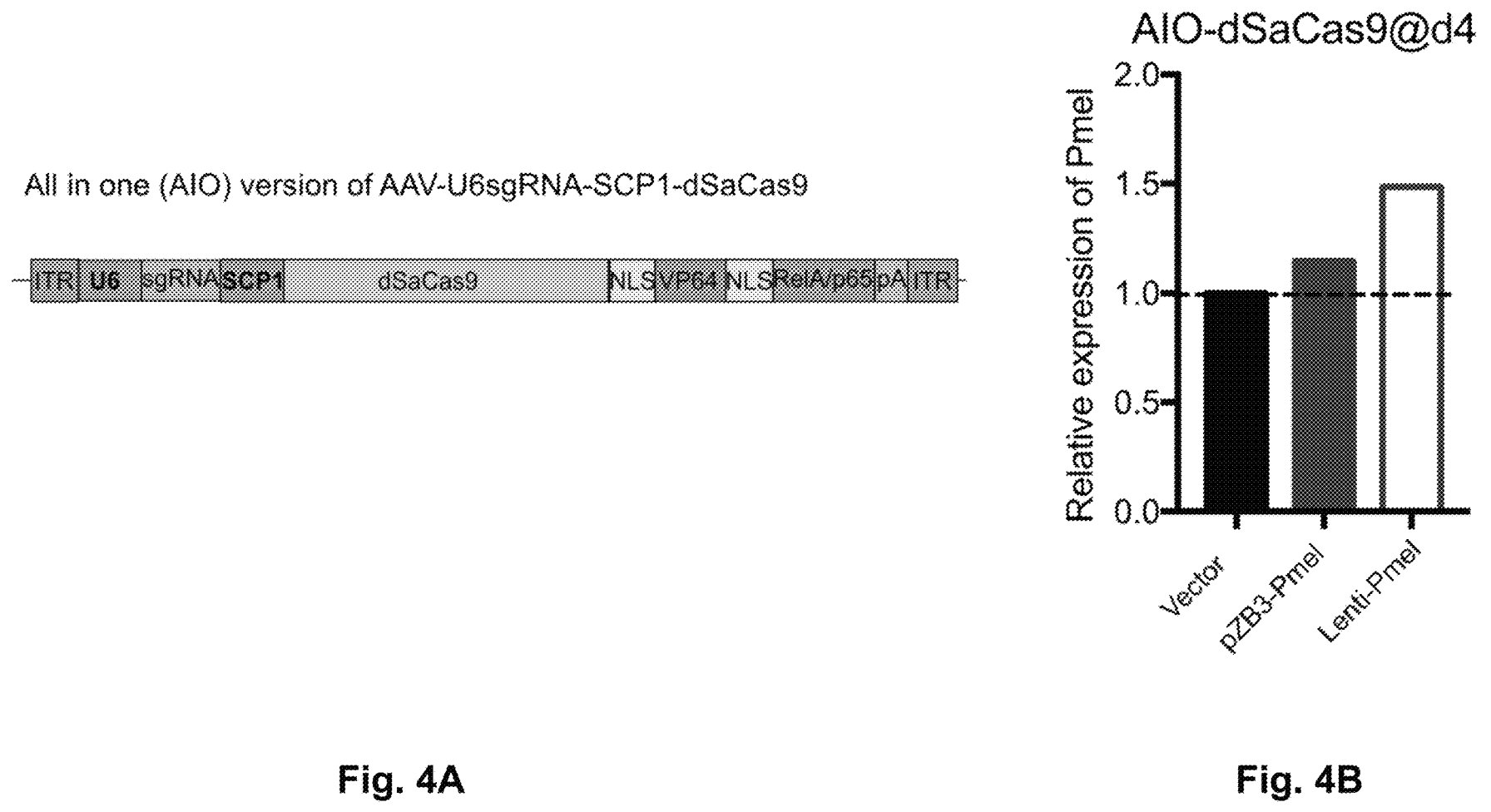

Additional vector systems were designed utilizing AAV to deliver CRISPRa components to target cells. The first was a dSaCas9-based AIO (all-in-one) CRISPRa system, which uses a single AAV vector (pZB3: SEQ ID NO: 10) to deliver all CRISPRa components (FIG. 4A). For in vitro testing of this system, Pmel was targeted with the AIO CRISPRa system. Four days post-infection, expression levels of Pmel were determined by quantitative RT-PCR, which revealed up-regulation of Pmel expression by the AAV-based (pZB3) vector (FIG. 4B). A lentiviral based version was used for comparison.

Figures 5A, 5B:
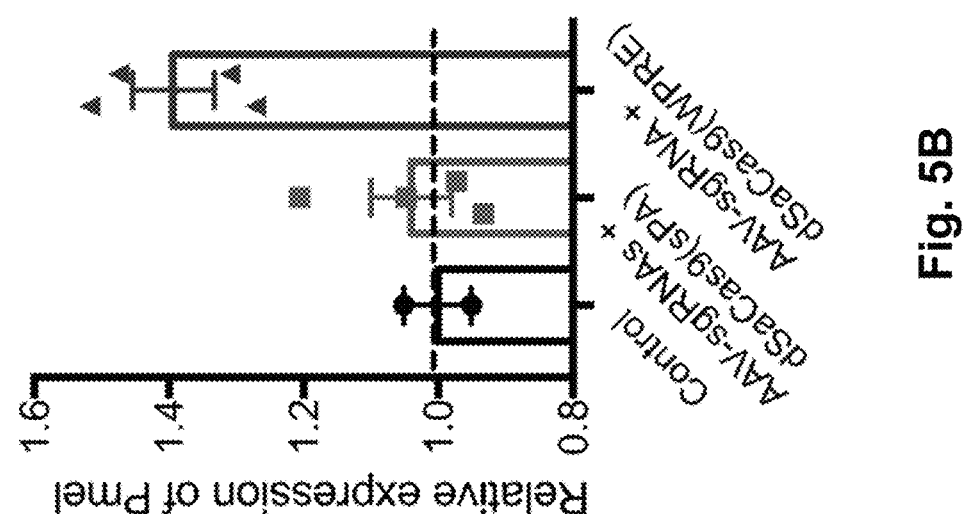
FIGS. 5A-5B illustrate an AAV based two-vector system with dSaCas9.

An AAV-based two-vector system with dSaCas9 was designed for use in endogenous gene activation and MAEGI. In this case, the dSaCas9 enzyme was delivered on a separate construct from the other CRISPRa components (pGW060: SEQ ID NO: 12 and pGW047: SEQ ID NO:11, respectively) (FIG. 5A). For in vitro testing, Pmel targeted sgRNA was cloned into the dual AAV-CRISPRa system.

Expression levels of Pmel were determined by quantitative RT-PCR four days after infection (FIG. 5B). A significant increase in Pmel expression was observed in cells transfected with the two-vector dSaCas9 system.

Figures 6A, 6B:
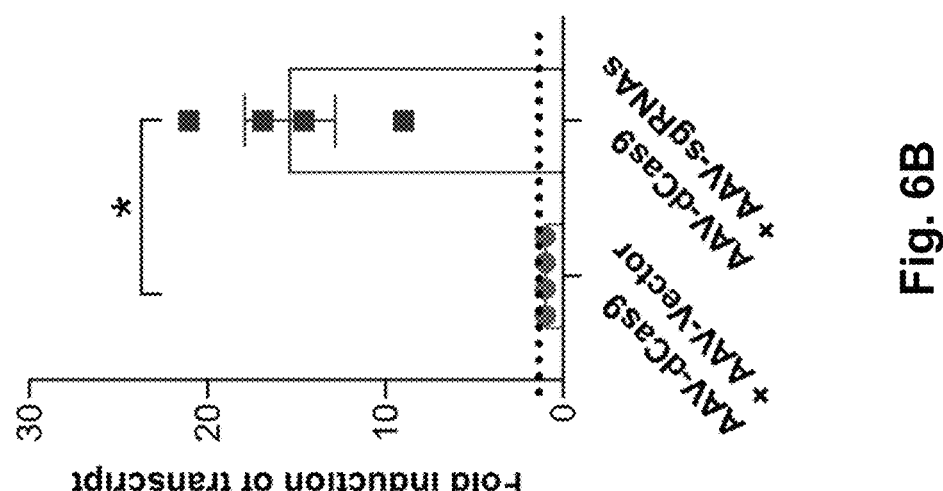
FIGS. 6A-6B illustrate an AAV based two-vector system with dSpCas9.

Another two-vector system was also designed, which utilized the dSpCas9 endonuclease. A schematic of the two constructs used in this dSpCas9-based dual-AAV delivery system is depicted in FIG. 6A (pGW045: SEQ ID NO: 13). For in vitro testing, Pmel targeted sgRNA was cloned into cells with the dual AAV-CRISPRa system (FIG. 6B). Four days post-infection, expression levels of Pmel were determined by quantitative RT-PCR, which demonstrated significant upregulation of Pmel transcript as compared to a non-sgRNA containing control.

Example 5: An AAV-Based Two-Vector System with dCas12a/dCpf1

AAV-based two-vector systems were generated that utilize dCas12a/dCpf1 to facilitate endogenous gene activation and MAEGI. Vectors comprising Cas12 (formerly known as Cpf1) derived from Lachnospiraceae bacterium ND2006 (dLbCas12a/dLbCpf1) or *Acidaminococcus* sp. (dAsCas12a/dAsCpf1) were generated. Vectors used in this system include: pRC119: pRC119 AAV EFS-denAsCas12a-SunTag3x-1 (SEQ ID NO: 14); pRC120: pRC120 AAV EFS-dLbCas12a-SunTag5x-1 (SEQ ID NO: 15); pRC121b: pRC121b AAV-EFS-LTR-scFV_Gcn4-Activ-Triplex-SapI-WPRE (SEQ ID NO: 16); pRC124: pRC124 AAV-EFS-LTR-NLS-dLbCpf1_574-NLS-Activ-Triplex-SapI-WPRE-1 (SEQ ID NO: 17); and pRC126: pRC126 AAV-EFS-LTR-NLS-Activ-dLbCpf1_1229-NLS-Activ-sPA-1 (SEQ ID NO: 18).

Figures 9A, 9B:
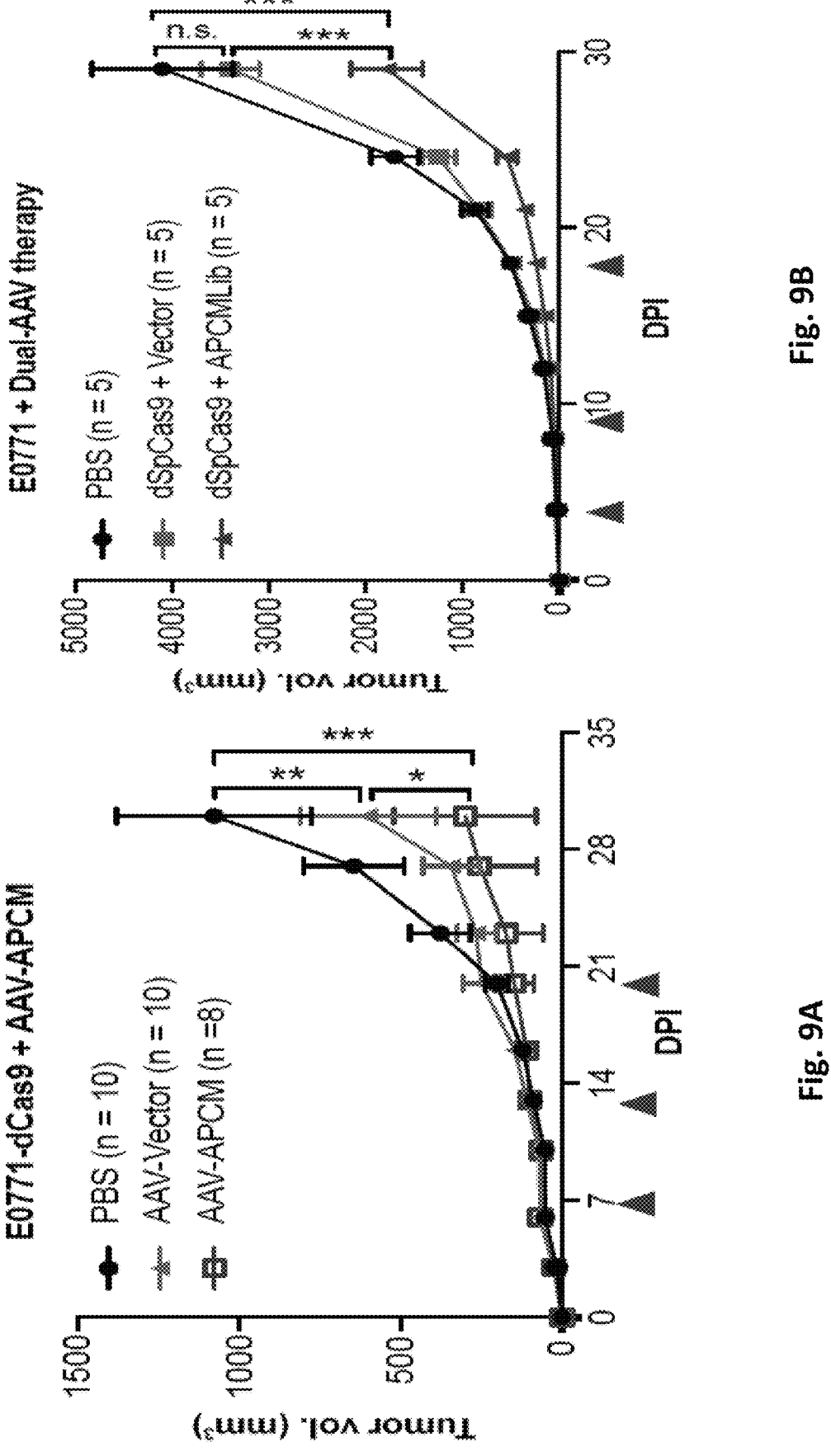
FIGS. 9A-9G illustrate multiplexed activation of endogenous genes as immunotherapy, by activating immune genes (APCM) or mutant genes (p-MAEGI).
Figures 9C, 9D, 9E:
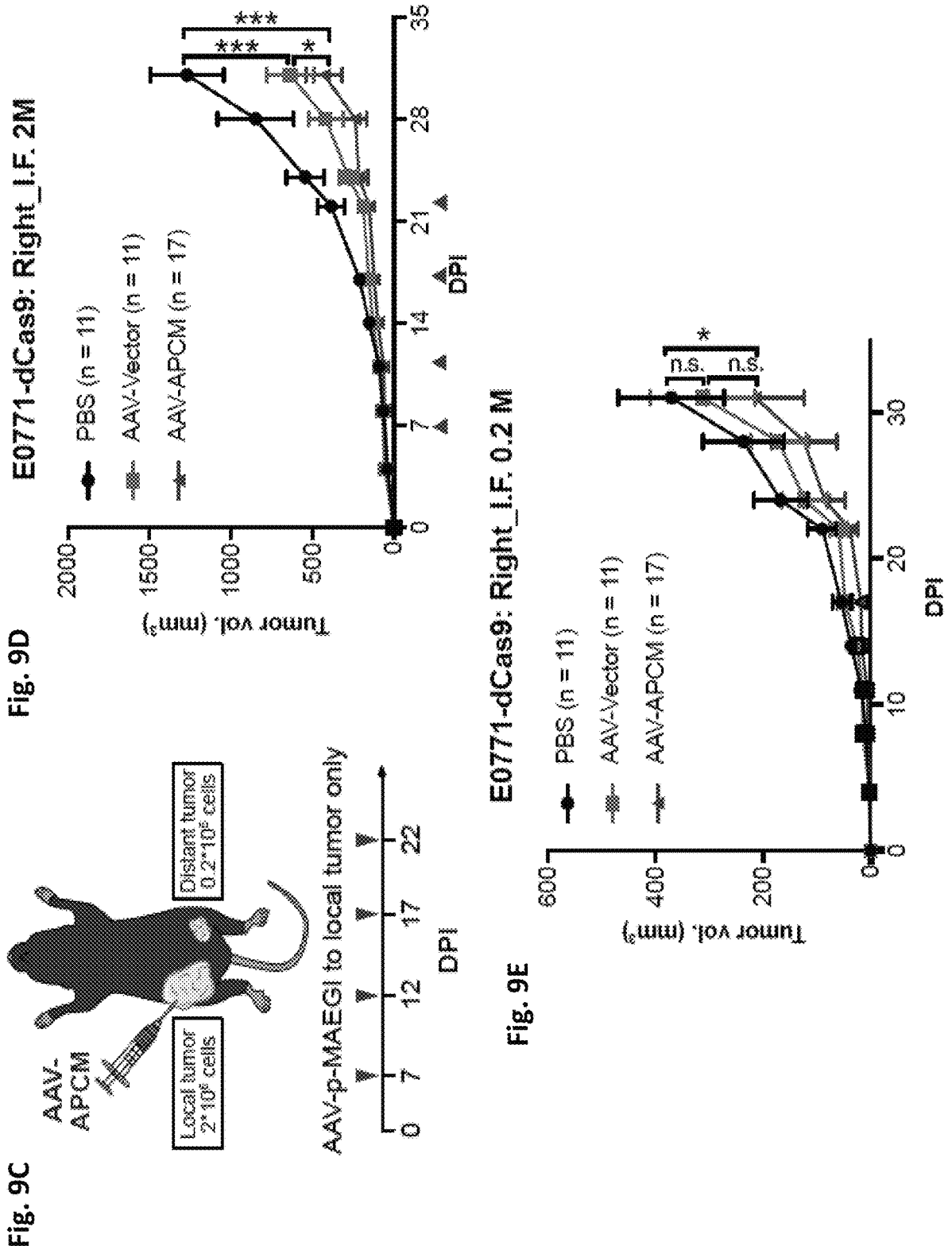
Figures 9F, 9G:

Example 6: Multiplexed Activation of Endogenous Genes by APCM as an Immune-Gene Therapy Approach Syngeneic orthotopic breast tumors were induced in mice by E0771 cells in C57BL/6 mice (FIGS. 9A-9D). These animals were treated with PBS, AAV-Vector, or AAV-APCM sgRNA library by intratumoral administration at indicated times (arrows), using either a single vector carrying the library alone into dCas9-VP64 expressing cells (FIG. 9A, against single tumor; and FIG. 9C, against both local and distant tumor), or using a dual-AAV approach (FIG. 9B). Survival of these animals treated with PBS, AAV-Vector, or AAV-APCM sgRNA library showed that AAV-APCM treatment extended the overall survival of treated animals (FIG. 9D). Syngeneic pancreatic tumors were induced in mice by Pan02 cells in C57BL/6 mice (FIG. 9E). These animals were treated with PBS, AAV-Vector, AAV-p-MAEGI(Pan02) or AAV-APCM sgRNA library by intratumoral administration with two doses per week, total of 3-4 doses starting at end of week 1.

Example 7: Molecular Characterization and Therapeutic Effect of Multiplexed Activation of Cd80, Light, Cxcl10, Gitrl, 41bbl, and IFNg in Tumor Cells by AAV-Delivered CRISPRa or AAV-ORFs (Polycistronic Open-Reading-Frames)

Figure 10A:
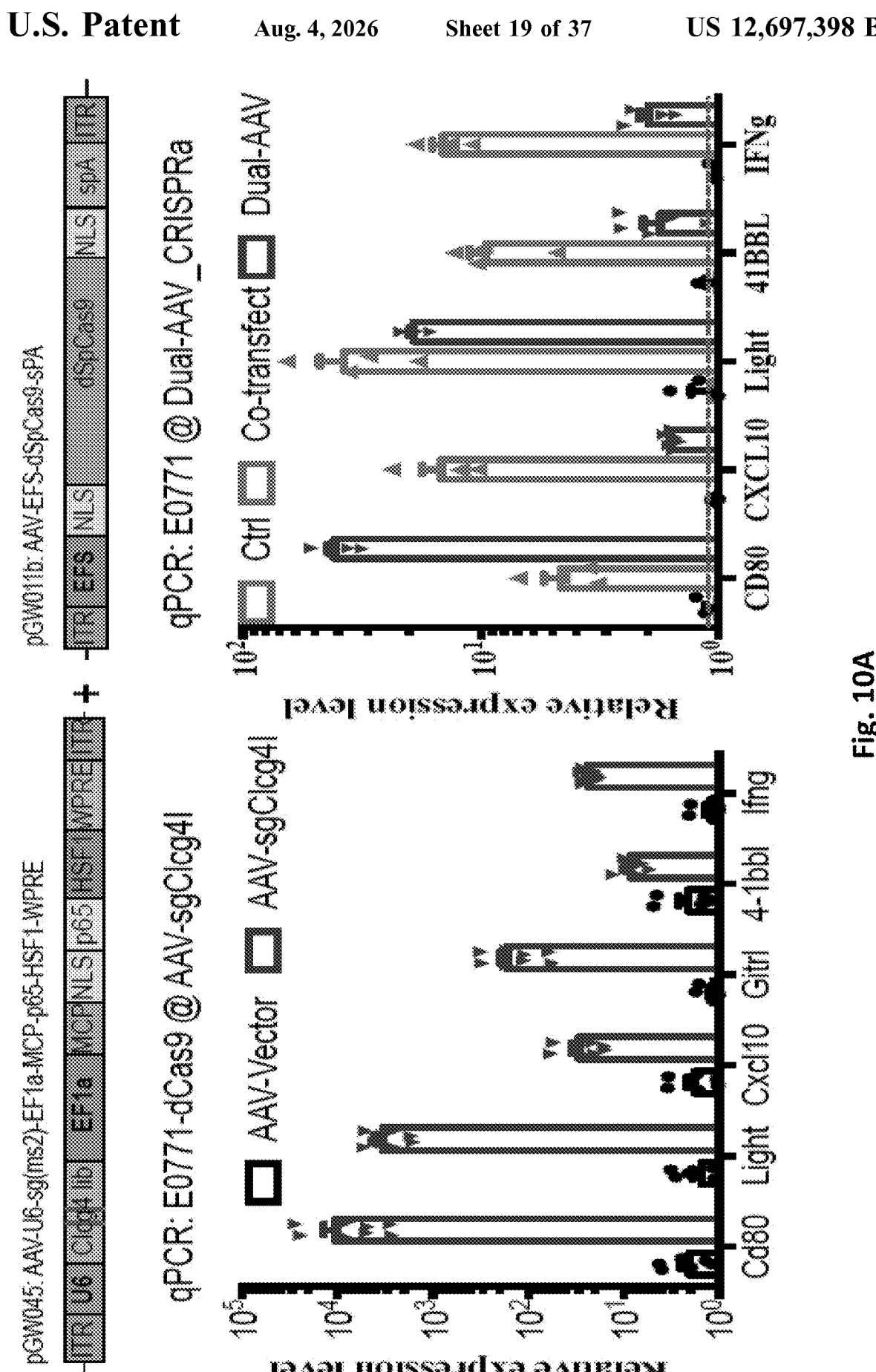
FIGS. 10A-10F illustrate therapeutic effects by multiplexed activation of Cd80, Light, Cxcl10, Gitrl, 41bbl, and IFNg in tumor cells by AAV-delivered CRISPRa or AAV-ORFs (polycistronic open-reading-frames).
Figure 10B:
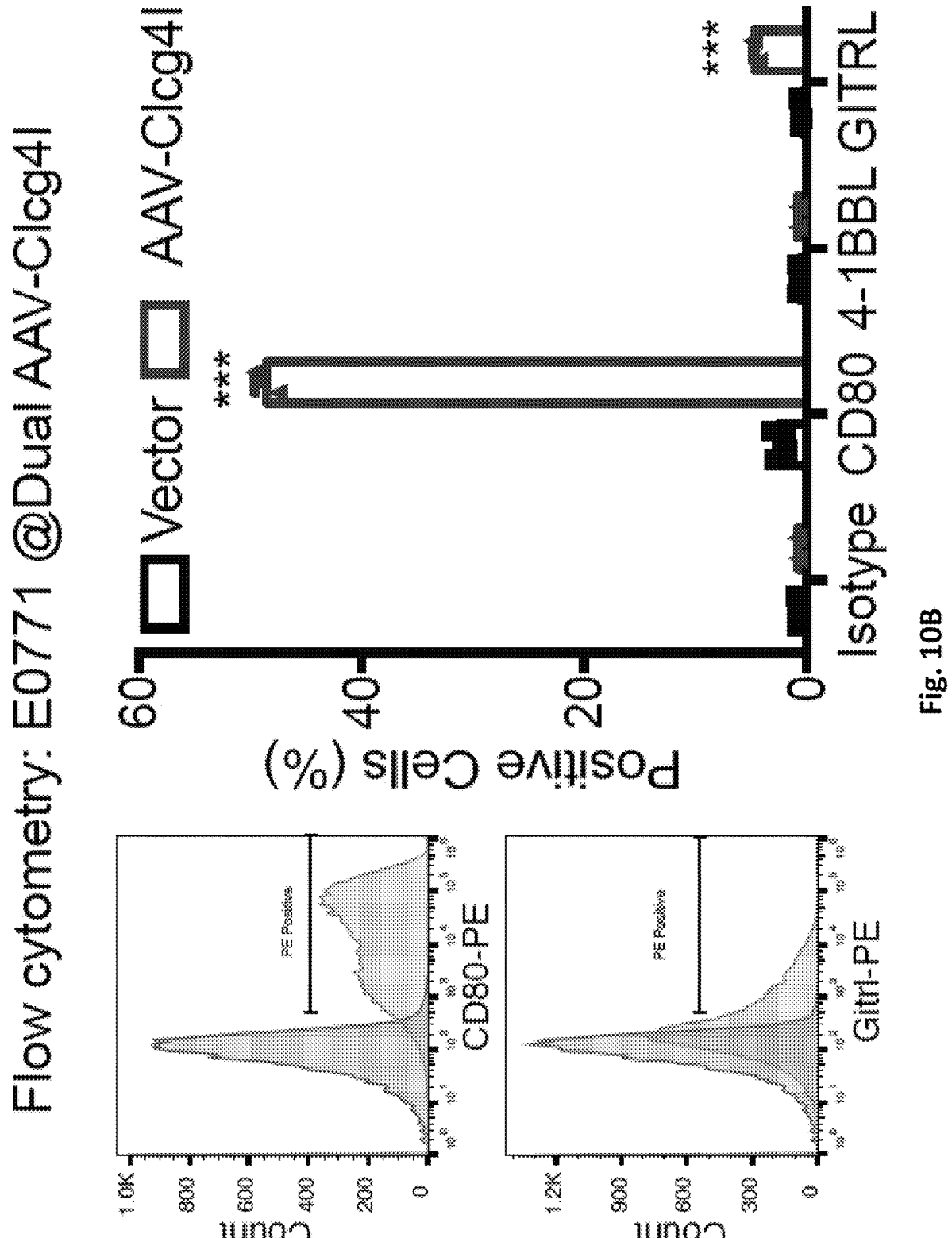
Figures 10C, 10D:
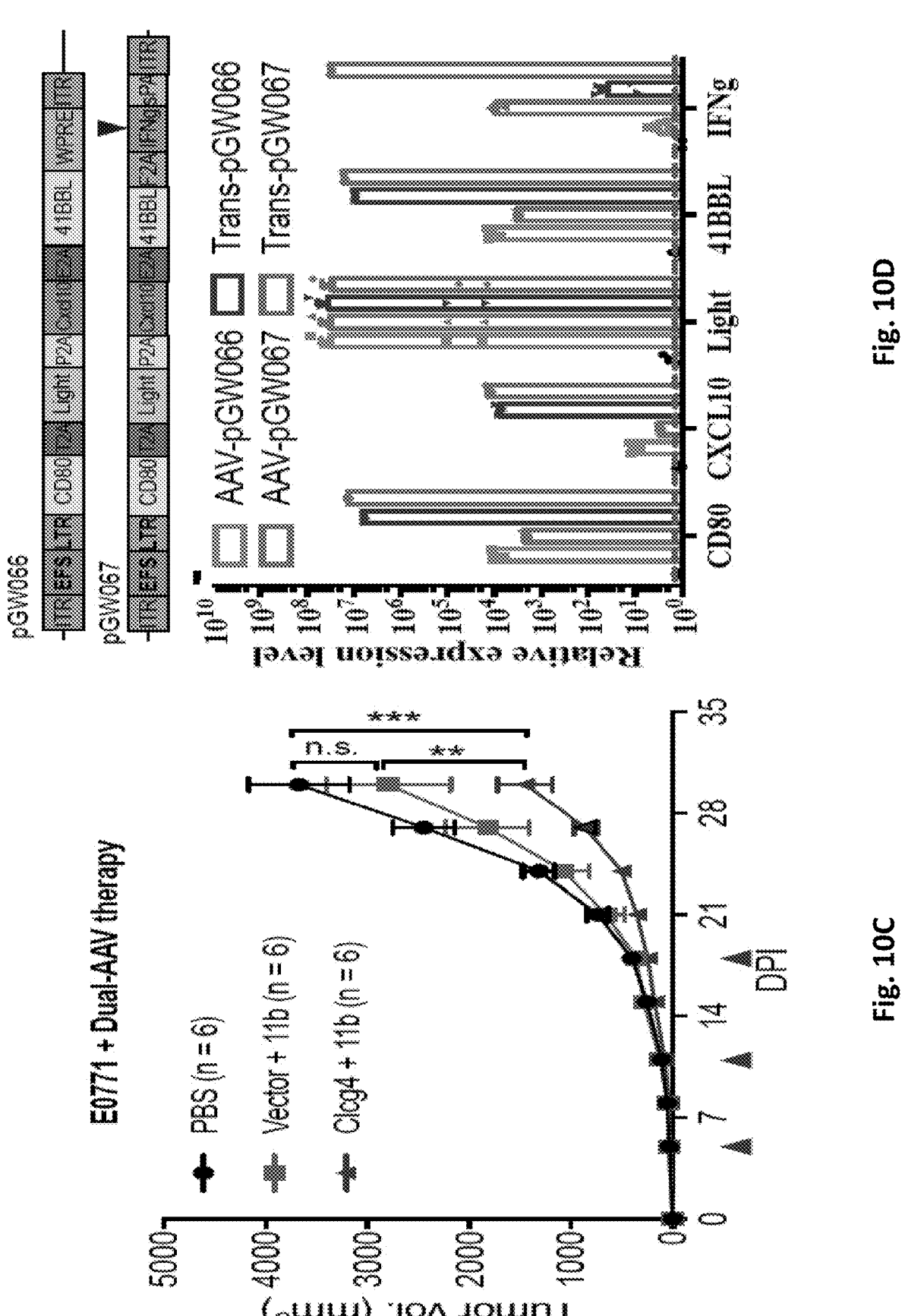
Figures 10E, 10F:
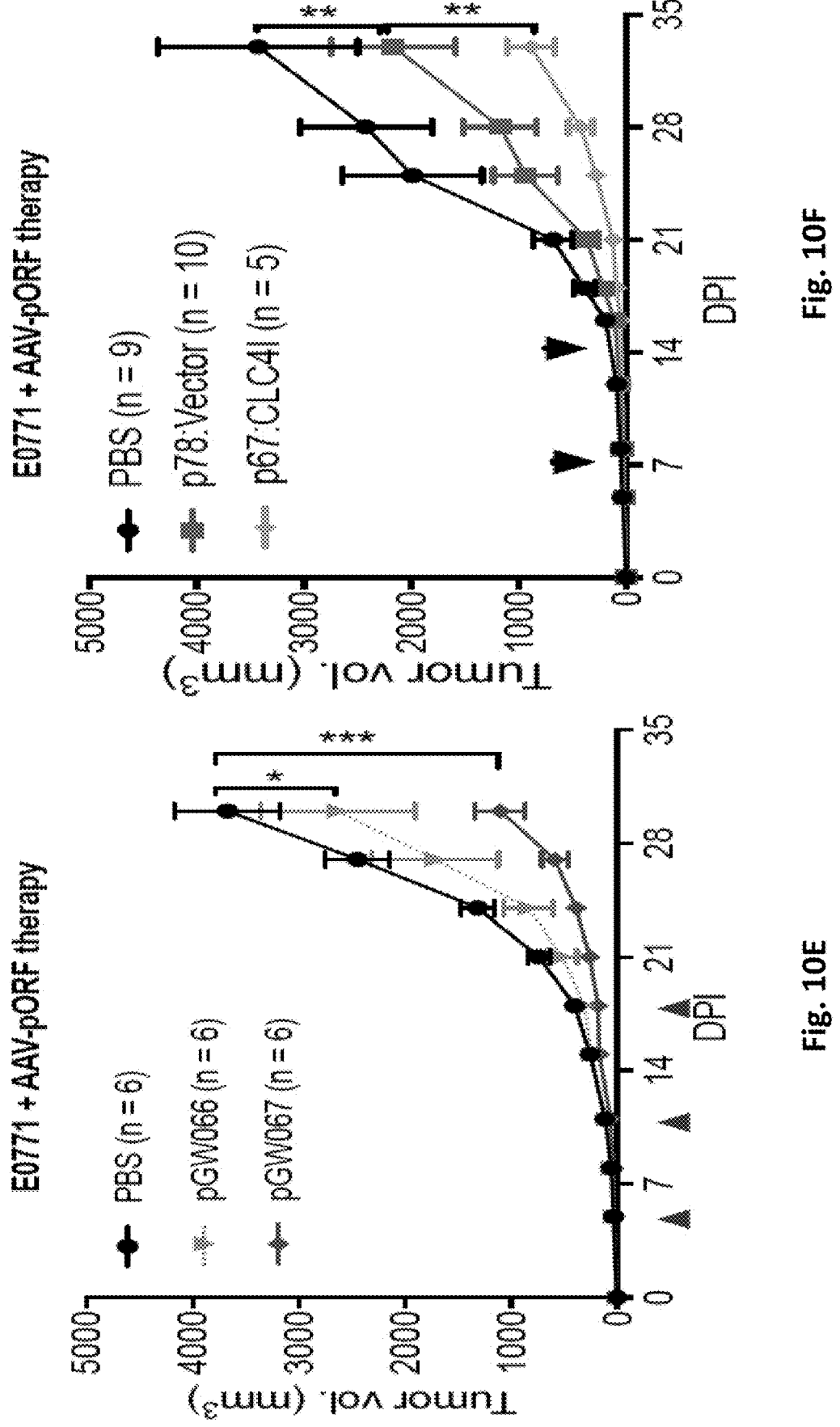

FIG. 10A left panel shows AAV-CRISPRa-mediated transcriptional activation of Cd80, Light, Cxcl10, Gitrl, 41bbl, and IFNg, normalized to vector-transduced controls; Right panel shows Co-transfection of or Dual AAV-CRISPRa-mediated transcriptional activation of Cd80, Light, Cxcl10, Gitrl, 41bbl, and IFNg, normalized to control. The results showed expression of CD80, 41BBL, and Gitrl in dual-AAV-CRISPRa infected cells assessed by flow cytometry (FIG. 10B). Therapeutic effects of intratumoral injected AAV-CRISPRa with dual-AAV mediated activation of Cd80, light/Tnfsf14, Cxcl10, 4-1BBL/Tnfsf9, and Ifng (CLC4I) are shown in FIG. 10C. Growth curves showed the time course sizes of E0771 tumors treated with PBS, AAV-dCas9+Vector, AAV-dCas9+CLCG4 (dual AAV delivered CRISRPa of Clcg)(FIG. 10C). QPCR results showed successful overexpression of Cd80, Light, Cxcl10, 41bbl, or/and IFNg using AAV polycistronic ORFs (FIG. 10D). Both transfection and AAV infection led to high levels of expression of these molecules. Results showed significant therapeutic effects of intratumoral injected AAV-ORFs expressing Cd80, Light, Cxcl10, 41bbl (orfClc4), or AAV expressing Cd80, Light, Cxcl10, 41bbl, Ifng (orfClc4I) (FIG. 10E). Significant therapeutic effects of intratumoral injected AAV-ORFs expressing Cd80, Light, Cxcl10, 41bbl, Ifng (orfClc4I) were also demonstrated (FIG. 10F).

Example 8: Immune Characterization of APCM Treated Tumors

Figures 11A, 11B, 11C:
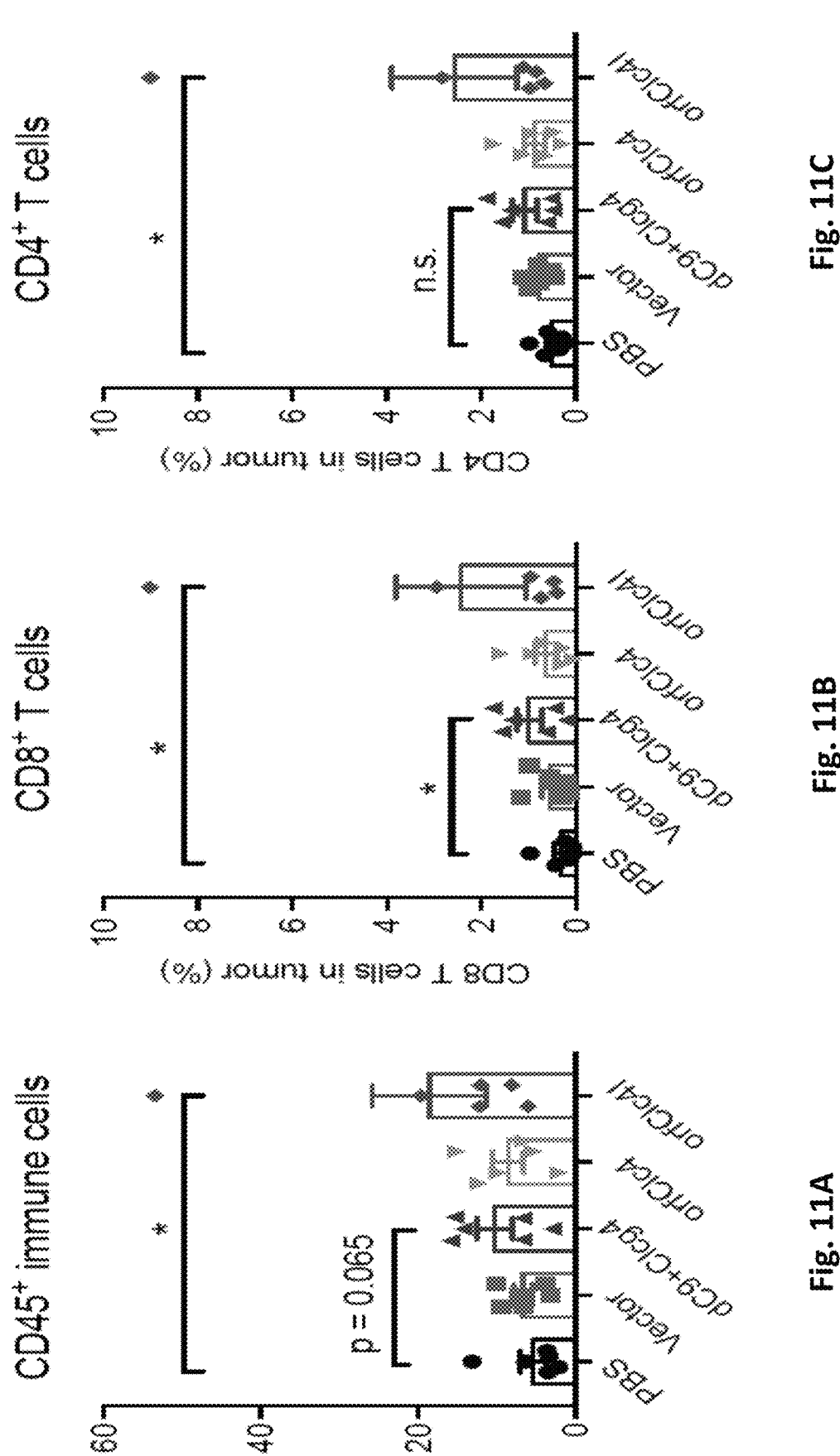
FIGS. 11A-11F illustrate the finding that AAV-mediated costimulatory molecule expression promotes tumor immune infiltration.
Figure 11F:
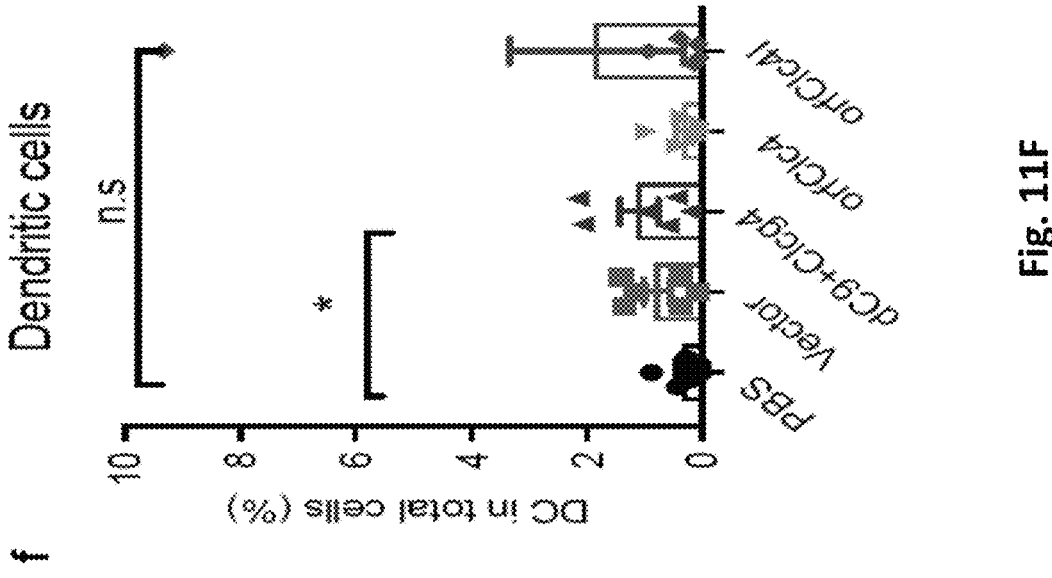
Figure 11E:
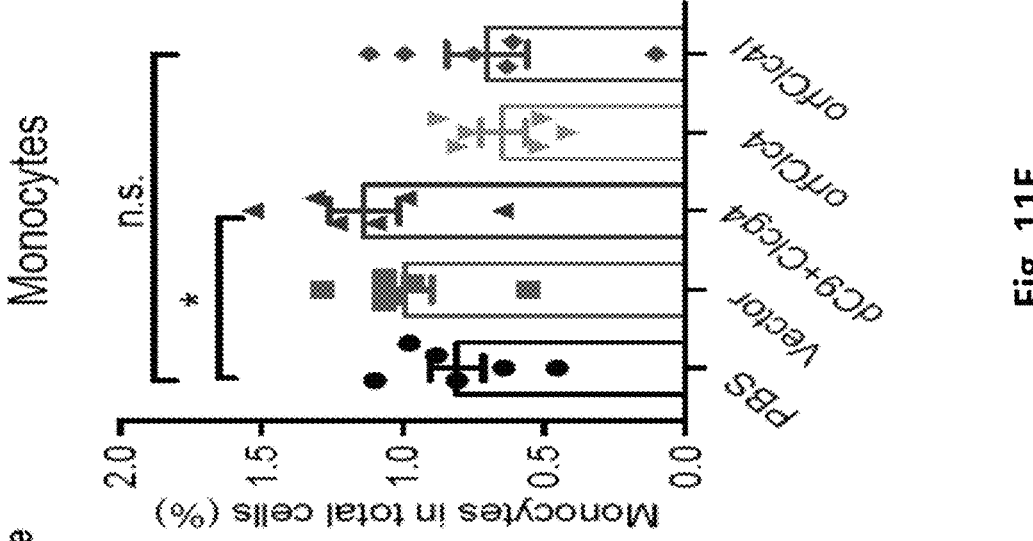
Figure 11D:
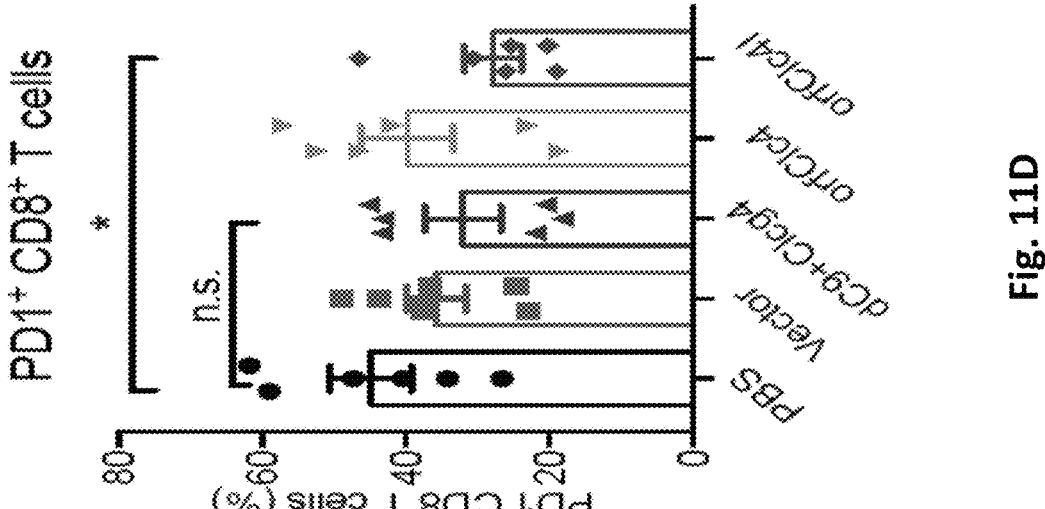

Immune profiling was performed to characterize AAV-mediated costimulatory molecule expression that promotes tumor immune infiltration (FIGS. 11A-11F). Results showed flow cytometry quantification of CD45+ immune cells in tumor microenvironment at DPI=30, showing percentages of CD45+ immune cells out of total cells in tumors treated with PBS, dual-AAV-vector, dual-AAV-Clcg4, AAV-orfClc4, AAV-orfClc4I (FIG. 11A). The percentages of CD8+ T cells out of total cells in tumors treated with PBS, dual-AAV-vector, dual-AAV-Clcg4, AAV-orfClc4, AAV-orfClc4I are shown in FIG. 11B. The percentages of of CD4+ T cells out of total cells in tumors treated with PBS, dual-AAV-vector, dual-AAV-Clcg4, AAV-orfClc4, AAV-orfClc4I are shown in FIG. 11C. Flow cytometry quantification of PD1+CD8+ T cells out of total CD8+ T cells in tumors treated with PBS, dual-AAV-vector, dual-AAV-Clcg4, AAV-orfClc4, AAV-orfClc4I is shown in FIG. 11D.) Flow cytometry quantification of monocytes out of total cells in tumors treated with PBS, dual-AAV-vector, dual-AAV-Clcg4, AAV-orfClc4, AAV-orfClc4I is shown in FIG. 11E. Flow cytometry quantification of monocytes out of total cells in tumors treated with PBS, dual-AAV-vector, dual-AAV-Clcg4, AAV-orfClc4, AAV-orfClc4I is shown in FIG. 11F.

Example 9: Rational Design of Off-the-Shelf Immune Gene Therapy by Composition Subtraction ("Minus-One Experiment")

Figures 12A, 12B:
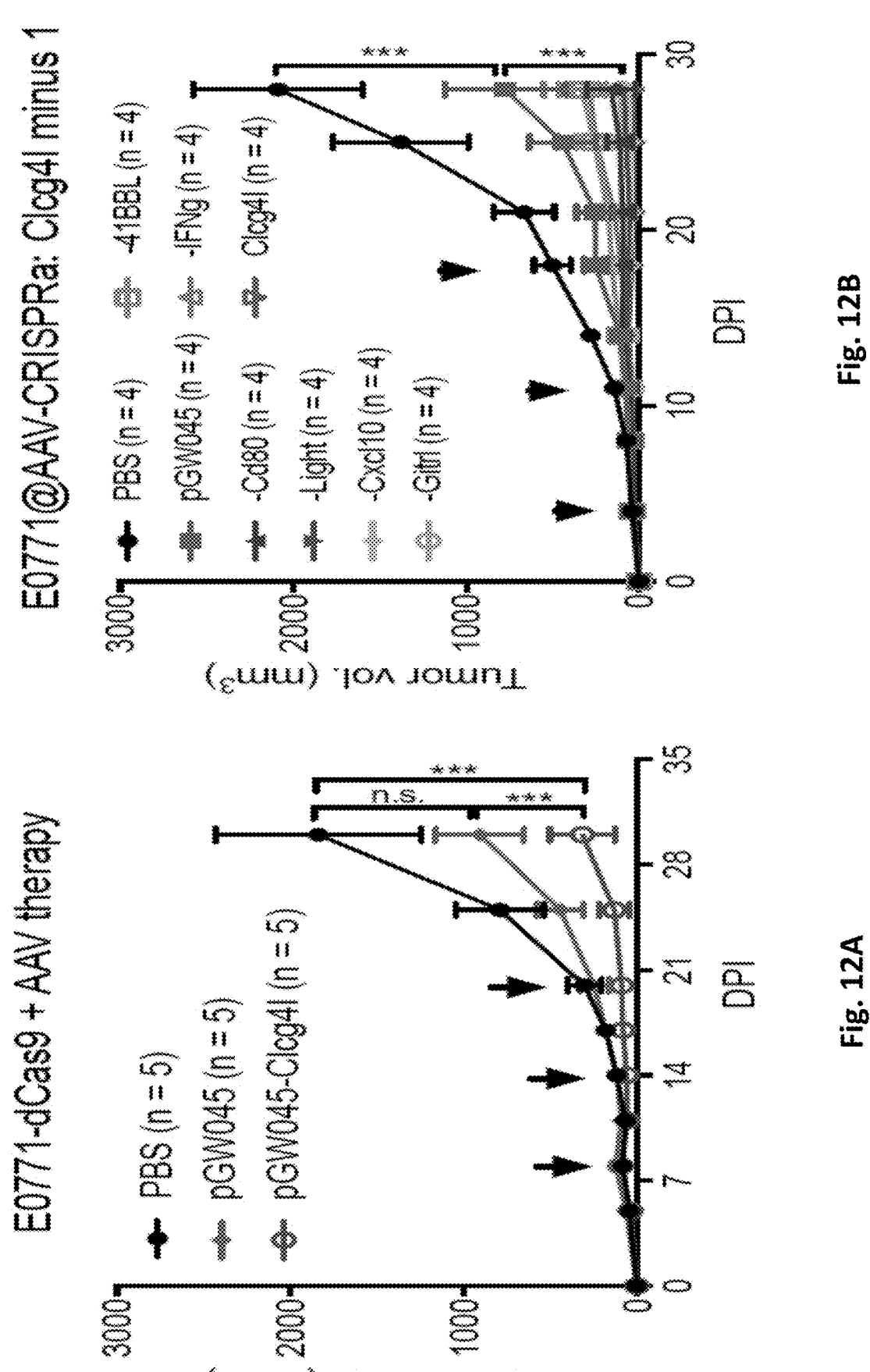
FIGS. 12A-12F illustrate optimized combinations of immune-stimulating molecules for tumor therapy.
Figures 12C, 12D:
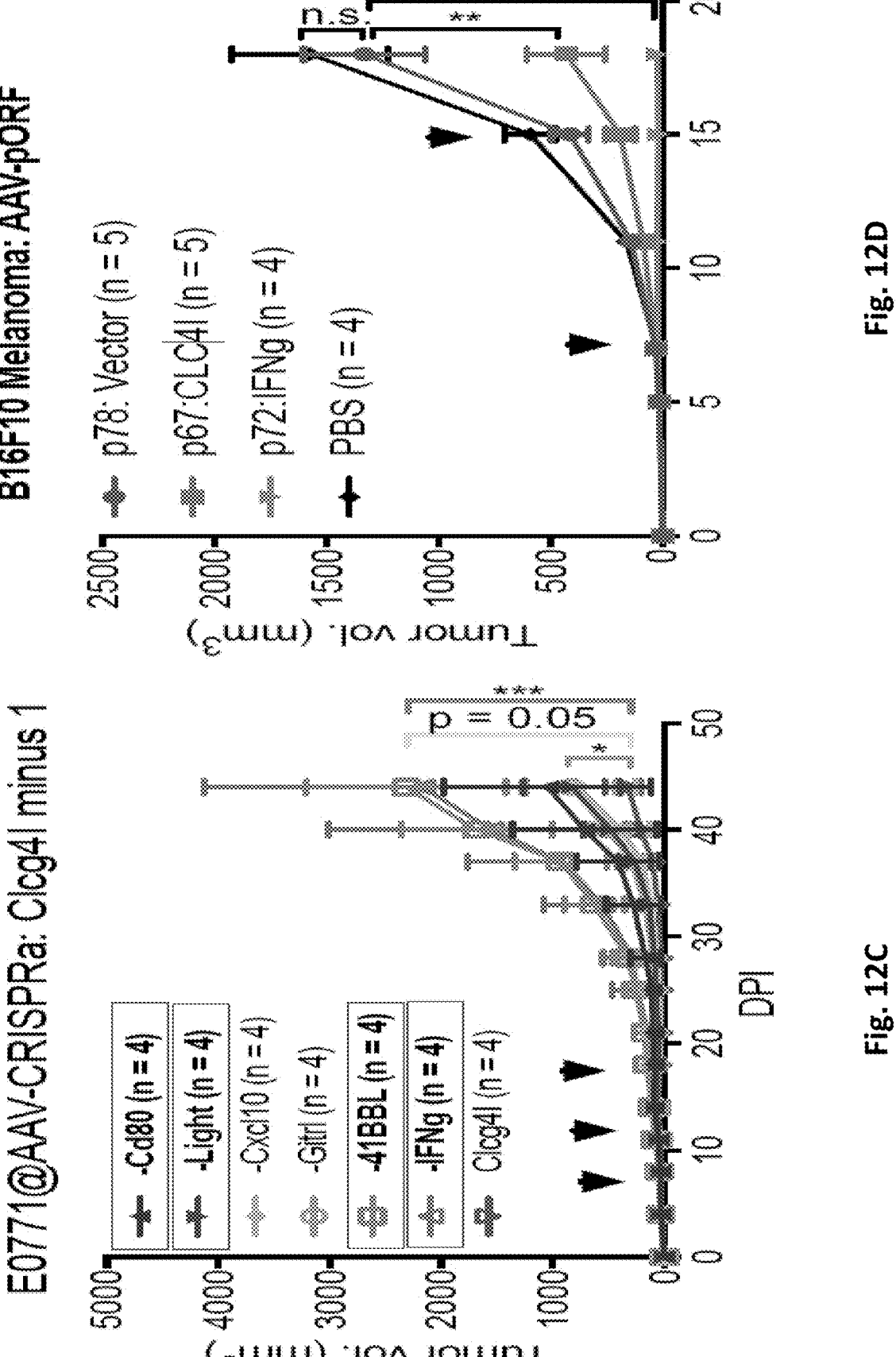
Figures 12E, 12F:
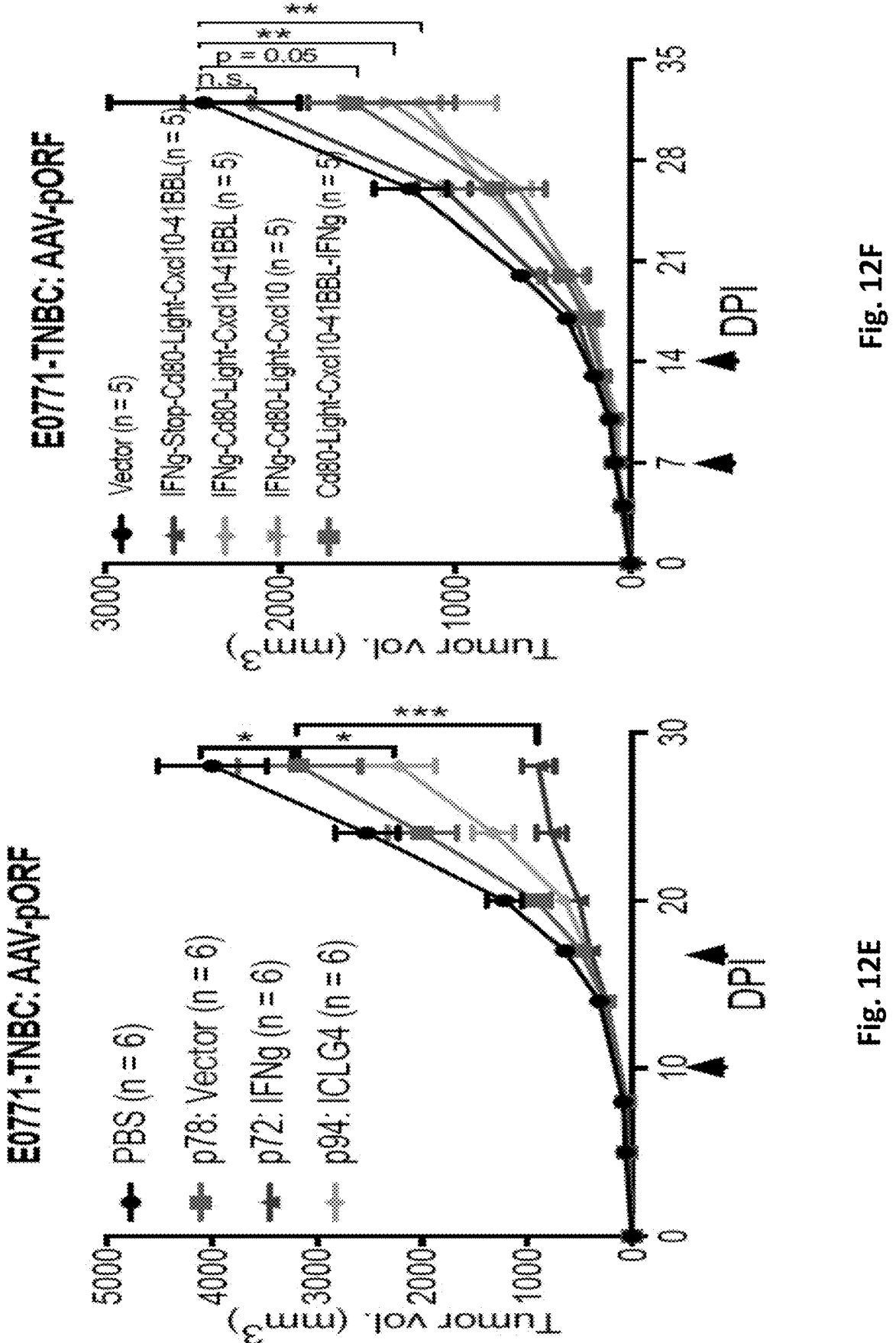

Composition subtraction and testing were performed to optimize the combinations of immune-stimulating molecules for tumor immune-gene therapy (FIGS. 12A-12F). Results demonstrated the therapeutic effects of intra-tumoral injected AAV-CRISPR activating Cd80, light, Cxcl10, 4-1BBL, Gitrl and Ifng (Clcg4I) (FIG. 12A). Growth curves of E0771 tumors treated with PBS (n=5), AAV-Vector (n=5), AAV-Clcg4I are shown in FIGS. 12B-12C. The "minus-one" experiment further optimized the combinatorial genes pool by removing one gene in each pool. Results showed the differential therapeutic efficacy of various different constructs of the full set and the "minus-one" constructs, with growth curves of E0771 tumors treated with PBS (n=4), AAV-Vector (n=4), AAV-Clcg4I (n=4), or AAV- Clcg4Iminus1 (n=4) (FIG. 12B). Growth curves of E0771 tumors treated with AAV-Clcg4I (n=4), or AAV-Clcg4Iminus1 (n=4) are shown in FIG. 12C. Growth curves of B16F10 melanoma treated with PBS (n=4), AAV-Vector (n=5), AAV-p67:Clc4I (Cd80, Light, Cxcl10, 41bbl, Ifng; n=5), AAV-P72:IFNg (n=4) are shown in FIG. 12D. Growth curves of E0771 tumors treated with PBS (n=6), AAV-Vector (n=6), AAV-P72:IFNg (n=6), AAV-p94:IClG4 (Ifng, Cd80, Light, Gitrl, 41bbl; n=6) are shown in FIG. 12E. Growth curves of E0771 tumors treated with AAV-Vector (n=5), AAV-polycistronic P119:IFNg-STOP-CD80-Light-Cxcl10-41BBL (n=5), AAV-polycistronic P118:IFNg-CD80-Light-Cxcl10-41BBL (n=5), AAV-polycistronic P100:IFNg-CD80-Light-Cxcl10 (n=5), AAV-P67: CD80-Light-Cxcl10-41BBL-IFNg (n=5) are shown in FIG. 12F.

Figure 13A:
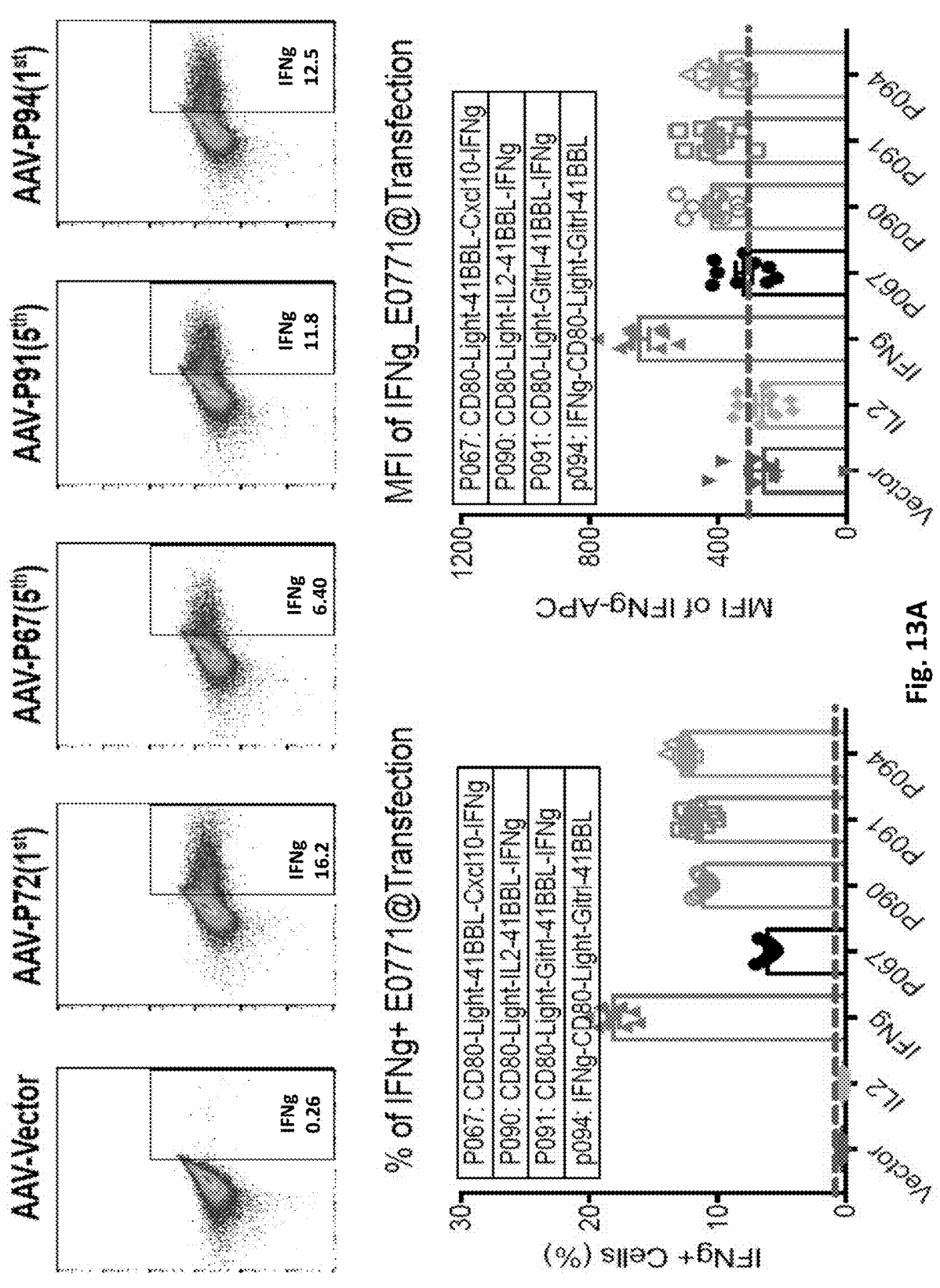
FIGS. 13A-13B illustrate the expression levels of IFNg and CD80 in transfected cells using different polycistronic AAV-ORFs.
Figure 13B:
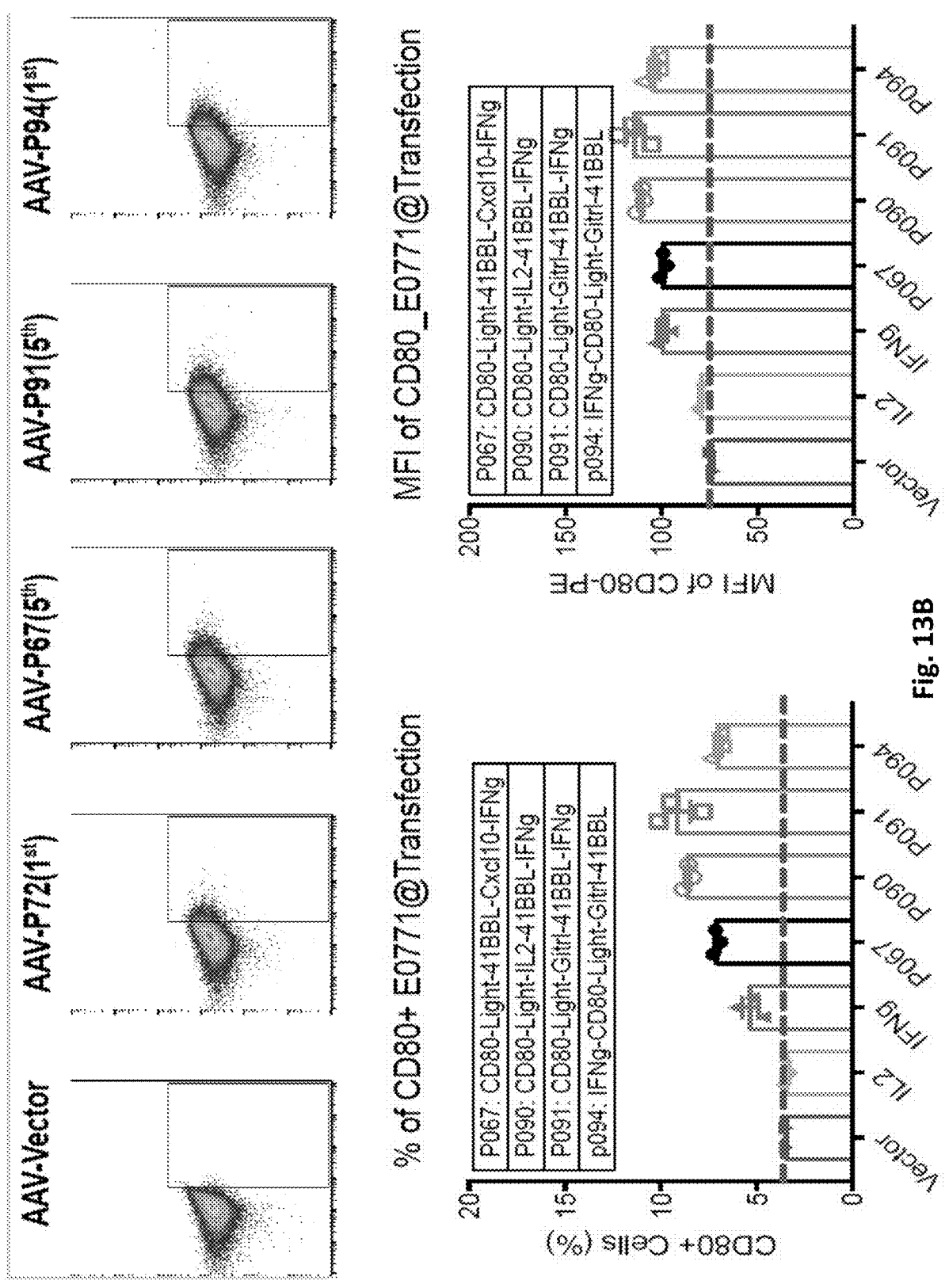

Example 10: Analysis of Expression Levels of IFNg and CD80 in Mammalian Cells Using Different Polycistronic AAV-ORFs AAV-ORFs-mediated expression of IFNg was demonstrated in different AAV constructs transfected into E0771 cells (FIG. 13A). The percentage of IFNg expressing cells in different constructs-transfected E0771 cells is shown in FIG. 13A, lower panel left. FIG. 13A, low panel (right) shows the median fluorescent intensity (MFI) of IFNg-APC in different constructs-transfected E0771 cells. FIG. 13B, upper panel shows representative flow cytometry plots demonstrating AAV-ORFs-mediated expression of CD80 in different AAV constructs transfected E0771 cells. FIG. 13B lower panel (left) shows the percentage of CD80+ cells in different constructs-transfected E0771 cells and FIG. 13B lower panel (right) shows the median fluorescent intensity (MFI) of CD80-PE in different constructs-transfected E0771 cells.

Figure 14A:
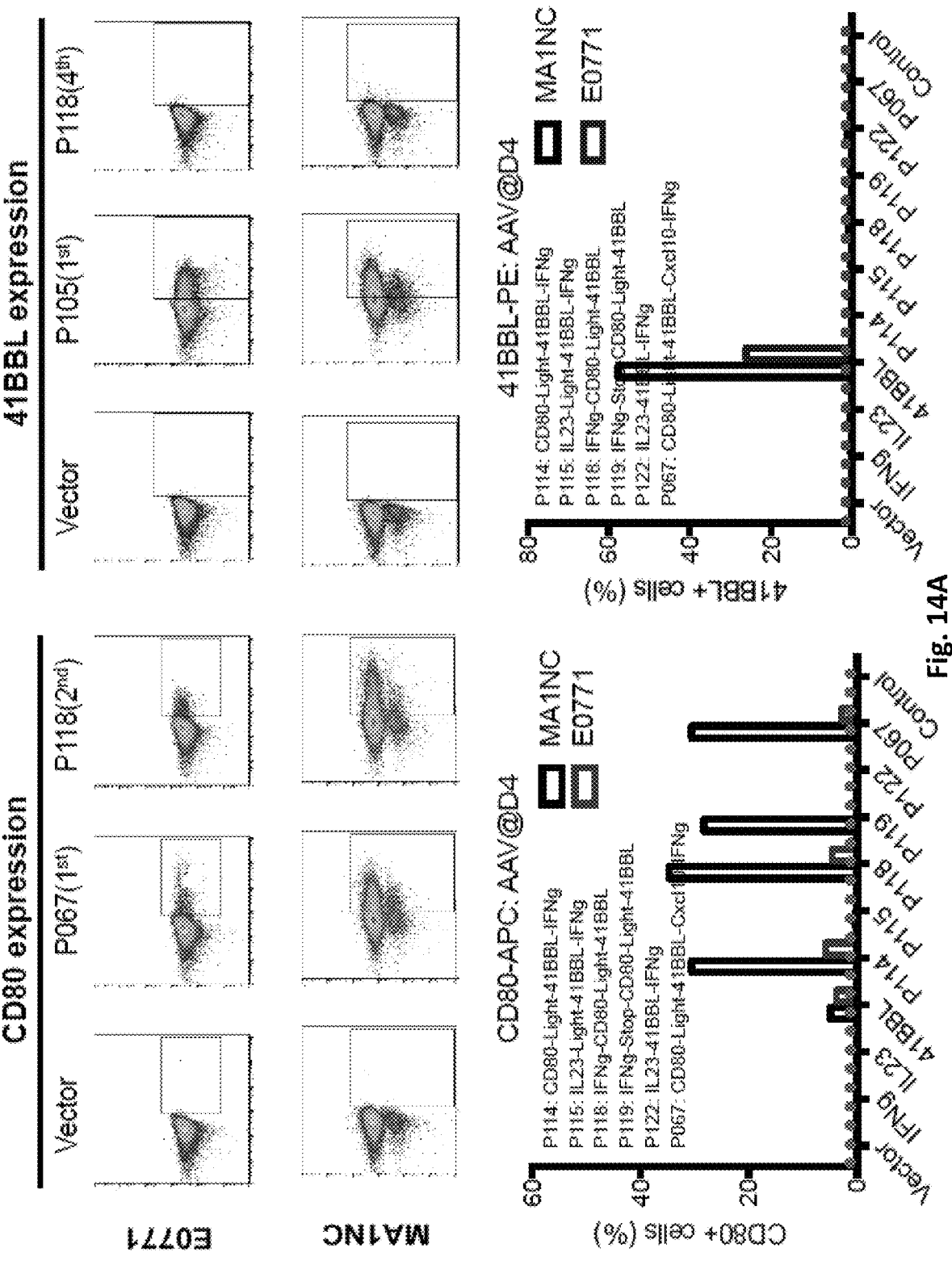
FIGS. 14A-14F illustrate optimizing costimulatory molecule combinations for tumor therapy.
Figure 14B:
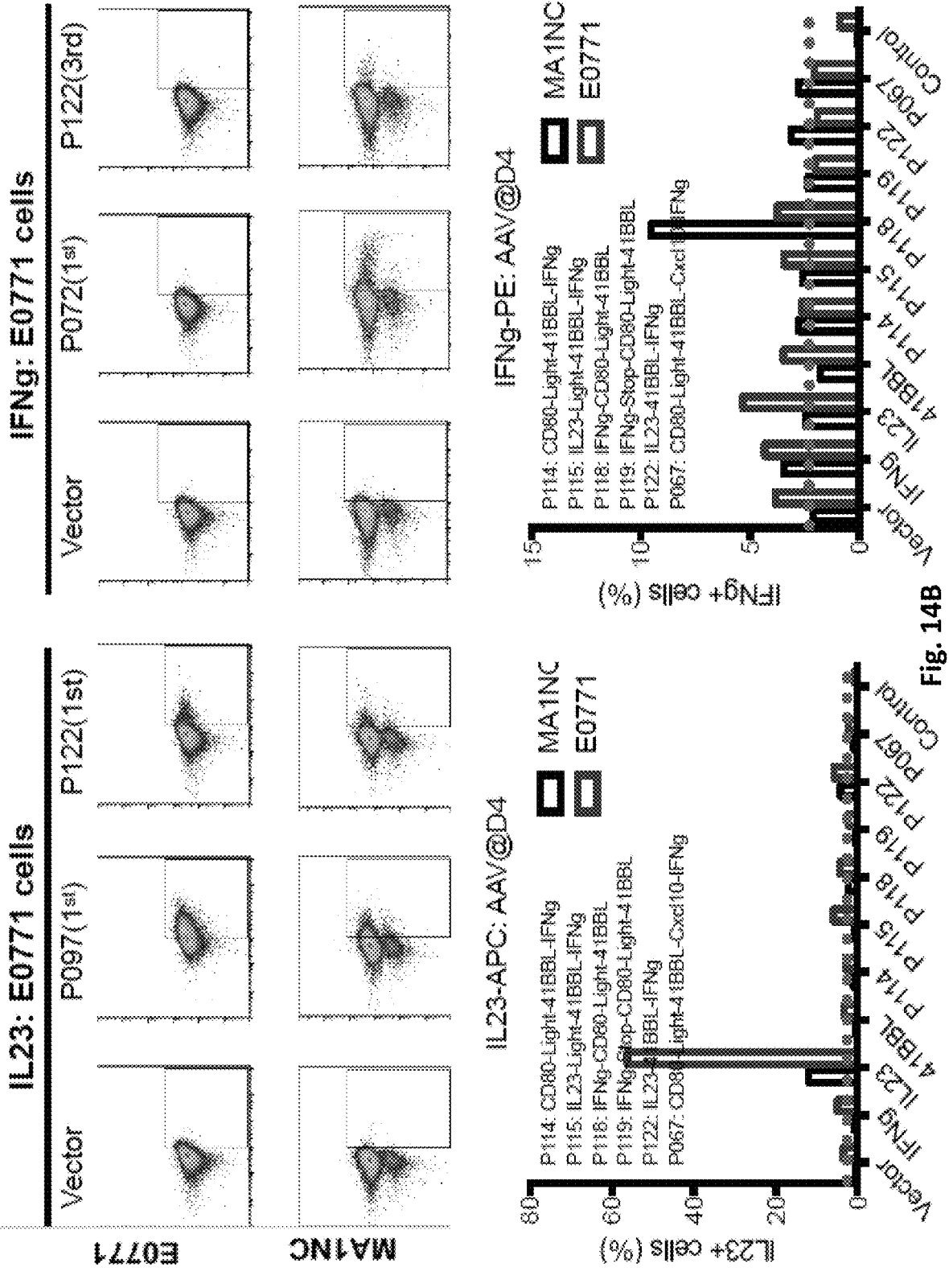
Figure 14D:
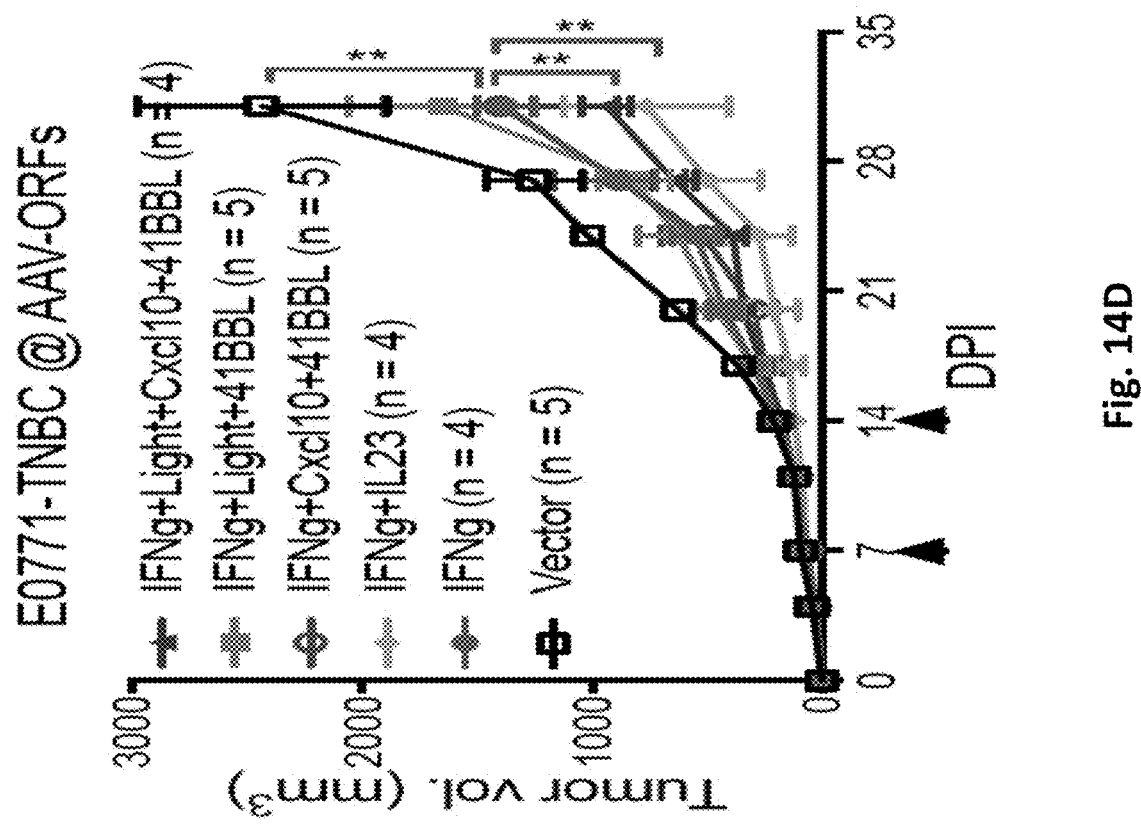
Figure 14C:
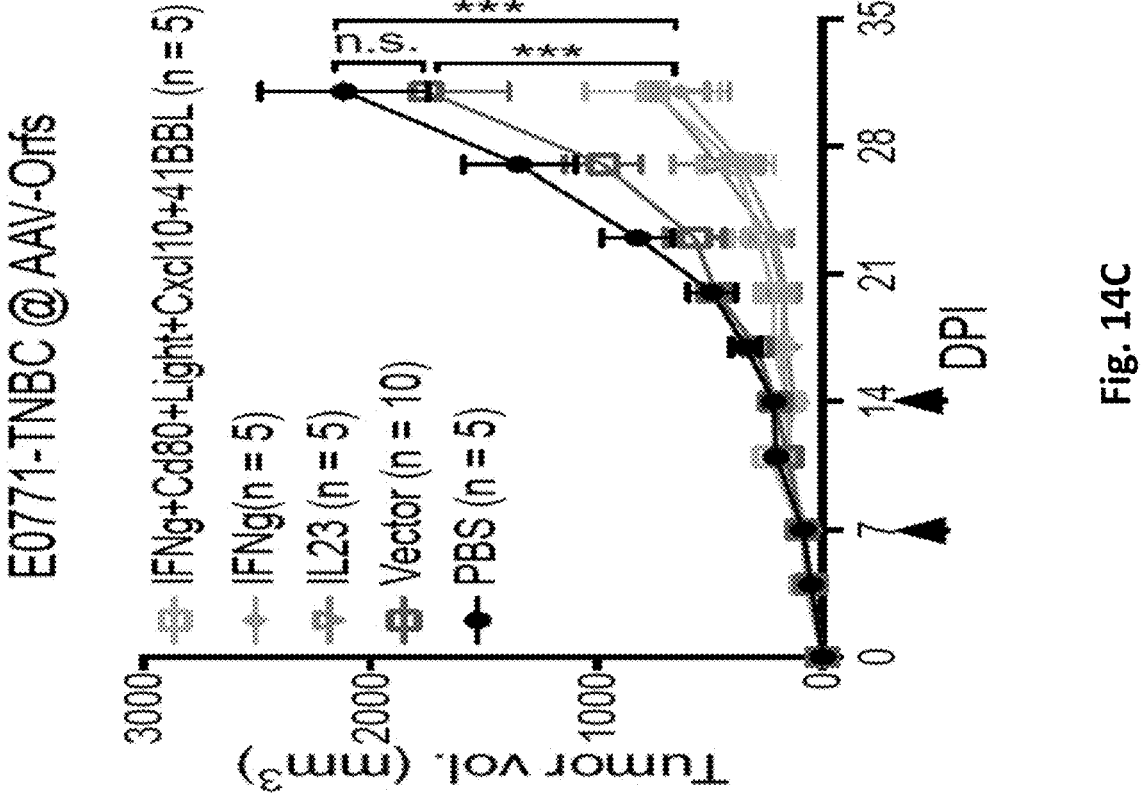
Figure 14F:
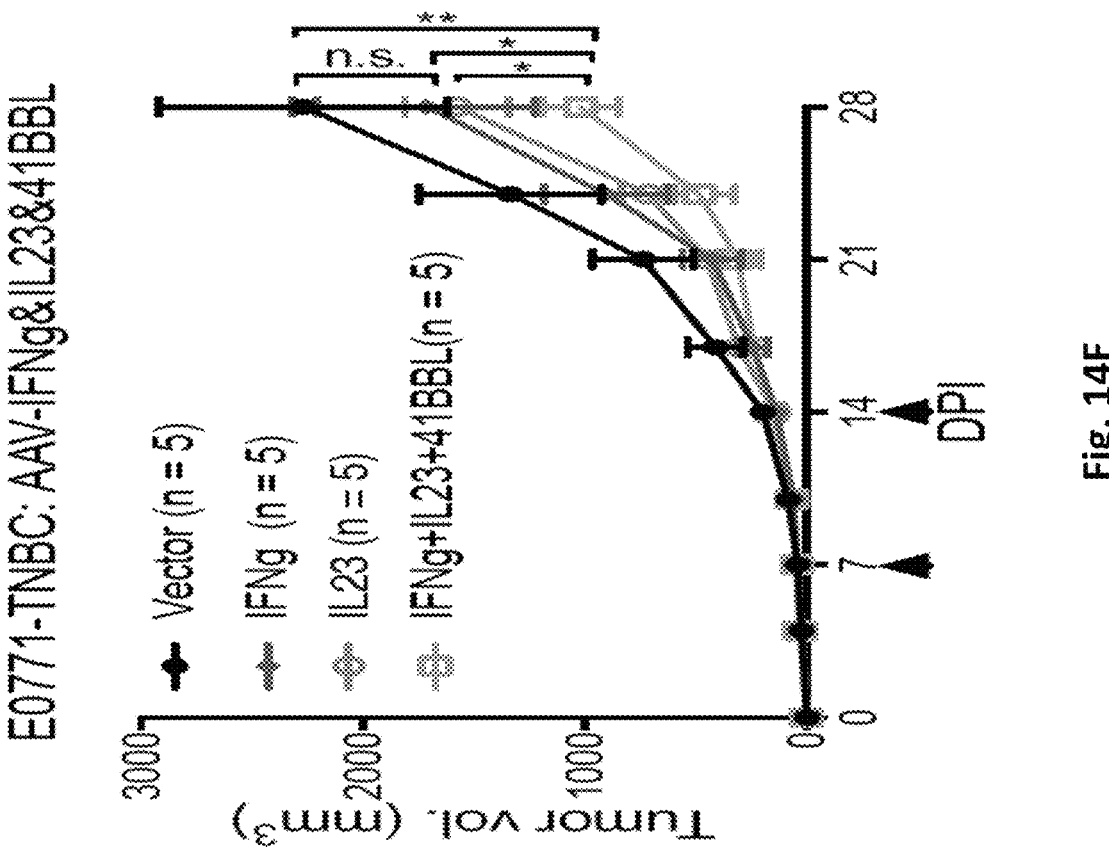
Figure 14E:
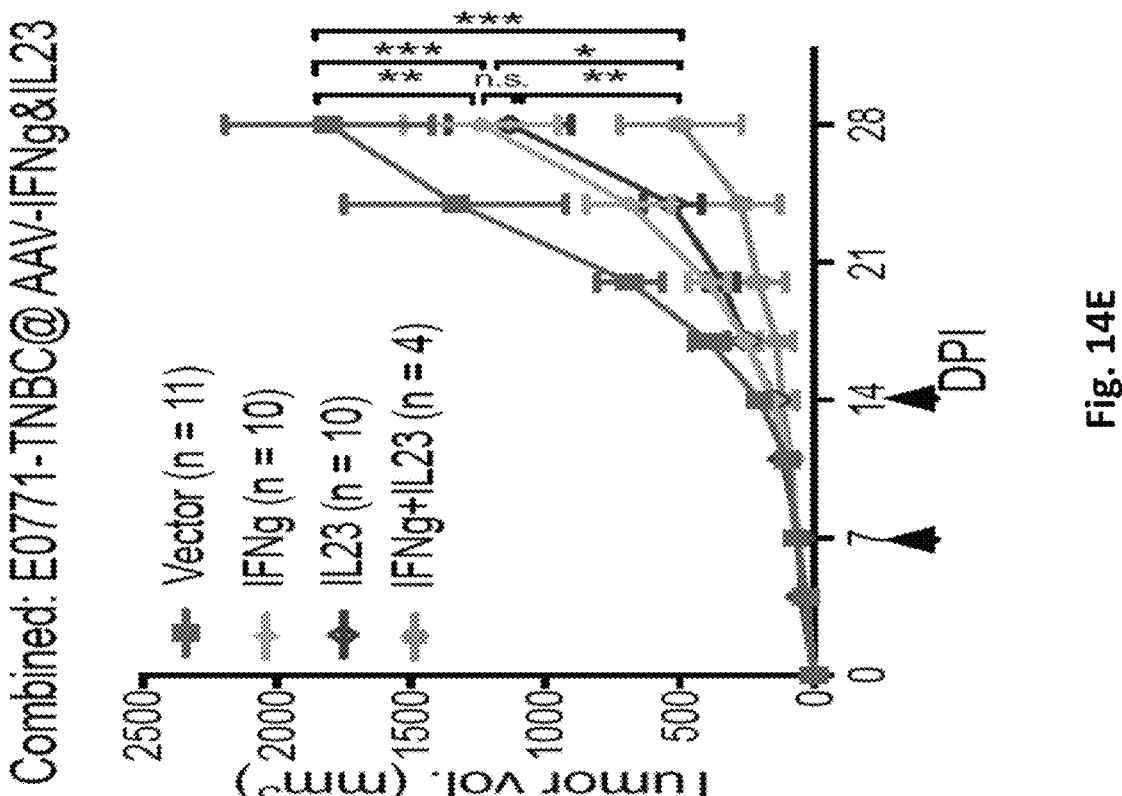

Example 11: Rational Design of Single AAV Vectors for Tumor Immune Gene Therapies The costimulatory molecule combinations in single AAV vectors as tumor immune gene therapies were optimized (FIGS. 14A-14F). FIG. 14A-14B upper panels show representative flow cytometry plots demonstrating AAV-ORFs-mediated expression of CD80, 41BBL, IL23 and IFNg in AAV-infected E0771 or MA1NC cells. FIGS. 14A-14B lower panels show the percentage of CD80, 41BBL, IL23, and IFNg positive cells in different AAV-infected E0771 and MA1NC cells. Result showed significant efficacy of indicated single AAV vectors with various defined combinations of transgenes expressing immune molecules as tumor immune gene therapies, where the tumor growth curves show the dynamics of E0771 tumors treated with PBS (n=5), AAV-Vector (n=10), AAV-IL23 (n=5), AAV-IFNg (n=6), Pooled AAVs(IFNg+CD80+LIGHT+CXCL10+41BBL; n=5) (FIG. 14C). Significant efficacy of indicated single AAV vectors was also demonstrated with various defined combinations of transgenes expressing immune molecules as tumor immune gene therapies, where the tumor growth curves show the dynamics of tumor growth curves of E0771 tumors treated AAV-Vector (n=5), AAV-IFNg (n=4), AAV-IFNg+AAV-IL23 (n=5), pooled AAVs (IFNg+CXCL10+41BBL; n=5), pooled AAVs (IFNg+LIGHT+41BBL; n=5), pooled AAV(IFNg+LIGHT+CXCL10+41BBL; n=5) (FIG. 14D). Significant efficacy of indicated single AAV vectors was demonstrated with various defined combinations of transgenes expressing immune molecules as tumor immune gene therapies, where the tumor growth curves show the dynamics of E0771 tumors treated AAV-Vector (n=11), AAV-IFNg (n=10), AAV-IL23 (n=10), AAV-IFNg+AAV-IL23 (n=4) (FIG. 14E). Tumor growth curves of E0771 tumors treated AAV-Vector (n=5), AAV-IFNg (n=5), AAV-IL23 (n=5), AAV-IFNg+AAV-IL23+AAV-41BBL (n=5) are shown in FIG. 14F.

OTHER EMBODIMENTS

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of developing a cancer immunotherapy, the method comprising:

a) administering a clustered regularly interspaced short palindromic repeats activation (CRISPRa) system comprising a single guide RNA (sgRNA) library targeting a plurality of genes to a plurality of cancer cells obtained from a human subject, thereby generating a plurality of modified cancer cells in which the expression of the plurality of targeted genes is increased as compared to an unmodified cancer cell from the subject, b) administering the plurality of modified cancer cells to an immunocompetent non-human mammal whereby the non-human mammal develops tumors from the plurality of modified cancer cells, c) isolating tumor tissue from the non-human mammal, wherein modified cancer cells comprising increased expression of targeted genes that enhance immune recognition by the non-human mammal's immune system are depleted in the isolated tumor tissue, d) determining the sgRNAs and thereby the plurality of targeted genes that are decreased in cells of the isolated tumor tissue as compared to an unmodified cancer cell from the subject, wherein determining the plurality of targeted genes in the cells of the isolated tumor tissue comprises nucleotide sequencing and analysis, and e) designing a cancer immunotherapy that increases the expression of targeted genes determined in step d) comprising packaging open reading frames (ORFs) encoding the targeted genes into a vector;

wherein the sgRNA library comprises every nucleic acid sequence of SEQ ID NOs. 86-192 or SEQ ID NOs. 193-411; and wherein the cancer immunotherapy is selected from the group consisting of Multiplexed Activation of Endogenous Genes as an Immunotherapy (MAEGI) and direct ORF-based viral immune gene therapy.

2. The method of claim 1, wherein the sgRNA library comprises every nucleic acid sequence of SEQ ID NOs. 193-411.

3. The method of claim 1, wherein the CRISPRa system comprises a vector comprising the nucleotide sequence set forth in SEQ ID NO: 1.

4. The method of claim 1, wherein the vector is an adeno-associated viral (AAV) vector or an adenoviral vector.

* * * * *

SEQUENCE LISTING

```
<160> NUMBER OF SEQ ID NOS: 411

<210> SEQ ID NO 1
<211> LENGTH: 10185
<212> TYPE: DNA
<213> ORGANISM: Artificial Sequence
<220> FEATURE:
<223> OTHER INFORMATION: pGW059

<400> SEQUENCE: 1
ttaatgtagt cttatgcaat actcttgtag tcttgcaaca tggtaacgat gagttagcaa         60
catgccttac aaggagagaa aaagcaccgt gcatgccgat tggtggaagt aaggtggtac        120
gatcgtgcct tattaggaag gcaacagacg ggtctgacat ggattggacg aaccactgaa        180
```

```
ttgccgcatt gcagagatat tgtatttaag tgcctagctc gatacataaa cgggtctctc      240
tggttagacc agatctgagc ctgggagctc tctggctaac tagggaaccc actgcttaag      300
cctcaataaa gcttgccttg agtgcttcaa gtagtgtgtg cccgtctgtt gtgtgactct      360
ggtaactaga gatccctcag accctttttag tcagtgtgga aaatctctag cagtggcgcc      420
cgaacaggga cttgaaagcg aaagggaaac cagaggagct ctctcgacgc aggactcggc      480
ttgctgaagc gcgcacggca agaggcgagg ggcggcgact ggtgagtacg ccaaaaattt      540
tgactagcgg aggctagaag gagagagatg ggtgcgagag cgtcagtatt aagcggggga      600
gaattagatc gcgatgggaa aaaattcggt taaggccagg gggaaagaaa aaatataaat      660
taaaacatat agtatgggca agcagggagc tagaacgatt cgcagttaat cctggcctgt      720
tagaaacatc agaaggctgt agacaaatac tgggacagct acaaccatcc cttcagacag      780
gatcagaaga acttagatca ttatataata cagtagcaac cctctattgt gtgcatcaaa      840
ggatagagat aaaagacacc aaggaagctt tagacaagat agaggaagag caaaacaaaa      900
gtaagaccac cgcacagcaa gcggccgctg atcttcagac ctggaggagg agatatgagg      960
gacaattgga gaagtgaatt atataaatat aaagtagtaa aaattgaacc attaggagta     1020
gcacccacca aggcaaagag aagagtggtg cagagagaaa aaagagcagt gggaatagga     1080
gctttgttcc ttgggttctt gggagcagca ggaagcacta tgggcgcagc gtcaatgacg     1140
ctgacggtac aggccagaca attattgtct ggtatagtgc agcagcagaa caatttgctg     1200
agggctattg aggcgcaaca gcatctgttg caactcacag tctggggcat caagcagctc     1260
caggcaagaa tcctggctgt ggaaagatac ctaaaggatc aacagctcct ggggatttgg     1320
ggttgctctg gaaaactcat ttgcaccact gctgtgcctt ggaatgctag ttggagtaat     1380
aaatctctgg aacagatttg gaatcacacg acctggatgg agtgggacag agaaattaac     1440
aattacacaa gcttaataca ctccttaatt gaagaatcgc aaaaccagca agaaaagaat     1500
gaacaagaat tattggaatt agataaatgg gcaagtttgt ggaattggtt taacataaca     1560
aattggctgt ggtatataaa attattcata atgatagtag gaggcttggt aggtttaaga     1620
atagtttttg ctgtactttc tatagtgaat agagttaggc agggatattc accattatcg     1680
tttcagaccc acctcccaac cccgagggga ccctctagag atccgacgcg ccatctctag     1740
gcccgcgccg gccccctcgc acggacttgt gggagaagct cggctactcc cctgccccgg     1800
ttaatttgca tataatattt cctagtaact atagaggctt aatgtgcgat aaaagacaga     1860
taatctgttc tttttaatac tagctacatt ttacatgata ggcttggatt tctataactt     1920
cgtatagcat acattatacg aagttataaa cagcacaaaa ggaaactcac cctaactgta     1980
aagtaattgt gtgttttgag actataagta tcccttggag aaccaccttg ttgggagacg     2040
ggataccgtc tctgtttaag agctaagctg gccaacatga ggatcaccca tgtctgcagg     2100
gccagcttag caagttaaaa taaggctagt ccgttatcaa cttggccaac atgaggatca     2160
cccatgtctg cagggccaag tggcaccgag tcggtgcttt tttggatcca agcttggcgt     2220
aactagatct tgagacaaat ggcagtattc atccacaatt ttaaaagaaa aggggggatt     2280
ggggggtaca gtgcagggga agaatagta gacataatag caacagacat acaaactaaa     2340
gaattacaaa aacaaattac aaaaattcaa aattttcggg tttattacag gacagcaga     2400 gatccacttt ggcgccggct cgagggggcc cgggtgcaaa gatggataaa gttttaaaca     2460
gagaggaatc tttgcagcta atggaccttc taggtcttga aaggagtggg aattggctcc     2520
```

-continued

```
ggtgcccgtc agtgggcaga gcgcacatcg cccacagtcc ccgagaagtt ggggggaggg      2580
gtcggcaatt gatccggtgc ctagagaagg tggcgcgggg taaactggga aagtgatgtc      2640
gtgtactggc tccgcctttt tcccgagggt gggggagaac cgtatataag tgcagtagtc      2700
gccgtgaacg ttcttttcg caacgggttt gccgccagaa cacaggtaag tgccgtgtgt       2760
ggttcccgcg ggcctggcct ctttacgggt tatggccctt gcgtgccttg aattacttcc      2820
actggctgca gtacgtgatt cttgatcccg agcttcgggt tggaagtggg tgggagagtt      2880
cgaggccttg cgcttaagga gccccttcgc ctcgtgcttg agttgaggcc tggcctgggc      2940
gctggggccg ccgcgtgcga atctggtggc accttcgcgc ctgtctcgct gctttcgata      3000
agtctctagc catttaaaat ttttgatgac ctgctgcgac gcttttttttc tggcaagata     3060 gtcttgtaaa tgcgggccaa gatctgcaca ctggtatttc ggttttggg gccgcgggcg       3120 gcgacggggc ccgtgcgtcc cagcgcacat gttcggcgag gcggggcctg cgagcgcggc      3180
caccgagaat cggacggggg tagtctcaag ctggccggcc tgctctggtg cctggcctcg      3240
cgccgccgtg tatcgccccg ccctgggcgg caaggctggc ccggtcggca ccagttgcgt      3300
gagcggaaag atggccgctt cccggccctg ctgcagggag ctcaaaatgg aggacgcggc      3360
gctcgggaga gcgggcgggt gagtcaccca cacaaaggaa aagggccttt ccgtcctcag      3420
ccgtcgcttc atgtgactcc acggagtacc gggcgccgtc caggcacctc gattagttct      3480
cgagcttttg gagtacgtcg tctttaggtt gggggaggg gttttatgcg atggagtttc       3540
cccacactga gtgggtggag actgaagtta ggccagcttg gcacttgatg taattctcct      3600
tggaatttgc cctttttgag tttggatctt ggttcattct caagcctcag acagtggttc      3660 aaagttttttt tcttccattt caggtgtcgt gacgtacggc caccatgacc gagtacaagc     3720
ccacggtgcg cctcgccacc cgcgacgacg tccccagggc cgtacgcacc ctcgccgccg      3780
cgttcgccga ctaccccgcc acgcgccaca ccgtcgatcc ggaccgccac atcgagcggg      3840
tcaccgagct gcaagaactc ttcctcacgc gcgtcgggct cgacatcggc aaggtgtggg      3900
tcgcggacga cggcgccgcc gtggcggtct ggaccacgcc ggagagcgtc gaagcggggg      3960
cggtgttcgc cgagatcggc ccgcgcatgg ccgagttgag cggttcccgg ctggccgcgc      4020
agcaacagat ggaaggcctc ctggcgccgc accggcccaa ggagcccgcg tggttcctgg      4080
ccaccgtcgg agtctcgccc gaccaccagg gcaaggtct gggcagcgcc gtcgtgctcc       4140
ccggagtgga ggcggccgag cgcgccgggg tgcccgcctt cctggagacc tccgcgcccc      4200
gcaacctccc cttctacgag cggctcggct tcaccgtcac cgccgacgtc gaggtgcccg      4260
aaggaccgcg cacctggtgc atgacccgca agcccggtgc cggatccggc gcaacaaact      4320
tctctctgct gaaacaagcc ggagatgtcg aagagaatcc tggaccgatg gaagacgcca      4380
aaaacataaa gaaaggcccg gcgccattct atccgctgga agatggaacc gctggagagc      4440
aactgcataa ggctatgaag agatacgccc tggttcctgg aacaattgct tttacagatg      4500
cacatatcga ggtggacatc acttacgctg agtacttcga aatgtccgtt cggttggcag      4560
aagctatgaa acgatatggg ctgaatacaa atcacagaat cgtcgtatgc agtgaaaact      4620
ctcttcaatt ctttatgccg gtgttgggcg cgttatttat cggagttgca gttgcgcccg      4680
cgaacgacat ttataatgaa cgtgaattgc tcaacagtat gggcatttcg cagcctaccg      4740
tggtgttcgt ttccaaaaag gggttgcaaa aaattttgaa cgtgcaaaaa aagctcccaa      4800
tcatccaaaa aattattatc atggattcta aaacggatta ccagggattt cagtcgatgt      4860
acacgttcgt cacatctcat ctacctcccg gttttaatga atacgatttt gtgccagagt      4920
```

-continued

```
ccttcgatag ggacaagaca attgcactga tcatgaactc ctctggatct actggtctgc      4980
ctaaaggtgt cgctctgcct catagaactg cctgcgtgag attctcgcat gccagagatc      5040 ctattttttgg caatcaaatc attccggata ctgcgatttt aagtgttgtt ccattccatc     5100
acggttttgg aatgtttact acactcggat atttgatatg tggatttcga gtcgtcttaa     5160
tgtatagatt tgaagaggag ctgtttctga ggagccttca ggattacaag attcaaagtg      5220
cgctgctggt gccaacccta ttctccttct tcgccaaaag cactctgatt gacaaatacg      5280
atttatctaa tttacacgaa attgcttctg gtggcgctcc cctctctaag gaagtcgggg     5340
aagcggttgc caagaggttc catctgccag gtatcaggca aggatatggg ctcactgaga      5400
ctacatcagc tattctgatt acacccgagg gggatgataa accgggcgcg gtcggtaaag      5460
ttgttccatt ttttgaagcg aaggttgtgg atctggatac cgggaaaacg ctgggcgtta     5520
atcaaagagg cgaactgtgt gtgagaggtc ctatgattat gtccggttat gtaaacaatc      5580
cggaagcgac caacgccttg attgacaagg atggatggct acattctgga gacatagctt      5640
actgggacga agacgaacac ttcttcatcg ttgaccgcct gaagtctctg attaagtaca      5700
aaggctatca ggtggctccc gctgaattgg aatccatctt gctccaacac cccaacatct      5760
tcgacgcagg tgtcgcaggt cttcccgacg atgacgccgg tgaacttccc gccgccgttg     5820 ttgtttttgga gcacggaaag acgatgacgg aaaaagagat cgtggattac gtcgccagtc      5880
aagtaacaac cgcgaaaaag ttgcgcggag gagttgtgtt tgtggacgaa gtaccgaaag      5940
gtcttaccgg aaaactcgac gcaagaaaaa tcagagagat cctcataaag gccaagaagg     6000
gcggaaagat cgccgtgtaa gaattcacgc gttaagtcga caatcaacct ctggattaca      6060
aaatttgtga aagattgact ggtattctta actatgttgc tccttttacg ctatgtggat     6120
acgctgcttt aatgcctttg tatcatgcta ttgcttcccg tatggctttc attttctcct      6180
ccttgtataa atcctggttg ctgtctcttt atgaggagtt gtggcccgtt gtcaggcaac      6240
gtggcgtggt gtgcactgtg tttgctgacg caaccccac tggttggggc attgccacca      6300
cctgtcagct cctttccggg actttcgctt tccccctccc tattgccacg gcggaactca      6360
tcgccgcctg ccttgcccgc tgctggacag gggctcggct gttgggcact gacaattccg      6420
tggtgttgtc ggggaaatca tcgtcctttc cttggctgct cgcctgtgtt gccacctgga      6480
ttctgcgcgg gacgtccttc tgctacgtcc cttcggccct caatccagcg gaccttcctt     6540
cccgcggcct gctgccggct ctgcggcctc ttccgcgtct tcgccttcgc cctcagacga     6600
gtcggatctc cctttgggcc gcctccccgc gtcgacttta agaccaatga cttacaaggc      6660
agctgtagat cttagccact tttaaaaga aaggggggga ctggaagggc taattcactc      6720
ccaacgaaga caagatctgc tttttgcttg tactgggtct ctctggttag accagatctg      6780
agcctgggag ctctctggct aactagggaa cccactgctt aagcctcaat aaagcttgcc      6840
ttgagtgctt caagtagtgt gtgcccgtct gttgtgtgac tctggtaact agagatccct      6900
cagacccttt tagtcagtgt ggaaaatctc tagcagtacg tatagtagtt catgtcatct      6960
tattattcag tatttataac ttgcaaagaa atgaatatca gagagtgaga ggaacttgtt     7020
tattgcagct tataatggtt acaaataaag caatagcatc acaaatttca caaataaagc      7080 attttttttca ctgcattcta gttgtggttt gtccaaactc atcaatgtat cttatcatgt      7140
ctggctctag ctatcccgcc cctaactccg cccatcccgc ccctaactcc gcccagttcc      7200
gcccattctc cgccccatgg ctgactaatt ttttttattt atgcagaggc cgaggccgcc      7260
```

-continued

```
tcggcctctg agctattcca gaagtagtga ggaggctttt ttggaggcct agggacgtac    7320
ccaattcgcc ctatagtgag tcgtattacg cgcgctcact ggccgtcgtt ttacaacgtc    7380
gtgactggga aaaccctggc gttacccaac ttaatcgcct tgcagcacat ccccctttcg    7440
ccagctggcg taatagcgaa gaggcccgca ccgatcgccc ttcccaacag ttgcgcagcc    7500
tgaatggcga atgggacgcg ccctgtagcg gcgcattaag cgcggcgggt gtggtggtta    7560
cgcgcagcgt gaccgctaca cttgccagcg ccctagcgcc cgctcctttc gctttcttcc    7620
cttcctttct cgccacgttc gccggctttc cccgtcaagc tctaaatcgg gggctccctt    7680
tagggttccg atttagtgct ttacggcacc tcgaccccaa aaaacttgat tagggtgatg    7740
gttcacgtag tgggccatcg ccctgataga cggtttttcg ccctttgacg ttggagtcca    7800
cgttctttaa tagtggactc ttgttccaaa ctggaacaac actcaaccct atctcggtct    7860
attcttttga tttataaggg attttgccga tttcggccta ttggttaaaa aatgagctga    7920
tttaacaaaa atttaacgcg aattttaaca aaatattaac gcttacaatt taggtggcac    7980
ttttcgggga aatgtgcgcg gaacccctat ttgtttattt ttctaaatac attcaaatat    8040
gtatccgctc atgagacaat aaccctgata aatgcttcaa taatattgaa aaaggaagag    8100
tatgagtatt caacatttcc gtgtcgccct tattcccttt tttgcggcat tttgccttcc    8160 tgttttttgct cacccagaaa cgctggtgaa agtaaaagat gctgaagatc agttgggtgc    8220
acgagtgggt tacatcgaac tggatctcaa cagcggtaag atccttgaga gttttcgccc    8280
cgaagaacgt tttccaatga tgagcacttt taaagttctg ctatgtggcg cggtattatc    8340
ccgtattgac gccgggcaag agcaactcgg tcgccgcata cactattctc agaatgactt    8400
ggttgagtac tcaccagtca cagaaaagca tcttacggat ggcatgacag taagagaatt    8460
atgcagtgct gccataacca tgagtgataa cactgcggcc aacttacttc tgacaacgat    8520
cggaggaccg aaggagctaa ccgctttttt gcacaacatg ggggatcatg taactcgcct    8580
tgatcgttgg gaaccggagc tgaatgaagc cataccaaac gacgagcgtg acaccacgat    8640
gcctgtagca atggcaacaa cgttgcgcaa actattaact ggcgaactac ttactctagc    8700
ttcccggcaa caattaatag actggatgga ggcggataaa gttgcaggac cacttctgcg    8760
ctcggccctt ccggctggct ggtttattgc tgataaatct ggagccggtg agcgtgggtc    8820
tcgcggtatc attgcagcac tggggccaga tggtaagccc tcccgtatcg tagttatcta    8880
cacgacgggg agtcaggcaa ctatggatga acgaaataga cagatcgctg agataggtgc    8940
ctcactgatt aagcattggt aactgtcaga ccaagtttac tcatatatac tttagattga    9000
tttaaaactt cattttaat ttaaaaggat ctaggtgaag atcctttttg ataatctcat    9060
gaccaaaatc ccttaacgtg agttttcgtt ccactgagcg tcagacccg tagaaaagat    9120 caaaggatct tcttgagatc cttttttct gcgcgtaatc tgctgcttgc aaacaaaaaa    9180
accaccgcta ccagcggtgg tttgtttgcc ggatcaagag ctaccaactc tttttccgaa    9240
ggtaactggc ttcagcagag cgcagatacc aaatactgtt cttctagtgt agccgtagtt    9300
aggccaccac ttcaagaact ctgtagcacc gcctacatac ctcgctctgc taatcctgtt    9360
accagtggct gctgccagtg gcgataagtc gtgtcttacc gggttggact caagacgata    9420
gttaccggat aaggcgcagc ggtcgggctg aacggggggt tcgtgcacac agcccagctt    9480
ggagcgaacg acctacaccg aactgagata cctacagcgt gagctatgag aaagcgccac    9540
gcttcccgaa gggagaaagg cggacaggta tccggtaagc ggcagggtcg aacaggaga    9600 gcgcacgagg gagcttccag ggggaaacgc ctggtatctt tatagtcctg tcgggtttcg    9660
```

```
ccacctctga cttgagcgtc gatttttgtg atgctcgtca ggggggcgga gcctatggaa    9720
aaacgccagc aacgcggcct ttttacggtt cctggccttt tgctggcctt ttgctcacat    9780
gttctttcct gcgttatccc ctgattctgt ggataaccgt attaccgcct ttgagtgagc    9840
tgataccgct cgccgcagcc gaacgaccga gcgcagcgag tcagtgagcg aggaagcgga    9900
agagcgccca atacgcaaac cgcctctccc cgcgcgttgg ccgattcatt aatgcagctg   9960
gcacgacagg tttcccgact ggaaagcggg cagtgagcgc aacgcaatta atgtgagtta   10020
gctcactcat taggcacccc aggctttaca ctttatgctt ccggctcgta tgttgtgtgg   10080
aattgtgagc ggataacaat ttcacacagg aaacagctat gaccatgatt acgccaagcg   10140
cgcaattaac cctcactaaa gggaacaaaa gctggagctg caagc                     10185
```

```
<210> SEQ ID NO 2
<211> LENGTH: 7138
<212> TYPE: DNA
<213> ORGANISM: Artificial Sequence
<220> FEATURE:
<223> OTHER INFORMATION: pGW066

<400> SEQUENCE: 2
```

```
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggcctcta gaaaggatct gcgatcgctc cggtgcccgt cagtgggcag    180
agcgcacatc gcccacagtc cccgagaagt tggggggagg ggtcggcaat tgaacgggtg    240
cctagagaag gtggcgcggg gtaaactggg aaagtgatgt cgtgtactgg ctccgccttt    300
ttcccgaggg tggggagaa ccgtatataa gtgcagtagt cgccgtgaac gttcttttc     360 gcaacgggtt tgccgccaga acacagctga agcttcgagg ggctcgcatc tctccttcac    420
gcgcccgccg ccctacctga ggccgccatc cacgccggtt gagtgcgtt ctgccgcctc     480 ccgcctgtgg tgcctcctga actgcgtccg ccgtctaggt aagtttaaag ctcaggtcga    540
gaccgggcct ttgtccggcg ctcccttgga gcctacctag actcagccgg ctctccacgc    600
tttgcctgac cctgcttgct caactctacg tctttgtttc gttttctgtt ctgcgccgtt    660
acagatctgg ctaactaccg gtgccaccat ggcttgcaat tgtcagttga tgcaggatac    720
accactcctc aagtttccat gtccaaggct cattcttctc tttgtgctgc tgattcgtct    780
ttcacaagtg tcttcagatg ttgatgaaca actgtccaag tcagtgaaag ataaggtatt    840
gctgccttgc cgttacaact ctcctcatga agatgagtct gaagaccgaa tctactggca    900
aaaacatgac aaagtggtgc tgtctgtcat tgctgggaaa ctaaaagtgt ggcccgagta    960
taagaaccgg actttatatg acaacactac ctactctctt atcatcctgg gcctggtcct   1020
ttcagaccgg ggcacataca gctgtgtcgt tcaaaagaag gaaagaggaa cgtatgaagt   1080
taaacacttg gctttagtaa agttgtccat caaagctgac ttctctaccc ccaacataac   1140
tgagtctgga aacccatctg cagacactaa aaggattacc tgctttgctt ccgggggttt   1200
cccaaagcct cgcttctctt ggttggaaaa tggaagagaa ttacctggca tcaatacgac   1260
aatttcccag gatcctgaat ctgaattgta caccattagt agccaactag atttcaatac   1320
gactcgcaac cacaccatta agtgtctcat aaatatgga gatgctcacg tgtcagagga   1380
cttcacctgg gaaaaacccc cagaagaccc tcctgatagc aagaacacac ttgtgctctt   1440 tgggggcagga ttcggcgcag taataacagt cgtcgtcatc gttgtcatca tcaaatgctt   1500
```

-continued

```
ctgtaagcac agaagctgtt tcagaagaaa tgaggcaagc agagaaacaa acaacagcct   1560
taccttcggg cctgaagaag cattagctga acagaccgtc ttccttcgta cgggcagtgg   1620
agagggcaga ggaagtctgc taacatgcgg tgacgtcgag gagaatcctg gcccaatgga   1680
gagtgtggta cagccttcag tgtttgtggt ggatggacag acggacatcc cattcaggcg   1740
gctggaacag aaccaccgga gacggcgctg tggcactgtc caggtcagcc tggccctggt   1800
gctgctgcta agtgctgggc tggccactca gggctggttt ctcctgagac tgcatcaacg   1860
tcttggagac atagtagctc atctgccaga tggaggcaaa ggctcctggg agaagctgat   1920
acaagatcaa cgatctcacc aggccaaccc agcagcacat cttacaggag ccaacgccag   1980
cttgataggt attggtggac ctctgttatg ggagacacga cttggcctgg ccttcttgag   2040
gggcttgacg tatcatgatg gggccctggt gaccatggag cccggttact actatgtgta   2100
ctccaaagtg cagctgagcg gcgtgggctg cccccagggg ctggccaatg gcctccccat   2160
cacccatgga ctatacaagc gcacatcccg ctacccgaag gagttagaac tgctggtcag   2220
tcggcggtca ccctgtggcc gggccaacag ctcccgagtc tggtgggaca gcagcttcct   2280
gggcggcgtg gtacatctgg aggctgggga agaggtggtg gtccgcgtgc ctggaaaccg   2340
cctggtcaga ccacgtgacg gcaccaggtc ctatttcgga gctttcatgg tcactagtgg   2400
atccggcgca acaaacttct ctctgctgaa acaagccgga gatgtcgaag agaatcctgg   2460
accgatgaac ccaagtgctg ccgtcatttt ctgcctcatc ctgctgggtc tgagtgggac   2520
tcaagggatc cctctcgcaa ggacggtccg ctgcaactgc atccatatcg atgacgggcc   2580
agtgagaatg agggccatag ggaagcttga aatcatccct gcgagcctat cctgcccacg   2640
tgttgagatc attgccacga tgaaaaagaa tgatgagcag agatgtctga atccggaatc   2700
taagaccatc aagaatttaa tgaaagcgtt tagccaaaaa aggtctaaaa gggctcctgc   2760
tagcagcggt acccagtgca ccaactacgc cctgctgaag ctggccggcg atgtggagag   2820
caaccccggg cccatggacc agcacacact tgatgtggag gataccgcgg atgccagaca   2880
tccagcaggt acttcgtgcc cctcggatgc ggcgctcctc agagataccg ggctcctcgc   2940
ggacgctgcg ctcctctcag atactgtgcg ccccacaaat gccgcgctcc ccacggatgc   3000
tgcctaccct gcggttaatg ttcgggatcg cgaggccgcg tggccgcctg cactgaactt   3060
ctgttcccgc cacccaaagc tctatggcct agtcgctttg gttttgctgc ttctgatcgc   3120
cgcctgtgtt cctatcttca cccgcaccga gcctcggcca gcgctcacaa tcaccacctc   3180
gcccaacctg ggtacccgag agaataatgc agaccaggtc acccctgttt cccacattgg   3240
ctgccccaac actacacaac agggctctcc tgtgttcgcc aagctactgg ctaaaaacca   3300
agcatcgttg tgcaatacaa ctctgaactg gcacagccaa gatggagctg ggagctcata   3360
cctatctcaa ggtctgaggt acgaagaaga caaaaaggag ttggtggtag acagtcccgg   3420
gctctactac gtattttgg aactgaagct cagtccaaca ttcacaaaca caggccacaa   3480
ggtgcagggc tgggtctctc ttgttttgca agcaaagcct caggtagatg actttgacaa   3540
cttggccctg acagtggaac tgttcccttg ctccatggag aacaagttag tggaccgttc   3600
ctggagtcaa ctgttgctcc tgaaggctgg ccaccgcctc agtgtgggtc tgagggctta   3660
tctgcatgga gcccaggatg catacagaga ctgggagctg tcttatccca acaccaccag   3720
ctttggactc tttcttatga aacccgacaa cccatgggaa tgagaattca cgcgttaagt   3780
cgacaatcaa cctctggatt acaaaatttg tgaaagattg actggtattc ttaactatgt   3840
tgctcctttt acgctatgtg gatacgctgc tttaatgcct ttgtatcatg ctattgcttc   3900
```

-continued

```
ccgtatggct ttcattttct cctccttgta taaatcctgg ttgctgtctc tttatgagga   3960
gttgtggccc gttgtcaggc aacgtggcgt ggtgtgcact gtgtttgctg acgcaacccc   4020
cactggttgg ggcattgcca ccacctgtca gctcctttcc gggactttcg ctttccccct   4080
ccctattgcc acggcggaac tcatcgccgc ctgccttgcc cgctgctgga caggggctcg   4140
gctgttgggc actgacaatt ccgtggtgtt gtcggggaaa tcatcgtcct ttccttggct   4200
gctcgcctgt gttgccacct ggattctgcg cgggacgtcc ttctgctacg tcccttcggc   4260
cctcaatcca gcggaccttc cttcccgcgg cctgctgccg gctctgcggc ctcttccgcg   4320
tcttcgcctt cgccctcaga cgagtcggat ctccctttgg gccgcctccc cgcgtcgact   4380
ttaagaccaa tgacggccgc aggaacccct agtgatggag ttggccactc cctctctgcg   4440
cgctcgctcg ctcactgagg ccgggcgacc aaaggtcgcc cgacgcccgg gctttgcccg   4500
ggcggcctca gtgagcgagc gagcgcgcag ctgcctgcag gggcgcctga tgcggtattt   4560
tctccttacg catctgtgcg gtatttcaca ccgcatacgt caaagcaacc atagtacgcg   4620
ccctgtagcg gcgcattaag cgcggcgggt gtggtggtta cgcgcagcgt gaccgctaca   4680
cttgccagcg ccttagcgcc cgctcctttc gctttcttcc cttcctttct cgccacgttc   4740
gccggctttc cccgtcaagc tctaaatcgg gggctccctt tagggttccg atttagtgct   4800
ttacggcacc tcgaccccaa aaaacttgat ttgggtgatg gttcacgtag tgggccatcg   4860
ccctgataga cggttttttcg ccctttgacg ttggagtcca cgttctttaa tagtggactc   4920
ttgttccaaa ctggaacaac actcaactct atctcgggct attcttttga tttataaggg   4980
attttgccga tttcggtcta ttggttaaaa aatgagctga tttaacaaaa atttaacgcg   5040
aattttaaca aaatattaac gtttacaatt ttatggtgca ctctcagtac aatctgctct   5100
gatgccgcat agttaagcca gccccgacac ccgccaacac ccgctgacgc gccctgacgg   5160
gcttgtctgc tcccggcatc cgcttacaga caagctgtga ccgtctccgg gagctgcatg   5220
tgtcagaggt tttcaccgtc atcaccgaaa cgcgcgagac gaaagggcct cgtgatacgc   5280
ctatttttat aggttaatgt catgataata atggtttctt agacgtcagg tggcactttt   5340
cggggaaatg tgcgcggaac ccctatttgt ttatttttct aaatacattc aaatatgtat   5400
ccgctcatga caataaacc ctgataaatg cttcaataat attgaaaaag gaagagtatg   5460
agtattcaac atttccgtgt cgcccttatt ccctttttttg cggcattttg ccttcctgtt   5520
tttgctcacc cagaaacgct ggtgaaagta aaagatgctg aagatcagtt gggtgcacga   5580
gtgggttaca tcgaactgga tctcaacagc ggtaagatcc ttgagagttt cgccccgaa   5640 gaacgttttc caatgatgag cacttttaaa gttctgctat gtggcgcggt attatcccgt   5700
attgacgccg ggcaagagca actcggtcgc cgcatacact attctcagaa tgacttggtt   5760
gagtactcac cagtcacaga aaagcatctt acggatggca tgacagtaag agaattatgc   5820
agtgctgcca taaccatgag tgataacact gcggccaact tacttctgac aacgatcgga   5880
ggaccgaagg agctaaccgc ttttttgcac aacatggggg atcatgtaac tcgccttgat   5940
cgttgggaac cggagctgaa tgaagccata ccaaacgacg agcgtgacac cacgatgcct   6000
gtagcaatgg caacaacgtt gcgcaaacta ttaactggcg aactacttac tctagcttcc   6060
cggcaacaat taatagactg gatggaggcg gataaagttg caggaccact tctgcgctcg   6120
gcccttccgg ctggctggtt tattgctgat aaatctggag ccggtgagcg tggaagccgc   6180
ggtatcattg cagcactggg gccagatggt aagccctccc gtatcgtagt tatctacacg   6240
```

-continued

```
acggggagtc aggcaactat ggatgaacga aatagacaga tcgctgagat aggtgcctca      6300
ctgattaagc attggtaact gtcagaccaa gtttactcat atatacttta gattgattta      6360
aaacttcatt tttaatttaa aaggatctag gtgaagatcc tttttgataa tctcatgacc      6420
aaaatccctt aacgtgagtt ttcgttccac tgagcgtcag accccgtaga aaagatcaaa      6480
ggatcttctt gagatccttt ttttctgcgc gtaatctgct gcttgcaaac aaaaaaacca      6540
ccgctaccag cggtggtttg tttgccggat caagagctac caactctttt tccgaaggta      6600
actggcttca gcagagcgca gataccaaat actgttcttc tagtgtagcc gtagttaggc      6660
caccacttca agaactctgt agcaccgcct acatacctcg ctctgctaat cctgttacca      6720
gtggctgctg ccagtggcga taagtcgtgt cttaccgggt tggactcaag acgatagtta      6780
ccggataagg cgcagcggtc gggctgaacg gggggttcgt gcacacagcc cagcttggag      6840
cgaacgacct acaccgaact gagataccta cagcgtgagc tatgagaaag cgccacgctt      6900
cccgaaggga aaaggcgga caggtatccg gtaagcggca gggtcggaac aggagagcgc      6960
acgagggagc ttccaggggg aaacgcctgg tatctttata gtcctgtcgg gtttcgccac      7020
ctctgacttg agcgtcgatt tttgtgatgc tcgtcagggg ggcggagcct atggaaaaac      7080
gccagcaacg cggccttttt acggttcctg gccttttgct ggccttttgc tcacatgt       7138
```

```
<210> SEQ ID NO 3
<211> LENGTH: 7109
<212> TYPE: DNA
<213> ORGANISM: Artificial Sequence
<220> FEATURE:
<223> OTHER INFORMATION: pGW067

<400> SEQUENCE: 3
```

```
cctgcaggca gctgcgcgct cgctcgctca ctgaggccgc ccgggcgtcg ggcgaccttt        60
ggtcgcccgg cctcagtgag cgagcgagcg cgcagagagg gagtggccaa ctccatcact       120
aggggttcct gcggcctcta gaaaggatct gcgatcgctc cggtgcccgt cagtgggcag       180
agcgcacatc gcccacagtc cccgagaagt tggggggagg ggtcggcaat tgaacgggtg       240
cctagagaag gtggcgcggg gtaaactggg aaagtgatgt cgtgtactgg ctccgccttt       300
ttcccgaggg tggggagaa ccgtatataa gtgcagtagt cgccgtgaac gttctttttc       360
gcaacgggtt tgccgccaga acacagctga agcttcgagg ggctcgcatc tctccttcac       420
gcgcccgccg ccctacctga ggccgccatc cacgccggtt gagtcgcgtt ctgccgcctc       480
ccgcctgtgg tgcctcctga actgcgtccg ccgtctaggt aagtttaaag ctcaggtcga       540
gaccgggcct ttgtccggcg ctcccttgga gcctacctag actcagccgg ctctccacgc       600
tttgcctgac cctgcttgct caactctacg tctttgtttc gttttctgtt ctgcgccgtt       660
acagatctgg ctaactaccg gtgccaccat ggcttgcaat tgtcagttga tgcaggatac       720
accactcctc aagtttccat gtccaaggct cattcttctc tttgtgctgc tgattcgtct       780
ttcacaagtg tcttcagatg ttgatgaaca actgtccaag tcagtgaaag ataaggtatt       840
gctgccttgc cgttacaact ctcctcatga agatgagtct gaagaccgaa tctactggca       900
aaaacatgac aaagtggtgc tgtctgtcat tgttgggaaa ctaaaagtgt ggcccgagta       960
taagaaccgg actttatatg acaacactac ctactctctt atcatcctgg gcctggtcct      1020
ttcagaccgg ggcacataca gctgtgtcgt tcaaaagaag gaaagaggaa cgtatgaagt      1080
taaacacttg gctttagtaa agttgtccat caaagctgac ttctctaccc ccaacataac      1140
tgagtctgga aacccatctg cagacactaa aaggattacc tgctttgctt ccgggggttt      1200
```

-continued

```
cccaaagcct cgcttctctt ggttggaaaa tggaagagaa ttacctggca tcaatacgac    1260
aatttcccag gatcctgaat ctgaattgta caccattagt agccaactag atttcaatac    1320
gactcgcaac cacaccatta agtgtctcat taaatatgga gatgctcacg tgtcagagga    1380
cttcacctgg gaaaaacccc cagaagaccc tcctgatagc aagaacacac ttgtgctctt    1440
tggggcagga ttcggcgcag taataacagt cgtcgtcatc gttgtcatca tcaaatgctt    1500
ctgtaagcac agaagctgtt tcagaagaaa tgaggcaagc agagaaacaa acaacagcct    1560
taccttcggg cctgaagaag cattagctga acagaccgtc ttccttcgta cgggcagtgg    1620
agagggcaga ggaagtctgc taacatgcgg tgacgtcgag gagaatcctg gcccaatgga    1680
gagtgtggta cagccttcag tgtttgtggt ggatggacag acggacatcc cattcaggcg    1740
gctggaacag aaccaccgga gacggcgctg tggcactgtc caggtcagcc tggccctggt    1800
gctgctgcta ggtgctgggc tggccactca gggctggttt ctcctgagac tgcatcaacg    1860
tcttggagac atagtagctc atctgccaga tggaggcaaa ggctcctggg agaagctgat    1920
acaagatcaa cgatctcacc aggccaaccc agcagcacat cttacaggag ccaacgccag    1980
cttgataggt attggtggac ctctgttatg ggagacacga cttggcctgg ccttcttgag    2040
gggcttgacg tatcatgatg gggccctggt gaccatggag cccggttact actatgtgta    2100
ctccaaagtg cagctgagcg gcgtgggctg ccccccaggggg ctggccaatg gcctccccat    2160
cacccatgga ctatacaagc gcacatcccg ctacccgaag gagttagaac tgctggtcag    2220
tcggcggtca ccctgtggcc gggccaacag ctcccgagtc tggtgggaca gcagcttcct    2280
gggcggcgtg gtacatctgg aggctgggga agaggtggtg gtccgcgtgc ctggaaaccg    2340
cctggtcaga ccacgtgacg gcaccaggtc ctatttcgga gctttcatgg tcactagtgg    2400
atccggcgca acaaacttct ctctgctgaa acaagccgga gatgtcgaag agaatcctgg    2460
accgatgaac ccaagtgctg ccgtcatttt ctgcctcatc ctgctgggtc tgagtgggac    2520
tcaagggatc cctctcgcaa ggacggtccg ctgcaactgc atccatatcg atgacgggcc    2580
agtgagaatg agggccatag ggaagcttga aatcatccct gcgagcctat cctgcccacg    2640
tgttgagatc attgccacga tgaaaaagaa tgatgagcag agatgtctga atccggaatc    2700
taagaccatc aagaatttaa tgaaagcgtt tagccaaaaa aggtctaaaa gggctcctgc    2760
tagcagcggt acccagtgca ccaactacgc cctgctgaag ctggccggcg atgtggagag    2820
caaccccggg cccatggacc agcacacact tgatgtggag gataccgcgg atgccagaca    2880
tccagcaggt acttcgtgcc cctcggatgc ggcgctcctc agagataccg ggctcctcgc    2940
ggacgctgcg ctcctctcag atactgtgcg ccccacaaat gccgcgctcc ccacggatgc    3000
tgcctaccct gcggttaatg ttcgggatcg cgaggccgcg tggccgcctg cactgaactt    3060
ctgttcccgc cacccaaagc tctatggcct agtcgctttg gttttgctgc ttctgatcgc    3120
cgcctgtgtt cctatcttca cccgcaccga gcctcggcca gcgctcacaa tcaccacctc    3180
gcccaacctg ggtacccgag agaataatgc agaccaggtc accctgtttt cccacattgg    3240
ctgccccaac actacacaac agggctctcc tgtgttcgcc aagctactgg ctaaaaacca    3300
agcatcgttg tgcaatacaa ctctgaactg gcacagccaa gatggagctg ggagctcata    3360
cctatctcaa ggtctgaggt acgaagaaga caaaaaggag ttggtggtag acagtcccgg    3420
gctctactac gtatttttgg aactgaagct cagtccaaca ttcacaaaca caggccacaa    3480
ggtgcagggc tgggtctctc ttgttttgca agcaaagcct caggtagatg actttgacaa    3540
```

-continued

```
cttggccctg acagtggaac tgttcccttg ctccatggag aacaagttag tggaccgttc    3600
ctggagtcaa ctgttgctcc tgaaggctgg ccaccgcctc agtgtgggtc tgagggctta    3660
tctgcatgga gcccaggatg catacagaga ctgggagctg tcttatccca acaccaccag    3720
ctttggactc tttcttgtga aacccgacaa cccatgggaa ggcatatgcg gtaccgtgaa    3780
gcagaccctg aacttcgatc tgctgaagct ggccggcgat gtggagagca accccgggcc    3840
catgaacgct acacactgca tcttggcttt gcagctcttc ctcatggctg tttctggctg    3900
ttactgccac ggcacagtca ttgaaagcct agaaagtctg aataactatt ttaactcaag    3960
tggcatagat gtggaagaaa agagtctctt cttggatatc tggaggaact ggcaaaagga    4020
tggtgacatg aaaatcctgc agagccagat tatctctttc tacctcagac tctttgaagt    4080
cttgaaagac aatcaggcca tcagcaacaa cataagcgtc attgaatcac acctgattac    4140
taccttcttc agcaacagca aggcgaaaaa ggatgcattc atgagtattg ccaagtttga    4200
ggtcaacaac ccacaggtcc agcgccaagc attcaatgag ctcatccgag tggtccacca    4260
gctgttgccg gaatccagcc tcaggaagcg gaaaaggagt cgctgctgag aattcaataa    4320
aagatcttta ttttcattag atctgtgtgt tggttttttg tgtgcggccg caggaacccc    4380
tagtgatgga gttggccact ccctctctgc gcgctcgctc gctcactgag gccgggcgac    4440
caaaggtcgc ccgacgcccg ggctttgccc gggcggcctc agtgagcgag cgagcgcgca    4500
gctgcctgca ggggcgcctg atgcggtatt ttctccttac gcatctgtgc ggtatttcac    4560
accgcatacg tcaaagcaac catagtacgc gccctgtagc ggcgcattaa gcgcggcggg    4620
tgtggtggtt acgcgcagcg tgaccgctac acttgccagc gccttagcgc ccgctccttt    4680
cgctttcttc ccttcctttc tcgccacgtt cgccggcttt ccccgtcaag ctctaaatcg    4740
ggggctccct ttagggttcc gatttagtgc tttacggcac ctcgacccca aaaaacttga    4800
tttgggtgat ggttcacgta gtgggccatc gccctgatag acggtttttc gccctttgac    4860
gttggagtcc acgttcttta atagtggact cttgttccaa actggaacaa cactcaactc    4920
tatctcgggc tattcttttg atttataagg gattttgccg atttcggtct attggttaaa    4980
aaatgagctg atttaacaaa aatttaacgc gaattttaac aaaatattaa cgtttacaat    5040
tttatggtgc actctcagta caatctgctc tgatgccgca tagttaagcc agccccgaca    5100
cccgccaaca cccgctgacg cgccctgacg ggcttgtctg ctcccggcat ccgcttacag    5160
acaagctgtg accgtctccg ggagctgcat gtgtcagagg ttttcaccgt catcaccgaa    5220
acgcgcgaga cgaaagggcc tcgtgatacg cctattttta taggttaatg tcatgataat    5280
aatggtttct tagacgtcag gtggcacttt tcggggaaat gtgcgcggaa cccctatttg    5340
tttatttttc taaatacatt caaatatgta tccgctcatg agacaataac cctgataaat    5400
gcttcaataa tattgaaaaa ggaagagtat gagtattcaa catttccgtg tcgcccttat    5460
tccctttttt gcggcatttt gccttcctgt ttttgctcac ccagaaacgc tggtgaaagt    5520
aaaagatgct gaagatcagt tgggtgcacg agtgggttac atcgaactgg atctcaacag    5580
cggtaagatc cttgagagtt ttcgccccga agaacgtttt ccaatgatga gcactttaa    5640 agttctgcta tgtggcgcgg tattatcccg tattgacgcc gggcaagagc aactcggtcg    5700
ccgcatacac tattctcaga atgacttggt tgagtactca ccagtcacag aaaagcatct    5760
tacggatggc atgacagtaa gagaattatg cagtgctgcc ataaccatga gtgataacac    5820
tgcggccaac ttacttctga caacgatcgg aggaccgaag gagctaaccg cttttttgca    5880
caacatgggg gatcatgtaa ctcgccttga tcgttgggaa ccggagctga atgaagccat    5940
```

```
accaaacgac gagcgtgaca ccacgatgcc tgtagcaatg gcaacaacgt tgcgcaaact    6000
attaactggc gaactactta ctctagcttc ccggcaacaa ttaatagact ggatggaggc    6060
ggataaagtt gcaggaccac ttctgcgctc ggcccttccg gctggctggt ttattgctga    6120
taaatctgga gccggtgagc gtggaagccg cggtatcatt gcagcactgg ggccagatgg    6180
taagccctcc cgtatcgtag ttatctacac gacggggagt caggcaacta tggatgaacg    6240
aaatagacag atcgctgaga taggtgcctc actgattaag cattggtaac tgtcagacca    6300
agtttactca tatatacttt agattgattt aaaacttcat ttttaattta aaaggatcta    6360
ggtgaagatc cttttgata atctcatgac caaaatccct taacgtgagt tttcgttcca    6420
ctgagcgtca gaccccgtag aaaagatcaa aggatcttct tgagatcctt tttttctgcg    6480
cgtaatctgc tgcttgcaaa caaaaaaacc accgctacca gcggtggttt gtttgccgga    6540
tcaagagcta ccaactcttt ttccgaaggt aactggcttc agcagagcgc agataccaaa    6600
tactgttctt ctagtgtagc cgtagttagg ccaccacttc aagaactctg tagcaccgcc    6660
tacatacctc gctctgctaa tcctgttacc agtggctgct gccagtggcg ataagtcgtg    6720
tcttaccggg ttggactcaa gacgatagtt accggataag gcgcagcggt cgggctgaac    6780
ggggggttcg tgcacacagc ccagcttgga gcgaacgacc tacaccgaac tgagatacct    6840
acagcgtgag ctatgagaaa gcgccacgct tcccgaaggg agaaaggcgg acaggtatcc    6900
ggtaagcggc agggtcggaa caggagagcg cacgagggag cttccagggg gaaacgcctg    6960
gtatctttat agtcctgtcg ggtttcgcca cctctgactt gagcgtcgat ttttgtgatg    7020
ctcgtcaggg gggcggagcc tatggaaaaa cgccagcaac gcggcctttt tacggttcct    7080
ggccttttgc tggcctttg ctcacatgt                                       7109
```

```
<210> SEQ ID NO 4
<211> LENGTH: 13393
<212> TYPE: DNA
<213> ORGANISM: Artificial Sequence
<220> FEATURE:
<223> OTHER INFORMATION: pGW029
<220> FEATURE:
<221> NAME/KEY: misc_feature
<222> LOCATION: (9532)..(9534)
<223> OTHER INFORMATION: n is a, c, g, or t
<220> FEATURE:
<221> NAME/KEY: misc_feature
<222> LOCATION: (9549)..(9551)
<223> OTHER INFORMATION: n is a, c, g, or t
<220> FEATURE:
<221> NAME/KEY: misc_feature
<222> LOCATION: (11851)..(11856)
<223> OTHER INFORMATION: n is a, c, g, or t

<400> SEQUENCE: 4
```

```
ctacagggcg cgtccattcg ccattcagga tcgaattaat tcttaattaa catcatcaat     60
aatatacctt attttggatt gaagccaata tgataatgag ggggtggagt ttgtgacgtg    120
gcgcggggcg tgggaacggg gcgggtgacg tagtagtgtg gcggaagtgt gatgttgcaa    180
gtgtggcgga acacatgtaa gcgacggatg tggcaaaagt gacgtttttg gtgtgcgccg    240
gtgtacacag gaagtgacaa ttttcgcgcg gtttttaggcg gatgttgtag taaatttggg    300
cgtaaccgag taagatttgg ccattttcgc gggaaaactg aataagagga agtgaaatct    360
gaataatttt gtgttactca tagcgcgtaa tactggtacc gcggccgcct cgagtctaga    420
aagagggcct atttcccatg attccttcat atttgcatat acgatacaag gctgttagag    480
```

-continued

```
agataattag aattaatttg actgtaaaca caaagatatt agtacaaaat acgtgacgta    540
gaaagtaata atttcttggg tagtttgcag ttttaaaatt atgtttttaaa atggactatc    600 atatgcttac cgtaacttga aagtatttcg atttcttggc tttatatatc ttgtggaaag    660
gacgaaacac cggaagagcg agctcttctg ttttagagct aggccaacat gaggatcacc    720
catgtctgca gggcctagca agttaaaata aggctagtcc gttatcaact tggccaacat    780
gaggatcacc catgtctgca gggccaagtg gcaccgagtc ggtgcttttt tgctagcgtc    840
agtgggcaga gcgcacatcg cccacagtcc ccgagaagtt ggggggaggg gtcggcaatt    900
gaacgggtgc ctagagaagg tggcgcgggg taaactggga aagtgatgtc gtgtactggc    960
tccgcctttt tcccgagggt gggggagaac cgtatataag tgcagtagtc gccgtgaacg   1020 ttcttttttcg caacgggttt gccgccagaa cacagctgaa gcttcgaggg gctcgcatct   1080
ctccttcacg cgcccgccgc cctacctgag gccgccatcc acgccggttg agtcgcgttc   1140
tgccgcctcc cgcctgtggt gcctcctgaa ctgcgtccgc cgtctaggta agtttaaagc   1200
tcaggtcgag accgggcctt tgtccggcgc tcccttggag cctacctaga ctcagccggc   1260
tctccacgct ttgcctgacc ctgcttgctc aactctacgt ctttgtttcg ttttctgttc   1320
tgcgccgtta cagatccaag ctcgtacggc caccatgaaa aggccggcgg ccacgaaaaa   1380
ggccggccag gcaaaaaaga aaaaggacaa gaagtacagc atcggcctgg ccatcggcac   1440
caactctgtg ggctgggccg tgatcaccga cgagtacaag gtgcccagca agaaattcaa   1500
ggtgctgggc aacaccgacc ggcacagcat caagaagaac ctgatcggag ccctgctgtt   1560
cgacagcggc gaaacagccg aggccacccg gctgaagaga accgcagaa gaagatacac   1620 cagacggaag aaccggatct gctatctgca agagatcttc agcaacgaga tggccaaggt   1680
ggacgacagc ttcttccaca gactggaaga gtccttcctg gtggaagagg ataagaagca   1740
cgagcggcac cccatcttcg gcaacatcgt ggacgaggtg gcctaccacg agaagtaccc   1800
caccatctac cacctgagaa agaaactggt ggacagcacc gacaaggccg acctgcggct   1860
gatctatctg gccctggccc acatgatcaa gttccggggc cacttcctga tcgagggcga   1920
cctgaacccc gacaacagcg acgtggacaa gctgttcatc cagctggtgc agacctacaa   1980
ccagctgttc gaggaaaacc ccatcaacgc cagcggcgtg gacgccaagg ccatcctgtc   2040
tgccagactg agcaagagca gacggctgga aaatctgatc gcccagctgc ccggcgagaa   2100
gaagaatggc ctgttcggca acctgattgc cctgagcctg ggcctgaccc ccaacttcaa   2160
gagcaacttc gacctggccg aggatgccaa actgcagctg agcaaggaca cctacgacga   2220
cgacctggac aacctgctgg cccagatcgg cgaccagtac gccgacctgt ttctggccgc   2280
caagaacctg tccgacgcca tcctgctgag cgacatcctg agagtgaaca ccgagatcac   2340
caaggccccc ctgagcgcct ctatgatcaa gagatacgac gagcaccacc aggacctgac   2400
cctgctgaaa gctctcgtgc ggcagcagct gcctgagaag tacaaagaga ttttcttcga   2460
ccagagcaag aacggctacg ccggctacat tgacggcgga gccagccagg aagagttcta   2520
caagttcatc aagcccatcc tggaaaagat ggacggcacc gaggaactgc tcgtgaagct   2580
gaacagagag gacctgctgc ggaagcagcg gaccttcgac aacggcagca tcccccacca   2640
gatccacctg ggagagctgc acgccattct gcggcggcag gaagattttt acccattcct   2700
gaaggacaac cgggaaaaga tcgagaagat cctgaccttc cgcatcccct actacgtggg   2760
ccctctggcc aggggaaaca gcagattcgc ctggatgacc agaaagagcg aggaaaccat   2820 cacccccctgg aacttcgagg aagtggtgga caagggcgct tccgcccaga gcttcatcga   2880
```

```
gcggatgacc aacttcgata agaacctgcc caacgagaag gtgctgccca agcacagcct   2940
gctgtacgag tacttcaccg tgtataacga gctgaccaaa gtgaaatacg tgaccgaggg   3000
aatgagaaag cccgccttcc tgagcggcga gcagaaaaag gccatcgtgg acctgctgtt   3060
caagaccaac cggaaagtga ccgtgaagca gctgaaagag gactacttca agaaaatcga   3120
gtgcttcgac tccgtggaaa tctccggcgt ggaagatcgg ttcaacgcct ccctgggcac   3180
ataccacgat ctgctgaaaa ttatcaagga caaggacttc ctggacaatg aggaaaacga   3240
ggacattctg gaagatatcg tgctgaccct gacactgttt gaggacagag agatgatcga   3300
ggaacggctg aaaacctatg cccacctgtt cgacgacaaa gtgatgaagc agctgaagcg   3360
gcggagatac accggctggg gcaggctgag ccggaagctg atcaacggca tccgggacaa   3420
gcagtccggc aagacaatcc tggatttcct gaagtccgac ggcttcgcca acagaaactt   3480
catgcagctg atccacgacg acagcctgac ctttaaagag gacatccaga aagcccaggt   3540
gtccggccag ggcgatagcc tgcacgagca cattgccaat ctggccggca gccccgccat   3600
taagaagggc atcctgcaga cagtgaaggt ggtggacgag ctcgtgaaag tgatgggccg   3660
gcacaagccc gagaacatcg tgatcgaaat ggccagagag aaccagacca cccagaaggg   3720
acagaagaac agccgcgaga gaatgaagcg gatcgaagag ggcatcaaag agctgggcag   3780
ccagatcctg aaagaacacc ccgtggaaaa cacccagctg cagaacgaga gctgtacct   3840 gtactacctg cagaatgggc gggatatgta cgtggaccag gaactggaca tcaaccggct   3900
gtccgactac gatgtggacc acatcgtgcc tcagagcttt ctgaaggacg actccatcga   3960
caacaaggtg ctgaccagaa gcgacaaggc ccggggcaag agcgacaacg tgccctccga   4020
agaggtcgtg aagaagatga agaactactg gcggcagctg ctgaacgcca agctgattac   4080
ccagagaaag ttcgacaatc tgaccaaggc cgagagaggc ggcctgagcg aactggataa   4140
ggccggcttc atcaagagac agctggtgga aacccggcag atcacaaagc acgtggcaca   4200
gatcctggac tcccggatga acactaagta cgacgagaat gacaagctga tccgggaagt   4260
gaaagtgatc accctgaagt ccaagctggt gtccgatttc cggaaggatt ccagttttta   4320
caaagtgcgc gagatcaaca actaccacca cgcccacgac gcctacctga acgccgtcgt   4380
gggaaccgcc ctgatcaaaa agtaccctaa gctggaaagc gagttcgtgt acggcgacta   4440
caaggtgtac gacgtgcgga agatgatcgc caagagcgag caggaaatcg gcaaggctac   4500
cgccaagtac ttcttctaca gcaacatcat gaactttttc aagaccgaga ttaccctggc   4560
caacggcgag atccggaagc ggcctctgat cgagacaaac ggcgaaaccg gggagatcgt   4620
gtgggataag ggccgggatt ttgccaccgt gcggaaagtg ctgagcatgc cccaagtgaa   4680
tatcgtgaaa aagaccgagg tgcagacagg cggcttcagc aaagagtcta tcctgcccaa   4740
gaggaacagc gataagctga tcgccagaaa gaaggactgg gaccctaaga gtacggcgg   4800 cttcgacagc cccaccgtgg cctattctgt gctggtggtg gccaaagtgg aaaagggcaa   4860
gtccaagaaa ctgaagagtg tgaaagagct gctggggatc accatcatgg aaagaagcag   4920
cttcgagaag aatcccatcg actttctgga agccaagggc tacaaagaag tgaaaaagga   4980
cctgatcatc aagctgccta gtactccct gttcgagctg gaaaacggcc ggaagagaat   5040
gctggcctct gccggcgaac tgcagaaggg aaacgaactg gccctgccct ccaaatatgt   5100
gaacttcctg tacctggcca gccactatga gaagctgaag ggctcccccg aggataatga   5160
gcagaaacag ctgtttgtgg aacagcacaa gcactacctg gacgagatca tcgagcagat   5220
```

-continued

```
cagcgagttc tccaagagag tgatcctggc cgacgctaat ctggacaaag tgctgtccgc    5280
ctacaacaag caccgggata agcccatcag agagcaggcc gagaatatca tccacctgtt    5340
taccctgacc aatctgggag cccctgccgc cttcaagtac tttgacacca ccatcgaccg    5400
gaagaggtac accagcacca aagaggtgct ggacgccacc ctgatccacc agagcatcac    5460
cggcctgtac gagacacgga tcgacctgtc tcagctggga ggcgacagcg ctggaggacc    5520
taagaaaaag aggaaggtgg gatccggacg ggctgacgca ttggacgatt ttgatctgga    5580
tatgctggga agtgacgccc tcgatgattt tgaccttgac atgcttggtt cggatgccct    5640
tgatgacttt gacctcgaca tgctcggcag tgacgccctt gatgatttcg acctggacat    5700
gctgattaac tgtacaggaa gcggagccac taacttctcc ctgttgaaac aagcaggga    5760 tgtcgaagag aatcccgggc cagccaccat ggcttcaaac tttactcagt tcgtgctcgt    5820
ggacaatggt gggacagggg atgtgacagt ggctccttct aatttcgcta atggggtggc    5880
agagtggatc agctccaact cacggagcca ggcctacaag gtgacatgca gcgtcaggca    5940
gtctagtgcc cagaagagaa agtataccat caaggtggag gtccccaaag tggctaccca    6000
gacagtgggc ggagtcgaac tgcctgtcgc cgcttggagg tcctacctga acatggagct    6060
cactatccca attttcgcta ccaattctga ctgtgaactc atcgtgaagg caatgcaggg    6120
gctcctcaaa gacggtaatc ctatcccttc cgccatcgcc gctaactcag gtatctacag    6180
cgctggagga ggtggaagcg gaggaggagg aagcggagga ggaggtagcg gacctaagaa    6240
aaagaggaag gtggcggccg ctggatcccc ttcagggcag atcagcaacc aggccctggc    6300
tctggcccct agtccgctc cagtgctggc ccagactatg gtgccctcta gtgctatggt    6360
gcctctggcc cagccacctg ctccagcccc tgtgctgacc ccaggaccac cccagtcact    6420
gagcgctcca gtgcccaagt ctacacaggc cggcgagggg actctgagtg aagctctgct    6480
gcacctgcag ttcgacgctg atgaggacct gggagctctg ctgggaaca gcaccgatcc    6540 cggagtgttc acagatctgg cctccgtgga caactctgag tttcagcagc tgctgaatca    6600
gggcgtgtcc atgtctcata gtacagccga accaatgctg atggagtacc ccgaagccat    6660 taccccggctg gtgaccggca gccagcggcc ccccgacccc gctccaactc ccctgggaac    6720
cagcggcctg cctaatgggc tgtccggaga tgaagacttc tcaagcatcg ctgatatgga    6780
ctttagtgcc ctgctgtcac agatttcctc tagtgggcag ggaggaggtg gaagcggctt    6840
cagcgtggac accagtgccc tgctggacct gttcagcccc tcggtgaccg tgcccgacat    6900
gagcctgcct gaccttgaca gcagcctggc cagtatccaa gagctcctgt ctccccagga    6960 gcccccagg cctcccgagg cagagaacag cagcccggat tcagggaagc agctggtgca    7020
ctacacagcg cagccgctgt tcctgctgga ccccggctcc gtggacaccg ggagcaacga    7080
cctgccggtg ctgtttgagc tgggagaggg ctcctacttc tccgaagggg acggcttcgc    7140
cgaggacccc accatctccc tgctgacagg ctcggagcct cccaaagcca aggaccccac    7200
tgtctcctaa gaattcgata tcaagcttaa taaaagatct ttattttcat tagatctgtg    7260
tgttggtttt ttgtgtagat ctgggcgtgg ttaagggtgg gaaagaatat ataaggtggg    7320
ggtcttatgt agttttgtat ctgttttgca gcagccgccg ccgccatgag caccaactcg    7380
tttgatggaa gcattgtgag ctcatatttg acaacgcgca tgcccccatg ggccgggtg    7440 cgtcagaatg tgatgggctc cagcattgat ggtcgccccg tcctgcccgc aaactctact    7500
accttgacct acgagaccgt gtctggaacg ccgttggaga ctgcagcctc cgccgccgct    7560
tcagccgctg cagccaccgc ccgcgggatt gtgactgact ttgctttcct gagcccgctt    7620
```

-continued

```
gcaagcagtg cagcttcccg ttcatccgcc cgcgatgaca agttgacggc tcttttggca    7680
caattggatt ctttgacccg ggaacttaat gtcgtttctc agcagctgtt ggatctgcgc    7740
cagcaggttt ctgccctgaa ggcttcctcc cctcccaatg cggtttaaaa cataaataaa    7800
aaaccagact ctgtttggat ttggatcaag caagtgtctt gctgtcttta tttaggggtt    7860
ttgcgcgcgc ggtaggcccg ggaccagcgg tctcggtcgt tgagggtcct gtgtattttt    7920
tccaggacgt ggtaaaggtg actctggatg ttcagataca tgggcataag cccgtctctg    7980
gggtggaggt agcaccactg cagagcttca tgctgcgggg tggtgttgta gatgatccag    8040
tcgtagcagg agcgctgggc gtggtgccta aaaatgtctt tcagtagcaa gctgattgcc    8100
aggggcaggc ccttggtgta agtgtttaca aagcggttaa gctgggatgg gtgcatacgt    8160
ggggatatga gatgcatctt ggactgtatt tttaggttgg ctatgttccc agccatatcc    8220
ctccggggat tcatgttgtg cagaaccacc agcacagtgt atccggtgca cttgggaaat    8280
ttgtcatgta gcttagaagg aaatgcgtgg aagaacttgg agacgccctt gtgacctcca    8340 agatttttcca tgcattcgtc cataatgatg gcaatgggcc cacgggcggc ggcctgggcg    8400
aagatatttc tgggatcact aacgtcatag ttgtgttcca ggatgagatc gtcataggcc    8460
atttttacaa agcgcgggcg gagggtgcca gactgcggta taatggttcc atccggccca    8520
ggggcgtagt taccctcaca gatttgcatt tcccacgctt tgagttcaga tgggggggatc    8580 atgtctacct gcggggcgat gaagaaaacg gtttccgggg taggggagat cagctgggaa    8640
gaaagcaggt tcctgagcag ctgcgactta ccgcagccgg tgggcccgta aatcacacct    8700
attaccgggt gcaactggta gttaagagag ctgcagctgc cgtcatccct gagcaggggg    8760
gccacttcgt taagcatgtc cctgactcgc atgttttccc tgaccaaatc cgccagaagg    8820
cgctcgccgc ccagcgatag cagttcttgc aaggaagcaa agttttttcaa cggtttgaga    8880 ccgtccgccg taggcatgct tttgagcgtt tgaccaagca gttccaggcg gtcccacagc    8940
tcggtcacct gctctacggc atctcgatcc agcatatctc ctcgtttcgc gggttgggggc    9000 ggctttcgct gtacggcagt agtcggtgct cgtccagacg ggccagggtc atgtctttcc    9060
acgggcgcag ggtcctcgtc agcgtagtct gggtcacggt gaaggggtgc gctccgggct    9120
gcgcgctggc cagggtgcgc ttgaggctgg tcctgctggt gctgaagcgc tgccggtctt    9180
cgccctgcgc gtcggccagg tagcatttga ccatggtgtc atagtccagc ccctccgcgg    9240
cgtggccctt ggcgcgcagc ttgcccttgg aggaggcgcc gcacgagggg cagtgcagac    9300 tttttgagggc gtagagcttg ggcgcgagaa ataccgattc cggggagtag gcatccgcgc    9360
cgcaggcccc gcagacggtc tcgcattcca cgagccaggt gagctctggc cgttcggggt    9420
caaaaaccag gtttccccca tgctttttga tgcgtttctt acctctggtt tccatgagcc    9480
ggtgtccacg ctcggtgacg aaaaggctgt ccgtgtcccc gtatacagac tnnngtttaa    9540
acgaattcnn ntataaaatg caaggtgctg ctcaaaaaat caggcaaagc ctcgcgcaaa    9600
aaagaaagca catcgtagtc atgctcatgc agataaaggc aggtaagctc cggaaccacc    9660
acagaaaaag acaccatttt tctctcaaac atgtctgcgg gtttctgcat aaacacaaaa    9720
taaaataaca aaaaaacatt taaacattag aagcctgtct tacaacagga aaacaaccc    9780 ttataagcat aagacggact acggccatgc cggcgtgacc gtaaaaaaac tggtcaccgt    9840
gattaaaaag caccaccgac agctcctcgg tcatgtccgg agtcataatg taagactcgg    9900
taaacacatc aggttgattc atcggtcagt gctaaaaagc gaccgaaata gcccggggga    9960
```

-continued

```
atacataccc gcaggcgtag agacaacatt acagcccccca taggaggtat aacaaaatta  10020
ataggagaga aaaacacata aacacctgaa aaaccctcct gcctaggcaa aatagcaccc  10080
tcccgctcca gaacaacata cagcgcttca cagcggcagc ctaacagtca gccttaccag  10140
taaaaaagaa aacctattaa aaaaacacca ctcgacacgg caccagctca atcagtcaca  10200
gtgtaaaaaa gggccaagtg cagagcgagt atatatagga ctaaaaaatg acgtaacggt  10260
taaagtccac aaaaaacacc cagaaaaccg cacgcgaacc tacgcccaga aacgaaagcc  10320
aaaaaaccca caacttcctc aaatcgtcac ttccgttttc ccacgttacg taacttccca  10380
ttttaagaaa actacaattc ccaacacata caagttactc cgccctaaaa cctacgtcac  10440 ccgcccgtt cccacgccc gcgccacgtc acaaactcca ccccctcatt atcatattgg  10500
cttcaatcca aaataaggta tattattgat gattaattaa ttaaggatcc cggtgtgaaa  10560
taccgcacag atgcgtaagg agaaaatacc gcatcaggcg ctcttacgct tcctcgctca  10620
ctgactcgct gcgctcggtc gttcggctgc ggcgagcggt atcagctcac tcaaaggcgg  10680
taatacggtt atccacagaa tcaggggata acgcaggaaa gaacatgtga gcaaaaggcc  10740
agcaaaaggc caggaaccgt aaaaaggccg cgttgctggc gtttttccat aggctccgcc  10800
cccctgacga gcatcacaaa aatcgacgct caagtcagag gtggcgaaac ccgacaggac  10860
tataaagata ccaggcgttt cccctggaa gctccctcgt gcgctctcct gttccgaccc  10920
tgccgcttac cggatacctg tccgcctttc tcccttcggg aagcgtggcg ctttctcata  10980
gctcacgctg taggtatctc agttcggtgt aggtcgttcg ctccaagctg ggctgtgtgc  11040 acgaacccc cgttcagccc gaccgctgcg ccttatccgg taactatcgt cttgagtcca  11100
acccggtaag acacgactta tcgccactgg cagcagccac tggtaacagg attagcagag  11160
cgaggtatgt aggcggtgct acagagttct tgaagtggtg gcctaactac ggctacacta  11220
gaaggacagt atttggtatc tgcgctctgc tgaagccagt taccttcgga aaaagagttg  11280
gtagctcttg atccggcaaa caaaccaccg ctggtagcgg tggtttttttt gtttgcaagc  11340 agcagattac gcgcagaaaa aaaggatctc aagaagatcc tttgatcttt tctacggggt  11400
ctgacgctca gtggaacgaa aactcacgtt aagggatttt ggtcatgaga ttatcaaaaa  11460
ggatcttcac ctagatcctt ttaaattaaa aatgaagttt taaatcaatc taaagtatat  11520
atgagtaaac ttggtctgac agttaccaat gcttaatcag tgaggcacct atctcagcga  11580
tctgtctatt tcgttcatcc atagttgcct gactccccgt cgtgtagata actacgatac  11640
gggagggctt accatctggc cccagtgctg caatgatacc gcgagaccca cgctcaccgg  11700
ctccagattt atcagcaata aaccagccag ccggaagggc cgagcgcaga agtggtcctg  11760
caactttatc cgcctccatc cagtctatta attgttgccg ggaagctaga gtaagtagtt  11820
cgccagttaa tagtttgcgc aacgttgttg nnnnnnaaaa aggatcttca cctagatcct  11880
tttcacgtag aaagccagtc cgcagaaacg gtgctgaccc cggatgaatg tcagctactg  11940
ggctatctgg acaagggaaa acgcaagcgc aaagagaaag caggtagctt gcagtgggct  12000
tacatggcga tagctagact gggcggtttt atggacagca agcgaaccgg aattgccagc  12060
tggggcgccc tctggtaagg ttgggaagcc ctgcaaagta aactggatgg ctttctcgcc  12120
gccaaggatc tgatggcgca ggggatcaag ctctgatcaa gagacaggat gaggatcgtt  12180
tcgcatgatt gaacaagatg gattgcacgc aggttctccg gccgcttggg tggagaggct  12240
attcggctat gactgggcac aacagacaat cggctgctct gatgccgccg tgttccggct  12300
gtcagcgcag gggcgcccgg ttctttttgt caagaccgac ctgtccggtg ccctgaatga  12360
```

-continued

```
actgcaagac gaggcagcgc ggctatcgtg gctggccacg acgggcgttc cttgcgcagc    12420
tgtgctcgac gttgtcactg aagcgggaag ggactggctg ctattgggcg aagtgccggg    12480
gcaggatctc ctgtcatctc accttgctcc tgccgagaaa gtatccatca tggctgatgc    12540
aatgcggcgg ctgcatacgc ttgatccggc tacctgccca ttcgaccacc aagcgaaaca    12600
tcgcatcgag cgagcacgta ctcggatgga agccggtctt gtcgatcagg atgatctgga    12660
cgaggagcat caggggctcg cgccagccga actgttcgcc aggctcaagg cgagcatgcc    12720
cgacggcgag gatctcgtcg tgacccatgg cgatgcctgc ttgccgaata tcatggtgga    12780
aaatggccgc ttttctggat tcatcgactg tggccggctg ggtgtggcgg accgctatca    12840
ggacatagcg ttggctaccc gtgatattgc tgaggagctt ggcggcgaat gggctgaccg    12900
cttcctcgtg ctttacggta tcgccgctcc cgattcgcag cgcatcgcct tctatcgcct    12960
tcttgacgag ttcttctgaa ttttgttaaa attttgtta aatcagctca tttttttaacc   13020 aataggccga aatcggcaac atcccttata aatcaaaaga atagaccgcg ataggggttga   13080 gtgttgttcc agtttggaac aagagtccac tattaaagaa cgtggactcc aacgtcaaag    13140
ggcgaaaaac cgtctatcag ggcgatggcc cactacgtga accatcaccc aaatcaagtt    13200
ttttgcggtc gaggtgccgt aaagctctaa atcggaaccc taaagggagc ccccgattta    13260
gagcttgacg gggaaagccg cgaacgtgg cgagaaagga agggaagaaa gcgaaaggag    13320
cgggcgctag ggcgctggca agtgtagcgg tcacgctgcg cgtaaccacc acacccgcgc    13380
gcttaatgcg ccg                                                     13393
```

```
<210> SEQ ID NO 5
<211> LENGTH: 13444
<212> TYPE: DNA
<213> ORGANISM: Artificial Sequence
<220> FEATURE:
<223> OTHER INFORMATION: pGW035
<220> FEATURE:
<221> NAME/KEY: misc_feature
<222> LOCATION: (9583)..(9585)
<223> OTHER INFORMATION: n is a, c, g, or t
<220> FEATURE:
<221> NAME/KEY: misc_feature
<222> LOCATION: (9600)..(9602)
<223> OTHER INFORMATION: n is a, c, g, or t
<220> FEATURE:
<221> NAME/KEY: misc_feature
<222> LOCATION: (11902)..(11907)
<223> OTHER INFORMATION: n is a, c, g, or t

<400> SEQUENCE: 5
```

```
ctacagggcg cgtccattcg ccattcagga tcgaattaat tcttaattaa catcatcaat      60
aatatacctt attttggatt gaagccaata tgataatgag ggggtggagt ttgtgacgtg      120
gcgcggggcg tgggaacggg gcgggtgacg tagtagtgtg gcggaagtgt gatgttgcaa     180
gtgtggcgga acacatgtaa gcgacggatg tggcaaaagt gacgtttttg tgtgtgcgccg     240 gtgtacacag gaagtgacaa ttttcgcgcg gttttaggcg gatgttgtag taaatttggg     300
cgtaaccgag taagatttgg ccattttcgc gggaaaactg aataagagga agtgaaatct      360
gaataatttt gtgttactca tagcgcgtaa tactggtacc gcggccgcct cgagtctaga      420
aagagggcct atttcccatg attccttcat atttgcatat acgatacaag gctgttagag      480
agataattag aattaatttg actgtaaaca caaagatatt agtacaaaat acgtgacgta      540
gaaagtaata atttcttggg tagtttgcag ttttaaaatt atgttttaaa atggactatc      600
```

```
atatgcttac cgtaacttga aagtatttcg atttcttggc tttatatatc ttgtggaaag     660
gacgaaacac cggaagagcg agctcttctg ttttagagct aggccaacat gaggatcacc     720
catgtctgca gggcctagca agttaaaata aggctagtcc gttatcaact tggccaacat     780
gaggatcacc catgtctgca gggccaagtg gcaccgagtc ggtgcttttt tgctagcgtc     840
agtgggcaga gcgcacatcg cccacagtcc ccgagaagtt ggggggaggg gtcggcaatt     900
gaacgggtgc ctagagaagg tggcgcgggg taaactggga aagtgatgtc gtgtactggc     960
tccgcctttt tcccgagggt gggggagaac cgtatataag tgcagtagtc gccgtgaacg    1020
ttctttttcg caacgggttt gccgccagaa cacagctgaa gcttcgaggg gctcgcatct    1080
ctccttcacg cgcccgccgc cctacctgag gccgccatcc acgccggttg agtcgcgttc    1140
tgccgcctcc cgcctgtggt gcctcctgaa ctgcgtccgc cgtctaggta agtttaaagc    1200
tcaggtcgag accgggcctt tgtccggcgc tcccttggag cctacctaga ctcagccggc    1260
tctccacgct ttgcctgacc ctgcttgctc aactctacgt ctttgtttcg ttttctgttc    1320
tgcgccgtta cagatccaag ctcgtacggc caccatgaaa aggccggcgg ccacgaaaaa    1380
ggccggccag gcaaaaaaga aaaaggacaa gaagtacagc atcggcctgg ccatcggcac    1440
caactctgtg ggctgggccg tgatcaccga cgagtacaag gtgcccagca agaaattcaa    1500
ggtgctgggc aacaccgacc ggcacagcat caagaagaac ctgatcggag ccctgctgtt    1560
cgacagcggg aaacagccg aggccacccg gctgaagaga accgccagaa gaagatacac    1620
cagacggaag aaccggatct gctatctgca agagatcttc agcaacgaga tggccaaggt    1680
ggacgacagc ttcttccaca gactggaaga gtccttcctg gtggaagagg ataagaagca    1740
cgagcggcac cccatcttcg gcaacatcgt ggacgaggtg gcctaccacg agaagtaccc    1800
caccatctac cacctgagaa agaaactggt ggacagcacc gacaaggccg acctgcggct    1860
gatctatctg gccctggccc acatgatcaa gttccggggc cacttcctga tcgagggcga    1920
cctgaacccc gacaacagcg acgtggacaa gctgttcatc cagctggtgc agacctacaa    1980
ccagctgttc gaggaaaacc ccatcaacgc cagcggcgtg gacgccaagg ccatcctgtc    2040
tgccagactg agcaagagca gacggctgga aaatctgatc gcccagctgc cggcgagaa    2100 gaagaatggc ctgttcggca acctgattgc cctgagcctg ggcctgaccc ccaacttcaa    2160
gagcaacttc gacctggccg aggatgccaa actgcagctg agcaaggaca cctacgacga    2220
cgacctggac aacctgctgg cccagatcgg cgaccagtac gccgacctgt ttctggccgc    2280
caagaacctg tccgacgcca tcctgctgag cgacatcctg agagtgaaca ccgagatcac    2340
caaggccccc ctgagcgcct ctatgatcaa gagatacgac gagcaccacc aggacctgac    2400
cctgctgaaa gctctcgtgc ggcagcagct gcctgagaag tacaaagaga ttttcttcga    2460
ccagagcaag aacggctacg ccggctacat tgacggcgga gccagccagg aagagttcta    2520
caagttcatc aagcccatcc tggaaaagat ggacggcacc gaggaactgc tcgtgaagct    2580
gaacagagag gacctgctgc ggaagcagcg gaccttcgac aacggcagca tcccccacca    2640
gatccacctg ggagagctgc acgccattct gcggcggcag gaagattttt acccattcct    2700
gaaggacaac cggaaaagaa tcgagaagat cctgaccttc cgcatcccct actacgtggg    2760
ccctctggcc aggggaaaca gcagattcgc ctggatgacc agaaagagcg aggaaaccat    2820 cacccctgg aacttcgagg aagtggtgga caagggcgct tccgcccaga gcttcatcga    2880
gcggatgacc aacttcgata agaacctgcc caacgagaag gtgctgccca gcacagcct    2940 gctgtacgag tacttcaccg tgtataacga gctgaccaaa gtgaaatacg tgaccgaggg    3000
```

```
aatgagaaag cccgccttcc tgagcggcga gcagaaaaag gccatcgtgg acctgctgtt    3060
caagaccaac cggaaagtga ccgtgaagca gctgaaagcg gactacttca agaaaatcga    3120
gtgcttcgac tccgtggaaa tctccggcgt ggaagatcgg ttcaacgcct ccctgggcac    3180
ataccacgat ctgctgaaaa ttatcaagga caaggacttc ctggacaatg aggaaaacga    3240
ggacattctg gaagatatcg tgctgaccct gacactgttt gaggacagag agatgatcga    3300
ggaacggctg aaaacctatg cccacctgtt cgacgacaaa gtgatgaagc agctgaagcg    3360
gcggagatac accggctggg gcaggctgag ccggaagctg atcaacggca tccgggacaa    3420
gcagtccggc aagacaatcc tggatttcct gaagtccgac ggcttcgcca acagaaactt    3480
catgcagctg atccacgacg acagcctgac ctttaaagag gacatccaga aagcccaggt    3540
gtccggccag ggcgatagcc tgcacgagca cattgccaat ctggccggca gccccgccat    3600
taagaagggc atcctgcaga cagtgaaggt ggtggacgag ctcgtgaaag tgatgggccg    3660
gcacaagccc gagaacatcg tgatcgaaat ggccagagag aaccagacca cccagaaggg    3720
acagaagaac agccgcgaga gaatgaagcg gatcgaagag ggcatcaaag agctgggcag    3780
ccagatcctg aaagaacacc ccgtggaaaa cacccagctg cagaacgaga gctgtacct    3840 gtactacctg cagaatgggc gggatatgta cgtggaccag gaactggaca tcaaccggct    3900
gtccgactac gatgtggacc acatcgtgcc tcagagcttt ctgaaggacg actccatcga    3960
caacaaggtg ctgaccagaa gcgacaaggc ccggggcaag agcgacaacg tgccctccga    4020
agaggtcgtg aagaagatga gaaactactg gcggcagctg ctgaacgcca agctgattac    4080
ccagagaaag ttcgacaatc tgaccaaggc cgagagaggc ggcctgagcg aactggataa    4140
ggccggcttc atcaagagac agctggtgga aacccggcag atcacaaagc acgtggcaca    4200
gatcctggac tcccggatga cactaagta cgacgagaat gacaagctga tccgggaagt    4260
gaaagtgatc accctgaagt ccaagctggt gtccgatttc cggaaggatt ccagttttta    4320
caaagtgcgc gagatcaaca ctaccacca cgcccacgac gcctacctga acgccgtcgt    4380
gggaaccgcc ctgatcaaaa agtaccctaa gctggaaagc gagttcgtgt acggcgacta    4440
caaggtgtac gacgtgcgga agatgatcgc caagagcgag caggaaatcg gcaaggctac    4500
cgccaagtac ttcttctaca gcaacatcat gaactttttc aagaccgaga ttaccctggc    4560
caacggcgag atccggaagc ggcctctgat cgagacaaac ggcgaaaccg gggagatcgt    4620
gtgggataag ggccgggatt ttgccaccgt gcggaaagtg ctgagcatgc cccaagtgaa    4680
tatcgtgaaa aagaccgagg tgcagacagg cggcttcagc aaagagtcta tcctgcccaa    4740
gaggaacagc gataagctga tcgccagaaa gaaggactgg gaccctaaga gtacggcgg    4800 cttcgacagc cccaccgtgg cctattctgt gctggtggtg gccaaagtgg aaaagggcaa    4860
gtccaagaaa ctgaagagtg tgaaagagct gctggggatc accatcatgg aaagaagcag    4920
cttcgagaag aatcccatcg actttctgga agccaagggc tacaaagaag tgaaaaagga    4980
cctgatcatc aagctgccta gtactccct gttcgagctg gaaaacggcc ggaagagaat    5040
gctggcctct gccggcgaac tgcagaaggg aaacgaactg gccctgcct ccaaatatgt    5100 gaacttcctg tacctggcca gccactatga gaagctgaag ggctcccccg aggataatga    5160
gcagaaacag ctgtttgtgg aacagcacaa gcactacctg gacgagatca tcgagcagat    5220
cagcgagttc tccaagagag tgatcctggc cgacgctaat ctggacaaag tgctgtccgc    5280
ctacaacaag caccgggata gcccatcag agagcaggcc gagaatatca tccacctgtt    5340
```

-continued

```
taccctgacc aatctgggag cccctgccgc cttcaagtac tttgacacca ccatcgaccg   5400
gaagaggtac accagcacca aagaggtgct ggacgccacc ctgatccacc agagcatcac   5460
cggcctgtac gagacacgga tcgacctgtc tcagctggga ggcgacagcg ctggaggagg   5520
tggaagcgga ggaggaggaa gcggaggagg aggtagcgga cctaagaaaa agaggaaggt   5580
ggcggccgct ggatccggac gggctgacgc attggacgat tttgatctgg atatgctggg   5640
aagtgacgcc ctcgatgatt ttgaccttga catgcttggt tcggatgccc ttgatgactt   5700
tgacctcgac atgctcggca gtgacgccct tgatgatttc gacctggaca tgctgattaa   5760
ctgtacagga agcggagcca ctaacttctc cctgttgaaa caagcagggg atgtcgaaga   5820
gaatcccggg ccagccacca tggcttcaaa ctttactcag ttcgtgctcg tggacaatgg   5880
tgggacaggg gatgtgacag tggctccttc taatttcgct aatggggtgg cagagtggat   5940
cagctccaac tcacggagcc aggcctacaa ggtgacatgc agcgtcaggc agtctagtgc   6000
ccagaagaga aagtatacca tcaaggtgga ggtccccaaa gtggctaccc agacagtggg   6060
cggagtcgaa ctgcctgtcg ccgcttggag gtcctacctg aacatggagc tcactatccc   6120
aattttcgct accaattctg actgtgaact catcgtgaag gcaatgcagg ggctcctcaa   6180
agacggtaat cctatccctt ccgccatcgc cgctaactca ggtatctaca gcgctggagg   6240
aggtggaagc ggaggaggag gaagcggagg aggaggtagc ggacctaaga aaaagaggaa   6300
ggtggcggcc gctggatccc cttcagggca gatcagcaac caggccctgg ctctggcccc   6360
tagctccgct ccagtgctgg cccagactat ggtgccctct agtgctatgg tgcctctggc   6420
ccagccacct gctccagccc ctgtgctgac cccaggacca ccccagtcac tgagcgctcc   6480
agtgcccaag tctacacagg ccggcgaggg gactctgagt gaagctctgc tgcacctgca   6540
gttcgacgct gatgaggacc tgggagctct gctggggaac agcaccgatc ccggagtgtt   6600
cacagatctg gcctccgtgg acaactctga gtttcagcag ctgctgaatc agggcgtgtc   6660
catgtctcat agtacagccg aaccaatgct gatggagtac cccgaagcca ttacccggct   6720
ggtgaccggc agccagcggc cccccgaccc cgctccaact cccctgggaa ccagcggcct   6780
gcctaatggg ctgtccggag atgaagactt ctcaagcatc gctgatatgg actttagtgc   6840
cctgctgtca cagatttcct ctagtgggca gggaggaggt ggaagcggct tcagcgtgga   6900
caccagtgcc ctgctggacc tgttcagccc ctcggtgacc gtgcccgaca tgagcctgcc   6960
tgaccttgac agcagcctgg ccagtatcca agagctcctg tctccccagg agccccccag   7020
gcctcccgag gcagagaaca gcagcccgga ttcaggggaag cagctggtgc actacacagc   7080
gcagccgctg ttcctgctgg accccggctc cgtggacacc gggagcaacg acctgccggt   7140
gctgtttgag ctgggagagg ctcctactt ctccgaaggg gacggcttcg ccgaggaccc   7200
caccatctcc ctgctgacag gctcggagcc tcccaaagcc aaggacccca ctgtctccta   7260
agaattcgat atcaagctta ataaaagatc tttattttca ttagatctgt gtgttggttt   7320
tttgtgtaga tctgggcgtg gttaagggtg ggaaagaata tataaggtgg gggtcttatg   7380 tagtttttgta tctgttttgc agcagccgcc gccgccatga gcaccaactc gtttgatgga   7440
agcattgtga gctcatattt gacaacgcgc atgcccccat gggccggggt gcgtcagaat   7500
gtgatgggct ccagcattga tggtcgcccc gtcctgcccg caaactctac taccttgacc   7560
tacgagaccg tgtctggaac gccgttggag actgcagcct ccgccgccgc ttcagccgct   7620
gcagccaccg cccgcgggat tgtgactgac tttgctttcc tgagcccgct tgcaagcagt   7680
gcagcttccc gttcatccgc ccgcgatgac aagttgacgg ctcttttggc acaattggat   7740
```

-continued

```
tctttgaccc gggaacttaa tgtcgtttct cagcagctgt tggatctgcg ccagcaggtt    7800
tctgccctga aggcttcctc ccctcccaat gcggtttaaa acataaataa aaaaccagac    7860
tctgtttgga tttggatcaa gcaagtgtct tgctgtcttt atttaggggt tttgcgcgcg    7920
cggtaggccc gggaccagcg gtctcggtcg ttgagggtcc tgtgtatttt ttccaggacg    7980
tggtaaaggt gactctggat gttcagatac atgggcataa gcccgtctct ggggtggagg    8040
tagcaccact gcagagcttc atgctgcggg gtggtgttgt agatgatcca gtcgtagcag    8100
gagcgctggg cgtggtgcct aaaaatgtct ttcagtagca agctgattgc caggggcagg    8160
cccttggtgt aagtgtttac aaagcggtta agctgggatg ggtgcatacg tggggatatg    8220
agatgcatct tggactgtat ttttaggttg gctatgttcc cagccatatc cctccgggga    8280
ttcatgttgt gcagaaccac cagcacagtg tatccggtgc acttgggaaa tttgtcatgt    8340
agcttagaag gaaatgcgtg gaagaacttg gagacgccct tgtgacctcc aagattttcc    8400
atgcattcgt ccataatgat ggcaatgggc ccacggcgg cggcctgggc gaagatattt     8460
ctgggatcac taacgtcata gttgtgttcc aggatgagat cgtcataggc cattttttaca   8520 aagcgcgggc ggagggtgcc agactgcggt ataatggttc catccggccc aggggcgtag    8580
ttaccctcac agatttgcat ttcccacgct ttgagttcag atggggggat catgtctacc    8640
tgcggggcga tgaagaaaac ggtttccggg gtaggggaga tcagctggga agaaagcagg    8700
ttcctgagca gctgcgactt accgcagccg gtgggcccgt aaatcacacc tattaccggg    8760
tgcaactggt agttaagaga gctgcagctg ccgtcatccc tgagcagggg ggccacttcg    8820
ttaagcatgt ccctgactcg catgttttcc ctgaccaaat ccgccagaag gcgctcgccg    8880
cccagcgata gcagttcttg caaggaagca aagttttttca acggtttgag accgtccgcc   8940
gtaggcatgc ttttgagcgt ttgaccaagc agttccaggc ggtcccacag ctcggtcacc    9000
tgctctacgg catctcgatc cagcatatct cctcgtttcg cgggttgggg cggctttcgc    9060
tgtacggcag tagtcggtgc tcgtccagac gggccagggt catgtctttc cacgggcgca    9120
gggtcctcgt cagcgtagtc tgggtcacg tgaaggggtg cgctccgggc tgcgcgctgg     9180
ccagggtgcg cttgaggctg gtcctgctgg tgctgaagcg ctgccggtct tcgccctgcg    9240
cgtcggccag gtagcatttg accatggtgt catagtccag cccctccgcg gcgtggccct    9300
tggcgcgcag cttgcccttg gaggaggcgc cgcacgaggg gcagtgcaga cttttgaggg    9360
cgtagagctt gggcgcgaga aataccgatt ccggggagta ggcatccgcg ccgcaggccc    9420
cgcagacggt ctcgcattcc acgagccagg tgagctctgg ccgttcgggg tcaaaaacca    9480
ggtttccccc atgcttttttg atgcgtttct tacctctggt ttccatgagc cggtgtccac    9540
gctcggtgac gaaaaggctg tccgtgtccc cgtatacaga ctnnngttta aacgaattcn    9600
nntataaaat gcaaggtgct gctcaaaaaa tcaggcaaag cctcgcgcaa aaagaaagc     9660 acatcgtagt catgctcatg cagataaagg caggtaagct ccggaaccac cacagaaaaa    9720
gacaccattt ttctctcaaa catgtctgcg ggtttctgca taaacacaaa ataaaataac    9780
aaaaaaacat ttaaacatta gaagcctgtc ttacaacagg aaaaacaacc cttataagca    9840
taagacggac tacggccatg ccggcgtgac cgtaaaaaaa ctggtcaccg tgattaaaaa    9900
gcaccaccga cagctcctcg gtcatgtccg gagtcataat gtaagactcg gtaaacacat    9960
caggttgatt catcggtcag tgctaaaaag cgaccgaaat agcccggggg aatacatacc   10020
cgcaggcgta gagacaacat tacagccccc ataggaggta taacaaaatt aataggagag   10080
```

```
aaaaacacat aaacacctga aaaaccctcc tgcctaggca aaatagcacc ctcccgctcc   10140
agaacaacat acagcgcttc acagcggcag cctaacagtc agccttacca gtaaaaaaga   10200
aaacctatta aaaaaacacc actcgacacg gcaccagctc aatcagtcac agtgtaaaaa   10260
agggccaagt gcagagcgag tatatatagg actaaaaaat gacgtaacgg ttaaagtcca   10320
caaaaaacac ccagaaaacc gcacgcgaac ctacgcccag aaacgaaagc caaaaaaccc   10380
acaacttcct caaatcgtca cttccgtttt cccacgttac gtaacttccc attttaagaa   10440
aactacaatt cccaacacat acaagttact ccgccctaaa acctacgtca cccgccccgt   10500
tcccacgccc cgcgccacgt cacaaactcc accccctcat tatcatattg gcttcaatcc   10560
aaaataaggt atattattga tgattaatta attaaggatc ccggtgtgaa ataccgcaca   10620
gatgcgtaag gagaaaatac cgcatcaggc gctcttacgc ttcctcgctc actgactcgc   10680
tgcgctcggt cgttcggctg cggcgagcgg tatcagctca ctcaaaggcg gtaatacggt   10740
tatccacaga atcaggggat aacgcaggaa agaacatgtg agcaaaaggc cagcaaaagg   10800
ccaggaaccg taaaaaggcc gcgttgctgg cgtttttcca taggctccgc cccctgacg   10860 agcatcacaa aaatcgacgc tcaagtcaga ggtggcgaaa cccgacagga ctataaagat   10920
accaggcgtt tcccctgga agctcctcg tgcgctctcc tgttccgacc ctgccgctta   10980
ccggatacct gtccgccttt ctcccttcgg gaagcgtggc gctttctcat agctcacgct   11040
gtaggtatct cagttcggtg taggtcgttc gctccaagct gggctgtgtg cacgaacccc   11100
ccgttcagcc cgaccgctgc gccttatccg gtaactatcg tcttgagtcc aacccggtaa   11160
gacacgactt atcgccactg gcagcagcca ctggtaacag gattagcaga gcgaggtatg   11220
taggcggtgc tacagagttc ttgaagtggt ggcctaacta cggctacact agaaggacag   11280
tatttggtat ctgcgctctg ctgaagccag ttaccttcgg aaaaagagtt ggtagctctt   11340
gatccggcaa acaaaccacc gctggtagcg gtggtttttt tgtttgcaag cagcagatta   11400
cgcgcagaaa aaaaggatct caagaagatc ctttgatctt ttctacgggg tctgacgctc   11460
agtggaacga aaactcacgt taagggattt tggtcatgag attatcaaaa aggatcttca   11520
cctagatcct tttaaattaa aaatgaagtt ttaaatcaat ctaaagtata tatgagtaaa   11580
cttggtctga cagttaccaa tgcttaatca gtgaggcacc tatctcagcg atctgtctat   11640
ttcgttcatc catagttgcc tgactccccg tcgtgtagat aactacgata cgggagggct   11700
taccatctgg ccccagtgct gcaatgatac cgcgagaccc acgctcaccg gctccagatt   11760
tatcagcaat aaaccagcca gccggaaggg ccgagcgcag aagtggtcct gcaactttat   11820
ccgcctccat ccagtctatt aattgttgcc gggaagctag agtaagtagt tcgccagtta   11880
atagtttgcg caacgttgtt gnnnnnnaaa aaggatcttc acctagatcc ttttcacgta   11940
gaaagccagt ccgcagaaac ggtgctgacc ccggatgaat gtcagctact gggctatctg   12000
dacaagggaa aacgcaagcg caaagagaaa gcaggtagct tgcagtgggc ttacatggcg   12060
atagctagac tgggcggttt tatggacagc aagcgaaccg gaattgccag ctggggcgcc   12120
ctctggtaag gttgggaagc cctgcaaagt aaactggatg gctttctcgc cgccaaggat   12180
ctgatggcgc aggggatcaa gctctgatca agagacagga tgaggatcgt ttcgcatgat   12240
tgaacaagat ggattgcacg caggttctcc ggccgcttgg gtggagaggc tattcggcta   12300
tgactgggca caacagacaa tcggctgctc tgatgccgcc gtgttccggc tgtcagcgca   12360 gggcgcccg gttctttttg tcaagaccga cctgtccggt gccctgaatg aactgcaaga   12420
cgaggcagcg cggctatcgt ggctggccac gacgggcgtt ccttgcgcag ctgtgctcga   12480
```

```
cgttgtcact gaagcgggaa gggactggct gctattgggc gaagtgccgg ggcaggatct   12540
cctgtcatct caccttgctc ctgccgagaa agtatccatc atggctgatg caatgcggcg   12600
gctgcatacg cttgatccgg ctacctgccc attcgaccac caagcgaaac atcgcatcga   12660
gcgagcacgt actcggatgg aagccggtct tgtcgatcag gatgatctgg acgaggagca   12720 tcagggggctc gcgccagccg aactgttcgc caggctcaag gcgagcatgc ccgacggcga   12780
ggatctcgtc gtgacccatg gcgatgcctg cttgccgaat atcatggtgg aaaatggccg   12840
cttttctgga ttcatcgact gtggccggct gggtgtggcg gaccgctatc aggacatagc   12900
gttggctacc cgtgatattg ctgaggagct tggcggcgaa tgggctgacc gcttcctcgt   12960
gctttacggt atcgccgctc ccgattcgca gcgcatcgcc ttctatcgcc ttcttgacga   13020
gttcttctga attttgttaa aattttttgtt aaatcagctc attttttaac caataggccg   13080
aaatcggcaa catcccttat aaatcaaaag aatagaccgc gatagggttg agtgttgttc   13140
cagtttggaa caagagtcca ctattaaaga acgtggactc caacgtcaaa gggcgaaaaa   13200
ccgtctatca gggcgatggc ccactacgtg aaccatcacc caaatcaagt tttttgcggt   13260
cgaggtgccg taaagctcta aatcggaacc ctaaagggag cccccgattt agagcttgac   13320
ggggaaagcc ggcgaacgtg gcgagaaagg aagggaagaa agcgaaagga gcgggcgcta   13380
gggcgctggc aagtgtagcg gtcacgctgc gcgtaaccac cacacccgcg cgcttaatgc   13440
gccg                                                                13444
```

```
<210> SEQ ID NO 6
<211> LENGTH: 11777
<212> TYPE: DNA
<213> ORGANISM: Artificial Sequence
<220> FEATURE:
<223> OTHER INFORMATION: pGW063

<400> SEQUENCE: 6
aattaattaa gctagcatca tcaataatat accttatttt ggattgaagc caatatgata     60
atgagggggt ggagtttgtg acgtggcgcg gggcgtggga acggggcggg tgacgtagta    120
gtgtggcgga agtgtgatgt tgcaagtgtg gcggaacaca tgtaagcgac ggatgtggca    180
aaagtgacgt ttttggtgtg cgccggtgta cacaggaagt gacaattttc gcgcggtttt    240
aggcggatgt tgtagtaaat ttgggcgtaa ccgagtaaga tttggccatt ttcgcgggaa    300
aactgaataa gaggaagtga aatctgaata attttgtgtt actcatagcg cgtaatattt    360 gtctaggggag atccggtacc gcggccgcct cgagtctaga aagagggcct atttcccatg    420
attccttcat atttgcatat acgatacaag gctgttagag agataattag aattaatttg    480
actgtaaaca caaagatatt agtacaaaat acgtgacgta gaaagtaata atttcttggg    540
tagtttgcag ttttaaaatt atgttttaaa atggactatc atatgcttac cgtaacttga    600
aagtatttcg atttcttggc tttatatatc ttgtggaaag gacgaaacac cggaagagcg    660
agctcttctg ttttagagct aggccaacat gaggatcacc catgtctgca gggcctagca    720
agttaaaata aggctagtcc gttatcaact tggccaacat gaggatcacc catgtctgca    780
gggccaagtg gcaccgagtc ggtgcttttt tgctagcgtc agtgggcaga gcgcacatcg    840
cccacagtcc ccgagaagtt ggggggaggg gtcggcaatt gaacgggtgc ctagagaagg    900
tggcgcgggg taaactggga aagtgatgtc gtgtactggc tccgcctttt tcccgagggt    960
gggggagaac cgtatataag tgcagtagtc gccgtgaacg ttcttttttcg caacgggttt   1020
```

-continued

```
gccgccagaa cacagctgaa gcttcgaggg gctcgcatct ctccttcacg cgcccgccgc   1080
cctacctgag gccgccatcc acgccggttg agtcgcgttc tgccgcctcc cgcctgtggt   1140
gcctcctgaa ctgcgtccgc cgtctaggta agtttaaagc tcaggtcgag accgggcctt   1200
tgtccggcgc tcccttggag cctacctaga ctcagccggc tctccacgct ttgcctgacc   1260
ctgcttgctc aactctacgt ctttgtttcg ttttctgttc tgcgccgtta cagatccaag   1320
ctcgtacggc caccatgaaa aggccggcgg ccacgaaaaa ggccggccag gcaaaaaaga   1380
aaaaggacaa gaagtacagc atcggcctgg ccatcggcac caactctgtg ggctgggccg   1440
tgatcaccga cgagtacaag gtgcccagca agaaattcaa ggtgctgggc aacaccgacc   1500
ggcacagcat caagaagaac ctgatcggag ccctgctgtt cgacagcggc gaaacagccg   1560
aggccacccg gctgaagaga accgccagaa gaagatacac cagacggaag aaccggatct   1620
gctatctgca agagatcttc agcaacgaga tggccaaggt ggacgacagc ttcttccaca   1680
gactggaaga gtccttcctg gtggaagagg ataagaagca cgagcggcac cccatcttcg   1740
gcaacatcgt ggacgaggtg gcctaccacg agaagtaccc caccatctac cacctgagaa   1800
agaaactggt ggacagcacc gacaaggccg acctgcggct gatctatctg gccctggccc   1860
acatgatcaa gttccggggc cacttcctga tcgagggcga cctgaacccc gacaacagcg   1920
acgtggacaa gctgttcatc cagctggtgc agacctacaa ccagctgttc gaggaaaacc   1980
ccatcaacgc cagcggcgtg gacgccaagg ccatcctgtc tgccagactg agcaagagca   2040
gacggctgga aaatctgatc gcccagctgc ccggcgagaa gaagaatggc ctgttcggca   2100
acctgattgc cctgagcctg ggcctgaccc ccaacttcaa gagcaacttc gacctggccg   2160
aggatgccaa actgcagctg agcaaggaca cctacgacga cgacctggac aacctgctgg   2220
cccagatcgg cgaccagtac gccgacctgt ttctggccgc caagaacctg tccgacgcca   2280
tcctgctgag cgacatcctg agagtgaaca ccgagatcac caaggccccc ctgagcgcct   2340
ctatgatcaa gagatacgac gagcaccacc aggacctgac cctgctgaaa gctctcgtgc   2400
ggcagcagct gcctgagaag tacaaagaga ttttcttcga ccagagcaag aacggctacg   2460
ccggctacat tgacggcgga gccagccagg aagagttcta caagttcatc aagcccatcc   2520
tggaaaagat ggacggcacc gaggaactgc tcgtgaagct gaacagagag gacctgctgc   2580
ggaagcagcg gaccttcgac aacggcagca tcccccacca gatccacctg ggagagctgc   2640
acgccattct gcggcggcag gaagattttt acccattcct gaaggacaac cgggaaaaga   2700
tcgagaagat cctgaccttc cgcatcccct actacgtggg ccctctggcc aggggaaaca   2760
gcagattcgc ctggatgacc agaaagagcg aggaaaccat cacccctgg aacttcgagg   2820 aagtggtgga caagggcgct tccgcccaga gcttcatcga gcggatgacc aacttcgata   2880
agaacctgcc caacgagaag gtgctgccca gcacagcct gctgtacgag tacttcaccg   2940
tgtataacga gctgaccaaa gtgaaatacg tgaccgaggg aatgagaaag cccgccttcc   3000
tgagcggcga gcagaaaaag gccatcgtgg acctgctgtt caagaccaac cggaaagtga   3060
ccgtgaagca gctgaaagag gactacttca gaaaatcga gtgcttcgac tccgtggaaa   3120
tctccggcgt ggaagatcgg ttcaacgcct ccctgggcac ataccacgat ctgctgaaaa   3180
ttatcaagga caaggacttc ctggacaatg aggaaaacga ggacattctg gaagatatcg   3240
tgctgaccct gacactgttt gaggacagag agatgatcga ggaacggctg aaaacctatg   3300
cccacctgtt cgacgacaaa gtgatgaagc agctgaagcg gcggagatac accggctggg   3360
gcaggctgag ccggaagctg atcaacggca tccgggacaa gcagtccggc aagacaatcc   3420
```

-continued

```
tggatttcct gaagtccgac ggcttcgcca acagaaactt catgcagctg atccacgacg   3480
acagcctgac ctttaaagag gacatccaga aagcccaggt gtccggccag ggcgatagcc   3540
tgcacgagca cattgccaat ctggccggca gccccgccat taagaagggc atcctgcaga   3600
cagtgaaggt ggtggacgag ctcgtgaaag tgatgggccg gcacaagccc gagaacatcg   3660
tgatcgaaat ggccagagag aaccagacca cccagaaggg acagaagaac agccgcgaga   3720
gaatgaagcg gatcgaagag ggcatcaaag agctgggcag ccagatcctg aaagaacacc   3780
ccgtggaaaa cacccagctg cagaacgaga agctgtacct gtactacctg cagaatgggc   3840
gggatatgta cgtggaccag gaactggaca tcaaccggct gtccgactac gatgtggacc   3900
acatcgtgcc tcagagcttt ctgaaggacg actccatcga caacaaggtg ctgaccagaa   3960
gcgacaaggc ccggggcaag agcgacaacg tgccctccga agaggtcgtg aagaagatga   4020
agaactactg gcggcagctg ctgaacgcca agctgattac ccagagaaag ttcgacaatc   4080
tgaccaaggc cgagagaggc ggcctgagcg aactggataa ggccggcttc atcaagagac   4140
agctggtgga aacccggcag atcacaaagc acgtggcaca gatcctggac tcccggatga   4200
acactaagta cgacgagaat gacaagctga tccgggaagt gaaagtgatc accctgaagt   4260
ccaagctggt gtccgatttc cggaaggatt tccagttta caaagtcgcc gagatcaaca   4320
actaccacca cgcccacgac gcctacctga acgccgtcgt gggaaccgcc ctgatcaaaa   4380
agtaccctaa gctggaaagc gagttcgtgt acggcgacta caaggtgtac gacgtgcgga   4440
agatgatcgc caagagcgag caggaaatcg gcaaggctac cgccaagtac ttcttctaca   4500
gcaacatcat gaactttttc aagaccgaga ttaccctggc caacggcgag atccggaagc   4560
ggcctctgat cgagacaaac ggcgaaaccg gggagatcgt gtgggataag ggccgggatt   4620
ttgccaccgt gcggaaagtg ctgagcatgc cccaagtgaa tatcgtgaaa aagaccgagg   4680
tgcagacagg cggcttcagc aaagagtcta tcctgcccaa gaggaacagc gataagctga   4740
tcgccagaaa gaaggactgg gaccctaaga gtacggcgg cttcgacagc cccaccgtgg   4800
cctattctgt gctggtggtg gccaaagtgg aaaagggcaa gtccaagaaa ctgaagagtg   4860
tgaaagagct gctgggggatc accatcatgg aaagaagcag cttcgagaag aatcccatcg   4920
actttctgga agccaagggc tacaaagaag tgaaaaagga cctgatcatc aagctgccta   4980
agtactccct gttcgagctg gaaaacggcc ggaagagaat gctggcctct gccggcgaac   5040
tgcagaaggg aaacgaactg gccctgccct ccaaatatgt gaacttcctg tacctggcca   5100
gccactatga gaagctgaag ggctcccccg aggataatga gcagaaacag ctgtttgtgg   5160
aacagcacaa gcactacctg gacgagatca tcgagcagat cagcgagttc tccaagagag   5220
tgatcctggc cgacgctaat ctggacaaag tgctgtccgc ctacaacaag caccggggata   5280 agcccatcag agagcaggcc gagaatatca tccacctgtt taccctgacc aatctgggag   5340
cccctgccgc cttcaagtac tttgacacca ccatcgaccg gaagaggtac accagcacca   5400
aagaggtgct ggacgccacc ctgatccacc agagcatcac cggcctgtac gagacacgga   5460
tcgacctgtc tcagctggga ggcgacagcg ctggaggagg tggaagcgga ggaggaggaa   5520
gcggaggagg aggtagcgga cctaagaaaa agaggaaggt ggcggccgct ggatcccctt   5580
cagggcagat cagcaaccag gccctggctc tggcccctag ctccgctcca gtgctggccc   5640
agactatggt gcccctctagt gctatggtgc ctctggccca gccacctgct ccagcccctg   5700
tgctgacccc aggaccaccc cagtcactga gcgctccagt gcccaagtct acacaggccg   5760
```

-continued

```
gcgaggggac tctgagtgaa gctctgctgc acctgcagtt cgacgctgat gaggacctgg      5820
gagctctgct ggggaacagc accgatcccg gagtgttcac agatctggcc tccgtggaca      5880
actctgagtt tcagcagctg ctgaatcagg gcgtgtccat gtctcatagt acagccgaac      5940
caatgctgat ggagtacccc gaagccatta cccggctggt gaccggcagc cagcggcccc      6000
ccgaccccgc tccaactccc ctgggaacca gcggcctgcc taatgggctg tccggagatg      6060
aagacttctc aagcatcgct gatatggact ttagtgccct gctgtcacag atttcctcta      6120
gtgggcaggg aggaggtgga agcggcttca gcgtggacac cagtgccctg ctggacctgt      6180
tcagcccctc ggtgaccgtg cccgacatga gcctgcctga ccttgacagc agcctggcca      6240
gtatccaaga gctcctgtct ccccaggagc cccccaggcc tcccgaggca gagaacagca      6300
gcccggattc agggaagcag ctggtgcact acacagcgca gccgctgttc ctgctggacc      6360
ccggctccgt ggacaccggg agcaacgacc tgccggtgct gtttgagctg ggagagggct      6420
cctacttctc cgaaggggac ggcttcgccg aggaccccac catctccctg ctgacaggct      6480
cggagcctcc caaagccaag gacccccactg tctcctaaga attcctgcag cccggggggat      6540 ccactagttc tagagcggcc gccaccgcgg ggagatccag acatgataag atacattgat      6600
gagtttggac aaaccacaac tagaatgcag tgaaaaaaat gctttatttg tgaaatttgt      6660
gatgctattg ctttatttgt aaccattata agctgcaata aacaagttaa caacaacaat      6720
tgcattcatt ttatgtttca ggttcagggg gaggtgtggg aggttttta aagcaagtaa      6780 aacctctaca aatgtggtat ggctgattat gatcccggct gcctcgcgcg tttcggtgat      6840
gacggtgaaa acctcttgac acatgcagct cccggagacg gtcacagctt gtctgtaagc      6900
ggatgccggg agcagacaag cccgtcaggg cgcgtcagcg ggtgttggcg ggtgtcgggg      6960
cgcagccatg aggtcgactc tagtccccgc ggtggcagat ctggaaggtg ctgaggtacg      7020
atgagacccg caccaggtgc agaccctgcg agtgtggcgg taaacatatt aggaaccagc      7080
ctgtgatgct ggatgtgacc gaggagctga ggcccgatca cttggtgctg gcctgcaccc      7140
gcgctgagtt tggctctagc gatgaagata cagattgagg tactgaaatg tgtgggcgtg      7200
gcttaagggg gggaaagaat atataaggt ggggtcttat gtagttttgt atctgttttg      7260
cagcagccgc cgccgccatg agcaccaact cgtttgatgg aagcattgtg agctcatatt      7320
tgacaacgcg catgccccca tgggccgggg tgcgtcagaa tgtgatgggc tccagcattg      7380
atggtcgccc cgtcctgccc gcaaactcta ctaccttgac ctacgagacc gtgtctggaa      7440
cgccgttgga gactgcagcc tccgccgccg cttcagccgc tgcagccacc gcccgcggga      7500
ttgtgactga ctttgctttc ctgagcccgc ttgcaagcag tgcagcttcc cgttcatccg      7560
cccgcgatga caagttgacg gctctttttgg cacaattgga ttctttgacc cgggaactta      7620
atgtcgtttc tcagcagctg ttggatctgc gccagcaggt ttctgccctg aaggcttcct      7680
cccctcccaa tgcggtttaa aacataaata aaaaaccaga ctctgtttgg atttggatca      7740
agcaagtgtc ttgctgtctt tatttagggg ttttgcgcgc gcggtaggcc cgggaccagc      7800
ggtctcggtc gttgagggtc ctgtgtattt tttccaggac gtggtaaagg tgactctgga      7860
tgttcagata catgggcata gcccgtctc tggggtggag gtagcaccac tgcagagctt      7920
catgctgcgg ggtggtgttg tagatgatcc agtcgtagca ggagcgctgg gcgtggtgcc      7980
taaaaatgtc tttcagtagc aagctgattg ccaggggcag gcccttggtg taagtgttta      8040
caaagcggtt aagctgggat gggtgcatac gtggggatat gagatgcatc ttggactgta      8100 ttttttaggtt ggctatgttc ccagccatat ccctccgggg attcatgttg tgcagaacca      8160
```

-continued

```
ccagcacagt gtatccggtg cacttgggaa atttgtcatg tagcttagaa ggaaatgcgt    8220
ggaagaactt ggagacgccc ttgtgacctc caagattttc catgcattcg tccataatga    8280
tggcaatggg cccacgggcg gcggcctggg cgaagatatt tctgggatca ctaacgtcat    8340
agttgtgttc caggatgaga tcgtcatagg ccatttttac aaagcgcggg cggagggtgc    8400
cagactgcgg tataatggtt ccatccggcc caggggcgta gttaccctca cagatttgca    8460
tttcccacgc tttgagttca gatgggggga tcatgtctac ctgcggggcg atgaagaaaa    8520
cggtttccgg ggtaggggag atcagctggg aagaaagcag gttcctgagc agctgcgact    8580
taccgcagcc ggtgggcccg taaatcacac ctattaccgg gtgcaactgg tagttaagag    8640
agctgcagct gccgtcatcc ctgagcaggg gggccacttc gttaagcatg tccctgactc    8700
gcatgttttc cctgaccaaa tccgccagaa ggcgctcgcc gcccagcgat agcagttctt    8760
gcaaggaagc aaagtttttc aacggtttga daccgtccgc cgtaggcatg cttttgagcg    8820
tttgaccaag cagttccagg cggtcccaca gctcggtcac ctgctctacg gcatctcgat    8880
ccagcatatc tcctcgtttc gcgggttggg gcggctttcg ctgtacggca gtagtcggtg    8940
ctcgtccaga cgggccaggg tcatgtcttt ccacgggcgc agggtcctcg tcagcgtagt    9000
ctgggtcacg gtgaagggt gcgctccggg ctgcgcgctg gccagggtgc gcttgaggct    9060
ggtcctgctg gtgctgaagc gctgccggtc ttcgccctgc gcgtcggcca ggtagcattt    9120
gaccatggtg tcatagtcca gcccctccgc ggcgtggccc ttggcgcgca gcttgccctt    9180
ggaggaggcg ccgcacgagg ggcagtgcag acttttgagg gcgtagagct tgggcgcgag    9240
aaataccgat tccggggagt aggcatccgc gccgcaggcc ccgcagacgg tctcgcattc    9300
cacgagccag gtgagctctg gccgttcggg gtcaaaaacc aggtttcccc catgcttttt    9360
gatgcgtttc ttacctctgg tttccatgag ccggtgtcca cgctcggtga cgaaaaggct    9420
gtccgtgtcc ccgtatacag acttgagagg cctgtcctcg accgatgccc ttgagagcct    9480
tcaacccagt cagctccttc cggtgggcgc ggggcatgac tatcgtcgcc gcacttatga    9540
ctgtcttctt tatcatgcaa ctcgtaggac aggtgccggc agcgctctgg gtcattttcg    9600
gcgaggaccg ctttcgctgg agcgcgacga tgatcggcct gtcgcttgcg gtattcggaa    9660
tcttgcacgc cctcgctcaa gccttcgtca ctggtcccgc caccaaacgt ttcggcgaga    9720
agcaggccat tatcgccggc atggcggccg acgcgctggg ctacgtcttg ctggcgttcg    9780
cgacgcgagg ctggatggcc ttccccatta tgattcttct cgcttccggc ggcatcggga    9840
tgcccgcgtt gcaggccatg ctgtccaggc aggtagatga cgaccatcag ggacagcttc    9900
aaggccagca aaaggccagg aaccgtaaaa aggccgcgtt gctggcgttt ttccataggc    9960
tccgcccccc tgacgagcat cacaaaaatc gacgctcaag tcagaggtgg cgaaacccga   10020
caggactata aagataccag gcgtttcccc ctggaagctc cctcgtgcgc tctcctgttc   10080
cgaccctgcc gcttaccgga tacctgtccg cctttctccc ttcgggaagc gtggcgcttt   10140
ctcatagctc acgctgtagg tatctcagtt cggtgtaggt cgttcgctcc aagctgggct   10200
gtgtgcacga accccccgtt cagcccgacc gctgcgcctt atccggtaac tatcgtcttg   10260
agtccaaccc ggtaagacac gacttatcgc cactggcagc agccactggt aacaggatta   10320
gcagagcgag gtatgtaggc ggtgctacag agttcttgaa gtggtggcct aactacggct   10380
acactagaag gacagtattt ggtatctgcg ctctgctgaa gccagttacc ttcggaaaaa   10440
gagttggtag ctcttgatcc ggcaaacaaa ccaccgctgg tagcggtggt ttttttgttt   10500
```

-continued

```
gcaagcagca gattacgcgc agaaaaaaag gatctcaaga agatcctttg atctttttcta  10560 cggggtctga cgctcagtgg aacgaaaact cacgttaagg gattttggtc atgagattat  10620
caaaaaggat cttcacctag atcctttttaa attaaaaatg aagtttttaaa tcaatctaaa  10680 gtatatatga gtaaacttgg tctgacagtt accaatgctt aatcagtgag gcacctatct  10740
cagcgatctg tctatttcgt tcatccatag ttgcctgact ccccgtcgtg tagataacta  10800
cgatacggga gggcttacca tctggcccca gtgctgcaat gataccgcga gacccacgct  10860
caccggctcc agatttatca gcaataaacc agccagccgg aagggccgag cgcagaagtg  10920
gtcctgcaac tttatccgcc tccatccagt ctattaattg ttgccgggaa gctagagtaa  10980
gtagttcgcc agttaatagt ttgcgcaacg ttgttgccat tgctgcaggc atcgtggtgt  11040
cacgctcgtc gtttggtatg gcttcattca gctccggttc ccaacgatca aggcgagtta  11100
catgatcccc catgttgtgc aaaaaagcgg ttagctcctt cggtcctccg atcgttgtca  11160
gaagtaagtt ggccgcagtg ttatcactca tggttatggc agcactgcat aattctctta  11220
ctgtcatgcc atccgtaaga tgcttttctg tgactggtga gtactcaacc aagtcattct  11280
gagaatagtg tatgcggcga ccgagttgct cttgcccggc gtcaacacgg gataataccg  11340
cgccacatag cagaactttaa aaagtgctca tcattggaaa acgttcttcg gggcgaaaac  11400
tctcaaggat cttaccgctg ttgagatcca gttcgatgta acccactcgt gcacccaact  11460
gatcttcagc atcttttact ttcaccagcg tttctgggtg agcaaaaaca ggaaggcaaa  11520
atgccgcaaa aaagggaata aagggcgacac ggaaatgttg aatactcata ctcttccttt  11580
ttcaatatta ttgaagcatt tatcagggtt attgtctcat gagcggatac atatttgaat  11640
gtatttagaa aaataaacaa ataggggttc cgcgcacatt tccccgaaaa gtgccacctg  11700
acgtctaaga aaccattatt atcatgacat taacctataa aaataggcgt atcacgaggc  11760
cctttcgtct tcaagaa                                                  11777
```

<210> SEQ ID NO 7
<211> LENGTH: 33477
<212> TYPE: DNA
<213> ORGANISM: Artificial Sequence
<220> FEATURE:
<223> OTHER INFORMATION: pAdEasy-1

<400> SEQUENCE: 7

```
attgtgagct catatttgac aacgcgcatg ccccccatggg ccggggtgcg tcagaatgtg    60
atgggctcca gcattgatgg tcgccccgtc ctgcccgcaa actctactac cttgacctac   120
gagaccgtgt ctggaacgcc gttggagact gcagcctccg ccgccgcttc agccgctgca   180
gccaccgccc gcgggattgt gactgacttt gctttcctga gcccgcttgc aagcagtgca   240
gcttcccgtt catccgcccg cgatgacaag ttgacggctc ttttggcaca attggattct   300
ttgacccggg aacttaatgt cgtttctcag cagctgttgg atctgcgcca gcaggtttct   360
gccctgaagg cttcctcccc tcccaatgcg gtttaaaaca taaataaaaa accagactct   420
gtttggattt ggatcaagca agtgtcttgc tgtctttatt taggggtttt gcgcgcgcgg   480
taggcccggg accagcggtc tcggtcgttg agggtcctgt gtattttttc caggacgtgg   540
taaaggtgac tctggatgtt cagatacatg ggcataagcc cgtctctggg gtggaggtag   600
caccactgca gagcttcatg ctgcggggtg tgttgtaga tgatccagtc gtagcaggag   660
cgctgggcgt ggtgcctaaa aatgtctttc agtagcaagc tgattgccag gggcaggccc   720
ttggtgtaag tgtttacaaa gcggttaagc tgggatgggt gcatacgtgg ggatatgaga   780
```

-continued

```
tgcatcttgg actgtatttt taggttggct atgttcccag ccatatccct ccggggattc      840
atgttgtgca gaaccaccag cacagtgtat ccggtgcact tgggaaattt gtcatgtagc      900
ttagaaggaa atgcgtggaa gaacttggag acgcccttgt gacctccaag attttccatg      960
cattcgtcca taatgatggc aatgggccca cgggcggcgg cctgggcgaa gatatttctg     1020
ggatcactaa cgtcatagtt gtgttccagg atgagatcgt cataggccat ttttacaaag     1080
cgcgggcgga gggtgccaga ctgcggtata atggttccat ccggcccagg ggcgtagtta     1140
ccctcacaga tttgcatttc ccacgctttg agttcagatg gggggatcat gtctacctgc     1200
ggggcgatga agaaaacggt ttccgggcgta ggggagatca gctgggaaga aagcaggttc     1260
ctgagcagct gcgacttacc gcagccggtg ggcccgtaaa tcacacctat taccggctgc     1320
aactggtagt taagagagct gcagctgccg tcatccctga gcaggggggc cacttcgtta     1380
agcatgtccc tgactcgcat gttttccctg accaaatccg ccagaaggcg ctcgccgccc     1440
agcgatagca gttcttgcaa ggaagcaaag tttttcaacg gtttgagacc gtccgccgta     1500
ggcatgcttt tgagcgtttg accaagcagt tccaggcggt cccacagctc ggtcacctgc     1560
tctacggcat ctcgatccag catatctcct cgtttcgcgg gttggggcgg ctttcgctgt     1620
acggcagtag tcggtgctcg tccagacggg ccagggtcat gtctttccac gggcgcaggg     1680
tcctcgtcag cgtagtctgg gtcacggtga aggggtgcgc tccgggctgc gcgctggcca     1740
gggtgcgctt gaggctggtc ctgctggtgc tgaagcgctg ccggtcttcg ccctgcgcgt     1800
cggccaggta gcatttgacc atggtgtcat agtccagccc ctccgcggcg tggcccttgg     1860
cgcgcagctt gcccttggag gaggcgccgc acgaggggca gtgcagactt ttgagggcgt     1920
agagcttggg cgcgagaaat accgattccg gggagtaggc atccgcgccg caggccccgc     1980
agacggtctc gcattccacg agccaggtga gctctggccg ttcggggtca aaaaccaggt     2040
ttcccccatg ctttttgatg cgtttcttac ctctggtttc catgagccgg tgtccacgct     2100
cggtgacgaa aaggctgtcc gtgtcccccgt atacagactt gagaggcctg tcctcgagcg     2160
gtgttccgcg gtcctcctcg tatagaaact cggaccactc tgagacaaag gctcgcgtcc     2220
aggccagcac gaaggaggct aagtgggagg ggtagcggtc gttgtccact aggggtccaa     2280
ctcgctccag ggtgtgaaga cacatgtcgc cctcttcggc atcaaggaag gtgattggtt     2340
tgtaggtgta ggcacgtgaa ccgggtgttc ctgaaggggg gctataaaag ggggtggggg     2400
cgcgttcgtc ctcactctct tccgcatcgc tgtctgcgag ggccagctgt tggggtgagt     2460
actccctctg aaaagcgggc atgacttctg cgctaagatt gtcagtttcc aaaaacgagg     2520
aggatttgat attcacctgg cccgcggtga tgcctttgag ggtggccgca tccatctggt     2580
cagaaaagac aatctttttg ttgtcaagct tggtggcaaa cgacccgtag agggcgttgg     2640
acagcaactt ggcgatggag cgcagggttt ggttttttgtc gcgatcggcg cgctccttgg     2700
ccgcgatgtt tagctgcacg tattcgcgcg caacgcaccg ccattcggga aagacggtgg     2760
tgcgctcgtc gggcaccagg tgcacgcgcc aaccgcggtt gtgcagggtg acaaggtcaa     2820
cgctggtggc tacctctccg cgtaggcgct cgttggtcca gcagaggcgg ccgcccttgc     2880
gcgagcagaa tggcggtagg gggtctagct gcgtctcgtc cggggggtct gcgtccacgg     2940
taaagacccc gggcagcagg cgcgcgtcga agtagtctat cttgcatcct tgcaagtcta     3000
gcgcctgctg ccatgcgcgg gcggcaagcg cgcgctcgta tgggttgagt gggggacccc     3060
atggcatggg gtgggtgagc gcggaggcgt acatgccgca aatgtcgtaa acgtagaggg     3120
```

-continued

```
gctctctgag tattccaaga tatgtagggt agcatcttcc accgcggatg ctggcgcgca    3180
cgtaatcgta tagttcgtgc gagggagcga ggaggtcggg accgaggttg ctacgggcgg    3240
gctgctctgc tcggaagact atctgcctga agatggcatg tgagttggat gatatggttg    3300
gacgctggaa gacgttgaag ctggcgtctg tgagacctac cgcgtcacgc acgaaggagg    3360
cgtaggagtc gcgcagcttg ttgaccagct cggcggtgac ctgcacgtct agggcgcagt    3420
agtccagggt ttccttgatg atgtcatact tatcctgtcc ctttttttttc cacagctcgc    3480 ggttgaggac aaactcttcg cggtctttcc agtactcttg gatcggaaac ccgtcggcct    3540
ccgaacggta agagcctagc atgtagaact ggttgacggc ctggtaggcg cagcatccct    3600
tttctacggg tagcgcgtat gcctgcgcgg ccttccggag cgaggtgtgg gtgagcgcaa    3660
aggtgtccct gaccatgact ttgaggtact ggtatttgaa gtcagtgtcg tcgcatccgc    3720
cctgctccca gagcaaaaag tccgtgcgct ttttggaacg cggatttggc agggcgaagg    3780
tgacatcgtt gaagagtatc tttcccgcgc gaggcataaa gttgcgtgtg atgcggaagg    3840
gtcccggcac ctcggaacgg ttgttaatta cctgggcggc gagcacgatc tcgtcaaagc    3900
cgttgatgtt gtggcccaca atgtaaagtt ccaagaagcg cgggatgccc ttgatggaag    3960
gcaatttttt aagttcctcg taggtgagct cttcagggga gctgagcccg tgctctgaaa    4020
gggcccagtc tgcaagatga gggttggaag cgacgaatga gctccacagg tcacgggcca    4080
ttagcatttg caggtggtcg cgaaaggtcc taaactggcg acctatggcc attttttctg    4140
gggtgatgca gtagaaggta agcgggtctt gttcccagcg gtcccatcca aggttcgcgg    4200
ctaggtctcg cgcggcagtc actagaggct catctccgcc gaacttcatg accagcatga    4260
agggcacgag ctgcttccca aaggccccca tccaagtata ggtctctaca tcgtaggtga    4320
caaagagacg ctcggtgcga ggatgcgagc cgatcgggaa gaactggatc tcccgccacc    4380
aattggagga gtggctattg atgtggtgaa agtagaagtc cctgcgacgg gccgaacact    4440
cgtgctggct tttgtaaaaa cgtgcgcagt actggcagcg gtgcacgggc tgtacatcct    4500
gcacgaggtt gacctgacga ccgcgcacaa ggaagcagag tgggaatttg agcccctcgc    4560
ctggcgggtt tggctggtgg tcttctactt cggctgcttg tccttgaccg tctggctgct    4620
cgaggggagt tacggtggat cggaccacca cgccgcgcga gcccaaagtc cagatgtccg    4680
cgcgcggcgg tcggagcttg atgacaacat cgcgcagatg ggagctgtcc atggtctgga    4740
gctcccgcgg cgtcaggtca ggcgggagct cctgcaggtt tacctcgcat agacgggtca    4800
gggcgcgggc tagatccagg tgatacctaa tttccagggg ctggttggtg gcggcgtcga    4860
tggcttgcaa gaggccgcat ccccgcggcg cgactacggt accgcgcggc gggcggtggg    4920
ccgcgggggt gtccttggat gatgcatcta aaagcggtga cgcgggcgag ccccgggagg    4980
tagggggggc tccggacccg ccgggagagg gggcagggc acgtcggcgc cgcgcgcggg    5040
caggagctgg tgctgcgcgc gtaggttgct ggcgaacgcg acgacgcggc ggttgatctc    5100
ctgaatctgg cgcctctgcg tgaagacgac gggcccggtg agcttgaacc tgaaagagag    5160
ttcgacagaa tcaatttcgg tgtcgttgac ggcggcctgg cgcaaaatct cctgcacgtc    5220
tcctgagttg tcttgatagg cgatctcggc catgaactgc tcgatctctt cctcctggag    5280
atctccgcgt ccggctcgct ccacggtggc ggcgaggtcg ttggaaatgc gggccatgag    5340
ctgcgagaag gcgttgaggc ctccctcgtt ccagacgcgg ctgtagacca cgccccttc     5400 ggcatcgcgg gcgcgcatga ccacctgcgc gagattgagc tccacgtgcc gggcgaagac    5460
ggcgtagttt cgcaggcgct gaaagaggta gttgagggtg gtggcggtgt gttctgccac    5520
```

-continued

```
gaagaagtac ataacccagc gtcgcaacgt ggattcgttg atatcccccca aggcctcaag    5580 gcgctccatg gcctcgtaga agtccacggc gaagttgaaa aactgggagt tgcgcgccga    5640
cacggttaac tcctcctcca gaagacggat gagctcggcg acagtgtcgc gcacctcgcg    5700
ctcaaaggct acaggggcct cttcttcttc ttcaatctcc tcttccataa gggcctcccc    5760
ttcttcttct tctggcggcg gtggggagg ggggacacgg cggcgacgac ggcgcaccgg     5820
gaggcggtcg acaaagcgct cgatcatctc cccgcggcga cggcgcatgg tctcggtgac    5880
ggcgcggccg ttctcgcggg ggcgcagttg gaagacgccg cccgtcatgt cccggttatg    5940
ggttggcggg gggctgccat gcggcaggga tacggcgcta acgatgcatc tcaacaattg    6000
ttgtgtaggt actccgccgc cgagggacct gagcgagtcc gcatcgaccg gatcggaaaa    6060
cctctcgaga aaggcgtcta accagtcaca gtcgcaaggt aggctgagca ccgtggcggg    6120
cggcagcggg cggcggtcgg ggttgtttct ggcggaggtg ctgctgatga tgtaattaaa    6180
gtaggcggtc ttgagacggc ggatggtcga cagaagcacc atgtccttgg gtccggcctg    6240
ctgaatgcgc aggcggtcgg ccatgcccca ggcttcgttt tgacatcggc gcaggtcttt    6300
gtagtagtct tgcatgagcc tttctaccgg cacttcttct tctccttcct cttgtcctgc    6360
atctcttgca tctatcgctg cggcggcggc ggagtttggc cgtaggtggc gccctcttcc    6420
tcccatgcgt gtgaccccga agccctcat cggctgaagc agggctaggt cggcgacaac    6480
gcgctcggct aatatggcct gctgcacctg cgtgagggta gactggaagt catccatgtc    6540
cacaaagcgg tggtatgcgc ccgtgttgat ggtgtaagtg cagttggcca taacggacca    6600
gttaacggtc tggtgacccg gctgcgagag ctcggtgtac ctgagacgcg agtaagccct    6660
cgagtcaaat acgtagtcgt tgcaagtccg caccaggtac tggtatccca ccaaaaagtg    6720
cggcggcggc tggcggtaga ggggccagcg tagggtggcc ggggctccgg gggcgagatc    6780
ttccaacata aggcgatgat atccgtagat gtacctggac atccaggtga tgccggcggc    6840
ggtggtggag gcgcgcggaa agtcgcggac gcggttccag atgttgcgca gcggcaaaaa    6900
gtgctccatg gtcgggacgc tctggccggt caggcgcgcg caatcgttga cgctctagcg    6960
tgcaaaagga gagcctgtaa gcgggcactc ttccgtggtc tggtggataa attcgcaagg    7020
gtatcatggc ggacgaccgg ggttcgagcc ccgtatccgg ccgtccgccg tgatccatgc    7080
ggttaccgcc cgcgtgtcga acccaggtgt gcgacgtcag acaacggggg agtgctcctt    7140
ttggcttcct tccaggcgcg gcggctgctg cgctagcttt tttggccact ggccgcgcgc    7200
agcgtaagcg gttaggctgg aaagcgaaag cattaagtgg ctcgctccct gtagccggag    7260
ggttattttc caagggttga gtcgcgggac ccccggttcg agtctcggac cggccggact    7320
gcggcgaacg ggggtttgcc tccccgtcat gcaagacccc gcttgcaaat tcctccggaa    7380
acagggacga gcccctttt tgcttttccc agatgcatcc ggtgctgcgg cagatgcgcc     7440
cccctcctca gcagcggcaa gagcaagagc agcggcagac atgcagggca ccctcccctc    7500
ctcctaccgc gtcaggaggg gcgacatccg cggttgacgc ggcagcagat ggtgattacg    7560 aaccccgcg gcgccgggcc cggcactacc tggacttgga ggaggcgag ggcctggcgc      7620 ggctaggagc gccctctcct gagcggcacc caagggtgca gctgaagcgt gatacgcgtg    7680
aggcgtacgt gccgcggcag aacctgtttc gcgaccgcga gggagaggag cccgaggaga    7740
tgcgggatcg aaagttccac gcagggcgcg agctgcggca tggcctgaat cgcgagcggt    7800
tgctgcgcga ggaggacttt gagcccgacg cgcgaaccgg gattagtccc gcgcgcgcac    7860
```

-continued

```
acgtggcggc cgccgacctg gtaaccgcat acgagcagac ggtgaaccag gagattaact   7920
ttcaaaaaag ctttaacaac cacgtgcgta cgcttgtggc gcgcgaggag gtggctatag   7980
gactgatgca tctgtgggac tttgtaagcg cgctggagca aaacccaaat agcaagccgc   8040
tcatggcgca gctgttcctt atagtgcagc acagcaggga caacgaggca ttcagggatg   8100
cgctgctaaa catagtagag cccgagggcc gctggctgct cgatttgata aacatcctgc   8160
agagcatagt ggtgcaggag cgcagcttga gcctggctga caaggtggcc gccatcaact   8220
attccatgct tagcctgggc aagttttacg cccgcaagat ataccatacc ccttacgttc   8280
ccatagacaa ggaggtaaag atcgaggggt tctacatgcg catggcgctg aaggtgctta   8340
ccttgagcga cgacctgggc gtttatcgca acgagcgcat ccacaaggcc gtgagcgtga   8400
gccggcggcg cgagctcagc gaccgcgagc tgatgcacag cctgcaaagg gccctggctg   8460
gcacgggcag cggcgataga gaggccgagt cctactttga cgcgggcgct gacctgcgct   8520
gggccccaag ccgacgcgcc ctggaggcag ctggggccgg acctgggctg gcggtggcac   8580
ccgcgcgcgc tggcaacgtc ggcggcgtgg aggaatatga cgaggacgat gagtacgagc   8640
cagaggacgg cgagtactaa gcggtgatgt ttctgatcag atgatgcaag acgcaacgga   8700
cccggcggtg cgggcggcgc tgcagagcca gccgtccggc cttaactcca cggacgactg   8760
gcgccaggtc atggaccgca tcatgtcgct gactgcgcgc aatcctgacg cgttccggca   8820
gcagccgcag gccaaccggc tctccgcaat tctggaagcg gtggtcccgg cgcgcgcaaa   8880
ccccacgcac gagaaggtgc tggcgatcgt aaacgcgctg gccgaaaaca gggccatccg   8940 gccccgacgag gccggcctgg tctacgacgc gctgcttcag cgcgtggctc gttacaacag   9000
cggcaacgtg cagaccaacc tggaccggct ggtgggggat gtgcgcgagg ccgtggcgca   9060
gcgtgagcgc gcgcagcagc agggcaacct gggctccatg gttgcactaa acgccttcct   9120
gagtacacag cccgccaacg tgccgcgggg acaggaggac tacaccaact ttgtgagcgc   9180
actgcggcta atggtgactg agacaccgca aagtgaggtg taccagtctg gccagacta   9240 ttttttccag accagtagac aaggcctgca gaccgtaaac ctgagccagg ctttcaaaaa   9300
cttgcagggg ctgtgggggg tgcgggctcc cacaggcgac cgcgcgaccg tgtctagctt   9360
gctgacgccc aactcgcgcc tgttgctgct gctaatagcg cccttcacgg acagtggcag   9420
cgtgtcccgg gacacatacc taggtcactt gctgacactg taccgcgagg ccataggtca   9480
ggcgcatgtg gacgagcata cttttccagga gattacaagt gtcagccgcg cgctgggggca   9540 ggaggacacg ggcagcctgg aggcaaccct aaactacctg ctgaccaacc ggcggcagaa   9600
gatcccctcg ttgcacagtt taaacagcga ggaggagcgc attttgcgct acgtgcagca   9660
gagcgtgagc cttaacctga tgcgcgacgg ggtaacgccc agcgtggcgc tggacatgac   9720
cgcgcgcaac atggaaccgg gcatgtatgc ctcaaaccgg ccgtttatca accgcctaat   9780
ggactacttg catcgcgcgg ccgccgtgaa ccccgagtat ttcaccaatg ccatcttgaa   9840
cccgcactgg ctaccgcccc ctggtttcta caccggggga ttcgaggtgc ccgagggtaa   9900
cgatggattc ctctgggacg acatagacga cagcgtgttt tccccgcaac cgcagaccct   9960
gctagagttg caacagcgcg agcaggcaga ggcggcgctg cgaaaggaaa gcttccgcag  10020
gccaagcagc ttgtccgatc taggcgctgc ggccccgcgg tcagatgcta gtagcccatt  10080
tccaagcttg atagggtctc ttaccagcac tcgcaccacc cgcccgcgcc tgctgggcga  10140
ggaggagtac ctaaacaact cgctgctgca gccgcagcgc gaaaaaaacc tgcctccggc  10200
atttcccaac aacgggatag agagcctagt ggacaagatg agtagatgga gacgtacgc  10260
```

-continued

```
gcaggagcac agggacgtgc caggcccgcg cccgcccacc cgtcgtcaaa ggcacgaccg   10320
tcagcggggt ctggtgtggg aggacgatga ctcggcagac gacagcagcg tcctggattt   10380
gggagggagt ggcaacccgt ttgcgcacct tcgccccagg ctggggagaa tgttttaaaa   10440
aaaaaaaagc atgatgcaaa ataaaaaact caccaaggcc atggcaccga gcgttggttt   10500
tcttgtattc cccttagtat gcggcgcgcg gcgatgtatg aggaaggtcc tcctccctcc   10560
tacgagagtg tggtgagcgc ggcgccagtg gcggcggcgc tgggttctcc cttcgatgct   10620
cccctggacc cgccgtttgt gcctccgcgg tacctgcggc ctaccggggg gagaaacagc   10680
atccgttact ctgagttggc acccctattc gacaccaccc gtgtgtacct ggtggacaac   10740
aagtcaacgg atgtggcatc cctgaactac cagaacgacc acagcaactt tctgaccacg   10800
gtcattcaaa acaatgacta cagcccgggg gaggcaagca cacagaccat caatcttgac   10860
gaccggtcgc actggggcgg cgacctgaaa accatcctgc ataccaacat gccaaatgtg   10920
aacgagttca tgtttaccaa taagtttaag gcgcgggtga tggtgtcgcg cttgcctact   10980
aaggacaatc aggtggagct gaaatacgag tgggtggagt tcacgctgcc cgagggcaac   11040
tactccgaga ccatgaccat agaccttatg aacaacgcga tcgtggagca ctacttgaaa   11100
gtgggcagac agaacggggt tctggaaagc gacatcgggg taaagtttga caccccgcaac  11160 ttcagactgg ggtttgaccc cgtcactggt cttgtcatgc ctgggggtata tacaaaacgaa  11220 gccttccatc cagacatcat tttgctgcca ggatgcgggg tggacttcac ccacagccgc   11280
ctgagcaact tgttgggcat ccgcaagcgg caacccttcc aggagggctt taggatcacc   11340
tacgatgatc tggagggtgg taacattccc gcactgttgg atgtggacgc ctaccaggcg   11400
agcttgaaag atgacaccga acagggcggg ggtggcgcag gcggcagcaa cagcagtggc   11460
agcggcgcgg aagagaactc caacgcggca gccgcggcaa tgcagccggt ggaggacatg   11520
aacgatcatg ccattcgcgg cgacaccttt gccacacggg ctgaggagaa gcgcgctgag   11580
gccgaagcag cggccgaagc tgccgccccc gctgcgcaac ccgaggtcga gaagcctcag   11640
aagaaaccgg tgatcaaacc cctgacagag gacagcaaga aacgcagtta caacctaata   11700
agcaatgaca gcaccttcac ccagtaccgc agctggtacc ttgcatacaa ctacggcgac   11760
cctcagaccg gaatccgctc atggaccctg ctttgcactc ctgacgtaac ctgcggctcg   11820
gagcaggtct actggtcgtt gccagacatg atgcaagacc ccgtgacctt ccgctccacg   11880
cgccagatca gcaactttcc ggtggtgggc gccgagctgt tgcccgtgca ctccaagagc   11940
ttctacaacg accaggccgt ctactcccaa ctcatccgcc agtttacctc tctgacccac   12000
gtgttcaatc gctttcccga gaaccagatt ttggcgcgcc cgccagcccc caccatcacc   12060
accgtcagtg aaaacgttcc tgctctcaca gatcacggga cgctaccgct gcgcaacagc   12120
atcggaggag tccagcgagt gaccattact gacgccagac gccgcacctg ccctacgtt    12180 tacaaggccc tgggcatagt ctcgccgcgc gtcctatcga gccgcacttt ttgagcaagc   12240
atgtccatcc ttatatcgcc cagcaataac acaggctggg gcctgcgctt cccaagcaag   12300
atgtttggcg gggccaagaa gcgctccgac caacacccag tgcgcgtgcg cgggcactac   12360
cgcgcgccct ggggcgcgca caaacgcggc cgcactgggc gcaccaccgt cgatgacgcc   12420
atcgacgcgg tggtggagga ggcgcgcaac tacacgccca cgccgccacc agtgtccaca   12480
gtggacgcgg ccattcagac cgtggtgcgc ggagcccggc gctatgctaa aatgaagaga   12540
cggcggaggc gcgtagcacg tcgccaccgc cgccgacccg gcactgccgc ccaacgcgcg   12600
```

-continued

```
gcggcggccc tgcttaaccg cgcacgtcgc accggccgac gggcggccat gcgggccgct   12660
cgaaggctgg ccgcgggtat tgtcactgtg cccccaggt ccaggcgacg agcggccgcc   12720
gcagcagccg cggccattag tgctatgact cagggtcgca ggggcaacgt gtattgggtg   12780
cgcgactcgg ttagcggcct gcgcgtgccc gtgcgcaccc gccccccgcg caactagatt   12840
gcaagaaaaa actacttaga ctcgtactgt tgtatgtatc cagcggcggc ggcgcgcaac   12900
gaagctatgt ccaagcgcaa aatcaaagaa gagatgctcc aggtcatcgc gccggagatc   12960 tatggcccc cgaagaagga agagcaggat tacaagcccc gaaagctaaa gcgggtcaaa   13020
aagaaaaaga aagatgatga tgatgaactt gacgacgagg tggaactgct gcacgctacc   13080
gcgcccaggc gacgggtaca gtggaaaggt cgacgcgtaa aacgtgtttt gcgacccggc   13140
accaccgtag tctttacgcc cggtgagcgc tccacccgca cctacaagcg cgtgtatgat   13200
gaggtgtacg gcgacgagga cctgcttgag caggccaacg agcgcctcgg ggagtttgcc   13260 tacgaaagc ggcataagga catgctggcg ttgccgctgg acgagggcaa cccaacacct   13320
agcctaaagc ccgtaacact gcagcaggtg ctgcccgcgc ttgcaccgtc cgaagaaaag   13380
cgcggcctaa agcgcgagtc tggtgacttg gcacccaccg tgcagctgat ggtacccaag   13440
cgccagcgac tggaagatgt cttggaaaaa atgaccgtgg aacctgggct ggagcccgag   13500
gtccgcgtgc ggccaatcaa gcaggtggcg ccgggactgg gcgtgcagac cgtggacgtt   13560 cagatacca ctaccagtag caccagtatt gccaccgcca cagagggcat ggagacacaa   13620
acgtccccgg ttgcctcagc ggtggcggat gccgcggtgc aggcggtcgc tgcggccgcg   13680
tccaagacct ctacggaggt gcaaacggac ccgtggatgt ttcgcgtttc agcccccgg   13740 cgcccgcgcc gttcgaggaa gtacggcgcc gccagcgcgc tactgcccga atatgcccta   13800
catccttcca ttgcgcctac ccccggctat cgtggctaca cctaccgccc cagaagacga   13860
gcaactaccc gacgccgaac caccactgga acccgccgcc gccgtcgccg tcgccagccc   13920
gtgctggccc cgatttccgt gcgcagggtg gctcgcgaag gaggcaggac cctggtgctg   13980
ccaacagcgc gctaccaccc cagcatcgtt taaaagccgg tctttgtggt tcttgcagat   14040
atggccctca cctgccgcct ccgtttcccg gtgccgggat tccgaggaag aatgcaccgt   14100
aggaggggca tggccggcca cggcctgacg ggcggcatgc gtcgtgcgca ccaccggcgg   14160
cggcgcgcgt cgcaccgtcg catgcgcggc ggtatcctgc ccctccttat tccactgatc   14220
gccgcggcga ttggcgccgt gcccggaatt gcatccgtgg ccttgcaggc gcagagacac   14280
tgattaaaaa caagttgcat gtggaaaaat caaaataaaa agtctggact ctcacgctcg   14340
cttggtcctg taactatttt gtagaatgga agacatcaac tttgcgtctc tggccccgcg   14400
acacggctcg cgcccgttca tgggaaactg gcaagatatc ggcaccagca atatgagcgg   14460
tggcgccttc agctggggct cgctgtggag cggcattaaa aatttcggtt ccaccgttaa   14520
gaactatggc agcaaggcct ggaacagcag cacaggccag atgctgaggg ataagttgaa   14580
agagcaaaat ttccaacaaa aggtggtaga tggcctggcc tctggcatta gcggggtggt   14640
ggacctggcc aaccaggcag tgcaaaataa gattaacagt aagcttgatc cccgccctcc   14700
cgtagaggag cctccaccgg ccgtggagac agtgtctcca gaggggcgtg gcgaaaagcg   14760
tccgcgcccc gacagggaag aaactctggt gacgcaaata gacgagcctc cctcgtacga   14820
ggaggcacta aagcaaggcc tgcccaccac ccgtcccatc gcgcccatgg ctaccggagt   14880
gctgggccag cacacacccg taacgctgga cctgcctccc cccgccgaca cccagcagaa   14940
acctgtgctg ccaggcccga ccgccgttgt tgtaacccgt cctagccgcg cgtccctgcg   15000
```

-continued

```
ccgcgccgcc agcggtccgc gatcgttgcg gcccgtagcc agtggcaact ggcaaagcac   15060
actgaacagc atcgtgggtc tgggggtgca atccctgaag cgccgacgat gcttctgata   15120
gctaacgtgt cgtatgtgtg tcatgtatgc gtccatgtcg ccgccagagg agctgctgag   15180
ccgccgcgcg cccgctttcc aagatggcta ccccttcgat gatgccgcag tggtcttaca   15240
tgcacatctc gggccaggac gcctcggagt acctgagccc cgggctggtg cagtttgccc   15300
gcgccaccga gacgtacttc agcctgaata acaagtttag aaaccccacg gtggcgccta   15360
cgcacgacgt gaccacagac cggtcccagc gtttgacgct gcggttcatc cctgtggacc   15420
gtgaggatac tgcgtactcg tacaaggcgc ggttcaccct agctgtgggt gataaccgtg   15480
tgctggacat ggcttccacg tactttgaca tccgcgcgcg tgctggacagg ggccctactt   15540 ttaagcccta ctctggcact gcctacaacg ccctggctcc caagggtgcc ccaaatcctt   15600
gcgaatggga tgaagctgct actgctcttg aaataaacct agaagaagag gacgatgaca   15660
acgaagacga agtagacgag caagctgagc agcaaaaaac tcacgtattt gggcaggcgc   15720
cttattctgg tataaatatt acaaaggagg gtattcaaat aggtgtcgaa ggtcaaacac   15780
ctaaatatgc cgataaaaca tttcaacctg aacctcaaat aggagaatct cagtggtacg   15840
aaacagaaat taatcatgca gctgggagag tcctaaaaaa gactacccca atgaaaccat   15900
gttacggttc atatgcaaaa cccacaaatg aaaatggagg gcaaggcatt cttgtaaagc   15960 aacaaatgg aaagctagaa agtcaagtgg aaatgcaatt tttctcaact actgaggcag   16020
ccgcaggcaa tggtgataac ttgactccta aagtggtatt gtacagtgaa gatgtagata   16080
tagaaacccc agacactcat atttcttaca tgcccactat taaggaaggt aactcacgag   16140
aactaatggg ccaacaatct atgcccaaca ggcctaatta cattgctttt agggacaatt   16200
ttattggtct aatgtattac aacagcacgg gtaatatggg tgttctggcg ggccaagcat   16260
cgcagttgaa tgctgttgta gatttgcaag acagaaacac agagctttca taccagcttt   16320
tgcttgattc cattggtgat agaaccaggt acttttctat gtggaatcag gctgttgaca   16380
gctatgatcc agatgttaga attattgaaa atcatggaac tgaagatgaa cttccaaatt   16440
actgctttcc actgggaggt gtgattaata cagagactct taccaaggta aaacctaaaa   16500
caggtcagga aaatgatgg gaaaaagatg ctacagaatt ttcagataaa aatgaaataa   16560
gagttggaaa taattttgcc atggaaatca atctaaatgc caacctgtgg agaaatttcc   16620
tgtactccaa catagcgctg tatttgcccg acaagctaaa gtacagtcct tccaacgtaa   16680
aaatttctga taacccaaac acctacgact acatgaacaa gcgagtggtg gctcccgggc   16740
tagtggactg ctacattaac cttggagcac gctggtccct tgactatatg gacaacgtca   16800
acccatttaa ccaccaccgc aatgctggcc tgcgctaccg ctcaatgttg ctgggcaatg   16860
gtcgctatgt gcccttccac atccaggtgc ctcagaagtt ctttgccatt aaaaacctcc   16920
ttctcctgcc gggctcatac acctacgagt ggaacttcag gaaggatgtt aacatggttc   16980
tgcagagctc cctaggaaat gacctaaggg ttgacggagc cagcattaag tttgatagca   17040 tttgcctta cgccaccttc ttccccatgg cccacaacac cgcctccacg cttgaggcca   17100
tgcttagaaa cgacaccaac gaccagtcct ttaacgacta tctctccgcc gccaacatgc   17160
tctaccctat acccgccaac gctaccaacg tgcccatatc catcccctcc cgcaactggg   17220
cggctttccg cggctgggcc ttcacgcgcc ttaagactaa ggaaacccca tcactgggct   17280
cgggctacga cccttattac acctactctg gctctatacc ctacctagat ggaacctttt   17340
```

-continued

```
acctcaacca caccttaag aaggtggcca ttaccttga ctcttctgtc agctggcctg      17400
gcaatgaccg cctgcttacc cccaacgagt ttgaaattaa gcgctcagtt gacggggagg      17460
gttacaacgt tgcccagtgt aacatgacca aagactggtt cctggtacaa atgctagcta      17520
actataacat tggctaccag ggcttctata tcccagagag ctacaaggac cgcatgtact      17580
ccttctttag aaacttccag cccatgagcc gtcaggtggt ggatgatact aaatacaagg      17640
actaccaaca ggtgggcatc ctacaccaac acaacaactc tggatttgtt ggctaccttg      17700
cccccaccat gcgcgaagga caggcctacc ctgctaactt cccctatccg cttataggca      17760
agaccgcagt tgacagcatt acccagaaaa agtttcttg cgatcgcacc ctttggcgca      17820
tcccattctc cagtaacttt atgtccatgg gcgcactcac agacctgggc caaaaccttc      17880
tctacgccaa ctccgcccac gcgctagaca tgactttga ggtggatccc atggacgagc      17940 ccaccttct ttatgttttg tttgaagtct ttgacgtggt ccgtgtgcac cagccgcacc      18000
gcggcgtcat cgaaaccgtg tacctgcgca cgcccttctc ggccggcaac gccacaacat      18060
aaagaagcaa gcaacatcaa caacagctgc cgccatgggc tccagtgagc aggaactgaa      18120
agccattgtc aaagatcttg gttgtgggcc atattttttg ggcacctatg acaagcgctt      18180
tccaggcttt gtttctccac acaagctcgc ctgcgccata gtcaatacgg ccggtcgcga      18240
gactgggggc gtacactgga tggcctttgc ctggaacccg cactcaaaaa catgctacct      18300
ctttgagccc tttggctttt ctgaccagcg actcaagcag gttaccagt ttgagtacga      18360 gtcactcctg cgccgtagcg ccattgcttc ttcccccgac cgctgtataa cgctggaaaa      18420
gtccacccaa agcgtacagg ggcccaactc ggccgcctgt ggactattct gctgcatgtt      18480
tctccacgcc tttgccaact ggccccaaac tcccatggat cacaacccca ccatgaacct      18540
tattaccggg gtacccaact ccatgctcaa cagtccccag gtacagccca ccctgcgtcg      18600
caaccaggaa cagctctaca gcttcctgga gcgccactcg ccctacttcc gcagccacag      18660
tgcgcagatt aggagcgcca cttcttttg tcacttgaaa aacatgtaaa aataatgtac      18720
tagagacact ttcaataaag gcaaatgctt ttatttgtac actctcgggt gattatttac      18780
ccccaccctt gccgtctgcg ccgtttaaaa atcaaagggg ttctgccgcg catcgctatg      18840
cgccactggc agggacacgt tgcgatactg gtgtttagtg ctccacttaa actcaggcac      18900
aaccatccgc ggcagctcgg tgaagttttc actccacagg ctgcgcacca tcaccaacgc      18960
gtttagcagg tcgggcgccg atatcttgaa gtcgcagttg gggcctccgc cctgcgcgcg      19020
cgagttgcga tacacagggt tgcagcactg gaacactatc agcgccgggt ggtgcacgct      19080
ggccagcacg ctcttgtcgg agatcagatc cgcgtccagg tcctccgcgt tgctcagggc      19140
gaacggagtc aactttggta gctgccttcc caaaaagggc gcgtgccag gctttgagtt      19200 gcactcgcac cgtagtggca tcaaaaggtg accgtgcccg gtctgggcgt taggatacag      19260
cgcctgcata aaagccttga tctgcttaaa agccacctga gcctttgcgc cttcagagaa      19320
gaacatgccg caagacttgc cggaaaactg attggccgga caggccgcgt cgtgcacgca      19380
gcaccttgcg tcggtgttgg agatctgcac cacatttcgg ccccaccggt tcttcacgat      19440
cttggccttg ctagactgct ccttcagcgc gcgctgcccg ttttcgctcg tcacatccat      19500
ttcaatcacg tgctccttat ttatcataat gcttccgtgt agacacttaa gctcgccttc      19560
gatctcagcg cagcggtgca gccacaacgc gcagcccgtg ggctcgtgat gcttgtaggt      19620
cacctctgca aacgactgca ggtacgcctg caggaatcgc cccatcatcg tcacaaaggt      19680
cttgttgctg gtgaaggtca gctgcaaccc gcggtgctcc tcgttcagcc aggtcttgca      19740
```

-continued

```
tacggccgcc agagcttcca cttggtcagg cagtagtttg aagttcgcct ttagatcgtt  19800
atccacgtgg tacttgtcca tcagcgcgcg cgcagcctcc atgcccttct cccacgcaga  19860
cacgatcggc acactcagcg ggttcatcac cgtaatttca ctttccgctt cgctgggctc  19920
ttcctcttcc tcttgcgtcc gcataccacg cgccactggg tcgtcttcat tcagccgccg  19980
cactgtgcgc ttacctcctt tgccatgctt gattagcacc ggtgggttgc tgaaacccac  20040
catttgtagc gccacatctt ctctttcttc ctcgctgtcc acgattacct ctggtgatgg  20100
cgggcgctcg ggcttgggag aagggcgctt ctttttcttc ttgggcgcaa tggccaaatc  20160
cgccgccgag gtcgatggcc gcgggctggg tgtgcgcggc accagcgcgt cttgtgatga  20220
gtcttcctcg tcctcggact cgatacgccg cctcatccgc ttttttgggg gcgcccgggg  20280
aggcggcggc gacggggacg gggacgacac gtcctccatg gttgggggac gtcgcgccgc  20340
accgcgtccg cgctcggggg tggtttcgcg ctgctcctct tcccgactgg ccatttcctt  20400
ctcctatagg cagaaaaaga tcatggagtc agtcgagaag aaggacagcc taaccgcccc  20460
ctctgagttc gccaccaccg cctccaccga tgccgccaac gcgcctacca ccttccccgt  20520
cgaggcaccc ccgcttgagg aggaggaagt gattatcgag caggacccag gttttgtaag  20580
cgaagacgac gaggaccgct cagtaccaac agaggataaa aagcaagacc aggacaacgc  20640
agaggcaaac gaggaacaag tcgggcgggg ggacgaaagg catggcgact acctagatgt  20700
gggagacgac gtgctgttga agcatctgca gcgccagtgc gccattatct cgacgcgtt  20760 gcaagagcgc agcgatgtgc ccctcgccat agcggatgtc agccttgcct acgaacgcca  20820
cctattctca ccgcgcgtac cccccaaacg ccaagaaaac ggcacatgcg agcccaaccc  20880
gcgcctcaac ttctaccccg tatttgccgt gccagaggtg cttgccacct atcacatctt  20940
tttccaaaac tgcaagatac ccctatcctg ccgtgccaac cgcagccgag cggacaagca  21000
gctggccttg cggcagggcg ctgtcatacc tgatatcgcc tcgctcaacg aagtgccaaa  21060
aatctttgag ggtcttggac gcgacgagaa gcgcgcggca aacgctctgc aacaggaaaa  21120
cagcgaaaat gaaagtcact ctggagtgtt ggtggaactc gagggtgaca acgcgcgcct  21180
agccgtacta aaacgcagca tcgaggtcac ccactttgcc tacccggcac ttaacctacc  21240
ccccaaggtc atgagcacag tcatgagtga gctgatcgtg cgccgtgcgc agcccctgga  21300
gagggatgca aatttgcaag aacaaacaga ggagggccta cccgcagttg gcgacgagca  21360
gctagcgcgc tggcttcaaa cgcgcgagcc tgccgacttg gaggagcgac gcaaactaat  21420
gatgccgcga gtgctcgtta ccgtggagct tgagtgcatg cagcggttct ttgctgaccc  21480
ggagatgcag cgcaagctag aggaaacatt gcactacacc tttcgacagg ctacgtacg  21540 ccaggcctgc aagatctcca acgtggagct ctgcaacctg gtctcctacc ttggaatttt  21600
gcacgaaaac cgccttgggc aaaacgtgct tcattccacg ctcaagggcg aggcgcgccg  21660
cgactacgtc cgcgactgcg tttacttatt tctatgctac acctggcaga cggccatggg  21720
cgtttggcag cagtgcttgg aggagtgcaa cctcaaggag ctgcagaaac tgctaaagca  21780
aaacttgaag gacctatgga cggccttcaa cgagcgctcc gtggccgcgc acctggcgga  21840
catcattttc cccgaacgcc tgcttaaaac cctgcaacag ggtctgccag acttcaccag  21900
tcaaagcatg ttgcagaact ttaggaactt tatcctagag cgctcaggaa tcttgcccgc  21960
cacctgctgt gcacttccta gcgactttgt gcccattaag taccgcgaat gccctccgcc  22020
gctttggggc cactgctacc ttctgcagct agccaactac cttgcctacc actctgacat  22080
```

-continued

```
aatggaagac gtgagcggtg acggtctact ggagtgtcac tgtcgctgca acctatgcac   22140
cccgcaccgc tccctggttt gcaattcgca gctgcttaac gaaagtcaaa ttatcggtac   22200
ctttgagctg cagggtccct cgcctgacga aaagtccgcg gctccggggt tgaaactcac   22260 tccgggggctg tggacgtcgg cttaccttcg caaatttgta cctgaggact accacgccca   22320
cgagattagg ttctacgaag accaatcccg cccgcctaat gcggagctta ccgcctgcgt   22380
cattacccag ggccacattc ttggccaatt gcaagccatc aacaaagccc gccaagagtt   22440
tctgctacga aagggacggg gggtttactt ggaccccag tccggcgagg agctcaaccc   22500
aatccccccg ccgccgcagc cctatcagca gcagccgcgg gcccttgctt cccaggatgg   22560
cacccaaaaa gaagctgcag ctgccgccgc cacccacgga cgaggaggaa tactgggaca   22620
gtcaggcaga ggaggttttg dacgaggagg aggaggacat gatggaagac tgggagagcc   22680
tagacgagga agcttccgag gtcgaagagg tgtcagacga aacaccgtca ccctcggtcg   22740
cattcccctc gccggcgccc cagaaatcgg caaccggttc cagcatggct acaacctccg   22800
ctcctcaggc gccgccggca ctgcccgttc gccgacccaa ccgtagatgg gacaccactg   22860
gaaccagggc cggtaagtcc aagcagccgc cgccgttagc ccaagagcaa caacagcgcc   22920
aaggctaccg ctcatggcgc gggcacaaga acgccatagt tgcttgcttg caagactgtg   22980
ggggcaacat ctccttcgcc cgccgctttc ttctctacca tcacggcgtg gccttccccc   23040
gtaacatcct gcattactac cgtcatctct acagcccata ctgcaccggc ggcagcggca   23100
gcaacagcag cggccacaca gaagcaaagg cgaccggata gcaagactct gacaaagccc   23160
aagaaatcca cagcggcggc agcagcagga ggaggagcgc tgcgtctggc gcccaacgaa   23220
cccgtatcga cccgcgagct tagaaacagg attttccca ctctgtatgc tatatttcaa   23280
cagagcaggc gccaagaaca agagctgaaa ataaaaaaca ggtctctgcg atccctcacc   23340
cgcagctgcc tgtatcacaa aagcgaagat cagcttcggc gcacgctgga agacgcggag   23400
gctctcttca gtaaatactg cgcgctgact cttaaggact agtttcgcgc cctttctcaa   23460
atttaagcgc gaaaactacg tcatctccag cggccacacc cggcgccagc acctgttgtc   23520
agcgccatta tgagcaagga aattcccacg ccctacatgt ggagttacca gccacaaatg   23580
ggacttgcgg ctggagctgc ccaagactac tcaacccgaa taaactacat gagcgcggga   23640
ccccacatga tatcccgggt caacggaata cgcgcccacc gaaaccgaat tctcctggaa   23700
caggcggcta ttaccaccac acctcgtaat aaccttaatc cccgtagttg gcccgctgcc   23760
ctggtgtacc aggaaagtcc cgctcccacc actgtggtac ttcccagaga cgcccaggcc   23820
gaagttcaga tgactaactc aggggcgcag cttgcgggcg gctttcgtca cagggtgcgg   23880
tcgcccgggc agggtataac tcacctgaca atcagagggc gaggtattca gctcaacgac   23940
gagtcggtga gctcctcgct tggtctccgt ccggacggga catttcagat cggcggcgcc   24000
ggccgctctt cattcacgcc tcgtcaggca atcctaactc tgcagaccctc gtcctctgag   24060 ccgcgctctg gaggcattgg aactctgcaa tttattgagg agtttgtgcc atcggtctac   24120
tttaacccct tctcgggacc tcccggccac tatccggatc aatttattcc taactttgac   24180
gcggtaaagg actcggcgga cggctacgac tgaatgttaa gtggagaggc agagcaactg   24240
cgcctgaaac acctggtcca ctgtcgccgc cacaagtgct ttgcccgcga ctccggtgag   24300
ttttgctact ttgaattgcc cgaggatcat atcgagggcc cggcgcacgg cgtccggctt   24360
accgcccagg gagagcttgc ccgtagcctg attcgggagt ttacccagcg cccccctgcta   24420 gttgagcggg acaggggacc ctgtgttctc actgtgattt gcaactgtcc taaccctgga   24480
```

-continued

```
ttacatcaag atcctctagt taatgtcagg tcgcctaagt cgattaacta gagtacccgg   24540
ggatcttatt ccctttaact aataaaaaaa aataataaag catcacttac ttaaaatcag   24600
ttagcaaatt tctgtccagt ttattcagca gcacctcctt gccctcctcc cagctctggt   24660
attgcagctt cctcctggct gcaaactttc tccacaatct aaatggaatg tcagtttcct   24720
cctgttcctg tccatccgca cccactatct tcatgttgtt gcagatgaag cgcgcaagac   24780
cgtctgaaga taccttcaac cccgtgtatc catatgacac ggaaaccggt cctccaactg   24840 tgcctttct tactcctccc tttgtatccc ccaatgggtt tcaagagagt cccctgggg    24900 tactctcttt gcgcctatcc gaacctctag ttacctccaa tggcatgctt gcgctcaaaa   24960
tgggcaacgg cctctctctg gacgaggccg gcaaccttac ctcccaaaat gtaaccactg   25020
tgagcccacc tctcaaaaaa accaagtcaa acataaacct ggaaatatct gcacccctca   25080
cagttacctc agaagcccta actgtggctg ccgccgcacc tctaatggtc gcgggcaaca   25140
cactcaccat gcaatcacag gccccgctaa ccgtgcacga ctccaaactt agcattgcca   25200
cccaaggacc cctcacagtg tcagaaggaa agctagccct gcaaacatca ggcccctca   25260 ccaccaccga tagcagtacc cttactatca ctgcctcacc ccctctaact actgccactg   25320
gtagcttggg cattgacttg aaagagccca tttatacaca aaatggaaaa ctaggactaa   25380 agtacgggc tcctttgcat gtaacagacg acctaaacac tttgaccgta gcaactggtc   25440
caggtgtgac tattaataat acttccttgc aaactaaagt tactggagcc ttgggttttg   25500
attcacaagg caatatgcaa cttaatgtag caggaggact aaggattgat tctcaaaaca   25560
gacgccttat acttgatgtt agttatccgt ttgatgctca aaaccaacta aatctaagac   25620
taggacaggg ccctcttttt ataaactcag cccacaactt ggatattaac tacaacaaag   25680
gcctttactt gtttacagct tcaaacaatt ccaaaaagct tgaggttaac ctaagcactg   25740 ccaagggggtt gatgtttgac gctacagcca tagccattaa tgcaggagat gggcttgaat   25800
ttggttcacc taatgcacca aacacaaatc ccctcaaaac aaaaattggc catggcctag   25860
aatttgattc aaacaaggct atggttccta aactaggaac tggccttagt tttgacagca   25920
caggtgccat tacagtagga aacaaaaata atgataagct aactttgtgg accacaccag   25980
ctccatctcc taactgtaga ctaaatgcag agaaagatgc taaactcact ttggtcttaa   26040
caaaatgtgg cagtcaaata cttgctacag tttcagtttt ggctgttaaa ggcagtttgg   26100
ctccaatatc tggaacagtt caaagtgctc atcttattat aagatttgac gaaaatggag   26160
tgctactaaa caattccttc ctggacccag aatattggaa ctttagaaat ggagatctta   26220
ctgaaggcac agcctataca aacgctgttg gatttatgcc taacctatca gcttatccaa   26280
aatctcacgg taaaactgcc aaaagtaaca ttgtcagtca agtttactta aacggagaca   26340
aaactaaacc tgtaacacta accattacac taaacggtac acaggaaaca ggagacacaa   26400
ctccaagtgc atactctatg tcattttcat gggactggtc tggccacaac tacattaatg   26460
aaatatttgc cacatcctct tacactttttt catacattgc ccaagaataa agaatcgttt   26520
gtgttatgtt tcaacgtgtt tattttttcaa ttgcagaaaa tttcaagtca tttttcattc   26580
agtagtatag ccccaccacc acatagctta tacagatcac cgtaccttaa tcaaactcac   26640
agaaccctag tattcaacct gccacctccc tcccaacaca cagagtacac agtcctttct   26700
ccccggctgg cctaaaaaag catcatatca tgggtaacag acatattctt aggtgttata   26760
ttccacacgg tttcctgtcg agccaaacgc tcatcagtga tattaataaa ctccccgggc   26820
```

-continued

```
agctcactta agttcatgtc gctgtccagc tgctgagcca caggctgctg tccaacttgc  26880
ggttgcttaa cgggcggcga aggagaagtc cacgcctaca tggggggtaga gtcataatcg  26940 tgcatcagga tagggcggtg gtgctgcagc agcgcgcgaa taaactgctg ccgccgccgc  27000
tccgtcctgc aggaatacaa catggcagtg gtctcctcag cgatgattcg caccgcccgc  27060
agcataaggc gccttgtcct ccgggcacag cagcgcaccc tgatctcact taaatcagca  27120
cagtaactgc agcacagcac cacaatattg ttcaaaatcc cacagtgcaa ggcgctgtat  27180
ccaaagctca tggcggggac cacagaaccc acgtggccat cataccacaa gcgcaggtag  27240
attaagtggc gacccctcat aaacacgctg gacataaaca ttacctcttt tggcatgttg  27300
taattcacca cctcccggta ccatataaac ctctgattaa acatggcgcc atccaccacc  27360
atcctaaacc agctggccaa aacctgcccg ccggctatac actgcaggga accgggactg  27420
gaacaatgac agtggagagc ccaggactcg taaccatgga tcatcatgct cgtcatgata  27480
tcaatgttgg cacaacacag gcacacgtgc atacacttcc tcaggattac aagctcctcc  27540
cgcgttagaa ccatatccca gggaacaacc cattcctgaa tcagcgtaaa tcccacactg  27600
cagggaagac ctcgcacgta actcacgttg tgcattgtca aagtgttaca ttcgggcagc  27660
agcggatgat cctccagtat ggtagcgcgg gtttctgtct caaaaggagg tagacgatcc  27720
ctactgtacg gagtgcgccg agacaaccga gatcgtgttg gtcgtagtgt catgccaaat  27780
ggaacgccgg acgtagtcat atttcctgaa gcaaaaccag gtgcgggcgt gacaaacaga  27840
tctgcgtctc cggtctcgcc gcttagatcg ctctgtgtag tagttgtagt atatccactc  27900
tctcaaagca tccaggcgcc ccctggcttc gggttctatg taaactcctt catgcgccgc  27960
tgccctgata acatccacca ccgcagaata agccacaccc agccaaccta cacattcgtt  28020
ctgcgagtca cacacgggag gagcgggaag agctggaaga accatgtttt tttttttatt  28080
ccaaaagatt atccaaaacc tcaaaatgaa gatctattaa gtgaacgcgc tcccctccgg  28140
tggcgtggtc aaactctaca gccaaagaac agataatggc atttgtaaga tgttgcacaa  28200
tggcttccaa aaggcaaacg gccctcacgt ccaagtggac gtaaaggcta aacccttcag  28260
ggtgaatctc ctctataaac attccagcac cttcaaccat gcccaaataa ttctcatctc  28320
gccaccttct caatatatct ctaagcaaat cccgaatatt aagtccggcc attgtaaaaa  28380
tctgctccag agcgccctcc accttcagcc tcaagcagcg aatcatgatt gcaaaaattc  28440
aggttcctca cagacctgta taagattcaa aagcggaaca ttaacaaaaa taccgcgatc  28500
ccgtaggtcc cttcgcaggg ccagctgaac ataatcgtgc aggtctgcac ggaccagcgc  28560
ggccacttcc ccgccaggaa ccatgacaaa agaacccaca ctgattatga cacgcatact  28620
cggagctatg ctaaccagcg tagccccgat gtaagcttgt tgcatgggcg gcgatataaa  28680
atgcaaggtg ctgctcaaaa aatcaggcaa agcctcgcgc aaaaaagaaa gcacatcgta  28740
gtcatgctca tgcagataaa ggcaggtaag ctccggaacc accacagaaa aagacaccat  28800
ttttctctca aacatgtctg cgggtttctg cataaacaca aaataaaata acaaaaaaac  28860
atttaaacat tagaagcctg tcttacaaca ggaaaaacaa cccttataag cataagacgg  28920
actacggcca tgccggcgtg accgtaaaaa aactggtcac cgtgattaaa aagcaccacc  28980
gacagctcct cggtcatgtc cggagtcata atgtaagact cggtaaacac atcaggttga  29040
ttcacatcgg tcagtgctaa aaagcgaccg aaatagcccg ggggaataca tacccgcagg  29100
cgtagagaca acattacagc ccccatagga ggtataacaa aattaatagg agagaaaaac  29160
acataaacac ctgaaaaacc ctcctgccta ggcaaaatag caccctcccg ctccagaaca  29220
```

-continued

```
acatacagcg cttccacagc ggcagccata acagtcagcc ttaccagtaa aaaagaaaac   29280
ctattaaaaa aacaccactc gacacggcac cagctcaatc agtcacagtg taaaaaaggg   29340
ccaagtgcag agcgagtata tataggacta aaaaatgacg taacggttaa agtccacaaa   29400
aaacacccag aaaaccgcac gcgaacctac gcccagaaac gaaagccaaa aaacccacaa   29460
cttcctcaaa tcgtcacttc cgttttccca cgttacgtca cttcccattt taagaaaact   29520
acaattccca acacatacaa gttactccgc cctaaaacct acgtcacccg ccccgttccc   29580
acgccccgcg ccacgtcaca aactccaccc cctcattatc atattggctt caatccaaaa   29640
taaggtatat tattgatgat gttaattaac atgcatggat cctacgtctc gaccgatgcc   29700
cttgagagcc ttcaacccag tcagctcctt ccggtgggcg cggggcatga ctatcgtcgc   29760
cgcacttatg actgtcttct ttatcatgca actcgtagga caggtgccgg cagcgctctg   29820
ggtcattttc ggcgaggacc gctttcgctg gagcgcgacg atgatcggcc tgtcgcttgc   29880
ggtattcgga atcttgcacg ccctcgctca agccttcgtc actggtcccg ccaccaaacg   29940
tttcggcgag aagcaggcca ttatcgccgg catggcggcc gacgcgctgg gctacgtctt   30000
gctggcgttc gcgacgcgag gctggatggc cttccccatt atgattcttc tcgcttccgg   30060
cggcatcggg atgcccgcgt tgcaggccat gctgtccagg caggtagatg acgaccatca   30120
gggacagctt caaggatcgc tcgcggctct taccagccta acttcgatca ttggaccgct   30180
gatcgtcacg gcgatttatg ccgcctcggc gagcacatgg aacgggttgg catggattgt   30240
aggcgccgcc ctataccttg tctgcctccc cgcgttgcgt cgcggtgcat ggagccgggc   30300
cacctcgacc tgaatggaag ccggcggcac ctcgctaacg gattcaccac tccaagaatt   30360
ggagccaatc aattcttgcg gagaactgtg aatgcgcaaa ccaacccttg gcagaacata   30420
tccatcgcgt ccgccatctc cagcagccgc acgcggcgca tctcgggcag cgttgggtcc   30480
tggccacggg tgcgcatgat cgtgctcctg tcgttgagga cccggctagg ctggcggggt   30540
tgccttactg gttagcagaa tgaatcaccg atacgcgagc gaacgtgaag cgactgctgc   30600
tgcaaaacgt ctgcgacctg agcaacaaca tgaatggtct tcggtttccg tgtttcgtaa   30660
agtctggaaa cgcggaagtc agcgccctgc accattatgt tccggatctg catcgcagga   30720
tgctgctggc taccctgtgg aacacctaca tctgtattaa cgaagcgctg gcattgaccc   30780
tgagtgattt ttctctggtc ccgccgcatc cataccgcca gttgtttacc ctcacaacgt   30840
tccagtaacc gggcatgttc atcatcagta acccgtatcg tgagcatcct ctctcgtttc   30900
atcggtatca ttacccccat gaacagaaat ccccttaca cggaggcatc agtgaccaaa   30960
caggaaaaaa ccgcccttaa catggcccgc tttatcagaa gccagacatt aacgcttctg   31020
gagaaactca acgagctgga cgcggatgaa caggcagaca tctgtgaatc gcttcacgac   31080
cacgctgatg agctttaccg cagctgcctc gcgcgtttcg gtgatgacgg tgaaaacctc   31140
tgacacatgc agctcccgga cacggtcaca gcttgtctgt aagcggatgc cgggagcaga   31200
caagcccgtc agggcgcgtc agcgggtgtt ggcgggtgtc ggggcgcagc catgacccag   31260
tcacgtagcg atagcggagt gtatactggc ttaactatgc ggcatcagag cagattgtac   31320
tgagagtgca ccatatgcgg tgtgaaatac cgcacagatg cgtaaggaga aaataccgca   31380
tcaggcgctc ttccgcttcc tcgctcactg actcgctgcg ctcggtcgtt cggctgcggc   31440
gagcggtatc agctcactca aaggcggtaa tacggttatc cacagaatca ggggataacg   31500
caggaaagaa catgtgagca aaaggccagc aaaaggccag gaaccgtaaa aaggccgcgt   31560
```

-continued

```
tgctggcgtt tttccatagg ctccgccccc ctgacgagca tcacaaaaat cgacgctcaa    31620
gtcagaggtg gcgaaacccg acaggactat aaagatacca ggcgtttccc cctggaagct    31680
ccctcgtgcg ctctcctgtt ccgaccctgc cgcttaccgg atacctgtcc gcctttctcc    31740
cttcgggaag cgtggcgctt tctcatagct cacgctgtag gtatctcagt tcggtgtagg    31800
tcgttcgctc caagctgggc tgtgtgcacg aaccccccgt tcagcccgac cgctgcgcct    31860
tatccggtaa ctatcgtctt gagtccaacc cggtaagaca cgacttatcg ccactggcag    31920
cagccactgg taacaggatt agcagagcga ggtatgtagg cggtgctaca gagttcttga    31980
agtggtggcc taactacggc tacactagaa ggacagtatt tggtatctgc gctctgctga    32040
agccagttac cttcggaaaa agagttggta gctcttgatc cggcaaacaa accaccgctg    32100
gtagcggtgg tttttttgtt tgcaagcagc agattacgcg cagaaaaaaa ggatctcaag    32160
aagatccttt gatcttttct acggggtctg acgctcagtg gaacgaaaac tcacgttaag    32220
ggattttggt catgagatta tcaaaaagga tcttcaccta gatcctttta aattaaaaat    32280
gaagttttaa atcaatctaa agtatatatg agtaaacttg gtctgacagt taccaatgct    32340
taatcagtga ggcacctatc tcagcgatct gtctatttcg ttcatccata gttgcctgac    32400
tccccgtcgt gtagataact acgatacggg agggcttacc atctggcccc agtgctgcaa    32460
tgataccgcg agacccacgc tcaccggctc cagatttatc agcaataaac cagccagccg    32520
gaagggccga gcgcagaagt ggtcctgcaa ctttatccgc ctccatccag tctattaatt    32580
gttgccggga agctagagta agtagttcgc cagttaatag tttgcgcaac gttgttgcca    32640
ttgctgcagg catcgtggtg tcacgctcgt cgtttggtat ggcttcattc agctccggtt    32700
cccaacgatc aaggcgagtt acatgatccc ccatgttgtg caaaaaagcg gttagctcct    32760
tcggtcctcc gatcgttgtc agaagtaagt tggccgcagt gttatcactc atggttatgg    32820
cagcactgca taattctctt actgtcatgc catccgtaag atgcttttct gtgactggtg    32880
agtactcaac caagtcattc tgagaatagt gtatgcggcg accgagttgc tcttgcccgg    32940
cgtcaacacg ggataatacc gcgccacata gcagaacttt aaaagtgctc atcattggaa    33000
aacgttcttc ggggcgaaaa ctctcaagga tcttaccgct gttgagatcc agttcgatgt    33060
aacccactcg tgcacccaac tgatcttcag catcttttac tttcaccagc gtttctgggt    33120
gagcaaaaac aggaaggcaa aatgccgcaa aaaagggaat aagggcgaca cggaaatgtt    33180
gaatactcat actcttcctt tttcaatatt attgaagcat ttatcagggt tattgtctca    33240
tgagcggata catatttgaa tgtatttaga aaaataaaca aataggggtt ccgcgcacat    33300
ttccccgaaa agtgccacct gtctagctac gaattcttcg acagcttcga aactagaatc    33360
gatttcgaaa ctagcttaag ggtgggaaag aatatataag gtgggggtct tatgtagttt    33420
tgtatctgtt ttgcagcagc cgccgccgcc atgagcacca actcgtttga tggaagc       33477
```

<210> SEQ ID NO 8
<211> LENGTH: 8108
<212> TYPE: DNA
<213> ORGANISM: Artificial Sequence
<220> FEATURE:
<223> OTHER INFORMATION: pAD_Track8509
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (352)..(354)
<223> OTHER INFORMATION: n is a, c, g, or t
<220> FEATURE:
<221> NAME/KEY: misc_feature
<222> LOCATION: (1942)..(1944)
<223> OTHER INFORMATION: n is a, c, g, or t
<220> FEATURE:
<221> NAME/KEY: misc_feature
<222> LOCATION: (2001)..(2003)
<223> OTHER INFORMATION: n is a, c, g, or t
<220> FEATURE:
<221> NAME/KEY: misc_feature
<222> LOCATION: (4244)..(4246)
<223> OTHER INFORMATION: n is a, c, g, or t
<220> FEATURE:
<221> NAME/KEY: misc_feature
<222> LOCATION: (4261)..(4263)
<223> OTHER INFORMATION: n is a, c, g, or t
<220> FEATURE:
<221> NAME/KEY: misc_feature
<222> LOCATION: (5246)..(5248)
<223> OTHER INFORMATION: n is a, c, g, or t
<220> FEATURE:
<221> NAME/KEY: misc_feature
<222> LOCATION: (5263)..(5265)
<223> OTHER INFORMATION: n is a, c, g, or t
<220> FEATURE:
<221> NAME/KEY: misc_feature
<222> LOCATION: (6566)..(6571)
<223> OTHER INFORMATION: n is a, c, g, or t

<400> SEQUENCE: 8
ttaattaann ntcccttcca gctctctgcc cctttggat tgaagccaat atgataatga       60
gggggtggag tttgtgacgt ggcgcggggc gtgggaacgg ggcgggtgac gtagtagtgt      120
ggcggaagtg tgatgttgca agtgtggcgg aacacatgta agcgacggat gtggcaaaag      180
tgacgttttt ggtgtgcgcc ggtgtacaca ggaagtgaca attttcgcgc ggtttttaggc     240 ggatgttgta gtaaatttgg gcgtaaccga gtaagatttg gccattttcg cgggaaaact      300
gaataagagg aagtgaaatc tgaataattt tgtgttactc atagcgcgta annncgcgtt      360
aagatacatt gatgagtttg gacaaaccac aactagaatg cagtgaaaaa aatgctttat      420
ttgtgaaatt tgtgatgcta ttgctttatt tgtaaccatt ataagctgca ataaacaagt      480
taacaacaac aattgcattc attttatgtt tcaggttcag ggggaggtgt gggaggtttt      540
ttaaagcaag taaaacctct acaaatgtgg tatggctgat tatgatcagt tatctagatc      600
cggtggatct gagtccggac ttgtacagct cgtccatgcc gagagtgatc ccggcggcgg      660
tcacgaactc cagcaggacc atgtgatcgc gcttctcgtt ggggtctttg ctcagggcgg      720
actgggtgct caggtagtgg ttgtcgggca gcagcacggg gccgtcgccg atggggggtgt     780 tctgctggta gtggtcggcg agctgcacgc tgccgtcctc gatgttgtgg cggatcttga      840
agttcacctt gatgccgttc ttctgcttgt cggccatgat atagacgttg tggctgttgt      900
agttgtactc cagcttgtgc cccaggatgt tgccgtcctc cttgaagtcg atgcccttca      960
gctcgatgcg gttcaccagg gtgtcgccct cgaacttcac ctcggcgcgg gtcttgtagt     1020
tgccgtcgtc cttgaagaag atggtgcgct cctggacgta gccttcgggc atggcggact     1080
tgaagaagtc gtgctgcttc atgtggtcgg ggtagcggct gaagcactgc acgccgtagg     1140
tcagggtggt cacgagggtg ggccagggca cgggcagctt gccggtggtg cagatgaact     1200
tcagggtcag cttgccgtag gtggcatcgc cctcgccctc gccggacacg ctgaacttgt     1260
ggccgtttac gtcgccgtcc agctcgacca ggatgggcac caccccggtg aacagctcct     1320
cgcccttgct caccatggtg gcgaccggta gcgctagcgg atctgacggt tcactaaacc     1380
agctctgctt atatagacct cccaccgtac acgcctaccg cccatttgcg tcaatggggc     1440

-continued

```
ggagttgtta cgacattttg gaaagtcccg ttgattttgg tgccaaaaca aactcccatt   1500
gacgtcaatg gggtggagac ttggaaatcc ccgtgagtca aaccgctatc cacgcccatt   1560
gatgtactgc caaaaccgca tcaccatggt aatagcgatg actaatacgt agatgtactg   1620
ccaagtagga aagtcccata aggtcatgta ctgggcataa tgccaggcgg gccatttacc   1680
gtcattgacg tcaataggggg gcgtacttgg catatgatac acttgatgta ctgccaagtg   1740
ggcagtttac cgtaaatact ccacccattg acgtcaatgg aaagtcccta ttggcgttac   1800
tatgggaaca tacgtcatta ttgacgtcaa tgggcggggg tcgttgggcg tcagccagg   1860 cgggccattt accgtaagtt atgtaacgcg gaactccata tatgggctat gaactaatga   1920
ccccgtaatt gattactatt annnctagca gatctggtac cgtcgacgcg gccgcgatat   1980
cctcgagaag ctttctagag nnntaagggt gggaaagaat atataaggtg ggggtcttat   2040
gtagttttgt atctgttttg cagcagccgc cgccgccatg agcaccaact cgtttgatgg   2100
aagcattgtg agctcatatt tgacaacgcg catgcccccca tgggccgggg tgcgtcagaa   2160
tgtgatgggc tccagcattg atggtcgccc cgtcctgccc gcaaactcta ctaccttgac   2220
ctacgagacc gtgtctggaa cgccgttgga gactgcagcc tccgccgccg cttcagccgc   2280
tgcagccacc gcccgcggga ttgtgactga ctttgctttc ctgagcccgc ttgcaagcag   2340
tgcagcttcc cgttcatccg cccgcgatga caagttgacg gctcttttgg cacaattgga   2400
ttctttgacc cgggaactta atgtcgtttc tcagcagctg ttggatctgc gccagcaggt   2460
ttctgccctg aaggcttcct cccctcccaa tgcggtttaa aacataaata aaaaaccaga   2520
ctctgtttgg atttggatca agcaagtgtc ttgctgtctt tatttagggg ttttgcgcgc   2580
gcggtaggcc cgggaccagc ggtctcggtc gttgagggtc ctgtgtattt tttccaggac   2640
gtggtaaagg tgactctgga tgttcagata catgggcata agcccgtctc tggggtggag   2700
gtagcaccac tgcagagctt catgctgcgg ggtggtgttg tagatgatcc agtcgtagca   2760
ggagcgctgg gcgtggtgcc taaaaatgtc tttcagtagc aagctgattg ccaggggcag   2820
gcccttggtg taagtgttta caaagcggtt aagctgggat gggtgcatac gtggggatat   2880
gagatgcatc ttggactgta ttttaggtt ggctatgttc ccagccatat ccctccgggg   2940
attcatgttg tgcagaacca ccagcacagt gtatccggtg cacttgggaa atttgtcatg   3000
tagcttagaa ggaaatgcgt ggaagaactt ggagacgccc ttgtgacctc caagattttc   3060
catgcattcg tccataatga tggcaatggg cccacgggcg gcggcctggg cgaagatatt   3120
tctgggatca ctaacgtcat agttgtgttc caggatgaga tcgtcatagg ccatttttac   3180
aaagcgcggg cggagggtgc cagactgcgg tataatggtt ccatccggcc caggggcgta   3240
gttaccctca cagatttgca tttcccacgc tttgagttca gatggggggga tcatgtctac   3300 ctgcggggcg atgaagaaaa cggtttccgg ggtaggggag atcagctggg aagaaagcag   3360
gttcctgagc agctgcgact taccgcagcc ggtgggcccg taaatcacac ctattaccgg   3420
gtgcaactgg tagttaagag agctgcagct gccgtcatcc ctgagcaggg gggccacttc   3480
gttaagcatg tccctgactc gcatgttttc cctgaccaaa tccgccagaa ggcgctcgcc   3540
gcccagcgat agcagttctt gcaaggaagc aaagttttc aacggtttga accgtccgc   3600 cgtaggcatg ctttttgagcg tttgaccaag cagttccagg cggtcccaca gctcggtcac   3660
ctgctctacg gcatctcgat ccagcatatc tcctcgtttc gcgggttggg gcggctttcg   3720
ctgtacggca gtagtcggtg ctcgtccaga cgggccaggt tcatgtcttt ccacgggcgc   3780
agggtcctcg tcagcgtagt ctgggtcacg gtgaaggggt gcgctccggg ctgcgcgctg   3840
```

```
gccagggtgc gcttgaggct ggtcctgctg gtgctgaagc gctgccggtc ttcgccctgc    3900
gcgtcggcca ggtagcattt gaccatggtg tcatagtcca gcccctccgc ggcgtggccc    3960
ttggcgcgca gcttgccctt ggaggaggcg ccgcacgagg ggcagtgcag acttttgagg    4020
gcgtagagct tgggcgcgag aaataccgat tccggggagt aggcatccgc gccgcaggcc    4080
ccgcagacgg tctcgcattc cacgagccag gtgagctctg gccgttcggg gtcaaaaacc    4140
aggtttcccc catgcttttt gatgcgtttc ttacctctgg tttccatgag ccggtgtcca    4200
cgctcggtga cgaaaaggct gtccgtgtcc ccgtatacag actnnngttt aaacgaattc    4260
nnntataaaa tgcaaggtgc tgctcaaaaa atcaggcaaa gcctcgcgca aaaaagaaag    4320
cacatcgtag tcatgctcat gcagataaag gcaggtaagc tccggaacca ccacagaaaa    4380
agacaccatt tttctctcaa acatgtctgc gggtttctgc ataaacacaa aataaaataa    4440
caaaaaaaca tttaaacatt agaagcctgt cttacaacag gaaaaacaac ccttataagc    4500
ataagacgga ctacggccat gccggcgtga ccgtaaaaaa actggtcacc gtgattaaaa    4560
agcaccaccg acagctcctc ggtcatgtcc ggagtcataa tgtaagactc ggtaaacaca    4620
tcaggttgat tcatcggtca gtgctaaaaa gcgaccgaaa tagcccgggg gaatacatac    4680
ccgcaggcgt agagacaaca ttacagcccc cataggaggt ataacaaaat taataggaga    4740
gaaaaacaca taaacacctg aaaaaccctc ctgcctaggc aaaatagcac cctcccgctc    4800
cagaacaaca tacagcgctt cacagcggca gcctaacagt cagccttacc agtaaaaaag    4860
aaaacctatt aaaaaaacac cactcgacac ggcaccagct caatcagtca cagtgtaaaa    4920
aagggccaag tgcagagcga gtatatatag gactaaaaaa tgacgtaacg gttaaagtcc    4980
acaaaaaaca cccagaaaac cgcacgcgaa cctacgccca gaaacgaaag ccaaaaaacc    5040
cacaacttcc tcaaatcgtc acttccgttt tcccacgtta cgtaacttcc cattttaaga    5100
aaactacaat tcccaacaca tacaagttac tccgccctaa aacctacgtc acccgccccg    5160
ttcccacgcc ccgcgccacg tcacaaactc cacccctca ttatcatatt ggcttcaatc    5220
caaaataagg tatattattg atgatnnntt aattaaggat ccnnncggtg tgaaataccg    5280
cacagatgcg taaggagaaa ataccgcatc aggcgctctt ccgcttcctc gctcactgac    5340
tcgctgcgct cggtcgttcg gctgcggcga gcggtatcag ctcactcaaa ggcggtaata    5400
cggttatcca cagaatcagg ggataacgca ggaaagaaca tgtgagcaaa aggccagcaa    5460
aaggccagga accgtaaaaa ggccgcgttg ctggcgtttt tccataggct ccgcccccct    5520
gacgagcatc acaaaaatcg acgctcaagt cagaggtggc gaaacccgac aggactataa    5580
agataccagg cgtttccccc tggaagctcc ctcgtgcgct ctcctgttcc gaccctgccg    5640
cttaccggat acctgtccgc ctttctccct tcgggaagcg tggcgctttc tcatagctca    5700
cgctgtaggt atctcagttc ggtgtaggtc gttcgctcca agctgggctg tgtgcacgaa    5760
ccccccgttc agcccgaccg ctgcgcctta tccggtaact atcgtcttga gtccaacccg    5820
gtaagacacg acttatcgcc actggcagca gccactggta acaggattag cagagcgagg    5880
tatgtaggcg gtgctacaga gttcttgaag tggtggccta actacggcta cactagaagg    5940
acagtatttg gtatctgcgc tctgctgaag ccagttacct tcggaaaaag agttggtagc    6000
tcttgatccg gcaaacaaac caccgctggt agcggtggtt tttttgtttg caagcagcag    6060
attacgcgca gaaaaaaagg atctcaagaa gatcctttga tcttttctac ggggtctgac    6120
gctcagtgga acgaaaactc acgttaaggg attttggtca tgagattatc aaaaaggatc    6180
```

-continued

```
ttcacctaga tccttttaaa ttaaaaatga agttttaaat caatctaaag tatatatgag      6240
taaacttggt ctgacagtta ccaatgctta atcagtgagg cacctatctc agcgatctgt      6300
ctatttcgtt catccatagt tgcctgactc cccgtcgtgt agataactac gatacgggag      6360
ggcttaccat ctggccccag tgctgcaatg ataccgcgag acccacgctc accggctcca      6420
gatttatcag caataaacca gccagccgga agggccgagc gcagaagtgg tcctgcaact      6480
ttatccgcct ccatccagtc tattaattgt tgccgggaag ctagagtaag tagttcgcca      6540
gttaatagtt tgcgcaacgt tgttgnnnnn naaaaaggat cttcacctag atccttttca      6600
cgtagaaagc cagtccgcag aaacggtgct gaccccggat gaatgtcagc tactgggcta      6660
tctggacaag ggaaaacgca agcgcaaaga gaaagcaggt agcttgcagt gggcttacat      6720
ggcgatagct agactgggcg gttttatgga cagcaagcga accggaattg ccagctgggg      6780
cgccctctgg taaggttggg aagccctgca aagtaaactg gatggctttc tcgccgccaa      6840
ggatctgatg gcgcagggga tcaagctctg atcaagagac aggatgagga tcgtttcgca      6900
tgattgaaca agatggattg cacgcaggtt ctccggccgc ttgggtggag aggctattcg      6960
gctatgactg ggcacaacag acaatcggct gctctgatgc cgccgtgttc cggctgtcag      7020
cgcaggggcg cccggttctt tttgtcaaga ccgacctgtc cggtgccctg aatgaactgc      7080
aagacgaggc agcgcggcta tcgtggctgg ccacgacggg cgttccttgc gcagctgtgc      7140
tcgacgttgt cactgaagcg ggaagggact ggctgctatt gggcgaagtg ccggggcagg      7200
atctcctgtc atctcacctt gctcctgccg agaaagtatc catcatggct gatgcaatgc      7260
ggcggctgca tacgcttgat ccggctacct gcccattcga ccaccaagcg aaacatcgca      7320
tcgagcgagc acgtactcgg atggaagccg gtcttgtcga tcaggatgat ctggacgaag      7380
agcatcaggg gctcgcgcca gccgaactgt tcgccaggct caaggcgagc atgcccgacg      7440
gcgaggatct cgtcgtgacc catggcgatg cctgcttgcc gaatatcatg gtggaaaatg      7500
gccgcttttc tggattcatc gactgtggcc ggctgggtgt ggcggaccgc tatcaggaca      7560
tagcgttggc tacccgtgat attgctgaag agcttggcgg cgaatgggct gaccgcttcc      7620
tcgtgcttta cggtatcgcc gctcccgatt cgcagcgcat cgccttctat cgccttcttg      7680
acgagttctt ctgaattttg ttaaaatttt tgttaaatca gctcatttt taaccaatag      7740 gccgaaatcg gcaacatccc ttataaatca aaagaataga ccgcgatagg gttgagtgtt      7800
gttccagttt ggaacaagag tccactatta aagaacgtgg actccaacgt caaagggcga      7860
aaaaccgtct atcagggcga tggcccacta cgtgaaccat cacccaaatc aagttttttg      7920
cggtcgaggt gccgtaaagc tctaaatcgg aaccctaaag ggagcccccg atttagagct      7980
tgacggggaa agccggcgaa cgtggcgaga aggaaggga agaaagcgaa aggagcgggc      8040
gctagggcgc tggcaagtgt agcggtcacg ctgcgcgtaa ccaccacacc cgcgcgctta      8100
atgcgccg                                                               8108
```

<210> SEQ ID NO 9
<211> LENGTH: 9237
<212> TYPE: DNA
<213> ORGANISM: Artificial Sequence
<220> FEATURE:
<223> OTHER INFORMATION: pAdTrack-CMV

<400> SEQUENCE: 9

```
tgttaacttg tttattgcag cttataatgg ttacaaataa agcaatagca tcacaaattt        60
cacaaataaa gcattttttt cactgcattc tagttgtggt ttgtccaaac tcatcaatgt       120
```

-continued

```
atcttaacgc ggaggtttat cgacgatctg ctagtgatta atagtaatca attacggggt      180
cattagttca tagcccatat atggagttcc gcgttacata acttacgta aatggcccgc       240 ctggctgacc gcccaacgac ccccgcccat tgacgtcaat aatgacgtat gttcccatag      300
taacgccaat agggactttc cattgacgtc aatgggtgga gtatttacgg taaactgccc      360
acttggcagt acatcaagtg tatcatatgc caagtacgcc ccctattgac gtcaatgacg      420
gtaaatggcc cgcctggcat tatgcccagt acatgacctt atgggacttt cctacttggc      480
agtacatcta cgtattagtc atcgctatta ccatggtgat gcggttttgg cagtacatca      540
atgggcgtgg atagcggttt gactcacggg gatttccaag tctccacccc attgacgtca      600
atgggagttt gttttggcac caaaatcaac gggactttcc aaaatgtcgt aacaactccg      660
ccccattgac gcaaatgggc ggtaggcgtg tacggtggga ggtctatata agcagagctg      720
gtttagtgaa ccgtcagatc cgctagcgct accggtcgcc accatggtga gcaagggcga      780
ggagctgttc accggggtgg tgcccatcct ggtcgagctg gacggcgacg taaacggcca      840
caagttcagc gtgtccggcg agggcgaggg cgatgccacc tacggcaagc tgaccctgaa      900
gttcatctgc accaccggca agctgcccgt gccctggccc accctcgtga ccaccctgac      960
ctacggcgtg cagtgcttca gccgctaccc cgaccacatg aagcagcacg acttcttcaa     1020
gtccgccatg cccgaaggct acgtccagga gcgcaccatc ttcttcaagg acgacggcaa     1080
ctacaagacc cgcgccgagg tgaagttcga gggcgacacc ctggtgaacc gcatcgagct     1140
gaagggcatc gacttcaagg aggacggcaa catcctgggg cacaagctgg agtacaacta     1200
caacagccac aacgtctata tcatggccga caagcagaag aacggcatca aggtgaactt     1260
caagatccgc cacaacatcg aggacggcag cgtgcagctc gccgaccact accagcagaa     1320
cacccccatc ggcgacggcc ccgtgctgct gcccgacaac cactacctga gcacccagtc     1380
cgccctgagc aaagacccca acgagaagcg cgatcacatg gtcctgctgg agttcgtgac     1440
cgccgccggg atcactctcg gcatggacga gctgtacaag tccggactca gatccaccgg     1500
atctagataa ctgatcataa tcagccatac cacatttgta gaggttttac ttgctttaaa     1560
aaacctccca cacctccccc tgaacctgaa acataaaatg aatgcaattg ttgttgttaa     1620
cttgtttatt gcagcttata atggttacaa ataaagcaat agcatcacaa atttcacaaa     1680
taaagcattt ttttcactgc attctagttg tggtttgtcc aaactcatca atgtatctta     1740
acgcgatcaa gctagcttgc tagactcgac tgactataat aataaaacgc caactttgac     1800
ccggaacgcg gaaaacacct gagaaaaaca cctgggcgag tctccacgta aacggtcaaa     1860
gtccccgcgg ccctagacaa atattacgcg ctatgagtaa cacaaaatta ttcagatttc     1920
acttcctctt attcagtttt cccgcgaaaa tggccaaatc ttactcggtt acgcccaaat     1980
ttactacaac atccgcctaa aaccgcgcga aaattgtcac ttcctgtgta caccggcgca     2040
caccaaaaac gtcactttg ccacatccgt cgcttacatg tgttccgcca cacttgcaac     2100
atcacacttc cgccacacta ctacgtcacc cgccccgttc ccacgccccg cgccacgtca     2160
caaactccac cccctcatta tcatattggc ttcaatccaa aataaggtat attattgatg     2220
atgttaatta agaattaatt cgatcctgaa tggcgaatgg acgcgccctg tagcggcgca     2280
ttaagcgcgg cgggtgtggt ggttacgcgc agcgtgaccg ctacacttgc cagcgcccta     2340
gcgcccgctc ctttcgcttt cttcccttcc tttctcgcca cgttcgccgg ctttccccgt     2400
caagctctaa atcgggggct ccctttaggg ttccgattta gtgctttacg gcacctcgac     2460
```

-continued

```
cccaaaaaac ttgattaggg tgatggttca cgtagtgggc catcgccctg atagacggtt      2520
tttcgccctt tgacgttgga gtccacgttc tttaatagtg gactcttgtt ccaaactgga      2580
acaacactca accctatctc ggtctattct tttgatttat aagggatttt gccgatttcg      2640
gcctattggt taaaaaatga gctgatttaa caaaaatttt aacaaaattc agaagaactc      2700
gtcaagaagg cgatagaagg cgatgcgctg cgaatcggga gcggcgatac cgtaaagcac      2760
gaggaagcgg tcagcccatt cgccgccaag ctcttcagca atatcacggg tagccaacgc      2820
tatgtcctga tagcggtccg ccacacccag ccggccacag tcgatgaatc cagaaaagcg      2880
gccattttcc accatgatat tcggcaagca ggcatcgcca tgggtcacga cgagatcctc      2940
gccgtcgggc atgctcgcct tgagcctggc gaacagttcg gctggcgcga gcccctgatg      3000
ctcttcgtcc agatcatcct gatcgacaag accggcttcc atccgagtac gtgctcgctc      3060
gatgcgatgt ttcgcttggt ggtcgaatgg gcaggtagcc ggatcaagcg tatgcagccg      3120
ccgcattgca tcagccatga tggatacttt ctcggcagga gcaaggtgag atgacaggag      3180
atcctgcccc ggcacttcgc ccaatagcag ccagtccctt cccgcttcag tgacaacgtc      3240
gagcacagct gcgcaaggaa cgcccgtcgt ggccagccac gatagccgcg ctgcctcgtc      3300
ttgcagttca ttcagggcac cggacaggtc ggtcttgaca aaaagaaccg ggcgcccctg      3360
cgctgacagc cggaacacgg cggcatcaga gcagccgatt gtctgttgtg cccagtcata      3420
gccgaatagc ctctccaccc aagcggccgg agaacctgcg tgcaatccat cttgttcaat      3480
catgcgaaac gatcctcatc ctgtctcttg atcagagctt gatcccctgc gccatcagat      3540
ccttggcggc aagaaagcca tccagtttac tttgcagggc ttcccaacct taccagaggg      3600
cgccccagct ggcaattccg gttcgcttgc tgtccataaa accgcccagt ctagctatcg      3660
ccatgtaagc ccactgcaag ctacctgctt tctctttgcg cttgcgtttt cccttgtcca      3720
gatagcccag tagctgacat tcatccgggg tcagcaccgt ttctgcggac tggctttcta      3780
cgtgaaaagg atctaggtga agatcctttt tgataatctc atggctgcag caatggcaac      3840
aacgttgcgc aaactattaa ctggcgaact acttactcta gcttcccggc aacaattaat      3900
agactggatg gaggcggata aagttgcagg accacttctg cgctcggccc ttccggctgg      3960
ctggtttatt gctgataaat ctggagccgg tgagcgtggg tctcgcggta tcattgcagc      4020
actggggcca gatggtaagc cctcccgtat cgtagttatc tacacgacgg ggagtcaggc      4080
aactatggat gaacgaaata gacagatcgc tgagataggt gcctcactga ttaagcattg      4140
gtaactgtca gaccaagttt actcatatat actttagatt gatttaaaac ttcattttta      4200
atttaaaagg atctaggtga agatcctttt tgataatctc atgaccaaaa tcccttaacg      4260
tgagttttcg ttccactgag cgtcagaccc cgtagaaaag atcaaaggat cttcttgaga      4320 tcctttttttc tgcgcgtaa tctgctgctt gcaaacaaaa aaaccaccgc taccagcggt      4380
ggtttgtttg ccggatcaag agctaccaac tctttttccg aaggtaactg gcttcagcag      4440
agcgcagata ccaaatactg tccttctagt gtagccgtag ttaggccacc acttcaagaa      4500
ctctgtagca ccgcctacat acctcgctct gctaatcctg ttaccagtgg ctgctgccag      4560
tggcgataag tcgtgtctta ccgggttgga ctcaagacga tagttaccgg ataaggcgca      4620
gcggtcgggc tgaacggggg gttcgtgcac acagcccagc ttggagcgaa cgacctacac      4680
cgaactgaga tacctacagc gtgagctatg agaaagcgcc acgcttcccg aagggagaaa      4740
ggcggacagg tatccggtaa gcggcagggt cggaacagga gagcgcacga gggagcttcc      4800 aggggggaaac gcctggtatc tttatagtcc tgtcgggttt cgccacctct gacttgagcg      4860
```

-continued

```
tcgatttttg tgatgctcgt cagggggcg gagcctatgg aaaaacgcca gcaacgcggc     4920 cttttacgg ttcctggcct tttgctggcc ttttgctcac atgttctttc ctgcgttatc      4980
ccctgattct gtggataacc gtattaccgc ctttgagtga gctgataccg ctcgccgcag      5040
ccgaacgacc gagcgcagcg agtcagtgag cgaggaagcg gaagagcgcc tgatgcggta      5100
ttttctcctt acgcatctgt gcggtatttc acaccgcata tggatccatg catgttaatt     5160
aacatcatca ataatatacc ttattttgga ttgaagccaa tatgataatg aggggtggga     5220
gtttgtgacg tggcgcgggg cgtgggaacg gggcgggtga cgtaggtttt agggcggagt      5280
aacttgtatg tgttgggaat tgtagttttc ttaaaatggg aagtgacgta acgtgggaaa      5340
acggaagtga cgatttgagg aagttgtggg tttttttggct ttcgtttctg ggcgtaggtt     5400
cgcgtgcggt tttctgggtg tttttgtgg actttaaccg ttacgtcatt tttagtcct       5460 atatatactc gctctgcact tggcccttt ttacactgtg actgattgag ctggtgccgt       5520
gtcgagtggt gtttttttaa taggtttct tttttactgg taaggctgac tgttatggct      5580
gccgctgtgg aagcgctgta tgttgttctg gagcgggagg gtgctatttt gcctaggcag     5640 gagggtttt caggtgttta tgtgtttttc tctcctatta attttgttat acctcctatg      5700
ggggctgtaa tgttgtctct acgcctgcgg gtatgtattc ccccgggcta tttcggtcgc     5760
tttttagcac tgaccgatgt gaatcaacct gatgtgttta ccgagtctta cattatgact      5820
ccggacatga ccgaggagct gtcggtggtg cttttttaatc acggtgacca gttttttttac    5880 ggtcacgccg gcatggccgt agtccgtctt atgcttataa gggttgtttt tcctgttgta      5940
agacaggctt ctaatgttta aatgtttttt tgttatttta ttttgtgttt atgcagaaac      6000
ccgcagacat gtttgagaga aaaatggtgt cttttttctgt ggtggttccg gagcttacct     6060
gcctttatct gcatgagcat gactacgatg tgctttcttt tttgcgcgag gctttgcctg      6120 atttttttgag cagcaccttg cattttatat cgccgcccat gcaacaagct attgaattcg     6180
tttaaactcc ctctcaagtc tgtatacggg gacacggaca gccttttcgt caccgagcgt      6240
ggacaccggc tcatggaaac cagaggtaag aaacgcatca aaaagcatgg gggaaacctg      6300 gttttttgacc ccgaacggcc agagctcacc tggctcgtgg aatgcgagac cgtctgcggg     6360
gcctgcggcg cggatgccta ctccccggaa tcggtatttc tcgcgcccaa gctctacgcc      6420
ctcaaaagtc tgcactgccc ctcgtgcggc gcctcctcca agggcaagct gcgcgccaag      6480
ggccacgccg cggaggggct ggactatgac accatggtca aatgctacct ggccgacgcg      6540
cagggcgaag accggcagcg cttcagcacc agcaggacca gcctcaagcg caccctggcc     6600
agcgcgcagc ccggagcgca ccccttcacc gtgacccaga ctacgctgac gaggaccctg      6660
cgcccgtgga aagacatgac cctggcccgt ctggacgagc accgactact gccgtacagc      6720
gaaagccgcc ccaacccgcg aaacgaggag atatgctgga tcgagatgcc gtagagcagg      6780
tgaccgagct gtgggaccgc ctggaactgc ttggtcaaac gctcaaaagc atgcctacgg      6840
cggacggtct caaaccgttg aaaaactttg cttccttgca agaactgcta tcgctgggcg      6900
gcgagcgcct tctggcggat ttggtcaggg aaaacatgcg agtcagggac atgcttaacg     6960
aagtggcccc cctgctcagg gatgacggca gctgcagctc tcttaactac cagttgcagc      7020
cggtaatagg tgtgatttac gggcccaccg gctgcggtaa gtcgcagctg ctcaggaacc     7080
tgctttcttc ccagctgatc tccctaccc cggaaaccgt tttcttcatc gccccgcagg       7140
tagacatgat cccccatct gaactcaaag cgtgggaaat gcaaatctgt gagggtaact       7200
```

-continued

```
acgcccctgg gccggatgga accattatac cgcagtctgg caccctccgc ccgcgctttg       7260
taaaaatggc ctatgacgat ctcatcctgg aacacaacta tgacgttagt gatcccagaa       7320
atatcttcgc ccaggccgcc gcccgtgggc ccattgccat cattatggac gaatgcatgg       7380
aaaatcttgg aggtcacaag ggcgtctcca agttcttcca cgcatttcct tctaagctac       7440
atgacaaatt tcccaagtgc accggataca ctgtgctggt ggttctgcac aacatgaatc       7500
cccggaggga tatggctggg aacatagcca acctaaaaat acagtccaag atgcatctca       7560
tatccccacg tatgcaccca tcccagctta accgctttgt aaacacttac accaagggcc       7620
tgcccctggc aatcagcttg ctactgaaag acatttttag gcaccacgcc cagcgctcct       7680
gctacgactg gatcatctac aacaccaccc cgcagcatga agctctgcag tggtgctacc       7740 tccacccag agacgggctt atgcccatgt atctgaacat ccagagtcac ctttaccacg       7800
tcctggaaaa aatacacagg accctcaacg accgagaccg ctggtcccgg gcctaccgcg       7860
cgcgcaaaac ccctaaataa agacagcaag acacttgctt gatccaaatc caaacagagt       7920
ctggtttttt atttatgttt taaaccgcat tgggagggga ggaagccttc agggcagaaa       7980
cctgctggcg cagatccaac agctgctgag aaacgacatt aagttcccgg gtcaaagaat       8040
ccaattgtgc caaaagagcc gtcaacttgt catcgcgggc ggatgaacgg gaagctgcac       8100
tgcttgcaag cgggctcagg aaagcaaagt cagtcacaat cccgcgggcg gtggctgcag       8160
cggctgaagc ggcggcggag gctgcagtct ccaacgcgcgt tccagacacg gtctcgtagg       8220
tcaaggtagt agagtttgcg ggcaggacgg ggcgaccatc aatgctggag cccatcacat       8280
tctgacgcac cccggcccat gggggcatgc gcgttgtcaa atatgagctc acaatgcttc       8340
catcaaacga gttggtgctc atggcggcgg cggctgctgc aaaacagata caaaactaca       8400 taagacccccc accttatata ttctttccca cccttaacca cgcccagatc ctctagcagt       8460
gataaacgtc taatagtaat caattacggg gtcattagtt catagcccat atatggagtt       8520
ccgcgttaca taacttacgg taaatggccc gcctggctga ccgcccaacg accccccgccc       8580 attgacgtca ataatgacgt atgttcccat agtaacgcca atagggactt tccattgacg       8640
tcaatgggtg gagtatttac ggtaaactgc ccacttggca gtacatcaag tgtatcatat       8700
gccaagtacg ccccctattg acgtcaatga cggtaaatgg cccgcctggc attatgccca       8760
gtacatgacc ttatgggact ttcctacttg gcagtacatc tacgtattag tcatcgctat       8820
taccatggtg atgcggtttt ggcagtacat caatgggcgt ggatagcggt ttgactcacg       8880
gggatttcca agtctccacc ccattgacgt caatgggagt ttgttttggc accaaaatca       8940
acgggacttt ccaaaatgtc gtaacaactc cgccccattg acgcaaatgg gcggtaggcg       9000
tgtacggtgg gaggtctata taagcagagc tggtttagtg aaccgtcaga tccgctagag       9060
atctggtacc gtcgacgcgg ccgctcgagc ctaagcttct agataagata tccgatccac       9120
cggatctaga taactgatca taatcagcca taccacattt gtagaggttt tacttgcttt       9180
aaaaaacctc ccacacctcc ccctgaacct gaaacataaa atgaatgcaa ttgttgt        9237
```

<210> SEQ ID NO 10
<211> LENGTH: 7658
<212> TYPE: DNA
<213> ORGANISM: Artificial Sequence
<220> FEATURE:
<223> OTHER INFORMATION: pZB3 AAV dSaCas9

<400> SEQUENCE: 10

```
aaaacctctg acacatgcag ctcccggaga cggtcacagc ttgtctgtaa gcggatgccg       60
```

-continued

```
ggagcagaca agcccgtcag ggcgcgtcag cgggtgttgg cgggtgtcgg ggctggctta      120
actatgcggc atcagagcag attgtactga gagtgcacca taaaattgta aacgttaata      180
ttttgttaaa attcgcgtta aatttttgtt aaatcagctc attttttaac caatagaccg      240
aaatcggcaa aatcccttat aaatcaaaag aatagcccga gatagagttg agtgttgttc      300
cagtttggaa caagagtcca ctattaaaga acgtggactc caacgtcaaa gggcgaaaaa      360
ccgtctatca gggcgatggc ccactacgtg aaccatcacc caaatcaagt ttttgggggt      420
cgaggtgccg taaagcacta aatcggaacc ctaaagggag cccccgattt agagcttgac      480
ggggaaagcc ggcgaacgtg gcgagaaagg aagggaagaa agcgaaagga gcgggcgcta      540
aggcgctggc aagtgtagcg gtcacgctgc gcgtaaccac cacacccgcc gcgcttaatg      600
cgccgctaca gggcgcgtac tatggttgct ttgacgtatg cggtgtgaaa taccgcacag      660
atgcgtaagg agaaaatacc gcatcaggcg cccctgcagg cagctgcgcg ctcgctcgct      720
cactgaggcc gcccgggcaa agcccgggcg tcgggcgacc tttggtcgcc cggcctcagt      780
gagcgagcga gcgcgcagag agggagtggc caactccatc actaggggtt cctgcggccg      840
cgagggccta tttcccatga ttccttcata tttgcatata cgatacaagg ctgttagaga      900
gataattgga attaatttga ctgtaaacac aaagatatta gtacaaaata cgtgacgtag      960
aaagtaataa tttcttgggt agtttgcagt tttaaaatta tgttttaaaa tggactatca     1020
tatgcttacc gtaacttgaa agtatttcga tttcttggct ttatatatct tgtggaaagg     1080
acgaaacacc gggagaccac ggcaggtctc agttttagta ctctggaggc caacatgagg     1140
atcacccatg tctgcagggc caacagaatc tactaaaaca aggcaaaatg ccgtgtttat     1200
ctcgtcaact tgttggcgag attttttttgg ccgcctcgag gtacttatat aaggggggtgg     1260 gggcgcgttc gtcctcagtc gcgatcgaac actcgagccg agcagacgtg cctacggacc     1320
gaccggtgcc accatggccc caaagaagaa gcggaaggtc ggtatccacg gagtcccagc     1380
agccaagcgg aactacatcc tgggcctggc catcggcatc accagcgtgg gctacggcat     1440
catcgactac gagacacggg acgtgatcga tgccggcgtg cggctgttca aagaggccaa     1500
cgtggaaaac aacgagggca ggcggagcaa gagaggcgcc agaaggctga agcggcggag     1560
gcggcataga atccagagag tgaagaagct gctgttcgac tacaacctgc tgaccgacca     1620
cagcgagctg agcggcatca acccctacga ggccagagtg aagggcctga ccagaagct     1680 gagcgaggaa gagttctctg ccgccctgct gcacctggcc aagagaagag gcgtgcacaa     1740
cgtgaacgag gtgaagagg acaccggcaa cgagctgtcc accaaagagc agatcagccg     1800
gaacagcaag gccctggaag agaaatacgt ggccgaactg cagctggaac ggctgaagaa     1860
agacggcgaa gtgcggggca gcatcaacag attcaagacc agcgactacg tgaaagaagc     1920
caaacagctg ctgaaggtgc agaaggccta ccaccagctg gaccagagct tcatcgacac     1980
ctacatcgac ctgctggaaa cccggcggac ctactatgag ggacctggcg agggcagccc     2040
cttcggctgg aaggacatca agaatggta cgagatgctg atgggccact gcacctactt     2100
ccccgaggaa ctgcggagcg tgaagtacgc ctacaacgcc gacctgtaca acgccctgaa     2160
cgacctgaac aatctcgtga tcaccaggga cgagaacgag aagctggaat attacgagaa     2220
gttccagatc atcgagaacg tgttcaagca gaagaagaag cccaccctga gcagatcgc     2280 caaagaaatc ctcgtgaacg aagaggatat taagggctac agagtgacca gcaccggcaa     2340
gcccgagttc accaacctga aggtgtacca cgacatcaag gacattaccg cccggaaaga     2400
```

-continued

```
gattattgag aacgccgagc tgctggatca gattgccaag atcctgacca tctaccagag       2460
cagcgaggac atccaggaag aactgaccaa tctgaactcc gagctgaccc aggaagagat       2520
cgagcagatc tctaatctga agggctatac cggcacccac aacctgagcc tgaaggccat       2580
caacctgatc ctggacgagc tgtggcacac caacgacaac cagatcgcta tcttcaaccg       2640
gctgaagctg gtgcccaaga aggtggacct gtcccagcag aaagagatcc ccaccaccct       2700
ggtggacgac ttcatcctga gccccgtcgt gaagagaagc ttcatccaga gcatcaaagt       2760
gatcaacgcc atcatcaaga agtacggcct gcccaacgac atcattatcg agctggcccg       2820
cgagaagaac tccaaggacg cccagaaaat gatcaacgag atgcagaagc ggaaccggca       2880
gaccaacgag cggatcgagg aaatcatccg gaccaccggc aaagagaacg ccaagtacct       2940
gatcgagaag atcaagctgc acgacatgca ggaaggcaag tgcctgtaca gcctggaagc       3000
catccctctg gaagatctgc tgaacaaccc cttcaactat gaggtggacc acatcatccc       3060
cagaagcgtg tccttcgaca acagcttcaa caacaaggtg ctcgtgaagc aggaagaagc       3120
cagcaagaag ggcaaccgga ccccattcca gtacctgagc agcagcgaca gcaagatcag       3180
ctacgaaacc ttcaagaagc acatcctgaa tctggccaag ggcaagggca gaatcagcaa       3240
gaccaagaaa gagtatctgc tggaagaacg ggacatcaac aggttctccg tgcagaaaga       3300
cttcatcaac cggaacctgg tggataccag atacgccacc agaggcctga tgaacctgct       3360
gcggagctac ttcagagtga caacctggga cgtgaaagtg aagtccatca tggcggctt       3420 caccagcttt ctgcggcgga gtggaagtt taagaaagag cggaacaagg ggtacaagca       3480
ccacgccgag gacgccctga tcattgccaa cgccgatttc atcttcaaag agtggaagaa       3540
actggacaag gccaaaaaag tgatggaaaa ccagatgttc gaggaaaagc aggccgagag       3600
catgcccgag atcgaaaccg agcaggagta caaagagatc ttcatcaccc cccaccagat       3660
caagcacatt aaggacttca aggactacaa gtacagccac cgggtggaca agaagcctaa       3720
tagagagctg attaacgaca ccctgtactc caccccggaag gacgacaagg gcaacaccct       3780
gatcgtgaac aatctgaacg gcctgtacga caaggacaat gacaagctga aaaagctgat       3840
caacaagagc cccgaaaagc tgctgatgta ccaccacgac ccccagacct accagaaact       3900
gaagctgatt atggaacagt acggcgacga gaagaatccc ctgtacaagt actacgagga       3960
aaccgggaac tacctgacca gtactccaa aaaggacaac ggccccgtga tcaagaagat       4020
taagtattac ggcaacaaac tgaacgccca tctggacatc accgacgact accccaacag       4080
cagaaacaag gtcgtgaagc tgtccctgaa gcccctacaga ttcgacgtgt acctggacaa       4140
tggcgtgtac aagttcgtga ccgtgaagaa tctggatgtg atcaaaaaag aaaactacta       4200
cgaagtgaat agcaagtgct atgaggaagc taagaagctg aagaagatca gcaaccaggc       4260
cgagtttatc gcctccttct acaacaacga tctgatcaag atcaacggcg agctgtatag       4320
agtgatcggc gtgaacaacg acctgctgaa ccggatcgaa gtgaacatga tcgacatcac       4380
ctaccgcgag tacctggaaa acatgaacga caagaggccc cccaggatca ttaagacaat       4440
cgcctccaag acccagagca ttaagaagta cagcacagac attctgggca acctgtatga       4500
agtgaaatct aagaagcacc ctcagatcat caaaaagggc aaaaggccgg cggccacgaa       4560
aaaggccggc caggcaaaaa agaaaaaggg gatccgaggcc agcggttccg gacgggctga       4620
cgcattggac gattttgatc tggatatgct gggaagtgac gccctcgatg attttgacct       4680
tgacatgctt ggttcggatg cccttgatga ctttgacctc gacatgctcg gcagtgacgc       4740
ccttgatgat ttcgacctgg acatgctgat taactctaga agttccggat ctccgaaaaa       4800
```

-continued

```
gaaacgcaaa gttggttcgg gaggtggttc gggtggctct ggatcagtgc tgcctcaggc    4860
tcctgctcct gcaccagctc cagccatggt gtctgcactg gctcaggcac cagcacccgt    4920
gcctgtgctg gctcctggac ctccacaggc tgtggctcca ccagccccta aacctacaca    4980
ggccggcgag ggcacactgt ctgaagctct gctgcagctg cagttcgacg acgaggatct    5040
gggagccctg ctgggaaaca gcaccgatcc tgccgtgttc accgacctgg ccagcgtgga    5100
caacagcgag ttccagcagc tgctgaacca gggcatccct gtggccctc acaccaccga    5160 gcccatgctg atggaatacc ccgaggccat caccGGCtc gtgacaggcg ctcagaggcc    5220
tcctgatcca gctcctgccc ctctgggagc accaggcctg cctaatggac tgctgtctgg    5280
cgacgaggac ttcagctcta tcgccgatat ggatttctca gccttgctgt caggcggtgg    5340
tagtggtggg agcggtagtg acctttccca tccgccccca aggggccatc tggatgagct    5400
gacaaccaca cttgagtcca tgaccgagga tctgaacctg gactcacccc tgaccccgga    5460
attgaacgag attctggata ccttcctgaa cgacgagtgc ctcttgcatg ccatgcatat    5520
cagcacagga ctgtccatct tcgacacatc tctgttttag gaattcaaat aaaatacgaa    5580
atgaaataaa atacgaaatg caattgggcc gcaggaaccc ctagtgatgg agttggccac    5640
tccctctctg cgcgctcgct cgctcactga ggccgggcga ccaaaggtcg cccgacgccc    5700
gggctttgcc cgagcggcct cagtgagcga gcgagcgcgc agctgcctgc aggacatgtg    5760
agcaaaaggc cagcaaaagg ccaggaaccg taaaaaggcc gcgttgctgg cgttttttcca   5820 taggctccgc cccctgacg agcatcacaa aaatcgacgc tcaagtcaga ggtggcgaaa     5880
cccgacagga ctataaagat accaggcgtt ccccctgga agctccctcg tgcgctctcc     5940
tgttccgacc ctgccgctta ccggatacct gtccgccttt ctcccttcgg gaagcgtggc    6000
gctttctcat agctcacgct gtaggtatct cagttcggtg taggtcgttc gctccaagct    6060
gggctgtgtg cacgaacccc ccgttcagcc cgaccgctgc gccttatccg gtaactatcg    6120
tcttgagtcc aacccggtaa gacacgactt atcgccactg gcagcagcca ctggtaacag    6180
gattagcaga gcgaggtatg taggcggtgc tacagagttc ttgaagtggt ggcctaacta    6240
cggctacact agaagaacag tatttggtat ctgcgctctg ctgaagccag ttaccttcgg    6300
aaaaagagtt ggtagctctt gatccggcaa acaaaccacc gctggtagcg gtggtttttt    6360
tgtttgcaag cagcagatta cgcgcagaaa aaaaggatct caagaagatc ctttgatctt    6420
ttctacgggg tctgacgctc agtggaacga aaactcacgt taagggattt tggtcatgag    6480
attatcaaaa aggatcttca cctagatcct tttaaattaa aaatgaagtt ttaaatcaat    6540
ctaaagtata tatgagtaaa cttggtctga cagttaccaa tgcttaatca gtgaggcacc    6600
tatctcagcg atctgtctat ttcgttcatc catagttgcc tgactccccg tcgtgtagat    6660
aactacgata cgggagggct taccatctgg ccccagtgct gcaatgatac cgcggcttcc    6720
acgctcaccg gctccagatt tatcagcaat aaaccagcca gccggaaggg ccgagcgcag    6780
aagtggtcct gcaactttat ccgcctccat ccagtctatt aattgttgcc gggaagctag    6840
agtaagtagt tcgccagtta atagtttgcg caacgttgtt gccattgcta caggcatcgt    6900
ggtgtcacgc tcgtcgtttg gtatggcttc attcagctcc ggttcccaac gatcaaggcg    6960
agttacatga tcccccatgt tgtgcaaaaa agcggttagc tccttcggtc ctccgatcgt    7020
tgtcagaagt aagttggccg cagtgttatc actcatggtt atggcagcac tgcataattc    7080
tcttactgtc atgccatccg taagatgctt ttctgtgact ggtgagtact caaccaagtc    7140
```

-continued

```
attctgagaa tagtgtatgc ggcgaccgag ttgctcttgc ccggcgtcaa tacgggataa    7200
taccgcgcca catagcagaa ctttaaaagt gctcatcatt ggaaaacgtt cttcggggcg    7260
aaaactctca aggatcttac cgctgttgag atccagttcg atgtaaccca ctcgtgcacc    7320
caactgatct tcagcatctt ttactttcac cagcgtttct gggtgagcaa aaacaggaag    7380
gcaaaatgcc gcaaaaaagg gaataagggc gacacggaaa tgttgaatac tcatactctt    7440 ccttttttcaa tattattgaa gcatttatca gggttattgt ctcatgagcg gatacatatt   7500
tgaatgtatt tagaaaaata aacaaatagg ggttccgcgc acatttcccc gaaaagtgcc    7560
acctgacgtc taagaaacca ttattatcat gacattaacc tataaaaata ggcgtatcac    7620
gaggcccttt cgtctcgcgc gtttcggtga tgacggtg                             7658
```

<210> SEQ ID NO 11
<211> LENGTH: 6668
<212> TYPE: DNA
<213> ORGANISM: Artificial Sequence
<220> FEATURE:
<223> OTHER INFORMATION: pGW047

<400> SEQUENCE: 11

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgttctag aaagagggcc tatttcccat     180
gattccttca tatttgcata tacgatacaa ggctgttaga gagataattg gaattaattt     240
gactgtaaac acaagatat tagtacaaaa tacgtgacgt agaaagtaat aatttcttgg      300
gtagtttgca gttttaaaat tatgttttaa aatggactat catatgctta ccgtaacttg     360
aaagtatttc gatttcttgg ctttatatat cttgtggaaa ggacgaaaca ccggaagagc     420
gagctcttct gtttagtac tctggaggcc aacatgagga tcacccatgt ctgcagggcc      480
aacagaatct actaaaacaa ggcaaaatgc cgtgtttatc tcgtcaactg gccaacatga     540
ggatcaccca tgtctgcagg gcctgttggc gagatttttt tgctagctgc aaagatggat     600
aaagttttaa acagagagga atctttgcag ctaatggacc ttctaggtct tgaaaggagt     660
gggaattggc tccggtgccc gtcagtgggc agagcgcaca tcgcccacag tccccgagaa     720 gttggggggga ggggtcggca attgaaccgg tgcctagaga aggtggcgcg gggtaaactg     780
ggaaagtgat gtcgtgtact ggctccgcct ttttcccgag ggtgggggag aaccgtatat     840
aagtgcagta gtcgccgtga cgttcttttt tcgcaacggg tttgccgcca gaacacaggt     900
aagtgccgtg tgtggttccc gcgggcctgg cctctttacg ggttatggcc cttgcgtgcc     960
ttgaattact tccacctggc tgcagtacgt gattcttgat cccgagcttc gggttggaag    1020
tgggtgggag agttcgaggc cttgcgctta aggagcccct tcgcctcgtg cttgagttga    1080
ggcctggcct gggcgctggg ccgccgcgt gcgaatctgg tggcaccttc gcgcctgtct     1140
cgctgctttc gataagtctc tagccattta aaattttga tgacctgctg cgacgctttt     1200
tttctggcaa gatagtcttg taaatgcggg ccaagatctg cacactggta tttcggtttt    1260
tggggccgcg ggcggcgacg gggcccgtgc gtcccagcgc acatgttcgg cgaggcgggg    1320
cctgcgagcg cggccaccga gaatcggacg ggggtagtct caagctggcc ggcctgctct    1380
ggtgcctggc ctcgcgccgc cgtgtatcgc cccgccctgg gcggcaaggc tggcccggtc    1440
ggcaccagtt gcgtgagcgg aaagatggcc gcttcccggc cctgctgcag ggagctcaaa    1500
atgaaggacg cggcgctcgg gagagcgggc gggtgagtca cccacacaaa ggaaaagggc    1560
```

```
ctttccgtcc tcagccgtcg cttcatgtga ctccacggag taccgggcgc cgtccaggca    1620
cctcgattag ttctcgagct tttggagtac gtcgtcttta ggttgggggg aggggtttta    1680
tgcgatggag tttccccaca ctgagtgggt ggagactgaa gttaggccag cttggcactt    1740
gatgtaattc tccttggaat ttgccctttt tgagtttgga tcttggttca ttctcaagcc    1800
tcagacagtg gttcaaagtt tttttcttcc atttcaggtg tcgtgacgta cggccaccat    1860
ggcttcaaac tttactcagt tcgtgctcgt ggacaatggt gggacagggg atgtgacagt    1920
ggctccttct aatttcgcta atggggtggc agagtggatc agctccaact cacggagcca    1980
ggcctacaag gtgacatgca gcgtcaggca gtctagtgcc cagaagagaa agtataccat    2040
caaggtggag gtccccaaag tggctaccca gacagtgggc ggagtcgaac tgcctgtcgc    2100
cgcttggagg tcctacctga acatggagct cactatccca attttcgcta ccaattctga    2160
ctgtgaactc atcgtgaagg caatgcaggg gctcctcaaa gacggtaatc ctatcccttc    2220
cgccatcgcc gctaactcag gtatctacag cgctggagga ggtggaagcg gaggaggagg    2280
aagcggagga ggaggtagcg gacctaagaa aaagaggaag gtggcggccg ctggatcccc    2340
ttcagggcag atcagcaacc aggccctggc tctggcccct agctccgctc cagtgctggc    2400
ccagactatg gtgccctcta gtgctatggt gcctctggcc cagccacctg ctccagcccc    2460
tgtgctgacc ccaggaccac cccagtcact gagcgctcca gtgcccaagt ctacacaggc    2520
cggcgagggg actctgagtg aagctctgct gcacctgcag ttcgacgctg atgaggacct    2580
gggagctctg ctggggaaca gcaccgatcc cggagtgttc acagatctgg cctccgtgga    2640
caactctgag tttcagcagc tgctgaatca gggcgtgtcc atgtctcata gtacagccga    2700
accaatgctg atggagtacc ccgaagccat taccccggctg gtgaccggca gccagcggcc    2760
ccccgacccc gctccaactc ccctgggaac cagcggcctg cctaatgggc tgtccggaga    2820
tgaagacttc tcaagcatcg ctgatatgga ctttagtgcc ctgctgtcac agatttcctc    2880
tagtgggcag ggaggaggtg gaagcggctt cagcgtggac accagtgccc tgctggacct    2940
gttcagcccc tcggtgaccg tgcccgacat gagcctgcct gaccttgaca gcagcctggc    3000
cagtatccaa gagctcctgt ctccccagga gccccccagg cctcccgagg cagagaacag    3060
cagcccggat tcagggaagc agctggtgca ctacacagcg cagccgctgt tcctgctgga    3120
ccccggctcc gtggacaccg ggagcaacga cctgccggtg ctgtttgagc tgggagaggg    3180
ctcctacttc tccgaagggg acggcttcgc cgaggacccc accatctccc tgctgacagg    3240
ctcggagcct cccaaagcca aggaccccac tgtctcctaa gaattcacgc gttaagtcga    3300
caatcaacct ctggattaca aaatttgtga agattgact ggtattctta actatgttgc    3360
tccttttacg ctatgtggat acgctgcttt aatgcctttg tatcatgcta ttgcttcccg    3420
tatggctttc attttctcct ccttgtataa atcctggttg ctgtctcttt atgaggagtt    3480
gtggcccgtt gtcaggcaac gtggcgtggt gtgcactgtg tttgctgacg caaccccccac    3540 tggttggggc attgccacca cctgtcagct cctttccggg actttcgctt tccccctccc    3600
tattgccacg gcggaactca tcgccgcctg ccttgcccgc tgctggacag gggctcggct    3660
gttgggcact gacaattccg tggtgttgtc ggggaaatca tcgtcctttc cttggctgct    3720
cgcctgtgtt gccacctgga ttctgcgcgg gacgtccttc tgctacgtcc cttcggccct    3780
caatccagcg gaccttcctt cccgcggcct gctgccggct ctgcggcctc ttccgcgtct    3840
tcgccttcgc cctcagacga gtcggatctc cctttgggcc gcctccccgc gtcgacttta    3900
```

-continued

```
agaccaatga cgtgcggacc gagcggccgc aggaacccct agtgatggag ttggccactc    3960
cctctctgcg cgctcgctcg ctcactgagg ccgggcgacc aaaggtcgcc cgacgcccgg    4020
gctttgcccg ggcggcctca gtgagcgagc gagcgcgcag ctgcctgcag gggcgcctga    4080
tgcggtattt tctccttacg catctgtgcg gtatttcaca ccgcatacgt caaagcaacc    4140
atagtacgcg ccctgtagcg gcgcattaag cgcggcgggt gtggtggtta cgcgcagcgt    4200
gaccgctaca cttgccagcg ccctagcgcc cgctcctttc gctttcttcc cttcctttct    4260
cgccacgttc gccggctttc cccgtcaagc tctaaatcgg gggctccctt tagggttccg    4320
atttagtgct ttacggcacc tcgaccccaa aaaacttgat ttgggtgatg gttcacgtag    4380
tgggccatcg ccctgataga cggtttttcg ccctttgacg ttggagtcca cgttctttaa    4440
tagtggactc ttgttccaaa ctggaacaac actcaaccct atctcgggct attcttttga    4500
tttataaggg attttgccga tttcggccta ttggttaaaa aatgagctga tttaacaaaa    4560
atttaacgcg aattttaaca aaatattaac gtttacaatt ttatggtgca ctctcagtac    4620
aatctgctct gatgccgcat agttaagcca gccccgacac ccgccaacac ccgctgacgc    4680
gccctgacgg gcttgtctgc tcccggcatc cgcttacaga caagctgtga ccgtctccgg    4740
gagctgcatg tgtcagaggt tttcaccgtc atcaccgaaa cgcgcgagac gaaagggcct    4800
cgtgatacgc ctatttttat aggttaatgt catgataata atggtttctt agacgtcagg    4860
tggcactttt cggggaaatg tgcgcggaac ccctatttgt ttatttttct aaatacattc    4920
aaatatgtat ccgctcatga dacaataacc ctgataaatg cttcaataat attgaaaaag    4980
gaagagtatg agtattcaac atttccgtgt cgcccttatt cccttttttg cggcattttg    5040
ccttcctgtt tttgctcacc cagaaacgct ggtgaaagta aaagatgctg aagatcagtt    5100
gggtgcacga gtgggttaca tcgaactgga tctcaacagc ggtaagatcc ttgagagttt    5160
tcgccccgaa gaacgttttc caatgatgag cacttttaaa gttctgctat gtggcgcggt    5220
attatcccgt attgacgccg ggcaagagca actcggtcgc cgcatacact attctcagaa    5280
tgacttggtt gagtactcac cagtcacaga aaagcatctt acggatggca tgacagtaag    5340
agaattatgc agtgctgcca taaccatgag tgataacact gcggccaact tacttctgac    5400
aacgatcgga ggaccgaagg agctaaccgc ttttttgcac aacatggggg atcatgtaac    5460
tcgccttgat cgttgggaac cggagctgaa tgaagccata ccaaacgacg agcgtgacac    5520
cacgatgcct gtagcaatgg caacaacgtt gcgcaaacta ttaactggcg aactacttac    5580
tctagcttcc cggcaacaat taatagactg gatggaggcg gataaagttg caggaccact    5640
tctgcgctcg gcccttccgg ctggctggtt tattgctgat aaatctggag ccggtgagcg    5700
tgggtctcgc ggtatcattg cagcactggg gccagatggt aagccctccc gtatcgtagt    5760
tatctacacg acggggagtc aggcaactat ggatgaacga aatagacaga tcgctgagat    5820
aggtgcctca ctgattaagc attggtaact gtcagaccaa gtttactcat atatacttta    5880
gattgattta aaacttcatt tttaatttaa aaggatctag gtgaagatcc tttttgataa    5940
tctcatgacc aaaatccctt aacgtgagtt ttcgttccac tgagcgtcag accccgtaga    6000
aaagatcaaa ggatcttctt gagatccttt ttttctgcgc gtaatctgct gcttgcaaac    6060
aaaaaaacca ccgctaccag cggtggtttg tttgccggat caagagctac caactctttt    6120
tccgaaggta actggcttca gcagagcgca gataccaaat actgtccttc tagtgtagcc    6180
gtagttaggc caccacttca agaactctgt agcaccgcct acatacctcg ctctgctaat    6240
cctgttacca gtggctgctg ccagtggcga taagtcgtgt cttaccgggt tggactcaag    6300
```

-continued

```
acgatagtta ccggataagg cgcagcggtc gggctgaacg gggggttcgt gcacacagcc      6360
cagcttggag cgaacgacct acaccgaact gagatacct a cagcgtgagc tatgagaaag      6420
cgccacgctt cccgaaggga gaaaggcgga caggtatccg gtaagcggca gggtcggaac      6480
aggagagcgc acgagggagc ttccaggggg aaacgcctgg tatctttata gtcctgtcgg      6540
gtttcgccac ctctgacttg agcgtcgatt tttgtgatgc tcgtcagggg ggcggagcct      6600
atggaaaaac gccagcaacg cggcctttt acggttcctg ccttttgct ggcctttgc      6660 tcacatgt                                                              6668

<210> SEQ ID NO 12
<211> LENGTH: 7489
<212> TYPE: DNA
<213> ORGANISM: Artificial Sequence
<220> FEATURE:
<223> OTHER INFORMATION: pGW060

<400> SEQUENCE: 12
cctgcaggca gctgcgcgct cgctcgctca ctgaggccgc ccgggcgtcg ggcgaccttt       60
ggtcgcccgg cctcagtgag cgagcgagcg cgcagagagg gagtggccaa ctccatcact      120
aggggttcct gcggcctcta gaaaggatct gcgatcgctc cggtgcccgt cagtgggcag      180
agcgcacatc gcccacagtc cccgagaagt tggggggagg ggtcggcaat tgaacgggtg      240
cctagagaag gtggcgcggg gtaaactggg aaagtgatgt cgtgtactgg ctccgccttt      300
ttcccgaggg tggggagaa ccgtatataa gtgcagtagt cgccgtgaac gttcttttc      360 gcaacgggtt tgccgccaga acacagctga agcttcgagg ggctcgcatc tctccttcac      420
gcgcccgccg ccctacctga ggccgccatc cacgccggtt gagtgcgcgtt ctgccgcctc      480 ccgcctgtgg tgcctcctga actgcgtccg ccgtctaggt aagtttaaag ctcaggtcga      540
gaccgggcct ttgtccggcg ctcccttgga gcctacctag actcagccgg ctctccacgc      600
tttgcctgac cctgcttgct caactctacg tctttgtttc gttttctgtt ctgcgccgtt      660
acagatctgg ctaactaccg gtgccaccat ggccccaaag aagaagcgga aggtcggtat      720
ccacggagtc ccagcagcca agcggaacta catcctgggc ctggccatcg gcatcaccag      780
cgtgggctac ggcatcatcg actacgagac acgggacgtg atcgatgccg gcgtgcggct      840
gttcaaagag gccaacgtgg aaaacaacga gggcaggcgg agcaagagag cgccagaag      900 gctgaagcgg cggaggcggc atagaatcca gagagtgaag aagctgctgt tcgactacaa      960
cctgctgacc gaccacagcg agctgagcgg catcaacccc tacgaggcca gagtgaaggg     1020
cctgagccag aagctgagcg aggaagagtt ctctgccgcc ctgctgcacc tggccaagag     1080
aagaggcgtg cacaacgtga cgaggtgga agaggacacc ggcaacgagc tgtccaccaa     1140
agagcagatc agccggaaca gcaaggccct ggaagagaaa tacgtggccg aactgcagct     1200
ggaacggctg aagaaagacg cgaagtgcg gggcagcatc aacagattca gaccagcga     1260 ctacgtgaaa gaagccaaac agctgctgaa ggtgcagaag gcctaccacc agctggacca     1320
gagcttcatc gacacctaca tcgacctgct ggaaacccgg cggacctact atgagggacc     1380
tggcgagggc agccccttcg gctggaagga catcaaagaa tggtacgaga tgctgatggg     1440
ccactgcacc tacttccccg aggaactgcg gagcgtgaag tacgcctaca acgccgacct     1500
gtacaacgcc ctgaacgacc tgaacaatct cgtgatcacc agggacgaga acgagaagct     1560
ggaatattac gagaagttcc agatcatcga gaacgtgttc aagcagaaga agaagcccac     1620
```

-continued

```
cctgaagcag atcgccaaag aaatcctcgt gaacgaagag gatattaagg gctacagagt   1680
gaccagcacc ggcaagcccg agttcaccaa cctgaaggtg taccacgaca tcaaggacat   1740
taccgcccgg aaagagatta ttgagaacgc cgagctgctg gatcagattg ccaagatcct   1800
gaccatctac cagagcagcg aggacatcca ggaagaactg accaatctga actccgagct   1860
gacccaggaa gagatcgagc agatctctaa tctgaagggc tataccggca cccacaacct   1920
gagcctgaag gccatcaacc tgatcctgga cgagctgtgg cacaccaacg acaaccagat   1980
cgctatcttc aaccggctga agctggtgcc caagaaggtg gacctgtccc agcagaaaga   2040
gatccccacc accctggtgg acgacttcat cctgagcccc gtcgtgaaga gaagcttcat   2100
ccagagcatc aaagtgatca cgccatcat caagaagtac ggcctgccca cgacatcat   2160 tatcgagctg gcccgcgaga agaactccaa ggacgcccag aaaatgatca cgagatgca   2220 gaagcggaac cggcagacca acgagcggat cgaggaaatc atccggacca ccggcaaaga   2280
gaacgccaag tacctgatcg agaagatcaa gctgcacgac atgcaggaag gcaagtgcct   2340
gtacagcctg gaagccatcc ctctggaaga tctgctgaac aaccccttca actatgaggt   2400
ggaccacatc atccccagaa gcgtgtgctt cgacaacagc ttcaacaaca aggtgctcgt   2460
gaagcaggaa gaagccagca agaagggcaa ccggacccca ttccagtacc tgagcagcag   2520
cgacagcaag atcagctacg aaaccttcaa gaagcacatc ctgaatctgg ccaagggcaa   2580
gggcagaatc agcaagacca agaaagagta tctgctggaa gaacgggaca tcaacaggtt   2640
ctccgtgcag aaagacttca tcaaccggaa cctggtggat accagatacg ccaccagagg   2700
cctgatgaac ctgctgcgga gctacttcag agtgaacaac ctggacgtga agtgaagtc   2760 catcaatggc ggcttcacca gctttctgcg gcggaagtgg aagtttaaga aagagcggaa   2820
caaggggtac aagcaccacg ccgaggacgc cctgatcatt gccaacgccg atttcatctt   2880
caaagagtgg aagaaactgg acaaggccaa aaaagtgatg gaaaaccaga tgttcgagga   2940
aaagcaggcc gagagcatgc ccgagatcga aaccgagcag gagtacaaag agatcttcat   3000 cacccccccac cagatcaagc acattaagga cttcaaggac tacaagtaca gccaccgggt   3060
ggacaagaag cctaatagag agctgattaa cgacaccctg tactccaccc ggaaggacga   3120
caagggcaac accctgatcg tgaacaatct gaacggcctg tacgacaagg acaatgacaa   3180
gctgaaaaag ctgatcaaca agagccccga aaagctgctg atgtaccacc acgacccccca   3240 gacctaccag aaactgaagc tgattatgga acagtacggc gacgagaaga tcccctgta   3300 caagtactac gaggaaaccg ggaactacct gaccaagtac tccaaaaagg caacggccc   3360 cgtgatcaag aagattaagt attacggcaa caaactgaac gcccatctgg acatcaccga   3420
cgactacccc aacagcagaa acaaggtcgt gaagctgtcc ctgaagccct acagattcga   3480
cgtgtacctg gacaatggcg tgtacaagtt cgtgaccgtg aagaatctgg atgtgatcaa   3540
aaaagaaaac tactacgaag tgaatagcaa gtgctatgag gaagctaaga gctgaagaa   3600 gatcagcaac caggccgagt ttatcgcctc cttctacaac aacgatctga tcaagatcaa   3660
cggcgagctg tatagagtga tcggcgtgaa caacgacctg ctgaaccgga tcgaagtgaa   3720
catgatcgac atcacctacc gcgagtacct ggaaaacatg aacgacaaga gacccccag   3780 gatcattaag acaatcgcct ccaagacccca gagcattaag aagtacagca cagacattct   3840
gggcaacctg tatgaagtga aatctaagaa gcaccctcag atcatcaaaa agggcaaaag   3900
gccggcggcc acgaaaaagg ccggccaggc aaaaaagaaa aagggatccg acgggctga   3960 cgcattggac gattttgatc tggatatgct gggaagtgac gccctcgatg attttgacct   4020
```

-continued

```
tgacatgctt ggttcggatg cccttgatga ctttgacctc gacatgctcg gcagtgacgc    4080
ccttgatgat ttcgacctgg acatgctgat ttaagaattc acgcgttaag tcgacaatca    4140
acctctggat tacaaaattt gtgaaagatt gactggtatt cttaactatg ttgctccttt    4200
tacgctatgt ggatacgctg ctttaatgcc tttgtatcat gctattgctt cccgtatggc    4260
tttcattttc tcctccttgt ataaatcctg gttgctgtct ctttatgagg agttgtggcc    4320
cgttgtcagg caacgtggcg tggtgtgcac tgtgtttgct gacgcaaccc ccactggttg    4380
gggcattgcc accacctgtc agctcctttc cgggactttc gctttccccc tccctattgc    4440
cacggcggaa ctcatcgccg cctgccttgc ccgctgctgg acaggggctc ggctgttggg    4500
cactgacaat tccgtggtgt tgtcggggaa atcatcgtcc tttccttggc tgctcgcctg    4560
tgttgccacc tggattctgc gcgggacgtc cttctgctac gtcccttcgg ccctcaatcc    4620
agcggacctt ccttcccgcg gcctgctgcc ggctctgcgg cctcttccgc gtcttcgcct    4680
tcgccctcag acgagtcgga tctccctttg ggccgcctcc ccgcgtcgac tttaagacca    4740
atgacggccg caggaacccc tagtgatgga gttggccact ccctctctgc gcgctcgctc    4800
gctcactgag gccgggcgac caaaggtcgc ccgacgcccg ggctttgccc gggcggcctc    4860
agtgagcgag cgagcgcgca gctgcctgca ggggcgcctg atgcggtatt ttctccttac    4920
gcatctgtgc ggtatttcac accgcatacg tcaaagcaac catagtacgc gccctgtagc    4980
ggcgcattaa gcgcggcggg tgtggtggtt acgcgcagcg tgaccgctac acttgccagc    5040
gccttagcgc ccgctccttt cgctttcttc ccttcctttc tcgccacgtt cgccggcttt    5100
ccccgtcaag ctctaaatcg ggggctccct ttagggttcc gatttagtgc tttacggcac    5160
ctcgacccca aaaaacttga tttgggtgat ggttcacgta gtgggccatc gccctgatag    5220
acggtttttc gccctttgac gttggagtcc acgttcttta atagtggact cttgttccaa    5280
actggaacaa cactcaactc tatctcgggc tattcttttg atttataagg attttgccg     5340 atttcggtct attggttaaa aaatgagctg atttaacaaa aatttaacgc gaattttaac    5400
aaaatattaa cgtttacaat tttatggtgc actctcagta caatctgctc tgatgccgca    5460
tagttaagcc agccccgaca cccgccaaca cccgctgacg cgccctgacg ggcttgtctg    5520
ctcccggcat ccgcttacag acaagctgtg accgtctccg ggagctgcat gtgtcagagg    5580
ttttcaccgt catcaccgaa acgcgcgaga cgaaagggcc tcgtgatacg cctatttta    5640 taggttaatg tcatgataat aatggtttct tagacgtcag gtggcacttt tcggggaaat    5700
gtgcgcggaa cccctatttg tttatttttc taaatacatt caaatatgta tccgctcatg    5760
agacaataac cctgataaat gcttcaataa tattgaaaaa ggaagagtat gagtattcaa    5820
catttccgtg tcgcccttat tcccttttt gcggcatttt gccttcctgt ttttgctcac    5880
ccagaaacgc tggtgaaagt aaaagatgct gaagatcagt tgggtgcacg agtgggttac    5940
atcgaactgg atctcaacag cggtaagatc cttgagagtt ttcgccccga gaacgttttt    6000
ccaatgatga gcacttttaa agttctgcta tgtggcgcgg tattatcccg tattgacgcc    6060
gggcaagagc aactcggtcg ccgcatacac tattctcaga atgacttggt tgagtactca    6120
ccagtcacag aaaagcatct tacggatggc atgacagtaa gagaattatg cagtgctgcc    6180
ataaccatga gtgataacac tgcggccaac ttacttctga caacgatcgg aggaccgaag    6240
gagctaaccg cttttttgca caacatgggg gatcatgtaa ctcgccttga tcgttgggaa    6300
ccggagctga atgaagccat accaaacgac gagcgtgaca ccacgatgcc tgtagcaatg    6360
```

-continued

```
gcaacaacgt tgcgcaaact attaactggc gaactactta ctctagcttc ccggcaacaa      6420
ttaatagact ggatggaggc ggataaagtt gcaggaccac ttctgcgctc ggcccttccg      6480
gctggctggt ttattgctga taaatctgga gccggtgagc gtggaagccg cggtatcatt      6540
gcagcactgg ggccagatgg taagccctcc cgtatcgtag ttatctacac gacggggagt      6600
caggcaacta tggatgaacg aaatagacag atcgctgaga taggtgcctc actgattaag      6660
cattggtaac tgtcagacca gtttactca tatatacttt agattgattt aaaacttcat       6720 tttaattta aaaggatcta ggtgaagatc ctttttgata atctcatgac caaaatccct        6780
taacgtgagt tttcgttcca ctgagcgtca gaccccgtag aaaagatcaa aggatcttct       6840
tgagatcctt ttttctgcg cgtaatctgc tgcttgcaaa caaaaaaacc accgctacca        6900
gcggtggttt gtttgccgga tcaagagcta ccaactcttt ttccgaaggt aactggcttc      6960
agcagagcgc agataccaaa tactgttctt ctagtgtagc cgtagttagg ccaccacttc      7020
aagaactctg tagcaccgcc tacatacctc gctctgctaa tcctgttacc agtggctgct      7080
gccagtggcg ataagtcgtg tcttaccggg ttggactcaa gacgatagtt accggataag      7140
gcgcagcggt cgggctgaac ggggggttcg tgcacacagc ccagcttgga gcgaacgacc      7200
tacaccgaac tgagatacct acagcgtgag ctatgagaaa gcgccacgct tcccgaaggg      7260
agaaaggcgg acaggtatcc ggtaagcggc agggtcggaa caggagagcg cacgagggag      7320
cttccagggg gaaacgcctg gtatctttat agtcctgtcg ggtttcgcca cctctgactt      7380
gagcgtcgat ttttgtgatg ctcgtcaggg gggcggagcc tatggaaaaa cgccagcaac      7440
gcggcctttt tacggttcct ggccttttgc tggccttttg ctcacatgt                  7489
```

```
<210> SEQ ID NO 13
<211> LENGTH: 6726
<212> TYPE: DNA
<213> ORGANISM: Artificial Sequence
<220> FEATURE:
<223> OTHER INFORMATION: pGW045

<400> SEQUENCE: 13
```

```
cctgcaggca gctgcgcgct cgctcgctca ctgaggccgc ccgggcaaag cccgggcgtc       60
gggcgacctt tggtcgcccg gcctcagtga gcgagcgagc gcgcagagag ggagtggcca      120
actccatcac taggggttcc tgcggccgca cgcgttctag aaagagggcc tatttcccat      180
gattccttca tatttgcata tacgatacaa ggctgttaga gagataattg gaattaattt      240
gactgtaaac acaaagatat tagtacaaaa tacgtgacgt agaaagtaat aatttcttgg      300
gtagtttgca gttttaaaat tatgttttaa aatggactat catatgctta ccgtaacttg      360
aaagtatttc gatttcttgg ctttatatat cttgtggaaa ggacgaaaca ccggaagagc      420
gagctcttct gttttagagc taggccaaca tgaggatcac ccatgtctgc agggcctagc      480
aagttaaaat aaggctagtc cgttatcaac ttggccaaca tgaggatcac ccatgtctgc      540
agggccaagt ggcaccgagt cggtgctttt ttggatccaa gcttggcgta actagatctt      600
gagacaaatg gcacagcaga gatccagttt ggttaattag ctagctgcaa agatggataa      660
agttttaaac agagaggaat ctttgcagct aatggacctt ctaggtcttg aaaggagtgg      720
gaattggctc cggtgcccgt cagtgggcag agcgcacatc gcccacagtc cccgagaagt      780
tggggggagg ggtcggcaat tgaaccggtg cctagagaag gtggcgcggg gtaaactggg      840
aaagtgatgt cgtgtactgg ctccgccttt ttccgagggt ggggagaa ccgtatataa        900 gtgcagtagt cgccgtgaac gttctttttc gcaacgggtt tgccgccaga acacaggtaa      960
```

-continued

```
gtgccgtgtg tggttcccgc gggcctggcc tctttacggg ttatggccct tgcgtgcctt      1020
gaattacttc cacctggctg cagtacgtga ttcttgatcc cgagcttcgg gttggaagtg      1080
ggtgggagag ttcgaggcct tgcgcttaag gagcccccttc gcctcgtgct tgagttgagg      1140
cctggcctgg gcgctggggc cgccgcgtgc gaatctggtg gcaccttcgc gcctgtctcg      1200
ctgctttcga taagtctcta gccatttaaa atttttgatg acctgctgcg acgctttttt      1260
tctggcaaga tagtcttgta aatgcgggcc aagatctgca cactggtatt tcggtttttg      1320
gggccgcggg cggcgacggg gcccgtgcgt cccagcgcac atgttcggcg aggcggggcc      1380
tgcgagcgcg gccaccgaga atcggacggg ggtagtctca agctggccgg cctgctctgg      1440
tgcctggcct cgcgccgccg tgtatcgccc cgccctgggc ggcaaggctg gcccggtcgg      1500
caccagttgc gtgagcggaa agatggccgc ttcccggccc tgctgcaggg agctcaaaat      1560
gaaggacgcg gcgctcggga gagcgggcgg gtgagtcacc cacacaaagg aaaagggcct      1620
ttccgtcctc agccgtcgct tcatgtgact ccacggagta ccgggcgccg tccaggcacc      1680
tcgattagtt ctcgagcttt tggagtacgt cgtctttagg ttggggggag gggttttatg      1740
cgatggagtt tccccacact gagtgggtgg agactgaagt taggccagct tggcacttga      1800
tgtaattctc cttggaattt gccctttttg agtttggatc ttggttcatt ctcaagcctc      1860
agacagtggt tcaaagtttt tttcttccat ttcaggtgtc gtgacgtacg gccaccatgg      1920
cttcaaactt tactcagttc gtgctcgtgg acaatggtgg gacaggggat gtgacagtgg      1980
ctccttctaa tttcgctaat ggggtggcag agtggatcag ctccaactca cggagccagg      2040
cctacaaggt gacatgcagc gtcaggcagt ctagtgccca gaagagaaag tataccatca      2100
aggtggaggt ccccaaagtg gctacccaga cagtgggcgg agtcgaactg cctgtcgccg      2160
cttggaggtc ctacctgaac atggagctca ctatcccaat tttcgctacc aattctgact      2220
gtgaactcat cgtgaaggca atgcaggggc tcctcaaaga cggtaatcct atcccttccg      2280
ccatcgccgc taactcaggt atctacagcg ctggaggagg tggaagcgga ggaggaggaa      2340
gcggaggagg aggtagcgga cctaagaaaa agaggaaggt ggcggccgct ggatcccctt      2400
cagggcagat cagcaaccag gccctggctc tggcccctag ctccgctcca gtgctggccc      2460
agactatggt gccctctagt gctatggtgc ctctggccca gccacctgct ccagccctg      2520 tgctgacccc aggaccaccc cagtcactga gcgctccagt gcccaagtct acacaggccg      2580 gcgagggac tctgagtgaa gctctgctgc acctgcagtt cgacgctgat gaggacctgg      2640
gagctctgct ggggaacagc accgatcccg gagtgttcac agatctggcc tccgtggaca      2700
actctgagtt tcagcagctg ctgaatcagg gcgtgtccat gtctcatagt acagccgaac      2760
caatgctgat ggagtacccc gaagccatta cccggctggt gaccggcagc cagcggcccc      2820 ccgacccgc tccaactccc ctgggaacca gcggcctgcc taatgggctg tccggagatg      2880
aagacttctc aagcatcgct gatatggact ttagtgccct gctgtcacag atttcctcta      2940
gtgggcaggg aggaggtgga agcggcttca gcgtggacac cagtgccctg ctggacctgt      3000
tcagcccctc ggtgaccgtg cccgacatga gcctgcctga ccttgacagc agcctggcca      3060
gtatccaaga gctcctgtct ccccaggagc cccccaggcc tcccgaggca gagaacagca      3120
gcccggattc agggaagcag ctggtgcact acacagcgca gccgctgttc ctgctggacc      3180
ccggctccgt ggacaccggg agcaacgacc tgccggtgct gtttgagctg ggagagggct      3240
cctacttctc cgaagggggac ggcttcgccg aggaccccac catctccctg ctgacaggct      3300
```

-continued

```
cggagcctcc caaagccaag gaccccactg tctcctaaga attcacgcgt taagtcgaca    3360
atcaacctct ggattacaaa atttgtgaaa gattgactgg tattcttaac tatgttgctc    3420
cttttacgct atgtggatac gctgctttaa tgcctttgta tcatgctatt gcttcccgta    3480
tggctttcat tttctcctcc ttgtataaat cctggttgct gtctctttat gaggagttgt    3540
ggcccgttgt caggcaacgt ggcgtggtgt gcactgtgtt tgctgacgca acccccactg    3600
gttggggcat tgccaccacc tgtcagctcc tttccgggac tttcgctttc ccctccccta    3660
ttgccacggc ggaactcatc gccgcctgcc ttgcccgctg ctggacaggg gctcggctgt    3720
tgggcactga caattccgtg gtgttgtcgg ggaaatcatc gtcctttcct ggctgctcg     3780 cctgtgttgc cacctggatt ctgcgcggga cgtccttctg ctacgtccct tcggccctca    3840
atccagcgga ccttccttcc cgcggcctgc tgccggctct gcggcctctt ccgcgtcttc    3900
gccttcgccc tcagacgagt cggatctccc tttgggccgc ctccccgcgt cgactttaag    3960
accaatgacg tgcggaccga gcggccgcag gaacccctag tgatggagtt ggccactccc    4020
tctctgcgcg ctcgctcgct cactgaggcc gggcgaccaa aggtcgcccg acgcccgggc    4080
tttgcccggg cggcctcagt gagcgagcga gcgcgcagct gcctgcaggg gcgcctgatg    4140
cggtattttc tccttacgca tctgtgcggt atttcacacc gcatacgtca aagcaaccat    4200
agtacgcgcc ctgtagcggc gcattaagcg cggcgggtgt ggtggttacg cgcagcgtga    4260
ccgctacact tgccagcgcc ctagcgcccg ctcctttcgc tttcttccct tcctttctcg    4320
ccacgttcgc cggctttccc cgtcaagctc taaatcgggg gctccctta gggttccgat     4380 ttagtgcttt acggcacctc gaccccaaaa aacttgattt gggtgatggt tcacgtagtg    4440
ggccatcgcc ctgatagacg gtttttcgcc ctttgacgtt ggagtccacg ttctttaata    4500
gtggactctt gttccaaact ggaacaacac tcaaccctat ctcgggctat tcttttgatt    4560
tataagggat tttgccgatt tcggcctatt ggttaaaaaa tgagctgatt taacaaaaat    4620
ttaacgcgaa ttttaacaaa atattaacgt ttacaatttt atggtgcact ctcagtacaa    4680
tctgctctga tgccgcatag ttaagccagc cccgacaccc gccaacaccc gctgacgcgc    4740
cctgacgggc ttgtctgctc ccggcatccg cttacagaca agctgtgacc gtctccggga    4800
gctgcatgtg tcagaggttt tcaccgtcat caccgaaacg cgcgagacga aagggcctcg    4860
tgatacgcct attttttatag gttaatgtca tgataataat ggtttcttag acgtcaggtg    4920
gcacttttcg gggaaatgtg cgcggaaccc ctatttgttt atttttctaa atacattcaa    4980
atatgtatcc gctcatgaga caataaccct gataaatgct tcaataatat tgaaaaagga    5040
agagtatgag tattcaacat ttccgtgtcg cccttattcc cttttttgcg gcattttgcc    5100
ttcctgtttt tgctcaccca gaaacgctgg tgaaagtaaa agatgctgaa gatcagttgg    5160
gtgcacgagt gggttacatc gaactggatc tcaacagcgg taagatcctt gagagttttc    5220
gccccgaaga acgttttcca atgatgagca cttttaaagt tctgctatgt ggcgcggtat    5280
tatcccgtat tgacgccggg caagagcaac tcggtcgccg catacactat tctcagaatg    5340
acttggttga gtactcacca gtcacagaaa agcatcttac ggatggcatg acagtaagag    5400
aattatgcag tgctgccata accatgagtg ataacactgc ggccaactta cttctgacaa    5460
cgatcggagg accgaaggag ctaaccgctt ttttgcacaa catgggggat catgtaactc    5520
gccttgatcg ttgggaaccg gagctgaatg aagccatacc aaacgacgag cgtgacacca    5580
cgatgcctgt agcaatggca acaacgttgc gcaaactatt aactggcgaa ctacttactc    5640
tagcttcccg gcaacaatta atagactgga tggaggcgga taaagttgca ggaccacttc    5700
```

```
tgcgctcggc ccttccggct ggctggttta ttgctgataa atctggagcc ggtgagcgtg    5760
ggtctcgcgg tatcattgca gcactggggc cagatggtaa gccctcccgt atcgtagtta    5820
tctacacgac ggggagtcag gcaactatgg atgaacgaaa tagacagatc gctgagatag    5880
gtgcctcact gattaagcat tggtaactgt cagaccaagt ttactcatat atactttaga    5940
ttgatttaaa acttcatttt taatttaaaa ggatctaggt gaagatcctt tttgataatc    6000
tcatgaccaa aatcccttaa cgtgagtttt cgttccactg agcgtcagac cccgtagaaa    6060
agatcaaagg atcttcttga gatcctttt ttctgcgcgt aatctgctgc ttgcaaacaa     6120
aaaaaccacc gctaccagcg gtggtttgtt tgccggatca gagctacca actcttttc     6180 cgaaggtaac tggcttcagc agagcgcaga taccaaatac tgtccttcta gtgtagccgt    6240
agttaggcca ccacttcaag aactctgtag caccgcctac atacctcgct ctgctaatcc    6300
tgttaccagt ggctgctgcc agtggcgata agtcgtgtct taccgggttg gactcaagac    6360
gatagttacc ggataaggcg cagcggtcgg gctgaacggg gggttcgtgc acacagccca    6420
gcttggagcg aacgacctac accgaactga gatacctaca gcgtgagcta tgagaaagcg    6480
ccacgcttcc cgaagggaga aaggcggaca ggtatccggt aagcggcagg gtcggaacag    6540
gagagcgcac gagggagctt ccaggggggaa acgcctggta tctttatagt cctgtcgggt    6600
ttcgccacct ctgacttgag cgtcgatttt tgtgatgctc gtcaggggggg cggagcctat    6660 ggaaaaacgc cagcaacgcg gccttttac ggttcctggc cttttgctgg cctttgctc     6720 acatgt                                                                 6726
```

<210> SEQ ID NO 14
<211> LENGTH: 7428
<212> TYPE: DNA
<213> ORGANISM: Artificial Sequence
<220> FEATURE:
<223> OTHER INFORMATION: pRC119

<400> SEQUENCE: 14

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac tagggggttcc tgcggccgca cgcgttctag gtcttgaaag gagtgggaat    180
tggctccggt gcccgtcagt gggcagagcg cacatcgccc acagtccccg agaagttggg    240 gggagggggtc ggcaattgat ccggtgccta gagaaggtgg cgcggggtaa actgggaaag    300
tgatgtcgtg tactggctcc gcctttttcc cgagggtggg ggagaaccgt atataagtgc     360
agtagtcgcc gtgaacgttc tttttcgcaa cgggtttgcc gccagaacac aggtgtcgtg    420
acgcgcgtac ggccaccatg acacagttcg agggctttac caacctgtat caggtgagca    480
agacactgcg gtttgagctg atcccacagg gcaagaccct gaagcacatc caggagcagg    540
gcttcatcga ggaggacaag gcccgcaatg atcactacaa ggagctgaag cccatcatcg    600
atcggatcta caagacctat gccgaccagt gcctgcagct ggtgcagctg gattgggaga    660
acctgagcgc cgccatcgac tcctatagaa aggagaaaac cgaggagaca aggaacgccc    720
tgatcgagga gcaggccaca tatcgcaatg ccatccacga ctacttcatc ggccggacag    780
acaacctgac cgatgccatc aataagagac acgccgagat ctacaagggc ctgttcaagg    840
ccgagctgtt taatggcaag gtgctgaagc agctgggcac cgtgaccaca accgagcacg    900
agaacgccct gctgcggagc ttcgacaagt ttacaaccta cttctccggc ttttatagaa    960
```

```
acaggaagaa cgtgttcagc gccgaggata tcagcacagc catcccacac cgcatcgtgc    1020
aggacaactt ccccaagttt aaggagaatt gtcacatctt cacacgcctg atcaccgccg    1080
tgcccagcct gcgggagcac tttgagaacg tgaagaaggc catcggcatc ttcgtgagca    1140
cctccatcga ggaggtgttt tccttccctt tttataacca gctgctgaca cagacccaga    1200
tcgacctgta taaccagctg ctgggaggaa tctctcggga ggcaggcacc gagaagatca    1260
agggcctgaa cgaggtgctg aatctggcca tccagaagaa tgatgagaca gcccacatca    1320
tcgcctccct gccacacaga ttcatccccc tgtttaagca gatcctgtcc gataggaaca    1380
ccctgtcttt catcctggag gagtttaaga gcgacgagga agtgatccag tccttctgca    1440
agtacaagac actgctgaga aacgagaacg tgctggagac agccgaggcc ctgtttaacg    1500
agctgaacag catcgacctg acacacatct tcatcagcca caagaagctg gagacaatca    1560
gcagcgccct gtgcgaccac tgggatacac tgaggaatgc cctgtatgag cggagaatct    1620
ccgagctgac aggcaagatc accaagtctg ccaaggagaa ggtgcagcgc agcctgaagc    1680
acgaggatat caacctgcag gagatcatct ctgccgcagg caaggagctg agcgaggcct    1740
tcaagcagaa aaccagcgag atcctgtccc acgcacacgc cgccctggat cagccactgc    1800
ctacaaccct gaagaagcag gaggagaagg agatcctgaa gtctcagctg gacagcctgc    1860
tgggcctgta ccacctgctg gactggtttg ccgtggatga gtccaacgag gtggaccccg    1920
agttctctgc ccggctgacc ggcatcaagc tggagatgga gccttctctg agcttctaca    1980
acaaggccag aaattatgcc accaagaagc cctactccgt ggagaagttc aagctgaact    2040
ttcagatgcc tacactggcc agaggctggg acgtgaatag agagaagaac aatggcgcca    2100
tcctgtttgt gaagaacggc ctgtactatc tgggcatcat gccaaagcag aagggcaggt    2160
ataaggccct gagcttcgag cccacagaga aaaccagcga gggctttgat aagatgtact    2220
atgactactt ccctgatgcc gccaagatga tcccaaagtg cagcacccag ctgaaggccg    2280
tgacagccca ctttcagacc cacacaaccc ccatcctgct gtccaacaat ttcatcgagc    2340
ctctggagat cacaaaggag atctacgacc tgaacaatcc tgagaaggag ccaaagaagt    2400
ttcagacagc ctacgccaag aaaaccggcg accagaaggg ctacagagag gccctgtgca    2460
agtggatcga cttcacaagg gattttctgt ccaagtatac caagacaacc tctatcgatc    2520
tgtctagcct gcggccatcc tctcagtata aggacctggg cgagtactat gccgagctga    2580
atcccctgct gtaccacatc agcttccaga gaatcgccga gaaggagatc atggatgccg    2640
tggagacagg caagctgtac ctgttccaga tctataacaa ggactttgcc aagggccacc    2700
acggcaagcc taatctgcac acactgtatt ggaccggcct gttttctcca gagaacctgg    2760
ccaagacaag catcaagctg aatggccagg ccgagctgtt ctaccgccct aagtccagga    2820
tgaagaggat ggcacaccgg ctgggagaga agatgctgaa caagaagctg aaggatcaga    2880 aaacccaat ccccgacacc ctgtaccagg agctgtacga ctatgtgaat cacagactgt    2940
cccacgacct gtctgatgag gccagggccc tgctgcccaa cgtgatcacc aaggaggtgt    3000
ctcacgagat catcaaggat aggcgcttta ccagcgacaa gttctttttc cacgtgccta    3060
tcacactgaa ctatcaggcc gccaattccc catctaagtt caaccagagg gtgaatgcct    3120
acctgaagga gcaccccgag acacctatca tcggcatcgc ccggggcgag agaaacctga    3180
tctatatcac agtgatcgac tccaccggca gatcctggga gcagcggagc ctgaacacca    3240
tccagcagtt tgattaccag aagaagctgg acaacaggga gaaggagagg gtggcagcaa    3300
ggcaggcctg gtctgtggtg ggcacaatca aggatctgaa gcagggctat ctgagccagg    3360
```

-continued

```
tcatccacga gatcgtggac ctgatgatcc actaccaggc cgtggtggtg ctggagaacc   3420
tgaatttcgg ctttaagagc aagaggaccg gcatcgccga gaaggccgtg taccagcagt   3480
tcgagaagat gctgatcgat aagctgaatt gcctggtgct gaaggactat ccagcagaga   3540
aagtgggagg cgtgctgaac ccataccagc tgacagacca gttcacctcc tttgccaaga   3600 tgggcacccca gtctggcttc ctgttttacg tgcctgcccc atatacatct aagatcgatc   3660
ccctgaccgg cttcgtggac cccttcgtgt ggaaaaccat caagaatcac gagagccgca   3720
agcacttcct ggagggcttc gactttctgc actacgacgt gaaaaccggc gacttcatcc   3780
tgcactttaa gatgaacaga aatctgtcct tccagagggg cctgcccggc tttatgcctg   3840
catgggatat cgtgttcgag aagaacgaga cacagtttga cgccaagggc acccctttca   3900
tcgccggcaa gagaatcgtg ccagtgatcg agaatcacag attcaccggc agataccggg   3960
acctgtatcc tgccaacgag ctgatcgccc tgctggagga gaagggcatc gtgttcaggg   4020
atggctccaa catcctgcca aagctgctgg agaatgacga ttctcacgcc atcgacacga   4080
tggtggccct gatccgcagc gtgctgcaga tgcggaactc caatgccgcc acaggcgagg   4140
actatatcaa cagccccgtg cgcgatctga atggcgtgtg cttcgactcc cggtttcaga   4200
acccagagtg gccaatggac gccgatgcca atggcgccta ccacatcgcc ctgaagggcc   4260
agctgctgct gaatcacctg aaggagagca aggatctgaa gctgcagaac ggcatctcca   4320
atcaggactg gctggcctac atccaggagc tgcgcaacaa aaggccggcg gccacgaaaa   4380
aggccggcca ggcaaaaaag aaaaagggca gtggtagtgg agaagagctg ttgtcaaaaa   4440
attatcactt ggagaatgag gtagcccgcc ttaagaaagg cagcggatca ggcgaggaac   4500
ttctgagcaa gaattaccat ctcgaaaacg aagtggcacg cttgaagaag ggttcaggtt   4560
ccggggagga gctcctctcc aagaactacc acctggagaa cgaagtcgct cgcctgaaga   4620
aatgaaataa aagatcttta ttttcattag atctgtgtgt tggttttttg tgtgcggacc   4680
gagcggccgc aggaaccccct agtgatggag ttggccactc cctctctgcg cgctcgctcg   4740
ctcactgagg ccgggcgacc aaaggtcgcc cgacgcccgg gctttgcccg gcggcctca   4800 gtgagcgagc gagcgcgcag ctgcctgcag gggcgcctga tgcggtattt tctccttacg   4860
catctgtgcg gtatttcaca ccgcatacgt caaagcaacc atagtacgcg ccctgtagcg   4920
gcgcattaag cgcggcgggt gtggtggtta cgcgcagcgt gaccgctaca cttgccagcg   4980
ccctagcgcc cgctcctttc gctttcttcc cttcctttct cgccacgttc gccggctttc   5040
cccgtcaagc tctaaatcgg gggctccctt tagggttccg atttagtgct ttacggcacc   5100
tcgaccccaa aaaacttgat ttgggtgatg gttcacgtag tgggccatcg ccctgataga   5160
cggtttttcg ccctttgacg ttggagtcca cgttctttaa tagtggactc ttgttccaaa   5220
ctggaacaac actcaaccct atctcgggct attcttttga tttataaggg attttgccga   5280
tttcggccta ttggttaaaa aatgagctga tttaacaaaa atttaacgcg aattttaaca   5340
aaatattaac gtttacaatt ttatggtgca ctctcagtac aatctgctct gatgccgcat   5400
agttaagcca gccccgacac ccgccaacac ccgctgacgc gccctgacgg gcttgtctgc   5460
tcccggcatc cgcttacaga caagctgtga ccgtctccgg gagctgcatg tgtcagaggt   5520
tttcaccgtc atcaccgaaa cgcgcgagac gaaagggcct cgtgatacgc ctatttttat   5580
aggttaatgt catgataata atggtttctt agacgtcagg tggcactttt cggggaaatg   5640
tgcgcggaac ccctatttgt ttatttttct aaatacattc aaatatgtat ccgctcatga   5700
```

```
gacaataacc ctgataaatg cttcaataat attgaaaaag gaagagtatg agtattcaac      5760
atttccgtgt cgcccttatt cccttttttg cggcattttg ccttcctgtt tttgctcacc      5820
cagaaacgct ggtgaaagta aaagatgctg aagatcagtt gggtgcacga gtgggttaca      5880
tcgaactgga tctcaacagc ggtaagatcc ttgagagttt cgcccccgaa gaacgttttc      5940
caatgatgag cacttttaaa gttctgctat gtggcgcggt attatcccgt attgacgccg      6000
ggcaagagca actcggtcgc cgcatacact attctcagaa tgacttggtt gagtactcac      6060
cagtcacaga aaagcatctt acggatggca tgacagtaag agaattatgc agtgctgcca      6120
taaccatgag tgataacact gcggccaact tacttctgac aacgatcgga ggaccgaagg      6180
agctaaccgc ttttttgcac aacatggggg atcatgtaac tcgccttgat cgttgggaac      6240
cggagctgaa tgaagccata ccaaacgacg agcgtgacac cacgatgcct gtagcaatgg      6300
caacaacgtt gcgcaaacta ttaactggcg aactacttac tctagcttcc cggcaacaat      6360
taatagactg gatggaggcg gataaagttg caggaccact tctgcgctcg gcccttccgg      6420
ctggctggtt tattgctgat aaatctggag ccggtgagcg tgggtctcgc ggtatcattg      6480
cagcactggg gccagatggt aagccctccc gtatcgtagt tatctacacg acggggagtc      6540
aggcaactat ggatgaacga aatagacaga tcgctgagat aggtgcctca ctgattaagc      6600
attggtaact gtcagaccaa gtttactcat atatacttta gattgattta aaacttcatt      6660
tttaatttaa aaggatctag gtgaagatcc tttttgataa tctcatgacc aaaatccctt      6720
aacgtgagtt ttcgttccac tgagcgtcag accccgtaga aaagatcaaa ggatcttctt      6780
gagatccttt ttttctgcgc gtaatctgct gcttgcaaac aaaaaaacca ccgctaccag      6840
cggtggtttg tttgccggat caagagctac caactctttt tccgaaggta actggcttca      6900
gcagagcgca gataccaaat actgtccttc tagtgtagcc gtagttaggc caccacttca      6960
agaactctgt agcaccgcct acatacctcg ctctgctaat cctgttacca gtggctgctg      7020
ccagtggcga taagtcgtgt cttaccgggt tggactcaag acgatagtta ccggataagg      7080
cgcagcggtc gggctgaacg gggggttcgt gcacacagcc cagcttggag cgaacgacct      7140
acaccgaact gagataccta cagcgtgagc tatgagaaag cgccacgctt cccgaaggga      7200
gaaaggcgga caggtatccg gtaagcggca gggtcggaac aggagagcgc acgagggagc      7260
ttccaggggg aaacgcctgg tatctttata gtcctgtcgg gtttcgccac ctctgacttg      7320
agcgtcgatt tttgtgatgc tcgtcagggg ggcggagcct atggaaaaac gccagcaacg      7380
cggccttttt acggttcctg gccttttgct ggccttttgc tcacatgt                   7428
```

```
<210> SEQ ID NO 15
<211> LENGTH: 7335
<212> TYPE: DNA
<213> ORGANISM: Artificial Sequence
<220> FEATURE:
<223> OTHER INFORMATION: pRC120

<400> SEQUENCE: 15
cctgcaggca gctgcgcgct cgctcgctca ctgaggccgc ccgggcaaag cccgggcgtc        60
gggcgacctt tggtcgcccg gcctcagtga gcgagcgagc gcgcagagag ggagtggcca       120
actccatcac tagggggttcc tgcggccgca cgcgttctag gtcttgaaag gagtgggaat      180
tggctccggt gcccgtcagt gggcagagcg cacatcgccc acagtccccg agaagttggg       240
gggaggggtc ggcaattgat ccggtgccta gagaaggtgg cgcggggtaa actgggaaag       300
tgatgtcgtg tactggctcc gcctttttcc cgagggtggg ggagaaccgt atataagtgc       360
```

-continued

```
agtagtcgcc gtgaacgttc tttttcgcaa cgggtttgcc gccagaacac aggtgtcgtg        420
acgcgcgtac ggccaccatg tcaaagctgg agaaattcac caactgttat agcctgtcta        480
agaccctgcg cttcaaggca atcccagtgg gcaagacaca agagaacatt gacaacaaac        540
ggctcctggt ggaggatgag aagagggctg aagattacaa gggcgttaag aagctgctgg        600
ataggtacta tctgtcattc atcaacgatg tcctccacag tatcaagctg aagaatctga        660
acaattacat ttctctgttc cggaagaaga cacggaccga gaaggagaac aaagagctgg        720
agaatctgga gatcaacctg aggaaagaaa tagctaaggc tttcaaaggg aacgagggtt        780
acaagtccct gttcaagaaa gacattatcg agactattct gcctgagttc ctggacgata        840
aagatgagat cgccctcgtc aattccttca atgggtttac cacagccttt accggcttct        900
tcgacaatag agagaatatg ttctctgaag aggccaaatc cactagcatc gcctttcgct        960
gcataaacga gaacctgact aggtacatca gcaatatgga catctttgag aaagtcgatg       1020
ccatattcga caaacatgag gtgcaggaga ttaaggagaa gatcctgaac tcagattacg       1080
atgtcgaaga tttcttcgag ggagagttct tcaacttcgt gctcacacaa gagggcattg       1140
atgtgtacaa tgcaatcatt ggagggttcg tgacagagag tggcgagaag ataaagggcc       1200
tgaacgagta tatcaacctc tacaaccaga aaaccaagca gaaactgcct aagttcaagc       1260
cactgtacaa acaagtgctc tcagataggg aaagcctgag cttctacggt gaagggtata       1320
catcagatga agaagtgctc gaagtgttcc gcaacaccct caataagaac agtgaaatct       1380
tctcttcaat caagaagctg gagaaactgt tcaagaattt cgatgagtac tcctctgccg       1440
gaatctttgt gaagaatggc cctgcaatat ccactattag caaagacatc tttggcgagt       1500
ggaacgttat cagggataag tggaatgccg agtacgatga tattcatctc aagaagaaag       1560
ccgtggttac agagaaatac gaggatgata gacgcaagag ctttaagaag attggtagct       1620
tctctctcga acagctgcag gagtacgccg acgctgacct gtcagtcgtg gagaaactca       1680
aggagatcat aatccagaag gtggatgaaa tctacaaagt gtatggaagc tctgagaaac       1740
tcttcgatgc agactttgtt ctggagaaga gtctgaagaa gaacgacgca gtggttgcta       1800
tcatgaagga cctgctggat tctgttaagt cttttcgaga attacattaag gcattctttg       1860 gtgaagggaa ggagacaaat aggggacgaga gcttctatgg cgactttgtt ctggcctacg       1920
acatcctcct caaggttgac cacatctatg acgctatacg gaattacgtt acccagaagc       1980
cctatagcaa agacaagttc aagctgtatt tccagaatcc acagtttatg ggtgggtggg       2040
ataaagacaa agaaacagat tacagggcca ctatcctgcg gtacggcagc aaatactatc       2100
tggctatcat ggataagaag tacgccaaat gcctccagaa gatcgacaag gacgacgtga       2160
acggtaacta cgagaagatc aattacaagc tcctgccagg acctaacaag atgctgccca       2220
aggtgttctt ctccaagaaa tggatggcct actataaccc aagcgaggac attcagaaga       2280
tatacaagaa tgggacattc aagaagggcg atatgttcaa cctcaacgac tgccacaagc       2340
tgattgattt cttcaaggat agcatttctc gctatcccaa gtggtctaat gcatacgatt       2400
tcaacttcag cgagactgag aagtacaaag acatcgctgg cttctaccgg gaggtggaag       2460
agcaaggcta taaggtgtca ttcgaatccg cttctaagaa ggaagtggat aagctcgtgg       2520
aagagggtaa gctgtacatg ttccagatat acaacaaaga cttcagcgat aagagccacg       2580
gcactccaaa cctccatact atgtatttca agctgctgtt tgacgagaac aaccacggac       2640
agattaggct gtcaggaggc gcagaactct tcatgcgcag agcttcactg aagaaggagg       2700
```

-continued

```
aactcgttgt ccacccagcc aatagcccta tagccaataa gaatccagac aatcctaaga   2760
aaaccactac tctgtcttac gatgtgtata aggataagag attctctgaa gatcagtacg   2820
aactgcacat acccattgcc attaacaagt gccctaagaa catcttcaag attaacacag   2880
aggttagagt gctcctgaaa cacgacgata acccttatgt tataggcatt gctcgcggag   2940
agagaaacct gctgtacatc gtcgtggtgg acggcaaagg caacatcgtg gaacagtaca   3000
gtctcaatga aatcattaac aatttcaacg gaatccgcat taagaccgac taccattctc   3060
tcctcgacaa gaaggagaaa gaaaggttcg aagcaagaca gaattggaca agtatagaga   3120
atatcaaaga actgaaggct gggtacatct ctcaggttgt gcacaagata tgtgagctgg   3180
tggagaagta cgacgctgtt atcgccctcg cggacctgaa tagcggcttc aagaactcca   3240
gggtgaaggt ggagaagcag gtgtatcaga agttcgagaa gatgctgatc gacaagctca   3300
actatatggt ggacaagaaa tccaatcctt gcgctactgg tggagccctg aagggctatc   3360
aaatcaccaa taagttcgaa tctttcaagt ctatgagcac ccagaatggc ttcatcttct   3420
acatacccgc atggctgaca tccaagattg atccctctac cggatttgtt aatctgctca   3480
agactaagta cacctctatt gctgactcaa agaagttcat atcatcattt gaccgcatca   3540
tgtacgtgcc agaagaggac ctgttcgagt ttgccctgga ttacaagaat ttctctcgga   3600
ctgacgccga ctacatcaag aagtggaagc tctactctta tggtaatcgg attcgcatat   3660
tccgcaatcc caagaagaat aacgtgttcg attgggagga agtttgcctc accagcgctt   3720
acaaggagct gttcaataag tatgggatta actaccagca gggcgacata agagccctgc   3780
tgtgcgaaca atctgataag gcattctatt cctctttcat ggcactgatg tcactgatgc   3840
tgcaaatgcg caattccatc accggaagaa cagacgtggc ctttctgatc tctcctgtca   3900
agaactcaga tggcatcttc tacgattccc gcaactatga agcacaggag aatgctatcc   3960
tgcctaagaa tgccgatgca aatggagcct ataacatcgc cagaaaggtc ctctgggcca   4020
taggacaatt caagaaagct gaagatgaga agctggacaa ggtgaagatc gccatttcaa   4080
acaaagagtg gctcgaatat gctcagacct cagtgaagca taaaaggccg gcggccacga   4140
aaaaggccgg ccaggcaaaa aagaaaaagg gcagcggtag tggggaggag cttctttcta   4200
aaaattatca tcttgaaaat gaagtggcac gactcaagaa aggctctggg tccggtgagg   4260
aactcctgtc caagaactat catcttgaaa acgaagtcgc ccgccttaaa aaaggctcag   4320
gctcaggtga agaattgttg agcaaaaact atcaccttga gaatgaggtt gcccggctca   4380
aaaaagggtc tggcagcggc gaggaactcc tttcaaagaa ctaccatctc gaaaatgaag   4440
ttgctcggtt gaagaagggt tcaggatctg gcgaggagct tctgtccaag aactaccatt   4500
tggagaacga ggtcgcaaga cttaaaaaat gaaataaaag atctttattt tcattagatc   4560
tgtgtgttgg ttttttgtgt gcggaccgag cggccgcagg aacccctagt gatggagttg   4620
gccactccct ctctgcgcgc tcgctcgctc actgaggccg ggcgaccaaa ggtcgcccga   4680
cgcccgggct ttgcccgggc ggcctcagtg agcgagcgag cgcgcagctg cctgcagggg   4740
cgcctgatgc ggtattttct ccttacgcat ctgtgcggta tttcacaccg catacgtcaa   4800
agcaaccata gtacgcgccc tgtagcggcg cattaagcgc ggcgggtgtg gtggttacgc   4860
gcagcgtgac cgctacactt gccagcgccc tagcgcccgc tcctttcgct ttcttccctt   4920
cctttctcgc cacgttcgcc ggctttcccc gtcaagctct aaatcggggg ctccctttag   4980
ggttccgatt tagtgcttta cggcacctcg accccaaaaa acttgatttg ggtgatggtt   5040
cacgtagtgg gccatcgccc tgatagacgg tttttcgccc tttgacgttg gagtccacgt   5100
```

```
tctttaatag tggactcttg ttccaaactg gaacaacact caaccctatc tcgggctatt       5160
cttttgattt ataagggatt ttgccgattt cggcctattg gttaaaaaat gagctgattt       5220
aacaaaaatt taacgcgaat tttaacaaaa tattaacgtt tacaatttta tggtgcactc       5280
tcagtacaat ctgctctgat gccgcatagt taagccagcc ccgacacccg ccaacacccg       5340
ctgacgcgcc ctgacgggct tgtctgctcc cggcatccgc ttacagacaa gctgtgaccg       5400
tctccgggag ctgcatgtgt cagaggtttt caccgtcatc accgaaacgc gcgagacgaa       5460
agggcctcgt gatacgccta ttttttatagg ttaatgtcat gataataatg gtttcttaga       5520
cgtcaggtgg cacttttcgg ggaaatgtgc gcggaacccc tatttgttta tttttctaaa       5580
tacattcaaa tatgtatccg ctcatgagac aataaccctg ataaatgctt caataatatt       5640
gaaaaaggaa gagtatgagt attcaacatt tccgtgtcgc ccttattccc tttttttgcgg       5700 cattttgcct tcctgttttt gctcacccag aaacgctggt gaaagtaaaa gatgctgaag       5760
atcagttggg tgcacgagtg ggttacatcg aactggatct caacagcggt aagatccttg       5820
agagttttcg ccccgaagaa cgttttccaa tgatgagcac ttttaaagtt ctgctatgtg       5880
gcgcggtatt atcccgtatt gacgccgggc aagagcaact cggtcgccgc atacactatt       5940
ctcagaatga cttggttgag tactcaccag tcacagaaaa gcatcttacg gatggcatga       6000
cagtaagaga attatgcagt gctgccataa ccatgagtga taacactgcg gccaacttac       6060
ttctgacaac gatcggagga ccgaaggagc taaccgcttt tttgcacaac atgggggatc       6120
atgtaactcg ccttgatcgt tgggaaccgg agctgaatga agccatacca aacgacgagc       6180
gtgacaccac gatgcctgta gcaatggcaa caacgttgcg caaactatta actggcgaac       6240
tacttactct agcttcccgg caacaattaa tagactggat ggaggcggat aaagttgcag       6300
gaccacttct gcgctcggcc cttccggctg gctggtttat tgctgataaa tctggagccg       6360
gtgagcgtgg gtctcgcggt atcattgcag cactggggcc agatggtaag ccctcccgta       6420
tcgtagttat ctacacgacg gggagtcagg caactatgga tgaacgaaat agacagatcg       6480
ctgagatagg tgcctcactg attaagcatt ggtaactgtc agaccaagtt tactcatata       6540
tactttagat tgatttaaaa cttcattttt aatttaaaag gatctaggtg aagatccttt       6600
ttgataatct catgaccaaa atcccttaac gtgagttttc gttccactga gcgtcagacc       6660
ccgtagaaaa gatcaaagga tcttcttgag atcctttttt tctgcgcgta atctgctgct       6720
tgcaaacaaa aaaaccaccg ctaccagcgg tggtttgttt gccggatcaa gagctaccaa       6780
ctctttttcc gaaggtaact ggcttcagca gagcgcagat accaaatact gtccttctag       6840
tgtagccgta gttaggccac cacttcaaga actctgtagc accgcctaca tacctcgctc       6900
tgctaatcct gttaccagtg gctgctgcca gtggcgataa gtcgtgtctt accgggttgg       6960
actcaagacg atagttaccg gataaggcgc agcggtcggg ctgaacgggg ggttcgtgca       7020
cacagcccag cttggagcga acgacctaca ccgaactgag atacctacag cgtgagctat       7080
gagaaagcgc cacgcttccc gaagggagaa aggcggacag gtatccggta agcggcaggg       7140
tcggaacagg agagcgcacg aggggagcttc caggggggaaa cgcctggtat ctttatagtc       7200
ctgtcgggtt tcgccacctc tgacttgagc gtcgattttt gtgatgctcg tcaggggggc       7260
ggagcctatg gaaaaacgcc agcaacgcgg cctttttacg gttcctggcc ttttgctggc       7320
cttttgctca catgt                                                        7335
```

<210> SEQ ID NO 16

<211> LENGTH: 5810
<212> TYPE: DNA
<213> ORGANISM: Artificial Sequence
<220> FEATURE:
<223> OTHER INFORMATION: pRC121b

<400> SEQUENCE: 16

```
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggcctcta gaaaggatct gcgatcgctc cggtgcccgt cagtgggcag     180
agcgcacatc gcccacagtc cccgagaagt tggggggagg ggtcggcaat tgaacgggtg     240
cctagagaag gtggcgcggg gtaaactggg aaagtgatgt cgtgtactgg ctccgccttt     300
ttcccgaggg tggggagaa ccgtatataa gtgcagtagt cgccgtgaac gttctttttc     360
gcaacgggtt tgccgccaga acacagctga agcttcgagg ggctcgcatc tctccttcac     420
gcgcccgccg ccctacctga ggccgccatc cacgccggtt gagtgcgcgtt ctgccgcctc     480 ccgcctgtgg tgcctcctga actgcgtccg ccgtctaggt aagtttaaag ctcaggtcga     540
gaccgggcct ttgtccggcg ctcccttgga gcctacctag actcagccgg ctctccacgc     600
tttgcctgac cctgcttgct caactctacg tctttgtttc gttttctgtt ctgcgccgtt     660
acagatctgg ctaactaccg gtgccaccat gggcccagcc gccaaacgag tcaagctgga     720
tggccccgat atcgtcatga ctcaatcacc ctcatcactg tcagccagcg tcggtgaccg     780
ggtaacaatt acttgtagat catcaactgg ggccgtcact acctccaact atgccagttg     840
ggttcaagag aaacccggca agctctttaa gggactgatc ggtgggacca ataatcgggc     900
ccccggtgtg ccttctcgct ttagcgggag tttgataggc gataaagcca cattgacaat     960
atcatctctt caacccgagg acttcgctac ctatttttgt gctttgtggt atagtaacca    1020
ttgggtattt ggccaaggaa ctaaggtaga gttgaagcgg ggggcggcg gctctggtgg    1080 aggaggtagt ggggcggtg gctcttccgg aggggttcc gaagtaaagc ttttggagag    1140
cggcggcggc ctggtccagc ctggaggatc tctcaagctt agctgcgccg tcagcggctt    1200
ttccctcact gattatggtg taaattgggt gaggcaggct ccaggcaggg ggttggagtg    1260
gataggggtg atatggggggg atggcatcac agattataat tctgcactta aggataggtt    1320
tattatcagt aaggacaacg gtaagaacac cgtttatctt cagatgtcta aggtgcggtc    1380
cgatgatact gccctctatt attgtgtaac cggccttttc gattactggg gccaagggac    1440
tttggtaacc gtgtcatcat atccctatga cgtccctgac tacgcagggg gaggaggggg    1500
atccggtggc ggtggtagtg gaggaggtgg atctggagga gggggaagcg gtaccccagc    1560
tgcgaaacga gttaaattgg atggtggtgg cgggtcctca ggtttgccca atggattgga    1620
tggtgatgaa gacttctcag acatcgcaga tatggacttt agtgccttgc tgagccaaat    1680
ctcatctggc tcatcaggtc ttcccaacg attggatggc gatgaggact tttccgacat    1740
cgcagacatg gactttttccg ctctgttgag ccagataagt tctggctcct ccggactccc    1800
taatggcttg gatggagatg aggattttag cgatatagca gacatggatt ttagcgcatt    1860
gctctcacaa atcccagtg gcggggggtgg tagtggattt tcagtggata cttccgcact    1920
tctcgatttg ttttctccca gtgtcaccgt cccagacatg agtcttcctg acctcgactc    1980
ttctctcgcc agtattcagg aactgctcag tccacaggag cctcctcgcc tcctgaagc    2040 agagaatagt tccccagatt caggaaagca gctggtgcac tacacagcac agccactgtt    2100
cctcttggac cctgggagtg tagacacagg ctcaaacgat ctccccgttc ttttttgaact    2160
```

-continued

```
tggcgaaggt tcctatttta gcgaggggga cggattcgcc gaggaccta ctatcagtct       2220 ccttacaggt agcgagccac ccaaagctaa agaccccacc gtgagctagt gactcgagga       2280
ttcgtcagta gggttgtaaa ggttttctt ttcctgagaa aacaacctt tgttttctca        2340 ggttttgctt tttggccttt ccctagcttt aaaaaaaaa aagcaaaact caccgaggca       2400
gttccatagg atggctagca agatcctggt attggtctgc gagaagagcg agctcttcaa      2460
tcaacctctg gattacaaaa tttgtgaaag attgactggt attcttaact atgttgctcc      2520
ttttacgcta tgtggatacg ctgctttaat gcctttgtat catgctattg cttcccgtat      2580
ggctttcatt ttctcctcct tgtataaatc ctggttgctg tctctttatg aggagttgtg      2640
gcccgttgtc aggcaacgtg gcgtggtgtg cactgtgttt gctgacgcaa cccccactgg      2700
ttggggcatt gccaccacct gtcagctcct ttccgggact ttcgctttcc ccctccctat      2760
tgccacggcg gaactcatcg ccgcctgcct tgcccgctgc tggacagggg ctcggctgtt      2820
gggcactgac aattccgtgg tgttgtcggg gaaatcatcg tcctttcctt ggctgctcgc      2880
ctgtgttgcc acctggattc tgcgcgggac gtccttctgc tacgtccctt cggccctcaa      2940
tccagcggac cttccttccc gcggcctgct gccggctctg cggcctcttc cgcgtcttcg      3000
ccttcgccct cagacgagtc ggatctccct ttgggccgcc tccccgcgtc gactttaaga      3060
ccaatcggcc gcaggaaccc ctagtgatgg agttggccac tccctctctg cgcgctcgct      3120
cgctcactga ggccgggcga ccaaaggtcg cccgacgccc gggctttgcc cgggcggcct      3180
cagtgagcga gcgagcgcgc agctgcctgc aggggcgcct gatgcggtat tttctcctta      3240
cgcatctgtg cggtatttca caccgcatac gtcaaagcaa ccatagtacg cgccctgtag      3300
cggcgcatta agcgcggcgg gtgtggtggt tacgcgcagc gtgaccgcta cacttgccag      3360
cgccttagcg cccgctcctt cgctttctt cccttccttt ctcgccacgt tcgccggctt       3420
tccccgtcaa gctctaaatc gggggctccc tttagggttc cgatttagtg ctttacggca      3480
cctcgacccc aaaaaacttg atttgggtga tggttcacgt agtgggccat cgccctgata      3540
gacggttttt cgccctttga cgttggagtc cacgttcttt aatagtggac tcttgttcca      3600
aactggaaca acactcaact ctatctcggg ctattctttt gatttataag ggattttgcc      3660
gatttcggtc tattggttaa aaaatgagct gatttaacaa aaatttaacg cgaattttaa      3720
caaaatatta acgtttacaa ttttatggtg cactctcagt acaatctgct ctgatgccgc      3780
atagttaagc cagccccgac acccgccaac acccgctgac gcgccctgac gggcttgtct      3840
gctcccggca tccgcttaca gacaagctgt gaccgtctcc gggagctgca tgtgtcagag      3900
gttttcaccg tcatcaccga aacgcgcgag acgaaagggc ctcgtgatac gcctattttt      3960
ataggttaat gtcatgataa taatggtttc ttagacgtca ggtggcactt ttcggggaaa      4020
tgtgcgcgga acccctattt gtttattttt ctaaatacat tcaaatatgt atccgctcat      4080
gagacaataa ccctgataaa tgcttcaata atattgaaaa aggaagagta tgagtattca      4140
acatttccgt gtcgccctta ttcccttttt tgcggcattt tgccttcctg ttttttgctca     4200 cccagaaacg ctggtgaaag taaaagatgc tgaagatcag ttgggtgcac gagtgggtta      4260
catcgaactg gatctcaaca gcggtaagat ccttgagagt tttcgccccg aagaacgttt      4320
tccaatgatg agcacttta aagttctgct atgtggcgcg gtattatccc gtattgacgc       4380
cgggcaagag caactcggtc gccgcataca ctattctcag aatgacttgg ttgagtactc      4440
accagtcaca gaaaagcatc ttacggatgg catgacagta agagaattat gcagtgctgc      4500
```

-continued

```
cataaccatg agtgataaca ctgcggccaa cttacttctg acaacgatcg gaggaccgaa    4560
ggagctaacc gctttttttgc acaacatggg ggatcatgta actcgccttg atcgttggga    4620
accggagctg aatgaagcca taccaaacga cgagcgtgac accacgatgc ctgtagcaat    4680
ggcaacaacg ttgcgcaaac tattaactgg cgaactactt actctagctt cccggcaaca    4740
attaatagac tggatggagg cggataaagt tgcaggacca cttctgcgct cggcccttcc    4800
ggctggctgg tttattgctg ataaatctgg agccggtgag cgtggaagcc gcggtatcat    4860
tgcagcactg gggccagatg gtaagccctc ccgtatcgta gttatctaca cgacggggag    4920
tcaggcaact atggatgaac gaaatagaca gatcgctgag ataggtgcct cactgattaa    4980
gcattggtaa ctgtcagacc aagtttactc atatatactt tagattgatt taaaacttca    5040 ttttttaattt aaaaggatct aggtgaagat cctttttgat aatctcatga ccaaaatccc    5100
ttaacgtgag ttttcgttcc actgagcgtc agaccccgta gaaaagatca aaggatcttc    5160
ttgagatcct ttttttctgc gcgtaatctg ctgcttgcaa acaaaaaaac caccgctacc    5220
agcggtggtt tgtttgccgg atcaagagct accaactctt tttccgaagg taactggctt    5280
cagcagagcg cagataccaa atactgttct tctagtgtag ccgtagttag gccaccactt    5340
caagaactct gtagcaccgc ctacatacct cgctctgcta atcctgttac cagtggctgc    5400
tgccagtggc gataagtcgt gtcttaccgg gttggactca agacgatagt taccggataa    5460
ggcgcagcgg tcgggctgaa cggggggttc gtgcacacag cccagcttgg agcgaacgac    5520
ctacaccgaa ctgagatacc tacagcgtga gctatgagaa agcgccacgc ttcccgaagg    5580
gagaaaggcg gacaggtatc cggtaagcgg cagggtcgga acaggagagc gcacgaggga    5640
gcttccaggg ggaaacgcct ggtatcttta tagtcctgtc gggtttcgcc acctctgact    5700
tgagcgtcga tttttgtgat gctcgtcagg ggggcggagc ctatggaaaa acgccagcaa    5760
cgcggccttt ttacggttcc tggccttttg ctggcctttt gctcacatgt              5810
```

```
<210> SEQ ID NO 17
<211> LENGTH: 6689
<212> TYPE: DNA
<213> ORGANISM: Artificial Sequence
<220> FEATURE:
<223> OTHER INFORMATION: pRC124

<400> SEQUENCE: 17
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggcctcta gaaaggatct gcgatcgctc cggtgcccgt cagtgggcag    180
agcgcacatc gcccacagtc cccgagaagt tggggggagg ggtcggcaat tgaacgggtg    240
cctagagaag gtggcgcggg gtaaactggg aaagtgatgt cgtgtactgg ctccgccttt    300
ttcccgaggg tggggagaa ccgtatataa gtgcagtagt cgccgtgaac gttcttttttc    360 gcaacgggtt tgccgccaga acacagctga agcttcgagg ggctcgcatc tctccttcac    420
gcgcccgccg ccctacctga ggccgccatc cacgccggtt gagtcgcgtt ctgccgcctc    480
ccgcctgtgg tgcctcctga actgcgtccg ccgtctaggt aagtttaaag ctcaggtcga    540
gaccgggcct ttgtccggcg ctcccttgga gcctacctag actcagccgg ctctccacgc    600
tttgcctgac cctgcttgct caactctacg tctttgtttc gttttctgtt ctgcgccgtt    660
acagatctgg ctaactaccg gtgccaccat gcccgctgcg aaacgagtta aattggatgg    720
atcctcaaag ctggagaaat tcaccaactg ttatagcctg tctaagaccc tgcgcttcaa    780
```

```
ggcaatccca gtgggcaaga cacaagagaa cattgacaac aaacggctcc tggtggagga     840
tgagaagagg gctgaagatt acaagggcgt taagaagctg ctggataggt actatctgtc     900
attcatcaac gatgtcctcc acagtatcaa gctgaagaat ctgaacaatt acatttctct     960
gttccggaag aagacacgga ccgagaagga gaacaaagac ctggagaatc tggagatcaa    1020
cctgaggaaa gaaatagcta aggctttcaa agggaacgag ggttacaagt ccctgttcaa    1080
gaaagacatt atcgagacta ttctgcctga gttcctggac gataaagatg agatcgccct    1140
cgtcaattcc ttcaatgggt ttaccacagc ctttaccggc ttcttcgaca atagagagaa    1200
tatgttctct gaagaggcca aatccactag catcgccttt cgctgcataa acgagaacct    1260
gactaggtac atcagcaata tggacatctt tgagaaagtc gatgccatat cgacaaaca    1320 tgaggtgcag gagattaagg agaagatcct gaactcagat tacgatgtcg aagatttctt    1380
cgagggagag ttcttcaact tcgtgctcac acaagagggc attgatgtgt acaatgcaat    1440
cattggaggg ttcgtgacag agagtggcga agaataaag ggcctgaacg agtatatcaa    1500
cctctacaac cagaaaacca agcagaaact gcctaagttc aagccactgt acaaacaagt    1560
gctctcagat agggaaagcc tgagcttcta cggtgaaggg tatacatcag atgaagaagt    1620
gctcgaagtg ttccgcaaca ccctcaataa gaacagtgaa atcttctctt caatcaagaa    1680
gctggagaaa ctgttcaaga atttcgatga gtactcctct gccggaatct ttgtgaagaa    1740
tggccctgca atatccacta ttagcaaaga catctttggc gagtggaacg ttatcaggga    1800
taagtggaat gccgagtacg atgatattca tctcaagaag aaagccgtgg ttacagagaa    1860
atacgaggat gatagacgca agagctttaa gaagattggt agcttctctc tcgaacagct    1920
gcaggagtac gccgacgctg acctgtcagt cgtggagaaa ctcaaggaga tcataatcca    1980
gaaggtggat gaaatctaca aagtgtatgg aagctctgag aaactcttcg atgcagactt    2040
tgttctggag aagagtctga agaagaacga cgcagtggtt gctatcatga aggacctgct    2100
ggattctgtt aagtctttcg agaattacat taaggcattc tttggtgaag ggaaggagac    2160
aaatagggac gagagcttct atggcgactt tgttctggcc tacgacatcc tcctcaaggt    2220
tgaccacatc tatgacgcta tacggaatta cgttacccag aagccctata gcaaagacaa    2280
gttcaagctg tatttccaga atccacagtt tatgggtggg tgggataaag acaaagaaac    2340
agattacagg gccactatcc tgcggtacgg cagcaaatac tatctggcta tcatggataa    2400
gaagtacgcc aaatgcctcc agaagatcga caaggacgac gtgggtacca gtccagctgc    2460
gaaacgagtt aaattggatg gtggtggcgg gtcctcaggt ttgcccaatg gattggatgg    2520
tgatgaagac ttctcagaca tcgcagatat ggactttagt gccttgctga gccaaatctc    2580
atctggctca tcaggtcttc ccaacggatt ggatggcgat gaggacttt ccgacatcgc    2640 agacatggac tttttccgctc tgttgagcca gataagttct ggctcctccg gactccctaa    2700
tggcttggat ggagatgagg attttagcga tatagcagac atggatttta gcgcattgct    2760
ctcacaaatc tccagtggcg ggggtggtag tggatttttca gtggatactt ccgcacttct    2820
cgatttgttt tctcccagtg tcaccgtccc agacatgagt cttcctgacc tcgactcttc    2880
tctcgccagt attcaggaac tgctcagtcc acaggagcct cctcgccctc ctgaagcaga    2940
gaatagttcc ccagattcag gaaagcagct ggtgcactac acagcacagc cactgttcct    3000
cttggaccct gggagtgtag acacaggctc aaacgatctc cccgttcttt ttgaacttgg    3060
cgaaggttcc tattttagcg aggggggacgg attcgccgag gaccctacta tcagtctcct    3120
```

-continued

```
tacaggtagc gagccaccca aagctaaaga ccccaccgtg agctagtgac tcgaggattc    3180
gtcagtaggg ttgtaaaggt ttttctttc ctgagaaaac aaccttttgt tttctcaggt    3240
tttgcttttt ggcctttccc tagctttaaa aaaaaaaag caaaactcac cgaggcagtt    3300
ccataggatg gctagcaaga tcctggtatt ggtctgcgag aagagcgagc tcttcaatca    3360
acctctggat tacaaaattt gtgaaagatt gactggtatt cttaactatg ttgctccttt    3420
tacgctatgt ggatacgctg ctttaatgcc tttgtatcat gctattgctt cccgtatggc    3480 tttcatttc tcctccttgt ataaatcctg gttgctgtct ctttatgagg agttgtggcc    3540
cgttgtcagg caacgtggcg tggtgtgcac tgtgtttgct gacgcaaccc ccactggttg    3600
gggcattgcc accacctgtc agctcctttc cgggactttc gctttccccc tccctattgc    3660
cacggcggaa ctcatcgccg cctgccttgc ccgctgctgg acaggggctc ggctgttggg    3720
cactgacaat tccgtggtgt tgtcggggaa atcatcgtcc tttccttggc tgctcgcctg    3780
tgttgccacc tggattctgc gcgggacgtc cttctgctac gtcccttcgg ccctcaatcc    3840
agcggacctt ccttcccgcg gcctgctgcc ggctctgcgg cctcttccgc gtcttcgcct    3900
tcgccctcag acgagtcgga tctcccttg ggccgcctcc ccgccggccg caggaacccc    3960
tagtgatgga gttggccact ccctctctgc gcgctcgctc gctcactgag gccgggcgac    4020
caaaggtcgc ccgacgcccg ggctttgccc gggcggcctc agtgagcgag cgagcgcgca    4080
gctgcctgca ggggcgcctg atgcggtatt ttctccttac gcatctgtgc ggtatttcac    4140
accgcatacg tcaaagcaac catagtacgc gccctgtagc ggcgcattaa gcgcggcggg    4200
tgtggtggtt acgcgcagcg tgaccgctac acttgccagc gccttagcgc ccgctccttt    4260
cgctttcttc ccttcctttc tcgccacgtt cgccggcttt ccccgtcaag ctctaaatcg    4320
ggggctccct ttagggttcc gatttagtgc tttacggcac ctcgacccca aaaaacttga    4380
tttgggtgat ggttcacgta gtgggccatc gccctgatag acggtttttc gccctttgac    4440
gttggagtcc acgttcttta atagtggact cttgttccaa actggaacaa cactcaactc    4500
tatctcgggc tattcttttg atttataagg gattttgccg atttcggtct attggttaaa    4560
aaatgagctg atttaacaaa aatttaacgc gaattttaac aaaatattaa cgtttacaat    4620
tttatggtgc actctcagta caatctgctc tgatgccgca tagttaagcc agccccgaca    4680
cccgccaaca cccgctgacg cgccctgacg ggcttgtctg ctcccggcat ccgcttacag    4740
acaagctgtg accgtctccg ggagctgcat gtgtcagagg ttttcaccgt catcaccgaa    4800
acgcgcgaga cgaaagggcc tcgtgatacg cctatttta taggttaatg tcatgataat    4860
aatggtttct tagacgtcag gtggcacttt tcggggaaat gtgcgcggaa cccctatttg    4920
tttatttttc taaatacatt caaatatgta tccgctcatg agacaataac cctgataaat    4980
gcttcaataa tattgaaaaa ggaagagtat gagtattcaa catttccgtg tcgcccttat    5040 tcccttttt gcggcatttt gccttcctgt ttttgctcac ccagaaacgc tggtgaaagt    5100
aaaagatgct gaagatcagt tgggtgcacg agtgggttac atcgaactgg atctcaacag    5160
cggtaagatc cttgagagtt ttcgccccga agaacgtttt ccaatgatga gcacttttaa    5220
agttctgcta tgtggcgcgg tattatcccg tattgacgcc gggcaagagc aactcggtcg    5280
ccgcatacac tattctcaga atgacttggt tgagtactca ccagtcacag aaaagcatct    5340
tacggatggc atgacagtaa gagaattatg cagtgctgcc ataaccatga gtgataacac    5400
tgcggccaac ttacttctga caacgatcgg aggaccgaag gagctaaccg cttttttgca    5460
caacatgggg gatcatgtaa ctcgccttga tcgttgggaa ccggagctga atgaagccat    5520
```

-continued

```
accaaacgac gagcgtgaca ccacgatgcc tgtagcaatg gcaacaacgt tgcgcaaact     5580
attaactggc gaactactta ctctagcttc ccggcaacaa ttaatagact ggatggaggc     5640
ggataaagtt gcaggaccac ttctgcgctc ggcccttccg gctggctggt ttattgctga     5700
taaatctgga gccggtgagc gtggaagccg cggtatcatt gcagcactgg ggccagatgg     5760
taagccctcc cgtatcgtag ttatctacac gacggggagt caggcaacta tggatgaacg     5820
aaatagacag atcgctgaga taggtgcctc actgattaag cattggtaac tgtcagacca     5880
agtttactca tatatacttt agattgattt aaaacttcat ttttaattta aaaggatcta     5940
ggtgaagatc cttttgata atctcatgac caaaatccct taacgtgagt tttcgttcca     6000
ctgagcgtca gaccccgtag aaaagatcaa aggatcttct tgagatcctt tttttctgcg     6060
cgtaatctgc tgcttgcaaa caaaaaaacc accgctacca gcggtggttt gtttgccgga     6120
tcaagagcta ccaactcttt ttccgaaggt aactggcttc agcagagcgc agataccaaa     6180
tactgttctt ctagtgtagc cgtagttagg ccaccacttc aagaactctg tagcaccgcc     6240
tacatacctc gctctgctaa tcctgttacc agtggctgct gccagtggcg ataagtcgtg     6300
tcttaccggg ttggactcaa gacgatagtt accggataag gcgcagcggt cgggctgaac     6360
ggggggttcg tgcacacagc ccagcttgga gcgaacgacc tacaccgaac tgagatacct     6420
acagcgtgag ctatgagaaa gcgccacgct tcccgaaggg agaaaggcgg acaggtatcc     6480
ggtaagcggc agggtcggaa caggagagcg cacgagggag cttccagggg gaaacgcctg     6540
gtatctttat agtcctgtcg ggtttcgcca cctctgactt gagcgtcgat ttttgtgatg     6600
ctcgtcaggg gggcggagcc tatggaaaaa cgccagcaac gcggccttt tacggttcct     6660 ggccttttgc tggccttttg ctcacatgt                                       6689
```

```
<210> SEQ ID NO 18
<211> LENGTH: 6904
<212> TYPE: DNA
<213> ORGANISM: Artificial Sequence
<220> FEATURE:
<223> OTHER INFORMATION: pRC126
```

```
<400> SEQUENCE: 18
```

```
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggcctcta gaaaggatct gcgatcgctc cggtgcccgt cagtgggcag     180
agcgcacatc gcccacagtc cccgagaagt tggggggagg ggtcggcaat gaacgggtg     240 cctagagaag gtggcgcggg gtaaactggg aaagtgatgt cgtgtactgg ctccgccttt      300
ttcccgaggg tgggggagaa ccgtatataa gtgcagtagt cgccgtgaac gttcttttc      360 gcaacgggtt tgccgccaga acacagctga agcttcgagg ggctcgcatc tctccttcac     420
gcgcccgccg ccctacctga ggccgccatc cacgccggtt gagtcgcgtt ctgccgcctc     480
ccgcctgtgg tgcctcctga actgcgtccg ccgtctaggt aagtttaaag ctcaggtcga     540
gaccgggcct ttgtccggcg ctcccttgga gcctacctag actcagccgg ctctccacgc     600
tttgcctgac cctgcttgct caactctacg tctttgtttc gttttctgtt ctgcgccgtt     660
acagatctgg ctaactaccg gtgccaccat gcccgctgcg aaacgagtta aattggatgg     720
tggtggcggg tcctcaggtt tgcccaatgg attggatggt gatgaagact ctctcagacat     780 cgcagatatg gactttagtg ccttgctgag ccaaatctca tctggctcat caggtcttcc     840
```

-continued

```
caacggattg gatggcgatg aggacttttc cgacatcgca gacatggact tttccgctct    900
gttgagccag ataagttctg gctcctccgg actccctaat ggcttggatg gagatgagga    960
ttttagcgat atagcagaca tggattttag cgcattgctc tcacaaatct ccagtggcgg    1020
gggtggtagt ggattttcag tggatacttc cgcacttctc gatttgtttt ctcccagtgt    1080
caccgtccca gacatgagtc ttcctgacct cgactcttct ctcgccagta ttcaggaact    1140
gctcagtcca caggagcctc ctcgccctcc tgaagcagag aatagttccc cagattcagg    1200
aaagcagctg gtgcactaca cagcacagcc actgttcctc ttggaccctg ggagtgtaga    1260
cacaggctca aacgatctcc ccgttctttt tgaacttggc gaaggttcct attttagcga    1320
gggggacgga ttcgccgagg accctactat cagtctcctt acaggtagcg agccacccaa    1380
agctaaagac cccaccgtga gcggtggtgg cgggtccggt aacggtaact acgagaagat    1440
caattacaag ctcctgccag gacctaacaa gatgctgccc aaggtgttct tctccaagaa    1500
atggatggcc tactataacc caagcgagga cattcagaag atatacaaga atgggacatt    1560
caagaagggc gatatgttca acctcaacga ctgccacaag ctgattgatt tcttcaagga    1620
tagcatttct cgctatccca agtggtctaa tgcatacgat ttcaacttca gcgagactga    1680
gaagtacaaa gacatcgctg gcttctaccg ggaggtggaa gagcaaggct ataaggtgtc    1740
attcgaatcc gcttctaaga aggaagtgga taagctcgtg gaagagggta agctgtacat    1800
gttccagata tacaacaaag acttcagcga taagagccac ggcactccaa acctccatac    1860
tatgtatttc aagctgctgt ttgacgagaa caaccacgga cagattaggc tgtcaggagg    1920
cgcagaactc ttcatgcgca gagcttcact gaagaaggag gaactcgttg tccacccagc    1980
caatagccct atagccaata agaatccaga caatcctaag aaaaccacta ctctgtctta    2040
cgatgtgtat aaggataaga gattctctga agatcagtac gaactgcaca tacccattgc    2100
cattaacaag tgccctaaga acatcttcaa gattaacaca gaggttagag tgctcctgaa    2160
acacgacgat aacccttatg ttataggcat tgctcgcgga gagagaaacc tgctgtacat    2220
cgtcgtggtg gacggcaaag gcaacatcgt ggaacagtac agtctcaatg aaatcattaa    2280
caatttcaac ggaatccgca ttaagaccga ctaccattct ctcctcgaca agaaggagaa    2340
agaaaggttc gaagcaagac agaattggac aagtatagag aatatcaaag aactgaaggc    2400
tgggtacatc tctcaggttg tgcacaagat atgtgagctg gtggagaagt acgacgctgt    2460
tatcgccctc gcggacctga atagcggctt caagaactcc agggtgaagg tggagaagca    2520
ggtgtatcag aagttcgaga gatgctgat cgacaagctc aactatatgg tggacaagaa    2580
atccaatcct tgcgctactg gtggagccct gaagggctat caaatcacca ataagttcga    2640
atctttcaag tctatgagca cccagaatgg cttcatcttc tacatacccg catggctgac    2700
atccaagatt gatccctcta ccggatttgt taatctgctc aagactaagt acacctctat    2760
tgctgactca aagaagttca tatcatcatt tgaccgcatc atgtacgtgc cagaagagga    2820
cctgttcgag tttgccctgg attacaagaa tttctctcgg actgacgccg actacatcaa    2880
gaagtggaag ctctactctt atggtaatcg gattcgcata ttccgcaatc ccaagaagaa    2940
taacgtgttc gattgggagg aagtttgcct caccagcgct tacaaggagc tgttcaataa    3000
gtatgggatt aactaccagc agggcgacat aagagccctg ctgtgcgaac aatctgataa    3060
ggcattctat tcctctttca tggcactgat gtcactgatg ctgcaaatgc gcaattccat    3120
caccggaaga acagacgtgg cctttctgat ctctcctgtc aagaactcag atggcatctt    3180
ctacgattcc cgcaactatg aagcacagga gaatgctatc ctgcctaaga atgccgatgc    3240
```

-continued

```
aaatggagcc tataacatcg ccagaaaggt cctctgggcc ataggacaat tcaagaaagc    3300
tgaagatgag aagctggaca aggtgaagat cgccatttca aacaaagagt ggctcgaata    3360
tgctcagacc tcagtgaagc atggtacccc cgctgcgaaa cgagttaaat tggatggtgg    3420
tggcgggtcc tcaggtttgc ccaatggatt ggatggtgat gaagacttct cagacatcgc    3480
agatatggac tttagtgcct tgctgagcca aatctcatct ggctcatcag gtcttcccaa    3540
cggattggat ggcgatgagg acttttccga catcgcagac atggactttt ccgctctgtt    3600
gagccagata agttctggct cctccggact ccctaatggc ttggatggag atgaggattt    3660
tagcgatata gcagacatgg attttagcgc attgctctca caaatctcca gtggcggggg    3720
tggtagtgga ttttcagtgg atacttccgc acttctcgat ttgtttttctc ccagtgtcac    3780 cgtcccagac atgagtcttc ctgacctcga ctcttctctc gccagtattc aggaactgct    3840
cagtccacag gagcctcctc gccctcctga agcagagaat agttccccag attcaggaaa    3900
gcagctggtg cactacacag cacagccact gttcctcttg gaccctggga gtgtagacac    3960
aggctcaaac gatctccccg ttcttttttga acttggcgaa ggttcctatt ttagcgaggg    4020
ggacggattc gccgaggacc ctactatcag tctccttaca ggtagcgagc cacccaaagc    4080
taaagacccc accgtgagct agtgactcga gaataaaaga tctttatttt cattagatct    4140
gtgtgttggt tttttgtgtc ggccgcagga acccctagtg atggagttgg ccactccctc    4200
tctgcgcgct cgctcgctca ctgaggccgg gcgaccaaag gtcgcccgac gcccgggctt    4260
tgcccgggcg gcctcagtga gcgagcgagc gcgcagctgc ctgcaggggc gcctgatgcg    4320
gtattttctc cttacgcatc tgtgcggtat ttcacaccgc atacgtcaaa gcaaccatag    4380
tacgcgccct gtagcggcgc attaagcgcg gcgggtgtgg tggttacgcg cagcgtgacc    4440
gctacacttg ccagcgccct agcgcccgct cctttcgctt tcttcccttc ctttctcgcc    4500
acgttcgccg gctttccccg tcaagctcta atcggggggc tccctttagg gttccgattt    4560
agtgctttac ggcacctcga ccccaaaaaa cttgatttgg gtgatggttc acgtagtggg    4620
ccatcgccct gatagacggt ttttcgccct ttgacgttgg agtccacgtt ctttaatagt    4680
ggactcttgt tccaaactgg aacaacactc aactctatct cgggctattc ttttgattta    4740
taagggattt tgccgatttc ggtctattgg ttaaaaaatg agctgattta acaaaaattt    4800
aacgcgaatt ttaacaaaat attaacgttt acaattttat ggtgcactct cagtacaatc    4860
tgctctgatg ccgcatagtt aagccagccc cgacacccgc caacacccgc tgacgcgccc    4920
tgacgggctt gtctgctccc ggcatccgct tacagacaag ctgtgaccgt ctccgggagc    4980
tgcatgtgtc agaggttttc accgtcatca ccgaaacgcg cgagacgaaa gggcctcgtg    5040
atacgcctat ttttataggt taatgtcatg ataataatgg tttcttagac gtcaggtggc    5100
acttttcggg gaaatgtgcg cggaacccct atttgtttat ttttctaaat acattcaaat    5160
atgtatccgc tcatgagaca ataaccctga taaatgcttc aataatattg aaaaaggaag    5220
agtatgagta ttcaacattt ccgtgtcgcc cttattccct tttttgcggc attttgcctt    5280 cctgttttttg ctcacccaga aacgctggtg aaagtaaaag atgctgaaga tcagttgggt    5340
gcacgagtgg gttacatcga actggatctc aacagcggta agatccttga gtttttcgc    5400 cccgaagaac gttttccaat gatgagcact tttaaagttc tgctatgtgg cgcggtatta    5460
tcccgtattg acgccgggca agagcaactc ggtcgccgca tacactattc tcagaatgac    5520
ttggttgagt actcaccagt cacagaaaag catcttacgg atggcatgac agtaagagaa    5580
```

-continued

```
ttatgcagtg ctgccataac catgagtgat aacactgcgg ccaacttact tctgacaacg      5640
atcggaggac cgaaggagct aaccgctttt ttgcacaaca tggggggatca tgtaactcgc      5700 cttgatcgtt gggaaccgga gctgaatgaa gccataccaa acgacgagcg tgacaccacg      5760
atgcctgtag caatggcaac aacgttgcgc aaactattaa ctggcgaact acttactcta      5820
gcttcccggc aacaattaat agactggatg gaggcggata aagttgcagg accacttctg      5880
cgctcggccc ttccggctgg ctggtttatt gctgataaat ctggagccgg tgagcgtgga      5940
agccgcggta tcattgcagc actggggcca gatggtaagc cctcccgtat cgtagttatc      6000
tacacgacgg ggagtcaggc aactatggat gaacgaaata gacagatcgc tgagataggt      6060
gcctcactga ttaagcattg gtaactgtca gaccaagttt actcatatat actttagatt      6120
gatttaaaac ttcattttta atttaaaagg atctaggtga agatcctttt tgataatctc      6180
atgaccaaaa tcccttaacg tgagttttcg ttccactgag cgtcagaccc cgtagaaaag      6240
atcaaaggat cttcttgaga tcctttttt ctgcgcgtaa tctgctgctt gcaaacaaaa      6300
aaaccaccgc taccagcggt ggtttgtttg ccggatcaag agctaccaac tcttttttccg      6360 aaggtaactg gcttcagcag agcgcagata ccaaatactg ttcttctagt gtagccgtag      6420
ttaggccacc acttcaagaa ctctgtagca ccgcctacat acctcgctct gctaatcctg      6480
ttaccagtgg ctgctgccag tggcgataag tcgtgtctta ccgggttgga ctcaagacga      6540
tagttaccgg ataaggcgca gcggtcgggc tgaacggggg gttcgtgcac acagcccagc      6600
ttggagcgaa cgacctacac cgaactgaga tacctacagc gtgagctatg agaaagcgcc      6660
acgcttcccg aagggagaaa ggcggacagg tatccggtaa gcggcagggt cggaacagga      6720
gagcgcacga gggagcttcc aggggggaaac gcctggtatc tttatagtcc tgtcgggttt      6780
cgccacctct gacttgagcg tcgatttttg tgatgctcgt caggggggcg gagcctatgg      6840
aaaaacgcca gcaacgcggc ctttttacgg ttcctggcct tttgctggcc ttttgctcac      6900
atgt                                                                 6904
```

<210> SEQ ID NO 19
<211> LENGTH: 20
<212> TYPE: DNA
<213> ORGANISM: Artificial Sequence
<220> FEATURE:
<223> OTHER INFORMATION: CD80 sg2

<400> SEQUENCE: 19

```
tccaggcctg ttctgagcac                                                  20
```

<210> SEQ ID NO 20
<211> LENGTH: 20
<212> TYPE: DNA
<213> ORGANISM: Artificial Sequence
<220> FEATURE:
<223> OTHER INFORMATION: LIGHT sg2

<400> SEQUENCE: 20

```
gaggaggtac gtgaggaaag                                                  20
```

<210> SEQ ID NO 21
<211> LENGTH: 20
<212> TYPE: DNA
<213> ORGANISM: Artificial Sequence
<220> FEATURE:
<223> OTHER INFORMATION: CXCL10 sg3

<400> SEQUENCE: 21

-continued

```
gcaatgccct cggtttacag                                              20

<210> SEQ ID NO 22
<211> LENGTH: 20
<212> TYPE: DNA
<213> ORGANISM: Artificial Sequence
<220> FEATURE:
<223> OTHER INFORMATION: 4-1BBL sg2

<400> SEQUENCE: 22
acagggcctg gacagggaag                                              20

<210> SEQ ID NO 23
<211> LENGTH: 20
<212> TYPE: DNA
<213> ORGANISM: Artificial Sequence
<220> FEATURE:
<223> OTHER INFORMATION: GITRL sg1

<400> SEQUENCE: 23
agtgcttagc agtgttccaa                                              20

<210> SEQ ID NO 24
<211> LENGTH: 7151
<212> TYPE: DNA
<213> ORGANISM: Artificial Sequence
<220> FEATURE:
<223> OTHER INFORMATION: pGW071

<400> SEQUENCE: 24
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggcctcta gaaaggatct gcgatcgctc cggtgcccgt cagtgggcag     180
agcgcacatc gcccacagtc cccgagaagt tggggggagg ggtcggcaat tgaacgggtg     240
cctagagaag gtggcgcggg gtaaactggg aaagtgatgt cgtgtactgg ctccgccttt     300
ttcccgaggg tggggagaa ccgtatataa gtgcagtagt cgccgtgaac gttcttttc      360 gcaacgggtt tgccgccaga acacagctga agcttcgagg ggctcgcatc tctccttcac     420
gcgcccgccg ccctacctga ggccgccatc cacgccggtt gagtcgcgtt ctgccgcctc     480
ccgcctgtgg tgcctcctga actgcgtccg ccgtctaggt aagtttaaag ctcaggtcga     540
gaccgggcct ttgtccggcg ctcccttgga gcctacctag actcagccgg ctctccacgc     600
tttgcctgac cctgcttgct caactctacg tctttgtttc gttttctgtt ctgcgccgtt     660
acagatctgg ctaactaccg gtgccaccat ggcttgcaat tgtcagttga tgcaggatac     720
accactcctc aagtttccat gtccaaggct cattcttctc tttgtgctgc tgattcgtct     780
ttcacaagtg tcttcagatg ttgatgaaca actgtccaag tcagtgaaag ataaggtatt     840
gctgccttgc cgttacaact ctcctcatga agatgagtct gaagaccgaa tctactggca     900
aaaacatgac aaagtggtgc tgtctgtcat tgttgggaaa ctaaaagtgt ggcccgagta     960
taagaaccgg actttatatg acaacactac ctactctctt atcatcctgg gcctggtcct    1020
ttcagaccgg ggcacataca gctgtgtcgt tcaaaagaag gaaagaggaa cgtatgaagt    1080
taaacacttg gctttagtaa agttgtccat caaagctgac ttctctaccc ccaacataac    1140
tgagtctgga aacccatctg cagacactaa aaggattacc tgctttgctt ccgggggttt    1200
cccaaagcct cgcttctctt ggttggaaaa tggaagagaa ttacctggca tcaatacgac    1260
```

-continued

```
aatttcccag gatcctgaat ctgaattgta caccattagt agccaactag atttcaatac      1320
gactcgcaac cacaccatta agtgtctcat taaatatgga gatgctcacg tgtcagagga      1380
cttcacctgg gaaaaacccc cagaagaccc tcctgatagc aagaacacac ttgtgctctt      1440
tggggcagga ttcggcgcag taataacagt cgtcgtcatc gttgtcatca tcaaatgctt      1500
ctgtaagcac agaagctgtt tcagaagaaa tgaggcaagc agagaaacaa acaacagcct      1560
taccttcggg cctgaagaag cattagctga acagaccgtc ttccttcgta cgggcagtgg      1620
agagggcaga ggaagtctgc taacatgcgg tgacgtcgag gagaatcctg gcccaatgga      1680
gagtgtggta cagccttcag tgtttgtggt ggatggacag acggacatcc cattcaggcg      1740
gctggaacag aaccaccgga gacggcgctg tggcactgtc caggtcagcc tggccctggt      1800
gctgctgcta ggtgctgggc tggccactca gggctggttt ctcctgagac tgcatcaacg      1860
tcttggagac atagtagctc atctgccaga tggaggcaaa ggctcctggg agaagctgat      1920
acaagatcaa cgatctcacc aggccaaccc agcagcacat cttacaggag ccaacgccag      1980
cttgataggt attggtggac ctctgttatg ggagacacga cttggcctgg ccttcttgag      2040
gggcttgacg tatcatgatg gggccctggt gaccatggag cccggttact actatgtgta      2100
ctccaaagtg cagctgagcg gcgtgggctg ccccagggg ctggccaatg cctcccat        2160 cacccatgga ctatacaagc gcacatcccg ctacccgaag gagttagaac tgctggtcag      2220
tcggcggtca ccctgtggcc gggccaacag ctcccgagtc tggtgggaca gcagcttcct      2280
gggcggcgtg gtacatctgg aggctgggga agaggtggtg gtccgcgtgc ctggaaaccg      2340
cctggtcaga ccacgtgacg gcaccaggtc ctatttcgga gctttcatgg tcactagtgg      2400
atccggcgca acaaacttct ctctgctgaa acaagccgga gatgtcgaag agaatcctgg      2460
accgatgaac ccaagtgctg ccgtcatttt ctgcctcatc ctgctgggtc tgagtgggac      2520
tcaagggatc cctctcgcaa ggacggtccg ctgcaactgc atccatatcg atgacgggcc      2580
agtgagaatg agggccatag ggaagcttga aatcatccct gcgagcctat cctgcccacg      2640
tgttgagatc attgccacga tgaaaaagaa tgatgagcag agatgtctga atccggaatc      2700
taagaccatc aagaatttaa tgaaagcgtt tagccaaaaa aggtctaaaa gggctcctgc      2760
tagcagcggt acccagtgca ccaactacgc cctgctgaag ctggccggcg atgtggagag      2820
caacccaggg cccatggacc agcacacact tgatgtggag gataccgcgg atgccagaca      2880
tccagcaggt acttcgtgcc cctcggatgc ggcgctcctc agagataccg ggctcctcgc      2940
ggacgctgcg ctcctctcag atactgtgcg ccccacaaat gccgcgctcc ccacggatgc      3000
tgcctaccct gcggttaatg ttcgggatcg cgaggccgcg tggccgcctg cactgaactt      3060
ctgttcccgc cacccaaagc tctatggcct agtcgctttg gttttgctgc ttctgatcgc      3120
cgcctgtgtt cctatcttca cccgcaccga gcctcggcca gcgctcacaa tcaccacctc      3180
gcccaacctg ggtacccgag agaataatgc agaccaggtc accctgtttt cccacattgg      3240
ctgccccaac actacacaac agggctctcc tgtgttcgcc aagctactgg ctaaaaacca      3300
agcatcgttg tgcaatacaa ctctgaactg gcacagccaa gatggagctg ggagctcata      3360
cctatctcaa ggtctgaggt acgaagaaga caaaaaggag ttggtggtag acagtcccgg      3420
gctctactac gtattttgg aactgaagct cagtccaaca ttcacaaaca caggccacaa      3480
ggtgcagggc tgggtctctc ttgtttttgca agcaaagcct caggtagatg actttgacaa      3540 cttgccctg acagtggaac tgttcccttg ctccatggag aacaagttag tggaccgttc      3600
ctggagtcaa ctgttgctcc tgaaggctgg ccaccgcctc agtgtgggtc tgagggctta      3660
```

-continued

```
tctgcatgga gcccaggatg catacagaga ctgggagctg tcttatccca acaccaccag   3720
ctttggactc tttcttgtga aacccgacaa cccatgggaa ggcatatgcg gtaccgtgaa   3780
gcagaccctg aacttcgatc tgctgaagct ggccggcgat gtggagagca accccgggcc   3840
catgtacagc atgcagctcg catcctgtgt cacattgaca cttgtgctcc ttgtcaacag   3900
cgcacccact tcaagctcca cttcaagctc tacagcggaa gcacagcagc agcagcagca   3960
gcagcagcag cagcagcagc acctggagca gctgttgatg gacctacagg agctcctgag   4020
caggatggag aattacagga acctgaaact ccccaggatg ctcaccttca aattttactt   4080
gcccaagcag gccacagaat tgaaagatct tcagtgccta gaagatgaac ttggacctct   4140
gcggcatgtt ctggatttga ctcaaagcaa aagctttcaa ttggaagatg ctgagaattt   4200
catcagcaat atcagagtaa ctgttgtaaa actaaagggc tctgacaaca catttgagtg   4260
ccaattcgat gatgagtcag caactgtggt ggactttctg aggagatgga tagccttctg   4320
tcaaagcatc atctcaacaa gccctcaata agaattcaat aaaagatctt tattttcatt   4380
agatctgtgt gttggttttt tgtgtgcggc cgcaggaacc cctagtgatg gagttggcca   4440
ctccctctct gcgcgctcgc tcgctcactg aggccgggcg accaaaggtc gcccgacgcc   4500
cgggctttgc ccgggcggcc tcagtgagcg agcgagcgcg cagctgcctg caggggcgcc   4560
tgatgcggta ttttctcctt acgcatctgt gcggtatttc acaccgcata cgtcaaagca   4620
accatagtac gcgccctgta gcggcgcatt aagcgcggcg ggtgtggtgg ttacgcgcag   4680
cgtgaccgct acacttgcca gcgccttagc gcccgctcct ttcgctttct tcccttcctt   4740
tctcgccacg ttcgccggct ttccccgtca agctctaaat cggggctcc ctttagggtt   4800 ccgatttagt gctttacggc acctcgaccc caaaaaactt gatttgggtg atggttcacg   4860
tagtgggcca tcgccctgat agacggtttt tcgccctttg acgttggagt ccacgttctt   4920
taatagtgga ctcttgttcc aaactggaac aacactcaac tctatctcgg gctattcttt   4980
tgatttataa gggattttgc cgatttcggt ctattggtta aaaaatgagc tgatttaaca   5040
aaaatttaac gcgaatttta acaaaatatt aacgtttaca atttatggt gcactctcag   5100 tacaatctgc tctgatgccg catagttaag ccagccccga cacccgccaa cacccgctga   5160
cgcgccctga cgggcttgtc tgctcccggc atccgcttac agacaagctg tgaccgtctc   5220
cgggagctgc atgtgtcaga ggttttcacc gtcatcaccg aaacgcgcga gacgaaaggg   5280
cctcgtgata cgcctatttt tataggttaa tgtcatgata ataatggttt cttagacgtc   5340
aggtggcact tttcggggaa atgtgcgcgg aaccccctatt tgtttatttt ctaaatacca   5400
ttcaaatatg tatccgctca tgagacaata accctgataa atgcttcaat aatattgaaa   5460
aaggaagagt atgagtattc aacatttccg tgtcgccctt attcccttt ttgcggcatt   5520 ttgccttcct gttttgctc acccagaaac gctggtgaaa gtaaaagatg ctgaagatca   5580
gttgggtgca cgagtgggt acatcgaact ggatctcaac agcggtaaga tccttgagag   5640
ttttcgcccc gaagaacgtt ttccaatgat gagcactttt aaagttctgc tatgtggcgc   5700
ggtattatcc cgtattgacg ccgggcaaga gcaactcggt cgccgcatac actattctca   5760
gaatgacttg gttgagtact caccagtcac agaaaagcat cttacggatg gcatgacagt   5820
aagagaatta tgcagtgctg ccataaccat gagtgataac actgcggcca acttacttct   5880
gacaacgatc ggaggaccga aggagctaac cgcttttttg cacaacatgg gggatcatgt   5940
aactcgcctt gatcgttggg aaccggagct gaatgaagcc ataccaaacg acgagcgtga   6000
```

-continued

```
caccacgatg cctgtagcaa tggcaacaac gttgcgcaaa ctattaactg gcgaactact      6060
tactctagct tcccggcaac aattaataga ctggatggag gcggataaag ttgcaggacc      6120
acttctgcgc tcggcccttc cggctggctg gtttattgct gataaatctg gagccggtga      6180
gcgtggaagc cgcggtatca ttgcagcact ggggccagat ggtaagccct cccgtatcgt      6240
agttatctac acgacgggga gtcaggcaac tatggatgaa cgaaatagac agatcgctga      6300
gataggtgcc tcactgatta agcattggta actgtcagac caagtttact catatatact      6360
ttagattgat ttaaaacttc attttttaatt taaaaggatc taggtgaaga tccttttttga     6420 taatctcatg accaaaatcc cttaacgtga gttttcgttc cactgagcgt cagacccgt       6480 agaaaagatc aaaggatctt cttgagatcc ttttttttctg cgcgtaatct gctgcttgca     6540
aacaaaaaaa ccaccgctac cagcggtggt ttgtttgccg gatcaagagc taccaactct      6600
ttttccgaag gtaactggct tcagcagagc gcagatacca aatactgttc ttctagtgta      6660
gccgtagtta ggccaccact tcaagaactc tgtagcaccg cctacatacc tcgctctgct      6720
aatcctgtta ccagtggctg ctgccagtgg cgataagtcg tgtcttaccg ggttggactc      6780
aagacgatag ttaccggata aggcgcagcg gtcgggctga acggggggtt cgtgcacaca      6840
gcccagcttg gagcgaacga cctacaccga actgagatac ctacagcgtg agctatgaga      6900
aagcgccacg cttcccgaag ggagaaaggc ggacaggtat ccggtaagcg gcagggtcgg      6960
aacaggagag cgcacgaggg agcttccagg gggaaacgcc tggtatcttt atagtcctgt      7020
cgggtttcgc cacctctgac ttgagcgtcg attttttgtga tgctcgtcag gggggcggag      7080
cctatggaaa aacgccagca acgcggcctt tttacggttc ctggcctttt gctggccttt      7140
tgctcacatg t                                                           7151
```

<210> SEQ ID NO 25
<211> LENGTH: 3956
<212> TYPE: DNA
<213> ORGANISM: Artificial Sequence
<220> FEATURE:
<223> OTHER INFORMATION: pGW072

<400> SEQUENCE: 25

```
cctgcaggca gctgcgcgct cgctcgctca ctgaggccgc ccgggcgtcg ggcgaccttt        60
ggtcgcccgg cctcagtgag cgagcgagcg cgcagagagg gagtggccaa ctccatcact       120
aggggttcct gcggcctcta gaaaggatct gcgatcgctc cggtgcccgt cagtgggcag       180
agcgcacatc gcccacagtc cccgagaagt tggggggagg ggtcggcaat tgaacgggtg       240
cctagagaag gtggcgcggg gtaaactggg aaagtgatgt cgtgtactgg ctccgccttt       300
ttcccgaggg tggggggagaa ccgtatataa gtgcagtagt cgccgtgaac gttcttttttc     360 gcaacgggtt tgccgccaga acacagctga agcttcgagg ggctcgcatc tctccttcac       420
gcgcccgccg ccctacctga ggccgccatc cacgccggtt gagtgcgcgtt ctgccgcctc       480 ccgcctgtgg tgcctcctga actgcgtccg ccgtctaggt aagtttaaag ctcaggtcga       540
gaccgggcct ttgtccggcg ctcccttgga gcctacctag actcagccgg ctctccacgc       600
tttgcctgac cctgcttgct caactctacg tctttgtttc gttttctgtt ctgcgccgtt       660
acagatctgg ctaactaccg gtgccaccat gaacgctaca cactgcatct tggctttgca       720
gctcttcctc atggctgttt ctggctgtta ctgccacggc acagtcattg aaagcctaga       780
aagtctgaat aactatttta actcaagtgg catagatgtg gaagaaaaga gtctcttctt       840
ggatatctgg aggaactggc aaaaggatgg tgacatgaaa atcctgcaga gccagattat       900
```

-continued

```
ctctttctac ctcagactct ttgaagtctt gaaagacaat caggccatca gcaacaacat      960
aagcgtcatt gaatcacacc tgattactac cttcttcagc aacagcaagg cgaaaaagga     1020
tgcattcatg agtattgcca agtttgaggt caacaaccca caggtccagc gccaagcatt     1080
caatgagctc atccgagtgg tccaccagct gttgccggaa tccagcctca ggaagcggaa     1140
aaggagtcgc tgctgagaat tcaataaaag atctttattt tcattagatc tgtgtgttgg     1200 tttttttgtgt gcggccgcag gaacccctag tgatggagtt ggccactccc tctctgcgcg     1260
ctcgctcgct cactgaggcc gggcgaccaa aggtcgcccg acgcccgggc tttgcccggg     1320
cggcctcagt gagcgagcga gcgcgcagct gcctgcaggg gcgcctgatg cggtattttc     1380
tccttacgca tctgtgcggt atttcacacc gcatacgtca aagcaaccat agtacgcgcc     1440
ctgtagcggc gcattaagcg cggcgggtgt ggtggttacg cgcagcgtga ccgctacact     1500
tgccagcgcc ttagcgcccg ctcctttcgc tttcttccct tcctttctcg ccacgttcgc     1560
cggctttccc cgtcaagctc taaatcgggg gctcccttta gggttccgat ttagtgcttt     1620
acggcacctc gaccccaaaa aacttgattt gggtgatggt tcacgtagtg ggccatcgcc     1680
ctgatagacg gtttttcgcc ctttgacgtt ggagtccacg ttctttaata gtggactctt     1740
gttccaaact ggaacaacac tcaactctat ctcgggctat tcttttgatt tataagggat     1800
tttgccgatt tcggtctatt ggttaaaaaa tgagctgatt taacaaaaat ttaacgcgaa     1860
ttttaacaaa atattaacgt ttacaatttt atggtgcact ctcagtacaa tctgctctga     1920
tgccgcatag ttaagccagc cccgacaccc gccaacaccc gctgacgcgc cctgacgggc     1980
ttgtctgctc ccggcatccg cttacagaca agctgtgacc gtctccggga gctgcatgtg     2040
tcagaggttt tcaccgtcat caccgaaacg cgcgagacga aagggcctcg tgatacgcct     2100 attttttatag gttaatgtca tgataataat ggtttcttag acgtcaggtg gcacttttcg     2160
gggaaatgtg cgcggaaccc ctatttgttt attttttctaa atacattcaa atatgtatcc     2220
gctcatgaga caataaccct gataaatgct tcaataatat tgaaaaagga agagtatgag     2280
tattcaacat ttccgtgtcg cccttattcc cttttttgcg gcattttgcc ttcctgtttt     2340
tgctcaccca gaaacgctgg tgaaagtaaa agatgctgaa gatcagttgg gtgcacgagt     2400
gggttacatc gaactggatc tcaacagcgg taagatcctt gagagttttc gccccgaaga     2460
acgttttcca atgatgagca cttttaaagt tctgctatgt ggcgcggtat tatcccgtat     2520
tgacgccggg caagagcaac tcggtcgccg catacactat tctcagaatg acttggttga     2580
gtactcacca gtcacagaaa agcatcttac ggatggcatg acagtaagag aattatgcag     2640
tgctgccata accatgagtg ataacactgc ggccaactta cttctgacaa cgatcggagg     2700
accgaaggag ctaaccgctt ttttgcacaa catgggggat catgtaactc gccttgatcg     2760
ttgggaaccg gagctgaatg aagccatacc aaacgacgag cgtgacacca cgatgcctgt     2820
agcaatggca acaacgttgc gcaaactatt aactggcgaa ctacttactc tagcttcccg     2880
gcaacaatta atagactgga tggaggcgga taaagttgca ggaccacttc tgcgctcggc     2940
ccttccggct ggctggttta ttgctgataa atctggagcc ggtgagcgtg aagccgcgg     3000 tatcattgca gcactggggc cagatggtaa gccctcccgt atcgtagtta tctacacgac     3060
ggggagtcag gcaactatgg atgaacgaaa tagacagatc gctgagatag gtgcctcact     3120
gattaagcat tggtaactgt cagaccaagt ttactcatat atactttaga ttgatttaaa     3180
acttcatttt taatttaaaa ggatctaggt gaagatcctt tttgataatc tcatgaccaa     3240
```

```
aatcccttaa cgtgagtttt cgttccactg agcgtcagac cccgtagaaa agatcaaagg      3300
atcttcttga gatccttttt ttctgcgcgt aatctgctgc ttgcaaacaa aaaaaccacc      3360
gctaccagcg gtggtttgtt tgccggatca agagctacca actctttttc cgaaggtaac      3420
tggcttcagc agagcgcaga taccaaatac tgttcttcta gtgtagccgt agttaggcca      3480
ccacttcaag aactctgtag caccgcctac atacctcgct ctgctaatcc tgttaccagt      3540
ggctgctgcc agtggcgata agtcgtgtct taccgggttg gactcaagac gatagttacc      3600
ggataaggcg cagcggtcgg gctgaacggg gggttcgtgc acacagccca gcttggagcg      3660
aacgacctac accgaactga gatacctaca gcgtgagcta tgagaaagcg ccacgcttcc      3720
cgaagggaga aaggcggaca ggtatccggt aagcggcagg gtcggaacag gagagcgcac      3780
gagggagctt ccagggggaa acgcctggta tctttatagt cctgtcgggt ttcgccacct      3840
ctgacttgag cgtcgatttt tgtgatgctc gtcaggggggg cggagcctat ggaaaaacgc      3900
cagcaacgcg gcctttttac ggttcctggc cttttgctgg ccttttgctc acatgt         3956
```

<210> SEQ ID NO 26
<211> LENGTH: 7163
<212> TYPE: DNA
<213> ORGANISM: Artificial Sequence
<220> FEATURE:
<223> OTHER INFORMATION: pGW073

<400> SEQUENCE: 26

```
cctgcaggca gctgcgcgct cgctcgctca ctgaggccgc ccgggcgtcg ggcgaccttt       60
ggtcgcccgg cctcagtgag cgagcgagcg cgcagagagg gagtggccaa ctccatcact      120
aggggttcct gcggcctcta gaaaggatct gcgatcgctc cggtgcccgt cagtgggcag      180
agcgcacatc gcccacagtc cccgagaagt tggggggagg ggtcggcaat tgaacgggtg      240
cctagagaag gtggcgcggg gtaaactggg aaagtgatgt cgtgtactgg ctccgccttt      300
ttcccgaggt ggggggagaa ccgtatataa gtgcagtagt cgccgtgaac gttctttttc      360
gcaacgggtt tgccgccaga acacagctga agcttcgagg ggctcgcatc tctccttcac      420
gcgcccgccg ccctacctga ggccgccatc cacgccggtt gagtcgcgtt ctgccgcctc      480
ccgcctgtgg tgcctcctga actgcgtccg ccgtctaggt aagtttaaag ctcaggtcga      540
gaccgggcct ttgtccggcg ctcccttgga gcctacctag actcagccgg ctctccacgc      600
tttgcctgac cctgcttgct caactctacg tctttgtttc gttttctgtt ctgcgccgtt      660
acagatctgg ctaactaccg gtgccaccat ggcttgcaat tgtcagttga tgcaggatac      720
accactcctc aagtttccat gtccaaggct cattcttctc tttgtgctgc tgattcgtct      780
ttcacaagtg tcttcagatg ttgatgaaca actgtccaag tcagtgaaag ataaggtatt      840
gctgccttgc cgttacaact ctcctcatga agatgagtct gaagaccgaa tctactggca      900
aaaacatgac aaagtggtgc tgtctgtcat tgttgggaaa ctaaaagtgt ggcccgagta      960
taagaaccgg actttatatg acaacactac ctactctctt atcatcctgg gcctggtcct     1020
ttcagaccgg ggcacataca gctgtgtcgt tcaaaagaag gaaagaggaa cgtatgaagt     1080
taaacacttg gctttagtaa agttgtccat caaagctgac ttctctaccc ccaacataac     1140
tgagtctgga aacccatctg cagacactaa aaggattacc tgctttgctt ccgggggttt     1200
cccaaagcct cgcttctctt ggttggaaaa tggaagagaa ttacctggca tcaatacgac     1260
aatttcccag gatcctgaat ctgaattgta caccattagt agccaactag atttcaatac     1320
gactcgcaac cacaccatta agtgtctcat aaatatggga gatgctcacg tgtcagagga     1380
```

-continued

```
cttcacctgg gaaaaacccc cagaagaccc tcctgatagc aagaacacac ttgtgctctt   1440
tggggcagga ttcggcgcag taataacagt cgtcgtcatc gttgtcatca tcaaatgctt   1500
ctgtaagcac agaagctgtt tcagaagaaa tgaggcaagc agagaaacaa acaacagcct   1560
taccttcggg cctgaagaag cattagctga acagaccgtc ttccttcgta cgggcagtgg   1620
agagggcaga ggaagtctgc taacatgcgg tgacgtcgag gagaatcctg gcccaatgga   1680
gagtgtggta cagccttcag tgtttgtggt ggatggacag acggacatcc cattcaggcg   1740
gctggaacag aaccaccgga dacggcgctg tggcactgtc caggtcagcc tggccctggt   1800
gctgctgcta ggtgctgggc tggccactca gggctggttt ctcctgagac tgcatcaacg   1860
tcttggagac atagtagctc atctgccaga tggaggcaaa ggctcctggg agaagctgat   1920
acaagatcaa cgatctcacc aggccaaccc agcagcacat cttacaggag ccaacgccag   1980
cttgataggt attggtggac ctctgttatg ggagacacga cttggcctgg ccttcttgag   2040
gggcttgacg tatcatgatg gggccctggt gaccatggag cccggttact actatgtgta   2100
ctccaaagtg cagctgagcg gcgtgggctg cccccagggg ctggccaatg gcctccccat   2160
cacccatgga ctatacaagc gcacatcccg ctacccgaag gagttagaac tgctggtcag   2220
tcggcggtca ccctgtggcc gggccaacag ctcccgagtc tggtgggaca gcagcttcct   2280
gggcggcgtg gtacatctgg aggctgggga agaggtggtg gtccgcgtgc ctggaaaccg   2340
cctggtcaga ccacgtgacg gcaccaggtc ctatttcgga gctttcatgg tcactagtgg   2400
atccggcgca acaaacttct ctctgctgaa acaagccgga gatgtcgaag agaatcctgg   2460
accgatgaac ccaagtgctg ccgtcatttt ctgcctcatc ctgctgggtc tgagtgggac   2520
tcaagggatc cctctcgcaa ggacggtccg ctgcaactgc atccatatcg atgacgggcc   2580
agtgagaatg agggccatag ggaagcttga aatcatccct gcgagcctat cctgcccacg   2640
tgttgagatc attgccacga tgaaaaagaa tgatgagcag agatgtctga atccggaatc   2700
taagaccatc aagaatttaa tgaaagcgtt tagccaaaaa aggtctaaaa gggctcctgc   2760
tagcagcggt acccagtgca ccaactacgc cctgctgaag ctggccggcg atgtggagag   2820 caacccccggg cccatggacc agcacacact tgatgtggag gataccgcgg atgccagaca   2880
tccagcaggt acttcgtgcc cctcggatgc ggcgctcctc agagataccg ggctcctcgc   2940
ggacgctgcg ctcctctcag atactgtgcg ccccacaaat gccgcgctcc ccacggatgc   3000
tgcctaccct gcggttaatg ttcgggatcg cgaggccgcg tggccgcctg cactgaactt   3060
ctgttcccgc cacccaaagc tctatggcct agtcgctttg gttttgctgc ttctgatcgc   3120
cgcctgtgtt cctatcttca cccgcaccga gcctcggcca gcgctcacaa tcaccacctc   3180
gcccaacctg ggtacccgag agaataatgc agaccaggtc acccctgttt cccacattgg   3240
ctgccccaac actacacaac agggctctcc tgtgttcgcc aagctactgg ctaaaaacca   3300
agcatcgttg tgcaatacaa ctctgaactg gcacagccaa gatggagctg ggagctcata   3360
cctatctcaa ggtctgaggt acgaagaaga caaaaaggag ttggtggtag acagtcccgg   3420
gctctactac gtatttttgg aactgaagct cagtccaaca ttcacaaaca caggccacaa   3480
ggtgcagggc tgggtctctc ttgttttgca agcaaagcct caggtagatg actttgacaa   3540
cttggccctg acagtggaac tgttcccttg ctccatggag aacaagttag tggaccgttc   3600
ctggagtcaa ctgttgctcc tgaaggctgg ccaccgcctc agtgtgggtc tgagggctta   3660
tctgcatgga gcccaggatg catacagaga ctgggagctg tcttatccca acaccaccag   3720
```

-continued

```
ctttggactc tttcttgtga aacccgacaa cccatgggaa ggcatatgcg gtaccgtgaa    3780
gcagaccctg aacttcgatc tgctgaagct ggccggcgat gtggagagca accccgggcc    3840
catggaggaa atgcctttga gagagtcaag tcctcaaagg gcagagaggt gcaagaagtc    3900
atggctcttg tgcatagtgg ctctgttact gatgctgctc tgttctttgg gtacactgat    3960
ctatacttca ctcaagccaa ctgccatcga gtcctgcatg gttaagtttg aactatcatc    4020
ctcaaaatgg cacatgacat ctcccaaacc tcactgtgtg aatacgacat ctgatgggaa    4080
gctgaagata ctgcagagtg gcacatattt aatctacggc caagtgattc ctgtggataa    4140
gaaatacata aaagacaatg cccccttcgt agtacagata tataaaaaga atgatgtcct    4200
acaaactcta atgaatgatt ttcaaatctt gcctatagga ggggtttatg aactgcatgc    4260
tggagataac atatatctga agttcaactc taaagaccat attcagaaaa ataacacata    4320 ctggggatc atcttaatgc ctgatctacc attcatctct taggaattca ataaaagatc    4380
tttattttca ttagatctgt gtgttggttt tttgtgtgcg gccgcaggaa cccctagtga    4440
tggagttggc cactccctct ctgcgcgctc gctcgctcac tgaggccggg cgaccaaagg    4500
tcgcccgacg cccgggcttt gcccgggcgg cctcagtgag cgagcgagcg cgcagctgcc    4560
tgcaggggcg cctgatgcgg tattttctcc ttacgcatct gtgcggtatt tcacaccgca    4620
tacgtcaaag caaccatagt acgcgccctg tagcggcgca ttaagcgcgg cgggtgtggt    4680
ggttacgcgc agcgtgaccg ctacacttgc cagcgcctta gcgcccgctc ctttcgcttt    4740
cttcccttcc tttctcgcca cgttcgccgg ctttccccgt caagctctaa atcggggget    4800 cccctttaggg ttccgattta gtgctttacg gcacctcgac cccaaaaaac ttgatttggg    4860
tgatggttca cgtagtgggc catcgccctg atagacggtt tttcgccctt tgacgttgga    4920
gtccacgttc tttaatagtg gactcttgtt ccaaactgga acaacactca actctatctc    4980
gggctattct tttgatttat aagggatttt gccgatttcg gtctattggt taaaaaatga    5040
gctgatttaa caaaaattta acgcgaattt taacaaaata ttaacgttta caattttatg    5100
gtgcactctc agtacaatct gctctgatgc cgcatagtta agccagcccc gacacccgcc    5160
aacacccgct gacgcgccct gacgggcttg tctgctcccg gcatccgctt acagacaagc    5220
tgtgaccgtc tccgggagct gcatgtgtca gaggttttca ccgtcatcac cgaaacgcgc    5280
gagacgaaag ggcctcgtga tacgcctatt tttataggtt aatgtcatga taataatggt    5340
ttcttagacg tcaggtggca cttttcgggg aaatgtgcgc ggaacccta tttgtttatt     5400 tttctaaata cattcaaata tgtatccgct catgagacaa taaccctgat aaatgcttca    5460
ataatattga aaaaggaaga gtatgagtat tcaacatttc cgtgtcgccc ttattccctt    5520
ttttgcggca ttttgccttc ctgtttttgc tcacccagaa acgctggtga agtaaaaga    5580 tgctgaagat cagttgggtg cacgagtggg ttacatcgaa ctggatctca acagcggtaa    5640
gatccttgag agttttcgcc ccgaagaacg ttttccaatg atgagcactt ttaaagttct    5700
gctatgtggc gcggtattat cccgtattga cgccgggcaa gagcaactcg gtcgccgcat    5760
acactattct cagaatgact tggttgagta ctcaccagtc acagaaaagc atcttacgga    5820
tggcatgaca gtaagagaat tatgcagtgc tgccataacc atgagtgata acactgcggc    5880
caacttactt ctgacaacga tcggaggacc gaaggagcta accgcttttt tgcacaacat    5940
gggggatcat gtaactcgcc ttgatcgttg ggaaccggag ctgaatgaag ccataccaaa    6000
cgacgagcgt gacaccacga tgcctgtagc aatggcaaca acgttgcgca aactattaac    6060
tggcgaacta cttactctag cttcccggca acaattaata gactggatgg aggcggataa    6120
```

```
agttgcagga ccacttctgc gctcggccct tccggctggc tggtttattg ctgataaatc    6180
tggagccggt gagcgtggaa gccgcggtat cattgcagca ctggggccag atggtaagcc    6240
ctcccgtatc gtagttatct acacgacggg gagtcaggca actatggatg aacgaaatag    6300
acagatcgct gagataggtg cctcactgat taagcattgg taactgtcag accaagttta    6360
ctcatatata ctttagattg atttaaaact tcattttaa tttaaaagga tctaggtgaa    6420
gatccttttt gataatctca tgaccaaaat cccttaacgt gagttttcgt tccactgagc    6480
gtcagacccc gtagaaaaga tcaaaggatc ttcttgagat cctttttttc tgcgcgtaat    6540
ctgctgcttg caaacaaaaa aaccaccgct accagcggtg gtttgtttgc cggatcaaga    6600
gctaccaact ctttttccga aggtaactgg cttcagcaga gcgcagatac caaatactgt    6660
tcttctagtg tagccgtagt taggccacca cttcaagaac tctgtagcac cgcctacata    6720
cctcgctctg ctaatcctgt taccagtggc tgctgccagt ggcgataagt cgtgtcttac    6780
cgggttggac tcaagacgat agttaccgga taaggcgcag cggtcgggct gaacggggg    6840 ttcgtgcaca cagcccagct tggagcgaac gacctacacc gaactgagat acctacagcg    6900
tgagctatga aaagcgcca cgcttcccga agggagaaag gcggacaggt atccggtaag    6960
cggcagggtc ggaacaggag agcgcacgag ggagcttcca gggggaaacg cctggtatct    7020
ttatagtcct gtcgggtttc gccacctctg acttgagcgt cgatttttgt gatgctcgtc    7080
aggggggcgg agcctatgga aaaacgccag caacgcggcc ttttacggt tcctggcctt    7140 ttgctggcct tttgctcaca tgt                                            7163
```

```
<210> SEQ ID NO 27
<211> LENGTH: 3491
<212> TYPE: DNA
<213> ORGANISM: Artificial Sequence
<220> FEATURE:
<223> OTHER INFORMATION: pGW078

<400> SEQUENCE: 27
```

```
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggcctcta gaaaggatct gcgatcgctc cggtgcccgt cagtgggcag     180
agcgcacatc gcccacagtc cccgagaagt tggggggagg ggtcggcaat tgaacgggtg     240
cctagagaag gtggcgcggg gtaaactggg aaagtgatgt cgtgtactgg ctccgccttt     300
ttcccgaggg tggggagaa ccgtatataa gtgcagtagt cgccgtgaac gttctttttc     360
gcaacgggtt tgccgccaga acacagctga agcttcgagg ggctcgcatc tctccttcac     420
gcgcccgccg ccctacctga ggccgccatc cacgccggtt gagtcgcgtt ctgccgcctc     480
ccgcctgtgg tgcctcctga actgcgtccg ccgtctaggt aagtttaaag ctcaggtcga     540
gaccgggcct ttgtccggcg ctcccttgga gcctacctag actcagccgg ctctccacgc     600
tttgcctgac cctgcttgct caactctacg tctttgtttc gttttctgtt ctgcgccgtt     660
acagatctgg ctaactaccg gtgccacctg agaattcaat aaaagatctt tattttcatt     720
agatctgtgt gttggttttt tgtgtgcggc gcaggaacc cctagtgatg gagttggcca     780
ctccctctct gcgcgctcgc tcgctcactg aggccgggcg accaaaggtc gcccgacgcc     840
cgggctttgc ccgggcggcc tcagtgagcg agcgagcgcg cagctgcctg caggggcgcc     900
tgatgcggta ttttctcctt acgcatctgt gcggtatttc acaccgcata cgtcaaagca     960
```

-continued

```
accatagtac gcgccctgta gcggcgcatt aagcgcggcg ggtgtggtgg ttacgcgcag    1020
cgtgaccgct acacttgcca gcgccttagc gcccgctcct ttcgctttct tcccttcctt    1080
tctcgccacg ttcgccggct ttccccgtca agctctaaat cgggggctcc ctttagggtt    1140
ccgatttagt gctttacggc acctcgaccc caaaaaactt gatttgggtg atggttcacg    1200
tagtgggcca tcgccctgat agacggtttt tcgcccetttg acgttggagt ccacgttctt    1260
taatagtgga ctcttgttcc aaactggaac aacactcaac tctatctcgg gctattcttt    1320
tgatttataa gggattttgc cgatttcggt ctattggtta aaaaatgagc tgatttaaca    1380
aaaatttaac gcgaattta acaaaatatt aacgtttaca attttatggt gcactctcag    1440
tacaatctgc tctgatgccg catagttaag ccagccccga cacccgccaa cacccgctga    1500
cgcgccctga cgggcttgtc tgctcccggc atccgcttac agacaagctg tgaccgtctc    1560
cgggagctgc atgtgtcaga ggttttcacc gtcatcaccg aaacgcgcga gacgaaaggg    1620
cctcgtgata cgcctatttt tataggttaa tgtcatgata ataatggttt cttagacgtc    1680
aggtggcact tttcggggaa atgtgcgcgg aaccccctatt tgtttatttt tctaaataca    1740
ttcaaatatg tatccgctca tgagacaata accctgataa atgcttcaat aatattgaaa    1800
aaggaagagt atgagtattc aacatttccg tgtcgccctt attcccttttt ttgcggcatt    1860 ttgccttcct gtttttgctc acccagaaac gctggtgaaa gtaaaagatg ctgaagatca    1920
gttgggtgca cgagtgggtt acatcgaact ggatctcaac agcggtaaga tccttgagag    1980
ttttcgcccc gaagaacgtt ttccaatgat gagcactttt aaagttctgc tatgtggcgc    2040
ggtattatcc cgtattgacg ccgggcaaga gcaactcggt cgccgcatac actattctca    2100
gaatgacttg gttgagtact caccagtcac agaaaagcat cttacggatg gcatgacagt    2160
aagagaatta tgcagtgctg ccataaccat gagtgataac actgcggcca acttacttct    2220
gacaacgatc ggaggaccga aggagctaac cgcttttttg cacaacatgg gggatcatgt    2280
aactcgcctt gatcgttggg aaccggagct gaatgaagcc ataccaaacg acgagcgtga    2340
caccacgatg cctgtagcaa tggcaacaac gttgcgcaaa ctattaactg gcgaactact    2400
tactctagct tcccggcaac aattaataga ctggatggag gcggataaag ttgcaggacc    2460
acttctgcgc tcggcccttc cggctggctg gtttattgct gataaatctg gagccggtga    2520
gcgtggaagc cgcggtatca ttgcagcact ggggccagat ggtaagccct cccgtatcgt    2580
agttatctac acgacgggga gtcaggcaac tatggatgaa cgaaatagac agatcgctga    2640
gataggtgcc tcactgatta agcattggta actgtcagac caagtttact catatatact    2700
ttagattgat ttaaaacttc attttttaatt taaaaggatc taggtgaaga tcctttttga    2760
taatctcatg accaaaatcc cttaacgtga gttttcgttc cactgagcgt cagacccgt    2820 agaaaagatc aaaggatctt cttgagatcc ttttttttctg cgcgtaatct gctgcttgca    2880
aacaaaaaaa ccaccgctac cagcggtggt ttgtttgccg gatcaagagc taccaactct    2940 tttttccgaag gtaactggct tcagcagagc gcagatacca aatactgttc ttctagtgta    3000
gccgtagtta ggccaccact tcaagaactc tgtagcaccg cctacatacc tcgctctgct    3060
aatcctgtta ccagtggctg ctgccagtgg cgataagtcg tgtcttaccg ggttggactc    3120
aagacgatag ttaccggata aggcgcagcg tcgggctga acggggggtt cgtgcacaca    3180
gcccagcttg gagcgaacga cctacaccga actgagatac ctacagcgtg agctatgaga    3240
aagcgccacg cttcccgaag ggagaaaggc ggacaggtat ccggtaagcg gcagggtcgg    3300
aacaggagag cgcacgaggg agcttccagg gggaaacgcc tggtatcttt atagtcctgt    3360
```

-continued

```
cgggtttcgc cacctctgac ttgagcgtcg atttttgtga tgctcgtcag gggggcggag    3420
cctatggaaa aacgccagca acgcggcctt tttacggttc ctggcctttt gctggccttt    3480
tgctcacatg t                                                          3491

<210> SEQ ID NO 28
<211> LENGTH: 7322
<212> TYPE: DNA
<213> ORGANISM: Artificial Sequence
<220> FEATURE:
<223> OTHER INFORMATION: pGW090

<400> SEQUENCE: 28
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact    120
aggggttcct gcggcctcta gaaaggatct gcgatcgctc cggtgcccgt cagtgggcag    180
agcgcacatc gcccacagtc cccgagaagt tggggggagg ggtcggcaat tgaacgggtg    240
cctagagaag gtggcgcggg gtaaactggg aaagtgatgt cgtgtactgg ctccgccttt    300
ttcccgaggg tggggagaa ccgtatataa gtgcagtagt cgccgtgaac gttcttttc     360 gcaacgggtt tgccgccaga acacagctga agcttcgagg ggctcgcatc tctccttcac    420
gcgcccgccg ccctacctga ggccgccatc cacgccggtt gagtcgcgtt ctgccgcctc    480
ccgcctgtgg tgcctcctga actgcgtccg ccgtctaggt aagtttaaag ctcaggtcga    540
gaccgggcct ttgtccggcg ctcccttgga gcctacctag actcagccgg ctctccacgc    600
tttgcctgac cctgcttgct caactctacg tctttgtttc gttttctgtt ctgcgccgtt    660
acagatctgg ctaactaccg gtgccaccat ggcttgcaat tgtcagttga tgcaggatac    720
accactcctc aagtttccat gtccaaggct cattcttctc tttgtgctgc tgattcgtct    780
ttcacaagtg tcttcagatg ttgatgaaca actgtccaag tcagtgaaag ataaggtatt    840
gctgccttgc cgttacaact ctcctcatga agatgagtct gaagaccgaa tctactggca    900
aaaacatgac aaagtggtgc tgtctgtcat tgttgggaaa ctaaaagtgt ggcccgagta    960
taagaaccgg actttatatg acaacactac ctactctctt atcatcctgg gcctggtcct   1020
ttcagaccgg ggcacataca gctgtgtcgt tcaaaagaag gaaagaggaa cgtatgaagt   1080
taaacacttg gctttagtaa agttgtccat caaagctgac ttctctaccc ccaacataac   1140
tgagtctgga aacccatctg cagacactaa aaggattacc tgctttgctt ccgggggttt   1200
cccaaagcct cgcttctctt ggttggaaaa tggaagagaa ttacctggca tcaatacgac   1260
aatttcccag gatcctgaat ctgaattgta caccattagt agccaactag atttcaatac   1320
gactcgcaac cacaccatta agtgtctcat taaatatgga gatgctcacg tgtcagagga   1380
cttcacctgg gaaaaacccc cagaagaccc tcctgatagc aagaacacac ttgtgctctt   1440
tggggcagga ttcggcgcag taataacagt cgtcgtcatc gttgtcatca tcaaatgctt   1500
ctgtaagcac agaagctgtt tcagaagaaa tgaggcaagc agagaaacaa acaacagcct   1560
taccttcggg cctgaagaag cattagctga acagaccgtc ttccttcgta cgggcagtgg   1620
agagggcaga ggaagtctgc taacatgcgg tgacgtcgag gagaatcctg gcccaatgga   1680
gagtgtggta cagccttcag tgtttgtggt ggatggacag acggacatcc cattcaggcg   1740
gctggaacag aaccaccgga gacggcgctg tggcactgtc caggtcagcc tggccctggt   1800
gctgctgcta ggtgctgggc tggccactca gggctggttt ctcctgagac tgcatcaacg   1860
```

-continued

```
tcttggagac atagtagctc atctgccaga tggaggcaaa ggctcctggg agaagctgat    1920
acaagatcaa cgatctcacc aggccaaccc agcagcacat cttacaggag ccaacgccag    1980
cttgataggt attggtggac ctctgttatg ggagacacga cttggcctgg ccttcttgag    2040
gggcttgacg tatcatgatg gggccctggt gaccatggag cccggttact actatgtgta    2100
ctccaaagtg cagctgagcg gcgtgggctg cccccagggg ctggccaatg gcctccccat    2160
cacccatgga ctatacaagc gcacatcccg ctacccgaag gagttagaac tgctggtcag    2220
tcggcggtca ccctgtggcc gggccaacag ctcccgagtc tggtgggaca gcagcttcct    2280
gggcggcgtg gtacatctgg aggctgggga agaggtggtg gtccgcgtgc ctggaaaccg    2340
cctggtcaga ccacgtgacg gcaccaggtc ctatttcgga gctttcatgg tcactagtgg    2400
atccggcgca acaaacttct ctctgctgaa acaagccgga gatgtcgaag agaatcctgg    2460
accgatgtac agcatgcagc tcgcatcctg tgtcacattg acacttgtgc tccttgtcaa    2520
cagcgcaccc acttcaagct ccacttcaag ctctacagcg gaagcacagc agcagcagca    2580
gcagcagcag cagcagcagc agcacctgga gcagctgttg atggacctac aggagctcct    2640
gagcaggatg gagaattaca ggaacctgaa actccccagg atgctcacct tcaaatttta    2700
cttgcccaag caggccacag aattgaaaga tcttcagtgc ctagaagatg aacttggacc    2760
tctgcggcat gttctggatt tgactcaaag caaaagcttt caattggaag atgctgagaa    2820
tttcatcagc aatatcagag taactgttgt aaaactaaag ggctctgaca acacatttga    2880
gtgccaattc gatgatgagt cagcaactgt ggtggacttt ctgaggagat ggatagcctt    2940
ctgtcaaagc atcatctcaa caagccctca agctagcagc ggtacccagt gcaccaacta    3000
cgccctgctg aagctggccg gcgatgtgga gagcaacccc gggcccatgg accagcacac    3060
acttgatgtg gaggataccg cggatgccag acatccagca ggtacttcgt gcccctcgga    3120
tgcggcgctc ctcagagata ccgggctcct cgcggacgct gcgctcctct cagatactgt    3180
gcgccccaca aatgccgcgc tccccacgga tgctgcctac cctgcggtta atgttcggga    3240
tcgcgaggcc gcgtggccgc ctgcactgaa cttctgttcc cgccacccaa agctctatgg    3300
cctagtcgct ttggttttgc tgcttctgat cgccgcctgt gttcctatct tcacccgcac    3360
cgagcctcgg ccagcgctca caatcaccac ctcgcccaac ctgggtaccc gagagaataa    3420
tgcagaccag gtcacccctg tttcccacat tggctgcccc aacactacac aacagggctc    3480
tcctgtgttc gccaagctac tggctaaaaa ccaagcatcg ttgtgcaata caactctgaa    3540
ctggcacagc caagatggag ctgggagctc atacctatct caaggtctga ggtacgaaga    3600
agacaaaaag gagttggtgg tagacagtcc cgggctctac tacgtatttt tggaactgaa    3660
gctcagtcca acattcacaa acacaggcca caaggtgcag ggctgggtct ctcttgtttt    3720
gcaagcaaag cctcaggtag atgactttga caacttggcc ctgacagtgg aactgttccc    3780
ttgctccatg gagaacaagt tagtggaccg ttcctggagt caactgttgc tcctgaaggc    3840
tggccaccgc ctcagtgtgg gtctgagggc ttatctgcat ggagcccagg atgcatacag    3900
agactgggag ctgtcttatc ccaacaccac cagctttgga ctctttcttg tgaaacccga    3960
caacccatgg gaaggcatat gcggtaccgt gaagcagacc ctgaacttcg atctgctgaa    4020
gctggccggc gatgtggaga gcaaccccgg gcccatgaac gctacacact gcatcttggc    4080
tttgcagctc ttcctcatgg ctgtttctgg ctgttactgc cacggcacag tcattgaaag    4140
cctagaaagt ctgaataact attttaactc aagtggcata gatgtggaag aaaagagtct    4200
cttcttggat atctggagga actggcaaaa ggatggtgac atgaaaatcc tgcagagcca    4260
```

-continued

```
gattatctct ttctacctca gactctttga agtcttgaaa gacaatcagg ccatcagcaa      4320
caacataagc gtcattgaat cacacctgat tactaccttc ttcagcaaca gcaaggcgaa      4380
aaaggatgca ttcatgagta ttgccaagtt tgaggtcaac aacccacagg tccagcgcca      4440
agcattcaat gagctcatcc gagtggtcca ccagctgttg ccggaatcca gcctcaggaa      4500
gcggaaaagg agtcgctgct gagaattcaa taaaagatct ttattttcat tagatctgtg      4560
tgttggtttt ttgtgtgcgg ccgcaggaac ccctagtgat ggagttggcc actccctctc      4620
tgcgcgctcg ctcgctcact gaggccgggc gaccaaaggt cgcccgacgc ccgggctttg      4680
cccgggcggc ctcagtgagc gagcgagcgc gcagctgcct gcaggggcgc ctgatgcggt      4740
attttctcct tacgcatctg tgcggtattt cacaccgcat acgtcaaagc aaccatagta      4800
cgcgccctgt agcggcgcat taagcgcggc gggtgtggtg gttacgcgca gcgtgaccgc      4860
tacacttgcc agcgccttag cgcccgctcc tttcgctttc ttcccttcct ttctcgccac      4920
gttcgccggc tttccccgtc aagctctaaa tcggggctc cctttagggt tccgatttag      4980
tgctttacgg cacctcgacc ccaaaaaact tgatttgggt gatggttcac gtagtgggcc      5040
atcgccctga tagacggttt ttcgcccttt gacgttggag tccacgttct ttaatagtgg      5100
actcttgttc caaactggaa caacactcaa ctctatctcg ggctattctt ttgatttata      5160
agggattttg ccgatttcgg tctattggtt aaaaaatgag ctgatttaac aaaaatttaa      5220
cgcgaatttt aacaaaatat taacgtttac aattttatgg tgcactctca gtacaatctg      5280
ctctgatgcc gcatagttaa gccagccccg acacccgcca acacccgctg acgcgccctg      5340
acgggcttgt ctgctcccgg catccgctta cagacaagct gtgaccgtct ccgggagctg      5400
catgtgtcag aggttttcac cgtcatcacc gaaacgcgcg agacgaaagg gcctcgtgat      5460
acgcctattt ttataggtta atgtcatgat aataatggtt tcttagacgt caggtggcac      5520
ttttcgggga aatgtgcgcg gaacccctat ttgtttattt ttctaaatac attcaaatat      5580
gtatccgctc atgagacaat aaccctgata aatgcttcaa taatattgaa aaaggaagag      5640
tatgagtatt caacatttcc gtgtcgccct tattcccttt tttgcggcat tttgccttcc      5700 tgttttttgct cacccagaaa cgctggtgaa agtaaaagat gctgaagatc agttgggtgc      5760
acgagtgggt tacatcgaac tggatctcaa cagcggtaag atccttgaga gttttcgccc      5820
cgaagaacgt tttccaatga tgagcacttt taaagttctg ctatgtggcg cggtattatc      5880
ccgtattgac gccgggcaag agcaactcgg tcgccgcata cactattctc agaatgactt      5940
ggttgagtac tcaccagtca cagaaaagca tcttacggat ggcatgacag taagagaatt      6000
atgcagtgct gccataacca tgagtgataa cactgcggcc aacttacttc tgacaacgat      6060
cggaggaccg aaggagctaa ccgcttttt gcacaacatg gggatcatg taactcgcct      6120 tgatcgttgg gaaccggagc tgaatgaagc cataccaaac gacgagcgtg acaccacgat      6180
gcctgtagca atggcaacaa cgttgcgcaa actattaact ggcgaactac ttactctagc      6240
ttcccggcaa caattaatag actggatgga ggcggataaa gttgcaggac cacttctgcg      6300
ctcggccctt ccggctggct ggtttattgc tgataaatct ggagccggtg agcgtggaag      6360
ccgcggtatc attgcagcac tggggccaga tggtaagccc tcccgtatcg tagttatcta      6420
cacgacgggg agtcaggcaa ctatggatga acgaaataga cagatcgctg agataggtgc      6480
ctcactgatt aagcattggt aactgtcaga ccaagtttac tcatatatac tttagattga      6540
tttaaaactt cattttttaat ttaaaaggat ctaggtgaag atcctttttg ataatctcat      6600
```

-continued

```
gaccaaaatc ccttaacgtg agttttcgtt ccactgagcg tcagaccccg tagaaaagat    6660
caaaggatct tcttgagatc cttttttttct gcgcgtaatc tgctgcttgc aaacaaaaaa    6720
accaccgcta ccagcggtgg tttgtttgcc ggatcaagag ctaccaactc tttttccgaa    6780
ggtaactggc ttcagcagag cgcagatacc aaatactgtt cttctagtgt agccgtagtt    6840
aggccaccac ttcaagaact ctgtagcacc gcctacatac ctcgctctgc taatcctgtt    6900
accagtggct gctgccagtg gcgataagtc gtgtcttacc gggttggact caagacgata    6960
gttaccggat aaggcgcagc ggtcgggctg aacggggggt tcgtgcacac agcccagctt    7020
ggagcgaacg acctacaccg aactgagata cctacagcgt gagctatgag aaagcgccac    7080
gcttcccgaa gggagaaagg cggacaggta tccggtaagc ggcagggtcg aacaggaga    7140 gcgcacgagg gagcttccag ggggaaacgc ctggtatctt tatagtcctg tcgggtttcg    7200
ccacctctga cttgagcgtc gatttttgtg atgctcgtca ggggggcgga gcctatggaa    7260
aaacgccagc aacgcggcct ttttacggtt cctggccttt tgctggcctt ttgctcacat    7320
gt                                                                   7322
```

<210> SEQ ID NO 29
<211> LENGTH: 7334
<212> TYPE: DNA
<213> ORGANISM: Artificial Sequence
<220> FEATURE:
<223> OTHER INFORMATION: pGW091

<400> SEQUENCE: 29

```
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggcctcta gaaaggatct gcgatcgctc cggtgcccgt cagtgggcag     180
agcgcacatc gcccacagtc cccgagaagt tggggggagg ggtcggcaat tgaacgggtg     240
cctagagaag gtggcgcggg gtaaactggg aaagtgatgt cgtgtactgg ctccgccttt     300
ttcccgaggg tgggggagaa ccgtatataa gtgcagtagt cgccgtgaac gttctttttc     360
gcaacgggtt tgccgccaga acacagctga agcttcgagg ggctcgcatc tctccttcac     420
gcgcccgccg ccctacctga ggccgccatc cacgccggtt gagtcgcgtt ctgccgcctc     480
ccgcctgtgg tgcctcctga actgcgtccg ccgtctaggt aagtttaaag ctcaggtcga     540
gaccgggcct ttgtccggcg ctcccttgga gcctacctag actcagccgg ctctccacgc     600
tttgcctgac cctgcttgct caactctacg tctttgtttc gttttctgtt ctgcgccgtt     660
acagatctgg ctaactaccg gtgccaccat ggcttgcaat tgtcagttga tgcaggatac     720
accactcctc aagtttccat gtccaaggct cattcttctc tttgtgctgc tgattcgtct     780
ttcacaagtg tcttcagatg ttgatgaaca actgtccaag tcagtgaaag ataaggtatt     840
gctgccttgc cgttacaact ctcctcatga agatgagtct gaagaccgaa tctactggca     900
aaaacatgac aaagtggtgc tgtctgtcat tgttgggaaa ctaaaagtgt ggcccgagta     960
taagaaccgg actttatatg acaacactac ctactctctt atcatcctgg gcctggtcct    1020
ttcagaccgg ggcacataca gctgtgtcgt tcaaaagaag gaaagaggaa cgtatgaagt    1080
taaacacttg gctttagtaa agttgtccat caaagctgac ttctctaccc ccaacataac    1140
tgagtctgga aacccatctg cagacactaa aaggattacc tgctttgctt ccggggggttt    1200 cccaaagcct cgcttctctt ggttggaaaa tggaagagaa ttacctggca tcaatacgac    1260
aatttcccag gatcctgaat ctgaattgta caccattagt agccaactag atttcaatac    1320
```

-continued

```
gactcgcaac cacaccatta agtgtctcat taaatatgga gatgctcacg tgtcagagga   1380
cttcacctgg gaaaaacccc cagaagaccc tcctgatagc aagaacacac ttgtgctctt   1440
tggggcagga ttcggcgcag taataacagt cgtcgtcatc gttgtcatca tcaaatgctt   1500
ctgtaagcac agaagctgtt tcagaagaaa tgaggcaagc agagaaacaa acaacagcct   1560
taccttcggg cctgaagaag cattagctga acagaccgtc ttccttcgta cgggcagtgg   1620
agagggcaga ggaagtctgc taacatgcgg tgacgtcgag gagaatcctg gcccaatgga   1680
gagtgtggta cagccttcag tgtttgtggt ggatggacag acggacatcc cattcaggcg   1740
gctggaacag aaccaccgga gacggcgctg tggcactgtc caggtcagcc tggccctggt   1800
gctgctgcta ggtgctgggc tggccactca gggctggttt ctcctgagac tgcatcaacg   1860
tcttggagac atagtagctc atctgccaga tggaggcaaa ggctcctggg agaagctgat   1920
acaagatcaa cgatctcacc aggccaaccc agcagcacat cttacaggag ccaacgccag   1980
cttgataggt attggtggac ctctgttatg ggagacacga cttggcctgg ccttcttgag   2040
gggcttgacg tatcatgatg gggccctggt gaccatggag cccggttact actatgtgta   2100
ctccaaagtg cagctgagcg gcgtgggctg cccccagggg ctggccaatg gcctccccat   2160
cacccatgga ctatacaagc gcacatcccg ctacccgaag gagttagaac tgctggtcag   2220
tcggcggtca ccctgtggcc gggccaacag ctcccgagtc tggtgggaca gcagcttcct   2280
gggcggcgtg gtacatctgg aggctgggga agaggtggtg gtccgcgtgc ctggaaaccg   2340
cctggtcaga ccacgtgacg gcaccaggtc ctatttcgga gctttcatgg tcactagtgg   2400
atccggcgca acaaacttct ctctgctgaa acaagccgga gatgtcgaag agaatcctgg   2460
accgatggag gaaatgcctt tgagagagtc aagtcctcaa agggcagaga ggtgcaagaa   2520
gtcatggctc ttgtgcatag tggctctgtt actgatgctg ctctgttctt tgggtacact   2580
gatctatact tcactcaagc caactgccat cgagtcctgc atggttaagt ttgaactatc   2640
atcctcaaaa tggcacatga catctcccaa acctcactgt gtgaatacga catctgatgg   2700
gaagctgaag atactgcaga gtggcacata tttaatctac ggccaagtga ttcctgtgga   2760
taagaaatac ataaaagaca atgccccctt cgtagtacag atatataaaa agaatgatgt   2820
cctacaaact ctaatgaatg attttcaaat cttgcctata ggaggggttt atgaactgca   2880
tgctggagat aacatatatc tgaagttcaa ctctaaagac catattcaga aaaataacac   2940
atactggggg atcatcttaa tgcctgatct accattcatc tctgctagca gcggtaccca   3000
gtgcaccaac tacgccctgc tgaagctggc cggcgatgtg gagagcaacc ccgggcccat   3060
ggaccagcac acacttgatg tggaggatac cgcggatgcc agacatccag caggtacttc   3120
gtgcccctcg gatgcggcgc tcctcagaga taccgggctc ctcgcggacg ctgcgctcct   3180
ctcagatact gtgcgcccca caaatgccgc gctccccacg gatgctgcct accctgcggt   3240
taatgttcgg gatcgcgagg ccgcgtggcc gcctgcactg aacttctgtt cccgccaccc   3300
aaagctctat ggcctagtcg ctttggtttt gctgcttctg atcgccgcct gtgttcctat   3360
cttcacccgc accagcctc ggccagcgct cacaatcacc acctcgccca acctgggtac   3420
ccgagagaat aatgcagacc aggtcacccc tgtttcccac attggctgcc ccaacactac   3480
acaacagggc tctcctgtgt tcgccaagct actggctaaa aaccaagcat cgttgtgcaa   3540
tacaactctg aactggcaca gccaagatgg agctgggagc tcatacctat ctcaaggtct   3600
gaggtacgaa gaagacaaaa aggagttggt ggtagacagt cccgggctct actacgtatt   3660
```

-continued

```
tttggaactg aagctcagtc caacattcac aaacacaggc cacaaggtgc agggctgggt    3720
ctctcttgtt ttgcaagcaa agcctcaggt agatgacttt gacaacttgg ccctgacagt    3780
ggaactgttc ccttgctcca tggagaacaa gttagtggac cgttcctgga gtcaactgtt    3840
gctcctgaag gctggccacc gcctcagtgt gggtctgagg gcttatctgc atggagccca    3900
ggatgcatac agagactggg agctgtctta tcccaacacc accagctttg gactctttct    3960
tgtgaaaccc gacaacccat gggaaggcat atgcggtacc gtgaagcaga ccctgaactt    4020
cgatctgctg aagctggccg gcgatgtgga gagcaacccc gggcccatga acgctacaca    4080
ctgcatcttg gctttgcagc tcttcctcat ggctgtttct ggctgttact gccacggcac    4140
agtcattgaa agcctagaaa gtctgaataa ctattttaac tcaagtggca tagatgtgga    4200
agaaaagagt ctcttcttgg atatctggag gaactggcaa aaggatggtg acatgaaaat    4260
cctgcagagc cagattatct ctttctacct cagactcttt gaagtcttga aagacaatca    4320
ggccatcagc aacaacataa gcgtcattga atcacacctg attactacct tcttcagcaa    4380
cagcaaggcg aaaaaggatg cattcatgag tattgccaag tttgaggtca acaacccaca    4440
ggtccagcgc caagcattca atgagctcat ccgagtggtc caccagctgt tgccggaatc    4500
cagcctcagg aagcggaaaa ggagtcgctg ctgagaattc aataaaagat ctttattttc    4560
attagatctg tgtgttggtt ttttgtgtgc ggccgcagga acccctagtg atggagttgg    4620
ccactccctc tctgcgcgct cgctcgctca ctgaggccgg gcgaccaaag gtcgcccgac    4680
gcccgggctt tgcccgggcg gcctcagtga gcgagcgagc gcgcagctgc ctgcaggggc    4740
gcctgatgcg gtattttctc cttacgcatc tgtgcggtat ttcacaccgc atacgtcaaa    4800
gcaaccatag tacgcgccct gtagcggcgc attaagcgcg gcgggtgtgg tggttacgcg    4860
cagcgtgacc gctacacttg ccagcgccct agcgcccgct cctttcgctt tcttcccttc    4920
ctttctcgcc acgttcgccg gctttccccg tcaagctcta aatcggggtc ccctttagg    4980 gttccgattt agtgctttac ggcacctcga ccccaaaaaa cttgatttgg gtgatggttc    5040
acgtagtggg ccatcgccct gatagacggt ttttcgccct ttgacgttgg agtccacgtt    5100
ctttaatagt ggactcttgt tccaaactgg aacaacactc aactctatct cgggctattc    5160
ttttgattta taggggatttt tgccgatttc ggtctattgg ttaaaaaatg agctgattta    5220
acaaaaattt aacgcgaatt ttaacaaaat attaacgttt acaattttat ggtgcactct    5280
cagtacaatc tgctctgatg ccgcatagtt aagccagccc cgacaccgc caacacccgc    5340 tgacgcgccc tgacgggctt gtctgctccc ggcatccgct tacagacaag ctgtgaccgt    5400
ctccgggagc tgcatgtgtc agaggttttc accgtcatca ccgaaacgcg cgagacgaaa    5460
gggcctcgtg atacgcctat ttttataggt taatgtcatg ataataatgg tttcttagac    5520
gtcaggtggc acttttcggg gaaatgtgcg cggaacccct atttgtttat ttttctaaat    5580
acattcaaat atgtatccgc tcatgagaca ataaccctga taaatgcttc aataatattg    5640
aaaaaggaag agtatgagta ttcaacattt ccgtgtcgcc cttattccct ttttgcggc     5700 attttgcctt cctgtttttg ctcacccaga aacgctggtg aaagtaaaag atgctgaaga    5760
tcagttgggt gcacgagtgg gttacatcga actggatctc aacagcggta agatccttga    5820
gagttttcgc cccgaagaac gttttccaat gatgagcact tttaaagttc tgctatgtgg    5880
cgcggtatta tcccgtattg acgccgggca agagcaactc ggtcgccgca tacactattc    5940
tcagaatgac ttggttgagt actcaccagt cacagaaaag catcttacgg atggcatgac    6000
agtaagagaa ttatgcagtg ctgccataac catgagtgat aacactgcgg ccaacttact    6060
```

-continued

```
tctgacaacg atcggaggac cgaaggagct aaccgctttt ttgcacaaca tgggggatca      6120
tgtaactcgc cttgatcgtt gggaaccgga gctgaatgaa gccataccaa acgacgagcg      6180
tgacaccacg atgcctgtag caatggcaac aacgttgcgc aaaactattaa ctggcgaact     6240 acttactcta gcttcccggc aacaattaat agactggatg gaggcggata aagttgcagg      6300
accacttctg cgctcggccc ttccggctgg ctggtttatt gctgataaat ctggagccgg      6360
tgagcgtgga agccgcggta tcattgcagc actgggggcca gatggtaagc cctcccgtat     6420
cgtagttatc tacacgacgg ggagtcaggc aactatggat gaacgaaata gacagatcgc      6480
tgagataggt gcctcactga ttaagcattg gtaactgtca gaccaagttt actcatatat      6540
actttagatt gatttaaaac ttcattttta atttaaaagg atctaggtga agatcctttt      6600
tgataatctc atgaccaaaa tcccttaacg tgagttttcg ttccactgag cgtcagaccc      6660
cgtagaaaag atcaaaggat cttcttgaga tcctttttttt ctgcgcgtaa tctgctgctt      6720
gcaaacaaaa aaaccaccgc taccagcggt ggtttgtttg ccggatcaag agctaccaac      6780 tcttttttccg aaggtaactg gcttcagcag agcgcagata ccaaatactg ttcttctagt     6840
gtagccgtag ttaggccacc acttcaagaa ctctgtagca ccgcctacat acctcgctct      6900
gctaatcctg ttaccagtgg ctgctgccag tggcgataag tcgtgtctta ccgggttgga      6960
ctcaagacga tagttaccgg ataaggcgca gcggtcgggc tgaacggggg gttcgtgcac      7020
acagcccagc ttggagcgaa cgacctacac cgaactgaga tacctacagc gtgagctatg     7080
agaaagcgcc acgcttcccg aagggagaaa ggcggacagg tatccggtaa gcggcagggt      7140
cggaacagga gagcgcacga gggagcttcc aggggggaaac gcctggtatc tttatagtcc      7200
tgtcgggttt cgccacctct gacttgagcg tcgatttttg tgatgctcgt cagggggggcg      7260 gagcctatgg aaaaacgcca gcaacgcggc ctttttacgg ttcctggcct tttgctggcc      7320
ttttgctcac atgt                                                        7334
```

<210> SEQ ID NO 30
<211> LENGTH: 7805
<212> TYPE: DNA
<213> ORGANISM: Artificial Sequence
<220> FEATURE:
<223> OTHER INFORMATION: pGW096

<400> SEQUENCE: 30

```
cctgcaggca gctgcgcgct cgctcgctca ctgaggccgc ccgggcgtcg ggcgaccttt        60
ggtcgcccgg cctcagtgag cgagcgagcg cgcagagagg gagtggccaa ctccatcact       120
aggggttcct gcggcctcta gaaaggatct gcgatcgctc cggtgcccgt cagtgggcag       180
agcgcacatc gcccacagtc cccgagaagt tggggggagg ggtcggcaat tgaacgggtg       240
cctagagaag gtggcgcggg gtaaactggg aaagtgatgt cgtgtactgg ctccgccttt       300
ttcccgaggg tggggagaa ccgtatataa gtgcagtagt cgccgtgaac gttcttttttc       360 gcaacgggtt tgccgccaga acacagctga agcttcgagg ggctcgcatc tctccttcac       420
gcgcccgccg ccctacctga ggccgccatc cacgccggtt gagtcgcgtt ctgccgcctc       480
ccgcctgtgg tgcctcctga actgcgtccg ccgtctaggt aagtttaaag ctcaggtcga       540
gaccgggcct ttgtccggcg ctcccttgga gcctacctag actcagccgg ctctccacgc       600
tttgcctgac cctgcttgct caactctacg tctttgtttc gttttctgtt ctgcgccgtt       660
acagatctgg ctaactaccg gtgccaccat gaacgctaca cactgcatct tggctttgca       720
```

-continued

```
gctcttcctc atggctgttt ctggctgtta ctgccacggc acagtcattg aaagcctaga      780
aagtctgaat aactatttta actcaagtgg catagatgtg gaagaaaaga gtctcttctt      840
ggatatctgg aggaactggc aaaaggatgg tgacatgaaa atcctgcaga gccagattat      900
ctctttctac ctcagactct ttgaagtctt gaaagacaat caggccatca gcaacaacat      960
aagcgtcatt gaatcacacc tgattactac cttcttcagc aacagcaagg cgaaaaagga     1020
tgcattcatg agtattgcca agtttgaggt caacaaccca caggtccagc gccaagcatt     1080
caatgagctc atccgagtgg tccaccagct gttgccggaa tccagcctca ggaagcggaa     1140
aaggagtcgc tgcggatccg cgcaacaaa  cttctctctg ctgaaacaag ccggagatgt     1200
cgaagagaat cctggaccga tggcttgcaa ttgtcagttg atgcaggata caccactcct     1260
caagtttcca tgtccaaggc tcattcttct ctttgtgctg ctgattcgtc tttcacaagt     1320
gtcttcagat gttgatgaac aactgtccaa gtcagtgaaa gataaggtat tgctgccttg     1380
ccgttacaac tctcctcatg aagatgagtc tgaagaccga atctactggc aaaaacatga     1440
caaagtggtg ctgtctgtca ttgttgggaa actaaaagtg tggcccgagt ataagaaccg     1500
gactttatat gacaacacta cctactctct tatcatcctg ggcctggtcc tttcagaccg     1560
gggcacatac agctgtgtcg ttcaaaagaa ggaaagagga acgtatgaag ttaaacactt     1620
ggctttagta aagttgtcca tcaaagctga cttctctacc cccaacataa ctgagtctgg     1680
aaacccatct gcagacacta aaaggattac ctgctttgct tccggggggtt tcccaaagcc     1740 tcgcttctct tggttggaaa atggaagaga attacctggc atcaatacga caatttccca     1800
ggatcctgaa tctgaattgt acaccattag tagccaacta gatttcaata cgactcgcaa     1860
ccacaccatt aagtgtctca ttaaatatgg agatgctcac gtgtcagagg acttcacctg     1920
ggaaaaaccc ccagaagacc ctcctgatag caagaacaca cttgtgctct ttgggggcagg     1980 attcggcgca gtaataacag tcgtcgtcat cgttgtcatc atcaaatgct ctgtaagca      2040 cagaagctgt ttcagaagaa atgaggcaag cagagaaaca aacaacagcc ttaccttcgg     2100
gcctgaagaa gcattagctg aacagaccgt cttccttcgt acgggcagtg agagggcag      2160 aggaagtctg ctaacatgcg gtgacgtcga ggagaatcct ggcccaatgg agagtgtggt     2220
acagccttca gtgtttgtgg tggatggaca gacggacatc ccattcaggc ggctggaaca     2280
gaaccaccgg agacggcgct gtggcactgt ccaggtcagc ctggccctgg tgctgctgct     2340
aggtgctggg ctggccactc agggctggtt tctcctgaga ctgcatcaac gtcttggaga     2400
catagtagct catctgccag atggaggcaa aggctcctgg gagaagctga tacaagatca     2460
acgatctcac caggccaacc cagcagcaca tcttacagga gccaacgcca gcttgatagg     2520
tattggtgga cctctgttat gggagacacg acttggcctg gccttcttga ggggcttgac     2580
gtatcatgat ggggccctgg tgaccatgga gcccggttac tactatgtgt actccaaagt     2640
gcagctgagc ggcgtgggct gccccccaggg gctggccaat ggcctcccca tcacccatgg     2700
actatacaag cgcacatccc gctacccgaa ggagttagaa ctgctggtca gtcggcggtc     2760
accctgtggc cgggccaaca gctcccgagt ctggtgggac agcagcttcc tgggcggcgt     2820
ggtacatctg gaggctgggg aagaggtggt ggtccgcgtg cctggaaacc gcctggtcag     2880
accacgtgac ggcaccaggt cctatttcgg agctttcatg gtcactagtg gatccggcgc     2940
aacaaacttc tctctgctga aacaagccgg agatgtcgaa gagaatcctg accgatgtg      3000 tcctcagaag ctaaccatct cctggtttgc catcgttttg ctggtgtctc cactcatggc     3060
catgtgggag ctggagaaag acgtttatgt tgtagaggtg gactggactc ccgatgcccc     3120
```

-continued

```
tggagaaaca gtgaacctca cctgtgacac gcctgaagaa gatgacatca cctggacctc    3180
agaccagaga catggagtca taggctctgg aaagaccctg accatcactg tcaaagagtt    3240
tctagatgct ggccagtaca cctgccacaa aggaggcgag actctgagcc actcacatct    3300
gctgctccac aagaaggaaa atggaatttg gtccactgaa attttaaaaa atttcaaaaa    3360
caagactttc ctgaagtgtg aagcaccaaa ttactccgga cggttcacgt gctcatggct    3420
ggtgcaaaga aacatggact tgaagttcaa catcaagagc agtagcagtt cccctgactc    3480
tcgggcagtg acatgtggaa tggcgtctct gtctgcagag aaggtcacac tggaccaaag    3540
ggactatgag aagtattcag tgtcctgcca ggaggatgtc acctgcccaa ctgccgagga    3600
gaccctgccc attgaactgg cgttggaagc acggcagcag aataaatatg agaactacag    3660
caccagcttc ttcatcaggg acatcatcaa accagacccg cccaagaact tgcagatgaa    3720
gcctttgaag aactcacagg tggaggtcag ctgggagtac cctgactcct ggagcactcc    3780
ccattcctac ttctccctca agttctttgt tcgaatccag cgcaagaaag aaaagatgaa    3840
ggagacagag gaggggtgta accagaaagg tgcgttcctc gtagagaaga catctaccga    3900
agtccaatgc aaaggcggga atgtctgcgt gcaagctcag gatcgctatt acaattcctc    3960
atgcagcaag tgggcatgtg ttccctgcag ggtccgatcc gctagcagcg gtacccagtg    4020
caccaactac gccctgctga agctggccgg cgatgtggag agcaaccccg gcccatgga    4080 ccagcacaca cttgatgtgg aggataccgc ggatgccaga catccagcag gtacttcgtg    4140
cccctcggat gcggcgctcc tcagagatac cgggctcctc gcggacgctg cgctcctctc    4200
agatactgtg cgccccacaa atgccgcgct ccccacggat gctgcctacc ctgcggttaa    4260
tgttcgggat cgcgaggccg cgtggccgcc tgcactgaac ttctgttccc gccacccaaa    4320
gctctatggc ctagtcgctt tggttttgct gcttctgatc gccgcctgtg ttcctatctt    4380 caccgcacc gagcctcggc cagcgctcac aatcaccacc tcgcccaacc tgggtacccg    4440
agagaataat gcagaccagg tcacccctgt ttcccacatt ggctgcccca acactacaca    4500
acagggctct cctgtgttcg ccaagctact ggctaaaaac caagcatcgt tgtgcaatac    4560
aactctgaac tggcacagcc aagatggagc tgggagctca tacctatctc aaggtctgag    4620
gtacgaagaa gacaaaaagg agttggtggt agacagtccc gggctctact acgtattttt    4680
ggaactgaag ctcagtccaa cattcacaaa cacaggccac aaggtgcagg ctgggtctc    4740 tcttgttttg caagcaaagc ctcaggtaga tgactttgac aacttggccc tgacagtgga    4800
actgttccct tgctccatgg agaacaagtt agtggaccgt tcctggagtc aactgttgct    4860
cctgaaggct ggccaccgcc tcagtgtggg tctgagggct tatctgcatg agcccagga    4920 tgcatacaga gactgggagc tgtcttatcc caacaccacc agctttggac tctttcttgt    4980
gaaacccgac aacccatggg aatgagaatt caataaaaga tctttatttt cattagatct    5040
gtgtgttggt tttttgtgtg cggccgcagg aaccccagt gatggagttg gccactccct    5100
ctctgcgcgc tcgctcgctc actgaggccg ggcgaccaaa ggtcgcccga cgcccgggct    5160
ttgcccgggc ggcctcagtg agcgagcgag cgcgcagctg cctgcagggg cgcctgatgc    5220
ggtattttct ccttacgcat ctgtgcggta tttcacaccg catacgtcaa agcaaccata    5280
gtacgcgccc tgtagcggcg cattaagcgc ggcgggtgtg gtggttacgc gcagcgtgac    5340
cgctacactt gccagcgcct tagcgcccgc tcctttcgct ttcttccctt cctttctcgc    5400
cacgttcgcc ggctttcccc gtcaagctct aaatcggggg ctcccttag ggttccgatt    5460
```

-continued

```
tagtgcttta cggcacctcg accccaaaaa acttgatttg ggtgatggtt cacgtagtgg    5520
gccatcgccc tgatagacgg tttttcgccc tttgacgttg gagtccacgt tctttaatag    5580
tggactcttg ttccaaactg gaacaacact caactctatc tcgggctatt cttttgattt    5640
ataagggatt ttgccgattt cggtctattg gttaaaaaat gagctgattt aacaaaaatt    5700
taacgcgaat tttaacaaaa tattaacgtt tacaatttta tggtgcactc tcagtacaat    5760
ctgctctgat gccgcatagt taagccagcc ccgacacccg ccaacacccg ctgacgcgcc    5820
ctgacgggct tgtctgctcc cggcatccgc ttacagacaa gctgtgaccg tctccgggag    5880
ctgcatgtgt cagaggtttt caccgtcatc accgaaacgc gcgagacgaa agggcctcgt    5940
gatacgccta ttttttatagg ttaatgtcat gataataatg gtttcttaga cgtcaggtgg    6000
cacttttcgg ggaaatgtgc gcggaacccc tatttgttta tttttctaaa tacattcaaa    6060
tatgtatccg ctcatgagac aataaccctg ataaatgctt caataatatt gaaaaaggaa    6120
gagtatgagt attcaacatt tccgtgtcgc ccttattccc ttttttgcgg cattttgcct    6180
tcctgttttt gctcacccag aaacgctggt gaaagtaaaa gatgctgaag atcagttggg    6240
tgcacgagtg ggttacatcg aactggatct caacagcggt aagatccttg agagttttcg    6300
ccccgaagaa cgttttccaa tgatgagcac ttttaaagtt ctgctatgtg gcgcggtatt    6360
atcccgtatt gacgccgggc aagagcaact cggtcgccgc atacactatt ctcagaatga    6420
cttggttgag tactcaccag tcacagaaaa gcatcttacg gatggcatga cagtaagaga    6480
attatgcagt gctgccataa ccatgagtga taacactgcg gccaacttac ttctgacaac    6540
gatcggagga ccgaaggagc taaccgcttt tttgcacaac atgggggatc atgtaactcg    6600
ccttgatcgt tgggaaccgg agctgaatga agccatacca aacgacgagc gtgacaccac    6660
gatgcctgta gcaatggcaa caacgttgcg caaactatta actggcgaac tacttactct    6720
agcttcccgg caacaattaa tagactggat ggaggcggat aaagttgcag gaccacttct    6780
gcgctcggcc cttccggctg gctggtttat tgctgataaa tctggagccg gtgagcgtgg    6840
aagccgcggt atcattgcag cactggggcc agatggtaag ccctcccgta tcgtagttat    6900
ctacacgacg gggagtcagg caactatgga tgaacgaaat agacagatcg ctgagatagg    6960
tgcctcactg attaagcatt ggtaactgtc agaccaagtt tactcatata ctttttagat    7020
tgatttaaaa cttcattttt aatttaaaag gatctaggtg aagatccttt ttgataatct    7080
catgaccaaa atcccttaac gtgagttttc gttccactga gcgtcagacc ccgtagaaaa    7140
gatcaaagga tcttcttgag atccttttttt tctgcgcgta atctgctgct tgcaaacaaa    7200
aaaaccaccg ctaccagcgg tggtttgttt gccggatcaa gagctaccaa ctctttttcc    7260
gaaggtaact ggcttcagca gagcgcagat accaaatact gttcttctag tgtagccgta    7320
gttaggccac cacttcaaga actctgtagc accgcctaca tacctcgctc tgctaatcct    7380
gttaccagtg gctgctgcca gtggcgataa gtcgtgtctt accgggttgg actcaagacg    7440
atagttaccg gataaggcgc agcggtcggg ctgaacgggg ggttcgtgca cacagcccag    7500
cttggagcga acgacctaca ccgaactgag atacctacag cgtgagctat gagaaagcgc    7560
cacgcttccc gaagggagaa aggcggacag gtatccggta agcggcaggg tcggaacagg    7620
agagcgcacg agggagcttc caggggggaaa cgcctggtat ctttatagtc ctgtcgggtt    7680
tcgccacctc tgacttgagc gtcgattttt gtgatgctcg tcaggggggc ggagcctatg    7740
gaaaaacgcc agcaacgcgg cctttttacg gttcctggcc ttttgctggc cttttgctca    7800
catgt                                                                7805
```

```
<210> SEQ ID NO 31
<211> LENGTH: 4495
<212> TYPE: DNA
<213> ORGANISM: Artificial Sequence
<220> FEATURE:
<223> OTHER INFORMATION: pGW097

<400> SEQUENCE: 31
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggcctcta gaaaggatct gcgatcgctc cggtgcccgt cagtgggcag     180
agcgcacatc gcccacagtc cccgagaagt tggggggagg ggtcggcaat tgaacgggtg     240
cctagagaag gtggcgcggg gtaaactggg aaagtgatgt cgtgtactgg ctccgccttt     300
ttcccgaggg tggggagaa ccgtatataa gtgcagtagt cgccgtgaac gttctttttc     360
gcaacgggtt tgccgccaga acacagctga agcttcgagg ggctcgcatc tctccttcac     420
gcgcccgccg ccctacctga ggccgccatc cacgccggtt gagtcgcgtt ctgccgcctc     480
ccgcctgtgg tgcctcctga actgcgtccg ccgtctaggt aagtttaaag ctcaggtcga     540
gaccgggcct ttgtccggcg ctcccttgga gcctacctag actcagccgg ctctccacgc     600
tttgcctgac cctgcttgct caactctacg tctttgtttc gttttctgtt ctgcgccgtt     660
acagatctgg ctaactaccg gtgccacatg tgtcctcaga agctaaccat ctcctggttt     720
gccatcgttt tgctggtgtc tccactcatg gccatgtggg agctggagaa agacgtttat     780
gttgtagagg tggactggac tcccgatgcc cctggagaaa cagtgaacct cacctgtgac     840
acgcctgaag aagatgacat cacctggacc tcagaccaga gacatggagt cataggctct     900
ggaaagaccc tgaccatcac tgtcaaagag tttctagatg ctggccagta cacctgccac     960
aaaggaggcg agactctgag ccactcacat ctgctgctcc acaagaagga aaatggaatt    1020
tggtccactg aaattttaaa aaatttcaaa aacaagactt tcctgaagtg tgaagcacca    1080
aattactccg gacggttcac gtgctcatgg ctggtgcaaa gaaacatgga cttgaagttc    1140
aacatcaaga gcagtagcag ttcccctgac tctcgggcag tgacatgtgg aatggcgtct    1200
ctgtctgcag agaaggtcac actggaccaa agggactatg agaagtattc agtgtcctgc    1260
caggaggatg tcacctgccc aactgccgag gagaccctgc ccattgaact ggcgttggaa    1320
gcacggcagc agaataaata tgagaactac agcaccagct tcttcatcag ggacatcatc    1380
aaaccagacc cgcccaagaa cttgcagatg aagcctttga agaactcaca ggtggaggtc    1440
agctgggagt accctgactc ctggagcact ccccattcct acttctccct caagttcttt    1500
gttcgaatcc agcgcaagaa agaaaagatg aaggagacag aggaggggtg taaccagaaa    1560
ggtgcgttcc tcgtagagaa gacatctacc gaagtccaat gcaaaggcgg gaatgtctgc    1620
gtgcaagctc aggatcgcta ttacaattcc tcatgcagca gtgggcatg tgttccctgc    1680 agggtccgat cctaggaatt caataaaaga tctttatttt cattagatct gtgtgttggt    1740
tttttgtgtg cggccgcagg aaccctagt gatggagttg gccactccct ctctgcgcgc    1800
tcgctcgctc actgaggccg ggcgaccaaa ggtcgcccga cgcccgggct ttgcccgggc    1860
ggcctcagtg agcgagcgag cgcgcagctg cctgcagggg cgcctgatgc ggtattttct    1920
ccttacgcat ctgtgcggta tttcacaccg catacgtcaa agcaaccata gtacgcgccc    1980
tgtagcggcg cattaagcgc ggcgggtgtg gtggttacgc gcagcgtgac cgctacactt    2040
```

-continued

```
gccagcgcct tagcgcccgc tcctttcgct ttcttccctt cctttctcgc cacgttcgcc    2100
ggctttcccc gtcaagctct aaatcggggg ctccctttag ggttccgatt tagtgcttta    2160
cggcacctcg accccaaaaa acttgatttg ggtgatggtt cacgtagtgg gccatcgccc    2220
tgatagacgt tttttcgccc tttgacgttg gagtccacgt tctttaatag tggactcttg    2280
ttccaaactg gaacaacact caactctatc tcgggctatt cttttgattt ataagggatt    2340
ttgccgattt cggtctattg gttaaaaaat gagctgattt aacaaaaatt taacgcgaat    2400
tttaacaaaa tattaacgtt tacaatttta tggtgcactc tcagtacaat ctgctctgat    2460
gccgcatagt taagccagcc ccgacacccg ccaacacccg ctgacgcgcc ctgacgggct    2520
tgtctgctcc cggcatccgc ttacagacaa gctgtgaccg tctccgggag ctgcatgtgt    2580
cagaggtttt caccgtcatc accgaaacgc gcgagacgaa agggcctcgt gatacgccta    2640 ttttttatagg ttaatgtcat gataataatg gtttcttaga cgtcaggtgg cactttttcgg    2700 ggaaatgtgc gcggaacccc tatttgttta tttttctaaa tacattcaaa tatgtatccg    2760
ctcatgagac aataaccctg ataaatgctt caataatatt gaaaaaggaa gagtatgagt    2820
attcaacatt tccgtgtcgc ccttattccc ttttttgcgg cattttgcct tcctgttttt    2880
gctcacccag aaacgctggt gaaagtaaaa gatgctgaag atcagttggg tgcacgagtg    2940
ggttacatcg aactggatct caacagcggt aagatccttg agagttttcg ccccgaagaa    3000
cgttttccaa tgatgagcac ttttttaaagtt ctgctatgtg gcgcggtatt atcccgtatt    3060
gacgccgggc aagagcaact cggtcgccgc atacactatt ctcagaatga cttggttgag    3120
tactcaccag tcacagaaaa gcatcttacg gatggcatga cagtaagaga attatgcagt    3180
gctgccataa ccatgagtga taacactgcg gccaacttac ttctgacaac gatcggagga    3240
ccgaaggagc taaccgcttt tttgcacaac atgggggatc atgtaactcg ccttgatcgt    3300
tgggaaccgg agctgaatga agccatacca aacgacgagc gtgacaccac gatgcctgta    3360
gcaatggcaa caacgttgcg caaactatta actggcgaac tacttactct agcttcccgg    3420
caacaattaa tagactggat ggaggcggat aaagttgcag gaccacttct gcgctcggcc    3480
cttccggctg gctggtttat tgctgataaa tctggagccg gtgagcgtgg aagccgcggt    3540
atcattgcag cactggggcc agatggtaag ccctcccgta tcgtagttat ctacacgacg    3600
gggagtcagg caactatgga tgaacgaaat agacagatcg ctgagatagg tgcctcactg    3660
attaagcatt ggtaactgtc agaccaagtt tactcatata cactttagat tgatttaaaa    3720 cttcatttttt aatttaaaag gatctaggtg aagatccttt ttgataatct catgaccaaa    3780
atcccttaac gtgagttttc gttccactga gcgtcagacc ccgtagaaaa gatcaaagga    3840
tcttcttgag atcctttttt tctgcgcgta atctgctgct tgcaaacaaa aaaaccaccg    3900
ctaccagcgg tggtttgttt gccggatcaa gagctaccaa ctctttttcc gaaggtaact    3960
ggcttcagca gagcgcagat accaaatact gttcttctag tgtagccgta gttaggccac    4020
cacttcaaga actctgtagc accgcctaca tacctcgctc tgctaatcct gttaccagtg    4080
gctgctgcca gtggcgataa gtcgtgtctt accgggttgg actcaagacg atagttaccg    4140
gataaggcgc agcggtcggg ctgaacgggg ggttcgtgca cacagcccag cttggagcga    4200
acgacctaca ccgaactgag atacctacag cgtgagctat gagaaagcgc cacgcttccc    4260
gaagggagaa aggcggacag gtatccggta agcggcaggg tcggaacagg agagcgcacg    4320
agggagcttc caggggggaaa cgcctggtat ctttatagtc ctgtcgggtt cgccacctc    4380 tgacttgagc gtcgattttt gtgatgctcg tcaggggggc ggagcctatg gaaaaacgcc    4440
```

-continued

```
agcaacgcgg cctttttacg gttcctggcc ttttgctggc cttttgctca catgt         4495

<210> SEQ ID NO 32
<211> LENGTH: 6803
<212> TYPE: DNA
<213> ORGANISM: Artificial Sequence
<220> FEATURE:
<223> OTHER INFORMATION: pGW098

<400> SEQUENCE: 32
cctgcaggca gctgcgcgct cgctcgctca ctgaggccgc ccgggcgtcg ggcgaccttt       60
ggtcgcccgg cctcagtgag cgagcgagcg cgcagagagg gagtggccaa ctccatcact      120
aggggttcct gcggcctcta gaaaggatct gcgatcgctc cggtgcccgt cagtgggcag      180
agcgcacatc gcccacagtc cccgagaagt tggggggagg ggtcggcaat tgaacgggtg      240
cctagagaag gtggcgcggg gtaaactggg aaagtgatgt cgtgtactgg ctccgccttt      300
ttcccgaggg tggggagaa ccgtatataa gtgcagtagt cgccgtgaac gttcttttc        360 gcaacgggtt tgccgccaga acacagctga agcttcgagg ggctcgcatc tctccttcac      420
gcgcccgccg ccctacctga ggccgccatc cacgccggtt gagtcgcgtt ctgccgcctc      480
ccgcctgtgg tgcctcctga actgcgtccg ccgtctaggt aagtttaaag ctcaggtcga      540
gaccgggcct ttgtccggcg ctcccttgga gcctacctag actcagccgg ctctccacgc      600
tttgcctgac cctgcttgct caactctacg tctttgtttc gttttctgtt ctgcgccgtt      660
acagatctgg ctaactaccg gtgccaccat gaacgctaca cactgcatct ggcttttgca      720
gctcttcctc atggctgttt ctggctgtta ctgccacggc acagtcattg aaagcctaga      780
aagtctgaat aactatttta actcaagtgg catagatgtg gaagaaaaga gtctcttctt      840
ggatatctgg aggaactggc aaaaggatgg tgacatgaaa atcctgcaga gccagattat      900
ctctttctac ctcagactct ttgaagtctt gaaagacaat caggccatca gcaacaacat      960
aagcgtcatt gaatcacacc tgattactac cttcttcagc aacagcaagg cgaaaaagga     1020
tgcattcatg agtattgcca gtttgaggt caacaaccca caggtccagc gccaagcatt      1080
caatgagctc atccgagtgg tccaccagct gttgccggaa tccagcctca ggaagcggaa     1140
aaggagtcgc tgcggatccg gcgcaacaaa cttctctctg ctgaaacaag ccggagatgt     1200
cgaagagaat cctggaccga tggcttgcaa ttgtcagttg atgcaggata caccactcct     1260
caagtttcca tgtccaaggc tcattcttct ctttgtgctg ctgattcgtc tttcacaagt     1320
gtcttcagat gttgatgaac aactgtccaa gtcagtgaaa gataaggtat tgctgccttg     1380
ccgttacaac tctcctcatg aagatgagtc tgaagaccga atctactggc aaaaacatga     1440
caaagtggtg ctgtctgtca ttgttgggaa actaaaagtg tggcccgagt ataagaaccg     1500
gactttatat gacaacacta cctactctct tatcatcctg ggcctggtcc tttcagaccg     1560
gggcacatac agctgtgtcg ttcaaaagaa ggaaagagag acgtatgaag ttaaacactt     1620
ggctttagta aagttgtcca tcaaagctga cttctctacc cccaacataa ctgagtctgg     1680
aaacccatct gcagacacta aaaggattac ctgctttgct ccggggggtt tcccaaagcc     1740
tcgcttctct tggttggaaa atggaagaga attacctggc atcaatacga caatttccca     1800
ggatcctgaa tctgaattgt acaccattag tagccaacta gatttcaata cgactcgcaa     1860
ccacaccatt aagtgtctca ttaaatatgg agatgctcac gtgtcagagg acttcacctg     1920
ggaaaaaccc ccagaagacc ctcctgatag caagaacaca cttgtgctct ttgggggcagg     1980
```

-continued

```
attcggcgca gtaataacag tcgtcgtcat cgttgtcatc atcaaatgct tctgtaagca   2040
cagaagctgt ttcagaagaa atgaggcaag cagagaaaca aacaacagcc ttaccttcgg   2100
gcctgaagaa gcattagctg aacagaccgt cttccttcgt acgggcagtg gagagggcag   2160
aggaagtctg ctaacatgcg gtgacgtcga ggagaatcct ggcccaatgg agagtgtggt   2220
acagccttca gtgtttgtgg tggatggaca gacggacatc ccattcaggc ggctggaaca   2280
gaaccaccgg agacggcgct gtggcactgt ccaggtcagc ctggccctgg tgctgctgct   2340
aggtgctggg ctggccactc agggctggtt tctcctgaga ctgcatcaac gtcttggaga   2400
catagtagct catctgccag atggaggcaa aggctcctgg gagaagctga tacaagatca   2460
acgatctcac caggccaacc cagcagcaca tcttacagga gccaacgcca gcttgatagg   2520
tattggtgga cctctgttat gggagacacg acttggcctg gccttcttga ggggcttgac   2580
gtatcatgat ggggccctgg tgaccatgga gcccggttac tactatgtgt actccaaagt   2640
gcagctgagc ggcgtgggct gcccccaggg gctggccaat ggcctcccca tcacccatgg   2700
actatacaag cgcacatccc gctacccgaa ggagttagac ctgctggtca gtcggcggtc   2760
accctgtggc cgggccaaca gctcccgagt ctggtgggac agcagcttcc tgggcggcgt   2820
ggtacatctg gaggctgggg aagaggtggt ggtccgcgtg cctggaaacc gcctggtcag   2880
accacgtgac ggcaccaggt cctatttcgg agctttcatg gtcactagtg gatccggcgc   2940
aacaaacttc tctctgctga aacaagccgg agatgtcgaa gagaatcctg gaccgatgtg   3000
tcctcagaag ctaaccatct cctggtttgc catcgttttg ctggtgtctc cactcatggc   3060
catgtgggag ctggagaaag acgtttatgt tgtagaggtg gactggactc ccgatgcccc   3120
tggagaaaca gtgaacctca cctgtgacac gcctgaagaa gatgacatca cctggacctc   3180
agaccagaga catggagtca taggctctgg aaagaccctg accatcactg tcaaagagtt   3240
tctagatgct ggccagtaca cctgccacaa aggaggcgag actctgagcc actcacatct   3300
gctgctccac aagaaggaaa atggaatttg gtccactgaa attttaaaaa atttcaaaaa   3360
caagactttc ctgaagtgtg aagcaccaaa ttactccgga cggttcacgt gctcatggct   3420
ggtgcaaaga aacatggact tgaagttcaa catcaagagc agtagcagtt cccctgactc   3480
tcgggcagtg acatgtggaa tggcgtctct gtctgcagag aaggtcacac tggaccaaag   3540
ggactatgag aagtattcag tgtcctgcca ggaggatgtc acctgcccaa ctgccgagga   3600
gaccctgccc attgaactgg cgttggaagc acggcagcag aataaatatg agaactacag   3660
caccagcttc ttcatcaggg acatcatcaa accagacccg cccaagaact tgcagatgaa   3720
gcctttgaag aactcacagg tggaggtcag ctgggagtac cctgactcct ggagcactcc   3780
ccattcctac ttctccctca gttctttgt tcgaatccag cgcaagaaag aaaagatgaa   3840
ggagacagag gaggggtgta accagaaagg tgcgttcctc gtagagaaga catctaccga   3900
agtccaatgc aaaggcggga atgtctgcgt gcaagctcag gatcgctatt acaattcctc   3960
atgcagcaag tgggcatgtg ttccctgcag ggtccgatcc tgagaattca ataaaagatc   4020
tttattttca ttagatctgt gtgttggttt tttgtgtgcg gccgcaggaa cccctagtga   4080
tggagttggc cactccctct ctgcgcgctc gctcgctcac tgaggccggg cgaccaaagg   4140
tcgcccgacg cccgggcttt gcccgggcgg cctcagtgag cgagcgagcg cgcagctgcc   4200
tgcaggggcg cctgatgcgg tattttctcc ttacgcatct gtgcggtatt tcacaccgca   4260
tacgtcaaag caaccatagt acgcgccctg tagcggcgca ttaagcgcgg cgggtgtggt   4320
ggttacgcgc agcgtgaccg ctacacttgc cagcgcctta gcgcccgctc ctttcgcttt   4380
```

-continued

```
cttcccttcc tttctcgcca cgttcgccgg ctttccccgt caagctctaa atcggggget      4440 cccttagggg ttccgattta gtgctttacg gcacctcgac cccaaaaaac ttgatttggg      4500
tgatggttca cgtagtgggc catcgccctg atagacggtt tttcgccctt tgacgttgga      4560
gtccacgttc tttaatagtg gactcttgtt ccaaactgga acaacactca actctatctc      4620
gggctattct tttgatttat aagggatttt gccgatttcg gtctattggt taaaaaatga      4680
gctgatttaa caaaaattta acgcgaattt taacaaaata ttaacgttta caattttatg      4740
gtgcactctc agtacaatct gctctgatgc cgcatagtta agccagcccc gacacccgcc      4800
aacacccgct gacgcgccct gacgggcttg tctgctcccg gcatccgctt acagacaagc      4860
tgtgaccgtc tccgggagct gcatgtgtca gaggttttca ccgtcatcac cgaaacgcgc      4920
gagacgaaag ggcctcgtga tacgcctatt tttataggtt aatgtcatga taataatggt      4980
ttcttagacg tcaggtggca cttttcgggg aaatgtgcgc ggaacccta tttgtttatt       5040 tttctaaata cattcaaata tgtatccgct catgagacaa taaccctgat aaatgcttca      5100
ataatattga aaaggaaga gtatgagtat tcaacatttc cgtgtcgccc ttattcccctt      5160 ttttgcggca ttttgccttc ctgttttttgc tcacccagaa acgctggtga agtaaaaga      5220 tgctgaagat cagttgggtg cacgagtggg ttacatcgaa ctggatctca acagcggtaa      5280
gatccttgag agttttcgcc ccgaagaacg ttttccaatg atgagcactt ttaaagttct      5340
gctatgtggc gcggtattat cccgtattga cgccgggcaa gagcaactcg gtcgccgcat      5400
acactattct cagaatgact tggttgagta ctcaccagtc acagaaaagc atcttacgga      5460
tggcatgaca gtaagagaat tatgcagtgc tgccataacc atgagtgata acactgcggc      5520
caacttactt ctgacaacga tcggaggacc gaaggagcta accgcttttt tgcacaacat      5580
gggggatcat gtaactcgcc ttgatcgttg ggaaccggag ctgaatgaag ccataccaaa      5640
cgacgagcgt gacaccacga tgcctgtagc aatggcaaca acgttgcgca aactattaac      5700
tggcgaacta cttactctag cttcccggca acaattaata gactggatgg aggcggataa      5760
agttgcagga ccacttctgc gctcggccct tccggctggc tggtttattg ctgataaatc      5820
tggagccggt gagcgtggaa gccgcggtat cattgcagca ctggggccag atggtaagcc      5880
ctcccgtatc gtagttatct acacgacggg gagtcaggca actatggatg aacgaaatag      5940
acagatcgct gagataggtg cctcactgat taagcattgg taactgtcag accaagttta      6000
ctcatatata ctttagattg atttaaaact tcatttttaa tttaaaagga tctaggtgaa      6060 gatcctttttt gataatctca tgaccaaaat cccttaacgt gagttttcgt tccactgagc      6120
gtcagacccc gtagaaaaga tcaaaggatc ttcttgagat cctttttttc tgcgcgtaat      6180
ctgctgcttg caaacaaaaa aaccaccgct accagcggtg gtttgtttgc cggatcaaga      6240
gctaccaact ctttttccga aggtaactgg cttcagcaga gcgcagatac caaatactgt      6300
tcttctagtg tagccgtagt taggccacca cttcaagaac tctgtagcac cgcctacata      6360
cctcgctctg ctaatcctgt taccagtggc tgctgccagt ggcgataagt cgtgtcttac      6420
cgggttggac tcaagacgat agttaccgga taaggcgcag cggtcgggct gaacggggg      6480 ttcgtgcaca cagcccagct tggagcgaac gacctacacc gaactgagat acctacagcg      6540
tgagctatga aaagcgcca cgcttcccga agggagaaag gcggacaggt atccggtaag      6600
cggcagggtc ggaacaggag agcgcacgag ggagcttcca gggggaaacg cctggtatct      6660
ttatagtcct gtcgggtttc gccacctctg acttgagcgt cgatttttgt gatgctcgtc      6720
```

-continued

```
aggggggcgg agcctatgga aaaacgccag caacgcggcc ttttacggt cctggcctt    6780 ttgctggcct tttgctcaca tgt                                         6803

<210> SEQ ID NO 33
<211> LENGTH: 6092
<212> TYPE: DNA
<213> ORGANISM: Artificial Sequence
<220> FEATURE:
<223> OTHER INFORMATION: pGW099

<400> SEQUENCE: 33
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggcctcta gaaaggatct gcgatcgctc cggtgcccgt cagtgggcag    180
agcgcacatc gcccacagtc cccgagaagt tggggggagg ggtcggcaat tgaacgggtg    240
cctagagaag gtggcgcggg gtaaactggg aaagtgatgt cgtgtactgg ctccgccttt    300
ttcccgaggg tggggagaa ccgtatataa gtgcagtagt cgccgtgaac gttctttttc    360
gcaacgggtt tgccgccaga acacagctga agcttcgagg ggctcgcatc tctccttcac    420
gcgcccgccg ccctacctga ggccgccatc cacgccggtt gagtcgcgtt ctgccgcctc    480
ccgcctgtgg tgcctcctga actgcgtccg ccgtctaggt aagtttaaag ctcaggtcga    540
gaccgggcct ttgtccggcg ctcccttgga gcctacctag actcagccgg ctctccacgc    600
tttgcctgac cctgcttgct caactctacg tctttgtttc gttttctgtt ctgcgccgtt    660
acagatctgg ctaactaccg gtgccaccat gaacgctaca cactgcatct ggctttgca     720 gctcttcctc atggctgttt ctggctgtta ctgccacggc acagtcattg aaagcctaga    780
aagtctgaat aactatttta actcaagtgg catagatgtg gaagaaaaga gtctcttctt    840
ggatatctgg aggaactggc aaaaggatgg tgacatgaaa atcctgcaga gccagattat    900
ctctttctac ctcagactct ttgaagtctt gaaagacaat caggccatca gcaacaacat    960
aagcgtcatt gaatcacacc tgattactac cttcttcagc aacagcaagg cgaaaaagga   1020
tgcattcatg agtattgcca gtttgaggt caacaaccca caggtccagc gccaagcatt    1080
caatgagctc atccgagtgg tccaccagct gttgccggaa tccagcctca ggaagcggaa    1140
aaggagtcgc tgcggatccg gcgcaacaaa cttctctctg ctgaaacaag ccggagatgt    1200
cgaagagaat cctggaccga tggcttgcaa ttgtcagttg atgcaggata caccactcct    1260
caagtttcca tgtccaaggc tcattcttct ctttgtgctg ctgattcgtc tttcacaagt    1320
gtcttcagat gttgatgaac aactgtccaa gtcagtgaaa gataaggtat tgctgccttg    1380
ccgttacaac tctcctcatg aagatgagtc tgaagaccga atctactggc aaaaacatga    1440
caaagtggtg ctgtctgtca ttgttgggaa actaaaagtg tggcccgagt ataagaaccg    1500
gactttatat gacaacacta cctactctct tatcatcctg ggcctggtcc tttcagaccg    1560
gggcacatac agctgtgtcg ttcaaaagaa ggaaagagga acgtatgaag ttaaacactt    1620
ggctttagta aagttgtcca tcaaagctga cttctctacc cccaacataa ctgagtctgg    1680
aaacccatct gcagacacta aaaggattac ctgctttgct tccggggggtt tcccaaagcc    1740 tcgcttctct tggttggaaa atggaagaga attacctggc atcaatacga caatttccca    1800
ggatcctgaa tctgaattgt acaccattag tagccaacta gatttcaata cgactcgcaa    1860
ccacaccatt aagtgtctca ttaaatatgg agatgctcac gtgtcagagg acttcacctg    1920
ggaaaaaccc ccagaagacc ctcctgatag caagaacaca cttgtgctct ttgggggcagg   1980
```

-continued

```
attcggcgca gtaataacag tcgtcgtcat cgttgtcatc atcaaatgct tctgtaagca      2040
cagaagctgt ttcagaagaa atgaggcaag cagagaaaca aacaacagcc ttaccttcgg      2100
gcctgaagaa gcattagctg aacagaccgt cttccttcgt acgggcagtg gagagggcag      2160
aggaagtctg ctaacatgcg gtgacgtcga ggagaatcct ggcccaatgg agagtgtggt      2220
acagccttca gtgtttgtgg tggatggaca gacggacatc ccattcaggc ggctggaaca      2280
gaaccaccgg agacggcgct gtggcactgt ccaggtcagc ctggccctgg tgctgctgct      2340
aggtgctggg ctggccactc agggctggtt tctcctgaga ctgcatcaac gtcttggaga      2400
catagtagct catctgccag atggaggcaa aggctcctgg gagaagctga tacaagatca      2460
acgatctcac caggccaacc cagcagcaca tcttacagga gccaacgcca gcttgatagg      2520
tattggtgga cctctgttat gggagacacg acttggcctg gccttcttga ggggcttgac      2580
gtatcatgat ggggccctgg tgaccatgga gcccggttac tactatgtgt actccaaagt      2640
gcagctgagc ggcgtgggct gcccccaggg gctggccaat ggcctcccca tcacccatgg      2700
actatacaag cgcacatccc gctacccgaa ggagttagaa ctgctggtca gtcggcggtc      2760
accctgtggc cgggccaaca gctcccgagt ctggtgggac agcagcttcc tgggcggcgt      2820
ggtacatctg gaggctgggg aagaggtggt ggtccgcgtg cctggaaacc gcctggtcag      2880
accacgtgac ggcaccaggt cctatttcgg agctttcatg gtcactagtg gatccggcgc      2940
aacaaacttc tctctgctga aacaagccgg agatgtcgaa gagaatcctg gaccgatgaa      3000
cccaagtgct gccgtcattt tctgcctcat cctgctgggt ctgagtggga ctcaagggat      3060
ccctctcgca aggacggtcc gctgcaactg catccatatc gatgacgggc cagtgagaat      3120
gagggccata gggaagcttg aaatcatccc tgcgagccta tcctgcccac gtgttgagat      3180
cattgccacg atgaaaaaga atgatgagca gagatgtctg aatccggaat ctaagaccat      3240
caagaattta atgaaagcgt ttagccaaaa aaggtctaaa agggctcctt gagaattcaa      3300
taaaagatct ttattttcat tagatctgtg tgttggtttt ttgtgtgcgg ccgcaggaac      3360
ccctagtgat ggagttggcc actccctctc tgcgcgctcg ctcgctcact gaggccgggc      3420
gaccaaaggt cgcccgacgc ccgggctttg cccgggcggc ctcagtgagc gagcgagcgc      3480
gcagctgcct gcaggggcgc ctgatgcggt attttctcct tacgcatctg tgcggtattt      3540
cacaccgcat acgtcaaagc aaccatagta cgcgccctgt agcggcgcat taagcgcggc      3600
gggtgtggtg gttacgcgca gcgtgaccgc tacacttgcc agcgccttag cgcccgctcc      3660
tttcgctttc ttcccttcct ttctcgccac gttcgccggc tttccccgtc aagctctaaa      3720
tcgggggctc cctttagggt tccgatttag tgctttacgg cacctcgacc ccaaaaaact      3780
tgatttgggt gatggttcac gtagtgggcc atcgccctga tagacggttt ttcgcccttt      3840
gacgttggag tccacgttct ttaatagtgg actcttgttc caaactggaa caacactcaa      3900
ctctatctcg ggctattctt ttgatttata agggattttg ccgatttcgg tctattggtt      3960
aaaaaatgag ctgatttaac aaaaatttaa cgcgaatttt aacaaaatat taacgtttac      4020
aattttatgg tgcactctca gtacaatctg ctctgatgcc gcatagttaa gccagccccg      4080
acacccgcca acacccgctg acgcgccctg acgggcttgt ctgctcccgg catccgctta      4140
cagacaagct gtgaccgtct ccgggagctg catgtgtcag aggttttcac cgtcatcacc      4200
gaaacgcgcg agacgaaagg gcctcgtgat acgcctattt ttataggtta atgtcatgat      4260
aataatggtt tcttagacgt caggtggcac ttttcgggga aatgtgcgcg gaacccctat      4320
```

-continued

```
ttgtttattt ttctaaatac attcaaatat gtatccgctc atgagacaat aaccctgata      4380
aatgcttcaa taatattgaa aaaggaagag tatgagtatt caacatttcc gtgtcgccct      4440
tattcccttt tttgcggcat tttgccttcc tgttttttgct cacccagaaa cgctggtgaa      4500
agtaaaagat gctgaagatc agttgggtgc acgagtgggt tacatcgaac tggatctcaa      4560
cagcggtaag atccttgaga gttttcgccc cgaagaacgt tttccaatga tgagcacttt      4620
taaagttctg ctatgtggcg cggtattatc ccgtattgac gccgggcaag agcaactcgg      4680
tcgccgcata cactattctc agaatgactt ggttgagtac tcaccagtca cagaaaagca      4740
tcttacggat ggcatgacag taagagaatt atgcagtgct gccataacca tgagtgataa      4800
cactgcggcc aacttacttc tgacaacgat cggaggaccg aaggagctaa ccgctttttt      4860
gcacaacatg ggggatcatg taactcgcct tgatcgttgg gaaccggagc tgaatgaagc      4920
cataccaaac gacgagcgtg acaccacgat gcctgtagca atggcaacaa cgttgcgcaa      4980
actattaact ggcgaactac ttactctagc ttcccggcaa caattaatag actggatgga      5040
ggcggataaa gttgcaggac cacttctgcg ctcggccctt ccggctggct ggtttattgc      5100
tgataaatct ggagccggtg agcgtggaag ccgcggtatc attgcagcac tggggccaga      5160
tggtaagccc tcccgtatcg tagttatcta cacgacgggg agtcaggcaa ctatggatga      5220
acgaaataga cagatcgctg agataggtgc ctcactgatt aagcattggt aactgtcaga      5280
ccaagtttac tcatatatac tttagattga tttaaaactt catttttaat ttaaaaggat      5340
ctaggtgaag atccttttttg ataatctcat gaccaaaatc ccttaacgtg agttttcgtt      5400
ccactgagcg tcagaccccg tagaaaagat caaaggatct tcttgagatc ctttttttct      5460
gcgcgtaatc tgctgcttgc aaacaaaaaa accaccgcta ccagcggtgg tttgtttgcc      5520
ggatcaagag ctaccaactc tttttccgaa ggtaactggc ttcagcagag cgcagatacc      5580
aaatactgtt cttctagtgt agccgtagtt aggccaccac ttcaagaact ctgtagcacc      5640
gcctacatac ctcgctctgc taatcctgtt accagtggct gctgccagtg gcgataagtc      5700
gtgtcttacc gggttggact caagacgata gttaccggat aaggcgcagc ggtcgggctg      5760
aacggggggt tcgtgcacac agcccagctt ggagcgaacg acctacaccg aactgagata      5820
cctacagcgt gagctatgag aaagcgccac gcttcccgaa gggagaaagg cggacaggta      5880
tccggtaagc ggcagggtcg aacaggaga gcgcacgagg gagcttccag ggggaaacgc      5940
ctggtatctt tatagtcctg tcgggtttcg ccacctctga cttgagcgtc gatttttgtg      6000
atgctcgtca gggggggcgga gcctatggaa aaacgccagc aacgcggcct ttttacggtt      6060
cctggccttt tgctggcctt ttgctcacat gt                                      6092
```

```
<210> SEQ ID NO 34
<211> LENGTH: 7094
<212> TYPE: DNA
<213> ORGANISM: Artificial Sequence
<220> FEATURE:
<223> OTHER INFORMATION: pGW100

<400> SEQUENCE: 34
```

```
cctgcaggca gctgcgcgct cgctcgctca ctgaggccgc ccgggcgtcg ggcgaccttt        60
ggtcgcccgg cctcagtgag cgagcgagcg cgcagagagg gagtggccaa ctccatcact       120
aggggttcct gcggcctcta gaaaggatct gcgatcgctc cggtgcccgt cagtgggcag       180
agcgcacatc gcccacagtc cccgagaagt tggggggagg ggtcggcaat tgaacgggtg       240
cctagagaag gtggcgcggg gtaaactggg aaagtgatgt cgtgtactgg ctccgccttt       300
```

-continued

```
ttcccgaggg tggggagaa  ccgtatataa gtgcagtagt cgccgtgaac gttctttttc    360
gcaacgggtt tgccgccaga acacagctga agcttcgagg ggctcgcatc tctccttcac    420
gcgcccgccg ccctacctga ggccgccatc cacgccggtt gagtcgcgtt ctgccgcctc    480
ccgcctgtgg tgcctcctga actgcgtccg ccgtctaggt aagtttaaag ctcaggtcga    540
gaccgggcct ttgtccggcg ctcccttgga gcctacctag actcagccgg ctctccacgc    600
tttgcctgac cctgcttgct caactctacg tctttgtttc gttttctgtt ctgcgccgtt    660
acagatctgg ctaactaccg gtgccaccat gaacgctaca cactgcatct tggctttgca    720
gctcttcctc atggctgttt ctggctgtta ctgccacggc acagtcattg aaagcctaga    780
aagtctgaat aactatttta actcaagtgg catagatgtg gaagaaaaga gtctcttctt    840
ggatatctgg aggaactggc aaaaggatgg tgacatgaaa atcctgcaga gccagattat    900
ctctttctac ctcagactct ttgaagtctt gaaagacaat caggccatca gcaacaacat    960
aagcgtcatt gaatcacacc tgattactac cttcttcagc aacagcaagg cgaaaaagga   1020
tgcattcatg agtattgcca agtttgaggt caacaaccca caggtccagc gccaagcatt   1080
caatgagctc atccgagtgg tccaccagct gttgccggaa tccagcctca ggaagcggaa   1140
aaggagtcgc tgcggatccg gcgcaacaaa cttctctctg ctgaaacaag ccggagatgt   1200
cgaagagaat cctggaccga tggcttgcaa ttgtcagttg atgcaggata caccactcct   1260
caagtttcca tgtccaaggc tcattcttct ctttgtgctg ctgattcgtc tttcacaagt   1320
gtcttcagat gttgatgaac aactgtccaa gtcagtgaaa gataaggtat tgctgccttg   1380
ccgttacaac tctcctcatg aagatgagtc tgaagaccga atctactggc aaaaacatga   1440
caaagtggtg ctgtctgtca ttgttgggaa actaaaagtg tggcccgagt ataagaaccg   1500
gactttatat gacaacacta cctactctct tatcatcctg ggcctggtcc tttcagaccg   1560
gggcacatac agctgtgtcg ttcaaaagaa ggaaagagga acgtatgaag ttaaacactt   1620
ggctttagta aagttgtcca tcaaagctga cttctctacc cccaacataa ctgagtctgg   1680
aaacccatct gcagacacta aaaggattac ctgctttgct tccgggggtt tcccaaagcc   1740
tcgcttctct tggttggaaa atggaagaga attacctggc atcaatacga caatttccca   1800
ggatcctgaa tctgaattgt acaccattag tagccaacta gatttcaata cgactcgcaa   1860
ccacaccatt aagtgtctca ttaaatatgg agatgctcac gtgtcagagg acttcacctg   1920
ggaaaaaccc ccagaagacc ctcctgatag caagaacaca cttgtgctct ttggggcagg   1980
attcggcgca gtaataacag tcgtcgtcat cgttgtcatc atcaaatgct ctgtaagca    2040 cagaagctgt ttcagaagaa atgaggcaag cagagaaaca aacaacagcc ttaccttcgg   2100
gcctgaagaa gcattagctg aacagaccgt cttccttcgt acgggcagtg agagggcag    2160 aggaagtctg ctaacatgcg gtgacgtcga ggagaatcct ggcccaatgg agagtgtggt   2220
acagccttca gtgtttgtgg tggatggaca cacggacatc ccattcaggc ggctggaaca   2280
gaaccaccgg agacggcgct gtggcactgt ccaggtcagc ctggccctgg tgctgctgct   2340
aagtgctggg ctggccactc agggctggtt tctcctgaga ctgcatcaac gtcttggaga   2400
catagtagct catctgccag atggaggcaa aggctcctgg gagaagctga tacaagatca   2460
acgatctcac caggccaacc cagcagcaca tcttacagga gccaacgcca gcttgatagg   2520
tattggtgga cctctgttat gggagacacg acttggcctg gccttcttga ggggcttgac   2580
gtatcatgat ggggccctgg tgaccatgga gcccggttac tactatgtgt actccaaagt   2640
```

-continued

```
gcagctgagc ggcgtgggct gccccccaggg gctggccaat ggcctcccca tcacccatgg    2700
actatacaag cgcacatccc gctacccgaa ggagttagaa ctgctggtca gtcggcggtc    2760
accctgtggc cgggccaaca gctcccgagt ctggtgggac agcagcttcc tgggcggcgt    2820
ggtacatctg gaggctgggg aagaggtggt ggtccgcgtg cctggaaacc gcctggtcag    2880
accacgtgac ggcaccaggt cctatttcgg agctttcatg gtcactagtg gatccggcgc    2940
aacaaacttc tctctgctga aacaagccgg agatgtcgaa gagaatcctg gaccgatgaa    3000
cccaagtgct gccgtcattt tctgcctcat cctgctgggt ctgagtggga ctcaagggat    3060
ccctctcgca aggacggtcc gctgcaactg catccatatc gatgacgggc cagtgagaat    3120
gagggccata gggaagcttg aaatcatccc tgcgagccta tcctgcccac gtgttgagat    3180
cattgccacg atgaaaaaga atgatgagca gagatgtctg aatccggaat ctaagaccat    3240
caagaattta atgaaagcgt ttagccaaaa aaggtctaaa agggctcctg ctagcagcgg    3300
tacccagtgc accaactacg ccctgctgaa gctggccggc gatgtggaga gcaacccccgg    3360 gcccatggac cagcacacac ttgatgtgga ggataccgcg gatgccagac atccagcagg    3420
tacttcgtgc ccctcggatg cggcgctcct cagagatacc gggctcctcg cggacgctgc    3480
gctcctctca gatactgtgc gccccacaaa tgccgcgctc cccacggatg ctgcctaccc    3540
tgcggttaat gttcgggatc gcgaggccgc gtggccgcct gcactgaact tctgttcccg    3600
ccacccaaag ctctatggcc tagtcgcttt ggttttgctg cttctgatcg ccgcctgtgt    3660
tcctatcttc acccgcaccg agcctcggcc agcgctcaca atcaccacct cgcccaacct    3720
gggtacccga gagaataatg cagaccaggt caccctgtt tcccacattg gctgccccaa    3780
cactacacaa cagggctctc ctgtgttcgc caagctactg gctaaaaacc aagcatcgtt    3840
gtgcaataca actctgaact ggcacagcca agatggagct gggagctcat acctatctca    3900
aggtctgagg tacgaagaag acaaaaagga gttggtggta gacagtcccg ggctctacta    3960 cgtattttg gaactgaagc tcagtccaac attcacaaac acaggccaca aggtgcaggg    4020
ctgggtctct cttgtttgc aagcaaagcc tcaggtagat gactttgaca acttggccct    4080
gacagtggaa ctgttcccctt gctccatgga gaacaagtta gtggaccgtt cctggagtca    4140
actgttgctc ctgaaggctg gccaccgcct cagtgtgggt ctgagggctt atctgcatgg    4200
agcccaggat gcatacagag actgggagct gtcttatccc aacaccacca gctttggact    4260
ctttcttgtg aaacccgaca acccatggga atgagaattc aataaaagat ctttattttc    4320
attagatctg tgtgttggtt ttttgtgtgc ggccgcagga accctagtg atggagttgg    4380 ccactccctc tctgcgcgct cgctcgctca ctgaggccgg gcgaccaaag tcgcccgac    4440 gcccgggctt tgcccgggcg gcctcagtga gcgagcgagc gcgcagctgc ctgcaggggc    4500
gcctgatgcg gtattttctc cttacgcatc tgtgcggtat ttcacaccgc atacgtcaaa    4560
gcaaccatag tacgcgccct gtagcggcgc attaagcgcg gcgggtgtgg tggttacgcg    4620
cagcgtgacc gctacacttg ccagcgccct agcgcccgct cctttcgctt tcttcccttc    4680
ctttctcgcc acgttcgccg gctttccccg tcaagctcta aatcgggggc tccctttagg    4740
gttccgattt agtgctttac ggcacctcga ccccaaaaaa cttgatttgg gtgatggttc    4800
acgtagtggg ccatcgccct gatagacggt ttttcgccct ttgacgttgg agtccacgtt    4860
ctttaatagt ggactcttgt tccaaactgg aacaacactc aactctatct cgggctattc    4920
ttttgattta taagggattt tgccgatttc ggtctattgg ttaaaaaatg agctgattta    4980
acaaaaattt aacgcgaatt ttaacaaaat attaacgttt acaattttat ggtgcactct    5040
```

-continued

```
cagtacaatc tgctctgatg ccgcatagtt aagccagccc cgacacccgc caacacccgc      5100
tgacgcgccc tgacgggctt gtctgctccc ggcatccgct tacagacaag ctgtgaccgt      5160
ctccgggagc tgcatgtgtc agaggttttc accgtcatca ccgaaacgcg cgagacgaaa      5220
gggcctcgtg atacgcctat ttttataggt taatgtcatg ataataatgg tttcttagac      5280
gtcaggtggc acttttcggg gaaatgtgcg cggaacccct atttgtttat ttttctaaat      5340
acattcaaat atgtatccgc tcatgagaca ataaccctga taaatgcttc aataatattg      5400
aaaaaggaag agtatgagta ttcaacattt ccgtgtcgcc cttattccct ttttttgcggc     5460 attttgcctt cctgtttttg ctcacccaga aacgctggtg aaagtaaaag atgctgaaga     5520
tcagttgggt gcacgagtgg gttacatcga actggatctc aacagcggta agatccttga     5580
gagttttcgc cccgaagaac gttttccaat gatgagcact tttaaagttc tgctatgtgg     5640
cgcggtatta tcccgtattg acgccgggca agagcaactc ggtcgccgca tacactattc     5700
tcagaatgac ttggttgagt actcaccagt cacagaaaag catcttacgg atggcatgac     5760
agtaagagaa ttatgcagtg ctgccataac catgagtgat aacactgcgg ccaacttact     5820
tctgacaacg atcggaggac cgaaggagct aaccgctttt ttgcacaaca tgggggatca     5880
tgtaactcgc cttgatcgtt gggaaccgga gctgaatgaa gccataccaa acgacgagcg     5940
tgacaccacg atgcctgtag caatggcaac aacgttgcgc aaactattaa ctggcgaact     6000
acttactcta gcttcccggc aacaattaat agactggatg gaggcggata agttgcagg      6060 accacttctg cgctcggccc ttccggctgg ctggtttatt gctgataaat ctggagccgg     6120
tgagcgtgga agccgcggta tcattgcagc actggggcca gatggtaagc cctcccgtat     6180
cgtagttatc tacacgacgg ggagtcaggc aactatggat gaacgaaata gacagatcgc     6240
tgagataggt gcctcactga ttaagcattg gtaactgtca gaccaagttt actcatatat     6300
actttagatt gatttaaaac ttcatttta atttaaaagg atctaggtga agatcctttt      6360
tgataatctc atgaccaaaa tcccttaacg tgagttttcg ttccactgag cgtcagaccc     6420
cgtagaaaag atcaaaggat cttcttgaga tccttttttt ctgcgcgtaa tctgctgctt     6480
gcaaacaaaa aaaccaccgc taccagcggt ggtttgtttg ccggatcaag agctaccaac     6540 tcttttccg aaggtaactg gcttcagcag agcgcagata ccaaatactg ttcttctagt      6600
gtagccgtag ttaggccacc acttcaagaa ctctgtagca ccgcctacat acctcgctct     6660
gctaatcctg ttaccagtgg ctgctgccag tggcgataag tcgtgtctta ccgggttgga     6720
ctcaagacga tagttaccgg ataaggcgca gcggtcgggc tgaacggggg gttcgtgcac     6780
acagcccagc ttggagcgaa cgacctacac cgaactgaga tacctacagc gtgagctatg     6840
agaaagcgcc acgcttcccg aagggagaaa ggcggacagg tatccggtaa gcggcagggt     6900
cggaacagga gagcgcacga gggagcttcc aggggaaac gcctggtatc tttatagtcc      6960
tgtcgggttt cgccacctct gacttgagcg tcgatttttg tgatgctcgt caggggggcg     7020
gagcctatgg aaaaacgcca gcaacgcggc ctttttacgg ttcctggcct tttgctggcc     7080
ttttgctcac atgt                                                       7094
```

<210> SEQ ID NO 35
<211> LENGTH: 6728
<212> TYPE: DNA
<213> ORGANISM: Artificial Sequence
<220> FEATURE:
<223> OTHER INFORMATION: pGW101

-continued

```
<400> SEQUENCE: 35
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggcctcta gaaaggatct gcgatcgctc cggtgcccgt cagtgggcag     180
agcgcacatc gcccacagtc cccgagaagt tggggggagg ggtcggcaat tgaacgggtg     240
cctagagaag gtggcgcggg gtaaactggg aaagtgatgt cgtgtactgg ctccgccttt     300
ttcccgaggg tggggagaa ccgtatataa gtgcagtagt cgccgtgaac gttcttttc     360 gcaacgggtt tgccgccaga acacagctga agcttcgagg ggctcgcatc tctccttcac     420
gcgcccgccg ccctacctga ggccgccatc cacgccggtt gagtcgcgtt ctgccgcctc     480
ccgcctgtgg tgcctcctga actgcgtccg ccgtctaggt aagtttaaag ctcaggtcga     540
gaccgggcct ttgtccggcg ctcccttgga gcctacctag actcagccgg ctctccacgc     600
tttgcctgac cctgcttgct caactctacg tctttgtttc gttttctgtt ctgcgccgtt     660
acagatctgg ctaactaccg gtgccaccat gaacgctaca cactgcatct tggctttgca     720
gctcttcctc atggctgttt ctggctgtta ctgccacggc acagtcattg aaagcctaga     780
aagtctgaat aactatttta actcaagtgg catagatgtg gaagaaaaga gtctcttctt     840
ggatatctgg aggaactggc aaaaggatgg tgacatgaaa atcctgcaga gccagattat     900
ctctttctac ctcagactct ttgaagtctt gaaagacaat caggccatca gcaacaacat     960
aagcgtcatt gaatcacacc tgattactac cttcttcagc aacagcaagg cgaaaaagga    1020
tgcattcatg agtattgcca gtttgaggt caacaaccca caggtccagc gccaagcatt    1080
caatgagctc atccgagtgg tccaccagct gttgccggaa tccagcctca ggaagcggaa    1140
aaggagtcgc tgcggatccg gcgcaacaaa cttctctctg ctgaaacaag ccggagatgt    1200
cgaagagaat cctggaccga tggcttgcaa ttgtcagttg atgcaggata caccactcct    1260
caagtttcca gtccaaggc tcattcttct cttttgtgctg ctgattcgtc tttcacaagt    1320
gtcttcagat gttgatgaac aactgtccaa gtcagtgaaa gataaggtat tgctgccttg    1380
ccgttacaac tctcctcatg aagatgagtc tgaagaccga atctactggc aaaaacatga    1440
caaagtggtg ctgtctgtca ttgttgggaa actaaaagtg tggcccgagt ataagaaccg    1500
gactttatat gacaacacta cctactctct tatcatcctg ggcctggtcc tttcagaccg    1560
gggcacatac agctgtgtcg ttcaaaagaa ggaaagagga acgtatgaag ttaaacactt    1620
ggctttagta aagttgtcca tcaaagctga cttctctacc cccaacataa ctgagtctgg    1680
aaacccatct gcagacacta aaaggattac ctgctttgct tccggggggtt tcccaaagcc    1740 tcgcttctct tggttggaaa atggaagaga attacctggc atcaatacga caatttccca    1800
ggatcctgaa tctgaattgt acaccattag tagccaacta gatttcaata cgactcgcaa    1860
ccacaccatt aagtgtctca ttaaatatgg agatgctcac gtgtcagagg acttcacctg    1920
ggaaaaaccc ccagaagacc ctcctgatag caagaacaca cttgtgctct ttgggggcagg    1980 attcggcgca gtaataacag tcgtcgtcat cgttgtcatc atcaaatgct tctgtaagca    2040
cagaagctgt ttcagaagaa atgaggcaag cagagaaaca aacaacagcc ttaccttcgg    2100
gcctgaagaa gcattagctg aacagaccgt cttccttcgt acgggcagtg agagggcag    2160 aggaagtctg ctaacatgcg gtgacgtcga ggagaatcct ggcccaatgg agagtgtggt    2220
acagccttca gtgtttgtgg tggatggaca gacggacatc ccattcaggc ggctggaaca    2280
gaaccaccgg agacggcgct gtggcactgt ccaggtcagc ctggccctgg tgctgctgct    2340
```

-continued

```
aggtgctggg ctggccactc agggctggtt tctcctgaga ctgcatcaac gtcttggaga    2400
catagtagct catctgccag atggaggcaa aggctcctgg gagaagctga tacaagatca    2460
acgatctcac caggccaacc cagcagcaca tcttacagga gccaacgcca gcttgatagg    2520
tattggtgga cctctgttat gggagacacg acttggcctg gccttcttga ggggcttgac    2580
gtatcatgat ggggccctgg tgaccatgga gcccggttac tactatgtgt actccaaagt    2640
gcagctgagc ggcgtgggct gcccccaggg gctggccaat ggcctcccca tcacccatgg    2700
actatacaag cgcacatccc gctacccgaa ggagttagaa ctgctggtca gtcggcggtc    2760
accctgtggc cgggccaaca gctcccgagt ctggtgggac agcagcttcc tgggcggcgt    2820
ggtacatctg gaggctgggg aagaggtggt ggtccgcgtg cctggaaacc gcctggtcag    2880
accacgtgac ggcaccaggt cctatttcgg agctttcatg gtcactagca gcggtaccca    2940
gtgcaccaac tacgccctgc tgaagctggc cggcgatgtg gagagcaacc ccgggcccat    3000
ggaccagcac acacttgatg tggaggatac cgcggatgcc agacatccag caggtacttc    3060
gtgcccctcg gatgcggcgc tcctcagaga taccgggctc ctcgcggacg ctgcgctcct    3120
ctcagatact gtgcgcccca caaatgccgc gctccccacg gatgctgcct accctgcggt    3180
taatgttcgg gatcgcgagg ccgcgtggcc gcctgcactg aacttctgtt cccgccaccc    3240
aaagctctat ggcctagtcg ctttggtttt gctgcttctg atcgccgcct gtgttcctat    3300
cttcacccgc accgagcctc ggccagcgct cacaatcacc acctcgccca acctgggtac    3360
ccgagagaat aatgcagacc aggtcacccc tgtttcccac attggctgcc ccaacactac    3420
acaacagggc tctcctgtgt tcgccaagct actggctaaa aaccaagcat cgttgtgcaa    3480
tacaactctg aactggcaca gccaagatgg agctgggagc tcatacctat ctcaaggtct    3540
gaggtacgaa gaagacaaaa aggagttggt ggtagacagt cccgggctct actacgtatt    3600
tttggaactg aagctcagtc caacattcac aaacacaggc cacaaggtgc agggctgggt    3660
ctctcttgtt ttgcaagcaa agcctcaggt agatgacttt gacaacttgg ccctgacagt    3720
ggaactgttc ccttgctcca tggagaacaa gttagtggac cgttcctgga gtcaactgtt    3780
gctcctgaag gctggccacc gcctcagtgt gggtctgagg gcttatctgc atggagccca    3840
ggatgcatac agagactggg agctgtctta tcccaacacc accagctttg gactctttct    3900
tgtgaaaccc gacaacccat gggaatgaga attcaataaa agatctttat tttcattaga    3960
tctgtgtgtt ggtttttttgt gtgcggccgc aggaacccct agtgatggag ttggccactc    4020
cctctctgcg cgctcgctcg ctcactgagg ccgggcgacc aaaggtcgcc cgacgcccgg    4080
gctttgcccg ggcggcctca gtgagcgagc gagcgcgcag ctgcctgcag gggcgcctga    4140
tgcggtattt tctccttacg catctgtgcg gtatttcaca ccgcatacgt caaagcaacc    4200
atagtacgcg ccctgtagcg gcgcattaag cgcggcgggt gtggtggtta cgcgcagcgt    4260
gaccgctaca cttgccagcg ccttagcgcc cgctcctttc gctttcttcc cttcctttct    4320
cgccacgttc gccggctttc cccgtcaagc tctaaatcgg gggctccctt tagggttccg    4380
atttagtgct ttacggcacc tcgaccccaa aaaacttgat ttgggtgatg gttcacgtag    4440
tgggccatcg ccctgataga cggttttttcg ccctttgacg ttggagtcca cgttctttaa    4500
tagtggactc ttgttccaaa ctggaacaac actcaactct atctcgggct attcttttga    4560
tttataaggg attttgccga tttcggtcta ttggttaaaa aatgagctga tttaacaaaa    4620
atttaacgcg aattttaaca aaatattaac gtttacaatt ttatggtgca ctctcagtac    4680
```

-continued

```
aatctgctct gatgccgcat agttaagcca gccccgacac ccgccaacac ccgctgacgc      4740
gccctgacgg gcttgtctgc tcccggcatc cgcttacaga caagctgtga ccgtctccgg      4800
gagctgcatg tgtcagaggt tttcaccgtc atcaccgaaa cgcgcgagac gaaagggcct      4860
cgtgatacgc ctattttat aggttaatgt catgataata atggtttctt agacgtcagg       4920
tggcactttt cggggaaatg tgcgcggaac ccctatttgt ttattttttct aaatacattc     4980 aaatatgtat ccgctcatga dacaataacc ctgataaatg cttcaataat attgaaaaag      5040
gaagagtatg agtattcaac atttccgtgt cgcccttatt cccttttttg cggcattttg      5100
ccttcctgtt tttgctcacc cagaaacgct ggtgaaagta aaagatgctg aagatcagtt      5160
gggtgcacga gtgggttaca tcgaactgga tctcaacagc ggtaagatcc ttgagagttt      5220
tcgccccgaa gaacgttttc caatgatgag cactttttaaa gttctgctat gtggcgcggt     5280
attatcccgt attgacgccg ggcaagagca actcggtcgc cgcatacact attctcagaa      5340
tgacttggtt gagtactcac cagtcacaga aaagcatctt acggatggca tgacagtaag      5400
agaattatgc agtgctgcca taaccatgag tgataacact gcggccaact tacttctgac      5460
aacgatcgga ggaccgaagg agctaaccgc ttttttgcac aacatggggg atcatgtaac      5520
tcgccttgat cgttgggaac cggagctgaa tgaagccata ccaaacgacg agcgtgacac      5580
cacgatgcct gtagcaatgg caacaacgtt gcgcaaacta ttaactggcg aactacttac      5640
tctagcttcc cggcaacaat taatagactg gatggaggcg gataaagttg caggaccact      5700
tctgcgctcg gcccttccgg ctggctggtt tattgctgat aaatctggag ccggtgagcg      5760
tggaagccgc ggtatcattg cagcactggg gccagatggt aagccctccc gtatcgtagt      5820
tatctacacg acggggagtc aggcaactat ggatgaacga aatagacaga tcgctgagat      5880
aggtgcctca ctgattaagc attggtaact gtcagaccaa gtttactcat atatacttta      5940
gattgattta aaacttcatt tttaatttaa aaggatctag gtgaagatcc tttttgataa      6000
tctcatgacc aaaatccctt aacgtgagtt ttcgttccac tgagcgtcag accccgtaga      6060
aaagatcaaa ggatcttctt gagatccttt ttttctgcgc gtaatctgct gcttgcaaac      6120
aaaaaaacca ccgctaccag cggtggtttg tttgccggat caagagctac caactctttt      6180
tccgaaggta actggcttca gcagagcgca gataccaaat actgttcttc tagtgtagcc      6240
gtagttaggc caccacttca agaactctgt agcaccgcct acatacctcg ctctgctaat      6300
cctgttacca gtggctgctg ccagtggcga taagtcgtgt cttaccgggt tggactcaag      6360
acgatagtta ccggataagg cgcagcggtc gggctgaacg ggggggttcgt gcacacagcc      6420 cagcttggag cgaacgacct acaccgaact gagataccta cagcgtgagc tatgagaaag      6480
cgccacgctt cccgaaggga gaaaggcgga caggtatccg gtaagcggca gggtcggaac      6540
aggagagcgc acgagggagc ttccaggggg aaacgcctgg tatctttata gtcctgtcgg      6600
gtttcgccac ctctgacttg agcgtcgatt tttgtgatgc tcgtcagggg ggcggagcct      6660
atggaaaaac gccagcaacg cggcctttttt acggttcctg gccttttgct ggcctttttgc     6720 tcacatgt                                                               6728
```

<210> SEQ ID NO 36
<211> LENGTH: 4412
<212> TYPE: DNA
<213> ORGANISM: Artificial Sequence
<220> FEATURE:
<223> OTHER INFORMATION: pGW102

<400> SEQUENCE: 36

-continued

```
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggcctcta gaaaggatct gcgatcgctc cggtgcccgt cagtgggcag     180
agcgcacatc gcccacagtc cccgagaagt tggggggagg ggtcggcaat tgaacgggtg     240
cctagagaag gtggcgcggg gtaaactggg aaagtgatgt cgtgtactgg ctccgccttt     300
ttcccgaggg tggggggagaa ccgtatataa gtgcagtagt cgccgtgaac gttctttttc    360
gcaacgggtt tgccgccaga acacagctga agcttcgagg ggctcgcatc tctccttcac     420
gcgcccgccg ccctacctga ggccgccatc cacgccggtt gagtcgcgtt ctgccgcctc     480
ccgcctgtgg tgcctcctga actgcgtccg ccgtctaggt aagtttaaag ctcaggtcga     540
gaccgggcct ttgtccggcg ctcccttgga gcctacctag actcagccgg ctctccacgc     600
tttgcctgac cctgcttgct caactctacg tctttgtttc gttttctgtt ctgcgccgtt     660
acagatctgg ctaactaccg gtgccaccat ggcttgcaat tgtcagttga tgcaggatac     720
accactcctc aagtttccat gtccaaggct cattcttctc tttgtgctgc tgattcgtct     780
ttcacaagtg tcttcagatg ttgatgaaca actgtccaag tcagtgaaag ataaggtatt     840
gctgccttgc cgttacaact ctcctcatga agatgagtct gaagaccgaa tctactggca     900
aaaacatgac aaagtggtgc tgtctgtcat tgttgggaaa ctaaaagtgt ggcccgagta     960
taagaaccgg actttatatg acaacactac ctactctctt atcatcctgg gcctggtcct    1020
ttcagaccgg ggcacataca gctgtgtcgt tcaaaagaag gaaagaggaa cgtatgaagt    1080
taaacacttg gctttagtaa agttgtccat caaagctgac ttctctaccc ccaacataac    1140
tgagtctgga aacccatctg cagacactaa aaggattacc tgctttgctt ccggggggttt   1200 cccaaagcct cgcttctctt ggttggaaaa tggaagagaa ttacctggca tcaatacgac    1260 aaatttcccag gatcctgaat ctgaattgta caccattagt agccaactag atttcaatac   1320
gactcgcaac cacaccatta agtgtctcat taaatatgga gatgctcacg tgtcagagga    1380
cttcacctgg gaaaaacccc cagaagaccc tcctgatagc aagaacacac ttgtgctctt    1440
tggggcagga ttcggcgcag taataacagt cgtcgtcatc gttgtcatca tcaaatgctt    1500
ctgtaagcac agaagctgtt tcagaagaaa tgaggcaagc agagaaacaa acaacagcct    1560
taccttcggg cctgaagaag cattagctga acagaccgtc ttccttcgtt aggaattcaa    1620
taaaagatct ttattttcat tagatctgtg tgttggtttt ttgtgtgcgg ccgcaggaac    1680
ccctagtgat ggagttggcc actccctctc tgcgcgctcg ctcgctcact gaggccgggc    1740
gaccaaaggt cgcccgacgc ccgggctttg cccgggcggc ctcagtgagc gagcgagcgc    1800
gcagctgcct gcaggggcgc ctgatgcggt attttctcct tacgcatctg tgcggtattt    1860
cacaccgcat acgtcaaagc aaccatagta cgcgccctgt agcggcgcat taagcgcggc    1920
gggtgtggtg gttacgcgca gcgtgaccgc tacacttgcc agcgccttag cgcccgctcc    1980
tttcgctttc ttcccttcct ttctcgccac gttcgccggc tttccccgtc aagctctaaa    2040 tcggggggctc cctttagggt tccgatttag tgctttacgg cacctcgacc ccaaaaaact    2100
tgatttgggt gatggttcac gtagtgggcc atcgccctga tagacggttt ttcgcccttt    2160
gacgttggag tccacgttct ttaatagtgg actcttgttc caaactggaa caacactcaa    2220
ctctatctcg ggctattctt ttgatttata agggattttg ccgatttcgg tctattggtt    2280
aaaaaatgag ctgatttaac aaaaatttaa cgcgaatttt aacaaaatat taacgtttac    2340
```

-continued

```
aattttatgg tgcactctca gtacaatctg ctctgatgcc gcatagttaa gccagccccg      2400
acacccgcca acacccgctg acgcgccctg acgggcttgt ctgctcccgg catccgctta      2460
cagacaagct gtgaccgtct ccgggagctg catgtgtcag aggttttcac cgtcatcacc      2520
gaaacgcgcg agacgaaagg gcctcgtgat acgcctattt ttataggtta atgtcatgat      2580
aataatggtt tcttagacgt caggtggcac ttttcgggga aatgtgcgcg gaacccctat      2640
ttgtttattt ttctaaatac attcaaatat gtatccgctc atgagacaat aaccctgata      2700
aatgcttcaa taatattgaa aaaggaagag tatgagtatt caacatttcc gtgtcgccct      2760
tattcccttt tttgcggcat tttgccttcc tgttttttgct cacccagaaa cgctggtgaa      2820
agtaaaagat gctgaagatc agttgggtgc acagtgggt tacatcgaac tggatctcaa      2880
cagcggtaag atccttgaga gttttcgccc cgaagaacgt tttccaatga tgagcacttt      2940
taaagttctg ctatgtggcg cggtattatc ccgtattgac gccgggcaag agcaactcgg      3000
tcgccgcata cactattctc agaatgactt ggttgagtac tcaccagtca cagaaaagca      3060
tcttacggat ggcatgacag taagagaatt atgcagtgct gccataacca tgagtgataa      3120
cactgcggcc aacttacttc tgacaacgat cggaggaccg aaggagctaa ccgcttttttt      3180 gcacaacatg ggggatcatg taactcgcct tgatcgttgg gaaccggagc tgaatgaagc      3240
cataccaaac gacgagcgtg acaccacgat gcctgtagca atggcaacaa cgttgcgcaa      3300
actattaact ggcgaactac ttactctagc ttcccggcaa caattaatag actggatgga      3360
ggcggataaa gttgcaggac cacttctgcg ctcggccctt ccggctggct ggtttattgc      3420
tgataaatct ggagccggtg agcgtggaag ccgcggtatc attgcagcac tggggccaga      3480
tggtaagccc tcccgtatcg tagttatcta cacgacgggg agtcaggcaa ctatggatga      3540
acgaaataga cagatcgctg agataggtgc ctcactgatt aagcattggt aactgtcaga      3600
ccaagtttac tcatatatac tttagattga tttaaaactt catttttaat ttaaaaggat      3660
ctaggtgaag atcctttttg ataatctcat gaccaaaatc ccttaacgtg agttttcgtt      3720
ccactgagcg tcagaccccg tagaaaagat caaaggatct tcttgagatc cttttttctt     3780
gcgcgtaatc tgctgcttgc aaacaaaaaa accaccgcta ccagcggtgg tttgtttgcc      3840
ggatcaagag ctaccaactc tttttccgaa ggtaactggc ttcagcagag cgcagatacc      3900
aaatactgtt cttctagtgt agccgtagtt aggccaccac ttcaagaact ctgtagcacc      3960
gcctacatac ctcgctctgc taatcctgtt accagtggct gctgccagtg gcgataagtc      4020
gtgtcttacc gggttggact caagacgata gttaccggat aaggcgcagc ggtcgggctg      4080
aacggggggt tcgtgcacac agcccagctt ggagcgaacg acctacaccg aactgagata      4140
cctacagcgt gagctatgag aaagcgccac gcttcccgaa gggagaaagg cggacaggta      4200
tccggtaagc ggcagggtcg aacaggaga gcgcacgagg gagcttccag ggggaaacgc      4260
ctggtatctt tatagtcctg tcgggtttcg ccacctctga cttgagcgtc gatttttgtg      4320
atgctcgtca ggggggcgga gcctatggaa aaacgccagc aacgcggcct ttttacggtt      4380
cctggccttt tgctggcctt ttgctcacat gt                                    4412
```

<210> SEQ ID NO 37
<211> LENGTH: 4208
<212> TYPE: DNA
<213> ORGANISM: Artificial Sequence
<220> FEATURE:
<223> OTHER INFORMATION: pGW103

<400> SEQUENCE: 37

```
cctgcaggca gctgcgcgct cgctcgctca ctgaggccgc ccgggcgtcg ggcgaccttt    60
ggtcgcccgg cctcagtgag cgagcgagcg cgcagagagg gagtggccaa ctccatcact   120
aggggttcct gcggcctcta gaaaggatct gcgatcgctc cggtgcccgt cagtgggcag   180
agcgcacatc gcccacagtc cccgagaagt tggggggagg ggtcggcaat tgaacgggtg   240
cctagagaag gtggcgcggg gtaaactggg aaagtgatgt cgtgtactgg ctccgccttt   300
ttcccgaggg tgggggagaa ccgtatataa gtgcagtagt cgccgtgaac gttcttttc    360 gcaacgggtt tgccgccaga acacagctga agcttcgagg ggctcgcatc tctccttcac   420
gcgcccgccg ccctacctga ggccgccatc cacgccggtt gagtcgcgtt ctgccgcctc   480
ccgcctgtgg tgcctcctga actgcgtccg ccgtctaggt aagtttaaag ctcaggtcga   540
gaccgggcct ttgtccggcg ctcccttgga gcctacctag actcagccgg ctctccacgc   600
tttgcctgac cctgcttgct caactctacg tctttgtttc gttttctgtt ctgcgccgtt   660
acagatctgg ctaactaccg gtgccaccat ggagagtgtg gtacagcctt cagtgtttgt   720
ggtggatgga cagacggaca tcccattcag gcggctggaa cagaaccacc ggagacggcg   780
ctgtggcact gtccaggtca gcctggccct ggtgctgctg ctaggtgctg ggctggccac   840
tcagggctgg tttctcctga gactgcatca acgtcttgga gacatagtag ctcatctgcc   900
agatggaggc aaaggctcct gggagaagct gatacaagat caacgatctc accaggccaa   960
cccagcagca catcttacag gagccaacgc cagcttgata ggtattggtg gacctctgtt  1020
atgggagaca cgacttggcc tggccttctt gaggggcttg acgtatcatg atggggccct  1080
ggtgaccatg gagcccggtt actactatgt gtactccaaa gtgcagctga gcggcgtggg  1140
ctgcccccag gggctggcca atggcctccc catcacccat ggactataca agcgcacatc  1200
ccgctacccg aaggagttag aactgctggt cagtcggcgg tcaccctgtg gccgggccaa  1260
cagctcccga gtctggtggg acagcagctt cctgggcggc gtggtacatc tggaggctgg  1320
ggaagaggtg gtggtccgcg tgcctggaaa ccgcctggtc agaccacgtg acggcaccag  1380
gtcctatttc ggagctttca tggtctgaga attcaataaa agatctttat tttcattaga  1440
tctgtgtgtt ggttttttgt gtgcggccgc aggaacccct agtgatggag ttggccactc  1500
cctctctgcg cgctcgctcg ctcactgagg ccgggcgacc aaaggtcgcc cgacgcccgg  1560
gctttgcccg ggcggcctca gtgagcgagc gagcgcgcag ctgcctgcag gggcgcctga  1620
tgcggtattt tctccttacg catctgtgcg gtatttcaca ccgcatacgt caaagcaacc  1680
atagtacgcg ccctgtagcg cgcattaag cgcggcgggt gtggtggtta cgcgcagcgt   1740
gaccgctaca cttgccagcg ccttagcgcc cgctcctttc gctttcttcc cttcctttct  1800
cgccacgttc gccggctttc cccgtcaagc tctaaatcgg gggctccctt tagggttccg  1860
atttagtgct ttacggcacc tcgaccccaa aaaacttgat ttgggtgatg gttcacgtag  1920
tgggccatcg ccctgataga cggtttttcg ccctttgacg ttggagtcca cgttctttaa  1980
tagtggactc ttgttccaaa ctggaacaac actcaactct atctcgggct attcttttga  2040
tttataaggg attttgccga tttcggtcta ttggttaaaa aatgagctga tttaacaaaa  2100
atttaacgcg aattttaaca aaatattaac gtttacaatt ttatggtgca ctctcagtac  2160
aatctgctct gatgccgcat agttaagcca gccccgacac ccgccaacac ccgctgacgc  2220
gccctgacgg gcttgtctgc tcccggcatc cgcttacaga caagctgtga ccgtctccgg  2280
gagctgcatg tgtcagaggt tttcaccgtc atcaccgaaa cgcgcgagac gaaagggcct  2340
```

```
cgtgatacgc ctattttat aggttaatgt catgataata atggtttctt agacgtcagg    2400
tggcactttt cggggaaatg tgcgcggaac ccctatttgt ttattttct aaatacattc      2460 aaatatgtat ccgctcatga acaataacc ctgataaatg cttcaataat attgaaaaag     2520
gaagagtatg agtattcaac atttccgtgt cgcccttatt ccctttttg cggcattttg     2580 ccttcctgtt tttgctcacc cagaaacgct ggtgaaagta aaagatgctg aagatcagtt   2640
gggtgcacga gtgggttaca tcgaactgga tctcaacagc ggtaagatcc ttgagagttt   2700
tcgccccgaa gaacgttttc caatgatgag cactttaaa gttctgctat gtggcgcggt    2760
attatcccgt attgacgccg ggcaagagca actcggtcgc cgcatacact attctcagaa    2820
tgacttggtt gagtactcac cagtcacaga aaagcatctt acggatggca tgacagtaag    2880
agaattatgc agtgctgcca taaccatgag tgataacact gcggccaact tacttctgac    2940
aacgatcgga ggaccgaagg agctaaccgc ttttttgcac aacatggggg atcatgtaac   3000
tcgccttgat cgttgggaac cggagctgaa tgaagccata ccaaacgacg agcgtgacac   3060
cacgatgcct gtagcaatgg caacaacgtt gcgcaaacta ttaactggcg aactacttac   3120
tctagcttcc cggcaacaat taatagactg gatggaggcg gataaagttg caggaccact   3180
tctgcgctcg gcccttccgg ctggctggtt tattgctgat aaatctggag ccggtgagcg   3240
tggaagccgc ggtatcattg cagcactggg gccagatggt aagccctccc gtatcgtagt   3300
tatctacacg acggggagtc aggcaactat ggatgaacga aatagacaga tcgctgagat   3360
aggtgcctca ctgattaagc attggtaact gtcagaccaa gtttactcat atatacttta   3420
gattgattta aaacttcatt tttaatttaa aaggatctag gtgaagatcc tttttgataa   3480
tctcatgacc aaaatccctt aacgtgagtt ttcgttccac tgagcgtcag accccgtaga   3540
aaagatcaaa ggatcttctt gagatccttt ttttctgcgc gtaatctgct gcttgcaaac   3600
aaaaaaacca ccgctaccag cggtggtttg tttgccggat caagagctac caactctttt   3660
tccgaaggta actggcttca gcagagcgca gataccaaat actgttcttc tagtgtagcc   3720
gtagttaggc caccacttca agaactctgt agcaccgcct acatacctcg ctctgctaat   3780
cctgttacca gtggctgctg ccagtggcga taagtcgtgt cttaccgggt tggactcaag   3840
acgatagtta ccggataagg cgcagcggtc gggctgaacg gggggttcgt gcacacagcc   3900
cagcttggag cgaacgacct acaccgaact gagataccta cagcgtgagc tatgagaaag   3960
cgccacgctt cccgaaggga gaaaggcgga caggtatccg gtaagcggca gggtcggaac   4020
aggagagcgc acgagggagc ttccaggggg aaacgcctgg tatctttata gtcctgtcgg   4080
gtttcgccac ctctgacttg agcgtcgatt tttgtgatgc tcgtcagggg ggcggagcct   4140
atggaaaaac gccagcaacg cggccttttt acggttcctg gccttttgct ggccttttgc   4200
tcacatgt                                                             4208

<210> SEQ ID NO 38
<211> LENGTH: 3785
<212> TYPE: DNA
<213> ORGANISM: Artificial Sequence
<220> FEATURE:
<223> OTHER INFORMATION: pGW104

<400> SEQUENCE: 38
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact    120
aggggttcct gcggcctcta gaaaggatct gcgatcgctc cggtgcccgt cagtgggcag    180
```

```
agcgcacatc gcccacagtc cccgagaagt tgggggggagg ggtcggcaat tgaacgggtg      240
cctagagaag gtggcgcggg gtaaactggg aaagtgatgt cgtgtactgg ctccgccttt      300
ttcccgaggg tgggggagaa ccgtatataa gtgcagtagt cgccgtgaac gttcttttttc     360 gcaacgggtt tgccgccaga acacagctga agcttcgagg ggctcgcatc tctccttcac      420
gcgcccgccg ccctacctga ggccgccatc cacgccggtt gagtcgcgtt ctgccgcctc      480
ccgcctgtgg tgcctcctga actgcgtccg ccgtctaggt aagtttaaag ctcaggtcga      540
gaccgggcct ttgtccggcg ctcccttgga gcctacctag actcagccgg ctctccacgc      600
tttgcctgac cctgcttgct caactctacg tctttgtttc gttttctgtt ctgcgccgtt      660
acagatctgg ctaactaccg gtgccaccat gaacccaagt gctgccgtca ttttctgcct      720
catcctgctg ggtctgagtg ggactcaagg gatccctctc gcaaggacgg tccgctgcaa      780
ctgcatccat atcgatgacg ggccagtgag aatgagggcc atagggaagc ttgaaatcat      840
ccctgcgagc ctatcctgcc cacgtgttga gatcattgcc acgatgaaaa agaatgatga      900
gcagagatgt ctgaatccgg aatctaagac catcaagaat ttaatgaaag cgtttagcca      960
aaaaaggtct aaaagggctc cttgagaatt caataaaaga tctttatttt cattagatct     1020
gtgtgttggt tttttgtgtg cggccgcagg aacccctagt gatggagttg gccactccct     1080
ctctgcgcgc tcgctcgctc actgaggccg ggcgaccaaa ggtcgcccga cgcccgggct     1140
ttgcccgggc ggcctcagtg agcgagcgag cgcgcagctg cctgcagggg cgcctgatgc     1200
ggtattttct ccttacgcat ctgtgcggta tttcacaccg catacgtcaa agcaaccata     1260
gtacgcgccc tgtagcggcg cattaagcgc ggcgggtgtg gtggttacgc gcagcgtgac     1320
cgctacactt gccagcgcct tagcgcccgc tcctttcgct ttcttccctt cctttctcgc     1380
cacgttcgcc ggctttcccc gtcaagctct aaatcggggg ctcccttttag ggttccgatt     1440 tagtgcttta cggcacctcg accccaaaaa acttgatttg ggtgatggtt cacgtagtgg     1500
gccatcgccc tgatagacgg ttttttcgccc tttgacgttg gagtccacgt tctttaatag     1560
tggactcttg ttccaaactg gaacaacact caactctatc tcgggctatt cttttgattt     1620
ataagggatt ttgccgattt cggtctattg gttaaaaaat gagctgattt aacaaaaatt     1680
taacgcgaat tttaacaaaa tattaacgtt tacaattttta tggtgcactc tcagtacaat     1740
ctgctctgat gccgcatagt taagccagcc ccgacacccg ccaacacccg ctgacgcgcc     1800
ctgacgggct tgtctgctcc cggcatccgc ttacagacaa gctgtgaccg tctccgggag     1860
ctgcatgtgt cagaggtttt caccgtcatc accgaaacgc gcgagacgaa agggcctcgt     1920
gatacgccta ttttttatagg ttaatgtcat gataataatg gtttcttaga cgtcaggtgg     1980 cactttttcgg ggaaatgtgc gcggaacccc tatttgttta tttttctaaa tacattcaaa     2040
tatgtatccg ctcatgagac aataaccctg ataaatgctt caataatatt gaaaaaggaa     2100
gagtatgagt attcaacatt tccgtgtcgc ccttattccc ttttttgcgg cattttgcct     2160
tcctgttttt gctcacccag aaacgctggt gaaagtaaaa gatgctgaag atcagttggg     2220
tgcacgagtg ggttacatcg aactggatct caacagcggt aagatccttg agagttttcg     2280
ccccgaagaa cgttttccaa tgatgagcac ttttaaagtt ctgctatgtg gcgcggtatt     2340
atcccgtatt gacgccgggc aagagcaact cggtcgccgc atacactatt ctcagaatga     2400
cttggttgag tactcaccag tcacagaaaa gcatcttacg gatggcatga cagtaagaga     2460
attatgcagt gctgccataa ccatgagtga taacactgcg gccaacttac ttctgacaac     2520
```

-continued

```
gatcggagga ccgaaggagc taaccgcttt tttgcacaac atgggggatc atgtaactcg     2580
ccttgatcgt tgggaaccgg agctgaatga agccatacca aacgacgagc gtgacaccac     2640
gatgcctgta gcaatggcaa caacgttgcg caaactatta actggcgaac tacttactct     2700
agcttcccgg caacaattaa tagactggat ggaggcggat aaagttgcag gaccacttct     2760
gcgctcggcc cttccggctg gctggtttat tgctgataaa tctggagccg gtgagcgtgg     2820
aagccgcggt atcattgcag cactgggggcc agatggtaag ccctcccgta tcgtagttat     2880
ctacacgacg gggagtcagg caactatgga tgaacgaaat agacagatcg ctgagatagg     2940
tgcctcactg attaagcatt ggtaactgtc agaccaagtt tactcatata tactttagat     3000
tgatttaaaa cttcattttt aatttaaaag gatctaggtg aagatccttt ttgataatct     3060
catgaccaaa atcccttaac gtgagttttc gttccactga gcgtcagacc ccgtagaaaa     3120
gatcaaagga tcttcttgag atcctttttt tctgcgcgta atctgctgct tgcaaacaaa     3180
aaaaccaccg ctaccagcgg tggtttgttt gccggatcaa gagctaccaa ctctttttcc     3240
gaaggtaact ggcttcagca gagcgcagat accaaatact gttcttctag tgtagccgta     3300
gttaggccac cacttcaaga actctgtagc accgcctaca tacctcgctc tgctaatcct     3360
gttaccagtg gctgctgcca gtggcgataa gtcgtgtctt accgggttgg actcaagacg     3420
atagttaccg gataaggcgc agcggtcggg ctgaacgggg ggttcgtgca cacagcccag     3480
cttggagcga acgacctaca ccgaactgag atacctacag cgtgagctat gagaaagcgc     3540
cacgcttccc gaagggagaa aggcggacag gtatccggta agcggcaggg tcggaacagg     3600
agagcgcacg agggagcttc cagggggaaa cgcctggtat ctttatagtc ctgtcgggtt     3660
tcgccacctc tgacttgagc gtcgatttt tgtgatgctcg tcaggggggc ggagcctatg     3720
gaaaaacgcc agcaacgcgg cctttttacg gttcctggcc ttttgctggc cttttgctca     3780
catgt                                                                 3785
```

```
<210> SEQ ID NO 39
<211> LENGTH: 4418
<212> TYPE: DNA
<213> ORGANISM: Artificial Sequence
<220> FEATURE:
<223> OTHER INFORMATION: pGW105

<400> SEQUENCE: 39
cctgcaggca gctgcgcgct cgctcgctca ctgaggccgc ccgggcgtcg ggcgaccttt       60
ggtcgcccgg cctcagtgag cgagcgagcg cgcagagagg gagtggccaa ctccatcact      120
aggggttcct gcggcctcta gaaaggatct gcgatcgctc cggtgcccgt cagtgggcag      180
agcgcacatc gcccacagtc cccgagaagt tggggggagg ggtcggcaat tgaacgggtg      240
cctagagaag gtggcgcggg gtaaactggg aaagtgatgt cgtgtactgg ctccgccttt      300
ttcccgaggg tggggagaa ccgtatataa gtgcagtagt cgccgtgaac gttctttttc      360
gcaacgggtt tgccgccaga acacagctga agcttcgagg ggctcgcatc tctccttcac      420
gcgcccgccg ccctacctga ggccgccatc cacgccggtt gagtcgcgtt ctgccgcctc      480
ccgcctgtgg tgcctcctga actgcgtccg ccgtctaggt aagtttaaag ctcaggtcga      540
gaccgggcct ttgtccggcg ctcccttgga gcctacctag actcagccgg ctctccacgc      600
tttgcctgac cctgcttgct caactctacg tctttgtttc gttttctgtt ctgcgccgtt      660
acagatctgg ctaactaccg gtgccaccat ggaccagcac acacttgatg tggaggatac      720
cgcggatgcc agacatccag caggtacttc gtgcccctcg gatgcggcgc tcctcagaga      780
```

```
taccgggctc ctcgcggacg ctgcgctcct ctcagatact gtgcgcccca caaatgccgc      840
gctccccacg gatgctgcct accctgcggt taatgttcgg gatcgcgagg ccgcgtggcc      900
gcctgcactg aacttctgtt cccgccaccc aaagctctat ggcctagtcg ctttggtttt      960
gctgcttctg atcgccgcct gtgttcctat cttcacccgc accgagcctc ggccagcgct     1020
cacaatcacc acctcgccca acctgggtac ccgagagaat aatgcagacc aggtcacccc     1080
tgtttcccac attggctgcc ccaacactac acaacagggc tctcctgtgt tcgccaagct     1140
actggctaaa aaccaagcat cgttgtgcaa tacaactctg aactggcaca gccaagatgg     1200
agctgggagc tcatacctat ctcaaggtct gaggtacgaa gaagacaaaa aggagttggt     1260
ggtagacagt cccgggctct actacgtatt tttggaactg aagctcagtc caacattcac     1320
aaacacaggc cacaaggtgc agggctgggt ctctcttgtt ttgcaagcaa agcctcaggt     1380
agatgacttt gacaacttgg ccctgacagt ggaactgttc ccttgctcca tggagaacaa     1440
gttagtggac cgttcctgga gtcaactgtt gctcctgaag gctggccacc gcctcagtgt     1500
gggtctgagg gcttatctgc atggagccca ggatgcatac agagactggg agctgtctta     1560
tcccaacacc accagctttg gactctttct tgtgaaaccc gacaacccat gggaatgaga     1620
attcaataaa agatctttat tttcattaga tctgtgtgtt ggttttttgt gtgcggccgc     1680
aggaacccct agtgatggag ttggccactc cctctctgcg cgctcgctcg ctcactgagg     1740
ccgggcgacc aaaggtcgcc cgacgcccgg gctttgcccg ggcggcctca gtgagcgagc     1800
gagcgcgcag ctgcctgcag gggcgcctga tgcggtattt tctccttacg catctgtgcg     1860
gtatttcaca ccgcatacgt caaagcaacc atagtacgcg ccctgtagcg cgcattaag     1920 cgcggcgggt gtggtggtta cgcgcagcgt gaccgctaca cttgccagcg ccttagcgcc     1980
cgctcctttc gctttcttcc cttcctttct cgccacgttc gccggctttc cccgtcaagc     2040
tctaaatcgg gggctccctt tagggttccg atttagtgct ttacggcacc tcgaccccaa     2100
aaaacttgat ttgggtgatg gttcacgtag tgggccatcg ccctgataga cggttttttcg     2160 ccctttgacg ttggagtcca cgttctttaa tagtggactc ttgttccaaa ctggaacaac     2220
actcaactct atctcgggct attctttttga tttataaggg attttgccga tttcggtcta     2280
ttggttaaaa aatgagctga tttaacaaaa atttaacgcg aattttaaca aaatattaac     2340
gtttacaatt ttatggtgca ctctcagtac aatctgctct gatgccgcat agttaagcca     2400
gccccgacac ccgccaacac ccgctgacgc gccctgacgg gcttgtctgc tcccggcatc     2460
cgcttacaga caagctgtga ccgtctccgg gagctgcatg tgtcagaggt tttcaccgtc     2520
atcaccgaaa cgcgcgagac gaaagggcct cgtgatacgc ctatttttat aggttaatgt     2580
catgataata atggtttctt agacgtcagg tggcactttt cggggaaatg tgcgcggaac     2640
ccctatttgt ttatttttct aaatacattc aaatatgtat ccgctcatga caataaacc     2700 ctgataaatg cttcaataat attgaaaaag gaagagtatg agtattcaac atttccgtgt     2760
cgcccttatt cccttttttg cggcattttg ccttcctgtt tttgctcacc cagaaacgct     2820
ggtgaaagta aaagatgctg aagatcagtt gggtgcacga gtgggttaca tcgaactgga     2880
tctcaacagc ggtaagatcc ttgagagttt tcgccccgaa gaacgttttc caatgatgag     2940
cacttttaaa gttctgctat gtggcgcggt attatcccgt attgacgccg ggcaagagca     3000
actcggtcgc cgcatacact attctcagaa tgacttggtt gagtactcac cagtcacaga     3060
aaagcatctt acggatggca tgacagtaag agaattatgc agtgctgcca taaccatgag     3120
```

-continued

```
tgataacact gcggccaact tacttctgac aacgatcgga ggaccgaagg agctaaccgc      3180 tttttttgcac aacatggggg atcatgtaac tcgccttgat cgttgggaac cggagctgaa     3240
tgaagccata ccaaacgacg agcgtgacac cacgatgcct gtagcaatgg caacaacgtt     3300
gcgcaaacta ttaactggcg aactacttac tctagcttcc cggcaacaat taatagactg     3360
gatggaggcg gataaagttg caggaccact tctgcgctcg gcccttccgg ctggctggtt     3420
tattgctgat aaatctggag ccggtgagcg tggaagccgc ggtatcattg cagcactggg     3480
gccagatggt aagccctccc gtatcgtagt tatctacacg acggggagtc aggcaactat     3540
ggatgaacga aatagacaga tcgctgagat aggtgcctca ctgattaagc attggtaact     3600
gtcagaccaa gtttactcat atatacttta gattgattta aaacttcatt tttaatttaa     3660
aaggatctag gtgaagatcc tttttgataa tctcatgacc aaaatccctt aacgtgagtt     3720
ttcgttccac tgagcgtcag accccgtaga aaagatcaaa ggatcttctt gagatccttt     3780
ttttctgcgc gtaatctgct gcttgcaaac aaaaaaacca ccgctaccag cggtggtttg     3840
tttgccggat caagagctac caactctttt tccgaaggta actggcttca gcagagcgca     3900
gataccaaat actgttcttc tagtgtagcc gtagttaggc caccacttca agaactctgt     3960
agcaccgcct acatacctcg ctctgctaat cctgttacca gtggctgctg ccagtggcga     4020
taagtcgtgt cttaccgggt tggactcaag acgatagtta ccggataagg cgcagcggtc     4080
gggctgaacg ggggggttcgt gcacacagcc cagcttggag cgaacgacct acaccgaact     4140
gagataccta cagcgtgagc tatgagaaag cgccacgctt cccgaaggga gaaaggcgga     4200
caggtatccg gtaagcggca gggtcggaac aggagagcgc acgagggagc ttccaggggg     4260
aaacgcctgg tatctttata gtcctgtcgg gtttcgccac ctctgacttg agcgtcgatt     4320
tttgtgatgc tcgtcagggg ggcggagcct atggaaaaac gccagcaacg cggccttttt     4380
acggttcctg gccttttgct ggccttttgc tcacatgt                             4418
```

<210> SEQ ID NO 40
<211> LENGTH: 6676
<212> TYPE: DNA
<213> ORGANISM: Artificial Sequence
<220> FEATURE:
<223> OTHER INFORMATION: pGW110

<400> SEQUENCE: 40

```
cctgcaggca gctgcgcgct cgctcgctca ctgaggccgc ccgggcgtcg ggcgaccttt        60
ggtcgcccgg cctcagtgag cgagcgagcg cgcagagagg gagtggccaa ctccatcact       120
aggggttcct gcggcctcta gaaaggatct gcgatcgctc cggtgcccgt cagtgggcag       180
agcgcacatc gcccacagtc cccgagaagt tggggggagg ggtcggcaat tgaacgggtg       240
cctagagaag gtggcgcggg gtaaactggg aaagtgatgt cgtgtactgg ctccgccttt       300
ttcccgaggg tggggagaa ccgtatataa gtgcagtagt cgccgtgaac gttctttttc        360
gcaacgggtt tgccgccaga acacagctga agcttcgagg ggctcgcatc tctccttcac       420
gcgcccgccg ccctacctga ggccgccatc cacgccggtt gagtcgcgtt ctgccgcctc       480
ccgcctgtgg tgcctcctga actgcgtccg ccgtctaggt aagtttaaag ctcaggtcga       540
gaccgggcct ttgtccggcg ctccttgga gcctacctag actcagccgg ctctccacgc        600
tttgcctgac cctgcttgct caactctacg tctttgtttc gttttctgtt ctgcgccgtt       660
acagatctgc taactaccg gtgccaccat ggcttgcaat tgtcagttga tgcaggatac       720
accactcctc aagtttccat gtccaaggct cattcttctc tttgtgctgc tgattcgtct       780
```

-continued

```
ttcacaagtg tcttcagatg ttgatgaaca actgtccaag tcagtgaaag ataaggtatt      840
gctgccttgc cgttacaact ctcctcatga agatgagtct gaagaccgaa tctactggca      900
aaaacatgac aaagtggtgc tgtctgtcat tgctgggaaa ctaaaagtgt ggcccgagta      960
taagaaccgg actttatatg acaacactac ctactctctt atcatcctgg gcctggtcct     1020
ttcagaccgg ggcacataca gctgtgtcgt tcaaaagaag gaaagaggaa cgtatgaagt     1080
taaacacttg gctttagtaa agttgtccat caaagctgac ttctctaccc ccaacataac     1140
tgagtctgga aacccatctg cagacactaa aaggattacc tgctttgctt ccggggggttt     1200 cccaaagcct cgcttctctt ggttggaaaa tggaagagaa ttacctggca tcaatacgac     1260
aatttcccag gatcctgaat ctgaattgta caccattagt agccaactag atttcaatac     1320
gactcgcaac cacaccatta agtgtctcat taaatatgga gatgctcacg tgtcagagga     1380
cttcacctgg gaaaaacccc cagaagaccc tcctgatagc aagaacacac ttgtgctctt     1440
tggggcagga ttcggcgcag taataacagt cgtcgtcatc gttgtcatca tcaaatgctt     1500
ctgtaagcac agaagctgtt tcagaagaaa tgaggcaagc agagaaacaa acaacagcct     1560
taccttcggg cctgaagaag cattagctga acagaccgtc ttccttcgta cgggcagtgg     1620
agagggcaga ggaagtctgc taacatgcgg tgacgtcgag gagaatcctg gcccaatgga     1680
gagtgtggta cagccttcag tgtttgtggt ggatggacag acggacatcc cattcaggcg     1740
gctggaacag aaccaccgga gacggcgctg tggcactgtc caggtcagcc tggccctggt     1800
gctgctgcta agtgctgggc tggccactca gggctggttt ctcctgagac tgcatcaacg     1860
tcttggagac atagtagctc atctgccaga tggaggcaaa ggctcctggg agaagctgat     1920
acaagatcaa cgatctcacc aggccaaccc agcagcacat cttacaggag ccaacgccag     1980
cttgataggt attggtggac ctctgttatg ggagacacga cttggcctgg ccttcttgag     2040
gggcttgacg tatcatgatg gggccctggt gaccatggag cccggttact actatgtgta     2100
ctccaaagtg cagctgagcg gcgtgggctg cccccagggg ctggccaatg gcctccccat     2160
cacccatgga ctatacaagc gcacatcccg ctacccgaag gagttagaac tgctggtcag     2220
tcggcggtca ccctgtggcc gggccaacag ctcccgagtc tggtgggaca gcagcttcct     2280
gggcggcgtg gtacatctgg aggctgggga agaggtggtg gtccgcgtgc ctggaaaccg     2340
cctggtcaga ccacgtgacg gcaccaggtc ctatttcgga gctttcatgg tcactagtgg     2400
atccggcgca acaaacttct ctctgctgaa acaagccgga gatgtcgaag agaatcctgg     2460
accgatgaac ccaagtgctg ccgtcatttt ctgcctcatc ctgctgggtc tgagtgggac     2520
tcaagggatc cctctcgcaa ggacggtccg ctgcaactgc atccatatcg atgacgggcc     2580
agtgagaatg agggccatag ggaagcttga aatcatccct gcgagcctat cctgcccacg     2640
tgttgagatc attgccacga tgaaaaagaa tgatgagcag agatgtctga atccggaatc     2700
taagaccatc aagaatttaa tgaaagcgtt tagccaaaaa aggtctaaaa gggctcctag     2760
cggtacccag tgcaccaact acgccctgct gaagctggcc ggcgatgtgg agagcaaccc     2820
cgggcccgct agcatgaacg ctacacactg catcttggct ttgcagctct tcctcatggc     2880
tgtttctggc tgttactgcc acggcacagt cattgaaagc ctagaaagtc tgaataacta     2940
ttttaactca agtggcatag atgtggaaga aaagagtctc ttcttggata tctggaggaa     3000
ctggcaaaag gatggtgaca tgaaaatcct gcagagccag attatctctt tctacctcag     3060
actctttgaa gtcttgaaag acaatcaggc catcagcaac aacataagcg tcattgaatc     3120
```

-continued

```
acacctgatt actaccttct tcagcaacag caaggcgaaa aaggatgcat tcatgagtat   3180
tgccaagttt gaggtcaaca acccacaggt gcagcgccaa gcattcaatg agctcatccg   3240
agtggtccac cagctgttgc cggaatccag cctcaggaag cggaaaagga gtcgctgctg   3300
agaattcacg cgttaagtcg acaatcaacc tctggattac aaaatttgtg aaagattgac   3360
tggtattctt aactatgttg ctccttttac gctatgtgga tacgctgctt taatgccttt   3420
gtatcatgct attgcttccc gtatggcttt cattttctcc tccttgtata aatcctggtt   3480
gctgtctctt tatgaggagt tgtggcccgt tgtcaggcaa cgtggcgtgg tgtgcactgt   3540
gtttgctgac gcaacccca ctggttgggg cattgccacc acctgtcagc tcctttccgg   3600
gactttcgct ttcccctcc ctattgccac ggcggaactc atcgccgcct gccttgcccg   3660
ctgctggaca ggggctcggc tgttgggcac tgacaattcc gtggtgttgt cggggaaatc   3720
atcgtccttt ccttggctgc tcgcctgtgt tgccacctgg attctgcgcg ggacgtcctt   3780
ctgctacgtc ccttcggccc tcaatccagc ggaccttcct tcccgcggcc tgctgccggc   3840
tctgcggcct cttccgcgtc ttcgccttcg ccctcagacg agtcggatct cccttgggc   3900 cgcctccccg cgtcgacttt aagaccaatg acggccgcag gaaccctag tgatggagtt   3960 ggccactccc tctctgcgcg ctcgctcgct cactgaggcc gggcgaccaa aggtcgcccg   4020
acgcccgggc tttgccgggg cggcctcagt gagcgagcga gcgcgcagct gcctgcaggg   4080
gcgcctgatg cggtatttttc tccttacgca tctgtgcggt atttcacacc gcatacgtca   4140
aagcaaccat agtacgcgcc ctgtagcggc gcattaagcg cggcgggtgt ggtggttacg   4200
cgcagcgtga ccgctacact tgccagcgcc ttagcgcccg ctcctttcgc tttcttccct   4260
tcctttctcg ccacgttcgc cggctttccc cgtcaagctc taaatcgggg gctcccttta   4320
gggttccgat ttagtgcttt acggcacctc gacccccaaa aacttgattt gggtgatggt   4380
tcacgtagtg ggccatcgcc ctgatagacg gttttttcgcc ctttgacgtt ggagtccacg   4440
ttctttaata gtggactctt gttccaaact ggaacaacac tcaactctat ctcgggctat   4500
tcttttgatt tataagggat tttgccgatt tcggtctatt ggttaaaaaa tgagctgatt   4560
taacaaaaat ttaacgcgaa ttttaacaaa atattaacgt ttacaatttt atggtgcact   4620
ctcagtacaa tctgctctga tgccgcatag ttaagccagc cccgacaccc gccaacaccc   4680
gctgacgcgc cctgacgggc ttgtctgctc ccggcatccg cttacagaca agctgtgacc   4740
gtctccggga gctgcatgtg tcagaggttt tcaccgtcat caccgaaacg cgcgagacga   4800
aagggcctcg tgatacgcct attttttatag gttaatgtca tgataataat ggtttcttag   4860
acgtcaggtg gcacttttcg gggaaatgtg cgcggaaccc ctatttgttt attttttctaa   4920 atacattcaa atatgtatcc gctcatgaga caataaccct gataaatgct tcaataatat   4980
tgaaaaagga agagtatgag tattcaacat ttccgtgtcg cccttattcc cttttttgcg   5040 gcatttttgcc ttcctgtttt tgctcaccca gaaacgctgg tgaaagtaaa agatgctgaa   5100
gatcagttgg gtgcacgagt gggttacatc gaactggatc tcaacagcgg taagatcctt   5160
gagagttttc gccccgaaga acgttttcca atgatgagca cttttaaagt tctgctatgt   5220
ggcgcggtat tatcccgtat tgacgccggg caagagcaac tcggtcgccg catacactat   5280
tctcagaatg acttggttga gtactcacca gtcacagaaa agcatcttac ggatggcatg   5340
acagtaagag aattatgcag tgctgccata accatgagtg ataacactgc ggccaactta   5400
cttctgacaa cgatcggagg accgaaggag ctaaccgctt ttttgcacaa catgggggat   5460
catgtaactc gccttgatcg ttgggaaccg gagctgaatg aagccatacc aaacgacgag   5520
```

```
cgtgacacca cgatgcctgt agcaatggca acaacgttgc gcaaactatt aactggcgaa    5580
ctacttactc tagcttcccg gcaacaatta atagactgga tggaggcgga taaagttgca    5640
ggaccacttc tgcgctcggc ccttccggct ggctggttta ttgctgataa atctggagcc    5700
ggtgagcgtg gaagccgcgg tatcattgca gcactggggc cagatggtaa gccctcccgt    5760
atcgtagtta tctacacgac ggggagtcag gcaactatgg atgaacgaaa tagacagatc    5820
gctgagatag gtgcctcact gattaagcat tggtaactgt cagaccaagt ttactcatat    5880
atactttaga ttgatttaaa acttcatttt taatttaaaa ggatctaggt gaagatcctt    5940
tttgataatc tcatgaccaa aatcccttaa cgtgagtttt cgttccactg agcgtcagac    6000
cccgtagaaa agatcaaagg atcttcttga tcctttttt ttctgcgcgt aatctgctgc    6060
ttgcaaacaa aaaaaccacc gctaccagcg gtggtttgtt tgccggatca agagctacca    6120
actctttttc cgaaggtaac tggcttcagc agagcgcaga taccaaatac tgttcttcta    6180
gtgtagccgt agttaggcca ccacttcaag aactctgtag caccgcctac atacctcgct    6240
ctgctaatcc tgttaccagt ggctgctgcc agtggcgata agtcgtgtct taccgggttg    6300
gactcaagac gatagttacc ggataaggcg cagcggtcgg gctgaacggg gggttcgtgc    6360
acacagccca gcttggagcg aacgacctac accgaactga gatacctaca gcgtgagcta    6420
tgagaaagcg ccacgcttcc cgaagggaga aaggcggaca ggtatccggt aagcggcagg    6480
gtcggaacag gagagcgcac gagggagctt ccagggggaa acgcctggta tctttatagt    6540
cctgtcgggt ttcgccacct ctgacttgag cgtcgatttt tgtgatgctc gtcaggggg    6600 cggagcctat ggaaaaacgc cagcaacgcg gccttttttac ggttcctggc cttttgctgg    6660
ccttttgctc acatgt    6676
```

```
<210> SEQ ID NO 41
<211> LENGTH: 5689
<212> TYPE: DNA
<213> ORGANISM: Artificial Sequence
<220> FEATURE:
<223> OTHER INFORMATION: pGW111

<400> SEQUENCE: 41
```

```
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggcctcta gaaaggatct gcgatcgctc cggtgcccgt cagtgggcag    180
agcgcacatc gcccacagtc cccgagaagt tggggggagg ggtcggcaat tgaacgggtg    240
cctagagaag gtggcgcggg gtaaactggg aaagtgatgt cgtgtactgg ctccgccttt    300
ttcccgaggg tggggagaa ccgtatataa gtgcagtagt cgccgtgaac gttcttttc     360 gcaacgggtt tgccgccaga acacagctga agcttcgagg ggctcgcatc tctccttcac    420
gcgcccgccg ccctacctga ggccgccatc cacgccggtt gagtcgcgtt ctgccgcctc    480
ccgcctgtgg tgcctcctga actgcgtccg ccgtctaggt aagtttaaag ctcaggtcga    540
gaccgggcct ttgtccggcg ctcccttgga gcctacctag actcagccgg ctctccacgc    600
tttgcctgac cctgcttgct caactctacg tctttgtttc gttttctgtt ctgcgccgtt    660
acagatctgg ctaactaccg gtgccaccat ggagagtgtg gtacagcctt cagtgtttgt    720
ggtggatgga cagacggaca tcccattcag gcggctggaa cagaaccacc ggagacggcg    780
ctgtggcact gtccaggtca gcctggccct ggtgctgctg ctaagtgctg gctggccac    840
```

-continued

```
tcagggctgg tttctcctga gactgcatca acgtcttgga gacatagtag ctcatctgcc    900
agatggaggc aaaggctcct gggagaagct gatacaagat caacgatctc accaggccaa    960
cccagcagca catcttacag gagccaacgc cagcttgata ggtattggtg gacctctgtt   1020
atgggagaca cgacttggcc tggccttctt gaggggcttg acgtatcatg atggggccct   1080
ggtgaccatg gagcccggtt actactatgt gtactccaaa gtgcagctga gcggcgtggg   1140
ctgcccccag gggctggcca atggcctccc catcacccat ggactataca agcgcacatc   1200
ccgctacccg aaggagttag aactgctggt cagtcggcgg tcaccctgtg gccgggccaa   1260
cagctcccga gtctggtggg acagcagctt cctgggcggc gtggtacatc tggaggctgg   1320
ggaagaggtg gtggtccgcg tgcctggaaa ccgcctggtc agaccacgtg acggcaccag   1380
gtcctatttc ggagctttca tggtcactag tggatccggc gcaacaaact tctctctgct   1440
gaaacaagcc ggagatgtcg aagagaatcc tggaccgatg aacccaagtg ctgccgtcat   1500
tttctgcctc atcctgctgg gtctgagtgg gactcaaggg atccctctcg caaggacggt   1560
ccgctgcaac tgcatccata tcgatgacgg gccagtgaga atgagggcca tagggaagct   1620
tgaaatcatc cctgcgagcc tatcctgccc acgtgttgag atcattgcca cgatgaaaaa   1680
gaatgatgag cagagatgtc tgaatccgga atctaagacc atcaagaatt taatgaaagc   1740
gtttagccaa aaaaggtcta aaagggctcc tagcggtacc cagtgcacca actacgccct   1800
gctgaagctg gccggcgatg tggagagcaa ccccgggccc gctagcatga cgctacaca   1860 ctgcatcttg gctttgcagc tcttcctcat ggctgtttct ggctgttact gccacggcac   1920
agtcattgaa agcctagaaa gtctgaataa ctattttaac tcaagtggca tagatgtgga   1980
agaaaagagt ctcttcttgg atatctggag gaactggcaa aaggatggtg acatgaaaat   2040
cctgcagagc cagattatct ctttctacct cagactcttt gaagtcttga agacaatca   2100 ggccatcagc aacaacataa gcgtcattga atcacacctg attactacct tcttcagcaa   2160
cagcaaggcg aaaaaggatg cattcatgag tattgccaag tttgaggtca acaacccaca   2220
ggtccagcgc caagcattca atgagctcat ccgagtggtc caccagctgt tgccggaatc   2280
cagcctcagg aagcggaaaa ggagtcgctg ctgagaattc acgcgttaag tcgacaatca   2340
acctctggat tacaaaattt gtgaaagatt gactggtatt cttaactatg ttgctccttt   2400
tacgctatgt ggatacgctg ctttaatgcc tttgtatcat gctattgctt cccgtatggc   2460
tttcattttc tcctccttgt ataaatcctg gttgctgtct ctttatgagg agttgtggcc   2520
cgttgtcagg caacgtggcg tggtgtgcac tgtgtttgct gacgcaaccc ccactggttg   2580
gggcattgcc accacctgtc agctcctttc cgggactttc gctttccccc tccctattgc   2640
cacggcggaa ctcatcgccg cctgccttgc ccgctgctgg acaggggctc ggctgttggg   2700
cactgacaat tccgtggtgt gtcgggggaa atcatcgtcc tttccttggc tgctcgcctg   2760
tgttgccacc tggattctgc gcgggacgtc cttctgctac gtcccttcgg ccctcaatcc   2820
agcggacctt ccttcccgcg gcctgctgcc ggctctgcgg cctcttccgc gtcttcgcct   2880
tcgccctcag acgagtcgga tctccctttg gccgcctcc ccgcgtcgac tttaagacca   2940
atgacggccg caggaacccc tagtgatgga gttggccact ccctctctgc gcgctcgctc   3000
gctcactgag gccgggcgac caaaggtcgc ccgacgcccg gctttgcccc gggcggcctc   3060
agtgagcgag cgagcgcgca gctgcctgca ggggcgcctg atgcggtatt ttctccttac   3120
gcatctgtgc ggtatttcac accgcatacg tcaaagcaac catagtacgc gccctgtagc   3180
ggcgcattaa gcgcggcggg tgtggtggtt acgcgcagcg tgaccgctac acttgccagc   3240
```

-continued

```
gccttagcgc ccgctccttt cgctttcttc ccttcctttc tcgccacgtt cgccggcttt    3300
ccccgtcaag ctctaaatcg ggggctccct ttagggttcc gatttagtgc tttacggcac    3360
ctcgacccca aaaaacttga tttgggtgat ggttcacgta gtgggccatc gccctgatag    3420 acggttttc gcccttttgac gttggagtcc acgttcttta atagtggact cttgttccaa    3480
actggaacaa cactcaactc tatctcgggc tattcttttg atttataagg gattttgccg    3540
atttcggtct attggttaaa aaatgagctg atttaacaaa aatttaacgc gaattttaac    3600
aaaatattaa cgtttacaat tttatggtgc actctcagta caatctgctc tgatgccgca    3660
tagttaagcc agccccgaca cccgccaaca cccgctgacg cgccctgacg ggcttgtctg    3720
ctcccggcat ccgcttacag acaagctgtg accgtctccg ggagctgcat gtgtcagagg    3780
ttttcaccgt catcaccgaa acgcgcgaga cgaaagggcc tcgtgatacg cctattttta    3840
taggttaatg tcatgataat aatggtttct tagacgtcag gtggcacttt tcggggaaat    3900
gtgcgcggaa cccctatttg tttatttttc taaatacatt caaatatgta tccgctcatg    3960
agacaataac cctgataaat gcttcaataa tattgaaaaa ggaagagtat gagtattcaa    4020
catttccgtg tcgcccttat tccctttttt gcggcatttt gccttcctgt ttttgctcac    4080
ccagaaacgc tggtgaaagt aaaagatgct gaagatcagt tgggtgcacg agtgggttac    4140
atcgaactgg atctcaacag cggtaagatc cttgagagtt ttcgccccga gaacgtttt    4200 ccaatgatga gcactttaa agttctgcta tgtggcgcgg tattatcccg tattgacgcc    4260
gggcaagagc aactcggtcg ccgcatacac tattctcaga atgacttggt tgagtactca    4320
ccagtcacag aaaagcatct tacggatggc atgacagtaa gagaattatg cagtgctgcc    4380
ataaccatga gtgataacac tgcggccaac ttacttctga caacgatcgg aggaccgaag    4440
gagctaaccg cttttttgca caacatgggg gatcatgtaa ctcgccttga tcgttgggaa    4500
ccggagctga atgaagccat accaaacgac gagcgtgaca ccacgatgcc tgtagcaatg    4560
gcaacaacgt tgcgcaaact attaactggc gaactactta ctctagcttc ccggcaacaa    4620
ttaatagact ggatggaggc ggataaagtt gcaggaccac ttctgcgctc ggcccttccg    4680
gctggctggt ttattgctga taaatctgga gccggtgagc gtggaagccg cggtatcatt    4740
gcagcactgg ggccagatgg taagccctcc cgtatcgtag ttatctacac gacggggagt    4800
caggcaacta tggatgaacg aaatagacag atcgctgaga taggtgcctc actgattaag    4860
cattggtaac tgtcagacca gtttactca tatatacttt agattgattt aaaacttcat    4920
ttttaattta aaaggatcta ggtgaagatc cttttttgata atctcatgac caaaatccct    4980
taacgtgagt tttcgttcca ctgagcgtca gaccccgtag aaaagatcaa aggatcttct    5040
tgagatcctt ttttctgcg cgtaatctgc tgcttgcaaa caaaaaaacc accgctacca    5100
gcggtggttt gtttgccgga tcaagagcta ccaactcttt ttccgaaggt aactggcttc    5160
agcagagcgc agataccaaa tactgttctt ctagtgtagc cgtagttagg ccaccacttc    5220
aagaactctg tagcaccgcc tacatacctc gctctgctaa tcctgttacc agtggctgct    5280
gccagtggcg ataagtcgtg tcttaccggg ttggactcaa gacgatagtt accggataag    5340
gcgcagcggt cgggctgaac ggggggttcg tgcacacagc ccagcttgga gcgaacgacc    5400
tacaccgaac tgagatacct acagcgtgag ctatgagaaa gcgccacgct tcccgaaggg    5460
agaaaggcgg acaggtatcc ggtaagcggc agggtcggaa caggagagcg cacgagggag    5520
cttccagggg gaaacgcctg gtatctttat agtcctgtcg ggtttcgcca cctctgactt    5580
```

-continued

```
gagcgtcgat ttttgtgatg ctcgtcaggg gggcggagcc tatggaaaaa cgccagcaac     5640
gcggcctttt tacggttcct ggccttttgc tggccttttg ctcacatgt                  5689

<210> SEQ ID NO 42
<211> LENGTH: 6679
<212> TYPE: DNA
<213> ORGANISM: Artificial Sequence
<220> FEATURE:
<223> OTHER INFORMATION: pGW112

<400> SEQUENCE: 42
cctgcaggca gctgcgcgct cgctcgctca ctgaggccgc ccgggcgtcg ggcgaccttt       60
ggtcgcccgg cctcagtgag cgagcgagcg cgcagagagg gagtggccaa ctccatcact      120
aggggttcct gcggcctcta gaaaggatct gcgatcgctc cggtgcccgt cagtgggcag      180
agcgcacatc gcccacagtc cccgagaagt tggggggagg ggtcggcaat tgaacgggtg      240
cctagagaag gtggcgcggg gtaaactggg aaagtgatgt cgtgtactgg ctccgccttt      300
ttcccgaggg tgggggagaa ccgtatataa gtgcagtagt cgccgtgaac gttctttttc      360
gcaacgggtt tgccgccaga acacagctga agcttcgagg ggctcgcatc tctccttcac      420
gcgcccgccg ccctacctga ggccgccatc cacgccggtt gagtcgcgtt ctgccgcctc      480
ccgcctgtgg tgcctcctga actgcgtccg ccgtctaggt aagtttaaag ctcaggtcga      540
gaccgggcct ttgtccggcg ctcccttgga gcctacctag actcagccgg ctctccacgc      600
tttgcctgac cctgcttgct caactctacg tctttgtttc gttttctgtt ctgcgccgtt      660
acagatctgg ctaactaccg gtgccaccat ggaccagcac acacttgatg tggaggatac      720
cgcggatgcc agacatccag caggtacttc gtgcccctcg gatgcggcgc tcctcagaga      780
taccgggctc ctcgcggacg ctgcgctcct ctcagatact gtgcgcccca caaatgccgc      840
gctccccacg gatgctgcct accctgcggt taatgttcgg gatcgcgagg ccgcgtggcc      900
gcctgcactg aacttctgtt cccgccaccc aaagctctat ggcctagtcg ctttggtttt      960
gctgcttctg atcgccgcct gtgttcctat cttcacccgc accgagcctc ggccagcgct     1020
cacaatcacc acctcgccca acctgggtac ccgagagaat aatgcagacc aggtcacccc     1080
tgtttcccac attggctgcc ccaacactac acaacagggc tctcctgtgt tcgccaagct     1140
actggctaaa aaccaagcat cgttgtgcaa tacaactctg aactggcaca gccaagatgg     1200
agctgggagc tcatacctat ctcaaggtct gaggtacgaa gaagacaaaa aggagttggt     1260
ggtagacagt cccgggctct actacgtatt tttggaactg aagctcagtc caacattcac     1320
aaacacaggc cacaaggtgc agggctgggt ctctcttgtt ttgcaagcaa gcctcaggt      1380 agatgacttt gacaacttgg ccctgacagt ggaactgttc ccttgctcca tggagaacaa     1440
gttagtggac cgttcctgga gtcaactgtt gctcctgaag gctggccacc gcctcagtgt     1500
gggtctgagg gcttatctgc atggagccca ggatgcatac agagactggg agctgtctta     1560
tcccaacacc accagctttg gactcttttct tgtgaaaccc gacaacccat gggaaggcag     1620
tggagagggc agaggaagtc tgctaacatg cggtgacgtc gaggagaatc ctggcccaat     1680
ggagagtgtg gtacagcctt cagtgtttgt ggtggatgga cagacggaca tcccattcag     1740
gcggctggaa cagaaccacc ggagacggcg ctgtggcact gtccaggtca gcctggccct     1800
ggtgctgctg ctaagtgctg ggctggccac tcagggctgg tttctcctga gactgcatca     1860
acgtcttgga gacatagtag ctcatctgcc agatggaggc aaaggctcct gggagaagct     1920
gatacaagat caacgatctc accaggccaa cccagcagca catcttacag gagccaacgc     1980
```

-continued

```
cagcttgata ggtattggtg gacctctgtt atgggagaca cgacttggcc tggccttctt     2040
gaggggcttg acgtatcatg atggggccct ggtgaccatg gagcccggtt actactatgt     2100
gtactccaaa gtgcagctga gcggcgtggg ctgcccccag gggctggcca atggcctccc     2160
catcacccat ggactataca agcgcacatc ccgctacccg aaggagttag aactgctggt     2220
cagtcggcgg tcaccctgtg gccgggccaa cagctcccga gtctggtggg acagcagctt     2280
cctgggcggc gtggtacatc tggaggctgg ggaagaggtg gtggtccgcg tgcctggaaa     2340
ccgcctggtc agaccacgtg acggcaccag gtcctatttc ggagctttca tggtcactag     2400
tggatccggc gcaacaaact tctctctgct gaaacaagcc ggagatgtcg aagagaatcc     2460
tggaccgatg aacccaagtg ctgccgtcat tttctgcctc atcctgctgg gtctgagtgg     2520
gactcaaggg atccctctcg caaggacggt ccgctgcaac tgcatccata tcgatgacgg     2580
gccagtgaga atgagggcca tagggaagct tgaaatcatc cctgcgagcc tatcctgccc     2640
acgtgttgag atcattgcca cgatgaaaaa gaatgatgag cagagatgtc tgaatccgga     2700
atctaagacc atcaagaatt taatgaaagc gtttagccaa aaaaggtcta aaagggctcc     2760
tagcggtacc cagtgcacca actacgccct gctgaagctg gccggcgatg tggagagcaa     2820
ccccgggccc gctagcatga acgctacaca ctgcatcttg gctttgcagc tcttcctcat     2880
ggctgtttct ggctgttact gccacggcac agtcattgaa agcctagaaa gtctgaataa     2940
ctattttaac tcaagtggca tagatgtgga agaaaagagt ctcttcttgg atatctggag     3000
gaactggcaa aaggatggtg acatgaaaat cctgcagagc cagattatct ctttctacct     3060
cagactcttt gaagtcttga agacaatca ggccatcagc aacaacataa gcgtcattga     3120
atcacacctg attactacct tcttcagcaa cagcaaggcg aaaaaggatg cattcatgag     3180
tattgccaag tttgaggtca acaacccaca ggtccagcgc caagcattca atgagctcat     3240
ccgagtggtc caccagctgt tgccggaatc cagcctcagg aagcggaaaa ggagtcgctg     3300
ctgagaattc acgcgttaag tcgacaatca acctctggat tacaaaattt gtgaaagatt     3360
gactggtatt cttaactatg ttgctccttt tacgctatgt ggatacgctg ctttaatgcc     3420
tttgtatcat gctattgctt cccgtatggc tttcattttc tcctccttgt ataaatcctg     3480
gttgctgtct ctttatgagg agttgtggcc cgttgtcagg caacgtggcg tggtgtgcac     3540
tgtgtttgct gacgcaaccc ccactggttg gggcattgcc accacctgtc agctcctttc     3600
cgggactttc gctttccccc tccctattgc cacggcggaa ctcatcgccg cctgccttgc     3660
ccgctgctgg acaggggctc ggctgttggg cactgacaat tccgtggtgt gtcggggaa     3720 atcatcgtcc tttccttggc tgctcgcctg tgttgccacc tggattctgc gcgggacgtc     3780
cttctgctac gtcccttcgg ccctcaatcc agcggacctt ccttcccgcg gcctgctgcc     3840
ggctctgcgg cctcttccgc gtcttcgcct tcgccctcag acgagtcgga tctccctttg     3900
ggccgcctcc ccgcgtcgac tttaagacca atgacttaacg caggaacccc tagtgatgga     3960
gttggccact ccctctctgc gcgctcgctc gctcactgag gccgggcgac caaaggtcgc     4020
ccgacgcccg ggctttgccc gggcggcctc agtgagcgag cgagcgcgca gctgcctgca     4080
ggggcgcctg atgcggtatt ttctccttac gcatctgtgc ggtatttcac accgcatacg     4140
tcaaagcaac catagtacgc gccctgtagc ggcgcattaa gcgcggcggg tgtggtggtt     4200
acgcgcagcg tgaccgctac acttgccagc gccttagcgc ccgctccttt cgctttcttc     4260
ccttcctttc tcgccacgtt cgccggcttt ccccgtcaag ctctaaatcg ggggctccct     4320
```

-continued

```
ttagggttcc gatttagtgc tttacggcac ctcgacccca aaaaacttga tttgggtgat    4380
ggttcacgta gtgggccatc gccctgatag acggttttc gcccttgac gttggagtcc     4440 acgttctta atagtggact cttgttccaa actggaacaa cactcaactc tatctcgggc     4500
tattcttttg atttataagg gattttgccg atttcggtct attggttaaa aaatgagctg    4560
atttaacaaa aatttaacgc gaattttaac aaaatattaa cgtttacaat tttatggtgc    4620
actctcagta caatctgctc tgatgccgca tagttaagcc agccccgaca cccgccaaca    4680
cccgctgacg cgccctgacg ggcttgtctg ctcccggcat ccgcttacag acaagctgtg    4740
accgtctccg ggagctgcat gtgtcagagg ttttcaccgt catcaccgaa acgcgcgaga    4800
cgaaagggcc tcgtgatacg cctattttta taggttaatg tcatgataat aatggtttct    4860
tagacgtcag gtggcacttt tcggggaaat gtgcgcggaa cccctatttg tttattttc    4920 taaatacatt caaatatgta tccgctcatg agacaataac cctgataaat gcttcaataa    4980
tattgaaaaa ggaagagtat gagtattcaa catttccgtg tcgcccttat tcccttttt    5040 gcggcatttt gccttcctgt ttttgctcac ccagaaacgc tggtgaaagt aaaagatgct    5100
gaagatcagt tgggtgcacg agtgggttac atcgaactgg atctcaacag cggtaagatc    5160
cttgagagtt ttcgccccga agaacgtttt ccaatgatga gcacttttaa agttctgcta    5220
tgtggcgcgg tattatcccg tattgacgcc gggcaagagc aactcggtcg ccgcatacac    5280
tattctcaga atgacttggt tgagtactca ccagtcacag aaaagcatct tacggatggc    5340
atgacagtaa gagaattatg cagtgctgcc ataaccatga gtgataacac tgcggccaac    5400
ttacttctga caacgatcgg aggaccgaag gagctaaccg cttttttgca caacatgggg    5460
gatcatgtaa ctcgccttga tcgttgggaa ccggagctga atgaagccat accaaacgac    5520
gagcgtgaca ccacgatgcc tgtagcaatg gcaacaacgt tgcgcaaact attaactggc    5580
gaactactta ctctagcttc ccggcaacaa ttaatagact ggatggaggc ggataaagtt    5640
gcaggaccac ttctgcgctc ggcccttccg gctggctggt ttattgctga taaatctgga    5700
gccggtgagc gtggaagccg cggtatcatt gcagcactgg ggccagatgg taagccctcc    5760
cgtatcgtag ttatctacac gacggggagt caggcaacta tggatgaacg aaatagacag    5820
atcgctgaga taggtgcctc actgattaag cattggtaac tgtcagacca agtttactca    5880
tatatacttt agattgattt aaaacttcat ttttaattta aaaggatcta ggtgaagatc    5940 cttttttgata atctcatgac caaaatccct taacgtgagt tttcgttcca ctgagcgtca    6000
gaccccgtag aaaagatcaa aggatcttct tgagatcctt tttttctgcg cgtaatctgc    6060
tgcttgcaaa caaaaaaacc accgctacca gcggtggttt gtttgccgga tcaagagcta    6120
ccaactcttt ttccgaaggt aactggcttc agcagagcgc agataccaaa tactgttctt    6180
ctagtgtagc cgtagttagg ccaccacttc aagaactctg tagcaccgcc tacatacctc    6240
gctctgctaa tcctgttacc agtggctgct gccagtggcg ataagtcgtg tcttaccggg    6300
ttggactcaa gacgatagtt accggataag gcgcagcggt cgggctgaac ggggggttcg    6360
tgcacacagc ccagcttgga gcgaacgacc tacaccgaac tgagatacct acagcgtgag    6420
ctatgagaaa gcgccacgct tcccgaaggg agaaaggcgg acaggtatcc ggtaagcggc    6480
agggtcggaa caggagagcg cacgagggag cttccagggg gaaacgcctg gtatctttat    6540
agtcctgtcg ggtttcgcca cctctgactt gagcgtcgat ttttgtgatg ctcgtcaggg    6600
gggcggagcc tatggaaaaa cgccagcaac gcggcctttt tacggttcct ggccttttgc    6660 tggcctttg ctcacatgt                                                  6679
```

-continued

```
<210> SEQ ID NO 43
<211> LENGTH: 6757
<212> TYPE: DNA
<213> ORGANISM: Artificial Sequence
<220> FEATURE:
<223> OTHER INFORMATION: pGW113

<400> SEQUENCE: 43
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggcctcta gaaaggatct gcgatcgctc cggtgcccgt cagtgggcag     180
agcgcacatc gcccacagtc cccgagaagt tggggggagg ggtcggcaat tgaacgggtg     240
cctagagaag gtggcgcggg gtaaactggg aaagtgatgt cgtgtactgg ctccgccttt     300
ttcccgaggg tggggagaa ccgtatataa gtgcagtagt cgccgtgaac gttctttttc      360
gcaacgggtt tgccgccaga acacagctga agcttcgagg ggctcgcatc tctccttcac     420
gcgcccgccg ccctacctga ggccgccatc cacgccggtt gagtcgcgtt ctgccgcctc     480
ccgcctgtgg tgcctcctga actgcgtccg ccgtctaggt aagtttaaag ctcaggtcga     540
gaccgggcct ttgtccggcg ctcccttgga gcctacctag actcagccgg ctctccacgc     600
tttgcctgac cctgcttgct caactctacg tctttgtttc gttttctgtt ctgcgccgtt     660
acagatctgg ctaactaccg gtgccaccat gtgtcctcag aagctaacca tctcctggtt     720
tgccatcgtt ttgctggtgt ctccactcat ggccatgtgg gagctggaga aagacgttta     780
tgttgtagag gtggactgga ctcccgatgc ccctggagaa acagtgaacc tcacctgtga     840
cacgcctgaa gaagatgaca tcacctggac ctcagaccag agacatggag tcataggctc     900
tggaaagacc ctgaccatca ctgtcaaaga gtttctagat gctggccagt acacctgcca     960
caaaggaggc gagactctga gccactcaca tctgctgctc cacaagaagg aaaatggaat    1020
ttggtccact gaaattttaa aaaatttcaa aaacaagact ttcctgaagt gtgaagcacc    1080
aaattactcc ggacggttca cgtgctcatg gctggtgcaa agaaacatgg acttgaagtt    1140
caacatcaag agcagtagca gttcccctga ctctcgggca gtgacatgtg aatggcgtc    1200 tctgtctgca gagaaggtca cactggacca aagggactat gagaagtatt cagtgtcctg    1260
ccaggaggat gtcacctgcc caactgccga ggagaccctg cccattgaac tggcgttgga    1320
agcacggcag cagaataaat atgagaacta gcaccagc ttcttcatca gggacatcat    1380
caaaccagac ccgcccaaga acttgcagat gaagcctttg aagaactcac aggtggaggt    1440
cagctgggag taccctgact cctggagcac tcccattccc tacttctccc tcaagttctt    1500
tgttcgaatc cagcgcaaga agaaaagat gaaggagaca gaggaggggt gtaaccagaa    1560
aggtgcgttc ctcgtagaga agacatctac cgaagtccaa tgcaaaggcg ggaatgtctg    1620
cgtgcaagct caggatcgct attacaattc ctcatgcagc aagtgggcat gtgttccctg    1680
cagggtccga tccggcagtg agagggcag aggaagtctg ctaacatgcg gtgacgtcga    1740
ggagaatcct ggcccaatgg agagtgtggt acagccttca gtgtttgtgg tggatggaca    1800 gacgacatc ccattcaggc ggctggaaca gaaccaccgg agacgcgct gtggcactgt     1860 ccaggtcagc ctggccctgg tgctgctgct aagtgctggg ctggccactc agggctggtt    1920
tctcctgaga ctgcatcaac gtcttggaga catagtagct catctgccag atggaggcaa    1980
aggctcctgg gagaagctga tacaagatca acgatctcac caggccaacc cagcagcaca    2040
```

```
tcttacagga gccaacgcca gcttgatagg tattggtgga cctctgttat gggagacacg    2100
acttggcctg gccttcttga ggggcttgac gtatcatgat ggggccctgg tgaccatgga    2160
gcccggttac tactatgtgt actccaaagt gcagctgagc ggcgtgggct gcccccaggg    2220
gctggccaat ggcctcccca tcacccatgg actatacaag cgcacatccc gctacccgaa    2280
ggagttagaa ctgctggtca gtcggcggtc accctgtggc cgggccaaca gctcccgagt    2340
ctggtgggac agcagcttcc tgggcggcgt ggtacatctg gaggctgggg aagaggtggt    2400
ggtccgcgtg cctggaaacc gcctggtcag accacgtgac ggcaccaggt cctatttcgg    2460
agctttcatg gtcactagtg gatccggcgc aacaaacttc tctctgctga aacaagccgg    2520
agatgtcgaa gagaatcctg gaccgatgaa cccaagtgct gccgtcattt tctgcctcat    2580
cctgctgggt ctgagtggga ctcaagggat ccctctcgca aggacggtcc gctgcaactg    2640
catccatatc gatgacgggc cagtgagaat gagggccata gggaagcttg aaatcatccc    2700
tgcgagccta tcctgcccac gtgttgagat cattgccacg atgaaaaaga atgatgagca    2760
gagatgtctg aatccggaat ctaagaccat caagaattta atgaaagcgt ttagccaaaa    2820
aaggtctaaa agggctccta gcggtaccca gtgcaccaac tacgccctgc tgaagctggc    2880
cggcgatgtg gagagcaacc ccgggcccgc tagcatgaac gctacacact gcatcttggc    2940
tttgcagctc ttcctcatgg ctgtttctgg ctgttactgc cacggcacag tcattgaaag    3000
cctagaaagt ctgaataact attttaactc aagtggcata gatgtggaag aaaagagtct    3060
cttcttggat atctggagga actggcaaaa ggatggtgac atgaaaatcc tgcagagcca    3120
gattatctct ttctacctca gactctttga agtcttgaaa gacaatcagg ccatcagcaa    3180
caacataagc gtcattgaat cacacctgat tactaccttc ttcagcaaca gcaaggcgaa    3240
aaaggatgca ttcatgagta ttgccaagtt tgaggtcaac aacccacagg tccagcgcca    3300
agcattcaat gagctcatcc gagtggtcca ccagctgttg ccggaatcca gcctcaggaa    3360
gcggaaaagg agtcgctgct gagaattcac gcgttaagtc gacaatcaac ctctggatta    3420
caaaatttgt gaaagattga ctggtattct taactatgtt gctccttta cgctatgtgg    3480 atacgctgct ttaatgcctt tgtatcatgc tattgcttcc cgtatggctt tcattttctc    3540
ctccttgtat aaatcctggt tgctgtctct ttatgaggag ttgtggcccg ttgtcaggca    3600
acgtggcgtg gtgtgcactg tgtttgctga cgcaacccc actggttggg gcattgccac    3660
cacctgtcag ctcctttccg ggactttcgc tttcccccc cctattgcca cggcggaact    3720
catcgccgcc tgccttgccc gctgctggac aggggctcgg ctgttgggca ctgacaattc    3780
cgtggtgttg tcggggaaat catcgtcctt tccttggctg ctcgcctgtg ttgccacctg    3840
gattctgcgc gggacgtcct tctgctacgt ccccttcggc ctcaatccag cggaccttcc    3900
ttcccgcggc ctgctgccgg ctctgcggcc tcttccgcgt cttcgccttc gccctcagac    3960
gagtcggatc tccctttggg ccgcctcccc gcgtcgactt taagaccaat gacggccgca    4020 ggaacccta gtgatggagt tggccactcc ctctctgcgc gctcgctcgc tcactgaggc    4080
cgggcgacca aaggtcgccc gacgcccggg ctttgcccgg gcggcctcag tgagcgagcg    4140
agcgcgcagc tgcctgcagg ggcgcctgat gcggtatttt ctccttacgc atctgtgcgg    4200
tatttcacac cgcatacgtc aaagcaacca tagtacgcgc cctgtagcgg cgcattaagc    4260
gcggcgggtg tggtggttac gcgcagcgtg accgctacac ttgccagcgc cttagcgccc    4320
gctcctttcg ctttcttccc ttcctttctc gccacgttcg ccggctttcc ccgtcaagct    4380
ctaaatcggg ggctcccttt agggttccga tttagtgctt tacggcacct cgaccccaaa    4440
```

-continued

```
aaacttgatt tgggtgatgg ttcacgtagt gggccatcgc cctgatagac ggttttttcgc      4500 cctttgacgt tggagtccac gttctttaat agtggactct tgttccaaac tggaacaaca      4560
ctcaactcta tctcgggcta ttcttttgat ttataaggga ttttgccgat ttcggtctat      4620
tggttaaaaa atgagctgat ttaacaaaaa tttaacgcga attttaacaa aatattaacg      4680
tttacaattt tatggtgcac tctcagtaca atctgctctg atgccgcata gttaagccag      4740
ccccgacacc cgccaacacc cgctgacgcg ccctgacggg cttgtctgct cccggcatcc      4800
gcttacagac aagctgtgac cgtctccggg agctgcatgt gtcagaggtt ttcaccgtca      4860
tcaccgaaac gcgcgagacg aaagggcctc gtgatacgcc tatttttata ggttaatgtc      4920
atgataataa tggtttctta gacgtcaggt ggcactttc ggggaaatgt gcgcggaacc      4980
cctatttgtt tattttttcta aatacattca aatatgtatc cgctcatgag acaataaccc      5040
tgataaatgc ttcaataata ttgaaaaagg aagagtatga gtattcaaca tttccgtgtc      5100
gcccttattc ccttttttgc ggcatttttgc cttcctgttt ttgctcaccc agaaacgctg      5160
gtgaaagtaa aagatgctga agatcagttg ggtgcacgag tgggttacat cgaactggat      5220
ctcaacagcg gtaagatcct tgagagtttt cgccccgaag aacgttttcc aatgatgagc      5280
acttttaaag ttctgctatg tggcgcggta ttatcccgta ttgacgccgg gcaagagcaa      5340
ctcggtcgcc gcatacacta ttctcagaat gacttggttg agtactcacc agtcacagaa      5400
aagcatctta cggatggcat gacagtaaga gaattatgca gtgctgccat aaccatgagt      5460
gataacactg cggccaactt acttctgaca acgatcggag gaccgaagga gctaaccgct      5520
tttttgcaca acatggggga tcatgtaact cgccttgatc gttgggaacc ggagctgaat      5580
gaagccatac caaacgacga gcgtgacacc acgatgcctg tagcaatggc aacaacgttg      5640
cgcaaactat taactggcga actacttact ctagcttccc ggcaacaatt aatagactgg      5700
atggaggcgg ataaagttgc aggaccactt ctgcgctcgg cccttccggc tggctggttt      5760
attgctgata atctggagc cggtgagcgt ggaagccgcg gtatcattgc agcactgggg      5820
ccagatggta agccctcccg tatcgtagtt atctacacga cggggagtca ggcaactatg      5880
gatgaacgaa atagacagat cgctgagata ggtgcctcac tgattaagca ttggtaactg      5940
tcagaccaag tttactcata tatactttag attgatttaa aacttcattt ttaatttaaa      6000
aggatctagg tgaagatcct ttttgataat ctcatgacca aaatccctta acgtgagttt      6060
tcgttccact gagcgtcaga ccccgtagaa aagatcaaag gatcttcttg agatcctttt      6120
tttctgcgcg taatctgctg cttgcaaaca aaaaaaccac cgctaccagc ggtggtttgt      6180
ttgccggatc aagagctacc aactcttttt ccgaaggtaa ctggcttcag cagagcgcag      6240
ataccaaata ctgttcttct agtgtagccg tagttaggcc accacttcaa gaactctgta      6300
gcaccgccta cataacctcgc tctgctaatc ctgttaccag tggctgctgc cagtggcgat      6360
aagtcgtgtc ttaccgggtt ggactcaaga cgatagttac cggataaggc gcagcggtcg      6420
ggctgaacgg ggggttcgtg cacacagccc agcttggagc gaacgaccta caccgaactg      6480
agatacctac agcgtgagct atgagaaagc gccacgcttc ccgaagggag aaaggcggac      6540
aggtatccgg taagcggcag ggtcggaaca ggagagcgca cgagggagct ccaggggga      6600 aacgcctggt atctttatag tcctgtcggg tttcgccacc tctgacttga gcgtcgattt      6660
ttgtgatgct cgtcaggggg gcggagccta tggaaaaacg ccagcaacgc ggcctttttta      6720 cggttcctgg ccttttgctg gcctttttgct cacatgt      6757
```

<210> SEQ ID NO 44
<211> LENGTH: 7309
<212> TYPE: DNA
<213> ORGANISM: Artificial Sequence
<220> FEATURE:
<223> OTHER INFORMATION: pGW114

<400> SEQUENCE: 44

```
cctgcaggca gctgcgcgct cgctcgctca ctgaggccgc ccgggcgtcg ggcgaccttt       60
ggtcgcccgg cctcagtgag cgagcgagcg cgcagagagg gagtggccaa ctccatcact      120
aggggttcct gcggcctcta gaaaggatct gcgatcgctc cggtgcccgt cagtgggcag      180
agcgcacatc gcccacagtc cccgagaagt tggggggagg ggtcggcaat tgaacgggtg      240
cctagagaag gtggcgcggg gtaaactggg aaagtgatgt cgtgtactgg ctccgccttt      300
ttcccgaggg tggggagaa ccgtatataa gtgcagtagt cgccgtgaac gttctttttc      360
gcaacgggtt tgccgccaga acacagctga agcttcgagg ggctcgcatc tctccttcac      420
gcgcccgccg ccctacctga ggccgccatc cacgccggtt gagtcgcgtt ctgccgcctc      480
ccgcctgtgg tgcctcctga actgcgtccg ccgtctaggt aagtttaaag ctcaggtcga      540
gaccgggcct ttgtccggcg ctcccttgga gcctacctag actcagccgg ctctccacgc      600
tttgcctgac cctgcttgct caactctacg tctttgtttc gttttctgtt ctgcgccgtt      660
acagatctgg ctaactaccg gtgccaccat ggcttgcaat tgtcagttga tgcaggatac      720
accactcctc aagtttccat gtccaaggct cattcttctc tttgtgctgc tgattcgtct      780
ttcacaagtg tcttcagatg ttgatgaaca actgtccaag tcagtgaaag ataaggtatt      840
gctgccttgc cgttacaact ctcctcatga agatgagtct gaagaccgaa tctactggca      900
aaaacatgac aaagtggtgc tgtctgtcat tgctgggaaa ctaaaagtgt ggcccgagta      960
taagaaccgg actttatatg acaacactac ctactctctt atcatcctgg gcctggtcct     1020
ttcagaccgg ggcacataca gctgtgtcgt tcaaaagaag gaaagaggaa cgtatgaagt     1080
taaacacttg gctttagtaa agttgtccat caaagctgac ttctctaccc ccaacataac     1140
tgagtctgga aacccatctg cagacactaa aaggattacc tgctttgctt ccggggggttt     1200 cccaaagcct cgcttctctt ggttggaaaa tggaagagaa ttacctggca tcaatacgac     1260
aatttcccag gatcctgaat ctgaattgta caccattagt agccaactag atttcaatac     1320
gactcgcaac cacaccatta agtgtctcat aaatatgga gatgctcacg tgtcagagga     1380
cttcacctgg gaaaaacccc cagaagaccc tcctgatagc aagaacacac ttgtgctctt     1440 tgggcagga ttcggcgcag taataacagt cgtcgtcatc gttgtcatca tcaaatgctt     1500
ctgtaagcac agaagctgtt tcagaagaaa tgaggcaagc agagaaacaa acaacagcct     1560
taccttcggg cctgaagaag cattagctga acagaccgtc ttccttcgta cgggcagtgg     1620
agagggcaga ggaagtctgc taacatgcgg tgacgtcgag gagaatcctg gcccaatgga     1680
gagtgtggta cagccttcag tgtttgtggt ggatggacag acggacatcc cattcaggcg     1740
gctggaacag aaccaccgga cgggcgctg tggcactgtc caggtcagcc tggccctggt     1800
gctgctgcta agtgctgggc tggccactca gggctggttt ctcctgagac tgcatcaacg     1860
tcttggagac atagtagctc atctgccaga tggaggcaaa ggctcctggg agaagctgat     1920
acaagatcaa cgatctcacc aggccaaccc agcagcacat cttacaggag ccaacgccag     1980
cttgataggt attggtggac ctctgttatg ggagacacga cttggcctgg ccttcttgag     2040
gggcttgacg tatcatgatg gggccctggt gaccatggag cccggttact actatgtgta     2100
```

-continued

```
ctccaaagtg cagctgagcg gcgtgggctg cccccagggg ctggccaatg gcctccccat    2160
cacccatgga ctatacaagc gcacatcccg ctacccgaag gagttagaac tgctggtcag    2220
tcggcggtca ccctgtggcc gggccaacag ctcccgagtc tggtgggaca gcagcttcct    2280
gggcggcgtg gtacatctgg aggctgggga agaggtggtg gtccgcgtgc ctggaaaccg    2340
cctggtcaga ccacgtgacg gcaccaggtc ctatttcgga gctttcatgg tcactagtgg    2400
atccggcgca acaaacttct ctctgctgaa acaagccgga gatgtcgaag agaatcctgg    2460
accgatggac cagcacacac ttgatgtgga ggataccgcg gatgccagac atccagcagg    2520
tacttcgtgc ccctcggatg cggcgctcct cagagatacc gggctcctcg cggacgctgc    2580
gctcctctca gatactgtgc gccccacaaa tgccgcgctc cccacggatg ctgcctaccc    2640
tgcggttaat gttcgggatc gcgaggccgc gtggccgcct gcactgaact tctgttcccg    2700
ccacccaaag ctctatggcc tagtcgcttt ggttttgctg cttctgatcg ccgcctgtgt    2760
tcctatcttc acccgcaccg agcctcggcc agcgctcaca atcaccacct cgcccaacct    2820
gggtacccga gagaataatg cagaccaggt cacccctgtt tcccacattg gctgccccaa    2880
cactacacaa cagggctctc ctgtgttcgc caagctactg gctaaaaacc aagcatcgtt    2940
gtgcaataca actctgaact ggcacagcca agatggagct gggagctcat acctatctca    3000
aggtctgagg tacgaagaag acaaaaagga gttggtggta gacagtcccg ggctctacta    3060 cgtattttg gaactgaagc tcagtccaac attcacaaac acaggccaca aggtgcaggg    3120
ctgggtctct cttgtttgc aagcaaagcc tcaggtagat gactttgaca acttggccct    3180
gacagtggaa ctgttccctt gctccatgga gaacaagtta gtggaccgtt cctggagtca    3240
actgttgctc ctgaaggctg gccaccgcct cagtgtgggt ctgagggctt atctgcatgg    3300
agcccaggat gcatacagag actgggagct gtcttatccc aacaccacca gctttggact    3360
ctttcttgtg aaacccgaca acccatggga aagcggtacc cagtgcacca actacgccct    3420
gctgaagctg gccggcgatg tggagagcaa ccccgggccc gctagcatga cgctacaca    3480 ctgcatcttg gctttgcagc tcttcctcat ggctgtttct ggctgttact gccacggcac    3540
agtcattgaa agcctagaaa gtctgaataa ctattttaac tcaagtggca tagatgtgga    3600
agaaaagagt ctcttcttgg atatctggag gaactggcaa aaggatggtg acatgaaaat    3660
cctgcagagc cagattatct ctttctacct cagactcttt gaagtcttga agacaatca    3720 ggccatcagc aacaacataa gcgtcattga atcacacctg attactacct tcttcagcaa    3780
cagcaaggcg aaaaaggatg cattcatgag tattgccaag tttgaggtca caacccaca    3840 ggtgcagcgc caagcattca atgagctcat ccgagtggtc caccagctgt gccggaatc    3900 cagcctcagg aagcggaaaa ggagtcgctg ctgagaattc acgcgttaag tcgacaatca    3960
acctctggat tacaaaattt gtgaaagatt gactggtatt cttaactatg ttgctccttt    4020
tacgctatgt ggatacgctg ctttaatgcc tttgtatcat gctattgctt cccgtatggc    4080 tttcatttc tcctccttgt ataaatcctg gttgctgtct ctttatgagg agttgtggcc    4140
cgttgtcagg caacgtggcg tggtgtgcac tgtgtttgct gacgcaaccc ccactggttg    4200
gggcattgcc accacctgtc agctcctttc cgggactttc gctttcccc tccctattgc    4260 cacggcggaa ctcatcgccg cctgccttgc ccgctgctgg acagggctc ggctgttggg    4320 cactgacaat tccgtggtgt gtctcgggga atcatcgtcc tttccttggc tgctcgcctg    4380
tgttgccacc tggattctgc gcgggacgtc cttctgctac gtcccttcgg ccctcaatcc    4440
```

-continued

```
agcggacctt ccttcccgcg gcctgctgcc ggctctgcgg cctcttccgc gtcttcgcct   4500
tcgccctcag acgagtcgga tctccctttg ggccgcctcc ccgcgtcgac tttaagacca   4560
atgacggccg caggaacccc tagtgatgga gttggccact ccctctctgc gcgctcgctc   4620
gctcactgag gccgggcgac caaaggtcgc ccgacgcccg ggctttgccc gggcggcctc   4680
agtgagcgag cgagcgcgca gctgcctgca ggggcgcctg atgcggtatt ttctccttac   4740
gcatctgtgc ggtatttcac accgcatacg tcaaagcaac catagtacgc gccctgtagc   4800
ggcgcattaa gcgcggcggg tgtggtggtt acgcgcagcg tgaccgctac acttgccagc   4860
gccttagcgc ccgctccttt cgctttcttc ccttcctttc tcgccacgtt cgccggcttt   4920
ccccgtcaag ctctaaatcg ggggctccct ttagggttcc gatttagtgc tttacggcac   4980
ctcgacccca aaaaacttga tttgggtgat ggttcacgta gtgggccatc gccctgatag   5040
acggtttttc gccctttgac gttggagtcc acgttcttta atagtggact cttgttccaa   5100
actggaacaa cactcaactc tatctcgggc tattcttttg atttataagg attttgccg   5160 atttcggtct attggttaaa aaatgagctg atttaacaaa aatttaacgc gaattttaac   5220
aaaatattaa cgtttacaat tttatggtgc actctcagta caatctgctc tgatgccgca   5280
tagttaagcc agccccgaca cccgccaaca cccgctgacg cgccctgacg ggcttgtctg   5340
ctcccggcat ccgcttacag acaagctgtg accgtctccg ggagctgcat gtgtcagagg   5400
ttttcaccgt catcaccgaa acgcgcgaga cgaaagggcc tcgtgatacg cctatttta   5460 taggttaatg tcatgataat aatggtttct tagacgtcag gtggcacttt tcggggaaat   5520
gtgcgcggaa cccctatttg tttatttttc taaatacatt caaatatgta tccgctcatg   5580
agacaataac cctgataaat gcttcaataa tattgaaaaa ggaagagtat gagtattcaa   5640
catttccgtg tcgcccttat tccctttttt gcggcatttt gccttcctgt ttttgctcac   5700
ccagaaacgc tggtgaaagt aaaagatgct gaagatcagt tgggtgcacg agtgggttac   5760
atcgaactga atctcaacag cggtaagatc cttgagagtt ttcgccccga agaacgtttt   5820
ccaatgatga gcacttttaa agttctgcta tgtggcgcgg tattatcccg tattgacgcc   5880
gggcaagagc aactcggtcg ccgcatacac tattctcaga atgacttggt tgagtactca   5940
ccagtcacag aaaagcatct tacggatggc atgacagtaa gagaattatg cagtgctgcc   6000
ataaccatga gtgataacac tgcggccaac ttacttctga caacgatcgg aggaccgaag   6060
gagctaaccg cttttttgca caacatgggg gatcatgtaa ctcgccttga tcgttgggaa   6120
ccggagctga atgaagccat accaaacgac gagcgtgaca ccacgatgcc tgtagcaatg   6180
gcaacaacgt tgcgcaaact attaactggc gaactactta ctctagcttc ccggcaacaa   6240
ttaatagact ggatggaggc ggataaagtt gcaggaccac ttctgcgctc ggcccttccg   6300
gctggctggt ttattgctga taaatctgga gccggtgagc gtggaagccg cggtatcatt   6360
gcagcactgg ggccagatgg taagccctcc cgtatcgtag ttatctacac gacggggagt   6420
caggcaacta tggatgaacg aaatagacag atcgctgaga taggtgcctc actgattaag   6480
cattggtaac tgtcagacca gtttactca tatatacttt agattgattt aaaacttcat   6540
ttttaattta aaaggatcta ggtgaagatc ctttttgata atctcatgac caaaatccct   6600
taacgtgagt tttcgttcca ctgagcgtca gaccccgtag aaaagatcaa aggatcttct   6660
tgagatcctt ttttttctgcg cgtaatctgc tgcttgcaaa caaaaaaacc accgctacca   6720
gcggtggttt gtttgccgga tcaagagcta ccaactcttt ttccgaaggt aactggcttc   6780
agcagagcgc agataccaaa tactgttctt ctagtgtagc cgtagttagg ccaccacttc   6840
```

-continued

```
aagaactctg tagcaccgcc tacataccct gctctgctaa tcctgttacc agtggctgct      6900
gccagtggcg ataagtcgtg tcttaccggg ttggactcaa gacgatagtt accggataag      6960
gcgcagcggt cgggctgaac ggggggttcg tgcacacagc ccagcttgga gcgaacgacc      7020
tacaccgaac tgagatacct acagcgtgag ctatgagaaa gcgccacgct tcccgaaggg      7080
agaaaggcgg acaggtatcc ggtaagcggc agggtcggaa caggagagcg cacgagggag      7140
cttccagggg gaaacgcctg gtatctttat agtcctgtcg ggtttcgcca cctctgactt      7200
gagcgtcgat ttttgtgatg ctcgtcaggg gggcggagcc tatggaaaaa cgccagcaac      7260
gcggcctttt tacggttcct ggccttttgc tggccttttg ctcacatgt               7309
```

```
<210> SEQ ID NO 45
<211> LENGTH: 7390
<212> TYPE: DNA
<213> ORGANISM: Artificial Sequence
<220> FEATURE:
<223> OTHER INFORMATION: pGW115

<400> SEQUENCE: 45
```

```
cctgcaggca gctgcgcgct cgctcgctca ctgaggccgc ccgggcgtcg ggcgaccttt        60
ggtcgcccgg cctcagtgag cgagcgagcg cgcagagagg gagtggccaa ctccatcact       120
aggggttcct gcggcctcta gaaaggatct gcgatcgctc cggtgcccgt cagtgggcag       180
agcgcacatc gcccacagtc cccgagaagt tggggggagg ggtcggcaat tgaacgggtg       240
cctagagaag gtggcgcggg gtaaactggg aaagtgatgt cgtgtactgg ctccgccttt       300
ttcccgaggg tggggagaa ccgtatataa gtgcagtagt cgccgtgaac gttcttttc       360 gcaacgggtt tgccgccaga acacagctga agcttcgagg ggctcgcatc tctccttcac       420
gcgcccgccg ccctacctga ggccgccatc cacgccggtt gagtcgcgtt ctgccgcctc       480
ccgcctgtgg tgcctcctga actgcgtccg ccgtctaggt aagtttaaag ctcaggtcga       540
gaccgggcct ttgtccggcg ctcccttgga gcctacctag actcagccgg ctctccacgc       600
tttgcctgac cctgcttgct caactctacg tctttgtttc gttttctgtt ctgcgccgtt       660
acagatctgg ctaactaccg gtgccaccat gtgtcctcag aagctaacca tctcctggtt       720
tgccatcgtt ttgctggtgt ctccactcat ggccatgtgg gagctggaga aagacgttta       780
tgttgtagag gtggactgga ctcccgatgc ccctggagaa acagtgaacc tcacctgtga       840
cacgcctgaa gaagatgaca tcacctggac ctcagaccag agacatggag tcataggctc       900
tggaaagacc ctgaccatca ctgtcaaaga gtttctagat gctggccagt acacctgcca       960
caaaggaggc gagactctga gccactcaca tctgctgctc cacaagaagg aaaatggaat      1020
ttggtccact gaaattttaa aaatttcaa aaacaagact ttcctgaagt gtgaagcacc      1080
aaattactcc ggacggttca cgtgctcatg ctggtgcaa agaaacatgg acttgaagtt      1140
caacatcaag agcagtagca gttcccctga ctctcgggca gtgacatgtg gaatggcgtc      1200
tctgtctgca gagaaggtca cactggacca aagggactat gagaagtatt cagtgtcctg      1260
ccaggaggat gtcacctgcc caactgccga ggagaccctg cccattgaac tggcgttgga      1320
agcacggcag cagaataaat atgagaacta cagcaccagc ttcttcatca gggacatcat      1380
caaaccagac ccgcccaaga acttgcagat gaagcctttg aagaactcac aggtggaggt      1440
cagctgggag tacctgact cctggagcac tcccattcc tacttctccc tcaagttctt      1500
tgttcgaatc cagcgcaaga agaaaagat gaaggagaca gaggagggggt gtaaccagaa      1560
```

-continued

```
aggtgcgttc ctcgtagaga agacatctac cgaagtccaa tgcaaaggcg ggaatgtctg    1620
cgtgcaagct caggatcgct attacaattc ctcatgcagc aagtgggcat gtgttccctg    1680
cagggtccga tccggcagtg gagagggcag aggaagtctg ctaacatgcg gtgacgtcga    1740
ggagaatcct ggcccaatgg agagtgtggt acagccttca gtgtttgtgg tggatggaca    1800
gacggacatc ccattcaggc ggctggaaca gaaccaccgg agacggcgct gtggcactgt    1860
ccaggtcagc ctggccctgg tgctgctgct aagtgctggg ctggccactc agggctggtt    1920
tctcctgaga ctgcatcaac gtcttggaga catagtagct catctgccag atggaggcaa    1980
aggctcctgg gagaagctga tacaagatca acgatctcac caggccaacc cagcagcaca    2040
tcttacagga gccaacgcca gcttgatagg tattggtgga cctctgttat gggagacacg    2100
acttggcctg gccttcttga ggggcttgac gtatcatgat ggggccctgg tgaccatgga    2160
gcccggttac tactatgtgt actccaaagt gcagctgagc ggcgtgggct gcccccaggg    2220
gctggccaat ggcctcccca tcacccatgg actatacaag cgcacatccc gctacccgaa    2280
ggagttagaa ctgctggtca gtcggcggtc accctgtggc cgggccaaca gctcccgagt    2340
ctggtgggac agcagcttcc tgggcggcgt ggtacatctg gaggctgggg aagaggtggt    2400
ggtccgcgtg cctggaaacc gcctggtcag accacgtgac ggcaccaggt cctatttcgg    2460
agctttcatg gtcactagtg gatccggcgc aacaaacttc tctctgctga aacaagccgg    2520
agatgtcgaa gagaatcctg gaccgatgga ccagcacaca cttgatgtgg aggataccgc    2580
ggatgccaga catccagcag gtacttcgtg cccctcggat gcggcgctcc tcagagatac    2640
cgggctcctc gcggacgctg cgctcctctc agatactgtg cgcccacaa atgccgcgct    2700 ccccacggat gctgcctacc ctgcggttaa tgttcgggat cgcgaggccg cgtggccgcc    2760
tgcactgaac ttctgttccc gccacccaaa gctctatggc ctagtcgctt tggttttgct    2820
gcttctgatc gccgcctgtg ttcctatctt caccccgcacc gagcctcggc cagcgctcac    2880
aatcaccacc tcgcccaacc tgggtacccg agagaataat gcagaccagg tcacccctgt    2940
ttcccacatt ggctgcccca acactacaca acagggctct cctgtgttcg ccaagctact    3000
ggctaaaaac caagcatcgt tgtgcaatac aactctgaac tggcacagcc aagatggagc    3060
tgggagctca tacctatctc aaggtctgag gtacgaagaa gacaaaaagg agttggtggt    3120
agacagtccc gggctctact acgtattttt ggaactgaag ctcagtccaa cattcacaaa    3180
cacaggccac aaggtgcagg gctgggtctc tcttgttttg caagcaaagc ctcaggtaga    3240
tgactttgac aacttggccc tgacagtgga actgttccct tgctccatgg agaacaagtt    3300
agtggaccgt tcctggagtc aactgttgct cctgaaggct ggccaccgcc tcagtgtggg    3360
tctgagggct tatctgcatg gagcccagga tgcatacaga gactgggagc tgtcttatcc    3420
caacaccacc agctttggac tctttcttgt gaaacccgac aacccatggg aaagcggtac    3480
ccagtgcacc aactacgccc tgctgaagct ggccggcgat gtggagagca accccgggcc    3540
cgctagcatg aacgctacac actgcatctt ggctttgcag ctcttcctca tggctgtttc    3600
tggctgttac tgccacggca cagtcattga aagcctagaa agtctgaata actatttaa    3660 ctcaagtggc atagatgtgg aagaaaagag tctcttcttg gatatctgga ggaactggca    3720
aaaggatggt gacatgaaaa tcctgcagag ccagattatc tctttctacc tcagactctt    3780
tgaagtcttg aaagacaatc aggccatcag caacaacata agcgtcattg aatcacacct    3840
gattactacc ttcttcagca acagcaaggc gaaaaaggat gcattcatga gtattgccaa    3900
gtttgaggtc aacaacccac aggtccagcg ccaagcattc aatgagctca tccgagtggt    3960
```

-continued

```
ccaccagctg ttgccggaat ccagcctcag gaagcggaaa aggagtcgct gctgagaatt    4020
cacgcgttaa gtcgacaatc aacctctgga ttacaaaatt tgtgaaagat tgactggtat    4080
tcttaactat gttgctcctt ttacgctatg tggatacgct gctttaatgc ctttgtatca    4140
tgctattgct tcccgtatgg ctttcatttt ctcctccttg tataaatcct ggttgctgtc    4200
tctttatgag gagttgtggc ccgttgtcag gcaacgtggc gtggtgtgca ctgtgtttgc    4260
tgacgcaacc cccactggtt ggggcattgc caccacctgt cagctccttt ccgggacttt    4320
cgctttcccc ctccctattg ccacggcgga actcatcgcc gcctgccttg cccgctgctg    4380 gacagggggct cggctgttgg gcactgacaa ttccgtggtg ttgtcgggga aatcatcgtc    4440
ctttccttgg ctgctcgcct gtgttgccac ctggattctg cgcgggacgt ccttctgcta    4500
cgtcccttcg gccctcaatc cagcggacct tccttcccgc ggcctgctgc cggctctgcg    4560
gcctcttccg cgtcttcgcc ttcgccctca gacgagtcgg atctcccttt gggccgcctc    4620
cccgcgtcga ctttaagacc aatgacggcc gcaggaaccc ctagtgatgg agttggccac    4680
tccctctctg cgcgctcgct cgctcactga ggccgggcga ccaaaggtcg cccgacgccc    4740
gggctttgcc cgggcggcct cagtgagcga gcgagcgcgc agctgcctgc aggggcgcct    4800
gatgcggtat tttctcctta cgcatctgtg cggtatttca caccgcatac gtcaaagcaa    4860
ccatagtacg cgccctgtag cggcgcatta agcgcggcgg gtgtggtggt tacgcgcagc    4920
gtgaccgcta cacttgccag cgccttagcg cccgctcctt tcgctttctt cccttccttt    4980
ctcgccacgt tcgccggctt tccccgtcaa gctctaaatc gggggctccc tttagggttc    5040
cgatttagtg ctttacggca cctcgacccc aaaaaacttg atttgggtga tggttcacgt    5100
agtgggccat cgccctgata gacggttttt cgccctttga cgttggagtc cacgttcttt    5160
aatagtggac tcttgttcca aactggaaca acactcaact ctatctcggg ctattctttt    5220
gatttataag ggattttgcc gatttcggtc tattggttaa aaaatgagct gatttaacaa    5280
aaatttaacg cgaattttaa caaaatatta cgtttacaa ttttatggtg cactctcagt    5340
acaatctgct ctgatgccgc atagttaagc cagccccgac accgccaac acccgctgac    5400 gcgccctgac gggcttgtct gctcccggca tccgcttaca gacaagctgt gaccgtctcc    5460
gggagctgca tgtgtcagag gttttcaccg tcatcaccga aacgcgcgag acgaaagggc    5520
ctcgtgatac gcctattttt ataggttaat gtcatgataa taatggtttc ttagacgtca    5580
ggtggcactt ttcggggaaa tgtgcgcgga accctatttt gtttattttt ctaaatacat    5640
tcaaatatgt atccgctcat gagacaataa ccctgataaa tgcttcaata atattgaaaa    5700
aggaagagta tgagtattca acatttccgt gtcgccctta ttccctttttt tgcggcattt    5760 tgccttcctg ttttttgctca cccagaaacg ctggtgaaag taaaagatgc tgaagatcag    5820
ttgggtgcac gagtgggtta catcgaactg gatctcaaca gcggtaagat ccttgagagt    5880
tttcgccccg aagaacgttt tccaatgatg agcactttta aagttctgct atgtggcgcg    5940
gtattatccc gtattgacgc cgggcaagag caactcggtc gccgcataca ctattctcag    6000
aatgacttgg ttgagtactc accagtcaca gaaaagcatc ttacggatgg catgacagta    6060
agagaattat gcagtgctgc cataaccatg agtgataaca ctgcggccaa cttacttctg    6120
acaacgatcg gaggaccgaa ggagctaacc gctttttttgc acaacatggg ggatcatgta    6180
actcgccttg atcgttggga accggagctg aatgaagcca taccaaacga cgagcgtgac    6240
accacgatgc ctgtagcaat ggcaacaacg ttgcgcaaac tattaactgg cgaactactt    6300
```

-continued

```
actctagctt cccggcaaca attaatagac tggatggagg cggataaagt tgcaggacca    6360
cttctgcgct cggcccttcc ggctggctgg tttattgctg ataaatctgg agccggtgag    6420
cgtggaagcc gcggtatcat tgcagcactg gggccagatg gtaagccctc ccgtatcgta    6480
gttatctaca cgacggggag tcaggcaact atggatgaac gaaatagaca gatcgctgag    6540
ataggtgcct cactgattaa gcattggtaa ctgtcagacc aagtttactc atatatactt    6600
tagattgatt taaaacttca ttttaattt aaaaggatct aggtgaagat ccttttttgat    6660 aatctcatga ccaaaatccc ttaacgtgag ttttcgttcc actgagcgtc agaccccgta    6720
gaaaagatca aaggatcttc ttgagatcct ttttttctgc gcgtaatctg ctgcttgcaa    6780
acaaaaaaac caccgctacc agcggtggtt tgtttgccgg atcaagagct accaactctt    6840
tttccgaagg taactggctt cagcagagcg cagataccaa atactgttct tctagtgtag    6900
ccgtagttag gccaccactt caagaactct gtagcaccgc ctacatacct cgctctgcta    6960
atcctgttac cagtggctgc tgccagtggc gataagtcgt gtcttaccgg gttggactca    7020
agacgatagt taccggataa ggcgcagcgg tcgggctgaa cggggggttc gtgcacacag    7080
cccagcttgg agcgaacgac ctacaccgaa ctgagatacc tacagcgtga gctatgagaa    7140
agcgccacgc ttcccgaagg gagaaaggcg acaggtatc cggtaagcgg cagggtcgga    7200
acaggagagc gcacgaggga gcttccaggg ggaaacgcct ggtatcttta tagtcctgtc    7260
gggtttcgcc acctctgact tgagcgtcga ttttttgtgat gctcgtcagg ggggcggagc    7320
ctatggaaaa acgccagcaa cgcggccttt ttacggttcc tggccttttg ctggcctttt    7380
gctcacatgt                                                           7390
```

```
<210> SEQ ID NO 46
<211> LENGTH: 6728
<212> TYPE: DNA
<213> ORGANISM: Artificial Sequence
<220> FEATURE:
<223> OTHER INFORMATION: pGW118

<400> SEQUENCE: 46
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggcctcta gaaaggatct gcgatcgctc cggtgcccgt cagtgggcag     180
agcgcacatc gcccacagtc cccgagaagt tggggggagg ggtcggcaat tgaacgggtg     240
cctagagaag gtggcgcggg gtaaactggg aaagtgatgt cgtgtactgg ctccgccttt     300
ttcccgaggg tggggagaa ccgtatataa gtgcagtagt cgccgtgaac gttctttttc     360
gcaacgggtt tgccgccaga acacagctga agcttcgagg ggctcgcatc tctccttcac     420
gcgcccgccg ccctacctga ggccgccatc cacgccggtt gagtcgcgtt ctgccgcctc     480
ccgcctgtgg tgcctcctga actgcgtccg ccgtctaggt aagtttaaag ctcaggtcga     540
gaccgggcct ttgtccggcg ctcccttgga gcctacctag actcagccgg ctctccacgc     600
tttgcctgac cctgcttgct caactctacg tctttgtttc gttttctgtt ctgcgccgtt     660
acagatctgg ctaactaccg gtgccaccat gaacgctaca cactgcatct tggctttgca     720
gctcttcctc atggctgttt ctggctgtta ctgccacggc acagtcattg aaagcctaga     780
aagtctgaat aactatttta actcaagtgg catagatgtg gaagaaaaga gtctcttctt     840
ggatatctga aggaactggc aaaaggatgg tgacatgaaa atcctgcaga gccagattat     900
ctctttctac ctcagactct ttgaagtctt gaaagacaat caggccatca gcaacaacat     960
```

-continued

```
aagcgtcatt gaatcacacc tgattactac cttcttcagc aacagcaagg cgaaaaagga    1020
tgcattcatg agtattgcca agtttgaggt caacaaccca caggtccagc gccaagcatt    1080
caatgagctc atccgagtgg tccaccagct gttgccggaa tccagcctca ggaagcggaa    1140
aaggagtcgc tgcggatccg cgcaacaaa cttctctctg ctgaaacaag ccggagatgt    1200
cgaagagaat cctggaccga tggcttgcaa ttgtcagttg atgcaggata caccactcct    1260
caagtttcca tgtccaaggc tcattcttct ctttgtgctg ctgattcgtc tttcacaagt    1320
gtcttcagat gttgatgaac aactgtccaa gtcagtgaaa gataaggtat tgctgccttg    1380
ccgttacaac tctcctcatg aagatgagtc tgaagaccga atctactggc aaaaacatga    1440
caaagtggtg ctgtctgtca ttgttgggaa actaaaagtg tggcccgagt ataagaaccg    1500
gactttatat gacaacacta cctactctct tatcatcctg ggcctggtcc tttcagaccg    1560
gggcacatac agctgtgtcg ttcaaaagaa ggaaagagga acgtatgaag ttaaacactt    1620
ggctttagta aagttgtcca tcaaagctga cttctctacc cccaacataa ctgagtctgg    1680
aaacccatct gcagacacta aaaggattac ctgctttgct tccggggggtt tcccaaagcc    1740 tcgcttctct tggttggaaa atggaagaga attacctggc atcaatacga caatttccca    1800
ggatcctgaa tctgaattgt acaccattag tagccaacta gatttcaata cgactcgcaa    1860
ccacaccatt aagtgtctca ttaaatatgg agatgctcac gtgtcagagg acttcacctg    1920
ggaaaaaccc ccagaagacc ctcctgatag caagaacaca cttgtgctct ttggggcagg    1980
attcggcgca gtaataacag tcgtcgtcat cgttgtcatc atcaaatgct tctgtaagca    2040
cagaagctgt ttcagaagaa atgaggcaag cagagaaaca aacaacagcc ttaccttcgg    2100
gcctgaagaa gcattagctg aacagaccgt cttccttcgt acgggcagtg gagagggcag    2160
aggaagtctg ctaacatgcg gtgacgtcga ggagaatcct ggcccaatgg agagtgtggt    2220
acagccttca gtgtttgtgg tggatggaca gacggacatc ccattcaggc ggctggaaca    2280
gaaccaccgg agacggcgct gtggcactgt ccaggtcagc ctggccctgg tgctgctgct    2340
aggtgctggg ctggccactc agggctggtt tctcctgaga ctgcatcaac gtcttggaga    2400
catagtagct catctgccag atggaggcaa aggctcctgg gagaagctga tacaagatca    2460
acgatctcac caggccaacc cagcagcaca tcttacagga gccaacgcca gcttgatagg    2520
tattggtgga cctctgttat gggagacacg acttggcctg gccttcttga ggggcttgac    2580
gtatcatgat ggggccctgg tgaccatgga gcccggttac tactatgtgt actccaaagt    2640
gcagctgagc ggcgtgggct gcccccaggg gctggccaat ggcctcccca tcacccatgg    2700
actatacaag cgcacatccc gctacccgaa ggagttagaa ctgctggtca gtcggcggtc    2760
accctgtggc cgggccaaca gctcccgagt ctggtgggac agcagcttcc tgggcggcgt    2820
ggtacatctg gaggctgggg aagaggtggt ggtccgcgtg cctggaaacc gcctggtcag    2880
accacgtgac ggcaccaggt cctatttcgg agctttcatg gtcactagca gcggtaccca    2940
gtgcaccaac tacgccctgc tgaagctggc cggcgatgtg gagagcaacc ccgggcccat    3000
ggaccagcac acacttgatg tggaggatac cgcggatgcc agacatccag caggtacttc    3060
gtgcccctcg gatgcggcgc tcctcagaga taccgggctc ctcgcggacg ctgcgctcct    3120
ctcagatact gtgcgcccca caaatgccgc gctccccacg gatgctgcct accctgcggt    3180
taatgttcgg gatcgcgagg ccgcgtggcc gcctgcactg aacttctgtt cccgccaccc    3240
aaagctctat ggcctagtcg ctttggtttt gctgcttctg atcgccgcct gtgttcctat    3300
```

-continued

```
cttcacccgc accgagcctc ggccagcgct cacaatcacc acctcgccca acctgggtac   3360
ccgagagaat aatgcagacc aggtcacccc tgtttcccac attggctgcc ccaacactac   3420
acaacagggc tctcctgtgt tcgccaagct actggctaaa aaccaagcat cgttgtgcaa   3480
tacaactctg aactggcaca gccaagatgg agctgggagc tcatacctat ctcaaggtct   3540
gaggtacgaa gaagacaaaa aggagttggt ggtagacagt cccgggctct actacgtatt   3600
tttggaactg aagctcagtc caacattcac aaacacaggc cacaaggtgc agggctgggt   3660
ctctcttgtt ttgcaagcaa agcctcaggt agatgacttt gacaacttgg ccctgacagt   3720
ggaactgttc ccttgctcca tggagaacaa gttagtggac cgttcctgga gtcaactgtt   3780
gctcctgaag gctggccacc gcctcagtgt gggtctgagg gcttatctgc atggagccca   3840
ggatgcatac agagactggg agctgtctta tcccaacacc accagctttg gactctttct   3900
tgtgaaaccc gacaacccat gggaatgaga attcaataaa agatctttat tttcattaga   3960
tctgtgtgtt ggtttttttgt gtgcggccgc aggaaccccct agtgatggag ttggccactc   4020
cctctctgcg cgctcgctcg ctcactgagg ccgggcgacc aaaggtcgcc cgacgcccgg   4080
gctttgcccg ggcggcctca gtgagcgagc gagcgcgcag ctgcctgcag gggcgcctga   4140
tgcggtattt tctccttacg catctgtgcg gtatttcaca ccgcatacgt caaagcaacc   4200
atagtacgcg ccctgtagcg gcgcattaag cgcggcgggt gtggtggtta cgcgcagcgt   4260
gaccgctaca cttgccagcg ccttagcgcc cgctcctttc gctttcttcc cttcctttct   4320
cgccacgttc gccggctttc cccgtcaagc tctaaatcgg gggctccctt tagggttccg   4380
atttagtgct ttacggcacc tcgaccccaa aaaacttgat ttgggtgatg gttcacgtag   4440
tgggccatcg ccctgataga cggtttttcg ccctttgacg ttggagtcca cgttctttaa   4500
tagtggactc ttgttccaaa ctggaacaac actcaactct atctcgggct attcttttga   4560
tttataaggg attttgccga tttcggtcta ttggttaaaa aatgagctga tttaacaaaa   4620
atttaacgcg aattttaaca aaatattaac gtttacaatt ttatggtgca ctctcagtac   4680
aatctgctct gatgccgcat agttaagcca gccccgacac ccgccaacac ccgctgacgc   4740
gccctgacgg gcttgtctgc tcccggcatc cgcttacaga caagctgtga ccgtctccgg   4800
gagctgcatg tgtcagaggt tttcaccgtc atcaccgaaa cgcgcgagac gaaagggcct   4860
cgtgatacgc ctatttttat aggttaatgt catgataata atggtttctt agacgtcagg   4920
tggcactttt cggggaaatg tgcgcggaac ccctatttgt ttatttttct aaatacattc   4980
aaatatgtat ccgctcatga cacaataacc ctgataaatg cttcaataat attgaaaaag   5040
gaagagtatg agtattcaac atttccgtgt cgcccttatt ccctttttttg cggcattttg   5100 ccttcctgtt tttgctcacc cagaaacgct ggtgaaagta aaagatgctg aagatcagtt   5160
gggtgcacga gtgggttaca tcgaactgga tctcaacagc ggtaagatcc ttgagagttt   5220
tcgccccgaa gaacgttttc caatgatgag cacttttaaa gttctgctat gtggcgcggt   5280
attatcccgt attgacgccg ggcaagagca actcggtcgc cgcatacact attctcagaa   5340
tgacttggtt gagtactcac cagtcacaga aaagcatctt acggatggca tgacagtaag   5400
agaattatgc agtgctgcca taaccatgag tgataacact gcggccaact tacttctgac   5460
aacgatcgga ggaccgaagg agctaaccgc ttttttgcac aacatggggg atcatgtaac   5520
tcgccttgat cgttgggaac cggagctgaa tgaagccata ccaaacgacg agcgtgacac   5580
cacgatgcct gtagcaatgg caacaacgtt gcgcaaacta ttaactggcg aactacttac   5640
tctagcttcc cggcaacaat taatagactg gatggaggcg gataaagttg caggaccact   5700
```

-continued

```
tctgcgctcg gcccttccgg ctggctggtt tattgctgat aaatctggag ccggtgagcg   5760
tggaagccgc ggtatcattg cagcactggg gccagatggt aagccctccc gtatcgtagt   5820
tatctacacg acggggagtc aggcaactat ggatgaacga aatagacaga tcgctgagat   5880
aggtgcctca ctgattaagc attggtaact gtcagaccaa gtttactcat atatacttta   5940
gattgattta aaacttcatt tttaatttaa aaggatctag gtgaagatcc ttttgataa   6000 tctcatgacc aaaatccctt aacgtgagtt ttcgttccac tgagcgtcag accccgtaga   6060
aaagatcaaa ggatcttctt gagatccttt ttttctgcgc gtaatctgct gcttgcaaac   6120
aaaaaaacca ccgctaccag cggtggtttg tttgccggat caagagctac caactctttt   6180
tccgaaggta actggcttca gcagagcgca gataccaaat actgttcttc tagtgtagcc   6240
gtagttaggc caccacttca agaactctgt agcaccgcct acatacctcg ctctgctaat   6300
cctgttacca gtggctgctg ccagtggcga taagtcgtgt cttaccgggt tggactcaag   6360
acgatagtta ccggataagg cgcagcggtc gggctgaacg gggggttcgt gcacacagcc   6420
cagcttggag cgaacgacct acaccgaact gagataccta cagcgtgagc tatgagaaag   6480
cgccacgctt cccgaaggga gaaaggcgga caggtatccg gtaagcggca gggtcggaac   6540
aggagagcgc acgagggagc ttccaggggg aaacgcctgg tatctttata gtcctgtcgg   6600
gtttcgccac ctctgacttg agcgtcgatt tttgtgatgc tcgtcagggg ggcggagcct   6660
atggaaaaac gccagcaacg cggccttttt acggttcctg gccttttgct ggccttttgc   6720
tcacatgt                                                              6728
```

<210> SEQ ID NO 47
<211> LENGTH: 6729
<212> TYPE: DNA
<213> ORGANISM: Artificial Sequence
<220> FEATURE:
<223> OTHER INFORMATION: pGW119

<400> SEQUENCE: 47

```
cctgcaggca gctgcgcgct cgctcgctca ctgaggccgc ccgggcgtcg ggcgaccttt    60
ggtcgcccgg cctcagtgag cgagcgagcg cgcagagagg gagtggccaa ctccatcact   120
aggggttcct gcggcctcta gaaaggatct gcgatcgctc cggtgcccgt cagtgggcag   180
agcgcacatc gcccacagtc cccgagaagt tggggggagg ggtcggcaat tgaacgggtg   240
cctagagaag gtggcgcggg gtaaactggg aaagtgatgt cgtgtactgg ctccgccttt   300
ttcccgaggg tggggagaa ccgtatataa gtgcagtagt cgccgtgaac gttctttttc    360
gcaacgggtt tgccgccaga acacagctga agcttcgagg ggctcgcatc tctccttcac   420
gcgcccgccg ccctacctga ggccgccatc cacgccggtt gagtcgcgtt ctgccgcctc   480
ccgcctgtgg tgcctcctga actgcgtccg ccgtctaggt aagtttaaag ctcaggtcga   540
gaccgggcct ttgtccggcg ctcccttgga gcctacctag actcagccgg ctctccacgc   600
tttgcctgac cctgcttgct caactctacg tctttgtttc gttttctgtt ctgcgccgtt   660
acagatctgg ctaactaccg gtgccaccat gaacgctaca cactgcatct tggctttgca   720
gctcttcctc atggctgttt ctggctgtta ctgccacggc acagtcattg aaagcctaga   780
aagtctgaat aactatttta actcaagtgg catagatgtg gaagaaaaga gtctcttctt   840
ggatatctgg aggaactggc aaaaggatgt tgacatgaaa atcctgcaga gccagattat   900
ctctttctac ctcagactct ttgaagtctt gaaagacaat caggccatca gcaacaacat   960
```

-continued

```
aagcgtcatt gaatcacacc tgattactac cttcttcagc aacagcaagg cgaaaaagga   1020
tgcattcatg agtattgcca agtttgaggt caacaaccca caggtccagc gccaagcatt   1080
caatgagctc atccgagtgg tccaccagct gttgccggaa tccagcctca ggaagcggaa   1140
aaggagtcgc tgctgaatcc ggcgcaacaa acttctctct gctgaaacaa gccggagatg   1200
tcgaagagaa tcctggaccg atggcttgca attgtcagtt gatgcaggat acaccactcc   1260
tcaagtttcc atgtccaagg ctcattcttc tctttgtgct gctgattcgt ctttcacaag   1320
tgtcttcaga tgttgatgaa caactgtcca agtcagtgaa agataaggta ttgctgcctt   1380
gccgttacaa ctctcctcat gaagatgagt ctgaagaccg aatctactgg caaaaacatg   1440
acaaagtggt gctgtctgtc attgttggga aactaaaagt gtggcccgag tataagaacc   1500
ggactttata tgacaacact acctactctc ttatcatcct gggcctggtc ctttcagacc   1560
ggggcacata cagctgtgtc gttcaaaaga aggaaagagg aacgtatgaa gttaaacact   1620
tggctttagt aaagttgtcc atcaaagctg acttctctac ccccaacata actgagtctg   1680
gaaacccatc tgcagacact aaaaggatta cctgctttgc ttccgggggt ttcccaaagc   1740
ctcgcttctc ttggttggaa aatggaagag aattacctgg catcaatacg acaatttccc   1800
aggatcctga atctgaattg tacaccatta gtagccaact agatttcaat acgactcgca   1860
accacaccat taagtgtctc attaaatatg agatgctca cgtgtcagag gacttcacct   1920
gggaaaaacc cccagaagac cctcctgata gcaagaacac acttgtgctc tttggggcag   1980
gattcggcgc agtaataaca gtcgtcgtca tcgttgtcat catcaaatgc ttctgtaagc   2040
acagaagctg tttcagaaga aatgaggcaa gcagagaaac aaacaacagc cttaccttcg   2100
ggcctgaaga agcattagct gaacagaccg tcttccttcg tacgggcagt ggagagggca   2160
gaggaagtct gctaacatgc ggtgacgtcg aggagaatcc tggcccaatg gagagtgtgg   2220
tacagccttc agtgtttgtg gtggatggac agacggacat cccattcagg cggctggaac   2280
agaaccaccg gagacggcgc tgtggcactg tccaggtcag cctggccctg gtgctgctgc   2340
taggtgctgg gctggccact cagggctggt ttctcctgag actgcatcaa cgtcttggag   2400
acatagtagc tcatctgcca gatggaggca aaggctcctg ggagaagctg atacaagatc   2460
aacgatctca ccaggccaac ccagcagcac atcttacagg agccaacgcc agcttgatag   2520
gtattggtgg acctctgtta tgggagacac gacttggcct ggccttcttg aggggcttga   2580
cgtatcatga tggggccctg gtgaccatgg agcccggtta ctactatgtg tactccaaag   2640
tgcagctgag cggcgtgggc tgcccccagg ggctggccaa tggcctcccc atcacccatg   2700
gactatacaa gcgcacatcc cgctacccga aggagttaga actgctggtc agtcggcggt   2760
caccctgtgg ccgggccaac agctcccgag tctggtggga cagcagcttc ctgggcggcg   2820
tggtacatct ggaggctggg aagaggtgg tggtccgcgt gcctggaaac cgcctggtca   2880
gaccacgtga cggcaccagg tcctatttcg gagctttcat ggtcactagc agcggtaccc   2940
agtgcaccaa ctacgccctg ctgaagctgg ccggcgatgt ggagagcaac cccgggccca   3000
tggaccagca cacacttgat gtggaggata ccgcggatgc cagacatcca gcaggtactt   3060
cgtgcccctc ggatgcggcg ctcctcagag ataccgggct cctcgcggac gctgcgctcc   3120
tctcagatac tgtgcgcccc acaaatgccg cgctcccac ggatgctgcc taccctgcgg   3180
ttaatgttcg ggatcgcgag gccgcgtggc cgcctgcact gaacttctgt tcccgccacc   3240
caaagctcta tggcctagtc gctttggttt tgctgcttct gatcgccgcc tgtgttccta   3300
tcttcacccg caccgagcct cggccagcgc tcacaatcac cacctcgccc aacctgggta   3360
```

547 548

```
cccgagagaa taatgcagac caggtcaccc ctgtttccca cattggctgc cccaacacta   3420
cacaacaggg ctctcctgtg ttcgccaagc tactggctaa aaaccaagca tcgttgtgca   3480
atacaactct gaactggcac agccaagatg gagctgggag ctcataccta tctcaaggtc   3540
tgaggtacga agaagacaaa aaggagttgg tggtagacag tcccgggctc tactacgtat   3600 tttttggaact gaagctcagt ccaacattca caaacacagg ccacaaggtg cagggctggg   3660
tctctcttgt tttgcaagca aagcctcagg tagatgactt tgacaacttg gccctgacag   3720
tggaactgtt cccttgctcc atggagaaca agttagtgga ccgttcctgg agtcaactgt   3780
tgctcctgaa ggctggccac cgcctcagtg tgggtctgag ggcttatctg catggagccc   3840
aggatgcata cagagactgg gagctgtctt atcccaacac caccagcttt ggactctttc   3900
ttgtgaaacc cgacaaccca tgggaatgag aattcaataa aagatcttta ttttcattag   3960
atctgtgtgt tggttttttg tgtgcggccg caggaacccc tagtgatgga gttggccact   4020
ccctctctgc gcgctcgctc gctcactgag gccgggcgac caaaggtcgc ccgacgcccg   4080
ggctttgccc gggcggcctc agtgagcgag cgagcgcgca gctgcctgca ggggcgcctg   4140
atgcggtatt ttctccttac gcatctgtgc ggtatttcac accgcatacg tcaaagcaac   4200
catagtacgc gccctgtagc ggcgcattaa gcgcggcggg tgtggtggtt acgcgcagcg   4260
tgaccgctac acttgccagc gccttagcgc ccgctccttt cgctttcttc ccttcctttc   4320
tcgccacgtt cgccggcttt ccccgtcaag ctctaaatcg gggctccct ttagggttcc   4380 gatttagtgc tttacggcac ctcgacccca aaaaacttga tttgggtgat ggttcacgta   4440
gtgggccatc gccctgatag acggtttttc gccctttgac gttggagtcc acgttcttta   4500
atagtggact cttgttccaa actgaacaa cactcaactc tatctcgggc tattcttttg   4560
atttataagg attttgccg atttcggtct attggttaaa aaatgagctg atttaacaaa   4620
aatttaacgc gaattttaac aaaatattaa cgtttacaat tttatggtgc actctcagta   4680
caatctgctc tgatgccgca tagttaagcc agccccgaca cccgccaaca cccgctgacg   4740
cgccctgacg ggcttgtctg ctcccggcat ccgcttacag acaagctgtg accgtctccg   4800
ggagctgcat gtgtcagagg ttttcaccgt catcaccgaa acgcgcgaga cgaaagggcc   4860
tcgtgatacg cctattttta taggttaatg tcatgataat aatggtttct tagacgtcag   4920
gtggcacttt tcggggaaat gtgcgcggaa ccccatttg tttatttttc taaatacatt   4980
caaatatgta tccgctcatg agacaataac cctgataaat gcttcaataa tattgaaaaa   5040
ggaagagtat gagtattcaa catttccgtg tcgcccttat tcccttttt gcggcatttt   5100 gccttcctgt ttttgctcac ccagaaacgc tggtgaaagt aaaagatgct gaagatcagt   5160
tgggtgcacg agtgggttac atcgaactgg atctcaacag cggtaagatc cttgagagtt   5220
ttcgccccga agaacgtttt ccaatgatga gcacttttaa agttctgcta tgtggcgcgg   5280
tattatcccg tattgacgcc gggcaagagc aactcggtcg ccgcatacac tattctcaga   5340
atgacttggt tgagtactca ccagtcacag aaaagcatct tacggatggc atgacagtaa   5400
gagaattatg cagtgctgcc ataaccatga gtgataacac tgcggccaac ttacttctga   5460
caacgatcgg aggaccgaag gagctaaccg ctttttttgca caacatgggg gatcatgtaa   5520
ctcgccttga tcgttgggaa ccggagctga atgaagccat accaaacgac gagcgtgaca   5580
ccacgatgcc tgtagcaatg gcaacaacgt tgcgcaaact attaactggc gaactactta   5640
ctctagcttc ccggcaacaa ttaatagact ggatggaggc ggataaagtt gcaggaccac   5700
```

-continued

```
ttctgcgctc ggcccttccg gctggctggt ttattgctga taaatctgga gccggtgagc    5760
gtggaagccg cggtatcatt gcagcactgg ggccagatgg taagccctcc cgtatcgtag    5820
ttatctacac gacgggagt caggcaacta tggatgaacg aaatagacag atcgctgaga      5880
taggtgcctc actgattaag cattggtaac tgtcagacca agtttactca tatatacttt    5940
agattgattt aaaacttcat ttttaattta aaaggatcta ggtgaagatc cttttttgata   6000 atctcatgac caaaatccct taacgtgagt tttcgttcca ctgagcgtca gaccccgtag    6060
aaaagatcaa aggatcttct tgagatcctt ttttctgcg cgtaatctgc tgcttgcaaa      6120
caaaaaaacc accgctacca gcggtggttt gtttgccgga tcaagagcta ccaactcttt    6180
ttccgaaggt aactggcttc agcagagcgc agataccaaa tactgttctt ctagtgtagc    6240
cgtagttagg ccaccacttc aagaactctg tagcaccgcc tacatacctc gctctgctaa    6300
tcctgttacc agtggctgct gccagtggcg ataagtcgtg tcttaccggg ttggactcaa    6360
gacgatagtt accggataag cgcagcggt cgggctgaac gggggggttcg tgcacacagc      6420 ccagcttgga gcgaacgacc tacaccgaac tgagatacct acagcgtgag ctatgagaaa    6480
gcgccacgct tcccgaaggg agaaaggcgg acaggtatcc ggtaagcggc agggtcggaa    6540
caggagagcg cacgagggag cttccagggg gaaacgcctg gtatctttat agtcctgtcg    6600
ggtttcgcca cctctgactt gagcgtcgat ttttgtgatg ctcgtcaggg gggcggagcc    6660
tatggaaaaa cgccagcaac gcggcctttt tacggttcct ggccttttgc tggccttttg    6720
ctcacatgt                                                            6729
```

```
<210> SEQ ID NO 48
<211> LENGTH: 6598
<212> TYPE: DNA
<213> ORGANISM: Artificial Sequence
<220> FEATURE:
<223> OTHER INFORMATION: pGW122

<400> SEQUENCE: 48
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggcctcta gaaaggatct gcgatcgctc cggtgcccgt cagtgggcag     180
agcgcacatc gcccacagtc cccgagaagt tggggggagg ggtcggcaat tgaacgggtg     240
cctagagaag gtggcgcggg gtaaactggg aaagtgatgt cgtgtactgg ctccgccttt     300
ttcccgaggg tggggagaa ccgtatataa gtgcagtagt cgccgtgaac gttcttttc        360 gcaacgggtt tgccgccaga acacagctga agcttcgagg ggctcgcatc tctccttcac     420
gcgcccgccg ccctacctga ggccgccatc cacgccggtt gagtcgcgtt ctgccgcctc     480
ccgcctgtgg tgcctcctga actgcgtccg ccgtctaggt aagtttaaag ctcaggtcga     540
gaccgggcct ttgtccggcg ctcccttgga gcctacctag actcagccgg ctctccacgc     600
tttgcctgac cctgcttgct caactctacg tctttgtttc gttttctgtt ctgcgccgtt     660
acagatctgg ctaactaccg gtgccaccat gtgtcctcag aagctaacca tctcctggtt     720
tgccatcgtt ttgctggtgt ctccactcat ggccatgtgg gagctggaga aagacgttta     780
tgttgtagag gtggactgga ctcccgatgc ccctggagaa acagtgaacc tcacctgtga     840
cacgcctgaa gaagatgaca tcacctggac ctcagaccag agacatggag tcataggctc     900
tggaaagacc ctgaccatca ctgtcaaaga gtttctagat gctggccagt acacctgcca     960
caaaggaggc gagactctga gccactcaca tctgctgctc cacaagaagg aaaatggaat    1020
```

```
ttggtccact gaaattttaa aaaatttcaa aaacaagact ttcctgaagt gtgaagcacc    1080
aaattactcc ggacggttca cgtgctcatg gctggtgcaa agaaacatgg acttgaagtt    1140
caacatcaag agcagtagca gttcccctga ctctcgggca gtgacatgtg gaatggcgtc    1200
tctgtctgca gagaaggtca cactggacca aagggactat gagaagtatt cagtgtcctg    1260
ccaggaggat gtcacctgcc caactgccga ggagaccctg cccattgaac tggcgttgga    1320
agcacggcag cagaataaat atgagaacta cagcaccagc ttcttcatca gggacatcat    1380
caaaccagac ccgcccaaga acttgcagat gaagcctttg aagaactcac aggtggaggt    1440
cagctgggag taccctgact cctggagcac tcccattcc tacttctccc tcaagttctt    1500
tgttcgaatc cagcgcaaga agaaaaagat gaaggagaca gaggaggggt gtaaccagaa    1560
aggtgcgttc ctcgtagaga agacatctac cgaagtccaa tgcaaaggcg ggaatgtctg    1620
cgtgcaagct caggatcgct attacaattc ctcatgcagc aagtgggcat gtgttccctg    1680
cagggtccga tccggcagtg gagagggcag aggaagtctg ctaacatgcg gtgacgtcga    1740
ggagaatcct ggcccaatgg accagcacac acttgatgtg gaggataccg cggatgccag    1800
acatccagca ggtacttcgt gcccctcgga tgcggcgctc ctcagagata ccgggctcct    1860
cgcggacgct gcgctcctct cagatactgt gcgccccaca aatgccgcgc tccccacgga    1920
tgctgcctac cctgcggtta atgttcggga tcgcgaggcc gcgtggccgc ctgcactgaa    1980
cttctgttcc cgccacccaa agctctatgg cctagtcgct ttggttttgc tgcttctgat    2040
cgccgcctgt gttcctatct tcacccgcac cgagcctcgg ccagcgctca caatcaccac    2100
ctcgcccaac ctgggtaccc gagagaataa tgcagaccag gtcacccctg tttcccacat    2160
tggctgcccc aacactacac aacagggctc tcctgtgttc gccaagctac tggctaaaaa    2220
ccaagcatcg ttgtgcaata caactctgaa ctggcacagc caagatggag ctgggagctc    2280
atacctatct caaggtctga ggtacgaaga agacaaaaag gagttggtgg tagacagtcc    2340
cgggctctac tacgtatttt tggaactgaa gctcagtcca acattcacaa acacaggcca    2400
caaggtgcag ggctgggtct ctcttgtttt gcaagcaaag cctcaggtag atgactttga    2460
caacttggcc ctgacagtgg aactgttccc ttgctccatg gagaacaagt tagtggaccg    2520
ttcctggagt caactgttgc tcctgaaggc tggccaccgc ctcagtgtgg gtctgagggc    2580
ttatctgcat ggagcccagg atgcatacag agactgggct ctgtcttatc ccaacaccac    2640
cagctttgga ctctttcttg tgaaacccga caacccatgg gaaggatccg gcgcaacaaa    2700
cttctctctg ctgaaacaag ccggagatgt cgaagagaat cctggaccgg ctagcatgaa    2760
cgctacacac tgcatcttgg ctttgcagct cttcctcatg gctgtttctg ctgttactg    2820 ccacggcaca gtcattgaaa gcctagaaag tctgaataac tattttaact caagtggcat    2880
agatgtggaa gaaaagagtc tcttcttgga tatctggagg aactggcaaa aggatggtga    2940
catgaaaatc ctgcagagcc agattatctc tttctacctc agactctttg aagtcttgaa    3000
agacaatcag gccatcagca caacataag cgtcattgaa tcacacctga ttactacctt    3060
cttcagcaac agcaaggcga aaaggatgc attcatgagt attgccaagt ttgaggtcaa    3120
caacccacag gtccagcgcc aagcattcaa tgagctcatc cgagtggtcc accagctgtt    3180
gccggaatcc agcctcagga agcggaaaag gagtcgctgc tgagaattca cgcgttaagt    3240
cgacaatcaa cctctggatt acaaaatttg tgaaagattg actggtattc ttaactatgt    3300
tgctcctttt acgctatgtg gatacgctgc tttaatgcct ttgtatcatg ctattgcttc    3360
```

-continued

```
ccgtatggct ttcattttct cctccttgta taaatcctgg ttgctgtctc tttatgagga     3420
gttgtggccc gttgtcaggc aacgtggcgt ggtgtgcact gtgtttgctg acgcaacccc     3480
cactggttgg ggcattgcca ccacctgtca gctcctttcc gggactttcg ctttccccct     3540
ccctattgcc acggcggaac tcatcgccgc ctgccttgcc cgctgctgga caggggctcg     3600
gctgttgggc actgacaatt ccgtggtgtt gtcggggaaa tcatcgtcct ttccttggct     3660
gctcgcctgt gttgccacct ggattctgcg cgggacgtcc ttctgctacg tcccttcggc     3720
cctcaatcca gcggaccttc cttcccgcgg cctgctgccg gctctgcggc ctcttccgcg     3780
tcttcgcctt cgccctcaga cgagtcggat ctccctttgg gccgcctccc cgcgtcgact     3840
ttaagaccaa tgacggccgc aggaacccct agtgatggag ttggccactc cctctctgcg     3900
cgctcgctcg ctcactgagg ccgggcgacc aaaggtcgcc cgacgcccgg gctttgcccg     3960
ggcggcctca gtgagcgagc gagcgcgcag ctgcctgcag gggcgcctga tgcggtattt     4020
tctccttacg catctgtgcg gtatttcaca ccgcatacgt caaagcaacc atagtacgcg     4080
ccctgtagcg gcgcattaag cgcggcgggt gtggtggtta cgcgcagcgt gaccgctaca     4140
cttgccagcg ccttagcgcc cgctcctttc gctttcttcc cttcctttct cgccacgttc     4200
gccggctttc cccgtcaagc tctaaatcgg gggctccctt tagggttccg atttagtgct     4260
ttacggcacc tcgaccccaa aaaacttgat ttgggtgatg gttcacgtag tgggccatcg     4320
ccctgataga cggtttttcg ccctttgacg ttggagtcca cgttctttaa tagtggactc     4380
ttgttccaaa ctggaacaac actcaactct atctcgggct attcttttga tttataaggg     4440
attttgccga tttcggtcta ttggttaaaa aatgagctga tttaacaaaa atttaacgcg     4500
aattttaaca aaatattaac gtttacaatt ttatggtgca ctctcagtac aatctgctct     4560
gatgccgcat agttaagcca gccccgacac ccgccaacac ccgctgacgc gccctgacgg     4620
gcttgtctgc tcccggcatc cgcttacaga caagctgtga ccgtctccgg gagctgcatg     4680
tgtcagaggt tttcaccgtc atcaccgaaa cgcgcgagac gaaagggcct cgtgatacgc     4740
ctatttttat aggttaatgt catgataata atggtttctt agacgtcagg tggcactttt     4800
cggggaaatg tgcgcggaac ccctatttgt ttatttttct aaatacattc aaatatgtat     4860
ccgctcatga gacaataacc ctgataaatg cttcaataat attgaaaaag gaagagtatg     4920
agtattcaac atttccgtgt cgcccttatt ccctttttg cggcattttg ccttcctgtt     4980
tttgctcacc cagaaacgct ggtgaaagta aaagatgctg aagatcagtt gggtgcacga     5040
gtgggttaca tcgaactgga tctcaacagc ggtaagatcc ttgagagttt tcgccccgaa     5100
gaacgttttc caatgatgag cacttttaaa gttctgctat gtggcgcggt attatcccgt     5160
attgacgccg ggcaagagca actcggtcgc cgcatacact attctcagaa tgacttggtt     5220
gagtactcac cagtcacaga aaagcatctt acggatggca tgacagtaag agaattatgc     5280
agtgctgcca taaccatgag tgataacact gcggccaact tacttctgac aacgatcgga     5340
ggaccgaagg agctaaccgc ttttttgcac aacatggggg atcatgtaac tcgccttgat     5400
cgttgggaac cggagctgaa tgaagccata ccaaacgacg agcgtgacac cacgatgcct     5460
gtagcaatgg caacaacgtt gcgcaaacta ttaactggcg aactacttac tctagcttcc     5520
cggcaacaat taatagactg gatggaggcg gataaagttg caggaccact tctgcgctcg     5580
gcccttccgg ctggctggtt tattgctgat aaatctggag ccggtgagcg tggaagccgc     5640
ggtatcattg cagcactggg gccagatggt aagccctccc gtatcgtagt tatctacacg     5700
acggggagtc aggcaactat ggatgaacga aatagacaga tcgctgagat aggtgcctca     5760
```

```
ctgattaagc attggtaact gtcagaccaa gtttactcat atatacttta gattgattta      5820
aaacttcatt tttaatttaa aaggatctag gtgaagatcc tttttgataa tctcatgacc      5880
aaaatccctt aacgtgagtt ttcgttccac tgagcgtcag accccgtaga aaagatcaaa      5940
ggatcttctt gagatccttt ttttctgcgc gtaatctgct gcttgcaaac aaaaaaacca      6000
ccgctaccag cggtggtttg tttgccggat caagagctac caactctttt tccgaaggta      6060
actggcttca gcagagcgca gataccaaat actgttcttc tagtgtagcc gtagttaggc      6120
caccacttca agaactctgt agcaccgcct acatacctcg ctctgctaat cctgttacca      6180
gtggctgctg ccagtggcga taagtcgtgt cttaccgggt tggactcaag acgatagtta      6240
ccggataagg cgcagcggtc gggctgaacg gggggttcgt gcacacagcc cagcttggag      6300
cgaacgacct acaccgaact gagataccta cagcgtgagc tatgagaaag cgccacgctt      6360
cccgaaggga gaaaggcgga caggtatccg gtaagcggca gggtcggaac aggagagcgc      6420
acgagggagc ttccaggggg aaacgcctgg tatctttata gtcctgtcgg gtttcgccac      6480
ctctgacttg agcgtcgatt tttgtgatgc tcgtcagggg ggcggagcct atggaaaaac      6540
gccagcaacg cggccttttt acggttcctg gccttttgct ggccttttgc tcacatgt      6598
```

```
<210> SEQ ID NO 49
<211> LENGTH: 6448
<212> TYPE: DNA
<213> ORGANISM: Artificial Sequence
<220> FEATURE:
<223> OTHER INFORMATION: pGW127b

<400> SEQUENCE: 49
```

```
cctgcaggca gctgcgcgct cgctcgctca ctgaggccgc ccgggcgtcg ggcgaccttt       60
ggtcgcccgg cctcagtgag cgagcgagcg cgcagagagg gagtggccaa ctccatcact      120
aggggttcct gcggcctcta gaaaggatct gcgatcgctc cggtgcccgt cagtgggcag      180
agcgcacatc gcccacagtc cccgagaagt tggggggagg ggtcggcaat tgaacgggtg      240
cctagagaag gtggcgcggg gtaaactggg aaagtgatgt cgtgtactgg ctccgccttt      300
ttcccgaggg tggggagaa ccgtatataa gtgcagtagt cgccgtgaac gttctttttc      360
gcaacgggtt tgccgccaga acacagctga agcttcgagg ggctcgcatc tctccttcac      420
gcgcccgccg ccctacctga ggccgccatc cacgccggtt gagtcgcgtt ctgccgcctc      480
ccgcctgtgg tgcctcctga actgcgtccg ccgtctaggt aagtttaaag ctcaggtcga      540
gaccgggcct ttgtccggcg ctcccttgga gcctacctag actcagccgg ctctccacgc      600
tttgcctgac cctgcttgct caactctacg tctttgtttc gttttctgtt ctgcgccgtt      660
acagatctgg ctaactaccg gtgccaccat gaaatataca agttatatct ggctttttca      720
gctctgcatc gttttgggtt ctcttggctg ttactgccag gacccatatg taaaagaagc      780
agaaaacctt aagaaatatt ttaatgcagg tcattcagat gtagcggata atggaactct      840
tttcttaggc attttgaaga attggaaaga ggagagtgac agaaaaataa tgcagagcca      900
aattgtctcc ttttacttca aacttttttaa aaacttttaaa gatgaccaga gcatccaaaa      960
gagtgtggag accatcaagg aagacatgaa tgtcaagttt ttcaatagca acaaaaagaa      1020
acgagatgac ttcgaaaagc tgactaatta ttcggtaact gacttgaatg tccaacgcaa      1080
agcaatacat gaactcatcc aagtgatggc tgaactgtcg ccagcagcta aaacaggaa       1140 gcgaaaaagg agtcagatgc tgtttcgagg tcgaagagca tcccagggcg gaggatccgg      1200
```

-continued

```
cgcaacaaac ttctctctgc tgaaacaagc cggagatgtc gaagagaatc ctggaccgat    1260
gtgtcaccag cagttggtca tctcttggtt ttccctggtt tttctggcat ctcccctcgt    1320
ggccatatgg gaactgaaga aagatgttta tgtcgtagaa ttggattggt atccggatgc    1380
ccctggagaa atggtggtcc tcacctgtga caccccctgaa gaagatggta tcacctggac    1440
cttggaccag agcagtgagg tcttaggctc tggcaaaacc ctgaccatcc aagtcaaaga    1500
gtttggagat gctggccagt acacctgtca caaaggaggc gaggttctaa gccattcgct    1560
cctgctgctt cacaaaaagg aagatggaat ttggtccact gatattttaa aggaccagaa    1620
agaacccaaa aataagacct ttctaagatg cgaggccaag aattattctg gacgtttcac    1680
ctgctggtgg ctgacgacaa tcagtactga tttgacattc agtgtcaaaa gcagcagagg    1740
ctcttctgac ccccaagggg tgacgtgcgg agctgctaca ctctctgcag agagagtcag    1800
aggggacaac aaggagtatg agtactcagt ggagtgccag gaggacagtg cctgcccagc    1860
tgctgaggag agtctgccca ttgaggtcat ggtggatgcc gttcacaagc tcaagtatga    1920
aaactacacc agcagcttct tcatcaggga catcatcaaa cctgacccac caagaacttt    1980
gcagctgaag ccattaaaga attctcggca ggtggaggtc agctgggagt accctgacac    2040
ctggagtact ccacattcct acttctccct gacattctgc gttcaggtcc agggcaagag    2100
caagagagaa aagaaagata gagtcttcac ggacaagacc tcagccacgg tcatctgccg    2160
caaaaatgcc agcattagcg tgcgggccca ggaccgctac tatagctcat cttggagcga    2220
atgggcatct gtgccctgca gtggcactag tggagagggc agaggaagtc tgctaacatg    2280
cggtgacgtc gaggagaatc ctggcccaat ggaatacgcc tctgacgctt cactggaccc    2340
cgaagccccg tggcctcccg cgccccgcgc tcgcgcctgc cgcgtactgc cttgggccct    2400
ggtcgcgggg ctgctgctgc tgctgctgct cgctgccgcc tgcgccgtct tcctcgcctg    2460
cccctgggcc gtgtccgggg ctcgcgcctc gcccggctcc gcggccagcc cgagactccg    2520
cgagggtccc gagctttcgc ccgacgatcc cgccggcctc ttggacctgc ggcagggcat    2580
gtttgcgcag ctggtggccc aaaatgttct gctgatcgat gggcccctga ctggtacag    2640 tgacccaggc ctggcaggcg tgtccctgac ggggggcctg agctacaaag aggacacgaa    2700
ggagctggtg gtggccaagg ctggagtcta ctatgtcttc tttcaactag agctgcggcg    2760
cgtggtggcc ggcgagggct caggctccgt ttcacttgcg ctgcacctgc agccactgcg    2820
ctctgctgct ggggccgccg ccctggcttt gaccgtggac ctgccacccg cctcctccga    2880
ggctcggaac tcggccttcg gtttccaggg ccgcttgctg cacctgagtg ccggccagcg    2940
cctgggcgtc catcttcaca ctgaggccag ggcacgccat gcctggcagc ttacccaggg    3000
cgccacagtc ttgggactct ccgggtgac ccccgaaatc ccagccggac tcccttcacc    3060
gaggtcggaa taagaattca cgcgttaagt cgacaatcaa cctctggatt acaaaatttg    3120
tgaaagattg actggtattc ttaactatgt tgctcctttt acgctatgtg gatacgctgc    3180
tttaatgcct ttgtatcatg ctattgcttc ccgtatggct ttcattttct cctccttgta    3240
taaatcctgg ttgctgtctc tttatgagga gttgtggccc gttgtcaggc aacgtggcgt    3300
ggtgtgcact gtgtttgctg acgcaacccc cactggttgg ggcattgcca ccacctgtca    3360
gctcctttcc gggactttcg ctttccccct ccctattgcc acggcggaac tcatcgccgc    3420
ctgccttgcc cgctgctgga caggggctcg gctgttgggc actgacaatt ccgtggtgtt    3480
gtcggggaaa tcatcgtcct ttccttggct gctcgcctgt gttgccacct ggattctgcg    3540
cgggacgtcc ttctgctacg tcccttcggc cctcaatcca gcggaccttc cttcccgcgg    3600
```

-continued

```
cctgctgccg gctctgcggc ctcttccgcg tcttcgcctt cgccctcaga cgagtcggat    3660 ctcctttgg gccgcctccc cgcgtcgact ttaagaccaa tgacggccgc aggaacccct      3720
agtgatggag ttggccactc cctctctgcg cgctcgctcg ctcactgagg ccgggcgacc      3780
aaaggtcgcc cgacgcccgg gctttgcccg ggcggcctca gtgagcgagc gagcgcgcag      3840
ctgcctgcag gggcgcctga tgcggtattt tctccttacg catctgtgcg gtatttcaca      3900
ccgcatacgt caaagcaacc atagtacgcg ccctgtagcg gcgcattaag cgcggcgggt      3960
gtggtggtta cgcgcagcgt gaccgctaca cttgccagcg ccttagcgcc cgctcctttc      4020
gctttcttcc cttcctttct cgccacgttc gccggctttc cccgtcaagc tctaaatcgg      4080
gggctccctt tagggttccg atttagtgct ttacggcacc tcgaccccaa aaaacttgat      4140
ttgggtgatg gttcacgtag tgggccatcg ccctgataga cggttttttcg cccttttgacg    4200 ttggagtcca cgttctttaa tagtggactc ttgttccaaa ctggaacaac actcaactct      4260
atctcgggct attctttttga tttataaggg attttgccga tttcggtcta ttggttaaaa     4320
aatgagctga tttaacaaaa atttaacgcg aattttaaca aaatattaac gtttacaatt      4380
ttatggtgca ctctcagtac aatctgctct gatgccgcat agttaagcca gccccgacac      4440
ccgccaacac ccgctgacgc gccctgacgg gcttgtctgc tcccggcatc cgcttacaga      4500
caagctgtga ccgtctccgg gagctgcatg tgtcagaggt tttcaccgtc atcaccgaaa      4560
cgcgcgagac gaaagggcct cgtgatacgc ctatttttat aggttaatgt catgataata      4620
atggtttctt agacgtcagg tggcacttttt cggggaaatg tgcgcggaac ccctatttgt     4680
ttatttttct aaatacattc aaatatgtat ccgctcatga caataaacc ctgataaatg       4740 cttcaataat attgaaaaag gaagagtatg agtattcaac atttccgtgt cgcccttatt      4800 ccctttttttg cggcattttg ccttcctgtt tttgctcacc cagaaacgct ggtgaaagta     4860
aaagatgctg aagatcagtt gggtgcacga gtgggttaca tcgaactgga tctcaacagc      4920
ggtaagatcc ttgagagttt tcgccccgaa gaacgttttc caatgatgag cactttttaaa    4980 gttctgctat gtggcgcggt attatcccgt attgacgccg ggcaagagca actcggtcgc      5040
cgcatacact attctcagaa tgacttggtt gagtactcac cagtcacaga aaagcatctt      5100
acggatggca tgacagtaag agaattatgc agtgctgcca taaccatgag tgataacact      5160
gcggccaact tacttctgac aacgatcgga ggaccgaagg agctaaccgc ttttttgcac      5220
aacatggggg atcatgtaac tcgccttgat cgttgggaac cggagctgaa tgaagccata      5280
ccaaacgacg agcgtgacac cacgatgcct gtagcaatgg caacaacgtt gcgcaaacta      5340
ttaactggcg aactacttac tctagcttcc cggcaacaat taatagactg gatggaggcg      5400
gataaagttg caggaccact tctgcgctcg gcccttccgg ctggctggtt tattgctgat      5460
aaatctggag ccggtgagcg tggaagccgc ggtatcattg cagcactggg gccagatggt      5520
aagccctccc gtatcgtagt tatctacacg acggggagtc aggcaactat ggatgaacga      5580
aatagacaga tcgctgagat aggtgcctca ctgattaagc attggtaact gtcagaccaa      5640
gtttactcat atatacttta gattgatttta aaacttcatt tttaatttaa aaggatctag      5700
gtgaagatcc tttttgataa tctcatgacc aaaatccctt aacgtgagtt ttcgttccac       5760
tgagcgtcag accccgtaga aaagatcaaa ggatcttctt gagatccttt ttttctgcgc      5820
gtaatctgct gcttgcaaac aaaaaaacca ccgctaccag cggtggtttg tttgccggat      5880
caagagctac caactctttt tccgaaggta actggcttca gcagagcgca gataccaaat      5940
```

```
actgttcttc tagtgtagcc gtagttaggc caccacttca agaactctgt agcaccgcct      6000
acatacctcg ctctgctaat cctgttacca gtggctgctg ccagtggcga taagtcgtgt      6060
cttaccgggt tggactcaag acgatagtta ccggataagg cgcagcggtc gggctgaacg      6120
gggggttcgt gcacacagcc cagcttggag cgaacgacct acaccgaact gagataccta      6180
cagcgtgagc tatgagaaag cgccacgctt cccgaaggga gaaaggcgga caggtatccg      6240
gtaagcggca gggtcggaac aggagagcgc acgagggagc ttccaggggg aaacgcctgg      6300
tatctttata gtcctgtcgg gtttcgccac ctctgacttg agcgtcgatt tttgtgatgc      6360
tcgtcagggg ggcggagcct atggaaaaac gccagcaacg cggccttttt acggttcctg      6420
gccttttgct ggccttttgc tcacatgt                                         6448

<210> SEQ ID NO 50
<211> LENGTH: 7267
<212> TYPE: DNA
<213> ORGANISM: Artificial Sequence
<220> FEATURE:
<223> OTHER INFORMATION: pGW128b

<400> SEQUENCE: 50
cctgcaggca gctgcgcgct cgctcgctca ctgaggccgc ccgggcgtcg ggcgaccttt        60
ggtcgcccgg cctcagtgag cgagcgagcg cgcagagagg gagtggccaa ctccatcact       120
aggggttcct gcggcctcta gaaaggatct gcgatcgctc cggtgcccgt cagtgggcag       180
agcgcacatc gcccacagtc cccgagaagt tggggggagg ggtcggcaat tgaacgggtg       240
cctagagaag gtggcgcggg gtaaactggg aaagtgatgt cgtgtactgg ctccgccttt       300
ttcccgaggg tgggggagaa ccgtatataa gtgcagtagt cgccgtgaac gttctttttc       360
gcaacgggtt tgccgccaga acacagctga agcttcgagg ggctcgcatc tctccttcac       420
gcgcccgccg ccctacctga ggccgccatc cacgccggtt gagtcgcgtt ctgccgcctc       480
ccgcctgtgg tgcctcctga actgcgtccg ccgtctaggt aagtttaaag ctcaggtcga       540
gaccgggcct ttgtccggcg ctcccttgga gcctacctag actcagccgg ctctccacgc       600
tttgcctgac cctgcttgct caactctacg tctttgtttc gttttctgtt ctgcgccgtt       660
acagatctgg ctaactaccg gtgccaccat gaaatataca agttatatct tggcttttca       720
gctctgcatc gttttgggtt ctcttggctg ttactgccag gacccatatg taaaagaagc       780
agaaaacctt aagaaatatt ttaatgcagg tcattcagat gtagcggata atggaactct       840
tttcttaggc attttgaaga attggaaaga ggagagtgac agaaaaataa tgcagagcca       900
aattgtctcc ttttacttca aactttttaa aaactttaaa gatgaccaga gcatccaaaa       960
gagtgtggag accatcaagg aagacatgaa tgtcaagttt ttcaatagca acaaaaagaa      1020
acgagatgac ttcgaaaagc tgactaatta ttcggtaact gacttgaatg tccaacgcaa      1080
agcaatacat gaactcatcc aagtgatggc tgaactgtcg ccagcagcta aaacagggaa      1140
gcgaaaaagg agtcagatgc tgtttcgagg tcgaagagca tcccagggcg gaggatccgg      1200
cgcaacaaac ttctctctgc tgaaacaagc cggagatgtc gaagagaatc ctggaccgat      1260
gtgtcaccag cagttggtca tctcttggtt ttccctggtt tttctggcat ctcccctcgt      1320
ggccatatgg gaactgaaga agatgtttta tgtcgtagaa ttggattggt atccggatgc      1380
ccctggagaa atggtggtcc tcacctgtga caccccgaa gaagatggta tcacctggac      1440
cttgaccagc agcagtgagg tcttaggctc tggcaaaacc ctgaccatcc aagtcaaaga      1500
gtttggagat gctggccagt acacctgtca caaaggaggc gaggttctaa gccattcgct      1560
```

```
cctgctgctt cacaaaaagg aagatggaat ttggtccact gatattttaa aggaccagaa    1620
agaacccaaa aataagacct ttctaagatg cgaggccaag aattattctg gacgtttcac    1680
ctgctggtgg ctgacgacaa tcagtactga tttgacattc agtgtcaaaa gcagcagagg    1740
ctcttctgac ccccaagggg tgacgtgcgg agctgctaca ctctctgcag agagagtcag    1800
aggggacaac aaggagtatg agtactcagt ggagtgccag gaggacagtg cctgcccagc    1860
tgctgaggag agtctgccca ttgaggtcat ggtggatgcc gttcacaagc tcaagtatga    1920
aaactacacc agcagcttct tcatcaggga catcatcaaa cctgacccac ccaagaactt    1980
gcagctgaag ccattaaaga attctcggca ggtggaggtc agctgggagt accctgacac    2040
ctggagtact ccacattcct acttctccct gacattctgc gttcaggtcc agggcaagag    2100
caagagagaa aagaaagata gagtcttcac ggacaagacc tcagccacgg tcatctgccg    2160
caaaaatgcc agcattagcg tgcgggccca ggaccgctac tatagctcat cttggagcga    2220
atgggcatct gtgccctgca gtggcagtgg agagggcaga ggaagtctgc taacatgcgg    2280
tgacgtcgag gagaatcctg gcccaatgga atacgcctct gacgcttcac tggaccccga    2340
agccccgtgg cctcccgcgc cccgcgctcg cgcctgccgc gtactgcctt gggccctggt    2400
cgcggggctg ctgctgctgc tgctgctcgc tgccgcctgc gccgtcttcc tcgcctgccc    2460
ctgggccgtg tccggggctc gcgcctcgcc cggctccgcg gccagcccga gactccgcga    2520
gggtcccgag ctttcgcccg acgatcccgc cggcctcttg gacctgcggc agggcatgtt    2580
tgcgcagctg gtggcccaaa atgttctgct gatcgatggg cccctgagct ggtacagtga    2640
cccaggcctg gcaggcgtgt ccctgacggg gggcctgagc tacaaagagg acacgaagga    2700
gctggtggtg gccaaggctg gagtctacta tgtcttcttt caactagagc tgcggcgcgt    2760
ggtggccggc gagggctcag gctccgtttc acttgcgctg cacctgcagc cactgcgctc    2820
tgctgctggg gccgccgccc tggctttgac cgtggacctg ccacccgcct cctccgaggc    2880
tcggaactcg gccttcggtt ccagggccg cttgctgcac ctgagtgccg gccagcgcct    2940
gggcgtccat cttcacactg aggccagggc acgccatgcc tggcagctta cccagggcgc    3000
cacagtcttg ggactcttcc gggtgacccc cgaaatccca gccggactcc cttcaccgag    3060
gtcggaaggt gctagcggta cccagtgcac caactacgcc ctgctgaagc tggccggcga    3120
tgtggagagc aaccccgggc ccatggagga gagtgtcgta cggccctcag tgtttgtggt    3180
ggatggacag accgacatcc cattcacgag gctgggacga agccaccgga gacagtcgtg    3240
cagtgtggcc cgggtgggtc tgggtctctt gctgttgctg atgggggccg ggctggccgt    3300
ccaaggctgg ttcctcctgc agctgcactg gcgtctagga gagatggtca cccgcctgcc    3360
tgacggacct gcaggctcct gggagcagct gatacaagag cgaaggtctc acgaggtcaa    3420
cccagcagcg catctcacag gggccaactc agcttgacc ggcagcgggg gccgctgtt    3480 atgggagact cagctgggcc tggccttcct gaggggcctc agctaccacg atggggccct    3540
tgtggtcacc aaagctggct actactacat ctactccaag gtgcagctgg cggtgtggg    3600 ctgcccgctg ggcctggcca gcaccatcac ccacggcctc tacaagcgca caccccgcta    3660
ccccgaggag ctggagctgt tggtcagcca gcagtcaccc tgcggacggg ccaccagcag    3720
ctcccgggtc tggtgggaca gcagcttcct gggtggtgtg gtacacctgg aggctgggga    3780
gaaggtggtc gtccgtgtgc tggatgaacg cctggttcga ctgcgtgatg gtacccggtc    3840
ttacttcggg gctttcatgg tgggtggagg cggttgcgga aagcgtaagt gagaattcac    3900
```

-continued

```
gcgttaagtc gacaatcaac ctctggatta caaaatttgt gaaagattga ctggtattct    3960
taactatgtt gctcctttta cgctatgtgg atacgctgct ttaatgcctt tgtatcatgc    4020
tattgcttcc cgtatggctt tcattttctc ctccttgtat aaatcctggt tgctgtctct    4080
ttatgaggag ttgtggcccg ttgtcaggca acgtggcgtg gtgtgcactg tgtttgctga    4140 cgcaacccc actggttggg gcattgccac cacctgtcag ctcctttccg ggactttcgc    4200 tttcccctc cctattgcca cggcggaact catcgccgcc tgccttgccc gctgctggac    4260
aggggctcgg ctgttgggca ctgacaattc cgtggtgttg tcgggaaat catcgtcctt    4320 tccttggctg ctcgcctgtg ttgccacctg gattctgcgc gggacgtcct tctgctacgt    4380
cccttcggcc ctcaatccag cggaccttcc ttcccgcggc ctgctgccgg ctctgcggcc    4440
tcttccgcgt cttcgccttc gccctcagac gagtcggatc tccctttggg ccgcctcccc    4500
gcgtcgactt taagaccaat gacggccgca ggaacccta gtgatggagt tggccactcc    4560
ctctctgcgc gctcgctcgc tcactgaggc cgggcgacca aaggtcgccc gacgcccggg    4620
ctttgcccgg gcggcctcag tgagcgagcg agcgcgcagc tgcctgcagg ggcgcctgat    4680
gcggtatttt ctccttacgc atctgtgcgg tatttcacac cgcatacgtc aaagcaacca    4740
tagtacgcgc cctgtagcgg cgcattaagc gcggcgggtg tggtggttac gcgcagcgtg    4800
accgctacac ttgccagcgc cttagcgccc gctcctttcg ctttcttccc ttcctttctc    4860
gccacgttcg ccggctttcc ccgtcaagct ctaaatcggg ggctcccttt agggttccga    4920
tttagtgctt tacggcacct cgaccccaaa aaacttgatt tgggtgatgg ttcacgtagt    4980
gggccatcgc cctgatagac ggtttttcgc cctttgacgt tggagtccac gttctttaat    5040
agtggactct tgttccaaac tggaacaaca ctcaactcta tctcgggcta ttcttttgat    5100
ttataaggga ttttgccgat ttcggtctat tggttaaaaa atgagctgat ttaacaaaaa    5160
tttaacgcga attttaacaa aatattaacg tttacaattt tatggtgcac tctcagtaca    5220
atctgctctg atgccgcata gttaagccag ccccgacacc cgccaacacc cgctgacgcg    5280
ccctgacggg cttgtctgct cccggcatcc gcttacagac aagctgtgac cgtctccggg    5340
agctgcatgt gtcagaggtt ttcaccgtca tcaccgaaac gcgcgagacg aaagggcctc    5400
gtgatacgcc tattttttata ggttaatgtc atgataataa tggtttctta gacgtcaggt    5460 ggcactttc ggggaaatgt gcgcggaacc cctatttgtt tatttttcta aatacattca    5520
aatatgtatc cgctcatgag acaataaccc tgataaatgc ttcaataata ttgaaaaagg    5580
aagagtatga gtattcaaca tttccgtgtc gcccttattc ccttttttgc ggcattttgc    5640
cttcctgttt ttgctcaccc agaaacgctg gtgaaagtaa aagatgctga agatcagttg    5700
ggtgcacgag tgggttacat cgaactggat ctcaacagcg gtaagatcct tgagagtttt    5760
cgccccgaag aacgttttcc aatgatgagc acttttaaag ttctgctatg tggcgcggta    5820
ttatcccgta ttgacgccgg gcaagagcaa ctcggtcgcc gcatacacta ttctcagaat    5880
gacttggttg agtactcacc agtcacagaa aagcatctta cggatggcat gacagtaaga    5940
gaattatgca gtgctgccat aaccatgagt gataacactg cggccaactt acttctgaca    6000
acgatcggag gaccgaagga gctaaccgct tttttgcaca acatggggga tcatgtaact    6060
cgccttgatc gttgggaacc ggagctgaat gaagccatac caaacgacga gcgtgacacc    6120
acgatgcctg tagcaatggc aacaacgttg cgcaaactat taactggcga actacttact    6180
ctagcttccc ggcaacaatt aatagactgg atggaggcgg ataaagttgc aggaccactt    6240
ctgcgctcgg cccttccggc tggctggttt attgctgata aatctggagc cggtgagcgt    6300
```

```
ggaagccgcg gtatcattgc agcactgggg ccagatggta agccctcccg tatcgtagtt      6360
atctacacga cggggagtca ggcaactatg gatgaacgaa atagacagat cgctgagata      6420
ggtgcctcac tgattaagca ttggtaactg tcagaccaag tttactcata tatactttag      6480
attgatttaa aacttcattt ttaatttaaa aggatctagg tgaagatcct ttttgataat      6540
ctcatgacca aaatccctta acgtgagttt tcgttccact gagcgtcaga ccccgtagaa      6600
aagatcaaag gatcttcttg agatcctttt tttctgcgcg taatctgctg cttgcaaaca      6660
aaaaaaccac cgctaccagc ggtggtttgt ttgccggatc aagagctacc aactctttt       6720 ccgaaggtaa ctggcttcag cagagcgcag ataccaaata ctgttcttct agtgtagccg      6780
tagttaggcc accacttcaa gaactctgta gcaccgccta catcctcgc tctgctaatc       6840 ctgttaccag tggctgctgc cagtggcgat aagtcgtgtc ttaccgggtt ggactcaaga      6900
cgatagttac cggataaggc gcagcggtcg ggctgaacgg ggggttcgtg cacacagccc      6960
agcttggagc gaacgaccta caccgaactg agatacctac agcgtgagct atgagaaagc      7020
gccacgcttc ccgaagggag aaaggcggac aggtatccgg taagcggcag ggtcggaaca      7080
ggagagcgca cgagggagct tccaggggga aacgcctggt atctttatag tcctgtcggg      7140
tttcgccacc tctgacttga gcgtcgattt ttgtgatgct cgtcaggggg cggagcccta      7200
tggaaaaacg ccagcaacgc ggcctttta cggttcctgg cctttgctg gcctttgct        7260 cacatgt                                                                7267
```

<210> SEQ ID NO 51
<211> LENGTH: 4619
<212> TYPE: DNA
<213> ORGANISM: Artificial Sequence
<220> FEATURE:
<223> OTHER INFORMATION: pGW145

<400> SEQUENCE: 51

```
cctgcaggca gctgcgcgct cgctcgctca ctgaggccgc ccgggcgtcg ggcgaccttt        60
ggtcgcccgg cctcagtgag cgagcgagcg cgcagagagg gagtggccaa ctccatcact       120
aggggttcct gcggcctcta gaaaggatct gcgatcgctc cggtgcccgt cagtgggcag       180
agcgcacatc gcccacagtc cccgagaagt tggggggagg ggtcggcaat tgaacgggtg       240
cctagagaag gtggcgcggg gtaaactggg aaagtgatgt cgtgtactgg ctccgccttt       300
ttcccgaggg tggggagaa ccgtatataa gtgcagtagt cgccgtgaac gttctttttc        360
gcaacgggtt tgccgccaga acacagctga agcttcgagg ggctcgcatc tctccttcac       420
gcgcccgccg ccctacctga ggccgccatc cacgccggtt gagtcgcgtt ctgccgcctc       480
ccgcctgtgg tgcctcctga actgcgtccg ccgtctaggt aagtttaaag ctcaggtcga      540
gaccgggcct ttgtccggcg ctccttggga gcctacctag actcagccgg ctctccacgc       600
tttgcctgac cctgcttgct caactctacg tctttgtttc gttttctgtt ctgcgccgtt       660
acagatctgg ctaactaccg gtgccaccat gaaatataca agttatatct tggctttca       720 gctctgcatc gtttttgggtt ctcttggctg ttactgccag gacccatatg taaaagaagc      780
agaaaacctt aagaaatatt ttaatgcagg tcattcagat gtagcggata atggaactct       840
tttcttaggc attttgaaga attggaaaga ggagagtgac agaaaaataa tgcagagcca       900
aattgtctcc ttttacttca aactttttaa aaactttaaa gatgaccaga gcatccaaaa       960
gagtgtggag accatcaagg aagacatgaa tgtcaagttt tcaatagca acaaaaagaa      1020
```

-continued

```
acgagatgac ttcgaaaagc tgactaatta ttcggtaact gacttgaatg tccaacgcaa   1080
agcaatacat gaactcatcc aagtgatggc tgaactgtcg ccagcagcta aaacagggaa   1140
gcgaaaaagg agtcagatgc tgtttcgagg tcgaagagca tcccagtgag aattcacgcg   1200
ttaagtcgac aatcaacctc tggattacaa aatttgtgaa agattgactg gtattcttaa   1260
ctatgttgct cctttttacgc tatgtggata cgctgcttta atgcctttgt atcatgctat   1320
tgcttcccgt atggctttca ttttctcctc cttgtataaa tcctggttgc tgtctcttta   1380
tgaggagttg tggcccgttg tcaggcaacg tggcgtggtg tgcactgtgt ttgctgacgc   1440 aaccccccact ggttggggca ttgccaccac ctgtcagctc ctttccggga ctttcgcttt   1500
ccccctccct attgccacgg cggaactcat cgccgcctgc cttgcccgct gctggacagg   1560
ggctcggctg ttgggcactg acaattccgt ggtgttgtcg gggaaatcat cgtcctttcc   1620
ttggctgctc gcctgtgttg ccacctggat tctgcgcggg acgtccttct gctacgtccc   1680
ttcggccctc aatccagcgg accttccttc ccgcggcctg ctgccggctc tgcggcctct   1740
tccgcgtctt cgccttcgcc ctcagacgag tcggatctcc ctttgggccg cctccccgcg   1800
tcgactttaa gaccaatgac ggccgaataa aagatcttta ttttcattag atctgtgtgt   1860
tggttttttg tgtgcggccg caggaacccc tagtgatgga gttggccact ccctctctgc   1920
gcgctcgctc gctcactgag gccgggcgac caaaggtcgc ccgacgcccg ggctttgccc   1980
gggcggcctc agtgagcgag cgagcgcgca gctgcctgca ggggcgcctg atgcggtatt   2040
ttctccttac gcatctgtgc ggtatttcac accgcatacg tcaaagcaac catagtacgc   2100
gccctgtagc ggcgcattaa gcgcggcggg tgtggtggtt acgcgcagcg tgaccgctac   2160
acttgccagc gccttagcgc ccgctccttt cgctttcttc ccttcctttc tcgccacgtt   2220
cgccggcttt ccccgtcaag ctctaaatcg ggggctccct ttagggttcc gatttagtgc   2280
tttacggcac ctcgacccca aaaaacttga tttgggtgat ggttcacgta gtgggccatc   2340
gccctgatag acggtttttc gcccttgac gttggagtcc acgttcttta atagtggact   2400
cttgttccaa actggaacaa cactcaactc tatctcgggc tattcttttg atttataagg   2460
gattttgccg atttcggtct attggttaaa aaatgagctg atttaacaaa aatttaacgc   2520
gaattttaac aaaatattaa cgtttacaat tttatggtgc actctcagta caatctgctc   2580
tgatgccgca tagttaagcc agccccgaca cccgccaaca cccgctgacg cgccctgacg   2640
ggcttgtctg ctcccggcat ccgcttacag acaagctgtg accgtctccg ggagctgcat   2700
gtgtcagagg ttttcaccgt catcaccgaa acgcgcgaga cgaaagggcc tcgtgatacg   2760
cctattttta taggttaatg tcatgataat aatggtttct tagacgtcag gtggcacttt   2820
tcggggaaat gtgcgcggaa cccctatttg tttatttttc taaatacatt caaatatgta   2880
tccgctcatg agacaataac cctgataaat gcttcaataa tattgaaaaa ggaagagtat   2940
gagtattcaa catttccgtg tcgcccttat tccctttttt gcggcatttt gccttcctgt   3000
ttttgctcac ccagaaacgc tggtgaaagt aaaagatgct gaagatcagt tgggtgcacg   3060
agtgggttac atcgaactgg atctcaacag cggtaagatc cttgagagtt ttcgccccga   3120
agaacgtttt ccaatgatga gcacttttaa agttctgcta tgtggcgcgg tattatcccg   3180
tattgacgcc gggcaagagc aactcggtcg ccgcatacac tattctcaga atgacttggt   3240
tgagtactca ccagtcacag aaaagcatct tacggatggc atgacagtaa gagaattatg   3300
cagtgctgcc ataaccatga gtgataacac tgcggccaac ttacttctga caacgatcgg   3360
aggaccgaag gagctaaccg cttttttgca aacatggggg gatcatgtaa ctcgccttga   3420
```

-continued

```
tcgttgggaa ccggagctga atgaagccat accaaacgac gagcgtgaca ccacgatgcc      3480
tgtagcaatg gcaacaacgt tgcgcaaact attaactggc gaactactta ctctagcttc      3540
ccggcaacaa ttaatagact ggatggaggc ggataaagtt gcaggaccac ttctgcgctc      3600
ggcccttccg gctggctggt ttattgctga taaatctgga gccggtgagc gtggaagccg      3660
cggtatcatt gcagcactgg ggccagatgg taagccctcc cgtatcgtag ttatctacac      3720
gacggggagt caggcaacta tggatgaacg aaatagacag atcgctgaga taggtgcctc      3780
actgattaag cattggtaac tgtcagacca agtttactca tatatacttt agattgattt      3840
aaaacttcat ttttaattta aaaggatcta ggtgaagatc cttttttgata atctcatgac      3900 caaaatccct taacgtgagt tttcgttcca ctgagcgtca accccgtag aaaagatcaa       3960 aggatcttct tgagatcctt tttttctgcg cgtaatctgc tgcttgcaaa caaaaaaacc      4020
accgctacca gcggtggttt gtttgccgga tcaagagcta ccaactcttt ttccgaaggt      4080
aactggcttc agcagagcgc agataccaaa tactgttctt ctagtgtagc cgtagttagg      4140
ccaccacttc aagaactctg tagcaccgcc tacatacctc gctctgctaa tcctgttacc      4200
agtggctgct gccagtggcg ataagtcgtg tcttaccggg ttggactcaa gacgatagtt      4260
accggataag gcgcagcggt cgggctgaac ggggggttcg tgcacacagc ccagcttgga      4320
gcgaacgacc tacaccgaac tgagatacct acagcgtgag ctatgagaaa gcgccacgct      4380
tcccgaaggg agaaaggcgg acaggtatcc ggtaagcggc agggtcggaa caggagagcg      4440
cacgagggag cttccagggg gaaacgcctg gtatctttat agtcctgtcg ggtttcgcca      4500
cctctgactt gagcgtcgat ttttgtgatg ctcgtcaggg gggcggagcc tatggaaaaa      4560
cgccagcaac gcggcctttt tacggttcct ggccttttgc tggccttttg ctcacatgt       4619
```

<210> SEQ ID NO 52
<211> LENGTH: 5105
<212> TYPE: DNA
<213> ORGANISM: Artificial Sequence
<220> FEATURE:
<223> OTHER INFORMATION: pGW146

<400> SEQUENCE: 52

```
cctgcaggca gctgcgcgct cgctcgctca ctgaggccgc ccgggcgtcg ggcgaccttt        60
ggtcgcccgg cctcagtgag cgagcgagcg cgcagagagg gagtggccaa ctccatcact       120
aggggttcct gcggcctcta gaaaggatct gcgatcgctc cggtgcccgt cagtgggcag       180
agcgcacatc gcccacagtc cccgagaagt tggggggagg ggtcggcaat tgaacgggtg       240
cctagagaag gtggcgcggg gtaaactggg aaagtgatgt cgtgtactgg ctccgccttt       300
ttcccgaggt gggggagaa ccgtatataa gtgcagtagt cgccgtgaac gttcttttc        360 gcaacgggtt tgccgccaga acacagctga agcttcgagg ggctcgcatc tctccttcac       420
gcgcccgccg ccctacctga ggccgccatc cacgccggtt gagtcgcgtt ctgccgcctc       480
ccgcctgtgg tgcctcctga actgcgtccg ccgtctaggt aagtttaaag ctcaggtcga       540
gaccgggcct ttgtccggcg ctcccttgga gcctacctag actcagccgg ctctccacgc       600
tttgcctgac cctgcttgct caactctacg tctttgtttc gttttctgtt ctgcgccgtt       660
acagatctgg ctaactaccg gtgccaccat gtgtcaccag cagttggtca tctcttggtt       720
ttccctggtt tttctggcat ctcccctcgt ggccatatgg gaactgaaga agatgtttta      780
tgtcgtagaa ttggattggt atccggatgc ccctggagaa atggtggtcc tcacctgtga      840
```

-continued

```
cacccctgaa gaagatggta tcacctggac cttggaccag agcagtgagg tcttaggctc      900
tggcaaaacc ctgaccatcc aagtcaaaga gtttggagat gctggccagt acacctgtca      960
caaaggaggc gaggttctaa gccattcgct cctgctgctt cacaaaaagg aagatggaat     1020
ttggtccact gatattttaa aggaccagaa agaacccaaa aataagacct ttctaagatg     1080
cgaggccaag aattattctg gacgtttcac ctgctggtgg ctgacgacaa tcagtactga     1140
tttgacattc agtgtcaaaa gcagcagagg ctcttctgac ccccaagggg tgacgtgcgg     1200
agctgctaca ctctctgcag agagagtcag aggggacaac aaggagtatg agtactcagt     1260
ggagtgccag gaggacagtg cctgcccagc tgctgaggag agtctgccca ttgaggtcat     1320
ggtggatgcc gttcacaagc tcaagtatga aaactacacc agcagcttct tcatcaggga     1380
catcatcaaa cctgacccac ccaagaactt gcagctgaag ccattaaaga attctcggca     1440
ggtggaggtc agctgggagt accctgacac ctggagtact ccacattcct acttctccct     1500
gacattctgc gttcaggtcc agggcaagag caagagagaa aagaaagata gagtcttcac     1560
ggacaagacc tcagccacgg tcatctgccg caaaaatgcc agcattagcg tgcgggccca     1620
ggaccgctac tatagctcat cttggagcga atgggcatct gtgccctgca gttgagaatt     1680
cacgcgttaa gtcgacaatc aacctctgga ttacaaaatt tgtgaaagat tgactggtat     1740
tcttaactat gttgctcctt ttacgctatg tggatacgct gctttaatgc ctttgtatca     1800
tgctattgct tcccgtatgg ctttcatttt ctcctccttg tataaatcct ggttgctgtc     1860
tctttatgag gagttgtggc ccgttgtcag gcaacgtggc gtggtgtgca ctgtgtttgc     1920
tgacgcaacc cccactggtt ggggcattgc caccacctgt cagctccttt ccgggacttt     1980
cgctttcccc ctccctattg ccacggcgga actcatcgcc gcctgccttg cccgctgctg     2040
gacagggggc cggctgttgg gcactgacaa ttccgtggtg ttgtcgggga aatcatcgtc     2100
ctttccttgg ctgctcgcct gtgttgccac ctggattctg cgcgggacgt ccttctgcta     2160
cgtcccttcg ccctcaatc cagcggacct tccttcccgc ggcctgctgc cggctctgcg     2220
gcctcttccg cgtcttcgcc ttcgccctca gacgagtcgg atctcccttt gggccgcctc     2280
cccgcgtcga ctttaagacc aatgacggcc gaataaaaga tctttatttt cattagatct     2340
gtgtgttggt tttttgtgtg cggccgcagg aacccctagt gatggagttg gccactccct     2400
ctctgcgcgc tcgctcgctc actgaggccg ggcgaccaaa ggtcgcccga cgcccgggct     2460
ttgcccgggc ggcctcagtg agcgagcgag cgcgcagctg cctgcagggg cgcctgatgc     2520
ggtattttct ccttacgcat ctgtgcggta tttcacaccg catacgtcaa agcaaccata     2580
gtacgcgccc tgtagcggcg cattaagcgc ggcgggtgtg gtggttacgc gcagcgtgac     2640
cgctacactt gccagcgcct tagcgcccgc tcctttcgct ttcttccctt cctttctcgc     2700
cacgttcgcc ggctttcccc gtcaagctct aaatcggggg ctccctttag ggttccgatt     2760
tagtgcttta cggcacctcg accccaaaaa acttgatttg ggtgatggtt cacgtagtgg     2820
gccatcgccc tgatagacgg tttttcgccc tttgacgttg gagtccacgt tctttaatag     2880
tggactcttg ttccaaactg gaacaacact caactctatc tcgggctatt cttttgattt     2940
ataagggatt ttgccgattt cggtctattg gttaaaaaat gagctgattt aacaaaaatt     3000
taacgcgaat tttaacaaaa tattaacgtt tacaattttt ggtgcactc tcagtacaat     3060 ctgctctgat gccgcatagt taagccagcc ccgacacccg ccaacacccg ctgacgcgcc     3120
ctgacgggct tgtctgctcc cggcatccgc ttacagacaa gctgtgaccg tctccgggag     3180
ctgcatgtgt cagaggtttt caccgtcatc accgaaacgc gcgagacgaa agggcctcgt     3240
```

-continued

```
gatacgccta tttttatagg ttaatgtcat gataataatg gtttcttaga cgtcaggtgg      3300
cacttttcgg ggaaatgtgc gcggaacccc tatttgttta tttttctaaa tacattcaaa      3360
tatgtatccg ctcatgagac aataaccctg ataaatgctt caataatatt gaaaaaggaa      3420
gagtatgagt attcaacatt tccgtgtcgc ccttattccc ttttttgcgg cattttgcct      3480
tcctgttttt gctcacccag aaacgctggt gaaagtaaaa gatgctgaag atcagttggg      3540
tgcacgagtg ggttacatcg aactggatct caacagcggt aagatccttg agagttttcg      3600
ccccgaagaa cgttttccaa tgatgagcac ttttaaagtt ctgctatgtg gcgcggtatt      3660
atcccgtatt gacgccgggc aagagcaact cggtcgccgc atacactatt ctcagaatga      3720
cttggttgag tactcaccag tcacagaaaa gcatcttacg gatggcatga cagtaagaga      3780
attatgcagt gctgccataa ccatgagtga taacactgcg gccaacttac ttctgacaac      3840
gatcggagga ccgaaggagc taaccgcttt tttgcacaac atgggggatc atgtaactcg      3900
ccttgatcgt tgggaaccgg agctgaatga agccatacca aacgacgagc gtgacaccac      3960
gatgcctgta gcaatggcaa caacgttgcg caaactatta actggcgaac tacttactct      4020
agcttcccgg caacaattaa tagactggat ggaggcggat aaagttgcag gaccacttct      4080
gcgctcggcc cttccggctg gctggtttat tgctgataaa tctggagccg gtgagcgtgg      4140
aagccgcggt atcattgcag cactggggcc agatggtaag ccctcccgta tcgtagttat      4200
ctacacgacg gggagtcagg caactatgga tgaacgaaat agacagatcg ctgagatagg      4260
tgcctcactg attaagcatt ggtaactgtc agaccaagtt tactcatata ctttttagat      4320
tgatttaaaa cttcattttt aatttaaaag gatctaggtg aagatccttt ttgataatct      4380
catgaccaaa atcccttaac gtgagttttc gttccactga gcgtcagacc ccgtagaaaa      4440
gatcaaagga tcttcttgag atccttttttt tctgcgcgta atctgctgct tgcaaacaaa      4500
aaaaccaccg ctaccagcgg tggtttgttt gccggatcaa gagctaccaa ctctttttcc      4560
gaaggtaact ggcttcagca gagcgcagat accaaatact gttcttctag tgtagccgta      4620
gttaggccac cacttcaaga actctgtagc accgcctaca tacctcgctc tgctaatcct      4680
gttaccagtg gctgctgcca gtggcgataa gtcgtgtctt accgggttgg actcaagacg      4740
atagttaccg gataaggcgc agcggtcggg ctgaacgggg ggttcgtgca cacagcccag      4800
cttggagcga acgacctaca ccgaactgag atacctacag cgtgagctat gagaaagcgc      4860
cacgcttccc gaagggagaa aggcggacag gtatccggta agcggcaggg tcggaacagg      4920
agagcgcacg agggagcttc caggggggaaa cgcctggtat cttttatagtc ctgtcgggtt      4980 tcgccacctc tgacttgagc gtcgattttt gtgatgctcg tcaggggggc ggagcctatg      5040
gaaaaacgcc agcaacgcgg cctttttacg gttcctggcc ttttgctggc cttttgctca      5100
catgt                                                                   5105
```

<210> SEQ ID NO 53
<211> LENGTH: 4883
<212> TYPE: DNA
<213> ORGANISM: Artificial Sequence
<220> FEATURE:
<223> OTHER INFORMATION: pGW147

<400> SEQUENCE: 53

```
cctgcaggca gctgcgcgct cgctcgctca ctgaggccgc ccgggcgtcg ggcgaccttt       60
ggtcgcccgg cctcagtgag cgagcgagcg cgcagagagg gagtggccaa ctccatcact      120
```

-continued

```
aggggttcct gcggcctcta gaaaggatct gcgatcgctc cggtgcccgt cagtgggcag      180
agcgcacatc gcccacagtc cccgagaagt tggggggagg ggtcggcaat tgaacgggtg      240
cctagagaag gtggcgcggg gtaaactggg aaagtgatgt cgtgtactgg ctccgccttt      300
ttcccgaggg tggggggagaa ccgtatataa gtgcagtagt cgccgtgaac gttcttttttc      360 gcaacgggtt tgccgccaga acacagctga agcttcgagg ggctcgcatc tctccttcac      420
gcgcccgccg ccctacctga ggccgccatc cacgccggtt gagtcgcgtt ctgccgcctc      480
ccgcctgtgg tgcctcctga actgcgtccg ccgtctaggt aagtttaaag ctcaggtcga      540
gaccgggcct ttgtccggcg ctcccttgga gcctacctag actcagccgg ctctccacgc      600
tttgcctgac cctgcttgct caactctacg tctttgtttc gttttctgtt ctgcgccgtt      660
acagatctgg ctaactaccg gtgccaccat ggaatacgcc tctgacgctt cactggaccc      720
cgaagccccg tggcctcccg cgccccgcgc tcgcgcctgc cgcgtactgc cttgggccct      780
ggtcgcgggg ctgctgctgc tgctgctgct cgctgccgcc tgcgccgtct tcctcgcctg      840
cccctgggcc gtgtccgggg ctcgcgcctc gcccggctcc gcggccagcc cgagactccg      900
cgagggtccc gagctttcgc ccgacgatcc cgccggcctc ttggacctgc ggcagggcat      960
gtttgcgcag ctggtggccc aaaatgttct gctgatcgat gggcccctga gctggtacag     1020
tgacccaggc ctggcaggcg tgtccctgac gggggggcctg agctacaaag aggacacgaa     1080
ggagctggtg gtgccaaagg ctggagtcta ctatgtcttc tttcaactag agctgcggcg     1140
cgtggtggcc ggcgagggct caggctccgt ttcacttgcg ctgcacctgc agccactgcg     1200
ctctgctgct ggggccgccg ccctggcttt gaccgtggac ctgccacccg cctcctccga     1260
ggctcggaac tcggccttcg gtttccaggg ccgcttgctg cacctgagtg ccggccagcg     1320
cctgggcgtc catcttcaca ctgaggccag ggcacgccat gcctggcagc ttacccaggg     1380
cgccacagtc ttgggactct tccgggtgac ccccgaaatc ccagccggac tcccttcacc     1440
gaggtcggaa tgagaattca cgcgttaagt cgacaatcaa cctctggatt acaaaatttg     1500
tgaaagattg actggtattc ttaactatgt tgctcctttt acgctatgtg gatacgctgc     1560
tttaatgcct ttgtatcatg ctattgcttc ccgtatggct ttcattttct cctccttgta     1620
taaatcctgg ttgctgtctc tttatgagga gttgtggccc gttgtcaggc aacgtggcgt     1680
ggtgtgcact gtgtttgctg acgcaacccc cactggttgg ggcattgcca ccacctgtca     1740
gctcctttcc gggactttcg ctttccccct ccctattgcc acggcggaac tcatcgccgc     1800
ctgccttgcc cgctgctgga caggggctcg gctgttgggc actgacaatt ccgtggtgtt     1860
gtcggggaaa tcatcgtcct ttccttggct gctcgcctgt gttgccacct ggattctgcg     1920
cgggacgtcc ttctgctacg tcccttcggc cctcaatcca gcggaccttc cttcccgcgg     1980
cctgctgccg gctctgcggc ctcttccgcg tcttcgcctt cgccctcaga cgagtcggat     2040
ctccctttgg gccgcctccc cgcgtcgact ttaagaccaa tgacggccga ataaagagatc     2100 tttattttca ttagatctgt gtgttggttt tttgtgtgcg gccgcaggaa cccctagtga     2160
tggagttggc cactccctct ctgcgcgctc gctcgctcac tgaggccggg cgaccaaagg     2220
tcgcccgacg cccgggcttt gcccgggcgg cctcagtgag cgagcgagcg cgcagctgcc     2280
tgcaggggcg cctgatgcgg tattttctcc ttacgcatct gtgcggtatt tcacaccgca     2340
tacgtcaaag caaccatagt acgcgccctg tagcggcgca ttaagcgcgg cgggtgtggt     2400
ggttacgcgc agcgtgaccg ctacacttgc cagcgcctta cgcccgctc ctttcgcttt     2460 cttcccttcc tttctcgcca cgttcgccgg ctttccccgt caagctctaa atcgggggct     2520
```

-continued

```
ccctttaggg ttccgattta gtgctttacg gcacctcgac cccaaaaaac ttgatttggg   2580
tgatggttca cgtagtgggc catcgccctg atagacggtt tttcgccctt tgacgttgga   2640
gtccacgttc tttaatagtg gactcttgtt ccaaactgga acaacactca actctatctc   2700
gggctattct tttgatttat aagggatttt gccgatttcg gtctattggt taaaaaatga   2760
gctgatttaa caaaaattta acgcgaattt taacaaaata ttaacgttta caattttatg   2820
gtgcactctc agtacaatct gctctgatgc cgcatagtta agccagcccc gacacccgcc   2880
aacacccgct gacgcgccct gacgggcttg tctgctcccg gcatccgctt acagacaagc   2940
tgtgaccgtc tccgggagct gcatgtgtca gaggttttca ccgtcatcac cgaaacgcgc   3000
gagacgaaag ggcctcgtga tacgcctatt tttataggtt aatgtcatga taataatggt   3060
ttcttagacg tcaggtggca cttttcgggg aaatgtgcgc ggaacccta tttgtttatt    3120 tttctaaata cattcaaata tgtatccgct catgagacaa taaccctgat aaatgcttca   3180
ataatattga aaaaggaaga gtatgagtat tcaacatttc cgtgtcgccc ttattccctt   3240
ttttgcggca ttttgccttc ctgtttttgc tcacccagaa acgctggtga agtaaaaga    3300 tgctgaagat cagttgggtg cacgagtggg ttacatcgaa ctggatctca acagcggtaa   3360
gatccttgag agttttcgcc ccgaagaacg ttttccaatg atgagcactt ttaaagttct   3420
gctatgtggc gcggtattat cccgtattga cgccgggcaa gagcaactcg gtcgccgcat   3480
acactattct cagaatgact tggttgagta ctcaccagtc acagaaaagc atcttacgga   3540
tggcatgaca gtaagagaat tatgcagtgc tgccataacc atgagtgata acactgcggc   3600
caacttactt ctgacaacga tcggaggacc gaaggagcta accgcttttt tgcacaacat   3660
gggggatcat gtaactcgcc ttgatcgttg ggaaccggag ctgaatgaag ccataccaaa   3720
cgacgagcgt gacaccacga tgcctgtagc aatggcaaca acgttgcgca aactattaac   3780
tggcgaacta cttactctag cttcccggca acaattaata gactggatgg aggcggataa   3840
agttgcagga ccacttctgc gctcggccct tccggctggc tggtttattg ctgataaatc   3900
tggagccggt gagcgtggaa gccgcggtat cattgcagca ctggggccag atggtaagcc   3960
ctcccgtatc gtagttatct acacgacggg gagtcaggca actatggatg aacgaaatag   4020
acagatcgct gagataggtg cctcactgat taagcattgg taactgtcag accaagttta   4080
ctcatatata ctttagattg atttaaaact tcatttttaa tttaaaagga tctaggtgaa   4140 gatcctttt gataatctca tgaccaaaat cccttaacgt gagttttcgt tccactgagc   4200
gtcagacccc gtagaaaaga tcaaaggatc ttcttgagat cctttttttc tgcgcgtaat   4260
ctgctgcttg caaacaaaaa aaccaccgct accagcggtg gtttgtttgc cggatcaaga   4320
gctaccaact ctttttccga aggtaactgg cttcagcaga gcgcagatac caaatactgt   4380
tcttctagtg tagccgtagt taggccacca cttcaagaac tctgtagcac cgcctacata   4440
cctcgctctg ctaatcctgt taccagtggc tgctgccagt ggcgataagt cgtgtcttac   4500
cgggttggac tcaagacgat agttaccgga taaggcgcag cggtcgggct gaacgggggg   4560
ttcgtgcaca cagcccagct tggagcgaac gacctacacc gaactgagat acctacagcg   4620
tgagctatga gaaagcgcca cgcttcccga agggagaaag gcggacaggt atccggtaag   4680
cggcagggtc ggaacaggag agcgcacgag ggagcttcca gggggaaacg cctggtatct   4740
ttatagtcct gtcgggtttc gccacctctg acttgagcgt cgatttttgt gatgctcgtc   4800 agggggggcgg agcctatgga aaaacgccag caacgcggcc tttttacggt tcctggcctt   4860
```

-continued

```
ttgctggcct tttgctcaca tgt                                              4883

<210> SEQ ID NO 54
<211> LENGTH: 4856
<212> TYPE: DNA
<213> ORGANISM: Artificial Sequence
<220> FEATURE:
<223> OTHER INFORMATION: pGW149

<400> SEQUENCE: 54
cctgcaggca gctgcgcgct cgctcgctca ctgaggccgc ccgggcgtcg ggcgaccttt         60
ggtcgcccgg cctcagtgag cgagcgagcg cgcagagagg gagtggccaa ctccatcact        120
aggggttcct gcggcctcta gaaaggatct gcgatcgctc cggtgcccgt cagtgggcag        180
agcgcacatc gcccacagtc cccgagaagt tggggggagg ggtcggcaat tgaacgggtg        240
cctagagaag gtggcgcggg gtaaactggg aaagtgatgt cgtgtactgg ctccgccttt        300
ttcccgaggg tggggagaa ccgtatataa gtgcagtagt cgccgtgaac gttcttttc         360 gcaacgggtt tgccgccaga acacagctga agcttcgagg ggctcgcatc tctccttcac        420
gcgcccgccg ccctacctga ggccgccatc cacgccggtt gagtcgcgtt ctgccgcctc        480
ccgcctgtgg tgcctcctga actgcgtccg ccgtctaggt aagtttaaag ctcaggtcga        540
gaccgggcct ttgtccggcg ctcccttgga gcctacctag actcagccgg ctctccacgc        600
tttgcctgac cctgcttgct caactctacg tctttgtttc gttttctgtt ctgcgccgtt        660
acagatctgg ctaactaccg gtgccaccat ggaggagagt gtcgtacggc cctcagtgtt        720
tgtggtggat ggacagaccg acatcccatt cacgaggctg ggacgaagcc accggagaca        780
gtcgtgcagt gtggcccggg tgggtctggg tctcttgctg ttgctgatgg gggccgggct        840
ggccgtccaa ggctggttcc tcctgcagct gcactggcgt ctaggagaga tggtcacccg        900
cctgcctgac ggacctgcag gctcctggca agagcgaagg tctcacgagg tcaacccagc        960
agcgcatctc acaggggcca actccagctt gaccggcagc ggggggccgc tgttatggga       1020
gactcagctg ggcctggcct tcctgagggg cctcagctac cacgatgggg cccttgtggt       1080
caccaaagct ggctactact acatctactc caaggtgcag ctgggcggtg tgggctgccc       1140
gctgggcctg gccagcacca tcacccacgg cctctacaag cgcacacccc gctaccccga       1200
ggagctggag ctgttggtca gccagcagtc accctgcgga cgggccacca gcagctcccg       1260
ggtctggtgg gacagcagct cctgggtgg tgtggtacac ctggaggctg gggagaaggt       1320
ggtcgtccgt gtgctggatg aacgcctggt tcgactgcgt gatggtaccc ggtcttactt       1380
cggggctttc atggtgggtg gaggcggttg cggaaagcgt aagtgagaat tcacgcgtta       1440
agtcgacaat caacctctgg attacaaaat ttgtgaaaga ttgactggta ttcttaacta       1500
tgttgctcct tttacgctat gtggatacgc tgctttaatg cctttgtatc atgctattgc       1560
ttcccgtatg gctttcattt tctcctcctt gtataaatcc tggttgctgt ctctttatga       1620
ggagttgtgg cccgttgtca ggcaacgtgg cgtggtgtgc actgtgtttg ctgacgcaac       1680
ccccactggt tggggcattg ccaccacctg tcagctcctt tccgggactt tcgctttccc       1740
cctccctatt gccacggcgg aactcatcgc cgcctgcctt gcccgctgct ggacaggggc       1800
tcggctgttg ggcactgaca attccgtggt gttgtcgggg aaatcatcgt cctttccttg       1860
gctgctcgcc tgtgttgcca cctggattct gcgcgggacg tccttctgct acgtcccttc       1920
ggccctcaat ccagcggacc ttccttcccg cggcctgctg ccggctctgc ggcctcttcc       1980
gcgtcttcgc cttcgccctc agacgagtcg gatctccctt tgggccgcct ccccgcgtcg       2040
```

-continued

```
actttaagac caatgacggc cgaataaaag atctttattt tcattagatc tgtgtgttgg   2100
ttttttgtgt gcggccgcag gaacccctag tgatggagtt ggccactccc tctctgcgcg   2160
ctcgctcgct cactgaggcc gggcgaccaa aggtcgcccg acgcccgggc tttgcccggg   2220
cggcctcagt gagcgagcga gcgcgcagct gcctgcaggg gcgcctgatg cggtattttc   2280
tccttacgca tctgtgcggt atttcacacc gcatacgtca aagcaaccat agtacgcgcc   2340
ctgtagcggc gcattaagcg cggcgggtgt ggtggttacg cgcagcgtga ccgctacact   2400
tgccagcgcc ttagcgcccg ctcctttcgc tttcttccct tcctttctcg ccacgttcgc   2460
cggctttccc cgtcaagctc taaatcgggg gctcccttta gggttccgat ttagtgcttt   2520
acggcacctc gaccccaaaa aacttgattt gggtgatggt tcacgtagtg ggccatcgcc   2580
ctgatagacg gttttcgccc tttgacgtt ggagtccacg ttctttaata gtggactctt   2640
gttccaaact ggaacaacac tcaactctat ctcgggctat tcttttgatt tataagggat   2700
tttgccgatt tcggtctatt ggttaaaaaa tgagctgatt taacaaaaat ttaacgcgaa   2760
ttttaacaaa atattaacgt ttacaatttt atggtgcact ctcagtacaa tctgctctga   2820
tgccgcatag ttaagccagc cccgacaccc gccaacaccc gctgacgcgc cctgacgggc   2880
ttgtctgctc ccggcatccg cttacagaca agctgtgacc gtctccggga gctgcatgtg   2940
tcagaggttt tcaccgtcat caccgaaacg cgcgagacga aagggcctcg tgatacgcct   3000
atttttatag gttaatgtca tgataataat ggtttcttag acgtcaggtg cacttttcg   3060 gggaaatgtg cgcggaaccc ctatttgttt attttttctaa atacattcaa atatgtatcc   3120
gctcatgaga caataaccct gataaatgct tcaataatat tgaaaaagga agagtatgag   3180
tattcaacat ttccgtgtcg cccttattcc cttttttgcg gcattttgcc ttcctgtttt   3240
tgctcaccca gaaacgctgg tgaaagtaaa agatgctgaa gatcagttgg gtgcacgagt   3300
gggttacatc gaactggatc tcaacagcgg taagatcctt gagagttttc gccccgaaga   3360
acgttttcca atgatgagca cttttaaagt tctgctatgt ggcgcggtat tatcccgtat   3420
tgacgccggg caagagcaac tcggtcgccg catacactat tctcagaatg acttggttga   3480
gtactcacca gtcacagaaa agcatcttac ggatggcatg acagtaagag aattatgcag   3540
tgctgccata accatgagtg ataacactgc ggccaactta cttctgacaa cgatcggagg   3600
accgaaggag ctaaccgctt ttttgcacaa catgggggat catgtaactc gccttgatcg   3660
ttgggaaccg gagctgaatg aagccatacc aaacgacgag cgtgacacca cgatgcctgt   3720
agcaatggca acaacgttgc gcaaactatt aactggcgaa ctacttactc tagcttcccg   3780
gcaacaatta atagactgga tggaggcgga taaagttgca ggaccacttc tgcgctcggc   3840
ccttccggct ggctggttta ttgctgataa atctggagcc ggtgagcgtg gaagccgcgg   3900
tatcattgca gcactggggc cagatggtaa gccctcccgt atcgtagtta tctacacgac   3960
ggggagtcag gcaactatgg atgaacgaaa tagacagatc gctgagatag gtgcctcact   4020
gattaagcat tggtaactgt cagaccaagt ttactcatat atactttaga ttgatttaaa   4080
acttcatttt taatttaaaa ggatctaggt gaagatcctt tttgataatc tcatgaccaa   4140
aatcccttaa cgtgagtttt cgttccactg agcgtcagac cccgtagaaa agatcaaagg   4200
atcttcttga tcctttttt ttctgcgcgt aatctgctgc ttgcaaacaa aaaaaccacc   4260
gctaccagcg gtggtttgtt tgccggatca gagctacca actctttttc cgaaggtaac   4320
tggcttcagc agagcgcaga taccaaatac tgttcttcta gtgtagccgt agttaggcca   4380
```

-continued

```
ccacttcaag aactctgtag caccgcctac atacctcgct ctgctaatcc tgttaccagt    4440
ggctgctgcc agtggcgata agtcgtgtct taccggggttg gactcaagac gatagttacc    4500
ggataaggcg cagcggtcgg gctgaacggg gggttcgtgc acacagccca gcttggagcg    4560
aacgacctac accgaactga gatacctaca gcgtgagcta tgagaaagcg ccacgcttcc    4620
cgaagggaga aaggcggaca ggtatccggt aagcggcagg gtcggaacag gagagcgcac    4680
gagggagctt ccagggggaa acgcctggta tctttatagt cctgtcgggt ttcgccacct    4740
ctgacttgag cgtcgatttt tgtgatgctc gtcaggggg cggagcctat ggaaaaacgc    4800
cagcaacgcg gcctttttac ggttcctggc cttttgctgg ccttttgctc acatgt       4856
```

```
<210> SEQ ID NO 55
<211> LENGTH: 6914
<212> TYPE: DNA
<213> ORGANISM: Artificial Sequence
<220> FEATURE:
<223> OTHER INFORMATION: pGW036

<400> SEQUENCE: 55
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggcctcta gaaaggatct gcgatcgctc cggtgcccgt cagtgggcag     180
agcgcacatc gcccacagtc cccgagaagt tggggggagg ggtcggcaat tgaacgggtg     240
cctagagaag gtggcgcggg gtaaactggg aaagtgatgt cgtgtactgg ctccgccttt     300
ttcccgaggg tgggggagaa ccgtatataa gtgcagtagt cgccgtgaac gttctttttc     360
gcaacgggtt tgccgccaga acacagctga agcttcgagg ggctcgcatc tctccttcac     420
gcgcccgccg ccctacctga ggccgccatc cacgccggtt gagtcgcgtt ctgccgcctc     480
ccgcctgtgg tgcctcctga actgcgtccg ccgtctaggt aagtttaaag ctcaggtcga     540
gaccgggcct ttgtccggcg ctcccttgga gcctacctag actcagccgg ctctccacgc     600
tttgcctgac cctgcttgct caactctacg tctttgtttc gttttctgtt ctgcgccgtt     660
acagatctgg ctaactaccg gtgccaccat ggccccaaag aagaagcgga aggtcggtat     720
ccacggagtc ccagcagcca agcggaacta catcctgggc ctggccatcg gcatcaccag     780
cgtgggctac ggcatcatcg actacgagac acgggacgtg atcgatgccg gcgtgcggct     840
gttcaaagag gccaacgtgg aaaacaacga gggcaggcgg agcaagagag gcgccagaag     900
gctgaagcgg cggaggcggc atagaatcca gagagtgaag aagctgctgt tcgactacaa     960
cctgctgacc gaccacagcg agctgagcgg catcaacccc tacgaggcca gagtgaaggg    1020
cctgagccag aagctgagcg aggaagagtt ctctgccgcc ctgctgcacc tggccaagag    1080
aagaggcgtg cacaacgtga cgaggtgga agaggacacc ggcaacgagc tgtccaccaa    1140
agagcagatc agccggaaca gcaaggccct ggaagagaaa tacgtggccg aactgcagct    1200
ggaacggctg aagaaagacg cgaagtgcg gggcagcatc aacagattca gaccagcga     1260 ctacgtgaaa gaagccaaac agctgctgaa ggtgcagaag gcctaccacc agctggacca    1320
gagcttcatc gacacctaca tcgacctgct ggaaacccgg cggacctact atgagggacc    1380
tggcgagggc agccccttcg gctggaagga catcaaagaa tggtacgaga tgctgatggg    1440
ccactgcacc tacttccccg aggaactgcg gagcgtgaag tacgcctaca acgccgacct    1500
gtacaacgcc ctgaacgacc tgaacaatct cgtgatcacc agggacgaga acgagaagct    1560
ggaatattac gagaagttcc agatcatcga gaacgtgttc aagcagaaga gaagcccac    1620
```

-continued

```
cctgaagcag atcgccaaag aaatcctcgt gaacgaagag gatattaagg gctacagagt   1680
gaccagcacc ggcaagcccg agttcaccaa cctgaaggtg taccacgaca tcaaggacat   1740
taccgcccgg aaagagatta ttgagaacgc cgagctgctg gatcagattg ccaagatcct   1800
gaccatctac cagagcagcg aggacatcca ggaagaactg accaatctga actccgagct   1860
gacccaggaa gagatcgagc agatctctaa tctgaagggc tataccggca cccacaacct   1920
gagcctgaag gccatcaacc tgatcctgga cgagctgtgg cacaccaacg acaaccagat   1980
cgctatcttc aaccggctga agctggtgcc caagaaggtg gacctgtccc agcagaaaga   2040
gatccccacc accctggtgg acgacttcat cctgagcccc gtcgtgaaga gaagcttcat   2100
ccagagcatc aaagtgatca acgccatcat caagaagtac ggcctgccca acgacatcat   2160
tatcgagctg gcccgcgaga agaactccaa ggacgcccag aaaatgatca acgagatgca   2220
gaagcggaac cggcagacca acgagcggat cgaggaaatc atccggacca ccggcaaaga   2280
gaacgccaag tacctgatcg agaagatcaa gctgcacgac atgcaggaag gcaagtgcct   2340
gtacagcctg gaagccatcc ctctggaaga tctgctgaac aaccccttca actatgaggt   2400
ggaccacatc atccccagaa gcgtgtcctt cgacaacagc ttcaacaaca aggtgctcgt   2460
gaagcaggaa gaagccagca agaaagggca accggacccca ttccagtacc tgagcagcag   2520
cgacagcaag atcagctacg aaaccttcaa gaagcacatc ctgaatctgg ccaagggcaa   2580
gggcagaatc agcaagacca agaaagagta tctgctggaa gaacgggaca tcaacaggtt   2640
ctccgtgcag aaagacttca tcaaccggaa cctggtggat accagatacg ccaccagagg   2700
cctgatgaac ctgctgcgga gctacttcag agtgaacaac ctggacgtga aagtgaagtc   2760
catcaatggc ggcttcacca gctttctgcg gcggaagtgg aagtttaaga aagagcggaa   2820
caagggntac aagcaccacg ccgaggacgc cctgatcatt gccaacgccg atttcatctt   2880
caaagagtgg aagaaactgg acaaggccaa aaaagtgatg gaaaaccaga tgttcgagga   2940
aaagcaggcc gagagcatgc ccgagatcga aaccgagcag gagtacaaag agatcttcat   3000 cacccccccac cagatcaagc acattaagga cttcaaggac tacaagtaca gccaccgggt   3060
ggacaagaag cctaatagag agctgattaa cgacaccctg tactccaccc ggaaggacga   3120
caagggcaac accctgatcg tgaacaatct gaacggcctg tacgacaagg acaatgacaa   3180
gctgaaaaag ctgatcaaca gagcccccga aaagctgctg atgtaccacc acgaccccca   3240
gacctaccag aaactgaagc tgattatgga acagtacggc gacgagaaga tcccctgta   3300 caagtactac gaggaaaccg ggaactacct gaccaagtac tccaaaaagg acaacggccc   3360
cgtgatcaag aagattaagt attacggcaa caaactgaac gcccatctgg acatcaccga   3420
cgactacccc aacagcagaa acaaggtcgt gaagctgtcc ctgaagcct acagattcga   3480 cgtgtacctg gacaatggcg tgtacaagtt cgtgaccgtg aagaatctgg atgtgatcaa   3540
aaaagaaaac tactacgaag tgaatagcaa gtgctatgag gaagctaaga gctgaagaa   3600 gatcagcaac caggccgagt ttatcgcctc cttctacaac aacgatctga tcaagatcaa   3660
cggcgagctg tatagagtga tcggcgtgaa caacgacctg ctgaaccgga tcgaagtgaa   3720
catgatcgac atcacctacc gcgagtacct ggaaaacatg aacgacaaga gcccccccag   3780
gatcattaag acaatcgcct ccaagacccca gagcattaag aagtacagca cagacattct   3840
gggcaacctg tatgaagtga aatctaagaa gcaccctcag atcatcaaaa agggcaaaag   3900
gccggcggcc acgaaaaagg ccggccaggc aaaaaagaaa aagggatccg gacgggctga   3960
```

-continued

```
cgcattggac gattttgatc tggatatgct gggaagtgac gccctcgatg attttgacct    4020
tgacatgctt ggttcggatg cccttgatga ctttgacctc gacatgctcg gcagtgacgc    4080
ccttgatgat ttcgacctgg acatgctgat ttaagaattc aataaaagat ctttattttc    4140
attagatctg tgtgttggtt ttttgtgtgc ggccgcagga acccctagtg atggagttgg    4200
ccactccctc tctgcgcgct cgctcgctca ctgaggccgg cgaccaaag gtcgcccgac      4260 gcccgggctt tgcccgggcg gcctcagtga gcgagcgagc gcgcagctgc ctgcaggggc    4320
gcctgatgcg gtattttctc cttacgcatc tgtgcggtat ttcacaccgc atacgtcaaa    4380
gcaaccatag tacgcgccct gtagcggcgc attaagcgcg gcgggtgtgg tggttacgcg    4440
cagcgtgacc gctacacttg ccagcgccct agcgcccgct cctttcgctt tcttcccttc    4500
ctttctcgcc acgttcgccg gctttccccg tcaagctcta aatcgggggc tccctttagg    4560
gttccgattt agtgctttac ggcacctcga ccccaaaaaa cttgatttgg gtgatggttc    4620
acgtagtggg ccatcgccct gatagacggt ttttcgccct ttgacgttgg agtccacgtt    4680
ctttaatagt ggactcttgt tccaaactgg aacaacactc aactctatct cgggctattc    4740
ttttgattta aagggatttt gccgatttc ggtctattgg ttaaaaaatg agctgattta     4800
acaaaaattt aacgcgaatt ttaacaaaat attaacgttt acaattttat ggtgcactct    4860
cagtacaatc tgctctgatg ccgcatagtt aagccagccc cgacacccgc caacacccgc    4920
tgacgcgccc tgacgggctt gtctgctccc ggcatccgct tacagacaag ctgtgaccgt    4980
ctccgggagc tgcatgtgtc agaggttttc accgtcatca ccgaaacgcg cgagacgaaa    5040
gggcctcgtg atacgcctat ttttataggt taatgtcatg ataataatgg tttcttagac    5100
gtcaggtggc acttttcggg gaaatgtgcg cggaacccct atttgtttat ttttctaaat    5160
acattcaaat atgtatccgc tcatgagaca ataaccctga taaatgcttc aataatattg    5220
aaaaaggaag agtatgagta ttcaacattt ccgtgtcgcc cttattccct ttttttgcggc   5280 attttgcctt cctgttttg ctcacccaga aacgctggtg aaagtaaaag atgctgaaga     5340
tcagttgggt gcacgagtgg gttacatcga actggatctc aacagcggta agatccttga    5400
gagttttcgc cccgaagaac gttttccaat gatgagcact tttaaagttc tgctatgtgg    5460
cgcggtatta tcccgtattg acgccgggca agagcaactc ggtcgccgca tacactattc    5520
tcagaatgac ttggttgagt actcaccagt cacagaaaag catcttacgg atggcatgac    5580
agtaagagaa ttatgcagtg ctgccataac catgagtgat aacactgcgg ccaacttact    5640
tctgacaacg atcggaggac cgaaggagct aaccgctttt ttgcacaaca tgggggatca    5700
tgtaactcgc cttgatcgtt gggaaccgga gctgaatgaa gccataccaa acgacgagcg    5760
tgacaccacg atgcctgtag caatggcaac aacgttgcgc aaactattaa ctggcgaact    5820
acttactcta gcttcccggc aacaattaat agactggatg gaggcggata aagttgcagg    5880
accacttctg cgctcggccc ttccggctgg ctggtttatt gctgataaat ctggagccgg    5940
tgagcgtgga agccgcggta tcattgcagc actggggcca gatggtaagc cctcccgtat    6000
cgtagttatc tacacgacgg ggagtcaggc aactatggat gaacgaaata gacagatcgc    6060
tgagataggt gcctcactga ttaagcattg gtaactgtca gaccaagttt actcatatat    6120
actttagatt gatttaaaac ttcatttta atttaaaagg atctaggtga agatcctttt     6180
tgataatctc atgaccaaaa tcccttaacg tgagttttcg ttccactgag cgtcagaccc    6240
cgtagaaaag atcaaaggat cttcttgaga tccttttttt ctgcgcgtaa tctgctgctt    6300
gcaaacaaaa aaaccaccgc taccagcggt ggtttgtttg ccggatcaag agctaccaac    6360
```

-continued

```
tctttttccg aaggtaactg gcttcagcag agcgcagata ccaaatactg ttcttctagt    6420
gtagccgtag ttaggccacc acttcaagaa ctctgtagca ccgcctacat acctcgctct    6480
gctaatcctg ttaccagtgg ctgctgccag tggcgataag tcgtgtctta ccgggttgga    6540
ctcaagacga tagttaccgg ataaggcgca gcggtcgggc tgaacggggg gttcgtgcac    6600
acagcccagc ttggagcgaa cgacctacac cgaactgaga tacctacagc gtgagctatg    6660
agaaagcgcc acgcttcccg aagggagaaa ggcggacagg tatccggtaa gcggcagggt    6720
cggaacagga gagcgcacga gggagcttcc aggggggaaac gcctggtatc tttatagtcc    6780
tgtcgggttt cgccacctct gacttgagcg tcgattttg tgatgctcgt cagggggggcg    6840 gagcctatgg aaaaacgcca gcaacgcggc cttttttacgg ttcctggcct tttgctggcc    6900
ttttgctcac atgt                                                      6914
```

<210> SEQ ID NO 56
<211> LENGTH: 7454
<212> TYPE: DNA
<213> ORGANISM: Artificial Sequence
<220> FEATURE:
<223> OTHER INFORMATION: pGW011b

<400> SEQUENCE: 56

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgttctag gtcttgaaag gagtgggaat     180
tggctccggt gcccgtcagt gggcagagcg cacatcgccc acagtccccg agaagttggg     240 gggagggggtc ggcaattgat ccggtgccta gagaaggtgg cgcggggtaa actgggaaag     300
tgatgtcgtg tactggctcc gcctttttcc cgagggtggg ggagaaccgt atataagtgc     360
agtagtcgcc gtgaacgttc tttttcgcaa cgggtttgcc gccagaacac aggtgtcgtg     420
acgcgcgtac gtaatacgac tcactatagg gccgccacca tgaaaaggcc ggcggccacg     480
aaaaaggccg gccaggcaaa aaagaaaaag acaagaagt acagcatcgg cctggccatc     540
ggcaccaact ctgtgggctg ggccgtgatc accgacgagt acaaggtgcc cagcaagaaa     600
ttcaaggtgc tgggcaacac cgaccggcac agcatcaaga gaaacctgat cggagccctg     660
ctgttcgaca gcggcgaaac agccgaggcc acccggctga gagaaccgc cagaagaaga     720 tacaccagac ggaagaaccg gatctgctat ctgcaagaga tcttcagcaa cgagatggcc     780
aaggtggacg acagcttctt ccacagactg gaagagtcct tcctggtgga agaggataag     840
aagcacgagc ggcaccccat cttcggcaac atcgtggacg aggtggccta ccacgagaag     900 tacccccacca tctaccacct gagaaagaaa ctggtggaca gcaccgacaa ggccgacctg     960
cggctgatct atctggccct ggcccacatg atcaagttcc ggggccactt cctgatcgag    1020
ggcgacctga accccgacaa cagcgacgtg gacaagctgt tcatccagct ggtgcagacc    1080
tacaaccagc tgttcgagga aaaccccatc aacgccagcg gcgtggacgc caaggccatc    1140
ctgtctgcca gactgagcaa gagcagacgg ctggaaaatc tgatcgccca gctgcccggc    1200
gagaagaaga atggcctgtt cggcaacctg attgccctga gctgggggcct gacccccaac    1260 ttcaagagca acttcgacct ggccgaggat gccaaactgc agctgagcaa ggacacctac    1320
gacgacgacc tggacaacct gctggcccag atcggcgacc agtacgccga cctgtttctg    1380
gccgccaaga acctgtccga cgccatcctg ctgagcgaca tcctgagagt gaacaccgag    1440
```

-continued

```
atcaccaagg cccccctgag cgcctctatg atcaagagat acgacgagca ccaccaggac    1500
ctgaccctgc tgaaagctct cgtgcggcag cagctgcctg agaagtacaa agagattttc    1560
ttcgaccaga gcaagaacgg ctacgccggc tacattgacg gcggagccag ccaggaagag    1620
ttctacaagt tcatcaagcc catcctggaa aagatggacg gcaccgagga actgctcgtg    1680
aagctgaaca gagaggacct gctgcggaag cagcggacct tcgacaacgg cagcatcccc    1740
caccagatcc acctgggaga gctgcacgcc attctgcggc ggcaggaaga tttttaccca    1800
ttcctgaagg acaaccggga aaagatcgag aagatcctga ccttccgcat cccctactac    1860
gtgggccctc tggccagggg aaacagcaga ttcgcctgga tgaccagaaa gagcgaggaa    1920
accatcaccc cctggaactt cgaggaagtg gtggacaagg gcgcttccgc ccagagcttc    1980
atcgagcgga tgaccaactt cgataagaac ctgcccaacg agaaggtgct gcccaagcac    2040
agcctgctgt acgagtactt caccgtgtat aacgagctga ccaaagtgaa atacgtgacc    2100
gagggaatga aaagcccgc cttcctgagc ggcgagcaga aaaaggccat cgtggacctg    2160
ctgttcaaga ccaaccggaa agtgaccgtg aagcagctga agaggacta cttcaagaaa    2220 atcgagtgct tcgactccgt ggaaatctcc ggcgtggaag atcggttcaa cgcctccctg    2280
ggcacatacc acgatctgct gaaaattatc aaggacaag acttcctgga caatgaggaa    2340
aacgaggaca ttctggaaga tatcgtgctg accctgacac tgtttgagga cagagagatg    2400
atcgaggaac ggctgaaaac ctatgcccac ctgttcgacg acaaagtgat gaagcagctg    2460
aagcggcgga gataccccgg ctggggcagg ctgagccgga agctgatcaa cggcatccgg    2520
gacaagcagt ccggcaagac aatcctggat ttcctgaagt ccgacggctt cgccaacaga    2580
aacttcatgc agctgatcca cgacgacagc ctgacctttta aagaggacat ccagaaagcc    2640
caggtgtccg gccagggcga tagcctgcac gagcacattg ccaatctggc cggcagcccc    2700
gccattaaga agggcatcct gcagacagtg aaggtggtgg acgagctcgt gaaagtgatg    2760
ggccggcaca gcccgagaa catcgtgatc gaaatggcca gagagaacca gaccacccag    2820
aagggacaga agaacagccg cgagagaatg aagcggatcg aagagggcat caaagagctg    2880
ggcagccaga tcctgaaaga acaccccgtg gaaaacaccc agctgcagaa cgagaagctg    2940
tacctgtact acctgcagaa tgggcgggat atgtacgtgg accaggaact ggacatcaac    3000
cggctgtccg actacgatgt ggaccacatc gtgcctcaga gctttctgaa ggacgactcc    3060
atcgacaaca aggtgctgac cagaagcgac aaggcccggg gcaagagcga caacgtgccc    3120
tccgaagagg tcgtgaagaa gatgaagaac tactggcggc agctgctgaa cgccaagctg    3180
attacccaga gaaagttcga caatctgacc aaggccgaga gaggcggcct gagcgaactg    3240
gataaggccg gcttcatcaa gagacagctg gtggaaaccc ggcagatcac aaagcacgtg    3300
gcacagatcc tggactcccg gatgaacact aagtacgacg agaatgacaa gctgatccgg    3360
gaagtgaaag tgatcaccct gaagtccaag ctggtgtccg atttccggaa ggatttccag    3420
ttttacaaag tgcgcgagat caacaactac caccacgccc acgacgccta cctgaacgcc    3480
gtcgtgggaa ccgccctgat caaaaagtac cctaagctgg aaagcgagtt cgtgtacggc    3540
gactacaagg tgtacgacgt gcggaagatg atcgccaaga gcgagcagga aatcggcaag    3600
gctaccgcca agtacttctt ctacagcaac atcatgaact ttttcaagac cgagattacc    3660
ctggccaacg gcgagatccg gaagcggcct ctgatcgaga caaacggcga aaccgggggag    3720 atcgtgtggg ataaagggccg ggattttgcc accgtgcgga aagtgctgag catgcccaa    3780 gtgaatatcg tgaaaaagac cgaggtgcag acaggcggct tcagcaaaga gtctatcctg    3840
```

-continued

```
cccaagagga acagcgataa gctgatcgcc agaaagaagg actgggaccc taagaagtac    3900
ggcggcttcg acagccccac cgtggcctat tctgtgctgg tggtggccaa agtggaaaag    3960
ggcaagtcca agaaactgaa gagtgtgaaa gagctgctgg ggatcaccat catggaaaga    4020
agcagcttcg agaagaatcc catcgacttt ctggaagcca agggctacaa agaagtgaaa    4080
aaggacctga tcatcaagct gcctaagtac tccctgttcg agctggaaaa cggccggaag    4140
agaatgctgg cctctgccgg cgaactgcag aagggaaacg aactggccct gccctccaaa    4200
tatgtgaact tcctgtacct ggccagccac tatgagaagc tgaagggctc ccccgaggat    4260
aatgagcaga aacagctgtt tgtggaacag cacaagcact acctggacga gatcatcgag    4320
cagatcagcg agttctccaa gagagtgatc ctggccgacg ctaatctgga caaagtgctg    4380
tccgcctaca acaagcaccg ggataagccc atcagagagc aggccgagaa tatcatccac    4440
ctgtttaccc tgaccaatct gggagcccct gccgccttca agtactttga caccaccatc    4500
gaccggaaga ggtacaccag caccaaagag gtgctggacg ccaccctgat ccaccagagc    4560
atcaccggcc tgtacgagac acggatcgac ctgtctcagc tgggaggcga cagccctaag    4620
aaaaagagga aggtgagctg agaattcaat aaataaaaga tctttatttt cattagatct    4680
gtgtgttggt tttttgtgtg cggaccgagc ggccgcagga acccctagtg atggagttgg    4740
ccactccctc tctgcgcgct cgctcgctca ctgaggccgg gcgaccaaag gtcgcccgac    4800
gcccgggctt tgcccgggcg gcctcagtga gcgagcgagc gcgcagctgc ctgcaggggc    4860
gcctgatgcg gtattttctc cttacgcatc tgtgcggtat ttcacaccgc atacgtcaaa    4920
gcaaccatag tacgcgccct gtagcggcgc attaagcgcg gcgggtgtgg tggttacgcg    4980
cagcgtgacc gctacacttg ccagcgccct agcgcccgct cctttcgctt tcttcccttc    5040
ctttctcgcc acgttcgccg gctttccccg tcaagctcta atcgggggc tccctttagg    5100 gttccgattt agtgctttac ggcacctcga ccccaaaaaa cttgatttgg gtgatggttc    5160
acgtagtggg ccatcgccct gatagacggt ttttcgccct ttgacgttgg agtccacgtt    5220
ctttaatagt ggactcttgt tccaaactgg aacaacactc aaccctatct cgggctattc    5280
ttttgattta taagggattt tgccgatttc ggcctattgg ttaaaaaatg agctgattta    5340
acaaaaattt aacgcgaatt ttaacaaaat attaacgttt acaattttat ggtgcactct    5400
cagtacaatc tgctctgatg ccgcatagtt aagccagccc cgacacccgc caacacccgc    5460
tgacgcgccc tgacgggctt gtctgctccc ggcatccgct tacagacaag ctgtgaccgt    5520
ctccgggagc tgcatgtgtc agaggttttc accgtcatca ccgaaacgcg cgagacgaaa    5580
gggcctcgtg atacgcctat ttttataggt taatgtcatg ataataatgg tttcttagac    5640
gtcaggtggc acttttcggg gaaatgtgcg cggaacccct atttgtttat ttttctaaat    5700
acattcaaat atgtatccgc tcatgagaca ataaccctga taaatgcttc aataatattg    5760
aaaaaggaag agtatgagta ttcaacattt ccgtgtcgcc cttattccct tttttgcggc    5820
attttgcctt cctgtttttg ctcacccaga aacgctggtg aaagtaaaag atgctgaaga    5880
tcagttgggt gcacgagtgg gttacatcga actggatctc aacagcggta agatccttga    5940
gagttttcgc cccgaagaac gttttccaat gatgagcact tttaaagttc tgctatgtgg    6000
cgcggtatta tccgtattg acgccgggca agagcaactc ggtcgccgca tacactattc     6060
tcagaatgac ttggttgagt actcaccagt cacagaaaag catcttacgg atggcatgac    6120
agtaagagaa ttatgcagtg ctgccataac catgagtgat aacactgcgg ccaacttact    6180
```

-continued

```
tctgacaacg atcggaggac cgaaggagct aaccgctttt ttgcacaaca tgggggatca    6240
tgtaactcgc cttgatcgtt gggaaccgga gctgaatgaa gccataccaa acgacgagcg    6300
tgacaccacg atgcctgtag caatggcaac aacgttgcgc aaactattaa ctggcgaact    6360
acttactcta gcttcccggc aacaattaat agactggatg gaggcggata aagttgcagg    6420
accacttctg cgctcggccc ttccggctgg ctggtttatt gctgataaat ctggagccgg    6480
tgagcgtggg tctcgcggta tcattgcagc actggggcca gatggtaagc cctcccgtat    6540
cgtagttatc tacacgacgg ggagtcaggc aactatggat gaacgaaata gacagatcgc    6600
tgagataggt gcctcactga ttaagcattg gtaactgtca gaccaagttt actcatatat    6660
actttagatt gatttaaaac ttcattttta atttaaaagg atctaggtga agatcctttt    6720
tgataatctc atgaccaaaa tcccttaacg tgagttttcg ttccactgag cgtcagaccc    6780
cgtagaaaag atcaaaggat cttcttgaga tcctttttt ctgcgcgtaa tctgctgctt    6840
gcaaacaaaa aaaccaccgc taccagcggt ggtttgtttg ccggatcaag agctaccaac    6900 tcttttttccg aaggtaactg gcttcagcag agcgcagata ccaaatactg tccttctagt    6960
gtagccgtag ttaggccacc acttcaagaa ctctgtagca ccgcctacat acctcgctct    7020
gctaatcctg ttaccagtgg ctgctgccag tggcgataag tcgtgtctta ccgggttgga    7080
ctcaagacga tagttaccgg ataaggcgca gcggtcgggc tgaacggggg gttcgtgcac    7140
acagcccagc ttggagcgaa cgacctacac cgaactgaga tacctacagc gtgagctatg    7200
agaaagcgcc acgcttcccg aagggagaaa ggcggacagg tatccggtaa gcggcagggt    7260
cggaacagga gagcgcacga gggagcttcc agggggaaac gcctggtatc tttatagtcc    7320
tgtcgggttt cgccacctct gacttgagcg tcgatttttg tgatgctcgt caggggggcg    7380
gagcctatgg aaaaacgcca gcaacgcggc ctttttacgg ttcctggcct tttgctggcc    7440
ttttgctcac atgt                                                      7454
```

<210> SEQ ID NO 57
<211> LENGTH: 3997
<212> TYPE: DNA
<213> ORGANISM: Artificial Sequence
<220> FEATURE:
<223> OTHER INFORMATION: pGW089

<400> SEQUENCE: 57

```
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggcctcta gaaaggatct gcgatcgctc cggtgcccgt cagtgggcag     180
agcgcacatc gcccacagtc cccgagaagt tggggggagg ggtcggcaat tgaacgggtg     240
cctagagaag gtggcgcggg gtaaactggg aaagtgatgt cgtgtactgg ctccgccttt     300
ttcccgaggg tgggggagaa ccgtatataa gtgcagtagt cgccgtgaac gttcttttttc     360 gcaacgggtt tgccgccaga acacagctga agcttcgagg ggctcgcatc tctccttcac     420
gcgcccgccg ccctacctga ggccgccatc cacgccggtt gagtcgcgtt ctgccgcctc     480
ccgcctgtgg tgcctcctga actgcgtccg ccgtctaggt aagtttaaag ctcaggtcga     540
gaccgggcct ttgtccggcg ctcccttgga gcctacctag actcagccgg ctctccacgc     600
tttgcctgac cctgcttgct caactctacg tctttgtttc gttttctgtt ctgcgccgtt     660
acagatctgg ctaactaccg gtgccacatg tacagcatgc agctcgcatc ctgtgtcaca     720
ttgacacttg tgctccttgt caacagcgca cccacttcaa gctccacttc aagctctaca     780
```

-continued

```
gcggaagcac agcagcagca gcagcagcag cagcagcagc agcagcacct ggagcagctg      840
ttgatggacc tacaggagct cctgagcagg atggagaatt acaggaacct gaaactcccc      900
aggatgctca ccttcaaatt ttacttgccc aagcaggcca cagaattgaa agatcttcag      960
tgcctagaag atgaacttgg acctctgcgg catgttctgg atttgactca aagcaaaagc     1020
tttcaattgg aagatgctga gaatttcatc agcaatatca gagtaactgt tgtaaaacta     1080
aagggctctg acaacacatt tgagtgccaa ttcgatgatg agtcagcaac tgtggtggac     1140
tttctgagga gatggatagc cttctgtcaa agcatcatct caacaagccc tcaataagaa     1200
ttcaataaaa gatctttatt ttcattagat ctgtgtgttg gttttttgtg tgcggccgca     1260 ggaacccta gtgatggagt tggccactcc ctctctgcgc gctcgctcgc tcactgaggc     1320
cgggcgacca aagtgcgccc gacgcccggg ctttgcccgg gcggcctcag tgagcgagcg     1380
agcgcgcagc tgcctgcagg ggcgcctgat gcggtatttt ctccttacgc atctgtgcgg     1440
tatttcacac cgcatacgtc aaagcaacca tagtacgcgc cctgtagcgg cgcattaagc     1500
gcggcgggtg tggtggttac gcgcagcgtg accgctacac ttgccagcgc cttagcgccc     1560
gctcctttcg ctttcttccc ttcctttctc gccacgttcg ccggctttcc ccgtcaagct     1620
ctaaatcggg ggctcccttt agggttccga tttagtgctt tacggcacct cgaccccaaa     1680
aaacttgatt tgggtgatgg ttcacgtagt gggccatcgc cctgatagac ggtttttcgc     1740
cctttgacgt tggagtccac gttctttaat agtggactct tgttccaaac tggaacaaca     1800
ctcaactcta tctcgggcta ttcttttgat ttataaggga ttttgccgat ttcggtctat     1860
tggttaaaaa atgagctgat ttaacaaaaa tttaacgcga attttaacaa aatattaacg     1920
tttacaattt tatggtgcac tctcagtaca atctgctctg atgccgcata gttaagccag     1980
ccccgacacc cgccaacacc cgctgacgcg ccctgacggg cttgtctgct cccggcatcc     2040
gcttacagac aagctgtgac cgtctccggg agctgcatgt gtcagaggtt ttcaccgtca     2100
tcaccgaaac gcgcgagacg aaagggcctc gtgatacgcc tatttttata ggttaatgtc     2160
atgataataa tggtttctta gacgtcaggt ggcactttc ggggaaatgt gcgcggaacc     2220
cctatttgtt tatttttcta aatacattca aatatgtatc cgctcatgag acaataaccc     2280
tgataaatgc ttcaataata ttgaaaaagg aagagtatga gtattcaaca tttccgtgtc     2340
gcccttattc cctttttgc ggcattttgc cttcctgttt ttgctcaccc agaaacgctg     2400
gtgaaagtaa aagatgctga agatcagttg ggtgcacgag tgggttacat cgaactggat     2460
ctcaacagcg gtaagatcct tgagagtttt cgccccgaag aacgttttcc aatgatgagc     2520
acttttaaag ttctgctatg tggcgcggta ttatcccgta ttgacgccgg gcaagagcaa     2580
ctcggtcgcc gcatacacta ttctcagaat gacttggttg agtactcacc agtcacagaa     2640
aagcatctta cggatggcat gacagtaaga gaattatgca gtgctgccat aaccatgagt     2700
gataacactg cggccaactt acttctgaca acgatcggag gaccgaagga gctaaccgct     2760
tttttgcaca acatggggga tcatgtaact cgccttgatc gttgggaacc ggagctgaat     2820
gaagccatac caaacgacga gcgtgacacc acgatgcctg tagcaatggc aacaacgttg     2880
cgcaaactat taactggcga actacttact ctagcttccc ggcaacaatt aatagactgg     2940
atggaggcgg ataaagttgc aggaccactt ctgcgctcgg cccttccggc tggctggttt     3000
attgctgata atctggagc cggtgagcgt ggaagccgcg gtatcattgc agcactgggg     3060
ccagatggta agccctcccg tatcgtagtt atctacacga cggggagtca ggcaactatg     3120
```

-continued

```
gatgaacgaa atagacagat cgctgagata ggtgcctcac tgattaagca ttggtaactg    3180
tcagaccaag tttactcata tatactttag attgatttaa aacttcattt ttaatttaaa    3240
aggatctagg tgaagatcct ttttgataat ctcatgacca aaatcccttaa cgtgagtttt   3300 tcgttccact gagcgtcaga ccccgtagaa aagatcaaag gatcttcttg agatcctttt   3360
tttctgcgcg taatctgctg cttgcaaaca aaaaaaccac cgctaccagc ggtggtttgt    3420
ttgccggatc aagagctacc aactcttttt ccgaaggtaa ctggcttcag cagagcgcag   3480
ataccaaata ctgttcttct agtgtagccg tagttaggcc accacttcaa gaactctgta   3540
gcaccgccta cataccctgc ctgctaatcc tgttaccag tggctgctgc cagtggcgat     3600
aagtcgtgtc ttaccgggtt ggactcaaga cgatagttac cggataaggc gcagcggtcg    3660
ggctgaacgg ggggttcgtg cacacagccc agcttggagc gaacgaccta caccgaactg    3720
agatacctac agcgtgagct atgagaaagc gccacgcttc ccgaagggag aaaggcggac    3780
aggtatccgg taagcggcag ggtcggaaca ggagagcgca cgagggagct tccagggggga   3840 aacgcctggt atctttatag tcctgtcggg tttcgccacc tctgacttga gcgtcgattt    3900
ttgtgatgct cgtcaggggg gcggagccta tggaaaaacg ccagcaacgc ggcctttttta   3960 cggttcctgg ccttttgctg gccttttgct cacatgt                            3997
```

<210> SEQ ID NO 58
<211> LENGTH: 7319
<212> TYPE: DNA
<213> ORGANISM: Artificial Sequence
<220> FEATURE:
<223> OTHER INFORMATION: pGW094

<400> SEQUENCE: 58

```
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact    120
aggggttcct gcggcctcta gaaaggatct gcgatcgctc cggtgcccgt cagtgggcag    180
agcgcacatc gcccacagtc cccgagaagt tggggggagg ggtcggcaat tgaacgggtg     240
cctagagaag gtggcgcggg gtaaactggg aaagtgatgt cgtgtactgg ctccgccttt    300
ttcccgaggg tggggaggaa ccgtatataa gtgcagtagt cgccgtgaac gttctttttc     360
gcaacgggtt tgccgccaga acacagctga agcttcgagg ggctcgcatc tctccttcac    420
gcgcccgccg ccctacctga ggccgccatc cacgccggtt gagtcgcgtt ctgccgcctc     480
ccgcctgtgg tgcctcctga actgcgtccg ccgtctaggt aagtttaaag ctcaggtcga    540
gaccgggcct ttgtccggcg ctcccttgga gcctacctag actcagccgg ctctccacgc    600
tttgcctgac cctgcttgct caactctacg tctttgtttc gttttctgtt ctgcgccgtt    660
acagatctgg ctaactaccg gtgccaccat gaacgctaca cactgcatct tggctttgca    720
gctcttcctc atggctgttt ctggctgtta ctgccacggc acagtcattg aaagcctaga    780
aagtctgaat aactatttta actcaagtgg catagatgtg gaagaaaaga gtctcttctt    840
ggatatctgg aggaactggc aaaaggatgg tgacatgaaa atcctgcaga gccagattat    900 ctcttctctac ctcagactct ttgaagtctt gaaagacaat caggccatca gcaacaacat    960
aagcgtcatt gaatcacacc tgattactac cttcttcagc aacagcaagg cgaaaaagga   1020
tgcattcatg agtattgcca gtttgaggt caacaaccca caggtccagc gccaagcatt     1080
caatgagctc atccgagtgg tccaccagct gttgccggaa tccagcctca ggaagcgaa    1140 aaggagtcgc tgcggatccg gcgcaacaaa cttctctctg ctgaaacaag ccggagatgt    1200
```

```
cgaagagaat cctggaccga tggcttgcaa ttgtcagttg atgcaggata caccactcct    1260
caagtttcca tgtccaaggc tcattcttct ctttgtgctg ctgattcgtc tttcacaagt    1320
gtcttcagat gttgatgaac aactgtccaa gtcagtgaaa gataaggtat tgctgccttg    1380
ccgttacaac tctcctcatg aagatgagtc tgaagaccga atctactggc aaaaacatga    1440
caaagtggtg ctgtctgtca ttgttgggaa actaaaagtg tggcccgagt ataagaaccg    1500
gactttatat gacaacacta cctactctct tatcatcctg ggcctggtcc tttcagaccg    1560
gggcacatac agctgtgtcg ttcaaaagaa ggaaagagga acgtatgaag ttaaacactt    1620
ggctttagta aagttgtcca tcaaagctga cttctctacc cccaacataa ctgagtctgg    1680
aaacccatct gcagacacta aaaggattac ctgctttgct tccgggggtt tcccaaagcc    1740
tcgcttctct tggttggaaa atggaagaga attacctggc atcaatacga caatttccca    1800
ggatcctgaa tctgaattgt acaccattag tagccaacta gatttcaata cgactcgcaa    1860
ccacaccatt aagtgtctca ttaaatatgg agatgctcac gtgtcagagg acttcacctg    1920
ggaaaaaccc ccagaagacc ctcctgatag caagaacaca cttgtgctct ttggggcagg    1980
attcggcgca gtaataacag tcgtcgtcat cgttgtcatc atcaaatgct ctgtaagca    2040 cagaagctgt ttcagaagaa atgaggcaag cagagaaaca aacaacagcc ttaccttcgg    2100
gcctgaagaa gcattagctg aacagaccgt cttccttcgt acgggcagtg agagggcag    2160 aggaagtctg ctaacatgcg gtgacgtcga ggagaatcct ggcccaatgg agagtgtggt    2220
acagccttca gtgtttgtgg tggatggaca cacggcatc ccattcaggc ggctggaaca    2280
gaaccaccgg agacggcgct gtggcactgt ccaggtcagc ctggccctgg tgctgctgct    2340
aggtgctggg ctggccactc agggctggtt tctcctgaga ctgcatcaac gtcttggaga    2400
catagtagct catctgccag atggaggcaa aggctcctgg gagaagctga tacaagatca    2460
acgatctcac caggccaacc cagcagcaca tcttacagga gccaacgcca gcttgatagg    2520
tattggtgga cctctgttat gggagacacg acttggcctg gccttcttga ggggcttgac    2580
gtatcatgat ggggccctgg tgaccatgga gcccggttac tactatgtgt actccaaagt    2640
gcagctgagc ggcgtgggct gcccccaggg gctggccaat ggcctcccca tcacccatgg    2700
actatacaag cgcacatccc gctacccgaa ggagttagaa ctgctggtca gtcggcggtc    2760
accctgtggc cgggccaaca gctcccgagt ctggtgggac agcagcttcc tgggcggcgt    2820
ggtacatctg gaggctgggg aagaggtggt ggtccgcgtg cctggaaacc gcctggtcag    2880
accacgtgac ggcaccaggt cctatttcgg agctttcatg gtcactagtg gatccggcgc    2940
aacaaacttc tctctgctga aacaagccgg agatgtcgaa gagaatcctg gaccgatgga    3000
ggaaatgcct ttgagagagt caagtcctca aagggcagag aggtgcaaga agtcatggct    3060
cttgtgcata gtggctctgt tactgatgct gctctgttct ttgggtacac tgatctatac    3120
ttcactcaag ccaactgcca tcgagtcctg catggttaag tttgaactat catcctcaaa    3180
atggcacatg acatctccca aacctcactg tgtgaatacg acatctgatg ggaagctgaa    3240
gatactgcag agtggcacat atttaatcta cggccaagtg attcctgtgg ataagaaata    3300
cataaaagac aatgcccct tcgtagtaca gatatataaa aagaatgatg tcctacaaac    3360
tctaatgaat gattttcaaa tcttgcctat aggaggggt tatgaactgc atgctggaga    3420
taacatatat ctgaagttca actctaaaga ccatattcag aaaaataaca catactgggg    3480
gatcatctta atgcctgatc taccattcat ctctgctagc agcggtaccc agtgcaccaa    3540
```

-continued

```
ctacgccctg ctgaagctgg ccggcgatgt ggagagcaac cccgggccca tggaccagca    3600
cacacttgat gtggaggata ccgcggatgc cagacatcca gcaggtactt cgtgcccctc    3660
ggatgcggcg ctcctcagag ataccgggct cctcgcggac gctgcgctcc tctcagatac    3720
tgtgcgcccc acaaatgccg cgctccccac ggatgctgcc taccctgcgg ttaatgttcg    3780
ggatcgcgag gccgcgtggc cgcctgcact gaacttctgt tcccgccacc caaagctcta    3840
tggcctagtc gctttggttt tgctgcttct gatcgccgcc tgtgttccta tcttcacccg    3900
caccgagcct cggccagcgc tcacaatcac cacctcgccc aacctgggta cccgagagaa    3960
taatgcagac caggtcaccc ctgtttccca cattggctgc cccaacacta cacaacaggg    4020
ctctcctgtg ttcgccaagc tactggctaa aaaccaagca tcgttgtgca atacaactct    4080
gaactggcac agccaagatg gagctgggag ctcataccta tctcaaggtc tgaggtacga    4140
agaagacaaa aaggagttgg tggtagacag tcccgggctc tactacgtat ttttggaact    4200
gaagctcagt ccaacattca caaacacagg ccacaaggtg cagggctggg tctctcttgt    4260
tttgcaagca aagcctcagg tagatgactt tgacaacttg gccctgacag tggaactgtt    4320
cccttgctcc atggagaaca gttagtgga ccgttcctgg agtcaactgt tgctcctgaa    4380
ggctggccac cgcctcagtg tgggtctgag ggcttatctg catggagccc aggatgcata    4440
cagagactgg gagctgtctt atcccaacac caccagcttt ggactctttc ttgtgaaacc    4500
cgacaaccca tgggaatgag aattcaataa aagatcttta ttttcattag atctgtgtgt    4560
tggttttttg tgtgcggccg caggaacccc tagtgatgga gttggccact ccctctctgc    4620
gcgctcgctc gctcactgag gccgggcgac caaaggtcgc ccgacgcccg ggctttgccc    4680
gggcggcctc agtgagcgag cgagcgcgca gctgcctgca ggggcgcctg atgcggtatt    4740
ttctccttac gcatctgtgc ggtatttcac accgcatacg tcaaagcaac catagtacgc    4800
gccctgtagc ggcgcattaa gcgcggcggg tgtggtggtt acgcgcagcg tgaccgctac    4860
acttgccagc gccttagcgc ccgctccttt cgctttcttc ccttcctttc tcgccacgtt    4920
cgccggcttt ccccgtcaag ctctaaatcg ggggctccct ttagggttcc gatttagtgc    4980
tttacggcac ctcgacccca aaaaacttga tttgggtgat ggttcacgta gtgggccatc    5040
gccctgatag acggtttttc gccctttgac gttggagtcc acgttcttta atagtggact    5100
cttgttccaa actggaacaa cactcaactc tatctcgggc tattcttttg atttataagg    5160
gattttgccg atttcggtct attggttaaa aaatgagctg atttaacaaa aatttaacgc    5220
gaattttaac aaaatattaa cgtttacaat tttatggtgc actctcagta caatctgctc    5280
tgatgccgca tagttaagcc agccccgaca cccgccaaca cccgctgacg cgccctgacg    5340
ggcttgtctg ctcccggcat ccgcttacag acaagctgtg accgtctccg ggagctgcat    5400
gtgtcagagg ttttcaccgt catcaccgaa acgcgcgaga cgaaagggcc tcgtgatacg    5460
cctattttta taggttaatg tcatgataat aatggtttct tagacgtcag gtggcacttt    5520
tcggggaaat gtgcgcggaa cccctatttg tttatttttc taaatacatt caaatatgta    5580
tccgctcatg agacaataac cctgataaat gcttcaataa tattgaaaaa ggaagagtat    5640
gagtattcaa catttccgtg tcgcccttat tccctttttt gcggcatttt gccttcctgt    5700
ttttgctcac ccagaaacgc tggtgaaagt aaaagatgct gaagatcagt tgggtgcacg    5760
agtgggttac atcgaactgg atctcaacag cggtaagatc cttgagagtt ttcgccccga    5820
agaacgtttt ccaatgatga gcacttttaa agttctgcta tgtggcgcgg tattatcccg    5880
tattgacgcc gggcaagagc aactcggtcg ccgcatacac tattctcaga atgacttggt    5940
```

```
tgagtactca ccagtcacag aaaagcatct tacggatggc atgacagtaa gagaattatg    6000
cagtgctgcc ataaccatga gtgataacac tgcggccaac ttacttctga caacgatcgg    6060
aggaccgaag gagctaaccg ctttttttgca caacatgggg gatcatgtaa ctcgccttga    6120
tcgttgggaa ccggagctga atgaagccat accaaacgac gagcgtgaca ccacgatgcc    6180
tgtagcaatg gcaacaacgt tgcgcaaact attaactggc gaactactta ctctagcttc    6240
ccggcaacaa ttaatagact ggatggaggc ggataaagtt gcaggaccac ttctgcgctc    6300
ggcccttccg gctggctggt ttattgctga taaatctgga gccggtgagc gtggaagccg    6360
cggtatcatt gcagcactgg ggccagatgg taagccctcc cgtatcgtag ttatctacac    6420
gacggggagt caggcaacta tggatgaacg aaatagacag atcgctgaga taggtgcctc    6480
actgattaag cattggtaac tgtcagacca agtttactca tatatacttt agattgattt    6540
aaaacttcat ttttaattta aaaggatcta ggtgaagatc ctttttgata atctcatgac    6600
caaaatccct taacgtgagt tttcgttcca ctgagcgtca gaccccgtag aaaagatcaa    6660
aggatcttct tgagatcctt ttttttctgcg cgtaatctgc tgcttgcaaa caaaaaaacc    6720
accgctacca gcggtggttt gtttgccgga tcaagagcta ccaactcttt ttccgaaggt    6780
aactggcttc agcagagcgc agataccaaa tactgttctt ctagtgtagc cgtagttagg    6840
ccaccacttc aagaactctg tagcaccgcc tacatacctc gctctgctaa tcctgttacc    6900
agtggctgct gccagtggcg ataagtcgtg tcttaccggg ttggactcaa gacgatagtt    6960
accggataag gcgcagcggt cgggctgaac ggggggttcg tgcacacagc ccagcttgga    7020
gcgaacgacc tacaccgaac tgagatacct acagcgtgag ctatgagaaa gcgccacgct    7080
tcccgaaggg agaaaggcgg acaggtatcc ggtaagcggc agggtcggaa caggagagcg    7140
cacgagggag cttccagggg gaaacgcctg gtatctttat agtcctgtcg ggtttcgcca    7200
cctctgactt gagcgtcgat ttttgtgatg ctcgtcaggg gggcggagcc tatggaaaaa    7260
cgccagcaac gcggcctttt tacggttcct ggccttttgc tggccttttg ctcacatgt    7319
```

```
<210> SEQ ID NO 59
<211> LENGTH: 589
<212> TYPE: DNA
<213> ORGANISM: Artificial Sequence
<220> FEATURE:
<223> OTHER INFORMATION: Ori

<400> SEQUENCE: 59
```

```
ttgagatcct ttttttctgc gcgtaatctg ctgcttgcaa acaaaaaaac caccgctacc     60
agcggtggtt tgtttgccgg atcaagagct accaactctt tttccgaagg taactggctt    120
cagcagagcg cagataccaa atactgttct tctagtgtag ccgtagttag gccaccactt    180
caagaactct gtagcaccgc ctacatacct cgctctgcta atcctgttac cagtggctgc    240
tgccagtggc gataagtcgt gtcttaccgg gttggactca agacgatagt taccggataa    300
ggcgcagcgg tcgggctgaa cggggggttc gtgcacacag cccagcttgg agcgaacgac    360
ctacaccgaa ctgagatacc tacagcgtga gctatgagaa agcgccacgc ttcccgaagg    420
gagaaaggcg gacaggtatc cggtaagcgg caggtcgga acaggagagc gcacgaggga    480
gcttccaggg ggaaacgcct ggtatcttta gtcctgtc gggtttcgcc acctctgact    540
tgagcgtcga tttttgtgat gctcgtcagg gggcggagc ctatggaaa                 589
```

```
<210> SEQ ID NO 60
```

<211> LENGTH: 456
<212> TYPE: DNA
<213> ORGANISM: Artificial Sequence
<220> FEATURE:
<223> OTHER INFORMATION: f1Ori

<400> SEQUENCE: 60
acgcgccctg tagcggcgca ttaagcgcgg cgggtgtggt ggttacgcgc agcgtgaccg        60
ctacacttgc cagcgcctta gcgcccgctc ctttcgcttt cttcccttcc tttctcgcca       120
cgttcgccgg ctttccccgt caagctctaa atcgggggct cccctttaggg ttccgattta      180 gtgctttacg gcacctcgac cccaaaaaac ttgatttggg tgatggttca cgtagtgggc       240
catcgccctg atagacggtt tttcgccctt tgacgttgga gtccacgttc tttaatagtg       300
gactcttgtt ccaaactgga acaacactca actctatctc gggctattct tttgatttat       360
aagggatttt gccgatttcg gtctattggt taaaaaatga gctgatttaa caaaaattta       420
acgcgaattt taacaaaata ttaacgttta caattt                                  456

<210> SEQ ID NO 61
<211> LENGTH: 105
<212> TYPE: DNA
<213> ORGANISM: Artificial Sequence
<220> FEATURE:
<223> OTHER INFORMATION: AmpR Promoter

<400> SEQUENCE: 61
cgcggaaccc ctatttgttt attttnctaa atacattcaa atatgtatcc gctcatgaga        60
caataaccct gataaatgct tcaataatat tgaaaaagga agagt                        105

<210> SEQ ID NO 62
<211> LENGTH: 861
<212> TYPE: DNA
<213> ORGANISM: Artificial Sequence
<220> FEATURE:
<223> OTHER INFORMATION: AmpR

<400> SEQUENCE: 62
atgagtattc aacatttccg tgtcgccctt attccctttt ttgcggcatt ttgccttcct        60 gttttttgctc acccagaaac gctggtgaaa gtaaaagatg ctgaagatca gttgggtgca      120
cgagtgggtt acatcgaact ggatctcaac agcggtaaga tccttgagag ttttttcgcccc    180 gaagaacgtt ttccaatgat gagcactttt aaagttctgc tatgtggcgc ggtattatcc       240
cgtattgacg ccgggcaaga gcaactcggt cgccgcatac actattctca gaatgacttg       300
gttgagtact caccagtcac agaaaagcat cttacggatg gcatgacagt aagagaatta       360
tgcagtgctg ccataaccat gagtgataac actgcggcca acttacttct gacaacgatc       420
ggaggaccga aggagctaac cgcttttttg cacaacatgg gggatcatgt aactcgcctt       480
gatcgttggg aaccggagct gaatgaagcc ataccaaacg acgagcgtga caccacgatg       540
cctgtagcaa tggcaacaac gttgcgcaaa ctattaactg gcgaactact tactctagct       600
tcccggcaac aattaataga ctggatggag gcggataaag ttgcaggacc acttctgcgc       660
tcggcccttc cggctggctg gtttattgct gataaatctg gagccggtga gcgtggaagc       720
cgcggtatca ttgcagcact ggggccagat ggtaagccct cccgtatcgt agttatctac       780
acgacgggga gtcaggcaac tatggatgaa cgaaatagac agatcgctga gataggtgcc       840
tcactgatta agcattggta a                                                   861

<210> SEQ ID NO 63
<211> LENGTH: 141
<212> TYPE: DNA
<213> ORGANISM: Artificial Sequence
<220> FEATURE:
<223> OTHER INFORMATION: AAV ITR

<400> SEQUENCE: 63
aggaacccct agtgatggag ttggccactc cctctctgcg cgctcgctcg ctcactgagg      60
ccgggcgacc aaaggtcgcc cgacgcccgg gctttgcccg ggcggcctca gtgagcgagc     120
gagcgcgcag ctgcctgcag g     141

<210> SEQ ID NO 64
<211> LENGTH: 212
<212> TYPE: DNA
<213> ORGANISM: Artificial Sequence
<220> FEATURE:
<223> OTHER INFORMATION: EFS core promoter

<400> SEQUENCE: 64
gggcagagcg cacatcgccc acagtccccg agaagttggg gggaggggtc ggcaattgaa      60
cgggtgccta gagaaggtgg cgcggggtaa actgggaaag tgatgtcgtg tactggctcc     120
gcctttttcc cgagggtggg ggagaaccgt atataagtgc agtagtcgcc gtgaacgttc     180
tttttcgcaa cgggtttgcc gccagaacac ag     212

<210> SEQ ID NO 65
<211> LENGTH: 269
<212> TYPE: DNA
<213> ORGANISM: Artificial Sequence
<220> FEATURE:
<223> OTHER INFORMATION: LTR promoter

<400> SEQUENCE: 65
ggggctcgca tctctccttc acgcgcccgc cgccctacct gaggccgcca tccacgccgg      60
ttgagtcgcg ttctgccgcc tcccgcctgt ggtgcctcct gaactgcgtc cgccgtctag     120
gtaagtttaa agctcaggtc gagaccgggc ctttgtccgg cgctcccttg gagcctacct     180
agactcagcc ggctctccac gctttgcctg accctgcttg ctcaactcta cgtctttgtt     240
tcgttttctg ttctgcgccg ttacagatc     269

<210> SEQ ID NO 66
<211> LENGTH: 493
<212> TYPE: DNA
<213> ORGANISM: Artificial Sequence
<220> FEATURE:
<223> OTHER INFORMATION: EFS LTR promoter

<400> SEQUENCE: 66
gggcagagcg cacatcgccc acagtccccg agaagttggg gggaggggtc ggcaattgaa      60
cgggtgccta gagaaggtgg cgcggggtaa actgggaaag tgatgtcgtg tactggctcc     120
gcctttttcc cgagggtggg ggagaaccgt atataagtgc agtagtcgcc gtgaacgttc     180
tttttcgcaa cgggtttgcc gccagaacac agctgaagct tcgagggget cgcatctctc     240 cttcacgcgc ccgccgccct acctgaggcc gccatccacg ccggttgagt cgcgttctgc     300
cgcctcccgc ctgtggtgcc tcctgaactg cgtccgccgt ctaggtaagt ttaaagctca     360
ggtcgagacc gggcctttgt ccggcgctcc cttggagcct acctagactc agccggctct     420
ccacgctttg cctgaccctg cttgctcaac tctacgtctt tgtttcgttt ctgttctgc     480

```
gccgttacag atc                                                           493

<210> SEQ ID NO 67
<211> LENGTH: 68
<212> TYPE: DNA
<213> ORGANISM: Artificial Sequence
<220> FEATURE:
<223> OTHER INFORMATION: T2A

<400> SEQUENCE: 67
gaggaagtct gctaacatgc ggtgacgtcg aggagaatcc tggcccaatg gagagtgtgg        60
tacagcct                                                                 68

<210> SEQ ID NO 68
<211> LENGTH: 72
<212> TYPE: DNA
<213> ORGANISM: Artificial Sequence
<220> FEATURE:
<223> OTHER INFORMATION: P2A

<400> SEQUENCE: 68
actagtggat ccggcgcaac aaacttctct ctgctgaaac aagccggaga tgtcgaagag        60
aatcctggac cg                                                            72

<210> SEQ ID NO 69
<211> LENGTH: 75
<212> TYPE: DNA
<213> ORGANISM: Artificial Sequence
<220> FEATURE:
<223> OTHER INFORMATION: E2A

<400> SEQUENCE: 69
gctagcagcg gtacccagtg caccaactac gccctgctga agctggccgg cgatgtggag        60
agcaaccccg ggccc                                                         75

<210> SEQ ID NO 70
<211> LENGTH: 81
<212> TYPE: DNA
<213> ORGANISM: Artificial Sequence
<220> FEATURE:
<223> OTHER INFORMATION: F2A

<400> SEQUENCE: 70
ggcatatgcg gtaccgtgaa gcagaccctg aacttcgatc tgctgaagct ggccggcgat        60
gtggagagca accccgggcc c                                                  81

<210> SEQ ID NO 71
<211> LENGTH: 589
<212> TYPE: DNA
<213> ORGANISM: Artificial Sequence
<220> FEATURE:
<223> OTHER INFORMATION: WPRE

<400> SEQUENCE: 71
aatcaacctc tggattacaa aatttgtgaa agattgactg gtattcttaa ctatgttgct        60
ccttttacgc tatgtggata cgctgcttta atgcctttgt atcatgctat tgcttcccgt       120
atggctttca ttttctcctc cttgtataaa tcctggttgc tgtctcttta tgaggagttg       180
tggcccgttg tcaggcaacg tggcgtggtg tgcactgtgt ttgctgacgc aacccccact       240
ggttggggca ttgccaccac ctgtcagctc ctttccggga ctttcgcttt ccccctccct       300
attgccacgg cggaactcat cgccgcctgc cttgcccgct gctggacagg ggctcggctg       360
```

-continued

```
ttgggcactg acaattccgt ggtgttgtcg gggaaatcat cgtcctttcc ttggctgctc       420
gcctgtgttg ccacctggat tctgcgcggg acgtccttct gctacgtccc ttcggccctc       480
aatccagcgg accttccttc ccgcggcctg ctgccggctc tgcggcctct tccgcgtctt       540
cgccttcgcc ctcagacgag tcggatctcc ctttgggccg cctccccgc                   589
```

```
<210> SEQ ID NO 72
<211> LENGTH: 49
<212> TYPE: DNA
<213> ORGANISM: Artificial Sequence
<220> FEATURE:
<223> OTHER INFORMATION: short PolyA

<400> SEQUENCE: 72
aataaaagat ctttattttc attagatctg tgtgttggtt ttttgtgtg               49
```

```
<210> SEQ ID NO 73
<211> LENGTH: 918
<212> TYPE: DNA
<213> ORGANISM: Artificial Sequence
<220> FEATURE:
<223> OTHER INFORMATION: ORF Cd80

<400> SEQUENCE: 73
atggcttgca attgtcagtt gatgcaggat acaccactcc tcaagtttcc atgtccaagg       60
ctcattcttc tctttgtgct gctgattcgt ctttcacaag tgtcttcaga tgttgatgaa      120
caactgtcca agtcagtgaa agataaggta ttgctgcctt gccgttacaa ctctcctcat      180
gaagatgagt ctgaagaccg aatctactgg caaaaacatg acaaagtggt gctgtctgtc      240
attgctggga aactaaaagt gtggcccgag tataagaacc ggactttata tgacaacact      300
acctactctc ttatcatcct gggcctggtc ctttcagacc ggggcacata cagctgtgtc      360
gttcaaaaga aggaaagagg aacgtatgaa gttaaacact tggctttagt aaagttgtcc      420
atcaaagctg acttctctac ccccaacata actgagtctg aaacccatc tgcagacact       480 aaaaggatta cctgctttgc ttccgggggt ttcccaaagc ctcgcttctc ttggttggaa      540
aatggaagag aattacctgg catcaatacg acaatttccc aggatcctga atctgaattg      600
tacaccatta gtagccaact agatttcaat acgactcgca accacaccat taagtgtctc      660
attaaatatg gagatgctca cgtgtcagag gacttcacct gggaaaaacc cccagaagac      720
cctcctgata gcaagaacac acttgtgctc tttgggggcag gattcggcgc agtaataaca      780
gtcgtcgtca tcgttgtcat catcaaatgc ttctgtaagc acagaagctg tttcagaaga      840
aatgaggcaa gcagagaaac aaacaacagc cttaccttcg ggcctgaaga agcattagct      900
gaacagaccg tcttcctt                                                    918
```

```
<210> SEQ ID NO 74
<211> LENGTH: 717
<212> TYPE: DNA
<213> ORGANISM: Artificial Sequence
<220> FEATURE:
<223> OTHER INFORMATION: ORF Light

<400> SEQUENCE: 74
atggagagtg tggtacagcc ttcagtgttt gtggtggatg gacagacgga catcccattc       60
aggcggctgg aacagaacca ccggagacgg cgctgtggca ctgtccaggt cagcctggcc      120
ctggtgctgc tgctaggtgc tgggctggcc actcagggct ggtttctcct gagactgcat      180
```

```
caacgtcttg gagacatagt agctcatctg ccagatggag gcaaaggctc ctgggagaag          240
ctgatacaag atcaacgatc tcaccaggcc aacccagcag cacatcttac aggagccaac          300
gccagcttga taggtattgg tggacctctg ttatgggaga cacgacttgg cctggccttc          360
ttgaggggct tgacgtatca tgatggggcc ctggtgacca tggagcccgg ttactactat          420
gtgtactcca aagtgcagct gagcggcgtg ggctgccccc aggggctggc caatggcctc          480
cccatcaccc atggactata caagcgcaca tcccgctacc cgaaggagtt agaactgctg          540
gtcagtcggc ggtcaccctg tggccgggcc aacagctccc gagtctggtg ggacagcagc          600
ttcctgggcg gcgtggtaca tctggaggct ggggaagagg tggtggtccg cgtgcctgga          660
aaccgcctgg tcagaccacg tgacggcacc aggtcctatt tcggagcttt catggtc           717

<210> SEQ ID NO 75
<211> LENGTH: 294
<212> TYPE: DNA
<213> ORGANISM: Artificial Sequence
<220> FEATURE:
<223> OTHER INFORMATION: ORF Cxcl10

<400> SEQUENCE: 75
atgaacccaa gtgctgccgt cattttctgc ctcatcctgc tgggtctgag tgggactcaa           60
gggatccctc tcgcaaggac ggtccgctgc aactgcatcc atatcgatga cgggccagtg          120
agaatgaggg ccatagggaa gcttgaaatc atccctgcga gcctatcctg cccacgtgtt          180
gagatcattg ccacgatgaa aaagaatgat gagcagagat gtctgaatcc ggaatctaag          240
accatcaaga atttaatgaa agcgtttagc caaaaaaggt ctaaaagggc tcct              294

<210> SEQ ID NO 76
<211> LENGTH: 927
<212> TYPE: DNA
<213> ORGANISM: Artificial Sequence
<220> FEATURE:
<223> OTHER INFORMATION: ORF 41BBL

<400> SEQUENCE: 76
atggaccagc acacacttga tgtggaggat accgcggatg ccagacatcc agcaggtact           60
tcgtgcccct cggatgcggc gctcctcaga gataccgggc tcctcgcgga cgctgcgctc          120
ctctcagata ctgtgcgccc cacaaatgcc gcgctcccca cggatgctgc ctaccctgcg          180
gttaatgttc gggatcgcga ggccgcgtgg ccgcctgcac tgaacttctg ttcccgccac          240
ccaaagctct atggcctagt cgctttggtt ttgctgcttc tgatcgccgc ctgtgttcct          300
atcttcaccc gcaccgagcc tcggccagcg ctcacaatca ccacctcgcc caacctgggt          360
acccgagaga taatgcaga ccaggtcacc cctgtttccc acattggctg ccccaacact          420
acacaacagg gctctcctgt gttcgccaag ctactggcta aaaaccaagc atcgttgtgc          480
aatacaactc tgaactggca cagccaagat ggagctggga gctcatacct atctcaaggt          540
ctgaggtacg aagaagacaa aaaggagttg gtggtagaca gtcccgggct ctactacgta          600
tttttggaac tgaagctcag tccaacattc acaaacacag gccacaaggt gcagggctgg          660
gtctctcttg ttttgcaagc aaagcctcag gtagatgact ttgacaactt ggccctgaca          720
gtggaactgt tcccttgctc catggagaac aagttagtgg accgttcctg gagtcaactg          780
ttgctcctga ggctggcca ccgcctcagt gtgggtctga gggcttatct gcatggagcc          840
caggatgcat acagagactg ggagctgtct tatcccaaca ccaccagctt tggactcttt          900
cttatgaaac ccgacaaccc atgggaa                                              927
```

<210> SEQ ID NO 77
<211> LENGTH: 468
<212> TYPE: DNA
<213> ORGANISM: Artificial Sequence
<220> FEATURE:
<223> OTHER INFORMATION: ORF IFNg

<400> SEQUENCE: 77
atgaacgcta cacactgcat cttggctttg cagctcttcc tcatggctgt ttctggctgt      60
tactgccacg gcacagtcat tgaaagccta gaaagtctga ataactattt taactcaagt     120
ggcatagatg tggaagaaaa gagtctcttc ttggatatct ggaggaactg gcaaaaggat     180
ggtgacatga aaatcctgca gagccagatt atctctttct acctcagact ctttgaagtc     240
ttgaaagaca tcaggccat cagcaacaac ataagcgtca ttgaatcaca cctgattact      300
accttcttca gcaacagcaa ggcgaaaaag gatgcattca tgagtattgc caagtttgag     360
gtcaacaacc cacaggtcca gcgccaagca ttcaatgagc tcatccgagt ggtccaccag     420
ctgttgccgg aatccagcct caggaagcgg aaaaggagtc gctgctga                  468

<210> SEQ ID NO 78
<211> LENGTH: 516
<212> TYPE: DNA
<213> ORGANISM: Artificial Sequence
<220> FEATURE:
<223> OTHER INFORMATION: ORF Il2

<400> SEQUENCE: 78
atgtacagca tgcagctcgc atcctgtgtc acattgacac ttgtgctcct tgtcaacagc      60
gcacccactt caagctccac ttcaagctct acagcggaag cacagcagca gcagcagcag     120
cagcagcagc agcagcagca cctggagcag ctgttgatgg acctacagga gctcctgagc     180
aggatggaga attacaggaa cctgaaactc cccaggatgc tcaccttcaa attttacttg     240
cccaagcagg ccacagaatt gaaagatctt cagtgcctag aagatgaact tggacctctg     300
cggcatgttc tggatttgac tcaaagcaaa gctttcaat tggaagatgc tgagaatttc      360
atcagcaata tcagagtaac tgttgtaaaa ctaaagggct ctgacaacac atttgagtgc     420
caattcgatg atgagtcagc aactgtggtg gactttctga ggagatggat agccttctgt     480
caaagcatca tctcaacaag ccctcaataa gaattc                               516

<210> SEQ ID NO 79
<211> LENGTH: 519
<212> TYPE: DNA
<213> ORGANISM: Artificial Sequence
<220> FEATURE:
<223> OTHER INFORMATION: ORF Gitrl

<400> SEQUENCE: 79
atggaggaaa tgcctttgag agagtcaagt cctcaaaggg cagagaggtg caagaagtca      60
tggctcttgt gcatagtggc tctgttactg atgctgctct gttctttggg tacactgatc     120
tatacttcac tcaagccaac tgccatcgag tcctgcatgg ttaagtttga actatcatcc     180
tcaaaatggc acatgacatc tcccaaacct cactgtgtga tacgacatc tgatgggaag      240 ctgaagatac tgcagagtgg cacatattta atctacggcc aagtgattcc tgtggataag     300
aaatacataa aagacaatgc cccctTcgta gtacagatat ataaaaagaa tgatgtccta     360
caaactctaa tgaatgattt tcaaatcttg cctataggag gggtttatga actgcatgct     420

```
ggagataaca tatatctgaa gttcaactct aaagaccata ttcagaaaaa taacacatac      480
tgggggatca tcttaatgcc tgatctacca ttcatctct                            519
```

<210> SEQ ID NO 80
<211> LENGTH: 1008
<212> TYPE: DNA
<213> ORGANISM: Artificial Sequence
<220> FEATURE:
<223> OTHER INFORMATION: ORF Il23

<400> SEQUENCE: 80

```
atgtgtcctc agaagctaac catctcctgg tttgccatcg ttttgctggt gtctccactc       60
atggccatgt gggagctgga gaaagacgtt tatgttgtag aggtggactg gactcccgat      120
gcccctggag aaacagtgaa cctcacctgt gacacgcctg aagaagatga catcacctgg      180
acctcagacc agagacatgg agtcataggc tctggaaaga ccctgaccat cactgtcaaa      240
gagtttctag atgctggcca gtacacctgc cacaaaggag gcgagactct gagccactca      300
catctgctgc tccacaagaa ggaaaatgga atttggtcca ctgaaatttt aaaaaatttc      360
aaaaacaaga ctttcctgaa gtgtgaagca ccaaattact ccggacggtt cacgtgctca      420
tggctggtgc aaagaaacat ggacttgaag ttcaacatca agagcagtag cagttcccct      480
gactctcggg cagtgacatg tggaatggcg tctctgtctg cagagaaggt cacactggac      540
caaagggact atgagaagta ttcagtgtcc tgccaggagg atgtcacctg cccaactgcc      600
gaggagaccc tgcccattga actggcgttg gaagcacggc agcagaataa atatgagaac      660
tacagcacca gcttcttcat cagggacatc atcaaaccag acccgcccaa gaacttgcag      720
atgaagcctt tgaagaactc acaggtggag gtcagctggg agtaccctga ctcctggagc      780
actccccatt cctacttctc cctcaagttc tttgttcgaa tccagcgcaa gaaagaaaag      840
atgaaggaga cagaggaggg tgtgtaaccag aaaggtgcgt tcctcgtaga gaagacatct      900
accgaagtcc aatgcaaagg cgggaatgtc tgcgtgcaag ctcaggatcg ctattacaat      960
tcctcatgca gcaagtgggc atgtgttccc tgcagggtcc gatcctag             1008
```

<210> SEQ ID NO 81
<211> LENGTH: 498
<212> TYPE: DNA
<213> ORGANISM: Artificial Sequence
<220> FEATURE:
<223> OTHER INFORMATION: ORF hIFNg

<400> SEQUENCE: 81

```
atgaaatata caagttatat cttggctttt cagctctgca tcgttttggg ttctcttggc       60
tgttactgcc aggacccata tgtaaaagaa gcagaaaacc ttaagaaata tttaatgca      120 ggtcattcag atgtagcgga taatggaact ctttttcttag cattttgaa gaattggaaa      180 gaggagagtg acagaaaaat aatgcagagc caaattgtct cctttactt caaactttt      240 aaaaactta aagatgacca gagcatccaa aagagtgtgg agaccatcaa ggaagacatg      300
aatgtcaagt ttttcaatag caacaaaaag aaacgagatg acttcgaaaa gctgactaat      360
tattcggtaa ctgacttgaa tgtccaacgc aaagcaatac atgaactcat ccaagtgatg      420
gctgaactgt cgccagcagc taaaacaggg aagcgaaaaa ggagtcagat gctgtttcga      480
ggtcgaagag catcccag                                                    498
```

<210> SEQ ID NO 82
<211> LENGTH: 983

-continued

```
<212> TYPE: DNA
<213> ORGANISM: Artificial Sequence
<220> FEATURE:
<223> OTHER INFORMATION: ORF hIL23

<400> SEQUENCE: 82
tgtgtcacca gcagttggtc atctcttggt tttccctggt ttttctggca tctcccctcg      60
tggccatatg ggaactgaag aaagatgttt atgtcgtaga attggattgg tatccggatg     120
cccctggaga aatggtggtc ctcacctgtg acacccctga agaagatggt atcacctgga     180
ccttggacca gagcagtgag gtcttaggct ctggcaaaac cctgaccatc caagtcaaag     240
agtttggaga tgctggccag tacacctgtc acaaaggagg cgaggttcta agccattcgc     300
tcctgctgct tcacaaaaag gaagatggaa tttggtccac tgatatttta aaggaccaga     360
aagaacccaa aaataagacc tttctaagat gcgaggccaa gaattattct ggacgtttca     420
cctgctggtg gctgacgaca atcagtactg atttgacatt cagtgtcaaa agcagcagag     480
gctcttctga ccccaagggg gtgacgtgcg gagctgctac actctctgca gagagagtca     540
gaggggacaa caaggagtat gagtactcag tggagtgcca ggaggacagt gcctgcccag     600
ctgctgagga gagtctgccc attgaggtca tggtggatgc cgttcacaag ctcaagtatg     660
aaaactacac cagcagcttc ttcatcaggg acatcatcaa acctgaccca cccaagaact     720
tgcagctgaa gccattaaag aattctcggc aggtggaggt cagctgggag taccctgaca     780
cctggagtac tccacattcc tacttctccc tgacattctg cgttcaggtc cagggcaaga     840
gcaagagaga aaagaaagat agagtcttca cggacaagac ctcagccacg gtcatctgcc     900
gcaaaaatgc cagcattagc gtgcgggccc aggaccgcta ctatagctca tcttggagcg     960
aatgggcatc tgtgccctgc agt                                             983

<210> SEQ ID NO 83
<211> LENGTH: 762
<212> TYPE: DNA
<213> ORGANISM: Artificial Sequence
<220> FEATURE:
<223> OTHER INFORMATION: ORF h41BBL

<400> SEQUENCE: 83
atggaatacg cctctgacgc ttcactggac cccgaagccc cgtggcctcc cgcgccccgc      60
gctcgcgcct gccgcgtact gccttgggcc ctggtcgcgg ggctgctgct gctgctgctg     120
ctcgctgccg cctgcgccgt cttcctcgcc tgccctgggg ccgtgtccgg ggctcgcgcc     180
tcgcccggct ccgcgccag cccgagactc cgcgagggtc ccgagctttc gcccgacgat     240
cccgccggcc tcttggacct gcggcagggc atgtttgcgc agctggtggc ccaaaatgtt     300
ctgctgatcg atgggcccct gagctggtac agtgacccag cctggcagg cgtgtccctg     360 acgggggggcc tgagctacaa agaggacacg aaggagctgg tggtggccaa ggctggagtc     420
tactatgtct tctttcaact agagctgcgg cgcgtggtgg ccggcgaggg ctcaggctcc     480
gtttcacttg cgctgcacct gcagccactg cgctctgctg ctggggccgc cgccctggct     540
ttgaccgtgg acctgccacc cgcctcctcc gaggctcgga actcggcctt cggtttccag     600
ggccgcttgc tgcacctgag tgccggccag cgcctgggcg tccatcttca cactgaggcc     660
agggcacgcc atgcctggca gcttacccag ggcgccacag tcttgggact cttccgggtg     720
acccccgaaa tccagccggg actcccttca ccgaggtcgg aa                        762

<210> SEQ ID NO 84
```

-continued

```
<211> LENGTH: 708
<212> TYPE: DNA
<213> ORGANISM: Artificial Sequence
<220> FEATURE:
<223> OTHER INFORMATION: ORF hLIGHT

<400> SEQUENCE: 84
atggaggaga gtgtcgtacg gccctcagtg tttgtggtgg atggacagac cgacatccca      60
ttcacgaggc tgggacgaag ccaccggaga cagtcgtgca gtgtggcccg ggtgggtctg     120
ggtctcttgc tgttgctgat gggggccggg ctggccgtcc aaggctggtt cctcctgcag     180
ctgcactggc gtctaggaga gatggtcacc cgcctgcctg acggacctgc aggtcctgg      240 caagagcgaa ggtctcacga ggtcaaccca gcagcgcatc tcacaggggc caactccagc     300
ttgaccggca gcggggggcc gctgttatgg gagactcagc tgggcctggc cttcctgagg     360
ggcctcagct accacgatgg ggcccttgtg gtcaccaaag ctggctacta ctacatctac     420
tccaaggtgc agctgggcgg tgtgggctgc ccgctgggcc tggccagcac catcaccccac    480 ggcctctaca agcgcacacc ccgctacccc gaggagctgg agctgttggt cagccagcag     540
tcaccctgcg gacgggccac cagcagctcc cgggtctggt gggacagcag cttcctgggt     600
ggtgtggtac acctggaggc tggggagaag gtggtcgtcc gtgtgctgga tgaacgcctg     660
gttcgactgc gtgatggtac ccggtcttac ttcgggggctt tcatggtg                  708

<210> SEQ ID NO 85
<211> LENGTH: 15
<212> TYPE: DNA
<213> ORGANISM: Artificial Sequence
<220> FEATURE:
<223> OTHER INFORMATION: CGKRK

<400> SEQUENCE: 85
tgcggaaagc gtaag                                                        15

<210> SEQ ID NO 86
<211> LENGTH: 20
<212> TYPE: DNA
<213> ORGANISM: Artificial Sequence
<220> FEATURE:
<223> OTHER INFORMATION: sgRNA

<400> SEQUENCE: 86
gcttcagttt gtctgtggga                                                   20

<210> SEQ ID NO 87
<211> LENGTH: 20
<212> TYPE: DNA
<213> ORGANISM: Artificial Sequence
<220> FEATURE:
<223> OTHER INFORMATION: sgRNA

<400> SEQUENCE: 87
attcactgag catctattag                                                   20

<210> SEQ ID NO 88
<211> LENGTH: 20
<212> TYPE: DNA
<213> ORGANISM: Artificial Sequence
<220> FEATURE:
<223> OTHER INFORMATION: sgRNA

<400> SEQUENCE: 88
atcaggaagc atccgcatcc                                                   20
```

-continued

```
<210> SEQ ID NO 89
<211> LENGTH: 20
<212> TYPE: DNA
<213> ORGANISM: Artificial Sequence
<220> FEATURE:
<223> OTHER INFORMATION: sgRNA

<400> SEQUENCE: 89
gagagttctg aatcagggtg                                               20

<210> SEQ ID NO 90
<211> LENGTH: 20
<212> TYPE: DNA
<213> ORGANISM: Artificial Sequence
<220> FEATURE:
<223> OTHER INFORMATION: sgRNA

<400> SEQUENCE: 90
tccaggcctg ttctgagcac                                               20

<210> SEQ ID NO 91
<211> LENGTH: 20
<212> TYPE: DNA
<213> ORGANISM: Artificial Sequence
<220> FEATURE:
<223> OTHER INFORMATION: sgRNA

<400> SEQUENCE: 91
ggacctttga gttgccctca                                               20

<210> SEQ ID NO 92
<211> LENGTH: 20
<212> TYPE: DNA
<213> ORGANISM: Artificial Sequence
<220> FEATURE:
<223> OTHER INFORMATION: sgRNA

<400> SEQUENCE: 92
ccaagtccgc gttgctgctg                                               20

<210> SEQ ID NO 93
<211> LENGTH: 20
<212> TYPE: DNA
<213> ORGANISM: Artificial Sequence
<220> FEATURE:
<223> OTHER INFORMATION: sgRNA

<400> SEQUENCE: 93
atctgcatga cccactcgat                                               20

<210> SEQ ID NO 94
<211> LENGTH: 20
<212> TYPE: DNA
<213> ORGANISM: Artificial Sequence
<220> FEATURE:
<223> OTHER INFORMATION: sgRNA

<400> SEQUENCE: 94
gtttgagggt catctagctg                                               20

<210> SEQ ID NO 95
<211> LENGTH: 20
<212> TYPE: DNA
<213> ORGANISM: Artificial Sequence
<220> FEATURE:
```

-continued

<223> OTHER INFORMATION: sgRNA

<400> SEQUENCE: 95
gcaggcagga gtgggtgggt                                                   20

<210> SEQ ID NO 96
<211> LENGTH: 20
<212> TYPE: DNA
<213> ORGANISM: Artificial Sequence
<220> FEATURE:
<223> OTHER INFORMATION: sgRNA

<400> SEQUENCE: 96
ctttgtagat tattcgagtt                                                   20

<210> SEQ ID NO 97
<211> LENGTH: 20
<212> TYPE: DNA
<213> ORGANISM: Artificial Sequence
<220> FEATURE:
<223> OTHER INFORMATION: sgRNA

<400> SEQUENCE: 97
gagttcggtt tcagtcttga                                                   20

<210> SEQ ID NO 98
<211> LENGTH: 20
<212> TYPE: DNA
<213> ORGANISM: Artificial Sequence
<220> FEATURE:
<223> OTHER INFORMATION: sgRNA

<400> SEQUENCE: 98
aaagagaatt ggaaagcaag                                                   20

<210> SEQ ID NO 99
<211> LENGTH: 20
<212> TYPE: DNA
<213> ORGANISM: Artificial Sequence
<220> FEATURE:
<223> OTHER INFORMATION: sgRNA

<400> SEQUENCE: 99
tgtgtacatc tctcttaaat                                                   20

<210> SEQ ID NO 100
<211> LENGTH: 20
<212> TYPE: DNA
<213> ORGANISM: Artificial Sequence
<220> FEATURE:
<223> OTHER INFORMATION: sgRNA

<400> SEQUENCE: 100
caggctctca gagaacctgt                                                   20

<210> SEQ ID NO 101
<211> LENGTH: 20
<212> TYPE: DNA
<213> ORGANISM: Artificial Sequence
<220> FEATURE:
<223> OTHER INFORMATION: sgRNA

<400> SEQUENCE: 101
gaaattcctc tgaggcagaa                                                   20

-continued

```
<210> SEQ ID NO 102
<211> LENGTH: 20
<212> TYPE: DNA
<213> ORGANISM: Artificial Sequence
<220> FEATURE:
<223> OTHER INFORMATION: sgRNA

<400> SEQUENCE: 102
cctgtgctat ttataaggga                                                20

<210> SEQ ID NO 103
<211> LENGTH: 20
<212> TYPE: DNA
<213> ORGANISM: Artificial Sequence
<220> FEATURE:
<223> OTHER INFORMATION: sgRNA

<400> SEQUENCE: 103
gtgagaatga tcttccttca                                                20

<210> SEQ ID NO 104
<211> LENGTH: 20
<212> TYPE: DNA
<213> ORGANISM: Artificial Sequence
<220> FEATURE:
<223> OTHER INFORMATION: sgRNA

<400> SEQUENCE: 104
agagtttcct ttcgactcct                                                20

<210> SEQ ID NO 105
<211> LENGTH: 20
<212> TYPE: DNA
<213> ORGANISM: Artificial Sequence
<220> FEATURE:
<223> OTHER INFORMATION: sgRNA

<400> SEQUENCE: 105
ttaagatggt gacagatagg                                                20

<210> SEQ ID NO 106
<211> LENGTH: 20
<212> TYPE: DNA
<213> ORGANISM: Artificial Sequence
<220> FEATURE:
<223> OTHER INFORMATION: sgRNA

<400> SEQUENCE: 106
atacctgatc gaaggctcct                                                20

<210> SEQ ID NO 107
<211> LENGTH: 20
<212> TYPE: DNA
<213> ORGANISM: Artificial Sequence
<220> FEATURE:
<223> OTHER INFORMATION: sgRNA

<400> SEQUENCE: 107
aaaccctact ctcagatccc                                                20

<210> SEQ ID NO 108
<211> LENGTH: 20
<212> TYPE: DNA
<213> ORGANISM: Artificial Sequence
<220> FEATURE:
<223> OTHER INFORMATION: sgRNA
```

-continued

```
<400> SEQUENCE: 108
tagttcttct aggtcagctg                                              20

<210> SEQ ID NO 109
<211> LENGTH: 20
<212> TYPE: DNA
<213> ORGANISM: Artificial Sequence
<220> FEATURE:
<223> OTHER INFORMATION: sgRNA

<400> SEQUENCE: 109
taaccacaaa ttgatcgtcc                                              20

<210> SEQ ID NO 110
<211> LENGTH: 20
<212> TYPE: DNA
<213> ORGANISM: Artificial Sequence
<220> FEATURE:
<223> OTHER INFORMATION: sgRNA

<400> SEQUENCE: 110
actttggaga tgactcagca                                              20

<210> SEQ ID NO 111
<211> LENGTH: 20
<212> TYPE: DNA
<213> ORGANISM: Artificial Sequence
<220> FEATURE:
<223> OTHER INFORMATION: sgRNA

<400> SEQUENCE: 111
tttattgtga cccatgaact                                              20

<210> SEQ ID NO 112
<211> LENGTH: 20
<212> TYPE: DNA
<213> ORGANISM: Artificial Sequence
<220> FEATURE:
<223> OTHER INFORMATION: sgRNA

<400> SEQUENCE: 112
gcaatgccct cggtttacag                                              20

<210> SEQ ID NO 113
<211> LENGTH: 20
<212> TYPE: DNA
<213> ORGANISM: Artificial Sequence
<220> FEATURE:
<223> OTHER INFORMATION: sgRNA

<400> SEQUENCE: 113
tttcaaagag tctacctgtg                                              20

<210> SEQ ID NO 114
<211> LENGTH: 20
<212> TYPE: DNA
<213> ORGANISM: Artificial Sequence
<220> FEATURE:
<223> OTHER INFORMATION: sgRNA

<400> SEQUENCE: 114
gcaatttata ctgttaatgc                                              20

<210> SEQ ID NO 115
<211> LENGTH: 20
```

```
<212> TYPE: DNA
<213> ORGANISM: Artificial Sequence
<220> FEATURE:
<223> OTHER INFORMATION: sgRNA

<400> SEQUENCE: 115
tccattcagt cagtgtatgg                                            20

<210> SEQ ID NO 116
<211> LENGTH: 20
<212> TYPE: DNA
<213> ORGANISM: Artificial Sequence
<220> FEATURE:
<223> OTHER INFORMATION: sgRNA

<400> SEQUENCE: 116
cacactcatc aagagcccgg                                            20

<210> SEQ ID NO 117
<211> LENGTH: 20
<212> TYPE: DNA
<213> ORGANISM: Artificial Sequence
<220> FEATURE:
<223> OTHER INFORMATION: sgRNA

<400> SEQUENCE: 117
gtgggcaaga agcgaaggaa                                            20

<210> SEQ ID NO 118
<211> LENGTH: 20
<212> TYPE: DNA
<213> ORGANISM: Artificial Sequence
<220> FEATURE:
<223> OTHER INFORMATION: sgRNA

<400> SEQUENCE: 118
agaggacaca cgtgtgctac                                            20

<210> SEQ ID NO 119
<211> LENGTH: 20
<212> TYPE: DNA
<213> ORGANISM: Artificial Sequence
<220> FEATURE:
<223> OTHER INFORMATION: sgRNA

<400> SEQUENCE: 119
aggcagagtc atacttccaa                                            20

<210> SEQ ID NO 120
<211> LENGTH: 20
<212> TYPE: DNA
<213> ORGANISM: Artificial Sequence
<220> FEATURE:
<223> OTHER INFORMATION: sgRNA

<400> SEQUENCE: 120
ctaccctggc tccctataaa                                            20

<210> SEQ ID NO 121
<211> LENGTH: 20
<212> TYPE: DNA
<213> ORGANISM: Artificial Sequence
<220> FEATURE:
<223> OTHER INFORMATION: sgRNA

<400> SEQUENCE: 121
```
ttatgacagc aacaagtgtt                                          20

<210> SEQ ID NO 122
<211> LENGTH: 20
<212> TYPE: DNA
<213> ORGANISM: Artificial Sequence
<220> FEATURE:
<223> OTHER INFORMATION: sgRNA

<400> SEQUENCE: 122
tggtgtcttc tgaccaagaa                                          20

<210> SEQ ID NO 123
<211> LENGTH: 20
<212> TYPE: DNA
<213> ORGANISM: Artificial Sequence
<220> FEATURE:
<223> OTHER INFORMATION: sgRNA

<400> SEQUENCE: 123
tcgtcgcaac ccacacttcc                                          20

<210> SEQ ID NO 124
<211> LENGTH: 20
<212> TYPE: DNA
<213> ORGANISM: Artificial Sequence
<220> FEATURE:
<223> OTHER INFORMATION: sgRNA

<400> SEQUENCE: 124
ttaactaatc ctgagtaagg                                          20

<210> SEQ ID NO 125
<211> LENGTH: 20
<212> TYPE: DNA
<213> ORGANISM: Artificial Sequence
<220> FEATURE:
<223> OTHER INFORMATION: sgRNA

<400> SEQUENCE: 125
aagtcactca attcataact                                          20

<210> SEQ ID NO 126
<211> LENGTH: 20
<212> TYPE: DNA
<213> ORGANISM: Artificial Sequence
<220> FEATURE:
<223> OTHER INFORMATION: sgRNA

<400> SEQUENCE: 126
caactccctg ttagcccgga                                          20

<210> SEQ ID NO 127
<211> LENGTH: 20
<212> TYPE: DNA
<213> ORGANISM: Artificial Sequence
<220> FEATURE:
<223> OTHER INFORMATION: sgRNA

<400> SEQUENCE: 127
agtgcttagc agtgttccaa                                          20

<210> SEQ ID NO 128
<211> LENGTH: 20
<212> TYPE: DNA
<213> ORGANISM: Artificial Sequence
<220> FEATURE:
<223> OTHER INFORMATION: sgRNA

<400> SEQUENCE: 128
gcaccaggcc aaacatacaa                                                                                      20

<210> SEQ ID NO 129
<211> LENGTH: 20
<212> TYPE: DNA
<213> ORGANISM: Artificial Sequence
<220> FEATURE:
<223> OTHER INFORMATION: sgRNA

<400> SEQUENCE: 129
cactacaagg gaagttcaga                                                                                      20

<210> SEQ ID NO 130
<211> LENGTH: 20
<212> TYPE: DNA
<213> ORGANISM: Artificial Sequence
<220> FEATURE:
<223> OTHER INFORMATION: sgRNA

<400> SEQUENCE: 130
cgccacctag tggtaacaag                                                                                      20

<210> SEQ ID NO 131
<211> LENGTH: 20
<212> TYPE: DNA
<213> ORGANISM: Artificial Sequence
<220> FEATURE:
<223> OTHER INFORMATION: sgRNA

<400> SEQUENCE: 131
gggccctgaa aggatagcga                                                                                      20

<210> SEQ ID NO 132
<211> LENGTH: 20
<212> TYPE: DNA
<213> ORGANISM: Artificial Sequence
<220> FEATURE:
<223> OTHER INFORMATION: sgRNA

<400> SEQUENCE: 132
ttctacatac acttcgaagc                                                                                      20

<210> SEQ ID NO 133
<211> LENGTH: 20
<212> TYPE: DNA
<213> ORGANISM: Artificial Sequence
<220> FEATURE:
<223> OTHER INFORMATION: sgRNA

<400> SEQUENCE: 133
tgtgactcag gtgggatgga                                                                                      20

<210> SEQ ID NO 134
<211> LENGTH: 20
<212> TYPE: DNA
<213> ORGANISM: Artificial Sequence
<220> FEATURE:
<223> OTHER INFORMATION: sgRNA

<400> SEQUENCE: 134
gaggaggtac gtgaggaaag                                                                                      20

-continued

<210> SEQ ID NO 135
<211> LENGTH: 20
<212> TYPE: DNA
<213> ORGANISM: Artificial Sequence
<220> FEATURE:
<223> OTHER INFORMATION: sgRNA

<400> SEQUENCE: 135
cagtgagagt gatcgaccgg                                                   20

<210> SEQ ID NO 136
<211> LENGTH: 20
<212> TYPE: DNA
<213> ORGANISM: Artificial Sequence
<220> FEATURE:
<223> OTHER INFORMATION: sgRNA

<400> SEQUENCE: 136
gagacttggg catgagttac                                                   20

<210> SEQ ID NO 137
<211> LENGTH: 20
<212> TYPE: DNA
<213> ORGANISM: Artificial Sequence
<220> FEATURE:
<223> OTHER INFORMATION: sgRNA

<400> SEQUENCE: 137
aacccaatcg gctgctgagc                                                   20

<210> SEQ ID NO 138
<211> LENGTH: 20
<212> TYPE: DNA
<213> ORGANISM: Artificial Sequence
<220> FEATURE:
<223> OTHER INFORMATION: sgRNA

<400> SEQUENCE: 138
ccgcctgtgc ccaattagcc                                                   20

<210> SEQ ID NO 139
<211> LENGTH: 20
<212> TYPE: DNA
<213> ORGANISM: Artificial Sequence
<220> FEATURE:
<223> OTHER INFORMATION: sgRNA

<400> SEQUENCE: 139
ccctccctcc cttccctccc                                                   20

<210> SEQ ID NO 140
<211> LENGTH: 20
<212> TYPE: DNA
<213> ORGANISM: Artificial Sequence
<220> FEATURE:
<223> OTHER INFORMATION: sgRNA

<400> SEQUENCE: 140
acagggcctg gacagggaag                                                   20

<210> SEQ ID NO 141
<211> LENGTH: 20
<212> TYPE: DNA
<213> ORGANISM: Artificial Sequence
<220> FEATURE:
<223> OTHER INFORMATION: sgRNA

<400> SEQUENCE: 141
agaaagttcc gggagtcgag                                                        20

<210> SEQ ID NO 142
<211> LENGTH: 20
<212> TYPE: DNA
<213> ORGANISM: Artificial Sequence
<220> FEATURE:
<223> OTHER INFORMATION: sgRNA

<400> SEQUENCE: 142
cagagggctg tcagagggag                                                        20

<210> SEQ ID NO 143
<211> LENGTH: 20
<212> TYPE: DNA
<213> ORGANISM: Artificial Sequence
<220> FEATURE:
<223> OTHER INFORMATION: sgRNA

<400> SEQUENCE: 143
aacttggttt ctgttgtagg                                                        20

<210> SEQ ID NO 144
<211> LENGTH: 20
<212> TYPE: DNA
<213> ORGANISM: Artificial Sequence
<220> FEATURE:
<223> OTHER INFORMATION: sgRNA

<400> SEQUENCE: 144
attccctagc cgggcagggc                                                        20

<210> SEQ ID NO 145
<211> LENGTH: 20
<212> TYPE: DNA
<213> ORGANISM: Artificial Sequence
<220> FEATURE:
<223> OTHER INFORMATION: sgRNA

<400> SEQUENCE: 145
aattgtagcg agatagacga                                                        20

<210> SEQ ID NO 146
<211> LENGTH: 20
<212> TYPE: DNA
<213> ORGANISM: Artificial Sequence
<220> FEATURE:
<223> OTHER INFORMATION: sgRNA

<400> SEQUENCE: 146
gtggttggtg tacactcacg                                                        20

<210> SEQ ID NO 147
<211> LENGTH: 20
<212> TYPE: DNA
<213> ORGANISM: Artificial Sequence
<220> FEATURE:
<223> OTHER INFORMATION: sgRNA

<400> SEQUENCE: 147
cgttctgtgg ctgagcctaa                                                        20

<210> SEQ ID NO 148

-continued

```
<211> LENGTH: 20
<212> TYPE: DNA
<213> ORGANISM: Artificial Sequence
<220> FEATURE:
<223> OTHER INFORMATION: sgRNA

<400> SEQUENCE: 148
tgcaggcaac ttgcagactg                                         20

<210> SEQ ID NO 149
<211> LENGTH: 20
<212> TYPE: DNA
<213> ORGANISM: Artificial Sequence
<220> FEATURE:
<223> OTHER INFORMATION: sgRNA

<400> SEQUENCE: 149
ttcacgcaag caagttaagg                                         20

<210> SEQ ID NO 150
<211> LENGTH: 20
<212> TYPE: DNA
<213> ORGANISM: Artificial Sequence
<220> FEATURE:
<223> OTHER INFORMATION: sgRNA

<400> SEQUENCE: 150
cgtgccgttc taccagcatt                                         20

<210> SEQ ID NO 151
<211> LENGTH: 20
<212> TYPE: DNA
<213> ORGANISM: Artificial Sequence
<220> FEATURE:
<223> OTHER INFORMATION: sgRNA

<400> SEQUENCE: 151
acgacctccg gatctgagtc                                         20

<210> SEQ ID NO 152
<211> LENGTH: 20
<212> TYPE: DNA
<213> ORGANISM: Artificial Sequence
<220> FEATURE:
<223> OTHER INFORMATION: sgRNA

<400> SEQUENCE: 152
ccgtgatatt tcaaacagcc                                         20

<210> SEQ ID NO 153
<211> LENGTH: 20
<212> TYPE: DNA
<213> ORGANISM: Artificial Sequence
<220> FEATURE:
<223> OTHER INFORMATION: sgRNA

<400> SEQUENCE: 153
agcatcaaca gctaggagac                                         20

<210> SEQ ID NO 154
<211> LENGTH: 20
<212> TYPE: DNA
<213> ORGANISM: Artificial Sequence
<220> FEATURE:
<223> OTHER INFORMATION: sgRNA

<400> SEQUENCE: 154
```

-continued gcggagtcta ggctgataaa                                                          20

<210> SEQ ID NO 155
<211> LENGTH: 20
<212> TYPE: DNA
<213> ORGANISM: Artificial Sequence
<220> FEATURE:
<223> OTHER INFORMATION: sgRNA

<400> SEQUENCE: 155
ggtctgggaa cgcgggagtg                                                          20

<210> SEQ ID NO 156
<211> LENGTH: 20
<212> TYPE: DNA
<213> ORGANISM: Artificial Sequence
<220> FEATURE:
<223> OTHER INFORMATION: sgRNA

<400> SEQUENCE: 156
tatttattgg tcacttcact                                                          20

<210> SEQ ID NO 157
<211> LENGTH: 20
<212> TYPE: DNA
<213> ORGANISM: Artificial Sequence
<220> FEATURE:
<223> OTHER INFORMATION: sgRNA

<400> SEQUENCE: 157
ctccagccct ctcatagttg                                                          20

<210> SEQ ID NO 158
<211> LENGTH: 20
<212> TYPE: DNA
<213> ORGANISM: Artificial Sequence
<220> FEATURE:
<223> OTHER INFORMATION: sgRNA

<400> SEQUENCE: 158
aggatttaac atggactgaa                                                          20

<210> SEQ ID NO 159
<211> LENGTH: 20
<212> TYPE: DNA
<213> ORGANISM: Artificial Sequence
<220> FEATURE:
<223> OTHER INFORMATION: sgRNA

<400> SEQUENCE: 159
ctgtgatcga acagacgaga                                                          20

<210> SEQ ID NO 160
<211> LENGTH: 20
<212> TYPE: DNA
<213> ORGANISM: Artificial Sequence
<220> FEATURE:
<223> OTHER INFORMATION: sgRNA

<400> SEQUENCE: 160
gcagtgtggc agccgccgat                                                          20

<210> SEQ ID NO 161
<211> LENGTH: 20
<212> TYPE: DNA

<213> ORGANISM: Artificial Sequence
<220> FEATURE:
<223> OTHER INFORMATION: sgRNA

<400> SEQUENCE: 161
aacagctggt aactgccgat                                                      20

<210> SEQ ID NO 162
<211> LENGTH: 20
<212> TYPE: DNA
<213> ORGANISM: Artificial Sequence
<220> FEATURE:
<223> OTHER INFORMATION: sgRNA

<400> SEQUENCE: 162
ctgcgtcacg cagcgtcggg                                                      20

<210> SEQ ID NO 163
<211> LENGTH: 20
<212> TYPE: DNA
<213> ORGANISM: Artificial Sequence
<220> FEATURE:
<223> OTHER INFORMATION: sgRNA

<400> SEQUENCE: 163
ggtcgcacta tgggccaatg                                                      20

<210> SEQ ID NO 164
<211> LENGTH: 20
<212> TYPE: DNA
<213> ORGANISM: Artificial Sequence
<220> FEATURE:
<223> OTHER INFORMATION: sgRNA

<400> SEQUENCE: 164
gtaggtctaa accagtcaaa                                                      20

<210> SEQ ID NO 165
<211> LENGTH: 20
<212> TYPE: DNA
<213> ORGANISM: Artificial Sequence
<220> FEATURE:
<223> OTHER INFORMATION: sgRNA

<400> SEQUENCE: 165
gggtcgacca cgcgttgtgg                                                      20

<210> SEQ ID NO 166
<211> LENGTH: 20
<212> TYPE: DNA
<213> ORGANISM: Artificial Sequence
<220> FEATURE:
<223> OTHER INFORMATION: sgRNA

<400> SEQUENCE: 166
tgatagggaa tgcattctcc                                                      20

<210> SEQ ID NO 167
<211> LENGTH: 20
<212> TYPE: DNA
<213> ORGANISM: Artificial Sequence
<220> FEATURE:
<223> OTHER INFORMATION: sgRNA

<400> SEQUENCE: 167
actttgagtt cccgaagccc                                                      20

```
<210> SEQ ID NO 168
<211> LENGTH: 20
<212> TYPE: DNA
<213> ORGANISM: Artificial Sequence
<220> FEATURE:
<223> OTHER INFORMATION: sgRNA

<400> SEQUENCE: 168
caagcctaag ggatctagcc                                                20

<210> SEQ ID NO 169
<211> LENGTH: 20
<212> TYPE: DNA
<213> ORGANISM: Artificial Sequence
<220> FEATURE:
<223> OTHER INFORMATION: sgRNA

<400> SEQUENCE: 169
agctggccgt gcagagagga                                                20

<210> SEQ ID NO 170
<211> LENGTH: 20
<212> TYPE: DNA
<213> ORGANISM: Artificial Sequence
<220> FEATURE:
<223> OTHER INFORMATION: sgRNA

<400> SEQUENCE: 170
tcatctggga gatgagcctc                                                20

<210> SEQ ID NO 171
<211> LENGTH: 20
<212> TYPE: DNA
<213> ORGANISM: Artificial Sequence
<220> FEATURE:
<223> OTHER INFORMATION: sgRNA

<400> SEQUENCE: 171
ttcggttggc attcggctaa                                                20

<210> SEQ ID NO 172
<211> LENGTH: 20
<212> TYPE: DNA
<213> ORGANISM: Artificial Sequence
<220> FEATURE:
<223> OTHER INFORMATION: sgRNA

<400> SEQUENCE: 172
gggtctgaga tgctttgaaa                                                20

<210> SEQ ID NO 173
<211> LENGTH: 20
<212> TYPE: DNA
<213> ORGANISM: Artificial Sequence
<220> FEATURE:
<223> OTHER INFORMATION: sgRNA

<400> SEQUENCE: 173
ggcgcctgtc aatttgcggg                                                20

<210> SEQ ID NO 174
<211> LENGTH: 20
<212> TYPE: DNA
<213> ORGANISM: Artificial Sequence
<220> FEATURE:
```

<223> OTHER INFORMATION: sgRNA

<400> SEQUENCE: 174
ttgctagtag cggccttgga                                        20

<210> SEQ ID NO 175
<211> LENGTH: 20
<212> TYPE: DNA
<213> ORGANISM: Artificial Sequence
<220> FEATURE:
<223> OTHER INFORMATION: sgRNA

<400> SEQUENCE: 175
ctagtctgtt cttgccttgt                                        20

<210> SEQ ID NO 176
<211> LENGTH: 20
<212> TYPE: DNA
<213> ORGANISM: Artificial Sequence
<220> FEATURE:
<223> OTHER INFORMATION: sgRNA

<400> SEQUENCE: 176
gggagggtgg ccgccggaaa                                        20

<210> SEQ ID NO 177
<211> LENGTH: 20
<212> TYPE: DNA
<213> ORGANISM: Artificial Sequence
<220> FEATURE:
<223> OTHER INFORMATION: sgRNA

<400> SEQUENCE: 177
gaatctggca gctctttaag                                        20

<210> SEQ ID NO 178
<211> LENGTH: 20
<212> TYPE: DNA
<213> ORGANISM: Artificial Sequence
<220> FEATURE:
<223> OTHER INFORMATION: sgRNA

<400> SEQUENCE: 178
ggacgctaag aagggtttgg                                        20

<210> SEQ ID NO 179
<211> LENGTH: 20
<212> TYPE: DNA
<213> ORGANISM: Artificial Sequence
<220> FEATURE:
<223> OTHER INFORMATION: sgRNA

<400> SEQUENCE: 179
ctgtcaccac cctccgttcc                                        20

<210> SEQ ID NO 180
<211> LENGTH: 20
<212> TYPE: DNA
<213> ORGANISM: Artificial Sequence
<220> FEATURE:
<223> OTHER INFORMATION: sgRNA

<400> SEQUENCE: 180
cttcacgtcc tttccctgaa                                        20

-continued

```
<210> SEQ ID NO 181
<211> LENGTH: 20
<212> TYPE: DNA
<213> ORGANISM: Artificial Sequence
<220> FEATURE:
<223> OTHER INFORMATION: sgRNA

<400> SEQUENCE: 181
tgggaaggcg cttcgagcga                                                    20

<210> SEQ ID NO 182
<211> LENGTH: 20
<212> TYPE: DNA
<213> ORGANISM: Artificial Sequence
<220> FEATURE:
<223> OTHER INFORMATION: sgRNA

<400> SEQUENCE: 182
ttcttagatc ttgcgcaaag                                                    20

<210> SEQ ID NO 183
<211> LENGTH: 20
<212> TYPE: DNA
<213> ORGANISM: Artificial Sequence
<220> FEATURE:
<223> OTHER INFORMATION: sgRNA

<400> SEQUENCE: 183
ccacgaagaa tagccctagg                                                    20

<210> SEQ ID NO 184
<211> LENGTH: 20
<212> TYPE: DNA
<213> ORGANISM: Artificial Sequence
<220> FEATURE:
<223> OTHER INFORMATION: sgRNA

<400> SEQUENCE: 184
agcggccggt ggcccatccc                                                    20

<210> SEQ ID NO 185
<211> LENGTH: 20
<212> TYPE: DNA
<213> ORGANISM: Artificial Sequence
<220> FEATURE:
<223> OTHER INFORMATION: sgRNA

<400> SEQUENCE: 185
gctgtcggga agacgactgt                                                    20

<210> SEQ ID NO 186
<211> LENGTH: 20
<212> TYPE: DNA
<213> ORGANISM: Artificial Sequence
<220> FEATURE:
<223> OTHER INFORMATION: sgRNA

<400> SEQUENCE: 186
gcacacgccc agttccggtg                                                    20

<210> SEQ ID NO 187
<211> LENGTH: 20
<212> TYPE: DNA
<213> ORGANISM: Artificial Sequence
<220> FEATURE:
<223> OTHER INFORMATION: sgRNA
```

<400> SEQUENCE: 187
tcgcagactc ttggatgact                                            20

<210> SEQ ID NO 188
<211> LENGTH: 20
<212> TYPE: DNA
<213> ORGANISM: Artificial Sequence
<220> FEATURE:
<223> OTHER INFORMATION: sgRNA

<400> SEQUENCE: 188
aatctttaca ggcatatctc                                            20

<210> SEQ ID NO 189
<211> LENGTH: 20
<212> TYPE: DNA
<213> ORGANISM: Artificial Sequence
<220> FEATURE:
<223> OTHER INFORMATION: sgRNA

<400> SEQUENCE: 189
tcacacggcc cagttgttgt                                            20

<210> SEQ ID NO 190
<211> LENGTH: 20
<212> TYPE: DNA
<213> ORGANISM: Artificial Sequence
<220> FEATURE:
<223> OTHER INFORMATION: sgRNA

<400> SEQUENCE: 190
gtacatctaa ttcctcattg                                            20

<210> SEQ ID NO 191
<211> LENGTH: 20
<212> TYPE: DNA
<213> ORGANISM: Artificial Sequence
<220> FEATURE:
<223> OTHER INFORMATION: sgRNA

<400> SEQUENCE: 191
ttcaaactat tctccattcc                                            20

<210> SEQ ID NO 192
<211> LENGTH: 20
<212> TYPE: DNA
<213> ORGANISM: Artificial Sequence
<220> FEATURE:
<223> OTHER INFORMATION: sgRNA

<400> SEQUENCE: 192
gactttctgc ttattattca                                            20

<210> SEQ ID NO 193
<211> LENGTH: 20
<212> TYPE: DNA
<213> ORGANISM: Artificial Sequence
<220> FEATURE:
<223> OTHER INFORMATION: sgRNA

<400> SEQUENCE: 193
cccacctcac tcacacactc                                            20

<210> SEQ ID NO 194
<211> LENGTH: 20

<210> SEQ ID NO 195
<211> LENGTH: 20
<212> TYPE: DNA
<213> ORGANISM: Artificial Sequence
<220> FEATURE:
<223> OTHER INFORMATION: sgRNA

<400> SEQUENCE: 194
gggaccctcg gctgctcccc                                                        20

<210> SEQ ID NO 195
<211> LENGTH: 20
<212> TYPE: DNA
<213> ORGANISM: Artificial Sequence
<220> FEATURE:
<223> OTHER INFORMATION: sgRNA

<400> SEQUENCE: 195
gagaactcgc ccctcccatc                                                        20

<210> SEQ ID NO 196
<211> LENGTH: 20
<212> TYPE: DNA
<213> ORGANISM: Artificial Sequence
<220> FEATURE:
<223> OTHER INFORMATION: sgRNA

<400> SEQUENCE: 196 tccccttct acaggaaacc                                                         20

<210> SEQ ID NO 197
<211> LENGTH: 20
<212> TYPE: DNA
<213> ORGANISM: Artificial Sequence
<220> FEATURE:
<223> OTHER INFORMATION: sgRNA

<400> SEQUENCE: 197
gtggactgga atggtgcagg                                                        20

<210> SEQ ID NO 198
<211> LENGTH: 20
<212> TYPE: DNA
<213> ORGANISM: Artificial Sequence
<220> FEATURE:
<223> OTHER INFORMATION: sgRNA

<400> SEQUENCE: 198
acccacaggg cccctttatt                                                        20

<210> SEQ ID NO 199
<211> LENGTH: 20
<212> TYPE: DNA
<213> ORGANISM: Artificial Sequence
<220> FEATURE:
<223> OTHER INFORMATION: sgRNA

<400> SEQUENCE: 199
aaacacagat ggactttggg                                                        20

<210> SEQ ID NO 200
<211> LENGTH: 20
<212> TYPE: DNA
<213> ORGANISM: Artificial Sequence
<220> FEATURE:
<223> OTHER INFORMATION: sgRNA

<400> SEQUENCE: 200

-continued

```
aaaaatgtca gtcagcgccc                                              20

<210> SEQ ID NO 201
<211> LENGTH: 20
<212> TYPE: DNA
<213> ORGANISM: Artificial Sequence
<220> FEATURE:
<223> OTHER INFORMATION: sgRNA

<400> SEQUENCE: 201
tttatgttct gagtttgtgt                                              20

<210> SEQ ID NO 202
<211> LENGTH: 20
<212> TYPE: DNA
<213> ORGANISM: Artificial Sequence
<220> FEATURE:
<223> OTHER INFORMATION: sgRNA

<400> SEQUENCE: 202
aaagcacaag ggaagttcag                                              20

<210> SEQ ID NO 203
<211> LENGTH: 20
<212> TYPE: DNA
<213> ORGANISM: Artificial Sequence
<220> FEATURE:
<223> OTHER INFORMATION: sgRNA

<400> SEQUENCE: 203
ttttctaaca cagtgacaga                                              20

<210> SEQ ID NO 204
<211> LENGTH: 20
<212> TYPE: DNA
<213> ORGANISM: Artificial Sequence
<220> FEATURE:
<223> OTHER INFORMATION: sgRNA

<400> SEQUENCE: 204
cttaagtgct gactctcatt                                              20

<210> SEQ ID NO 205
<211> LENGTH: 20
<212> TYPE: DNA
<213> ORGANISM: Artificial Sequence
<220> FEATURE:
<223> OTHER INFORMATION: sgRNA

<400> SEQUENCE: 205
accagatcaa atacaacaaa                                              20

<210> SEQ ID NO 206
<211> LENGTH: 20
<212> TYPE: DNA
<213> ORGANISM: Artificial Sequence
<220> FEATURE:
<223> OTHER INFORMATION: sgRNA

<400> SEQUENCE: 206
agcaatatgg taattagtag                                              20

<210> SEQ ID NO 207
<211> LENGTH: 20
<212> TYPE: DNA
<213> ORGANISM: Artificial Sequence
```

-continued

```
<220> FEATURE:
<223> OTHER INFORMATION: sgRNA

<400> SEQUENCE: 207 ttttttttcct ctgggctaac                                              20

<210> SEQ ID NO 208
<211> LENGTH: 20
<212> TYPE: DNA
<213> ORGANISM: Artificial Sequence
<220> FEATURE:
<223> OTHER INFORMATION: sgRNA

<400> SEQUENCE: 208
acagtcactc aaatcagaac                                               20

<210> SEQ ID NO 209
<211> LENGTH: 20
<212> TYPE: DNA
<213> ORGANISM: Artificial Sequence
<220> FEATURE:
<223> OTHER INFORMATION: sgRNA

<400> SEQUENCE: 209
tttaacgctg caacttttgc                                               20

<210> SEQ ID NO 210
<211> LENGTH: 20
<212> TYPE: DNA
<213> ORGANISM: Artificial Sequence
<220> FEATURE:
<223> OTHER INFORMATION: sgRNA

<400> SEQUENCE: 210
agagtttcct ttagactcct                                               20

<210> SEQ ID NO 211
<211> LENGTH: 20
<212> TYPE: DNA
<213> ORGANISM: Artificial Sequence
<220> FEATURE:
<223> OTHER INFORMATION: sgRNA

<400> SEQUENCE: 211
taaataccag cagccagagg                                               20

<210> SEQ ID NO 212
<211> LENGTH: 20
<212> TYPE: DNA
<213> ORGANISM: Artificial Sequence
<220> FEATURE:
<223> OTHER INFORMATION: sgRNA

<400> SEQUENCE: 212
atcctcagga gacttcaatt                                               20

<210> SEQ ID NO 213
<211> LENGTH: 20
<212> TYPE: DNA
<213> ORGANISM: Artificial Sequence
<220> FEATURE:
<223> OTHER INFORMATION: sgRNA

<400> SEQUENCE: 213
aactaaggtt ttgtggcatt                                               20
```

-continued

```
<210> SEQ ID NO 214
<211> LENGTH: 20
<212> TYPE: DNA
<213> ORGANISM: Artificial Sequence
<220> FEATURE:
<223> OTHER INFORMATION: sgRNA

<400> SEQUENCE: 214
aagatgagat ggtgacagat                                                  20

<210> SEQ ID NO 215
<211> LENGTH: 20
<212> TYPE: DNA
<213> ORGANISM: Artificial Sequence
<220> FEATURE:
<223> OTHER INFORMATION: sgRNA

<400> SEQUENCE: 215
cggagcgcgg ggcggggccg                                                  20

<210> SEQ ID NO 216
<211> LENGTH: 20
<212> TYPE: DNA
<213> ORGANISM: Artificial Sequence
<220> FEATURE:
<223> OTHER INFORMATION: sgRNA

<400> SEQUENCE: 216
gctgtgtggc agccgctgat                                                  20

<210> SEQ ID NO 217
<211> LENGTH: 20
<212> TYPE: DNA
<213> ORGANISM: Artificial Sequence
<220> FEATURE:
<223> OTHER INFORMATION: sgRNA

<400> SEQUENCE: 217
caggggctag ggccgggtcc                                                  20

<210> SEQ ID NO 218
<211> LENGTH: 20
<212> TYPE: DNA
<213> ORGANISM: Artificial Sequence
<220> FEATURE:
<223> OTHER INFORMATION: sgRNA

<400> SEQUENCE: 218
cccaggtttc ggctcacccc                                                  20

<210> SEQ ID NO 219
<211> LENGTH: 20
<212> TYPE: DNA
<213> ORGANISM: Artificial Sequence
<220> FEATURE:
<223> OTHER INFORMATION: sgRNA

<400> SEQUENCE: 219
ggctgcgcgt cgccttcgtc                                                  20

<210> SEQ ID NO 220
<211> LENGTH: 20
<212> TYPE: DNA
<213> ORGANISM: Artificial Sequence
<220> FEATURE:
<223> OTHER INFORMATION: sgRNA
```

-continued

<400> SEQUENCE: 220
ggcgagtgtc tgggcgagcg                                                    20

<210> SEQ ID NO 221
<211> LENGTH: 20
<212> TYPE: DNA
<213> ORGANISM: Artificial Sequence
<220> FEATURE:
<223> OTHER INFORMATION: sgRNA

<400> SEQUENCE: 221
ggctgggccc ggtcctgggc                                                    20

<210> SEQ ID NO 222
<211> LENGTH: 20
<212> TYPE: DNA
<213> ORGANISM: Artificial Sequence
<220> FEATURE:
<223> OTHER INFORMATION: sgRNA

<400> SEQUENCE: 222
accaactcgt taccgccgag                                                    20

<210> SEQ ID NO 223
<211> LENGTH: 20
<212> TYPE: DNA
<213> ORGANISM: Artificial Sequence
<220> FEATURE:
<223> OTHER INFORMATION: sgRNA

<400> SEQUENCE: 223
aagaaaagga aactgaaaac                                                    20

<210> SEQ ID NO 224
<211> LENGTH: 20
<212> TYPE: DNA
<213> ORGANISM: Artificial Sequence
<220> FEATURE:
<223> OTHER INFORMATION: sgRNA

<400> SEQUENCE: 224
agacaggtga cggtccctgc                                                    20

<210> SEQ ID NO 225
<211> LENGTH: 20
<212> TYPE: DNA
<213> ORGANISM: Artificial Sequence
<220> FEATURE:
<223> OTHER INFORMATION: sgRNA

<400> SEQUENCE: 225
gtgcccagcc aatcaggaca                                                    20

<210> SEQ ID NO 226
<211> LENGTH: 20
<212> TYPE: DNA
<213> ORGANISM: Artificial Sequence
<220> FEATURE:
<223> OTHER INFORMATION: sgRNA

<400> SEQUENCE: 226
gaaagtccct ctctctaacc                                                    20

<210> SEQ ID NO 227

```
<211> LENGTH: 20
<212> TYPE: DNA
<213> ORGANISM: Artificial Sequence
<220> FEATURE:
<223> OTHER INFORMATION: sgRNA

<400> SEQUENCE: 227
caagccagcg acgcagtgcc                                                    20

<210> SEQ ID NO 228
<211> LENGTH: 20
<212> TYPE: DNA
<213> ORGANISM: Artificial Sequence
<220> FEATURE:
<223> OTHER INFORMATION: sgRNA

<400> SEQUENCE: 228
gagtctcgtg atgtttaaga                                                    20

<210> SEQ ID NO 229
<211> LENGTH: 20
<212> TYPE: DNA
<213> ORGANISM: Artificial Sequence
<220> FEATURE:
<223> OTHER INFORMATION: sgRNA

<400> SEQUENCE: 229
tgagtttgct gtctgtacat                                                    20

<210> SEQ ID NO 230
<211> LENGTH: 20
<212> TYPE: DNA
<213> ORGANISM: Artificial Sequence
<220> FEATURE:
<223> OTHER INFORMATION: sgRNA

<400> SEQUENCE: 230
caggggcaag ggctggtgcc                                                    20

<210> SEQ ID NO 231
<211> LENGTH: 20
<212> TYPE: DNA
<213> ORGANISM: Artificial Sequence
<220> FEATURE:
<223> OTHER INFORMATION: sgRNA

<400> SEQUENCE: 231
ccactattcc agactccaaa                                                    20

<210> SEQ ID NO 232
<211> LENGTH: 20
<212> TYPE: DNA
<213> ORGANISM: Artificial Sequence
<220> FEATURE:
<223> OTHER INFORMATION: sgRNA

<400> SEQUENCE: 232
ggagttgggg ggactgtgtc                                                    20

<210> SEQ ID NO 233
<211> LENGTH: 20
<212> TYPE: DNA
<213> ORGANISM: Artificial Sequence
<220> FEATURE:
<223> OTHER INFORMATION: sgRNA

<400> SEQUENCE: 233
```

```
ttctcagatg tgtctccggc                                    20

<210> SEQ ID NO 234
<211> LENGTH: 20
<212> TYPE: DNA
<213> ORGANISM: Artificial Sequence
<220> FEATURE:
<223> OTHER INFORMATION: sgRNA

<400> SEQUENCE: 234
gaagaacaag gtctagcgga                                    20

<210> SEQ ID NO 235
<211> LENGTH: 20
<212> TYPE: DNA
<213> ORGANISM: Artificial Sequence
<220> FEATURE:
<223> OTHER INFORMATION: sgRNA

<400> SEQUENCE: 235
gacacaagga gctgcagtcg                                    20

<210> SEQ ID NO 236
<211> LENGTH: 20
<212> TYPE: DNA
<213> ORGANISM: Artificial Sequence
<220> FEATURE:
<223> OTHER INFORMATION: sgRNA

<400> SEQUENCE: 236
tctagatgag agagcagtga                                    20

<210> SEQ ID NO 237
<211> LENGTH: 20
<212> TYPE: DNA
<213> ORGANISM: Artificial Sequence
<220> FEATURE:
<223> OTHER INFORMATION: sgRNA

<400> SEQUENCE: 237
gagacagaga ctcgaatttc                                    20

<210> SEQ ID NO 238
<211> LENGTH: 20
<212> TYPE: DNA
<213> ORGANISM: Artificial Sequence
<220> FEATURE:
<223> OTHER INFORMATION: sgRNA

<400> SEQUENCE: 238
aagaaaactg aaatagcctc                                    20

<210> SEQ ID NO 239
<211> LENGTH: 20
<212> TYPE: DNA
<213> ORGANISM: Artificial Sequence
<220> FEATURE:
<223> OTHER INFORMATION: sgRNA

<400> SEQUENCE: 239
attttggaaa ctccccttag                                    20

<210> SEQ ID NO 240
<211> LENGTH: 20
<212> TYPE: DNA
```

-continued

<213> ORGANISM: Artificial Sequence
<220> FEATURE:
<223> OTHER INFORMATION: sgRNA

<400> SEQUENCE: 240
gccctttata gggccagttg                                                    20

<210> SEQ ID NO 241
<211> LENGTH: 20
<212> TYPE: DNA
<213> ORGANISM: Artificial Sequence
<220> FEATURE:
<223> OTHER INFORMATION: sgRNA

<400> SEQUENCE: 241
ttatgatacc ggccaatgct                                                    20

<210> SEQ ID NO 242
<211> LENGTH: 20
<212> TYPE: DNA
<213> ORGANISM: Artificial Sequence
<220> FEATURE:
<223> OTHER INFORMATION: sgRNA

<400> SEQUENCE: 242
tggccgcggg cggaggggcg                                                    20

<210> SEQ ID NO 243
<211> LENGTH: 20
<212> TYPE: DNA
<213> ORGANISM: Artificial Sequence
<220> FEATURE:
<223> OTHER INFORMATION: sgRNA

<400> SEQUENCE: 243
gggcgtggcc gcgggcggag                                                    20

<210> SEQ ID NO 244
<211> LENGTH: 20
<212> TYPE: DNA
<213> ORGANISM: Artificial Sequence
<220> FEATURE:
<223> OTHER INFORMATION: sgRNA

<400> SEQUENCE: 244
gaaaggctct gggctgggaa                                                    20

<210> SEQ ID NO 245
<211> LENGTH: 20
<212> TYPE: DNA
<213> ORGANISM: Artificial Sequence
<220> FEATURE:
<223> OTHER INFORMATION: sgRNA

<400> SEQUENCE: 245
cgcagagtca cggggacgag                                                    20

<210> SEQ ID NO 246
<211> LENGTH: 20
<212> TYPE: DNA
<213> ORGANISM: Artificial Sequence
<220> FEATURE:
<223> OTHER INFORMATION: sgRNA

<400> SEQUENCE: 246
aaagcggaga gagatccgag                                                    20

```
<210> SEQ ID NO 247
<211> LENGTH: 20
<212> TYPE: DNA
<213> ORGANISM: Artificial Sequence
<220> FEATURE:
<223> OTHER INFORMATION: sgRNA

<400> SEQUENCE: 247
agagaaacaa caccacagcc                                                        20

<210> SEQ ID NO 248
<211> LENGTH: 20
<212> TYPE: DNA
<213> ORGANISM: Artificial Sequence
<220> FEATURE:
<223> OTHER INFORMATION: sgRNA

<400> SEQUENCE: 248
ctttgtcatg tttgtggatg                                                        20

<210> SEQ ID NO 249
<211> LENGTH: 20
<212> TYPE: DNA
<213> ORGANISM: Artificial Sequence
<220> FEATURE:
<223> OTHER INFORMATION: sgRNA

<400> SEQUENCE: 249
ccaagcaaga gcactgtccc                                                        20

<210> SEQ ID NO 250
<211> LENGTH: 20
<212> TYPE: DNA
<213> ORGANISM: Artificial Sequence
<220> FEATURE:
<223> OTHER INFORMATION: sgRNA

<400> SEQUENCE: 250
tccaaataac ttctgccggc                                                        20

<210> SEQ ID NO 251
<211> LENGTH: 20
<212> TYPE: DNA
<213> ORGANISM: Artificial Sequence
<220> FEATURE:
<223> OTHER INFORMATION: sgRNA

<400> SEQUENCE: 251
tttgtagtca ttctcatcag                                                        20

<210> SEQ ID NO 252
<211> LENGTH: 20
<212> TYPE: DNA
<213> ORGANISM: Artificial Sequence
<220> FEATURE:
<223> OTHER INFORMATION: sgRNA

<400> SEQUENCE: 252
gctttacact catgctccga                                                        20

<210> SEQ ID NO 253
<211> LENGTH: 20
<212> TYPE: DNA
<213> ORGANISM: Artificial Sequence
<220> FEATURE:
```

<223> OTHER INFORMATION: sgRNA

<400> SEQUENCE: 253
cccggcgggc cccgcgcgcc                                              20

<210> SEQ ID NO 254
<211> LENGTH: 20
<212> TYPE: DNA
<213> ORGANISM: Artificial Sequence
<220> FEATURE:
<223> OTHER INFORMATION: sgRNA

<400> SEQUENCE: 254
gcgcggcgaa gcgcggcggc                                              20

<210> SEQ ID NO 255
<211> LENGTH: 20
<212> TYPE: DNA
<213> ORGANISM: Artificial Sequence
<220> FEATURE:
<223> OTHER INFORMATION: sgRNA

<400> SEQUENCE: 255
gccccttccc gacaggcccc                                              20

<210> SEQ ID NO 256
<211> LENGTH: 20
<212> TYPE: DNA
<213> ORGANISM: Artificial Sequence
<220> FEATURE:
<223> OTHER INFORMATION: sgRNA

<400> SEQUENCE: 256
ccggcatgca gcggggctcc                                              20

<210> SEQ ID NO 257
<211> LENGTH: 20
<212> TYPE: DNA
<213> ORGANISM: Artificial Sequence
<220> FEATURE:
<223> OTHER INFORMATION: sgRNA

<400> SEQUENCE: 257
gaggtctcgg cgaagcggcg                                              20

<210> SEQ ID NO 258
<211> LENGTH: 20
<212> TYPE: DNA
<213> ORGANISM: Artificial Sequence
<220> FEATURE:
<223> OTHER INFORMATION: sgRNA

<400> SEQUENCE: 258
ggtgtgcggc tgcgcagact                                              20

<210> SEQ ID NO 259
<211> LENGTH: 20
<212> TYPE: DNA
<213> ORGANISM: Artificial Sequence
<220> FEATURE:
<223> OTHER INFORMATION: sgRNA

<400> SEQUENCE: 259
taacgcgaga gcgcgcgggg                                              20

-continued

```
<210> SEQ ID NO 260
<211> LENGTH: 20
<212> TYPE: DNA
<213> ORGANISM: Artificial Sequence
<220> FEATURE:
<223> OTHER INFORMATION: sgRNA

<400> SEQUENCE: 260
gaaggcgacg gccccgcccc                                                 20

<210> SEQ ID NO 261
<211> LENGTH: 20
<212> TYPE: DNA
<213> ORGANISM: Artificial Sequence
<220> FEATURE:
<223> OTHER INFORMATION: sgRNA

<400> SEQUENCE: 261
cccgtatccg actccacccc                                                 20

<210> SEQ ID NO 262
<211> LENGTH: 20
<212> TYPE: DNA
<213> ORGANISM: Artificial Sequence
<220> FEATURE:
<223> OTHER INFORMATION: sgRNA

<400> SEQUENCE: 262
ggtggactca ctgcctctcc                                                 20

<210> SEQ ID NO 263
<211> LENGTH: 20
<212> TYPE: DNA
<213> ORGANISM: Artificial Sequence
<220> FEATURE:
<223> OTHER INFORMATION: sgRNA

<400> SEQUENCE: 263
cattttctgc cccaaattcc                                                 20

<210> SEQ ID NO 264
<211> LENGTH: 20
<212> TYPE: DNA
<213> ORGANISM: Artificial Sequence
<220> FEATURE:
<223> OTHER INFORMATION: sgRNA

<400> SEQUENCE: 264
tgcacggggg ttactctgga                                                 20

<210> SEQ ID NO 265
<211> LENGTH: 20
<212> TYPE: DNA
<213> ORGANISM: Artificial Sequence
<220> FEATURE:
<223> OTHER INFORMATION: sgRNA

<400> SEQUENCE: 265
gaggcgtagg cgtcaccagt                                                 20

<210> SEQ ID NO 266
<211> LENGTH: 20
<212> TYPE: DNA
<213> ORGANISM: Artificial Sequence
<220> FEATURE:
<223> OTHER INFORMATION: sgRNA
```

-continued

<400> SEQUENCE: 266
agatcgatcc ggagtcccga                                              20

<210> SEQ ID NO 267
<211> LENGTH: 20
<212> TYPE: DNA
<213> ORGANISM: Artificial Sequence
<220> FEATURE:
<223> OTHER INFORMATION: sgRNA

<400> SEQUENCE: 267
tgttctctaa agaatttctc                                              20

<210> SEQ ID NO 268
<211> LENGTH: 20
<212> TYPE: DNA
<213> ORGANISM: Artificial Sequence
<220> FEATURE:
<223> OTHER INFORMATION: sgRNA

<400> SEQUENCE: 268
gaccacaaac ttgattgtgc                                              20

<210> SEQ ID NO 269
<211> LENGTH: 20
<212> TYPE: DNA
<213> ORGANISM: Artificial Sequence
<220> FEATURE:
<223> OTHER INFORMATION: sgRNA

<400> SEQUENCE: 269
aaaccctagt ctcagatcca                                              20

<210> SEQ ID NO 270
<211> LENGTH: 20
<212> TYPE: DNA
<213> ORGANISM: Artificial Sequence
<220> FEATURE:
<223> OTHER INFORMATION: sgRNA

<400> SEQUENCE: 270
tttctctcct aaactctgat                                              20

<210> SEQ ID NO 271
<211> LENGTH: 20
<212> TYPE: DNA
<213> ORGANISM: Artificial Sequence
<220> FEATURE:
<223> OTHER INFORMATION: sgRNA

<400> SEQUENCE: 271
tccctctgct cctctttttt                                              20

<210> SEQ ID NO 272
<211> LENGTH: 20
<212> TYPE: DNA
<213> ORGANISM: Artificial Sequence
<220> FEATURE:
<223> OTHER INFORMATION: sgRNA

<400> SEQUENCE: 272
ctgcaacatg ggacttcccc                                              20

<210> SEQ ID NO 273
<211> LENGTH: 20

-continued

```
<212> TYPE: DNA
<213> ORGANISM: Artificial Sequence
<220> FEATURE:
<223> OTHER INFORMATION: sgRNA

<400> SEQUENCE: 273
ttattgtagc ctccaagtta                                                   20

<210> SEQ ID NO 274
<211> LENGTH: 20
<212> TYPE: DNA
<213> ORGANISM: Artificial Sequence
<220> FEATURE:
<223> OTHER INFORMATION: sgRNA

<400> SEQUENCE: 274
gttgacttag caaaacctgc                                                   20

<210> SEQ ID NO 275
<211> LENGTH: 20
<212> TYPE: DNA
<213> ORGANISM: Artificial Sequence
<220> FEATURE:
<223> OTHER INFORMATION: sgRNA

<400> SEQUENCE: 275
tcggtcccca acttgagcac                                                   20

<210> SEQ ID NO 276
<211> LENGTH: 20
<212> TYPE: DNA
<213> ORGANISM: Artificial Sequence
<220> FEATURE:
<223> OTHER INFORMATION: sgRNA

<400> SEQUENCE: 276
gggttagggg catgcaggaa                                                   20

<210> SEQ ID NO 277
<211> LENGTH: 20
<212> TYPE: DNA
<213> ORGANISM: Artificial Sequence
<220> FEATURE:
<223> OTHER INFORMATION: sgRNA

<400> SEQUENCE: 277
tggacttgtc agcgcctgcc                                                   20

<210> SEQ ID NO 278
<211> LENGTH: 20
<212> TYPE: DNA
<213> ORGANISM: Artificial Sequence
<220> FEATURE:
<223> OTHER INFORMATION: sgRNA

<400> SEQUENCE: 278
tttcactgtt tagcgttgcg                                                   20

<210> SEQ ID NO 279
<211> LENGTH: 20
<212> TYPE: DNA
<213> ORGANISM: Artificial Sequence
<220> FEATURE:
<223> OTHER INFORMATION: sgRNA

<400> SEQUENCE: 279
```

-continued tttctctcac actaaaagaa                                                          20

<210> SEQ ID NO 280
<211> LENGTH: 20
<212> TYPE: DNA
<213> ORGANISM: Artificial Sequence
<220> FEATURE:
<223> OTHER INFORMATION: sgRNA

<400> SEQUENCE: 280
ctggaacaat gatgtgagct                                                          20

<210> SEQ ID NO 281
<211> LENGTH: 20
<212> TYPE: DNA
<213> ORGANISM: Artificial Sequence
<220> FEATURE:
<223> OTHER INFORMATION: sgRNA

<400> SEQUENCE: 281
ttccgttcct cattgactat                                                          20

<210> SEQ ID NO 282
<211> LENGTH: 20
<212> TYPE: DNA
<213> ORGANISM: Artificial Sequence
<220> FEATURE:
<223> OTHER INFORMATION: sgRNA

<400> SEQUENCE: 282
tagttccttg ccatatccta                                                          20

<210> SEQ ID NO 283
<211> LENGTH: 20
<212> TYPE: DNA
<213> ORGANISM: Artificial Sequence
<220> FEATURE:
<223> OTHER INFORMATION: sgRNA

<400> SEQUENCE: 283
aaacagtcag caaaacactg                                                          20

<210> SEQ ID NO 284
<211> LENGTH: 20
<212> TYPE: DNA
<213> ORGANISM: Artificial Sequence
<220> FEATURE:
<223> OTHER INFORMATION: sgRNA

<400> SEQUENCE: 284
tcggtcccca acttgagcac                                                          20

<210> SEQ ID NO 285
<211> LENGTH: 20
<212> TYPE: DNA
<213> ORGANISM: Artificial Sequence
<220> FEATURE:
<223> OTHER INFORMATION: sgRNA

<400> SEQUENCE: 285
gggttagggg catgcaggaa                                                          20

<210> SEQ ID NO 286
<211> LENGTH: 20
<212> TYPE: DNA
<213> ORGANISM: Artificial Sequence -continued

```
<220> FEATURE:
<223> OTHER INFORMATION: sgRNA

<400> SEQUENCE: 286
tggacttgtc agcgcctgcc                                               20

<210> SEQ ID NO 287
<211> LENGTH: 20
<212> TYPE: DNA
<213> ORGANISM: Artificial Sequence
<220> FEATURE:
<223> OTHER INFORMATION: sgRNA

<400> SEQUENCE: 287
tttcactgtt tagcgttgcg                                               20

<210> SEQ ID NO 288
<211> LENGTH: 20
<212> TYPE: DNA
<213> ORGANISM: Artificial Sequence
<220> FEATURE:
<223> OTHER INFORMATION: sgRNA

<400> SEQUENCE: 288
gccgggagtg aggcaggaag                                               20

<210> SEQ ID NO 289
<211> LENGTH: 20
<212> TYPE: DNA
<213> ORGANISM: Artificial Sequence
<220> FEATURE:
<223> OTHER INFORMATION: sgRNA

<400> SEQUENCE: 289
gctactcagg ggccaggggc                                               20

<210> SEQ ID NO 290
<211> LENGTH: 20
<212> TYPE: DNA
<213> ORGANISM: Artificial Sequence
<220> FEATURE:
<223> OTHER INFORMATION: sgRNA

<400> SEQUENCE: 290
gcgggacttg gcgccggctg                                               20

<210> SEQ ID NO 291
<211> LENGTH: 20
<212> TYPE: DNA
<213> ORGANISM: Artificial Sequence
<220> FEATURE:
<223> OTHER INFORMATION: sgRNA

<400> SEQUENCE: 291
tgttggttgg gcgggaggtg                                               20

<210> SEQ ID NO 292
<211> LENGTH: 20
<212> TYPE: DNA
<213> ORGANISM: Artificial Sequence
<220> FEATURE:
<223> OTHER INFORMATION: sgRNA

<400> SEQUENCE: 292
cgatgcccac gccggccaac                                               20
```

<210> SEQ ID NO 293
<211> LENGTH: 20
<212> TYPE: DNA
<213> ORGANISM: Artificial Sequence
<220> FEATURE:
<223> OTHER INFORMATION: sgRNA

<400> SEQUENCE: 293
tcttcgtgga gtgtgaagat                                                                    20

<210> SEQ ID NO 294
<211> LENGTH: 20
<212> TYPE: DNA
<213> ORGANISM: Artificial Sequence
<220> FEATURE:
<223> OTHER INFORMATION: sgRNA

<400> SEQUENCE: 294
accgtcccat acgcccccta                                                                    20

<210> SEQ ID NO 295
<211> LENGTH: 20
<212> TYPE: DNA
<213> ORGANISM: Artificial Sequence
<220> FEATURE:
<223> OTHER INFORMATION: sgRNA

<400> SEQUENCE: 295
atgtcggggc ttgcgcggga                                                                    20

<210> SEQ ID NO 296
<211> LENGTH: 20
<212> TYPE: DNA
<213> ORGANISM: Artificial Sequence
<220> FEATURE:
<223> OTHER INFORMATION: sgRNA

<400> SEQUENCE: 296
acttggctcc ctgccttccc                                                                    20

<210> SEQ ID NO 297
<211> LENGTH: 20
<212> TYPE: DNA
<213> ORGANISM: Artificial Sequence
<220> FEATURE:
<223> OTHER INFORMATION: sgRNA

<400> SEQUENCE: 297
gtactgactg ataacctccc                                                                    20

<210> SEQ ID NO 298
<211> LENGTH: 20
<212> TYPE: DNA
<213> ORGANISM: Artificial Sequence
<220> FEATURE:
<223> OTHER INFORMATION: sgRNA

<400> SEQUENCE: 298
acacgcatac acaacatttt                                                                    20

<210> SEQ ID NO 299
<211> LENGTH: 20
<212> TYPE: DNA
<213> ORGANISM: Artificial Sequence
<220> FEATURE:
<223> OTHER INFORMATION: sgRNA -continued

<400> SEQUENCE: 299
tacagacttg tatgtttcca                                                                           20

<210> SEQ ID NO 300
<211> LENGTH: 20
<212> TYPE: DNA
<213> ORGANISM: Artificial Sequence
<220> FEATURE:
<223> OTHER INFORMATION: sgRNA

<400> SEQUENCE: 300
taataggaga cactctcctt                                                                           20

<210> SEQ ID NO 301
<211> LENGTH: 20
<212> TYPE: DNA
<213> ORGANISM: Artificial Sequence
<220> FEATURE:
<223> OTHER INFORMATION: sgRNA

<400> SEQUENCE: 301
agctgcttgg ctacaaaagg                                                                           20

<210> SEQ ID NO 302
<211> LENGTH: 20
<212> TYPE: DNA
<213> ORGANISM: Artificial Sequence
<220> FEATURE:
<223> OTHER INFORMATION: sgRNA

<400> SEQUENCE: 302
ttggaaggcc ggaaacggaa                                                                           20

<210> SEQ ID NO 303
<211> LENGTH: 20
<212> TYPE: DNA
<213> ORGANISM: Artificial Sequence
<220> FEATURE:
<223> OTHER INFORMATION: sgRNA

<400> SEQUENCE: 303
ggcggggagg ggttgggggc                                                                           20

<210> SEQ ID NO 304
<211> LENGTH: 20
<212> TYPE: DNA
<213> ORGANISM: Artificial Sequence
<220> FEATURE:
<223> OTHER INFORMATION: sgRNA

<400> SEQUENCE: 304
atgtctcctg cctgaaggtc                                                                           20

<210> SEQ ID NO 305
<211> LENGTH: 20
<212> TYPE: DNA
<213> ORGANISM: Artificial Sequence
<220> FEATURE:
<223> OTHER INFORMATION: sgRNA

<400> SEQUENCE: 305
caggatgcag gcagtggccc                                                                           20

<210> SEQ ID NO 306

-continued

```
<211> LENGTH: 20
<212> TYPE: DNA
<213> ORGANISM: Artificial Sequence
<220> FEATURE:
<223> OTHER INFORMATION: sgRNA

<400> SEQUENCE: 306
caactgcctc cacccacttt                                        20

<210> SEQ ID NO 307
<211> LENGTH: 20
<212> TYPE: DNA
<213> ORGANISM: Artificial Sequence
<220> FEATURE:
<223> OTHER INFORMATION: sgRNA

<400> SEQUENCE: 307
atgtccggcc ggtcgagggg                                        20

<210> SEQ ID NO 308
<211> LENGTH: 20
<212> TYPE: DNA
<213> ORGANISM: Artificial Sequence
<220> FEATURE:
<223> OTHER INFORMATION: sgRNA

<400> SEQUENCE: 308
tcagactggc agcggttgga                                        20

<210> SEQ ID NO 309
<211> LENGTH: 20
<212> TYPE: DNA
<213> ORGANISM: Artificial Sequence
<220> FEATURE:
<223> OTHER INFORMATION: sgRNA

<400> SEQUENCE: 309
ggcaactctg aggctcaccc                                        20

<210> SEQ ID NO 310
<211> LENGTH: 20
<212> TYPE: DNA
<213> ORGANISM: Artificial Sequence
<220> FEATURE:
<223> OTHER INFORMATION: sgRNA

<400> SEQUENCE: 310
gggacttgag caattggcga                                        20

<210> SEQ ID NO 311
<211> LENGTH: 20
<212> TYPE: DNA
<213> ORGANISM: Artificial Sequence
<220> FEATURE:
<223> OTHER INFORMATION: sgRNA

<400> SEQUENCE: 311 cagggggcggg cccaagggct                                       20

<210> SEQ ID NO 312
<211> LENGTH: 20
<212> TYPE: DNA
<213> ORGANISM: Artificial Sequence
<220> FEATURE:
<223> OTHER INFORMATION: sgRNA

<400> SEQUENCE: 312
```
gtcaggttgg tttgagaggc                                             20

<210> SEQ ID NO 313
<211> LENGTH: 20
<212> TYPE: DNA
<213> ORGANISM: Artificial Sequence
<220> FEATURE:
<223> OTHER INFORMATION: sgRNA

<400> SEQUENCE: 313
cggaacgctg ggttcccaga                                             20

<210> SEQ ID NO 314
<211> LENGTH: 20
<212> TYPE: DNA
<213> ORGANISM: Artificial Sequence
<220> FEATURE:
<223> OTHER INFORMATION: sgRNA

<400> SEQUENCE: 314
gtggtgaggc caatagaaat                                             20

<210> SEQ ID NO 315
<211> LENGTH: 20
<212> TYPE: DNA
<213> ORGANISM: Artificial Sequence
<220> FEATURE:
<223> OTHER INFORMATION: sgRNA

<400> SEQUENCE: 315
ggcatagacc aatgacaaag                                             20

<210> SEQ ID NO 316
<211> LENGTH: 20
<212> TYPE: DNA
<213> ORGANISM: Artificial Sequence
<220> FEATURE:
<223> OTHER INFORMATION: sgRNA

<400> SEQUENCE: 316
caatggaaaa agacggccat                                             20

<210> SEQ ID NO 317
<211> LENGTH: 20
<212> TYPE: DNA
<213> ORGANISM: Artificial Sequence
<220> FEATURE:
<223> OTHER INFORMATION: sgRNA

<400> SEQUENCE: 317
tgggtataaa agtgcaaggc                                             20

<210> SEQ ID NO 318
<211> LENGTH: 20
<212> TYPE: DNA
<213> ORGANISM: Artificial Sequence
<220> FEATURE:
<223> OTHER INFORMATION: sgRNA

<400> SEQUENCE: 318
cttcgtcggt tcactatgtt                                             20

<210> SEQ ID NO 319
<211> LENGTH: 20
<212> TYPE: DNA

```
<213> ORGANISM: Artificial Sequence
<220> FEATURE:
<223> OTHER INFORMATION: sgRNA

<400> SEQUENCE: 319
gcggggagag gcaggggagg                                                                  20

<210> SEQ ID NO 320
<211> LENGTH: 20
<212> TYPE: DNA
<213> ORGANISM: Artificial Sequence
<220> FEATURE:
<223> OTHER INFORMATION: sgRNA

<400> SEQUENCE: 320
ggggagaggc aggggaggcg                                                                  20

<210> SEQ ID NO 321
<211> LENGTH: 20
<212> TYPE: DNA
<213> ORGANISM: Artificial Sequence
<220> FEATURE:
<223> OTHER INFORMATION: sgRNA

<400> SEQUENCE: 321
gagggagaag ggaggtggga                                                                  20

<210> SEQ ID NO 322
<211> LENGTH: 20
<212> TYPE: DNA
<213> ORGANISM: Artificial Sequence
<220> FEATURE:
<223> OTHER INFORMATION: sgRNA

<400> SEQUENCE: 322
gggagggaag gggatggatg                                                                  20

<210> SEQ ID NO 323
<211> LENGTH: 20
<212> TYPE: DNA
<213> ORGANISM: Artificial Sequence
<220> FEATURE:
<223> OTHER INFORMATION: sgRNA

<400> SEQUENCE: 323
gcaggggagg ctgggatggg                                                                  20

<210> SEQ ID NO 324
<211> LENGTH: 20
<212> TYPE: DNA
<213> ORGANISM: Artificial Sequence
<220> FEATURE:
<223> OTHER INFORMATION: sgRNA

<400> SEQUENCE: 324
gaggccggga ggggctggga                                                                  20

<210> SEQ ID NO 325
<211> LENGTH: 20
<212> TYPE: DNA
<213> ORGANISM: Artificial Sequence
<220> FEATURE:
<223> OTHER INFORMATION: sgRNA

<400> SEQUENCE: 325
aaggacaggg aagcctggag                                                                  20
```

```
<210> SEQ ID NO 326
<211> LENGTH: 20
<212> TYPE: DNA
<213> ORGANISM: Artificial Sequence
<220> FEATURE:
<223> OTHER INFORMATION: sgRNA

<400> SEQUENCE: 326
actgataggg agggacctgg                                                                      20

<210> SEQ ID NO 327
<211> LENGTH: 20
<212> TYPE: DNA
<213> ORGANISM: Artificial Sequence
<220> FEATURE:
<223> OTHER INFORMATION: sgRNA

<400> SEQUENCE: 327
gcggggcgcg gggcggggcg                                                                      20

<210> SEQ ID NO 328
<211> LENGTH: 20
<212> TYPE: DNA
<213> ORGANISM: Artificial Sequence
<220> FEATURE:
<223> OTHER INFORMATION: sgRNA

<400> SEQUENCE: 328
gggaggaggc actttggctt                                                                      20

<210> SEQ ID NO 329
<211> LENGTH: 20
<212> TYPE: DNA
<213> ORGANISM: Artificial Sequence
<220> FEATURE:
<223> OTHER INFORMATION: sgRNA

<400> SEQUENCE: 329
gggagggagc gccccctcc                                                                       20

<210> SEQ ID NO 330
<211> LENGTH: 20
<212> TYPE: DNA
<213> ORGANISM: Artificial Sequence
<220> FEATURE:
<223> OTHER INFORMATION: sgRNA

<400> SEQUENCE: 330
tgggtctccg cgcccagcgc                                                                      20

<210> SEQ ID NO 331
<211> LENGTH: 20
<212> TYPE: DNA
<213> ORGANISM: Artificial Sequence
<220> FEATURE:
<223> OTHER INFORMATION: sgRNA

<400> SEQUENCE: 331
agtcccctgc ggggtcgcgg                                                                      20

<210> SEQ ID NO 332
<211> LENGTH: 20
<212> TYPE: DNA
<213> ORGANISM: Artificial Sequence
<220> FEATURE:
```

-continued

<223> OTHER INFORMATION: sgRNA

<400> SEQUENCE: 332
gccccgcaag aagggacgcg                                              20

<210> SEQ ID NO 333
<211> LENGTH: 20
<212> TYPE: DNA
<213> ORGANISM: Artificial Sequence
<220> FEATURE:
<223> OTHER INFORMATION: sgRNA

<400> SEQUENCE: 333
ggaaagacga taccagcccc                                              20

<210> SEQ ID NO 334
<211> LENGTH: 20
<212> TYPE: DNA
<213> ORGANISM: Artificial Sequence
<220> FEATURE:
<223> OTHER INFORMATION: sgRNA

<400> SEQUENCE: 334
acctggccac cactcgccgc                                              20

<210> SEQ ID NO 335
<211> LENGTH: 20
<212> TYPE: DNA
<213> ORGANISM: Artificial Sequence
<220> FEATURE:
<223> OTHER INFORMATION: sgRNA

<400> SEQUENCE: 335
gggcggggcg gggacggggc                                              20

<210> SEQ ID NO 336
<211> LENGTH: 20
<212> TYPE: DNA
<213> ORGANISM: Artificial Sequence
<220> FEATURE:
<223> OTHER INFORMATION: sgRNA

<400> SEQUENCE: 336
ggggcgctgc gcggcggctc                                              20

<210> SEQ ID NO 337
<211> LENGTH: 20
<212> TYPE: DNA
<213> ORGANISM: Artificial Sequence
<220> FEATURE:
<223> OTHER INFORMATION: sgRNA

<400> SEQUENCE: 337
cggcgcccag gtccgcgtcc                                              20

<210> SEQ ID NO 338
<211> LENGTH: 20
<212> TYPE: DNA
<213> ORGANISM: Artificial Sequence
<220> FEATURE:
<223> OTHER INFORMATION: sgRNA

<400> SEQUENCE: 338
cgagaccgcc ccgggacagg                                              20

<210> SEQ ID NO 339
<211> LENGTH: 20
<212> TYPE: DNA
<213> ORGANISM: Artificial Sequence
<220> FEATURE:
<223> OTHER INFORMATION: sgRNA

<400> SEQUENCE: 339
tcgccagagg agccaggccg                                                    20

<210> SEQ ID NO 340
<211> LENGTH: 20
<212> TYPE: DNA
<213> ORGANISM: Artificial Sequence
<220> FEATURE:
<223> OTHER INFORMATION: sgRNA

<400> SEQUENCE: 340
gtgtgcccgt cggccggagg                                                    20

<210> SEQ ID NO 341
<211> LENGTH: 20
<212> TYPE: DNA
<213> ORGANISM: Artificial Sequence
<220> FEATURE:
<223> OTHER INFORMATION: sgRNA

<400> SEQUENCE: 341
ggcaggtcgg cctgtccgcc                                                    20

<210> SEQ ID NO 342
<211> LENGTH: 20
<212> TYPE: DNA
<213> ORGANISM: Artificial Sequence
<220> FEATURE:
<223> OTHER INFORMATION: sgRNA

<400> SEQUENCE: 342
ctgggcagag ccgaactttc                                                    20

<210> SEQ ID NO 343
<211> LENGTH: 20
<212> TYPE: DNA
<213> ORGANISM: Artificial Sequence
<220> FEATURE:
<223> OTHER INFORMATION: sgRNA

<400> SEQUENCE: 343
ttctcctccc ctaggccgcc                                                    20

<210> SEQ ID NO 344
<211> LENGTH: 20
<212> TYPE: DNA
<213> ORGANISM: Artificial Sequence
<220> FEATURE:
<223> OTHER INFORMATION: sgRNA

<400> SEQUENCE: 344
gcctccctca ccaccgtgca                                                    20

<210> SEQ ID NO 345
<211> LENGTH: 20
<212> TYPE: DNA
<213> ORGANISM: Artificial Sequence
<220> FEATURE:
<223> OTHER INFORMATION: sgRNA

```
<400> SEQUENCE: 345
gcttttgtag aggctgtggc                                        20

<210> SEQ ID NO 346
<211> LENGTH: 20
<212> TYPE: DNA
<213> ORGANISM: Artificial Sequence
<220> FEATURE:
<223> OTHER INFORMATION: sgRNA

<400> SEQUENCE: 346
caaacaccct gtccaactcc                                        20

<210> SEQ ID NO 347
<211> LENGTH: 20
<212> TYPE: DNA
<213> ORGANISM: Artificial Sequence
<220> FEATURE:
<223> OTHER INFORMATION: sgRNA

<400> SEQUENCE: 347
tagaagaaga cggcagcaga                                        20

<210> SEQ ID NO 348
<211> LENGTH: 20
<212> TYPE: DNA
<213> ORGANISM: Artificial Sequence
<220> FEATURE:
<223> OTHER INFORMATION: sgRNA

<400> SEQUENCE: 348
aatggtgccc gagaagagtg                                        20

<210> SEQ ID NO 349
<211> LENGTH: 20
<212> TYPE: DNA
<213> ORGANISM: Artificial Sequence
<220> FEATURE:
<223> OTHER INFORMATION: sgRNA

<400> SEQUENCE: 349
catgaaacac cacgagcacc                                        20

<210> SEQ ID NO 350
<211> LENGTH: 20
<212> TYPE: DNA
<213> ORGANISM: Artificial Sequence
<220> FEATURE:
<223> OTHER INFORMATION: sgRNA

<400> SEQUENCE: 350
ttaaagaaag ttagctgggt                                        20

<210> SEQ ID NO 351
<211> LENGTH: 20
<212> TYPE: DNA
<213> ORGANISM: Artificial Sequence
<220> FEATURE:
<223> OTHER INFORMATION: sgRNA

<400> SEQUENCE: 351
gagtttaaac tgcaaggaaa                                        20

<210> SEQ ID NO 352
<211> LENGTH: 20
```

<212> TYPE: DNA
<213> ORGANISM: Artificial Sequence
<220> FEATURE:
<223> OTHER INFORMATION: sgRNA

<400> SEQUENCE: 352
tcaaaatctg tagagaaaag                                                    20

<210> SEQ ID NO 353
<211> LENGTH: 20
<212> TYPE: DNA
<213> ORGANISM: Artificial Sequence
<220> FEATURE:
<223> OTHER INFORMATION: sgRNA

<400> SEQUENCE: 353
ttaaatttct tcctcaagtg                                                    20

<210> SEQ ID NO 354
<211> LENGTH: 20
<212> TYPE: DNA
<213> ORGANISM: Artificial Sequence
<220> FEATURE:
<223> OTHER INFORMATION: sgRNA

<400> SEQUENCE: 354
gctcatctta acgtcatgtc                                                    20

<210> SEQ ID NO 355
<211> LENGTH: 20
<212> TYPE: DNA
<213> ORGANISM: Artificial Sequence
<220> FEATURE:
<223> OTHER INFORMATION: sgRNA

<400> SEQUENCE: 355
ctccctttgg gggtttccca                                                    20

<210> SEQ ID NO 356
<211> LENGTH: 20
<212> TYPE: DNA
<213> ORGANISM: Artificial Sequence
<220> FEATURE:
<223> OTHER INFORMATION: sgRNA

<400> SEQUENCE: 356
gacgggggcg gggacggggg                                                    20

<210> SEQ ID NO 357
<211> LENGTH: 20
<212> TYPE: DNA
<213> ORGANISM: Artificial Sequence
<220> FEATURE:
<223> OTHER INFORMATION: sgRNA

<400> SEQUENCE: 357
ccgcccccgc gcgcccgggc                                                    20

<210> SEQ ID NO 358
<211> LENGTH: 20
<212> TYPE: DNA
<213> ORGANISM: Artificial Sequence
<220> FEATURE:
<223> OTHER INFORMATION: sgRNA

<400> SEQUENCE: 358

-continued gcgcacgcgg cgagggcggc                                                  20

<210> SEQ ID NO 359
<211> LENGTH: 20
<212> TYPE: DNA
<213> ORGANISM: Artificial Sequence
<220> FEATURE:
<223> OTHER INFORMATION: sgRNA

<400> SEQUENCE: 359
ccccgcgtga cgcccagcgc                                                  20

<210> SEQ ID NO 360
<211> LENGTH: 20
<212> TYPE: DNA
<213> ORGANISM: Artificial Sequence
<220> FEATURE:
<223> OTHER INFORMATION: sgRNA

<400> SEQUENCE: 360
cgacgcgaac tcggggcgcc                                                  20

<210> SEQ ID NO 361
<211> LENGTH: 20
<212> TYPE: DNA
<213> ORGANISM: Artificial Sequence
<220> FEATURE:
<223> OTHER INFORMATION: sgRNA

<400> SEQUENCE: 361
gggtctcgcg cgccccctcc                                                  20

<210> SEQ ID NO 362
<211> LENGTH: 20
<212> TYPE: DNA
<213> ORGANISM: Artificial Sequence
<220> FEATURE:
<223> OTHER INFORMATION: sgRNA

<400> SEQUENCE: 362
cgctttcgct tccccagcca                                                  20

<210> SEQ ID NO 363
<211> LENGTH: 20
<212> TYPE: DNA
<213> ORGANISM: Artificial Sequence
<220> FEATURE:
<223> OTHER INFORMATION: sgRNA

<400> SEQUENCE: 363
aggcgagtga gactcattgc                                                  20

<210> SEQ ID NO 364
<211> LENGTH: 20
<212> TYPE: DNA
<213> ORGANISM: Artificial Sequence
<220> FEATURE:
<223> OTHER INFORMATION: sgRNA

<400> SEQUENCE: 364
ggctccagtt ccgctgtctg                                                  20

<210> SEQ ID NO 365
<211> LENGTH: 20
<212> TYPE: DNA
<213> ORGANISM: Artificial Sequence
<220> FEATURE:
<223> OTHER INFORMATION: sgRNA

<400> SEQUENCE: 365
ttcattctgg gctgggccgc                                            20

<210> SEQ ID NO 366
<211> LENGTH: 20
<212> TYPE: DNA
<213> ORGANISM: Artificial Sequence
<220> FEATURE:
<223> OTHER INFORMATION: sgRNA

<400> SEQUENCE: 366
tacagtgcga accagagttc                                            20

<210> SEQ ID NO 367
<211> LENGTH: 20
<212> TYPE: DNA
<213> ORGANISM: Artificial Sequence
<220> FEATURE:
<223> OTHER INFORMATION: sgRNA

<400> SEQUENCE: 367
tctcgcgcgc cccctcccgg                                            20

<210> SEQ ID NO 368
<211> LENGTH: 20
<212> TYPE: DNA
<213> ORGANISM: Artificial Sequence
<220> FEATURE:
<223> OTHER INFORMATION: sgRNA

<400> SEQUENCE: 368
agtaaaatac agttgtctca                                            20

<210> SEQ ID NO 369
<211> LENGTH: 20
<212> TYPE: DNA
<213> ORGANISM: Artificial Sequence
<220> FEATURE:
<223> OTHER INFORMATION: sgRNA

<400> SEQUENCE: 369
aggcgagtga gactcattgc                                            20

<210> SEQ ID NO 370
<211> LENGTH: 20
<212> TYPE: DNA
<213> ORGANISM: Artificial Sequence
<220> FEATURE:
<223> OTHER INFORMATION: sgRNA

<400> SEQUENCE: 370
gctccagttc cgctgtctgc                                            20

<210> SEQ ID NO 371
<211> LENGTH: 20
<212> TYPE: DNA
<213> ORGANISM: Artificial Sequence
<220> FEATURE:
<223> OTHER INFORMATION: sgRNA

<400> SEQUENCE: 371
tacagtgcga accagagttc                                            20

-continued

```
<210> SEQ ID NO 372
<211> LENGTH: 20
<212> TYPE: DNA
<213> ORGANISM: Artificial Sequence
<220> FEATURE:
<223> OTHER INFORMATION: sgRNA

<400> SEQUENCE: 372
cggcgccgcc aggaggcgcc                                                    20

<210> SEQ ID NO 373
<211> LENGTH: 20
<212> TYPE: DNA
<213> ORGANISM: Artificial Sequence
<220> FEATURE:
<223> OTHER INFORMATION: sgRNA

<400> SEQUENCE: 373
ggaggcaggg agaggcgaga                                                    20

<210> SEQ ID NO 374
<211> LENGTH: 20
<212> TYPE: DNA
<213> ORGANISM: Artificial Sequence
<220> FEATURE:
<223> OTHER INFORMATION: sgRNA

<400> SEQUENCE: 374
ttcccacccc agcctcaggg                                                    20

<210> SEQ ID NO 375
<211> LENGTH: 20
<212> TYPE: DNA
<213> ORGANISM: Artificial Sequence
<220> FEATURE:
<223> OTHER INFORMATION: sgRNA

<400> SEQUENCE: 375
aaagcagccc cgcagcaccc                                                    20

<210> SEQ ID NO 376
<211> LENGTH: 20
<212> TYPE: DNA
<213> ORGANISM: Artificial Sequence
<220> FEATURE:
<223> OTHER INFORMATION: sgRNA

<400> SEQUENCE: 376
ggctgcctcg tcacttgtct                                                    20

<210> SEQ ID NO 377
<211> LENGTH: 20
<212> TYPE: DNA
<213> ORGANISM: Artificial Sequence
<220> FEATURE:
<223> OTHER INFORMATION: sgRNA

<400> SEQUENCE: 377
actggtgcaa gtggaaaggc                                                    20

<210> SEQ ID NO 378
<211> LENGTH: 20
<212> TYPE: DNA
<213> ORGANISM: Artificial Sequence
<220> FEATURE:
<223> OTHER INFORMATION: sgRNA
```

-continued

<400> SEQUENCE: 378
gcgcggcgct aacgtgtgta                                                    20

<210> SEQ ID NO 379
<211> LENGTH: 20
<212> TYPE: DNA
<213> ORGANISM: Artificial Sequence
<220> FEATURE:
<223> OTHER INFORMATION: sgRNA

<400> SEQUENCE: 379
agcgcagcgc gacgtgcgcc                                                    20

<210> SEQ ID NO 380
<211> LENGTH: 20
<212> TYPE: DNA
<213> ORGANISM: Artificial Sequence
<220> FEATURE:
<223> OTHER INFORMATION: sgRNA

<400> SEQUENCE: 380
ctcttccagg aagcgtggcc                                                    20

<210> SEQ ID NO 381
<211> LENGTH: 20
<212> TYPE: DNA
<213> ORGANISM: Artificial Sequence
<220> FEATURE:
<223> OTHER INFORMATION: sgRNA

<400> SEQUENCE: 381
cgcccactcc tccgtcctat                                                    20

<210> SEQ ID NO 382
<211> LENGTH: 20
<212> TYPE: DNA
<213> ORGANISM: Artificial Sequence
<220> FEATURE:
<223> OTHER INFORMATION: sgRNA

<400> SEQUENCE: 382
tagactcaca ctcctaagga                                                    20

<210> SEQ ID NO 383
<211> LENGTH: 20
<212> TYPE: DNA
<213> ORGANISM: Artificial Sequence
<220> FEATURE:
<223> OTHER INFORMATION: sgRNA

<400> SEQUENCE: 383
gcgcactgag gtttcgcgta                                                    20

<210> SEQ ID NO 384
<211> LENGTH: 20
<212> TYPE: DNA
<213> ORGANISM: Artificial Sequence
<220> FEATURE:
<223> OTHER INFORMATION: sgRNA

<400> SEQUENCE: 384
gcattgcgga gctcgctagt                                                    20

<210> SEQ ID NO 385

-continued

```
<211> LENGTH: 20
<212> TYPE: DNA
<213> ORGANISM: Artificial Sequence
<220> FEATURE:
<223> OTHER INFORMATION: sgRNA

<400> SEQUENCE: 385
cgttatccct tttttccggc                                              20

<210> SEQ ID NO 386
<211> LENGTH: 20
<212> TYPE: DNA
<213> ORGANISM: Artificial Sequence
<220> FEATURE:
<223> OTHER INFORMATION: sgRNA

<400> SEQUENCE: 386
tgaaagggag aagtgaaagt                                              20

<210> SEQ ID NO 387
<211> LENGTH: 20
<212> TYPE: DNA
<213> ORGANISM: Artificial Sequence
<220> FEATURE:
<223> OTHER INFORMATION: sgRNA

<400> SEQUENCE: 387
atggtcctct ctctattcag                                              20

<210> SEQ ID NO 388
<211> LENGTH: 20
<212> TYPE: DNA
<213> ORGANISM: Artificial Sequence
<220> FEATURE:
<223> OTHER INFORMATION: sgRNA

<400> SEQUENCE: 388
gaagactttg ctctgtgcat                                              20

<210> SEQ ID NO 389
<211> LENGTH: 20
<212> TYPE: DNA
<213> ORGANISM: Artificial Sequence
<220> FEATURE:
<223> OTHER INFORMATION: sgRNA

<400> SEQUENCE: 389
tatttttcac ctgcactcaa                                              20

<210> SEQ ID NO 390
<211> LENGTH: 20
<212> TYPE: DNA
<213> ORGANISM: Artificial Sequence
<220> FEATURE:
<223> OTHER INFORMATION: sgRNA

<400> SEQUENCE: 390
caactaggga atttagaaaa                                              20

<210> SEQ ID NO 391
<211> LENGTH: 20
<212> TYPE: DNA
<213> ORGANISM: Artificial Sequence
<220> FEATURE:
<223> OTHER INFORMATION: sgRNA

<400> SEQUENCE: 391
```

```
actgactcag gccccgcccc                                      20

<210> SEQ ID NO 392
<211> LENGTH: 20
<212> TYPE: DNA
<213> ORGANISM: Artificial Sequence
<220> FEATURE:
<223> OTHER INFORMATION: sgRNA

<400> SEQUENCE: 392
atccaaagga aggaggccgg                                      20

<210> SEQ ID NO 393
<211> LENGTH: 20
<212> TYPE: DNA
<213> ORGANISM: Artificial Sequence
<220> FEATURE:
<223> OTHER INFORMATION: sgRNA

<400> SEQUENCE: 393
agacgaccca ggcgtccctg                                      20

<210> SEQ ID NO 394
<211> LENGTH: 20
<212> TYPE: DNA
<213> ORGANISM: Artificial Sequence
<220> FEATURE:
<223> OTHER INFORMATION: sgRNA

<400> SEQUENCE: 394
aggaccttgc ctgcaagtcc                                      20

<210> SEQ ID NO 395
<211> LENGTH: 20
<212> TYPE: DNA
<213> ORGANISM: Artificial Sequence
<220> FEATURE:
<223> OTHER INFORMATION: sgRNA

<400> SEQUENCE: 395
gtctctactt cccatacagc                                      20

<210> SEQ ID NO 396
<211> LENGTH: 20
<212> TYPE: DNA
<213> ORGANISM: Artificial Sequence
<220> FEATURE:
<223> OTHER INFORMATION: sgRNA

<400> SEQUENCE: 396
gtagggattg gactttctga                                      20

<210> SEQ ID NO 397
<211> LENGTH: 20
<212> TYPE: DNA
<213> ORGANISM: Artificial Sequence
<220> FEATURE:
<223> OTHER INFORMATION: sgRNA

<400> SEQUENCE: 397
gtctgtagca gactgtctac                                      20

<210> SEQ ID NO 398
<211> LENGTH: 20
<212> TYPE: DNA
```

-continued

```
<213> ORGANISM: Artificial Sequence
<220> FEATURE:
<223> OTHER INFORMATION: sgRNA

<400> SEQUENCE: 398
ttccaatcca aaatcctgca                                             20

<210> SEQ ID NO 399
<211> LENGTH: 20
<212> TYPE: DNA
<213> ORGANISM: Artificial Sequence
<220> FEATURE:
<223> OTHER INFORMATION: sgRNA

<400> SEQUENCE: 399
acccgcagca agcaccacca                                             20

<210> SEQ ID NO 400
<211> LENGTH: 20
<212> TYPE: DNA
<213> ORGANISM: Artificial Sequence
<220> FEATURE:
<223> OTHER INFORMATION: sgRNA

<400> SEQUENCE: 400
taaacttgcc caaagccatg                                             20

<210> SEQ ID NO 401
<211> LENGTH: 20
<212> TYPE: DNA
<213> ORGANISM: Artificial Sequence
<220> FEATURE:
<223> OTHER INFORMATION: sgRNA

<400> SEQUENCE: 401
gtggcactgg accaagctgg                                             20

<210> SEQ ID NO 402
<211> LENGTH: 20
<212> TYPE: DNA
<213> ORGANISM: Artificial Sequence
<220> FEATURE:
<223> OTHER INFORMATION: sgRNA

<400> SEQUENCE: 402
tcttgaacac aaatgaatct                                             20

<210> SEQ ID NO 403
<211> LENGTH: 20
<212> TYPE: DNA
<213> ORGANISM: Artificial Sequence
<220> FEATURE:
<223> OTHER INFORMATION: sgRNA

<400> SEQUENCE: 403
caaggtttct ctcctatcat                                             20

<210> SEQ ID NO 404
<211> LENGTH: 20
<212> TYPE: DNA
<213> ORGANISM: Artificial Sequence
<220> FEATURE:
<223> OTHER INFORMATION: sgRNA

<400> SEQUENCE: 404
tgtgctcttg aagaggggag                                             20
```

```
<210> SEQ ID NO 405
<211> LENGTH: 20
<212> TYPE: DNA
<213> ORGANISM: Artificial Sequence
<220> FEATURE:
<223> OTHER INFORMATION: sgRNA

<400> SEQUENCE: 405
ctccttcctt cgtttacaga                                                    20

<210> SEQ ID NO 406
<211> LENGTH: 20
<212> TYPE: DNA
<213> ORGANISM: Artificial Sequence
<220> FEATURE:
<223> OTHER INFORMATION: sgRNA

<400> SEQUENCE: 406
gtgcattctc tagcagggta                                                    20

<210> SEQ ID NO 407
<211> LENGTH: 20
<212> TYPE: DNA
<213> ORGANISM: Artificial Sequence
<220> FEATURE:
<223> OTHER INFORMATION: sgRNA

<400> SEQUENCE: 407
aacttggttt ctgttgtagg                                                    20

<210> SEQ ID NO 408
<211> LENGTH: 20
<212> TYPE: DNA
<213> ORGANISM: Artificial Sequence
<220> FEATURE:
<223> OTHER INFORMATION: sgRNA

<400> SEQUENCE: 408
ggggaggtct tctgagccac                                                    20

<210> SEQ ID NO 409
<211> LENGTH: 20
<212> TYPE: DNA
<213> ORGANISM: Artificial Sequence
<220> FEATURE:
<223> OTHER INFORMATION: sgRNA

<400> SEQUENCE: 409
agctgcacct tctttcagcg                                                    20

<210> SEQ ID NO 410
<211> LENGTH: 20
<212> TYPE: DNA
<213> ORGANISM: Artificial Sequence
<220> FEATURE:
<223> OTHER INFORMATION: sgRNA

<400> SEQUENCE: 410
cccagcaagg actcattatc                                                    20

<210> SEQ ID NO 411
<211> LENGTH: 20
<212> TYPE: DNA
<213> ORGANISM: Artificial Sequence
<220> FEATURE:
```

-continued

```
<223> OTHER INFORMATION: sgRNA

<400> SEQUENCE: 411
ttgaacagga aggcgttttg                                                   20
```